(12) United States Patent
Obrecht et al.

(10) Patent No.: US 11,629,171 B2
(45) Date of Patent: Apr. 18, 2023

(54) BETA-HAIRPIN PEPTIDOMIMETICS

(71) Applicant: POLYPHOR AG, Allschwil (CH)

(72) Inventors: Daniel Obrecht, Bättwil (CH); Anatol Luther, Binzen (DE); Francesca Bernardini, Hésingue (FR); Glenn E. Dale, Basel (CH); Nicolas Desjonqueres, Kembs (FR); Emile Brabet, Saint Louis (FR); Grégory Upert, Kembs (FR)

(73) Assignee: Spexis AG, Allschwil (CH)

( * ) Notice: Subject to any disclaimer, the term of this patent is extended or adjusted under 35 U.S.C. 154(b) by 0 days.

(21) Appl. No.: 16/762,394

(22) PCT Filed: Nov. 12, 2018

(86) PCT No.: PCT/EP2018/025290
§ 371 (c)(1),
(2) Date: May 7, 2020

(87) PCT Pub. No.: WO2019/091601
PCT Pub. Date: May 16, 2019

(65) Prior Publication Data
US 2021/0284693 A1 Sep. 16, 2021

(30) Foreign Application Priority Data

Nov. 10, 2017 (EP) ..................... 17020526

(51) Int. Cl.
*C07K 7/64* (2006.01)
*C07K 1/06* (2006.01)
*A61K 38/00* (2006.01)

(52) U.S. Cl.
CPC ............. *C07K 7/64* (2013.01); *C07K 1/061* (2013.01); *A61K 38/00* (2013.01)

(58) Field of Classification Search
CPC . C07K 7/64; C07K 1/061; C07K 1/10; A61K 38/00; Y02A 50/30; A61P 31/00
See application file for complete search history.

(56) References Cited

U.S. PATENT DOCUMENTS 10,829,520 B2 * 11/2020 Obrecht ................. A61P 11/00

FOREIGN PATENT DOCUMENTS

| WO | 2014/161781 A1 | 10/2014 |
| WO | 2014/161782 A1 | 10/2014 |
| WO | 2016/050360 A1 | 4/2016 |
| WO | 2016/150576 A1 | 9/2016 |

OTHER PUBLICATIONS

He et al, Molecules, 2019, 24, 1855, 1-34 (Year: 2019).*
Lu et al, International Journal of Molecular Sciences, 2016, 17, 561, 1-22 (Year: 2016).*
Chen et al. Adv. Drug Deliv. Rev. 65:1357-1369, 2013 (Year: 2013).*
International Search Report issued in Int'l Appl. No. PCT/EP2018/025290, dated Jan. 22, 2019.

* cited by examiner

*Primary Examiner* — Sudhakar Katakam
(74) *Attorney, Agent, or Firm* — Medler Ferro Woodhouse & Mills PLLC

(57) ABSTRACT

Beta-hairpin peptidomimetics of the general formula (I), and pharmaceutically acceptable salts thereof, with P, X, Q., and optionally L being elements as defined in the description and the claims, have Gram-negative antimicrobial activity to e.g. inhibit the growth or to kill microorganisms such as *Klebsiella pneumoniae* and/or *Acinetobacter baumannii* and/or *Escherichia coli* and/or *Pseudomonas aeruginosa* and/or *Enterobacter cloacae*. They can be used as medicaments to treat or prevent infections or as disinfectants for foodstuffs, cosmetics, medicaments or other nutrient-containing materials. These peptidomimetics can be manufactured by a process which is based on a mixed solid- and solution phase synthetic strategy.

3 Claims, No Drawings

BETA-HAIRPIN PEPTIDOMIMETICS

The present invention provides β-hairpin peptidomimetics having Gram-negative antimicrobial activity.

The β-hairpin peptidomimetics of the invention are compounds of the general formula (I), as depicted below, and pharmaceutically acceptable salts thereof, with P, X, Q, and optionally L being elements as described herein below.

In addition, the present invention provides an efficient synthetic process by which these compounds can, if desired, be made in parallel library-format. Moreover, the β-hairpin peptidomimetics of the invention show improved efficacy and desired pharmacological properties like e.g. reduced hemolysis of red blood cells.

A major cause of death worldwide and a leading cause of mortality in developed countries are infectious diseases. They result from the presence of pathogenic microbial agents including pathogenic viruses and pathogenic bacteria. The problem of bacterial resistance to established antibiotics has stimulated intense interest in developing novel antimicrobial agents with new modes of action (D. Obrecht, J. A. Robinson, F. Bernadini, C. Bisang, S. J. DeMarco, K. Moehle, F. O. Gombert, *Curr. Med. Chem.* 2009, 16, 42-65; H. Breithaupt, *Nat. Biotechnol.* 1999, 17, 1165-1169).

A growing unmet medical need is represented by Gram-negative bacteria causing 60% of nosocomial pneumonias (R. Frechette, *Ann. Rep. Med. Chem.*, Elsevier, 2007, 349-64). Extended spectrum beta lactamase (ESBL)-producing Gram-negative bacteria have also compromised the utility of many front-line beta-lactam drugs (S. J. Projan, P. A. Bradford, *Curr. Opin. Microbiol.*, 2007, 10, 441). The lack of suitable new compounds is forcing clinicians to use previously discarded antibiotics like colistin, despite well-known toxicity problems (M. E. Falagas, S. K. Kasiakou, *Crit. Care,* 2006, 10, R 27). Therefore, novel approaches are needed to treat inter alia resistant strains of *Klebsiella pneumoniae, Acinetobacter baumannii, Escherichia coli* (H. W. Boucher, G. H. Talbot, J. S. Bradley, J. E. Edwards Jr, D. Gilbert, L. B. Rice, M. Scheid, B. Spellberg, J. Bartlett, *IDSA Report on Development Pipeline, CID* 2009, 48, 1), as well as *Pseudomonas aeruginosa* or *Enterobacter cloacae*.

Antibiotic drug discovery in the last 20 years focused on the development of novel antibiotics against Gram-positive bacteria, while the discovery of novel agents against Gram-negative pathogens has been particularly sparse. There is an urgent need for novel classes of antibiotics with novel mechanisms of action, in particular against Gram-negative MDR ESKAPE pathogens (D. Obrecht, F. Bernardini, G. Dale, K. Dembowsky, *Ann. Reps Med. Chem.* 2011, 46, 245), due to emergence of resistance against the last resort antibiotics, colistin and polymyxin B (M. Vaara, *Curr. Opin. Microbiol.* 2010, 13, 574). Gram-negative ESKAPE pathogens encompass *Klebsiella pneumoniae, Acinetobacter baumannii, Pseudomonas aeruginosa,* and *Enterobacter* species (L. B. Rice, *J. Infect. Dis.* 2008, 197, 1079). Gram-negative organisms are particularly hard to kill due to the highly negatively charged outer membrane which is composed of up to 75% with lipopolysaccharides forming a formidable shield to prevent entry of antibacterials (C. Alexander, E. T. Rietschel, *J. Endotox. Res.* 2001, 7, 167; D. S. Kabanov, I. R. Prokhorenko, *Biochemistry (Moscow),* 2010, 75, 383).

One emerging class of antibiotics is based on naturally occurring cationic peptides (T. Ganz, R. I. Lehrer, *Mol. Medicine Today* 1999, 5, 292-297; R. M. Epand, H. J. Vogel, *Biochim. Biophys. Acta* 1999, 1462, 11-28). These include disulfide-bridged β-hairpin and β-sheet peptides (such as the protegrins [V. N. Kokryakov, S. S. L. Harwig, E. A. Panyutich, A. A. Shevchenko, G. M. Aleshina, O. V. Shamova, H. A. Korneva, R. I. Lehrer, *FEBS Lett.* 1993, 327, 231-236], tachyplesins [T. Nakamura, H. Furunaka, T. Miyata, F. Tokunaga, T. Muta, S. Iwanaga, M. Niwa, T. Takao, Y. Shimonishi, *J. Biol. Chem.* 1988, 263, 16709-16713], and the defensins [R. I. Lehrer, A. K. Lichtenstein, T. Ganz, *Annu. Rev. Immunol.* 1993, 11, 105-128]), amphipathic α-helical peptides (e.g. cecropins, dermaseptins, magainins, and mellitins [A. Tossi, L. Sandri, A. Giangaspero, *Biopolymers* 2000, 55, 4-30]), as well as other linear and loop-structured peptides. Although the mechanisms of action of antimicrobial cationic peptides are not yet fully understood, their primary site of interaction is the microbial cell membrane (H. W. Huang, Biochemistry 2000, 39, 8347-8352). Upon exposure to these agents, the cell membrane undergoes permeabilization, which is followed by rapid cell death. However, more complex mechanisms of action, for example, involving receptor-mediated signaling, cannot presently be ruled out (M. Wu, E. Maier, R. Benz, R. E. Hancock, *Biochemistry* 1999, 38, 7235-7242).

The compounds of the invention, comprising a module A and a module B, being linked directly or via linker L, as described below, exhibit Gram-negative antimicrobial activity, in particular against Gram-negative pathogens of the so-called ESKAPE pathogens (L. B. Rice, *J. Infect. Dis.* 2008, 197, 1079).

In module A the β-hairpin conformations of the cationic peptide mimetics are stabilized by the introduction of inter-strand (β-strand) linkages.

In addition, a module B, being a cyclic heptapeptide derived from the polymyxin family (T. Velkov, P. E. Thompson, R. L. Nation, J. Li, J. Med. Chem. 2010, 53, 1898; T. Velkov, K. D. Roberts, R. L. Nation, J. Wang, P. E. Thompson, J. Li, *ACS Chem. Biol.* 2014, 9, 1172), is covalently linked to module A, either directly or via a peptide linker L, as described below.

Template-bound hairpin mimetic peptides have been described in the literature (D. Obrecht, M. Altorfer, J. A. Robinson, *Adv. Med. Chem.* 1999, 4, 1-68; J. A. Robinson, *Syn. Lett.* 2000, 4, 429-441) and the ability to generate β-hairpin peptidomimetics using combinatorial and parallel synthesis methods has been established (L. Jiang, K. Moehle, B. Dhanapal, D. Obrecht, J. A. Robinson, *Helv. Chim. Acta.* 2000, 83, 3097-3112). Antibacterial template-fixed peptidomimetics and methods for their synthesis have been described in international patent applications WO02/070547 A1, WO2004/018503 A1, WO2007/079605 A2, WO2012/016595 A1, WO2014/161781 A1 and WO2014/161782 A1. The molecules described in the latter two patent applications show Gram-negative antimicrobial activity having high potency against *Klebsiella pneumoniae* and/or *Acinetobacter baumannii* and/or *Escherichia coli*. Moreover, the β-hairpin peptidomimetics described in WO2016/150576 A1 have potency against *Pseudomonas aeruginosa*. In addition, the compounds of the present invention show inter alia high potency against *Enterobacter cloacae*.

In a first embodiment (1) the present invention relates to novel β-hairpin peptidomimetics of formula (I),

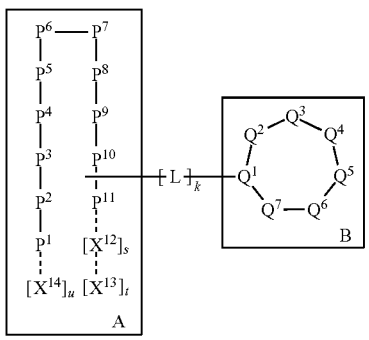

comprising a module A consisting of single elements P or X being connected in either direction from the carbonyl (C=O) point of attachment to the nitrogen (N) of the next element
wherein
$s=0$, $t=0$, and $u=0$; or $s=1$, $t=0$, and $u=0$; or $s=0$, $t=0$, and $u=1$; or $s=1$, $t=1$, and $u=0$; or $s=1$, $t=0$, and $u=1$; or $s=1$, $t=1$, and $u=1$;
if $s=1$, $t=1$, and $u=1$; and $X^{14}$ and $X^{13}$ taken together and/or $P^1$ and $X^{12}$ taken together and/or $P^2$ and $P^{11}$ taken together and/or $P^4$ and $P^9$ taken together form naturally or non-naturally cross-linking α-amino acids or non-naturally cross-linking acids containing each in total 1 to 12 carbon- and/or heteroatoms in a single side-chain which together are connecting $X^{14}$ and $X^{13}$ and/or $P^1$ and $X^{12}$ and/or $P^2$ and $P^{11}$ and/or $P^4$ and $P^9$ by covalent interaction (interstrand linkage) or by electrostatic interaction (salt bridge); then $X^{14}$ is pGlu; $^D$pGlu; Ac-pGlu; Ac-$^D$pGlu; or a naturally or non-naturally occurring basic L α-amino acid containing in total 1 to 25 carbon- and/or heteroatoms in a single side-chain comprising at least one amino function or one guanidino function; or a naturally or non-naturally occurring alcoholic D α-amino acid containing in total 1 to 25 carbon- and/or heteroatoms in a single side-chain; or an aliphatic acid containing in total 1 to 25 carbon- and/or heteroatoms in a single side-chain;

$P^1$ is a naturally or non-naturally occurring aliphatic L or D α-amino acid containing in total 1 to 25 carbon- and/or heteroatoms in a single side-chain; or a naturally or non-naturally occurring aromatic L α-amino acid containing in total 1 to 25 carbon- and/or heteroatoms in a single side-chain; or a naturally or non-naturally occurring alcoholic L α-amino acid containing in total 1 to 25 carbon- and/or heteroatoms in a single side-chain;

$P^2$ is a naturally or non-naturally occurring aliphatic L α-amino acid containing in total 1 to 25 carbon- and/or heteroatoms in a single side-chain; or a naturally or non-naturally occurring basic L α-amino acid containing in total 1 to 25 carbon- and/or heteroatoms in a single side-chain comprising at least one amino function or one guanidino function; or a naturally or non-naturally occurring alcoholic L α-amino acid containing in total 1 to 25 carbon- and/or heteroatoms in a single side-chain;

$P^3$ is a naturally or non-naturally occurring aliphatic L α-amino acid containing in total 1 to 25 carbon- and/or heteroatoms in a single side-chain; or a naturally or non-naturally occurring aromatic L α-amino acid containing in total 1 to 25 carbon- and/or heteroatoms in a single side-chain; or a naturally or non-naturally occurring alcoholic L α-amino acid containing in total 1 to 25 carbon- and/or heteroatoms in a single side-chain;

$P^4$ is Gly; or a naturally or non-naturally occurring aromatic L α-amino acid containing in total 1 to 25 carbon- and/or heteroatoms in a single side-chain; or a naturally or non-naturally occurring basic L α-amino acid containing in total 1 to 25 carbon- and/or heteroatoms in a single side-chain comprising at least one amino function or one guanidino function; or a naturally or non-naturally occurring alcoholic L α-amino acid containing in total 1 to 25 carbon- and/or heteroatoms in a single side-chain;

$P^5$ is Gly; or a naturally or non-naturally occurring aliphatic L α-amino acid containing in total 1 to 25 carbon- and/or heteroatoms in a single side-chain; or a naturally or non-naturally occurring aromatic L α-amino acid containing in total 1 to 25 carbon- and/or heteroatoms in a single side-chain; or a naturally or non-naturally occurring basic L α-amino acid containing in total 1 to 25 carbon- and/or heteroatoms in a single side-chain comprising at least one amino function or one guanidino function; or a naturally or non-naturally occurring alcoholic L α-amino acid containing in total 1 to 25 carbon- and/or heteroatoms in a single side-chain;

$P^6$ is Gly; or a naturally or non-naturally occurring basic D α-amino acid containing in total 1 to 25 carbon- and/or heteroatoms in a single side-chain comprising at least one amino function or one guanidino function; or a naturally or non-naturally occurring alcoholic D α-amino acid containing in total 1 to 25 carbon- and/or heteroatoms in a single side-chain; or a naturally or non-naturally occurring aliphatic D α-amino acid containing in total 1 to 25 carbon- and/or heteroatoms in a single side-chain;

$P^7$ is Gly; or a naturally or non-naturally occurring aliphatic L α-amino acid containing in total 1 to 25 carbon- and/or heteroatoms in a single side-chain; or a naturally or non-naturally occurring basic L α-amino acid containing in total 1 to 25 carbon- and/or heteroatoms in a single side-chain comprising at least one amino function or one guanidino function; or a naturally or non-naturally occurring alcoholic L or D α-amino acid containing in total 1 to 25 carbon- and/or heteroatoms in a single side-chain;

$P^8$ is a naturally or non-naturally occurring aliphatic L α-amino acid containing in total 1 to 25 carbon- and/or heteroatoms in a single side-chain; or a naturally or non-naturally occurring aromatic L α-amino acid containing in total 1 to 25 carbon- and/or heteroatoms in a single side-chain;

$P^9$ is Gly; or a naturally or non-naturally occurring aliphatic L α-amino acid containing in total 1 to 25 carbon- and/or heteroatoms in a single side-chain; or a naturally or non-naturally occurring aromatic L α-amino acid containing in total 1 to 25 carbon- and/or heteroatoms in a single side-chain; or a naturally or non-naturally occurring basic L α-amino acid containing in total 1 to 25 carbon- and/or heteroatoms in a single side-chain comprising at least one amino function or one guanidino function; or a naturally or non-naturally occurring alcoholic L α-amino acid containing in total 1 to 25 carbon- and/or heteroatoms in a single side-chain; or a naturally or non-naturally occurring L α-amino acid containing in total 1 to 25 carbon- and/or heteroatoms in a single side-chain comprising at least one carboxylic acid function or phosphonic acid function;

$P^{10}$ is a naturally or non-naturally occurring aliphatic L α-amino acid containing in total 1 to 25 carbon- and/or heteroatoms in a single side-chain; or a naturally or non-naturally occurring alcoholic L α-amino acid containing in total 1 to 25 carbon- and/or heteroatoms in a single side-chain; or a naturally or non-naturally occurring aromatic L α-amino acid containing in total 1 to 25 carbon- and/or heteroatoms in a single side-chain;

$P^{11}$ is a naturally or non-naturally occurring aliphatic L α-amino acid containing in total 1 to 25 carbon- and/or heteroatoms in a single side-chain; or a naturally or non-naturally occurring basic L α-amino acid containing in total 1 to 25 carbon- and/or heteroatoms in a single side-chain comprising at least one amino function or one guanidino function; or a naturally or non-naturally occurring alcoholic L α-amino acid containing in total 1 to 25 carbon- and/or heteroatoms in a single side-chain; or a naturally or non-naturally occurring L α-amino acid containing in total 1 to 25 carbon- and/or heteroatoms in a single side-chain comprising at least one carboxylic acid function or phosphonic acid function;

$X^{12}$ is Gly; or a naturally or non-naturally occurring aliphatic L or D α-amino acid containing in total 1 to 25 carbon- and/or heteroatoms in a single side-chain; or a naturally or non-naturally occurring aromatic L α-amino acid containing in total 1 to 25 carbon- and/or heteroatoms in a single side-chain; or a naturally or non-naturally occurring basic L α-amino acid containing in total 1 to 25 carbon- and/or heteroatoms in a single side-chain comprising at least one amino function or one guanidino function; or a naturally or non-naturally occurring alcoholic L α-amino acid containing in total 1 to 25 carbon- and/or heteroatoms in a single side-chain;

$X^{13}$ is Glyol; or a naturally or non-naturally occurring aliphatic D α-amino acid containing in total 1 to 25 carbon- and/or heteroatoms in a single side-chain; or a naturally or non-naturally occurring alcoholic D α-amino acid containing in total 1 to 25 carbon- and/or heteroatoms in a single side-chain;

with the proviso that, if $P^1$ is a naturally or non-naturally occurring alcoholic L α-amino acid containing in total 1 to 25 carbon- and/or heteroatoms in a single side-chain; then $X^{12}$ is naturally or non-naturally occurring aliphatic L or D α-amino acid
containing in total 1 to 25 carbon- and/or heteroatoms in a single side-chain; and if $P^3$ is a naturally or non-naturally occurring alcoholic L α-amino acid containing in total 1 to 25 carbon- and/or heteroatoms in a single side-chain; or a naturally or non-naturally occurring aliphatic L α-amino acid containing in total 1 to 25 carbon- and/or heteroatoms in a single side-chain;

then $P^1$; $P^{10}$; or $X^{12}$; is a naturally or non-naturally occurring aromatic L α-amino acid containing in total 1 to 25 carbon- and/or heteroatoms in a single side-chain; and if $P^8$ is a naturally or non-naturally occurring aliphatic L α-amino acid containing in total 1 to 25 carbon- and/or heteroatoms in a single side-chain; then $P^{10}$ is a naturally or non-naturally occurring aromatic L α-amino acid containing in total 1 to 25 carbon- and/or heteroatoms in a single side-chain; and if $P^{10}$ is a naturally or non-naturally occurring alcoholic L α-amino acid containing in total 1 to 25 carbon- and/or heteroatoms in a single side-chain; then $X^{12}$ is a naturally or non-naturally occurring aliphatic L or D α-amino acid containing in total 1 to 25 carbon- and/or heteroatoms in a single side-chain; and the combined number of the amino acid residue Gly in above module A must not exceed two; and the positions P of the amino acid residues Gly must not be in direct vicinity;

with the further proviso that, the combined number of interstrand linkages and salt bridges in above module A must not exceed two;

if $X^{14}$ and $X^{13}$ taken together form an interstrand linkage or salt bridge, as defined above; then $P^1$ and $X^{12}$ taken together are not forming an interstrand linkage or salt bridge, as defined above;

if $P^1$ and $X^{12}$ taken together form an interstrand linkage or salt bridge, as defined above; then $P^2$ and $P^{11}$ taken together are not forming an interstrand linkage or a salt bridge, as defined above;

the carbonyl (C=O) point of attachment of $X^{13}$ and the nitrogen (N) point of attachment of $X^{14}$ are appropriately saturated to form the corresponding naturally or non-naturally occurring terminal α-amino acids optionally having modified carbonyl (C=O) functional groups and/or nitrogen (N) functional groups;

with the further proviso that, if linker L, as defined below, is connected with module A by a carbonyl (C=O) point of attachment of $P^5$; $P^6$; or $P^7$; then $P^5$; $P^6$; or $P^7$; is a naturally or non-naturally occurring α-amino acid containing in total 1 to 25 carbon- and/or heteroatoms in a single side-chain comprising at least one carboxyl function;

if s=1, t=0, and u=1; and $P^1$ and $X^{12}$ taken together and/or $P^2$ and $P^{11}$ taken together and/or $P^4$ and $P^9$ taken together form naturally or non-naturally cross-linking α-amino acids containing each in total 1 to 12 carbon- and/or heteroatoms in a single side-chain which together are connecting $P^1$ and $X^{12}$ and/or $P^2$ and $P^{11}$ and/or $P^4$ and $P^9$ by covalent interaction (interstrand linkage) or by electrostatic interaction (salt bridge); then $X^{14}$; $P^1$; $P^2$; $P^3$; $P^4$; $P^5$; $P^6$; $P^7$; $P^8$; $P^9$; $P^{10}$; and $P^{11}$ are as defined above for module A, wherein s=1, t=1, and u=1;

$X^{12}$ is Glyol; or a naturally or non-naturally occurring aliphatic L α-amino acid containing in total 1 to 25 carbon- and/or heteroatoms in a single side-chain; or a naturally or non-naturally occurring aromatic L α-amino acid containing in total 1 to 25 carbon- and/or heteroatoms in a single side-chain; or a naturally or non-naturally occurring basic L α-amino acid containing in total 1 to 25 carbon- and/or heteroatoms in a single side-chain comprising at least one amino function or one guanidino function; or a naturally or non-naturally occurring alcoholic L α-amino acid containing in total 1 to 25 carbon- and/or heteroatoms in a single side-chain; or an aliphatic amino alcohol containing in total 1 to 25 carbon- and/or heteroatoms in a single side-chain; or an aromatic amino alcohol containing in total 1 to 25 carbon- and/or heteroatoms in a single side-chain; or basic amino alcohol containing in total 1 to 25 carbon- and/or heteroatoms in a single side-chain comprising at least one amino function or one guanidino function; or an alcoholic amino alcohol containing in total 1 to 25 carbon- and/or heteroatoms in a single side-chain comprising at least one hydroxyl function;

with the proviso that, if $P^1$ is a naturally or non-naturally occurring alcoholic L α-amino acid containing in total 1 to 25 carbon- and/or heteroatoms in a single side-chain; then $X^{12}$ is naturally or non-naturally occurring aliphatic L α-amino acid containing in total 1 to 25 carbon- and/or heteroatoms in a single side-chain; and if $P^3$ is a naturally or non-naturally occurring alcoholic L α-amino acid containing in total 1 to 25 carbon- and/or heteroatoms in a single side-chain; or a naturally or non-naturally occurring aliphatic L α-amino acid containing in total 1 to 25 carbon- and/or heteroatoms in a single side-chain;

then $P^1$; or $P^m$; is a naturally or non-naturally occurring aromatic L α-amino acid containing in total 1 to 25 carbon- and/or heteroatoms in a single side-chain; or $X^{12}$ is a naturally or non-naturally occurring aromatic L α-amino acid containing in total 1 to 25 carbon- and/or heteroatoms in a single side-chain; or an aromatic amino alcohol containing in total 1 to 25 carbon- and/or heteroatoms in a single side-chain;

and if $P^8$ is a naturally or non-naturally occurring aliphatic L α-amino acid containing in total 1 to 25 carbon- and/or heteroatoms in a single side-chain; then $P^{10}$ is a naturally or non-naturally occurring aromatic L α-amino acid containing in total 1 to 25 carbon- and/or heteroatoms in a single side-chain; and if $P^{10}$ is a naturally or non-naturally occurring alcoholic L α-amino acid containing in total 1 to 25 carbon- and/or heteroatoms in a single side-chain; then $X^{12}$ is a naturally or non-naturally occurring aliphatic L α-amino acid containing in total 1 to 25 carbon- and/or heteroatoms in a single side-chain; and the combined number of the amino acid residue Gly in above module A must not exceed two; and the positions P of the amino acid residues Gly must not be in direct vicinity;

with the further proviso that, if $P^1$ and $X^{12}$ taken together form an interstrand linkage or salt bridge, as defined above; then $P^2$ and $P^{11}$ taken together are not forming an interstrand linkage or salt bridge, as defined above;

the carbonyl (C=O) point of attachment of $X^{12}$ and the nitrogen (N) point of attachment of $X^{14}$ are appropriately saturated to form the corresponding naturally or non-naturally occurring terminal α-amino acids optionally having modified carbonyl (C=O) functional groups and/or nitrogen (N) functional groups;

with the further proviso that, if linker L, as defined below, is connected with module A by a carbonyl (C=O) point of attachment of $P^5$; $P^6$; or $P^7$; then $P^5$; $P^6$; or $P^7$; is a naturally or non-naturally occurring α-amino acid containing in total 1 to 25 carbon- and/or heteroatoms in a single side-chain comprising at least one carboxyl function;

if s=1, t=1, and u=0; and $P^1$ and $X^{12}$ taken together and/or $P^2$ and $P^{11}$ taken together and/or $P^4$ and $P^9$ taken together form naturally or non-naturally cross-linking α-amino acids or non-naturally cross-linking acids containing each in total 1 to 12 carbon- and/or heteroatoms in a single side-chain which together are connecting $P^1$ and $X^{12}$ and/or $P^2$ and $P^{11}$ and/or $P^4$ and $P^9$ by covalent interaction (interstrand linkage) or by electrostatic interaction (salt bridge); then $P^1$ is pGlu; $^D$pGlu; Ac-pGlu; Ac-$^D$pGlu; or a naturally or non-naturally occurring aliphatic L or D α-amino acid containing in total 1 to 25 carbon- and/or heteroatoms in a single side-chain; or a naturally or non-naturally occurring aromatic L α-amino acid containing in total 1 to 25 carbon- and/or heteroatoms in a single side-chain; or a naturally or non-naturally occurring alcoholic L α-amino acid containing in total 1 to 25 carbon- and/or heteroatoms in a single side-chain; or an aliphatic L α-hydroxy acid containing in total 1 to 25 carbon- and/or heteroatoms in a single side-chain; or an aromatic L α-hydroxy acid containing in total 1 to 25 carbon- and/or heteroatoms in a single side-chain; or an alcoholic L α-amino acid containing in total 1 to 25 carbon- and/or heteroatoms in a single side-chain; or an aliphatic acid containing in total 1 to 25 carbon- and/or heteroatoms in a single side-chain;

$P^2$; $P^3$; $P^4$; $P^5$; $P^6$; $P^7$; $P^8$; $P^9$; $P^{10}$; $P^{11}$; and $X^{12}$ are as defined above for module A, wherein s=1, t=1, and u=1;

$X^{13}$ is Glyol; or a naturally or non-naturally occurring aliphatic D α-amino acid containing in total 1 to 25 carbon- and/or heteroatoms in a single side-chain; or a naturally or non-naturally occurring alcoholic L or D α-amino acid containing in total 1 to 25 carbon- and/or heteroatoms in a single side-chain; or a naturally or non-naturally occurring L or D α-amino acid containing in total 1 to 25 carbon- and/or heteroatoms in a single side-chain comprising at least one carboxylic acid function or phosphonic acid function; or a naturally or non-naturally occurring L α-amino acid containing in total 1 to 25 carbon- and/or heteroatoms in a single side-chain comprising at least one carboxylic amide function;

with the proviso that, if $P^1$ is a naturally or non-naturally occurring alcoholic L α-amino acid containing in total 1 to 25 carbon- and/or heteroatoms in a single side-chain; then $X^{12}$ is naturally or non-naturally occurring aliphatic L or D α-amino acid containing in total 1 to 25 carbon- and/or heteroatoms in a single side-chain; and if $P^3$ is a naturally or non-naturally occurring alcoholic L α-amino acid containing in total 1 to 25 carbon- and/or heteroatoms in a single side-chain; or a naturally or non-naturally occurring aliphatic L α-amino acid containing in total 1 to 25 carbon- and/or heteroatoms in a single side-chain;

then $P^1$; $P^m$; or $X^{12}$; is a naturally or non-naturally occurring aromatic L α-amino acid containing in total 1 to 25 carbon- and/or heteroatoms in a single side-chain; and if $P^8$ is a naturally or non-naturally occurring aliphatic L α-amino acid containing in total 1 to 25 carbon- and/or heteroatoms in a single side-chain; then $P^{10}$ is a naturally or non-naturally occurring aromatic L α-amino acid containing in total 1 to 25 carbon- and/or heteroatoms in a single side-chain; and if $P^{10}$ is a naturally or non-naturally occurring alcoholic L α-amino acid containing in total 1 to 25 carbon- and/or heteroatoms in a single side-chain; then $X^{12}$ is a naturally or non-naturally occurring aliphatic L or D α-amino acid containing in total 1 to 25 carbon- and/or heteroatoms in a single side-chain; and the combined number of the amino acid residue Gly in above module A must not exceed two; and the positions P of the amino acid residues Gly must not be in direct vicinity;

with the further proviso that, if $P^1$ and $X^{12}$ taken together form an interstrand linkage or salt bridge, as defined above; then $P^2$ and $P^{11}$ taken together are not forming an interstrand linkage or salt bridge, as defined above;

the carbonyl (C=O) point of attachment of $X^{13}$ and the nitrogen (N) point of attachment of $P^1$ are appropriately saturated to form the corresponding naturally or non-naturally occurring terminal α-amino acids optionally having modified carbonyl (C=O) functional groups and/or nitrogen (N) functional groups;

with the further proviso that, if linker L, as defined below, is connected with module A by a carbonyl (C=O) point of attachment of $P^5$; $P^6$; or $P^7$; then $P^5$; $P^6$; or $P^7$; is a naturally or non-naturally occurring α-amino acid containing in total 1 to 25 carbon- and/or heteroatoms in a single side-chain comprising at least one carboxyl function;

if s=0, t=0, and u=1; and $P^2$ and $P^{11}$ taken together and/or $P^4$ and $P^9$ taken together form naturally or non-naturally cross-linking α-amino acids containing each in total 1 to 12 carbon- and/or heteroatoms in a single side-chain which together are connecting $P^2$ and $P^{11}$ and/or $P^4$ and $P^9$ by covalent interaction (interstrand linkage) or by electrostatic interaction (salt bridge); then $X^{14}$; $P^1$; $P^2$; $P^3$; $P^4$; $P^5$; $P^6$; $P^7$; $P^8$; $P^9$; and $P^{10}$ are as defined above for module A, wherein s=1, t=1, and u=1;

$P^{11}$ is a naturally or non-naturally occurring aliphatic L α-amino acid containing in total 1 to 25 carbon- and/or heteroatoms in a single side-chain; or a naturally or non-naturally occurring basic L α-amino acid containing in total 1 to 25 carbon- and/or heteroatoms in a single side-chain comprising at least one amino function or guanidino function; or a naturally or non-naturally occurring alcoholic L α-amino acid containing in total 1 to 25 carbon- and/or heteroatoms in a single side-chain; or a naturally or non-naturally occurring L α-amino acid containing in total 1 to 25 carbon- and/or heteroatoms in a single side-chain comprising at least one carboxylic acid function or phosphonic acid function;

with the proviso that, if $P^3$ is a naturally or non-naturally occurring alcoholic L α-amino acid containing in total 1 to 25 carbon- and/or heteroatoms in a single side-chain; or a naturally or non-naturally occurring aliphatic L α-amino acid containing in total 1 to 25 carbon- and/or heteroatoms in a single side-chain;

then $P^1$; or $P^{10}$; is a naturally or non-naturally occurring aromatic L α-amino acid containing in total 1 to 25 carbon- and/or heteroatoms in a single side-chain; and if $P^8$ is a naturally or non-naturally occurring aliphatic L α-amino acid containing in total 1 to 25 carbon- and/or heteroatoms in a single side-chain; then $P^{10}$ is a naturally or non-naturally occurring aromatic L α-amino acid containing in total 1 to 25 carbon- and/or heteroatoms in a single side-chain; and the combined number of the amino acid residue Gly in above module A must not exceed two; and the positions P of the amino acid residues Gly must not be in direct vicinity;

with the further proviso that, the carbonyl (C=O) point of attachment of $P^{11}$ and the nitrogen (N) point of attachment of $X^{14}$ are appropriately saturated to form the corresponding naturally or non-naturally occurring terminal α-amino acids optionally having modified carbonyl (C=O) functional groups and/or nitrogen (N) functional groups;

with the further proviso that, if linker L, as defined below, is connected with module A by a carbonyl (C=O) point of attachment of $P^5$; $P^6$; or $P^7$; then $P^5$; $P^6$; or $P^7$; is a naturally or non-naturally occurring α-amino acid containing in total 1 to 25 carbon- and/or heteroatoms in a single side-chain comprising at least one carboxyl function;

if s=1, t=0, and u=0; and $P^1$ and $X^{12}$ taken together and/or $P^2$ and $P^{11}$ taken together and/or $P^4$ and $P^9$ taken together form naturally or non-naturally cross-linking α-amino acids or non-naturally cross-linking acids containing each in total 1 to 12 carbon- and/or heteroatoms in a single side-chain which together are connecting $P^1$ and $X^{12}$ and/or $P^2$ and $P^{11}$ and/or $P^4$ and $P^9$ by covalent interaction (interstrand linkage) or by electrostatic interaction (salt bridge); then $P^1$ is pGlu; $^D$pGlu; Ac-pGlu; Ac-$^D$pGlu; or a naturally or non-naturally occurring aliphatic L or D α-amino acid containing in total 1 to 25 carbon- and/or heteroatoms in a single side-chain; or a naturally or non-naturally occurring aromatic L α-amino acid containing in total 1 to 25 carbon- and/or heteroatoms in a single side-chain; or a naturally or non-naturally occurring alcoholic L α-amino acid containing in total 1 to 25 carbon- and/or heteroatoms in a single side-chain; or an aliphatic α-hydroxy acid containing in total 1 to 25 carbon- and/or heteroatoms in a single side-chain; or an aromatic L α-hydroxy acid containing in total 1 to 25 carbon- and/or heteroatoms in a single side-chain; or an alcoholic L α-hydroxy acid containing in total 1 to 25 carbon- and/or heteroatoms in a single side-chain; or an aliphatic acid containing in total 1 to 25 carbon- and/or heteroatoms in a single side-chain;

$P^2$; $P^3$; $P^4$; $P^5$; $P^6$; $P^7$; $P^8$; $P^9$; $P^{10}$; and $P^{11}$ are as defined above for module A, wherein s=1, t=1, and u=1;

$X^{12}$ is Glyol; or a naturally or non-naturally occurring aliphatic L α-amino acid containing in total 1 to 25 carbon- and/or heteroatoms in a single side-chain; or a naturally or non-naturally occurring aromatic L α-amino acid containing in total 1 to 25 carbon- and/or heteroatoms in a single side-chain; or a naturally or non-naturally occurring basic L α-amino acid containing in total 1 to 25 carbon- and/or heteroatoms in a single side-chain comprising at least one amino function or one guanidino function; or a naturally or non-naturally occurring alcoholic L or D α-amino acid containing in total 1 to 25 carbon- and/or heteroatoms in a single side-chain; or a naturally or non-naturally occurring L α-amino acid containing in total 1 to 25 carbon- and/or heteroatoms in a single side-chain comprising at least one carboxylic amide function; or an aliphatic amino alcohol containing in total 1 to 25 carbon- and/or heteroatoms in a single side-chain; or an aromatic amino alcohol containing in total 1 to 25 carbon- and/or heteroatoms in a single side-chain; or a basic amino alcohol containing in total 1 to 25 carbon- and/or heteroatoms in a single side-chain comprising at least one amino function or one guanidino function; or an alcoholic amino alcohol containing in total 1 to 25 carbon- and/or heteroatoms in a single side-chain comprising at least one hydroxyl function;

with the proviso that, if $P^1$ is a naturally or non-naturally occurring alcoholic L α-amino acid containing in total 1 to 25 carbon- and/or heteroatoms in a single side-chain; then $X^{12}$ is naturally or non-naturally occurring aliphatic L α-amino acid containing in total 1 to 25 carbon- and/or heteroatoms in a single side-chain; or a naturally or non-naturally occurring alcoholic L or D α-amino acid containing in total 1 to 25 carbon- and/or heteroatoms in a single side-chain; and if $P^3$ is a naturally or non-naturally occurring alcoholic L α-amino acid containing in total 1 to 25 carbon- and/or heteroatoms in a single side-chain; or a naturally or non-naturally occurring aliphatic L α-amino acid containing in total 1 to 25 carbon- and/or heteroatoms in a single side-chain;

then P$^1$; or P$^{10}$; is a naturally or non-naturally occurring aromatic L α-amino acid containing in total 1 to 25 carbon- and/or heteroatoms in a single side-chain; or X$^{12}$ is a naturally or non-naturally occurring aromatic L α-amino acid containing in total 1 to 25 carbon- and/or heteroatoms in a single side-chain; or an aromatic amino alcohol containing in total 1 to 25 carbon- and/or heteroatoms in a single side-chain; and if P$^8$ is a naturally or non-naturally occurring aliphatic L α-amino acid containing in total 1 to 25 carbon- and/or heteroatoms in a single side-chain; then P$^{10}$ is a naturally or non-naturally occurring aromatic L α-amino acid containing in total 1 to 25 carbon- and/or heteroatoms in a single side-chain; and if P$^{10}$ is a naturally or non-naturally occurring alcoholic L α-amino acid containing in total 1 to 25 carbon- and/or heteroatoms in a single side-chain; then X$^{12}$ is a naturally or non-naturally occurring aliphatic L α-amino acid containing in total 1 to 25 carbon- and/or heteroatoms in a single side-chain; and the combined number of the amino acid residue Gly in above module A must not exceed two; and the positions P of the amino acid residues Gly must not be in direct vicinity;

with the further proviso that, if P$^1$ and X$^{12}$ taken together form an interstrand linkage or salt bridge, as defined above; then P$^2$ and P$^{11}$ taken together are not forming an interstrand linkage or salt bridge, as defined above;

the carbonyl (C=O) point of attachment of X$^{12}$ and the nitrogen (N) point of attachment of P$^1$ are appropriately saturated to form the corresponding naturally or non-naturally occurring terminal α-amino acids optionally having modified carbonyl (C=O) functional groups and/or nitrogen (N) functional groups;

with the further proviso that, if linker L, as defined below, is connected with module A by a carbonyl (C=O) point of attachment of P$^5$; P$^6$; or P$^7$; then P$^5$; P$^6$; or P$^7$; is a naturally or non-naturally occurring α-amino acid
containing in total 1 to 25 carbon- and/or heteroatoms in a single side-chain comprising at least one carboxyl function;

if s=0, t=0, and u=0; and

P$^2$ and P$^{11}$ taken together and/or P$^4$ and P$^9$ taken together form naturally or non-naturally cross-linking α-amino acids containing each in total 1 to 12 carbon- and/or heteroatoms in a single side-chain which together are connecting P$^2$ and P$^{11}$ and/or P$^4$ and P$^9$ by covalent interaction (interstrand linkage) or by electrostatic interaction (salt bridge); then P$^1$ is pGlu; $^D$pGlu; Ac-pGlu; Ac-$^D$pGlu; or a naturally or non-naturally occurring aliphatic L or D α-amino acid containing in total 1 to 25 carbon- and/or heteroatoms in a single side-chain; or a naturally or non-naturally occurring aromatic L α-amino acid containing in total 1 to 25 carbon- and/or heteroatoms in a single side-chain; or a naturally or non-naturally occurring alcoholic L α-amino acid containing in total 1 to 25 carbon- and/or heteroatoms in a single side-chain; or an aliphatic α-hydroxy acid containing in total 1 to 25 carbon- and/or heteroatoms in a single side-chain; or an aromatic L α-hydroxy acid containing in total 1 to 25 carbon- and/or heteroatoms in a single side-chain; or an alcoholic L α-hydroxy acid containing in total 1 to 25 carbon- and/or heteroatoms in a single side-chain; or an aliphatic acid containing in total 1 to 25 carbon- and/or heteroatoms in a single side-chain;

P$^2$; P$^3$; P$^4$; P$^5$; P$^6$; P$^7$; P$^8$; P$^9$; and P$^{10}$ are as defined above for module A, wherein s=1, t=1, and u=1;

P$^{11}$ is a naturally or non-naturally occurring aliphatic L α-amino acid containing in total 1 to 25 carbon- and/or heteroatoms in a single side-chain; or a naturally or non-naturally occurring basic L α-amino acid containing in total 1 to 25 carbon- and/or heteroatoms in a single side-chain comprising at least one amino function or guanidino function; or a naturally or non-naturally occurring alcoholic L α-amino acid containing in total 1 to 25 carbon- and/or heteroatoms in a single side-chain; or a naturally or non-naturally occurring L α-amino acid containing in total 1 to 25 carbon- and/or heteroatoms in a single side-chain comprising at least one carboxylic acid function or phosphonic acid function;

with the proviso that, if P$^3$ is a naturally or non-naturally occurring alcoholic L α-amino acid containing in total 1 to 25 carbon- and/or heteroatoms in a single side-chain; or a naturally or non-naturally occurring aliphatic L α-amino acid containing in total 1 to 25 carbon- and/or heteroatoms in a single side-chain;

then P$^1$; or P$^{10}$; is a naturally or non-naturally occurring aromatic L a amino acid containing in total 1 to 25 carbon- and/or heteroatoms in a single side-chain; and if P$^8$ is a naturally or non-naturally occurring aliphatic L α-amino acid containing in total 1 to 25 carbon- and/or heteroatoms in a single side-chain; then P$^{10}$ is a naturally or non-naturally occurring aromatic L α-amino acid containing in total 1 to 25 carbon- and/or heteroatoms in a single side-chain; and the combined number of the amino acid residue Gly in above module A must not exceed two; and the positions P of the amino acid residues Gly must not be in direct vicinity;

with the further proviso that, the carbonyl (C=O) point of attachment of P$^{11}$ and the nitrogen (N) point of attachment of P$^1$ are appropriately saturated to form the corresponding naturally or non-naturally occurring terminal α-amino acids optionally having modified carbonyl (C=O) functional groups and/or nitrogen (N) functional groups;

with the further proviso that, if linker L, as defined below, is connected with module A by a carbonyl (C=O) point of attachment of P$^5$; P$^6$; or P$^7$; then P$^5$; P$^6$; or P$^7$; is a naturally or non-naturally occurring α-amino acid containing in total 1 to 25 carbon- and/or heteroatoms in a single side-chain comprising at least one carboxyl function;

if s=0, t=0, and u=0; and alternatively

P$^{11}$ is connected from the α-carbonyl point of attachment to the ω-nitrogen (N) of P$^2$; then P$^1$ is a naturally or non-naturally occurring aliphatic L or D α-amino acid containing in total 1 to 25 carbon- and/or heteroatoms in a single side-chain; or a naturally or non-naturally occurring aromatic L α-amino acid containing in total 1 to 25 carbon- and/or heteroatoms in a single side-chain; or a naturally or non-naturally occurring alcoholic L α-amino acid containing in total 1 to 25 carbon- and/or heteroatoms in a single side-chain; or an aliphatic α-hydroxy acid containing in total 1 to 25 carbon- and/or heteroatoms in a single side-chain; or an aromatic L α-hydroxy acid containing in total 1 to 25 carbon- and/or heteroatoms in a single side-chain; or an alcoholic L α-hydroxy acid containing in total 1 to 25 carbon- and/or heteroatoms in a single side-chain; or an aliphatic acid containing in total 1 to 25 carbon- and/or heteroatoms in a single side-chain;

$P^2$ is a naturally or non-naturally occurring basic L α-amino acid containing in total 1 to 25 carbon- and/or heteroatoms in a single side-chain comprising at least one amino function;

$P^3$; $P^4$; $P^5$; $P^6$; $P^7$; $P^8$; $P^9$; and $P^{10}$ are as defined above for module A, wherein s=1, t=1, and u=1;

$P^{11}$ is a naturally or non-naturally occurring aliphatic D α-amino acid containing in total 1 to 25 carbon- and/or heteroatoms in a single side-chain; or a naturally or non-naturally occurring aromatic D α-amino acid containing in total 1 to 25 carbon- and/or heteroatoms in a single side-chain; or a naturally or non-naturally occurring basic D α-amino acid containing in total 1 to 25 carbon- and/or heteroatoms in a single side-chain comprising at least one amino function or guanidino function; or a naturally or non-naturally occurring alcoholic D α-amino acid containing in total 1 to 25 carbon- and/or heteroatoms in a single side-chain; or a naturally or non-naturally occurring D α-amino acid containing in total 1 to 25 carbon- and/or heteroatoms in a single side-chain comprising at least one carboxylic acid function or phosphonic acid function; or a naturally or non-naturally occurring D α-amino acid containing in total 1 to 25 carbon- and/or heteroatoms in a single side-chain comprising at least one amide function;

with the proviso that, if $P^3$ is a naturally or non-naturally occurring alcoholic L α-amino acid containing in total 1 to 25 carbon- and/or heteroatoms in a single side-chain; or a naturally or non-naturally occurring aliphatic L α-amino acid containing in total 1 to 25 carbon- and/or heteroatoms in a single side-chain;

then $P^1$; or $P^{10}$; is a naturally or non-naturally occurring aromatic L a amino acid containing in total 1 to 25 carbon- and/or heteroatoms in a single side-chain; and if $P^8$ is a naturally or non-naturally occurring aliphatic L α-amino acid containing in total 1 to 25 carbon- and/or heteroatoms in a single side-chain;

then $P^{10}$ is a naturally or non-naturally occurring aromatic L α-amino acid containing in total 1 to 25 carbon- and/or heteroatoms in a single side-chain; and the combined number of the amino acid residue Gly in above module A must not exceed two; and the positions P of the amino acid residues Gly must not be in direct vicinity;

with the further proviso that, the nitrogen (N) point of attachment of $P^1$ is appropriately saturated to form the corresponding naturally or non-naturally occurring terminal α-amino acid optionally having a modified nitrogen (N) functional group;

with the further proviso that, if linker L, as defined below, is connected with module A by a carbonyl (C=O) point of attachment of $P^5$; $P^6$; or $P^7$; then $P^5$; $P^6$; or $P^7$; is a naturally or non-naturally occurring α-amino acid containing in total 1 to 25 carbon- and/or heteroatoms in a single side-chain comprising at least one carboxyl function;

and a module B consisting of single elements Q being connected in either direction from the carbonyl (C=O) point of attachment to the nitrogen (N) of the next element with the proviso that $Q^7$ is connected from the α-carbonyl (C=O) point of attachment to the ω-nitrogen (N) of $Q^1$, and wherein $Q^1$ is a naturally or non-naturally occurring basic L or D α-amino acid containing in total 1 to 25 carbon- and/or heteroatoms in a single side-chain comprising at least one amino function;

$Q^2$, $Q^5$, and $Q^6$ are independently a naturally or non-naturally occurring basic L α-amino acid containing in total 1 to 25 carbon- and/or heteroatoms in a single side-chain comprising at least one amino function;

$Q^3$ is a naturally or non-naturally occurring aliphatic D α-amino acid containing in total 1 to 25 carbon- and/or heteroatoms in a single side-chain; or a naturally or non-naturally occurring aromatic D α-amino acid containing in total 1 to 25 carbon- and/or heteroatoms in a single side-chain;

$Q^4$ is a naturally or non-naturally occurring aliphatic L α-amino acid containing in total 1 to 25 carbon- and/or heteroatoms in a single side-chain; or a naturally or non-naturally occurring alcoholic L α-amino acid containing in total 1 to 25 carbon- and/or heteroatoms in a single side-chain;

$Q^7$ is a naturally or non-naturally occurring alcoholic L α-amino acid containing in total 1 to 25 carbon- and/or heteroatoms in a single side-chain; or a naturally or non-naturally occurring aliphatic L α-amino acid containing in total 1 to 25 carbon- and/or heteroatoms in a single side-chain;

and a linker L consisting of k=0-3 single elements L being connected in either direction from the carbonyl (C=O) point of attachment to the nitrogen (N) of the next element, and wherein, if k=1, $L^1$ is Gly; Sar; Aib; or a naturally or non-naturally occurring aliphatic L or D α-amino acid containing in total 1 to 25 carbon- and/or heteroatoms in a single side-chain; or a naturally or non-naturally occurring basic L or D α-amino acid containing in total 1 to 25 carbon- and/or heteroatoms in a single side-chain comprising at least one amino function; or a naturally or non-naturally occurring alcoholic L or D α-amino acid containing in total 1 to 25 carbon- and/or heteroatoms in a single side-chain;

if k=2, the additional element $L^2$ is Gly; Sar; Aib; or a naturally or non-naturally occurring aliphatic L or D α-amino acid containing in total 1 to 25 carbon- and/or heteroatoms in a single side-chain; or a naturally or non-naturally occurring basic L or D α-amino acid containing in total 1 to 25 carbon- and/or heteroatoms in a single side-chain comprising at least one amino function; or a naturally or non-naturally occurring alcoholic L or D α-amino acid containing in total 1 to 25 carbon- and/or heteroatoms in a single side-chain;

if k=3, the additional element $L^3$ is Gly; Sar; Aib; or a naturally or non-naturally occurring aliphatic L or D α-amino acid containing in total 1 to 25 carbon- and/or heteroatoms in a single side-chain; or a naturally or non-naturally occurring basic L or D α-amino acid containing in total 1 to 25 carbon- and/or heteroatoms in a single side-chain comprising at least one amino function; or a naturally or non-naturally occurring alcoholic L or D α-amino acid containing in total 1 to 25 carbon- and/or heteroatoms in a single side-chain;

said linker L being connected with module B from the carbonyl (C═O) point of attachment of $L^k$ to the α-nitrogen (N) of $Q^1$ and, if k=1-3, being connected with module A from the carbonyl (C═O) point of attachment of $P^5$; $P^6$; or $P^7$; to the nitrogen (N) of 12; or, if k=0, then $Q^1$ being directly connected with module A from the carbonyl (C═O) point of attachment of $P^5$; $P^6$; or $P^7$; to the α-nitrogen (N) of $Q^1$;

or a tautomer or rotamer thereof; or a salt; or a pharmaceutically acceptable salt; or a hydrate; or a solvate thereof.

In a preferred embodiment (2) the present invention relates to novel β-hairpin peptidomimetics of formula (I), according to embodiment (1), comprising a module A consisting of single elements P or X being connected in either direction from the carbonyl (C═O) point of attachment to the nitrogen (N) of the next element wherein s=0, t=0, and u=0; or s=1, t=0, and u=0; or s=0, t=0, and u=1;

if s=0, t=0, and u=1; and $P^2$ and $P^{11}$ taken together and/or $P^4$ and $P^9$ taken together form naturally or non-naturally cross-linking α-amino acids containing each in total 1 to 12 carbon- and/or heteroatoms in a single side-chain which together are connecting $P^2$ and $P^{11}$ and/or $P^4$ and $P^9$ by covalent interaction (interstrand linkage) or by electrostatic interaction (salt bridge); then)

$X^{14}$; $P^1$; $P^2$; $P^3$; $P^4$; $P^5$; $P^6$; $P^7$; $P^8$; $P^9$; and $P^{10}$ are as defined above for module A in embodiment 1, wherein s=1, t=1, and u=1;

$P^{11}$ is a naturally or non-naturally occurring aliphatic L α-amino acid containing in total 1 to 25 carbon- and/or heteroatoms in a single side-chain; or a naturally or non-naturally occurring basic L α-amino acid containing in total 1 to 25 carbon- and/or heteroatoms in a single side-chain comprising at least one amino function or guanidino function; or a naturally or non-naturally occurring alcoholic L α-amino acid containing in total 1 to 25 carbon- and/or heteroatoms in a single side-chain; or a naturally or non-naturally occurring L α-amino acid containing in total 1 to 25 carbon- and/or heteroatoms in a single side-chain comprising at least one carboxylic acid function or phosphonic acid function;

with the proviso that, if $P^3$ is a naturally or non-naturally occurring alcoholic L α-amino acid containing in total 1 to 25 carbon- and/or heteroatoms in a single side-chain; or a naturally or non-naturally occurring aliphatic L α-amino acid containing in total 1 to 25 carbon- and/or heteroatoms in a single side-chain;

then $P^1$; or $P^{10}$; is a naturally or non-naturally occurring aromatic L α-amino acid containing in total 1 to 25 carbon- and/or heteroatoms in a single side-chain; and if $P^8$ is a naturally or non-naturally occurring aliphatic L α-amino acid containing in total 1 to 25 carbon- and/or heteroatoms in a single side-chain; then $P^{10}$ is a naturally or non-naturally occurring aromatic L α-amino acid and the combined number of the amino acid residue Gly in above module A must not exceed two; and the positions P of the amino acid residues Gly must not be in direct vicinity;

with the further proviso that, the carbonyl (C═O) point of attachment of $P^{11}$ and the nitrogen (N) point of attachment of $X^{14}$ are appropriately saturated to form the corresponding naturally or non-naturally occurring terminal α-amino acids optionally having modified carbonyl (C═O) functional groups and/or nitrogen (N) functional groups;

with the further proviso that, if linker L, as defined below, is connected with module A by a carbonyl (C═O) point of attachment of $P^5$; $P^6$; or $P^7$; then $P^5$; $P^6$; or $P^7$; is a naturally or non-naturally occurring α-amino acid containing in total 1 to 25 carbon- and/or heteroatoms in a single side-chain comprising at least one carboxyl function;

if s=1, t=0, and u=0; and $P^1$ and $X^{12}$ taken together and/or $P^2$ and $P^{11}$ taken together and/or $P^4$ and $P^9$ taken together form naturally or non-naturally cross-linking α-amino acids or non-naturally cross-linking acids containing each in total 1 to 12 carbon- and/or heteroatoms in a single side-chain which together are connecting $P^1$ and $X^{12}$ and/or $P^2$ and $P^{11}$ and/or $P^4$ and $P^9$ by covalent interaction (interstrand linkage) or by electrostatic interaction (salt bridge); then $P^1$ is pGlu; $^D$pGlu; Ac-pGlu; Ac-$^D$pGlu; or a naturally or non-naturally occurring aliphatic L or D α-amino acid containing in total 1 to 25 carbon- and/or heteroatoms in a single side-chain; or a naturally or non-naturally occurring aromatic L α-amino acid containing in total 1 to 25 carbon- and/or heteroatoms in a single side-chain; or a naturally or non-naturally occurring alcoholic L α-amino acid containing in total 1 to 25 carbon- and/or heteroatoms in a single side-chain; or an aliphatic α-hydroxy acid containing in total 1 to 25 carbon- and/or heteroatoms in a single side-chain; or an aromatic L α-hydroxy acid containing in total 1 to 25 carbon- and/or heteroatoms in a single side-chain; or an alcoholic L α-hydroxy acid containing in total 1 to 25 carbon- and/or heteroatoms in a single side-chain; or an aliphatic acid containing in total 1 to 25 carbon- and/or heteroatoms in a single side-chain;

$P^2$; $P^3$; $P^4$; $P^5$; $P^6$; $P^7$; $P^8$; $P^9$; $P^{10}$; and $P^{11}$ are as defined above for module A in embodiment 1, wherein s=1, t=1, and u=1;

$X^{12}$ is Glyol; or a naturally or non-naturally occurring aliphatic L α-amino acid containing in total 1 to 25 carbon- and/or heteroatoms in a single side-chain; or a naturally or non-naturally occurring aromatic L α-amino acid containing in total 1 to 25 carbon- and/or heteroatoms in a single side-chain; or a naturally or non-naturally occurring basic L α-amino acid containing in total 1 to 25 carbon- and/or heteroatoms in a single side-chain comprising at least one amino function or one guanidino function; or a naturally or non-naturally occurring alcoholic L or D α-amino acid containing in total 1 to 25 carbon- and/or heteroatoms in a single side-chain; or a naturally or non-naturally occurring L α-amino acid containing in total 1 to 25 carbon- and/or heteroatoms in a single side-chain comprising at least one carboxylic amide function; or an aliphatic amino alcohol containing in total 1 to 25 carbon- and/or heteroatoms in a single side-chain; or an aromatic amino alcohol containing in total 1 to 25 carbon- and/or heteroatoms in a single side-chain; or a basic amino alcohol containing in total 1 to 25 carbon- and/or heteroatoms in a single side-chain comprising at least one amino function or one guanidino function; or an alcoholic amino alcohol containing in total 1 to 25 carbon- and/or heteroatoms in a single side-chain comprising at least one hydroxyl function;
with the proviso that,
if $P^1$ is a naturally or non-naturally occurring alcoholic L α-amino acid containing in total 1 to 25 carbon- and/or heteroatoms in a single side-chain; then $X^{12}$ is naturally or non-naturally occurring aliphatic L α-amino acid containing in total 1 to 25 carbon- and/or heteroatoms in a single side-chain; or a naturally or non-naturally occurring alcoholic L or D α-amino acid
containing in total 1 to 25 carbon- and/or heteroatoms in a single side-chain; and
if $P^3$ is a naturally or non-naturally occurring alcoholic L α-amino acid containing in total 1 to 25 carbon- and/or heteroatoms in a single side-chain; or a naturally or non-naturally occurring aliphatic L α-amino acid containing in total 1 to 25 carbon- and/or heteroatoms in a single side-chain;
then $P^1$; or $P^m$; is a naturally or non-naturally occurring aromatic L α-amino acid containing in total 1 to 25 carbon- and/or heteroatoms in a single side-chain; or $X^{12}$ is a naturally or non-naturally occurring aromatic L α-amino acid containing in total 1 to 25 carbon- and/or heteroatoms in a single side-chain; or an aromatic amino alcohol containing in total 1 to 25 carbon- and/or heteroatoms in a single side-chain; and
if $P^8$ is a naturally or non-naturally occurring aliphatic L α-amino acid containing in total 1 to 25 carbon- and/or heteroatoms in a single side-chain;
then $P^{10}$ is a naturally or non-naturally occurring aromatic L α-amino acid containing in total 1 to 25 carbon- and/or heteroatoms in a single side-chain; and
if $P^{10}$ is a naturally or non-naturally occurring alcoholic L α-amino acid containing in total 1 to 25 carbon- and/or heteroatoms in a single side-chain;
then $X^{12}$ is a naturally or non-naturally occurring aliphatic L α-amino acid containing in total 1 to 25 carbon- and/or heteroatoms in a single side-chain; and
the combined number of the amino acid residue Gly in above module A must not exceed two; and
with the further proviso that,
if $P^1$ and $X^{12}$ taken together form an interstrand linkage or salt bridge, as defined above; then $P^2$ and $P^{11}$ taken together are not forming an interstrand linkage or salt bridge, as defined above;
the carbonyl (C=O) point of attachment of $X^{12}$ and the nitrogen (N) point of attachment of $P^1$ are appropriately saturated to form the corresponding naturally or non-naturally occurring terminal α-amino acids optionally having modified carbonyl (C=O) functional groups and/or nitrogen (N) functional groups;
with the further proviso that,
if linker L, as defined below, is connected with module A by a carbonyl (C=O) point of attachment of $P^5$; $P^6$; or $P^7$; then
$P^5$; $P^6$; or $P^7$; is a naturally or non-naturally occurring α-amino acid containing in total 1 to 25 carbon- and/or heteroatoms in a single side-chain comprising at least one carboxyl function;
if s=0, t=0, and u=0; and
$P^2$ and $P^{11}$ taken together and/or $P^4$ and $P^9$ taken together form naturally or non-naturally cross-linking α-amino acids containing each in total 1 to 12 carbon- and/or heteroatoms in a single side-chain which together are connecting $P^2$ and $P^{11}$ and/or $P^4$ and $P^9$ by covalent interaction (interstrand linkage) or by electrostatic interaction (salt bridge); then $P^1$ is pGlu; $^D$pGlu; Ac-pGlu; Ac-$^D$pGlu; or a naturally or non-naturally occurring aliphatic L or D α-amino acid containing in total 1 to 25 carbon- and/or heteroatoms in a single side-chain; or a naturally or non-naturally occurring aromatic L α-amino acid containing in total 1 to 25 carbon- and/or heteroatoms in a single side-chain; or a naturally or non-naturally occurring alcoholic L α-amino acid containing in total 1 to 25 carbon- and/or heteroatoms in a single side-chain; or an aliphatic α-hydroxy acid containing in total 1 to 25 carbon- and/or heteroatoms in a single side-chain; or an aromatic L α-hydroxy acid containing in total 1 to 25 carbon- and/or heteroatoms in a single side-chain; or an alcoholic L α-hydroxy acid containing in total 1 to 25 carbon- and/or heteroatoms in a single side-chain; or an aliphatic acid containing in total 1 to 25 carbon- and/or heteroatoms in a single side-chain;
$P^2$; $P^3$; $P^4$; $P^5$; $P^6$; $P^7$; $P^8$; $P^9$; and $P^{10}$ are as defined above for module A in embodiment 1,
wherein s=1, t=1, and u=1;
$P^{11}$ is a naturally or non-naturally occurring aliphatic L α-amino acid containing in total 1 to 25 carbon- and/or heteroatoms in a single side-chain; or a naturally or non-naturally occurring basic L α-amino acid containing in total 1 to 25 carbon- and/or heteroatoms in a single side-chain comprising at least one amino function or guanidino function; or a naturally or non-naturally occurring alcoholic L α-amino acid containing in total 1 to 25 carbon- and/or heteroatoms in a single side-chain; or a naturally or non-naturally occurring L α-amino acid containing in total 1 to 25 carbon- and/or heteroatoms in a single side-chain comprising at least one carboxylic acid function or phosphonic acid function;
with the proviso that,
if $P^3$ is a naturally or non-naturally occurring alcoholic L α-amino acid containing in total 1 to 25 carbon- and/or heteroatoms in a single side-chain; or a naturally or non-naturally occurring aliphatic L α-amino acid containing in total 1 to 25 carbon- and/or heteroatoms in a single side-chain;
then $P^1$; or $P^{10}$; is a naturally or non-naturally occurring aromatic L a amino acid containing in total 1 to 25 carbon- and/or heteroatoms in a single side-chain; and
if $P^8$ is a naturally or non-naturally occurring aliphatic L α-amino acid containing in total 1 to 25 carbon- and/or heteroatoms in a single side-chain;
then $P^{10}$ is a naturally or non-naturally occurring aromatic L α-amino acid containing in total 1 to 25 carbon- and/or heteroatoms in a single side-chain; and
the combined number of the amino acid residue Gly in above module A must not exceed two; and
the positions P of the amino acid residues Gly must not be in direct vicinity;
with the further proviso that,
the carbonyl (C=O) point of attachment of $P^{11}$ and the nitrogen (N) point of attachment of $P^1$ are appropriately saturated to form the corresponding naturally or non-naturally occurring terminal α-amino acids optionally having modified carbonyl (C=O) functional groups and/or nitrogen (N) functional groups;
with the further proviso that,
if linker L, as defined below, is connected with module A by a carbonyl (C=O) point of attachment of $P^5$; $P^6$; or $P^7$; then
$P^5$; $P^6$; or $P^7$; is a naturally or non-naturally occurring α-amino acid containing in total 1 to 25 carbon- and/or heteroatoms in a single side-chain comprising at least one carboxyl function;
if s=0, t=0, and u=0; and alternatively
$P^{11}$ is connected from the α-carbonyl point of attachment to the ω-nitrogen (N) of $P^2$; then P¹ is a naturally or non-naturally occurring aliphatic L or D α-amino acid containing in total 1 to 25 carbon- and/or heteroatoms in a single side-chain; or a naturally or non-naturally occurring aromatic L α-amino acid containing in total 1 to 25 carbon- and/or heteroatoms in a single side-chain; or a naturally or non-naturally occurring alcoholic L α-amino acid containing in total 1 to 25 carbon- and/or heteroatoms in a single side-chain; or an aliphatic α-hydroxy acid containing in total 1 to 25 carbon- and/or heteroatoms in a single side-chain; or an aromatic L α-hydroxy acid containing in total 1 to 25 carbon- and/or heteroatoms in a single side-chain; or an alcoholic L α-hydroxy acid containing in total 1 to 25 carbon- and/or heteroatoms in a single side-chain; or an aliphatic acid containing in total 1 to 25 carbon- and/or heteroatoms in a single side-chain;

P² is a naturally or non-naturally occurring basic L α-amino acid containing in total 1 to 25 carbon- and/or heteroatoms in a single side-chain comprising at least one amino function;

P³; P⁴; P⁵; P⁶; P⁷; P⁸; P⁹; and P¹⁰ are as defined above for module A in embodiment 1, wherein s=1, t=1, and u=1;

P¹¹ is a naturally or non-naturally occurring aliphatic D α-amino acid containing in total 1 to 25 carbon- and/or heteroatoms in a single side-chain; or a naturally or non-naturally occurring aromatic D α-amino acid containing in total 1 to 25 carbon- and/or heteroatoms in a single side-chain; or a naturally or non-naturally occurring basic D α-amino acid containing in total 1 to 25 carbon- and/or heteroatoms in a single side-chain comprising at least one amino function or guanidino function; or a naturally or non-naturally occurring alcoholic D α-amino acid containing in total 1 to 25 carbon- and/or heteroatoms in a single side-chain; or a naturally or non-naturally occurring D α-amino acid containing in total 1 to 25 carbon- and/or heteroatoms in a single side-chain comprising at least one carboxylic acid function or phosphonic acid function; or a naturally or non-naturally occurring D α-amino acid containing in total 1 to 25 carbon- and/or heteroatoms in a single side-chain comprising at least one amide function;

with the proviso that,
if P³ is a naturally or non-naturally occurring alcoholic L α-amino acid containing in total 1 to 25 carbon- and/or heteroatoms in a single side-chain; or a naturally or non-naturally occurring aliphatic L α-amino acid containing in total 1 to 25 carbon- and/or heteroatoms in a single side-chain;
then P¹; or P¹⁰; is a naturally or non-naturally occurring aromatic L a amino acid containing in total 1 to 25 carbon- and/or heteroatoms in a single side-chain; and
if P⁸ is a naturally or non-naturally occurring aliphatic L α-amino acid containing in total 1 to 25 carbon- and/or heteroatoms in a single side-chain;
then P¹⁰ is a naturally or non-naturally occurring aromatic L α-amino acid containing in total 1 to 25 carbon- and/or heteroatoms in a single side-chain; and
the combined number of the amino acid residue Gly in above module A must not exceed two; and
the positions P of the amino acid residues Gly must not be in direct vicinity;
with the further proviso that,
the nitrogen (N) point of attachment of P¹ is appropriately saturated to form the corresponding naturally or non-naturally occurring terminal α-amino acid optionally having a modified nitrogen (N) functional group;

with the further proviso that,
if linker L, as defined below, is connected with module A by a carbonyl (C=O) point of attachment of P⁵; P⁶; or P⁷; then
P⁵; P⁶; or P⁷; is a naturally or non-naturally occurring α-amino acid containing in total 1 to 25 carbon- and/or heteroatoms in a single side-chain comprising at least one carboxyl function;
and a module B consisting of single elements Q being connected in either direction from the carbonyl (C=O) point of attachment to the nitrogen (N) of the next element with the proviso that Q⁷ is connected from the α-carbonyl (C=O) point of attachment to the ω-nitrogen (N) of Q¹, and wherein Q¹ is a naturally or non-naturally occurring basic L or D α-amino acid containing in total 1 to 25 carbon- and/or heteroatoms in a single side-chain comprising at least one amino function;

Q²; Q⁵, and Q⁶ are independently
a naturally or non-naturally occurring basic L α-amino acid containing in total 1 to 25 carbon- and/or heteroatoms in a single side-chain comprising at least one amino function;

Q³ is a naturally or non-naturally occurring aliphatic D α-amino acid containing in total 1 to 25 carbon- and/or heteroatoms in a single side-chain; or a naturally or non-naturally occurring aromatic D α-amino acid containing in total 1 to 25 carbon- and/or heteroatoms in a single side-chain;

Q⁴ is a naturally or non-naturally occurring aliphatic L α-amino acid containing in total 1 to 25 carbon- and/or heteroatoms in a single side-chain; or a naturally or non-naturally occurring alcoholic L α-amino acid containing in total 1 to 25 carbon- and/or heteroatoms in a single side-chain;

Q⁷ is a naturally or non-naturally occurring alcoholic L α-amino acid containing in total 1 to 25 carbon- and/or heteroatoms in a single side-chain; or a naturally or non-naturally occurring aliphatic L α-amino acid containing in total 1 to 25 carbon- and/or heteroatoms in a single side-chain;

and a linker L consisting of k=0-3 single elements L being connected in either direction from the carbonyl (C=O) point of attachment to the nitrogen (N) of the next element, and wherein,
if k=1,
L¹ is Gly; Sar; Aib; or a naturally or non-naturally occurring aliphatic L or D α-amino acid containing in total 1 to 25 carbon- and/or heteroatoms in a single side-chain; or a naturally or non-naturally occurring basic L or D α-amino acid containing in total 1 to 25 carbon- and/or heteroatoms in a single side-chain comprising at least one amino function; or a naturally or non-naturally occurring alcoholic L or D α-amino acid containing in total 1 to 25 carbon- and/or heteroatoms in a single side-chain;

if k=2, the additional element
L² is Gly; Sar; Aib; or a naturally or non-naturally occurring aliphatic L or D α-amino acid containing in total 1 to 25 carbon- and/or heteroatoms in a single side-chain; or a naturally or non-naturally occurring basic L or D α-amino acid containing in total 1 to 25 carbon- and/or heteroatoms in a single side-chain comprising at least one amino function; or a naturally or non-naturally occurring alcoholic L or D α-amino acid containing in total 1 to 25 carbon- and/or heteroatoms in a single side-chain;

if k=3, the additional element
L³ is Gly; Sar; Aib; or a naturally or non-naturally occurring aliphatic L or D α-amino acid containing in total 1 to 25 carbon- and/or heteroatoms in a single side-chain; or a naturally or non-naturally occurring basic L or D α-amino acid containing in total 1 to 25 carbon- and/or heteroatoms in a single side-chain comprising at least one amino function; or a naturally or non-naturally occurring alcoholic L or D α-amino acid containing in total 1 to 25 carbon- and/or heteroatoms in a single side-chain;

said linker L being connected with module B from the carbonyl (C=O) point of attachment of $L^k$ to the α-nitrogen (N) of $Q^1$ and, if k=1-3, being connected with module A from the carbonyl (C=O) point of attachment of $P^5$; $P^6$; or $P^7$; to the nitrogen (N) of $L^1$; or, if k=0, then $Q^1$ being directly connected with module A from the carbonyl (C=O) point of attachment of $P^5$; $P^6$; or $P^7$; to the α-nitrogen (N) of $Q^1$;

or a tautomer or rotamer thereof; or a salt; or a pharmaceutically acceptable salt; or a hydrate; or a solvate thereof.

In a more preferred embodiment (3) the present invention relates to novel β-hairpin peptidomimetics of formula (I), according to embodiment (1), comprising a module A consisting of single elements P or X being connected in either direction from the carbonyl (C=O) point of attachment to the nitrogen (N) of the next element wherein s=1, t=0, and u=0;

$P^1$ and $X^{12}$ taken together and/or $P^2$ and $P^{11}$ taken together and/or $P^4$ and $P^9$ taken together form naturally or non-naturally cross-linking α-amino acids or non-naturally cross-linking acids containing each in total 1 to 12 carbon- and/or heteroatoms in a single side-chain which together are connecting $P^1$ and $X^{12}$ and/or $P^2$ and $P^{11}$ and/or $P^4$ and $P^9$ by covalent interaction (interstrand linkage) or by electrostatic interaction (salt bridge);

$P^1$ is pGlu; $^D$pGlu; Ac-pGlu; Ac-$^D$pGlu; or a naturally or non-naturally occurring aliphatic L or D α-amino acid containing in total 1 to 25 carbon- and/or heteroatoms in a single side-chain; or a naturally or non-naturally occurring aromatic L α-amino acid containing in total 1 to 25 carbon- and/or heteroatoms in a single side-chain; or a naturally or non-naturally occurring alcoholic L α-amino acid containing in total 1 to 25 carbon- and/or heteroatoms in a single side-chain; or an aliphatic α-hydroxy acid containing in total 1 to 25 carbon- and/or heteroatoms in a single side-chain; or an aromatic L α-hydroxy acid containing in total 1 to 25 carbon- and/or heteroatoms in a single side-chain; or an alcoholic L α-hydroxy acid containing in total 1 to 25 carbon- and/or heteroatoms in a single side-chain; or an aliphatic acid containing in total 1 to 25 carbon- and/or heteroatoms in a single side-chain;

$P^2$; $P^3$; $P^4$; $P^5$; $P^6$; $P^7$; $P^8$; $P^9$; $P^{10}$; and $P^{11}$ are as defined above for module A in embodiment 1, wherein s=1, t=1, and u=1;

$X^{12}$ is Glyol; or a naturally or non-naturally occurring aliphatic L α-amino acid containing in total 1 to 25 carbon- and/or heteroatoms in a single side-chain; or a naturally or non-naturally occurring aromatic L α-amino acid containing in total 1 to 25 carbon- and/or heteroatoms in a single side-chain; or a naturally or non-naturally occurring basic L α-amino acid containing in total 1 to 25 carbon- and/or heteroatoms in a single side-chain comprising at least one amino function or one guanidino function; or a naturally or non-naturally occurring alcoholic L or D α-amino acid containing in total 1 to 25 carbon- and/or heteroatoms in a single side-chain; or a naturally or non-naturally occurring L α-amino acid containing in total 1 to 25 carbon- and/or heteroatoms in a single side-chain comprising at least one carboxylic amide function; or an aliphatic amino alcohol containing in total 1 to 25 carbon- and/or heteroatoms in a single side-chain; or an aromatic amino alcohol containing in total 1 to 25 carbon- and/or heteroatoms in a single side-chain; or a basic amino alcohol containing in total 1 to 25 carbon- and/or heteroatoms in a single side-chain comprising at least one amino function or one guanidino function; or an alcoholic amino alcohol containing in total 1 to 25 carbon- and/or heteroatoms in a single side-chain comprising at least one hydroxyl function;

with the proviso that, if $P^1$ is a naturally or non-naturally occurring alcoholic L α-amino acid containing in total 1 to 25 carbon- and/or heteroatoms in a single side-chain;

then $X^{12}$ is naturally or non-naturally occurring aliphatic L α-amino acid containing in total 1 to 25 carbon- and/or heteroatoms in a single side-chain; or a naturally or non-naturally occurring alcoholic L or D α-amino acid containing in total 1 to 25 carbon- and/or heteroatoms in a single side-chain; and if $P^3$ is a naturally or non-naturally occurring alcoholic L α-amino acid containing in total 1 to 25 carbon- and/or heteroatoms in a single side-chain;

or a naturally or non-naturally occurring aliphatic L α-amino acid containing in total 1 to 25 carbon- and/or heteroatoms in a single side-chain;

then $P^1$; or $P^{10}$; is a naturally or non-naturally occurring aromatic L α-amino acid containing in total 1 to 25 carbon- and/or heteroatoms in a single side-chain; or $X^{12}$ is a naturally or non-naturally occurring aromatic L α-amino acid containing in total 1 to 25 carbon- and/or heteroatoms in a single side-chain; or an aromatic amino alcohol containing in total 1 to 25 carbon- and/or heteroatoms in a single side-chain; and if $P^8$ is a naturally or non-naturally occurring aliphatic L α-amino acid containing in total 1 to 25 carbon- and/or heteroatoms in a single side-chain;

then $P^{10}$ is a naturally or non-naturally occurring aromatic L α-amino acid containing in total 1 to 25 carbon- and/or heteroatoms in a single side-chain; and if $P^{10}$ is a naturally or non-naturally occurring alcoholic L α-amino acid containing in total 1 to 25 carbon- and/or heteroatoms in a single side-chain;

then $X^{12}$ is a naturally or non-naturally occurring aliphatic L α-amino acid containing in total 1 to 25 carbon- and/or heteroatoms in a single side-chain; and the combined number of the amino acid residue Gly in above module A must not exceed two; and the positions P of the amino acid residues Gly must not be in direct vicinity;

with the further proviso that, if $P^1$ and $X^{12}$ taken together form an interstrand linkage or salt bridge, as defined above; then $P^2$ and $P^{11}$ taken together are not forming an interstrand linkage or salt bridge, as defined above;

the carbonyl (C=O) point of attachment of $X^{12}$ and the nitrogen (N) point of attachment of $P^1$ are appropriately saturated to form the corresponding naturally or non-naturally occurring terminal α-amino acids optionally having modified carbonyl (C=O) functional groups and/or nitrogen (N) functional groups;
with the further proviso that,
if linker L, as defined below, is connected with module A by a carbonyl (C=O) point of attachment of $P^5$; $P^6$; or $P^7$; then
$P^5$; $P^6$; or $P^7$; is a naturally or non-naturally occurring α-amino acid containing in total 1 to 25 carbon- and/or heteroatoms in a single side-chain comprising at least one carboxyl function;
and a module B consisting of single elements Q being connected in either direction from the carbonyl (C=O) point of attachment to the nitrogen (N) of the next element with the proviso that $Q^7$ is connected from the α-carbonyl (C=O) point of attachment to the ω-nitrogen (N) of $Q^1$, and wherein
$Q^1$ is a naturally or non-naturally occurring basic L or D α-amino acid containing in total 1 to 25 carbon- and/or heteroatoms in a single side-chain comprising at least one amino function;
$Q^2$, $Q^5$, and $Q^6$ are independently
a naturally or non-naturally occurring basic L α-amino acid containing in total 1 to 25 carbon- and/or heteroatoms in a single side-chain comprising at least one amino function;
$Q^3$ is a naturally or non-naturally occurring aliphatic D α-amino acid containing in total 1 to 25 carbon- and/or heteroatoms in a single side-chain; or a naturally or non-naturally occurring aromatic D α-amino acid containing in total 1 to 25 carbon- and/or heteroatoms in a single side-chain;
$Q^4$ is a naturally or non-naturally occurring aliphatic L α-amino acid containing in total 1 to 25 carbon- and/or heteroatoms in a single side-chain; or a naturally or non-naturally occurring alcoholic L α-amino acid containing in total 1 to 25 carbon- and/or heteroatoms in a single side-chain;
$Q^7$ is a naturally or non-naturally occurring alcoholic L α-amino acid containing in total 1 to 25 carbon- and/or heteroatoms in a single side-chain; or a naturally or non-naturally occurring aliphatic L α-amino acid containing in total 1 to 25 carbon- and/or heteroatoms in a single side-chain;
and a linker L consisting of k=0-3 single elements L being connected in either direction from the carbonyl (C=O) point of attachment to the nitrogen (N) of the next element, and wherein,
if k=1,
$L^1$ is Gly; Sar; Aib; or a naturally or non-naturally occurring aliphatic L or D α-amino acid containing in total 1 to 25 carbon- and/or heteroatoms in a single side-chain; or a naturally or non-naturally occurring basic L or D α-amino acid containing in total 1 to 25 carbon- and/or heteroatoms in a single side-chain comprising at least one amino function; or a naturally or non-naturally occurring alcoholic L or D α-amino acid containing in total 1 to 25 carbon- and/or heteroatoms in a single side-chain;
if k=2, the additional element
$L^2$ is Gly; Sar; Aib; or a naturally or non-naturally occurring aliphatic L or D α-amino acid containing in total 1 to 25 carbon- and/or heteroatoms in a single side-chain; or a naturally or non-naturally occurring basic L or D α-amino acid containing in total 1 to 25 carbon- and/or heteroatoms in a single side-chain comprising at least one amino function; or a naturally or non-naturally occurring alcoholic L or D α-amino acid containing in total 1 to 25 carbon- and/or heteroatoms in a single side-chain;
if k=3, the additional element
$L^3$ is Gly; Sar; Aib; or a naturally or non-naturally occurring aliphatic L or D α-amino acid containing in total 1 to 25 carbon- and/or heteroatoms in a single side-chain; or a naturally or non-naturally occurring basic L or D α-amino acid containing in total 1 to 25 carbon- and/or heteroatoms in a single side-chain comprising at least one amino function; or a naturally or non-naturally occurring alcoholic L or D α-amino acid containing in total 1 to 25 carbon- and/or heteroatoms in a single side-chain;
said linker L being connected with module B from the carbonyl (C=O) point of attachment of $L^k$ to the α-nitrogen (N) of $Q^1$ and,
if k=1-3, being connected with module A from the carbonyl (C=O) point of attachment of $P^5$; $P^6$; or $P^7$; to the nitrogen (N) of $L^1$; or,
if k=0, then
$Q^1$ being directly connected with module A from the carbonyl (C=O) point of attachment of $P^5$; $P^6$; or $P^7$; to the α-nitrogen (N) of $Q^1$;
or a tautomer or rotamer thereof; or a salt; or a pharmaceutically acceptable salt; or a hydrate; or a solvate thereof.

A further embodiment (4) of the invention relates to compounds of formula (I) according to embodiment (1),
comprising a module A consisting of single elements P or X being connected in either direction from the carbonyl (C=O) point of attachment to the nitrogen (N) of the next element, wherein
if s=1, t=1, and u=1; and
$X^{14}$ and $X^{13}$ taken together form an interstrand linking bis(amino acid)-structure of one of the formulae

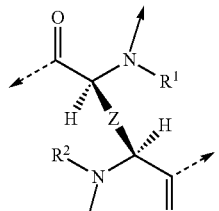

AA16

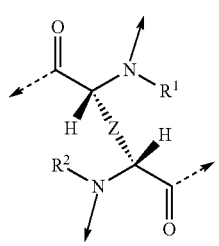

AA16$^D$ based on the linkage of two α-amino acid residues;
or an interstrand linking (amino acid)-(acid)-structure of one of the formulae

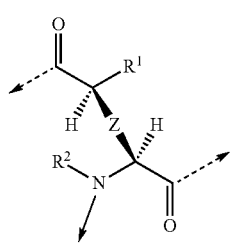

AA17

-continued

AA17$^D$

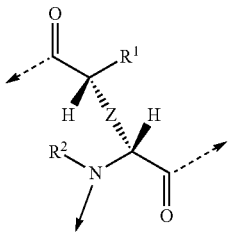

based on the linkage of an α-amino acid residue and an acid residue;

or a salt bridge of one of the formulae

AA18

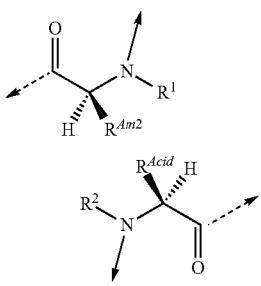

AA18$^D$

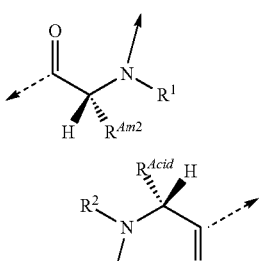

AA19

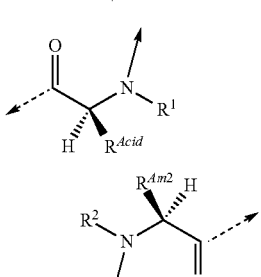

AA19$^D$

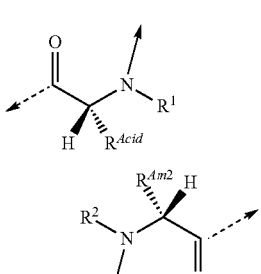

based on the electrostatic interaction between two α-amino acid residue as defined herein below; and/or $P^1$ and $X^{12}$ taken together form an interstrand linking bis (amino acid)-structure of one of the formulae AA16; or AA16$^D$; or a salt bridge of one of the formulae AA18; AA18$^D$; AA19; or AA19$^D$; and/or $P^2$ and $P^{11}$ taken together form an interstrand linking bis (amino acid)-structure of one of the formulae AA16; or AA16$^D$; or a salt bridge of one of the formulae AA18; AA18$^D$; AA19; or AA19$^D$; and/or $P^4$ and $P^9$ taken together form an interstrand linking bis (amino acid)-structure of one of the formulae AA16; or AA16$^D$; or a salt bridge of one of the formulae AA18; AA18$^D$; AA19; or AA19$^D$;

$X^{14}$ is pGlu; $^D$pGlu; Ac-pGlu; Ac-$^D$pGlu; or an α-amino acid residue of one of the formulae AA3b

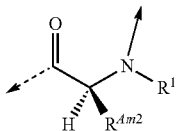

AA4$^D$

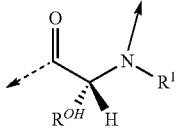

or an acid residue of one of the formulae

AA15a

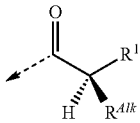

AA15b

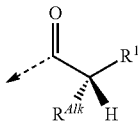

an α-amino acid residue of one of the formulae
$P^1$ is an α-amino acid residue of one of the formulae

AA1

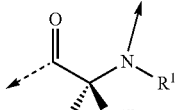

AA1$^D$

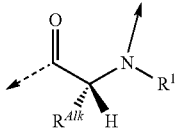

AA2

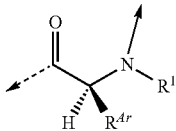

AA4
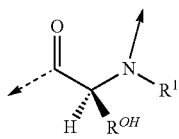
P² is an L α-amino acid residue of one of the formulae
AA1
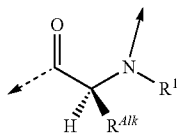
AA3b
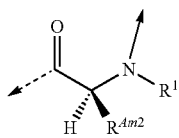
AA4
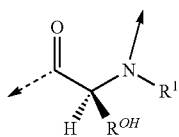
P³ is an L α-amino acid residue of one of the formulae
AA1
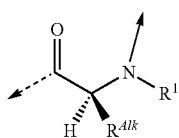
AA2
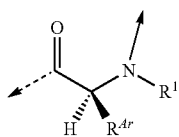
AA4

P⁴ is Gly; or an L α-amino acid residue of one of the formulae
AA3b
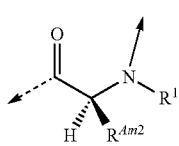
AA4
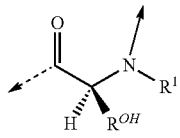
AA2
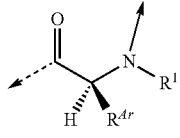
P⁵ is Gly; or an L α-amino acid residue of formula
AA3b
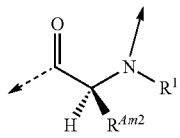
AA1
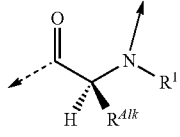
AA2
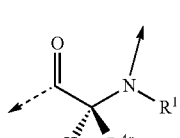
AA4
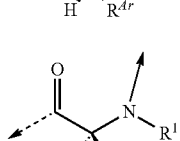
P⁶ is Gly; or a D α-amino acid residue of formula
AA1$^D$
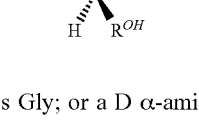
AA3a$^D$
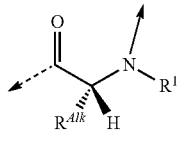
AA4$^D$
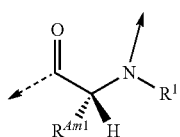

P⁷ is Gly; or an α-amino acid residue of one of the formulae
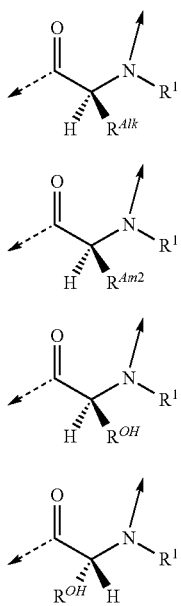
AA1
AA3b
AA4
AA4ᴰ
P⁸ is an L α-amino acid residue of one of the formulae
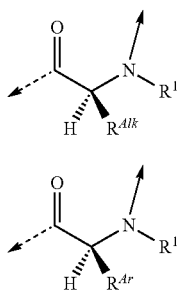
AA1
AA2
P⁹ is Gly, or an L α-amino acid residue of one of the formulae
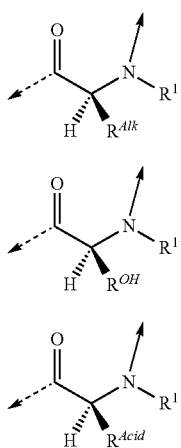
AA1
AA4
AA5
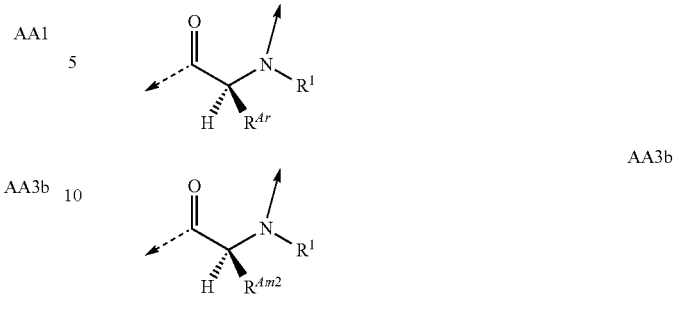
AA2
AA3b
P¹⁰ is an L α-amino acid residue of one of the formulae
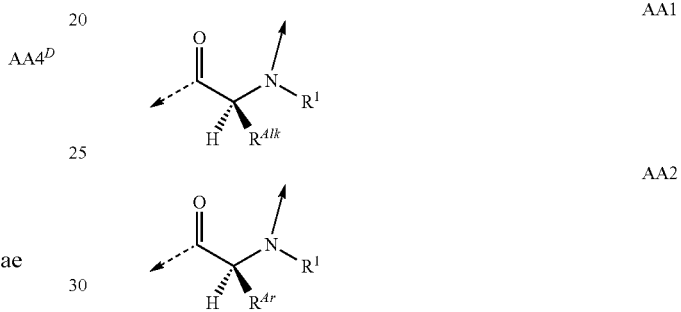
AA1
AA2
AA4
P¹¹ is an L α-amino acid residue of one of the formulae
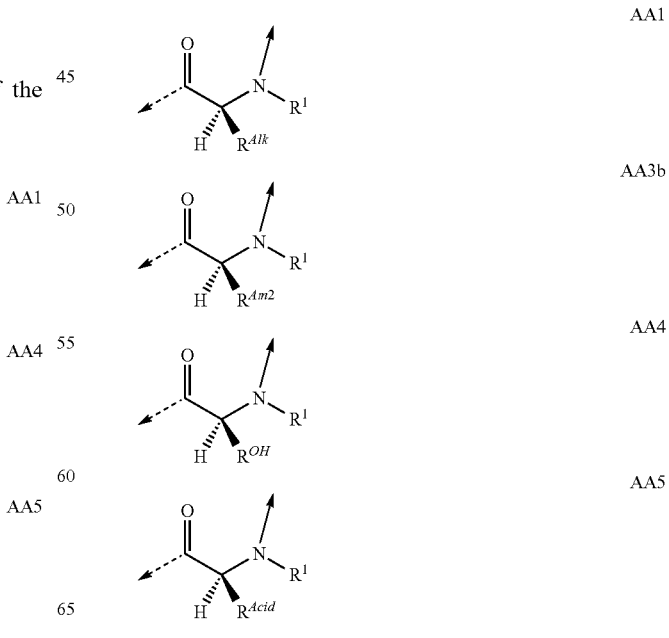
AA1
AA3b
AA4
AA5

$X^{12}$ is Gly; or an α-amino acid residue of one of the formulae

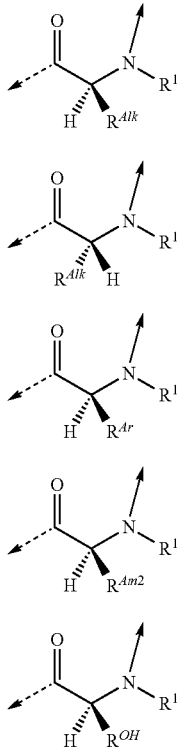

AA1

AA1$^D$

AA2

AA3

AA4

$X^{13}$ is Glyol; or an α-amino acid residue of one of the formulae

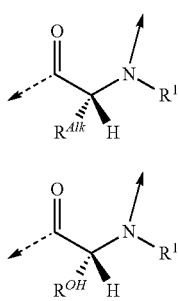

AA1$^D$

AA4$^D$ with the proviso that,
if $P^1$ is an α-amino acid residue of formula AA4;
then $X^{12}$ is an α-amino acid residue of formula AA1; or AA1D; and
if $P^3$ is an α-amino acid residue of one of the formulae AA1; or AA4;
then $P^1$; $P^{10}$; or $X^{12}$; is an α-amino acid residue of formula AA2; and
if $P^8$ is an α-amino acid residue of formula AA1;
then $P^{10}$ is an α-amino acid residue of formula AA2; and
if $P^{10}$ is an α-amino acid residue of formula AA4;
then $X^{12}$ is an α-amino acid residue of formula AA1; or AA1D; and
the combined number of the amino acid residue Gly in above module A must not exceed two; and
the positions P of the amino acid residues Gly must not be in direct vicinity;
with the further proviso that,
the combined number of interstrand linkages and salt bridges in above module A must not exceed two;
if $X^{14}$ and $X^{13}$ taken together form an interstrand linkage or salt bridge, as defined above; then $P^1$ and $X^{12}$ taken together are not forming an interstrand linkage or salt bridge, as defined above;
if $P^1$ and $X^{12}$ taken together form an interstrand linkage or salt bridge, as defined above; then $P^2$ and $P^{11}$ taken together are not forming an interstrand linkage or a salt bridge, as defined above;
$X^{13}$ having a carbonyl (C=O) point of attachment not connected as aforementioned, being appropriately saturated by linkage with $R^{30}$ to form the corresponding naturally or non-naturally occurring terminal α-amino acid residue; optionally having a modified carbonyl (C=O) functional group;
$X^{14}$ having a nitrogen (N) not connected as aforementioned, being appropriately saturated by linkages with Fe, as already depicted above, and $R^{31}$ to form the corresponding naturally or non-naturally occurring terminal α-amino acid residue; optionally having a modified nitrogen (N) functional group;
with the further proviso that,
if linker L, as defined below, is connected with module A by a carbonyl (C=O) point of attachment of $P^5$; $P^6$; or $P^7$; then
$P^5$; $P^6$; or $P^7$; is an α-amino acid residue of one of the formulae

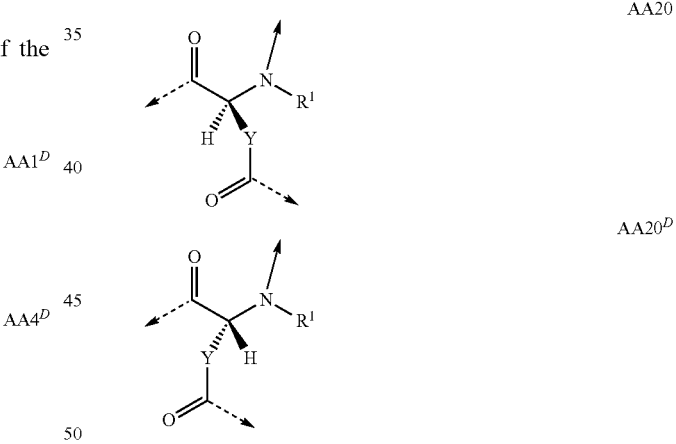

AA20

AA20$^D$ if s=1, t=0, and u=1; and
$P^1$ and $X^{12}$ taken together form an interstrand linking bis (amino acid) structure of one of the formulae AA16; or AA16$^D$; or a salt bridge of one of the formulae AA18; AA18$^D$; AA19; or AA19$^D$; and/or
$P^2$ and $P^{11}$ taken together form an interstrand linking bis (amino acid) structure of one of the formulae AA16; or AA16$^D$; or a salt bridge of one of the formulae AA18; AA18$^D$; AA19; or AA19$^D$; and/or
$P^4$ and $P^9$ taken together form an interstrand linking bis (amino acid) structure of one of the formulae AA16; or AA16$^D$; or a salt bridge one of the formulae AA18; AA18$^D$; AA19; or AA19$^D$;
$X^{14}$; $P^1$; $P^2$; $P^3$; $P^4$; $P^5$; $P^6$; $P^7$; $P^8$; $P^9$; $P^{10}$; and $P^{11}$ are as defined above for module A in this embodiment, wherein s=1, t=1, and u=1;

$X^{12}$ is Glyol; or an L α-amino acid residue of one of the formulae

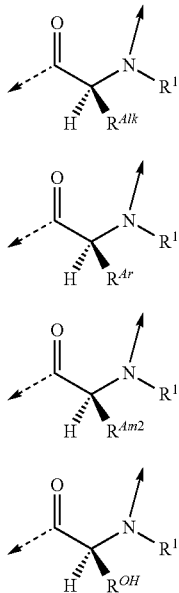

AA1

AA2

AA3

AA4 or an amino alcohol residue of one of the formulae

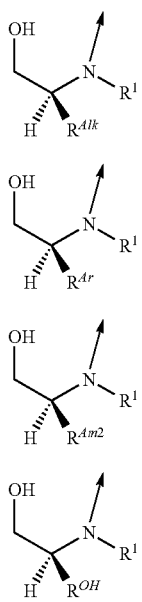

AA7

AA8

AA9

AA10 with the proviso that,
if $P^1$ is an α-amino acid residue of formula AA4;
then $X^{12}$ is an α-amino acid residue of formula AA1; and
if $P^3$ is an α-amino acid residue of one of the formulae AA1; or AA4;
then $P^1$; or $P^{10}$; is an α-amino acid residue of formula AA2; or $X^{12}$ is an α-amino acid residue of formula AA2; or an amino alcohol residue of formula AA8; and
if $P^8$ is an α-amino acid residue of formula AA1;
then $P^{10}$ is an α-amino acid residue of formula AA2; and
if $P^{10}$ is an α-amino acid residue of formula AA4;
then $X^{12}$ is an α-amino acid residue of formula AA1; and the combined number of the amino acid residue Gly in above module A must not exceed two; and the positions P of the amino acid residues Gly must not be in direct vicinity;

with the further proviso that, if $P^1$ and $X^{12}$ taken together form an interstrand linkage or salt bridge, as defined above; then $P^2$ and $P^{11}$ taken together are not forming an interstrand linkage or salt bridge, as defined above;

$X^{12}$ having a carbonyl (C=O) point of attachment not connected as aforementioned, being appropriately saturated by linkage with $R^{30}$ to form the corresponding naturally or non-naturally occurring terminal α-amino acid residue; optionally having a modified carbonyl (C=O) functional group;

$X^{14}$ having a nitrogen (N) not connected as aforementioned, being appropriately saturated by linkages with Fe, as already depicted above, and $R^{31}$ to form the corresponding naturally or non-naturally occurring terminal α-amino acid residue; optionally having a modified nitrogen (N) functional group;

with the further proviso that, if linker L, as defined below, is connected with module A by a carbonyl (C=O) point of attachment of $P^5$; $P^6$; or $P^7$; then $P^5$; $P^6$; or $P^7$; is an α-amino acid residue of one of the formulae

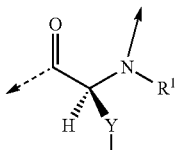

AA20

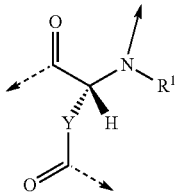

AA20$^D$ if s=1, t=1, and u=0; and $P^1$ and $X^{12}$ taken together form an interstrand linking bis (amino acid) structure of one of the formulae AA16; or AA16$^D$; or an interstrand linking (amino acid)-(acid)-structure of one of the formulae AA17; or AA17$^D$; or a salt bridge of one of the formulae AA18; AA18$^D$; AA19; or AA19$^D$; and/or $P^2$ and $P^{11}$ taken together form an interstrand linking bis (amino acid) structure of one of the formulae AA16; or AA16$^D$; or a salt bridge of one of the formulae AA18; AA18$^D$; AA19; or AA19$^D$; and/or $P^4$ and $P^9$ taken together form an interstrand linking bis (amino acid) structure of one of the formulae AA16; or AA16$^D$; or a salt bridge of one of the formulae AA18; AA18$^D$; AA19; or AA19$^D$;

P¹ is pGlu; $^D$pGlu; Ac-pGlu; Ac-$^D$pGlu; or an α-amino acid residue of one of the formulae

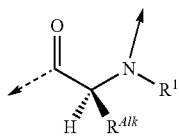
AA1

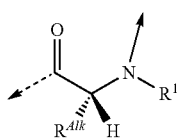
AA2

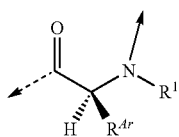
AA4

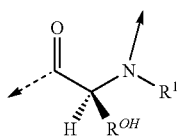
AA11 or an L α-hydroxy acid residue of one of the formulae

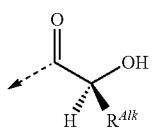
AA11

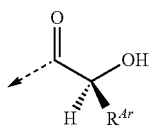
AA12

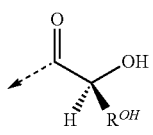
AA14 or an acid residue of one of the formulae

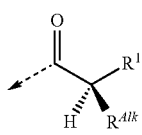
AA15a

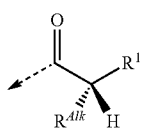
AA15b

P²; P³; P⁴; P⁵; P⁶; P⁷; P⁸; P⁹; P¹⁰; P¹¹; and X¹² are as defined above for module A in this embodiment, wherein s=1, t=1, and u=1;

X¹³ is Glyol; or an α-amino acid residue of one of the formulae

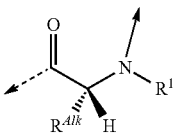
AA1$^D$

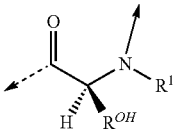
AA4

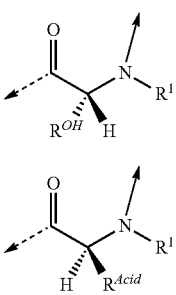
AA4$^D$

AA5

AA5$^D$

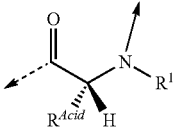
AA6 with the proviso that,
if P¹ is an α-amino acid residue of formula AA4;
then X¹² is an α-amino acid residue of formula AA1; or AA1D; and
if P³ is an α-amino acid residue of one of the formulae AA1; or AA4;
then P¹; P¹⁰; or X¹²; is an α-amino acid residue of formula AA2; and
if P⁸ is an α-amino acid residue of formula AA1;
then P¹⁰ is an α-amino acid residue of formula AA2; and
if P¹⁰ is an α-amino acid residue of formula AA4;
then X¹² is an α-amino acid residue of formula AA1; or AA1D; and
the combined number of the amino acid residue Gly in above module A must not exceed two; and
the positions P of the amino acid residues Gly must not be in direct vicinity;
with the further proviso that,
if P¹ and X¹² taken together form an interstrand linkage or salt bridge, as defined above; then P² and P¹¹ taken together are not forming an interstrand linkage or salt bridge, as defined above;

$X^{13}$ having a carbonyl (C=O) point of attachment not connected as aforementioned, being appropriately saturated by linkage with $R^{30}$ to form the corresponding naturally or non-naturally occurring terminal α-amino acid residue; optionally having a modified carbonyl (C=O) functional group;

$P^1$ having a nitrogen (N) not connected as aforementioned, being appropriately saturated by linkages with $R^1$, as already depicted above, and $R^{31}$ to form the corresponding naturally or non-naturally occurring terminal α-amino acid residue; optionally having a modified nitrogen (N) functional group;

with the further proviso that, if linker L, as defined below, is connected with module A by a carbonyl (C=O) point of attachment of $P^5$; $P^6$; or $P^7$; then $P^5$; $P^6$; or $P^7$; is an α-amino acid residue of one of the formulae

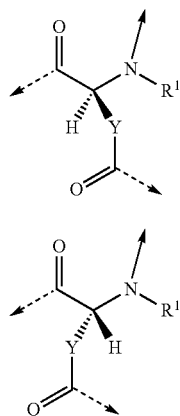

if s=0, t=0, and u=1; and $P^2$ and $P^{11}$ taken together form an interstrand linking bis(amino acid) structure of one of the formulae AA16; or AA16$^D$; or a salt bridge of one of the formulae AA18; AA18$^D$; AA19; or AA19$^D$; and/or $P^4$ and $P^9$ taken together form an interstrand linking bis(amino acid) structure of one of the formulae AA16; or AA16$^D$; or a salt bridge of one of the formulae AA18; AA18$^D$; AA19; or AA19D;

$X^{14}$; $P^1$; $P^2$; $P^3$; $P^4$; $P^5$; $P^6$; $P^7$; $P^8$; $P^9$; and $P^{10}$ are as defined above for module A in this embodiment, wherein s=1, t=1, and u=1;

$P^{11}$ is an L α-amino acid residue of one of the formulae

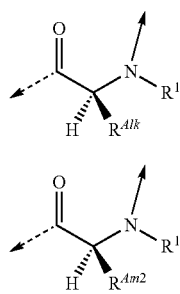

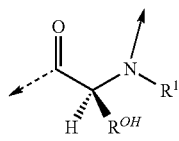

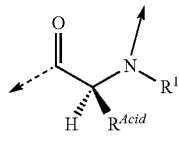

with the proviso that, if $P^3$ is an α-amino acid residue of one of the formulae AA1; or AA4;

then $P^1$; or $P^{10}$; is an α-amino acid residue of formula AA2; and if $P^8$ is an α-amino acid residue of formula AA1;

then $P^{10}$ is an α-amino acid residue of formula AA2; and the combined number of the amino acid residue Gly in above module A must not exceed two; and the positions P of the amino acid residues Gly must not be in direct vicinity;

with the further proviso that, $P^{11}$ having a carbonyl (C=O) point of attachment not connected as aforementioned, being appropriately saturated by linkage with $R^{39}$ to form the corresponding naturally or non-naturally occurring terminal α-amino acid residue; optionally having a modified carbonyl (C=O) functional group;

$X^{14}$ having a nitrogen (N) not connected as aforementioned, being appropriately saturated by linkages with Fe, as already depicted above, and $R^{31}$ to form the corresponding naturally or non-naturally occurring terminal α-amino acid residue; optionally having a modified nitrogen (N) functional group;

with the further proviso that, if linker L, as defined below, is connected with module A by a carbonyl (C=O) point of attachment of $P^5$; $P^6$; or $P^7$; then $P^5$; $P^6$; or $P^7$; is an α-amino acid residue of one of the formulae

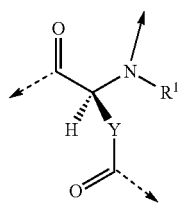

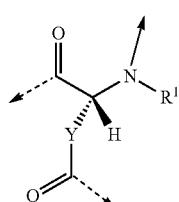

if s=1, t=0, and u=0; and $P^1$ and $X^{12}$ taken together form an interstrand linking bis(amino acid) structure of one of the formulae AA16; or AA16$^D$; or an interstrand linking (amino acid)-(acid)- structure of one of the formulae AA17; or AA17$^D$; or a salt bridge of one of the formulae AA18; AA18$^D$; AA19; or AA19$^D$; and/or P$^2$ and P$^{11}$ taken together form an interstrand linking bis (amino acid) structure of one of the formulae AA16; or AA16$^D$; or a salt bridge of one of the formulae AA18; AA18$^D$; AA19; or AA19$^D$; and/or P$^4$ and P$^9$ taken together form an interstrand linking bis (amino acid) structure of one of the formulae AA16; or AA16$^D$; or a salt bridge of one of the formulae AA18; AA18$^D$; AA19; or AA19$^D$;

P$^1$ is pGlu; $^D$pGlu; Ac-pGlu; Ac-$^D$pGlu; or an α-amino acid residue of one of the formulae

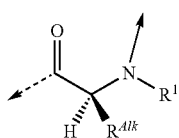

AA1

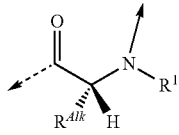

AA1$^D$

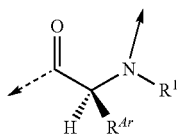

AA2

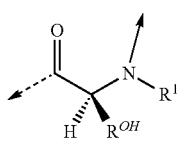

AA4 or an L α-hydroxy acid residue of one of the formulae

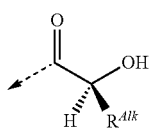

AA11

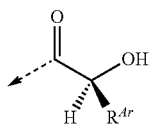

AA12

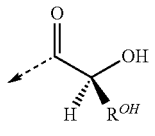

AA14 or an acid residue of one of the formulae

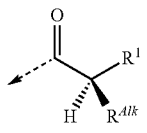

AA15a

-continued

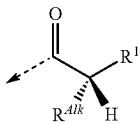

AA15b

P$^2$; P$^3$; P$^4$; P$^5$; P$^6$; P$^7$; P$^8$; P$^9$; P$^{10}$; and P$^{11}$ are as defined above for module A in this embodiment, wherein s=1, t=1, and u=1;

X$^{12}$ is Glyol; or an α-amino acid residue of one of the formulae

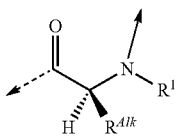

AA1

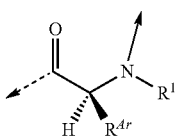

AA2

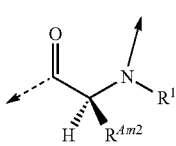

AA3

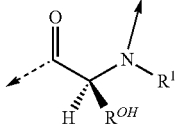

AA4

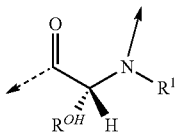

AA4$^D$

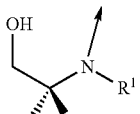

AA6 or an amino alcohol residue of one of the formulae

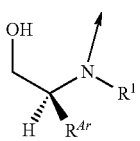

AA7

AA8

-continued

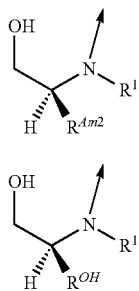
AA9

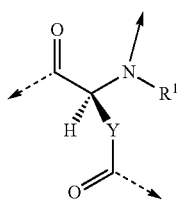
AA10 with the proviso that,
if $P^1$ is an α-amino acid residue of formula AA4;
then $X^{12}$ is an α-amino acid residue of formula AA1; AA4; or AA4$^D$; and
if $P^3$ is an α-amino acid residue of one of the formulae AA1; or AA4;
then $P^1$; or $P^{10}$; is an α-amino acid residue of formula AA2; or $X^{12}$ is an α-amino acid residue of formula AA2; or an amino alcohol residue of formula AA8; and
if $P^8$ is an α-amino acid residue of formula AA1;
then $P^{10}$ is an α-amino acid residue of formula AA2; and
if $P^{10}$ is an α-amino acid residue of formula AA4;
then $X^{12}$ is an α-amino acid residue of formula AA1; and
the combined number of the amino acid residue Gly in above module A must not exceed two; and
the positions P of the amino acid residues Gly must not be in direct vicinity;
with the further proviso that,
if $P^1$ and $X^{12}$ taken together form an interstrand linkage or salt bridge, as defined above; then $P^2$ and $P^{11}$ taken together are not forming an interstrand linkage or salt bridge, as defined above;
$X^{12}$ having a carbonyl (C=O) point of attachment not connected as aforementioned, being appropriately saturated by linkage with $R^{30}$ to form the corresponding naturally or non-naturally occurring terminal α-amino acid residue; optionally having a modified carbonyl (C=O) functional group;
$P^1$ having a nitrogen (N) not connected as aforementioned, being appropriately saturated by linkages with Fe, as already depicted above, and $R^{31}$ to form the corresponding naturally or non-naturally occurring terminal α-amino acid residue; optionally having a modified nitrogen (N) functional group;
with the further proviso that,
if linker L, as defined below, is connected with module A by a carbonyl (C=O) point of attachment of $P^5$; $P^6$; or $P^7$; then
$P^5$; $P^6$; or $P^7$; is an α-amino acid residue of one of the formulae

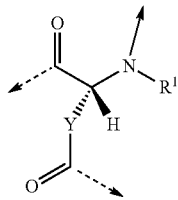
AA20

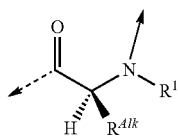
AA20$^D$ if s=0, t=0, and u=0; and
$P^2$ and $P^{11}$ taken together form an interstrand linking bis (amino acid) structure of one of the formulae AA16; or AA16$^D$; or a salt bridge of one of the formulae AA18; AA18$^D$; AA19; or AA19$^D$; and/or
$P^4$ and $P^9$ taken together form an interstrand linking bis (amino acid) structure of one of the formulae AA16; or AA16$^D$; or a salt bridge of one of the formulae AA18; AA18$^D$; AA19; or AA19$^D$;
$P^1$ is pGlu; $^D$pGlu; Ac-pGlu; Ac-$^D$pGlu; or an α-amino acid residue of one of the formulae

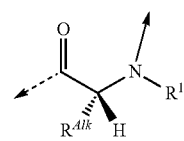
AA1

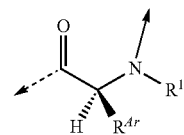
AA1$^D$

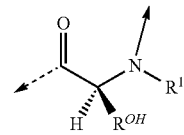
AA2

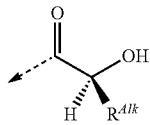
AA4 or an L α-hydroxy acid residue of one of the formulae

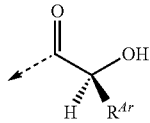
AA11

AA12

-continued

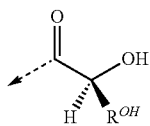
AA14 or an acid residue of one of the formulae

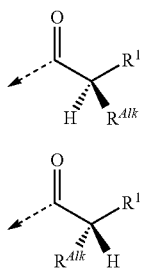
AA15a

AA15b $P^2$; $P^3$; $P^4$; $P^5$; $P^6$; $P^7$; $P^8$; $P^9$; and $P^{10}$ are as defined above for module A in this embodiment, wherein s=1, t=1, and u=1;

$P^{11}$ is an L α-amino acid residue of one of the formulae

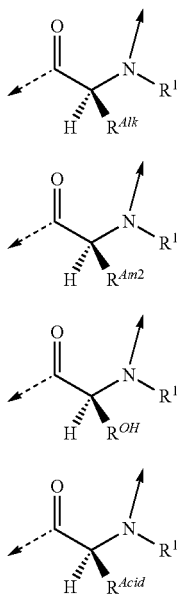
AA1

AA3b

AA4

AA5 with the proviso that,
if $P^3$ is an α-amino acid residue of one of the formulae AA1; or AA4;
then $P^1$; or $P^{10}$; is an α-amino acid residue of formula AA2; and
if $P^8$ is an α-amino acid residue of formula AA1;
then $P^{10}$ is an α-amino acid residue of formula AA2; and
the combined number of the amino acid residue Gly in above module A must not exceed two; and
the positions P of the amino acid residues Gly must not be in direct vicinity;
with the further proviso that,
$P^{11}$ having a carbonyl (C=O) point of attachment not connected as aforementioned, being appropriately saturated by linkage with $R^{30}$ to form the corresponding naturally or non-naturally occurring terminal α-amino acid residue; optionally having a modified carbonyl (C=O) functional group;

$P^1$ having a nitrogen (N) not connected as aforementioned, being appropriately saturated by linkages with $R^1$, as already depicted above, and $R^{31}$ to form the corresponding naturally or non-naturally occurring terminal α-amino acid residue; optionally having a modified nitrogen (N) functional group;

with the further proviso that,
if linker L, as defined below, is connected with module A by a carbonyl (C=O) point of attachment of $P^5$; $P^6$; or $P^7$; then
$P^5$; $P^6$; or $P^7$; is an α-amino acid residue of one of the formulae

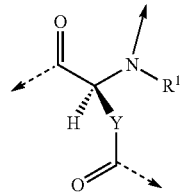
AA20

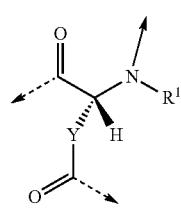
AA20$^D$ if s=0, t=0, and u=0; and alternatively
$P^{11}$ is connected from the α-carbonyl point of attachment to the ω-nitrogen (N) of $P^2$;
$P^1$ is pGlu; or an α-amino acid residue of one of the formulae

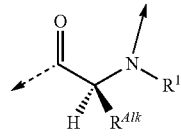
AA1

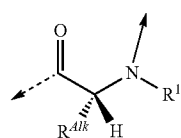
AA1$^D$

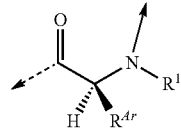
AA2

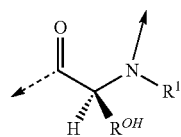
AA4 or an L α-hydroxy acid residue of one of the formulae

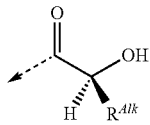
AA11

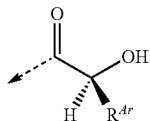
AA12

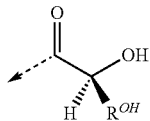
AA14 or an acid residue of one of the formulae

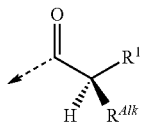
AA15a

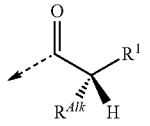
AA15b $P^2$ is an L α-amino acid residue of formula

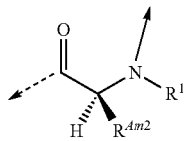
AA3b $P^3$; $P^4$; $P^5$; $P^6$; $P^7$; $P^8$; $P^9$; and $P^{10}$ are as defined above for module A in this embodiment, wherein s=1, t=1, and u=1;

$P^{11}$ is an α-amino acid residue of one of the formulae

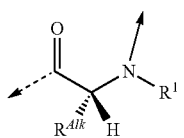
$AA1^D$

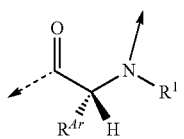
$AA2^D$

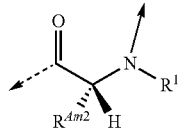
$AA3b^D$

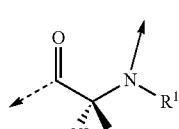
$AA4^D$

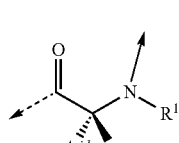
$AA5^D$

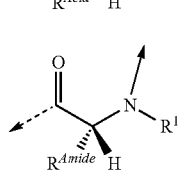
$AA6^D$ with the proviso that, if $P^3$ is an α-amino acid residue of one of the formulae AA1; or AA4;

then $P^1$; or $P^m$; is an α-amino acid residue of formula AA2; and if $P^8$ is an α-amino acid residue of formula AA1;

then $P^{10}$ is an α-amino acid residue of formula AA2; and the combined number of the amino acid residue Gly in above module A must not exceed two; and the positions P of the amino acid residues Gly must not be in direct vicinity;

with the further proviso that, $P^1$ having a nitrogen (N) not connected as aforementioned, being appropriately saturated by linkages with Fe, as already depicted above, and $R^{31}$ to form the corresponding naturally or non-naturally occurring terminal α-amino acid residue; optionally having a modified nitrogen (N) functional group;

with the further proviso that, if linker L, as defined below, is connected with module A by a carbonyl (C=O) point of attachment of $P^5$; $P^6$; or $P^7$; then $P^5$; $P^6$; or $P^7$; is an α-amino acid residue of one of the formulae

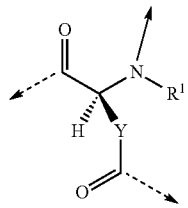
AA20

-continued

AA20$^D$

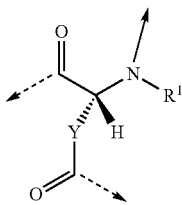

and a module B consisting of single elements Q being connected in either direction from the carbonyl (C=O) point of attachment to the nitrogen (N) of the next element with the proviso that $Q^7$ is connected from the α-carbonyl (C=O) point of attachment to the ω-nitrogen (N) of $Q^1$, and wherein $Q^1$ is an α-amino acid residue of one of the formulae

AA21

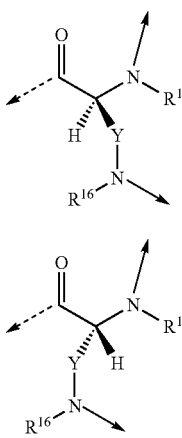

AA21$^D$ $Q^2$, $Q^5$, and $Q^6$ are independently an L α-amino acid residue of formula AA3b

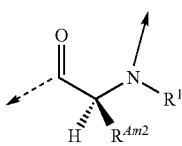

$Q^3$ is a D α-amino acid residue of one of the formulae

AA1$^D$

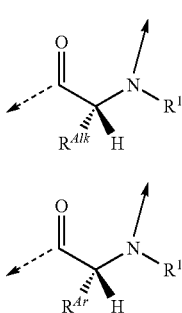

AA2$^D$ $Q^4$ is an L α-amino acid residue of one of the formulae

AA1

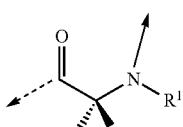

AA4

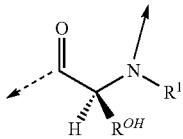

$Q^7$ is an L α-amino acid residue of one of the formulae

AA1

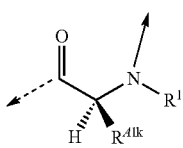

AA4

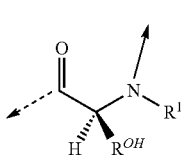

and a linker L consisting of k=0-3 single elements L being connected in either direction from the carbonyl (C=O) point of attachment to the nitrogen (N) of the next element, and wherein, if k=1, $L^1$ is Gly; Sar; Aib; or an α-amino acid residue of one of the formulae AA3b; AA3b$^D$; AA4; AA4$^D$; AA1; or AA1$^D$, as depicted above;

if k=2, the additional element $L^2$ is Gly; Sar; Aib; or an α-amino acid residue of one of the formulae AA3b; AA3b$^D$; AA4; AA4$^D$; AA1; or AA1$^D$, as depicted above;

if k=3, the additional element $L^3$ is Gly; Sar; Aib; or an α-amino acid residue of one of the formulae AA3b; AA3b$^D$; AA4; AA4$^D$; AA1; or AA1$^D$, as depicted above;

said linker L being connected with module B from the carbonyl (C=O) point of attachment of $L^k$ to the α-nitrogen (N) of $Q^1$ and, if k=1-3, being connected with module A from the carbonyl (C=O) point of attachment of $P^5$; $P^6$; or $P^7$; to the nitrogen (N) of $L^1$; or, if k=0, then $Q^1$ being directly connected with module A from the carbonyl (C=O) point of attachment of $P^5$; $P^6$; or $P^7$; to the α-nitrogen (N) of $Q^1$;

$R^{Alk}$ is, with the proviso of containing less than 26 carbon- and/or heteroatoms, $C_{1-12}$-alkyl; $C_{2-12}$-alkenyl; cycloalkyl; cycloalkyl-$C_{1-6}$-alkyl; or $C_{1-6}$-alkoxy-$C_{1-6}$-alkyl;

$R^{Ar}$ is, with the proviso of containing less than 26 carbon- and/or heteroatoms, —$(CR^1R^4)_nR^{19}$; —$(CH_2)_nO(CH_2)_mR^{19}$; —$(CH_2)_nS(CH_2)_mR^{19}$; or —$(CH_2)_nNR^{14}(CH_2)_mR^{19}$;

R$^{Am1}$ is, with the proviso of containing less than 26 carbon- and/or heteroatoms, —(CR$^1$R$^{13}$)$_q$NR$^{15}$R$^{16}$; —(CH$_2$)$_q$C(=NR$^{13}$)NR$^{15}$R$^{16}$; —(CH$_2$)$_q$C(=NNR$^{15}$R$^{16}$)NR$^{17}$R$^{18}$; —(CR$^1$R$^{13}$)$_q$NR$^2$C(=NR$^{17}$)NR$^{15}$R$^{16}$; —(CR$^1$R$^{13}$)$_q$N=C(NR$^{15}$R$^{16}$)NR$^{17}$R$^{18}$; —(CH$_2$)$_n$O(CH$_2$)$_m$NR$^{15}$R$^{16}$; —(CH$_2$)$_n$O(CH$_2$)$_m$C(=NR$^{17}$)NR$^{15}$R$^{16}$; —(CH$_2$)$_n$O(CH$_2$)$_m$C(=NNR$^{15}$R$^{16}$)NR$^{17}$R$^{18}$; —(CH$_2$)$_n$O(CH$_2$)$_m$NR$^1$C(=NR$^{17}$)NR$^{15}$R$^{16}$; —(CH$_2$)$_n$O(CH$_2$)$_m$N=C(NR$^{15}$R$^{16}$)NR$^{17}$R$^{18}$; —(CH$_2$)$_n$S(CH$_2$)$_m$NR$^{15}$R$^{16}$; —(CH$_2$)$_n$S(CH$_2$)$_m$C(=NR$^{17}$)NR$^{15}$R$^{16}$; —(CH$_2$)$_n$S(CH$_2$)$_m$C(=NNR$^{15}$R$^{16}$)NR$^{17}$R$^{18}$; —(CH$_2$)$_n$S(CH$_2$)$_m$NR$^1$C(=NR$^{17}$)NR$^{15}$R$^{16}$; —(CH$_2$)$_n$S(CH$_2$)$_m$N=C(NR$^{15}$R$^{16}$)NR$^{17}$R$^{18}$; or —(CR$^1$R$^{13}$)$_q$NR$^{14}$R$^{27}$;

R$^{Am2}$ is, with the proviso of containing less than 26 carbon- and/or heteroatoms, —(CR$^1$R$^{13}$)$_q$NR$^{15}$R$^{16}$; —(CH$_2$)$_n$O(CH$_2$)$_m$NR$^{15}$R$^{16}$; or —(CH$_2$)$_n$S(CH$_2$)$_m$NR$^{15}$R$^{16}$ R$^{Acid}$ is, with the proviso of containing less than 26 carbon- and/or heteroatoms, —(CR$^1$R$^{13}$)$_q$COOH; or —(CR$^1$R$^{13}$)$_q$PO(OH)$_2$;

R$^{OH}$ is, with the proviso of containing less than 26 carbon- and/or heteroatoms, —(CR$^1$R$^{13}$)$_q$OH; —(CR$^1$R$^{13}$)$_q$SH; —(CH$_2$)$_n$O(CH$_2$)$_m$OH; —(CH$_2$)$_n$S(CH$_2$)$_m$OH; —(CH$_2$)$_n$NR$^1$(CH$_2$)$_m$OH; hydroxy-C$_{1-8}$-alkyl; hydroxy-C$_{2-8}$-alkenyl; hydroxy-cycloalkyl; or hydroxy-heterocycloalkyl;

R$^{Amide}$ is, with the proviso of containing less than 26 carbon- and/or heteroatoms, —(CR$^1$R$^{13}$)$_q$CONR$^{15}$R$^{16}$;

Y is, with the proviso of containing less than 25 carbon- and/or heteroatoms, —(CR$^1$R$^{13}$)$_q$—;

Z is, with the proviso of containing less than 25 carbon- and/or heteroatoms, —(CH$_2$)$_n$—S—S—(CH$_2$)$_m$—; —(CR$^{28}$R$^{29}$)$_n$—S—S—(CR$^{28}$R$^{29}$)$_m$—; —(CH$_2$)$_n$CH=CH(CH$_2$)$_m$—; —(CR$^{28}$R$^{29}$)$_n$CH=CH(CR$^{28}$R$^{29}$)$_m$—; —(CH$_2$)$_n$-heteroaryl-(CH$_2$)$_m$—; —(CR$^{28}$R$^{29}$)$_n$-heteroaryl-(CR$^{28}$R$^{29}$)$_m$—; —(CH$_2$)$_n$CONR$^1$(CH$_2$)$_m$—; —(CH$_2$)$_n$NR$^1$CO(CH$_2$)$_m$—; —(CR$^{28}$R$^{29}$)$_n$CONR$^1$(CR$^{28}$R$^{29}$)$_m$—; —(CR$^{28}$R$^{29}$)$_n$R$^1$CO(CR$^{28}$R$^{29}$)$_m$—; —(CH$_2$)$_n$NR$^1$CONR$^2$(CH$_2$)$_m$—; or —(CR$^{28}$R$^{29}$)$_n$NR$^1$CONR$^2$(CR$^{28}$R$^{29}$)$_m$—;

R$^1$ and R$^2$ are independently
  H; CF$_3$; C$_{1-8}$-alkyl; or C$_{2-8}$-alkenyl;
R$^4$ is H; F; CF$_3$; C$_{1-8}$-alkyl; C$_{2-8}$-alkenyl; cycloalkyl; heterocycloalkyl; aryl; heteroaryl; aryl-C$_{1-6}$-alkyl; heteroaryl-C$_{1-6}$-alkyl; —(CHR$^{13}$)$_o$OR$^{15}$; —O(CO)R$^{15}$; —(CHR$^{13}$)$_o$SR$^{15}$; —(CHR$^{13}$)$_o$NR$^{15}$R$^{16}$; —(CHR$^{13}$)$_o$OCONR$^{15}$R$^{16}$; —(CHR$^{13}$)$_o$NR$^1$CONR$^{15}$R$^{16}$; —(CHR$^{13}$)$_o$NR$^1$COR$^{15}$; —(CHR$^{13}$)$_o$COOR$^{15}$; —(CHR$^{13}$)$_o$CONR$^{15}$R$^{16}$; —(CHR$^{13}$)$_o$PO(OR$^1$)$_2$; —(CHR$^{13}$)$_o$SO$_2$R$^{15}$; —(CHR$^{13}$)$_o$NR$^1$SO$_2$R$^{15}$; —(CHR$^{13}$)$_o$SO$_2$NR$^{15}$R$^{16}$; —(CR$^1$R$^{13}$)$_o$R$^{19}$; or —(CHR$^1$)$_n$O(CHR$^2$)$_m$R$^{23}$; or R$^{13}$ is H; F; CF$_3$; C$_{2-8}$-alkyl; C$_{2-8}$-alkenyl; cycloalkyl; heterocycloalkyl; cycloalkyl-C$_{1-6}$-alkyl; heterocycloalkyl-C$_{1-6}$-alkyl; aryl; heteroaryl; aryl-C$_{1-6}$-alkyl; heteroaryl-C$_{1-6}$-alkyl; —(CHR$^1$)$_o$OR$^{15}$; —OCOR$^1$; —(CHR$^1$)$_o$NR$^{15}$R$^{16}$; —(CHR$^1$)$_q$NR$^2$C(=NR$^{17}$)NR$^{15}$R$^{16}$; —(CHR$^1$)$_q$NR$^2$CONR$^{15}$R$^{16}$; —COOR$^{15}$; —CONR$^{15}$R$^{16}$; or —SO$_2$R$^{15}$; or —SO$_2$NR$^{15}$R$^{16}$;

R$^{14}$ is H; CF$_3$; C$_{1-8}$-alkyl; C$_{2-8}$-alkenyl; cycloalkyl; heterocycloalkyl; cycloalkyl-C$_{1-6}$-alkyl; heterocycloalkyl-C$_{1-6}$-alkyl; aryl; heteroaryl; aryl-C$_{1-6}$-alkyl; heteroaryl-C$_{1-6}$-alkyl; cycloalkyl-aryl; heterocycloalkyl-aryl; cycloalkyl-heteroaryl; heterocycloalkyl-heteroaryl; aryl-cycloalkyl; aryl-heterocycloalkyl; heteroaryl-cycloalkyl; heteroaryl-heterocycloalkyl; —(CHR$^1$)$_o$OR$^{15}$; —(CHR$^1$)$_o$SR$^{15}$; —(CHR$^1$)$_o$NR$^{15}$R$^{16}$; —(CHR$^1$)$_o$COOR$^{15}$; —(CHR$^1$)$_o$CONR$^{15}$R$^{16}$; or —(CHR$^1$)$_o$SO$_2$R$^{15}$;

R$^{15}$, R$^{16}$, R$^{17}$ and R$^{18}$ are independently
  H; C$_{1-8}$-alkyl; C$_{2-8}$-alkenyl; C$_{1-6}$-alkoxy; cycloalkyl; heterocycloalkyl; cycloalkyl-C$_{1-6}$-alkyl; heterocycloalkyl-C$_{1-6}$-alkyl; aryl; heteroaryl; aryl-C$_{1-6}$-alkyl; heteroaryl-C$_{1-6}$-alkyl; cycloalkyl-aryl; heterocycloalkyl-aryl; cycloalkyl-heteroaryl; heterocycloalkyl-heteroaryl; aryl-cycloalkyl; aryl-heterocycloalkyl; heteroaryl-cycloalkyl; or heteroaryl-heterocycloalkyl; or the structural elements —NR$^{15}$R$^{16}$ and —NR$^{17}$R$^{18}$ can independently form: heterocycloalkyl; aryl-heterocycloalkyl; or heteroaryl-heterocycloalkyl;

R$^{19}$ is an aryl group of one of the formulae

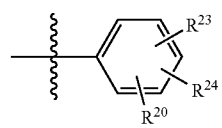

AR1

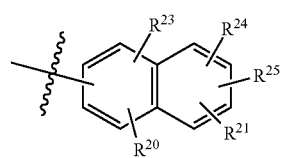

AR2 or a group of one of the formulae

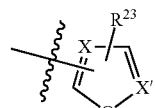

H1

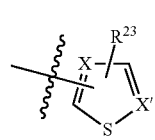

H2

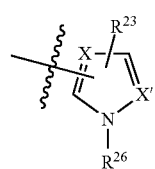

H3

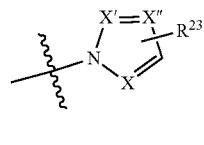

H4

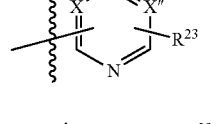

H5

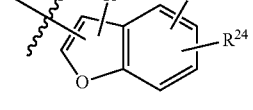

H6

-continued

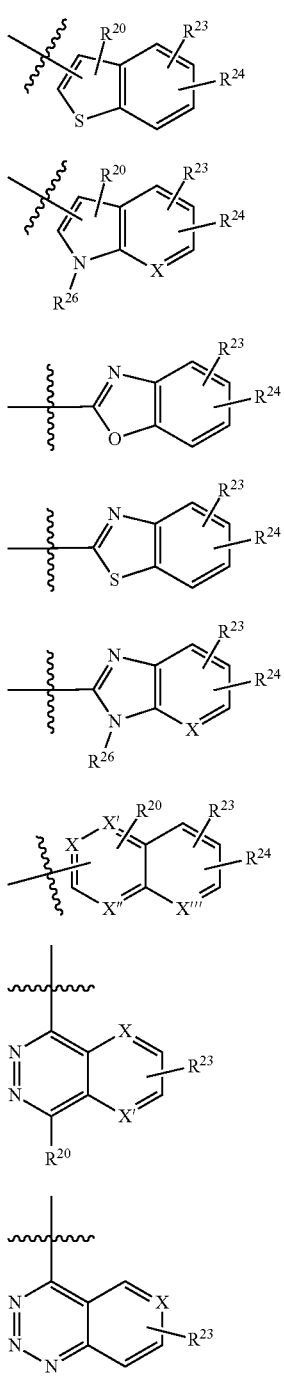

X, X', X" and X'" are independently
—CR$^{20}$; or N;

R$^{20}$ and R$^{21}$ are independently
H; F; Cl; Br; I; OH; NH$_2$; NO$_2$; CN; CF$_3$; OCHF$_2$; OCF$_3$; C$_{1-8}$-alkyl; C$_{2-8}$-alkenyl; aryl; heteroaryl; aryl-C$_{1-6}$-alkyl; heteroaryl-C$_{1-6}$-alkyl; —(CH$_2$)$_o$R$^{22}$; —(CH$_2$)$_o$OR$^{15}$; —O(CO)R$^{15}$; —O(CH$_2$)$_o$R$^{22}$; —(CH$_2$)$_o$SR$^{15}$; —(CH$_2$)$_o$NR$^{15}$R$^{16}$; —(CH$_2$)$_o$OCONR$^{15}$R$^{16}$; —(CH$_2$)$_o$NR$^1$R$^{15}$; —(CH$_2$)$_o$NR$^1$COR$^{15}$; —(CH$_2$)$_o$COOR$^{15}$; —(CH$_2$)$_o$OCNR$^{15}$R$^{16}$; —(CH$_2$)$_o$PO(OR$^1$)$_2$; —(CH$_2$)$_o$SO$_2$R$^{15}$; or —(CH$_2$)$_o$COR$^{15}$;

R$^{22}$ is an aryl group of the formula

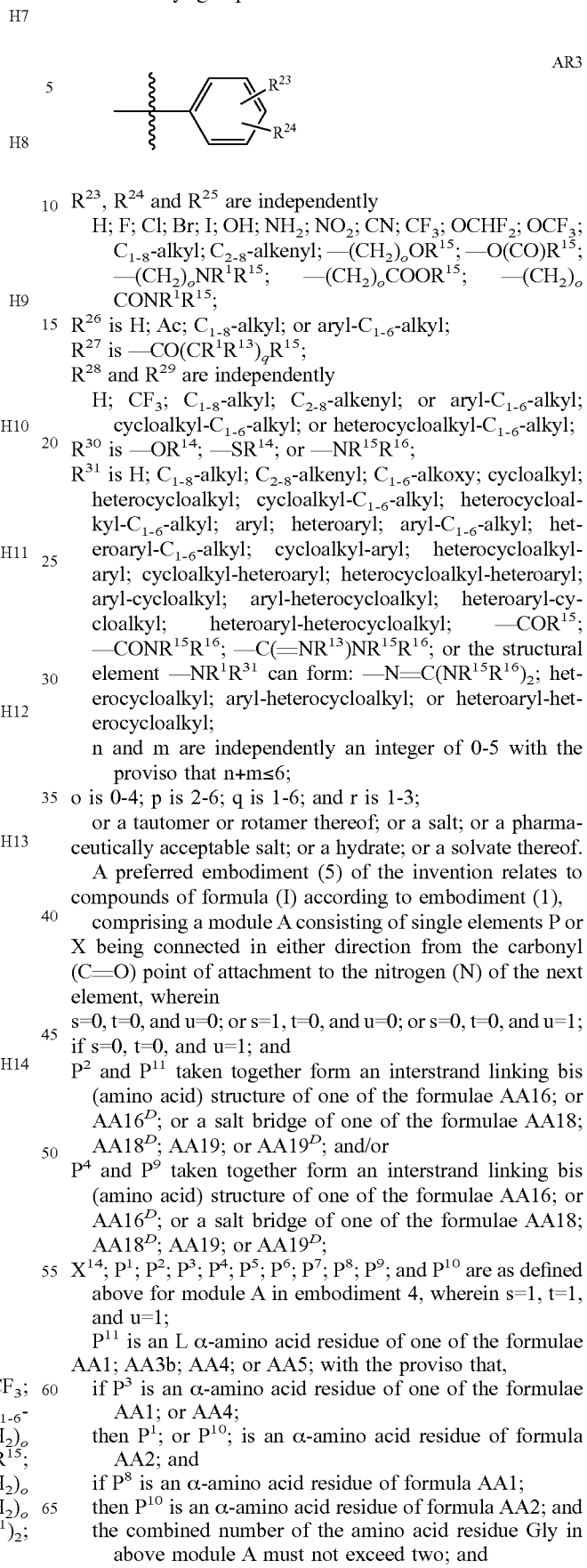

R$^{23}$, R$^{24}$ and R$^{25}$ are independently
H; F; Cl; Br; I; OH; NH$_2$; NO$_2$; CN; CF$_3$; OCHF$_2$; OCF$_3$; C$_{1-8}$-alkyl; C$_{2-8}$-alkenyl; —(CH$_2$)$_o$OR$^{15}$; —O(CO)R$^{15}$; —(CH$_2$)$_o$NR$^1$R$^{15}$; —(CH$_2$)$_o$COOR$^{15}$; —(CH$_2$)$_o$CONR$^1$R$^{15}$;

R$^{26}$ is H; Ac; C$_{1-8}$-alkyl; or aryl-C$_{1-6}$-alkyl;

R$^{27}$ is —CO(CR$^1$R$^{13}$)$_q$R$^{15}$;

R$^{28}$ and R$^{29}$ are independently
H; CF$_3$; C$_{1-8}$-alkyl; C$_{2-8}$-alkenyl; or aryl-C$_{1-6}$-alkyl; cycloalkyl-C$_{1-6}$-alkyl; or heterocycloalkyl-C$_{1-6}$-alkyl;

R$^{30}$ is —OR$^{14}$; —SR$^{14}$; or —NR$^{15}$R$^{16}$;

R$^{31}$ is H; C$_{1-8}$-alkyl; C$_{2-8}$-alkenyl; C$_{1-6}$-alkoxy; cycloalkyl; heterocycloalkyl; cycloalkyl-C$_{1-6}$-alkyl; heterocycloalkyl-C$_{1-6}$-alkyl; aryl; heteroaryl; aryl-C$_{1-6}$-alkyl; heteroaryl-C$_{1-6}$-alkyl; cycloalkyl-aryl; heterocycloalkyl-aryl; cycloalkyl-heteroaryl; heterocycloalkyl-heteroaryl; aryl-cycloalkyl; aryl-heterocycloalkyl; heteroaryl-cycloalkyl; heteroaryl-heterocycloalkyl; —COR$^{15}$; —CONR$^{15}$R$^{16}$; —C(=NR$^{13}$)NR$^{15}$R$^{16}$; or the structural element —NR$^1$R$^{31}$ can form: —N=C(NR$^{15}$R$^{16}$)$_2$; heterocycloalkyl; aryl-heterocycloalkyl; or heteroaryl-heterocycloalkyl;

n and m are independently an integer of 0-5 with the proviso that n+m≤6;

o is 0-4; p is 2-6; q is 1-6; and r is 1-3;

or a tautomer or rotamer thereof; or a salt; or a pharmaceutically acceptable salt; or a hydrate; or a solvate thereof.

A preferred embodiment (5) of the invention relates to compounds of formula (I) according to embodiment (1), comprising a module A consisting of single elements P or X being connected in either direction from the carbonyl (C=O) point of attachment to the nitrogen (N) of the next element, wherein s=0, t=0, and u=0; or s=1, t=0, and u=0; or s=0, t=0, and u=1; if s=0, t=0, and u=1; and P$^2$ and P$^{11}$ taken together form an interstrand linking bis(amino acid) structure of one of the formulae AA16; or AA16$^D$; or a salt bridge of one of the formulae AA18; AA18$^D$; AA19; or AA19$^D$; and/or P$^4$ and P$^9$ taken together form an interstrand linking bis(amino acid) structure of one of the formulae AA16; or AA16$^D$; or a salt bridge of one of the formulae AA18; AA18$^D$; AA19; or AA19$^D$;

X$^{14}$; P$^1$; P$^2$; P$^3$; P$^4$; P$^5$; P$^6$; P$^7$; P$^8$; P$^9$; and P$^{10}$ are as defined above for module A in embodiment 4, wherein s=1, t=1, and u=1;

P$^{11}$ is an L α-amino acid residue of one of the formulae AA1; AA3b; AA4; or AA5; with the proviso that, if P$^3$ is an α-amino acid residue of one of the formulae AA1; or AA4;

then P$^1$; or P$^{10}$; is an α-amino acid residue of formula AA2; and if P$^8$ is an α-amino acid residue of formula AA1;

then P$^{10}$ is an α-amino acid residue of formula AA2; and the combined number of the amino acid residue Gly in above module A must not exceed two; and the positions P of the amino acid residues Gly must not be in direct vicinity;

with the further proviso that, $P^{11}$ having a carbonyl (C=O) point of attachment not connected as aforementioned, being appropriately saturated by linkage with $R^{30}$ to form the corresponding naturally or non-naturally occurring terminal α-amino acid residue; optionally having a modified carbonyl (C=O) functional group;

$X^{14}$ having a nitrogen (N) not connected as aforementioned, being appropriately saturated by linkages with $R^1$, as already depicted above, and $R^{31}$ to form the corresponding naturally or non-naturally occurring terminal α-amino acid residue; optionally having a modified nitrogen (N) functional group;

with the further proviso that, if linker L, as defined below, is connected with module A by a carbonyl (C=O) point of attachment of $P^5$; $P^6$; or $P^7$; then $P^5$; $P^6$; or $P^7$; is an α-amino acid residue of one of the formulae AA20; or AA20$^D$;

if s=1, t=0, and u=0; and $P^1$ and $X^{12}$ taken together form an interstrand linking bis(amino acid) structure of one of the formulae AA16; or AA16$^D$; or an interstrand linking (amino acid)-(acid)-structure of one of the formulae AA17; or AA17$^D$; or a salt bridge of one of the formulae AA18; AA18$^D$; AA19; or AA19$^D$; and/or $P^2$ and $P^{11}$ taken together form an interstrand linking bis(amino acid) structure of one of the formulae AA16; or AA16$^D$; or a salt bridge of one of the formulae AA18; AA18$^D$; AA19; or AA19$^D$; and/or $P^4$ and $P^9$ taken together form an interstrand linking bis(amino acid) structure of one of the formulae AA16; or AA16$^D$; or a salt bridge of one of the formulae AA18; AA18$^D$; AA19; or AA19$^D$;

$P^1$ is pGlu; $^D$pGlu; Ac-pGlu; Ac-$^D$pGlu; or an α-amino acid residue of one of the formulae AA1; AA1$^D$; AA2; or AA4; or an L α-hydroxy acid residue of one of the formulae AA11; AA12; or AA14; or an acid residue of one of the formulae AA15a; or AA15b;

$P^2$; $P^3$; $P^4$; $P^5$; $P^6$; $P^7$; $P^8$; $P^9$; $P^{10}$; and $P^{11}$ are as defined above for module A in embodiment 4, wherein s=1, t=1, and u=1;

$X^{12}$ is Glyol; or an α-amino acid residue of one of the formulae AA1; AA2; AA3; AA4; AA4$^D$; or AA6; or an amino alcohol residue of one of the formulae AA7; AA8; AA9; or AA10;

with the proviso that, if $P^1$ is an α-amino acid residue of formula AA4;

then $X^{12}$ is an α-amino acid residue of formula AA1; AA4; or AA4$^D$; and if $P^3$ is an α-amino acid residue of one of the formulae AA1; or AA4;

then $P^1$; or $P^{10}$; is an α-amino acid residue of formula AA2; or $X^{12}$ is an α-amino acid residue of formula AA2; or an amino alcohol residue of formula AA8; and if $P^8$ is an α-amino acid residue of formula AA1;

then $P^{10}$ is an α-amino acid residue of formula AA2; and if $P^{10}$ is an α-amino acid residue of formula AA4;

then $X^{12}$ is an α-amino acid residue of formula AA1; and the combined number of the amino acid residue Gly in above module A must not exceed two; and the positions P of the amino acid residues Gly must not be in direct vicinity;

with the further proviso that, if $P^1$ and $X^{12}$ taken together form an interstrand linkage or salt bridge, as defined above; then $P^2$ and $P^{11}$ taken together are not forming an interstrand linkage or salt bridge, as defined above;

$X^{12}$ having a carbonyl (C=O) point of attachment not connected as aforementioned, being appropriately saturated by linkage with $R^{30}$ to form the corresponding naturally or non-naturally occurring terminal α-amino acid residue; optionally having a modified carbonyl (C=O) functional group;

$P^1$ having a nitrogen (N) not connected as aforementioned, being appropriately saturated by linkages with Fe, as already depicted above, and $R^{31}$ to form the corresponding naturally or non-naturally occurring terminal α-amino acid residue; optionally having a modified nitrogen (N) functional group;

with the further proviso that, if linker L, as defined below, is connected with module A by a carbonyl (C=O) point of attachment of $P^5$; $P^6$; or $P^7$; then $P^5$; $P^6$; or $P^7$; is an α-amino acid residue of one of the formulae AA20; or AA20$^D$;

if s=0, t=0, and u=0; and $P^2$ and $P^{11}$ taken together form an interstrand linking bis(amino acid) structure of one of the formulae AA16; or AA16$^D$; or a salt bridge of one of the formulae AA18; AA18$^D$; AA19; or AA19$^D$; and/or $P^4$ and $P^9$ taken together form an interstrand linking bis(amino acid) structure of one of the formulae AA16; or AA16$^D$; or a salt bridge of one of the formulae AA18; AA18$^D$; AA19; or AA19$^D$;

$P^1$ is pGlu; $^D$pGlu; Ac-pGlu; Ac-$^D$pGlu; or an α-amino acid residue of one of the formulae AA1; AA1$^D$; AA2; or AA4; or an L α-hydroxy acid residue of one of the formulae AA11; AA12; or AA14; or an acid residue of one of the formulae AA15a; or AA15b;

$P^2$; $P^3$; $P^4$; $P^5$; $P^6$; $P^7$; $P^8$; $P^9$; $P^{10}$ are as defined above for module A in embodiment 4, wherein s=1, t=1, and u=1;

$P^{11}$ is an L α-amino acid residue of one of the formulae AA1; AA3b; AA4; or AA5; with the proviso that, if $P^3$ is an α-amino acid residue of one of the formulae AA1; or AA4;

then $P^1$; or $P^{10}$; is an α-amino acid residue of formula AA2; and if $P^8$ is an α-amino acid residue of formula AA1;

then $P^{10}$ is an α-amino acid residue of formula AA2; and the combined number of the amino acid residue Gly in above module A must not exceed two; and the positions P of the amino acid residues Gly must not be in direct vicinity;

with the further proviso that, $P^{11}$ having a carbonyl (C=O) point of attachment not connected as aforementioned, being appropriately saturated by linkage with $R^{30}$ to form the corresponding naturally or non-naturally occurring terminal α-amino acid residue; optionally having a modified carbonyl (C=O) functional group;

$P^1$ having a nitrogen (N) not connected as aforementioned, being appropriately saturated by linkages with $R^1$, as already depicted above, and $R^{31}$ to form the corresponding naturally or non-naturally occurring terminal α-amino acid residue; optionally having a modified nitrogen (N) functional group;

with the further proviso that,
  if linker L, as defined below, is connected with module A by a carbonyl (C=O) point of attachment of $P^5$; $P^6$; or $P^7$; then
  $P^5$; $P^6$; or $P^7$; is an α-amino acid residue of one of the formulae AA20; or AA20$^D$;
if s=0, t=0, and u=0; and alternatively
$P^{11}$ is connected from the α-carbonyl point of attachment to the ω-nitrogen (N) of $P^2$;
$P^1$ is pGlu; or an α-amino acid residue of one of the formulae AA1; AA1$^D$; AA2; or AA4; or an L α-hydroxy acid residue of one of the formulae AA11; AA12; or AA14; or an acid residue of one of the formulae AA15a; or AA15b;
$P^2$ is an L α-amino acid residue of formula AA3b;
$P^3$; $P^4$; $P^5$; $P^6$; $P^7$; $P^8$; $P^9$; and $P^{10}$ are as defined above for module A in embodiment 4, wherein s=1, t=1, and u=1;
$P^{11}$ is an D α-amino acid residue of one of the formulae AA1$^D$; AA2$^D$; AA3b$^D$; AA4$^D$; AA5$^D$; or AA6$^D$;
with the proviso that,
  if $P^3$ is an α-amino acid residue of one of the formulae AA1; or AA4;
  then $P^1$; or $P^{10}$; is an α-amino acid residue of formula AA2; and
  if $P^8$ is an α-amino acid residue of formula AA1;
  then $P^{10}$ is an α-amino acid residue of formula AA2; and
  the combined number of the amino acid residue Gly in above module A must not exceed two; and
  the positions P of the amino acid residues Gly must not be in direct vicinity;
with the further proviso that,
  $P^1$ having a nitrogen (N) not connected as aforementioned, being appropriately saturated by linkages with $R^1$, as already depicted above, and $R^{31}$ to form the corresponding naturally or non-naturally occurring terminal α-amino acid residue; optionally having a modified nitrogen (N) functional group;
with the further proviso that,
  if linker L, as defined below, is connected with module A by a carbonyl (C=O) point of attachment of $P^5$; $P^6$; or $P^7$; then
  $P^5$; $P^6$; or $P^7$; is an α-amino acid residue of one of the formulae AA20; or AA20$^D$;
and a module B consisting of single elements Q being connected in either direction from the carbonyl (C=O) point of attachment to the nitrogen (N) of the next element with the proviso that $Q^7$ is connected from the α-carbonyl (C=O) point of attachment to the ω-nitrogen (N) of $Q^1$, and wherein
$Q^1$ is an α-amino acid residue of one of the formulae AA21; or AA21$^D$;
$Q^2$, $Q^5$, and $Q^6$ are independently an L α-amino acid residue of formula AA3b;
$Q^3$ is a D α-amino acid residue of one of the formulae AA1$^D$; or AA2$^D$;
$Q^4$ is an L α-amino acid residue of one of the formulae AA1; or AA4;
$Q^7$ is an L α-amino acid residue of one of the formulae AA1; or AA4;
and a linker L consisting of k=0-3 single elements L being connected in either direction from the carbonyl (C=O) point of attachment to the nitrogen (N) of the next element, and wherein,
if k=1,
$L^1$ is Gly; Sar; Aib; or an α-amino acid residue of one of the formulae AA3b; AA3b$^D$; AA4; AA4$^D$; AA1; or AA1$^D$, as depicted above;
if k=2, the additional element
$L^2$ is Gly; Sar; Aib; or an α-amino acid residue of one of the formulae AA3b; AA3b$^D$; AA4; AA4$^D$; AA1; or AA1$^D$, as depicted above;
if k=3, the additional element
$L^3$ is Gly; Sar; Aib; or an α-amino acid residue of one of the formulae AA3b; AA3b$^D$; AA4; AA4$^D$; AA1; or AA1$^D$, as depicted above;
said linker L being connected with module B from the carbonyl (C=O) point of attachment of $L^k$ to the α-nitrogen (N) of $Cl^1$ and,
if k=1-3, being connected with module A from the carbonyl (C=O) point of attachment of $P^5$; $P^6$; or $P^7$; to the nitrogen (N) of $L^1$; or,
if k=0, then
$Q^1$ being directly connected with module A from the carbonyl (C=O) point of attachment of $P^5$; $P^6$; or $P^7$; to the α-nitrogen (N) of $Q^1$;
$R^{Alk}$ is, with the proviso of containing less than 26 carbon- and/or heteroatoms, $C_{1-12}$-alkyl; $C_{2-12}$-alkenyl; cycloalkyl; cycloalkyl-$C_{1-6}$-alkyl; or $C_{1-6}$-alkoxy-$C_{1-6}$-alkyl;
$R^{Ar}$ is, with the proviso of containing less than 26 carbon- and/or heteroatoms, $-(CR^1R^4)_nR^{19}$; $-(CH_2)_nO(CH_2)_mR^{19}$; $-(CH_2)_nS(CH_2)_mR^{19}$; or $-(CH_2)_nNR^{14}(CH_2)_mR^{19}$;
$R^{Arn1}$ is, with the proviso of containing less than 26 carbon- and/or heteroatoms, $-(CR^1R^{13})_qNR^{15}R^{16}$; $-(CH_2)_qC(=NR^{13})NR^{15}R^{16}$; $-(CH_2)_qC(=NNR^{15}R^{16})NR^{17}R^{18}$; $-(CR^1R^{13})_qNR^2C(=NR^{17})NR^{15}R^{16}$; $-(CR^1R^{13})_qN=C(NR^{15}R^{16})NR^{17}R^{18}$; $-(CH_2)_nO(CH_2)_mNR^{15}R^{16}$; $-(CH_2)_nO(CH_2)_mC(=NR^{17})NR^{15}R^{16}$; $-(CH_2)_nO(CH_2)_mC(=NNR^{15}R^{16})NR^{17}R^{18}$; $-(CH_2)_nO(CH_2)_mNR^1C(=NR^{17})NR^{15}R^{16}$; $-(CH_2)_nO(CH_2)_mN=C(NR^{15}R^{16})NR^{17}R^{18}$; $-(CH_2)_nS(CH_2)_mNR^{15}R^{16}$; $-(CH_2)_nS(CH_2)_mC(=NR^{17})NR^{15}R^{16}$; $-(CH_2)_nS(CH_2)_mC(=NNR^{15}R^{16})NR^{17}R^{18}$; $-(CH_2)_nS(CH_2)_mNR^1C(=NR^{17})NR^{15}R^{16}$; $-(CH_2)_nS(CH_2)_mN=C(NR^{15}R^{16})NR^{17}R^{18}$; or $-(CR^1R^{13})_qNR^{14}R^{27}$;
$R^{Arn2}$ is, with the proviso of containing less than 26 carbon- and/or heteroatoms, $-(CR^1R^{13})_qNR^{15}R^{16}$; $-(CH_2)_nO(CH_2)_mNR^{15}R^{16}$; or $-(CH_2)_nS(CH_2)_mNR^{15}R^{16}$
$R^{Acid}$ is, with the proviso of containing less than 26 carbon- and/or heteroatoms, $-(CR^1R^{13})_qCOOH$; or $-(CR^1R^{13})_qPO(OH)_2$;
$R^{OH}$ is, with the proviso of containing less than 26 carbon- and/or heteroatoms, $-(CR^1R^{13})_qOH$; $-(CR^1R^{13})_qSH$; $-(CH_2)_nO(CH_2)_mOH$; $-(CH_2)_nS(CH_2)_mOH$; $-(CH_2)_nNR^1(CH_2)_mOH$; hydroxy-$C_{1-8}$-alkyl; hydroxy-$C_{2-8}$-alkenyl; hydroxy-cycloalkyl; or hydroxy-heterocycloalkyl;
$R^{Amide}$ is, with the proviso of containing less than 26 carbon- and/or heteroatoms, $-(CR^1R^{13})_qCONR^{15}R^{16}$;
Y is, with the proviso of containing less than 25 carbon- and/or heteroatoms, $-(CR^1R^{13})_q-$;
Z is, with the proviso of containing less than 25 carbon- and/or heteroatoms, $-(CH_2)_n-S-S-(CH_2)_m-$; $-(CR^{28}R^{29})_n-S-S-(CR^{28}R^{29})_m-$; $-(CH_2)_nCH=CH(CH_2)_m-$; $-(CR^{28}R^{29})_nCH=CH(CR^{28}R^{29})_m-$; $-(CH_2)_n$-heteroaryl-$(CH_2)_m-$; $-(CR^{28}R^{29})_n$-heteroaryl-$(CR^{28}R^{29})_m-$; $-(CH_2)_nCONR^1(CH_2)_m-$; $-(CH_2)_nNR^1CO(CH_2)_m-$; $-(CR^{28}R^{29})_nCONR^1(CR^{28}R^{29})_m-$; $-(CR^{28}R^{29})_nNR^1CO(CR^{28}R^{29})_m-$; $-(CH_2)_nNR^1CONR^2(CH_2)_m-$; or $-(CR^{28}R^{29})_nNR^1CONR^2(CR^{28}R^{29})_m-$;
$R^1$ and $R^2$ are independently H; $CF_3$; $C_{1-8}$-alkyl; or $C_{2-8}$-alkenyl;
$R^4$ is H; F; $CF_3$; $C_{1-8}$-alkyl; $C_{2-8}$-alkenyl; cycloalkyl; heterocycloalkyl; aryl; heteroaryl; aryl-$C_{1-6}$-alkyl; heteroaryl-$C_{1-6}$-alkyl; $-(CHR^{13})_oOR^{15}$; $-O(CO)R^{15}$;

—(CHR$^{13}$)$_o$SR$^{15}$; —(CHR$^{13}$)$_o$NR$^{15}$R$^{16}$; —(CHR$^{13}$)$_o$OCONR$^{15}$R$^{16}$; —(CHR$^{13}$)$_o$NR$^1$CONR$^{15}$R$^{16}$; —(CHR$^{13}$)$_o$ NR$^1$COR$^{15}$; —(CHR$^{13}$)$_o$COOR$^{15}$; —(CHR$^{13}$)$_o$CONR$^{15}$R$^{16}$; —(CHR$^{13}$)$_o$PO(OR$^1$)$_2$; —(CHR$^{13}$)$_o$SO$_2$R$^{15}$; —(CHR$^{13}$)$_o$NR$^1$SO$_2$R$^{15}$; —(CHR$^{13}$)$_o$SO$_2$NR$^{15}$R$^{16}$; —(CR$^1$R$^{13}$)$_o$R$^{19}$; or —(CHR$^1$)$_n$O(CHR$^2$)$_m$R$^{23}$; or

R$^{13}$ is H; F; CF$_3$; C$_{1-8}$-alkyl; C$_{2-8}$-alkenyl; cycloalkyl; heterocycloalkyl; cycloalkyl-C$_{1-6}$-alkyl; heterocycloalkyl-C$_{1-6}$-alkyl; aryl; heteroaryl; aryl-C$_{1-6}$-alkyl; heteroaryl-C$_{1-6}$-alkyl; —(CHR$^1$)$_o$OR$^{15}$; —OCOR$^1$; —(CHR$^1$)$_o$NR$^{15}$R$^{16}$; —CHR$^1$OR$^2$C(=NR$^{17}$)NR$^{15}$R$^{16}$; —(CHR$^1$OR$^2$CONR$^{15}$R$^{16}$; —COOR$^{15}$; —CONR$^{15}$R$^{16}$; or —SO$_2$R$^{15}$; or —SO$_2$NR$^{15}$R$^{16}$;

R$^{14}$ is H; CF$_3$; C$_{1-8}$-alkyl; C$_{2-8}$-alkenyl; cycloalkyl; heterocycloalkyl; cycloalkyl-C$_{1-6}$-alkyl; heterocycloalkyl-C$_{1-6}$-alkyl; aryl; heteroaryl; aryl-C$_{1-6}$-alkyl; heteroaryl-C$_{1-6}$-alkyl; cycloalkyl-aryl; heterocycloalkyl-aryl; cycloalkyl-heteroaryl; heterocycloalkyl-heteroaryl; aryl-cycloalkyl; aryl-heterocycloalkyl; heteroaryl-cycloalkyl; heteroaryl-heterocycloalkyl; —(CHR$^1$)$_o$OR$^{15}$; —(CHR$^1$)$_o$SR$^{15}$; —(CHR$^1$)$_o$NR$^{15}$R$^{16}$; —(CHR$^1$)$_o$COOR$^{15}$; —(CHR$^1$)$_o$CONR$^{15}$R$^{16}$; or —(CHR$^1$)$_o$SO$_2$R$^{15}$;

R$^{15}$, R$^{16}$, R$^{17}$ and R$^{18}$ are independently

H; C$_{1-8}$-alkyl; C$_{2-8}$-alkenyl; C$_{1-6}$-alkoxy; cycloalkyl; heterocycloalkyl; cycloalkyl-C$_{1-6}$-alkyl; heterocycloalkyl-C$_{1-6}$-alkyl; aryl; heteroaryl; aryl-C$_{1-6}$-alkyl; heteroaryl-C$_{1-6}$-alkyl; cycloalkyl-aryl; heterocycloalkyl-aryl; cycloalkyl-heteroaryl; heterocycloalkyl-heteroaryl; aryl-cycloalkyl; aryl-heterocycloalkyl; heteroaryl-cycloalkyl; or heteroaryl-heterocycloalkyl; or the structural elements —NR$^{15}$R$^{16}$ and —NR$^{17}$R$^{18}$ can independently form: heterocycloalkyl; aryl-heterocycloalkyl; or heteroaryl-heterocycloalkyl;

R$^{19}$ is an aryl group of one of the formulae

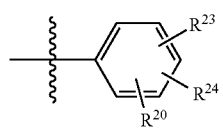

AR1

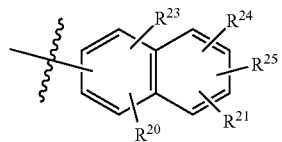

AR2 or a group of one of the formulae

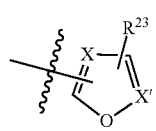

H1

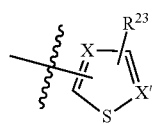

H2

-continued

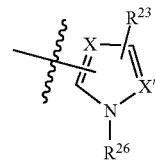

H3

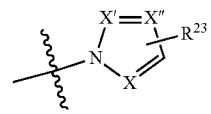

H4

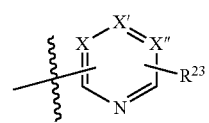

H5

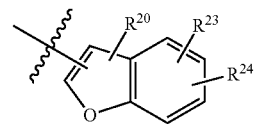

H6

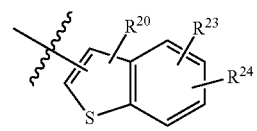

H7

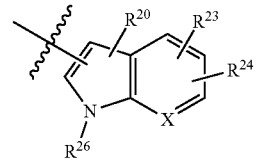

H8

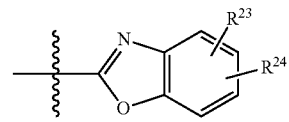

H9

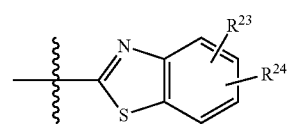

H10

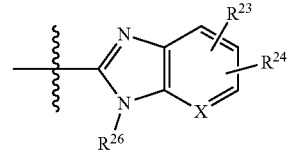

H11

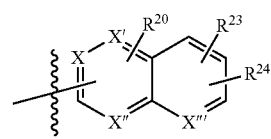

H12

-continued

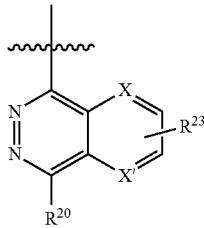
H13

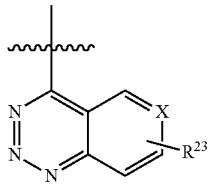
H14

X, X', X" and X'" are independently
—CR²⁰; or N;
R²⁰ and R²¹ are independently
H; F; Cl; Br; I; OH; NH₂; NO₂; CN; CF₃; OCHF₂; OCF₃; $C_{1-8}$-alkyl; $C_{2-8}$-alkenyl; aryl; heteroaryl; aryl-$C_{1-6}$-alkyl; heteroaryl-$C_{1-6}$-alkyl; —(CH₂)$_o$R²²; —(CH₂)$_o$OR¹⁵; —O(CO)R¹⁵; —O(CH₂)$_o$R²²; —(CH₂)$_o$SR¹⁵; —(CH₂)$_o$NR¹⁵R¹⁶; —(CH₂)$_o$OCONR¹⁵R¹⁶; —(CH₂)$_o$NR¹CONR¹⁵R¹⁶; —(CH₂)$_o$NR¹COR¹⁵; —(CH₂)$_o$COOR¹⁵; —(CH₂)$_o$CONR¹⁵R¹⁶; —(CH₂)$_o$PO(OR¹)₂; —(CH₂)$_o$SO₂R¹⁵; or —(CH₂)$_o$COR¹⁵;
R²² is an aryl group of the formula

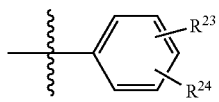
AR3

R²³, R²⁴ and R²⁵ are independently
H; F; Cl; Br; I; OH; NH₂; NO₂; CN; CF₃; OCHF₂; OCF₃; $C_{1-8}$-alkyl; $C_{2-8}$-alkenyl; —(CH₂)$_o$OR¹⁵; —O(CO)R¹⁵; —(CH₂)$_o$NR¹R¹⁵; —(CH₂)$_o$COOR¹⁵; —(CH₂)$_o$CONR¹R¹⁵; R²⁶ is H; Ac; $C_{1-8}$-alkyl; or aryl-$C_{1-6}$-alkyl;
R²⁷ is —CO(CR¹R¹³)$_q$R¹⁵;
R²⁸ and R²⁹ are independently
H; CF₃; $C_{1-8}$-alkyl; $C_{2-8}$-alkenyl; or aryl-$C_{1-6}$-alkyl; cycloalkyl-$C_{1-6}$-alkyl; or heterocycloalkyl-$C_{1-6}$-alkyl;
R³⁰ is —OR¹⁴; —SR¹⁴; or —NR¹⁵R¹⁶;
R³¹ is H; $C_{1-8}$-alkyl; $C_{2-8}$-alkenyl; $C_{1-6}$-alkoxy; cycloalkyl; heterocycloalkyl; cycloalkyl-$C_{1-6}$-alkyl; heterocycloalkyl-$C_{1-6}$-alkyl; aryl; heteroaryl; aryl-$C_{1-6}$-alkyl; heteroaryl-$C_{1-6}$-alkyl; cycloalkyl-aryl; heterocycloalkyl-aryl; cycloalkyl-heteroaryl; heterocycloalkyl-heteroaryl; aryl-cycloalkyl; aryl-heterocycloalkyl; heteroaryl-cycloalkyl; heteroaryl-heterocycloalkyl; —COR¹⁵; —CONR¹⁵R¹⁶; —C(=NR¹³)NR¹⁵R¹⁶; or the structural element —NR¹R³¹ can form: —N=C(NR¹⁵R¹⁶)₂; heterocycloalkyl; aryl-heterocycloalkyl; or heteroaryl-heterocycloalkyl;
n and m are independently an integer of 0-5 with the proviso that n+m≤6;
o is 0-4; p is 2-6; q is 1-6; and r is 1-3;
or a tautomer or rotamer thereof; or a salt; or a pharmaceutically acceptable salt; or a hydrate; or a solvate thereof.

A more preferred embodiment (6) of the invention relates to compounds of formula (I) according to embodiment (1), comprising a module A consisting of single elements P or X being connected in either direction from the carbonyl (C=O) point of attachment to the nitrogen (N) of the next element, wherein
s=1, t=0, and u=0;
P¹ and X¹² taken together form an interstrand linking bis (amino acid) structure of one of the formulae AA16; or AA16$^D$; or an interstrand linking (amino acid)-(acid)-structure of one of the formulae AA17; or AA17$^D$; or a salt bridge of one of the formulae AA18; AA18$^D$; AA19; or AA19$^D$; and/or
P² and P¹¹ taken together form an interstrand linking bis (amino acid) structure of one of the formulae AA16; or AA16$^D$; or a salt bridge of one of the formulae AA18; AA18$^D$; AA19; or AA19$^D$; and/or
P⁴ and P⁹ taken together form an interstrand linking bis (amino acid) structure of one of the formulae AA16; or AA16$^D$; or a salt bridge of one of the formulae AA18; AA18$^D$; AA19; or AA19$^D$;
P¹ is pGlu; $^D$pGlu; Ac-pGlu; Ac-$^D$pGlu; or an α-amino acid residue of one of the formulae AA1; AA1$^D$; AA2; or AA4; or an L α-hydroxy acid residue of one of the formulae AA11; AA12; or AA14; or an acid residue of one of the formulae AA15a; or AA15b;
P²; P³; P⁴; P⁵; P⁶; P⁷; P⁸; P⁹; P¹⁰; and P¹¹ are as defined above for module A in embodiment 4, wherein s=1, t=1, and u=1;
X¹² is Glyol; or an α-amino acid residue of one of the formulae AA1; AA2; AA3; AA4; AA4$^D$; or AA6; or an amino alcohol residue of one of the formulae AA7; AA8; AA9; or AA10;
with the proviso that,
if P¹ is an α-amino acid residue of formula AA4;
then X¹² is an α-amino acid residue of formula AA1; AA4; or AA4$^D$; and
if P³ is an α-amino acid residue of one of the formulae AA1; or AA4;
then P¹; or P¹⁰; is an α-amino acid residue of formula AA2; or X¹² is an α-amino acid residue of formula AA2; or an amino alcohol residue of formula AA8; and
if P⁸ is an α-amino acid residue of formula AA1;
then P¹⁰ is an α-amino acid residue of formula AA2; and
if P¹⁰ is an α-amino acid residue of formula AA4;
then X¹² is an α-amino acid residue of formula AA1; and
the combined number of the amino acid residue Gly in above module A must not exceed two; and
the positions P of the amino acid residues Gly must not be in direct vicinity;
with the further proviso that,
if P¹ and X¹² taken together form an interstrand linkage or salt bridge, as defined above; then P² and P¹¹ taken together are not forming an interstrand linkage or salt bridge, as defined above;
X¹² having a carbonyl (C=O) point of attachment not connected as aforementioned, being appropriately saturated by linkage with R³⁰ to form the corresponding naturally or non-naturally occurring terminal α-amino acid residue; optionally having a modified carbonyl (C=O) functional group;
P¹ having a nitrogen (N) not connected as aforementioned, being appropriately saturated by linkages with R¹, as already depicted above, and R³¹ to form the corresponding naturally or non-naturally occurring terminal α-amino acid residue; optionally having a modified nitrogen (N) functional group;

with the further proviso that,
if linker L, as defined below, is connected with module A by a carbonyl (C=O) point of attachment of $P^5$; $P^6$; or $P^7$; then
$P^5$; $P^6$; or $P^7$; is an α-amino acid residue of one of the formulae AA20; or AA20$^D$;
and a module B consisting of single elements Q being connected in either direction from the carbonyl (C=O) point of attachment to the nitrogen (N) of the next element with the proviso that $Q^7$ is connected from the α-carbonyl (C=O) point of attachment to the ω-nitrogen (N) of $Q^1$, and wherein
$Q^1$ is an α-amino acid residue of one of the formulae AA21; or AA21$^D$;
$Q^2$, $Q^5$, and $Q^6$ are independently an L α-amino acid residue of formula AA3b;
$Q^3$ is a D α-amino acid residue of one of the formulae AA1$^D$; or AA2$^D$;
$Q^4$ is an L α-amino acid residue of one of the formulae AA1; or AA4;
$Q^7$ is an L α-amino acid residue of one of the formulae AA1; or AA4;
and a linker L consisting of k=0-3 single elements L being connected in either direction from the carbonyl (C=O) point of attachment to the nitrogen (N) of the next element, and wherein,
if k=1,
$L^1$ is Gly; Sar; Aib; or an α-amino acid residue of one of the formulae
AA3b; AA3b$^D$; AA4; AA4$^D$; AA1; or AA1$^D$, as depicted above;
if k=2, the additional element
$L^2$ is Gly; Sar; Aib; or an α-amino acid residue of one of the formulae
AA3b; AA3b$^D$; AA4; AA4$^D$; AA1; or AA1$^D$, as depicted above;
if k=3, the additional element
$L^3$ is Gly; Sar; Aib; or an α-amino acid residue of one of the formulae
AA3b; AA3b$^D$; AA4; AA4$^D$; AA1; or AA1$^D$, as depicted above;
said linker L being connected with module B from the carbonyl (C=O) point of attachment of $L^k$ to the α-nitrogen (N) of Wand,
if k=1-3, being connected with module A from the carbonyl (C=O) point of attachment of $P^5$; $P^6$; or $P^7$; to the nitrogen (N) of 12; or,
if k=0, then
$Q^1$ being directly connected with module A from the carbonyl (C=O) point of attachment of $P^5$; $P^6$; or $P^7$; to the α-nitrogen (N) of $Q^1$;
$R^{Alk}$ is, with the proviso of containing less than 26 carbon- and/or heteroatoms, $C_{1-12}$-alkyl; $C_{2-12}$-alkenyl; cycloalkyl; cycloalkyl-$C_{1-6}$-alkyl; or $C_{1-6}$-alkoxy-$C_{1-6}$-alkyl;
$R^{Ar}$ is, with the proviso of containing less than 26 carbon- and/or heteroatoms, $-(CR^1R^4)_nR^{19}$; $-(CH_2)_nO(CH_2)_mR^{19}$; $-(CH_2)_nS(CH_2)_mR^{19}$; or $-(CH_2)_nNR^{14}(CH_2)_mR^{19}$;
$R^{Am1}$ is, with the proviso of containing less than 26 carbon- and/or heteroatoms, $-(CR^1R^{13})_qNR^{15}R^{16}$; $-(CH_2)_qC(=NR^{13})NR^{15}R^{16}$; $-(CH_2)_qC(=NNR^{15}R^{16})NR^{17}R^{18}$; $-(CR^1R^{13})_qNR^2C(=NR^{17})NR^{15}R^{16}$; $-(CR^1R^{13})_qN=C(NR^{15}R^{16})NR^{17}R^{18}$; $-(CH_2)_nO(CH_2)_mNR^{15}R^{16}$; $-(CH_2)_nO(CH_2)_mC(=NR^{17})NR^{15}R^{16}$; $-(CH_2)_nO(CH_2)_mC(=NNR^{15}R^{16})NR^{17}R^{18}$; $-(CH_2)_nO(CH_2)_mNR^1C(=NR^{17})NR^{15}R^{16}$; $-(CH_2)_nO(CH_2)_nN=C(NR^{15}R^{16})NR^{17}R^{18}$; $-(CH_2)_nS(CH_2)_nNR^{15}R^{16}$; $-(CH_2)_nS(CH_2)_mC(=NR^{17})NR^{15}R^{16}$; $-(CH_2)_nS(CH_2)_mC(=NNR^{15}R^{16})NR^{17}R^{18}$; $-(CH_2)_nS(CH_2)_nNR^1C(=NR^{17})NR^{15}R^{16}$; $-(CH_2)_nS(CH_2)_mN=C(NR^{15}R^{16})NR^{17}R^{18}$; or $-(CR^1R^{13})_qNR^{14}R^{27}$.

$R^{Am2}$ is, with the proviso of containing less than 26 carbon- and/or heteroatoms, $-(CR^1R^{13})_qNR^{15}R^{16}$; $-(CH_2)_nO(CH_2)_mNR^{15}R^{16}$; or $-(CH_2)_nS(CH_2)_mNR^{15}R^{16}$ $R^{Acid}$ is, with the proviso of containing less than 26 carbon- and/or heteroatoms, $-(CR^1R^{13})_qCOOH$; or $-(CR^1R^{13})_qPO(OH)_2$;

$R^{OH}$ is, with the proviso of containing less than 26 carbon- and/or heteroatoms, $-(CR^1R^{13})_qOH$; $-(CR^1R^{13})_qSH$; $-(CH_2)_nO(CH_2)_mOH$; $-(CH_2)_nS(CH_2)_mOH$; $-(CH_2)_nNR^1(CH_2)_mOH$; hydroxy-$C_{1-8}$-alkyl; hydroxy-$C_{2-8}$-alkenyl; hydroxy-cycloalkyl; or hydroxy-heterocycloalkyl;

$R^{Amide}$ is, with the proviso of containing less than 26 carbon- and/or heteroatoms, $-(CR^1R^{13})_qCONR^{15}R^{16}$;

Y is, with the proviso of containing less than 25 carbon- and/or heteroatoms, $-(CR^1R^{13})_q-$;

Z is, with the proviso of containing less than 25 carbon- and/or heteroatoms, $-(CH_2)_n-S-S-(CH_2)_m-$; $-(CR^{28}R^{29})_n-S-S-(CR^{28}R^{29})_m-$; $-(CH_2)_nCH=CH(CH_2)_m-$; $-(CR^{28}R^{29})_nCH=CH(CR^{28}R^{29})_m-$; $-(CH_2)_n$-heteroaryl-$(CH_2)_m-$; $-(CR^{28}R^{29})_n$-heteroaryl-$(CR^{28}R^{29})_m-$; $-(CH_2)_nCONR^1(CH_2)_m-$; $-(CH_2)_nNR^1CO(CH_2)_m-$; $-(CR^{28}R^{29})_nCONR^1(CR^{28}R^{29})_m-$; $-(CR^{28}R^{29})NR^1CO(CR^{28}R^{29})_m-$; $-(CH_2)_nNR^1CONR^2(CH_2)_m-$; or $-(CR^{28}R^{29})_nNR^1CONR^2(CR^{28}R^{29})_m-$;

$R^1$ and $R^2$ are independently
H; $CF_3$; $C_{1-8}$-alkyl; or $C_{2-8}$-alkenyl;

$R^4$ is H; F; $CF_3$; $C_{1-8}$-alkyl; $C_{2-8}$-alkenyl; cycloalkyl; heterocycloalkyl; aryl; heteroaryl; aryl-$C_{1-6}$-alkyl; heteroaryl-$C_{1-6}$-alkyl; $-(CHR^{13})_oOR^{15}$; $-O(CO)R^{15}$; $-(CHR^{13})_oSR^{15}$; $-(CHR^{13})_oNR^{15}R^{16}$; $-(CHR^{13})_oOCONR^{15}R^{16}$; $-(CHR^{13})_oNR^1CONR^{15}R^{16}$; $-(CHR^{13})_oNR^1COR^{15}$; $-(CHR^{13})_oCOOR^{15}$; $-(CHR^{13})_oCONR^{15}R^{16}$; $-(CHR^{13})_oPO(OR^1)_2$; $-(CHR^{13})_oSO_2R^{15}$; $-(CHR^{13})_oNR^1SO_2R^{15}$; $-(CHR^{13})_oSO_2NR^{15}R^{16}$; $-(CR^1R^{13})_oR^{19}$; or $-(CHR^1)_nO(CHR^2)_mR^{23}$; or $R^{13}$ is H; F; $CF_3$; $C_{1-8}$-alkyl; $C_{2-8}$-alkenyl; cycloalkyl; heterocycloalkyl; cycloalkyl-$C_{1-6}$-alkyl; heterocycloalkyl-$C_{1-6}$-alkyl; aryl; heteroaryl; aryl-$C_{1-6}$-alkyl; heteroaryl-$C_{1-6}$-alkyl; $-(CHR^1)_oOR^{15}$; $-OCOR^1$; $-(CHR^1)_oNR^{15}R^{16}$; $CHR^1OR^2C(=NR^{17})NR^{15}R^{16}$; $-(CHR^1OR^2CONR^{15}R^{16}$; $-COOR^{15}$; $-CONR^{15}R^{16}$; or $-SO_2R^{15}$; or $-SO_2NR^{15}R^{16}$;

$R^{14}$ is H; $CF_3$; $C_{1-8}$-alkyl; $C_{2-8}$-alkenyl; cycloalkyl; heterocycloalkyl; cycloalkyl-$C_{1-6}$-alkyl; heterocycloalkyl-$C_{1-6}$-alkyl; aryl; heteroaryl; aryl-$C_{1-6}$-alkyl; heteroaryl-$C_{1-6}$-alkyl; cycloalkyl-aryl; heterocycloalkyl-aryl; cycloalkyl-heteroaryl; heterocycloalkyl-heteroaryl; aryl-cycloalkyl; aryl-heterocycloalkyl; heteroaryl-cycloalkyl; heteroaryl-heterocycloalkyl; $-(CHR^1)_oOR^{15}$; $-(CHR^1)_oSR^{15}$; $-(CHR^1)_oNR^{15}R^{16}$; $-(CHR^1)_oCOOR^{15}$; $-(CHR^1)_oCONR^{15}R^{16}$; or $-(CHR^1)_oSO_2R^{15}$;

$R^{15}$, $R^{16}$, $R^{17}$ and $R^{18}$ are independently
H; $C_{1-8}$-alkyl; $C_{2-8}$-alkenyl; $C_{1-6}$-alkoxy; cycloalkyl; heterocycloalkyl; cycloalkyl-$C_{1-6}$-alkyl; heterocycloalkyl-$C_{1-6}$-alkyl; aryl; heteroaryl; aryl-$C_{1-6}$-alkyl; heteroaryl-$C_{1-6}$-alkyl; cycloalkyl-aryl; heterocycloalkyl-aryl; cycloalkyl-heteroaryl; heterocycloalkyl-heteroaryl; aryl-cycloalkyl; aryl-heterocycloalkyl; heteroaryl-cycloalkyl; or heteroaryl-heterocycloalkyl; or the structural elements $-NR^{15}R^{16}$ and $-NR^{17}R^{18}$ can independently form: heterocycloalkyl; aryl-heterocycloalkyl; or heteroaryl-heterocycloalkyl;

$R^{19}$ is an aryl group of one of the formulae

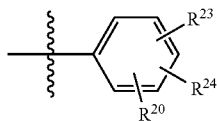
AR1

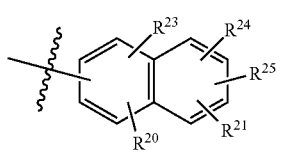
AR2 or a group of one of the formulae

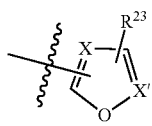
H1

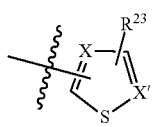
H2

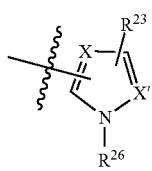
H3

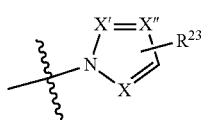
H4

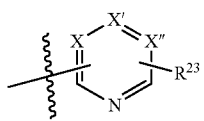
H5

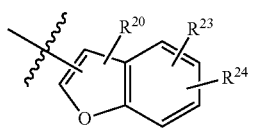
H6

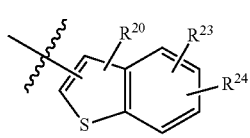
H7

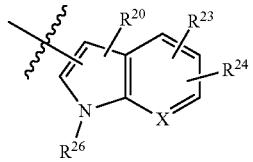
H8

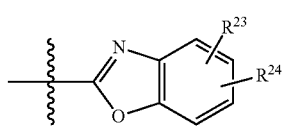
H9

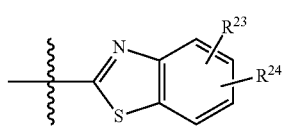
H10

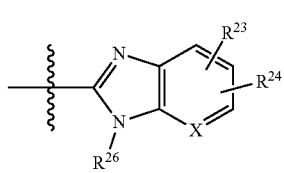
H11

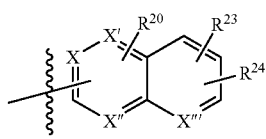
H12

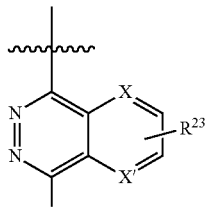
H13

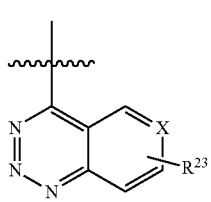
H14

X, X', X" and X'" are independently
  —$CR^{20}$; or N;

$R^{20}$ and $R^{21}$ are independently

H; F; Cl; Br; I; OH; $NH_2$; $NO_2$; CN; $CF_3$; $OCHF_2$; $OCF_3$; $C_{1-8}$-alkyl; $C_{2-8}$-alkenyl; aryl; heteroaryl; aryl-$C_{1-6}$-alkyl; heteroaryl-$C_{1-6}$-alkyl; —$(CH_2)_oR^{22}$; —$(CH_2)_oOR^{15}$; —$O(CO)R^{15}$; —$O(CH_2)_oR^{22}$; —$(CH_2)_oSR^{15}$; —$(CH_2)_oNR^{15}R^{16}$; —$(CH_2)_oOCONR^{15}R^{16}$; —$(CH_2)_oNR^1CONR^{15}R^{16}$; —$(CH_2)_oNR^1COR^{15}$; —$(CH_2)_oCOOR^{15}$; —$(CH_2)_oCONR^{15}R^{16}$; —$(CH_2)_oPO(OR^1)_2$; —$(CH_2)_oSO_2R^{15}$; or —$(CH_2)_oCOR^{15}$;

$R^{22}$ is an aryl group of the formula

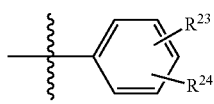

AR3

$R^{23}$, $R^{24}$ and $R^{25}$ are independently
H; F; Cl; Br; I; OH; $NH_2$; $NO_2$; CN; $CF_3$; $OCHF_2$; $OCF_3$; $C_{1-8}$-alkyl; $C_{2-8}$-alkenyl; —$(CH_2)_oOR^{15}$; —$O(CO)R^{15}$; —$(CH_2)_oNR^1R^{15}$; —$(CH_2)_oCOOR^{15}$; —$(CH_2)_oCONR^1R^{15}$;
$R^{26}$ is H; Ac; $C_{1-8}$-alkyl; or aryl-$C_{1-6}$-alkyl;
$R^{27}$ is —$CO(CR^1R^{13})_qR^{15}$;
$R^{28}$ and $R^{29}$ are independently
H; $CF_3$; $C_{1-8}$-alkyl; $C_{2-8}$-alkenyl; or aryl-$C_{1-6}$-alkyl; cycloalkyl-$C_{1-6}$-alkyl; or heterocycloalkyl-$C_{1-6}$-alkyl;
$R^{30}$ is —$OR^{14}$; —$SR^{14}$; or —$NR^{15}R^{16}$;
$R^{31}$ is H; $C_{1-8}$-alkyl; $C_{2-8}$-alkenyl; $C_{1-6}$-alkoxy; cycloalkyl; heterocycloalkyl; cycloalkyl-$C_{1-6}$-alkyl; heterocycloalkyl-$C_{1-6}$-alkyl; aryl; heteroaryl; aryl-$C_{1-6}$-alkyl; heteroaryl-$C_{1-6}$-alkyl; cycloalkyl-aryl; heterocycloalkyl-aryl; cycloalkyl-heteroaryl; heterocycloalkyl-heteroaryl; aryl-cycloalkyl; aryl-heterocycloalkyl; heteroaryl-cycloalkyl; heteroaryl-heterocycloalkyl; —$COR^{15}$; —$CONR^{15}R^{16}$; —$C(=NR^{13})NR^{15}R^{16}$; or the structural element —$NR^1R^{31}$ can form: —$N=C(NR^{15}R^{16})_2$; heterocycloalkyl; aryl-heterocycloalkyl; or heteroaryl-heterocycloalkyl;
n and m are independently an integer of 0-5 with the proviso that n+m≤6;
o is 0-4; p is 2-6; q is 1-6; and r is 1-3;
or a tautomer or rotamer thereof; or a salt; or a pharmaceutically acceptable salt; or a hydrate; or a solvate thereof.

Each single group "$R^x$" with the same index-number x for x=1-31 is independently selected on each occurrence in a specific formula and, therefore, they can be the same or different.

As used in this description, the term "alkyl", taken alone or in combinations (i.e. as part of another group, such as "aryl-$C_{1-6}$-alkyl") designates saturated, straight-chain or branched hydrocarbon radicals and may be optionally substituted. The term "$C_{x-y}$-alkyl" (x and y each being an integer) refers to an alkyl group as defined before containing x to y carbon atoms. For example a $C_{1-6}$-alkyl group contains one to six carbon atoms. Representative examples of alkyl groups include methyl, ethyl, n-propyl, iso-propyl, n-butyl, iso-butyl, sec-butyl, tert-butyl, n-pentyl, n-hexyl and the like.

The term "alkenyl", taken alone or in combinations, designates straight chain or branched hydrocarbon radicals containing at least one or, depending on the chain length, up to four olefinic double bonds. Such alkenyl moieties are optionally substituted and can independently exist as E or Z configurations per double bond, which are all part of the invention. The term "$C_{x-y}$-alkenyl" (x and y each being an integer) refers to an alkenyl group as defined before containing x to y carbon atoms.

The term "cycloalkyl", taken alone or in combinations, refers to a saturated or partially unsaturated alicyclic moiety having from three to ten carbon atoms and may be optionally substituted. Examples of this moiety include, but are not limited to, cyclohexyl, norbornyl, decalinyl and the like.

The term "heterocycloalkyl", taken alone or in combinations, describes a saturated or partially unsaturated mono- or bicyclic moiety having from three to nine ring carbon atoms and one or more ring heteroatoms selected from nitrogen, oxygen or sulphur. This term includes, for example, morpholino, piperazino, azetidinyl, pyrrolidinyl, tetrahydrofuranyl, piperidinyl, octahydro-1H-indolyl, 1,7-diazaspiro[4.4] nonyl and the like. Said heterocycloalkyl ring(s) might be optionally substituted.

The term "aryl", taken alone or in combinations, designates aromatic carbocyclic hydrocarbon radicals containing one or two six-membered rings, such as phenyl or naphthyl, which may be optionally substituted by up to three substituents such as Br, Cl, F, $CF_3$, OH, $OCF_3$, $OCHF_2$, $NH_2$, $N(CH_3)_2$, $NO_2$, CN, $C_{1-6}$-alkyl, $C_{2-6}$-alkenyl, phenyl or phenoxy.

The term "heteroaryl", taken alone or in combinations, designates aromatic heterocyclic radicals containing one or two five- and/or six-membered rings, at least one of them containing up to three heteroatoms selected from the group consisting of O, S and N and whereby the heteroaryl radicals or tautomeric forms thereof may be attached via any suitable atom. Said heteroaryl ring(s) are optionally substituted, e.g. as indicated above for "aryl".

The term "aryl-$C_{x-y}$-alkyl", as used herein, refers to an $C_{x-y}$-alkyl group as defined above, substituted by an aryl group, as defined above. Representative examples of aryl-$C_{x-y}$-alkyl moieties include, but are not limited to, benzyl, 1-phenylethyl, 2-phenylethyl, 3-phenylpropyl, 2-phenylpropyl and the like.

The term "heteroaryl-$C_{x-y}$-alkyl", as used herein, refers to an $C_{x-y}$-alkyl group as defined above, substituted by a heteroaryl group, as defined above. Examples of heteroaryl-$C_{x-y}$-alkyl groups include pyridin-3-ylmethyl, (1H-pyrrol-2-yl)ethyl and the like.

The term "aryl-cycloalkyl", as used herein, refers to a cycloalkyl group as defined above, substituted or annelated by an aryl group, as defined above. Examples of aryl-cycloalkyl moieties include, but are not limited to, phenyl-cyclopentyl, 2,3-dihydro-1H-indenyl, 1,2,3,4-tetrahydronaphthalenyl and the like.

The term "aryl-heterocycloalkyl", as used herein, refers to a heterocycloalkyl group as defined above, substituted or annelated by an aryl group, as defined above. Examples of aryl-heterocycloalkyl moieties include, but are not limited to, indolinyl, 1,2,3,4-tetrahydroquinolinyl and the like.

The term "heteroaryl-cycloalkyl", as used herein, refers to a cycloalkyl group as defined above, substituted or annelated by a heteroaryl group, as defined above. Examples of heteroaryl-cycloalkyl moieties include, but are not limited to, 5,6,7,8-tetrahydroquinolinyl and the like.

The term "heteroaryl-heterocycloalkyl", as used herein, refers to a heterocycloalkyl group as defined above, substituted or annelated by a heteroaryl group, as defined above. Examples of heteroaryl-heterocycloalkyl moieties include, but are not limited to, 4-(thiazol-2-yl)piperazinyl, 5,6,7,8-tetrahydro-1,6-naphthyridinyl and the like.

The terms "cycloalkyl-aryl", "heterocycloalkyl-aryl", "cycloalkyl-heteroaryl", and "heterocycloalkyl-heteroaryl", as used herein, are defined analogously to the terms "aryl-cycloalkyl", "aryl-heterocycloalkyl", "heteroaryl-cycloalkyl" and "heteroaryl-heterocycloalkyl", as defined above, but connected in the opposite direction, e.g. instead of 4-(thiazol-2-yl)piperazinyl the term refers to 2-(piperazin-1-yl)thiazolyl and the like.

The terms "hydroxy", "alkoxy" and "aryloxy", taken alone or in combinations, refer to the groups of —OH, —O-alkyl and —O-aryl respectively, wherein an alkyl group or an aryl group is as defined above. The term "$C_{x-y}$-alkoxy" (x and y each being an integer) refers to an —O-alkyl group as defined before containing x to y carbon atoms attached to an oxygen atom. Representative examples of alkoxy groups include methoxy, ethoxy, n-propoxy, isopropoxy, n-butoxy, tert-butoxy and the like. Examples of aryloxy include e.g. phenoxy. For avoidance of doubt e.g. the term "hydroxy-$C_{1-8}$-alkyl" represents, among others, groups like e.g. hydroxymethyl, 1-hydroxypropyl, 2-hydroxypropyl or 3-hydroxy-2,3-dimethylbutyl.

The term "optionally substituted" is in intended to mean that a group, such as, but not limited to $C_{x-y}$-alkyl, $C_{x-y}$-alkenyl, cycloalkyl, aryl, heteroaryl, heterocycloalkyl, $C_{x-y}$-alkoxy and aryloxy may be substituted with one or more substituents independently selected from amino (—$NH_2$), dimethylamino, nitro (—$NO_2$), halogen (F, Cl, Br, I), $CF_3$, cyano (—CN), hydroxy, methoxy, ethoxy, phenyloxy, benzyloxy, acetoxy, oxo (=O), carboxy, carboxamido, methyl, ethyl, phenyl, benzyl, sulfonic acid, sulfate, phosphonic acid, phosphate, or phosphonate.

In the context of this invention the term "naturally or non-naturally occurring α-amino acid" typically comprises any natural α-amino acid, such as the proteogenic amino acids (examples listed below), their natural or semi-synthetic derivatives as well as α-amino acids of purely synthetic origin. This term includes as well α-amino acids which are optionally substituted at the α-nitrogen of the amino acid such as, but not limited to, acetylation or alkylation, e.g. methylation, or benzylation. The term "amino alcohol" typically comprises any 1,2-amino alcohol, such as those derived from proteogenic amino acids by transformation of the α-carboxylic function to the corresponding alcohol function. The term "ahydroxy acid" typically comprises any 2-hydroxy acid, such as those derived from proteinogenic amino acids by transformation of the α-amino function the corresponding alcohol function. The term "acid" typically comprises organic acids, optionally substituted to form a "non-naturally cross-linking acid", as defined herein below.

It has to be noted that the above mentioned possible transformations of α-amino acids to e.g. amino alcohols or ahydroxy acids do not comprise modifications of the side chains of the underlying α-amino acids. Therefore, certain physico-chemical properties e.g. the physico-chemical properties caused by or assigned to the side chains are shared among structurally related α-amino acids and 1,2-amino alcohols, α-hydroxy acids and acids, respectively. Examples for such a structural relationship are the α-amino acid Thr and the 1,2-amino alcohol Throl sharing the same side-chain 2-hydroxyethyl or the α-amino acid Val, the α-hydroxy acid HOVal and the acid 3-methyl-butanoic acid having the same side-chain 2-methylethyl in common.

The term "aliphatic α-amino acid" refers to α-amino acids with an aliphatic side-chain, such as, but not limited to, alanine, valine, leucine, isoleucine, n-octylglycine etc.

The term "aromatic α-amino acid" refer to α-amino acids with a side-chain comprising an aromatic or heteroaromatic group, such as, but not limited to, phenylalanine, tryptophan, histidine, O-methyl-tyrosine, 4-trifluormethyl-phenylalanine, 3,4-dichloro-homophenylalanine etc.

The term "basic α-amino acid" refers to α-amino acids with a side-chain comprising at least one amino group, such as, but not limited to, lysine, ornithine etc. and further substituted derivatives thereof. The aforesaid amino group can be substituted by amidino groups to form α-amino acids, such as, but not limited to, arginine, homoarginine etc. and further substituted derivatives thereof, or by diamino methylidine groups.

The term "alcoholic α-amino acid" refers to α-amino acids with a side-chain comprising an alcoholic or thioalcoholic group, i.e. a hydroxy or sulfhydryl function, such as, but not limited to, serine, threonine etc.

The term "α-amino acids with a side-chain comprising at least one carboxylic acid function or phosphonic acid function" encompasses, but is not limited to, aspartic acid, glutamic acid, etc.

The term "α-amino acids with a side-chain comprising at least one amide function" encompasses, but is not limited to, asparagine, glutamine etc.

The term "cross-linking α-amino acid" refers to α-amino acids with a side-chain comprising a function able to cross-link to a second α-amino acid by a covalent bond, such as, but not limited to, cysteine, homocysteine etc.

The term "non-naturally cross-linking acid" refers to an organic acid with a side-chain comprising a function able to cross-link to an α-amino acid by a covalent bond, such as, but not limited to, 3-mercapto-propanoic acid etc.

For the avoidance of doubt the term "single side-chain" in the context of an α-amino acid refers to a structure where the α-carbon of the amino acid is covalently connected to the (in-chain) groups of the carbonyl (C=O) and nitrogen (N) as well as to one hydrogen (H) and one variable side-chain, e.g. as defined above.

The term "single side-chain" in the context of a 1,2-amino alcohol refers to a structure where the β-carbon of the amino alcohol is covalently connected to the group of hydroxymethyl ($CH_2OH$) and the (in-chain) group of nitrogen (N) as well as to one hydrogen (H) and one variable side-chain, e.g. as defined above.

The term "single side-chain" in the context of an α-hydroxy acid refers to a structure where the α-carbon of the hydroxy acid is covalently connected to the group of hydroxyl (OH) and the (in-chain) group of the carbonyl (C=O) as well as to one hydrogen (H) and one variable side-chain, e.g. as defined above.

For the avoidance of doubt the term "heteroatom" refers to any atom that is not carbon or hydrogen.

The descriptors L respectively D refer to the stereochemistry at the α-position of an α-amino acid and an α-hydroxy acid, and to the stereochemistry at the β-position of a 1,2-amino alcohol and are used according the Fischer-Rosanoff convention of the IUPAC.

The peptidomimetics of the present invention can also be diastereomers (e.g. epimers) of compounds of formula (I) if no specific stereochemistry of the chiral center is determined in the description. These stereoisomers can be prepared by a modification of the process described below in which the appropriate isomers (e.g. epimers/enantiomers) of chiral starting materials are used. In case of ambiguous stereochemistry in the above description each single epimer is part of the present invention as well as a mixture of both.

A further embodiment of the present invention may also include compounds, which are identical to the compounds of formula (I), except that one or more atoms are replaced by an atom having an atomic mass number or mass different from the atomic mass number or mass usually found in nature, e.g. compounds enriched in $^2H$ (D), $^3H$, $^{11}C$, $^{14}C$, $^{127}I$ etc. These isotopic analogs and their pharmaceutical salts and formulations are considered useful agents in the therapy and/or diagnostic, for example, but not limited to, where a fine-tuning of in vivo half-life time could lead to an optimized dosage regimen.

In a particular embodiment (7) of the invention the elements of formula (I) are defined as follows,
for module A,
s=1, t=1, and u=1; and $X^{14}$ and $X^{13}$ taken together form an interstrand linking bis(amino acid)-structure of formula AA16; with Z being, with the proviso of containing less than 25 carbon- and/or heteroatoms, $-(CR^{28}R^{29})_n-S-S-(CR^{28}R^{29})_m-$; or $-(CR^{28}R^{29})_n NR^1 CO(CR^{28}R^{29})_m-$;

or an interstrand linking (amino acid)-(acid)-structure of formula AA17; with Z being, with the proviso of containing less than 25 carbon- and/or heteroatoms, $-(CR^{28}R^{29})_n-S-S-(CR^{28}R^{29})_m-$; or a salt bridge of one of the formulae AA18; or AA19; and/or $P^2$ and $P^{11}$ taken together form an interstrand linking bis(amino acid)-structure of formula AA16; with Z being, with the proviso of containing less than 25 carbon- and/or heteroatoms, $-(CR^{28}R^{29})_n-S-S-(CR^{28}R^{29})_m-$; or a salt bridge of one of formula AA18;

$X^{14}$ is pGlu; $^D$pGlu; or a D α-amino acid residue of formula AA4$^D$;

$P^1$ is an L α-amino acid residue of one of the formulae AA1; or AA4;

$P^2$ is an L α-amino acid residue of formula AA4;

$P^3$ is an L α-amino acid residue of formula AA2;

$P^4$ is Gly; or an L α-amino acid residue of one of the formulae AA3b; or AA4;

$P^6$ is Gly; or a D α-amino acid residue of one of the formulae AA1$^D$; AA4$^D$; or AA3b$^D$;

$P^7$ is Gly; or an L α-amino acid residue of one of the formulae AA1; AA3b; or AA4;

$P^8$ is an L α-amino acid residue of formula AA2;

$P^9$ is Gly; or an L α-amino acid residue of one of the formulae AA1; AA4; or AA5;

$P^{10}$ is an L α-amino acid residue of formula AA1;

$P^{11}$ is an L α-amino acid residue of one of the formulae AA1; or AA4;

$X^{12}$ is an L α-amino acid residue of one of the formulae AA1; or AA4;

$X^{13}$ is a D α-amino acid residue of one of the formulae AA1$^D$; or AA4$^D$;

with the proviso that,
if $P^1$ is an α-amino acid residue of formula AA4;
then $X^{12}$ is an α-amino acid residue of formula AA1; and
the combined number of the amino acid residue Gly in above module A must not exceed two; and
the positions P of the amino acid residues Gly must not be in direct vicinity;

with the further proviso that,
$X^{13}$ having a carbonyl (C=O) point of attachment not connected as aforementioned, being appropriately saturated by linkage with $R^{30}$ to form the corresponding naturally or non-naturally occurring terminal α-amino acid residue; optionally having a modified carbonyl (C=O) functional group;
$X^{14}$ having a nitrogen (N) not connected as aforementioned, being appropriately saturated by linkages with Fe, as already depicted above, and
$R^{31}$ to form the corresponding naturally or non-naturally occurring terminal α-amino acid residue; optionally having a modified nitrogen (N) functional group;

with the further proviso that,
if linker L, as defined below, is connected with module A by a carbonyl (C=O) point of attachment of $P^5$; then $P^5$ is Glu;

for module B consisting of single elements Q being connected in either direction from the carbonyl (C=O) point of attachment to the nitrogen (N) of the next element with the proviso that $Q^7$ is connected from the α-carbonyl (C=O) point of attachment to the ω-nitrogen (N) of $Q^1$, $Q^1$ is an L α-amino acid residue of formula AA21;

$Q^2$, $Q^5$, and $Q^6$ are independently an L α-amino acid residue of formula AA3b;

$Q^3$ is a D α-amino acid residue of one of the formulae AA1$^D$; or AA2$^D$;

$Q^4$ is an L α-amino acid residue of one of the formulae AA1; or AA4;

$Q^7$ is an L α-amino acid residue of one of the formulae AA1; or AA4;

for a linker L consisting of k=1 or 3 single elements L being connected in either direction from the carbonyl (C=O) point of attachment to the nitrogen (N) of the next element,
if k=1,
$L^1$ is an α-amino acid residue of one of the formulae AA3b; or AA3b$^D$;
if k=3,
$L^1$ is an α-amino acid residue of one of the formulae AA3b; or AA3b$^D$;
$L^2$ is an α-amino acid residue of one of the formulae AA4; or AA4$^D$;
$L^3$ is an α-amino acid residue of one of the formulae AA3b; or AA3b$^D$;

said linker L being connected with module B from the carbonyl (C=O) point of attachment of $L^k$ to the α-nitrogen (N) of $Q^1$ and,
if k=1 or 3, being connected with module A from the carbonyl (C=O) point of attachment of $P^5$; $P^6$; or $P^7$; to the nitrogen (N) of $L^1$;
or a pharmaceutically acceptable salt thereof.

In another particular embodiment (8) of the invention the elements of formula (I) are defined as follows,
for module A,
s=1, t=0, and u=1; and $P^2$ and $P^{11}$ taken together form an interstrand linking bis(amino acid)-structure of formula AA16; with Z being, with the proviso of containing less than 25 carbon- and/or heteroatoms, $-(CR^{28}R^{29})_n-S-S-(CR^{28}R^{29})_m-$; and/or $P^4$ and $P^9$ taken together form an interstrand linking bis(amino acid)-structure of formula AA16; with Z being, with the proviso of containing less than 25 carbon- and/or heteroatoms, $-(CR^{28}R^{29})_n-S-S-(CR^{28}R^{29})_m-$;

$X^{14}$ is pGlu; $^D$pGlu; or an L α-amino acid residue of formula AA3b; or an acid residue of one of the formulae AA15a; or AA15b;

$P^1$ is an L α-amino acid residue of one of the formulae AA1; or AA4;

$P^2$ is an L α-amino acid residue of formula AA4;

$P^3$ is an L α-amino acid residue of formula AA2;

$P^4$ is Gly; or an L α-amino acid residue of one of the formulae AA3b; or AA4;

$P^6$ is Gly; or a D α-amino acid residue of one of the formulae AA1$^D$; AA4$^D$; or AA3b$^D$;

$P^7$ is Gly; or an L α-amino acid residue of one of the formulae AA1; AA3b; or AA4;

$P^8$ is an L α-amino acid residue of formula AA2;

$P^9$ is Gly; or an L α-amino acid residue of one of the formulae AA1; or AA4;

$P^{10}$ is an L α-amino acid residue of formula AA1;

$P^{11}$ is an L α-amino acid residue of formula AA1;

$X^{12}$ is Glyol; or an L α-amino acid residue of one of the formulae AA1; or AA4; or an amino alcohol residue of formula AA10;

with the proviso that,
if $P^1$ is an α-amino acid residue of formula AA4;
then $X^{12}$ is an α-amino acid residue of formula AA1; and
the combined number of the amino acid residue Gly in above module A must not exceed two; and the positions P of the amino acid residues Gly must not be in direct vicinity;
with the further proviso that,
  $X^{13}$ having a carbonyl (C=O) point of attachment not connected as aforementioned, being appropriately saturated by linkage with $R^{30}$ to form the corresponding naturally or non-naturally occurring terminal α-amino acid residue; optionally having a modified carbonyl (C=O) functional group;
  $X^{14}$ having a nitrogen (N) not connected as aforementioned, being appropriately saturated by linkages with $R^1$, as already depicted above, and $R^{31}$ to form the corresponding naturally or non-naturally occurring terminal α-amino acid residue; optionally having a modified nitrogen (N) functional group;
with the further proviso that,
  if linker L, as defined below, is connected with module A by a carbonyl (C=O) point of attachment of $P^5$; then $P^5$ is Glu;
for module B consisting of single elements Q being connected in either direction from the carbonyl (C=O) point of attachment to the nitrogen (N) of the next element with the proviso that $Q^7$ is connected from the α-carbonyl (C=O) point of attachment to the ω-nitrogen (N) of $Q^1$
$Q^1$ is an L α-amino acid residue of formula AA21;
$Q^2$, $Q^5$, and $Q^6$ are independently an L α-amino acid residue of formula AA3b;
$Q^3$ is a D α-amino acid residue of one of the formulae $AA1^D$; or $AA2^D$;
$Q^4$ is an L α-amino acid residue of one of the formulae AA1; or AA4;
$Q^7$ is an L α-amino acid residue of one of the formulae AA1; or AA4;
for a linker L consisting of k=1 or 3 single elements L being connected in either direction from the carbonyl (C=O) point of attachment to the nitrogen (N) of the next element,
if k=1,
$L^1$ is an α-amino acid residue of one of the formulae AA3b; or $AA3b^D$;
if k=3,
$L^1$ is an α-amino acid residue of one of the formulae AA3b; or $AA3b^D$;
$L^2$ is an α-amino acid residue of one of the formulae AA4; or $AA4^D$;
$L^3$ is an α-amino acid residue of one of the formulae AA3b; or $AA3b^D$;
said linker L being connected with module B from the carbonyl (C=O) point of attachment of $L^k$ to the α-nitrogen (N) of $Q^1$ and,
if k=1 or 3, being connected with module A from the carbonyl (C=O) point of attachment of $P^5$; $P^6$; or $P^7$; to the nitrogen (N) of $L^1$;
or a pharmaceutically acceptable salt thereof.

In another particular embodiment (9) of the invention the elements of formula (I) are defined as follows,
for module A,
s=1, t=1, and u=0; and
$P^2$ and $P^{11}$ taken together form an interstrand linking bis (amino acid)-structure of formula AA16; with Z being, with the proviso of containing less than 25 carbon- and/or heteroatoms, —$(CR^{28}R^{29})_n$—S—S—$(CR^{28}R^{29})_m$—; and/or
$P^4$ and $P^9$ taken together form an interstrand linking bis (amino acid)-structure of formula AA16; with Z being, with the proviso of containing less than 25 carbon- and/or heteroatoms, —$(CR^{28}R^{29})_n$—S—S—$(CR^{28}R^{29})_m$—;

$P^1$ is an L α-amino acid residue of one formula AA1; or an L α-hydroxy acid residue of formula AA11;
$P^2$ is an L α-amino acid residue of formula AA4;
$P^3$ is an L α-amino acid residue of one of the formula AA1; or AA4;
$P^4$ is Gly; or an L α-amino acid residue of one of the formulae AA3b; or AA4;
$P^6$ is Gly; or a D α-amino acid residue of one of the formulae $AA1^D$; $AA4^D$; or $AA3b^D$;
$P^7$ is Gly; or an L α-amino acid residue of one of the formulae AA1; AA3b; or AA4;
$P^8$ is an L α-amino acid residue of formula AA2;
$P^9$ is Gly; or an L α-amino acid residue of one of the formulae AA1; or AA4;
$P^{10}$ is an L α-amino acid residue of formula AA1;
$P^{11}$ is an L α-amino acid residue of one of the formulae AA1; or AA4;
$X^{12}$ is Gly; or an L α-amino acid residue of the formula AA2; or an α-amino acid residue of one of the formulae AA1; or $AA1^D$;
$X^{13}$ is Glyol; or an L α-amino acid residue of formula AA1; or an α-amino acid residue of one of the formulae AA4; or $AA4^D$; or an α-amino acid residue of one of the formulae AA5; or $AA5^D$; or an L α-amino acid residue of formula AA6;
with the proviso that,
  the combined number of the amino acid residue Gly in above module A must not exceed two; and
  the positions P of the amino acid residues Gly must not be in direct vicinity;
with the further proviso that,
  $X^{13}$ having a carbonyl (C=O) point of attachment not connected as aforementioned, being appropriately saturated by linkage with $R^{30}$ to form the corresponding naturally or non-naturally occurring terminal α-amino acid residue; optionally having a modified carbonyl (C=O) functional group;
  $X^{14}$ having a nitrogen (N) not connected as aforementioned, being appropriately saturated by linkages with $R^1$, as already depicted above, and $R^{31}$ to form the corresponding naturally or non-naturally occurring terminal α-amino acid residue; optionally having a modified nitrogen (N) functional group;
with the further proviso that,
  if linker L, as defined below, is connected with module A by a carbonyl (C=O) point of attachment of $P^5$; then $P^5$ is Glu;
for module B consisting of single elements Q being connected in either direction from the carbonyl (C=O) point of attachment to the nitrogen (N) of the next element with the proviso that $Q^7$ is connected from the α-carbonyl (C=O) point of attachment to the ω-nitrogen (N) of $Q^1$,
$Q^1$ is an L α-amino acid residue of formula AA21;
$Q^2$, $Q^5$, and $Q^6$ are independently an L α-amino acid residue of formula AA3b;
$Q^3$ is a D α-amino acid residue of one of the formulae $AA1^D$; or $AA2^D$;
$Q^4$ is an L α-amino acid residue of one of the formulae AA1; or AA4;
$Q^7$ is an L α-amino acid residue of one of the formulae AA1; or AA4;
for a linker L consisting of k=1 or 3 single elements L being connected in either direction from the carbonyl (C=O) point of attachment to the nitrogen (N) of the next element,
if k=1,
$L^1$ is an α-amino acid residue of one of the formulae AA3b; or $AA3b^D$;

if k=3,
L$^1$ is an α-amino acid residue of one of the formulae AA3b; or AA3b$^D$;
L$^2$ is an α-amino acid residue of one of the formulae AA4; or AA4D;
L$^3$ is an α-amino acid residue of one of the formulae AA3b; or AA3b$^D$;
said linker L being connected with module B from the carbonyl (C=O) point of attachment of L$^k$ to the α-nitrogen (N) of Q$^1$ and,
if k=1 or 3, being connected with module A from the carbonyl (C=O) point of attachment of P$^5$; P$^6$; or P$^7$; to the nitrogen (N) of L$^1$;
or a pharmaceutically acceptable salt thereof.

In a particular preferred embodiment (10) of the invention the elements of formula (I) are defined as follows,
for module A,
s=0, t=0, and u=1; and
P$^2$ and P$^{11}$ taken together form an interstrand linking bis (amino acid)-structure of formula AA16; with Z being, with the proviso of containing less than 25 carbon- and/or heteroatoms, —(CR$^{28}$R$^{29}$)$_n$—S—S—(CR$^{28}$R$^{29}$)$_m$—; and/or
P$^4$ and P$^9$ taken together form an interstrand linking bis (amino acid)-structure of formula AA16; with Z being, with the proviso of containing less than 25 carbon- and/or heteroatoms, —(CR$^{28}$R$^{29}$)$_n$—S—S—(CR$^{28}$R$^{29}$)$_m$—;
X$^{14}$ is pGlu; $^D$pGlu; or an L α-amino acid residue of formula AA3b;
P$^1$ is an L α-amino acid residue of one of the formulae AA1; or AA4;
P$^2$ is an L α-amino acid residue of formula AA4;
P$^3$ is an L α-amino acid residue of formula AA2;
P$^4$ is Gly; or an L α-amino acid residue of one of the formulae AA3b; or AA4;
P$^6$ is Gly; or a D α-amino acid residue of one of the formulae AA1$^D$; AA4$^D$; or AA3b$^D$;
P$^7$ is Gly; or an L α-amino acid residue of one of the formulae AA1; AA3b; or AA4;
P$^8$ is an L α-amino acid residue of formula AA2;
P$^9$ is Gly; or an L α-amino acid residue of formula AA4;
P$^{10}$ is an L α-amino acid residue of formula AA1;
P$^{11}$ is an L α-amino acid residue of one of the formulae AA1; or AA3b; with the proviso that,
the combined number of the amino acid residue Gly in above module A must not exceed two; and
the positions P of the amino acid residues Gly must not be in direct vicinity;
with the further proviso that,
X$^{13}$ having a carbonyl (C=O) point of attachment not connected as aforementioned, being appropriately saturated by linkage with R$^{30}$ to form the corresponding naturally or non-naturally occurring terminal α-amino acid residue; optionally having a modified carbonyl (C=O) functional group;
X$^{14}$ having a nitrogen (N) not connected as aforementioned, being appropriately saturated by linkages with Fe, as already depicted above, and R$^{31}$ to form the corresponding naturally or non-naturally occurring terminal α-amino acid residue; optionally having a modified nitrogen (N) functional group;
with the further proviso that,
if linker L, as defined below, is connected with module A by a carbonyl (C=O) point of attachment of P$^5$; then P$^5$ is Glu;
for module B consisting of single elements Q being connected in either direction from the carbonyl (C=O) point of attachment to the nitrogen (N) of the next element with the proviso that Q$^7$ is connected from the α-carbonyl (C=O) point of attachment to the ω-nitrogen (N) of Q$^1$,
Q$^1$ is an L α-amino acid residue of formula AA21;
Q$^2$, Q$^5$, and Q$^6$ are independently an L α-amino acid residue of formula AA3b;
Q$^3$ is a D α-amino acid residue of one of the formulae AA1$^D$; or AA2$^D$;
Q$^4$ is an L α-amino acid residue of one of the formulae AA1; or AA4;
Q$^7$ is an L α-amino acid residue of one of the formulae AA1; or AA4;
for a linker L consisting of k=1 or 3 single elements L being connected in either direction from the carbonyl (C=O) point of attachment to the nitrogen (N) of the next element,
if k=1,
L$^1$ is an α-amino acid residue of one of the formulae AA3b; or AA3b$^D$;
if k=3,
L$^1$ is an α-amino acid residue of one of the formulae AA3b; or AA3b$^D$;
L$^2$ is an α-amino acid residue of one of the formulae AA4; or AA4$^D$;
L$^3$ is an α-amino acid residue of one of the formulae AA3b; or AA3b$^D$;
said linker L being connected with module B from the carbonyl (C=O) point of attachment of L$^k$ to the α-nitrogen (N) of Q$^1$ and,
if k=1 or 3, being connected with module A from the carbonyl (C=O) point of attachment of P$^5$; P$^6$; or P$^7$; to the nitrogen (N) of L$^1$;
or a pharmaceutically acceptable salt thereof.

In a more preferred particular embodiment (11) of the invention the elements of formula (I) are defined as follows,
for module A,
s=1, t=0, and u=0; and
P$^1$ and X$^{12}$ taken together form an interstrand linking bis (amino acid)-structure of formula AA16; with Z being, with the proviso of containing less than 25 carbon- and/or heteroatoms, —(CR$^{28}$R$^{29}$)$_n$—S—S—(CR$^{28}$R$^{29}$)$_m$—; and/or
P$^2$ and P$^{11}$ taken together form an interstrand linking bis (amino acid)-structure of formula AA16; with Z being, with the proviso of containing less than 25 carbon- and/or heteroatoms, —(CR$^{28}$R$^{29}$)$_n$—S—S—(CR$^{28}$R$^{29}$)$_m$—; —(CR$^{28}$R$^{29}$)$_n$CONR$^1$(CR$^{28}$R$^{29}$)$_m$—; or —(CR$^{28}$R$^{29}$)$_n$NR$^1$CO(CR$^{28}$R$^{29}$)$_m$—; or
a salt bridge of one of the formulae AA18; or AA19; and/or
P$^4$ and P$^9$ taken together form an interstrand linking bis (amino acid)-structure of formula AA16; with Z being, with the proviso of containing less than 25 carbon- and/or heteroatoms, —(CR$^{28}$R$^{29}$)$_n$—S—S—(CR$^{28}$R$^{29}$)$_m$—; —(CR$^{28}$R$^{29}$)$_n$CONR$^1$(CR$^{28}$R$^{29}$)$_m$—; or —(CR$^{28}$R$^{29}$)$_n$NR$^1$CO(CR$^{28}$R$^{29}$)$_m$—; or a salt bridge of one of the formulae AA18; or AA19;
P$^1$ is pGlu; or an α-amino acid residue of one of the formulae AA1; AA1$^D$; AA2; or AA4; or an L α-hydroxy acid residue of formula AA11; or an acid residue of one of the formulae AA15a; or AA15b;
P$^2$ is an L α-amino acid residue of one of the formulae AA1; AA3b; or AA4;
P$^3$ is an L α-amino acid residue of one of the formula AA1; AA2; or AA4;
P$^4$ is Gly; or an L α-amino acid residue of one of the formulae AA3b; or AA4; or AA2;

P⁵ is Gly; or an L α-amino acid residue of one of the formulae AA3b; AA1; AA2; or AA4;
P⁶ is Gly; or a D α-amino acid residue of one of the formulae AA1$^D$; AA4$^D$; or AA3a$^D$;
P⁷ is Gly; or an L α-amino acid residue of one of the formulae AA1; AA3b; or AA4;
P⁸ is an L α-amino acid residue of one of the formulae AA1; or AA2;
P⁹ is Gly; or an L α-amino acid residue of one of the formulae AA1; AA2; AA3b; AA4; or AA5;
P¹⁰ is an L α-amino acid residue of one of the formulae AA1; or AA2;
P¹¹ is an L α-amino acid residue of one of the formulae AA1; AA3b; AA4; or AA5;
X¹² is Glyol; or an L α-amino acid residue of one of the formulae AA1; AA2; AA3b; AA6; AA4; or AA4$^D$; or an amino alcohol residue of one of the formulae AA8; AA10; or AA10$^D$;
with the proviso that,
 if P¹ is an α-amino acid residue of formula AA4;
 then X¹² is an α-amino acid residue of formula AA1; AA4; or AA4$^D$; and
 if P³ is an α-amino acid residue of one of the formulae AA1; or AA4;
 then P¹; or P¹⁰; is an α-amino acid residue of formula AA2; or X¹² is an α-amino acid residue of formula AA2; or an amino alcohol residue of formula AA8; and
 if P⁸ is an α-amino acid residue of formula AA1;
 then P¹⁰ is an α-amino acid residue of formula AA2; and
 the combined number of the amino acid residue Gly in above module A must not exceed two; and
 the positions P of the amino acid residues Gly must not be in direct vicinity;
with the further proviso that,
 if P¹ and X¹² taken together form an interstrand linkage or salt bridge, as defined above; then P² and P¹¹ taken together are not forming an interstrand linkage or salt bridge, as defined above;
 X¹³ having a carbonyl (C=O) point of attachment not connected as aforementioned, being appropriately saturated by linkage with R³⁰ to form the corresponding naturally or non-naturally occurring terminal α-amino acid residue; optionally having a modified carbonyl (C=O) functional group;
 X¹⁴ having a nitrogen (N) not connected as aforementioned, being appropriately saturated by linkages with Fe, as already depicted above, and R³¹ to form the corresponding naturally or non-naturally occurring terminal α-amino acid residue; optionally having a modified nitrogen (N) functional group;
if linker L, as defined below, is connected with module A by a carbonyl (C=O) point of attachment of P⁵; P⁶; or P⁷; then
 P⁵; P⁶; or P⁷; is Glu; or $^D$Glu;
for module B consisting of single elements Q being connected in either direction from the carbonyl (C=O) point of attachment to the nitrogen (N) of the next element with the proviso that Q⁷ is connected from the α-carbonyl (C=O) point of attachment to the ω-nitrogen (N) of Q¹,
Q¹ is an L α-amino acid residue of formula AA21;
Q², Q⁵, and Q⁶ are independently an L α-amino acid residue of formula AA3b;
Q³ is a D α-amino acid residue of one of the formulae AA1$^D$; or AA2$^D$;
Q⁴ is an L α-amino acid residue of one of the formulae AA1; or AA4;

Q⁷ is an L α-amino acid residue of one of the formulae AA1; or AA4;
for a linker L consisting of k=1 or 3 single elements L being connected in either direction from the carbonyl (C=O) point of attachment to the nitrogen (N) of the next element,
 if k=1,
 L¹ is an α-amino acid residue of one of the formulae AA3b; or AA3b$^D$;
 if k=3,
 L¹ is an α-amino acid residue of one of the formulae AA3b; or AA3b$^D$;
 L² is an α-amino acid residue of one of the formulae AA4; or AA4$^D$;
 L³ is an α-amino acid residue of one of the formulae AA3b; or AA3b$^D$;
 said linker L being connected with module B from the carbonyl (C=O) point of attachment of L$^k$ to the α-nitrogen (N) of Q¹ and,
 if k=1 or 3, being connected with module A from the carbonyl (C=O) point of attachment of P⁵; P⁶; or P⁷; to the nitrogen (N) of L¹;
or a pharmaceutically acceptable salt thereof.
 In a particular preferred particular embodiment (12) of the invention the elements of formula (I) are defined as follows,
for module A,
s=0, t=0, and u=0; and
P² and P¹¹ taken together form an interstrand linking bis (amino acid)-structure of formula AA16; with Z being, with the proviso of containing less than 25 carbon- and/or heteroatoms, —(CR²⁸R²⁹)$_n$—S—S—(CR²⁸R²⁹)$_m$—; and/or
P⁴ and P⁹ taken together form an interstrand linking bis (amino acid)-structure of formula AA16; with Z being, with the proviso of containing less than 25 carbon- and/or heteroatoms, —(CR²⁸R²⁹)$_n$—S—S—(CR²⁸R²⁹)$_m$—;
P¹ is an L α-amino acid residue of formula AA1; or an L α-hydroxy acid residue of formula AA11;
P² is an L α-amino acid residue of formula AA4;
P³ is an L α-amino acid residue of formula AA2;
P⁴ is Gly; or an L α-amino acid residue of one of the formulae AA3b; or AA4;
P⁶ is Gly; or a D α-amino acid residue of one of the formulae AA1$^D$; AA4$^D$; or AA3b$^D$;
P⁷ is Gly; or an L α-amino acid residue of one of the formulae AA1; AA3b; or AA4;
P⁸ is an L α-amino acid residue of formula AA2;
P⁹ is Gly; or an L α-amino acid residue of one of the formulae AA1; or AA4;
P¹⁰ is an L α-amino acid residue of formula AA1;
P¹¹ is an L α-amino acid residue of one of the formulae AA1; or AA4; with the proviso that,
 the combined number of the amino acid residue Gly in above module A must not exceed two; and
 the positions P of the amino acid residues Gly must not be in direct vicinity;
with the further proviso that,
 X¹³ having a carbonyl (C=O) point of attachment not connected as aforementioned, being appropriately saturated by linkage with R³⁰ to form the corresponding naturally or non-naturally occurring terminal α-amino acid residue; optionally having a modified carbonyl (C=O) functional group;
 X¹⁴ having a nitrogen (N) not connected as aforementioned, being appropriately saturated by linkages with Fe, as already depicted above, and R³¹ to form the corresponding naturally or non-naturally occurring terminal α-amino acid residue; optionally having a modified nitrogen (N) functional group;
with the further proviso that,
if linker L, as defined below, is connected with module A by a carbonyl (C=O) point of attachment of $P^5$; then $P^5$ is Glu;
for module B consisting of single elements Q being connected in either direction from the carbonyl (C=O) point of attachment to the nitrogen (N) of the next element with the proviso that $Q^7$ is connected from the α-carbonyl (C=O) point of attachment to the ω-nitrogen (N) of $Q^1$,
$Q^1$ is an L α-amino acid residue of formula AA21;
$Q^2$, $Q^5$, and $Q^6$ are independently an L α-amino acid residue of formula AA3b;
$Q^3$ is a D α-amino acid residue of one of the formulae $AA1^D$; or $AA2^D$;
$Q^4$ is an L α-amino acid residue of one of the formulae AA1; or AA4;
$Q^7$ is an L α-amino acid residue of one of the formulae AA1; or AA4;
for a linker L consisting of k=1 or 3 single elements L being connected in either direction from the carbonyl (C=O) point of attachment to the nitrogen (N) of the next element,
if k=1,
$L^1$ is an α-amino acid residue of one of the formulae AA3b; or $AA3b^D$;
if k=3,
$L^1$ is an α-amino acid residue of one of the formulae AA3b; or $AA3b^D$;
$L^2$ is an α-amino acid residue of one of the formulae AA4; or $AA4^D$;
$L^3$ is an α-amino acid residue of one of the formulae AA3b; or $AA3b^D$;
said linker L being connected with module B from the carbonyl (C=O) point of attachment of $L^k$ to the α-nitrogen (N) of $Q^1$ and,
if k=1 or 3, being connected with module A from the carbonyl (C=O) point of attachment of $P^5$; $P^6$; or $P^7$; to the nitrogen (N) of $L^1$;
or a pharmaceutically acceptable salt thereof.

In a particular preferred embodiment (13) of the invention the elements of formula (I) are defined as follows,
for module A,
s=0, t=0, and u=0; and
$P^{11}$ is connected from the α-carbonyl point of attachment to the ω-nitrogen (N) of $P^2$;
$P^1$ is an L α-amino acid residue of one of the formulae AA1; or AA2; or an L α-hydroxy acid residue of formula AA11;
$P^2$ is an L α-amino acid residue of formula AA3b;
$P^3$ is an L α-amino acid residue of formula AA2;
$P^4$ is Gly; or an L α-amino acid residue of one of the formulae AA3b; or AA4;
$P^6$ is Gly; or a D α-amino acid residue of one of the formulae $AA1^D$; $AA4^D$; or $AA3b^D$;
$P^7$ is Gly; or an L α-amino acid residue of one of the formulae AA1; AA3b; or AA4;
$P^8$ is an L α-amino acid residue of formula AA2;
$P^9$ is Gly; or an L α-amino acid residue of one of the formulae AA1; or AA4;
$P^{10}$ is an L α-amino acid residue of formula AA1;
$P^{11}$ is a D α-amino acid residue of one of the formulae $AA1^D$; $AA2^D$; $AA3b^D$; $AA4^D$; $AA5^D$; or $AA6^D$;
with the proviso that,
the combined number of the amino acid residue Gly in above module A must not exceed two; and
the positions P of the amino acid residues Gly must not be in direct vicinity;
with the further proviso that,
$X^{13}$ having a carbonyl (C=O) point of attachment not connected as aforementioned, being appropriately saturated by linkage with $R^{30}$ to form the corresponding naturally or non-naturally occurring terminal α-amino acid residue; optionally having a modified carbonyl (C=O) functional group;
$X^{14}$ having a nitrogen (N) not connected as aforementioned, being appropriately saturated by linkages with Fe, as already depicted above, and $R^{31}$ to form the corresponding naturally or non-naturally occurring terminal α-amino acid residue; optionally having a modified nitrogen (N) functional group;
with the further proviso that,
if linker L, as defined below, is connected with module A by a carbonyl (C=O) point of attachment of $P^5$; then $P^5$ is Glu;
for module B consisting of single elements Q being connected in either direction from the carbonyl (C=O) point of attachment to the nitrogen (N) of the next element with the proviso that $Q^7$ is connected from the α-carbonyl (C=O) point of attachment to the ω-nitrogen (N) of $Q^1$,
$Q^1$ is an L α-amino acid residue of formula AA21;
$Q^2$, $Q^5$, and $Q^6$ are independently an L α-amino acid residue of formula AA3b;
$Q^3$ is a D α-amino acid residue of one of the formulae $AA1^D$; or $AA2^D$;
$Q^4$ is an L α-amino acid residue of one of the formulae AA1; or AA4;
$Q^7$ is an L α-amino acid residue of one of the formulae AA1; or AA4;
for a linker L consisting of k=1 or 3 single elements L being connected in either direction from the carbonyl (C=O) point of attachment to the nitrogen (N) of the next element,
if k=1,
$L^1$ is an α-amino acid residue of one of the formulae AA3b; or $AA3b^D$;
if k=3,
$L^1$ is an α-amino acid residue of one of the formulae AA3b; or $AA3b^D$;
$L^2$ is an α-amino acid residue of one of the formulae AA4; or $AA4^D$;
$L^3$ is an α-amino acid residue of one of the formulae AA3b; or $AA3b^D$;
said linker L being connected with module B from the carbonyl (C=O) point of attachment of $L^k$ to the α-nitrogen (N) of $Q^1$ and,
if k=1 or 3, being connected with module A from the carbonyl (C=O) point of attachment of $P^5$; $P^6$; or $P^7$; to the nitrogen (N) of $L^1$;
or a pharmaceutically acceptable salt thereof.

In another embodiment (14) of the invention the elements of formula (I) are defined as follows,
for module A,
if s=1, t=1, and u=1; and
$X^{14}$ and $X^{13}$ taken together form an interstrand linking bis(amino acid)-structure or (amino acid)-(acid) structure based on the linkage of two L amino acid residues; or an amino acid residue and an acid residue; following connection of the side chain of Cys; Pen; Hcy; Ac-Cys; Ac-Pen; Ac-Hcy; or 3MPA with the side chain of Cys; Pen; Hcy; Cys-$NH_2$; Pen-$NH_2$; or Hcy-$NH_2$; by a disulfide linkage; or connection of the side chain of Ac-Dab; Ac-Dap; Dab; or Dap; at $X^{14}$ with the side chain of Glu-$NH_2$; Asp-$NH_2$; Glu; or Asp; at $X^{13}$; or the side chain of Ac-Glu; Ac-Asp; Glu; or Asp; at $X^{14}$ with the side chain of Dab-$NH_2$; Dap-$NH_2$; Dab; or Dap; at $X^{13}$; by a lactam linkage; or X$^{14}$ and X$^{13}$ taken together form a salt bridge based on the electrostatic interaction between the side chain of Ac-Dab; Ac-Dap; Ac-Lys; Dab; Dap; or Lys; at X$^{14}$ and the side chain of Glu-NH$_2$; Asp-NH$_2$; Glu; or Asp; at X$^{13}$; or the side chain of Ac-Glu; Ac-Asp; Glu; or Asp; at X$^{14}$ and the side chain of Dab-NH$_2$; Dap-NH$_2$; Lys-NH$_2$; Dab; Dap; or Lys; at X$^{13}$; and/or P$^1$ and X$^{12}$ taken together form an interstrand linking bis (amino acid)-structure based on the linkage of two L amino acid residues; following
connection of the side chain of Cys; Pen; or Hcy; with the side chain of Cys; Pen; or Hcy; by a disulfide linkage; and/or
P$^2$ and P$^{11}$ taken together form an interstrand linking bis (amino acid)-structure based on the linkage of two L amino acid residues; following
connection of the side chain of Cys; Pen; or Hcy; with the side chain of Cys; Pen; or Hcy; by a disulfide linkage; or
connection of the side chain of Dab; Dab(Me); or Dap; at P$^2$ with the side chain of Glu; or Asp; at P$^{11}$; or the side chain Glu; or Asp; at P$^2$ with the side chain of Dab; or Dap; at P$^{11}$; by a lactam linkage; or
P$^2$ and P$^{11}$ taken together form a salt bridge based on the electrostatic interaction between the side chain of Dab; Dap; or Lys; at P$^2$ and the side chain of Glu; or Asp; at P$^{11}$; or the side chain of Glu; or Asp; at P$^2$ and the side chain of Dab; Dap; or Lys; at P$^{11}$; and/or
P$^4$ and P$^9$ taken together form an interstrand linking bis (amino acid)-structure based on the linkage of two L amino acid residues; following
connection of the side chain of Cys; Pen; or Hcy; with the side chain of Cys; Pen; or Hcy; by a disulfide linkage; or
connection of the side chain of Asp; or Glu; with the side chain of Dab; or Dap; by a lactam linkage; or
P$^4$ and P$^9$ taken together form a salt bridge based on the electrostatic interaction between the side chain of Dab; Dap; or Lys; at P$^4$ and the side chain of Glu; or Asp; at P$^9$; or the side chain of Glu; or Asp; at P$^4$ and the side chain of Dab; Dap; or Lys; at P$^9$;
X$^{14}$ is Glu; pGlu; Ac-Dab; Dab; 6MeHeptA; Ac-pGlu; Ac-$^D$pGlu; or Ac-$^D$Ser;
P$^1$ is Val; NMeVal; $^D$Val; Leu; Ile; Nle; Phe; Tyr; Ser; Leu(3R)OH; or Nva;
P$^2$ is Thr; Dap; Ala; Val tBuGly; or Dab;
P$^3$ is Tyr; Val; Ser; or Thr;
P$^4$ is Dab; Dap; Ser; His; or Gly;
P$^5$ is Gly; Ala; Val; Abu; His; Thr; or Orn;
P$^6$ is $^D$Dab; $^D$Arg; $^D$Ser; $^D$Hse; $^D$Ala; or Gly;
P$^7$ is Ser; Hse; Thr; Dab; Dap; Ala; or Gly;
P$^8$ is Trp; or Val;
P$^9$ is Ser; Hse; Thr; alloThr; Dab; His; Glu; Ala; or Gly;
P$^{10}$ is Val; tBuGly; Tyr; Trp; Ser; Nva; or Ile;
P$^{11}$ is Ala; Ser; Thr; Dab; or Glu;
X$^{12}$ is Val; Ser; Thr; Dab; $^D$Ala; Gly; or Tyr;
X$^{13}$ is $^D$Ala; $^D$Ala-NH$_2$; $^D$Ser; $^D$Ser-N H$_2$; or Glyol;
with the proviso that,
 if P$^1$ is Ser; or Leu(3R)OH; then X$^{12}$ is Val; or $^D$Ala; and
 if P$^3$ is Ser; Thr; or Val; then P$^1$; P$^{10}$; or X$^{12}$; is Tyr; and
 if P$^8$ is Val; then P$^{10}$ is Trp; and
 if P$^{10}$ is Ser; then X$^{12}$ is Val; or $^D$Ala; and
 the combined number of the amino acid residue Gly in above module A must not exceed two; and
 the positions P of the amino acid residues Gly must not be in direct vicinity;
with the further proviso that,
 the combined number of interstrand linkages and salt bridges in above module A must not exceed two;

if X$^{14}$ and X$^{13}$ taken together form an interstrand linkage or salt bridge, as defined above; then P$^1$ and X$^{12}$ taken together are not forming an interstrand linkage or salt bridge, as defined above;
if P$^1$ and X$^{12}$ taken together form an interstrand linkage or salt bridge, as defined above; then P$^2$ and P$^{11}$ taken together are not forming an interstrand linkage or a salt bridge, as defined above;
with the further proviso that,
 if linker L, as defined below, is connected with module A by a carbonyl (C=O) point of attachment of P$^5$; P$^6$; or P$^7$; then
 P$^5$; P$^6$; or P$^7$; is Glu; or $^D$Glu;
if s=1, t=0, and u=1; and
P$^1$ and X$^{12}$ taken together form an interstrand linking bis (amino acid)-structure based on the linkage of two L amino acid residues; following
connection of the side chain of Cys; Pen; or Hcy; with the side chain of Cys; Pen; Hcy; Cys-NH$_2$; Pen-NH$_2$; or Hcy-NH$_2$ by a disulfide linkage; and/or
P$^2$ and P$^{11}$ taken together form an interstrand linking bis (amino acid)-structure based on the linkage of two L amino acid residues; following
connection of the side chain of Cys; Pen; or Hcy; with the side chain of Cys; Pen; or Hcy; by a disulfide linkage; or
connection of the side chain of Dab; Dab(Me); or Dap; with the side chain of Glu; or Asp; by a lactam linkage; or
P$^2$ and P$^{11}$ taken together form a salt bridge based on the electrostatic interaction between the side chain of Dab; Dap; or Lys; at P$^2$ and the side chain of Glu; or Asp; at P$^{11}$; or the side chain of Glu; or Asp; at P$^2$ and the side chain of Dab; Dap; or Lys; at P$^{11}$; and/or
P$^4$ and P$^9$ taken together form an interstrand linking bis (amino acid)-structure based on the linkage of two L amino acid residues; following
connection of the side chain of Cys; Pen; or Hcy; with the side chain of Cys; Pen; or Hcy; by a disulfide linkage; or
connection of the side chain of Asp; or Glu; with the side chain of Dab; or Dap; by a lactam linkage; or
P$^4$ and P$^9$ taken together form a salt bridge based on the electrostatic interaction between the side chain of Dab; Dap; or Lys; at P$^4$ and the side chain of Glu; or Asp; at P$^9$; or the side chain of Glu; or Asp; at P$^4$ and the side chain of Dab; Dap; or Lys; at P$^9$;
X$^{14}$; P$^1$; P$^2$; P$^3$; P$^4$; P$^5$; P$^6$; P$^7$; P$^8$; P$^9$; P$^{10}$; and P$^{11}$ are as defined above for module A in this embodiment, wherein s=1, t=1, and u=1;
X$^{12}$ is Val; Ser; Thr; Dab; Tyr; Serol; Throl; $^D$Throl; Tyrol; Glyol; Val-NH$_2$; Ser-NH$_2$; Ser-NHMe; Ser-OiPr; Thr-NH$_2$; Dab-NH$_2$; Tyr-NH$_2$;
with the proviso that,
 if P$^1$ is Ser; or Leu(3R)OH; then X$^{12}$ is Val; or Val-NH$_2$; and
 if P$^3$ is Ser; Thr; or Val; then P$^1$; or P$^m$; is Tyr; or X$^{12}$ is Tyr; Tyrol; or Tyr-NH$_2$; and
 if P$^8$ is Val; then P$^{10}$ is Trp; and
 if P$^{10}$ is Ser; then X$^{12}$ is Val; or Val-NH$_2$; and
 the combined number of the amino acid residue Gly in above module A must not exceed two; and
 the positions P of the amino acid residues Gly must not be in direct vicinity;
with the further proviso that,
 if P$^1$ and X$^{12}$ taken together form an interstrand linkage, as defined above;
 then P$^2$ and P$^{11}$ taken together are not forming an interstrand linkage or salt bridge, as defined above;

with the further proviso that,
  if linker L, as defined below, is connected with module A by a carbonyl (C=O) point of attachment of $P^5$; $P^6$; or $P^7$; then
    $P^5$; $P^6$; or $P^7$; is Glu; or $^D$Glu;
if s=1, t=1, and u=0; and
$P^1$ and $X^{12}$ taken together form an interstrand linking bis (amino acid)-structure based on the linkage of two L amino acid residues; following connection of the side chain of Cys; Pen; Hcy; Ac-Cys; Ac-Pen; or Ac-Hcy; with the side chain of Cys; Pen; or Hcy; by a disulfide linkage; and/or
$P^2$ and $P^{11}$ taken together form an interstrand linking bis (amino acid)-structure based on the linkage of two L amino acid residues; following
connection of the side chain of Cys; Pen; or Hcy; with the side chain of Cys; Pen; or Hcy; by a disulfide linkage; or
connection of the side chain of Dab; Dab(Me); or Dap; with the side chain of Glu; or Asp; by a lactam linkage; or
$P^2$ and $P^{11}$ taken together form a salt bridge based on the electrostatic interaction between the side chain of Dab; Dap; or Lys; at $P^2$ and the side chain of Glu; or Asp; at $P^{11}$; or the side chain of Glu; or Asp; at $P^2$ and the side chain of Dab; Dap; or Lys; at $P^{11}$; and/or
$P^4$ and $P^9$ taken together form an interstrand linking bis (amino acid)-structure based on the linkage of two L amino acid residues; following
connection of the side chain of Cys; Pen; or Hcy; with the side chain of Cys; Pen; or Hcy; by a disulfide linkage; or
connection of the side chain of Asp; or Glu; with the side chain of Dab; or Dap; by a lactam linkage; or
$P^4$ and $P^9$ taken together form a salt bridge based on the electrostatic interaction between the side chain of Dab; Dap; or Lys; at $P^4$ and the side chain of Glu; or Asp; at $P^9$; or the side chain of Glu; or Asp; at $P^4$ and the side chain of Dab; Dap; or Lys; at $P^9$;
$P^1$ is Val; NMeVal; $^D$Val; Leu; Ile; Nle; Phe; Tyr; Ser; Leu(3R)OH; Nva; HOVal; Ac-Val; Ac-$^D$Val; Ac-Leu; Ac-Ile; Ac-Phe; Prop-Val; Ac-Nle; Ac-Tyr; Ac-Ser; Ac-Leu(3R)OH; Ac-Nva; 3MeButA; 2MePropA; or 6MeHeptA;
$P^2$; $P^3$; $P^4$; $P^5$; $P^6$; $P^7$; $P^8$; $P^9$; $P^{10}$; $P^{11}$; and $X^{12}$ are as defined above for module A in this embodiment, wherein s=1, t=1, and u=1;
$X^{13}$ is $^D$Ala; $^D$Ala-NH$_2$; $^D$Ser; $^D$Ser-N H$_2$; $^D$Thr; $^D$Asp; Ser; Asp; Asn; or Glyol;
with the proviso that,
  if $P^1$ is Ser; Ac-Ser; Leu(3R)OH; or Ac-Leu(3R)OH; then $X^{12}$ is Val; and
  if $P^3$ is Ser; Thr; or Val; then $P^1$; is Tyr; or Ac-Tyr; or $P^{10}$; or $X^{12}$; is Tyr; and
  if $P^8$ is Val; then $P^{10}$ is Trp; and
  if $P^{10}$ is Ser; then $X^{12}$ is Val; or $^D$Ala; and
  the combined number of the amino acid residue Gly in above module A must not exceed two; and
  the positions P of the amino acid residues Gly must not be in direct vicinity;
with the further proviso that,
  if $P^1$ and $X^{12}$ taken together form an interstrand linkage, as defined above;
  then $P^2$ and $P^{11}$ taken together are not forming an interstrand linkage or salt bridge, as defined above;
with the further proviso that,
  if linker L, as defined below, is connected with module A by a carbonyl (C=O) point of attachment of $P^5$; $P^6$; or $P^7$; then
    $P^5$; $P^6$; or $P^7$; is Glu; or $^D$Glu;
if s=0, t=0, and u=1; and $P^2$ and $P^{11}$ taken together form an interstrand linking bis (amino acid)-structure based on the linkage of two L amino acid residues; following
connection of the side chain of Cys; Pen; or Hcy; with the side chain of Cys; Pen; Hcy; Cys-NH$_2$; Pen-NH$_2$; or Hcy-NH$_2$; by a disulfide linkage; or
connection of the side chain of Dab; Dab(Me); or Dap; at $P^2$ with the side chain of Glu; Asp; Glu-NH$_2$; or Asp-NH$_2$; at $P^{11}$; or the side chain Glu; or Asp; at $P^2$ with the side chain of Dab; Dap; Dab-NH$_2$; or Dap-NH$_2$; at $P^{11}$; by a lactam linkage; or
$P^2$ and $P^{11}$ taken together form a salt bridge based on the electrostatic interaction between the side chain of Dab; Dap; or Lys; at $P^2$ and the side chain of Glu; Asp; Glu-NH$_2$; or Asp-NH$_2$; at $P^{11}$; or the side chain of Glu; or Asp; at $P^2$ and the side chain of Dab; Dap; Lys; Dab-NH$_2$; Dap-NH$_2$; or Lys-NH$_2$; at $P^{11}$; and/or
$P^4$ and $P^9$ taken together form an interstrand linking bis (amino acid)-structure based on the linkage of two L amino acid residues; following
connection of the side chain of Cys; Pen; or Hcy; with the side chain of Cys; Pen; or Hcy; by a disulfide linkage; or
connection of the side chain of Asp; or Glu; with the side chain of Dab; or Dap; by a lactam linkage; or
$P^4$ and $P^9$ taken together form a salt bridge based on the electrostatic interaction between the side chain of Dab; Dap; or Lys; at $P^4$ and the side chain of Glu; or Asp; at $P^9$; or the side chain of Glu; or Asp; at $P^4$ and the side chain of Dab; Dap; or Lys; at $P^9$;
$X^{14}$; $P^1$; $P^2$; $P^3$; $P^4$; $P^5$; $P^6$; $P^7$; $P^8$; $P^9$; and $P^{10}$ are as defined above for module A in this embodiment, wherein s=1, t=1, and u=1;
$P^{11}$ is Ala; Ser; Thr; Dab; Glu; Ser-NH$_2$; Dab-NH$_2$; Ala-NH$_2$; Thr-NH$_2$; or Glu-NH$_2$;
with the proviso that,
  if $P^3$ is Ser; Thr; or Val; then $P^1$; or $P^{10}$; is Tyr; and
  if $P^8$ is Val; then $P^{10}$ is Trp; and
  the combined number of the amino acid residue Gly in above module A must not exceed two; and
  the positions P of the amino acid residues Gly must not be in direct vicinity;
with the further proviso that,
  if linker L, as defined below, is connected with module A by a carbonyl (C=O) point of attachment of $P^5$; $P^6$; or $P^7$; then
    $P^5$; $P^6$; or $P^7$; is Glu; or $^D$Glu;
if s=1, t=0, and u=0; and
$P^1$ and $X^{12}$ taken together form an interstrand linking bis (amino acid)-structure based on the linkage of two L amino acid residues; following
connection of the side chain of Cys; Pen; Hcy; Ac-Cys; Ac-Pen; or Ac-Hcy; with the side chain of Cys; Pen; Hcy; Cys-NH$_2$; Pen-NH$_2$; or Hcy-NH$_2$; by a disulfide linkage; and/or
$P^2$ and $P^{11}$ taken together form an interstrand linking bis (amino acid)-structure based on the linkage of two L amino acid residues; following
connection of the side chain of Cys; Pen; or Hcy; with the side chain of Cys; Pen; or Hcy; by a disulfide linkage; or
connection of the side chain of Dab; Dab(Me); or Dap; with the side chain of Glu; or Asp; by a lactam linkage; or
$P^2$ and $P^{11}$ taken together form a salt bridge based on the electrostatic interaction between the side chain of Dab; Dap; or Lys; at $P^2$ and the side chain of Glu; or Asp; at $P^{11}$; or the side chain of Glu; or Asp; at $P^2$ and the side chain of Dab; Dap; or Lys; at $P^{11}$; and/or P⁴ and P⁹ taken together form an interstrand linking bis (amino acid)-structure based on the linkage of two L amino acid residues; following
connection of the side chain of Cys; Pen; or Hcy; with the side chain of Cys; Pen; or Hcy; by a disulfide linkage; or
connection of the side chain of Asp; or Glu; with the side chain of Dab; or Dap; by a lactam linkage; or
P⁴ and P⁹ taken together form a salt bridge based on the electrostatic interaction between the side chain of Dab; Dap; or Lys; at P⁴ and the side chain of Glu; or Asp; at P⁹; or the side chain of Glu; or Asp; at P⁴ and the side chain of Dab; Dap; or Lys; at P⁹;

P¹ is Val; NMeVal; ᴰVal; Leu; Ile; Nle; Phe; Tyr; Ser; Leu(3R)OH; Nva; HOVal; Ac-Val; Ac-ᴰVal; Ac-Leu; Ac-Ile; Ac-Phe; Prop-Val; Ac-Nle; Ac-Tyr; Ac-Ser; Ac-Leu(3R)OH; Ac-Nva; 3MeButA; 2MePropA; or 6MeHeptA;

P²; P³; P⁴; P⁵; P⁶; P⁷; P⁸; P⁹; and P¹⁰ and P¹¹ are as defined above for module A in this embodiment, wherein s=1, t=1, and u=1;

X¹² is Val; Ser; Thr; Dab; Tyr; Serol; Throl; ᴰThrol; Tyrol; Glyol; Val-NH₂; Ser-NH₂; Ser-NHMe; Ser-OiPr; Thr-NH₂; Leu(3R)OH; Asn; Dab-NH₂; or Tyr-NH₂;

with the proviso that,
if P¹ is Ser; Ac-Ser; Leu(3R)OH; or Ac-Leu(3R)OH; then X¹² is Val; Val-NH₂; Ser-NH₂; Ser-NHMe; Ser-OiPr; Thr-NH₂; or Leu(3R)OH; and
if P³ is Ser; Thr; or Val; then P¹; is Tyr; or Ac-Tyr; or P¹⁰ is Tyr; or X¹² is Tyr; Tyrol; or Tyr-NH₂; and
if P⁸ is Val; then P¹⁰ is Trp; and
if P¹⁰ is Ser; then X¹² is Val; or Val-NH₂; and
the combined number of the amino acid residue Gly in above module A must not exceed two; and
the positions P of the amino acid residues Gly must not be in direct vicinity;
with the further proviso that,
if P¹ and X¹² taken together form an interstrand linkage, as defined above; then P² and P¹¹ taken together are not forming an interstrand linkage or salt bridge, as defined above;
with the further proviso that,
if linker L, as defined below, is connected with module A by a carbonyl (C=O) point of attachment of P⁵; P⁶; or P⁷; then
P⁵; P⁶; or P⁷; is Glu; or ᴰGlu;

if s=0, t=0, and u=0; and
P² and P¹¹ taken together form an interstrand linking bis (amino acid)-structure based on the linkage of two L amino acid residues; following
connection of the side chain of Cys; Pen; or Hcy; with the side chain of Cys; Pen; Hcy; Cys-NH₂; Pen-NH₂; or Hcy-NH₂; by a disulfide linkage; or
connection of the side chain of Dab; Dab(Me); or Dap; at P² with the side chain of Glu; Asp; Glu-NH₂; or Asp-NH₂; at P¹¹; or the side chain Glu; or Asp; at P² with the side chain of Dab; Dap; Dab-NH₂; or Dap-NH₂; at P¹¹; by a lactam linkage; or
P² and P¹¹ taken together form a salt bridge based on the electrostatic interaction between the side chain of Dab; Dap; or Lys; at P² and the side chain of Glu; Asp; Glu-NH₂; or Asp-NH₂; at P¹¹; or the side chain of Glu; or Asp; at P² and the side chain of Dab; Dap; Lys; Dab-NH₂; Dap-NH₂; or Lys-NH₂; at P¹¹; and/or
P⁴ and P⁹ taken together form an interstrand linking bis (amino acid)-structure based on the linkage of two L amino acid residues; following
connection of the side chain of Cys; Pen; or Hcy; with the side chain of Cys; Pen; or Hcy; by a disulfide linkage; or
connection of the side chain of Asp; or Glu; with the side chain of Dab; or Dap; by a lactam linkage; or
P⁴ and P⁹ taken together form a salt bridge based on the electrostatic interaction between the side chain of Dab; Dap; or Lys; at P⁴ and the side chain of Glu; or Asp; at P⁹; or the side chain of Glu; or Asp; at P⁴ and the side chain of Dab; Dap; or Lys; at P⁹;

P¹ is Val; NMeVal; ᴰVal; Leu; Ile; Nle; Phe; Tyr; Ser; Leu(3R)OH; Nva; HOVal; Ac-Val; Ac-ᴰVal; Ac-Leu; Ac-Ile; Ac-Phe; Prop-Val; Ac-Nle; Ac-Tyr; Ac-Ser; Ac-Leu(3R)OH; Ac-Nva; 3MeButA; 2MePropA; or 6MeHeptA;

P²; P³; P⁴; P⁵; P⁶; P⁷; P⁸; P⁹; and P¹⁰ are as defined above for module A in this embodiment, wherein s=1, t=1, and u=1;

P¹¹ is Ala; Ser; Thr; Dab; Glu; Ser-NH₂; Dab-NH₂; Ala-NH₂; Thr-NH₂; or Glu-NH₂;

with the proviso that,
if P³ is Ser; Thr; or Val; then P¹; is Tyr; or Ac-Tyr; or P¹⁰ is Tyr; and
if P⁸ is Val; then P¹⁰ is Trp; and
the combined number of the amino acid residue Gly in above module A must not exceed two; and
the positions P of the amino acid residues Gly must not be in direct vicinity; with the further proviso that,
if linker L, as defined below, is connected with module A by a carbonyl (C=O) point of attachment of P⁵; P⁶; or P⁷; then
P⁵; P⁶; or P⁷; is Glu; or ᴰGlu;

if s=0, t=0, and u=0; and alternatively
P¹¹ is connected from the α-carbonyl point of attachment to the ω-nitrogen (N) of P²;

P¹ is Val; NMeVal; ᴰVal; Leu; Ile; Nle; Phe; Tyr; Ser; Leu(3R)OH; Nva; HOVal; Ac-Val; Ac-ᴰVal; Ac-Leu; Ac-Ile; Ac-Phe; Prop-Val; Ac-Nle; Ac-Tyr; Ac-Ser; Ac-Leu(3R)OH; Ac-Nva; 3MeButA; 2MePropA; or 6MeHeptA;

P² is Orn; or Dab;
P³; P⁴; P⁵; P⁶; P⁷; P⁸; P⁹; and P¹⁰ are as defined above for module A in this embodiment, wherein s=1, t=1, and u=1;
P¹¹ is ᴰThr; ᴰHse; ᴰAsn; ᴰGln; ᴰGlu; ᴰVal; ᴰTyr; ᴰDab; ᴰOrn; ᴰLys;

with the proviso that,
if P³ is Ser; Thr; or Val; then P¹; is Tyr; or Ac-Tyr; or P¹⁰ is Tyr; and
if P⁸ is Val; then P¹⁰ is Trp; and
the combined number of the amino acid residue Gly in above module A must not exceed two; and
the positions P of the amino acid residues Gly must not be in direct vicinity;
with the further proviso that,
if linker L, as defined below, is connected with module A by a carbonyl (C=O) point of attachment of P⁵; P⁶; or P⁷; then
P⁵; P⁶; or P⁷; is Glu; or ᴰGlu;

for module B consisting of single elements Q being connected in either direction from the carbonyl (C=O) point of attachment to the nitrogen (N) of the next element with the proviso that Q⁷ is connected from the α-carbonyl (C=O) point of attachment to the ω-nitrogen (N) of Q¹, Q¹ is Dab;
Q², Q⁵ and Q⁶ are Dab;
Q³ is ᴰLeu; or ᴰPhe;
Q⁴ is Leu; Ile; Leu(3R)OH; Abu; Nva; Thr; or alloThr;
Q⁷ is Thr; or Leu;

for a linker L consisting of k=1 or 3 single elements L being connected in either direction from the carbonyl (C=O) point of attachment to the nitrogen (N) of the next element,
if k=1,
$L^1$ is $^D$Dab;
If k=3,
$L^1$ is Dab; $^D$Dab; $^D$Dap; or NMeDab;
$L^2$ is Thr; Hse; or Ser;
$L^3$ is Dap; Dab; $^D$Dab; or $^D$Dap;
said linker L being connected with module B from the carbonyl (C=O) point of attachment of $L^k$ to the α-nitrogen (N) of $Q^1$ and,
if k=1 or 3, being connected with module A from the carbonyl (C=O) point of attachment of $P^5$; $P^6$; or $P^7$; to the nitrogen (N) of $L^1$;
or a pharmaceutically acceptable salt thereof.

In a preferred embodiment (15) of the invention the elements of formula (I) are defined as follows,
for module A,
s=0, t=0, and u=0; or s=1, t=0, and u=0; or s=0, t=0, and u=1;
if s=0, t=0, and u=1; and
$P^2$ and $P^{11}$ taken together form an interstrand linking bis (amino acid)-structure based on the linkage of two L amino acid residues; following
connection of the side chain of Cys; Pen; or Hcy; with the side chain of Cys; Pen; Hcy; Cys-$NH_2$; Pen-$NH_2$; or Hcy-$NH_2$; by a disulfide linkage; or
connection of the side chain of Dab; Dab(Me); or Dap; at $P^2$ with the side chain of Glu; Asp; Glu-$NH_2$; or Asp-$NH_2$; at $P^{11}$; or the side chain Glu; or Asp; at $P^2$ with the side chain of Dab; Dap; Dab-$NH_2$; or Dap-$NH_2$; at $P^{11}$; by a lactam linkage; or
$P^2$ and $P^{11}$ taken together form a salt bridge based on the electrostatic interaction between the side chain of Dab; Dap; or Lys; at $P^2$ and the side chain of Glu; Asp; Glu-$NH_2$; or Asp-$NH_2$; at $P^{11}$; or the side chain of Glu; or Asp; at $P^2$ and the side chain of Dab; Dap; Lys; Dab-$NH_2$; Dap-$NH_2$; or Lys-$NH_2$; at $P^{11}$; and/or
$P^4$ and $P^9$ taken together form an interstrand linking bis (amino acid)-structure based on the linkage of two L amino acid residues; following
connection of the side chain of Cys; Pen; or Hcy; with the side chain of Cys; Pen; or Hcy; by a disulfide linkage; or
connection of the side chain of Asp; or Glu; with the side chain of Dab; or Dap; by a lactam linkage; or
$P^4$ and $P^9$ taken together form a salt bridge based on the electrostatic interaction between the side chain of Dab; Dap; or Lys; at $P^4$ and the side chain of Glu; or Asp; at $P^9$; or the side chain of Glu; or Asp; at $P^4$ and the side chain of Dab; Dap; or Lys; at $P^9$;
$X^{14}$; $P^1$; $P^2$; $P^3$; $P^4$; $P^5$; $P^6$; $P^7$; $P^8$; $P^9$; and $P^{10}$ are as defined above for module A in embodiment 14, wherein s=1, t=1, and u=1;
$P^{11}$ is Ala; Ser; Thr; Dab; Glu; Ser-$NH_2$; Dab-$NH_2$; Ala-$NH_2$; Thr-$NH_2$; or Glu-$NH_2$;
with the proviso that,
if $P^3$ is Ser; Thr; or Val; then $P^1$; or $P^{10}$; is Tyr; and
if $P^8$ is Val; then $P^{10}$ is Trp; and
the combined number of the amino acid residue Gly in above module A must not exceed two; and
the positions P of the amino acid residues Gly must not be in direct vicinity;
with the further proviso that,
if linker L, as defined below, is connected with module A by a carbonyl (C=O) point of attachment of $P^5$; $P^6$; or $P^7$; then
$P^5$; $P^6$; or $P^7$; is Glu; or $^D$Glu;
if s=1, t=0, and u=0; and
$P^1$ and $X^{12}$ taken together form an interstrand linking bis (amino acid)-structure based on the linkage of two L amino acid residues; following
connection of the side chain of Cys; Pen; Hcy; Ac-Cys; Ac-Pen; or Ac-Hcy; with the side chain of Cys; Pen; Hcy; Cys-$NH_2$; Pen-$NH_2$; or Hcy-$NH_2$; by a disulfide linkage; and/or
$P^2$ and $P^{11}$ taken together form an interstrand linking bis (amino acid)-structure based on the linkage of two L amino acid residues; following
connection of the side chain of Cys; Pen; or Hcy; with the side chain of Cys; Pen; or Hcy; by a disulfide linkage; or
connection of the side chain of Dab; Dab(Me); or Dap; with the side chain of Glu; or Asp; by a lactam linkage; or
$P^2$ and $P^{11}$ taken together form a salt bridge based on the electrostatic interaction between the side chain of Dab; Dap; or Lys; at $P^2$ and the side chain of Glu; or Asp; at $P^{11}$; or the side chain of Glu; or Asp; at $P^2$ and the side chain of Dab; Dap; or Lys; at $P^{11}$; and/or
$P^4$ and $P^9$ taken together form an interstrand linking bis (amino acid)-structure based on the linkage of two L amino acid residues; following
connection of the side chain of Cys; Pen; or Hcy; with the side chain of Cys; Pen; or Hcy; by a disulfide linkage; or
connection of the side chain of Asp; or Glu; with the side chain of Dab; or Dap; by a lactam linkage; or
$P^4$ and $P^9$ taken together form a salt bridge based on the electrostatic interaction between the side chain of Dab; Dap; or Lys; at $P^4$ and the side chain of Glu; or Asp; at $P^9$; or the side chain of Glu; or Asp; at $P^4$ and the side chain of Dab; Dap; or Lys; at $P^9$;
$P^1$ is Val; NMeVal; $^D$Val; Leu; Ile; Nle; Phe; Tyr; Ser; Leu(3R)OH; Nva; HOVal; Ac-Val; Ac-$^D$Val; Ac-Leu; Ac-Ile; Ac-Phe; Prop-Val; Ac-Nle; Ac-Tyr; Ac-Ser; Ac-Leu(3R)OH; Ac-Nva; 3MeButA; 2MePropA; or 6MeHeptA;
$P^2$; $P^3$; $P^4$; $P^5$; $P^6$; $P^7$; $P^8$; $P^9$; and $P^{10}$; and $P^{11}$ are as defined above for module A in embodiment 14, wherein s=1, t=1, and u=1;
$X^{12}$ is Val; Ser; Thr; Dab; Tyr; Serol; Throl; $^D$Throl; Tyrol; Glyol; Val-$NH_2$; Ser-$NH_2$; Ser-NHMe; Ser-OiPr; Thr-$NH_2$; Leu(3R)OH; Asn; Dab-$NH_2$; or Tyr-$NH_2$;
with the proviso that,
if $P^1$ is Ser; Ac-Ser; Leu(3R)OH; or Ac-Leu(3R)OH; then $X^{12}$ is Val; Val-$NH_2$; Ser-$NH_2$; Ser-NHMe; Ser-OiPr; Thr-$NH_2$; or Leu(3R)OH; and
if $P^3$ is Ser; Thr; or Val; then $P^1$; is Tyr; or Ac-Tyr; or $P^{10}$ is Tyr; or $X^{12}$ is Tyr; Tyrol; or Tyr-$NH_2$; and
if $P^8$ is Val; then $P^{10}$ is Trp; and
if $P^{10}$ is Ser; then $X^{12}$ is Val; or Val-$NH_2$; and
the combined number of the amino acid residue Gly in above module A must not exceed two; and
the positions P of the amino acid residues Gly must not be in direct vicinity;
with the further proviso that,
if $P^1$ and $X^{12}$ taken together form an interstrand linkage, as defined above; then $P^2$ and $P^{11}$ taken together are not forming an interstrand linkage or salt bridge, as defined above;
with the further proviso that,
if linker L, as defined below, is connected with module A by a carbonyl (C=O) point of attachment of $P^5$; $P^6$; or $P^7$; then
$P^5$; $P^6$; or $P^7$; is Glu; or $^D$Glu;

if s=0, t=0, and u=0; and
P² and P¹¹ taken together form an interstrand linking bis (amino acid)-structure based on the linkage of two L amino acid residues; following
connection of the side chain of Cys; Pen; or Hcy; with the side chain of Cys; Pen; Hcy; Cys-NH₂; Pen-NH₂; or Hcy-NH₂; by a disulfide linkage; or
connection of the side chain of Dab; Dab(Me); or Dap; at P² with the side chain of Glu; Asp; Glu-NH₂; or Asp-NH₂; at P¹¹; or the side chain Glu; or Asp; at P² with the side chain of Dab; Dap; Dab-NH₂; or Dap-NH₂; at P¹¹; by a lactam linkage; or
P² and P¹¹ taken together form a salt bridge based on the electrostatic interaction between the side chain of Dab; Dap; or Lys; at P² and the side chain of Glu; Asp; Glu-NH₂; or Asp-NH₂; at P¹¹; or the side chain of Glu; or Asp; at P² and the side chain of Dab; Dap; Lys; Dab-NH₂; Dap-NH₂; or Lys-NH₂; at P¹¹; and/or
P⁴ and P⁹ taken together form an interstrand linking bis (amino acid)-structure based on the linkage of two L amino acid residues; following
connection of the side chain of Cys; Pen; or Hcy; with the side chain of Cys; Pen; or Hcy; by a disulfide linkage; or
connection of the side chain of Asp; or Glu; with the side chain of Dab; or Dap; by a lactam linkage; or
P⁴ and P⁹ taken together form a salt bridge based on the electrostatic interaction between the side chain of Dab; Dap; or Lys; at P⁴ and the side chain of Glu; or Asp; at P⁹; or the side chain of Glu; or Asp; at P⁴ and the side chain of Dab; Dap; or Lys; at P⁹;
P¹ is Val; NMeVal; $^D$Val; Leu; Ile; Nle; Phe; Tyr; Ser; Leu(3R)OH; Nva; HOVal; Ac-Val; Ac-$^D$Val; Ac-Leu; Ac-Ile; Ac-Phe; Prop-Val; Ac-Nle; Ac-Tyr; Ac-Ser; Ac-Leu(3R)OH; Ac-Nva; 3MeButA; 2MePropA; or 6MeHeptA;
P²; P³; P⁴; P⁵; P⁶; P⁷; P⁸; P⁹; and P¹⁰ are as defined above for module A in embodiment 14, wherein s=1, t=1, and u=1;
P¹¹ is Ala; Ser; Thr; Dab; Glu; Ser-NH₂; Dab-NH₂; Ala-NH₂; Thr-NH₂; or Glu-NH₂;
with the proviso that,
if P³ is Ser; Thr; or Val; then P¹; is Tyr; or Ac-Tyr; or P¹⁰ is Tyr; and
if P⁸ is Val; then P¹⁰ is Trp; and
the combined number of the amino acid residue Gly in above module A must not exceed two; and
the positions P of the amino acid residues Gly must not be in direct vicinity;
with the further proviso that,
if linker L, as defined below, is connected with module A by a carbonyl (C=O) point of attachment of P⁵; P⁶; or P⁷; then
P⁵; P⁶; or P⁷; is Glu; or $^D$Glu;
if s=0, t=0, and u=0; and alternatively
P¹¹ is connected from the α-carbonyl point of attachment to the ω-nitrogen (N) of P²;
P¹ is Val; NMeVal; $^D$Val; Leu; Ile; Nle; Phe; Tyr; Ser; Leu(3R)OH; Nva; HOVal; Ac-Val; Ac-$^D$Val; Ac-Leu; Ac-Ile; Ac-Phe; Prop-Val; Ac-Nle; Ac-Tyr; Ac-Ser; Ac-Leu(3R)OH; Ac-Nva; 3MeButA; 2MePropA; or 6MeHeptA;
P² is Orn; or Dab;
P²; P³; P⁴; P⁵; P⁶; P⁷; P⁸; P⁹; and P¹⁰ are as defined above for module A in embodiment 14, wherein s=1, t=1, and u=1;
P¹¹ is $^D$Thr; $^D$Hse; $^D$Asn; $^D$Gln; $^D$Glu; $^D$Val; $^D$Tyr; $^D$Dab; $^D$Orn; $^D$Lys;

with the proviso that,
if P³ is Ser; Thr; or Val; then P¹; is Tyr; or Ac-Tyr; or P¹⁰ is Tyr; and
if P⁸ is Val; then P¹⁰ is Trp; and
the combined number of the amino acid residue Gly in above module A must not exceed two; and
the positions P of the amino acid residues Gly must not be in direct vicinity;
with the further proviso that,
if linker L, as defined below, is connected with module A by a carbonyl (C=O) point of attachment of P⁵; P⁶; or P⁷; then
P⁵; P⁶; or P⁷; is Glu; or $^D$Glu;
for module B consisting of single elements Q being connected in either direction from the carbonyl (C=O) point of attachment to the nitrogen (N) of the next element with the proviso that Q⁷ is connected from the α-carbonyl (C=O) point of attachment to the ω-nitrogen (N) of Q¹,
Q¹ is Dab;
Q², Q⁵ and Q⁶ are Dab;
Q³ is $^D$Leu; or $^D$Phe;
Q⁴ is Leu; Ile; Leu(3R)OH; Abu; Nva; Thr; or alloThr;
Q⁷ is Thr; or Leu;
for a linker L consisting of k=1 or 3 single elements L being connected in either direction from the carbonyl (C=O) point of attachment to the nitrogen (N) of the next element,
if k=1,
L¹ is $^D$Dab;
If k=3,
L¹ is Dab; $^D$Dab; $^D$Dap; or NMeDab;
L² is Thr; Hse; or Ser;
L³ is Dap; Dab; $^D$Dab; or $^D$Dap;
said linker L being connected with module B from the carbonyl (C=O) point of attachment of L$^k$ to the α-nitrogen (N) of Q¹ and,
if k=1 or 3, being connected with module A from the carbonyl (C=O) point of attachment of P⁵; P⁶; or P⁷; to the nitrogen (N) of L¹;
or a pharmaceutically acceptable salt thereof.

In a more preferred embodiment (16) of the invention the elements of formula (I) are defined as follows,
for module A,
s=1, t=0, and u=0;
P¹ and X¹² taken together form an interstrand linking bis (amino acid)-structure based on the linkage of two L amino acid residues; following
connection of the side chain of Cys; Pen; Hcy; Ac-Cys; Ac-Pen; or Ac-Hcy; with the side chain of Cys; Pen; Hcy; Cys-NH₂; Pen-NH₂; or Hcy-NH₂; by a disulfide linkage; and/or
P² and P¹¹ taken together form an interstrand linking bis (amino acid)-structure based on the linkage of two L amino acid residues; following
connection of the side chain of Cys; Pen; or Hcy; with the side chain of Cys; Pen; or Hcy; by a disulfide linkage; or
connection of the side chain of Dab; Dab(Me); or Dap; with the side chain of Glu; or Asp; by a lactam linkage; or
P² and P¹¹ taken together form a salt bridge based on the electrostatic interaction between the side chain of Dab; Dap; or Lys; at P² and the side chain of Glu; or Asp; at P¹¹; or the side chain of Glu; or Asp; at P² and the side chain of Dab; Dap; or Lys; at P¹¹; and/or
P⁴ and P⁹ taken together form an interstrand linking bis (amino acid)-structure based on the linkage of two L amino acid residues; following
connection of the side chain of Cys; Pen; or Hcy; with the side chain of Cys; Pen; or Hcy; by a disulfide linkage; or connection of the side chain of Asp; or Glu; with the side chain of Dab; or Dap; by a lactam linkage; or $P^4$ and $P^9$ taken together form a salt bridge based on the electrostatic interaction between the side chain of Dab; Dap; or Lys; at $P^4$ and the side chain of Glu; or Asp; at $P^9$; or the side chain of Glu; or Asp; at $P^4$ and the side chain of Dab; Dap; or Lys; at $P^9$;

$P^1$ is Val; NMeVal; $^D$Val; Leu; Ile; Nle; Phe; Tyr; Ser; Leu(3R)OH; Nva; HOVal; Ac-Val; Ac-$^D$Val; Ac-Leu; Ac-Ile; Ac-Phe; Prop-Val; Ac-Nle; Ac-Tyr; Ac-Ser; Ac-Leu(3R)OH; Ac-Nva; 3MeButA; 2MePropA; or 6MeHeptA;

$P^2$; $P^3$; $P^4$; $P^5$; $P^6$; $P^7$; $P^8$; $P^9$; and $P^{10}$; and $P^{11}$ are as defined above for module A in embodiment 14, wherein s=1, t=1, and u=1;

$X^{12}$ is Val; Ser; Thr; Dab; Tyr; Serol; Throl; $^D$Throl; Tyrol; Glyol; Val-NH$_2$; Ser-NH$_2$; Ser-NHMe; Ser-OiPr; Thr-NH$_2$; Leu(3R)OH; Asn; Dab-NH$_2$; or Tyr-NH$_2$;

with the proviso that,
if $P^1$ is Ser; Ac-Ser; Leu(3R)OH; or Ac-Leu(3R)OH; then $X^{12}$ is Val; Val-NH$_2$; Ser-NH$_2$; Ser-NHMe; Ser-OiPr; Thr-NH$_2$; or Leu(3R)OH; and
if $P^3$ is Ser; Thr; or Val; then $P^1$; is Tyr; or Ac-Tyr; or $P^{10}$ is Tyr; or $X^{12}$ is Tyr; Tyrol; or Tyr-NH$_2$; and
if $P^8$ is Val; then $P^{10}$ is Trp; and
if $P^{10}$ is Ser; then $X^{12}$ is Val; or Val-NH$_2$; and
the combined number of the amino acid residue Gly in above module A must not exceed two; and
the positions P of the amino acid residues Gly must not be in direct vicinity;
with the further proviso that,
if $P^1$ and $X^{12}$ taken together form an interstrand linkage, as defined above;
then $P^2$ and $P^{11}$ taken together are not forming an interstrand linkage or salt bridge, as defined above;
with the further proviso that,
if linker L, as defined below, is connected with module A by a carbonyl (C=O) point of attachment of $P^5$; $P^6$; or $P^7$; then
$P^5$; $P^6$; or $P^7$; is Glu; or $^D$Glu;

for module B consisting of single elements Q being connected in either direction from the carbonyl (C=O) point of attachment to the nitrogen (N) of the next element with the proviso that $Q^7$ is connected from the α-carbonyl (C=O) point of attachment to the ω-nitrogen (N) of $Q^1$,
$Q^1$ is Dab;
$Q^2$, $Q^5$ and $Q^6$ are Dab;
$Q^3$ is $^D$Leu; or $^D$Phe;
$Q^4$ is Leu; Ile; Leu(3R)OH; Abu; Nva; Thr; or alloThr;
$Q^7$ is Thr; or Leu;

for a linker L consisting of k=1 or 3 single elements L being connected in either direction from the carbonyl (C=O) point of attachment to the nitrogen (N) of the next element,
if k=1,
$L^1$ is $^D$Dab;
If k=3,
$L^1$ is Dab; $^D$Dab; $^D$Dap; or NMeDab;
$L^2$ is Thr; Hse; or Ser;
$L^3$ is Dap; Dab; $^D$Dab; or $^D$Dap;
said linker L being connected with module B from the carbonyl (C=O) point of attachment of $L^k$ to the α-nitrogen (N) of $Q^1$ and,
if k=1 or 3, being connected with module A from the carbonyl (C=O) point of attachment of $P^5$; $P^6$; or $P^7$; to the nitrogen (N) of $L^1$;
or a pharmaceutically acceptable salt thereof.

In another embodiment (17) of the invention the elements of formula (I) are defined as follows,
for module A,
if s=1, t=1, and u=1; and
$X^{14}$ and $X^{13}$ taken together form an interstrand linking bis(amino acid)-structure based on the linkage of two L amino acid residues; following
connection of the side chain of Ac-Cys; or 3MPA with the side chain of Cys-NH$_2$ by a disulfide linkage; or
connection of the side chain of Ac-Dab; at $X^{14}$ with the side chain of Glu-NH$_2$; at $X^{13}$; by a lactam linkage; or
$X^{14}$ and $X^{13}$ taken together form a salt bridge based on the electrostatic interaction between the side chain of Ac-Dab at $X^{14}$ and the side chain of Glu-NH$_2$ at $X^{13}$; or the side chain of Ac-Glu at $X^{14}$ and the side chain of Dab-NH$_2$ at $X^{13}$; and/or
$P^2$ and $P^{11}$ taken together form an interstrand linking bis (amino acid)-structure based on the linkage of two L amino acid residues; following
connection of the side chain of Cys; with the side chain of Cys by a disulfide linkage; or
$P^2$ and $P^{11}$ taken together form a salt bridge based on the electrostatic interaction between the side chain of Dab; at $P^2$ and the side chain of Glu; at $P^{11}$;
$X^{14}$ is $^D$Ser; pGlu; or $^D$pGlu;
$P^1$ is Val; Leu; or Leu(3R)OH;
$P^2$ is Thr;
$P^3$ is Tyr;
$P^4$ is Dab; Dap; Ser; or Gly;
$P^6$ is $^D$Dab; $^D$Ser; $^D$Hse; $^D$Ala; or Gly;
$P^7$ is Ser; Hse; Thr; Dab; Ala; or Gly;
$P^8$ is Trp;
$P^9$ is Ser; Hse; Glu; Ala; or Gly;
$P^{10}$ is Val; or tBuGly; Ile; or Nva;
$P^{11}$ is Ala; or Ser;
$X^{12}$ is Val; Ser; or Thr;
$X^{13}$ is $^D$Ala; $^D$Ser; $^D$Ala-NH$_2$; or $^D$Ser-NH$_2$;
with the proviso that,
if $P^1$ is Leu(3R)OH; then $X^{12}$ is Val; and
the combined number of the amino acid residue Gly in above module A must not exceed two; and
the positions P of the amino acid residues Gly must not be in direct vicinity;
with the further proviso that,
if linker L, as defined below, is connected with module A by a carbonyl (C=O) point of attachment of $P^5$; then
$P^5$ is Glu;

if s=1, t=0, and u=1; and
$P^2$ and $P^{11}$ taken together form an interstrand linking bis (amino acid)-structure based on the linkage of two L amino acid residues; following
connection of the side chain of Cys; with the side chain of Cys by a disulfide linkage; and/or
$P^4$ and $P^9$ taken together form an interstrand linking bis (amino acid) structure based on the linkage of two L amino acid residues; following
connection of the side chain of Cys; with the side chain of Cys by a disulfide linkage;
$X^{14}$ is pGu; $^D$pGlu; Ac-Dab; or 6MeHeptA;
$P^1$ is Val; Leu; or Leu(3R)OH;
$P^2$ is Thr;
$P^3$ is Tyr;
$P^4$ is Dap; Dab; Ser; or Gly;
$P^6$ is $^D$Dab; $^D$Ser; $^D$Hse; $^D$Ala; or Gly;
$P^7$ is Ser; Thr; Dab; Hse; Ala; or Gly;
$P^8$ is Trp;
$P^9$ is Ser; Hse; Ala; or Gly;

P¹⁰ is Val; tBuGly; Ile; or Nva;
P¹¹ is Ala;
X¹² is Val-NH₂; Ser-NH₂; Thr-NH₂; Throl; Glyol; Val; Ser; or Thr;
with the proviso that,
  if P¹ is Leu(3R)OH; then X¹² is Val; or Val-NH₂; and
  the combined number of the amino acid residue Gly in above module A must not exceed two; and
  the positions P of the amino acid residues Gly must not be in direct vicinity;
with the further proviso that,
  if linker L, as defined below, is connected with module A by a carbonyl (C=O) point of attachment of P⁵; then P⁵ is Glu;
if s=1, t=1, and u=0; and
P² and P¹¹ taken together form an interstrand linking bis (amino acid)-structure based on the linkage of two L amino acid residues; following
connection of the side chain of Cys; with the side chain of Cys by a disulfide linkage; and/or
P⁴ and P⁹ taken together form an interstrand linking bis (amino acid) structure based on the linkage of two L amino acid residues; following
connection of the side chain of Cys; with the side chain of Cys by a disulfide linkage;
P¹ is Val; HOVal; or Ac-Val;
P² is Thr;
P³ is Val; Ser; or Thr;
P⁴ is Dab; Dap; Ser; or Gly;
P⁶ is ᴰDab; ᴰSer; ᴰHse; ᴰAla; or Gly;
P⁷ is Hse; Ser; Thr; Dab; Ala; or Gly;
P⁸ is Trp;
P⁹ is Ser; Hse; Ala; or Gly;
P¹⁰ is tBuGly; Val; Ile; or Nva;
P¹¹ is Ala; or Ser;
X¹² is Tyr; Ala; Gly; or ᴰAla;
X¹³ is Glyol; ᴰAla; ᴰSer; ᴰThr; ᴰAsp; ᴰAla-NH₂; ᴰSer-NH₂; Asp; or Asn;
with the proviso that,
  the combined number of the amino acid residue Gly in above module A must not exceed two; and
  the positions P of the amino acid residues Gly must not be in direct vicinity;
with the further proviso that,
  if linker L, as defined below, is connected with module A by a carbonyl (C=O) point of attachment of P⁵; then P⁵ is Glu;
if s=0, t=0, and u=1; and
P² and P¹¹ taken together form an interstrand linking bis (amino acid)-structure based on the linkage of two L amino acid residues; following
connection of the side chain of Cys; with the side chain of Cys by a disulfide linkage; and/or
P⁴ and P⁹ taken together form an interstrand linking bis (amino acid) structure based on the linkage of two L amino acid residues; following
connection of the side chain of Cys; with the side chain of Cys by a disulfide linkage;
X¹⁴ is Ac-Dab; pGlu; or ᴰpGlu;
P¹ is Val; Leu; or Leu(3R)OH;
P² is Thr;
P³ is Tyr;
P⁴ is Dap; Dab; Ser; or Gly;
P⁶ is ᴰDab; ᴰSer; ᴰHse; ᴰAla; or Gly;
P⁷ is Ser; Hse; Thr; Dab; Ala; or Gly;
P⁸ is Trp;
P⁹ is Ser; Hse; Ala; or Gly;

P¹⁰ is tBuGly; Val; Ile; or Nva;
P¹¹ is Dab-NH₂; Ala-NH₂; Dab; or Ala;
with the proviso that,
  the combined number of the amino acid residue Gly in above module A must not exceed two; and
  the positions P of the amino acid residues Gly must not be in direct vicinity;
with the further proviso that,
  if linker L, as defined below, is connected with module A by a carbonyl (C=O) point of attachment of P⁵; then P⁵ is Glu;
if s=1, t=0, and u=0; and
P¹ and X¹² taken together form an interstrand linking bis (amino acid) structure based on the linkage of two L amino acid residues; following
connection of the side chain of Ac-Pen; with the side chain of Cys-NH₂; by a disulfide linkage; and/or
P² and P¹¹ taken together form an interstrand linking bis (amino acid)-structure based on the linkage of two L amino acid residues; following
connection of the side chain of Cys; hCys; or Pen; with the side chain of Cys; or Pen; by a disulfide linkage; or
connection of the side chain of Dab; or Dab(Me); with the side chain of Asp; or Glu; by a lactam linkage; or
P² and P¹¹ taken together form a salt bridge based on the electrostatic interaction between the side chain of Asp; or Glu; at P² and the side chain of Lys; or Dab; at P¹¹; or
the side chain of Dab at P² and the side chain of Asp; or Glu; at P¹¹; and/or
P⁴ and P⁹ taken together form an interstrand linking bis (amino acid) structure based on the linkage of two L amino acid residues; following
connection of the side chain of Cys; or Pen; with the side chain of Cys; or Pen; by a disulfide linkage; or
connection of the side chain of Dab; with the side chain of Asp; by a lactam linkage; or
P⁴ and P⁹ taken together form a salt bridge based on the electrostatic interaction between the side chain of Glu; at P⁴ and the side chain of Dap; at P⁹; or the side chain of Dab; or Lys; at P⁴ and the side chain of Asp; or Glu; at P⁹;
P¹ is Val; Ac-Val; NMeVal; HOVal; Ac-ᴰVal; Prop-Val; Leu; Nle; Ac-Nle; Tyr; Ac-Tyr; Ser; Ac-Ser; Ac-Leu(3R)OH; pGlu; 3MeButA; 2MePropA; or 6MeHeptA;
P² is Ala; Val; tBuGly; Dab; Dap; or Thr;
P³ is Val; Ser; Thr; or Tyr;
P⁴ is Dab; Dap; Ser; Thr; His; or Gly
P⁵ is Gly; Ala; Val; Abu; His; Thr; or Orn;
P⁶ is Gly; ᴰDab; ᴰSer; ᴰHse; ᴰAla; or ᴰArg;
P⁷ is Ser; Hse; Thr; Dab; Dap; Ala; or Gly;
P⁸ is Trp; or Val;
P⁹ is Ser; Thr; Hse; Glu; Ala; His; Dab; alloThr; or Gly;
P¹⁰ is tBuGly; Val; Ile; Nva; Tyr; or Trp;
P¹¹ is Ala; Ser; Thr; Glu; or Dab;
X¹² is Glyol; Ser; Serol; Ser-NH₂; Ser-NHMe; Ser-OiPr; Thr-NH₂; Leu(3R)OH; Asn; Throl; ᴰThrol; Val-NH₂; Tyr-NH₂; Tyrol; or Dab-NH₂;
with the proviso that,
  if P¹ is Ser; Ac-Leu(3R)OH; or Ac-Ser; then X¹² is Val-NH₂; or Leu(3R)OH; and
  if P³ is Ser; Thr; or Val; then P¹ is Tyr; or Ac-Tyr; or P¹⁰ is Tyr; or X¹² is Tyr-NH₂; or Tyrol; and
  if P⁸ is Val; then P¹⁰ is Trp; and
  the combined number of the amino acid residue Gly in above module A must not exceed two; and
  the positions P of the amino acid residues Gly must not be in direct vicinity;

with the further proviso that,
if $P^1$ and $X^{12}$ taken together form an interstrand linkage or salt bridge, as defined above; then $P^2$ and $P^{11}$ taken together are not forming an interstrand linkage or salt bridge, as defined above;
with the further proviso that,
if linker L, as defined below, is connected with module A by a carbonyl (C=O) point of attachment of $P^5$; $P^6$; or $P^7$; then;
$P^5$; $P^6$; or $P^7$ is Glu; or $^D$Glu;
if s=0, t=0, and u=0; and
$P^2$ and $P^{11}$ taken together form an interstrand linking bis (amino acid)-structure based on the linkage of two L amino acid residues; following
connection of the side chain of Cys with the side chain of Cys by a disulfide linkage; and/or
$P^4$ and $P^9$ taken together form an interstrand linking bis (amino acid) structure based on the linkage of two L amino acid residues; following
connection of the side chain of Cys with the side chain of Cys by a disulfide linkage;
$P^1$ is Ac-Val; NMeVal; HOVal; or Val;
$P^2$ is Thr;
$P^3$ is Tyr;
$P^4$ is Dab; Dap; Ser; Thr; or Gly;
$P^6$ is $^D$Dab; $^D$Ser; $^D$Hse; $^D$Ala; or Gly;
$P^7$ is Ser; Hse; Thr; Dab; Ala; or Gly;
$P^8$ is Trp;
$P^9$ is Ser; Hse; Ala; or Gly;
$P^{10}$ is tBuGly; Val; Ile; or Nva;
$P^{11}$ is Ser-NH$_2$; Ser; Ala; or Ala-NH$_2$;
with the proviso that,
the combined number of the amino acid residue Gly in above module A must not exceed two; and
the positions P of the amino acid residues Gly must not be in direct vicinity;
with the further proviso that,
if linker L, as defined below, is connected with module A by a carbonyl (C=O) point of attachment of $P^5$ then $P^5$ is Glu;
if s=0, t=0, and u=0; and alternatively
$P^{11}$ is connected from the α-carbonyl point of attachment to the ω-nitrogen (N) of $P^2$;
$P^1$ is Ac-Val; HOVal; Ac-Leu; Ac-Ile; Ac-Nle; or Ac-Phe; Val; Leu; Ile; Nle; or Phe;
$P^2$ is Orn; or Dab;
$P^3$ is Tyr;
$P^4$ is Dab; Dap; Ser; Thr; or Gly;
$P^6$ is $^D$Dab; $^D$Ser; $^D$Hse; $^D$Ala; or Gly;
$P^7$ is Ser; Hse; Thr; Dab; Ala; or Gly;
$P^8$ is Trp;
$P^9$ is Ser; Hse; Ala; or Gly;
$P^{10}$ is tBuGly; Val; Ile; or Nva;
$P^{11}$ is $^D$Thr; $^D$Hse; $^D$Asn; $^D$Gln; $^D$Glu; $^D$Val; $^D$Tyr; $^D$Dab; $^D$Orn; $^D$Lys;
with the proviso that,
the combined number of the amino acid residue Gly in above module A must not exceed two; and
the positions P of the amino acid residues Gly must not be in direct vicinity;
with the further proviso that,
if linker L, as defined below, is connected with module A by a carbonyl (C=O) point of attachment of $P^5$ then $P^5$ is Glu;
or a pharmaceutically acceptable salt thereof.

In a preferred embodiment (18) of the invention the elements of formula (I) are defined as follows,
for module A,
s=0, t=0, and u=0; or s=1, t=0, and u=0; or s=0, t=0, and u=1;
if s=0, t=0, and u=1; and
$P^2$ and $P^{11}$ taken together form an interstrand linking bis (amino acid)-structure based on the linkage of two L amino acid residues; following
connection of the side chain of Cys; with the side chain of Cys by a disulfide linkage; and/or
$P^4$ and $P^9$ taken together form an interstrand linking bis (amino acid) structure based on the linkage of two L amino acid residues; following
connection of the side chain of Cys; with the side chain of Cys by a disulfide linkage;
$X^{14}$ is Ac-Dab; pGlu; or $^D$pGlu;
$P^1$ is Val; Leu; or Leu(3R)OH;
$P^2$ is Thr;
$P^3$ is Tyr;
$P^4$ is Dap; Dab; Ser; or Gly;
$P^6$ is $^D$Dab; $^D$Ser; $^D$Hse; $^D$Ala; or Gly;
$P^7$ is Ser; Hse; Thr; Dab; Ala; or Gly;
$P^8$ is Trp;
$P^9$ is Ser; Hse; Ala; or Gly;
$P^{10}$ is tBuGly; Val; Ile; or Nva;
$P^{11}$ is Dab-NH$_2$; Ala-NH$_2$; Dab; or Ala;
with the proviso that,
the combined number of the amino acid residue Gly in above module A must not exceed two; and
the positions P of the amino acid residues Gly must not be in direct vicinity;
with the further proviso that,
if linker L, as defined below, is connected with module A by a carbonyl (C=O) point of attachment of $P^5$; then $P^5$ is Glu;
if s=1, t=0, and u=0; and
$P^1$ and $X^{12}$ taken together form an interstrand linking bis (amino acid) structure based on the linkage of two L amino acid residues; following
connection of the side chain of Ac-Pen; with the side chain of Cys-NH$_2$; by a disulfide linkage; and/or
$P^2$ and $P^{11}$ taken together form an interstrand linking bis (amino acid)-structure based on the linkage of two L amino acid residues; following
connection of the side chain of Cys; hCys; or Pen; with the side chain of Cys; or Pen; by a disulfide linkage; or
connection of the side chain of Dab; or Dab(Me); with the side chain of Asp; or Glu; by a lactam linkage; or
$P^2$ and $P^{11}$ taken together form a salt bridge based on the electrostatic interaction between the side chain of Asp; or Glu; at $P^2$ and the side chain of Lys; or Dab; at $P^{11}$; or
the side chain of Dab at $P^2$ and the side chain of Asp; or Glu; at $P^{11}$; and/or
$P^4$ and $P^9$ taken together form an interstrand linking bis (amino acid) structure based on the linkage of two L amino acid residues; following
connection of the side chain of Cys; or Pen; with the side chain of Cys; or Pen; by a disulfide linkage; or
connection of the side chain of Dab; with the side chain of Asp; by a lactam linkage; or
$P^4$ and $P^9$ taken together form a salt bridge based on the electrostatic interaction between the side chain of Glu; at $P^4$ and the side chain of Dap; at $P^9$; or the side chain of Dab; or Lys; at $P^4$ and the side chain of Asp; or Glu; at $P^9$;
$P^1$ is Val; Ac-Val; NMeVal; HOVal; Ac-$^D$Val; Prop-Val; Leu; Nle; Ac-Nle; Tyr; Ac-Tyr; Ser; Ac-Ser; Ac-Leu(3R)OH; pGlu; 3MeButA; 2MePropA; or 6MeHeptA;
$P^2$ is Ala; Val; tBuGly; Dab; Dap; or Thr;
$P^3$ is Val; Ser; Thr; or Tyr;

P⁴ is Dab; Dap; Ser; Thr; His; or Gly
P⁵ is Gly; Ala; Val; Abu; His; Thr; or Orn;
P⁶ is Gly; ᴰDab; ᴰSer; ᴰHse; ᴰAla; or ᴰArg;
P⁷ is Ser; Hse; Thr; Dab; Dap; Ala; or Gly;
P⁸ is Trp; or Val;
P⁹ is Ser; Thr; Hse; Glu; Ala; His; Dab; alloThr; or Gly;
P¹⁰ is tBuGly; Val; Ile; Nva; Tyr; or Trp;
P¹¹ is Ala; Ser; Thr; Glu; or Dab;
X¹² is Glyol; Ser; Serol; Ser-NH₂; Ser-NHMe; Ser-OiPr; Thr-NH₂; Leu(3R)OH; Asn; Throl; ᴰThrol; Val-NH₂; Tyr-NH₂; Tyrol; or Dab-NH₂;
with the proviso that,
  if P¹ is Ser; Ac-Leu(3R)OH; or Ac-Ser; then X¹² is Val-NH₂; or Leu(3R)OH; and
  if P³ is Ser; Thr; or Val; then P¹ is Tyr; or Ac-Tyr; or P¹⁰ is Tyr; or X¹² is Tyr-NH₂; or Tyrol; and
  if P⁸ is Val; then P¹⁰ is Trp; and
  the combined number of the amino acid residue Gly in above module A must not exceed two; and
  the positions P of the amino acid residues Gly must not be in direct vicinity;
with the further proviso that,
  if P¹ and X¹² taken together form an interstrand linkage or salt bridge, as defined above; then P² and P¹¹ taken together are not forming an interstrand linkage or salt bridge, as defined above;
with the further proviso that,
  if linker L, as defined below, is connected with module A by a carbonyl (C=O) point of attachment of P⁵; P⁶; or P⁷; then;
P⁵; P⁶; or P⁷ is Glu; or ᴰGlu;
if s=0, t=0, and u=0; and
P² and P¹¹ taken together form an interstrand linking bis (amino acid)-structure based on the linkage of two L amino acid residues; following
connection of the side chain of Cys with the side chain of Cys by a disulfide linkage; and/or
P⁴ and P⁹ taken together form an interstrand linking bis (amino acid) structure based on the linkage of two L amino acid residues; following
connection of the side chain of Cys with the side chain of Cys by a disulfide linkage;
P¹ is Ac-Val; NMeVal; HOVal; or Val;
P² is Thr;
P³ is Tyr;
P⁴ is Dab; Dap; Ser; Thr; or Gly;
P⁶ is ᴰDab; ᴰSer; ᴰHse; ᴰAla; or Gly;
P⁷ is Ser; Hse; Thr; Dab; Ala; or Gly;
P⁸ is Trp;
P⁹ is Ser; Hse; Ala; or Gly;
P¹⁰ is tBuGly; Val; Ile; or Nva;
P¹¹ is Ser-NH₂; Ser; Ala; or Ala-NH₂;
with the proviso that,
  the combined number of the amino acid residue Gly in above module A must not exceed two; and
  the positions P of the amino acid residues Gly must not be in direct vicinity;
with the further proviso that,
  if linker L, as defined below, is connected with module A by a carbonyl (C=O) point of attachment of P⁵ then P⁵ is Glu;
if s=0, t=0, and u=0; and alternatively
P¹¹ is connected from the α-carbonyl point of attachment to the ω-nitrogen (N) of P²;
P¹ is Ac-Val; HOVal; Ac-Leu; Ac-Ile; Ac-Nle; or Ac-Phe; Val; Leu; Ile; Nle; or Phe;
P² is Orn; or Dab;

Pᵃ is Tyr;
P⁴ is Dab; Dap; Ser; Thr; or Gly;
P⁶ is ᴰDab; ᴰSer; ᴰHse; ᴰAla; or Gly;
P⁷ is Ser; Hse; Thr; Dab; Ala; or Gly;
P⁸ is Trp;
P⁹ is Ser; Hse; Ala; or Gly;
P¹⁰ is tBuGly; Val; Ile; or Nva;
P¹¹ is ᴰThr; ᴰHse; ᴰAsn; ᴰGln; ᴰGlu; ᴰVal; ᴰTyr; ᴰDab; ᴰOrn; or ᴰLys;
with the proviso that,
  the combined number of the amino acid residue Gly in above module A must not exceed two; and
  the positions P of the amino acid residues Gly must not be in direct vicinity;
with the further proviso that,
  if linker L, as defined below, is connected with module A by a carbonyl (C=O) point of attachment of P⁵ then P⁵ is Glu;
or a pharmaceutically acceptable salt thereof.
  In a more preferred embodiment (19) of the invention the elements of formula (I) are defined as follows,
for module A,
s=1, t=0, and u=0;
P¹ and X¹² taken together form an interstrand linking bis (amino acid) structure based on the linkage of two L amino acid residues; following
connection of the side chain of Ac-Pen; with the side chain of Cys-NH₂; by a disulfide linkage; and/or
P² and P¹¹ taken together form an interstrand linking bis (amino acid)-structure based on the linkage of two L amino acid residues; following
connection of the side chain of Cys; hCys; or Pen; with the side chain of Cys; or Pen; by a disulfide linkage; or
connection of the side chain of Dab; or Dab(Me); with the side chain of Asp; or Glu; by a lactam linkage; or
P² and P¹¹ taken together form a salt bridge based on the electrostatic interaction between the side chain of Asp; or Glu; at P² and the side chain of Lys; or Dab; at P¹¹; or
the side chain of Dab at P² and the side chain of Asp; or Glu; at P¹¹; and/or
P⁴ and P⁹ taken together form an interstrand linking bis (amino acid) structure based on the linkage of two L amino acid residues; following
connection of the side chain of Cys; or Pen; with the side chain of Cys; or Pen; by a disulfide linkage; or
connection of the side chain of Dab; with the side chain of Asp; by a lactam linkage; or
P⁴ and P⁹ taken together form a salt bridge based on the electrostatic interaction between the side chain of Glu; at P⁴ and the side chain of Dap; at P⁹; or the side chain of Dab; or Lys; at P⁴ and the side chain of Asp; or Glu; at P⁹;
P¹ is Val; Ac-Val; NMeVal; HOVal; Ac-ᴰVal; Prop-Val; Leu; Nle; Ac-Nle; Tyr; Ac-Tyr; Ser; Ac-Ser; Ac-Leu(3R)OH; pGlu; 3MeButA; 2MePropA; or 6MeHeptA;
P² is Ala; Val; tBuGly; Dab; Dap; or Thr;
P³ is Val; Ser; Thr; or Tyr;
P⁴ is Dab; Dap; Ser; Thr; His; or Gly
P⁵ is Gly; Ala; Val; Abu; His; Thr; or Orn;
P⁶ is Gly; ᴰDab; ᴰSer; ᴰHse; ᴰAla; or ᴰArg;
P⁷ is Ser; Hse; Thr; Dab; Dap; Ala; or Gly;
P⁸ is Trp; or Val;
P⁹ is Ser; Thr; Hse; Glu; Ala; His; Dab; alloThr; or Gly;
P¹⁰ is tBuGly; Val; Ile; Nva; Tyr; or Trp;
P¹¹ is Ala; Ser; Thr; Glu; or Dab;
X¹² is Glyol; Ser; Serol; Ser-NH₂; Ser-NHMe; Ser-OiPr; Thr-NH₂; Leu(3R)OH; Asn; Throl; ᴰThrol; Val-NH₂; Tyr-NH₂; Tyrol; or Dab-NH₂;

with the proviso that,
if $P^1$ is Ser; Ac-Leu(3R)OH; or Ac-Ser; then $X^{12}$ is Val-NH$_2$; or Leu(3R)OH; and
if $P^3$ is Ser; Thr; or Val; then $P^1$ is Tyr; or Ac-Tyr; or $P^{10}$ is Tyr; or $X^{12}$ is Tyr-NH$_2$; or Tyrol; and
if $P^8$ is Val; then $P^{10}$ is Trp; and
the combined number of the amino acid residue Gly in above module A must not exceed two; and
the positions P of the amino acid residues Gly must not be in direct vicinity;
with the further proviso that,
if $P^1$ and $X^{12}$ taken together form an interstrand linkage or salt bridge, as defined above; then $P^2$ and $P^{11}$ taken together are not forming an interstrand linkage or salt bridge, as defined above;
with the further proviso that,
if linker L, as defined below, is connected with module A by a carbonyl (C=O) point of attachment of $P^5$; $P^6$; or $P^7$; then;
$P^5$; $P^6$; or $P^7$ is Glu; or $^D$Glu;
or a pharmaceutically acceptable salt thereof.

In a preferred embodiment (20) of the invention the elements of formula (I) are defined as follows,
for module B consisting of single elements Q being connected in either direction from the carbonyl (C=O) point of attachment to the nitrogen (N) of the next element with the proviso that $Q^7$ is connected from the α-carbonyl (C=O) point of attachment to the ω-nitrogen (N) of $Q^1$,
$Q^1$ is Dab;
$Q^2$, $Q^5$ and $Q^6$ are Dab;
$Q^3$ is $^D$Leu; or $^D$Phe;
$Q^4$ is Leu; Ile; Leu(3R)OH; Abu; Nva; Thr; or alloThr;
$Q^7$ is Thr; or Leu;
or a pharmaceutically acceptable salt thereof.

In a preferred embodiment (21) of the invention the elements of formula (I) are defined as follows,
for a linker L consisting of k=1 or 3 single elements L being connected in either direction from the carbonyl (C=O) point of attachment to the nitrogen (N) of the next element,
if k=1,
$L^1$ is $^D$Dab;
If k=3,
$L^1$ is Dab; $^D$Dab; $^D$Dap; or NMeDab;
$L^2$ is Thr; Hse; or Ser;
$L^3$ is Dap; Dab; $^D$Dab; or $^D$Dap;
said linker L being connected with module B from the carbonyl (C=O) point of attachment of $L^k$ to the α-nitrogen (N) of $Q^1$ and,
if k=1 or 3, being connected with module A from the carbonyl (C=O) point of attachment of $P^5$; $P^6$; or $P^7$; to the nitrogen (N) of $L^1$;
or a pharmaceutically acceptable salt thereof.

In another particular embodiment (22) of the invention the elements of formula (I) are defined as follows,
for module A,
s=1, t=1, and u=1; and
$X^{14}$ and $X^{13}$ taken together form an interstrand linking bis(amino acid)-structure based on the linkage of two L amino acid residues; following
connection of the side chain of Ac-Cys; or 3MPA with the side chain of Cys-NH$_2$ by a disulfide linkage; or connection of the side chain of Ac-Dab; at $X^{14}$ with the side chain of Glu-NH$_2$; at $X^{13}$; by a lactam linkage; or
$X^{14}$ and $X^{13}$ taken together form a salt bridge based on the electrostatic interaction between the side chain of Ac-Dab at $X^{14}$ and the side chain of Glu-NH$_2$ at $X^{13}$; or the side chain of Ac-Glu at $X^{14}$ and the side chain of Dab-NH$_2$ at $X^{13}$; and/or
$P^2$ and $P^{11}$ taken together form an interstrand linking bis (amino acid)-structure based on the linkage of two L amino acid residues; following
connection of the side chain of Cys; with the side chain of Cys by a disulfide linkage; or
$P^2$ and $P^{11}$ taken together form a salt bridge based on the electrostatic interaction between the side chain of Dab; at $P^2$ and the side chain of Glu; at $P^{11}$;
$X^{14}$ is $^D$Ser;
$P^1$ is Val;
$P^2$ is Thr;
$P^3$ is Tyr;
$P^4$ is Ala; Dab; Dap; or Ser;
$P^6$ is $^D$Dab;
$P^7$ is Ser; Hse; Thr; or Dab;
$P^8$ is Trp;
$P^9$ is Ser; or Glu;
$P^{10}$ is Val; or tBuGly;
$P^{11}$ is Ala; or Ser;
$X^{12}$ is Val; Ser; or Thr;
$X^{13}$ is $^D$Ala; or $^D$Ser;
with the proviso that,
if linker L, as defined below, is connected with module A by a carbonyl (C=O) point of attachment of $P^5$; then $P^5$ is Glu;
for module B consisting of single elements Q being connected in either direction from the carbonyl (C=O) point of attachment to the nitrogen (N) of the next element with the proviso that $Q^7$ is connected from the α-carbonyl (C=O) point of attachment to the ω-nitrogen (N) of $Q^1$,
$Q^1$ is Dab;
$Q^2$, $Q^5$ and $Q^6$ are Dab;
$Q^3$ is $^D$Leu;
$Q^4$ is Leu;
$Q^1$ is Thr;
for a linker L consisting of k=3 single elements L being connected in either direction from the carbonyl (C=O) point of attachment to the nitrogen (N) of the next element,
$L^1$ is Dab;
$L^2$ is Thr;
$L^3$ is Dab; or Dap;
said linker L being connected with module B from the carbonyl (C=O) point of attachment of $L^k$ to the α-nitrogen (N) of $Q^1$ and,
if k=3, being connected with module A from the carbonyl (C=O) point of attachment of $P^5$ to the nitrogen (N) of $L^1$;
or a pharmaceutically acceptable salt thereof.

In another particular embodiment (23) of the invention the elements of formula (I) are defined as follows,
s=1, t=0, and u=1; and
$P^2$ and $P^{11}$ taken together form an interstrand linking bis (amino acid)-structure based on the linkage of two L amino acid residues; following
connection of the side chain of Cys; with the side chain of Cys by a disulfide linkage; and/or
$P^4$ and $P^9$ taken together form an interstrand linking bis (amino acid) structure based on the linkage of two L amino acid residues; following
connection of the side chain of Cys; with the side chain of Cys by a disulfide linkage;
$X^{14}$ is pGu; $^D$pGlu; Ac-Dab; or 6MeHeptA;
$P^1$ is Val; Leu; or Leu(3R)OH;
$P^2$ is Thr;
$P^3$ is Tyr;

P⁴ is Dap;
P⁶ is ᴰDab;
P⁷ is Ser; Thr; Dab;
P⁸ is Trp;
P⁹ is Ser;
P¹⁰ is Val; or tBuGly;
P¹¹ is Ala;
X¹² is Val-NH₂; Ser-NH₂; or Throl;
with the proviso that,
  if P¹ is Leu(3R)OH; then X¹² is Val-NH₂;
with the further proviso that,
  if linker L, as defined below, is connected with module A by a carbonyl (C=O) point of attachment of P⁵; then P⁵ is Glu;
for module B consisting of single elements Q being connected in either direction from the carbonyl (C=O) point of attachment to the nitrogen (N) of the next element with the proviso that Q⁷ is connected from the α-carbonyl (C=O) point of attachment to the ω-nitrogen (N) of Q¹,
Q¹ is Dab;
Q², Q⁵ and Q⁶ are Dab;
Q³ is ᴰLeu;
Q⁴ is Leu;
Q⁷ is Thr;
for a linker L consisting of k=3 single elements L being connected in either direction from the carbonyl (C=O) point of attachment to the nitrogen (N) of the next element,
L¹ is Dab;
L² is Thr;
L³ is Dap;
said linker L being connected with module B from the carbonyl (C=O) point of attachment of Lᵏ to the α-nitrogen (N) of Q¹ and,
if k=3, being connected with module A from the carbonyl (C=O) point of attachment of P⁵ to the nitrogen (N) of L¹;
or a pharmaceutically acceptable salt thereof.

In another particular embodiment (24) of the invention the elements of formula (I) are defined as follows,
for module A,
s=1, t=1, and u=0; and
P² and P¹¹ taken together form an interstrand linking bis (amino acid)-structure based on the linkage of two L amino acid residues; following
connection of the side chain of Cys; with the side chain of Cys by a disulfide linkage; and/or
P⁴ and P⁹ taken together form an interstrand linking bis (amino acid) structure based on the linkage of two L amino acid residues; following
connection of the side chain of Cys; with the side chain of Cys by a disulfide linkage;
P¹ is HOVal; or Ac-Val;
P² is Thr;
P³ is Val; Ser; or Thr;
P⁴ is Dab;
P⁶ is ᴰDab;
P⁷ is Hse;
P⁸ is Trp;
P⁹ is Ser;
P¹⁰ is tBuGly;
P¹¹ is Ala;
X¹² is Tyr; Ala; Gly; or ᴰAla;
X¹³ is Glyol; ᴰAla; ᴰSer; ᴰThr; ᴰAsp; ᴰAla-NH₂; ᴰSer-NH₂; Asp; or Asn;
with the proviso that,
  if linker L, as defined below, is connected with module A by a carbonyl (C=O) point of attachment of P⁵; then P⁵ is Glu;
for module B consisting of single elements Q being connected in either direction from the carbonyl (C=O) point of attachment to the nitrogen (N) of the next element with the proviso that Q⁷ is connected from the α-carbonyl (C=O) point of attachment to the ω-nitrogen (N) of Q¹,
Q¹ is Dab;
Q², Q⁵ and Q⁶ are Dab;
Q³ is ᴰLeu;
Q⁴ is Leu;
Q⁷ is Thr;
for a linker L consisting of k=3 single elements L being connected in either direction from the carbonyl (C=O) point of attachment to the nitrogen (N) of the next element,
L¹ is Dab;
L² is Thr;
L³ is Dab;
said linker L being connected with module B from the carbonyl (C=O) point of attachment of Lᵏ to the α-nitrogen (N) of Q¹ and,
if k=3, being connected with module A from the carbonyl (C=O) point of attachment of P⁵ to the nitrogen (N) of L¹;
or a pharmaceutically acceptable salt thereof.

In a particular preferred embodiment (25) of the invention the elements of formula (I) are defined as follows,
for module A,
s=0, t=0, and u=1; and
P² and P¹¹ taken together form an interstrand linking bis (amino acid)-structure based on the linkage of two L amino acid residues; following
connection of the side chain of Cys; with the side chain of Cys by a disulfide linkage; and/or
P⁴ and P⁹ taken together form an interstrand linking bis (amino acid) structure based on the linkage of two L amino acid residues; following
connection of the side chain of Cys; with the side chain of Cys by a disulfide linkage;
X¹⁴ is Ac-Dab;
P¹ is Val;
P² is Thr;
P³ is Tyr;
P⁴ is Dap;
P⁶ is ᴰDab;
P⁷ is Ser; or Dab;
P⁸ is Trp;
P⁹ is Ser;
P¹⁰ is tBuGly;
P¹¹ is Dab-NH₂;
with the proviso that,
  if linker L, as defined below, is connected with module A by a carbonyl (C=O) point of attachment of P⁵; then P⁵ is Glu;
for module B consisting of single elements Q being connected in either direction from the carbonyl (C=O) point of attachment to the nitrogen (N) of the next element with the proviso that Q⁷ is connected from the α-carbonyl (C=O) point of attachment to the ω-nitrogen (N) of Q¹,
Q¹ is Dab;
Q², Q⁵ and Q⁶ are Dab;
Q³ is ᴰLeu;
Q⁴ is Leu;
Q⁷ is Thr;
for a linker L consisting of k=3 single elements L being connected in either direction from the carbonyl (C=O) point of attachment to the nitrogen (N) of the next element,
L¹ is Dab;
L² is Thr;
L³ is Dap;

said linker L being connected with module B from the carbonyl (C=O) point of attachment of $L^k$ to the α-nitrogen (N) of $Q^1$ and,
if k=3, being connected with module A from the carbonyl (C=O) point of attachment of $P^5$ to the nitrogen (N) of $L^1$;
or a pharmaceutically acceptable salt thereof.

In a more particular preferred embodiment (26) of the invention the elements of formula (I) are defined as follows,
for module A,
s=1, t=0, and u=0; and
$P^1$ and $X^{12}$ taken together form an interstrand linking bis (amino acid) structure based on the linkage of two L amino acid residues; following
connection of the side chain of Ac-Pen; with the side chain of Cys-$NH_2$; by a disulfide linkage; and/or
$P^2$ and $P^{11}$ taken together form an interstrand linking bis (amino acid)-structure based on the linkage of two L amino acid residues; following
connection of the side chain of Cys; hCys; or Pen; with the side chain of Cys; or Pen; by a disulfide linkage; or connection of the side chain of Dab; or Dab(Me); with the side chain of Asp; or Glu; by a lactam linkage; or
$P^2$ and $P^{11}$ taken together form a salt bridge based on the electrostatic interaction between the side chain of Asp; or Glu; at $P^2$ and the side chain of Lys; or Dab; at $P^{11}$; or the side chain of Dab at $P^2$ and the side chain of Asp; or Glu; at $P^{11}$; and/or
$P^4$ and $P^9$ taken together form an interstrand linking bis (amino acid) structure based on the linkage of two L amino acid residues; following
connection of the side chain of Cys; or Pen; with the side chain of Cys; or Pen; by a disulfide linkage; or connection of the side chain of Dab; or Dap; with the side chain of Asp; or Glu; by a lactam linkage; or
$P^4$ and $P^9$ taken together form a salt bridge based on the electrostatic interaction between the side chain of Glu; at $P^4$ and the side chain of Dap; at $P^9$; or the side chain of Dab; or Lys; at $P^4$ and the side chain of Asp; or Glu; at $P^9$;
$P^1$ is Val; Ac-Val; NMeVal; HOVal; Ac-$^D$Val; Prop-Val; Nle; Ac-Nle; Tyr; Ac-Tyr; Ac-Ser; Ac-Leu(3R)OH; pGlu; 3MeButA; or 2MePropA;
$P^2$ is Ala; Val; tBuGly; Dab; Dap; or Thr;
$P^3$ is Val; Ser; Thr; or Tyr;
$P^4$ is Dab; Dap; Ser; Thr; or His;
$P^5$ is Gly; Ala; Val; Abu; His; Thr; or Orn;
$P^6$ is Gly; $^D$Dab; or $^D$Arg;
$P^7$ is Ser; Hse; Thr; Dap; or Dab;
$P^8$ is Trp; Val;
$P^9$ is Ser; Thr; alloThr; Hse; Glu; His; Dab; or Gly;
$P^{10}$ is tBuGly; Val; Ile; Nva; Tyr; or Trp;
$P^{11}$ is Ala; Ser; Thr; Glu; or Dab;
$X^{12}$ is Glyol; Ser; Serol; Ser-$NH_2$; Ser-NHMe; Ser-OiPr; Thr-$NH_2$; Leu(3R)OH; Throl; $^D$Throl; Asn; Val-$NH_2$; Tyr-$NH_2$; Tyrol; or Dab-$NH_2$;
with the proviso that,
if $P^1$ is Ac-Ser; or Ac-Leu(3R)OH; then $X^{12}$ is Val-$NH_2$; or Leu(3R)OH; and
if $P^3$ is Ser; Thr; or Val; then $P^1$ is Ac-Tyr; or $P^{10}$ is Tyr; or $X^{12}$ is Tyr-$NH_2$; or Tyrol; and
if $P^8$ is Val; then $P^{10}$ is Trp; and
the combined number of the amino acid residue Gly in above module A must not exceed two; and
the positions P of the amino acid residues Gly must not be in direct vicinity;

with the further proviso that,
if $P^1$ and $X^{12}$ taken together form an interstrand linkage or salt bridge, as defined above; then $P^2$ and $P^{11}$ taken together are not forming an interstrand linkage or salt bridge, as defined above;
with the further proviso that,
if linker L, as defined below, is connected with module A by a carbonyl (C=O) point of attachment of $P^5$; $P^6$; or $P^7$; then;
$P^5$; $P^6$; or $P^7$ is Glu; or $^D$Glu;
for module B consisting of single elements Q being connected in either direction from the carbonyl (C=O) point of attachment to the nitrogen (N) of the next element with the proviso that $Q^7$ is connected from the α-carbonyl (C=O) point of attachment to the ω-nitrogen (N) of $Q^1$,
$Q^1$ is Dab;
$Q^2$, $Q^5$ and $Q^6$ are Dab;
$Q^3$ is $^D$Leu; or $^D$Phe;
$Q^4$ is Leu; Ile; Leu(3R)OH; Abu; Nva; Thr; or alloThr;
$Q^7$ is Thr; or Leu;
for a linker L consisting of k=1 or 3 single elements L being connected in either direction from the carbonyl (C=O) point of attachment to the nitrogen (N) of the next element,
if k=1,
$L^1$ is $^D$Dab;
if k=3,
$L^1$ is Dab; $^D$Dab; $^D$Dap; or NMeDab;
$L^2$ is Thr; Hse; or Ser;
$L^3$ is Dap; Dab; $^D$Dab; or $^D$Dap;
said linker L being connected with module B from the carbonyl (C=O) point of attachment of $L^k$ to the α-nitrogen (N) of $Q^1$ and,
if k=1 or 3, being connected with module A from the carbonyl (C=O) point of attachment of $P^5$; $P^6$; or $P^7$; to the nitrogen (N) of $L^1$;
or a pharmaceutically acceptable salt thereof.

In a particular preferred particular embodiment (27) of the invention the elements of formula (I) are defined as follows,
for module A,
s=0, t=0, and u=0; and
$P^2$ and $P^{11}$ taken together form an interstrand linking bis (amino acid)-structure based on the linkage of two L amino acid residues; following
connection of the side chain of Cys with the side chain of Cys by a disulfide linkage; and/or
$P^4$ and $P^9$ taken together form an interstrand linking bis (amino acid) structure based on the linkage of two L amino acid residues; following
connection of the side chain of Cys with the side chain of Cys by a disulfide linkage;
$P^1$ is Ac-Val; NMeVal; or HOVal;
$P^2$ is Thr;
$P^3$ is Tyr;
$P^4$ is Dab; or Dap;
$P^6$ is $^D$Dab;
$P^7$ is Ser; Hse; or Dab;
$P^8$ is Trp;
$P^9$ is Ser; or Hse;
$P^{10}$ is tBuGly; or Val;
$P^{11}$ is Ser-$NH_2$;
with the proviso that,
if linker L, as defined below, is connected with module A by a carbonyl (C=O) point of attachment of $P^5$ then $P^5$ is Glu;
for module B consisting of single elements Q being connected in either direction from the carbonyl (C=O) point of attachment to the nitrogen (N) of the next element with the proviso that $Q^7$ is connected from the α-carbonyl (C=O) point of attachment to the ω-nitrogen (N) of $Q^1$,
$Q^1$ is Dab;
$Q^2$, $Q^5$ and $Q^6$ are Dab;
$Q^3$ is $^D$Leu;
$Q^4$ is Leu;
$Q^7$ is Thr;
for a linker L consisting of k=3 single elements L being connected in either direction from the carbonyl (C=O) point of attachment to the nitrogen (N) of the next element,
$L^1$ is Dab;
$L^2$ is Thr;
$L^3$ is Dap; or Dab;
said linker L being connected with module B from the carbonyl (C=O) point of attachment of $L^k$ to the α-nitrogen (N) of $Q^1$ and,
if k=3, being connected with module A from the carbonyl (C=O) point of attachment of $P^5$ to the nitrogen (N) of $L^1$; or a pharmaceutically acceptable salt thereof.

In a particular preferred particular embodiment (28) of the invention the elements of formula (I) are defined as follows, for module A,
s=0, t=0, and u=0; and
$P^{11}$ is connected from the α-carbonyl point of attachment to the ω-nitrogen (N) of $P^2$;
$P^1$ is Ac-Val; HOVal; Ac-Leu; Ac-Ile; Ac-Nle; or Ac-Phe;
$P^2$ is Orn; or Dab;
$P^3$ is Tyr;
$P^4$ is Dab; Dap; Ser; or Thr;
$P^6$ is $^D$Dab;
$P^7$ is Ser; Hse; or Dab;
$P^8$ is Trp;
$P^9$ is Ser;
$P^{10}$ is tBuGly; or Val;
$P^{11}$ is $^D$Thr; $^D$Hse; $^D$Asn; $^D$Gln; $^D$Glu; $^D$Val; $^D$Tyr; $^D$Dab; $^D$Orn; or $^D$Lys;
with the proviso that,
if linker L, as defined below, is connected with module A by a carbonyl (C=O) point of attachment of $P^5$ then
$P^5$ is Glu;
for module B consisting of single elements Q being connected in either direction from the carbonyl (C=O) point of attachment to the nitrogen (N) of the next element with the proviso that $Q^7$ is connected from the α-carbonyl (C=O) point of attachment to the ω-nitrogen (N) of $Q^1$,
$Q^1$ is Dab;
$Q^2$, $Q^5$ and $Q^6$ are Dab;
$Q^3$ is $^D$Leu;
$Q^4$ is Leu;
$Q^7$ is Thr;
for a linker L consisting of k=3 single elements L being connected in either direction from the carbonyl (C=O) point of attachment to the nitrogen (N) of the next element,
$L^1$ is Dab;
$L^2$ is Thr;
$L^3$ is Dap; or Dab;
said linker L being connected with module B from the carbonyl (C=O) point of attachment of $L^k$ to the α-nitrogen (N) of $Q^1$ and,
if k=3, being connected with module A from the carbonyl (C=O) point of attachment of $P^5$ to the nitrogen (N) of $L^1$; or a pharmaceutically acceptable salt thereof.

In another embodiment (29) of the invention the elements of formula (I) are defined as follows,
for module A,
if s=1, t=1, and u=1; and
$X^{14}$ and $X^{13}$ taken together form an interstrand linking bis(amino acid)-structure or (amino acid)-(acid) structure based on the linkage of two L amino acid residues; or an amino acid residue and an acid residue; following connection of the side chain of Cys; Pen; Hcy; Ac-Cys; Ac-Pen; Ac-Hcy; or 3MPA with the side chain of Cys; Pen; Hcy; Cys-NH$_2$ Pen-NH$_2$; or Hcy-NH$_2$; by a disulfide linkage; or
connection of the side chain of Ac-Dab; Ac-Dap; Dab; or Dap; at $X^{14}$ with the side chain of Glu-NH$_2$; Asp-NH$_2$; Glu; or Asp; at $X^{13}$; or the side chain of Ac-Glu; Ac-Asp; Glu; or Asp at $X^{14}$ with the side chain of Dab-NH$_2$; Dap-NH$_2$; Dab; or Dap; at $X^{13}$; by a lactam linkage; or
$X^{14}$ and $X^{13}$ taken together form a salt bridge based on the electrostatic interaction between the side chain of Ac-Dab; Ac-Dap; Ac-Lys; Dab; Dap; or Lys; at $X^{14}$ and the side chain of Glu-NH$_2$; Asp-NH$_2$; Glu; or Asp; at $X^{13}$; or the side chain of Ac-Glu; Ac-Asp; Glu; or Asp; at $X^{14}$ and the side chain of Dab-NH$_2$; Dap-NH$_2$; Lys-NH$_2$; Dab; Dap; or Lys; at $X^{13}$; and/or
$P^2$ and $P^{11}$ taken together form an interstrand linking bis(amino acid)-structure based on the linkage of two L amino acid residues; following
connection of the side chain of Cys; Pen; or Hcy; with the side chain of Cys; Pen; or Hcy; by a disulfide linkage; or
connection of the side chain of Dab; or Dap; at $P^2$ with the side chain of Glu; or Asp; at $P^{11}$; or the side chain Glu; or Asp; at $P^2$ with the side chain of Dab; or Dap; at $P^{11}$; by a lactam linkage; or
$P^2$ and $P^{11}$ taken together form a salt bridge based on the electrostatic interaction between the side chain of Dab; Dap; or Lys; at $P^2$ and the side chain of Glu; or Asp; at $P^{11}$; or the side chain of Glu; or Asp; at $P^2$ and the side chain of Dab; Dap; or Lys; at $P^{11}$;
$X^{14}$ is $^D$Ser;
$P^1$ is Val;
$P^2$ is Thr;
$P^3$ is Tyr;
$P^4$ is Ser; Dap; Dap; or Gly;
$P^5$ is Orn; His; or Gly;
$P^6$ is $^D$Dab; $^D$Ser; $^D$Hse; $^D$Ala; or Gly;
$P^7$ is Dab; Thr; Ser; Hse; Ala; or Gly;
$P^8$ is Trp;
$P^9$ is Glu; Ala; Dab; Ser; or Hse;
$P^{10}$ is tBuGly; Val; or Ile
$P^{11}$ is Ala; or Ser;
$X^{12}$ is Thr;
$X^{13}$ is $^D$Ala; or $^D$Ser;
with the proviso that,
the combined number of the amino acid residue Gly in above module A must not exceed two; and
the positions P of the amino acid residues Gly must not be in direct vicinity;
with the further proviso that,
if linker L, as defined below, is connected with module A by a carbonyl (C=O) point of attachment of $P^5$; $P^6$; or $P^7$; then
$P^5$; $P^6$; or $P^7$; is Glu; or $^D$Glu;
if s=1, t=0, and u=1; and
$P^2$ and $P^{11}$ taken together form an interstrand linking bis(amino acid)-structure based on the linkage of two L amino acid residues; following
connection of the side chain of Cys; Pen; or Hcy; with the side chain of Cys; Pen; or Hcy; by a disulfide linkage; or
connection of the side chain of Dab; or Dap; with the side chain of Glu; or Asp; by a lactam linkage; or P² and P¹¹ taken together form a salt bridge based on the electrostatic interaction between the side chain of Dab; Dap; or Lys; at P² and the side chain of Glu; or Asp; at P¹¹; or the side chain of Glu; or Asp; at P² and the side chain of Dab; Dap; or Lys; at P¹¹; and/or P⁴ and P⁹ taken together form an interstrand linking bis (amino acid)-structure based on the linkage of two L amino acid residues; following connection of the side chain of Cys; Pen; or Hcy; with the side chain of Cys; Pen; or Hcy; by a disulfide linkage; or connection of the side chain of Asp; or Glu; with the side chain of Dab; or Dap; by a lactam linkage; or P⁴ and P⁹ taken together form a salt bridge based on the electrostatic interaction between the side chain of Dab; Dap; or Lys; at P⁴ and the side chain of Glu; or Asp; at P⁹; or the side chain of Glu; or Asp; at P⁴ and the side chain of Dab; Dap; or Lys; at P⁹;

$X^{14}$ pGu; or $^D$pGlu;

$P^1$; $P^2$; $P^3$; $P^4$; $P^5$; $P^6$; $P^7$; $P^8$; $P^9$; $P^{10}$; and $P^{11}$ are as defined above for module A in this embodiment, wherein s=1, t=1, and u=1;

$X^{12}$ is Throl; Thr-NH$_2$; or Thr;

with the proviso that,
the combined number of the amino acid residue Gly in above module A must not exceed two; and
the positions P of the amino acid residues Gly must not be in direct vicinity;
with the further proviso that,
if linker L, as defined below, is connected with module A by a carbonyl (C=O) point of attachment of P⁵; P⁶; or P⁷; then
P⁵; P⁶; or P⁷; is Glu; or $^D$Glu;

if s=1, t=1, and u=0; and

P² and P¹¹ taken together form an interstrand linking bis (amino acid)-structure based on the linkage of two L amino acid residues; following connection of the side chain of Cys; with the side chain of Cys by a disulfide linkage; and/or P⁴ and P⁹ taken together form an interstrand linking bis (amino acid) structure based on the linkage of two L amino acid residues; following connection of the side chain of Cys; with the side chain of Cys by a disulfide linkage;

P¹ is Val; HOVal; or Ac-Val;

$P^2$; $P^3$; $P^4$; $P^5$; $P^6$; $P^7$; $P^8$; $P^9$; $P^{10}$; $P^{11}$; and $X^{12}$ are as defined above for module A in this embodiment, wherein s=1, t=1, and u=1;

$X^{13}$ is Glyol;

with the proviso that,
the combined number of the amino acid residue Gly in above module A must not exceed two; and
the positions P of the amino acid residues Gly must not be in direct vicinity;
with the further proviso that,
if linker L, as defined below, is connected with module A by a carbonyl (C=O) point of attachment of P⁵; P⁶; or P⁷; then
P⁵; P⁶; or P⁷; is Glu; or $^D$Glu;

if s=0, t=0, and u=1; and

P² and P¹¹ taken together form an interstrand linking bis (amino acid)-structure based on the linkage of two L amino acid residues; following connection of the side chain of Cys; Pen; or Hcy; with the side chain of Cys; Pen; Hcy; Cys-NH$_2$; Pen-NH$_2$; or Hcy-NH$_2$; by a disulfide linkage; or connection of the side chain of Dab; or Dap; at P² with the side chain of Glu; Asp; Glu-NH$_2$; or Asp-NH$_2$; at P¹¹; or the side chain Glu; or Asp; at P² with the side chain of Dab; Dap; Dab-NH$_2$; or Dap-NH$_2$; at P¹¹; by a lactam linkage; or P² and P¹¹ taken together form a salt bridge based on the electrostatic interaction between the side chain of Dab; Dap; or Lys; at P² and the side chain of Glu; Asp; Glu-NH$_2$; or Asp-NH$_2$; at P¹¹; or the side chain of Glu; or Asp; at P² and the side chain of Dab; Dap; Lys; Dab-NH$_2$; Dap-NH$_2$; or Lys-NH$_2$; at P¹¹; and/or P⁴ and P⁹ taken together form an interstrand linking bis (amino acid)-structure based on the linkage of two L amino acid residues; following connection of the side chain of Cys; Pen; or Hcy; with the side chain of Cys; Pen; or Hcy; by a disulfide linkage; or connection of the side chain of Asp; or Glu; with the side chain of Dab; or Dap; by a lactam linkage; or P⁴ and P⁹ taken together form a salt bridge based on the electrostatic interaction between the side chain of Dab; Dap; or Lys; at P⁴ and the side chain of Glu; or Asp; at P⁹; or the side chain of Glu; or Asp; at P⁴ and the side chain of Dab; Dap; or Lys; at P⁹;

$X^{14}$ is Ac-Dab;

$P^2$; $P^3$; $P^4$; $P^5$; $P^6$; $P^7$; $P^8$; $P^9$; and $P^{10}$ are as defined above for module A in this embodiment, wherein s=1, t=1, and u=1;

$P^{11}$ is Dab-NH$_2$; or Dab;

with the proviso that,
the combined number of the amino acid residue Gly in above module A must not exceed two; and
the positions P of the amino acid residues Gly must not be in direct vicinity;
with the further proviso that,
if linker L, as defined below, is connected with module A by a carbonyl (C=O) point of attachment of P⁵; P⁶; or P⁷; then
P⁵; P⁶; or P⁷; is Glu; or $^D$Glu;

if s=1, t=0, and u=0; and

P² and P¹¹ taken together form an interstrand linking bis (amino acid)-structure based on the linkage of two L amino acid residues; following connection of the side chain of Cys; Pen; or Hcy; with the side chain of Cys; Pen; or Hcy; by a disulfide linkage; or connection of the side chain of Dab; or Dap; with the side chain of Glu; or Asp; by a lactam linkage; or P² and P¹¹ taken together form a salt bridge based on the electrostatic interaction between the side chain of Dab; Dap; or Lys; at P² and the side chain of Glu; or Asp; at P¹¹; or the side chain of Glu; or Asp; at P² and the side chain of Dab; Dap; or Lys; at P¹¹; and/or P⁴ and P⁹ taken together form an interstrand linking bis (amino acid)-structure based on the linkage of two L amino acid residues; following connection of the side chain of Cys; Pen; or Hcy; with the side chain of Cys; Pen; or Hcy; by a disulfide linkage; or connection of the side chain of Asp; or Glu; with the side chain of Dab; or Dap; by a lactam linkage; or P⁴ and P⁹ taken together form a salt bridge based on the electrostatic interaction between the side chain of Dab; Dap; or Lys; at P⁴ and the side chain of Glu; or Asp; at P⁹; or the side chain of Glu; or Asp; at P⁴ and the side chain of Dab; Dap; or Lys; at P⁹;

P¹ is Val; Ac-Val; NMeVal; HOVal; Prop-Val; Ac-Nle; Ac-Tyr; Nle; or Tyr;

$P^2$; $P^3$; $P^4$; $P^5$; $P^6$; $P^7$; $P^8$; $P^9$; and $P^{10}$; are as defined above for module A in this embodiment, wherein s=1, t=1, and u=1;

P¹¹ is Ala; Ser; Thr; Glu; or Dab;

$X^{12}$ is Glyol; Ser; Serol; Ser-NH$_2$; Ser-NHMe; Thr; Thr-NH$_2$; Throl; Val-NH$_2$; or Tyrol;

with the proviso that,
the combined number of the amino acid residue Gly in above module A must not exceed two; and
the positions P of the amino acid residues Gly must not be in direct vicinity;

with the further proviso that,
if linker L, as defined below, is connected with module A by a carbonyl (C=O) point of attachment of $P^5$; $P^6$; or $P^7$; then
$P^5$; $P^6$; or $P^7$; is Glu; or $^D$Glu;

if s=0, t=0, and u=0; and
$P^2$ and $P^{11}$ taken together form an interstrand linking bis (amino acid)-structure based on the linkage of two L amino acid residues; following
connection of the side chain of Cys with the side chain of Cys by a disulfide linkage; and/or
$P^4$ and $P^9$ taken together form an interstrand linking bis (amino acid) structure based on the linkage of two L amino acid residues; following
connection of the side chain of Cys with the side chain of Cys by a disulfide linkage;

$P^1$ is Ac-Val; NMeVal; HOVal; or Val;
$P^2$; $P^3$; $P^4$; $P^5$; $P^6$; $P^7$; $P^8$; $P^9$; and $P^{10}$ are as defined above for module A in this embodiment, wherein s=1, t=1, and u=1;
$P^{11}$ is Ser-NH$_2$; or Ser;

with the proviso that,
the combined number of the amino acid residue Gly in above module A must not exceed two; and
the positions P of the amino acid residues Gly must not be in direct vicinity;

with the further proviso that,
if linker L, as defined below, is connected with module A by a carbonyl (C=O) point of attachment of $P^5$; $P^6$; or $P^7$; then
$P^5$; $P^6$; or $P^7$; is Glu; or $^D$Glu;

if s=0, t=0, and u=0; and alternatively
$P^{11}$ is connected from the α-carbonyl point of attachment to the ω-nitrogen (N) of $P^2$;
$P^1$ is Ac-Val; HOVal; Ac-Leu; Ac-Ile; Ac-Nle; Ac-Phe; Val; Leu; Nle; Ile; or Phe;
$P^2$ is Orn; or Dab;
$P^3$; $P^4$; $P^5$; $P^6$; $P^7$; $P^8$; $P^9$; and $P^{10}$ are as defined above for module A in this embodiment, wherein s=1, t=1, and u=1;
$P^{11}$ is $^D$Thr; $^D$Hse; $^D$Asn; $^D$Gln; $^D$Glu; $^D$Val; $^D$Tyr; $^D$Dab; $^D$Orn; $^D$Lys;

with the proviso that,
the combined number of the amino acid residue Gly in above module A must not exceed two; and
the positions P of the amino acid residues Gly must not be in direct vicinity;

with the further proviso that,
if linker L, as defined below, is connected with module A by a carbonyl (C=O) point of attachment of $P^5$; $P^6$; or $P^7$; then
$P^5$; $P^6$; or $P^7$; is Glu; or $^D$Glu;

for module B consisting of single elements Q being connected in either direction from the carbonyl (C=O) point of attachment to the nitrogen (N) of the next element with the proviso that $Q^7$ is connected from the α-carbonyl (C=O) point of attachment to the ω-nitrogen (N) of $Q^1$,
$Q^1$ is Dab;
$Q^2$, $Q^5$ and $Q^6$ are Dab;
$Q^3$ is $^D$Leu;
$Q^4$ is Leu;
$Q^7$ is Thr;

for a linker L consisting of k=3 single elements L being connected in either direction from the carbonyl (C=O) point of attachment to the nitrogen (N) of the next element,
$L^1$ is Dab; or $^D$Dab;
$L^2$ is Thr;
$L^3$ is Dap; or Dab;
said linker L being connected with module B from the carbonyl (C=O) point of attachment of $L^k$ to the α-nitrogen (N) of $Q^1$ and,
if k=3, being connected with module A from the carbonyl (C=O) point of attachment of $P^5$ to the nitrogen (N) of $L^1$;
or a pharmaceutically acceptable salt thereof.

In a preferred embodiment (30) of the invention the elements of formula (I) are defined as follows,
for module A,
s=0, t=0, and u=0; or s=1, t=0, and u=0; or s=0, t=0, and u=1;

if s=0, t=0, and u=1; and
$P^2$ and $P^{11}$ taken together form an interstrand linking bis (amino acid)-structure based on the linkage of two L amino acid residues; following
connection of the side chain of Cys; Pen; or Hcy; with the side chain of Cys; Pen; Hcy; Cys-NH$_2$; Pen-NH$_2$; or Hey-NH$_2$; by a disulfide linkage; or
connection of the side chain of Dab; or Dap; at $P^2$ with the side chain of Glu; Asp; Glu-NH$_2$; or Asp-NH$_2$; at $P^{11}$; or the side chain Glu; or Asp; at $P^2$ with the side chain of Dab; Dap; Dab-NH$_2$; or Dap-NH$_2$; at $P^{11}$; by a lactam linkage; or
$P^2$ and $P^{11}$ taken together form a salt bridge based on the electrostatic interaction between the side chain of Dab; Dap; or Lys; at $P^2$ and the side chain of Glu; Asp; Glu-NH$_2$; or Asp-NH$_2$; at $P^{11}$; or the side chain of Glu; or Asp; at $P^2$ and the side chain of Dab; Dap; Lys; Dab-NH$_2$; Dap-NH$_2$; or Lys-NH$_2$; at $P^{11}$; and/or
$P^4$ and $P^9$ taken together form an interstrand linking bis (amino acid)-structure based on the linkage of two L amino acid residues; following
connection of the side chain of Cys; Pen; or Hcy; with the side chain of Cys; Pen; or Hcy; by a disulfide linkage; or
connection of the side chain of Asp; or Glu; with the side chain of Dab; or Dap; by a lactam linkage; or
$P^4$ and $P^9$ taken together form a salt bridge based on the electrostatic interaction between the side chain of Dab; Dap; or Lys; at $P^4$ and the side chain of Glu; or Asp; at $P^9$; or the side chain of Glu; or Asp; at $P^4$ and the side chain of Dab; Dap; or Lys; at $P^9$;
$X^{14}$ is Ac-Dab;
$P^1$; $P^2$; $P^3$; $P^4$; $P^5$; $P^6$; $P^7$; $P^8$; $P^9$; and $P^{10}$ are as defined above for module A in embodiment 29, wherein s=1, t=1, and u=1;
$P^{11}$ is Dab-NH$_2$; or Dab;

with the proviso that,
the combined number of the amino acid residue Gly in above module A must not exceed two; and
the positions P of the amino acid residues Gly must not be in direct vicinity;

with the further proviso that,
if linker L, as defined below, is connected with module A by a carbonyl (C=O) point of attachment of $P^5$; $P^6$; or $P^7$; then
$P^5$; $P^6$; or $P^7$; is Glu; or $^D$Glu;

if s=1, t=0, and u=0; and
$P^2$ and $P^{11}$ taken together form an interstrand linking bis (amino acid)-structure based on the linkage of two L amino acid residues; following
connection of the side chain of Cys; Pen; or Hcy; with the side chain of Cys; Pen; or Hcy; by a disulfide linkage; or connection of the side chain of Dab; or Dap; with the side chain of Glu; or Asp; by a lactam linkage; or $P^2$ and $P^{11}$ taken together form a salt bridge based on the electrostatic interaction between the side chain of Dab; Dap; or Lys; at $P^2$ and the side chain of Glu; or Asp; at $P^{11}$; or the side chain of Glu; or Asp; at $P^2$ and the side chain of Dab; Dap; or Lys; at $P^{11}$; and/or $P^4$ and $P^9$ taken together form an interstrand linking bis(amino acid)-structure based on the linkage of two L amino acid residues; following
connection of the side chain of Cys; Pen; or Hcy; with the side chain of Cys; Pen; or Hcy; by a disulfide linkage; or
connection of the side chain of Asp; or Glu; with the side chain of Dab; or Dap; by a lactam linkage; or $P^4$ and $P^9$ taken together form a salt bridge based on the electrostatic interaction between the side chain of Dab; Dap; or Lys; at $P^4$ and the side chain of Glu; or Asp; at $P^9$; or the side chain of Glu; or Asp; at $P^4$ and the side chain of Dab; Dap; or Lys; at $P^9$;

$P^1$ is Val; Ac-Val; NMeVal; HOVal; Prop-Val; Ac-Nle; Ac-Tyr; Nle; or Tyr;

$P^2$; $P^3$; $P^4$; $P^5$; $P^6$; $P^7$; $P^8$; $P^9$; and $P^{10}$; are as defined above for module A in embodiment 29, wherein s=1, t=1, and u=1;

$P^{11}$ is Ala; Ser; Thr; Glu; or Dab;

$X^{12}$ is Glyol; Ser; Serol; Ser-NH$_2$; Ser-NHMe; Thr; Thr-NH$_2$; Throl; Val-NH$_2$; or Tyrol;

with the proviso that,
the combined number of the amino acid residue Gly in above module A must not exceed two; and
the positions P of the amino acid residues Gly must not be in direct vicinity;
with the further proviso that,
if linker L, as defined below, is connected with module A by a carbonyl (C=O) point of attachment of $P^5$; $P^6$; or $P^7$; then
$P^5$; $P^6$; or $P^7$; is Glu; or $^D$Glu;
if s=0, t=0, and u=0; and
$P^2$ and $P^{11}$ taken together form an interstrand linking bis(amino acid)-structure based on the linkage of two L amino acid residues; following
connection of the side chain of Cys with the side chain of Cys by a disulfide linkage; and/or
$P^4$ and $P^9$ taken together form an interstrand linking bis(amino acid) structure based on the linkage of two L amino acid residues; following
connection of the side chain of Cys with the side chain of Cys by a disulfide linkage;
$P^1$ is Ac-Val; NMeVal; HOVal; or Val;
$P^2$; $P^3$; $P^4$; $P^5$; $P^6$; $P^7$; $P^8$; $P^9$; and $P^{10}$ are as defined above for module A in embodiment 29,
wherein s=1, t=1, and u=1;
$P^{11}$ is Ser-NH$_2$; or Ser;
with the proviso that,
the combined number of the amino acid residue Gly in above module A must not exceed two; and
the positions P of the amino acid residues Gly must not be in direct vicinity;
with the further proviso that,
if linker L, as defined below, is connected with module A by a carbonyl (C=O) point of attachment of $P^5$; $P^6$; or $P^7$; then
$P^5$; $P^6$; or $P^7$; is Glu; or $^D$Glu;
if s=0, t=0, and u=0; and alternatively
$P^{11}$ is connected from the α-carbonyl point of attachment to the ω-nitrogen (N) of $P^2$;

$P^1$ is Ac-Val; HOVal; Ac-Leu; Ac-Ile; Ac-Nle; Ac-Phe; Val; Leu; Nle; Ile; or Phe;

$P^2$ is Orn; or Dab;

$P^3$; $P^4$; $P^5$; $P^6$; $P^7$; $P^8$; $P^9$; and $P^{10}$ are as defined above for module A in embodiment 29, wherein s=1, t=1, and u=1;

$P^{11}$ is $^D$Thr; $^D$Hse; $^D$Asn; $^D$Gln; $^D$Glu; $^D$Val; $^D$Tyr; $^D$Dab; $^D$Orn; $^D$Lys;

with the proviso that,
the combined number of the amino acid residue Gly in above module A must not exceed two; and
the positions P of the amino acid residues Gly must not be in direct vicinity;
with the further proviso that,
if linker L, as defined below, is connected with module A by a carbonyl (C=O) point of attachment of $P^5$; $P^6$; or $P^7$; then
$P^5$; $P^6$; or $P^7$; is Glu; or $^D$Glu;

for module B consisting of single elements Q being connected in either direction from the carbonyl (C=O) point of attachment to the nitrogen (N) of the next element with the proviso that $Q^7$ is connected from the α-carbonyl (C=O) point of attachment to the ω-nitrogen (N) of $Q^1$, $Q^1$ is Dab;
$Q^2$, $Q^5$ and $Q^6$ are Dab;
$Q^3$ is $^D$Leu;
$Q^4$ is Leu;
$Q^7$ is Thr;

for a linker L consisting of k=3 single elements L being connected in either direction from the carbonyl (C=O) point of attachment to the nitrogen (N) of the next element, $L^1$ is Dab; or $^D$Dab;
$L^2$ is Thr;
$L^3$ is Dap; or Dab;

said linker L being connected with module B from the carbonyl (C=O) point of attachment of $L^k$ to the α-nitrogen (N) of $Q^1$ and,
if k=3, being connected with module A from the carbonyl (C=O) point of attachment of $P^5$ to the nitrogen (N) of $L^1$;
or a pharmaceutically acceptable salt thereof.

In a more preferred embodiment (31) of the invention the elements of formula (I) are defined as follows,
for module A,
s=1, t=0, and u=0;
$P^2$ and $P^{11}$ taken together form an interstrand linking bis(amino acid)-structure based on the linkage of two L amino acid residues; following
connection of the side chain of Cys; Pen; or Hcy; with the side chain of Cys; Pen; or Hcy; by a disulfide linkage; or
connection of the side chain of Dab; or Dap; with the side chain of Glu; or Asp; by a lactam linkage; or
$P^2$ and $P^{11}$ taken together form a salt bridge based on the electrostatic interaction between the side chain of Dab; Dap; or Lys; at $P^2$ and the side chain of Glu; or Asp; at $P^{11}$; or the side chain of Glu; or Asp; at $P^2$ and the side chain of Dab; Dap; or Lys; at $P^{11}$; and/or
$P^4$ and $P^9$ taken together form an interstrand linking bis(amino acid)-structure based on the linkage of two L amino acid residues; following
connection of the side chain of Cys; Pen; or Hcy; with the side chain of Cys; Pen; or Hcy; by a disulfide linkage; or
connection of the side chain of Asp; or Glu; with the side chain of Dab; or Dap; by a lactam linkage; or
$P^4$ and $P^9$ taken together form a salt bridge based on the electrostatic interaction between the side chain of Dab; Dap; or Lys; at $P^4$ and the side chain of Glu; or Asp; at $P^9$; or the side chain of Glu; or Asp; at $P^4$ and the side chain of Dab; Dap; or Lys; at $P^9$;

P¹ is Val; Ac-Val; NMeVal; HOVal; Prop-Val; Ac-Nle; Ac-Tyr; Nle; or Tyr;
P², P³, P⁴, P⁵, P⁶, P⁷, P⁸, P⁹; and P¹⁰; are as defined above for module A in embodiment 29, wherein s=1, t=1, and u=1;
P¹¹ is Ala; Ser; Thr; Glu; or Dab;
X¹² is Glyol; Ser; Serol; Ser-NH$_2$; Ser-NHMe; Thr; Thr-NH$_2$; Throl; Val-NH$_2$; or Tyrol;
with the proviso that,
the combined number of the amino acid residue Gly in above module A must not exceed two; and
the positions P of the amino acid residues Gly must not be in direct vicinity;
with the further proviso that,
if linker L, as defined below, is connected with module A by a carbonyl (C=O) point of attachment of P⁵; P⁶; or P⁷; then
P⁵; P⁶; or P⁷; is Glu; or $^D$Glu;
for module B consisting of single elements Q being connected in either direction from the carbonyl (C=O) point of attachment to the nitrogen (N) of the next element with the proviso that Q⁷ is connected from the α-carbonyl (C=O) point of attachment to the ω-nitrogen (N) of Q¹,
Q¹ is Dab;
Q², Q⁵ and Q⁶ are Dab;
Q³ is $^D$Leu;
Q⁴ is Leu;
Q⁷ is Thr;
for a linker L consisting of k=3 single elements L being connected in either direction from the carbonyl (C=O) point of attachment to the nitrogen (N) of the next element,
L¹ is Dab; or $^D$Dab;
L² is Thr;
L³ is Dap; or Dab;
said linker L being connected with module B from the carbonyl (C=O) point of attachment of L$^k$ to the α-nitrogen (N) of Q¹ and,
if k=3, being connected with module A from the carbonyl (C=O) point of attachment of P⁵ to the nitrogen (N) of L¹;
or a pharmaceutically acceptable salt thereof.

In another particular embodiment (32) of the invention the elements of formula (I) are defined as follows,
for module A,
s=1, t=1, and u=1; and
X¹⁴ and X¹³ taken together form an interstrand linking bis(amino acid)-structure based on the linkage of two L amino acid residues; following
connection of the side chain of Ac-Cys; or 3MPA with the side chain of Cys-NH$_2$ by a disulfide linkage; or
connection of the side chain of Ac-Dab; at X¹⁴ with the side chain of Glu-NH$_2$; at X¹³; by a lactam linkage; or
X¹⁴ and X¹³ taken together form a salt bridge based on the electrostatic interaction between the side chain of Ac-Dab at X¹⁴ and the side chain of Glu-NH$_2$ at X¹³; or the side chain of Ac-Glu at X¹⁴ and the side chain of Dab-NH$_2$ at X¹³; and/or
P² and P¹¹ taken together form an interstrand linking bis(amino acid)-structure based on the linkage of two L amino acid residues; following
connection of the side chain of Cys; with the side chain of Cys by a disulfide linkage; or P² and P¹¹ taken together form a salt bridge based on the electrostatic interaction between the side chain of Dab; at P² and the side chain of Glu; at P¹¹;
X¹⁴ is $^D$Ser;
P¹ is Val;
P² is Thr;
P³ is Tyr;
P⁴ is Ser;
P⁶ is $^D$Dab;
P⁷ is Dab;
P⁸ is Trp;
P⁹ is Glu;
P¹⁰ is tBuGly;
P¹¹ is Ala;
X¹² is Thr;
X¹³ is $^D$Ala; or $^D$Ser;
with the proviso that,
if linker L, as defined below, is connected with module A by a carbonyl (C=O) point of attachment of P⁵; then
P⁵ is Glu;
for module B consisting of single elements Q being connected in either direction from the carbonyl (C=O) point of attachment to the nitrogen (N) of the next element with the proviso that Q⁷ is connected from the α-carbonyl (C=O) point of attachment to the ω-nitrogen (N) of Q¹,
Q¹ is Dab;
Q², Q⁵ and Q⁶ are Dab;
Q³ is $^D$Leu;
Q⁴ is Leu;
Q⁷ is Thr;
for a linker L consisting of k=3 single elements L being connected in either direction from the carbonyl (C=O) point of attachment to the nitrogen (N) of the next element,
L¹ is Dab;
L² is Thr;
L³ is Dap;
said linker L being connected with module B from the carbonyl (C=O) point of attachment of L$^k$ to the α-nitrogen (N) of Q¹ and,
if k=3, being connected with module A from the carbonyl (C=O) point of attachment of P⁵ to the nitrogen (N) of L¹;
or a pharmaceutically acceptable salt thereof.

In another particular embodiment (33) of the invention the elements of formula (I) are defined as follows,
s=1, t=0, and u=1; and
P² and P¹¹ taken together form an interstrand linking bis (amino acid)-structure based on the linkage of two L amino acid residues; following
connection of the side chain of Cys; with the side chain of Cys by a disulfide linkage; and/or
P⁴ and P⁹ taken together form an interstrand linking bis (amino acid) structure based on the linkage of two L amino acid residues; following
connection of the side chain of Cys; with the side chain of Cys by a disulfide linkage;
X¹⁴ is pGu; or $^D$pGlu;
P¹ is Val;
P² is Thr;
P³ is Tyr;
P⁴ is Dap;
P⁶ is $^D$Dab;
P⁷ is Thr;
P⁸ is Trp;
P⁹ is Ser;
P¹⁰ is tBuGly;
P¹¹ is Ala;
X¹² is Throl;
with the proviso that,
if linker L, as defined below, is connected with module A by a carbonyl (C=O) point of attachment of P⁵; then
P⁵ is Glu;
for module B consisting of single elements Q being connected in either direction from the carbonyl (C=O) point of attachment to the nitrogen (N) of the next element with the proviso that $Q^7$ is connected from the α-carbonyl (C=O) point of attachment to the ω-nitrogen (N) of $Q^1$,
$Q^1$ is Dab;
$Q^2$, $Q^5$ and $Q^6$ are Dab;
$Q^3$ is $^D$Leu;
$Q^4$ is Leu;
$Q^7$ is Thr;
for a linker L consisting of k=3 single elements L being connected in either direction from the carbonyl (C=O) point of attachment to the nitrogen (N) of the next element,
$L^1$ is Dab;
$L^2$ is Thr;
$L^3$ is Dap;
said linker L being connected with module B from the carbonyl (C=O) point of attachment of $L^k$ to the α-nitrogen (N) of $Q^1$ and,
if k=3, being connected with module A from the carbonyl (C=O) point of attachment of $P^5$ to the nitrogen (N) of $L^1$;
or a pharmaceutically acceptable salt thereof.

In a particular preferred embodiment (34) of the invention the elements of formula (I) are defined as follows,
for module A,
s=0, t=0, and u=1; and
$P^2$ and $P^{11}$ taken together form an interstrand linking bis (amino acid)-structure based on the linkage of two L amino acid residues; following
connection of the side chain of Cys; with the side chain of Cys-NH$_2$ by a disulfide linkage; and/or
$P^4$ and $P^9$ taken together form an interstrand linking bis (amino acid) structure based on the linkage of two L amino acid residues; following
connection of the side chain of Cys; with the side chain of Cys by a disulfide linkage;
$X^{14}$ is Ac-Dab;
$P^1$ is Val;
$P^2$ is Thr;
$P^3$ is Tyr;
$P^4$ is Dap;
$P^6$ is $^D$Dab;
$P^7$ is Dab;
$P^8$ is Trp;
$P^9$ is Ser;
$P^{10}$ is tBuGly;
$P^{11}$ is Dab-NH$_2$;
with the proviso that,
  if linker L, as defined below, is connected with module A by a carbonyl (C=O) point of attachment of $P^5$; then $P^5$ is Glu;
for module B consisting of single elements Q being connected in either direction from the carbonyl (C=O) point of attachment to the nitrogen (N) of the next element with the proviso that $Q^7$ is connected from the α-carbonyl (C=O) point of attachment to the ω-nitrogen (N) of $Q^1$,
$Q^1$ is Dab;
$Q^2$, $Q^5$ and $Q^6$ are Dab;
$Q^3$ is $^D$Leu;
$Q^4$ is Leu;
$Q^7$ is Thr;
for a linker L consisting of k=3 single elements L being connected in either direction from the carbonyl (C=O) point of attachment to the nitrogen (N) of the next element,
$L^1$ is Dab;
$L^2$ is Thr;
$L^3$ is Dap;
said linker L being connected with module B from the carbonyl (C=O) point of attachment of $L^k$ to the α-nitrogen (N) of $Q^1$ and,
if k=3, being connected with module A from the carbonyl (C=O) point of attachment of $P^5$ to the nitrogen (N) of $L^1$;
or a pharmaceutically acceptable salt thereof.

In a more particular preferred particular embodiment (35) of the invention the elements of formula (I) are defined as follows,
for module A,
s=1, t=0, and u=0; and
$P^2$ and $P^{11}$ taken together form an interstrand linking bis (amino acid)-structure based on the linkage of two L amino acid residues; following
connection of the side chain of Cys; or Pen; with the side chain of Cys; by a disulfide linkage; or
connection of the side chain of Dab; with the side chain of Asp; or Glu; by a lactam linkage; and/or
$P^4$ and $P^9$ taken together form an interstrand linking bis (amino acid) structure based on the linkage of two L amino acid residues; following
connection of the side chain of Cys; with the side chain of Cys; or Pen; by a disulfide linkage; or
connection of the side chain of Dab; with the side chain of Asp; by a lactam linkage; or
$P^4$ and $P^9$ taken together form a salt bridge based on the electrostatic interaction between the side chain of Dab; or Lys; at $P^4$ and the side chain of Glu; at $P^9$;
$P^1$ is Val; Ac-Val; NMeVal; HOVal; Prop-Val; Ac-Nle; or Ac-Tyr;
$P^2$ is Ala; Val; or Thr;
$P^3$ is Val; or Tyr;
$P^4$ is Dab; Dap; or Ser;
$P^5$ is Gly; His; or Orn;
$P^6$ is $^D$Dab;
$P^7$ is Ser; Hse; Thr; or Dab;
$P^8$ is Trp;
$P^9$ is Ser; Hse; Dab; or Glu;
$P^{10}$ is tBuGly; Val; or Ile;
$P^{11}$ is Ala; Ser; Thr; Glu; or Dab;
$X^{12}$ is Glyol; Ser; Serol; Ser-NH$_2$; Ser-NHMe; Thr-NH$_2$; Throl; Val-NH$_2$; or Tyrol;
with the proviso that,
  if $P^3$ is Val; then $P^1$ is Ac-Tyr; or $X^{12}$ is Tyrol;
with the further proviso that,
  if $P^1$ and $X^{12}$ taken together form an interstrand linkage or salt bridge, as defined above; then $P^2$ and $P^{11}$ taken together are not forming an interstrand linkage or salt bridge, as defined above;
with the further proviso that,
  if linker L, as defined below, is connected with module A by a carbonyl (C=O) point of attachment of $P^5$; $P^6$; or $P^7$; then;
  $P^5$; or $P^7$ is Glu; or $P^6$ is $^D$Glu;
for module B consisting of single elements Q being connected in either direction from the carbonyl (C=O) point of attachment to the nitrogen (N) of the next element with the proviso that $Q^7$ is connected from the α-carbonyl (C=O) point of attachment to the ω-nitrogen (N) of $Q^1$,
$Q^1$ is Dab;
$Q^2$, $Q^5$ and $Q^6$ are Dab;
$Q^3$ is $^D$Leu;
$Q^4$ is Leu; Ile; Leu(3R)OH; Abu; Nva; Thr; or alloThr;
$Q^7$ is Thr;
for a linker L consisting of k=3 single elements L being connected in either direction from the carbonyl (C=O) point of attachment to the nitrogen (N) of the next element,
$L^1$ is Dab; or $^D$Dab;
$L^2$ is Thr; or Ser;
$L^3$ is Dap; or Dab;

said linker L being connected with module B from the carbonyl (C=O) point of attachment of $L^k$ to the α-nitrogen (N) of $Q^1$ and,
if k=3, being connected with module A from the carbonyl (C=O) point of attachment of $P^5$; $P^6$; or $P^7$; to the nitrogen (N) of $L^1$;
or a pharmaceutically acceptable salt thereof.

In a more particular preferred particular embodiment (36) of the invention the elements of formula (I) are defined as follows,
for module A,
s=1, t=0, and u=0; and
$P^2$ and $P^{11}$ taken together form an interstrand linking bis (amino acid)-structure based on the linkage of two L amino acid residues; following
connection of the side chain of Cys; with the side chain of Cys; by a disulfide linkage; or
$P^4$ and $P^9$ taken together form an interstrand linking bis (amino acid) structure based on the linkage of two L amino acid residues; following
connection of the side chain of Cys; with the side chain of Cys; or Pen; by a disulfide linkage; or
$P^4$ and $P^9$ taken together form a salt bridge based on the electrostatic interaction between the side chain of Dab at $P^4$ and the side chain of Glu; at $P^9$;
$P^1$ is Val; Ac-Val; NMeVal; HOVal; Ac-Nle; or Ac-Tyr;
$P^2$ is Thr;
$P^3$ is Val; Ser; or Tyr;
$P^4$ is Dab; Dap; Thr; or Ser;
$P^5$ is Orn; Ala; Val; Abu; His; or Thr;
$P^6$ is $^D$Dab; $^D$Ser; or $^D$Hse;
$P^7$ is Ser; Hse; Thr; or Dab;
$P^8$ is Trp;
$P^9$ is Ser; Hse; alloThr; Dab; or Glu;
$P^{10}$ is tBuGly; Val; or Ile;
$P^{11}$ is Ala;
$X^{12}$ is Ser; Serol; Ser-NH$_2$; Thr-NH$_2$; Throl; Tyr-NH$_2$; Asn; or Tyrol;
with the proviso that,
    if $P^3$ is Ser; or Val; then $P^1$ is Ac-Tyr; or $X^{12}$ is Tyr-NH$_2$; or Tyrol;
with the further proviso that,
    if linker L, as defined below, is connected with module A by a carbonyl (C=O) point of attachment of $P^5$; or $P^6$; then;
    $P^5$; is Glu; or $P^6$ is $^D$Glu;
for module B consisting of single elements Q being connected in either direction from the carbonyl (C=O) point of attachment to the nitrogen (N) of the next element with the proviso that $Q^7$ is connected from the α-carbonyl (C=O) point of attachment to the ω-nitrogen (N) of $Q^1$,
$Q^1$ is Dab;
$Q^2$, $Q^5$ and $Q^6$ are Dab;
$Q^3$ is $^D$Leu;
$Q^4$ is Leu; Ile; Abu; or Thr;
$Q^7$ is Thr;
for a linker L consisting of k=3 single elements L being connected in either direction from the carbonyl (C=O) point of attachment to the nitrogen (N) of the next element,
$L^1$ is Dab; or $^D$Dab;
$L^2$ is Thr; or Ser;
$L^3$ is Dap; Dab; or $^D$Dab;
said linker L being connected with module B from the carbonyl (C=O) point of attachment of $L^k$ to the α-nitrogen (N) of $Q^1$ and,
if k=3, being connected with module A from the carbonyl (C=O) point of attachment of $P^5$; or $P^6$; to the nitrogen (N) of $L^1$;
or a pharmaceutically acceptable salt thereof.

In a further embodiment (37) of the invention the elements of formula (I) are defined for module A as defined in embodiment (17), for module B as defined in embodiment (20) and for linker L as defined in embodiment (21); or a pharmaceutically acceptable salt thereof.

In a preferred embodiment (38) of the invention the elements of formula (I) are defined for module A as defined in embodiment (18), for module B as defined in embodiment (20) and for linker L as defined in embodiment (21); or a pharmaceutically acceptable salt thereof.

In a more preferred embodiment (39) of the invention the elements of formula (I) are defined for module A as defined in embodiment (19), for module B as defined in embodiment (20) and for linker L as defined in embodiment (21), or a pharmaceutically acceptable salt thereof.

With respect to embodiments 2, 5, 15, 38, 30, the order of preference is 30>38>15>>2, embodiment 30 being the absolutely preferred embodiment among these embodiments.

With respect to embodiments 3, 6, 16, 39, 31, the order of preference is 31>39>16>6>3, embodiment 31 being the absolutely preferred embodiment among these embodiments.

With respect to embodiments 8, 23, 33, the order of preference is 33>23>8, embodiment 33 being the absolutely preferred embodiment among these embodiments.

With respect to embodiments 10, 25, 34, the order of preference is 34>25>10, embodiment 34 being the absolutely preferred embodiment among these embodiments.

With respect to embodiments 11, 26, 35, 36, the order of preference is 36>35>26, >11, embodiment 36 being the absolutely preferred embodiment among these embodiments.

With respect to embodiments 12 and 27, the order of preference is 27>12, embodiment 27 being the absolutely preferred embodiment among these embodiments.

With respect to embodiments 13 and 28, the order of preference is 28>13, embodiment 28 being the absolutely preferred embodiment among these embodiments.

In a even more particular preferred embodiment (40) of the invention the elements of formula (I) are defined as follows,
for module A,
s=1, t=0, and u=0; and
$P^2$ and $P^{11}$ taken together form an interstrand linking bis (amino acid)-structure based on the linkage of two L amino acid residues; following
connection of the side chain of Cys; with the side chain of Cys; by a disulfide linkage; or
$P^4$ and $P^9$ taken together form an interstrand linking bis (amino acid) structure based on the linkage of two L amino acid residues; following
connection of the side chain of Cys; with the side chain of Cys; or Pen; by a disulfide linkage; or
$P^4$ and $P^9$ taken together form a salt bridge based on the electrostatic interaction between the side chain of Dab at $P^4$ and the side chain of Glu; at $P^9$;
$P^1$ is Val; Ac-Val; NMeVal; HOVal; Ac-Nle; or Ac-Tyr;
$P^2$ is Thr;
$P^3$ is Val; Ser; or Tyr;
$P^4$ is Dab; or Ser;
$P^5$ is Orn;
$P^6$ is $^D$Dab; or $^D$Ser;
$P^7$ is Ser; Hse; Thr; or Dab;

P⁸ is Trp;
P⁹ is Ser; Hse; alloThr; Dab; or Glu;
P¹⁰ is Val; or Ile;
P¹¹ is Ala;
X¹² is Ser; Ser-NH₂; Thr-NH₂; Tyrol; or Tyr-NH₂;
with the proviso that,
    if P³ is Ser; or Val; then P¹ is Ac-Tyr; or X¹² is Tyrol; or Tyr-NH₂;
with the further proviso that,
    if P⁷ is Dab; then P⁴ is Ser and Q⁴ of module B is Abu; or Thr;
with the further proviso that,
    if linker L, as defined below, is connected with module A by a carbonyl (C=O) point of attachment of P⁵; or P⁶; then;
P⁵; is Glu; or P⁶ is ᴰGlu;
for module B consisting of single elements Q being connected in either direction from the carbonyl (C=O) point of attachment to the nitrogen (N) of the next element with the proviso that Q⁷ is connected from the α-carbonyl (C=O) point of attachment to the ω-nitrogen (N) of Q¹,
Q¹ is Dab;
Q², Q⁵ and Q⁶ are Dab;
Q³ is ᴰLeu;
Q⁴ is Leu; Ile; Abu; or Thr;
Q⁷ is Thr;
for a linker L consisting of k=3 single elements L being connected in either direction from the carbonyl (C=O) point of attachment to the nitrogen (N) of the next element,
L¹ is Dab; or ᴰDab;
L² is Thr; or Ser;
L³ is Dap; Dab; or ᴰDab;
said linker L being connected with module B from the carbonyl (C=O) point of attachment of $L^k$ to the α-nitrogen (N) of Q¹ and,
if k=3, being connected with module A from the carbonyl (C=O) point of attachment of P⁵; or P⁶; to the nitrogen (N) of L¹;
or a pharmaceutically acceptable salt thereof.

In another embodiment (41) the present invention relates to novel β-hairpin peptidomimetics of formula (I), comprising a module A consisting of single elements P or X being connected in either direction from the carbonyl (C=O) point of attachment to the nitrogen (N) of the next element
wherein
s=0, t=0, and u=0; or s=1, t=0, and u=0; or s=0, t=0, and u=1; or s=1, t=1, and u=0; or s=1, t=0, and u=1; or s=1, t=1, and u=1;
if s=1, t=1, and u=1; and
X¹⁴ and X¹³ taken together and/or P¹ and X¹² taken together and/or P² and P¹¹ taken together and/or P⁴ and P⁹ taken together form naturally or non-naturally cross-linking α-amino acids or non-naturally cross-linking acids containing each in total 1 to 12 carbon- and/or heteroatoms in a single side-chain which together are connecting X¹⁴ and X¹³ and/or P¹ and X¹² and/or P² and P¹¹ and/or P⁴ and P⁹ by covalent interaction (interstrand linkage) or by electrostatic interaction (salt bridge); then
X¹⁴ is pGlu; ᴰpGlu; Ac-pGlu; Ac-ᴰpGlu; or a naturally or non-naturally occurring basic L α-amino acid containing in total 1 to 25 carbon- and/or heteroatoms in a single side-chain comprising at least one amino function or one guanidino function; or a naturally or non-naturally occurring alcoholic D α-amino acid containing in total 1 to 25 carbon- and/or heteroatoms in a single side-chain; or an aliphatic acid containing in total 1 to 25 carbon- and/or heteroatoms in a single side-chain;
P¹ is a naturally or non-naturally occurring aliphatic L or D α-amino acid containing in total 1 to 25 carbon- and/or heteroatoms in a single side-chain; or a naturally or non-naturally occurring aromatic L α-amino acid containing in total 1 to 25 carbon- and/or heteroatoms in a single side-chain; or a naturally or non-naturally occurring alcoholic L α-amino acid containing in total 1 to 25 carbon- and/or heteroatoms in a single side-chain;
P² is a naturally or non-naturally occurring aliphatic L α-amino acid containing in total 1 to 25 carbon- and/or heteroatoms in a single side-chain; or a naturally or non-naturally occurring basic L α-amino acid containing in total 1 to 25 carbon- and/or heteroatoms in a single side-chain comprising at least one amino function or one guanidino function; or a naturally or non-naturally occurring alcoholic L α-amino acid containing in total 1 to 25 carbon- and/or heteroatoms in a single side-chain;
P³ is a naturally or non-naturally occurring aliphatic L α-amino acid containing in total 1 to 25 carbon- and/or heteroatoms in a single side-chain; or a naturally or non-naturally occurring aromatic L α-amino acid containing in total 1 to 25 carbon- and/or heteroatoms in a single side-chain; or a naturally or non-naturally occurring alcoholic L α-amino acid containing in total 1 to 25 carbon- and/or heteroatoms in a single side-chain;
P⁴ is Gly; or a naturally or non-naturally occurring basic L α-amino acid containing in total 1 to 25 carbon- and/or heteroatoms in a single side-chain comprising at least one amino function or one guanidino function; or a naturally or non-naturally occurring alcoholic L α-amino acid containing in total 1 to 25 carbon- and/or heteroatoms in a single side-chain;
P⁵ is Gly; or a naturally or non-naturally occurring basic L α-amino acid containing in total 1 to 25 carbon- and/or heteroatoms in a single side-chain comprising at least one amino function or one guanidino function;
P⁶ is Gly; or a naturally or non-naturally occurring basic D α-amino acid containing in total 1 to 25 carbon- and/or heteroatoms in a single side-chain comprising at least one amino function or one guanidino function; or a naturally or non-naturally occurring alcoholic D α-amino acid containing in total 1 to 25 carbon- and/or heteroatoms in a single side-chain; or a naturally or non-naturally occurring aliphatic D α-amino acid containing in total 1 to 25 carbon- and/or heteroatoms in a single side-chain;
P⁷ is Gly; or a naturally or non-naturally occurring aliphatic L α-amino acid containing in total 1 to 25 carbon- and/or heteroatoms in a single side-chain; or a naturally or non-naturally occurring basic L α-amino acid containing in total 1 to 25 carbon- and/or heteroatoms in a single side-chain comprising at least one amino function or one guanidino function; or a naturally or non-naturally occurring alcoholic L α-amino acid containing in total 1 to 25 carbon- and/or heteroatoms in a single side-chain;
P⁸ is a naturally or non-naturally occurring aliphatic L α-amino acid containing in total 1 to 25 carbon- and/or heteroatoms in a single side-chain; or a naturally or non-naturally occurring aromatic L α-amino acid containing in total 1 to 25 carbon- and/or heteroatoms in a single side-chain;
P⁹ is Gly; or a naturally or non-naturally occurring aliphatic L α-amino acid containing in total 1 to 25 carbon- and/or heteroatoms in a single side-chain; or a naturally or non-naturally occurring alcoholic L α-amino acid containing in total 1 to 25 carbon- and/or heteroatoms in a single side-chain; or a naturally or non-naturally occurring L α-amino acid containing in total 1 to 25 carbon- and/or heteroatoms in a single side-chain comprising at least one carboxylic acid function or phosphonic acid function;

$P^{10}$ is a naturally or non-naturally occurring aliphatic L α-amino acid containing in total 1 to 25 carbon- and/or heteroatoms in a single side-chain; or a naturally or non-naturally occurring alcoholic L α-amino acid containing in total 1 to 25 carbon- and/or heteroatoms in a single side-chain; or a naturally or non-naturally occurring aromatic L α-amino acid containing in total 1 to 25 carbon- and/or heteroatoms in a single side-chain;

$P^{11}$ is a naturally or non-naturally occurring aliphatic L α-amino acid containing in total 1 to 25 carbon- and/or heteroatoms in a single side-chain; or a naturally or non-naturally occurring basic L α-amino acid containing in total 1 to 25 carbon- and/or heteroatoms in a single side-chain comprising at least one amino function or one guanidino function; or a naturally or non-naturally occurring alcoholic L α-amino acid containing in total 1 to 25 carbon- and/or heteroatoms in a single side-chain; or a naturally or non-naturally occurring L α-amino acid containing in total 1 to 25 carbon- and/or heteroatoms in a single side-chain comprising at least one carboxylic acid function or phosphonic acid function;

$X^{12}$ is a naturally or non-naturally occurring aliphatic L α-amino acid containing in total 1 to 25 carbon- and/or heteroatoms in a single side-chain; or a naturally or non-naturally occurring aromatic L α-amino acid containing in total 1 to 25 carbon- and/or heteroatoms in a single side-chain; or a naturally or non-naturally occurring basic L α-amino acid containing in total 1 to 25 carbon- and/or heteroatoms in a single side-chain comprising at least one amino function or one guanidino function; or a naturally or non-naturally occurring alcoholic L α-amino acid containing in total 1 to 25 carbon- and/or heteroatoms in a single side-chain;

$X^{13}$ is Glyol; or a naturally or non-naturally occurring aliphatic D α-amino acid containing in total 1 to 25 carbon- and/or heteroatoms in a single side-chain; or a naturally or non-naturally occurring alcoholic D α-amino acid containing in total 1 to 25 carbon- and/or heteroatoms in a single side-chain;

with the proviso that,
if $P^1$ is a naturally or non-naturally occurring alcoholic L α-amino acid containing in total 1 to 25 carbon- and/or heteroatoms in a single side-chain; then $X^{12}$ is naturally or non-naturally occurring aliphatic L α-amino acid containing in total 1 to 25 carbon- and/or heteroatoms in a single side-chain; and if $P^3$ is a naturally or non-naturally occurring alcoholic L α-amino acid containing in total 1 to 25 carbon- and/or heteroatoms in a single side-chain; or a naturally or non-naturally occurring aliphatic L α-amino acid containing in total 1 to 25 carbon- and/or heteroatoms in a single side-chain; then $P^1$; $P^m$; or $X^{12}$; is a naturally or non-naturally occurring aromatic L α-amino acid containing in total 1 to 25 carbon- and/or heteroatoms in a single side-chain; and if $P^8$ is a naturally or non-naturally occurring aliphatic L α-amino acid containing in total 1 to 25 carbon- and/or heteroatoms in a single side-chain; then $P^{10}$ is a naturally or non-naturally occurring aromatic L α-amino acid containing in total 1 to 25 carbon- and/or heteroatoms in a single side-chain; and if $P^{10}$ is a naturally or non-naturally occurring alcoholic L α-amino acid containing in total 1 to 25 carbon- and/or heteroatoms in a single side-chain; then $X^{12}$ is a naturally or non-naturally occurring aliphatic L α-amino acid containing in total 1 to 25 carbon- and/or heteroatoms in a single side-chain; and the combined number of the amino acid residue Gly in above module A must not exceed two; and the positions P of the amino acid residues Gly must not be in direct vicinity;

with the further proviso that,
the combined number of interstrand linkages and salt bridges in above module A must not exceed two;

if $X^{14}$ and $X^{13}$ taken together form an interstrand linkage or salt bridge, as defined above; then $P^1$ and $X^{12}$ taken together are not forming an interstrand linkage or salt bridge, as defined above;

if $P^1$ and $X^{12}$ taken together form an interstrand linkage or salt bridge, as defined above; then $P^2$ and $P^{11}$ taken together are not forming an interstrand linkage or a salt bridge, as defined above;

the carbonyl (C=O) point of attachment of $X^{13}$ and the nitrogen (N) point of attachment of $X^{14}$ are appropriately saturated to form the corresponding naturally or non-naturally occurring terminal α-amino acids optionally having modified carbonyl (C=O) functional groups and/or nitrogen (N) functional groups;

with the further proviso that,
if linker L, as defined below, is connected with module A by a carbonyl (C=O) point of attachment of $P^5$; $P^6$; or $P^7$; then $P^5$; $P^6$; or $P^7$; is a naturally or non-naturally occurring α-amino acid containing in total 1 to 25 carbon- and/or heteroatoms in a single side-chain comprising at least one carboxyl function;

if s=1, t=0, and u=1; and
$P^1$ and $X^{12}$ taken together and/or $P^2$ and $P^{11}$ taken together and/or $P^4$ and $P^9$ taken together form naturally or non-naturally cross-linking α-amino acids containing each in total 1 to 12 carbon- and/or heteroatoms in a single side-chain which together are connecting $P^1$ and $X^{12}$ and/or $P^2$ and $P^{11}$ and/or $P^4$ and $P^9$ by covalent interaction (interstrand linkage) or by electrostatic interaction (salt bridge); then)

$X^{14}$; $P^1$; $P^2$; $P^3$; $P^4$; $P^5$; $P^6$; $P^7$; $P^8$; $P^9$; $P^{10}$; and $P^{11}$ are as defined above for module A, wherein s=1, t=1, and u=1;

$X^{12}$ is Glyol; or a naturally or non-naturally occurring aliphatic L α-amino acid containing in total 1 to 25 carbon- and/or heteroatoms in a single side-chain; or a naturally or non-naturally occurring aromatic L α-amino acid containing in total 1 to 25 carbon- and/or heteroatoms in a single side-chain; or a naturally or non-naturally occurring basic L α-amino acid containing in total 1 to 25 carbon- and/or heteroatoms in a single side-chain comprising at least one amino function or one guanidino function; or a naturally or non-naturally occurring alcoholic L α-amino acid containing in total 1 to 25 carbon- and/or heteroatoms in a single side-chain; or an aliphatic amino alcohol containing in total 1 to 25 carbon- and/or heteroatoms in a single side-chain; or an aromatic amino alcohol containing in total 1 to 25 carbon- and/or heteroatoms in a single side-chain; or basic amino alcohol containing in total 1 to 25 carbon- and/or heteroatoms in a single side-chain comprising at least one amino function or one guanidino function; or an alcoholic amino alcohol containing in total 1 to 25 carbon- and/or heteroatoms in a single side-chain comprising at least one hydroxyl function;

with the proviso that,
  if $P^1$ is a naturally or non-naturally occurring alcoholic L α-amino acid containing in total 1 to 25 carbon- and/or heteroatoms in a single side-chain; then $X^{12}$ is naturally or non-naturally occurring aliphatic L α-amino acid containing in total 1 to 25 carbon- and/or heteroatoms in a single side-chain; and
  if $P^3$ is a naturally or non-naturally occurring alcoholic L α-amino acid containing in total 1 to 25 carbon- and/or heteroatoms in a single side-chain; or a naturally or non-naturally occurring aliphatic L α-amino acid containing in total 1 to 25 carbon- and/or heteroatoms in a single side-chain;
  then $P^1$; or $P^{10}$; is a naturally or non-naturally occurring aromatic L α-amino acid containing in total 1 to 25 carbon- and/or heteroatoms in a single side-chain; or $X^{12}$ is a naturally or non-naturally occurring aromatic L α-amino acid containing in total 1 to 25 carbon- and/or heteroatoms in a single side-chain; or an aromatic amino alcohol containing in total 1 to 25 carbon- and/or heteroatoms in a single side-chain;
  and
  if $P^8$ is a naturally or non-naturally occurring aliphatic L α-amino acid containing in total 1 to 25 carbon- and/or heteroatoms in a single side-chain;
  then $P^{10}$ is a naturally or non-naturally occurring aromatic L α-amino acid containing in total 1 to 25 carbon- and/or heteroatoms in a single side-chain; and
  if $P^{10}$ is a naturally or non-naturally occurring alcoholic L α-amino acid containing in total 1 to 25 carbon- and/or heteroatoms in a single side-chain;
  then $X^{12}$ is a naturally or non-naturally occurring aliphatic L α-amino acid containing in total 1 to 25 carbon- and/or heteroatoms in a single side-chain; and
  the combined number of the amino acid residue Gly in above module A must not exceed two; and
  the positions P of the amino acid residues Gly must not be in direct vicinity;
with the further proviso that,
  if $P^1$ and $X^{12}$ taken together form an interstrand linkage or salt bridge, as defined above; then $P^2$ and $P^{11}$ taken together are not forming an interstrand linkage or salt bridge, as defined above;
  the carbonyl (C=O) point of attachment of $X^{12}$ and the nitrogen (N) point of attachment of $X^{14}$ are appropriately saturated to form the corresponding naturally or non-naturally occurring terminal α-amino acids optionally having modified carbonyl (C=O) functional groups and/or nitrogen (N) functional groups;
with the further proviso that,
  if linker L, as defined below, is connected with module A by a carbonyl (C=O) point of attachment of $P^5$; $P^6$; or $P^7$; then
  $P^5$; $P^6$; or $P^7$; is a naturally or non-naturally occurring α-amino acid containing in total 1 to 25 carbon- and/or heteroatoms in a single side-chain comprising at least one carboxyl function;
if s=1, t=1, and u=0; and
$P^1$ and $X^{12}$ taken together and/or $P^2$ and $P^{11}$ taken together and/or $P^4$ and $P^9$ taken together form naturally or non-naturally cross-linking α-amino acids or non-naturally cross-linking acids containing each in total 1 to 12 carbon- and/or heteroatoms in a single side-chain which together are connecting $P^1$ and $X^{12}$ and/or $P^2$ and $P^{11}$ and/or $P^4$ and $P^9$ by covalent interaction (interstrand linkage) or by electrostatic interaction (salt bridge); then $P^1$ is pGlu; $^D$pGlu; Ac-pGlu; Ac-$^D$pGlu; or a naturally or non-naturally occurring aliphatic L or D α-amino acid containing in total 1 to 25 carbon- and/or heteroatoms in a single side-chain; or a naturally or non-naturally occurring aromatic L α-amino acid containing in total 1 to 25 carbon- and/or heteroatoms in a single side-chain; or a naturally or non-naturally occurring alcoholic L α-amino acid containing in total 1 to 25 carbon- and/or heteroatoms in a single side-chain; or an aliphatic L α-hydroxy acid containing in total 1 to 25 carbon- and/or heteroatoms in a single side-chain; or an aromatic L α-hydroxy acid containing in total 1 to 25 carbon- and/or heteroatoms in a single side-chain; or an alcoholic L α-amino acid containing in total 1 to 25 carbon- and/or heteroatoms in a single side-chain; or an aliphatic acid containing in total 1 to 25 carbon- and/or heteroatoms in a single side-chain;
$P^2$; $P^3$; $P^4$; $P^5$; $P^6$; $P^7$; $P^8$; $P^9$; $P^{10}$; $P^{11}$; and $X^{12}$ are as defined above for module A, wherein s=1, t=1, and u=1;
$X^{13}$ is Glyol; or a naturally or non-naturally occurring aliphatic D α-amino acid containing in total 1 to 25 carbon- and/or heteroatoms in a single side-chain; or a naturally or non-naturally occurring alcoholic D α-amino acid containing in total 1 to 25 carbon- and/or heteroatoms in a single side-chain;
with the proviso that,
  if $P^1$ is a naturally or non-naturally occurring alcoholic L α-amino acid containing in total 1 to 25 carbon- and/or heteroatoms in a single side-chain;
  then $X^{12}$ is naturally or non-naturally occurring aliphatic L α-amino acid containing in total 1 to 25 carbon- and/or heteroatoms in a single side-chain; and
  if $P^3$ is a naturally or non-naturally occurring alcoholic L α-amino acid containing in total 1 to 25 carbon- and/or heteroatoms in a single side-chain; or a naturally or non-naturally occurring aliphatic L α-amino acid containing in total 1 to 25 carbon- and/or heteroatoms in a single side-chain;
  then $P^1$; $P^m$; or $X^{12}$; is a naturally or non-naturally occurring aromatic L α-amino acid containing in total 1 to 25 carbon- and/or heteroatoms in a single side-chain; and
  if $P^8$ is a naturally or non-naturally occurring aliphatic L α-amino acid containing in total 1 to 25 carbon- and/or heteroatoms in a single side-chain;
  then $P^{10}$ is a naturally or non-naturally occurring aromatic L α-amino acid containing in total 1 to 25 carbon- and/or heteroatoms in a single side-chain; and
  if $P^{10}$ is a naturally or non-naturally occurring alcoholic L α-amino acid containing in total 1 to 25 carbon- and/or heteroatoms in a single side-chain;
  then $X^{12}$ is a naturally or non-naturally occurring aliphatic L α-amino acid containing in total 1 to 25 carbon- and/or heteroatoms in a single side-chain; and
  the combined number of the amino acid residue Gly in above module A must not exceed two; and
  the positions P of the amino acid residues Gly must not be in direct vicinity;
with the further proviso that,
  if $P^1$ and $X^{12}$ taken together form an interstrand linkage or salt bridge, as defined above; then $P^2$ and $P^{11}$ taken together are not forming an interstrand linkage or salt bridge, as defined above;
  the carbonyl (C=O) point of attachment of $X^{13}$ and the nitrogen (N) point of attachment of $P^1$ are appropriately saturated to form the corresponding naturally or non-naturally occurring terminal α-amino acids optionally having modified carbonyl (C=O) functional groups and/or nitrogen (N) functional groups;

with the further proviso that,
if linker L, as defined below, is connected with module A by a carbonyl (C=O) point of attachment of $P^5$; $P^6$; or $P^7$; then
$P^5$; $P^6$; or $P^7$; is a naturally or non-naturally occurring α-amino acid containing in total 1 to 25 carbon- and/or heteroatoms in a single side-chain comprising at least one carboxyl function;

if s=0, t=0, and u=1; and
$P^2$ and $P^{11}$ taken together and/or $P^4$ and $P^9$ taken together form naturally or non-naturally cross-linking α-amino acids containing each in total 1 to 12 carbon- and/or heteroatoms in a single side-chain which together are connecting $P^2$ and $P^{11}$ and/or $P^4$ and $P^9$ by covalent interaction (interstrand linkage) or by electrostatic interaction (salt bridge); then
$X^{14}$; $P^1$; $P^2$; $P^3$; $P^4$; $P^5$; $P^6$; $P^7$; $P^8$; $P^9$; and $P^{10}$ are as defined above for module A, wherein s=1, t=1, and u=1;
$P^{11}$ is a naturally or non-naturally occurring aliphatic L α-amino acid containing in total 1 to 25 carbon- and/or heteroatoms in a single side-chain; or a naturally or non-naturally occurring basic L α-amino acid containing in total 1 to 25 carbon- and/or heteroatoms in a single side-chain comprising at least one amino function or guanidino function; or a naturally or non-naturally occurring alcoholic L α-amino acid containing in total 1 to 25 carbon- and/or heteroatoms in a single side-chain; or a naturally or non-naturally occurring L α-amino acid containing in total 1 to 25 carbon- and/or heteroatoms in a single side-chain comprising at least one carboxylic acid function or with the proviso that,
if $P^3$ is a naturally or non-naturally occurring alcoholic L α-amino acid containing in total 1 to 25 carbon- and/or heteroatoms in a single side-chain; or a naturally or non-naturally occurring aliphatic L α-amino acid containing in total 1 to 25 carbon- and/or heteroatoms in a single side-chain;
then $P^1$; or $P^m$; is a naturally or non-naturally occurring aromatic L α-amino acid containing in total 1 to 25 carbon- and/or heteroatoms in a single side-chain; and
if $P^8$ is a naturally or non-naturally occurring aliphatic L α-amino acid containing in total 1 to 25 carbon- and/or heteroatoms in a single side-chain;
then $P^{10}$ is a naturally or non-naturally occurring aromatic L α-amino acid containing in total 1 to 25 carbon- and/or heteroatoms in a single side-chain; and
the combined number of the amino acid residue Gly in above module A must not exceed two; and
the positions P of the amino acid residues Gly must not be in direct vicinity;

with the further proviso that,
the carbonyl (C=O) point of attachment of $P^{11}$ and the nitrogen (N) point of attachment of $X^{14}$ are appropriately saturated to form the corresponding naturally or non-naturally occurring terminal α-amino acids optionally having modified carbonyl (C=O) functional groups and/or nitrogen (N) functional groups;

with the further proviso that,
if linker L, as defined below, is connected with module A by a carbonyl (C=O) point of attachment of $P^5$; $P^6$; or $P^7$; then
$P^5$; $P^6$; or $P^7$; is a naturally or non-naturally occurring α-amino acid containing in total 1 to 25 carbon- and/or heteroatoms in a single side-chain comprising at least one carboxyl function;

if s=1, t=0, and u=0; and
$P^1$ and $X^{12}$ taken together and/or $P^2$ and $P^{11}$ taken together and/or $P^4$ and $P^9$ taken together form naturally or non-naturally cross-linking α-amino acids or non-naturally cross-linking acids containing each in total 1 to 12 carbon- and/or heteroatoms in a single side-chain which together are connecting $P^1$ and $X^{12}$ and/or $P^2$ and $P^{11}$ and/or $P^4$ and $P^9$ by covalent interaction (interstrand linkage) or by electrostatic interaction (salt bridge); then
$P^1$ is pGlu; $^D$pGlu; Ac-pGlu; Ac-$^D$pGlu; or a naturally or non-naturally occurring aliphatic L or D α-amino acid containing in total 1 to 25 carbon- and/or heteroatoms in a single side-chain; or a naturally or non-naturally occurring aromatic L α-amino acid containing in total 1 to 25 carbon- and/or heteroatoms in a single side-chain; or a naturally or non-naturally occurring alcoholic L α-amino acid containing in total 1 to 25 carbon- and/or heteroatoms in a single side-chain; or an aliphatic α-hydroxy acid containing in total 1 to 25 carbon- and/or heteroatoms in a single side-chain; or an aromatic L α-hydroxy acid containing in total 1 to 25 carbon- and/or heteroatoms in a single side-chain; or an alcoholic L α-hydroxy acid containing in total 1 to 25 carbon- and/or heteroatoms in a single side-chain; or an aliphatic acid containing in total 1 to 25 carbon- and/or heteroatoms in a single side-chain;
$P^2$; $P^3$; $P^4$; $P^5$; $P^6$; $P^7$; $P^8$; $P^9$; $P^{10}$; and $P^{11}$ are as defined above for module A, wherein s=1, t=1, and u=1;
$X^{12}$ is Glyol; or a naturally or non-naturally occurring aliphatic L α-amino acid containing in total 1 to 25 carbon- and/or heteroatoms in a single side-chain; or a naturally or non-naturally occurring aromatic L α-amino acid containing in total 1 to 25 carbon- and/or heteroatoms in a single side-chain; or a naturally or non-naturally occurring basic L α-amino acid containing in total 1 to 25 carbon- and/or heteroatoms in a single side-chain comprising at least one amino function or one guanidino function; or a naturally or non-naturally occurring alcoholic L α-amino acid containing in total 1 to 25 carbon- and/or heteroatoms in a single side-chain; or an aliphatic amino alcohol containing in total 1 to 25 carbon- and/or heteroatoms in a single side-chain; or an aromatic amino alcohol containing in total 1 to 25 carbon- and/or heteroatoms in a single side-chain; or a basic amino alcohol containing in total 1 to 25 carbon- and/or heteroatoms in a single side-chain comprising at least one amino function or one guanidino function; or an alcoholic amino alcohol containing in total 1 to 25 carbon- and/or heteroatoms in a single side-chain comprising at least one hydroxyl function;

with the proviso that,
if $P^1$ is a naturally or non-naturally occurring alcoholic L α-amino acid containing in total 1 to 25 carbon- and/or heteroatoms in a single side-chain;
then $X^{12}$ is naturally or non-naturally occurring aliphatic L α-amino acid containing in total 1 to 25 carbon- and/or heteroatoms in a single side-chain; and
if $P^3$ is a naturally or non-naturally occurring alcoholic L α-amino acid containing in total 1 to 25 carbon- and/or heteroatoms in a single side-chain;
or a naturally or non-naturally occurring aliphatic L α-amino acid containing in total 1 to 25 carbon- and/or heteroatoms in a single side-chain;
then $P^1$; or $P^m$; is a naturally or non-naturally occurring aromatic L α-amino acid containing in total 1 to 25 carbon- and/or heteroatoms in a single side-chain; or
$X^{12}$ is a naturally or non-naturally occurring aromatic L α-amino acid containing in total 1 to 25 carbon- and/or heteroatoms in a single side-chain; or an aromatic amino alcohol containing in total 1 to 25 carbon- and/or heteroatoms in a single side-chain; and if $P^8$ is a naturally or non-naturally occurring aliphatic L α-amino acid containing in total 1 to 25 carbon- and/or heteroatoms in a single side-chain;

then $P^{10}$ is a naturally or non-naturally occurring aromatic L α-amino acid containing in total 1 to 25 carbon- and/or heteroatoms in a single side-chain; and if $P^{10}$ is a naturally or non-naturally occurring alcoholic L α-amino acid containing in total 1 to 25 carbon- and/or heteroatoms in a single side-chain;

then $X^{12}$ is a naturally or non-naturally occurring aliphatic L α-amino acid containing in total 1 to 25 carbon- and/or heteroatoms in a single side-chain; and the combined number of the amino acid residue Gly in above module A must not exceed two; and the positions P of the amino acid residues Gly must not be in direct vicinity;

with the further proviso that, if $P^1$ and $X^{12}$ taken together form an interstrand linkage or salt bridge, as defined above; then $P^2$ and $P^{11}$ taken together are not forming an interstrand linkage or salt bridge, as defined above;

the carbonyl (C=O) point of attachment of $X^{12}$ and the nitrogen (N) point of attachment of $P^1$ are appropriately saturated to form the corresponding naturally or non-naturally occurring terminal α-amino acids optionally having modified carbonyl (C=O) functional groups and/or nitrogen (N) functional groups;

with the further proviso that, if linker L, as defined below, is connected with module A by a carbonyl (C=O) point of attachment of $P^5$; $P^6$; or $P^7$; then $P^5$; $P^6$; or $P^7$; is a naturally or non-naturally occurring α-amino acid containing in total 1 to 25 carbon- and/or heteroatoms in a single side-chain comprising at least one carboxyl function;

if s=0, t=0, and u=0; and $P^2$ and $P^{11}$ taken together and/or $P^4$ and $P^9$ taken together form naturally or non-naturally cross-linking α-amino acids containing each in total 1 to 12 carbon- and/or heteroatoms in a single side-chain which together are connecting $P^2$ and $P^{11}$ and/or $P^4$ and $P^9$ by covalent interaction (interstrand linkage) or by electrostatic interaction (salt bridge); then $P^1$ is pGlu; $^D$pGlu; Ac-pGlu; Ac-$^D$pGlu; or a naturally or non-naturally occurring aliphatic L or D α-amino acid containing in total 1 to 25 carbon- and/or heteroatoms in a single side-chain; or a naturally or non-naturally occurring aromatic L α-amino acid containing in total 1 to 25 carbon- and/or heteroatoms in a single side-chain; or a naturally or non-naturally occurring alcoholic L α-amino acid containing in total 1 to 25 carbon- and/or heteroatoms in a single side-chain; or an aliphatic α-hydroxy acid containing in total 1 to 25 carbon- and/or heteroatoms in a single side-chain; or an aromatic L α-hydroxy acid containing in total 1 to 25 carbon- and/or heteroatoms in a single side-chain; or an alcoholic L α-hydroxy acid containing in total 1 to 25 carbon- and/or heteroatoms in a single side-chain; or an aliphatic acid containing in total 1 to 25 carbon- and/or heteroatoms in a single side-chain;

$P^2$; $P^3$; $P^4$; $P^5$; $P^6$; $P^7$; $P^8$; $P^9$; and $P^{10}$ are as defined above for module A, wherein s=1, t=1, and u=1;

$P^{11}$ is a naturally or non-naturally occurring aliphatic L α-amino acid containing in total 1 to 25 carbon- and/or heteroatoms in a single side-chain; or a naturally or non-naturally occurring basic L α-amino acid containing in total 1 to 25 carbon- and/or heteroatoms in a single side-chain comprising at least one amino function or guanidino function; or a naturally or non-naturally occurring alcoholic L α-amino acid containing in total 1 to 25 carbon- and/or heteroatoms in a single side-chain; or a naturally or non-naturally occurring L α-amino acid containing in total 1 to 25 carbon- and/or heteroatoms in a single side-chain comprising at least one carboxylic acid function or phosphonic acid function;

with the proviso that, if $P^3$ is a naturally or non-naturally occurring alcoholic L α-amino acid containing in total 1 to 25 carbon- and/or heteroatoms in a single side-chain; or a naturally or non-naturally occurring aliphatic L α-amino acid containing in total 1 to 25 carbon- and/or heteroatoms in a single side-chain;

then $P^7$; or $P'''$; is a naturally or non-naturally occurring aromatic L a amino acid containing in total 1 to 25 carbon- and/or heteroatoms in a single side-chain; and if $P^8$ is a naturally or non-naturally occurring aliphatic L α-amino acid containing in total 1 to 25 carbon- and/or heteroatoms in a single side-chain;

then $P^{10}$ is a naturally or non-naturally occurring aromatic L α-amino acid containing in total 1 to 25 carbon- and/or heteroatoms in a single side-chain; and the combined number of the amino acid residue Gly in above module A must not exceed two; and the positions P of the amino acid residues Gly must not be in direct vicinity;

with the further proviso that, the carbonyl (C=O) point of attachment of $P^{11}$ and the nitrogen (N) point of attachment of P' are appropriately saturated to form the corresponding naturally or non-naturally occurring terminal α-amino acids optionally having modified carbonyl (C=O) functional groups and/or nitrogen (N) functional groups;

with the further proviso that, if linker L, as defined below, is connected with module A by a carbonyl (C=O) point of attachment of $P^5$; $P^6$; or $P^7$; then $P^5$; $P^6$; or $P^7$; is a naturally or non-naturally occurring α-amino acid containing in total 1 to 25 carbon- and/or heteroatoms in a single side-chain comprising at least one carboxyl function;

if s=0, t=0, and u=0; and $P^{11}$ is connected from the α-carbonyl point of attachment to the ω-nitrogen (N) of $P^2$; then $P^1$ is a naturally or non-naturally occurring aliphatic L or D α-amino acid containing in total 1 to 25 carbon- and/or heteroatoms in a single side-chain; or a naturally or non-naturally occurring aromatic L α-amino acid containing in total 1 to 25 carbon- and/or heteroatoms in a single side-chain; or a naturally or non-naturally occurring alcoholic L α-amino acid containing in total 1 to 25 carbon- and/or heteroatoms in a single side-chain; or an aliphatic α-hydroxy acid containing in total 1 to 25 carbon- and/or heteroatoms in a single side-chain; or an aromatic L α-hydroxy acid containing in total 1 to 25 carbon- and/or heteroatoms in a single side-chain; or an alcoholic L α-hydroxy acid containing in total 1 to 25 carbon- and/or heteroatoms in a single side-chain; or an aliphatic acid containing in total 1 to 25 carbon- and/or heteroatoms in a single side-chain;

$P^2$ is a naturally or non-naturally occurring basic L α-amino acid containing in total 1 to 25 carbon- and/or heteroatoms in a single side-chain comprising at least one amino function;

$P^3$; $P^4$; $P^5$; $P^6$; $P^7$; $P^8$; $P^9$; and $P^{10}$ are as defined above for module A, wherein s=1, t=1, and u=1;

$P^{11}$ is a naturally or non-naturally occurring aliphatic D α-amino acid containing in total 1 to 25 carbon- and/or heteroatoms in a single side-chain; or a naturally or non-naturally occurring aromatic D α-amino acid containing in total 1 to 25 carbon- and/or heteroatoms in a single side-chain; or a naturally or non-naturally occurring basic D α-amino acid containing in total 1 to 25 carbon- and/or heteroatoms in a single side-chain comprising at least one amino function or guanidino function; or a naturally or non-naturally occurring alcoholic D α-amino acid containing in total 1 to 25 carbon- and/or heteroatoms in a single side-chain; or a naturally or non-naturally occurring D α-amino acid containing in total 1 to 25 carbon- and/or heteroatoms in a single side-chain comprising at least one carboxylic acid function or phosphonic acid function; or a naturally or non-naturally occurring D α-amino acid containing in total 1 to 25 carbon- and/or heteroatoms in a single side-chain comprising at least one amide function;

with the proviso that, if $P^3$ is a naturally or non-naturally occurring alcoholic L α-amino acid containing in total 1 to 25 carbon- and/or heteroatoms in a single side-chain; or a naturally or non-naturally occurring aliphatic L α-amino acid containing in total 1 to 25 carbon- and/or heteroatoms in a single side-chain;

then $P^7$; or $P^{10}$; is a naturally or non-naturally occurring aromatic L α amino acid containing in total 1 to 25 carbon- and/or heteroatoms in a single side-chain; and if $P^8$ is a naturally or non-naturally occurring aliphatic L α-amino acid containing in total 1 to 25 carbon- and/or heteroatoms in a single side-chain;

then $P^{10}$ is a naturally or non-naturally occurring aromatic L α-amino acid containing in total 1 to 25 carbon- and/or heteroatoms in a single side-chain; and the combined number of the amino acid residue Gly in above module A must not exceed two; and the positions P of the amino acid residues Gly must not be in direct vicinity;

with the further proviso that, the nitrogen (N) point of attachment of $P^1$ is appropriately saturated to form the corresponding naturally or non-naturally occurring terminal α-amino acid optionally having a modified nitrogen (N) functional group;

with the further proviso that, if linker L, as defined below, is connected with module A by a carbonyl (C=O) point of attachment of $P^5$; $P^6$; or $P^7$; then $P^5$; $P^6$; or $P^7$; is a naturally or non-naturally occurring α-amino acid containing in total 1 to 25 carbon- and/or heteroatoms in a single side-chain comprising at least one carboxyl function;

and a module B consisting of single elements Q being connected in either direction from the carbonyl (C=O) point of attachment to the nitrogen (N) of the next element with the proviso that $Q^7$ is connected from the α-carbonyl (C=O) point of attachment to the ω-nitrogen (N) of $Q^1$, and wherein $Q^1$ is a naturally or non-naturally occurring basic L or D α-amino acid containing in total 1 to 25 carbon- and/or heteroatoms in a single side-chain comprising at least one amino function;

$Q^2$, $Q^5$, and $Q^6$ are independently
a naturally or non-naturally occurring basic L α-amino acid containing in total 1 to 25 carbon- and/or heteroatoms in a single side-chain comprising at least one amino function;

$Q^3$ is a naturally or non-naturally occurring aliphatic D α-amino acid containing in total 1 to 25 carbon- and/or heteroatoms in a single side-chain; or a naturally or non-naturally occurring aromatic D α-amino acid containing in total 1 to 25 carbon- and/or heteroatoms in a single side-chain;

$Q^4$ is a naturally or non-naturally occurring aliphatic L α-amino acid containing in total 1 to 25 carbon- and/or heteroatoms in a single side-chain; or a naturally or non-naturally occurring alcoholic L α-amino acid containing in total 1 to 25 carbon- and/or heteroatoms in a single side-chain;

$Q^7$ is a naturally or non-naturally occurring alcoholic L α-amino acid containing in total 1 to 25 carbon- and/or heteroatoms in a single side-chain; or a naturally or non-naturally occurring aliphatic L α-amino acid containing in total 1 to 25 carbon- and/or heteroatoms in a single side-chain;

and a linker L consisting of k=0-3 single elements L being connected in either direction from the carbonyl (C=O) point of attachment to the nitrogen (N) of the next element, and wherein, if k=1, $L^1$ is Gly; Sar; Aib; or a naturally or non-naturally occurring aliphatic L or D α-amino acid containing in total 1 to 25 carbon- and/or heteroatoms in a single side-chain; or a naturally or non-naturally occurring basic L or D α-amino acid containing in total 1 to 25 carbon- and/or heteroatoms in a single side-chain comprising at least one amino function; or a naturally or non-naturally occurring alcoholic L or D α-amino acid containing in total 1 to 25 carbon- and/or heteroatoms in a single side-chain;

if k=2, the additional element $L^2$ is Gly; Sar; Aib; or a naturally or non-naturally occurring aliphatic L or D α-amino acid containing in total 1 to 25 carbon- and/or heteroatoms in a single side-chain; or a naturally or non-naturally occurring basic L or D α-amino acid containing in total 1 to 25 carbon- and/or heteroatoms in a single side-chain comprising at least one amino function; or a naturally or non-naturally occurring alcoholic L or D α-amino acid containing in total 1 to 25 carbon- and/or heteroatoms in a single side-chain;

if k=3, the additional element $L^3$ is Gly; Sar; Aib; or a naturally or non-naturally occurring aliphatic L or D α-amino acid containing in total 1 to 25 carbon- and/or heteroatoms in a single side-chain; or a naturally or non-naturally occurring basic L or D α-amino acid containing in total 1 to 25 carbon- and/or heteroatoms in a single side-chain comprising at least one amino function; or a naturally or non-naturally occurring alcoholic L or D α-amino acid containing in total 1 to 25 carbon- and/or heteroatoms in a single side-chain;

said linker L being connected with module B from the carbonyl (C=O) point of attachment of $L^k$ to the α-nitrogen (N) of $Q^1$ and, if k=1-3, being connected with module A from the carbonyl (C=O) point of attachment of $P^5$; $P^6$; or $P^7$; to the nitrogen (N) of 12; or, if k=0, then $Q^1$ being directly connected with module A from the carbonyl (C=O) point of attachment of $P^5$; $P^6$; or $P^7$; to the α-nitrogen (N) of $0^1$;

or a tautomer or rotamer thereof; or a salt; or a pharmaceutically acceptable salt; or a hydrate; or a solvate thereof.

Another embodiment (42) of the invention relates to compounds of general formula (I) according to embodiment (1), comprising a module A consisting of single elements P or X being connected in either direction from the carbonyl (C=O) point of attachment to the nitrogen (N) of the next element, wherein if s=1, t=1, and u=1; and $X^{14}$ and $X^{13}$ taken together form an interstrand linking bis(amino acid)-structure of one of the formulae AA16; or AA16$^D$; based on the linkage of two α-amino acid residues;

or an interstrand linking (amino acid)-(acid)-structure of one of the formulae AA17; or AA17$^D$; based on the linkage of an α-amino acid residue and an acid residue;

or a salt bridge of one of the formulae AA18; AA18$^D$, AA19; or AA19$^D$; based on the electrostatic interaction between two α-amino acid residue as defined herein below; and/or $P^1$ and $X^{12}$ taken together form an interstrand linking bis(amino acid)-structure of one of the formulae AA16; or AA16$^D$; or a salt bridge of one of the formulae AA18; AA18$^D$; AA19; or AA19$^D$; and/or $P^2$ and $P^{11}$ taken together form an interstrand linking bis(amino acid)-structure of one of the formulae AA16; or AA16$^D$; or a salt bridge of one of the formulae AA18; AA18$^D$; AA19; or AA19$^D$; and/or $P^4$ and $P^9$ taken together form an interstrand linking bis(amino acid)-structure of one of the formulae AA16; or AA16$^D$; or a salt bridge of one of the formulae AA18; AA18$^D$; AA19; or AA19$^D$;

$X^{14}$ is pGlu; $^D$pGlu; Ac-pGlu; Ac-$^D$pGlu; or an α-amino acid residue of one of the formulae AA3b; or AA4$^D$;

or an acid residue of one of the formulae AA15a; or AA15b;

$P^1$ is an α-amino acid residue of one of the formulae AA1; AA1$^D$; AA2; or AA4;

$P^2$ is an L α-amino acid residue of one of the formulae AA1; AA3b; or AA4;

$P^3$ is an L α-amino acid residue of one of the formulae AA1; AA2; or AA4;

$P^4$ is Gly; or an L α-amino acid residue of one of the formulae AA3b; or AA4;

$P^5$ is Gly; or an L α-amino acid residue of formula AA3b;

$P^6$ is Gly; or a D α-amino acid residue of formula AA1$^D$; AA3a$^D$; or AA4$^D$;

$P^7$ is Gly; or an L α-amino acid residue of one of the formulae AA1; AA3b; or AA4;

$P^8$ is an L α-amino acid residue of one of the formulae AA1; or AA2;

$P^9$ is Gly, or an L α-amino acid residue of one of the formulae AA1; AA4; or AA5;

$P^m$ is an L α-amino acid residue of one of the formulae AA1; AA2; or AA4;

$P^{11}$ is an L α-amino acid residue of one of the formulae AA1; AA3b; AA4; or AA5;

$X^{12}$ is an L α-amino acid residue of one of the formulae AA1; AA2; AA3; or AA4;

$X^{13}$ is Glyol; or an α-amino acid residue of one of the formulae AA1$^D$; or AA4$^D$;

with the proviso that, if $P^1$ is an α-amino acid residue of formula AA4;
then $X^{12}$ is an α-amino acid residue of formula AA1; and if $P^3$ is an α-amino acid residue of one of the formulae AA1; or AA4;

then $P^1$; $P^{10}$; or $X^{12}$; is an α-amino acid residue of formula AA2; and if $P^8$ is an α-amino acid residue of formula AA1;
then $P^{10}$ is an α-amino acid residue of formula AA2; and if $P^{10}$ is an α-amino acid residue of formula AA4;
then $X^{12}$ is an α-amino acid residue of formula AA1; and the combined number of the amino acid residue Gly in above module A must not exceed two; and the positions P of the amino acid residues Gly must not be in direct vicinity;

with the further proviso that, the combined number of interstrand linkages and salt bridges in above module A must not exceed two;

if $X^{14}$ and $X^{13}$ taken together form an interstrand linkage or salt bridge, as defined above; then $P^1$ and $X^{12}$ taken together are not forming an interstrand linkage or salt bridge, as defined above;

if $P^1$ and $X^{12}$ taken together form an interstrand linkage or salt bridge, as defined above; then $P^2$ and $P^{11}$ taken together are not forming an interstrand linkage or a salt bridge, as defined above;

$X^{13}$ having a carbonyl (C=O) point of attachment not connected as aforementioned, being appropriately saturated by linkage with $R^{30}$ to form the corresponding naturally or non-naturally occurring terminal α-amino acid residue; optionally having a modified carbonyl (C=O) functional group;

$X^{14}$ having a nitrogen (N) not connected as aforementioned, being appropriately saturated by linkages with $R^1$, as already depicted above, and $R^{31}$ to form the corresponding naturally or non-naturally occurring terminal α-amino acid residue; optionally having a modified nitrogen (N) functional group;

with the further proviso that, if linker L, as defined below, is connected with module A by a carbonyl (C=O) point of attachment of $P^5$; $P^6$; or $P^7$; then $P^5$; $P^6$; or $P^7$; is an α-amino acid residue of one of the formulae AA20; or AA20$^D$;

if s=1, t=0, and u=1; and $P^1$ and $X^{12}$ taken together form an interstrand linking bis(amino acid) structure of one of the formulae AA16; or AA16$^D$; or a salt bridge of one of the formulae AA18; AA18$^D$; AA19; or AA19$^D$; and/or $P^2$ and $P^{11}$ taken together form an interstrand linking bis(amino acid) structure of one of the formulae AA16; or AA16$^D$; or a salt bridge of one of the formulae AA18; AA18$^D$; AA19; or AA19$^D$; and/or $P^4$ and $P^9$ taken together form an interstrand linking bis(amino acid) structure of one of the formulae AA16; or AA16$^D$; or a salt bridge one of the formulae AA18; AA18$^D$; AA19; or AA19$^D$;

$X^{14}$; $P^1$; $P^2$; $P^3$; $P^4$; $P^5$; $P^6$; $P^7$; $P^8$; $P^9$; $P^{10}$; and $P^{11}$ are as defined above for module A, wherein s=1, t=1, and u=1;

$X^{12}$ is Glyol; or an L α-amino acid residue of one of the formulae AA1; AA2; AA3; or AA4; or an amino alcohol residue of one of the formulae AA7; AA8; AA9; or AA10;

with the proviso that, if $P^1$ is an α-amino acid residue of formula AA4;
then $X^{12}$ is an α-amino acid residue of formula AA1; and if $P^3$ is an α-amino acid residue of one of the formulae AA1; or AA4;

then $P^1$; or $P^m$; is an α-amino acid residue of formula AA2; or $X^{12}$ is an α-amino acid residue of formula AA2; or an amino alcohol residue of formula AA8; and if $P^8$ is an α-amino acid residue of formula AA1;
then $P^{10}$ is an α-amino acid residue of formula AA2; and if $P^{10}$ is an α-amino acid residue of formula AA4;

then $X^{12}$ is an α-amino acid residue of formula AA1; and
the combined number of the amino acid residue Gly in above module A must not exceed two; and
the positions P of the amino acid residues Gly must not be in direct vicinity;
with the further proviso that,
if $P^1$ and $X^{12}$ taken together form an interstrand linkage or salt bridge, as defined above; then $P^2$ and $P^{11}$ taken together are not forming an interstrand linkage or salt bridge, as defined above;
$X^{12}$ having a carbonyl (C=O) point of attachment not connected as aforementioned, being appropriately saturated by linkage with $R^{30}$ to form the corresponding naturally or non-naturally occurring terminal α-amino acid residue; optionally having a modified carbonyl (C=O) functional group;
$X^{14}$ having a nitrogen (N) not connected as aforementioned, being appropriately saturated by linkages with Fe, as already depicted above, and $R^{31}$ to form the corresponding naturally or non-naturally occurring terminal α-amino acid residue; optionally having a modified nitrogen (N) functional group;
with the further proviso that,
if linker L, as defined below, is connected with module A by a carbonyl (C=O) point of attachment of $P^5$; $P^6$; or $P^7$; then
$P^5$; $P^6$; or $P^7$; is an α-amino acid residue of one of the formulae AA20; or AA20$^D$;
if s=1, t=1, and u=0; and
$P^1$ and $X^{12}$ taken together form an interstrand linking bis (amino acid) structure of one of the formulae AA16; or AA16$^D$; or an interstrand linking (amino acid)-(acid)-structure of one of the formulae AA17; or AA17$^D$; or a salt bridge of one of the formulae AA18; AA18$^D$; AA19; or AA19$^D$; and/or
$P^2$ and $P^{11}$ taken together form an interstrand linking bis (amino acid) structure of one of the formulae AA16; or AA16$^D$; or a salt bridge of one of the formulae AA18; AA18$^D$; AA19; or AA19$^D$; and/or
$P^4$ and $P^9$ taken together form an interstrand linking bis (amino acid) structure of one of the formulae AA16; or AA16$^D$; or a salt bridge of one of the formulae AA18; AA18$^D$; AA19; or AA19$^D$;
$P^1$ is pGlu; $^D$pGlu; Ac-pGlu; Ac-$^D$pGlu; or an α-amino acid residue of one of the formulae AA1; AA1$^D$; AA2; or AA4;
or an L α-hydroxy acid residue of one of the formulae AA11; AA12; or AA14;
or an acid residue of one of the formulae AA15a; or AA15b;
$P^2$; $P^3$; $P^4$; $P^5$; $P^6$; $P^7$; $P^8$; $P^9$; $P^{10}$; $P^{11}$; and $X^{12}$ are as defined above for module A, wherein s=1, t=1, and u=1;
$X^{13}$ is Glyol; or an α-amino acid residue of one of the formulae AA1$^D$; or AA4$^D$;
with the proviso that,
if $P^1$ is an α-amino acid residue of formula AA4;
then $X^{12}$ is an α-amino acid residue of formula AA1; and
if $P^3$ is an α-amino acid residue of one of the formulae AA1; or AA4;
then $P^1$; $P^{10}$; or $X^{12}$; is an α-amino acid residue of formula AA2; and
if $P^8$ is an α-amino acid residue of formula AA1;
then $P^{10}$ is an α-amino acid residue of formula AA2; and
if $P^{10}$ is an α-amino acid residue of formula AA4;
then $X^{12}$ is an α-amino acid residue of formula AA1; and
the combined number of the amino acid residue Gly in above module A must not exceed two; and the positions P of the amino acid residues Gly must not be in direct vicinity;
with the further proviso that,
if $P^1$ and $X^{12}$ taken together form an interstrand linkage or salt bridge, as defined above; then $P^2$ and $P^{11}$ taken together are not forming an interstrand linkage or salt bridge, as defined above;
$X^{13}$ having a carbonyl (C=O) point of attachment not connected as aforementioned, being appropriately saturated by linkage with $R^{30}$ to form the corresponding naturally or non-naturally occurring terminal α-amino acid residue; optionally having a modified carbonyl (C=O) functional group;
$P^1$ having a nitrogen (N) not connected as aforementioned, being appropriately saturated by linkages with Fe, as already depicted above, and $R^{31}$ to form the corresponding naturally or non-naturally occurring terminal α-amino acid residue; optionally having a modified nitrogen (N) functional group;
with the further proviso that,
if linker L, as defined below, is connected with module A by a carbonyl (C=O) point of attachment of $P^5$; $P^6$; or $P^7$; then
$P^5$; $P^6$; or $P^7$; is an α-amino acid residue of one of the formulae AA20; or AA20$^D$;
if s=0, t=0, and u=1; and
$P^2$ and $P^{11}$ taken together form an interstrand linking bis (amino acid) structure of one of the formulae AA16; or AA16$^D$; or a salt bridge of one of the formulae AA18; AA18$^D$; AA19; or AA19$^D$; and/or
$P^4$ and $P^9$ taken together form an interstrand linking bis (amino acid) structure of one of the formulae AA16; or AA16$^D$; or a salt bridge of one of the formulae AA18; AA18$^D$; AA19; or AA19$^D$;
$X^{14}$; $P^1$; $P^2$; $P^3$; $P^4$; $P^5$; $P^6$; $P^7$; $P^8$; $P^9$; and $P^{10}$ are as defined above for module A, wherein s=1, t=1, and u=1;
$P^{11}$ is an L α-amino acid residue of one of the formulae AA1; AA3b; AA4; or AA5;
with the proviso that,
if $P^3$ is an α-amino acid residue of one of the formulae AA1; or AA4;
then $P^1$; or $P^m$; is an α-amino acid residue of formula AA2; and
if $P^8$ is an α-amino acid residue of formula AA1;
then $P^{10}$ is an α-amino acid residue of formula AA2; and
the combined number of the amino acid residue Gly in above module A must not exceed two; and
the positions P of the amino acid residues Gly must not be in direct vicinity;
with the further proviso that,
$P^{11}$ having a carbonyl (C=O) point of attachment not connected as aforementioned, being appropriately saturated by linkage with $R^{30}$ to form the corresponding naturally or non-naturally occurring terminal α-amino acid residue; optionally having a modified carbonyl (C=O) functional group;
$X^{14}$ having a nitrogen (N) not connected as aforementioned, being appropriately saturated by linkages with Fe, as already depicted above, and $R^{31}$ to form the corresponding naturally or non-naturally occurring terminal α-amino acid residue; optionally having a modified nitrogen (N) functional group;
with the further proviso that,
if linker L, as defined below, is connected with module A by a carbonyl (C=O) point of attachment of $P^5$; $P^6$; or $P^7$; then P⁵; P⁶; or P⁷; is an α-amino acid residue of one of the formulae AA20; or AA20^D;
if s=1, t=0, and u=0; and
P¹ and X¹² taken together form an interstrand linking bis (amino acid) structure of one of the formulae AA16; or AA16^D; or an interstrand linking (amino acid)-(acid)- structure of one of the formulae AA17; or AA17^D; or a salt bridge of one of the formulae AA18; AA18^D; AA19; or AA19^D; and/or
P² and P¹¹ taken together form an interstrand linking bis (amino acid) structure of one of the formulae AA16; or AA16^D; or a salt bridge of one of the formulae AA18; AA18^D; AA19; or AA19^D; and/or
P⁴ and P⁹ taken together form an interstrand linking bis (amino acid) structure of one of the formulae AA16; or AA16^D; or a salt bridge of one of the formulae AA18; AA18^D; AA19; or AA19^D;
P¹ is pGlu; ^DpGlu; Ac-pGlu; Ac-^DpGlu; or an α-amino acid residue of one of the formulae AA1; AA1^D; AA2; AA4; or an L α-hydroxy acid residue of one of the formulae AA11; AA12; or AA14; or an acid residue of one of the formulae AA15a; or AA15b;
P²; P³; P⁴; P⁵; P⁶; P⁷; P⁸; P⁹; P¹⁰; and P¹¹ are as defined above for module A, wherein s=1, t=1, and u=1;
X¹² is Glyol; or an L α-amino acid residue of one of the formulae AA1; AA2; AA3; or AA4; or an amino alcohol residue of one of the formulae AA7; AA8; AA9; or AA10;
with the proviso that,
  if P¹ is an α-amino acid residue of formula AA4;
  then X¹² is an α-amino acid residue of formula AA1; and
  if P³ is an α-amino acid residue of one of the formulae AA1; or AA4;
  then P¹; or P¹⁰; is an α-amino acid residue of formula AA2; or X¹² is an α-amino acid residue of formula AA2; or an amino alcohol residue of formula AA8; and
  if P⁸ is an α-amino acid residue of formula AA1;
  then P¹⁰ is an α-amino acid residue of formula AA2; and
  if P¹⁰ is an α-amino acid residue of formula AA4;
  then X¹² is an α-amino acid residue of formula AA1; and
  the combined number of the amino acid residue Gly in above module A must not exceed two; and
  the positions P of the amino acid residues Gly must not be in direct vicinity;
with the further proviso that,
  if P¹ and X¹² taken together form an interstrand linkage or salt bridge, as defined above; then P² and P¹¹ taken together are not forming an interstrand linkage or salt bridge, as defined above;
  X¹² having a carbonyl (C=O) point of attachment not connected as aforementioned, being appropriately saturated by linkage with R³⁰ to form the corresponding naturally or non-naturally occurring terminal α-amino acid residue; optionally having a modified carbonyl (C=O) functional group;
  P¹ having a nitrogen (N) not connected as aforementioned, being appropriately saturated by linkages with R¹, as already depicted above, and R³¹ to form the corresponding naturally or non-naturally occurring terminal α-amino acid residue; optionally having a modified nitrogen (N) functional group;
with the further proviso that,
  if linker L, as defined below, is connected with module A by a carbonyl (C=O) point of attachment of P⁵; P⁶; or P⁷; then
  P⁵; P⁶; or P⁷; is an α-amino acid residue of one of the formulae AA20; or AA20^D;
if s=0, t=0, and u=0; and
P² and P¹¹ taken together form an interstrand linking bis (amino acid) structure of one of the formulae AA16; or AA16^D; or a salt bridge of one of the formulae AA18; AA18^D; AA19; or AA19^D; and/or
P⁴ and P⁹ taken together form an interstrand linking bis (amino acid) structure of one of the formulae AA16; or AA16^D; or a salt bridge of one of the formulae AA18; AA18^D; AA19; or AA19^D;
P¹ is pGlu; ^DpGlu; Ac-pGlu; Ac-^DpGlu; or an α-amino acid residue of one of the formulae AA1; AA1^D; AA2; or AA4; or an L α-hydroxy acid residue of one of the formulae AA11; AA12; or AA14; or an acid residue of one of the formulae AA15a; or AA15b;
P²; P³; P⁴; P⁵; P⁶; P⁷; P⁸; P⁹; and P¹⁰ are as defined above for module A, wherein s=1, t=1, and u=1;
P¹¹ is an L α-amino acid residue of one of the formulae AA1; AA3b; AA4; or AA5; with the proviso that,
  if P³ is an α-amino acid residue of one of the formulae AA1; or AA4;
  then P¹; or P¹⁰; is an α-amino acid residue of formula AA2; and
  if P⁸ is an α-amino acid residue of formula AA1;
  then P¹⁰ is an α-amino acid residue of formula AA2; and
  the combined number of the amino acid residue Gly in above module A must not exceed two; and
  the positions P of the amino acid residues Gly must not be in direct vicinity;
with the further proviso that,
  P¹¹ having a carbonyl (C=O) point of attachment not connected as aforementioned, being appropriately saturated by linkage with R³⁰ to form the corresponding naturally or non-naturally occurring terminal α-amino acid residue; optionally having a modified carbonyl (C=O) functional group;
  P¹ having a nitrogen (N) not connected as aforementioned, being appropriately saturated by linkages with Fe, as already depicted above, and R³¹ to form the corresponding naturally or non-naturally occurring terminal α-amino acid residue; optionally having a modified nitrogen (N) functional group;
with the further proviso that,
  if linker L, as defined below, is connected with module A by a carbonyl (C=O) point of attachment of P⁵; P⁶; or P⁷; then
  P⁵; P⁶; or P⁷; is an α-amino acid residue of one of the formulae AA20; or AA20^D;
if s=0, t=0, and u=0; and
P¹¹ is connected from the α-carbonyl point of attachment to the ω-nitrogen (N) of P²;
P¹ is pGlu; or an α-amino acid residue of one of the formulae AA1; AA1^D; AA2; or AA4; or an L α-hydroxy acid residue of one of the formulae AA11; AA12; or AA14; or an acid residue of one of the formulae AA15a; or AA15b;
P² is an L α-amino acid residue of formula AA3b;
P³; P⁴; P⁵; P⁶; P⁷; P⁸; P⁹; and P¹⁰ are as defined above for module A,
wherein s=1, t=1, and u=1;
P¹¹ is an α-amino acid residue of one of the formulae AA1^D; AA2^D; AA3b^D; AA4^D; AA5^D; or AA6^D;
with the proviso that,
  if P³ is an α-amino acid residue of one of the formulae AA1; or AA4;
  then P¹; or P^m; is an α-amino acid residue of formula AA2; and
  if P⁸ is an α-amino acid residue of formula AA1;
  then P¹⁰ is an α-amino acid residue of formula AA2; and
  the combined number of the amino acid residue Gly in above module A must not exceed two; and the positions P of the amino acid residues Gly must not be in direct vicinity;
with the further proviso that,
P$^1$ having a nitrogen (N) not connected as aforementioned, being appropriately saturated by linkages with R$^1$, as already depicted above, and R$^{31}$ to form the corresponding naturally or non-naturally occurring terminal α-amino acid residue; optionally having a modified nitrogen (N) functional group;
with the further proviso that,
if linker L, as defined below, is connected with module A by a carbonyl (C=O) point of attachment of P$^5$; P$^6$; or P$^7$; then
P$^5$; P$^6$; or P$^7$; is an α-amino acid residue of one of the formulae AA20; or AA20$^D$;
and a module B consisting of single elements Q being connected in either direction from the carbonyl (C=O) point of attachment to the nitrogen (N) of the next element with the proviso that Q$^7$ is connected from the α-carbonyl (C=O) point of attachment to the ω-nitrogen (N) of Q$^1$, and wherein
Q$^1$ is an α-amino acid residue of one of the formulae AA21; or AA21$^D$;
Q$^2$, Q$^5$, and Q$^6$ are independently an L α-amino acid residue of formula AA3b;
Q$^3$ is a D α-amino acid residue of one of the formulae AA1$^D$; or AA2$^D$;
Q$^4$ is an L α-amino acid residue of one of the formulae AA1; or AA4;
Q$^7$ is an L α-amino acid residue of one of the formulae AA1; or AA4;
and a linker L consisting of k=0-3 single elements L being connected in either direction from the carbonyl (C=O) point of attachment to the nitrogen (N) of the next element, and wherein,
if k=1,
L$^1$ is Gly; Sar; Aib; or an α-amino acid residue of one of the formulae
AA3b; AA3b$^D$; AA4; AA4$^D$; AA1; or AA1$^D$, as depicted above;
if k=2, the additional element
L$^2$ is Gly; Sar; Aib; or an α-amino acid residue of one of the formulae
AA3b; AA3b$^D$; AA4; AA4$^D$; AA1; or AA1$^D$, as depicted above;
if k=3, the additional element
L$^3$ is Gly; Sar; Aib; or an α-amino acid residue of one of the formulae
AA3b; AA3b$^D$; AA4; AA4$^D$; AA1; or AA1$^D$, as depicted above;
said linker L being connected with module B from the carbonyl (C=O) point of attachment of L$^k$ to the α-nitrogen (N) of Q$^1$ and,
if k=1-3, being connected with module A from the carbonyl (C=O) point of attachment of P$^5$; P$^6$; or P$^7$; to the nitrogen (N) of 12; or,
if k=0, then
Q$^1$ being directly connected with module A from the carbonyl (C=O) point of attachment of P$^5$; P$^6$; or P$^7$; to the α-nitrogen (N) of Q$^1$;
R$^{Alk}$ is, with the proviso of containing less than 26 carbon- and/or heteroatoms, C$_{1-12}$-alkyl; C$_{2-12}$-alkenyl; cycloalkyl; cycloalkyl-C$_{1-6}$-alkyl; or C$_{1-6}$-alkoxy-C$_{1-6}$-alkyl;
R$^{Ar}$ is, with the proviso of containing less than 26 carbon- and/or heteroatoms, —(CR$^1$R$^4$)$_n$R$^{19}$; —(CH$_2$)$_n$O(CH$_2$)$_m$R$^{19}$; —(CH$_2$)$_n$NR$^{14}$(CH$_2$)$_m$R$^{19}$; or —(CH$_2$)$_n$NR$^{14}$(CH$_2$)$_m$R$^{19}$;

R$^{Am1}$ is, with the proviso of containing less than 26 carbon- and/or heteroatoms, —(CR$^1$R$^{13}$)$_q$NR$^{15}$R$^{16}$; —(CH$_2$)$_q$C(=NR$^{13}$)NR$^{15}$R$^{16}$; —(CH$_2$)$_q$C(=NNR$^{15}$R$^{16}$)NR$^{17}$R$^{18}$; —(CR$^1$R$^{13}$)$_q$NR$^2$C(=NR$^{17}$)NR$^{15}$R$^{16}$; —(CR$^1$R$^{13}$)$_q$N=C(NR$^{15}$R$^{16}$)NR$^{17}$R$^{18}$; —(CH$_2$)$_n$O(CH$_2$)$_m$NR$^{15}$R$^{16}$; —(CH$_2$)$_n$O(CH$_2$)$_m$C(=NR$^{17}$)NR$^{15}$R$^{16}$; —(CH$_2$)$_n$O(CH$_2$)$_m$C(=NNR$^{15}$R$^{16}$)NR$^{17}$R$^{18}$; —(CH$_2$)$_n$O(CH$_2$)$_m$NR$^1$C(=NR$^{17}$)NR$^{15}$R$^{16}$; —(CH$_2$)$_n$O(CH$_2$)$_m$N=C(NR$^{15}$R$^{16}$)NR$^{17}$R$^{18}$; —(CH$_2$)$_n$S(CH$_2$)$_m$NR$^{15}$R$^{16}$; —(CH$_2$)$_n$S(CH$_2$)$_m$C(=NR$^{17}$)NR$^{15}$R$^{16}$; —(CH$_2$)$_n$S(CH$_2$)$_m$C(=NNR$^{15}$R$^{16}$)NR$^{17}$R$^{18}$; —(CH$_2$)$_n$S(CH$_2$)$_m$NR$^1$C(=NR$^{17}$)NR$^{15}$R$^{16}$; —(CH$_2$)$_n$S(CH$_2$)$_m$N=C(NR$^{15}$R$^{16}$)NR$^{17}$R$^{18}$; or —(CR$^1$R$^{13}$)$_q$NR$^{14}$R$^{27}$;

R$^{Am2}$ is, with the proviso of containing less than 26 carbon- and/or heteroatoms, —(CR$^1$R$^{13}$)$_q$NR$^{15}$R$^{16}$; —(CH$_2$)$_n$O(CH$_2$)$_n$NR$^{15}$R$^{16}$; or —(CH$_2$)$_n$S(CH$_2$)$_m$NR$^{15}$R$^{16}$ R$^{Acid}$ is, with the proviso of containing less than 26 carbon- and/or heteroatoms, —(CR$^1$R$^{13}$)$_q$COOH; or —(CR$^1$R$^{13}$)$_q$PO(OH)$_2$;

R$^{OH}$ is, with the proviso of containing less than 26 carbon- and/or heteroatoms, —(CR$^1$R$^{13}$)$_q$OH; —(CR$^1$R$^{13}$)$_q$SH; —(CH$_2$)$_n$O(CH$_2$)$_m$OH; —(CH$_2$)$_n$S(CH$_2$)$_m$OH; —(CH$_2$)$_n$NR$^1$(CH$_2$)$_m$OH; hydroxy-C$_{1-8}$-alkyl; hydroxy-C$_{2-8}$-alkenyl; hydroxy-cycloalkyl; or hydroxy-heterocycloalkyl;

R$^{Amide}$ is, with the proviso of containing less than 26 carbon- and/or heteroatoms, —(CR$^1$R$^{13}$)$_q$CONR$^{15}$R$^{16}$;

Y is, with the proviso of containing less than 25 carbon- and/or heteroatoms, —(CR$^1$R$^{13}$)$_q$—;

Z is, with the proviso of containing less than 25 carbon- and/or heteroatoms, —(CH$_2$)$_n$—S—S—(CH$_2$)$_m$—; —(CR$^{28}$R$^{29}$)$_n$—S—S—(CR$^{28}$R$^{29}$)$_m$—; —(CH$_2$)$_n$CH=CH(CH$_2$)$_m$—; —(CR$^{28}$R$^{29}$)CH=CH(CR$^{28}$R$^{29}$)$_m$—; —(CH$_2$)$_n$-heteroaryl-(CH$_2$)$_m$—; —(CR$^{28}$R$^{29}$)$_n$-heteroaryl-(CR$^{28}$R$^{29}$)$_m$—; —(CH$_2$)$_n$CONR$^1$(CH$_2$)$_m$—; —(CH$_2$)$_n$NR$^1$CO(CH$_2$)$_m$—; —(CR$^{28}$R$^{29}$)$_n$CONR$^1$(CR$^{28}$R$^{29}$)$_m$—; —(CR$^{28}$R$^{29}$)NR$^1$CO(CR$^{28}$R$^{29}$)$_m$—; —(CH$_2$)$_n$NR$^1$CONR$^2$(CH$_2$)$_m$—; or —(CR$^{28}$R$^{29}$)$_n$NR$^1$CONR$^2$(CR$^{28}$R$^{29}$)$_m$—;

R$^1$ and R$^2$ are independently
H; CF$_3$; C$_{1-8}$-alkyl; or C$_{2-8}$-alkenyl;

R$^4$ is H; F; CF$_3$; C$_{1-8}$-alkyl; C$_{2-8}$-alkenyl; cycloalkyl; heterocycloalkyl; aryl; heteroaryl; aryl-C$_{1-6}$-alkyl; heteroaryl-C$_{1-6}$-alkyl; —(CHR$^{13}$)$_o$OR$^{15}$; —O(CO)R$^{15}$; —(CHR$^{13}$)$_o$SR$^{15}$; —(CHR$^{13}$)$_o$NR$^{15}$R$^{16}$; —(CHR$^{13}$)$_o$CONR$^{15}$R$^{16}$; —(CHR$^{13}$)$_o$NR$^1$CONR$^{15}$R$^{16}$; —(CHR$^{13}$)$_o$NR$^1$COR$^{15}$; —(CHR$^{13}$)$_o$COOR$^{15}$; —(CHR$^{13}$)$_o$CONR$^{15}$R$^{16}$; —(CHR$^{13}$)$_o$PO(OR$^1$)$_2$; —(CHR$^{13}$)$_o$SO$_2$R$^{15}$; —(CHR$^{13}$)$_o$NR$^1$SO$_2$R$^{15}$; —(CHR$^{13}$)$_o$SO$_2$NR$^{15}$R$^{16}$; —(CR$^1$R$^{13}$)$_o$R$^{19}$; or —(CHR$^1$)$_n$O(CHR$^2$)$_m$R$^{23}$; or R$^{13}$ is H; F; CF$_3$; C$_{1-8}$-alkyl; C$_{2-8}$-alkenyl; cycloalkyl; heterocycloalkyl; cycloalkyl-C$_{1-6}$-alkyl; heterocycloalkyl-C$_{1-6}$-alkyl; aryl; heteroaryl; aryl-C$_{1-6}$-alkyl; heteroaryl-C$_{1-6}$-alkyl; —(CHR$^1$)$_o$OR$^{15}$; —OCOR$^1$; —(CHR$^1$)$_o$NR$^{15}$R$^{16}$; CHR$^1$OR$^2$C(=NR$^{17}$)NR$^{15}$R$^{16}$; —(CHR$^1$OR$^2$CONR$^{15}$R$^{16}$; —COOR$^{15}$; —CONR$^{15}$R$^{16}$; or —SO$_2$R$^{15}$; or —SO$_2$NR$^{15}$R$^{16}$;

R$^{14}$ is H; CF$_3$; C$_{1-8}$-alkyl; C$_{2-8}$-alkenyl; cycloalkyl; heterocycloalkyl; cycloalkyl-C$_{1-6}$-alkyl; heterocycloalkyl-C$_{1-6}$-alkyl; aryl; heteroaryl; aryl-C$_{1-6}$-alkyl; heteroaryl-C$_{1-6}$-alkyl; cycloalkyl-aryl; heterocycloalkyl-aryl; cycloalkyl-heteroaryl; heterocycloalkyl-heteroaryl; aryl-cycloalkyl; aryl-heterocycloalkyl; heteroaryl-cycloalkyl; heteroaryl-heterocycloalkyl; —(CHR¹)$_o$OR¹⁵; —(CHR¹)$_o$SR¹⁵; —(CHR¹)$_o$NR¹⁵R¹⁶; —(CHR¹)$_o$COOR¹⁵; —(CHR¹)$_o$CONR¹⁵R¹⁶; or —(CHR¹)$_o$SO$_2$R¹⁵;

R¹⁵, R¹⁶, R¹⁷ and R¹⁸ are independently

H; C$_{1-8}$-alkyl; C$_{2-8}$-alkenyl; C$_{1-6}$-alkoxy; cycloalkyl; heterocycloalkyl; cycloalkyl-C$_{1-6}$-alkyl; heterocycloalkyl-C$_{1-6}$-alkyl; aryl; heteroaryl; aryl-C$_{1-6}$-alkyl; heteroaryl-C$_{1-6}$-alkyl; cycloalkyl-aryl; heterocycloalkyl-aryl; cycloalkyl-heteroaryl; heterocycloalkyl-heteroaryl; aryl-cycloalkyl; aryl-heterocycloalkyl; heteroaryl-cycloalkyl; or heteroaryl-heterocycloalkyl; or the structural elements —NR¹⁵R¹⁶ and —NR¹⁷R¹⁸ can independently form: heterocycloalkyl; aryl-heterocycloalkyl; or heteroaryl-heterocycloalkyl;

R¹⁹ is an aryl group of one of the formulae

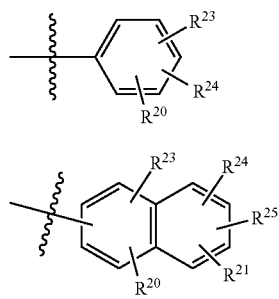

AR1

AR2 or a group of one of the formulae

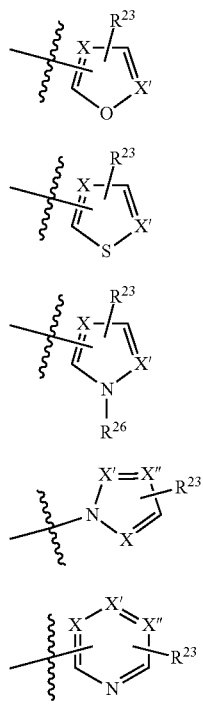

H1

H2

H3

H4

H5

H6

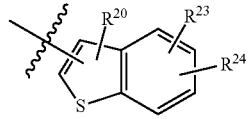

H7

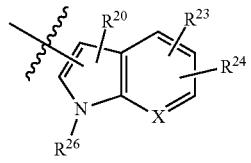

H8

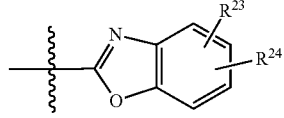

H9

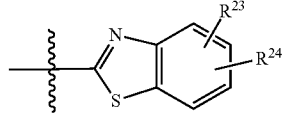

H10

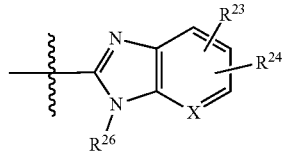

H11

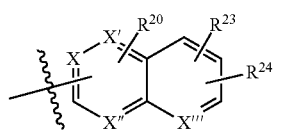

H12

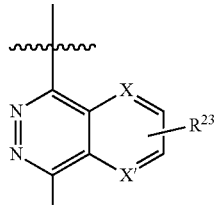

H13

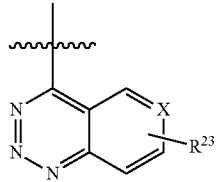

H14

X, X', X" and X'" are independently
—CR²⁰; or N;

R²⁰ and R²¹ are independently

H; F; Cl; Br; I; OH; NH$_2$; NO$_2$; CN; CF$_3$; OCHF$_2$; OCF$_3$; C$_{1-8}$-alkyl; C$_{2-8}$-alkenyl; aryl; heteroaryl; aryl-C$_{1-6}$-alkyl; heteroaryl-C$_{1-6}$-alkyl; —(CH$_2$)$_o$R²²; —(CH$_2$)$_o$OR¹⁵; —O(CO)R¹⁵; —O(CH$_2$)$_o$R²²; —(CH$_2$)$_o$SR¹⁵; —(CH$_2$)$_o$NR¹⁵R¹⁶; —(CH$_2$)$_o$CONR¹⁵R¹⁶; —(CH$_2$)$_o$NR¹CONR¹⁵R¹⁶; —(CH$_2$)$_o$NR¹COR¹⁵; —(CH$_2$)$_o$COOR¹⁵; —(CH$_2$)$_o$CONR¹⁵R¹⁶; —(CH$_2$)$_o$PO(OR¹)$_2$; —(CH$_2$)$_o$SO$_2$R¹⁵; or —(CH$_2$)$_o$COR¹⁵;

$R^{22}$ is an aryl group of the formula

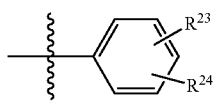

AR3

$R^{23}$, $R^{24}$ and $R^{25}$ are independently
  H; F; Cl; Br; I; OH; $NH_2$; $NO_2$; CN; $CF_3$; $OCHF_2$; $OCF_3$;
  $C_{1-8}$-alkyl; $C_{2-8}$-alkenyl; $—(CH_2)_oOR^{15}$; $—O(CO)R^{15}$;
  $—(CH_2)_oNR^1R^{15}$; $—(CH_2)_oCOOR^{15}$; $—(CH_2)_o$
  $CONR^1R^{15}$;
$R^{26}$ is H; Ac; $C_{1-8}$-alkyl; or aryl-$C_{1-6}$-alkyl;
$R^{27}$ is $—CO(CR^1R^{13})_qR^{15}$;
$R^{28}$ and $R^{29}$ are independently
  H; $CF_3$; $C_{1-8}$-alkyl; $C_{2-8}$-alkenyl; or aryl-$C_{1-6}$-alkyl;
  cycloalkyl-$C_{1-6}$-alkyl; or heterocycloalkyl-$C_{1-6}$-alkyl;
$R^{30}$ is $—OR^{14}$; $—SR^{14}$; or $—NR^{15}R^{16}$;
$R^{31}$ is H; $C_{1-8}$-alkyl; $C_{2-8}$-alkenyl; $C_{1-6}$-alkoxy; cycloalkyl;
  heterocycloalkyl; cycloalkyl-$C_{1-6}$-alkyl; heterocycloalkyl-$C_{1-6}$-alkyl; aryl; heteroaryl; aryl-$C_{1-6}$-alkyl; heteroaryl-$C_{1-6}$-alkyl; cycloalkyl-aryl; heterocycloalkyl-aryl; cycloalkyl-heteroaryl; heterocycloalkyl-heteroaryl; aryl-cycloalkyl; aryl-heterocycloalkyl; heteroaryl-cycloalkyl; heteroaryl-heterocycloalkyl; $—COR^{15}$; $—CONR^{15}R^{16}$; $—C(=NR^{13})NR^{15}R^{16}$; or the structural element $—NR^1R^{31}$ can form: $—N=C(NR^{15}R^{16})_2$; heterocycloalkyl; aryl-heterocycloalkyl; or heteroaryl-heterocycloalkyl;
  n and m are independently an integer of 0-5 with the proviso that n+m≤6; o is 0-4; p is 2-6; q is 1-6; and r is 1-3;
or a tautomer or rotamer thereof; or a salt; or a pharmaceutically acceptable salt; or a hydrate; or a solvate thereof.

In another particular embodiment (43) of the invention the elements of general formula (I) are defined as follows,
for module A,
if s=1, t=1, and u=1; and
$X^{14}$ and $X^{13}$ taken together form an interstrand linking bis(amino acid)-structure of formula AA16; with Z being, with the proviso of containing less than 25 carbon- and/or heteroatoms, $—(CR^{28}R^{29})_n—S—S—(CR^{28}R^{29})_m—$; or $—(CR^{28}R^{29})_nNR^1CO(CR^{28}R^{29})_m—$; or an interstrand linking (amino acid)-(acid)-structure of formula AA17; with Z being, with the proviso of containing less than 25 carbon- and/or heteroatoms, $—(CR^{28}R^{29})_n—S—S—(CR^{28}R^{29})_m—$; or
a salt bridge of one of the formulae AA18; or AA19;
and/or
$P^2$ and $P^{11}$ taken together form an interstrand linking bis (amino acid)-structure of formula AA16; with Z being, with the proviso of containing less than 25 carbon- and/or heteroatoms, $—(CR^{28}R^{29})_n—S—S—(CR^{28}R^{29})_m—$;
or a salt bridge of one of formula AA18;
$X^{14}$ is pGlu; $^D$pGlu; or a D α-amino acid residue of formula $AA4^D$;
$P^1$ is an L α-amino acid residue of one of the formulae AA1; or AA4;
$P^2$ is an L α-amino acid residue of formula AA4;
$P^3$ is an L α-amino acid residue of formula AA2;
$P^4$ is Gly; or an L α-amino acid residue of one of the formulae AA3b; or AA4;
$P^6$ is Gly; or a D α-amino acid residue of one of the formulae $AA1^D$; $AA4^D$; or $AA3b^D$;
$P^7$ is Gly; or an L α-amino acid residue of one of the formulae AA1; AA3b; or AA4;
$P^8$ is an L α-amino acid residue of formula AA2;
$P^9$ is Gly; or an L α-amino acid residue of one of the formulae AA1; AA4; or AA5;
$P^{10}$ is an L α-amino acid residue of formula AA1;
$P^{11}$ is an L α-amino acid residue of one of the formulae AA1; or AA4;
$X^{12}$ is an L α-amino acid residue of one of the formulae AA1; or AA4;
$X^{13}$ is a D α-amino acid residue of one of the formulae $AA1^D$; or $AA4^D$;
with the proviso that,
  if $P^1$ is an α-amino acid residue of formula AA4;
  then $X^{12}$ is an α-amino acid residue of formula AA1; and
  the combined number of the amino acid residue Gly in above module A must not exceed two; and
  the positions P of the amino acid residues Gly must not be in direct vicinity;
with the further proviso that,
  $X^{13}$ having a carbonyl (C=O) point of attachment not connected as aforementioned, being appropriately saturated by linkage with $R^{30}$ to form the corresponding naturally or non-naturally occurring terminal α-amino acid residue; optionally having a modified carbonyl (C=O) functional group;
  $X^{14}$ having a nitrogen (N) not connected as aforementioned, being appropriately saturated by linkages with Fe, as already depicted above, and $R^{31}$ to form the corresponding naturally or non-naturally occurring terminal α-amino acid residue; optionally having a modified nitrogen (N) functional group;
with the further proviso that,
  if linker L, as defined below, is connected with module A by a carbonyl (C=O) point of attachment of $P^5$; then $P^5$ is Glu;
for module B consisting of single elements Q being connected in either direction from the carbonyl (C=O) point of attachment to the nitrogen (N) of the next element with the proviso that $Q^7$ is connected from the α-carbonyl (C=O) point of attachment to the ω-nitrogen (N) of $Q^1$,
$Q^1$ is an L α-amino acid residue of formula AA3b;
$Q^2$, $Q^5$, and $Q^6$ are independently an L α-amino acid residue of formula AA3b;
$Q^3$ is a D α-amino acid residue of one of the formulae $AA1^D$; or $AA2^D$;
$Q^4$ is an L α-amino acid residue of one of the formulae AA1; or AA4;
$Q^7$ is an L α-amino acid residue of one of the formulae AA1; or AA4;
for a linker L consisting of k=1 or 3 single elements L being connected in either direction from the carbonyl (C=O) point of attachment to the nitrogen (N) of the next element,
if k=1,
$L^1$ is an α-amino acid residue of one of the formulae AA3b; or $AA3b^D$;
if k=3,
$L^1$ is an α-amino acid residue of one of the formulae AA3b; or $AA3b^D$;
$L^2$ is an α-amino acid residue of one of the formulae AA4; or $AA4^D$;
$L^3$ is an α-amino acid residue of one of the formulae AA3b; or $AA3b^D$;
said linker L being connected with module B from the carbonyl (C=O) point of attachment of $L^k$ to the α-nitrogen (N) of $Q^1$ and,
if k=1 or 3, being connected with module A from the carbonyl (C=O) point of attachment of $P^5$; $P^6$; or $P^7$; to the nitrogen (N) of $L^1$;
or a pharmaceutically acceptable salt thereof.

In another particular embodiment (44) of the invention the elements of general formula (I) are defined as follows,
for module A,
if s=1, t=0, and u=1; and
$P^2$ and $P^{11}$ taken together form an interstrand linking bis (amino acid)-structure of formula AA16; with Z being, with the proviso of containing less than 25 carbon- and/or heteroatoms, —$(CR^{28}R^{29})_n$—S—S—$(CR^{28}R^{29})_m$—; and/or
$P^4$ and $P^9$ taken together form an interstrand linking bis (amino acid)-structure of formula AA16; with Z being, with the proviso of containing less than 25 carbon- and/or heteroatoms, —$(CR^{28}R^{29})_n$—S—S—$(CR^{28}R^{29})_m$—;
$X^{14}$ is pGlu; $^D$pGlu; or an L α-amino acid residue of formula AA3b; or an acid residue of one of the formulae AA15a; or AA15b;
$P^1$ is an L α-amino acid residue of one of the formulae AA1; or AA4;
$P^2$ is an L α-amino acid residue of formula AA4;
$P^3$ is an L α-amino acid residue of formula AA2;
$P^4$ is Gly; or an L α-amino acid residue of one of the formulae AA3b; or AA4;
$P^6$ is Gly; or a D α-amino acid residue of one of the formulae AA1$^D$; AA4$^D$; or AA3b$^D$;
$P^7$ is Gly; or an L α-amino acid residue of one of the formulae AA1; AA3b; or AA4;
$P^8$ is an L α-amino acid residue of formula AA2;
$P^9$ is Gly; or an L α-amino acid residue of one of the formulae AA1; or AA4;
$P^{10}$ is an L α-amino acid residue of formula AA1;
$P^{11}$ is an L α-amino acid residue of formula AA1;
$X^{12}$ is Glyol; or an L α-amino acid residue of one of the formulae AA1; or AA4; or an amino alcohol residue of formula AA10;
with the proviso that,
  if $P^1$ is an α-amino acid residue of formula AA4;
  then $X^{12}$ is an α-amino acid residue of formula AA1; and
  the combined number of the amino acid residue Gly in above module A must not exceed two; and
  the positions P of the amino acid residues Gly must not be in direct vicinity;
with the further proviso that,
  $X^{13}$ having a carbonyl (C=O) point of attachment not connected as aforementioned, being appropriately saturated by linkage with $R^{30}$ to form the corresponding naturally or non-naturally occurring terminal α-amino acid residue; optionally having a modified carbonyl (C=O) functional group;
  $X^{14}$ having a nitrogen (N) not connected as aforementioned, being appropriately saturated by linkages with $R^1$, as already depicted above, and $R^{31}$ to form the corresponding naturally or non-naturally occurring terminal α-amino acid residue; optionally having a modified nitrogen (N) functional group;
with the further proviso that,
  if linker L, as defined below, is connected with module A by a carbonyl (C=O) point of attachment of $P^5$; then $P^5$ is Glu;
for module B consisting of single elements Q being connected in either direction from the carbonyl (C=O) point of attachment to the nitrogen (N) of the next element with the proviso that $Q^7$ is connected from the α-carbonyl (C=O) point of attachment to the ω-nitrogen (N) of $Q^1$,
$Q^1$ is an L α-amino acid residue of formula AA3b;
$Q^2$, $Q^5$, and $Q^6$ are independently an L α-amino acid residue of formula AA3b;
$Q^3$ is a D α-amino acid residue of one of the formulae AA1$^D$; or AA2$^D$;
$Q^4$ is an L α-amino acid residue of one of the formulae AA1; or AA4;
$Q^7$ is an L α-amino acid residue of one of the formulae AA1; or AA4;
for a linker L consisting of k=1 or 3 single elements L being connected in either direction from the carbonyl (C=O) point of attachment to the nitrogen (N) of the next element,
  if k=1,
  $L^1$ is an α-amino acid residue of one of the formulae AA3b; or AA3b$^D$;
  if k=3,
  $L^1$ is an α-amino acid residue of one of the formulae AA3b; or AA3b$^D$;
  $L^2$ is an α-amino acid residue of one of the formulae AA4; or AA4$^D$;
  $L^3$ is an α-amino acid residue of one of the formulae AA3b; or AA3b$^D$;
  said linker L being connected with module B from the carbonyl (C=O) point of attachment of $L^k$ to the α-nitrogen (N) of $Q^1$ and,
  if k=1 or 3, being connected with module A from the carbonyl (C=O) point of attachment of $P^5$; $P^6$; or $P^7$; to the nitrogen (N) of $L^1$;
or a pharmaceutically acceptable salt thereof.

In another particular embodiment (45) of the invention the elements of general formula (I) are defined as follows,
for module A,
if s=1, t=1, and u=0; and
$P^2$ and $P^{11}$ taken together form an interstrand linking bis (amino acid)-structure of formula AA16; with Z being, with the proviso of containing less than 25 carbon- and/or heteroatoms, —$(CR^{28}R^{29})_n$—S—S—$(CR^{28}R^{29})_m$—; and/or
$P^4$ and $P^9$ taken together form an interstrand linking bis (amino acid)-structure of formula AA16; with Z being, with the proviso of containing less than 25 carbon- and/or heteroatoms, —$(CR^{28}R^{29})_n$—S—S—$(CR^{28}R^{29})_m$—;
$P^1$ is an L α-amino acid residue of one formula AA1; or an L α-hydroxy acid residue of formula AA11;
$P^2$ is an L α-amino acid residue of formula AA4;
$P^3$ is an L α-amino acid residue of one of the formula AA1; or AA4;
$P^4$ is Gly; or an L α-amino acid residue of one of the formulae AA3b; or AA4;
$P^6$ is Gly; or a D α-amino acid residue of one of the formulae AA1$^D$; AA4$^D$; or AA3b$^D$;
$P^7$ is Gly; or an L α-amino acid residue of one of the formulae AA1; AA3b; or AA4;
$P^8$ is an L α-amino acid residue of formula AA2;
$P^9$ is Gly; or an L α-amino acid residue of one of the formulae AA1; or AA4;
$P^{10}$ is an L α-amino acid residue of formula AA1;
$P^{11}$ is an L α-amino acid residue of one of the formulae AA1; or AA4;
$X^{12}$ is an L α-amino acid residue of one of the formulae AA2;
$X^{13}$ is Glyol; or a D α-amino acid residue of one of the formulae AA1$^D$; or AA4$^D$;
with the proviso that,
  the combined number of the amino acid residue Gly in above module A must not exceed two; and
  the positions P of the amino acid residues Gly must not be in direct vicinity;

with the further proviso that,
- $X^{13}$ having a carbonyl (C=O) point of attachment not connected as aforementioned, being appropriately saturated by linkage with $R^{30}$ to form the corresponding naturally or non-naturally occurring terminal α-amino acid residue; optionally having a modified carbonyl (C=O) functional group;
- $X^{14}$ having a nitrogen (N) not connected as aforementioned, being appropriately saturated by linkages with $R^1$, as already depicted above, and $R^{31}$ to form the corresponding naturally or non-naturally occurring terminal α-amino acid residue; optionally having a modified nitrogen (N) functional group;

with the further proviso that,
if linker L, as defined below, is connected with module A by a carbonyl (C=O) point of attachment of $P^5$; then $P^5$ is Glu;

for module B consisting of single elements Q being connected in either direction from the carbonyl (C=O) point of attachment to the nitrogen (N) of the next element with the proviso that $Q^7$ is connected from the α-carbonyl (C=O) point of attachment to the ω-nitrogen (N) of $Q^1$,
$Q^1$ is an L α-amino acid residue of formula AA3b;
$Q^2$, $Q^5$, and $Q^6$ are independently an L α-amino acid residue of formula AA3b;
$Q^3$ is a D α-amino acid residue of one of the formulae $AA1^D$; or $AA2^D$;
$Q^4$ is an L α-amino acid residue of one of the formulae AA1; or AA4;
$Q^7$ is an L α-amino acid residue of one of the formulae AA1; or AA4;

for a linker L consisting of k=1 or 3 single elements L being connected in either direction from the carbonyl (C=O) point of attachment to the nitrogen (N) of the next element,
if k=1,
$L^1$ is an α-amino acid residue of one of the formulae AA3b; or $AA3b^D$;
if k=3,
12 is an α-amino acid residue of one of the formulae AA3b; or $AA3b^D$;
$L^2$ is an α-amino acid residue of one of the formulae AA4; or $AA4^D$;
$L^3$ is an α-amino acid residue of one of the formulae AA3b; or $AA3b^D$;
said linker L being connected with module B from the carbonyl (C=O) point of attachment of $L^k$ to the α-nitrogen (N) of $Q^1$ and,
if k=1 or 3, being connected with module A from the carbonyl (C=O) point of attachment of $P^5$; $P^6$; or $P^7$; to the nitrogen (N) of $L^1$;
or a pharmaceutically acceptable salt thereof.

In another particular embodiment (46) of the invention the elements of general formula (I) are defined as follows,
for module A,
if s=0, t=0, and u=1; and
$P^2$ and $P^{11}$ taken together form an interstrand linking bis (amino acid)-structure of formula AA16; with Z being, with the proviso of containing less than 25 carbon- and/or heteroatoms, $-(CR^{28}R^{29})_n-S-S-(CR^{28}R^{29})_m-$; and/or
$P^4$ and $P^9$ taken together form an interstrand linking bis (amino acid)-structure of formula AA16; with Z being, with the proviso of containing less than 25 carbon- and/or heteroatoms, $-(CR^{28}R^{29})_n-S-S-(CR^{28}R^{29})_m-$;
$X^{14}$ is pGlu; $^D$pGlu; or an L α-amino acid residue of formula AA3b;

$P^1$ is an L α-amino acid residue of one of the formulae AA1; or AA4;
$P^2$ is an L α-amino acid residue of formula AA4;
$P^3$ is an L α-amino acid residue of formula AA2;
$P^4$ is Gly; or an L α-amino acid residue of one of the formulae AA3b; or AA4;
$P^6$ is Gly; or a D α-amino acid residue of one of the formulae $AA1^D$; $AA4^D$; or $AA3b^D$;
$P^7$ is Gly; or an L α-amino acid residue of one of the formulae AA1; AA3b; or AA4;
$P^8$ is an L α-amino acid residue of formula AA2;
$P^9$ is Gly; or an L α-amino acid residue of formula AA4;
$P^{10}$ is an L α-amino acid residue of formula AA1;
$P^{11}$ is an L α-amino acid residue of one of the formulae AA1; or AA3b;

with the proviso that,
the combined number of the amino acid residue Gly in above module A must not exceed two; and
the positions P of the amino acid residues Gly must not be in direct vicinity;

with the further proviso that,
- $X^{13}$ having a carbonyl (C=O) point of attachment not connected as aforementioned, being appropriately saturated by linkage with $R^{30}$ to form the corresponding naturally or non-naturally occurring terminal α-amino acid residue; optionally having a modified carbonyl (C=O) functional group;
- $X^{14}$ having a nitrogen (N) not connected as aforementioned, being appropriately saturated by linkages with $R^1$, as already depicted above, and $R^{31}$ to form the corresponding naturally or non-naturally occurring terminal α-amino acid residue; optionally having a modified nitrogen (N) functional group;

with the further proviso that,
if linker L, as defined below, is connected with module A by a carbonyl (C=O) point of attachment of $P^5$; then $P^5$ is Glu;

for module B consisting of single elements Q being connected in either direction from the carbonyl (C=O) point of attachment to the nitrogen (N) of the next element with the proviso that $Q^7$ is connected from the α-carbonyl (C=O) point of attachment to the ω-nitrogen (N) of $Q^1$,
$Q^1$ is an L α-amino acid residue of formula AA3b;
$Q^2$, $Q^5$, and $Q^6$ are independently an L α-amino acid residue of formula AA3b;
$Q^3$ is a D α-amino acid residue of one of the formulae $AA1^D$; or $AA2^D$;
$Q^4$ is an L α-amino acid residue of one of the formulae AA1; or AA4;
$Q^7$ is an L α-amino acid residue of one of the formulae AA1; or AA4;

for a linker L consisting of k=1 or 3 single elements L being connected in either direction from the carbonyl (C=O) point of attachment to the nitrogen (N) of the next element,
if k=1,
$L^1$ is an α-amino acid residue of one of the formulae AA3b; or $AA3b^D$;
if k=3,
$L^1$ is an α-amino acid residue of one of the formulae AA3b; or $AA3b^D$;
$L^2$ is an α-amino acid residue of one of the formulae AA4; or $AA4^D$;
$L^3$ is an α-amino acid residue of one of the formulae AA3b; or $AA3b^D$;
said linker L being connected with module B from the carbonyl (C=O) point of attachment of $L^k$ to the α-nitrogen (N) of $Q^1$ and, if k=1 or 3, being connected with module A from the carbonyl (C=O) point of attachment of $P^5$; $P^6$; or $P^7$; to the nitrogen (N) of $L^1$;

or a pharmaceutically acceptable salt thereof.

In another particular embodiment (47) of the invention the elements of general formula (I) are defined as follows, for module A, if s=1, t=0, and u=0; and $P^1$ and $X^{12}$ taken together form an interstrand linking bis (amino acid)-structure of formula AA16; with Z being, with the proviso of containing less than 25 carbon- and/or heteroatoms, $-(CR^{28}R^{29})_n-S-S-(CR^{28}R^{29})_m-$; and/or $P^2$ and $P^{11}$ taken together form an interstrand linking bis (amino acid)-structure of formula AA16; with Z being, with the proviso of containing less than 25 carbon- and/or heteroatoms, $-(CR^{28}R^{29})_n-S-S-(CR^{28}R^{29})_m-$; $-(CR^{28}R^{29})_nCONR^1(CR^{28}R^{29})_m-$; or $-(CR^{28}R^{29})_nNR^1CO(CR^{28}R^{29})_m-$; or a salt bridge of one of the formulae AA18; or AA19; and/or $P^4$ and $P^9$ taken together form an interstrand linking bis (amino acid)-structure of formula AA16; with Z being, with the proviso of containing less than 25 carbon- and/or heteroatoms, $-(CR^{28}R^{29})_n-S-S-(CR^{28}R^{29})_m-$; $-(CR^{28}R^{29})_nCONR^1(CR^{28}R^{29})_m-$; or $-(CR^{28}R^{29})_nNR^1CO(CR^{28}R^{29})_m-$; or a salt bridge of one of the formulae AA18; or AA19;

$P^1$ is pGlu; or an α-amino acid residue of one of the formulae AA1; AA1$^D$; AA2; or AA4; or an L α-hydroxy acid residue of formula AA11; or an acid residue of one of the formulae AA15a; or AA15b;

$P^2$ is an L α-amino acid residue of one of the formulae AA1; AA3b; or AA4;

$P^3$ is an L α-amino acid residue of one of the formula AA1; AA2; or AA4;

$P^4$ is Gly; or an L α-amino acid residue of one of the formulae AA3b; or AA4;

$P^5$ is Gly; or an L α-amino acid residue of formula AA3b;

$P^6$ is Gly; or a D α-amino acid residue of one of the formulae AA1$^D$; AA4$^D$; or AA3a$^D$;

$P^7$ is Gly; or an L α-amino acid residue of one of the formulae AA1; AA3b; or AA4;

$P^8$ is an L α-amino acid residue of one of the formulae AA1; or AA2;

$P^9$ is Gly; or an L α-amino acid residue of one of the formulae AA1; AA4; or AA5;

$P^{10}$ is an L α-amino acid residue of one of the formulae AA1; or AA2;

$P^{11}$ is an L α-amino acid residue of one of the formulae AA1; AA3b; AA4; or AA5;

$X^{12}$ is Glyol; or an L α-amino acid residue of one of the formulae AA1; AA2; AA3b; or AA4; or an amino alcohol residue of one of the formulae AA8; AA10; or AA10$^D$;

with the proviso that, if $P^1$ is an α-amino acid residue of formula AA4;
then $X^{12}$ is an α-amino acid residue of formula AA1; and
if $P^3$ is an α-amino acid residue of one of the formulae AA1; or AA4;
then $P^1$; or $P^{10}$; is an α-amino acid residue of formula AA2; or $X^{12}$ is an α-amino acid residue of formula AA2; or an amino alcohol residue of formula AA8; and
if $P^8$ is an α-amino acid residue of formula AA1;
then $P^{10}$ is an α-amino acid residue of formula AA2; and
the combined number of the amino acid residue Gly in above module A must not exceed two; and the positions P of the amino acid residues Gly must not be in direct vicinity;

with the further proviso that, if $P^1$ and $X^{12}$ taken together form an interstrand linkage or salt bridge, as defined above; then $P^2$ and $P^{11}$ taken together are not forming an interstrand linkage or salt bridge, as defined above;

$X^{13}$ having a carbonyl (C=O) point of attachment not connected as aforementioned, being appropriately saturated by linkage with $R^{30}$ to form the corresponding naturally or non-naturally occurring terminal α-amino acid residue; optionally having a modified carbonyl (C=O) functional group;

$X^{14}$ having a nitrogen (N) not connected as aforementioned, being appropriately saturated by linkages with $R^1$, as already depicted above, and $R^{31}$ to form the corresponding naturally or non-naturally occurring terminal α-amino acid residue; optionally having a modified nitrogen (N) functional group;

if linker L, as defined below, is connected with module A by a carbonyl (C=O) point of attachment of $P^5$; $P^6$; or $P^7$; then
$P^5$; $P^6$; or $P^7$; is Glu; or $^D$Glu;

for module B consisting of single elements Q being connected in either direction from the carbonyl (C=O) point of attachment to the nitrogen (N) of the next element with the proviso that $Q^7$ is connected from the α-carbonyl (C=O) point of attachment to the ω-nitrogen (N) of $Q^1$, $Q^1$ is an L α-amino acid residue of formula AA3b;

$Q^2$, $Q^5$, and $Q^6$ are independently an L α-amino acid residue of formula AA3b;

$Q^3$ is a D α-amino acid residue of one of the formulae AA1$^D$; or AA2$^D$;

$Q^4$ is an L α-amino acid residue of one of the formulae AA1; or AA4;

$Q^7$ is an L α-amino acid residue of one of the formulae AA1; or AA4;

for a linker L consisting of k=1 or 3 single elements L being connected in either direction from the carbonyl (C=O) point of attachment to the nitrogen (N) of the next element, if k=1, $L^1$ is an α-amino acid residue of one of the formulae AA3b; or AA3b$^D$;

if k=3, $L^1$ is an α-amino acid residue of one of the formulae AA3b; or AA3b$^D$;

$L^2$ is an α-amino acid residue of one of the formulae AA4; or AA4$^D$;

$L^3$ is an α-amino acid residue of one of the formulae AA3b; or AA3b$^D$;

said linker L being connected with module B from the carbonyl (C=O) point of attachment of $L^k$ to the α-nitrogen (N) of $Q^1$ and, if k=1 or 3, being connected with module A from the carbonyl (C=O) point of attachment of $P^5$; $P^6$; or $P^7$; to the nitrogen (N) of $L^1$;

or a pharmaceutically acceptable salt thereof.

In another particular embodiment (48) of the invention the elements of general formula (I) are defined as follows, for module A, if s=0, t=0, and u=0; and $P^2$ and $P^{11}$ taken together form an interstrand linking bis (amino acid)-structure of formula AA16; with Z being, with the proviso of containing less than 25 carbon- and/or heteroatoms, $-(CR^{28}R^{29})_n-S-S-(CR^{28}R^{29})_m-$; and/or P⁴ and P⁹ taken together form an interstrand linking bis (amino acid)-structure of formula AA16; with Z being, with the proviso of containing less than 25 carbon- and/or heteroatoms, —$(CR^{28}R^{29})_n$—S—S—$(CR^{28}R^{29})_m$—;

P¹ is an L α-amino acid residue of formula AA1; or an L α-hydroxy acid residue of formula AA11;

P² is an L α-amino acid residue of formula AA4;

P³ is an L α-amino acid residue of formula AA2;

P⁴ is Gly; or an L α-amino acid residue of one of the formulae AA3b; or AA4;

P⁶ is Gly; or a D α-amino acid residue of one of the formulae AA1$^D$; AA4$^D$; or AA3b$^D$;

P⁷ is Gly; or an L α-amino acid residue of one of the formulae AA1; AA3b; or AA4;

P⁸ is an L α-amino acid residue of formula AA2;

P⁹ is Gly; or an L α-amino acid residue of one of the formulae AA1; or AA4;

P¹⁰ is an L α-amino acid residue of formula AA1;

P¹¹ is an L α-amino acid residue of one of the formulae AA1; or AA4;

with the proviso that,
the combined number of the amino acid residue Gly in above module A must not exceed two; and
the positions P of the amino acid residues Gly must not be in direct vicinity;

with the further proviso that,
X¹³ having a carbonyl (C=O) point of attachment not connected as aforementioned, being appropriately saturated by linkage with R³⁰ to form the corresponding naturally or non-naturally occurring terminal α-amino acid residue; optionally having a modified carbonyl (C=O) functional group;
X¹⁴ having a nitrogen (N) not connected as aforementioned, being appropriately saturated by linkages with R¹, as already depicted above, and R³¹ to form the corresponding naturally or non-naturally occurring terminal α-amino acid residue; optionally having a modified nitrogen (N) functional group;

with the further proviso that,
if linker L, as defined below, is connected with module A by a carbonyl (C=O) point of attachment of P⁵; then P⁵ is Glu;

for module B consisting of single elements Q being connected in either direction from the carbonyl (C=O) point of attachment to the nitrogen (N) of the next element with the proviso that Q⁷ is connected from the α-carbonyl (C=O) point of attachment to the ω-nitrogen (N) of Q¹, Q¹ is an L α-amino acid residue of formula AA3b;

Q², Q⁵, and Q⁶ are independently an L α-amino acid residue of formula AA3b;

Q³ is a D α-amino acid residue of one of the formulae AA1$^D$; or AA2$^D$;

Q⁴ is an L α-amino acid residue of one of the formulae AA1; or AA4;

Q⁷ is an L α-amino acid residue of one of the formulae AA1; or AA4;

for a linker L consisting of k=1 or 3 single elements L being connected in either direction from the carbonyl (C=O) point of attachment to the nitrogen (N) of the next element, if k=1,
L¹ is an α-amino acid residue of one of the formulae AA3b; or AA3b$^D$;

if k=3,
L¹ is an α-amino acid residue of one of the formulae AA3b; or AA3b$^D$;
L² is an α-amino acid residue of one of the formulae AA4; or AA4$^D$;

L³ is an α-amino acid residue of one of the formulae AA3b; or AA3b$^D$;

said linker L being connected with module B from the carbonyl (C=O) point of attachment of L$^k$ to the α-nitrogen (N) of Q¹ and, if k=1 or 3, being connected with module A from the carbonyl (C=O) point of attachment of P⁵; P⁶; or P⁷; to the nitrogen (N) of L¹;

or a pharmaceutically acceptable salt thereof.

In another particular embodiment (49) of the invention the elements of general formula (I) are defined as follows,
for module A,
if s=0, t=0, and u=0; and
P¹¹ is connected from the α-carbonyl point of attachment to the ω-nitrogen (N) of P²;

P¹ is an L α-amino acid residue of one of the formulae AA1; or AA2; or an L α-hydroxy acid residue of formula AA11;

P² is an L α-amino acid residue of formula AA3b;

P³ is an L α-amino acid residue of formula AA2;

P⁴ is Gly; or an L α-amino acid residue of one of the formulae AA3b; or AA4;

P⁶ is Gly; or a D α-amino acid residue of one of the formulae AA1$^D$; AA4$^D$; or AA3b$^D$;

P⁷ is Gly; or an L α-amino acid residue of one of the formulae AA1; AA3b; or AA4;

P⁸ is an L α-amino acid residue of formula AA2;

P⁹ is Gly; or an L α-amino acid residue of one of the formulae AA1; or AA4;

P¹⁰ is an L α-amino acid residue of formula AA1;

P¹¹ is a D α-amino acid residue of one of the formulae AA1$^D$; AA2$^D$; AA3b$^D$; AA4$^D$; AA5$^D$; or AA6$^D$;

with the proviso that,
the combined number of the amino acid residue Gly in above module A must not exceed two; and
the positions P of the amino acid residues Gly must not be in direct vicinity;

with the further proviso that,
X¹³ having a carbonyl (C=O) point of attachment not connected as aforementioned, being appropriately saturated by linkage with R³⁰ to form the corresponding naturally or non-naturally occurring terminal α-amino acid residue; optionally having a modified carbonyl (C=O) functional group;
X¹⁴ having a nitrogen (N) not connected as aforementioned, being appropriately saturated by linkages with Fe, as already depicted above, and R³¹ to form the corresponding naturally or non-naturally occurring terminal α-amino acid residue; optionally having a modified nitrogen (N) functional group;

with the further proviso that,
if linker L, as defined below, is connected with module A by a carbonyl (C=O) point of attachment of P⁵; then P⁵ is Glu;

for module B consisting of single elements Q being connected in either direction from the carbonyl (C=O) point of attachment to the nitrogen (N) of the next element with the proviso that Q⁷ is connected from the α-carbonyl (C=O) point of attachment to the ω-nitrogen (N) of Q¹, Q¹ is an L α-amino acid residue of formula AA3b;

Q², Q⁵, and Q⁶ are independently an L α-amino acid residue of formula AA3b;

Q³ is a D α-amino acid residue of one of the formulae AA1$^D$; or AA2$^D$;

Q⁴ is an L α-amino acid residue of one of the formulae AA1; or AA4;

Q⁷ is an L α-amino acid residue of one of the formulae AA1; or AA4;

for a linker L consisting of k=1 or 3 single elements L being connected in either direction from the carbonyl (C=O) point of attachment to the nitrogen (N) of the next element,
if k=1,
$L^1$ is an α-amino acid residue of one of the formulae AA3b; or AA3b$^D$;
if k=3,
$L^1$ is an α-amino acid residue of one of the formulae AA3b; or AA3b$^D$;
$L^2$ is an α-amino acid residue of one of the formulae AA4; or AA4$^D$;
$L^3$ is an α-amino acid residue of one of the formulae AA3b; or AA3b$^D$;
said linker L being connected with module B from the carbonyl (C=O) point of attachment of $L^k$ to the α-nitrogen (N) of $Q^1$ and,
if k=1 or 3, being connected with module A from the carbonyl (C=O) point of attachment of $P^5$; $P^6$; or $P^7$; to the nitrogen (N) of $L^1$;
or a pharmaceutically acceptable salt thereof.

In another particular embodiment (50) of the invention the elements of general formula (I) are defined as follows,
for module A,
if s=1, t=1, and u=1; and
$X^{14}$ and $X^{13}$ taken together form an interstrand linking bis(amino acid)-structure or (amino acid)-(acid) structure based on the linkage of two L amino acid residues; or an amino acid residue and an acid residue; following
connection of the side chain of Cys; Pen; Hcy; Ac-Cys; Ac-Pen; Ac-Hcy; or 3MPA with the side chain of Cys; Pen; Hcy; Cys-NH$_2$; Pen-NH$_2$; or Hcy-NH$_2$; by a disulfide linkage; or
connection of the side chain of Ac-Dab; Ac-Dap; Dab; or Dap; at $X^{14}$ with the side chain of Glu-NH$_2$; Asp-NH$_2$; Glu; or Asp; at $X^{13}$; or the side chain of Ac-Glu; Ac-Asp; Glu; or Asp; at $X^{14}$ with the side chain of Dab-NH$_2$; Dap-NH$_2$; Dab; or Dap; at $X^{13}$; by a lactam linkage; or
$X^{14}$ and $X^{13}$ taken together form a salt bridge based on the electrostatic interaction between the side chain of Ac-Dab; Ac-Dap; Ac-Lys; Dab; Dap; or Lys; at $X^{14}$ and the side chain of Glu-NH$_2$; Asp-NH$_2$; Glu; or Asp; at $X^{13}$; or the side chain of Ac-Glu; Ac-Asp; Glu; or Asp; at $X^{14}$ and the side chain of Dab-NH$_2$; Dap-NH$_2$; Lys-NH$_2$; Dab; Dap; or Lys; at $X^{13}$; and/or
$P^1$ and $X^{12}$ taken together form an interstrand linking bis(amino acid)-structure based on the linkage of two L amino acid residues; following
connection of the side chain of Cys; Pen; or Hcy; with the side chain of Cys; Pen; or Hcy; by a disulfide linkage; and/or
$P^2$ and $P^{11}$ taken together form an interstrand linking bis(amino acid)-structure based on the linkage of two L amino acid residues; following
connection of the side chain of Cys; Pen; or Hcy; with the side chain of Cys; Pen; or Hcy; by a disulfide linkage; or
connection of the side chain of Dab; or Dap; at $P^2$ with the side chain of Glu; or Asp; at $P^{11}$; or the side chain Glu; or Asp; at $P^2$ with the side chain of Dab; or Dap; at $P^{11}$; by a lactam linkage; or
$P^2$ and $P^{11}$ taken together form a salt bridge based on the electrostatic interaction between the side chain of Dab; Dap; or Lys; at $P^2$ and the side chain of Glu; or Asp; at $P^{11}$; or the side chain of Glu; or Asp; at $P^2$ and the side chain of Dab; Dap; or Lys; at $P^{11}$; and/or
$P^4$ and $P^9$ taken together form an interstrand linking bis(amino acid)-structure based on the linkage of two L amino acid residues; following
connection of the side chain of Cys; Pen; or Hcy; with the side chain of Cys; Pen; or Hcy; by a disulfide linkage; or
connection of the side chain of Asp; or Glu; with the side chain of Dab; or Dap; by a lactam linkage; or
$P^4$ and $P^9$ taken together form a salt bridge based on the electrostatic interaction between the side chain of Dab; Dap; or Lys; at $P^4$ and the side chain of Glu; or Asp; at $P^9$; or the side chain of Glu; or Asp; at $P^4$ and the side chain of Dab; Dap; or Lys; at $P^9$;
$X^{14}$ is $^D$Ser; pGlu; $^D$pGlu; Ac-Dab; Dab; 6MeHeptA; Ac-pGlu; Ac-DpGlu; or Ac-$^D$Ser;
$P^1$ is Val; NMeVal; $^D$Val; Leu; Ile; Nle; Phe; Tyr; Ser; Leu(3R)OH; or Nva;
$P^2$ is Thr; Dap; Ala; Val tBuGly; or Dab;
$P^a$ is Tyr; Val; Ser; or Thr;
$P^4$ is Dab; Dap; Ser; or Gly;
$P^5$ is Gly; or Orn;
$P^6$ is $^D$Dab; $^D$Arg; $^D$Ser; $^D$Hse; $^D$Ala; or Gly;
$P^7$ is Ser; Hse; Thr; Dab; Ala; or Gly;
$P^8$ is Trp; or Val;
$P^9$ is Ser; Hse; Thr; Glu; Ala; or Gly;
$P^{10}$ is Val; tBuGly; Tyr; Trp; Ser; Nva; or Ile;
$P^{11}$ is Ala; Ser; Thr; Dab; or Glu;
$X^{12}$ is Val; Ser; Thr; Dab; or Tyr;
$X^{13}$ is $^D$Ala; $^D$Ala-NH$_2$; $^D$Ser; $^D$Ser-NH$_2$; or Glyol;
with the proviso that,
if $P^1$ is Ser; or Leu(3R)OH; then $X^{12}$ is Val; and
if $P^3$ is Ser; Thr; or Val; then $P^1$; $P^{10}$; or $X^{12}$; is Tyr; and
if $P^8$ is Val; then $P^{10}$ is Trp; and
if $P^{10}$ is Ser; then $X^{12}$ is Val; and
the combined number of the amino acid residue Gly in above module A must not exceed two; and
the positions P of the amino acid residues Gly must not be in direct vicinity;
with the further proviso that,
the combined number of interstrand linkages and salt bridges in above module A must not exceed two;
if $X^{14}$ and $X^{13}$ taken together form an interstrand linkage or salt bridge, as defined above; then $P^1$ and $X^{12}$ taken together are not forming an interstrand linkage or salt bridge, as defined above;
if $P^1$ and $X^{12}$ taken together form an interstrand linkage or salt bridge, as defined above; then $P^2$ and $P^{11}$ taken together are not forming an interstrand linkage or a salt bridge, as defined above;
with the further proviso that,
if linker L, as defined below, is connected with module A by a carbonyl (C=O) point of attachment of $P^5$; $P^6$; or $P^7$; then
$P^5$; $P^6$; or $P^7$; is Glu; or $^D$Glu;
if s=1, t=0, and u=1; and
$P^1$ and $X^{12}$ taken together form an interstrand linking bis(amino acid)-structure based on the linkage of two L amino acid residues; following
connection of the side chain of Cys; Pen; or Hcy; with the side chain of Cys; Pen; Hcy; Cys-NH$_2$; Pen-NH$_2$; or Hcy-NH$_2$ by a disulfide linkage; and/or
$P^2$ and $P^{11}$ taken together form an interstrand linking bis(amino acid)-structure based on the linkage of two L amino acid residues; following
connection of the side chain of Cys; Pen; or Hcy; with the side chain of Cys; Pen; or Hcy; by a disulfide linkage; or
connection of the side chain of Dab; or Dap; with the side chain of Glu; or Asp; by a lactam linkage; or
$P^2$ and $P^{11}$ taken together form a salt bridge based on the electrostatic interaction between the side chain of Dab; Dap;

or Lys; at P² and the side chain of Glu; or Asp; at P¹¹; or the side chain of Glu; or Asp; at P² and the side chain of Dab; Dap; or Lys; at P¹¹; and/or P⁴ and P⁹ taken together form an interstrand linking bis (amino acid)-structure based on the linkage of two L amino acid residues; following connection of the side chain of Cys; Pen; or Hcy; with the side chain of Cys; Pen; or Hcy; by a disulfide linkage; or connection of the side chain of Asp; or Glu; with the side chain of Dab; or Dap; by a lactam linkage; or P⁴ and P⁹ taken together form a salt bridge based on the electrostatic interaction between the side chain of Dab; Dap; or Lys; at P⁴ and the side chain of Glu; or Asp; at P⁹; or the side chain of Glu; or Asp; at P⁴ and the side chain of Dab; Dap; or Lys; at P⁹;

X¹⁴; P¹; P²; P³; P⁴; P⁵; P⁶; P⁷; P⁸; P⁹; P¹⁰; and P¹¹ are as defined above for module A, wherein s=1, t=1, and u=1;

X¹² is Val; Ser; Thr; Dab; Tyr; Serol; Throl; $^D$Throl; Tyrol; Glyol; Val-NH₂; Ser-NH₂; Ser-NHMe; Ser-OiPr; Thr-NH₂; Dab-NH₂; Tyr-NH₂;

with the proviso that,
 if P¹ is Ser; or Leu(3R)OH; then X¹² is Val; or Val-NH₂; and
 if P³ is Ser; Thr; or Val; then P¹; or P^m; is Tyr; or X¹² is Tyr; Tyrol;
 or Tyr-NH₂; and
 if P⁸ is Val; then P¹⁰ is Trp; and
 if P¹⁰ is Ser; then X¹² is Val; or Val-NH₂; and
 the combined number of the amino acid residue Gly in above module A must not exceed two; and
 the positions P of the amino acid residues Gly must not be in direct vicinity;
with the further proviso that,
 if P¹ and X¹² taken together form an interstrand linkage, as defined above;
 then P² and P¹¹ taken together are not forming an interstrand linkage or salt bridge, as defined above;
with the further proviso that,
 if linker L, as defined below, is connected with module A by a carbonyl (C=O) point of attachment of P⁵; P⁶; or P⁷; then
  P⁵; P⁶; or P⁷; is Glu; or $^D$Glu;
if s=1, t=1, and u=0; and P¹ and X¹² taken together form an interstrand linking bis (amino acid)-structure based on the linkage of two L amino acid residues; following connection of the side chain of Cys; Pen; Hcy; Ac-Cys; Ac-Pen; or Ac-Hcy; with the side chain of Cys; Pen; or Hcy; by a disulfide linkage; and/or P² and P¹¹ taken together form an interstrand linking bis (amino acid)-structure based on the linkage of two L amino acid residues; following connection of the side chain of Cys; Pen; or Hcy; with the side chain of Cys; Pen; or Hcy; by a disulfide linkage; or connection of the side chain of Dab; or Dap; with the side chain of Glu; or Asp; by a lactam linkage; or P² and P¹¹ taken together form a salt bridge based on the electrostatic interaction between the side chain of Dab; Dap; or Lys; at P² and the side chain of Glu; or Asp; at P¹¹; or the side chain of Glu; or Asp; at P² and the side chain of Dab; Dap; or Lys; at P¹¹; and/or P⁴ and P⁹ taken together form an interstrand linking bis (amino acid)-structure based on the linkage of two L amino acid residues; following connection of the side chain of Cys; Pen; or Hcy; with the side chain of Cys; Pen; or Hcy; by a disulfide linkage; or connection of the side chain of Asp; or Glu; with the side chain of Dab; or Dap; by a lactam linkage; or P⁴ and P⁹ taken together form a salt bridge based on the electrostatic interaction between the side chain of Dab; Dap; or Lys; at P⁴ and the side chain of Glu; or Asp; at P⁹; or the side chain of Glu; or Asp; at P⁴ and the side chain of Dab; Dap; or Lys; at P⁹;

P¹ is Val; NMeVal; $^D$Val; Leu; Ile; Nle; Phe; Tyr; Ser; Leu(3R)OH; Nva; HOVal; Ac-Val; Ac-$^D$Val; Ac-Leu; Ac-Ile; Ac-Phe; Prop-Val; Ac-Nle; Ac-Tyr; Ac-Ser; Ac-Leu(3R)OH; Ac-Nva; 3MeButA; 2MePropA; or 6MeHeptA;

P²; P³; P⁴; P⁵; P⁶; P⁷; P⁸; P⁹; P¹⁰; P¹¹; and X¹² are as defined above for module A, wherein s=1, t=1, and u=1;

X¹³ is $^D$Ala; $^D$Ala-NH₂; $^D$Ser; $^D$Ser-N H₂; or Glyol;

with the proviso that,
 if P¹ is Ser; Ac-Ser; Leu(3R)OH; or Ac-Leu(3R)OH; then X¹² is Val; and
 if P³ is Ser; Thr; or Val; then P¹; is Tyr; or Ac-Tyr; or P¹⁰; or X¹²; is Tyr; and
 if P⁸ is Val; then P¹⁰ is Trp; and
 if P¹⁰ is Ser; then X¹² is Val; and
 the combined number of the amino acid residue Gly in above module A must not exceed two; and
 the positions P of the amino acid residues Gly must not be in direct vicinity;
with the further proviso that,
 if P¹ and X¹² taken together form an interstrand linkage, as defined above;
 then P² and P¹¹ taken together are not forming an interstrand linkage or salt bridge, as defined above;
with the further proviso that,
 if linker L, as defined below, is connected with module A by a carbonyl (C=O) point of attachment of P⁵; P⁶; or P⁷; then
  P⁵; P⁶; or P⁷; is Glu; or $^D$Glu;
if s=0, t=0, and u=1; and P² and P¹¹ taken together form an interstrand linking bis (amino acid)-structure based on the linkage of two L amino acid residues; following connection of the side chain of Cys; Pen; or Hcy; with the side chain of Cys; Pen; Hcy; Cys-NH₂; Pen-NH₂; or Hcy-NH₂; by a disulfide linkage; or connection of the side chain of Dab; or Dap; at P² with the side chain of Glu; Asp; Glu-NH₂; or Asp-NH₂; at P¹¹; or the side chain Glu; or Asp; at P² with the side chain of Dab; Dap; Dab-NH₂; or Dap-NH₂; at P¹¹; by a lactam linkage; or P² and P¹¹ taken together form a salt bridge based on the electrostatic interaction between the side chain of Dab; Dap; or Lys; at P² and the side chain of Glu; Asp; Glu-NH₂; or Asp-NH₂; at P¹¹; or the side chain of Glu; or Asp; at P² and the side chain of Dab; Dap; Lys; Dab-NH₂; Dap-NH₂; or Lys-NH₂; at P¹¹; and/or P⁴ and P⁹ taken together form an interstrand linking bis (amino acid)-structure based on the linkage of two L amino acid residues; following connection of the side chain of Cys; Pen; or Hcy; with the side chain of Cys; Pen; or Hcy; by a disulfide linkage; or connection of the side chain of Asp; or Glu; with the side chain of Dab; or Dap; by a lactam linkage; or P⁴ and P⁹ taken together form a salt bridge based on the electrostatic interaction between the side chain of Dab; Dap; or Lys; at P⁴ and the side chain of Glu; or Asp; at P⁹; or the side chain of Glu; or Asp; at P⁴ and the side chain of Dab; Dap; or Lys; at P⁹;

X¹⁴; P¹; P²; P³; P⁴; P⁵; P⁶; P⁷; P⁸; P⁹; and P¹⁰ are defined above for module A, wherein s=1, t=1, and u=1;

$P^{11}$ is Ala; Ser; Thr; Dab; Glu; Ser-$NH_2$; Dab-$NH_2$; Ala-$NH_2$; Thr-$NH_2$; or Glu-$NH_2$;
with the proviso that,
  if $P^3$ is Ser; Thr; or Val; then $P^1$; or $P^{10}$; is Tyr; and
  if $P^8$ is Val; then $P^{10}$ is Trp; and
  the combined number of the amino acid residue Gly in above module A must not exceed two; and
  the positions P of the amino acid residues Gly must not be in direct vicinity;
with the further proviso that,
  if linker L, as defined below, is connected with module A by a carbonyl (C=O) point of attachment of $P^5$; $P^6$; or $P^7$; then
    $P^5$; $P^6$; or $P^7$; is Glu; or $^D$Glu;
if s=1, t=0, and u=0; and
$P^1$ and $X^{12}$ taken together form an interstrand linking bis (amino acid)-structure based on the linkage of two L amino acid residues; following
connection of the side chain of Cys; Pen; Hcy; Ac-Cys; Ac-Pen; or Ac-Hcy; with the side chain of Cys; Pen; Hcy; Cys-$NH_2$; Pen-$NH_2$; or Hcy-$NH_2$; by a disulfide linkage; and/or
$P^2$ and $P^{11}$ taken together form an interstrand linking bis (amino acid)-structure based on the linkage of two L amino acid residues; following
connection of the side chain of Cys; Pen; or Hcy; with the side chain of Cys; Pen; or Hcy; by a disulfide linkage; or
connection of the side chain of Dab; or Dap; with the side chain of Glu; or Asp; by a lactam linkage; or
$P^2$ and $P^{11}$ taken together form a salt bridge based on the electrostatic interaction between the side chain of Dab; Dap; or Lys; at $P^2$ and the side chain of Glu; or Asp; at $P^{11}$; or the side chain of Glu; or Asp; at $P^2$ and the side chain of Dab; Dap; or Lys; at $P^{11}$; and/or
$P^4$ and $P^9$ taken together form an interstrand linking bis (amino acid)-structure based on the linkage of two L amino acid residues; following
connection of the side chain of Cys; Pen; or Hcy; with the side chain of Cys; Pen; or Hcy; by a disulfide linkage; or
connection of the side chain of Asp; or Glu; with the side chain of Dab; or Dap; by a lactam linkage; or
$P^4$ and $P^9$ taken together form a salt bridge based on the electrostatic interaction between the side chain of Dab; Dap; or Lys; at $P^4$ and the side chain of Glu; or Asp; at $P^9$; or the side chain of Glu; or Asp; at $P^4$ and the side chain of Dab; Dap; or Lys; at $P^9$;
$P^1$ is Val; NMeVal; $^D$Val; Leu; Ile; Nle; Phe; Tyr; Ser; Leu(3R)OH; Nva; HOVal; Ac-Val; Ac-$^D$Val; Ac-Leu; Ac-Ile; Ac-Phe; Prop-Val; Ac-Nle; Ac-Tyr; Ac-Ser; Ac-Leu(3R)OH; Ac-Nva; 3MeButA; 2MePropA; or 6MeHeptA;
$P^2$; $P^3$; $P^4$; $P^5$; $P^6$; $P^7$; $P^8$; $P^9$; $P^{10}$; and $P^{11}$ are as defined above for module A,
wherein s=1, t=1, and u=1;
$X^{12}$ is Val; Ser; Thr; Dab; Tyr; Serol; Throl; $^D$Throl; Tyrol; Glyol; Val-$NH_2$; Ser-$NH_2$; Ser-NHMe; Ser-OiPr; Thr-$NH_2$; Dab-$NH_2$; or Tyr-$NH_2$;
with the proviso that,
  if $P^1$ is Ser; Ac-Ser; Leu(3R)OH; or Ac-Leu(3R)OH; then $X^{12}$ is Val; or Val-$NH_2$; and
  if $P^3$ is Ser; Thr; or Val; then $P^1$; is Tyr; or Ac-Tyr; or $P^{10}$ is Tyr; or $X^{12}$ is Tyr; Tyrol; or Tyr-$NH_2$; and
  if $P^8$ is Val; then $P^{10}$ is Trp; and
  if $P^{10}$ is Ser; then $X^{12}$ is Val; or Val-$NH_2$; and
  the combined number of the amino acid residue Gly in above module A must not exceed two; and
  the positions P of the amino acid residues Gly must not be in direct vicinity;
with the further proviso that,
  if $P^1$ and $X^{12}$ taken together form an interstrand linkage, as defined above;
  then $P^2$ and $P^{11}$ taken together are not forming an interstrand linkage or salt bridge, as defined above;
with the further proviso that,
  if linker L, as defined below, is connected with module A by a carbonyl (C=O) point of attachment of $P^5$; $P^6$; or $P^7$; then
    $P^5$; $P^6$; or $P^7$; is Glu; or $^D$Glu;
if s=0, t=0, and u=0; and
$P^2$ and $P^{11}$ taken together form an interstrand linking bis (amino acid)-structure based on the linkage of two L amino acid residues; following
connection of the side chain of Cys; Pen; or Hcy; with the side chain of Cys; Pen; Hcy; Cys-$NH_2$; Pen-$NH_2$; or Hcy-$NH_2$; by a disulfide linkage; or
connection of the side chain of Dab; or Dap; at $P^2$ with the side chain of Glu; Asp; Glu-$NH_2$; or Asp-$NH_2$; at $P^{11}$; or the side chain Glu; or Asp; at $P^2$ with the side chain of Dab; Dap; Dab-$NH_2$; or Dap-$NH_2$; at $P^{11}$; by a lactam linkage; or
$P^2$ and $P^{11}$ taken together form a salt bridge based on the electrostatic interaction between the side chain of Dab; Dap; or Lys; at $P^2$ and the side chain of Glu; Asp; Glu-$NH_2$; or Asp-$NH_2$; at $P^{11}$; or the side chain of Glu; or Asp; at $P^2$ and the side chain of Dab; Dap; Lys; Dab-$NH_2$; Dap-$NH_2$; or Lys-$NH_2$; at $P^{11}$; and/or
$P^4$ and $P^9$ taken together form an interstrand linking bis (amino acid)-structure based on the linkage of two L amino acid residues; following
connection of the side chain of Cys; Pen; or Hcy; with the side chain of Cys; Pen; or Hcy; by a disulfide linkage; or
connection of the side chain of Asp; or Glu; with the side chain of Dab; or Dap; by a lactam linkage; or
$P^4$ and $P^9$ taken together form a salt bridge based on the electrostatic interaction between the side chain of Dab; Dap; or Lys; at $P^4$ and the side chain of Glu; or Asp; at $P^9$; or the side chain of Glu; or Asp; at $P^4$ and the side chain of Dab; Dap; or Lys; at $P^9$;
$P^1$ is Val; NMeVal; $^D$Val; Leu; Ile; Nle; Phe; Tyr; Ser; Leu(3R)OH; Nva; HOVal; Ac-Val; Ac-$^D$Val; Ac-Leu; Ac-Ile; Ac-Phe; Prop-Val; Ac-Nle; Ac-Tyr; Ac-Ser; Ac-Leu(3R)OH; Ac-Nva; 3MeButA; 2MePropA; or 6MeHeptA;
$P^2$; $P^3$; $P^4$; $P^5$; $P^6$; $P^7$; $P^8$; $P^9$; and $P^{10}$ are as defined above for module A,
wherein s=1, t=1, and u=1;
$P^{11}$ is Ala; Ser; Thr; Dab; Glu; Ser-$NH_2$; Dab-$NH_2$; Ala-$NH_2$; Thr-$NH_2$; or Glu-$NH_2$;
with the proviso that,
  if $P^3$ is Ser; Thr; or Val; then $P^1$; is Tyr; or Ac-Tyr; or $P^{10}$ is Tyr; and
  if $P^8$ is Val; then $P^{10}$ is Trp; and
  the combined number of the amino acid residue Gly in above module A must not exceed two; and
  the positions P of the amino acid residues Gly must not be in direct vicinity;
with the further proviso that,
  if linker L, as defined below, is connected with module A by a carbonyl (C=O) point of attachment of $P^5$; $P^6$; or $P^7$; then
    $P^5$; $P^6$; or $P^7$; is Glu; or $^D$Glu;
if s=0, t=0, and u=0; and
$P^{11}$ is connected from the α-carbonyl point of attachment to the ω-nitrogen (N) of $P^2$;

P$^1$ is Val; NMeVal; $^D$Val; Leu; Ile; Nle; Phe; Tyr; Ser; Leu(3R)OH; Nva; HOVal; Ac-Val; Ac-$^D$Val; Ac-Leu; Ac-Ile; Ac-Phe; Prop-Val; Ac-Nle; Ac-Tyr; Ac-Ser; Ac-Leu(3R)OH; Ac-Nva; 3MeButA; 2MePropA; or 6MeHeptA;

P$^2$ is Orn; or Dab;

P$^3$; P$^4$; P$^5$; P$^6$; P$^7$; P$^8$; P$^9$; and P$^{10}$ are as defined above for module A, wherein s=1, t=1, and u=1;

P$^{11}$ is $^D$Thr; $^D$Hse; $^D$Asn; $^D$Gln; $^D$Glu; $^D$Val; $^D$Tyr; $^D$Dab; $^D$Orn; or $^D$Lys;

with the proviso that,
   if P$^3$ is Ser; Thr; or Val; then P$^1$; is Tyr; or Ac-Tyr; or P$^{10}$ is Tyr; and
   if P$^8$ is Val; then P$^{10}$ is Trp; and
   the combined number of the amino acid residue Gly in above module A must not exceed two; and
   the positions P of the amino acid residues Gly must not be in direct vicinity;

with the further proviso that,
   if linker L, as defined below, is connected with module A by a carbonyl (C=O) point of attachment of P$^5$; P$^6$; or P$^7$; then
     P$^5$; P$^6$; or P$^7$; is Glu; or $^D$Glu;

for module B consisting of single elements Q being connected in either direction from the carbonyl (C=O) point of attachment to the nitrogen (N) of the next element with the proviso that Q$^7$ is connected from the α-carbonyl (C=O) point of attachment to the ω-nitrogen (N) of Q$^1$, Q$^1$ is Dab;
Q$^2$, Q$^5$ and Q$^6$ are Dab;
Q$^3$ is $^D$Leu; or $^D$Phe;
Q$^4$ is Leu; Ile; Leu(3R)OH; Abu; Nva; Thr; or alloThr;
Q$^7$ is Thr; or Leu;

for a linker L consisting of k=1 or 3 single elements L being connected in either direction from the carbonyl (C=O) point of attachment to the nitrogen (N) of the next element,
if k=1,
L$^1$ is $^D$Dab;
If k=3,
L$^1$ is Dab; or NMeDab;
L$^2$ is Thr; or Ser;
L$^3$ is Dap; or Dab;

said linker L being connected with module B from the carbonyl (C=O) point of attachment of L$^k$ to the α-nitrogen (N) of Q$^1$ and,
if k=1 or 3, being connected with module A from the carbonyl (C=O) point of attachment of P$^5$; P$^6$; or P$^7$; to the nitrogen (N) of L$^1$;
or a pharmaceutically acceptable salt thereof.

In another particular embodiment (51) of the invention the elements of general formula (I) are defined as follows,
for module A,
if s=1, t=1, and u=1; and
X$^{14}$ and X$^{13}$ taken together form an interstrand linking bis(amino acid)-structure based on the linkage of two L amino acid residues; following
connection of the side chain of Ac-Cys; or 3MPA with the side chain of Cys-NH$_2$ by a disulfide linkage; or
connection of the side chain of Ac-Dab; at X$^{14}$ with the side chain of Glu-NH$_2$; at X$^{13}$; by a lactam linkage; or
X$^{14}$ and X$^{13}$ taken together form a salt bridge based on the electrostatic interaction between the side chain of Ac-Dab at X$^{14}$ and the side chain of Glu-NH$_2$ at X$^{13}$; or the side chain of Ac-Glu at X$^{14}$ and the side chain of Dab-NH$_2$ at X$^{13}$; and/or P$^2$ and P$^{11}$ taken together form an interstrand linking bis (amino acid)-structure based on the linkage of two L amino acid residues; following
connection of the side chain of Cys; with the side chain of Cys by a disulfide linkage; or P$^2$ and P$^{11}$ taken together form a salt bridge based on the electrostatic interaction between the side chain of Dab; at P$^2$ and the side chain of Glu; at P$^{11}$;

X$^{14}$ is $^D$Ser; pGlu; or $^D$pGlu;
P$^1$ is Val; Leu; or Leu(3R)OH;
P$^2$ is Thr;
P$^3$ is Tyr;
P$^4$ is Dab; Dap; Ser; or Gly;
P$^6$ is $^D$Dab; $^D$Ser; $^D$Hse; $^D$Ala; or Gly;
P$^7$ is Ser; Hse; Thr; Dab; Ala; or Gly;
P$^8$ is Trp;
P$^9$ is Ser; Hse; Glu; Ala; or Gly;
P$^{10}$ is Val; or tBuGly; Ile; or Nva;
P$^{11}$ is Ala; or Ser;
X$^{12}$ is Val; Ser; or Thr;
X$^{13}$ is $^D$Ala; $^D$Ser; $^D$Ala-N H$_2$; or $^D$Ser-NH$_2$;

with the proviso that,
   if P$^1$ is Leu(3R)OH; then X$^{12}$ is Val; and
   the combined number of the amino acid residue Gly in above module A must not exceed two; and
   the positions P of the amino acid residues Gly must not be in direct vicinity;

with the further proviso that,
   if linker L, as defined below, is connected with module A by a carbonyl (C=O) point of attachment of P$^5$; then
     P$^5$ is Glu;

if s=1, t=0, and u=1; and

P$^2$ and P$^{11}$ taken together form an interstrand linking bis (amino acid)-structure based on the linkage of two L amino acid residues; following
connection of the side chain of Cys; with the side chain of Cys by a disulfide linkage; and/or
P$^4$ and P$^9$ taken together form an interstrand linking bis (amino acid) structure based on the linkage of two L amino acid residues; following
connection of the side chain of Cys; with the side chain of Cys by a disulfide linkage;

X$^{14}$ is pGu; $^D$pGlu; Ac-Dab; or 6MeHeptA;
P$^1$ is Val; Leu; or Leu(3R)OH;
P$^2$ is Thr;
P$^3$ is Tyr;
P$^4$ is Dap; Dab; Ser; or Gly;
P$^6$ is $^D$Dab; $^D$Ser; $^D$Hse; $^D$Ala; or Gly;
P$^7$ is Ser; Thr; Dab; Hse; Ala; or Gly;
P$^8$ is Trp;
P$^9$ is Ser; Hse; Ala; or Gly;
P$^{10}$ is Val; tBuGly; Ile; or Nva;
P$^{11}$ is Ala;
X$^{12}$ is Val-NH$_2$; Ser-NH$_2$; Thr-NH$_2$; Throl; Glyol; Val; Ser; or Thr;

with the proviso that,
   if P$^1$ is Leu(3R)OH; then X$^{12}$ is Val; or Val-NH$_2$; and
   the combined number of the amino acid residue Gly in above module A must not exceed two; and
   the positions P of the amino acid residues Gly must not be in direct vicinity;

with the further proviso that,
   if linker L, as defined below, is connected with module A by a carbonyl (C=O) point of attachment of P$^5$; then
     P$^5$ is Glu;

if s=1, t=1, and u=0; and
P² and P¹¹ taken together form an interstrand linking bis (amino acid)-structure based on the linkage of two L amino acid residues; following
connection of the side chain of Cys; with the side chain of Cys by a disulfide linkage; and/or
P⁴ and P⁹ taken together form an interstrand linking bis (amino acid) structure based on the linkage of two L amino acid residues; following
connection of the side chain of Cys; with the side chain of Cys by a disulfide linkage;
P¹ is Val; HOVal; or Ac-Val;
P² is Thr;
P³ is Val; Ser; or Thr;
P⁴ is Dab; Dap; Ser; or Gly;
P⁶ is $^D$Dab; $^D$Ser; $^D$Hse; $^D$Ala; or Gly;
P⁷ is Hse; Ser; Thr; Dab; Ala; or Gly;
P⁸ is Trp;
P⁹ is Ser; Hse; Ala; or Gly;
P¹⁰ is tBuGly; Val; Ile; or Nva;
P¹¹ is Ala; or Ser;
X¹² is Tyr;
X¹³ is Glyol; $^D$Ala; $^D$Ser; $^D$Ala-NH₂; or $^D$Ser-NH₂;
with the proviso that,
the combined number of the amino acid residue Gly in above module A must not exceed two; and
the positions P of the amino acid residues Gly must not be in direct vicinity;
with the further proviso that,
if linker L, as defined below, is connected with module A by a carbonyl (C=O) point of attachment of P⁵; then P⁵ is Glu;
if s=0, t=0, and u=1; and
P² and P¹¹ taken together form an interstrand linking bis (amino acid)-structure based on the linkage of two L amino acid residues; following
connection of the side chain of Cys; with the side chain of Cys by a disulfide linkage; and/or
P⁴ and P⁹ taken together form an interstrand linking bis (amino acid) structure based on the linkage of two L amino acid residues; following
connection of the side chain of Cys; with the side chain of Cys by a disulfide linkage;
X¹⁴ is Ac-Dab; pGlu; or $^D$pGlu;
P¹ is Val; Leu; or Leu(3R)OH;
P² is Thr;
P³ is Tyr;
P⁴ is Dap; Dab; Ser; or Gly;
P⁶ is $^D$Dab; $^D$Ser; $^D$Hse; $^D$Ala; or Gly;
P⁷ is Ser; Hse; Thr; Dab; Ala; or Gly;
P⁸ is Trp;
P⁹ is Ser; Hse; Ala; or Gly;
P¹⁰ is tBuGly; Val; Ile; or Nva;
P¹¹ is Dab-NH₂; Ala-NH₂; Dab; or Ala;
with the proviso that,
the combined number of the amino acid residue Gly in above module A must not exceed two; and
the positions P of the amino acid residues Gly must not be in direct vicinity;
with the further proviso that,
if linker L, as defined below, is connected with module A by a carbonyl (C=O) point of attachment of P⁵; then P⁵ is Glu;
if s=1, t=0, and u=0; and
P¹ and X¹² taken together form an interstrand linking bis (amino acid) structure based on the linkage of two L amino acid residues; following
connection of the side chain of Ac-Pen; with the side chain of Cys-NH₂; by a disulfide linkage; and/or
P² and P¹¹ taken together form an interstrand linking bis (amino acid)-structure based on the linkage of two L amino acid residues; following
connection of the side chain of Cys; hCys; or Pen; with the side chain of Cys; or Pen; by a disulfide linkage; or
connection of the side chain of Dab; with the side chain of Asp; or Glu; by a lactam linkage; or
P² and P¹¹ taken together form a salt bridge based on the electrostatic interaction between the side chain of Asp; or Glu; at P² and the side chain of Lys; or Dab; at P¹¹; or the side chain of Dab at P² and the side chain of Asp; or Glu; at P¹¹; and/or
P⁴ and P⁹ taken together form an interstrand linking bis (amino acid) structure based on the linkage of two L amino acid residues; following
connection of the side chain of Cys; or Pen; with the side chain of Cys; or Pen; by a disulfide linkage; or
connection of the side chain of Dab; with the side chain of Asp; by a lactam linkage; or
P⁴ and P⁹ taken together form a salt bridge based on the electrostatic interaction between the side chain of Glu; at P⁴ and the side chain of Dap; at P⁹; or the side chain of Dab; or Lys; at P⁴ and the side chain of Asp; or Glu; at P⁹;
P¹ is Val; Ac-Val; NMeVal; HOVal; Ac-$^D$Val; Prop-Val; Leu; Nle; Ac-Nle; Tyr; Ac-Tyr; Ser; Ac-Ser; pGlu; 3MeButA; 2MePropA; or 6MeHeptA;
P² is Ala; Val; tBuGly; Dab; Dap; or Thr;
P³ is Val; Ser; Thr; or Tyr;
P⁴ is Dab; Dap; Ser; Thr; or Gly
P⁵ is Gly; or Orn;
P⁶ is Gly; $^D$Dab; $^D$Ser; $^D$Hse; $^D$Ala; or $^D$Arg;
P⁷ is Ser; Hse; Thr; Dab; Ala; or Gly;
P⁸ is Trp; Val;
P⁹ is Ser; Thr; Hse; Glu; Ala; or Gly;
P¹⁰ is tBuGly; Val; Ile; Nva; Tyr; or Trp;
P¹¹ is Ala; Ser; Thr; Glu; or Dab;
X¹² is Glyol; Ser; Serol; Ser-NH₂; Ser-NHMe; Ser-OiPr; Thr-NH₂; Throl; $^D$Throl; Val-NH₂; Tyr-NH₂; Tyrol; or Dab-NH₂;
with the proviso that,
if P¹ is Ser; or Ac-Ser; then X¹² is Val-NH₂; and
if P³ is Ser; Thr; or Val; then P¹ is Tyr; or Ac-Tyr; or P¹⁰ is Tyr; or X¹² is Tyr-NH₂; or Tyrol; and
if P⁸ is Val; then P¹⁰ is Trp; and
the combined number of the amino acid residue Gly in above module A must not exceed two; and
the positions P of the amino acid residues Gly must not be in direct vicinity;
with the further proviso that,
if P¹ and X¹² taken together form an interstrand linkage or salt bridge, as defined above; then P² and P¹¹ taken together are not forming an interstrand linkage or salt bridge, as defined above;
with the further proviso that,
if linker L, as defined below, is connected with module A by a carbonyl (C=O) point of attachment of P⁵; P⁶; or P⁷; then;
P⁵; P⁶; or P⁷ is Glu; or $^D$Glu;
if s=0, t=0, and u=0; and
P² and P¹¹ taken together form an interstrand linking bis (amino acid)-structure based on the linkage of two L amino acid residues; following
connection of the side chain of Cys with the side chain of Cys by a disulfide linkage; and/or P⁴ and P⁹ taken together form an interstrand linking bis(amino acid) structure based on the linkage of two L amino acid residues; following
connection of the side chain of Cys with the side chain of Cys by a disulfide linkage;
P¹ is Ac-Val; NMeVal; HOVal; or Val;
P² is Thr;
P³ is Tyr;
P⁴ is Dab; Dap; Ser; or Gly;
P⁶ is $^D$Dab; $^D$Ser; $^D$Hse; $^D$Ala; or Gly;
P⁷ is Ser; Hse; Thr; Dab; Ala; or Gly;
P⁸ is Trp;
P⁹ is Ser; Hse; Ala; or Gly;
P¹⁰ is tBuGly; Val; Ile; or Nva;
P¹¹ is Ser-NH₂; Ser; Ala; or Ala-NH₂;
with the proviso that,
  the combined number of the amino acid residue Gly in above module A must not exceed two; and
  the positions P of the amino acid residues Gly must not be in direct vicinity;
with the further proviso that,
  if linker L, as defined below, is connected with module A by a carbonyl (C=O) point of attachment of P⁵ then P⁵ is Glu;
if s=0, t=0, and u=0; and
P¹¹ is connected from the α-carbonyl point of attachment to the ω-nitrogen (N) of P²;
P¹ is Ac-Val; HOVal; Ac-Leu; Ac-Ile; Ac-Nle; or Ac-Phe; Val; Leu; Ile; Nle; or Phe;
P² is Orn; or Dab;
P³ is Tyr;
P⁴ is Dab; Dap; Ser; Thr; or Gly;
P⁶ is $^D$Dab; $^D$Ser; $^D$Hse; $^D$Ala; or Gly;
P⁷ is Ser; Hse; Thr; Dab; Ala; or Gly;
P⁸ is Trp;
P⁹ is Ser; Hse; Ala; or Gly;
P¹⁰ is tBuGly; Val; Ile; or Nva;
P¹¹ is $^D$Thr; $^D$Hse; $^D$Asn; $^D$Gln; $^D$Glu; $^D$Val; $^D$Tyr; $^D$Dab; $^D$Orn; $^D$Lys;
with the proviso that,
  the combined number of the amino acid residue Gly in above module A must not exceed two; and
  the positions P of the amino acid residues Gly must not be in direct vicinity;
with the further proviso that,
  if linker L, as defined below, is connected with module A by a carbonyl (C=O) point of attachment of P⁵ then P⁵ is Glu;
or a pharmaceutically acceptable salt thereof.

In another particular embodiment (52) of the invention the elements of general formula (I) are defined as follows,
for a linker L consisting of k=1 or 3 single elements L being connected in either direction from the carbonyl (C=O) point of attachment to the nitrogen (N) of the next element,
if k=1,
L¹ is $^D$Dab;
If k=3,
L¹ is Dab; or NMeDab;
L² is Thr; or Ser;
L³ is Dap; or Dab;
said linker L being connected with module B from the carbonyl (C=O) point of attachment of $L^k$ to the α-nitrogen (N) of Q¹ and,
if k=1 or 3, being connected with module A from the carbonyl (C=O) point of attachment of P⁵; P⁶; or P⁷; to the nitrogen (N) of L¹;
or a pharmaceutically acceptable salt thereof.

In another particular embodiment (53) of the invention the elements of general formula (I) are defined as follows,
for module A,
if s=1, t=1, and u=0; and
P² and P¹¹ taken together form an interstrand linking bis(amino acid)-structure based on the linkage of two L amino acid residues; following
connection of the side chain of Cys; with the side chain of Cys by a disulfide linkage; and/or
P⁴ and P⁹ taken together form an interstrand linking bis(amino acid) structure based on the linkage of two L amino acid residues; following
connection of the side chain of Cys; with the side chain of Cys by a disulfide linkage;
P¹ is HOVal; or Ac-Val;
P² is Thr;
P³ is Val; Ser; or Thr;
P⁴ is Dab;
P⁶ is $^D$Dab;
P⁷ is Hse;
P⁸ is Trp;
P⁹ is Ser;
P^m is tBuGly;
P¹¹ is Ala;
X¹² is Tyr;
X¹³ is Glyol;
with the proviso that,
  if linker L, as defined below, is connected with module A by a carbonyl (C=O) point of attachment of P⁵; then P⁵ is Glu;
for module B consisting of single elements Q being connected in either direction from the carbonyl (C=O) point of attachment to the nitrogen (N) of the next element with the proviso that Q⁷ is connected from the α-carbonyl (C=O) point of attachment to the ω-nitrogen (N) of Q¹,
Q¹ is Dab;
Q², Q⁵ and Q⁶ are Dab;
Q³ is $^D$Leu;
Q⁴ is Leu;
Q⁷ is Thr;
for a linker L consisting of k=3 single elements L being connected in either direction from the carbonyl (C=O) point of attachment to the nitrogen (N) of the next element,
L¹ is Dab;
L² is Thr;
L³ is Dab;
said linker L being connected with module B from the carbonyl (C=O) point of attachment of $L^k$ to the α-nitrogen (N) of Q¹ and,
if k=3, being connected with module A from the carbonyl (C=O) point of attachment of P⁵ to the nitrogen (N) of L¹;
or a pharmaceutically acceptable salt thereof.

In another particular embodiment (54) of the invention the elements of general formula (I) are defined as follows,
for module A,
if s=1, t=0, and u=0; and
P¹ and X¹² taken together form an interstrand linking bis(amino acid) structure based on the linkage of two L amino acid residues; following
connection of the side chain of Ac-Pen; with the side chain of Cys-NH₂; by a disulfide linkage; and/or
P² and P¹¹ taken together form an interstrand linking bis(amino acid)-structure based on the linkage of two L amino acid residues; following
connection of the side chain of Cys; hCys; or Pen; with the side chain of Cys; or Pen; by a disulfide linkage; or connection of the side chain of Dab; with the side chain of Asp; or Glu; by a lactam linkage; or $P^2$ and $P^{11}$ taken together form a salt bridge based on the electrostatic interaction between the side chain of Asp; or Glu; at $P^2$ and the side chain of Lys; or Dab; at $P^{11}$; or the side chain of Dab at $P^2$ and the side chain of Asp; or Glu; at $P^{11}$; and/or $P^4$ and $P^9$ taken together form an interstrand linking bis (amino acid) structure based on the linkage of two L amino acid residues; following connection of the side chain of Cys; or Pen; with the side chain of Cys; or Pen; by a disulfide linkage; or connection of the side chain of Dab; with the side chain of Asp; by a lactam linkage; or $P^4$ and $P^9$ taken together form a salt bridge based on the electrostatic interaction between the side chain of Glu; at $P^4$ and the side chain of Dap; at $P^9$; or the side chain of Dab; or Lys; at $P^4$ and the side chain of Asp; or Glu; at $P^9$;

$P^1$ is Val; Ac-Val; NMeVal; HOVal; Ac-$^D$Val; Prop-Val; Nle; Ac-Nle; Tyr; Ac-Tyr; Ser-NH$_2$; pGlu; 3MeButA; or 2MePropA;

$P^2$ is Ala; Val; tBuGly; Dab; Dap; or Thr;

$P^3$ is Val; Ser; Thr; or Tyr;

$P^4$ is Dab; Dap; Ser; or Thr;

$P^5$ is Gly; or Orn;

$P^6$ is Gly; $^D$Dab; or $^D$Arg;

$P^7$ is Ser; Hse; Thr; or Dab;

$P^8$ is Trp; Val;

$P^9$ is Ser; Thr; Hse; Glu; or Gly;

$P^{10}$ is tBuGly; Val; Ile; Nva; Tyr; or Trp;

$P^{11}$ is Ala; Ser; Thr; Glu; or Dab;

$X^{12}$ is Glyol; Ser; Serol; Ser-NH$_2$; Ser-NHMe; Ser-OiPr; Thr-NH$_2$; Throl; $^D$Throl; Val-NH$_2$; Tyr-NH$_2$; Tyrol; or Dab-NH$_2$;

with the proviso that,
if $P^1$ is Ser-NH$_2$; then $X^{12}$ is Val-NH$_2$; and
if $P^3$ is Ser; Thr; or Val; then $P^1$ is Ac-Tyr; or $P^{10}$ is Tyr; or $X^{12}$ is Tyr-NH$_2$; or Tyrol; and
if $P^8$ is Val; then $P^{10}$ is Trp; and
the combined number of the amino acid residue Gly in above module A must not exceed two; and
the positions P of the amino acid residues Gly must not be in direct vicinity;

with the further proviso that,
if $P^1$ and $X^{12}$ taken together form an interstrand linkage or salt bridge, as defined above; then $P^2$ and $P^{11}$ taken together are not forming an interstrand linkage or salt bridge, as defined above;

with the further proviso that,
if linker L, as defined below, is connected with module A by a carbonyl (C=O) point of attachment of $P^5$; $P^6$; or $P^7$; then;

$P^5$; $P^6$; or $P^7$ is Glu; or $^D$Glu;

for module B consisting of single elements Q being connected in either direction from the carbonyl (C=O) point of attachment to the nitrogen (N) of the next element with the proviso that $Q^7$ is connected from the α-carbonyl (C=O) point of attachment to the ω-nitrogen (N) of $Q^1$, $Q^1$ is Dab;

$Q^2$, $Q^5$ and $Q^6$ are Dab;

$Q^3$ is $^D$Leu; or $^D$Phe;

$Q^4$ is Leu; Ile; Leu(3R)OH; Abu; Nva; Thr; or alloThr;

$Q^7$ is Thr; or Leu;

for a linker L consisting of k=1 or 3 single elements L being connected in either direction from the carbonyl (C=O) point of attachment to the nitrogen (N) of the next element, if k=1,
$L^1$ is $^D$Dab;

if k=3,
$L^1$ is Dab; or NMeDab;
$L^2$ is Thr; or Ser;
$L^3$ is Dap; or Dab;

said linker L being connected with module B from the carbonyl (C=O) point of attachment of $L^k$ to the α-nitrogen (N) of $Q^1$ and, if k=1 or 3, being connected with module A from the carbonyl (C=O) point of attachment of $P^5$; $P^6$; or $P^7$; to the nitrogen (N) of $L^1$;

or a pharmaceutically acceptable salt thereof.

In another particular embodiment (55) of the invention the elements of general formula (I) are defined as follows, for module A,
if s=1, t=1, and u=1; and
$X^{14}$ and $X^{13}$ taken together form an interstrand linking bis(amino acid)-structure or (amino acid)-(acid) structure based on the linkage of two L amino acid residues; or an amino acid residue and an acid residue; following connection of the side chain of Cys; Pen; Hcy; Ac-Cys; Ac-Pen; Ac-Hcy; or 3MPA with the side chain of Cys; Pen; Hcy; Cys-NH$_2$ Pen-NH$_2$; or Hey-NH$_2$; by a disulfide linkage; or connection of the side chain of Ac-Dab; Ac-Dap; Dab; or Dap; at $X^{14}$ with the side chain of Glu-NH$_2$; Asp-NH$_2$; Glu; or Asp; at $X^{13}$; or the side chain of Ac-Glu; Ac-Asp; Glu; or Asp; at $X^{14}$ with the side chain of Dab-NH$_2$; Dap-NH$_2$; Dab; or Dap; at $X^{13}$; by a lactam linkage; or $X^{14}$ and $X^{13}$ taken together form a salt bridge based on the electrostatic interaction between the side chain of Ac-Dab; Ac-Dap; Ac-Lys; Dab; Dap; or Lys; at $X^{14}$ and the side chain of Glu-NH$_2$; Asp-NH$_2$; Glu; or Asp; at $X^{13}$; or the side chain of Ac-Glu; Ac-Asp; Glu; or Asp; at $X^{14}$ and the side chain of Dab-NH$_2$; Dap-NH$_2$; Lys-NH$_2$; Dab; Dap; or Lys; at $X^{13}$; and/or $P^2$ and $P^{11}$ taken together form an interstrand linking bis (amino acid)-structure based on the linkage of two L amino acid residues; following connection of the side chain of Cys; Pen; or Hcy; with the side chain of Cys; Pen; or Hcy; by a disulfide linkage; or connection of the side chain of Dab; or Dap; at $P^2$ with the side chain of Glu; or Asp; at $P^{11}$; or the side chain Glu; or Asp; at $P^2$ with the side chain of Dab; or Dap; at $P^{11}$; by a lactam linkage; or $P^2$ and $P^{11}$ taken together form a salt bridge based on the electrostatic interaction between the side chain of Dab; Dap; or Lys; at $P^2$ and the side chain of Glu; or Asp; at $P^{11}$; or the side chain of Glu; or Asp; at $P^2$ and the side chain of Dab; Dap; or Lys; at $P^{11}$;

$X^{14}$ is $^D$Ser;

$P^1$ is Val;

$P^2$ is Thr;

$P^3$ is Tyr;

$P^4$ is Ser; Dap; Dap; or Gly;

$P^5$ is Orn; or Gly;

$P^6$ is $^D$Dab; $^D$Ser; $^D$Hse; $^D$Ala; or Gly;

$P^7$ is Dab; Thr; Ser; Hse; Ala; or Gly;

$P^8$ is Trp;

$P^9$ is Glu; Ala; Ser; or Hse;

$P^{10}$ is tBuGly; Val; or Ile $P^{11}$ is Ala; or Ser;

$X^{12}$ is Thr;

$X^{13}$ is $^D$Ala; or $^D$Ser;

with the proviso that,
the combined number of the amino acid residue Gly in above module A must not exceed two; and the positions P of the amino acid residues Gly must not be in direct vicinity;
with the further proviso that,
if linker L, as defined below, is connected with module A by a carbonyl (C=O) point of attachment of $P^5$; $P^6$; or $P^7$; then
$P^5$; $P^6$; or $P^7$; is Glu; or $^D$Glu;
if s=1, t=0, and u=1; and
$P^2$ and $P^{11}$ taken together form an interstrand linking bis (amino acid)-structure based on the linkage of two L amino acid residues; following
connection of the side chain of Cys; Pen; or Hcy; with the side chain of Cys; Pen; or Hcy; by a disulfide linkage; or
connection of the side chain of Dab; or Dap; with the side chain of Glu; or Asp; by a lactam linkage; or
$P^2$ and $P^{11}$ taken together form a salt bridge based on the electrostatic interaction between the side chain of Dab; Dap; or Lys; at $P^2$ and the side chain of Glu; or Asp; at $P^{11}$; or the side chain of Glu; or Asp; at $P^2$ and the side chain of Dab; Dap; or Lys; at $P^{11}$; and/or
$P^4$ and $P^9$ taken together form an interstrand linking bis (amino acid)-structure based on the linkage of two L amino acid residues; following
connection of the side chain of Cys; Pen; or Hcy; with the side chain of Cys; Pen; or Hcy; by a disulfide linkage; or
connection of the side chain of Asp; or Glu; with the side chain of Dab; or Dap; by a lactam linkage; or
$P^4$ and $P^9$ taken together form a salt bridge based on the electrostatic interaction between the side chain of Dab; Dap; or Lys; at $P^4$ and the side chain of Glu; or Asp; at $P^9$; or the side chain of Glu; or Asp; at $P^4$ and the side chain of Dab; Dap; or Lys; at $P^9$;
$X^{14}$ pGu; or $^D$pGlu;
$P^1$; $P^2$; $P^3$; $P^4$; $P^5$; $P^6$; $P^7$; $P^8$; $P^9$; $P^{10}$; and $P^{11}$ are as defined above for module A, wherein s=1, t=1, and u=1;
$X^{12}$ is Throl; Thr-NH$_2$; or Thr;
with the proviso that,
the combined number of the amino acid residue Gly in above module A must not exceed two; and
the positions P of the amino acid residues Gly must not be in direct vicinity;
with the further proviso that,
if linker L, as defined below, is connected with module A by a carbonyl (C=O) point of attachment of $P^5$; $P^6$; or $P^7$; then
$P^5$; $P^6$; or $P^7$; is Glu; or $^D$Glu;
if s=1, t=1, and u=0; and
$P^2$ and $P^{11}$ taken together form an interstrand linking bis (amino acid)-structure based on the linkage of two L amino acid residues; following
connection of the side chain of Cys; with the side chain of Cys by a disulfide linkage; and/or
$P^4$ and $P^9$ taken together form an interstrand linking bis (amino acid) structure based on the linkage of two L amino acid residues; following
connection of the side chain of Cys; with the side chain of Cys by a disulfide linkage;
$P^1$ is Val; HOVal; or Ac-Val;
$P^2$; $P^3$; $P^4$; $P^5$; $P^6$; $P^7$; $P^8$; $P^9$; $P^{10}$; $P^{11}$; and $X^{12}$ are as defined above for module A, wherein s=1, t=1, and u=1;
$X^{13}$ is Glyol;
with the proviso that,
the combined number of the amino acid residue Gly in above module A must not exceed two; and
the positions P of the amino acid residues Gly must not be in direct vicinity;
with the further proviso that,
if linker L, as defined below, is connected with module A by a carbonyl (C=O) point of attachment of $P^5$; $P^6$; or $P^7$; then
$P^5$; $P^6$; or $P^7$; is Glu; or $^D$Glu;
if s=0, t=0, and u=1; and
$P^2$ and $P^{11}$ taken together form an interstrand linking bis (amino acid)-structure based on the linkage of two L amino acid residues; following
connection of the side chain of Cys; Pen; or Hcy; with the side chain of Cys; Pen; Hcy; Cys-NH$_2$; Pen-NH$_2$; or Hcy-NH$_2$; by a disulfide linkage; or
connection of the side chain of Dab; or Dap; at $P^2$ with the side chain of Glu; Asp; Glu-NH$_2$; or Asp-NH$_2$; at $P^{11}$; or the side chain Glu; or Asp; at $P^2$ with the side chain of Dab; Dap; Dab-NH$_2$; or Dap-NH$_2$; at $P^{11}$; by a lactam linkage; or
$P^2$ and $P^{11}$ taken together form a salt bridge based on the electrostatic interaction between the side chain of Dab; Dap; or Lys; at $P^2$ and the side chain of Glu; Asp; Glu-NH$_2$; or Asp-NH$_2$; at $P^{11}$; or the side chain of Glu; or Asp; at $P^2$ and the side chain of Dab; Dap; Lys; Dab-NH$_2$; Dap-NH$_2$; or Lys-NH$_2$; at $P^{11}$; and/or
$P^4$ and $P^9$ taken together form an interstrand linking bis (amino acid)-structure based on the linkage of two L amino acid residues; following
connection of the side chain of Cys; Pen; or Hcy; with the side chain of Cys; Pen; or Hcy; by a disulfide linkage; or
connection of the side chain of Asp; or Glu; with the side chain of Dab; or Dap; by a lactam linkage; or
$P^4$ and $P^9$ taken together form a salt bridge based on the electrostatic interaction between the side chain of Dab; Dap; or Lys; at $P^4$ and the side chain of Glu; or Asp; at $P^9$; or the side chain of Glu; or Asp; at $P^4$ and the side chain of Dab; Dap; or Lys; at $P^9$;
$X^{14}$ is Ac-Dab;
$P^1$; $P^2$; $P^3$; $P^4$; $P^5$; $P^6$; $P^7$; $P^8$; $P^9$; and $P^{10}$ are as defined above for module A,
wherein s=1, t=1, and u=1;
$P^{11}$ is Dab-NH$_2$; or Dab;
with the proviso that,
the combined number of the amino acid residue Gly in above module A must not exceed two; and
the positions P of the amino acid residues Gly must not be in direct vicinity;
with the further proviso that,
if linker L, as defined below, is connected with module A by a carbonyl (C=O) point of attachment of $P^5$; $P^6$; or $P^7$; then
$P^5$; $P^6$; or $P^7$; is Glu; or $^D$Glu;
if s=1, t=0, and u=0; and
$P^2$ and $P^{11}$ taken together form an interstrand linking bis (amino acid)-structure based on the linkage of two L amino acid residues; following
connection of the side chain of Cys; Pen; or Hcy; with the side chain of Cys; Pen; or Hcy; by a disulfide linkage; or
connection of the side chain of Dab; or Dap; with the side chain of Glu; or Asp; by a lactam linkage; or
$P^2$ and $P^{11}$ taken together form a salt bridge based on the electrostatic interaction between the side chain of Dab; Dap; or Lys; at $P^2$ and the side chain of Glu; or Asp; at $P^{11}$; or the side chain of Glu; or Asp; at $P^2$ and the side chain of Dab; Dap; or Lys; at $P^{11}$; and/or
$P^4$ and $P^9$ taken together form an interstrand linking bis (amino acid)-structure based on the linkage of two L amino acid residues; following
connection of the side chain of Cys; Pen; or Hcy; with the side chain of Cys; Pen; or Hcy; by a disulfide linkage; or connection of the side chain of Asp; or Glu; with the side chain of Dab; or Dap; by a lactam linkage; or $P^4$ and $P^9$ taken together form a salt bridge based on the electrostatic interaction between the side chain of Dab; Dap; or Lys; at $P^4$ and the side chain of Glu; or Asp; at $P^9$; or the side chain of Glu; or Asp; at $P^4$ and the side chain of Dab; Dap; or Lys; at $P^9$;

$P^1$ is Val; Ac-Val; NMeVal; HOVal; Prop-Val; Ac-Nle; Ac-Tyr; Nle; or Tyr;

$P^2$; $P^3$; $P^4$; $P^5$; $P^6$; $P^7$; $P^8$; $P^9$; and $P^{10}$; are as defined above for module A, wherein s=1, t=1, and u=1;

$P^{11}$ is Ala; Ser; Thr; Glu; or Dab;

$X^{12}$ is Glyol; Ser; Serol; Ser-NH$_2$; Ser-NHMe; Thr; Thr-NH$_2$; Throl; Val-NH$_2$; or Tyrol;

with the proviso that,
   the combined number of the amino acid residue Gly in above module A must not exceed two; and
   the positions P of the amino acid residues Gly must not be in direct vicinity;

with the further proviso that,
   if linker L, as defined below, is connected with module A by a carbonyl (C=O) point of attachment of $P^5$; $P^6$; or $P^7$; then
   $P^5$; $P^6$; or $P^7$; is Glu; or $^D$Glu;

if s=0, t=0, and u=0; and $P^2$ and $P^{11}$ taken together form an interstrand linking bis(amino acid)-structure based on the linkage of two L amino acid residues; following
connection of the side chain of Cys with the side chain of Cys by a disulfide linkage; and/or $P^4$ and $P^9$ taken together form an interstrand linking bis(amino acid) structure based on the linkage of two L amino acid residues; following
connection of the side chain of Cys with the side chain of Cys by a disulfide linkage;

$P^1$ is Ac-Val; NMeVal; HOVal; or Val;

$P^2$; $P^3$; $P^4$; $P^5$; $P^6$; $P^7$; $P^8$; $P^9$; and $P^{10}$ are as defined above for module A, wherein s=1, t=1, and u=1;

$P^{11}$ is Ser-NH$_2$; or Ser;

with the proviso that,
   the combined number of the amino acid residue Gly in above module A must not exceed two; and
   the positions P of the amino acid residues Gly must not be in direct vicinity;

with the further proviso that,
   if linker L, as defined below, is connected with module A by a carbonyl (C=O) point of attachment of $P^5$; $P^6$; or $P^7$; then
   $P^5$; $P^6$; or $P^7$; is Glu; or $^D$Glu;

if s=0, t=0, and u=0; and $P^{11}$ is connected from the α-carbonyl point of attachment to the ω-nitrogen (N) of $P^2$;

$P^1$ is Ac-Val; HOVal; Ac-Leu; Ac-Ile; Ac-Nle; Ac-Phe; Val; Leu; Nle; Ile; or Phe;

$P^2$ is Orn; or Dab;

$P^3$; $P^4$; $P^5$; $P^6$; $P^7$; $P^8$; $P^9$; and $P^{10}$ are as defined above for module A, wherein s=1, t=1, and u=1;

$P^{11}$ is $^D$Thr; $^D$Hse; $^D$Asn; $^D$Gln; $^D$Val; $^D$Tyr; $^D$Dab; $^D$Orn; or $^D$Lys with the proviso that,
   the combined number of the amino acid residue Gly in above module A must not exceed two; and
   the positions P of the amino acid residues Gly must not be in direct vicinity;

with the further proviso that,
   if linker L, as defined below, is connected with module A by a carbonyl (C=O) point of attachment of $P^5$; $P^6$; or $P^7$; then
   $P^5$; $P^6$; or $P^7$; is Glu; or $^D$Glu;

for module B consisting of single elements Q being connected in either direction from the carbonyl (C=O) point of attachment to the nitrogen (N) of the next element with the proviso that $Q^7$ is connected from the α-carbonyl (C=O) point of attachment to the ω-nitrogen (N) of $Q^1$, $Q^1$ is Dab;
$Q^2$, $Q^5$ and $Q^6$ are Dab;
$Q^3$ is $^D$Leu;
$Q^4$ is Leu;
$Q^7$ is Thr;

for a linker L consisting of k=3 single elements L being connected in either direction from the carbonyl (C=O) point of attachment to the nitrogen (N) of the next element, $L^1$ is Dab;
$L^2$ is Thr;
$L^3$ is Dap; or Dab;

said linker L being connected with module B from the carbonyl (C=O) point of attachment of $L^k$ to the α-nitrogen (N) of $Q^1$ and, if k=3, being connected with module A from the carbonyl (C=O) point of attachment of $P^5$ to the nitrogen (N) of $L^1$;

or a pharmaceutically acceptable salt thereof.

In another particular embodiment (56) of the invention the elements of general formula (I) are defined as follows, for module A, if s=1, t=1, and u=1; and $X^{14}$ and $X^{13}$ taken together form an interstrand linking bis(amino acid)-structure based on the linkage of two L amino acid residues; following
connection of the side chain of Ac-Cys; or 3MPA with the side chain of Cys-NH$_2$ by a disulfide linkage; or
connection of the side chain of Ac-Dab; at $X^{14}$ with the side chain of Glu-NH$_2$; at $X^{13}$; by a lactam linkage; or $X^{14}$ and $X^{13}$ taken together form a salt bridge based on the electrostatic interaction between the side chain of Ac-Dab at $X^{14}$ and the side chain of Glu-NH$_2$ at $X^{13}$; or the side chain of Ac-Glu at $X^{14}$ and the side chain of Dab-NH$_2$ at $X^{13}$;

and/or $P^2$ and $P^{11}$ taken together form an interstrand linking bis(amino acid)-structure based on the linkage of two L amino acid residues; following
connection of the side chain of Cys; with the side chain of Cys by a disulfide linkage; or $P^2$ and $P^{11}$ taken together form a salt bridge based on the electrostatic interaction between the side chain of Dab; at $P^2$ and the side chain of Glu; at $P^{11}$;

$X^1$ is $^D$Ser;
$P^1$ is Val;
$P^2$ is Thr;
$P^3$ is Tyr;
$P^4$ is Ser;
$P^6$ is $^D$Dab;
$P^7$ is Dab;
$P^8$ is Trp;
$P^9$ is Glu;
$P^{10}$ is tBuGly;
$P^{11}$ is Ala;
$X^{12}$ is Thr;
$X^{13}$ is $^D$Ala; or $^D$Ser;

with the proviso that,
   if linker L, as defined below, is connected with module A by a carbonyl (C=O) point of attachment of $P^5$; then
   $P^5$ is Glu;

for module B consisting of single elements Q being connected in either direction from the carbonyl (C=O) point of attachment to the nitrogen (N) of the next element with the proviso that $Q^7$ is connected from the α-carbonyl (C=O) point of attachment to the ω-nitrogen (N) of $Q^1$,
$Q^1$ is Dab;
$Q^2$, $Q^5$ and $Q^6$ are Dab;
$Q^3$ is $^D$Leu;
$Q^4$ is Leu;
$Q^7$ is Thr;
for a linker L consisting of k=3 single elements L being connected in either direction from the carbonyl (C=O) point of attachment to the nitrogen (N) of the next element,
$L^1$ is Dab;
$L^2$ is Thr;
$L^3$ is Dap;
said linker L being connected with module B from the carbonyl (C=O) point of attachment of $L^k$ to the α-nitrogen (N) of $Q^1$ and,
if k=3, being connected with module A from the carbonyl (C=O) point of attachment of $P^5$ to the nitrogen (N) of $L^1$;
or a pharmaceutically acceptable salt thereof.

In another particular embodiment (57) of the invention the elements of general formula (I) are defined as follows,
for module A,
if s=1, t=0, and u=0; and
$P^2$ and $P^{11}$ taken together form an interstrand linking bis (amino acid)-structure based on the linkage of two L amino acid residues; following
connection of the side chain of Cys; or Pen; with the side chain of Cys; by a disulfide linkage; or
connection of the side chain of Dab; with the side chain of Asp; or Glu; by a lactam linkage; and/or
$P^4$ and $P^9$ taken together form an interstrand linking bis (amino acid) structure based on the linkage of two L amino acid residues; following
connection of the side chain of Cys; with the side chain of Cys; or Pen; by a disulfide linkage; or
connection of the side chain of Dab; with the side chain of Asp; by a lactam linkage; or
$P^4$ and $P^9$ taken together form a salt bridge based on the electrostatic interaction between the side chain of Dab; or Lys; at $P^4$ and the side chain of Glu; at $P^9$;
$P^1$ is Val; Ac-Val; NMeVal; HOVal; Prop-Val; Ac-Nle; or Ac-Tyr;
$P^2$ is Ala; Val; or Thr;
$P^3$ is Val; or Tyr;
$P^4$ is Dab; Dap; or Ser;
$P^5$ is Gly; or Orn;
$P^6$ is $^D$Dab;
$P^7$ is Ser; Hse; Thr; or Dab;
$P^8$ is Trp;
$P^9$ is Ser; Hse; or Glu;
$P^{10}$ is tBuGly; Val; or Ile;
$P^{11}$ is Ala; Ser; Thr; Glu; or Dab;
$X^{12}$ is Glyol; Ser; Serol; Ser-NH$_2$; Ser-NHMe; Thr-NH$_2$; Throl; Val-NH$_2$; or Tyrol;
with the proviso that,
  if $P^3$ is Val; then $P^1$ is Ac-Tyr; or $X^{12}$ is Tyrol;
with the further proviso that,
  if $P^1$ and $X^{12}$ taken together form an interstrand linkage or salt bridge, as defined above; then $P^2$ and $P^{11}$ taken together are not forming an interstrand linkage or salt bridge, as defined above;
with the further proviso that,
  if linker L, as defined below, is connected with module A by a carbonyl (C=O) point of attachment of $P^5$; $P^6$; or $P^7$; then;
  $P^5$; or $P^7$ is Glu; or $P^6$ is $^D$Glu;
for module B consisting of single elements Q being connected in either direction from the carbonyl (C=O) point of attachment to the nitrogen (N) of the next element with the proviso that $Q^7$ is connected from the α-carbonyl (C=O) point of attachment to the ω-nitrogen (N) of $Q^1$,
$Q^1$ is Dab;
$Q^2$, $Q^5$ and $Q^6$ are Dab;
$Q^3$ is $^D$Leu;
$Q^4$ is Leu; Ile; Leu(3R)OH; Abu; Nva; Thr; or alloThr;
$Q^7$ is Thr;
for a linker L consisting of k=3 single elements L being connected in either direction from the carbonyl (C=O) point of attachment to the nitrogen (N) of the next element,
$L^1$ is Dab;
$L^2$ is Thr; or Ser;
$L^3$ is Dap; or Dab;
said linker L being connected with module B from the carbonyl (C=O) point of attachment of $L^k$ to the α-nitrogen (N) of $Q^1$ and,
if k=3, being connected with module A from the carbonyl (C=O) point of attachment of $P^5$; $P^6$; or $P^7$; to the nitrogen (N) of $L^1$;
or a pharmaceutically acceptable salt thereof.

In another particular embodiment (58) of the invention the elements of general formula (I) are defined as follows,
for module A,
if s=1, t=0, and u=0; and
$P^2$ and $P^{11}$ taken together form an interstrand linking bis (amino acid)-structure based on the linkage of two L amino acid residues; following
connection of the side chain of Cys; with the side chain of Cys; by a disulfide linkage; or
$P^4$ and $P^9$ taken together form an interstrand linking bis (amino acid) structure based on the linkage of two L amino acid residues; following
connection of the side chain of Cys; with the side chain of Cys; or Pen; by a disulfide linkage; or
$P^4$ and $P^9$ taken together form a salt bridge based on the electrostatic interaction between the side chain of Dab at $P^4$ and the side chain of Glu; at $P^9$;
$P^1$ is Val; Ac-Val; NMeVal; HOVal; Ac-Nle; or Ac-Tyr;
$P^2$ is Thr;
$P^3$ is Val; Ser; or Tyr;
$P^4$ is Dab; Dap; Thr; or Ser;
$P^5$ is Orn;
$P^6$ is $^D$Dab;
$P^7$ is Ser; Hse; Thr; or Dab;
$P^8$ is Trp;
$P^9$ is Ser; Hse; or Glu;
$P^{10}$ is tBuGly; Val; or Ile;
$P^{11}$ is Ala;
$X^{12}$ is Ser; Serol; Ser-NH$_2$; Thr-NH$_2$; Throl; Tyr-NH$_2$; or Tyrol;
with the proviso that,
  if $P^3$ is Ser; or Val; then $P^1$ is Ac-Tyr; or $X^{12}$ is Tyr-NH$_2$; or Tyrol;
with the further proviso that,
  if linker L, as defined below, is connected with module A by a carbonyl (C=O) point of attachment of $P^5$; or $P^6$; then;
  $P^5$; is Glu; or $P^6$ is $^D$Glu;
for module B consisting of single elements Q being connected in either direction from the carbonyl (C=O) point of attachment to the nitrogen (N) of the next element with the proviso that $Q^7$ is connected from the α-carbonyl (C=O) point of attachment to the ω-nitrogen (N) of $Q^1$,
$Q^1$ is Dab;
$Q^2$, $Q^5$ and $Q^6$ are Dab;
$Q^3$ is $^D$Leu;
$Q^4$ is Leu; Ile; Abu; or Thr;
$Q^7$ is Thr;
for a linker L consisting of k=3 single elements L being connected in either direction from the carbonyl (C=O) point of attachment to the nitrogen (N) of the next element,
$L^1$ is Dab;
$L^2$ is Thr; or Ser;
$L^3$ is Dap; or Dab;
said linker L being connected with module B from the carbonyl (C=O) point of attachment of $L^k$ to the α-nitrogen (N) of $Q^1$ and,
if k=3, being connected with module A from the carbonyl (C=O) point of attachment of $P^5$; or $P^6$; to the nitrogen (N) of $L^1$;
or a pharmaceutically acceptable salt thereof.

In another particular embodiment (59) of the invention the elements of general formula (I) are defined as follows,
for module A,
if s=1, t=0, and u=0; and
$P^2$ and $P^{11}$ taken together form an interstrand linking bis (amino acid)-structure based on the linkage of two L amino acid residues; following
connection of the side chain of Cys; with the side chain of Cys; by a disulfide linkage; or
$P^4$ and $P^9$ taken together form an interstrand linking bis (amino acid) structure based on the linkage of two L amino acid residues; following
connection of the side chain of Cys; with the side chain of Cys; or Pen; by a disulfide linkage; or
$P^4$ and $P^9$ taken together form a salt bridge based on the electrostatic interaction between the side chain of Dab at $P^4$ and the side chain of Glu; at $P^9$;
$P^1$ is Val; Ac-Val; NMeVal; HOVal; Ac-Nle; or Ac-Tyr;
$P^2$ is Thr;
$P^3$ is Val; Ser; or Tyr;
$P^4$ is Dab; or Ser;
$P^5$ is Orn;
$P^6$ is $^D$Dab;
$P^7$ is Ser; Hse; Thr; or Dab;
$P^8$ is Trp;
$P^9$ is Ser; Hse; or Glu;
$P^{10}$ is Val; or Ile;
$P^{11}$ is Ala;
$X^{12}$ is Ser; Ser-NH$_2$; Thr-NH$_2$; Tyrol; or Tyr-NH$_2$;
with the proviso that,
    if $P^3$ is Ser; or Val; then $P^1$ is Ac-Tyr; or $X^{12}$ is Tyrol; or Tyr-NH$_2$;
with the further proviso that,
    if $P^7$ is Dab; then $P^4$ is Ser and $Q^4$ of module B is Abu; or Thr;
with the further proviso that,
    if linker L, as defined below, is connected with module A by a carbonyl (C=O) point of attachment of $P^5$; or $P^6$; then;
        $P^5$; is Glu; or $P^6$ is $^D$Glu;
for module B consisting of single elements Q being connected in either direction from the carbonyl (C=O) point of attachment to the nitrogen (N) of the next element with the proviso that $Q^7$ is connected from the α-carbonyl (C=O) point of attachment to the ω-nitrogen (N) of $Q^1$,
$Q^1$ is Dab;
$Q^2$, $Q^5$ and $Q^6$ are Dab;
$Q^3$ is $^D$Leu;
$Q^4$ is Leu; Ile; Abu; or Thr;
$Q^7$ is Thr;
for a linker L consisting of k=3 single elements L being connected in either direction from the carbonyl (C=O) point of attachment to the nitrogen (N) of the next element,
$L^1$ is Dab;
$L^2$ is Thr; or Ser;
$L^3$ is Dap; or Dab;
said linker L being connected with module B from the carbonyl (C=O) point of attachment of $L^k$ to the α-nitrogen (N) of $Q^1$ and,
if k=3, being connected with module A from the carbonyl (C=O) point of attachment of $P^5$; or $P^6$; to the nitrogen (N) of $L^1$;
or a pharmaceutically acceptable salt thereof.

Hereinafter follows a list of abbreviations, corresponding to ly adopted usual practice, of amino acids, amino alcohols, hydroxy acids, and acids which, or the residues of which, are suitable for the purposes of the present invention and referred to in this document.

In spite of this specific determination of amino acids, amino alcohols, hydroxy acids, and acids, it is noted that, for a person skilled in the art, it is obvious that derivatives of these amino acids, amino alcohols, hydroxy acids, and acids, resembling alike structural and physico-chemical properties, lead to functional analogs with similar biological activity, and therefore still form part of the gist of this invention.

Ala L-Alanine
Arg L-Arginine
Asn L-Asparagine
Asp L-Aspartic acid
Cit L-Citrulline
Cys L-Cysteine
Gln L-Glutamine
Glu L-Glutamic acid
Gly Glycine
His L-Histidine
Ile L-Isoleucine
Leu L-Leucine
Lys L-Lysine
Met L-Methionine
Orn L-Ornithine
Phe L-Phenylalanine
Ser L-Serine
Thr L-Threonine
Trp L-Tryptophan
Tyr L-Tyrosine
Val L-Valine
Abu (S)-2-aminobutanoic acid
Abu(4N$_3$) (S)-2-amino-4-azidobutanoic acid
Agp (S)-2-amino-3-guanidinopropanoic acid
Ala(tBu) (S)-2-amino-4,4-dimethylpentanoic acid
Ala(4butoxyPhUr) (S)-2-amino-3-(3-(4-butoxyphenyl) ureido)propanoic acid
Ala(cHex) (S)-2-amino-3-cyclohexylpropanoic acid
Ala(cPr) (S)-2-amino-3-cyclopropylpropanoic acid
Ala(iPrUr) (S)-2-amino-3-(3-isopropylureido)propanoic acid
Ala(2ClPhUr) (S)-2-amino-3-(3-(2-chlorophenyl)ureido) propanoic acid
Ala(4ClPhUr) (S)-2-amino-3-(3-(4-chlorophenyl)ureido) propanoic acid
Ala(2Furyl) (S)-2-amino-3-(furan-2-yl)propanoic acid
Ala(3Furyl) (S)-2-amino-3-(furan-3-yl)propanoic acid
Ala(1Im) (S)-2-amino-3-(1H-imidazol-1-yl)propanoic acid Ala(2Im) (S)-2-amino-3-(1H-imidazol-2-yl)propanoic acid
Ala(Ppz) (S)-2-amino-3-(piperazin-1-yl)propanoic acid
Ala(cPr) (S)-2-amino-3-cyclopropylpropanoic acid
Ala(Pyrazinyl) (S)-2-amino-3-(pyrazin-2-yl)propanoic acid
Ala(1Pyrazolyl) (S)-2-amino-3-(1H-pyrazol-1-yl)propanoic acid
Ala(3Pyrazolyl) (S)-2-amino-3-(1H-pyrazol-3-yl)propanoic acid
Ala(2Pyrimidin) (S)-2-amino-3-(pyrimidin-2-yl)propanoic acid
Ala(4Pyrimidin) (S)-2-amino-3-(pyrimidin-4-yl)propanoic acid
Ala(5Pyrimidin) (S)-2-amino-3-(pyrimidin-5-yl)propanoic acid
Ala(3PyrMeUr) (S)-2-amino-3-(3-(pyridin-3-ylmethyl)ureido)propanoic acid
Ala(2Quin) (S)-2-amino-3-(quinolin-2-yl)propanoic acid
Ala(3Quin) (S)-2-amino-3-(quinolin-3-yl)propanoic acid
Ala(4Quin) (S)-2-amino-3-(quinolin-4-yl)propanoic acid
Alb (S)-2-amino-3-ureidopropanoic acid
tBuGly (S)-2-amino-3,3-dimethylbutanoic acid
Bbta (S)-2-amino-3-(1-benzothiophen-3-yl)propanoic acid
Bip (S)-2-amino-3-(4-biphenylyl)propanoic acid
Cpa (S)-2-amino-3-cyclopentylpropanoic acid
Cha (S)-2-amino-3-cyclohexylpropanoic acid
Cpg (S)-2-amino-2-cyclopentylacetic acid
Chg (S)-2-amino-2-cyclohexylacetic acid
Dab (S)-2,4-diaminobutanoic acid
Dab(Ac) (S)-4-acetamido-2-aminobutanoic acid
Dab(cPr) (S)-2-amino-4-(cyclopropylamino)butanoic acid
Dab(iPr) (S)-2-amino-4-(isopropylamino)butanoic acid
Dab(Me) (S)-2-amino-4-(methylamino)butanoic acid
Dab(2PyrMe) (S)-2-amino-4-(pyridin-2-ylmethylamino)butanoic acid
Dab(Arg) (S)-2-amino-4-((S)-2-amino-5-guanidino-pentanamido)butanoic acid
Dap (S)-2,3-diaminopropanoic acid
Dap(Ac) (S)-3-acetamido-2-aminopropanoic acid
Dap(AcThr) (S)-3-((2S,3R)-2-acetamido-3-hydroxybutanamido)-2-aminopropanoic acid
Dap(cPr) (S)-2-amino-3-(cyclopropylamino)propanoic acid
Dap(iPr) (S)-2-amino-3-(isopropylamino)propanoic acid
Dap(MeSO$_2$) (S)-2-amino-3-(methylsulfonamido)propanoic acid
Dap(2,3-OHpropionyl) (2S)-2-amino-3-(2,3-dihydroxypropanamido)propanoic acid
Dap(Thr) (S)-2-amino-3-((2S,3R)-2-amino-3-hydroxybutanamido)-propanoic acid
Dap(Glu) (S)-4-amino-5-((S)-2-amino-2-carboxyethylamino)-5-oxo-pentanoic acid
Dab(Trp) (S)-2-amino-4-((2S)-2-amino-3-(1H-indol-3-yl)propanamido)-butanoic acid
Gly(cPr) (S)-2-amino-2-cyclopropylacetic acid
hAla(1lm) (S)-2-amino-3-(1H-imidazol-1-yl)-butanoic acid
hAla(2lm) (S)-2-amino-3-(1H-imidazol-2-yl)-butanoic acid
hArg (S)-2-amino-6-guanidinohexanoic acid
hCha (S)-2-amino-4-cyclohexylbutanoic acid
hCys, hCy, Hcy (S)-2-amino-4-mercaptobutanoic acid
hGlu (S)-2-amino-hexanedioic acid
hHis (S)-2-amino-4-(1H-imidazol-5-yl)butanoic acid
hLeu (S)-2-amino-5-methylhexanoic acid
hLys (S)-2,7-diaminoheptanoic acid
h2Pal (S)-2-amino-4-(pyridine-2-yl)-butanoic acid
h3Pal (S)-2-amino-4-(pyridine-3-yl)-butanoic acid
h4Pal (S)-2-amino-4-(pyridine-4-yl)-butanoic acid
hSer, Hse (S)-2-amino-4-hydroxybutanoic acid
hTrp (S)-2-amino-4-(1H-indol-3-yl)butanoic acid
hTyr (S)-2-amino-4-(4-hydroxyphenyl)butanoic acid
His(Me) (S)-2-amino-3-(1-methyl-1H-imidazol-5-yl)propanoic acid
His(Bn) (S)-2-amino-3-(1-benzyl-1H-imidazol-5-yl)propanoic acid
Leu(3R)OH (2S,3R)-2-amino-3-hydroxy-4-methylpentanoic acid
Lys(Bz) (S)-2-amino-6-benzamidohexanoic acid
Lys(Me) (S)-2-amino-6-(methylamino)hexanoic acid
Lys(Nic) (S)-2-amino-6-(nicotinamido)hexanoic acid
Met(O$_2$) (S)-2-amino-4-(methylsulfonyl)butanoic acid
1Nal (S)-2-amino-3-naphthalen-1-ylpropanoic acid
2Nal (S)-2-amino-3-naphthalen-2-ylpropanoic acid
Nle (S)-2-amino-hexanoic acid
Nle(6OBn) (S)-2-amino-6-(benzyloxy)hexanoic acid
NMeGly N-Methylglycine
NMeAla L-N-Methylalanine
NMeAbu N-Methyl-(S)-2-aminobutanoic acid
NMeAsp L-N-Methylaspartic acid
NMeDap (S)-2-methylamino-3-aminopropanoic acid
NMeGlu L-N-Methylglutamic acid
NMehGlu (S)2methylamino-hexanedioic acid
NMeVal L-N-Methylvaline
NMeNva L-N-Norvaline
NMeLeu L-N-Methylleucine
NMeIle L-N-Methylisoleucine
NMeNle L-N-Methylnorleucine
NMeAla L-N-Methylalanine
NMeAbu (S)-2-methylaminobutanoic acid
NMeTrp L-N-Methyltryptophan
NMeTyr L-N-Methyltyrosine
NMePhe L-N-Methylphenylalanine
NMeCys L-N-Methylcysteine
NMehCy (S)-2-methylamino-4-mercaptobutanoic acid
NMePen (S)-2-methylamino-3-methyl-3-sulfanyl-butanoic acid
NMeDab (S)-2-methylamino-4-aminobutanoic acid
NMeOrn L-N-Methylornithine
NMeLys L-N-Methyllysine
Nva (S)-2-aminopentanoic acid
OctG (S)-2-aminodecanoic acid
Orn(Ac) (S)-5-acetamido-2-aminopentanoic acid
Orn(cPr) (S)-2-amino-5-(cyclopropylamino)pentanoic acid
Orn(iPr) (S)-2-amino-5-(isopropylamino)pentanoic acid
2Pal (S)-2-amino-3-(pyridine-2-yl) propionic acid
3Pal (S)-2-amino-3-(pyridine-3-yl)propionic acid
4Pal (S)-2-amino-3-(pyridine-4-yl)propionic acid
Pen (R)-2-amino-3-methyl-3-sulfanyl-butanoic acid
pGlu L-pyroglutamic acid, (S)-2-pyrrolidone-5-carboxylic acid
Phe(2Cl) (S)-2-amino-3-(2-chlorophenyl)propanoic acid
Phe(3Cl) (S)-2-amino-3-(3-chlorophenyl)propanoic acid
Phe(4Cl) (S)-2-amino-3-(4-chlorophenyl)propanoic acid
Phe(3,4Cl$_2$) (S)-2-amino-3-(3,4-dichlorophenyl)propanoic acid
Phe(2F) (S)-2-amino-3-(2-fluorophenyl)propanoic acid
Phe(3F) (S)-2-amino-3-(3-fluorophenyl)propanoic acid
Phe(4F) (S)-2-amino-3-(4-fluorophenyl)propanoic acid
Phe(3,4F$_2$) (S)-2-amino-3-(3,4-difluorophenyl)propanoic acid
Phe(3CN) (S)-2-amino-3-(3-cyanophenyl)propanoic acid
Phe(4CN) (S)-2-amino-3-(4-cyanophenyl)propanoic acid
Phe(2CF$_3$) (S)-2-amino-3-(2-(trifluoromethyl)phenyl)propanoic acid
Phe(3CF$_3$) (S)-2-amino-3-(3-(trifluoromethyl)phenyl)propanoic acid Phe(4CF₃) (S)-2-amino-3-(4-(trifluoromethyl)phenyl)propanoic acid
Phe(3,4(CF₃)₂) (S)-2-amino-3-(3,4-bis(trifluoromethyl)phenyl)propanoic acid
Phe(4COOMe) (S)-2-amino-3-(4-(methoxycarbonyl)phenyl)propanoic acid
Phe(4NH₂) (S)-2-amino-3-(4-aminophenyl)propanoic acid
Phe(3OH) (S)-2-amino-3-(3-hydroxyphenyl)propanoic acid
Phg (S)-2-amino-2-phenylacetic acid
Pip 4-aminopiperidine-4-carboxylic acid
Pra L-propargylglycine
Sar; NMeGly N-Methylglycine
Ser(Bn) (S)-2-amino-3-(benzyloxy)propanoic acid
Ser(Me) (S)-2-amino-3-methoxy-propanoic acid
Thi (S)-2-amino-3-(thiophen-2-yl)propanoic acid
alloThr (2S,3S)-2-amino-3-hydroxybutanoic acid
Thr(Bn) (2S,3R)-2-amino-3-(benzyloxy)butanoic acid
Thr(Me) (2S,3R)-2-amino-3-(methyloxy)butanoic acid
Trp(7Aza) (S)-2-amino-3-(1H-pyrrolo[2,3-b]pyridin-3-yl)propanoic acid
Trp(5Br) (S)-2-amino-3-(5-bromo-1H-indol-3-yl)propanoic acid
Trp(6Br) (S)-2-amino-3-(6-bromo-1H-indol-3-yl)propanoic acid
Trp(6CF₃) (S)-2-amino-3-(6-(trifluoromethyl)-1H-indol-3-yl)propanoic acid
Trp(5Cl) (S)-2-amino-3-(5-chloro-1H-indol-3-yl)propanoic acid
Trp(6Cl) (S)-2-amino-3-(6-chloro-1H-indol-3-yl)propanoic acid
Trp(5,6Cl) (S)-2-amino-3-(5,6-dichloro-1H-indol-3-yl)propanoic acid
Trp(5OH) (S)-2-amino-3-(5-hydroxy-1H-indol-3-yl)propanoic acid
Tyr(Bn) (S)-2-amino-3-(4-(benzyloxy)phenyl)propanoic acid
Tyr(Me) (S)-2-amino-3-(4-methoxyphenyl)propanoic acid
Tyr(Ph) (S)-2-amino-3-(4-phenoxyphenyl)propanoic acid
Tyr(4OHPh) (S)-2-amino-3-[4-(4-hydroxyphenoxy)phenyl]propanoic acid
Tyr(3F) (S)-2-amino-3-(3-fluoro-4-hydroxyphenyl)propanoic acid
Tza (S)-2-amino-3-(thiazol-4-yl)propanoic acid
Glyol 2-amino-ethanol
Serol 2-amino-propane-1,3-diol
Throl (2R,3R)-2-amino-butane-1,3-diol
Tyrol (2S)-2-amino-3-(4-hydroxyphenyl)-propane-1-ol
HOVal (S)-2-hydroxy-3-methyl-butanoic acid
3MPA 3-mercaptopropanoic acid
3MeButA 3-methyl-butanoic acid
2MePropA 2-methyl-propanoic acid
6MeHeptA 6-methyl-heptanoic acid The abbreviation of D-isomers, e.g. $^D$Lys corresponds to the epimer at the 2-position of the appropriate amino acid described above. Same applies for the generic descriptions of the amino acids, e.g. AA1 which has AA1$^D$ as the corresponding α-epimer.

The abbreviation "Ac-" followed by an abbreviation of an amino acid, or amino acid residue, as listed above, corresponds to the N-acetylated amino acid, or amino acid residue, like, for example:
Ac-Trp N-acetyl-L-tryptophan
((S)-2-acetylamino-3-(1H-indol-3-yl)propanoic acid The abbreviation "Prop-" followed by an abbreviation of an amino acid, or amino acid residue, as listed above, corresponds to the N-acetylated amino acid, or amino acid residue, like, for example:

Prop-Val N-propanoyl-L-valine
(S)-2-propanoylamino-3-methyl-butanoic acid

The abbreviation of an amino acid, or amino acid residue, as listed above, followed by "—NH₂" corresponds to the C-terminal amidated amino acid, or amino acid residue, like, for example:
Cys-N H₂ (R)-2-amino-3-mercaptopropanamide The abbreviation of an amino acid, or amino acid residue, as listed above, followed by "—NHMe" corresponds to the C-terminal amidated amino acid, or amino acid residue, like, for example:
Ser-NHMe (S)-2-amino-3-hydroxy-N-methylpropanamide
(S)-2-amino-3-hydroxy-propanoic acid methylamide The abbreviation of an amino acid, or amino acid residue, as listed above, followed by "—OiPr" corresponds to the C-terminal ester of an amino acid, or amino acid residue, like, for example:
Ser-OiPr (S)-2-amino-3-hydroxy-propanoic acid isopropyl ester
(S)-isopropyl 2-amino-3-hydroxypropanoate In a preferred embodiment (60) of the invention the β-hairpin peptidomimetics of formula (I) are selected from the group consisting of
Ex. 1 to 385, the sequences of which are shown in Table 1;
or a pharmaceutically acceptable salt thereof.

In a more preferred embodiment (61) of the invention the β-hairpin peptidomimetics of formula (I) are selected from the group consisting of
Ex. 3, 41, 72, 73, 79, 84, 88, 92, 96, 99, 100, 103-117, 119, 120, 126, 128, 129, 132-145, 147, 148, 150, 151, 153, 154, 156, 159, 161, 166, 168, 172, 185, 193, 199, 201-204, 206, 219, 221-226, 232, 233, 250, 276, 281, 282, 289, 297, 310, 334, 340, 341, 350, t351, 359, 365, 375, 379, the sequences of which are shown in Table 1;
or a pharmaceutically acceptable salt thereof.

In another even more preferred embodiment (62) of the invention the β-hairpin peptidomimetics of formula (I) are selected from the group consisting of Ex. 39, 41-43, 58, 65, 92, 96, 100, 113-116, 128, 132, 137, 139, 143, 150, 161, 188, 215, 219, 257-261, 266, 270, 274-284, 289, 293-300, 306, 309-311, 331-341, 343-345, 350, 351, 358, 359, 361-365, 370, 375, 376, 379, 380-383, the sequences of which are shown in Table 1;
or a pharmaceutically acceptable salt thereof.

In a particular preferred embodiment (63) of the invention the β-hairpin peptidomimetics of formula (I) are selected from the group consisting of Ex. 1-39, 41-68, 72-231, 251-366, 384 and 385, the sequences of which are shown in Table 1;
or a pharmaceutically acceptable salt thereof.

In a more particular preferred embodiment (64) of the invention the β-hairpin peptidomimetics of formula (I) are selected from the group consisting of Ex. 1-5, 39, 41-56, 58-68, 72-124, 127-217, 219-231, 251-365, 366 and 385, the sequences of which are shown in Table 1;
or a pharmaceutically acceptable salt thereof.

In a most particular preferred embodiment (65) of the invention the β-hairpin peptidomimetics of formula (I) are selected from the group consisting of Ex. 39, 100, 113, 114, 115, 128, 132, 137, 260, 276-279, 281, 282, 289, 293, 297, 306, 310, 334, 340, 341, 350, and 351, the sequences of which are shown in Table 1;
or a pharmaceutically acceptable salt thereof.

In a preferred embodiment (66) of the invention the β-hairpin peptidomimetics of general formula (I) are selected from the group consisting of Ex. 1 to 266, the sequences of which are shown in Table 1;
or a pharmaceutically acceptable salt thereof.

In another preferred embodiment (67) of the invention the β-hairpin peptidomimetics of general formula (I) are selected from the group consisting of Ex. 3, 41, 72, 73, 79, 84, 88, 92, 96, 99, 100, 103-117, 119, 120, 126, 128, 129, 132-145, 147, 148, 150, 151, 153, 154, 156, 159, 161, 166, 168, 172, 185, 193, 199, 201-204, 206, 219, 221-226, 232, 233 and 250, the sequences of which are shown in Table 1;
or a pharmaceutically acceptable salt thereof.

In another preferred embodiment (68) of the invention the β-hairpin peptidomimetics of general formula (I) are selected from the group consisting of Ex. 39, 41-43, 58, 65, 92, 96, 100, 113-116, 128, 132, 137, 139, 143, 150, 161, 188, 215, 219, 257-261, and 266, the sequences of which are shown in Table 1;
or a pharmaceutically acceptable salt thereof.

In another preferred embodiment (69) of the invention the β-hairpin peptidomimetics of general formula (I) are selected from the group consisting of Ex. 39, 100, 113, 114, 115, 128, and 132, the sequences of which are shown in Table 1;
or a pharmaceutically acceptable salt thereof.

In accordance with the present invention these β-hairpin peptidomimetics can be prepared by the process as described herein below.

The described process is based on an on-resin fragment coupling strategy and comprises:

(I) generating a fully protected peptide fragment (module B and linker L) comprising amino acid residues of module B and linker L, as defined above,
if coupling to the solid support of the amino acid residue at position $Q^7$ of module B, as defined above, is via a hydroxyl group of said amino acid residue, by performing steps comprising:
(a) coupling an appropriately functionalized solid support with an appropriately N-protected derivative of that amino acid which in the desired end-product is at position $Q^7$ of module B, as defined above, any functional group which may be present in said N-protected amino acid derivative being likewise appropriately protected;
(b) removing the N-protecting group from the product obtained in step (a);
(c) coupling the product thus obtained with an appropriately N-protected derivative of that amino acid which in the desired end-product corresponds to $Q^6$, any functional group which may be present in said N-protected amino acid derivative being likewise appropriately protected;
(d) if desired, selectively deprotecting one or several protected functional group(s) present in the molecule and appropriately substituting the reactive group(s) thus liberated by attaching one or several moieties derived from acids, amino acids or amines;
(e) further effecting steps substantially corresponding to steps (b) to (d) using appropriately N-protected derivatives of amino acids which in the desired end-product are at positions $Q^5$ to $Q^1$, any functional group(s) which may be present in said N-protected amino acid derivatives being likewise appropriately protected;
(f) if desired or required, selectively removing an N-protecting group at position $Q^1$ and a carboxyl-protecting group at position $Q^7$; and generating a macrolactam cycle, as defined above, by formation of an amide bond between the thus liberated carboxyl group at position $Q^7$ and the amino group at $Q^1$ of module B;
(g) if L is present (k=1, 2, or 3), as defined above, effecting steps substantially corresponding to steps (b) to (d) using appropriately N-protected derivatives of amino acids which in the desired end-product are at positions $L^k$ to $L^1$, any functional group(s) which may be present in said N-protected amino acid derivatives being likewise appropriately protected; and, if desired or required, following the coupling, selectively removing an N-protecting group at position $Q^1$ and a carboxyl-protecting group at position $Q^7$; and generating a macrolactam cycle, as defined above, by formation of an amide bond between the thus liberated carboxyl group at position $Q^7$ and the amino group at $Q^1$ of module B;
(h) if L is present and if desired, removing an N-protecting group at position $L^1$;
(i) if L is not present and if desired, removing an N-protecting group at position $Q^1$;
(j) detaching the product thus obtained from the solid support;
(k) if desired, selectively protecting the thus liberated hydroxyl group at position $Q^7$;
(l) if L is present, and required, removing an N-protecting group at position $L^1$; and
(m) if L is not present, and required, removing an N-protecting group at position $Q^1$;
if coupling to the solid support of the amino acid residue at position $Q^7$ of module B, as defined above, is via a carboxyl group of said amino acid residue, by performing steps comprising:
(a) coupling an appropriately functionalized solid support with an appropriately N-protected derivative of that amino acid which in the desired end-product is at position $Q^7$ of module B, as defined above, any functional group which may be present in said N-protected amino acid derivative being likewise appropriately protected;
(b) removing the N-protecting group from the product obtained in step (a);
(c) coupling the product thus obtained with an appropriately N-protected derivative of that amino acid which in the desired end-product corresponds to $Q^6$, any functional group which may be present in said N-protected amino acid derivative being likewise appropriately protected;
(d) if desired, selectively deprotecting one or several protected functional group(s) present in the molecule and appropriately substituting the reactive group(s) thus liberated by attaching one or several moieties derived from acids, amino acids or amines;
(e) further effecting steps substantially corresponding to steps (b) to (d) using appropriately N-protected derivatives of amino acids which in the desired end-product are at positions $Q^5$ to $Q^1$, any functional group(s) which may be present in said N-protected amino acid derivatives being likewise appropriately protected;
(f) if L is present (k=1, 2, or 3), as defined above, effecting steps substantially corresponding to steps (b) to (d) using appropriately N-protected derivatives of amino acids which in the desired end-product are at positions $L^k$ to $L^1$, any functional group(s) which may be present in said N-protected amino acid derivatives being likewise appropriately protected;
(g) if desired, selectively removing an N-protecting group at position $Q^1$;

(h) detaching the product thus obtained from the solid support;
(i) if desired and required, selectively removing an N-protecting group at position $Q^1$;
(j) generating a macrolactam cycle, as defined above, by formation of an amide bond between the liberated carboxyl group at position $Q^7$ and the amino group at $Q^1$ of module B;
(k) if L is present, removing an N-protecting group at position $L^1$; and
(l) if L is not present, removing an N-protecting group at position $Q^1$;

(II) generating a peptide (module A, module B and linker L) comprising residues of module A, module B and linker L, as defined above,
if s=1, t=1, and u=1;
by performing steps comprising:
(a) coupling an appropriately functionalized solid support with an appropriately N-protected derivative of that amino acid or, if desired, an appropriately N-protected derivative of that amino alcohol, which in the desired end-product is at position $X^{13}$ of module A, as defined above, any functional group which may be present in said N-protected amino acid derivative or N-protected amino alcohol derivative being likewise appropriately protected;
(b) removing the N-protecting group from the product thus obtained;
(c) coupling the product thus obtained with an appropriately N-protected derivative of that amino acid which in the desired end-product is at position $X^{12}$, any functional group which may be present in said N-protected amino acid derivative being likewise appropriately protected;
(d) if desired, selectively deprotecting one or several protected functional group(s) present in the molecule and appropriately substituting the reactive group(s) thus liberated by attaching one or several moieties derived from acids, amino acids or amines;
(e) further effecting steps substantially corresponding to steps (b) to (d) using appropriately N-protected derivatives of amino acids which in the desired end-product are at positions $P^{11}$ to $P^n$ (n=5, 6, or 7), any functional group(s) which may be present in said N-protected amino acid derivatives being likewise appropriately protected;
(f) selectively removing a carboxyl-protecting group at $P^n$ (n=5, 6, or 7); and coupling of the protected peptide fragment (module B and linker L) by formation of an amide bond between the free amino function in the peptide fragment obtained from procedure (I) and the liberated carboxyl function at $P^n$;
(g) further effecting steps substantially corresponding to steps (b) to (d) using appropriately N-protected derivatives of amino acids which in the desired end-product are at positions $P^{n-1}$ (n=5, 6, or 7) to $P^1$, any functional group(s) which may be present in said N-protected amino acid derivatives being likewise appropriately protected; and, if desired, following coupling of the amino acid, selectively deprotecting one or several protected functional group(s) present in the molecule and chemically transforming the reactive group(s) thus liberated to form an interstrand linkage(s), as defined above;
(h) further effecting steps substantially corresponding to steps (b) to (d) using an appropriately N-protected derivative of an amino acid, or if desired, an appropriately protected derivative of an acid, which in the desired end-product is at position $X^{14}$, any functional group(s) which may be present in said N-protected amino acid derivative or acid derivative, being likewise appropriately protected; and, if desired, following the coupling, selectively deprotecting one or several protected functional group(s) present in the molecule and chemically transforming the reactive group(s) thus liberated to form an interstrand linkage(s), as defined above;
(i) if desired, selectively removing the N-protecting group at position $X^{14}$, and chemically transforming the thus obtained amino function;
(j) if desired, implementing additional chemical transformations of one or more group(s) present in the molecule;
(k) detaching the product thus obtained from the solid support;
(l) if desired, implementing additional chemical transformations of one or more group(s) present in the molecule to form, for example, an interstrand linkage(s), as defined above;
(m) if desired, selectively deprotecting one or several protected functional group(s) present in the molecule and chemically transforming the reactive group(s) thus liberated to form an interstrand linkage(s), as defined above;
(n) removing any protecting groups present on functional groups of any members of the chain of residues and, if desired, any protecting group(s) which may in addition be present in the molecule;
(o) if desired, implementing additional chemical transformations of one or more reactive group(s) present in the molecule;
(p) if desired and required, implementing additional chemical transformations of two or more group(s) present in the molecule to form an interstrand linkage(s), as defined above; and
(q) if desired, converting the product thus obtained into a pharmaceutically acceptable salt or converting a pharmaceutically acceptable, or unacceptable, salt thus obtained into the corresponding free compound of formula (I) or into a different, pharmaceutically acceptable salt;

if s=1, t=0, and u=1;
by performing steps comprising:
(a) coupling an appropriately functionalized solid support with an appropriately N-protected derivative of that amino acid or, if required, an appropriately N-protected derivative of that amino alcohol, which in the desired end-product is at position $X^{12}$ of module A, as defined above, any functional group which may be present in said N-protected amino acid derivative or N-protected amino alcohol derivative being likewise appropriately protected;
(b) removing the N-protecting group from the product thus obtained;
(c) coupling the product thus obtained with an appropriately N-protected derivative of that amino acid which in the desired end-product is at position $P^{11}$, any functional group which may be present in said N-protected amino acid derivative being likewise appropriately protected;
(d) if desired, selectively deprotecting one or several protected functional group(s) present in the molecule and appropriately substituting the reactive group(s)

thus liberated by attaching one or several moieties derived from acids, amino acids or amines;

(e) further effecting steps substantially corresponding to steps (b) to (d) using appropriately N-protected derivatives of amino acids which in the desired end-product are at positions $P^{10}$ to $P''$ (n=5, 6, or 7), any functional group(s) which may be present in said N-protected amino acid derivatives being likewise appropriately protected;

(f) selectively removing a carboxyl-protecting group at $P''$ (n=5, 6, or 7); and coupling of the protected peptide fragment (module B and linker L) by formation of an amide bond between the free amino function in the peptide fragment obtained from procedure (I) and the liberated carboxyl function at $P''$;

(g) further effecting steps substantially corresponding to steps (b) to (d) using appropriately N-protected derivatives of amino acids which in the desired end-product are at positions $P^{n-1}$ (n=5, 6, or 7) to $P^1$, any functional group(s) which may be present in said N-protected amino acid derivatives being likewise appropriately protected; and, if desired, following coupling of the amino acid, selectively deprotecting one or several protected functional group(s) present in the molecule and chemically transforming the reactive group(s) thus liberated to form an interstrand linkage(s), as defined above;

(h) further effecting steps substantially corresponding to steps (b) to (d) using an appropriately N-protected derivative of an amino acid, or if desired, an appropriately protected derivative of an acid, which in the desired end-product is at position $X^{14}$, any functional group(s) which may be present in said N-protected amino acid derivative or acid derivative, being likewise appropriately protected; and, if desired, following the coupling, selectively deprotecting one or several protected functional group(s) present in the molecule and chemically transforming the reactive group(s) thus liberated to form an interstrand linkage(s), as defined above;

(i) if desired, selectively removing the N-protecting group at position $X^{14}$, and chemically transforming the thus obtained amino function;

(j) if desired, implementing additional chemical transformations of one or more group(s) present in the molecule;

(k) detaching the product thus obtained from the solid support;

(l) if desired, implementing additional chemical transformations of one or more group(s) present in the molecule to form, for example, an interstrand linkage(s), as defined above;

(m) if desired, selectively deprotecting one or several protected functional group(s) present in the molecule and chemically transforming the reactive group(s) thus liberated to form an interstrand linkage(s), as defined above;

(n) removing any protecting groups present on functional groups of any members of the chain of residues and, if desired, any protecting group(s) which may in addition be present in the molecule;

(o) if desired, implementing additional chemical transformations of one or more reactive group(s) present in the molecule;

(p) if desired and required, implementing additional chemical transformations of two or more group(s) present in the molecule to form an interstrand linkage(s), as defined above; and (q) if desired, converting the product thus obtained into a pharmaceutically acceptable salt or converting a pharmaceutically acceptable, or unacceptable, salt thus obtained into the corresponding free compound of formula (I) or into a different, pharmaceutically acceptable salt;

if s=1, t=1, and u=0;

by performing steps comprising:

(a) coupling an appropriately functionalized solid support with an appropriately N-protected derivative of that amino acid or, if desired, an appropriately N-protected derivative of that amino alcohol, which in the desired end-product is at position $X^{13}$ of module A, as defined above, any functional group which may be present in said N-protected amino acid derivative or N-protected amino alcohol derivative being likewise appropriately protected;

(b) removing the N-protecting group from the product thus obtained;

(c) coupling the product thus obtained with an appropriately N-protected derivative of that amino acid which in the desired end-product is at position $X^{12}$, any functional group which may be present in said N-protected amino acid derivative being likewise appropriately protected;

(d) if desired, selectively deprotecting one or several protected functional group(s) present in the molecule and appropriately substituting the reactive group(s) thus liberated by attaching one or several moieties derived from acids, amino acids or amines;

(e) further effecting steps substantially corresponding to steps (b) to (d) using appropriately N-protected derivatives of amino acids which in the desired end-product are at positions $P^{11}$ to $P''$ (n=5, 6, or 7), any functional group(s) which may be present in said N-protected amino acid derivatives being likewise appropriately protected;

(f) selectively removing a carboxyl-protecting group at $P''$ (n=5, 6, or 7); and coupling of the protected peptide fragment (module B and linker L) by formation of an amide bond between the free amino function in the peptide fragment obtained from procedure (I) and the liberated carboxyl function at $P''$;

(g) further effecting steps substantially corresponding to steps (b) to (d) using appropriately N-protected derivatives of amino acids which in the desired end-product are at positions $P^{n-1}$ (n=5, 6, or 7) to $P^2$, any functional group(s) which may be present in said N-protected amino acid derivatives being likewise appropriately protected; and, if desired, following coupling of the amino acid, selectively deprotecting one or several protected functional group(s) present in the molecule and chemically transforming the reactive group(s) thus liberated to form an interstrand linkage(s), as defined above;

(h) further effecting steps substantially corresponding to steps (b) to (d) using an appropriately N-protected derivative of an amino acid, or if desired, an appropriately protected derivative of a hydroxy acid, or if desired, an appropriately protected derivative of an acid, which in the desired end-product is at position $P^1$, any functional group(s) which may be present in said N-protected amino acid derivative, hydroxy acid derivative, or acid derivative, being likewise appropriately protected; and, if desired, following the coupling, selectively deprotecting one or several protected functional group(s) present in the molecule and chemically transforming the reactive group(s) thus liberated to form an interstrand linkage(s), as defined above;
(i) if desired, selectively removing the N-protecting group at position $P^1$, and chemically transforming the thus obtained amino function;
(j) if desired, implementing additional chemical transformations of one or more group(s) present in the molecule;
(k) detaching the product thus obtained from the solid support;
(l) if desired, implementing additional chemical transformations of one or more group(s) present in the molecule to form, for example, an interstrand linkage(s), as defined above;
(m) if desired, selectively deprotecting one or several protected functional group(s) present in the molecule and chemically transforming the reactive group(s) thus liberated to form an interstrand linkage(s), as defined above;
(n) removing any protecting groups present on functional groups of any members of the chain of residues and, if desired, any protecting group(s) which may in addition be present in the molecule;
(o) if desired, implementing additional chemical transformations of one or more reactive group(s) present in the molecule;
(p) if desired and required, implementing additional chemical transformations of two or more group(s) present in the molecule to form an interstrand linkage(s), as defined above; and
(q) if desired, converting the product thus obtained into a pharmaceutically acceptable salt or converting a pharmaceutically acceptable, or unacceptable, salt thus obtained into the corresponding free compound of formula (I) or into a different, pharmaceutically acceptable salt;
if s=0, t=0, and u=1;
by performing steps comprising:
(a) coupling an appropriately functionalized solid support with an appropriately N-protected derivative of that amino acid, which in the desired end-product is at position $P^{11}$ of module A, as defined above, any functional group which may be present in said N-protected amino acid derivative being likewise appropriately protected;
(b) removing the N-protecting group from the product thus obtained;
(c) coupling the product thus obtained with an appropriately N-protected derivative of that amino acid which in the desired end-product is at position $P^{10}$, any functional group which may be present in said N-protected amino acid derivative being likewise appropriately protected;
(d) if desired, selectively deprotecting one or several protected functional group(s) present in the molecule and appropriately substituting the reactive group(s) thus liberated by attaching one or several moieties derived from acids, amino acids or amines;
(e) further effecting steps substantially corresponding to steps (b) to (d) using appropriately N-protected derivatives of amino acids which in the desired end-product are at positions $P^9$ to $P''$ (n=5, 6, or 7), any functional group(s) which may be present in said N-protected amino acid derivatives being likewise appropriately protected;
(f) selectively removing a carboxyl-protecting group at $P''$ (n=5, 6, or 7); and coupling of the protected peptide fragment (module B and linker L) by formation of an amide bond between the free amino function in the peptide fragment obtained from procedure (I) and the liberated carboxyl function at $P''$;
(g) further effecting steps substantially corresponding to steps (b) to (d) using appropriately N-protected derivatives of amino acids which in the desired end-product are at positions $P^{n-1}$ (n=5, 6, or 7) to $P^1$, any functional group(s) which may be present in said N-protected amino acid derivatives being likewise appropriately protected; and, if desired, following coupling of the amino acid, selectively deprotecting one or several protected functional group(s) present in the molecule and chemically transforming the reactive group(s) thus liberated to form an interstrand linkage(s), as defined above;
(h) further effecting steps substantially corresponding to steps (b) to (d) using an appropriately N-protected derivative of an amino acid, or if desired, an appropriately protected derivative of an acid, which in the desired end-product is at position $X^{14}$, any functional group(s) which may be present in said N-protected amino acid derivative or acid derivative, being likewise appropriately protected; and, if desired, following the coupling, selectively deprotecting one or several protected functional group(s) present in the molecule and chemically transforming the reactive group(s) thus liberated to form an interstrand linkage(s), as defined above;
(i) if desired, selectively removing the N-protecting group at position $X^{14}$, and chemically transforming the thus obtained amino function;
(j) if desired, implementing additional chemical transformations of one or more group(s) present in the molecule;
(k) detaching the product thus obtained from the solid support;
(l) if desired, implementing additional chemical transformations of one or more group(s) present in the molecule to form, for example, an interstrand linkage(s), as defined above;
(m) if desired, selectively deprotecting one or several protected functional group(s) present in the molecule and chemically transforming the reactive group(s) thus liberated to form an interstrand linkage(s), as defined above;
(n) removing any protecting groups present on functional groups of any members of the chain of residues and, if desired, any protecting group(s) which may in addition be present in the molecule;
(o) if desired, implementing additional chemical transformations of one or more reactive group(s) present in the molecule;
(p) if desired and required, implementing additional chemical transformations of two or more group(s) present in the molecule to form an interstrand linkage(s), as defined above; and
(q) if desired, converting the product thus obtained into a pharmaceutically acceptable salt or converting a pharmaceutically acceptable, or unacceptable, salt thus obtained into the corresponding free compound of formula (I) or into a different, pharmaceutically acceptable salt;
if s=1, t=0, and u=0;

by performing steps comprising:
(a) coupling an appropriately functionalized solid support with an appropriately N-protected derivative of that amino acid or, if desired, an appropriately N-protected derivative of that amino alcohol, which in the desired end-product is at position $X^{12}$ of module A, as defined above, any functional group which may be present in said N-protected amino acid derivative or N-protected amino alcohol derivative being likewise appropriately protected;
(b) removing the N-protecting group from the product thus obtained;
(c) coupling the product thus obtained with an appropriately N-protected derivative of that amino acid which in the desired end-product is at position $P^{11}$, any functional group which may be present in said N-protected amino acid derivative being likewise appropriately protected;
(d) if desired, selectively deprotecting one or several protected functional group(s) present in the molecule and appropriately substituting the reactive group(s) thus liberated by attaching one or several moieties derived from acids, amino acids or amines;
(e) further effecting steps substantially corresponding to steps (b) to (d) using appropriately N-protected derivatives of amino acids which in the desired end-product are at positions $P^{10}$ to $P^n$ (n=5, 6, or 7), any functional group(s) which may be present in said N-protected amino acid derivatives being likewise appropriately protected;
(f) selectively removing a carboxyl-protecting group at $P^n$ (n=5, 6, or 7); and coupling of the protected peptide fragment (module B and linker L) by formation of an amide bond between the free amino function in the peptide fragment obtained from procedure (I) and the liberated carboxyl function at $P^n$;
(g) further effecting steps substantially corresponding to steps (b) to (d) using appropriately N-protected derivatives of amino acids which in the desired end-product are at positions $P^{n-1}$ (n=5, 6, or 7) to $P^2$, any functional group(s) which may be present in said N-protected amino acid derivatives being likewise appropriately protected; and, if desired, following coupling of the amino acid, selectively deprotecting one or several protected functional group(s) present in the molecule and chemically transforming the reactive group(s) thus liberated to form an interstrand linkage(s), as defined above;
(h) further effecting steps substantially corresponding to steps (b) to (d) using an appropriately N-protected derivative of an amino acid, or if desired, an appropriately protected derivative of a hydroxy acid, or if desired, an appropriately protected derivative of an acid, which in the desired end-product is at position $P^1$, any functional group(s) which may be present in said N-protected amino acid derivative, hydroxy acid derivative, or acid derivative, being likewise appropriately protected; and, if desired, following the coupling, selectively deprotecting one or several protected functional group(s) present in the molecule and chemically transforming the reactive group(s) thus liberated to form an interstrand linkage(s), as defined above;
(i) if desired, selectively removing the N-protecting group at position $P^1$, and chemically transforming the thus obtained amino function;
(j) if desired, implementing additional chemical transformations of one or more group(s) present in the molecule;
(k) detaching the product thus obtained from the solid support;
(l) if desired, implementing additional chemical transformations of one or more group(s) present in the molecule to form, for example, an interstrand linkage(s), as defined above;
(m) if desired, selectively deprotecting one or several protected functional group(s) present in the molecule and chemically transforming the reactive group(s) thus liberated to form an interstrand linkage(s), as defined above;
(n) removing any protecting groups present on functional groups of any members of the chain of residues and, if desired, any protecting group(s) which may in addition be present in the molecule;
(o) if desired, implementing additional chemical transformations of one or more reactive group(s) present in the molecule;
(p) if desired and required, implementing additional chemical transformations of two or more group(s) present in the molecule to form an interstrand linkage(s), as defined above; and
(q) if desired, converting the product thus obtained into a pharmaceutically acceptable salt or converting a pharmaceutically acceptable, or unacceptable, salt thus obtained into the corresponding free compound of formula (I) or into a different, pharmaceutically acceptable salt;
if s=0, t=0, and u=0; and $P^{11}$ is not connected from the α-carbonyl point of attachment to the ω-nitrogen (N) of $P^2$;
by performing steps comprising:
(a) coupling an appropriately functionalized solid support with an appropriately N-protected derivative of that amino acid which in the desired end-product is at position $P^{11}$ of module A, as defined above, any functional group which may be present in said N-protected amino acid derivative being likewise appropriately protected;
(b) removing the N-protecting group from the product thus obtained;
(c) coupling the product thus obtained with an appropriately N-protected derivative of that amino acid which in the desired end-product is at position $P^{10}$, any functional group which may be present in said N-protected amino acid derivative being likewise appropriately protected;
(d) if desired, selectively deprotecting one or several protected functional group(s) present in the molecule and appropriately substituting the reactive group(s) thus liberated by attaching one or several moieties derived from acids, amino acids or amines;
(e) further effecting steps substantially corresponding to steps (b) to (d) using appropriately N-protected derivatives of amino acids which in the desired end-product are at positions $P^9$ to $P^n$ (n=5, 6, or 7), any functional group(s) which may be present in said N-protected amino acid derivatives being likewise appropriately protected;
(f) selectively removing a carboxyl-protecting group at $P^n$ (n=5, 6, or 7); and coupling of the protected peptide fragment (module B and linker L) by formation of an amide bond between the free amino function in the peptide fragment obtained from procedure (I) and the liberated carboxyl function at $P^n$;
(g) further effecting steps substantially corresponding to steps (b) to (d) using appropriately N-protected derivatives of amino acids which in the desired end-product are at positions $P^{n-1}$ (n=5, 6, or 7) to $P^2$, any functional group(s) which may be present in said N-protected amino acid derivatives being likewise appropriately protected; and, if desired, following coupling of the amino acid, selectively deprotecting one or several protected functional group(s) present in the molecule and chemically transforming the reactive group(s) thus liberated to form an interstrand linkage(s), as defined above;

(h) further effecting steps substantially corresponding to steps (b) to (d) using an appropriately N-protected derivative of an amino acid, or if desired, an appropriately protected derivative of a hydroxy acid, or if desired, an appropriately protected derivative of an acid, which in the desired end-product is at position $P^1$, any functional group(s) which may be present in said N-protected amino acid derivative, hydroxy acid derivative, or acid derivative, being likewise appropriately protected; and, if desired, following the coupling, selectively deprotecting one or several protected functional group(s) present in the molecule and chemically transforming the reactive group(s) thus liberated to form an interstrand linkage(s), as defined above;

(i) if desired, selectively removing the N-protecting group at position $P^1$, and chemically transforming the thus obtained amino function;

(j) if desired, implementing additional chemical transformations of one or more group(s) present in the molecule;

(k) detaching the product thus obtained from the solid support;

(l) if desired, implementing additional chemical transformations of one or more group(s) present in the molecule to form, for example, an interstrand linkage(s), as defined above;

(m) if desired, selectively deprotecting one or several protected functional group(s) present in the molecule and chemically transforming the reactive group(s) thus liberated to form an interstrand linkage(s), as defined above;

(n) removing any protecting groups present on functional groups of any members of the chain of residues and, if desired, any protecting group(s) which may in addition be present in the molecule;

(o) if desired, implementing additional chemical transformations of one or more reactive group(s) present in the molecule;

(p) if desired and required, implementing additional chemical transformations of two or more group(s) present in the molecule to form an interstrand linkage(s), as defined above; and (q) if desired, converting the product thus obtained into a pharmaceutically acceptable salt or converting a pharmaceutically acceptable, or unacceptable, salt thus obtained into the corresponding free compound of formula (I) or into a different, pharmaceutically acceptable salt;

if s=0, t=0, and u=0; and $P^{11}$ is connected from the α-carbonyl point of attachment to the ω-nitrogen (N) of $P^2$;

by performing steps comprising:

(a) coupling an appropriately functionalized solid support with an appropriately N-protected derivative of that amino acid, which in the desired end-product is at position $P^{11}$ of module A, as defined above, any functional group which may be present in said N-protected amino acid derivative being likewise appropriately protected;

(b) removing the N-protecting group from the product thus obtained;

(c) coupling the product thus obtained with an appropriately N-protected derivative of that amino acid which in the desired end-product is at position $P^{10}$, any functional group which may be present in said N-protected amino acid derivative being likewise appropriately protected;

(d) if desired, selectively deprotecting one or several protected functional group(s) present in the molecule and appropriately substituting the reactive group(s) thus liberated by attaching one or several moieties derived from acids, amino acids or amines;

(e) further effecting steps substantially corresponding to steps (b) to (d) using appropriately N-protected derivatives of amino acids which in the desired end-product are at positions $P^9$ to $P^n$ (n=5, 6, or 7), any functional group(s) which may be present in said N-protected amino acid derivatives being likewise appropriately protected;

(f) selectively removing a carboxyl-protecting group at $P^n$ (n=5, 6, or 7); and coupling of the protected peptide fragment (module B and linker L) by formation of an amide bond between the free amino function in the peptide fragment obtained from procedure (I) and the liberated carboxyl function at $P^n$;

(g) further effecting steps substantially corresponding to steps (b) to (d) using appropriately N-protected derivatives of amino acids which in the desired end-product are at positions $P^{n-1}$ (n=5, 6, or 7) to $P^2$, any functional group(s) which may be present in said N-protected amino acid derivatives being likewise appropriately protected;

(h) further effecting steps substantially corresponding to steps (b) to (d) using an appropriately N-protected derivative of an amino acid, or if desired, an appropriately protected derivative of a hydroxy acid, or if desired, an appropriately protected derivative of an acid, which in the desired end-product is at position $P^1$, any functional group(s) which may be present in said N-protected amino acid derivative, hydroxy acid derivative, or acid derivative, being likewise appropriately protected;

(i) if desired, selectively removing the N-protecting group at position $P^1$, and chemically transforming the thus obtained amino function;

(j) if desired, implementing additional chemical transformations of one or more group(s) present in the molecule;

(k) if desired, selectively removing an N-protecting group at position $P^2$; (l) detaching the product thus obtained from the solid support;

(m) if desired, formation of an interstrand linkage, as defined above, by formation of an amide bond between the thus liberated carboxyl group at position $P^{11}$ and the amino group at position $P^2$;

(n) if desired and required, selectively removing an N-protecting group at position $P^2$; and formation of an interstrand linkage, as defined above, by formation of an amide bond between the carboxyl group at position $P^{11}$ and the thus liberated amino group at position $P^2$;

(o) removing any protecting groups present on functional groups of any members of the chain of residues and, if desired, any protecting group(s) which may in addition be present in the molecule;
(p) if desired, implementing additional chemical transformations of one or more reactive group(s) present in the molecule; and
(q) if desired, converting the product thus obtained into a pharmaceutically acceptable salt or converting a pharmaceutically acceptable, or unacceptable, salt thus obtained into the corresponding free compound of formula (I) or into a different, pharmaceutically acceptable salt.

Enantiomers of the compounds defined herein before form also part of the present invention. These enantiomers can be prepared by a modification of the above process wherein enantiomers of all chiral starting materials are utilized.

The β hairpin peptidomimetics of the invention can be obtained by applying the process as described herein above, the main process steps of which are described in more detail in the following sections.

The process of the invention can advantageously be carried out as parallel array synthesis to yield libraries of β-hairpin peptidomimetics of the invention. Such parallel syntheses allow one to obtain arrays of numerous (normally 12 to 576, typically 96) compounds as described above in moderate to high yields and defined purities, minimizing the formation of dimeric and polymeric by-products. The proper choice of the functionalized solid-support (i.e. solid support plus linker molecule) plays thereby key roles.

The functionalized solid support is conveniently derived from polystyrene crosslinked with, preferably 1-5%, divinylbenzene; polystyrene coated with polyethyleneglycol spacers (Tentagel™); and polyacrylamide resins (see also D. Obrecht, J.-M. Villalgordo, "Solid-Supported Combinatorial and Parallel Synthesis of Small-Molecular-Weight Compound Libraries", *Tetrahedron Organic Chemistry Series*, Vol. 17, Pergamon, Elsevier Science, 1998).

The solid support is functionalized by means of a linker, i.e. a bifunctional spacer molecule which contains on one end an anchoring group for attachment to the solid support and on the other end a selectively cleavable functional group used for the subsequent chemical transformations and cleavage procedures. For the purposes of the present invention two types of linkers are used:

Type 1 linkers are designed to release the amide group under acidic conditions (H. Rink, *Tetrahedron Lett.* 1987, 28, 3783-3790). Linkers of this kind form amides of the carboxyl group of the amino acids; examples of resins functionalized by such linker structures include 4-[(((2,4-dimethoxyphenyl)Fmoc-aminomethyl) phenoxyacetamido) aminomethyl] PS resin, 4-[(((2,4-dimethoxyphenyl) Fmoc-aminomethyl)phenoxyacetamido) aminomethyl]-4-methylbenzydrylamine PS resin (Rink amide MBHA PS Resin), and 4-[(((2,4-dimethoxy-phenyl) Fmoc-aminomethyl)phenoxyacetamido) aminomethyl] benzhydrylamine PS-resin (Rink amide BHA PS resin). Preferably, the support is derived from polystyrene crosslinked with, most preferably 1-5%, divinylbenzene and functionalized by means of the 4-(((2,4-dimethoxy-phenyl) Fmoc-aminomethyl)phenoxyacetamido) linker.

Type 2 linkers are designed to eventually release the carboxyl group under acidic conditions. Linkers of this kind form acid-labile esters with the carboxyl group of the amino acids, usually acid-labile benzyl, benzhydryl and trityl esters; examples of such linker structures include 2-methoxy-4-hydroxymethylphenoxy (Sasrin™ linker), 4-(2,4-dimethoxyphenyl-hydroxymethyl)-phenoxy (Rink linker), 4-(4-hydroxymethyl-3-methoxyphenoxy)butyric acid (HMPB linker), trityl and 2-chlorotrityl. Preferably, the support is derived from polystyrene crosslinked with, most preferably 1-5%, divinylbenzene and functionalized by means of the 2-chlorotrityl linker. When carried out as parallel array synthesis the process of the invention can be advantageously carried out as described herein below but it will be immediately apparent to those skilled in the art how these procedures will have to be modified in case it is desired to synthesize one single compound of the invention.

A number of reaction vessels (normally 12 to 576, typically 96) equal to the total number of compounds to be synthesized by the parallel method are loaded with 25 to 1000 mg, preferably 60 mg, of the appropriate functionalized solid support, preferably 1 to 5% cross-linked polystyrene or Tentagel resin.

The solvent to be used must be capable of swelling the resin and includes, but is not limited to, dichloromethane (DCM), dimethylformamide (DMF), N-methylpyrrolidone (NMP), dioxane, toluene, tetrahydrofuran (THF), ethanol (EtOH), trifluoroethanol (TFE), isopropylalcohol and the like. Solvent mixtures containing as at least one component a polar solvent (e.g. 20% TFE/DCM, 35% THF/NMP) are beneficial for ensuring high reactivity and solvation of the resin-bound peptide chains (G. B. Fields, C. G. Fields, *J. Am. Chem. Soc.* 1991, 113, 4202-4207).

With the development of various linkers that release the C-terminal carboxylic acid group under mild acidic conditions, not affecting acid-labile groups protecting functional groups in the side chain(s), considerable progresses have been made in the synthesis of protected peptide fragments. The 2-methoxy-4-hydroxybenzylalcohol-derived linker (Sasrin™ linker, Mergler et al., *Tetrahedron Lett.* 1988, 29 4005-4008) is cleavable with diluted trifluoroacetic acid (0.5-1% TFA in DCM) and is stable to Fmoc deprotection conditions during the peptide synthesis, Boc/tBu-based additional protecting groups being compatible with this protection scheme. Other linkers which are suitable for the process of the invention include the super acid labile 4-(2, 4-dimethoxyphenyl-hydroxymethyl)-phenoxy linker (Rink linker, H. Rink, *Tetrahedron Lett.* 1987, 28, 3787-3790), where the removal of the peptide requires 10% acetic acid in DCM or 0.2% trifluoroacetic acid in DCM; the 4-(4-hydroxymethyl-3-methoxyphenoxy)butyric acid-derived linker (HMPB-linker, Florsheimer & Riniker, 1991, Peptides 1990: Proceedings of the Twenty-First European Peptide Symposium, 131) which is also cleaved with 1% TFA/DCM in order to yield a peptide fragment containing all acid labile side-chain protective groups; and, in addition, the 2-chlorotritylchloride linker (Barlos et al., *Tetrahedron Lett.* 1989, 30, 3943-3946), which allows the peptide detachment using a mixture of glacial acetic acid/trifluoroethanol/ DCM (1:2:7) for 30 min. Attachment to the linker via an alcohol group provides alternative strategies for the synthesis of peptides using, for example, the 2-chlorotritylchloride linker (L. Rizzi et al., *Tetrahedron Lett.* 2011, 52, 2808-2811).

Suitable protecting groups for amino acids and, respectively, for their residues are, for example, for the amino group (as is present e.g. also in the side-chain of lysine)
Cbz benzyloxycarbonyl
Boc tert.-butyloxycarbonyl
Fmoc 9-fluorenylmethoxycarbonyl
Alloc allyloxycarbonyl
Teoc trimethylsilylethoxycarbonyl
Tcc trichloroethoxycarbonyl Nps o-nitrophenylsulfonyl
Trt triphenylmethyl or trityl
ivDde 1-(4,4-dimethyl-2,6-dioxocyclohex-1-ylidene)-3-methylbutyl;
for the carboxyl group (as is present e.g. also in the side-chain of aspartic and glutamic acid) by conversion into esters with the alcohol components
tBu tert.-butyl
Bn benzyl
Me methyl
Ph phenyl
Pac phenacyl
allyl
Tse trimethylsilylethyl
Tce trichloroethyl
Dmab 4-N-(1-[dimethyl-2,6-dioxocyclohexylidene]-3-methylbutyl)-amino benzyl 2-PhiPr 2-phenyl-isopropyl;
for the guanidino group (as is present e.g. in the side-chain of arginine)
Pmc 2,2,5,7,8-pentamethylchroman-6-sulfonyl
Ts tosyl (i.e. p-toluenesulfonyl)
Cbz benzyloxycarbonyl
Pbf pentamethyldihydrobenzofuran-5-sulfonyl;
and for the hydroxy group (as is present e.g. in the side-chain of threonine and serine)
tBu tert.-butyl
Bn benzyl
Trt trityl
Alloc allyloxycarbonyl.

The 9-fluorenylmethoxycarbonyl-(Fmoc)-protected amino acid derivatives are preferably used as the building blocks for the construction of the β-hairpin peptidomimetics of the invention. For the deprotection, i.e. cleaving off of the Fmoc group, 20% piperidine in DMF or 2% DBU/2% piperidine in DMF can be used as well as 25% hexafluoroisopropanol in CH$_2$Cl$_2$.

The quantity of the reactant, i.e. of the amino acid derivative, is usually 1 to 20 equivalents (eq) based on the milliequivalents per gram (meq/g) loading of the functionalized solid support (typically 0.1 to 2.85 meq/g for polystyrene resins) originally weighed into the reaction tube. Additional equivalents of reactants can be used, if required, to drive the reaction to completion in a reasonable time. The preferred workstations (without, however, being limited thereto) are Labsource's Combi-chem station, Protein Technologies' Symphony and MultiSyn Tech's-Syro synthesizer, the latter additionally equipped with a transfer unit and a reservoir box during the process of detachment of the fully protected linear peptide from the solid support. All synthesizers are able to provide a controlled environment, for example, reactions can be accomplished at temperatures different from room temperature as well as under inert gas atmosphere, if desired.

Amide bond formation requires the activation of a carboxyl group for the acylation step. When this activation is being carried out by means of the commonly used carbodiimides such as dicyclohexylcarbodiimide (DCC, Sheehan & Hess, *J. Am. Chem. Soc.* 1955, 77, 1067-1068) or diisopropylcarbodiimide (DIC, Sarantakis et al *Biochem. Biophys. Res. Commun.* 1976, 73, 336-342), the resulting dicyclohexylurea and, respectively, diisopropylurea is insoluble and, respectively, soluble in the solvents ly used. In a variation of the carbodiimide method 1-hydroxy benzotriazole (HOBt, König & Geiger, *Chem. Ber.* 1970, 103, 788-798) is included as an additive to the coupling mixture. HOBt prevents dehydration, suppresses racemization of the activated amino acids and acts as a catalyst to improve the sluggish coupling reactions.

Ethyl(hydroxyimino)cyanoacetate (Oxyma Pure) is an alternative to HOBt in carbodiimide-mediated coupling reactions (M. Itoh, *Bull. Chem. Soc. Jpn* 1973, 46, 2219-2221; J. Izdebski, *Pol. J. Chem.* 1979, 53, 1049-1057).

Certain phosphonium reagents have been used as direct coupling reagents, such as benzotriazol-1-yl-oxy-tris-(dimethyl-amino)-phosphonium hexafluorophosphate (BOP, Castro et al., *Tetrahedron Lett.* 1975, 14, 1219-1222; *Synthesis* 1976, 751-752), or benzotriazol-1-yl-oxy-tris-pyrrolidino-phosphonium hexaflurophoshate (Py-BOP, Coste et al., *Tetrahedron Lett.* 1990, 31, 205-208), or 2-(1H-benzotriazol-1-yl-)1,1,3,3-tetramethyluronium tetrafluoroborate (TBTU), or hexafluorophosphate (HBTU, Knorr et al., *Tetrahedron Lett.* 1989, 30, 1927-1930); these phosphonium reagents are also suitable for in situ formation of HOBt esters with the protected amino acid derivatives. More recently diphenoxyphosphoryl azide (DPPA) or O-(7-aza-benzotriazol-1-yl)-N,N,N',N'-tetramethyluronium tetrafluoro borate (TATU) or O-(7-aza-benzotriazol-1-yl)-N,N,N',N'-tetramethyluronium hexa fluorophosphate (HATU)/7-aza-1-hydroxybenzotriazole (HOAt, Carpino et al., *Tetrahedron Lett.* 1994, 35, 2279-2281) or O-(6-Chloro-1H-benzotriazol-1-yl-)-N,N,N',N'-1,1,3,3-tetramethyl uronium tetrafluoroborate (TCTU), or hexafluoro phosphate (HCTU, Marder, Shivo and Albericio: HCTU and TCTU: New Coupling Reagents: Development and Industrial Applications, Poster Presentation, Gordon Conference February 2002) have also been used as coupling reagents as well as 1,1,3,3-bis(tetramethylene)chlorouronium hexafluorophosphate (PyClU) especially for coupling of N-methylated amino acids (J. Coste, E. Frerot, P. Jouin, B. Castro, *Tetrahedron Lett.* 1991, 32, 1967) or pentafluorophenyl diphenylphosphinate (FDPP, S. Chen, J. Xu, *Tetrahedron Lett.* 1991, 32, 6711).

Due to the fact that near-quantitative coupling reactions are essential, it is desirable to have experimental evidence for completion of the reactions. The ninhydrin test (Kaiser et al., *Anal. Biochemistry* 1970, 34, 595), where a positive colorimetric response to an aliquot of resin-bound peptide or peptide indicates qualitatively the presence of the primary amine, can easily and quickly be performed after each coupling step. Fmoc chemistry allows the spectrophotometric detection of the Fmoc chromophore when it is released with the base (Meienhofer et al., *Int. J. Peptide Protein Res.* 1979, 13, 35-42).

The resin-bound intermediate within each reaction vessel is washed free of excess of retained reagents, of solvents, and of by-products by repetitive exposure to pure solvent(s).

Washing procedures are repeated up to about 30 times (preferably about 5 times), monitoring the efficiency of reagent, solvent, and by-product removal by methods such as TLC, GC, LC-MS or inspection of the washings.

The above described procedure of reacting the resin-bound compound with reagents within the reaction wells followed by removal of excess reagents, by-products, and solvents is repeated with each successive transformation until the final resin-bound fully protected linear peptide has been obtained.

Before the fully protected linear peptide fragment (module B and linker L) or the fully protected peptide (module B, module A and linker L) are detached from the solid support, it is possible, if desired, either to chemically transform one or more groups present in the molecule, e.g. by formation of a disulfide bridge starting from still trityl-protected Cys residues, as described below, or to selectively deprotect one or several protected functional group(s) present in the molecule and to chemically transform the reactive group(s) thus liberated to form an interstrand linkage(s), as defined above, or to selectively deprotect two protected functional group(s) present in the molecule and to chemically transform the reactive group(s) thus liberated to form a macrolactam cycle (module B), as defined above. To this effect, the functional group(s) in question must initially be protected by a protecting group which can be selectively removed without affecting the remaining protecting groups present. Alloc (allyloxycarbonyl) is an example for such an amino protecting group which can be selectively removed, e.g. by means of Pd° and phenylsilane in $CH_2Cl_2$, without affecting the remaining protecting groups, such as Fmoc, present in the molecule. The reactive group thus liberated can then be treated with an agent suitable for introducing the desired substituent. Thus, for example, an amino group can be acylated by means of an acylating agent corresponding to the acyl substituent to be introduced. Other well known orthogonal protecting groups which can be selectively removed are allyl, dmab or 2-PhiPr, examples for carboxyl protecting groups, or ivdDe, a further amino protecting group. The selective removal of the allyl protecting group by e.g. means of Pd° and phenylsilane in $CH_2Cl_2$ can be used, for example, in the course of the macrolactam formation of module B (as described above, on solid support, or in the course of coupling of the protected peptide fragment [module B and linker L]), whereas an ivdDe deprotection step of an amino group being conducted by e.g. means of 5% of hydrazine in DMF (v/v) while the fully protected peptide is still attached on solid support can, for example, play a key role in the course of formation of a lactam interstrand linkage.

After detachment of the fully protected peptide from the solid support (cleavage) the individual solutions/extracts are then manipulated as needed to isolate the the fully protected peptides. Typical manipulations include, but are not limited to, evaporation, concentration, liquid/liquid extraction, acidification, basification, neutralization or additional reactions in solution.

The solutions containing fully protected peptide derivatives which have been cleaved off from the solid support and neutralized with a base, are evaporated.

Macrolactam formation of module B, as described above, or, if desired, formation of an interstrand linkage(s), as described above, is then effected in solution using solvents such as DCM, DMF, dioxane, THF and the like. Various coupling reagents which were mentioned earlier as activators for the amide bond formation can be used for the cyclization. The duration of the cyclization is about 6-48 hours, preferably about 16 hours. The progress of the reaction is followed, e.g. by RP-HPLC (Reverse Phase High Performance Liquid Chromatography). Then the solvent is removed by evaporation, the fully protected cyclic peptide derivative is dissolved in a solvent which is not miscible with water, such as DCM, and the solution is extracted with water or a mixture of water-miscible solvents, in order to remove any excess of the coupling reagent.

Finally, the fully protected peptide derivative (module A, module B and linker L) is treated with 95% TFA, 2.5% $H_2O$, 2.5% TIS, or 87.5% TFA, 2.5% DODT, 5% thioanisol, 5% $H_2O$ or another combination of scavengers for effecting the cleavage of protecting groups. The cleavage reaction time is commonly 30 minutes to 12 hours, preferably about 2.5 hours. The volatiles are evaporated to dryness and the crude peptide is dissolved in 20% AcOH in water and extracted with isopropyl ether or other solvents which are suitable therefore. The aqueous layer is collected and evaporated to dryness, and the fully deprotected peptide is obtained. Alternatively the deprotected peptide can be precipitated and washed using cold $Et_2O$. If desired, formation of an interstrand linkage(s), e.g. the formation of a disulfide bridge(s), as described above, is then effected.

For some compounds of the present invention according general formula (I) additional synthetic steps are required. These transformations can be applied either on a fully protected or partially deprotected peptide, attached to or already released from the solid support or on the final deprotected molecule.

Various methods are known to form interstrand linkages including those described by: J. P. Tam et al., *Synthesis* 1979, 955-957; J. M. Stewart et al., *Solid Phase Peptide Synthesis*, 2d Ed., Pierce Chemical Company, Rockford, Ill., 1984; A. K. Ahmed et al., *J. Biol. Chem.* 1975, 250, 8477-8482; and M. W. Pennington et al., *Peptides*, pages 164-166, Giralt and Andreu, Eds., ESCOM Leiden, The Netherlands, 1990; C. E. Schafmeister et al., *J. Am. Chem. Soc.* 2000, 122, 5891. The most widely known linkage is the disulfide bridge formed by e.g. cysteines and homo-cysteines positioned at opposite positions of the β-strand.

For instance, the formation of a disulfide bridge can be carried out after assembly of the linear peptide on resin by employing, for example, on trityl protected cysteine amino acid residues, 10 eq of iodine solution in DMF for 1.5 h and repetition of the oxidation step with a fresh iodine solution for additional 3 h. Alternatively, disulfide bridge formation can be performed in solution before deprotection of the peptide by employing, for example, on trityl protected cysteine amino acid residues, 2 eq of an iodine solution in a hexafluoroisopropanol/$CH_2Cl_2$-mixture for 1 h followed by addition of 1M aqueous solution of ascorbic acid to quench the oxidation reaction. Another possibility to form disulfide bridges remains after deprotection of the peptide (module A, module B and linker L), for example, in a mixture of DMSO and ammonium acetate after adjusting to pH 8 with ammoniumhydroxid solution by stirring for 24 h, or in water after adjusting to pH 8 with ammonium hydroxide solution by stirring for 24 h.

Another well established interstrand linkage is the lactam bridge formed by linking e.g. the amino group-bearing side chains of ornithine and lysine, respectively, with the carboxyl group-bearing side chains of glutamic and aspartic acid residues located at opposite β-strand positions by means of an amide bond formation. Preferred protective groups for the side chain amino-groups of ornithine and lysine are allyloxycarbonyl (alloc) and for the side chain carboxyl-groups of aspartic and glutamic acid allylesters (allyl).

For instance, the formation of a lactam bridge can be carried out after assembly of the linear peptide on resin by applying 0.2 eq tetrakis(triphenyl-phosphine)palladium(0) (10 mM) in dry $CH_2Cl_2$ and 10 eq phenylsilane to selectively remove alloc- and allyl-protecting groups from amino and carboxyl functional groups of the side chains of amino acid residues to be linked. After repetition of the above procedure, the lactam bridge is formed by adding 4 eq of DIPEA in DMF and subsequent addition of 2 eq HATU in DMF.

By applying an appropriate orthogonal protecting group strategy lactam bridges may also be formed in a later stage of the synthesis, e.g. after detachment of the fully protected peptide (module A, module B, linker L) from the solid support (cleavage).

Interstrand linkages can also be established by linking side chain amino groups of amino acid residues like e.g. L-1,3-diamino propionic acid and ornithine located at opposite β-strand positions with reagents such as N,N-carbonylimidazole or di(N-succinimidyl)carbonate to form cyclic ureas. Allyloxycarbonyl (alloc) as orthogonal protecting group for amino functions may be preferably used.

For instance, the formation of an urea bridge can be carried out in solution before full deprotection of the peptide, by applying 30 eq phenylsilane as well as a solution of 0.2 eq tetrakis(triphenylphosphine)-palladium(0) in $CH_2Cl_2$. After removal of the alloc protecting groups and precipitation of the selectively deprotected peptide the urea bridge is formed by adding 6 eq DIPEA dissolved in $CH_2Cl_2$ and subsequent dropwise addition of 1.2 eq of di(N-succinimidyl)carbonate in $CH_2Cl_2$.

Recently, a further type of interstrand linkages based on 1,4-disubstituted 1,2,3-triazole-containing alkanediyl groups have been introduced. The linkage is obtained through a 1,3-dipolar cycloaddition between the ω-yne group of the side chain of an amino acid residue like e.g. L-propargylglycine and the w-azido group of the side chain of an amino acid residue like e.g. (S)-2-amino-4-azidobutanoic acid, both residues located at opposite β-strand positions.

For instance, the formation of such a triazole-containing bridge is performed by stirring the purified fully deprotected peptide (module A, module B and linker L) in a mixture of $H_2O/tBuOH$, 4.4 eq of $CuSO_4x5H_2O$ and 6.6 eq of ascorbic acid for 12 h. Depending on its purity, the final product as obtained following the procedures above can be used directly for biological assays, or has to be further purified, for example by preparative HPLC.

As mentioned earlier, it is thereafter possible, if desired, to convert the fully deprotected product thus obtained into a pharmaceutically acceptable salt or to convert a pharmaceutically acceptable, or unacceptable, salt thus obtained into the corresponding free or into a different, pharmaceutically acceptable, salt. Any of these operations can be carried out by methods well known in the art.

In the building blocks for the peptidomimetics of the present invention can be synthesized according to the literature methods, which are known to a person skilled in the art or are commercially available. All other corresponding amino acids and amino alcohols have been described either as unprotected or as Boc- or Fmoc-protected racemates, (D)- or (L)-isomers. It will be appreciated that unprotected amino acid and amino alcohol building blocks can be easily transformed into the corresponding Fmoc-protected amino acid and amino alcohol building blocks required for the present invention by standard protecting group manipulations. Reviews describing methods for the synthesis of α-amino acids include: R. Duthaler, Tetrahedron (Report) 1994, 349, 1540-1650; R. M. Williams, "Synthesis of optically active α-amino acids", Tetrahedron Organic Chemistry Series, Vol. 7, J. E. Baldwin, P. D. Magnus (Eds.), Pergamon Press., Oxford 1989. An especially useful method for the synthesis of optically active α-amino acids relevant for this invention includes kinetic resolution using hydrolytic enzymes (M. A. Verhovskaya, I. A. Yamskov, Russian Chem. Rev. 1991, 60, 1163-1179; R. M. Williams, "Synthesis of optically active α-amino acids", Tetrahedron Organic Chemistry Series, Vol. 7, J. E. Baldwin, P. D. Magnus (Eds.), Pergamon Press., Oxford 1989, Chapter 7, p. 257-279). Kinetic resolution using hydrolytic enzymes involves hydrolysis of amides and nitriles by aminopeptidases or nitrilases, cleavage of N-acyl groups by acylases, and ester hydrolysis by lipases or proteases. It is well documented that certain enzymes will lead specifically to pure (L)-enantiomers whereas others yield the corresponding (D)-enantiomers (e.g.: R. Duthaler, Tetrahedron Report 1994, 349, 1540-1650; R. M. Williams, "Synthesis of optically active α-amino acids", Tetrahedron Organic Chemistry Series, Vol. 7, J. E. Baldwin, P. D. Magnus (Eds.), Pergamon Press., Oxford 1989).

A person skilled in the art is easily able to implement alternative processes, e.g. a process embracing the coupling of a fully protected peptide fragment (module A and linker L) with a fully protected peptide fragment (module B) which can be performed in solution according to methods known in the art (see e.g. W. C. Chan, P. D. White "Fmoc solid phase peptide synthesis: A practical approach", Oxford University Press Inc., New York, 2000, reprinted 2003, chapter 9, section 4.1, page 223f).

Finally, it will be apparent to those skilled in the art how to modify or adapt the above described process, or the process steps of which, to obtain the 13 hairpin peptidomimetics of the invention.

The β-hairpin peptidomimetics of the invention can be used in a wide range of applications in order to inhibit the growth of or to kill microorganisms leading to the desired therapeutic effect in man or, due to their similar etiology, in other mammals. In particular they can be used to inhibit the growth of or to kill Gram-negative bacteria such as *Klebsiella pneumoniae* and/or *Acinetobacter baumannii* and/or *Escherichia coli* and/or *Pseudomonas aeruginosa* and/or *Enterobacter cloacae*.

They can be used for example as disinfectants or as preservatives for materials such as foodstuffs, cosmetics, medicaments and other nutrient-containing materials.

The β-hairpin peptidomimetics of the invention can also be used to treat or prevent diseases related to microbial infection in plants and animals.

For use as disinfectants or preservatives the β-hairpin peptidomimetics can be added to the desired material singly, as mixtures of several β-hairpin peptidomimetics or in combination with other antimicrobial agents.

The β-hairpin peptidomimetics of the invention can be used to treat or prevent infections or diseases related to such infections, particularly nosocomial infections caused by Gram-negative bacteria related to diseases such as ventilator-associated pneumonia (VAP), ventilator-associated bacterial pneumonia (VABP), hospital-acquired pneumonia (HAP), hospital-acquired bacterial pneumonia (HABP), healthcare-associated pneumonia (HCAP); catheter-related and non-catheter-related infections such as urinary tract infections (UTIs) or bloodstream infections (BSIs); infections related to respiratory diseases such as cystic fibrosis, emphysema, asthma or pneumonia; infections related to skin or soft tissue diseases such as surgical wounds, traumatic wounds or burn; infections related to gastrointestinal diseases such as epidemic diarrhea, necrotizing enterocolitis, typhlitis, gastroenteritis or pancreatitis; infections related to eye diseases such as keratitis and endophthalmitis; infections related to ear diseases such as otitis; infections related to CNS diseases such as brain abscess and meningitis or encephalitis; infections related to bone diseases such as osteochondritis and osteomyelitis; infections related to cardiovascular diseases such as endocartitis and pericarditis; infections related to genitourinary diseases such as epididymitis, prostatitis and urethritis; or infection-induced sepsis. They can be administered singly, as mixtures of several β-hairpin peptidomimetics, in combination with other antimicrobial or antibiotic agents, or anti cancer agents, or antiviral (e.g. anti-HIV) agents, or in combination with other pharmaceutically active agents.

The β-hairpin peptidomimetics can be administered per se or as pharmaceutical compositions.

The β-hairpin peptidomimetics of the invention may be administered per se or may be applied as an appropriate formulation together with carriers, diluents or excipients well known in the art.

Pharmaceutical compositions comprising β-hairpin peptidomimetics of the invention may be manufactured by means of conventional mixing, dissolving, granulating, coated tablet-making, levigating, emulsifying, encapsulating, entrapping or lyophilizing processes. Pharmaceutical compositions may be formulated in conventional manner using one or more physiologically acceptable carriers, diluents, excipients or auxiliaries which facilitate processing of the active β-hairpin peptidomimetics into preparations which can be used pharmaceutically. Proper formulation depends upon the method of administration chosen.

For topical administration the β-hairpin peptidomimetics of the invention may be formulated as solutions, gels, ointments, creams, suspensions, etc. as are well-known in the art.

Systemic formulations include those designed for administration by injection, e.g. subcutaneous, intravenous, intramuscular, intrathecal or intraperitoneal injection, as well as those designed for transdermal, transmucosal, oral or pulmonary administration.

For injections, the β-hairpin peptidomimetics of the invention may be formulated in adequate solutions, preferably in physiologically compatible buffers such as Hink's solution, Ringer's solution, or physiological saline buffer. The solutions may contain formulatory agents such as suspending, stabilizing and/or dispersing agents. Alternatively, the β-hairpin peptidomimetics of the invention may be in powder form for combination with a suitable vehicle, e.g., sterile pyrogen-free water, before use. For transmucosal administration, penetrants appropriate to the barrier to be permeated are used in the formulation as known in the art.

For oral administration, the compounds can be readily formulated by combining the active β-hairpin peptidomimetics of the invention with pharmaceutically acceptable carriers well known in the art. Such carriers enable the β-hairpin peptidomimetics of the invention to be formulated as tablets, pills, dragees, capsules, liquids, gels, syrups, slurries, suspensions etc., for oral ingestion by a patient to be treated. For oral formulations such as, for example, powders, capsules and tablets, suitable excipients include fillers such as sugars, such as lactose, sucrose, mannitol and sorbitol; cellulose preparations such as maize starch, wheat starch, rice starch, potato starch, gelatin, gum tragacanth, methyl cellulose, hydroxypropylmethyl cellulose, sodium carboxymethylcellulose, and/or polyvinylpyrrolidone (PVP); granulating agents; and binding agents. If desired, desintegrating agents may be added, such as cross-linked polyvinylpyrrolidones, agar, or alginic acid or a salt thereof, such as sodium alginate. If desired, solid dosage forms may be sugar-coated or enteric-coated using standard techniques.

For oral liquid preparations such as, for example, suspensions, elixirs and solutions, suitable carriers, excipients or diluents include water, glycols, oils, alcohols, etc. In addition, flavoring agents, preservatives, coloring agents and the like may be added. For buccal administration, the composition may take the form of tablets, lozenges, etc. formulated as usual.

For administration by inhalation, the β-hairpin peptidomimetics of the invention are conveniently delivered in form of an aerosol spray from pressurized packs or a nebulizer, with the use of a suitable propellant, e.g. dichlorodifluoromethane, trichlorofluromethane, carbon dioxide or another suitable gas. In the case of a pressurized aerosol the dose unit may be determined by providing a valve to deliver a metered amount. Capsules and cartridges of e.g. gelatin for use in an inhaler or insufflator may be formulated containing a powder mix of the β-hairpin peptidomimetics of the invention and a suitable powder base such as lactose or starch. The compounds may also be formulated in rectal or vaginal compositions such as suppositories together with appropriate suppository bases such as cocoa butter or other glycerides.

In addition to the formulations described above, the β-hairpin peptidomimetics of the invention may also be formulated as depot preparations. Such long acting formulations may be administered by implantation (e.g. subcutaneously or intramuscularly) or by intramuscular injection. For the manufacture of such depot preparations the β-hairpin peptidomimetics of the invention may be formulated with suitable polymeric or hydrophobic materials (e.g. as an emulsion in an acceptable oil) or ion exchange resins, or as sparingly soluble salts.

In addition, other pharmaceutical delivery systems may be employed such as liposomes and emulsions well known in the art. Certain organic solvents such as dimethylsulfoxide may also be employed. Additionally, the β-hairpin peptidomimetics of the invention may be delivered using a sustained-release system, such as semipermeable matrices of solid polymers containing the therapeutic agent (e.g. for coated stents). Various sustained-release materials have been established and are well known by those skilled in the art. Sustained-release capsules may, depending on their chemical nature, release the compounds for a few weeks up to over 100 days. Depending on the chemical nature and the biological stability of the therapeutic agent, additional strategies for protein stabilization may be employed.

As the β-hairpin peptidomimetics of the invention may contain charged residues, they may be included in any of the above-described formulations as such or as pharmaceutically acceptable salts. Pharmaceutically acceptable salts tend to be more soluble in aqueous and other protic solvents than are the corresponding free forms. The β-hairpin peptidomimetics of the invention, or compositions thereof, will ly be used in an amount effective to achieve the intended purpose. It is to be understood that the amount used will depend on a particular application.

For example, for use as a disinfectant or preservative, an antimicrobially effective amount of a β-hairpin peptidomimetic of the invention, or a composition thereof, is applied or added to the material to be desinfected or preserved. By antimicrobially effective amount is meant an amount of a β-hairpin peptidomimetic of the invention, or a composition thereof, that inhibits the growth of, or is lethal to, a target microbe population. While the antimicrobially effective amount will depend on a particular application, for use as disinfectants or preservatives the β-hairpin peptidomimetics of the invention, or compositions thereof, are usually added or applied to the material to be desinfected or preserved in relatively low amounts. Typically, the β-hairpin peptidomimetics of the invention comprise less than about 5% by weight of a disinfectant solution or material to be preserved, preferably less than 1% by weight and more preferably less than 0.1% by weight. An ordinary skilled expert will be able to determine antimicrobially effective amounts of particular β-hairpin peptidomimetics of the invention for particular applications without undue experimentation using, for example, the results of the in vitro assays provided in the examples.

For use to treat or prevent microbial infections or diseases related to such infections, the β-hairpin peptidomimetics of the invention, or compositions thereof, are administered or applied in a therapeutically effective amount. By therapeutically effective amount is meant an amount effective in ameliorating the symptoms of, or in ameliorating, treating or preventing microbial infections or diseases related thereto. Determination of a therapeutically effective amount is well within the capacities of those skilled in the art, especially in view of the detailed disclosure provided herein. As in the case of disinfectants and preservatives, for topical administration to treat or prevent bacterial infections and/or viral infections a therapeutically effective dose can be determined using, for example, the results of the in vitro assays provided in the examples. The treatment may be applied while the infection is visible, or even when it is not visible. An ordinary skilled expert will be able to determine therapeutically effective amounts to treat topical infections without undue experimentation.

For systemic administration, a therapeutically effective dose can be estimated initially from in vitro assays. For example, a dose can be formulated in animal models to achieve a circulating β-hairpin peptidomimetic concentration range that includes the $IC_{50}$ as determined in the cell culture (i.e. the concentration of a test compound that is lethal to 50% of a cell culture). Such information can be used to more accurately determine useful doses in humans.

Initial dosages can also be determined from in vivo data, e.g. animal models, using techniques that are well known in the art. One having ordinary skill in the art could readily optimize administration to humans based on animal data.

Dosage amounts for applications as anti-infective agents may be adjusted individually to provide plasma levels of the β-hairpin peptidomimetics of the invention which are sufficient to maintain the therapeutic effect. Therapeutically effective serum levels may be achieved by administering multiple doses each day.

In cases of local administration or selective uptake, the effective local concentration of the β-hairpin peptidomimetics of the invention may not be related to plasma concentration. One having the ordinary skill in the art will be able to optimize therapeutically effective local dosages without undue experimentation.

The amount of β-hairpin peptidomimetics administered will, of course, be dependent on the subject being treated, on the subject's weight, the severity of the affliction, the manner of administration and the judgement of the prescribing physician.

The antimicrobial therapy may be repeated intermittently while infections are detectable or even when they are not detectable. The therapy may be provided alone or in combination with other drugs, such as for example anti-HIV agents or anti-cancer agents, or other antimicrobial agents.

Normally, a therapeutically effective dose of the β-hairpin peptidomimetics described herein will provide therapeutic benefit without causing substantial toxicity.

Toxicity of the β-hairpin peptidomimetics of the invention can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. Compounds which exhibit high therapeutic indices are preferred. The data obtained from these cell culture assays and animal studies can be used in formulating a dosage range that is not toxic for use in humans. The dosage of the β-hairpin peptidomimetics of the invention lies preferably within a range of circulating concentrations that include the effective dose with little or no toxicity. The dosage may vary within the range depending upon the dosage form employed and the route of administration utilized. The exact formulation, route of administration and dose can be chosen by the individual physician in view of the patient's condition (see, e.g. Fingl et al. 1975, In: *The Pharmacological Basis of Therapeutics*, Ch. 1, p. 1). The following Examples illustrate the present invention but are not to be construed as limiting its scope in any way.

Abbreviations:
Ac Acetyl;
BSA Bovine serum albumin;
Boc tert-Butyloxycarbonyl;
$CH_2Cl_2$ Dichloromethane;
DCHA Dicyclohexylamine;
DEAD Diethyl azodicarboxylate;
DIC N,N'-Diisopropylcarbodiimide;
DIPEA Diisopropylethylamine;
DMEM Dulbecco's Modified Eagle's Medium;
DMF Dimethylformamide;
DMSO Dimethyl sulfoxide;
$Et_2O$ Diethyl ether;
eq equivalent;
FCS Fetal Calf Serum;
FDPP Pentafluorophenyl diphenyl-phosphinate;
Fmoc Fluorenylmethyloxycarbonyl;
HATU O-(7-Azabenzotriazol-1-yl)-N,N,N',N'-tetramethyluronium hexafluorophosphate;
HBSS Hank's Buffered Salt Solution;
HBTU O-(Benzotriazol-1-yl)-N,N,N',N'-tetramethyluronium hexafluorophosphate;
HCTU O-(6-Chlorobenzotriazol-1-yl)-N,N,N',N'-tetramethyluronium hexafluorophosphate;
Hepes 4-(2-hydroxyethyl)piperazine-1-ethanesulfonic acid;
HFIP Hexafluoroisopropanol;
iPrOH Isopropanol;
$iPr_2O$ Diisopropyl ether;
HOAt 1-Hydroxy-7-azabenzotriazole;
IMDM Iscove's Modified Dulbecco's Media;
MeOH Methanol;
NMM N-Methylmorpholine;
NMP N-Methyl-2-pyrrolidone;
Oxyma Pure Ethyl(hydroxyimino)cyanoacetate;
PyBop® (Benzotriazol-1-yloxy)tripyrrolidinophosphonium hexafluorophosphate;
TFA Trifluoroacetic acid;
THF Tetrahydrofuran;
TIS Triisopropylsilane;
TPP Triphenylphosphine;
RPMI Roswell Park Memorial Institute medium;
rt Room temperature.

EXAMPLES

1. Peptide Synthesis
1.1 Synthetic Procedures

A method for the synthesis of the peptidomimetics of the present invention is exemplified in the following. This is to demonstrate the principal concept and does not limit or restrict the present invention in any way. A person skilled in the art is easily able to modify these procedures, especially, but not limited to, choosing a different strategy for formation of a disulfide interstrand linkage and a different fragment coupling strategy, to still achieve the preparation of the claimed cyclic peptidomimetic compounds of the present invention.

1.1.1 Coupling of the First Protected Residue to the Resin 1.1.1.1 Coupling of an Fmoc-Protected Amino Acid to the Resin Via a Side Chain Hydroxyl Group In a dried flask, 2-chlorotritylchloride resin (polystyrene, 1% crosslinked; loading: 1.4 mMol/g) was swollen in dry 1,2 dichloroethane for 30 min (4.5 mL 1,2 dichloroethane per g resin). A suspension of 3.2 eq of the Fmoc-protected amino acid and 2 eq of NMM in dry 1,2-dichloroethane (10 mL per g resin) was added. After stirring under reflux for 1-2 h the resin was filtered off and washed with 1,2 dichloroethane (3×) and with $CH_2Cl_2$. Then a solution of dry $CH_2Cl_2$/MeOH/DIPEA (17:2:1, v/v/v) was added (10 mL per g resin). After shaking for 3×30 min the resin was filtered off in a pre-weighed sintered funnel and washed successively with $CH_2Cl_2$, DMF, $CH_2Cl_2$, MeOH, $CH_2Cl_2$, MeOH, $CH_2Cl_2$ (2×) and $Et_2O$ (2×). The resin was dried under high vacuum overnight. The final mass of resin was calculated before the qualitative control.

Loading was typically 0.2-0.3 mMol/g.

The following preloaded resin was prepared: Fmoc-Thr(-2-chlorotrityl resin)-allyl.

1.1.1.2 Coupling of an Fmoc-Protected Amino Alcohol to the Resin Via a Hydroxyl Group In a dried flask, 2-chlorotritylchloride resin (polystyrene, 1% crosslinked; loading: 1.4 mMol/g) was swollen in dry 1,2 dichloroethane for 30 min (4.5 mL 1,2 dichloroethane per g resin). A suspension of 3.2 eq of the Fmoc-protected amino alcohol and 2 eq of NMM in dry 1,2-dichloroethane (10 mL per g resin) was added. After stirring under reflux for 1-2 h the resin was filtered off and washed with 1,2 dichloroethane (3×) and with $CH_2Cl_2$. Then a solution of dry $CH_2Cl_2$/MeOH/DIPEA (17:2:1, v/v/v) was added (10 mL per g resin). After shaking for 3×30 min the resin was filtered off in a pre-weighed sintered funnel and washed successively with $CH_2Cl_2$, DMF, $CH_2Cl_2$, MeOH, $CH_2Cl_2$, MeOH, $CH_2Cl_2$ (2×) and $Et_2O$ (2×). The resin was dried under high vacuum overnight. The final mass of resin was calculated before the qualitative control.

Loading was typically 0.2-0.3 mMol/g.

The following preloaded resins were prepared: Fmoc-Glyol-2-chlorotrityl resin, Fmoc-Serol(tBu)-2-chlorotrityl resin, Fmoc-Throl(tBu)-2-chlorotrityl resin, Fmoc-$^D$Throl(tBu)-2-chlorotrityl resin, and Fmoc-Tyrol(tBu)-2-chlorotrityl resin.

1.1.1.3 Coupling of an Fmoc-Protected Amino Acid to the Resin Via a Carboxyl Group In a dried flask, 2-chlorotritylchloride resin (polystyrene, 1% crosslinked; loading: 1.4 mMol/g) was swollen in dry $CH_2Cl_2$ for 30 min (7 mL $CH_2Cl_2$ per g resin). A solution of 0.8 eq of the Fmoc-protected amino acid and 6 eq of DIPEA in dry $CH_2Cl_2$/DMF (4/1, v/v) (10 mL per g resin) was added. After shaking for 2-4 h at rt the resin was filtered off and washed successively with $CH_2Cl_2$, DMF, $CH_2Cl_2$, DMF and $CH_2Cl_2$. Then a solution of dry $CH_2Cl_2$/MeOH/DIPEA (17:2:1, v/v/v) was added (10 mL per g resin). After shaking for 3×30 min the resin was filtered off in a pre-weighed sintered funnel and washed successively with $CH_2Cl_2$, DMF, $CH_2Cl_2$, MeOH, $CH_2Cl_2$, MeOH, $CH_2Cl_2$ (2×) and $Et_2O$ (2×). The resin was dried under high vacuum overnight. The final mass of resin was calculated before the qualitative control.

Loading was typically 0.6-0.7 mMol/g.

The following preloaded resins were prepared: Fmoc-$^D$Ala-2-chlorotrityl resin, Fmoc-$^D$Asn(Trityl)-2-chlorotrityl resin, Fmoc-Cys(Trityl)-2-chlorotrityl resin, Fmoc-$^D$Dab(Boc)-2-chlorotrityl resin, Fmoc-$^D$Gln(Trityl)-2-chlorotrityl resin, Fmoc-$^D$Glu(tBu)-2-chlorotrityl resin, Fmoc-$^D$Hse(tBu)-2-chlorotrityl resin, Fmoc-Leu(3R)OtBu-2-chlorotrityl resin, Fmoc-$^D$Lys(Boc)-2-chlorotrityl resin, Fmoc-Ser(tBu)-2-chlorotrityl resin, Fmoc-$^D$Ser(tBu)-2-chlorotrityl resin, Fmoc-Thr(tBu)-2-chlorotrityl resin, Fmoc-$^D$Thr(tBu)-2-chlorotrityl resin, Fmoc-$^D$Val-2-chlorotrityl resin and Fmoc-$^D$Tyr(tBu)-2-chlorotrityl resin.

1.1.2 Methods for Synthesis on Solid Support of the Fully Protected Peptide and of the Fully Protected Peptide Fragment for Fragment Coupling The synthesis was carried out on a Syro-peptide synthesizer (MultiSynTech GmbH) using 24 to 96 reaction vessels. Unless otherwise indicated, in each vessel were placed 0.05 mMol of the resin, obtained from procedures 1.1.1.1, 1.1.1.2, or 1.1.1.3, as described above, or 0.05 mMol of Sieber amide resin, as described below, and the resin was swelled in $CH_2Cl_2$ and DMF for 15 min, respectively.

The following reaction cycles were programmed and carried out as described in the methods A-K, as described herein below:

| Step | Reagent | Time |
|---|---|---|
| 1 | $CH_2Cl_2$, wash and swell (manual) | 1 × 3 min |
| 2 | DMF, wash and swell | 2 × 30 min |
| 3 | 20% piperidine/DMF | 1 × 5 min and 1 × 15 min |
| 4 | DMF, wash | 5 × 1 min |
| 5[a)] | 3.6 eq appropriately protected amino acid and 3.6 eq HOAt in DMF or NMP + 3.6 eq DIC in DMF | 1 × 40 min |
| 6 | 3.6 eq appropriately protected amino acid and 3.6 eq HOAt in DMF or NMP + 3.6 eq HATU + 7.2 eq DIPEA in NMP | 1 × 40 min |
| 7 | DMF, wash | 5 × 1 min |
| 8 | 20% piperidine/DMF | 1 × 5 min and 1 × 15 min or 2 × 2 min[b)] |
| 9 | DMF, wash | 5 × 1 min |
| 10 | $CH_2Cl_2$, wash (at the end of the synthesis) | 3 × 1 min |

[a)]In the coupling cycle following coupling of an N-alkyl amino acid residue and for coupling of the first protected amino acid residue to Sieber amide resin, step 5 was omitted and step 6 was performed twice instead.
[b)]Reduced times were used for Fmoc deprotection of an amino acid residue having a carboxyl group protected as allyl ester, and for the Fmoc deprotection step of the following coupling cycle.

The term "macrolactam cycle", as used herein below, refers to a cyclic peptide moiety that is generated through formation of an amide bond between two amino acid residues of module B, involving an α-carboxyl group and a side-chain amino group.

The term "lactam interstrand linkage", as used herein, refers to a linkage of two amino acid residues of module A by an amide bond, involving a side-chain carboxyl group and a side-chain amino group; or, an α-carboxyl group and a side-chain amino group.

1.1.2.1 Method A

The reaction cycles, as described herein above, were applied for the assembly of the fully protected peptide fragment (module B and linker L) using 0.05 mMol of the resin obtained from procedure 1.1.1.1 and appropriately protected Fmoc amino acid building blocks.

In a first part, a fully protected peptide fragment encompassing amino acid residues of module B was prepared. Steps 5 to 9 are repeated to add each amino acid residue of module B, except for the last amino acid residue of this peptide fragment, which was added by steps 5 to 7. Subsequently, allyl and alloc deprotection (module B) and macrolactam cycle formation (module B) were performed as described in the corresponding section of procedure A herein below, followed by steps 8 to 9 for Fmoc deprotection and washing.

Assembly of the fully protected peptide fragment was then continued. Steps 5 to 9 were repeated to add each amino acid residue of linker L.

1.1.2.2 Method B

The reaction cycles, as described herein above, were applied for the assembly of the fully protected peptide (module A, module B and linker L), using 0.05 mMol of the resin obtained from procedure 1.1.1.2 and appropriately protected Fmoc amino acid building blocks, except for coupling of the protected peptide fragment (module B and linker L) and the last coupling, as described herein below. For the latter, an appropriately protected Boc-amino acid building block was used.

In a first part, steps 5 to 9 are repeated to add each amino acid residue of module A, except for the case, where the carboxyl group-bearing side chain of the added amino acid residue of module A is connected with the amino acid residue at position 12 of linker L. In this case, coupling of the allyl protected Fmoc amino acid by steps 5 to 7 was followed by allyl deprotection and coupling of the protected peptide fragment (module B and linker L) as described in the corresponding sections of procedure A herein below. Subsequently, steps 8 to 9 for Fmoc protection and washing were performed.

Assembly of the fully protected peptide was then continued. Steps 5 to 9 were repeated to add each remaining amino acid residue of module A, except for the last amino acid residue, which was added by steps 5 to 7, followed by step 10.

1.1.2.3 Method C

The reaction cycles, as described herein above, were applied for the assembly of the fully protected peptide (module A, module B and linker L), using 0.05 mMol of the resin obtained from procedure 1.1.1.2 and appropriately protected Fmoc amino acid building blocks, except for coupling of the protected peptide fragment (module B and linker L), as described herein below.

In a first part, steps 5 to 9 are repeated to add each amino acid residue of module A, except for the case, where the carboxyl group-bearing side chain of the added amino acid residue of module A is connected with amino acid residue at position $L^1$ of linker L. In this case, coupling of the allyl protected Fmoc amino acid by steps 5 to 7 was followed by allyl deprotection and coupling of the protected peptide fragment (module B and linker L) as described in the corresponding sections of procedure A herein below. Subsequently, steps 8 to 9 for Fmoc protection and washing were performed. Assembly of the fully protected peptide was then continued. Steps 5 to 9 were repeated to add each remaining amino acid residue of module A.

1.1.2.4 Method D

The reaction cycles, as described herein above, were applied for the assembly of the fully protected peptide (module A, module B and linker L), using 0.05 mMol of the resin obtained from procedure 1.1.1.2 and appropriately protected Fmoc amino acid building blocks, except for coupling of the protected peptide fragment (module B and linker L) and the last coupling, as described herein below. For the latter, an acid building block was used.

In a first part, steps 5 to 9 are repeated to add each amino acid residue of module A, except for the case, where the carboxyl group-bearing side chain of the added amino acid residue of module A is connected with amino acid residue at position $L^1$ of linker L. In this case, coupling of the allyl protected Fmoc amino acid by steps 5 to 7 was followed by allyl deprotection and coupling of the protected peptide fragment (module B and linker L) as described in the corresponding sections of procedure A herein below. Subsequently, steps 8 to 9 for Fmoc protection and washing were performed.

Assembly of the fully protected peptide was then continued. Steps 5 to 9 were repeated to add each remaining amino acid residue of module A, except for the acid residue, which was added by steps 5 to 7, followed by step 10.

1.1.2.5 Method E

The reaction cycles, as described herein above, were applied for the assembly of the fully protected peptide (module A, module B and linker L), using 0.05 mMol of the resin obtained from procedure 1.1.1.2 and appropriately protected Fmoc amino acid building blocks, except for coupling of the protected peptide fragment (module B and linker L) and the last coupling, as described herein below. For the latter, an appropriately protected hydroxy acid building block was used.

In a first part, steps 5 to 9 are repeated to add each amino acid residue of module A, except for the case, where the carboxyl group-bearing side chain of the added amino acid residue of module A is connected with the amino acid residue at position 12 of linker L. In this case, coupling of the allyl protected Fmoc amino acid by steps 5 to 7 was followed by allyl deprotection and coupling of the protected peptide fragment (module B and linker L) as described in the corresponding sections of procedure A herein below. Subsequently, steps 8 to 9 for Fmoc protection and washing were performed.

Assembly of the fully protected peptide was then continued. Steps 5 to 9 were repeated to add each remaining amino acid residue of module A, except for the hydroxy acid residue, which was added by steps 5 to 7, followed by step 10.

1.1.2.6 Method F

The reaction cycles, as described herein above, were applied for the assembly of the fully protected peptide (module A, module B and linker L), using 0.05 mMol of the resin obtained from procedure 1.1.1.3 and appropriately protected Fmoc amino acid building blocks, except for coupling of the protected peptide fragment (module B and linker L) and the last coupling, as described herein below. For the latter, an appropriately protected Boc-amino acid building block was used.

In a first part, steps 5 to 9 are repeated to add each amino acid residue of module A, except for the case, where the carboxyl group-bearing side chain of the added amino acid residue of module A is connected with the amino acid residue at position 12 of linker L. In this case, coupling of the allyl protected Fmoc amino acid by steps 5 to 7 was followed by allyl deprotection and coupling of the protected peptide fragment (module B and linker L) as described in the corresponding sections of procedure A herein below. Subsequently, steps 8 to 9 for Fmoc protection and washing were performed.

Assembly of the fully protected peptide was then continued. Steps 5 to 9 were repeated to add each remaining amino acid residue of module A, except for the last amino acid residue, which was added by steps 5 to 7, followed by step 10.

1.1.2.7 Method G

The reaction cycles, as described herein above, were applied for the assembly of the fully protected peptide (module A, module B and linker L), using 0.05 mMol of the resin obtained from procedure 1.1.1.3 and appropriately protected Fmoc amino acid building blocks, except for coupling of the protected peptide fragment (module B and linker L), as described herein below.

In a first part, steps 5 to 9 are repeated to add each amino acid residue of module A, except for the case, where the carboxyl group-bearing side chain of the added amino acid residue of module A is connected with the amino acid residue at position 12 of linker L. In this case, coupling of the allyl protected Fmoc amino acid by steps 5 to 7 was followed by allyl deprotection and coupling of the protected peptide fragment (module B and linker L) as described in the corresponding sections of procedure A herein below. Subsequently, steps 8 to 9 for Fmoc protection and washing were performed.

Assembly of the fully protected peptide was then continued. Steps 5 to 9 were repeated to add each remaining amino acid residue of module A.

1.1.2.8 Method H

The reaction cycles, as described herein above, were applied for the assembly of the fully protected peptide (module A, module B and linker L), using 0.05 mMol of the resin obtained from procedure 1.1.1.3 and appropriately protected Fmoc amino acid building blocks, except for coupling of the protected peptide fragment (module B and linker L) and the last coupling, as described herein below. For the latter, an appropriately protected hydroxy acid building block was used.

In a first part, steps 5 to 9 are repeated to add each amino acid residue of module A, except for the case, where the carboxyl group-bearing side chain of the added amino acid residue of module A is connected with the amino acid residue at position 12 of linker L. In this case, coupling of the allyl protected Fmoc amino acid by steps 5 to 7 was followed by allyl deprotection and coupling of the protected peptide fragment (module B and linker L) as described in the corresponding section of procedure A herein below. Subsequently, steps 8 to 9 for Fmoc protection and washing were performed.

Assembly of the fully protected peptide was then continued. Steps 5 to 9 were repeated to add each remaining amino acid residue of module A, except for the hydroxy acid residue, which was added by steps 5 to 7, followed by step 10.

1.1.2.9 Method I

The reaction cycles, as described herein above, were applied for the assembly of the fully protected peptide (module A, module B and linker L), using 0.05 mMol of Sieber amide resin (polystyrene, 1% crosslinked; loading: 0.65 mMol/g) and appropriately protected Fmoc amino acid building blocks, except for coupling of the protected peptide fragment (module B and linker L), and the last coupling, as described herein below. For the latter, an appropriately protected Boc-amino acid building block was used.

In a first part, steps 5 to 9 are repeated to add each amino acid residue of module A, except for the case, where the carboxyl group-bearing side chain of the added amino acid residue of module A is connected with the amino acid residue at position 12 of linker L. In this case, coupling of the allyl protected Fmoc amino acid by steps 5 to 7 was followed by allyl deprotection and coupling of the protected peptide fragment (module B and linker L) as described in the corresponding sections of procedure A herein below. Subsequently, steps 8 to 9 for Fmoc protection and washing were performed.

Assembly of the fully protected peptide was then continued. Steps 5 to 9 were repeated to add each remaining amino acid residue of module A, except for the last amino acid residue, which was added by steps 5 to 7, followed by step 10.

1.1.2.10 Method J

The reaction cycles, as described herein above, were applied for the assembly of the fully protected peptide (module A, module B and linker L), using 0.05 mMol of Sieber amide resin (polystyrene, 1% crosslinked; loading: 0.65 mMol/g) and appropriately protected Fmoc amino acid building blocks, except for coupling of the protected peptide fragment (module B and linker L), as described herein below.

In a first part, steps 5 to 9 are repeated to add each amino acid residue of module A, except for the case, where the carboxyl group-bearing side chain of the added amino acid residue of module A is connected with the amino acid residue at position 12 of linker L. In this case, coupling of the allyl protected Fmoc amino acid by steps 5 to 7 was followed by allyl deprotection and coupling of the protected peptide fragment (module B and linker L) as described in the corresponding sections of procedure A herein below. Subsequently, steps 8 to 9 for Fmoc protection and washing were performed.

Assembly of the fully protected peptide was then continued. Steps 5 to 9 were repeated to add each remaining amino acid residue of module A.

1.1.2.11 Method K

The reaction cycles, as described herein above, were applied for the assembly of the fully protected peptide (module A, module B and linker L), using 0.05 mMol of Sieber amide resin (polystyrene, 1% crosslinked; loading: 0.65 mMol/g) and appropriately protected Fmoc amino acid building blocks, except for coupling of the protected peptide fragment (module B and linker L) and the last coupling, as described herein below. For the latter, an appropriately protected hydroxy acid building block was used. In a first part, steps 5 to 9 are repeated to add each amino acid residue of module A, except for the case, where the carboxyl group-bearing side chain of the added amino acid residue of module A is connected with the amino acid residue at position 12 of linker L. In this case, coupling of the allyl protected Fmoc amino acid by steps 5 to 7 was followed by allyl deprotection and coupling of the protected peptide fragment (module B and linker L) as described in the corresponding sections of procedure A herein below. Subsequently, steps 8 to 9 for Fmoc protection and washing were performed.

Assembly of the fully protected peptide was then continued. Steps 5 to 9 were repeated to add each remaining amino acid residue of module A, except for the hydroxy acid residue, which was added by steps 5 to 7, followed by step 10.

1.1.2.12 Method L

The reaction cycles, as described herein above, were applied for the assembly of the fully protected peptide (module A, module B and linker L), using 0.05 mMol of Sieber amide resin (polystyrene, 1% crosslinked; loading: 0.65 mMol/g) and appropriately protected Fmoc amino acid building blocks, except for coupling of the protected peptide fragment (module B and linker L) and the last coupling, as described herein below. For the latter, an acid building block was used.

In a first part, steps 5 to 9 are repeated to add each amino acid residue of module A, except for the case, where the carboxyl group-bearing side chain of the added amino acid residue of module A is connected with the amino acid residue at position 12 of linker L. In this case, coupling of the allyl protected Fmoc amino acid by steps 5 to 7 was followed by allyl deprotection and coupling of the protected peptide fragment (module B and linker L) as described in the corresponding sections of procedure A herein below. Subsequently, steps 8 to 9 for Fmoc protection and washing were performed.

Assembly of the fully protected peptide was then continued. Steps 5 to 9 were repeated to add each remaining amino acid residue of module A, except for the acid residue, which was added by steps 5 to 7, followed by step 10.

1.1.3 Procedures for the Preparation of the Peptides

One of the procedures A Q, as described herein below, was adopted for preparation of the peptides.

1.1.3.1 Procedure A:

Preparation of a Peptide Having a Disulfide Interstrand Linkage(s) in Module A Having an Amino Alcohol Residue Attached to the C-Terminal Amino Acid Residue and Having a Free N-Terminal Amino Group The peptide was prepared based on an on-resin fragment coupling strategy.

(I) Preparation of a Protected Peptide Fragment (Module B and Linker L)

The appropriately protected peptide fragment encompassing amino acid residues of module B and linker L was assembled on solid support according to Method A as described above. Allyl and alloc deprotection, and macrolactam cycle formation were performed as follows:

Allyl and Alloc Deprotection (Module B)

For selective removal of the allyl and alloc protecting groups from carboxyl and amino functions present in the resin bound peptide, the latter (0.05 mMol) was swollen in 1 mL dry $CH_2Cl_2$ for at least 10 min, washed twice with iPrOH and twice with $iPr_2O$, followed by addition of 40 eq triphenylsilane in 0.5 mL NMP, shaking of the mixture for 1 minute, and addition of 0.2 eq tetrakis(triphenylphosphine) palladium(0) in 0.5 mL dry $CH_2Cl_2$. After shaking the reaction mixture for 5 min at rt, the resin was filtered off and washed three times with 1 mL dry $CH_2Cl_2$. The deprotection procedure was repeated with fresh solutions of reagents, applying a shaking time of 15 min after addition of the palladium catalyst. LC-MS was used to monitor the deprotection reaction and, if required, the deprotection procedure was repeated. Subsequently the resin was thoroughly washed with $CH_2Cl_2$, DMF, iPrOH, and finally again with $CH_2Cl_2$.

Macrolactam Cycle Formation (Module B)

1 eq OxymaPure in 0.4 mL $CH_2Cl_2$ and 2 eq DIC in 0.6 mL $CH_2Cl_2$ were added to the resin in $CH_2Cl_2$. After stirring the reaction mixture for approximately 2-3 h, the resin was filtered, and fresh solutions of reagents were added to repeat the procedure. The resin was subsequently filtered and washed with $CH_2Cl_2$, DMF, iPrOH, and finally again with $CH_2Cl_2$.

Subsequently the following steps were performed:

Cleavage of Peptide Fragment from Resin (Module B and Linker L)

The resin was swollen in 1 mL $CH_2Cl_2$ (2×10 min). After filtration, the resin was suspended in 1 mL of 1% TFA in $CH_2Cl_2$ (v/v) for 5 min. The resin was then filtered and washed three times with 1 mL of $CH_2Cl_2$, and a solution of 1 mL of 40% DIPEA in $CH_2Cl_2$ (v/v) was added to the combined filtrate and washings. The cleavage procedure was repeated 6 times. LC-MS was used to monitor the cleavage and, if required, the cleavage procedure was repeated further.

The combined filtrate and washings were evaporated to dryness.

Preparation of Free Base Peptide Fragment (Module B and Linker L)

The obtained protected peptide fragment was then dissolved in 4 mL of $MeOH/CH_2Cl_2$ (1:4, v/v) and washed twice with 2 mL of aq. $Na_2CO_3$ (0.1 M). The organic layer was dried ($Na_2SO_4$), filtered, and evaporated to dryness.

(II) Preparation of the Peptide (Module A, Module B and Linker L)

The fully protected peptide (module A, module B and linker L) was assembled on solid support according to Method B as described above. Appropriately protected Fmoc amino acid building blocks with a thiol group protected as trityl thioether were used for the addition of amino acid residues that are involved in the formation of a disulfide interstrand linkage(s). Allyl deprotection and coupling of the protected peptide fragment (module B and linker L) were performed as follows:

Allyl Deprotection

Selective removal of the allyl protecting group from a carboxyl function was performed as described in the corresponding section above for allyl and alloc deprotection (module B).

Coupling of Protected Peptide Fragment (Module B and Linker L)

The resin was swollen in 1 mL DMF for 10 min and then filtered off. The swelling procedure was repeated once with fresh DMF. Subsequently, 1 eq OxymaPure in 0.4 mL $CH_2Cl_2$/DMSO (1:1, v/v) and 2 eq DIC in 0.6 mL $CH_2Cl_2$ were added to the resin in DMF. After stirring the reaction mixture for approximately 5-10 minutes, 1.2 eq protected peptide fragment (module B and linker L) in 0.5 mL $CH_2Cl_2$/DMSO (1:1, v/v) were added. The reaction mixture was then stirred for approximately 16 h. Afterwards, the resin was filtered and washed three times with $CH_2Cl_2$/DMSO (1:1, v/v), and finally with DMF.

Subsequently, cleavage of the peptide from the resin and disulfide bridge formation were performed as follows:

Cleavage of Peptide from Resin

The resin was swollen in 1 mL $CH_2Cl_2$ (2×10 min). After filtration, the resin was suspended in 1 mL of 1% TFA in $CH_2Cl_2$ (v/v) for 5 min. The resin was then filtered and washed three times with 1 mL of $CH_2Cl_2$, and a solution of 1 mL of 40% DIPEA in $CH_2Cl_2$ (v/v) was added to the combined filtrate and washings. The cleavage procedure was repeated 6 times. LC-MS was used to monitor the cleavage and, if required, the cleavage procedure was repeated further.

The combined filtrate and washings were evaporated to dryness.

Formation of Disulfide Interstrand Linkage(s) (Module A)

The protected peptide was dissolved in 8 mL of HFIP/$CH_2Cl_2$ (1:4, v/v) and 2 eq iodine in 2 mL of HFIP/$CH_2Cl_2$ (1:4, v/v) were added. After shaking for 20-45 minutes, 3 mL of a 1 M aqueous solution of ascorbic acid were added to quench excess reagent, and the mixture was further shaken for 10 min. The aqueous phase was discarded, optionally applying a centrifugation step for phase separation. The organic phase was washed with 4 mL of $H_2O$, and concentrated to dryness.

Full Deprotection

To fully deprotect the peptide, 7 mL of cleavage cocktail TFA/TIS/$H_2O$ (95:2.5:2.5, v/v/v) were added, and the mixture was kept for 2.5-4 h at room temperature. The reaction mixture was evaporated close to dryness, the peptide precipitated with 7 mL of cold $Et_2O$/pentane (1:1, v/v) and finally washed three times with 3 mL of cold $Et_2O$/pentane (1:1, v/v).

Finally, the peptide was purified by preparative reverse phase LC-MS, as described herein below.

1.1.3.2 Procedure B

Preparation of a Peptide Having a Disulfide Interstrand Linkage(s) in Module A Having an Amino Alcohol Residue Attached to the C-Terminal Amino Acid Residue and being Acylated at the N-Terminal Amino Group The peptide was prepared based on an on-resin fragment coupling strategy.

(I) Preparation of a Protected Peptide Fragment (Module B and Linker L)

The appropriately protected peptide fragment encompassing amino acid residues of module B and linker L was prepared as described in the corresponding section of procedure A.

(II) Preparation of a Peptide (Module a, Module B and Linker L)

The fully protected peptide (module A, module B and linker L) was assembled on solid support according to Method C as described above. Appropriately protected Fmoc amino acid building blocks with a thiol group protected as trityl thioether were used for the addition of amino acid residues that are involved in the formation of a disulfide interstrand linkage(s). Allyl deprotection and coupling of the protected peptide fragment (module B and linker L) were performed as indicated in the corresponding sections of procedure A.

Acylation of the N-terminal amino group was then carried out as follows:

Acylation

After assembly of the peptide on the resin, steps 5 to 7 of the programmed reaction cycles were performed using 3.6 eq appropriate acid instead of 3.6 eq protected amino acid, followed by step 10.

Subsequently, cleavage of the peptide from the resin, formation of a disulfide interstrand linkage(s), and full deprotection were performed as indicated in the corresponding sections of procedure A, following the same order.

Finally, the peptide was purified by preparative reverse phase LC-MS, as described herein below.

1.1.3.3 Procedure C

Preparation of a Peptide Having a Disulfide Interstrand Linkage(s) in Module A Having an Amino Alcohol Residue Attached to the C-Terminal Amino Acid Residue and Having an Acid Residue Attached to the N-Terminal Amino Acid Residue The peptide was prepared based on an on-resin fragment coupling strategy.

(I) Preparation of a Protected Peptide Fragment (Module B and Linker L)

The protected peptide fragment encompassing amino acid residues of module B and linker L was prepared as described in the corresponding section of procedure A.

(II) Preparation of a Peptide (Module a, Module B and Linker L)

The fully protected peptide (module A, module B and linker L) was assembled on solid support according to Method D as described above. Appropriately protected Fmoc amino acid building blocks with a thiol group protected as trityl thioether were used for the addition of amino acid residues that are involved in the formation of a disulfide interstrand linkage(s). Allyl deprotection and coupling of the protected peptide fragment (module B and linker L) were performed as indicated in the corresponding sections of procedure A.

Subsequently, cleavage of the peptide from the resin, formation of a disulfide interstrand linkage(s), and full deprotection were performed as indicated in the corresponding sections of procedure A, following the same order.

Finally, the peptide was purified by preparative reverse phase LC-MS, as described herein below.

1.1.3.4 Procedure D:

Preparation of a Peptide Having a Disulfide Interstrand Linkage(s) in Module a Having an Amino Alcohol Residue Attached to the C-Terminal Amino Acid Residue and Having an α-Hydroxy Acid Residue Attached to the N-Terminal Amino Acid Residue The peptide was prepared based on an on-resin fragment coupling strategy.

(I) Preparation of a Protected Peptide Fragment (Module B and Linker L)

The protected peptide fragment encompassing amino acid residues of module B and linker L was prepared as described in the corresponding section of procedure A.

(II) Preparation of a Peptide (Module a, Module B and Linker L)

The fully protected peptide (module A, module B and linker L) was assembled on solid support according to Method E as described above. Appropriately protected Fmoc amino acid building blocks with a thiol group protected as trityl thioether were used for the addition of amino acid residues that are involved in the formation of a disulfide interstrand linkage(s). Allyl deprotection and coupling of the protected peptide fragment (module B and linker L) were performed as indicated in the corresponding sections of procedure A.

Subsequently, cleavage of the peptide from the resin, formation of a disulfide interstrand linkage(s), and full deprotection were performed as indicated in the corresponding sections of procedure A, following the same order.

Finally, the peptide was purified by preparative reverse phase LC-MS, as described herein below.

1.1.3.5 Procedure E:

Preparation of a Peptide Having a Disulfide Interstrand Linkage(s) in Module A Having a Free C-Terminal Carboxyl Group and Having a Free N-Terminal Amino Group The peptide was prepared based on an on-resin fragment coupling strategy.

(I) Preparation of a protected peptide fragment (module B and linker L)

The protected peptide fragment encompassing amino acid residues of module B and linker L was prepared as described in the corresponding section of procedure A.

(II) Preparation of a Peptide (Module a, Module B and Linker L)

The fully protected peptide (module A, module B and linker L) was assembled on solid support according to Method F as described above. Appropriately protected Fmoc amino acid building blocks with a thiol group protected as trityl thioether were used for the addition of amino acid residues that are involved in the formation of a disulfide interstrand linkage(s). Allyl deprotection and coupling of the protected peptide fragment (module B and linker L) were performed as indicated in the corresponding sections of procedure A.

Subsequently, cleavage of the peptide from the resin, formation of a disulfide interstrand linkage(s), and full deprotection were performed as indicated in the corresponding sections of procedure A, following the same order.

Finally, the peptide was purified by preparative reverse phase LC-MS, as described herein below.

1.1.3.6 Procedure F:

Preparation of a Peptide Having a Disulfide Interstrand Linkage(s) in Module a Having a Free C-Terminal Carboxyl Group and being Acylated at the N-Terminal Amino Group The peptide was prepared based on an on-resin fragment coupling strategy.

(I) Preparation of a Protected Peptide Fragment (Module 13 and Linker L)

The protected peptide fragment encompassing amino acid residues of module B and linker L was prepared as described in the corresponding section of procedure A.

(II) Preparation of a Peptide (Module a, Module 13 and Linker L)

The fully protected peptide (module A, module B and linker L) was assembled on solid support according to Method G as described above. Appropriately protected Fmoc amino acid building blocks with a thiol group protected as trityl thioether were used for the addition of amino acid residues that are involved in the formation of a disulfide interstrand linkage(s). Allyl deprotection and coupling of the protected peptide fragment (module B and linker L) were performed as indicated in the corresponding sections of procedure A.

Acylation of the N-terminal amino group was then carried out as indicated in the corresponding section of procedure B.

Subsequently, cleavage of the peptide from the resin, formation of a disulfide interstrand linkage(s), and full deprotection were performed as indicated in the corresponding sections of procedure A, following the same order.

Finally, the peptide was purified by preparative reverse phase LC-MS, as described herein below.

1.1.3.7 Procedure G

Preparation of a Peptide Having a Lactam Interstrand Linkage Between a Side-Chain Carboxyl Group and a Side-Chain Amino Group in Module a Having a Free C-Terminal Carboxyl Group and Having a Free N-Terminal Amino Group The peptide was prepared based on an on-resin fragment coupling strategy.

(I) Preparation of a Protected Peptide Fragment (Module B and Linker L)

The protected peptide fragment encompassing amino acid residues of module B and linker L was prepared as described in the corresponding section of procedure A.

(II Preparation of a Peptide (Module a, Module B and Linker L)

The fully protected peptide (module A, module B and linker L) was assembled on solid support according to Method F as described above. Allyl deprotection and coupling of the protected peptide fragment (module B and linker L) were performed as indicated in the corresponding sections of procedure A.

Subsequently, the following steps were performed:

Allyl Deprotection

Selective removal of the allyl protecting group from the carboxyl function was performed as described in the corresponding section for allyl and alloc deprotection (module B) in procedure A.

ivDde Deprotection

The resin was swollen in 1 mL DMF for 10 min and subsequently filtered off. For deprotection, 1 mL of a 5% solution of hydrazine monohydrate in DMF (v/v) was added and the reaction mixture was shaken for 30 min. The reaction mixture was then filtered off and washed with 1 mL DMF. The deprotection step was repeated by employing the same amount of reagents. LC-MS was used to monitor the deprotection reaction and, if required, the deprotection procedure was repeated again. Finally, the resin was thoroughly washed with DMF, $CH_2Cl_2$, DMF, and iPrOH, and finally washed with $CH_2Cl_2$.

Formation of Lactam Interstrand Linkage

To the resin swollen in $CH_2Cl_2$, 2 eq FDPP in 0.5 mL DMF and 2 eq DIPEA in 0.5 mL $CH_2Cl_2$ were added. After stirring the reaction mixture for approximately 16 h at rt, the resin was filtered off, and fresh solutions of reagents were added to repeat the procedure. Subsequently, the resin was washed three times with DMF.

Cleavage of peptide from resin and full deprotection were then performed as indicated in the corresponding sections of procedure A.

Finally, the peptide was purified by preparative reverse phase LC-MS, as described herein below 1.1.3.8 Procedure H:

Preparation of a Peptide Having a Disulfide Interstrand Linkage in Module A Having a Carboxy Methylamide Group at the C-Terminus and being Acylated at the N-Terminal Amino Group The peptide was prepared based on an on-resin fragment coupling strategy.

(I) Preparation of a Protected Peptide Fragment (Module B and Linker L)

The protected peptide fragment encompassing amino acid residues of module B and linker L was prepared as described in the corresponding section of procedure A.

(II) Preparation of a Peptide (Module a, Module B and Linker L)

The fully protected peptide (module A, module B and linker L) was assembled on solid support according to Method G as described above. Appropriately protected Fmoc amino acid building blocks with a thiol group protected as trityl thioether were used for the addition of amino acid residues that are involved in the formation of a disulfide interstrand linkage(s). Allyl deprotection and coupling of the protected peptide fragment (module B and linker L) were performed as indicated in the corresponding sections of procedure A.

Acylation of the N-terminal amino group was then carried out as indicated in the corresponding section of procedure B. Subsequently, cleavage of the peptide from the resin was performed as indicated in the corresponding section of procedure A.

Afterwards the following step was performed:

Formation of the Carboxy Methylamide Group

The protected peptide was solubilized in 0.5 mL $CH_2Cl_2$, followed by the addition of 1 mL DMF and of 4 eq. $CH_3NH_2$ (100 µl, 2M $CH_3NH_2$ in THF). Then 2 eq NMM in 2 mL DMF, and 2 eq HATU and 1 eq HOAt in 2 mL DMF were added, and the reaction mixture was stirred for approximately 16 h. The volatiles were removed by evaporation. The crude cyclic peptide was dissolved in 7 mL of $CH_2Cl_2$ and washed three times with 4.5 mL 10% acetonitrile in water (v/v). The $CH_2Cl_2$ layer was then evaporated to dryness.

Subsequently, formation of a disulfide interstrand linkage(s) and full deprotection were performed as indicated in the corresponding sections of procedure A.

Finally, the peptide was purified by preparative reverse phase LC-MS, as described herein below 1.1.3.9 Procedure I:

Preparation of a Peptide Having a Disulfide Interstrand Linkage(s) in Module A

Having a Carboxyisopropyl Ester Group at the C-Terminus and being Acylated at the N-Terminal Amino Group The peptide was prepared based on an on-resin fragment coupling strategy.

(I) Preparation of a Protected Peptide Fragment (Module B and Linker L)

The protected peptide fragment encompassing amino acid residues of module B and linker L was prepared as described in the corresponding section of procedure A.

(II) Preparation of a Peptide (Module a, Module B and Linker L)

The fully protected peptide (module A, module B and linker L) was assembled on solid support according to Method G as described above. Appropriately protected Fmoc amino acid building blocks with a thiol group protected as trityl thioether were used for the addition of amino acid residues that are involved in the formation of a disulfide interstrand linkage(s). Allyl deprotection and coupling of the protected peptide fragment (module B and linker L) were performed as indicated in the corresponding sections of procedure A.

Acylation of the N-terminal amino group was then carried out as indicated in the corresponding section of procedure B.

Subsequently, the following step was performed:

Cleavage of Peptide from Resin and Formation of the Carboxyisopropyl Ester Group The resin (0.05 mMol) was swollen in 1 mL $CH_2Cl_2$ (2×10 min). To the resin in 0.6 mL $CH_2Cl_2$, 108 eq. acetyl chloride (1.8 mL, freshly prepared solution of 3M acetyl chloride in iPrOH at 0° C.) were added. After shaking the reaction mixture for 24 hours, the resin was filtered off and washed with three times 1 ml $CH_2Cl_2$, and the combined filtrate and washings were evaporated to dryness.

Subsequently, full deprotection and formation of a disulfide interstrand linkage(s) were performed as indicated in the corresponding sections of procedure M2.

Finally, the peptide was purified by preparative reverse phase LC-MS, as described herein below.

1.1.3.10 Procedure J:

Preparation of a Peptide Having a Lactam Interstrand Linkage Between a Side-Chain Amino Group and the C-Terminal Carboxyl Group in Module A and being Acylated at the N-Terminal Amino Group The peptide was prepared based on an on-resin fragment coupling strategy.

(I) Preparation of a Protected Peptide Fragment (Module B and Linker L)

The protected peptide fragment encompassing amino acid residues of module B and linker L was prepared as described in the corresponding section of procedure A.

(II) Preparation of a Peptide (Module a, Module B and Linker L)

The fully protected peptide (module A, module B and linker L) was assembled on solid support according to Method G as described above. Allyl deprotection and coupling of the protected peptide fragment (module B and linker L) were performed as indicated in the corresponding sections of procedure A.

Acylation of the N-terminal amino group was then carried out as indicated in the corresponding section of procedure B.

Subsequently, removal of the alloc protecting group from the amino function and cleavage of the peptide from the resin, in this order, were performed as described for allyl and alloc deprotection (module B), and cleavage of peptide from resin in the corresponding sections of procedure A.

Formation of a lactam interstrand linkage was then carried out as follows:

Lactam Interstrand Linkage Formation

The protected peptide was first solubilized in 0.5 mL $CH_2Cl_2$, followed by the addition of 8 mL DMF. Then 6 eq NMM in 2 mL DMF, and 2 eq HATU and 1 eq HOAt in 2 mL DMF were added, and the reaction mixture was stirred for approximately 16 h. The volatiles were removed by evaporation. The crude cyclic peptide was dissolved in 7 mL of $CH_2Cl_2$ and washed three times with 4.5 mL 10% acetonitrile in water (v/v). The $CH_2Cl_2$ layer was then evaporated to dryness.

Full deprotection was afterwards performed as indicated in the corresponding section of procedure A.

Finally, the peptide was purified by preparative reverse phase LC-MS, as described herein below.

1.1.3.11 Procedure K:

Preparation of a Peptide Having a Lactam Interstrand Linkage Between a Side-Chain Amino Group and the C-Terminal Carboxyl Group in Module A and Having an α-Hydroxy Acid at the N-Terminus The peptide was prepared based on an on-resin fragment coupling strategy.

(I) Preparation of a Protected Peptide Fragment (Module B and Linker L)

The protected peptide fragment encompassing amino acid residues of module B and linker L was prepared as described in the corresponding section of procedure A.

(II) Preparation of a Peptide (Module a, Module B and Linker L)

The fully protected peptide fragment was assembled on solid support according to Method H as described above. Allyl deprotection and coupling of the protected peptide fragment (module B and linker L) were performed as indicated in the corresponding sections of procedure A.

Subsequently, removal of the alloc protecting group from the amino function, cleavage of the peptide from the resin, formation of a lactam interstrand linkage, and full deprotection, in this order, were then performed as indicated in procedure J.

Finally, the peptide was purified by preparative reverse phase LC-MS, as described herein below.

1.1.3.12 Procedure L:

Preparation of a Peptide Having a Disulfide Interstrand Linkage(s) in Module A Having a Carboxylamide Group at the C-Terminus and Having a Free N-Terminal Amino Group The peptide was prepared based on an on-resin fragment coupling strategy.

(I) Preparation of a Protected Peptide Fragment (Module B and Linker L)

The protected peptide fragment encompassing amino acid residues of module B and linker L was prepared as described in the corresponding section of procedure A.

(II) Preparation of a Peptide (Module A, Module B and Linker L)

The fully protected peptide (module A, module B and linker L) was assembled on solid support according to Method I as described above. Appropriately protected Fmoc amino acid building blocks with a thiol group protected as trityl thioether were used for the addition of amino acid residues that are involved in the formation of a disulfide interstrand linkage(s). Allyl deprotection and coupling of the protected peptide fragment (module B and linker L) were performed as indicated in the corresponding sections of procedure A.

Subsequently, cleavage of the peptide from the resin was carried out as follows:

Cleavage of Peptide from Resin

The resin was swollen in 1 mL $CH_2Cl_2$ (2×10 min). After filtration, the resin was suspended in 1 mL of 1% TFA in $CH_2Cl_2$ (v/v) for 10-30 min. The resin was then filtered and washed three times with 1 mL of $CH_2Cl_2$, and a solution of 1 mL of 40% DIPEA in $CH_2Cl_2$ (v/v) was added to the combined filtrate and washings. LC-MS was used to monitor the cleavage and, if required, the cleavage procedure was repeated 3-5 times. The combined filtrate and washings were evaporated to dryness.

Formation of a disulfide interstrand linkage(s) and full deprotection were performed as indicated in the corresponding sections of procedure A.

Finally, the peptide was purified by preparative reverse phase LC-MS, as described herein below.

1.1.3.13 Procedure M1:

Preparation of a Peptide Having a Disulfide Interstrand Linkage(s) in Module A Having a Carboxylamide Group at the C-Terminus and being Acylated at the N-Terminal Amino Group The peptide was prepared based on an on-resin fragment coupling strategy.

(I) Preparation of a Protected Peptide Fragment (Module B and Linker L)

The protected peptide fragment encompassing amino acid residues of module B and linker L was prepared as described in the corresponding section of procedure A.

(II) Preparation of a Peptide (Module a, Module B and Linker L)

The fully protected peptide (module A, module B and linker L) was assembled on solid support according to Method J as described above. Appropriately protected Fmoc amino acid building blocks with a thiol group protected as trityl thioether were used for the addition of amino acid residues that are involved in the formation of a disulfide interstrand linkage(s). Allyl deprotection and coupling of the protected peptide fragment (module B and linker L) were performed as indicated in the corresponding sections of procedure A.

Acylation of the N-terminal amino group was then carried out as indicated in the corresponding section of procedure B.

Subsequently, cleavage of the peptide from the resin, formation of a disulfide interstrand linkage(s), and full deprotection were performed as indicated in the corresponding sections of procedure L, following the same order.

Finally, the peptide was purified by preparative reverse phase LC-MS, as described herein below.

1.1.3.14 Procedure M2:

Preparation of a Peptide Having a Disulfide Interstrand Linkage(s) in Module A Having a Carboxylamide Group at the C-Terminus and being Acylated at the N-Terminal Amino Group The peptide was prepared based on an on-resin fragment coupling strategy.

(I) Preparation of a Protected Peptide Fragment (Module B and Linker L)

The protected peptide fragment encompassing amino acid residues of module B and linker L was prepared as described in the corresponding section of procedure A.

(I) Preparation of a Peptide (Module a, Module B and Linker L)

The fully protected peptide (module A, module B and linker L) was assembled on solid support according to Method J as described above. Appropriately protected Fmoc amino acid building blocks with a thiol group protected as trityl thioether were used for the addition of amino acid residues that are involved in the formation of a disulfide interstrand linkage(s). Allyl deprotection and coupling of the protected peptide fragment (module B and linker L) were performed as indicated in the corresponding sections of procedure A.

Acylation of the N-terminal amino group was then carried out as indicated in the corresponding section of procedure B.

Subsequently, cleavage of the peptide from the resin was performed as indicated in the corresponding section of procedure L.

Afterwards full deprotection and formation of a disulfide interstrand linkage(s) were performed as follows:

Full Deprotection

To fully deprotect the peptide, 7 mL of cleavage cocktail TFA/TIS/thioanisole/anisole/water (82.5:2.5:5:5:5, v/v/v/v/v) were added, and the mixture was kept for 2.5-4 h at room temperature. The reaction mixture was evaporated close to dryness, the peptide precipitated with 7 mL of cold $Et_2O$/pentane (1:1, v/v) and finally washed 3 times with 4 mL of cold $Et_2O$/pentane.

Formation of a Disulfide Interstrand Linkage(s)

The deprotected peptide was dissolved in 0.8 mL DMSO, 7.2 mL aq. $NH_4OAc$ (0.5 M, adjusted to pH 8 with aq. $NH_4OH$ (28% in water, w/v)) were added, and the reaction mixture was then stirred for 24 h at rt. LC-MS was used to monitor the formation of the disulfide interstrand linkages and, if required, the reaction mixture was stirred for further 24 h at rt, followed again by LC-MS monitoring.

Thereafter, the reaction mixture was adjusted to pH 5-6 by addition of acetic acid and evaporated to dryness.

Finally, the peptide was purified by preparative reverse phase LC-MS, as described herein below.

1.1.3.15 Procedure N1:

Preparation of a Peptide Having a Lactam Interstrand Linkage Between a Side-Chain Carboxyl Group and a Side-Chain Amino Group in Module a Having a Carboxylamide Group at the C-Terminus and being Acylated at the N-Terminal Amino Group The peptide was prepared based on an on-resin fragment coupling strategy.

(I) Preparation of a Protected Peptide Fragment (Module B and Linker L)

The protected peptide fragment encompassing amino acid residues of module B and linker L was prepared as described in the corresponding section of procedure A.

(II) Preparation of a Peptide (Module a, Module B and Linker L)

The fully protected peptide (module A, module B and linker L) was assembled on solid support according to Method J as described above. Allyl deprotection and coupling of the protected peptide fragment (module B and linker L) were performed as indicated in the corresponding sections of procedure A.

Acylation of the N-terminal amino group was then carried out as indicated in the corresponding section of procedure B.

Subsequently, removal of the alloc protecting group from the amino function was performed as described for allyl and alloc deprotection (module B) in the corresponding section of procedure A.

Thereafter, the following steps was carried out:
Cleavage of Peptide from Resin and Removal of the 2-Phenyl-Isopropyl Protecting Group from the Carboxyl Function The resin was swollen in 1 mL $CH_2Cl_2$ (2×10 min). After filtration, the resin was suspended in 1 mL of 1% TFA in $CH_2Cl_2$ (v/v) for 10-30 min. The resin was then filtered and washed three times with 1 mL of $CH_2Cl_2$, and a solution of 1 mL of 40% DIPEA in $CH_2Cl_2$ (v/v) was added to the combined filtrate and washings. LC-MS was used to monitor the cleavage and, if required, the cleavage procedure was repeated 3-5 times. The combined filtrate and washings were evaporated to dryness.

Lactam Interstrand Linkage Formation

The protected peptide was first solubilized in 0.5 mL $CH_2Cl_2$, followed by the addition of 8 mL DMF. Then 6 eq NMM in 2 mL DMF, and 2 eq HATU and 1 eq HOAt in 2 mL DMF were added, and the reaction mixture was stirred for approximately 16 h. The volatiles were removed by evaporation. The crude cyclic peptide was dissolved in 7 mL of $CH_2Cl_2$ and washed three times with 4.5 mL 10% acetonitrile in water (v/v). The $CH_2Cl_2$ layer was then evaporated to dryness.

Full deprotection was then performed as indicated in the corresponding section of procedure A.

Finally, the peptide was purified by preparative reverse phase LC-MS, as described herein below.

1.1.3.16 Procedure N2:

Preparation of a Peptide Having a Lactam Interstrand Linkage Between a Side-Chain Carboxyl Group and a Side-Chain Amino Group in Module A Having a Carboxylamide Group at the C-Terminus and being Acylated at the N-Terminal Amino Group The peptide was prepared based on an on-resin fragment coupling strategy.

(I) Preparation of a Protected Peptide Fragment (Module B and Linker L)

The protected peptide fragment encompassing amino acid residues of module B and linker L was prepared as described in the corresponding section of procedure A.

(II) Preparation of a Peptide (Module a, Module B and Linker L)

The fully protected peptide (module A, module B and linker L) was assembled on solid support according to Method J as described above. Allyl deprotection and coupling of the protected peptide fragment (module B and linker L) were performed as indicated in the corresponding sections of procedure A.

Acylation of the N-terminal amino group was then carried out as indicated in the corresponding section of procedure B.

Subsequently, the following step was performed:
ivDde Deprotection

The resin was swollen in 1 mL DMF for 10 min and subsequently filtered off. For deprotection, 1 mL of a 5% solution of hydrazine monohydrate in DMF (v/v) was added and the reaction mixture was shaken for 30 min. The reaction mixture was then filtered off and washed with 1 mL DMF. The deprotection step was repeated by employing the same amount of reagents. LC-MS was used to monitor the deprotection reaction and, if required, the deprotection procedure was repeated again. Finally, the resin was thoroughly washed with DMF, $CH_2Cl_2$, DMF, and iPrOH, and finally washed again with $CH_2Cl_2$.

Cleavage of peptide from resin and removal of the 2-phenyl-isopropyl protecting group from the carboxyl function, formation of the lactam interstrand linkage and full deprotection were then performed as indicated in the corresponding section of procedure N1, in the same order.

Finally, the peptide was purified by preparative reverse phase LC-MS, as described herein below.

1.1.3.17 Procedure O:

Preparation of a Peptide Having a Disulfide Interstrand Linkage(s) in Module A Having a Carboxylamide Group at the C-Terminus and Having an α-Hydroxy Acid Residue Attached to the N-Terminal Amino Acid Residue The peptide was prepared based on an on-resin fragment coupling strategy.

(I) Preparation of a Protected Peptide Fragment (Module B and Linker L)

The protected peptide fragment encompassing amino acid residues of module B and linker L was prepared as described in the corresponding section of procedure A.

(II) Preparation of a Peptide (Module a, Module B and Linker L)

The fully protected peptide (module A, module B and linker L) was assembled on solid support according to Method K as described above. Appropriately protected Fmoc amino acid building blocks with a thiol group protected as trityl thioether were used for the addition of amino acid residues that are involved in the formation of a disulfide interstrand linkage(s). Allyl deprotection and coupling of the protected peptide fragment (module B and linker L) were performed as indicated in the corresponding sections of procedure A.

Subsequently, cleavage of the peptide from the resin, formation of a disulfide interstrand linkage(s), and full deprotection were performed as indicated in the corresponding sections of procedure L, following the same order.

Finally, the peptide was purified by preparative reverse phase LC-MS, as described herein below.

1.1.3.18 Procedure P:

Preparation of a Peptide Having a Disulfide Interstrand Linkage(s) in Module A Having a Carboxylamide Group at the C-Terminus and Having a Thiol-Substituted Acid Residue Attached to the N-Terminal Amino Acid Residue The peptide was prepared based on an on-resin fragment coupling strategy.

(I) Preparation of a Protected Peptide Fragment (Module B and Linker L)

The protected peptide fragment encompassing amino acid residues of module B and linker L was prepared as described in the corresponding section of procedure A.

(II) Preparation of a Peptide (Module a, Module B and Linker L)

The fully protected peptide (module A, module B and linker L) was assembled on solid support according to Method L as described above. An appropriately protected Fmoc amino acid building block(s) with a thiol group protected as trityl thioether and an appropriately protected acid building block with a thiol group protected as trityl thioether were used for the addition of the residues that are involved in the formation of a disulfide interstrand linkage(s). Allyl deprotection and coupling of the protected peptide fragment (module B and linker L) were performed as indicated in the corresponding sections of procedure A.

Subsequently, cleavage of the peptide from the resin, formation of a disulfide interstrand linkage(s), and full deprotection were performed as indicated in the corresponding sections of procedure L, following the same order.

Finally, the peptide was purified by preparative reverse phase LC-MS, as described herein below.

1.1.3.19 Procedure Q:

Preparation of a Peptide Having a Salt Bridge(s) in Module A Having a Carboxylamide Group at the C-Terminus and being Acylated at the N-Terminal Amino Group The peptide was prepared based on an on-resin fragment coupling strategy.

(I) Preparation of a Protected Peptide Fragment (Module B and Linker L)

The protected peptide fragment encompassing amino acid residues of module B and linker L was prepared as described in the corresponding section of procedure A.

(II) Preparation of a Peptide (Module a, Module B and Linker L)

The fully protected peptide (module A, module B and linker L) was assembled on solid support according to Method J as described above. Allyl deprotection and coupling of the protected peptide fragment (module B and linker L) were performed as indicated in the corresponding sections of procedure A.

Acylation of the N-terminal amino group was then carried out as indicated in the corresponding section of procedure B.

Subsequently, cleavage of the peptide from the resin and full deprotection were performed as indicated in the corresponding sections of procedure L.

Finally, the peptide was purified by preparative reverse phase LC-MS, as described herein below.

1.1.3.20 Procedure R:

Preparation of a Peptide Having a Lactam Interstrand Linkage Between a Side-Chain Carboxyl Group and a Side-Chain Amino Group in Module A Having a Carboxylamide Group at the C-Terminus and being Acetylated at the N-Terminal Amino Group The peptide was prepared based on an on-resin fragment coupling strategy.

(I) Preparation of a Protected Peptide Fragment (Module B and Linker L)

The protected peptide fragment encompassing amino acid residues of module B and linker L was prepared as described in the corresponding section of procedure A.

(II Preparation of a Peptide (Module a, Module B and Linker L)

The fully protected peptide (module A, module B and linker L) was assembled on solid support according to Method J as described above. Allyl deprotection and coupling of the protected peptide fragment (module B and linker L) were performed as indicated in the corresponding sections of procedure A.

Acylation of the N-terminal amino group was then carried out as indicated in the corresponding section of procedure B.

Subsequently, allyl-deprotection, ivDde deprotection, and formation of lactam interstrand linkage were performed as indicated in the corresponding section of procedure G, following the same order.

Cleavage of peptide from resin and full deprotection were then performed as indicated in the corresponding sections of procedure A.

Finally, the peptide was purified by preparative reverse phase LC-MS, as described herein below.

1.1.3.21 Procedure S:

Preparation of a Peptide Having a Lactam Interstrand Linkage Between a Side-Chain Carboxyl Group and a Side-Chain Amino Group in Module A Having a Carboxylamide Group at the C-Terminus and Having an α-Hydroxy Acid at the N-Terminus The peptide was prepared based on an on-resin fragment coupling strategy.

(I) Preparation of a Protected Peptide Fragment (Module B and Linker L)

The protected peptide fragment encompassing amino acid residues of module B and linker L was prepared as described in the corresponding section of procedure A.

(II) Preparation of a Peptide (Module a, Module B and Linker L)

The fully protected peptide (module A, module B and linker L) was assembled on solid support according to Method K as described above. Allyl deprotection and coupling of the protected peptide fragment (module B and linker L) were performed as indicated in the corresponding sections of procedure A.

Subsequently, removal of the alloc protecting group from the amino function was performed as described for allyl and alloc deprotection (module B) in the corresponding section of procedure A.

Thereafter, the following steps was carried out:

Cleavage of Peptide from Resin and Removal of the 2-Phenyl-Isopropyl Protecting Group from the Carboxyl Function The resin was swollen in 1 mL $CH_2Cl_2$ (2×10 min). After filtration, the resin was suspended in 1 mL of 1% TFA in $CH_2Cl_2$ (v/v) for 10-30 min. The resin was then filtered and washed three times with 1 mL of $CH_2Cl_2$, and a solution of 1 mL of 40% DIPEA in $CH_2Cl_2$ (v/v) was added to the combined filtrate and washings. LC-MS was used to monitor the cleavage and, if required, the cleavage procedure was repeated 3-5 times. The combined filtrate and washings were evaporated to dryness.

Lactam Interstrand Linkage Formation

The protected peptide was first solubilized in 0.5 mL $CH_2Cl_2$, followed by the addition of 8 mL DMF. Then 6 eq NMM in 2 mL DMF, and 2 eq HATU and 1 eq HOAt in 2 mL DMF were added, and the reaction mixture was stirred for approximately 16 h. The volatiles were removed by evaporation. The crude cyclic peptide was dissolved in 7 mL of $CH_2Cl_2$ and washed three times with 4.5 mL 10% acetonitrile in water (v/v). The $CH_2Cl_2$ layer was then evaporated to dryness.

Full deprotection was then performed as indicated in the corresponding section of procedure A.

Finally, the peptide was purified by preparative reverse phase LC-MS, as described herein below.

1.1.4 Purification Procedure (Preparative Reverse Phase LC-MS)

Compounds were purified by reverse phase chromatography using a Waters XBridge C8 OBD column, 30×150 mm, 5 μm (Cat No. 186003083), a Waters XSelect C18 OBD column, 30×150 mm, 5 μm (Cat. 186005426), or a Waters CSH XSelect Phenyl Hexyl column, 50×300 mm, 5 μm.

Mobile phases used were:

A: 0.1% TFA in Water/Acetonitrile 98/2 v/v

B: 0.1% TFA in Acetonitrile

Gradient slopes in the preparative runs were adapted each time based on analytical LC-MS analysis of the crude product. As an example, a typical run (purification of Ex. 204) was executed using two Waters CSH XSelect Phenyl Hexyl columns in series with a flow rate of 130 mL/min and at a column temperature of 50° C., running a gradient from 0-2.1 min 0% B, at 2.2 min 14% B to 38.2 min 18% B, and finally 48.0-55.0 min 100% B (retention time: 20.7 min in this case).

Detection: MS and UV @ 220 nm

Fractions collected were evaporated using a Genevac HT4/HT12 evaporator a Buchi system.

Alternatively for larger amounts the following LC-purification system was used:

Column: Waters XBridge C18 OBD column, 50×250 mm, 10 μm (Cat No. 186003900)

Mobile phase A: 0.1% TFA in Water/Acetonitrile 98/2 v/v
Mobile phase B: 0.1% TFA in Acetonitrile
Flow rate: 150 mL/min
Detection: UV @ 220 nm After lyophilisation the products were obtained typically as white to off-white powders. Unless otherwise indicated the obtained products as TFA salts were analysed by HPLC-ESI-MS methods as described below. Salt exchange to obtain the corresponding products as acetate salts or chloride salts was performed using procedures described under 1.1.5, and obtained products as acetate salts or chloride salts were analysed by HPLC-ESI-MS methods as described below.

1.1.5 Salt Exchange Procedure

Purification of compounds according to procedure 1.1.4 above provided the products as TFA salts. Conversion of the products to the corresponding acetate salts was performed using AG® 1-X2 Resin (acetate form, 2% crosslinkage, 200-400 dry mesh size; Bio-Rad, 140-1253). For the conversion of the products to the corresponding chloride salts AG® 1-X2 Resin (chloride form, 2% crosslinkage, 200-400 dry mesh; Bio-Rad, 140-1251) was used. Salt exchanges were carried out based on the corresponding instruction manual of the supplier.

After lyophilisation the products were obtained typically as white to off-white powders and analysed by HPLC-ESI-MS methods as described below.

1.2 Analytical Methods 1.2.1 Analytical Method A

Analytical HPLC retention times (rt, in minutes) were determined using an Ascentis Express C8 column 100×3 mm, 2.7 μm (Supelco, 53852-U) with the following solvents A (H$_2$O+0.1% TFA) and B (CH$_3$CN+0.085% TFA) and the gradient: 0-0.1 min: 95% A, 5% B; 7 min: 45% A, 55% B; 7.02-7.5 min: 3% A, 97% B; 7.52-7.8 min: 95% A, 5% B. Flow rate=1.4 mL/min at 55° C.

1.2.2 Analytical Method B

Analytical HPLC retention times (rt, in minutes) were determined using a Poroshell Bonus RP 100×3 mm, 2.7 μm (Agilent technologies, 695968-301) with the following solvents A (H$_2$O+0.1% TFA) and B (CH$_3$CN+0.085% TFA) and the gradient: 0-0.1 min: 95% A, 5% B; 7 min: 45% A, 55% B; 7.02-7.5 min: 3% A, 97% B; 7.52-7.8 min: 95% A, 5% B. Flow rate=1.4 mL/min at 55° C.

1.2.3 Analytical Method C

Analytical HPLC retention times (rt, in minutes) were determined using an Ascentis Express C8 column, 100×3 mm, 2.7 μm (Supelco, 53852-U) with the following solvents A (H$_2$O+0.1% TFA) and B (CH$_3$CN+0.085% TFA) and the gradient: 0-0.1 min: 95% A, 5% B; 7 min: 15% A, 85% B; 7.02-7.5 min: 3% A, 97% B; 7.52-7.8 min: 95% A, 5% B. Flow rate=1.4 mL/min at 55° C.

1.2.4 Analytical Method D

Analytical HPLC retention times (rt, in minutes) were determined using an Ascentis Express C8 column 100×3 mm, 2.7 μm (Supelco, 53852-U) with the following solvents A (H$_2$O+0.1% TFA) and B (CH$_3$CN+0.085% TFA) and the gradient: 0-0.1 min: 95% A, 5% B; 7 min: 45% A, 55% B; 7.02-7.5 min: 3% A, 97% B; 7.52-7.8 min: 95% A, 5% B. Flow rate=1.4 mL/min at 70° C.

1.2.5 Analytical Method E

Analytical HPLC retention times (rt, in minutes) were determined using an Ascentis Express C8 column 100×3 mm, 2.7 μm (Supelco, 53852-U) with the following solvents A (H$_2$O+0.1% TFA) and B (CH$_3$CN+0.085% TFA) and the gradient: 0-0.1 min: 95% A, 5% B; 11 min: 45% A, 55% B; 11.02-12.5 min: 3% A, 97% B; 12.55-13.5 min: 95% A, 5% B. Flow rate=1.4 mL/min at 55° C.

1.2.6 Analytical Method F

Analytical HPLC retention times (rt, in minutes) were determined using a Poroshell Bonus RP 100×3 mm, 2.7 μm (Agilent technologies, 695968-301) with the following solvents A (H$_2$O+0.1% TFA) and B (CH$_3$CN+0.085% TFA) and the gradient: 0-0.1 min: 95% A, 5% B; 7 min: 45% A, 55% B; 7.02-7.5 min: 3% A, 97% B; 7.52-7.8 min: 95% A, 5% B. Flow rate=1.4 mL/min at 70° C.

1.2.7 Analytical Method G

Analytical HPLC retention times (rt, in minutes) were determined using a XSelect CSH Phenyl-Hexyl 150×3 mm, 2.5 μm (Waters, 186006734) with the following solvents A (H2O 2O+0.1% TFA) and B (CH3CN+0.085% TFA) and the gradient: 0-0.1 min: 95% A, 5% B; 7 min: 45% A, 55% B; 7.02-7.7 min: 3% A, 97% B; 7.72-9.95 min: 95% A, 5% B. Flow rate=1.3 mL/min at 55° C.

1.2.8 Analytical Method H

Analytical HPLC retention times (rt, in minutes) were determined using a Ascentis Express C8 100×3 mm, 2.7 μm (Supelco, 53852-U) with the following solvents A (H2O 2O+0.1% TFA) and B (CH3CN+0.085% TFA) and the gradient: 0-0.1 min: 95% A, 5% B; 12.1 min: 45% A, 55% B; 12.12-13.1 min: 3% A, 97% B; 13.12-14.8 min: 95% A, 5% B. Flow rate=0.750 mL/min at 55° C.

1.2.8 Analytical Method I

Analytical HPLC retention times (rt, in minutes) were determined using a Poroshell Bonus RP 100×3 mm, 2.7 μm (Agilent technologies, 695968-301) with the following solvents A (H2O 2O+0.1% TFA) and B (CH3CN+0.085% TFA) and the gradient: 0-0.1 min: 95% A, 5% B; 12.1 min: 45% A, 55% B; 12.12-13.1 min: 3% A, 97% B; 13.12-15.2 min: 95% A, 5% B. Flow rate=0.750 mL/min at 55° C.

1.3 Synthesis of Peptide Sequences

Example 1 is shown in Table 1.

Procedure C, as described above, was used for the preparation of the peptide, applying an on-resin fragment coupling strategy.

(I) The protected peptide fragment (module B and linker L) was synthesized starting with the amino acid Fmoc-Thr-allyl ester, which was grafted to the resin (Fmoc-Thr(-2-chlorotrityl resin)-allyl). The peptide fragment was synthesized on solid support according to method A as described above. Following coupling of Fmoc-Dab(Alloc)-OH for addition of the amino acid residue at $Q^1$, allyl and alloc deprotection (module B), and macrolactam cycle formation (module B) by an amide bond between the liberated α-carboxyl group of Thr at $Q^7$ and the liberated γ-amino group of Dab at $Q^1$ was performed as indicated in the corresponding sections of procedure A above. Assembly of the peptide fragment was in the following sequence:

Resin-Thr-$Q^6$-$Q^5$-$Q^4$-$Q^3$-$Q^2$-$Q^1$-$L^3$-$L^2$-$L^1$.

Subsequently, cleavage of the protected peptide fragment from the resin and preparation of the free base of the protected peptide fragment were performed as indicated in procedure A above.

(II) The fully protected peptide (module A, module B and linker L) was assembled on solid support according to method D as described above.

The peptide was synthesized starting with the amino alcohol Fmoc-Glyol, which was grafted to the resin (Fmoc-Glyol-2-chlorotrityl resin), using Fmoc-Glu(Allyl)-OH for addition of the amino acid residue at at $P^5$ and using 3-methyl-butanoic acid for addition of the acid residue at $P^1$. Coupling of the protected peptide fragment (module B and linker L) was performed as indicated in the corresponding section of procedure A above by formation of an amide bond between the γ-carboxyl group of Glu at $P^5$ and the α-amino group of Dab at $L^1$. Assembly of the peptide was in the following sequence, showing only residues of module A:

Resin-Glyol-$P^{11}$-$P^{10}$-$P^9$-$P^8$-$P^7$-$P^6$-$P^5$-$P^4$-$P^3$-$P^2$-$P^1$.

Subsequently, cleavage of the peptide from the resin, formation of the disulfide interstrand linkage between $P^2$ and $P^{11}$, and full deprotection were performed as indicated in procedure C above. Finally, the peptide was purified, as described above, and characterized by HPLC-MS. For analytical data, see Ex. 1 in Table 2.

Examples 2 and 4 are shown in Table 1.

Procedure C, as described above, was used for the preparation of the peptides, applying an on-resin fragment coupling strategy.

(I) The protected peptide fragment (module B and linker L) was synthesized as described above in the corresponding section in the synthesis of Ex. 1. Assembly of the peptide fragment was in the following sequence:

Resin-Thr-$Q^6$-$Q^5$-$Q^4$-$Q^3$-$Q^2$-$Q^1$-$L^3$-$L^2$-$L^1$.

(II) The fully protected peptides (module A, module B and linker L) were assembled on solid support according to method D as described above.

The peptides were synthesized starting with the amino alcohol Fmoc-Throl(tBu), which was grafted to the resin (Fmoc-Throl(tBu)-2-chlorotrityl resin), using Fmoc-Glu(Allyl)-OH for addition of the amino acid residue at $P^5$ and using 3-methyl-butanoic acid for addition of the acid residue at $P^1$. Coupling of the protected peptide fragment (module B and linker L) was performed as indicated in the corresponding section of procedure A above by formation of an amide bond between the γ-carboxyl group of Glu at $P^5$ and the α-amino group of Dab at $L^1$. Assembly of the peptides was in the following sequence, showing only residues of module A:

Resin-Throl-$P^{11}$-$P^{10}$-$P^9$-$P^8$-$P^7$-$P^6$-$P^5$-$P^4$-$P^3$-$P^2$-$P^1$.

Subsequently, cleavage of the peptides from the resin, formation of the disulfide interstrand linkage between $P^2$ and $P^{11}$, and full deprotection were performed as indicated in procedure C above. Finally, the peptides were purified, as described above, and characterized by HPLC-MS. For analytical data, see Ex. 2 and 4 in Table 2. Example 3 is shown in Table 1.

Procedure C, as described above, was used for the preparation of the peptide, applying an on-resin fragment coupling strategy.

(I) The protected peptide fragment (module B and linker L) was synthesized as described above in the corresponding section in the synthesis of Ex. 1. Assembly of the peptide fragment was in the following sequence:

Resin-Thr-$Q^6$-$Q^5$-$Q^4$-$Q^3$-$Q^2$-$Q^1$-$L^3$-$L^2$-$L^1$.

(II) The fully protected peptide (module A and linker L) was assembled on solid support according to method D as described above.

The peptide was synthesized starting with the amino alcohol Fmoc-Throl(tBu), which was grafted to the resin (Fmoc-Throl(tBu)-2-chlorotrityl resin), using Fmoc-Glu(Allyl)-OH for addition of the amino acid residue at $P^5$ and using isobutyric acid for addition of the acid residue at $P^1$. Coupling of the protected fragment (module B and linker L) was performed as indicated in the corresponding section of procedure A above by formation of an amide bond between the γ-carboxyl group of Glu at $P^5$ and the α-amino group of Dab at $L^1$. Assembly of the peptide was in the following sequence, showing only residues of module A:

Resin-Throl-$P^{11}$-$P^{10}$-$P^9$-$P^8$-$P^7$-$P^6$-$P^5$-$P^4$-$P^3$-$P^2$-$P^1$.

Subsequently, cleavage of the peptide from the resin, formation of the disulfide interstrand linkage between $P^2$ and $P^{11}$, and full deprotection were performed as indicated in procedure C above. Finally, the peptide was purified, as described above, and characterized by HPLC-MS. For analytical data, see Ex. 3 in Table 2.

Example 5 is shown in Table 1.

Procedure C, as described above, was used for the preparation of the peptide, applying an on-resin fragment coupling strategy.

(I) The protected peptide fragment (module B and linker L) was synthesized as described above in the corresponding section in the synthesis of Ex. 1.

Assembly of the peptide fragment was in the following sequence:

Resin-Thr-$Q^6$-$Q^5$-$Q^4$-$Q^3$-$Q^2$-$Q^1$-$L^3$-$L^2$-$L^1$.

(II) The fully protected peptide (module A, module B and linker L) was assembled on solid support according to method D as described above.

The peptide was synthesized starting with the amino alcohol Fmoc-Serol(tBu), which was grafted to the resin (Fmoc-Serol(tBu)-2-chlorotrityl resin), using Fmoc-Glu(Allyl)-OH for addition of the amino acid residue at $P^5$ and using 3-methyl-butanoic acid for addition of the acid residue at $P^1$. Coupling of the protected peptide fragment (module B and linker L) was performed as indicated in the corresponding section of procedure A above by formation of an amide bond between the γ-carboxyl group of Glu at $P^5$ and the α-amino group of Dab at $L^1$. Assembly of the peptide was in the following sequence, showing only residues of module A:

Resin-Throl-$P^{11}$-$P^{10}$-$P^9$-$P^8$-$P^7$-$P^6$-$P^5$-$P^4$-$P^3$-$P^2$-$P^1$.

Subsequently, cleavage of the peptide from the resin, formation of the disulfide interstrand linkage between $P^2$ and $P^{11}$, and full deprotection were performed as indicated in procedure C above. Finally, the peptide was purified, as described above, and characterized by HPLC-MS. For analytical data, see Ex. 5 in Table 2.

Examples 6, 8 and 10 are shown in Table 1.

Procedure M1, as described above, was used for the preparation of the peptides, applying an on-resin fragment coupling strategy.

(I) The protected peptide fragment (module B and linker L) was synthesized as described above in the corresponding section in the synthesis of Ex. 1.

Assembly of the peptide fragment was in the following sequence:

Resin-Thr-$Q^6$-$Q^5$-$Q^4$-$Q^3$-$Q^2$-$Q^1$-$L^3$-$L^2$-$L^1$.

(II) The fully protected peptides (module A, module B and linker L) were assembled on solid support according to method J.

The peptides were synthesized starting with an appropriately protected Fmoc-amino acid, which was used in the first coupling cycle for grafting the amino acid residue at $P^{11}$ to Sieber amide resin, and using Fmoc-Glu(Allyl)-OH for addition of the amino acid residue at $P^5$. Coupling of the protected peptide fragment (module B and linker L) was performed as indicated in the corresponding section of procedure A above by formation of an amide bond between the γ-carboxyl group of Glu at $P^5$ and the α-amino group of Dab at $L^1$. Assembly of the peptides was in the following sequence, showing only residues of module A:

Resin-Throl-$P^{11}$-$P^{10}$-$P^9$-$P^8$-$P^7$-$P^6$-$P^5$-$P^4$-$P^3$-$P^2$-$P^1$.

Subsequently, acylation with acetic acid at $P^1$, cleavage of the peptides from the resin, formation of the disulfide interstrand linkage between $P^2$ and $P^{11}$, and full deprotection were performed as indicated in procedure M1 above. Finally, the peptides were purified, as described above, and characterized by HPLC-MS. For analytical data, see Ex. 6, 8 and 10 in Table 2.

Example 7 is shown in Table 1.

Procedure O, as described above, was used for the preparation of the peptide, applying an on-resin fragment coupling strategy.

(I) The protected peptide fragment (module B and linker L) was synthesized as described above in the corresponding section in the synthesis of Ex. 1. Assembly of the peptide fragment was in the following sequence:

Resin-Thr-$Q^6$-$Q^5$-$Q^4$-$Q^3$-$Q^2$-$Q^1$-$L^3$-$L^2$-$L^1$ (II) The fully protected peptide (module A, module B and linker L) was assembled on solid support according to method K as described above.

The peptide was synthesized starting with an appropriately protected Fmoc-amino acid, which was used in the first coupling cycle for grafting the amino acid residue at $P^{11}$ to Sieber amide resin, and using Fmoc-Glu(Allyl)-OH for addition of the amino acid residue at $P^5$. Coupling of the protected peptide fragment (module B and linker L) was performed as indicated in the corresponding section of procedure A above by formation of an amide bond between the γ-carboxyl group of Glu at $P^5$ and the α-amino group of Dab at $L^1$. Assembly of the peptide was in the following sequence, showing only residues of module A:

Resin-$P^{11}$-$P^{10}$-$P^9$-$P^8$-$P^7$-$P^6$-$P^5$-$P^4$-$P^3$-$P^2$-$P^1$.

Subsequently, cleavage of the peptide from the resin, formation of the disulfide interstrand linkage between $P^2$ and $P^{11}$, and full deprotection were performed as indicated in procedure O above. Finally, the peptide was purified, as described above, and characterized by HPLC-MS. For analytical data, see Ex. 7 in Table 2.

Examples 9 and 57 are shown in Table 1.

Procedure L, as described above, was used for the preparation of the peptides, applying an on-resin fragment coupling strategy.

(I) The protected peptide fragments (module B and linker L) were synthesized as described above in the corresponding section in the synthesis of Ex. 1.

Assembly of the peptide fragments was in the following sequence:

Resin-Thr-$Q^6$-$Q^5$-$Q^4$-$Q^3$-$Q^2$-$Q^1$-$L^3$-$L^2$-$L^1$.

(II) The fully protected peptides (module A, module B and linker L) were assembled on solid support according to method I as described above.

The peptides were synthesized starting with an appropriately protected Fmoc-amino acid, which was used in the first coupling cycle for grafting the amino acid residue at $P^{11}$ to Sieber amide resin, and using Fmoc-Glu(Allyl)-OH for addition of the amino acid residue at $P^5$. Coupling of the protected peptide fragment (module B and linker L) was performed as indicated in the corresponding section of procedure A above by formation of an amide bond between the γ-carboxyl group of Glu at $P^5$ and the α-amino group of Dab at $L^1$. Assembly of the peptides was in the following sequence, showing only residues of module A:

Resin-$P^{11}$-$P^{10}$-$P^9$-$P^8$-$P^7$-$P^6$-$P^5$-$P^4$-$P^3$-$P^2$-$P^1$.

Subsequently, cleavage of the peptide from the resin, formation of the disulfide interstrand linkage between $P^2$ and $P^{11}$, and full deprotection were performed as indicated in procedure L above. Finally, the peptides were purified, as described above, and characterized by HPLC-MS. For analytical data, see Ex. 9 and 57 in Table 2.

Example 11 is shown in Table 1.

Procedure M1, as described above, was used for the preparation of the peptide, applying an on-resin fragment coupling strategy.

(I) The protected peptide fragment (module B and linker L) was synthesized as described above in the corresponding section in the synthesis of Ex. 1.

Assembly of the peptide fragment was in the following sequence:

Resin-Thr-$Q^6$-$Q^5$-$Q^4$-$Q^3$-$Q^2$-$Q^1$-$L^3$-$L^2$-$L^1$.

(II) The fully protected peptide (module A, module B and linker L) was assembled on solid support according to method J as described above.

The peptide was synthesized starting with an appropriately protected Fmoc-amino acid, which was used in the first coupling cycle for grafting the amino acid residue at $P^{11}$ to Sieber amide resin, and using Fmoc-Glu(Allyl)-OH for addition of the amino acid residue at $P^5$. Coupling of the protected peptide fragment (module B and linker L) was performed as indicated in the corresponding section of procedure A above by formation of an amide bond between the γ-carboxyl group of Glu at $P^5$ and the α-amino group of Dab at $L^1$. Assembly of the peptide was in the following sequence, showing only residues of module A:

Resin-$P^{11}$-$P^{10}$-$P^9$-$P^8$-$P^7$-$P^6$-$P^5$-$P^4$-$P^3$-$P^2$-$P^1$.

Subsequently, acylation with acetic acid at $P^1$, cleavage of the peptide from the resin, formation of the disulfide interstrand linkage between $P^4$ and $P^9$, and full deprotection were performed as indicated in procedure M1 above. Finally, the peptide was purified, as described above, and characterized by HPLC-MS. For analytical data, see Ex. 11 in Table 2.

Example 12 is shown in Table 1.

Procedure L, as described above, was used for the preparation of the peptide, applying an on-resin fragment coupling strategy.

(I) The protected peptide fragment (module B and linker L) was synthesized as described above in the corresponding section in the synthesis of Ex. 1. Assembly of the peptide fragment was in the following sequence:

Resin-Thr-$Q^6$-$Q^5$-$Q^4$-$Q^3$-$Q^2$-$Q^1$-$L^3$-$L^2$-$L^1$.

(II) The fully protected peptide (module A, module B and linker L) was assembled on solid support according to method I as described above.

The peptide was synthesized starting with an appropriately protected Fmoc-amino acid, which was used in the first coupling cycle for grafting the amino acid residue at $P^{11}$ to Sieber amide resin, and using Fmoc-Glu(Allyl)-OH for addition of the amino acid residue at $P^5$. Coupling of the protected peptide fragment (module B and linker L) was performed as indicated in the corresponding section of procedure A above by formation of an amide bond between the γ-carboxyl group of Glu at $P^5$ and the α-amino group of Dab at $L^1$. Assembly of the peptide was in the following sequence, showing only residues of module A:

Resin-$P^{11}$-$P^{10}$-$P^9$-$P^8$-$P^7$-$P^6$-$P^5$-$P^4$-$P^3$-$P^2$-$P^1$.

Subsequently, cleavage of the peptide from the resin, formation of the disulfide interstrand linkage between $P^4$ and $P^9$, and full deprotection were performed as indicated in procedure L above. Finally, the peptide was purified, as described above, and characterized by HPLC-MS. For analytical data, see Ex. 12 in Table 2.

Examples 13 and 14 are shown in Table 1.

Procedure M1, as described above, was used for the preparation of the peptides, applying an on-resin fragment coupling strategy.

(I) The protected peptide fragment (module B and linker L) was synthesized as described above in the corresponding section in the synthesis of Ex. 1.

Assembly of the peptide fragment was in the following sequence:

Resin-Thr-$Q^6$-$Q^5$-$Q^4$-$Q^3$-$Q^2$-$Q^1$-$L^3$-$L^2$-$L^1$.

(II) The fully protected peptides (module A, module B and linker L) were assembled on solid support according to method J.

The peptides were synthesized starting with an appropriately protected Fmoc-amino acid, which was used in the first coupling cycle for grafting the amino acid residue at $P^{10}$ to Sieber amide resin, and using Fmoc-Glu(Allyl)-OH for addition of the amino acid residue at $P^5$. Coupling of the protected peptide fragment (module B and linker L) was performed as indicated in the corresponding section of procedure A above by formation of an amide bond between the γ-carboxyl group of Glu at $P^5$ and the α-amino group of Dab at $L^1$. Assembly of the peptides was in the following sequence, showing only residues of module A:

Resin-$P^{11}$-$P^{10}$-$P^9$-$P^8$-$P^7$-$P^6$-$P^5$-$P^4$-$P^3$-$P^2$-$P^1$.

Subsequently, acylation with acetic acid at $X^{14}$, cleavage of the peptides from the resin, formation of the disulfide interstrand linkage between $P^4$ and $P^9$, and full deprotection were performed as indicated in procedure M1 above. Finally, the peptides were purified, as described above, and characterized by HPLC-MS. For analytical data, see Ex. 13 and 14 in Table 2.

Examples 15 to 18, 23, 25 and 31 to 38 are shown in Table 1.

Procedure J, as described above, was used for the preparation of the peptides, applying an on-resin fragment coupling strategy.

(I) The protected peptide fragments (module B and linker L) were synthesized as described above in the corresponding section in the synthesis of Ex. 1. Assembly of the peptide fragments was in the following sequence:

Resin-Thr-$Q^6$-$Q^5$-$Q^4$-$Q^3$-$Q^2$-$Q^1$-$L^3$-$L^2$-$L^1$.

(II) The fully protected peptides (module A, module B and linker L) were assembled on solid support according to method G as described above.

The peptides were synthesized starting with the amino acid Fmoc-$^D$Thr(tBu)-OH, which was grafted to the resin (Fmoc-$^D$Thr(tBu)-2-chlorotrityl resin) and using Fmoc-Glu(Allyl)-OH for addition of the amino acid residue at $P^5$. Coupling of the protected peptide fragment (module B and linker L) was performed as indicated in the corresponding section of procedure A above by formation of an amide bond between the γ-carboxyl group of Glu at $P^5$ and the α-amino group of Dab at $L^1$. Assembly of the peptides was in the following sequence, showing only residues of module A:

Resin-$^D$Thr-$P^{10}$-$P^9$-$P^8$-$P^7$-$P^6$-$P^5$-$P^4$-$P^3$-$P^2$-$P^1$.

Subsequently, removal of the alloc protecting group at $P^2$, cleavage of the peptides from the resin, formation of the lactam interstrand linkage by an amide bond between the liberated side-chain amino group of the amino acid residue at $P^2$ and the liberated α-carboxyl group of $^D$Thr at $P^{11}$, and full deprotection were performed as indicated in procedure J above. Finally, the peptides were purified, as described above, and characterized by HPLC-MS. For analytical data, see Ex. 15 to 18, 23, 25 and 31 to 38 in Table 2.

Example 19 is shown in Table 1.

Procedure J, as described above, was used for the preparation of the peptide, applying an on-resin fragment coupling strategy.

(I) The protected peptide fragment (module B and linker L) was synthesized as described above in the corresponding section in the synthesis of Ex. 1.

Assembly of the peptide fragment was in the following sequence:

Resin-Thr-$Q^6$-$Q^5$-$Q^4$-$Q^3$-$Q^2$-$Q^1$-$L^3$-$L^2$-$L^1$.

(II) The fully protected peptide (module A, module B and linker L) was assembled on solid support according to method G as described above.

The peptide was synthesized starting with the amino acid Fmoc-$^D$Asn(Trityl)-OH, which was grafted to the resin (Fmoc-$^D$Asn(Trityl)-2-chlorotrityl resin) and using Fmoc-Glu(Allyl)-OH for addition of the amino acid residue at $P^5$. Coupling of the protected peptide fragment (module B and linker L) was performed as indicated in the corresponding section of procedure A above by formation of an amide bond between the γ-carboxyl group of Glu at $P^5$ and the α-amino group of Dab at $L^1$. Assembly of the peptide was in the following sequence, showing only residues of module A:

Resin-$^D$Asn-$P^{10}$-$P^9$-$P^8$-$P^7$-$P^6$-$P^5$-$P^4$-$P^3$-$P^2$-$P^1$.

Subsequently, removal of the alloc protecting group at $P^2$, cleavage of the peptide from the resin, formation of the lactam interstrand linkage by an amide bond between the δ-amino group of Orn at $P^2$ and the liberated α-carboxyl group of $^D$Asn at $P^{11}$, and full deprotection were performed as indicated in procedure J above. Finally, the peptide was purified, as described above, and characterized by HPLC-MS. For analytical data, see Ex. 19 in Table 2.

Example 20 is shown in Table 1.

Procedure J, as described above, was used for the preparation of the peptide, applying an on-resin fragment coupling strategy.

(I) The protected peptide fragment (module B and linker L) was synthesized as described above in the corresponding section in the synthesis of Ex. 1.

Assembly of the peptide fragment was in the following sequence:

Resin-Thr-$Q^6$-$Q^5$-$Q^4$-$Q^3$-$Q^2$-$Q^1$-$L^3$-$L^2$-$L^1$.

(II) The fully protected peptide (module A, module B and linker L) was assembled on solid support according to method G as described above.

The peptide was synthesized starting with the amino acid Fmoc-$^D$Gln(Trityl)-OH, which was grafted to the resin (Fmoc-$^D$Gln(Trityl)-2-chlorotrityl resin) and using Fmoc-Glu(Allyl)-OH for addition of the amino acid residue at $P^5$. Coupling of the protected peptide fragment (module B and linker L) was performed as indicated in the corresponding section of procedure A above by formation of an amide bond between the γ-carboxyl group of Glu at $P^5$ and the α-amino group of Dab at $L^1$. Assembly of the peptide was in the following sequence, showing only residues of module A:

Resin-$^D$Gln-$P^{10}$-$P^9$-$P^8$-$P^7$-$P^6$-$P^5$-$P^4$-$P^3$-$P^2$-$P^1$.

Subsequently, removal of the alloc protecting group at $P^2$, cleavage of the peptide from the resin, formation of the lactam interstrand linkage by an amide bond between the δ-amino group of Orn at $P^2$ and the liberated α-carboxyl group of $^D$Gln at $P^{11}$, and full deprotection were performed as indicated in procedure J above. Finally, the peptide was purified, as described above, and characterized by HPLC-MS. For analytical data, see Ex. 20 in Table 2.

Example 21 is shown in Table 1.

Procedure J, as described above, was used for the preparation of the peptide, applying an on-resin fragment coupling strategy.

(I) The protected peptide fragment (module B and linker L) was synthesized as described above in the corresponding section in the synthesis of Ex. 1.

Assembly of the peptide fragment was in the following sequence:

Resin-Thr-$Q^6$-$Q^5$-$Q^4$-$Q^3$-$Q^2$-$Q^1$-$L^3$-$L^2$-$L^1$.

(II) The fully protected peptide (module A, module B and linker L) was assembled on solid support according to method G as described above.

The peptide was synthesized starting with the amino acid Fmoc-$^D$Glu(tBu)-OH, which was grafted to the resin (Fmoc-$^D$Glu(tBu)-2-chlorotrityl resin) and using Fmoc-Glu(Allyl)-OH for addition of the amino acid residue at $P^5$. Coupling of the protected peptide fragment (module B and linker L) was performed as indicated in the corresponding section of procedure A above by formation of an amide bond between the γ-carboxyl group of Glu at $P^5$ and the α-amino group of Dab at $L^1$. Assembly of the peptide was in the following sequence, showing only residues of module A:

Resin-$^D$Glu-$P^{10}$-$P^9$-$P^8$-$P^7$-$P^6$-$P^5$-$P^4$-$P^3$-$P^2$-$P^1$.

Subsequently, removal of the alloc protecting group at $P^2$, cleavage of the peptide from the resin, formation of the lactam interstrand linkage by an amide bond between the δ-amino group of Orn at $P^2$ and the liberated α-carboxyl group of $^D$Glu at $P^{11}$, and full deprotection were performed as indicated in procedure J above. Finally, the peptide was purified, as described above, and characterized by HPLC-MS. For analytical data, see Ex. 21 in Table 2.

Example 22 is shown in Table 1.

Procedure J, as described above, was used for the preparation of the peptide, applying an on-resin fragment coupling strategy.

(I) The protected peptide fragment (module B and linker L) was synthesized as described above in the corresponding section in the synthesis of Ex. 1.

Assembly of the peptide fragment was in the following sequence:

Resin-Thr-$Q^6$-$Q^5$-$Q^4$-$Q^3$-$Q^2$-$Q^1$-$L^3$-$L^2$-$L^1$.

(II) The fully protected peptide (module A, module B and linker L) was assembled on solid support according to method G as described above.

The peptide was synthesized starting with the amino acid Fmoc-$^D$Hse(tBu)-OH, which was grafted to the resin (Fmoc-$^D$Hse(tBu)-2-chlorotrityl resin) and using Fmoc-Glu(Allyl)-OH for addition of the amino acid residue at $P^5$. Coupling of the protected peptide fragment (module B and linker L) was performed as indicated in the corresponding section of procedure A above by formation of an amide bond between the γ-carboxyl group of Glu at $P^5$ and the α-amino group of Dab at $L^1$. Assembly of the peptide was in the following sequence, showing only residues of module A:

Resin-$^D$Hse-$P^{10}$-$P^9$-$P^8$-$P^7$-$P^6$-$P^5$-$P^4$-$P^3$-$P^2$-$P^1$.

Subsequently, removal of the alloc protecting group at $P^2$, cleavage of the peptide from the resin, formation of the lactam interstrand linkage by an amide bond between the δ-amino group of Orn at $P^2$ and the liberated α-carboxyl group of $^D$Hse at $P^{11}$, and full deprotection were performed as indicated in procedure J above. Finally, the peptide was purified, as described above, and characterized by HPLC-MS. For analytical data, see Ex. 22 in Table 2.

Example 24 is shown in Table 1.

Procedure K, as described above, was used for the preparation of the peptide, applying an on-resin fragment coupling strategy.

(I) The protected peptide fragment (module B and linker L) was synthesized as described above in the corresponding section in the synthesis of Ex. 1.

Assembly of the peptide fragment was in the following sequence:

Resin-Thr-$Q^6$-$Q^5$-$Q^4$-$Q^3$-$Q^2$-$Q^1$-$L^3$-$L^2$-$L^1$.

(II) The fully protected peptide (module A, module B and linker L) was assembled on solid support according to method H as described above.

The peptide was synthesized starting with the amino acid Fmoc-$^D$Thr(tBu)-OH, which was grafted to the resin (Fmoc-$^D$Thr(tBu)-2-chlorotrityl resin), using Fmoc-Glu(Allyl)-OH for addition of the amino acid residue at $P^5$, and using alpha-hydroxyisovaleric acid (Hiv) for addition of the hydroxy acid residue at $P^1$. Coupling of the protected peptide fragment (module B and linker L) was performed as indicated in the corresponding section of procedure A above by formation of an amide bond between the γ-carboxyl group of Glu at $P^5$ and the α-amino group of Dab at $L^1$. Assembly of the peptide was in the following sequence, showing only residues of module A:

Resin-$^D$Thr-$P^{10}$-$P^9$-$P^8$-$P^7$-$P^6$-$P^5$-$P^4$-$P^3$-$P^2$-$P^1$.

Subsequently, removal of the alloc protecting group at $P^2$, cleavage of the peptide from the resin, formation of the lactam interstrand linkage by an amide bond between the δ-amino group of Orn at $P^2$ and the liberated α-carboxyl group of $^D$Thr at $P^{11}$, and full deprotection were performed as indicated in procedure K above. Finally, the peptide was purified, as described above, and characterized by HPLC-MS. For analytical data, see Ex. 24 in Table 2.

Example 26 is shown in Table 1.

Procedure J, as described above, was used for the preparation of the peptide, applying an on-resin fragment coupling strategy.

(I) The protected peptide fragment (module B and linker L) was synthesized as described above in the corresponding section in the synthesis of Ex. 1.

Assembly of the peptide fragment was in the following sequence:

Resin-Thr-$Q^6$-$Q^5$-$Q^4$-$Q^3$-$Q^2$-$Q^1$-$L^3$-$L^2$-$L^1$.

(II) The fully protected peptide (module A, module B and linker L) was assembled on solid support according to method G as described above.

The peptide was synthesized starting with the amino acid Fmoc-$^D$Tyr(tBu)-OH, which was grafted to the resin (Fmoc-$^D$Tyr(tBu)-2-chlorotrityl resin) and using Fmoc-Glu(Allyl)-OH for addition of the amino acid residue at $P^5$. Coupling of the protected peptide fragment (module B and linker L) was performed as indicated in the corresponding section of procedure A above by formation of an amide bond between the γ-carboxyl group of Glu at $P^5$ and the α-amino group of Dab at $L^1$. Assembly of the peptide was in the following sequence, showing only residues of module A:

Resin-$^D$Tyr-$P^{10}$-$P^9$-$P^8$-$P^7$-$P^6$-$P^5$-$P^4$-$P^3$-$P^2$-$P^1$.

Subsequently, removal of the alloc protecting group at $P^2$, cleavage of the peptide from the resin, formation of the lactam interstrand linkage by an amide bond between the δ-amino group of Orn at $P^2$ and the liberated α-carboxyl group of $^D$Tyr at $P^{11}$, and full deprotection were performed as indicated in procedure J above. Finally, the peptide was purified, as described above, and characterized by HPLC-MS. For analytical data, see Ex. 26 in Table 2.

Example 27 is shown in Table 1.

Procedure J, as described above, was used for the preparation of the peptide, applying an on-resin fragment coupling strategy.

(I) The protected peptide fragment (module B and linker L) was synthesized as described above in the corresponding section in the synthesis of Ex. 1.

Assembly of the peptide fragment was in the following sequence:

Resin-Thr-$Q^6$-$Q^5$-$Q^4$-$Q^3$-$Q^2$-$Q^1$-$L^3$-$L^2$-$L^1$.

(II) The fully protected peptide (module A, module B and linker L) was assembled on solid support according to method G as described above.

The peptide was synthesized starting with the amino acid Fmoc-$^D$Val-OH, which was grafted to the resin (Fmoc-$^D$Val-2-chlorotrityl resin) and using Fmoc-Glu(Allyl)-OH for addition of the amino acid residue at $P^5$. Coupling of the protected peptide fragment (module B and linker L) was performed as indicated in the corresponding section of procedure A above by formation of an amide bond between the γ-carboxyl group of Glu at $P^5$ and the α-amino group of Dab at $L^1$. Assembly of the peptide was in the following sequence, showing only residues of module A:

Resin-$^D$Val-$P^{10}$-$P^9$-$P^8$-$P^7$-$P^6$-$P^5$-$P^4$-$P^3$-$P^2$-$P^1$.

Subsequently, removal of the alloc protecting group at $P^2$, cleavage of the peptide from the resin, formation of the lactam interstrand linkage by an amide bond between the δ-amino group of Orn at $P^2$ and the liberated α-carboxyl group of $^D$Val at $P^{11}$, and full deprotection were performed as indicated in procedure J above. Finally, the peptide was purified, as described above, and characterized by HPLC-MS. For analytical data, see Ex. 27 in Table 2.

Example 28 is shown in Table 1.

Procedure J, as described above, was used for the preparation of the peptide, applying an on-resin fragment coupling strategy.

(I) The protected peptide fragment (module B and linker L) was synthesized as described above in the corresponding section in the synthesis of Ex. 1.

Assembly of the peptide fragment was in the following sequence:

Resin-Thr-$Q^6$-$Q^5$-$Q^4$-$Q^3$-$Q^2$-$Q^1$-$L^3$-$L^2$-$L^1$.

(II) The fully protected peptide (module A, module B and linker L) was assembled on solid support according to method G as described above.

The peptide was synthesized starting with the amino acid Fmoc-$^D$Dab(Boc)-OH, which was grafted to the resin (Fmoc-$^D$Dab(Boc)-2-chlorotrityl resin) and using Fmoc-Glu(Allyl)-OH for addition of the amino acid residue at $P^5$. Coupling of the protected peptide fragment (module B and linker L) was performed as indicated in the corresponding section of procedure A above by formation of an amide bond between the γ-carboxyl group of Glu at $P^5$ and the α-amino group of Dab at $L^1$. Assembly of the peptide was in the following sequence, showing only residues of module A:

Resin-$^D$Dab-$P^{10}$-$P^9$-$P^8$-$P^7$-$P^6$-$P^5$-$P^4$-$P^3$-$P^2$-$P^1$.

Subsequently, removal of the alloc protecting group at $P^2$, cleavage of the peptide from the resin, formation of the lactam interstrand linkage by an amide bond between the δ-amino group of Orn at $P^2$ and the liberated α-carboxyl group of $^D$Dab at $P^{11}$, and full deprotection were performed as indicated in procedure J above. Finally, the peptide was purified, as described above, and characterized by HPLC-MS. For analytical data, see Ex. 28 in Table 2.

Example 29 is shown in Table 1.

Procedure J, as described above, was used for the preparation of the peptide, applying an on-resin fragment coupling strategy.

(I) The protected peptide fragment (module B and linker L) was synthesized as described above in the corresponding section in the synthesis of Ex. 1.

Assembly of the peptide fragment was in the following sequence:

Resin-Thr-$Q^6$-$Q^5$-$Q^4$-$Q^3$-$Q^2$-$Q^1$-$L^3$-$L^2$-$L^1$.

(II) The fully protected peptide (module A, module B and linker L) was assembled on solid support according to method G as described above.

The peptide was synthesized starting with the amino acid Fmoc-$^D$Orn(Boc)-OH, which was grafted to the resin (Fmoc-$^D$Orn(Boc)-2-chlorotrityl resin) and using Fmoc-Glu(Allyl)-OH for addition of the amino acid residue at $P^5$. Coupling of the protected peptide fragment (module B and linker L) was performed as indicated in the corresponding section of procedure A above by formation of an amide bond between the γ-carboxyl group of Glu at $P^5$ and the α-amino group of Dab at $L^1$. Assembly of the peptide was in the following sequence, showing only residues of module A:

Resin-$^D$Orn-$P^{10}$-$P^9$-$P^8$-$P^7$-$P^6$-$P^5$-$P^4$-$P^3$-$P^2$-$P^1$.

Subsequently, removal of the alloc protecting group at $P^2$, cleavage of the peptide from the resin, formation of the lactam interstrand linkage by an amide bond between the δ-amino group of Orn at $P^2$ and the liberated α-carboxyl group of $^D$Orn at $P^{11}$, and full deprotection were performed as indicated in procedure J above. Finally, the peptide was purified, as described above, and characterized by HPLC-MS. For analytical data, see Ex. 29 in Table 2.

Example 30 is shown in Table 1.

Procedure J, as described above, was used for the preparation of the peptide, applying an on-resin fragment coupling strategy.

(I) The protected peptide fragment (module B and linker L) was synthesized as described above in the corresponding section in the synthesis of Ex. 1.

Assembly of the peptide fragment was in the following sequence:

Resin-Thr-$Q^6$-$Q^5$-$Q^4$-$Q^3$-$Q^2$-$Q^1$-$L^3$-$L^2$-$L^1$.

(II) The fully protected peptide (module A, module B and linker L) was assembled on solid support according to method G as described above.

The peptide was synthesized starting with the amino acid Fmoc-$^D$Lys(Boc)-OH, which was grafted to the resin (Fmoc-$^D$Lys(Boc)-2-chlorotrityl resin) and using Fmoc-Glu(Allyl)-OH for addition of the amino acid residue at $P^5$. Coupling of the protected peptide fragment (module B and linker L) was performed as indicated in the corresponding section of procedure A above by formation of an amide bond between the γ-carboxyl group of Glu at $P^5$ and the α-amino group of Dab at $L^1$. Assembly of the peptide was in the following sequence, showing only residues of module A:

Resin-$^D$Lys-$P^{10}$-$P^9$-$P^8$-$P^7$-$P^6$-$P^5$-$P^4$-$P^3$-$P^2$-$P^1$.

Subsequently, removal of the alloc protecting group at $P^2$, cleavage of the peptide from the resin, formation of the lactam interstrand linkage by an amide bond between the δ-amino group of Orn at $P^2$ and the liberated α-carboxyl group of $^D$Lys at $P^{11}$, and full deprotection were performed as indicated in procedure J above. Finally, the peptide was purified, as described above, and characterized by HPLC-MS. For analytical data, see Ex. 30 in Table 2.

Examples 39 to 41, 44 to 46, 49, 62 to 68, 119 and 144 are shown in Table 1.

Procedure M1, as described above, was used for the preparation of the peptides, applying an on-resin fragment coupling strategy.

(I) The protected peptide fragments (module B and linker L) were synthesized as described above in the corresponding section in the synthesis of Ex. 1.

Assembly of the peptide fragments was in the following sequence:

Resin-Thr-$Q^6$-$Q^5$-$Q^4$-$Q^3$-$Q^2$-$Q^1$-$L^3$-$L^2$-$L^1$.

(II) The fully protected peptides (module A, module B and linker L) were assembled on solid support according to method J as described above.

The peptides were synthesized starting with an appropriately protected Fmoc-amino acid, which was used in the first coupling cycle for grafting the amino acid residue at $X^{12}$ to Sieber amide resin, and using Fmoc-Glu(Allyl)-OH for addition of the amino acid residue at $P^5$. Coupling of the protected peptide fragment (module B and linker L) was performed as indicated in the corresponding section of procedure A above by formation of an amide bond between the γ-carboxyl group of Glu at $P^5$ and the α-amino group of Dab at C. Assembly of the peptides was in the following sequence, showing only residues of module A:

Resin-$X^{11}$-$P^{11}$-$P^{10}$-$P^9$-$P^8$-$P^7$-$P^6$-$P^5$-$P^4$-$P^3$-$P^2$-$P^1$.

Subsequently, acylation with acetic acid at $P^1$ (Ex. 39, 41, 44 to 46, 49, and 62 to 68) or acylation with 6-methyl heptanoic acid at $P^1$ (Ex. 40) or acylation with propionic acid at $P^1$ (Ex. 119 and 144), cleavage of the peptides from the resin, formation of the disulfide interstrand linkage between $P^2$ and $P^{11}$, and full deprotection were performed as indicated in procedure M1 above. Finally, the peptides were purified, as described above, and characterized by HPLC-MS. For analytical data, see Ex. 39 to 41, 44 to 46, 49, 62 to 68, 119 and 144 in Table 2.

Examples 100, 113, 114, 117, 120, 121, 128, 130 to 143, 150 to 156, 158, 159, 251 to 264, 267 to 269, 272, 275, 276, 278, 280 to 284, 289, 294 to 300, 305 to 318, 328 to 339, 342, 343, 345, 350, 352 and 353 are shown in Table 1.

Procedure M2, as described above, was used for the preparation of the peptides, applying an on-resin fragment coupling strategy.

(I) The protected peptide fragments (module B and linker L) were synthesized as described above in the corresponding section in the synthesis of Ex. 1.

Assembly of the peptide fragments was in the following sequence:

Resin-Thr-$Q^6$-$Q^5$-$Q^4$-$Q^3$-$Q^2$-$Q^1$-$L^3$-$L^2$-$L^1$.

(II) The fully protected peptides (module A, module B and linker L) were assembled on solid support according to method J as described above.

The peptides were synthesized starting with an appropriately protected Fmoc-amino acid, which was used in the first coupling cycle for grafting the amino acid residue at $X^{12}$ to Sieber amide resin, and using Fmoc-Glu(Allyl)-OH for addition of the amino acid residue at $P^5$. Coupling of the protected peptide fragment (module B and linker L) was performed as indicated in the corresponding section of procedure A above by formation of an amide bond between the γ-carboxyl group of Glu at $P^5$ and the α-amino group of Dab at $L^1$. Assembly of the peptides was in the following sequence, showing only residues of module A:

Resin-$X^{12}$-$P^{11}$-$P^{10}$-$P^9$-$P^8$-$P^7$-$P^6$-$P^5$-$P^4$-$P^3$-$P^2$-$P^1$.

Subsequently, acylation with acetic acid at $P^1$, cleavage of the peptides from the resin, full deprotection, and formation of the disulfide interstrand linkage between $P^2$ and $P^{11}$ were performed as indicated in procedure M2 above. Finally, the peptides were purified, as described above, and characterized by HPLC-MS. For analytical data, see Ex. 100, 113, 114, 117, 120, 121, 128, 130 to 143, 150 to 156, 158, 159, 251 to 264, 267 to 269, 272, 275, 276, 278, 280 to 284, 289, 294 to 300, 305 to 318, 328 to 339, 342, 343, 345, 350, 352 and 353 in Table 2.

Example 42 is shown in Table 1.

Procedure E, as described above, was used for the preparation of the peptide, applying an on-resin fragment coupling strategy.

(I) The protected peptide fragment (module B and linker L) was synthesized as described above in the corresponding section in the synthesis of Ex. 1.

Assembly of the peptide fragment was in the following sequence:

Resin-Thr-$Q^6$-$Q^5$-$Q^4$-$Q^3$-$Q^2$-$Q^1$-$L^3$-$L^2$-$L^1$.

(II) The fully protected peptide (module A, module B and linker L) was assembled on solid support according to method F as described above.

The peptide was synthesized starting with the amino acid Fmoc-Ser(tBu)-OH, which was grafted to the resin (Fmoc-Ser(tBu)-2-chlorotrityl resin) and using Fmoc-Glu(Allyl)-OH for addition of the amino acid residue at $P^5$. Coupling of the protected peptide fragment (module B and linker L) was performed as indicated in the corresponding section of procedure A above by formation of an amide bond between the γ-carboxyl group of Glu at $P^5$ and the α-amino group of Dab at $L^1$. Assembly of the peptide was in the following sequence, showing only residues of module A:

Resin-Ser-$P^{11}$-$P^{10}$-$P^9$-$P^8$-$P^7$-$P^6$-$P^5$-$P^4$-$P^3$-$P^2$-$P^1$.

Subsequently, cleavage of the peptide from the resin, formation of the disulfide interstrand linkage between $P^2$ and $P^{11}$, and full deprotection were performed as indicated in procedure E above. Finally, the peptide was purified, as described above, and characterized by HPLC-MS. For analytical data, see Ex. 42 in Table 2.

Examples 43, 47, 48, 50 and 51 are shown in Table 1.

Procedure L, as described above, was used for the preparation of the peptides, applying an on-resin fragment coupling strategy.

(I) The protected peptide fragment (module B and linker L) was synthesized as described above in the corresponding section in the synthesis of Ex. 1.

Assembly of the peptide fragment was in the following sequence:

Resin-Thr-$Q^6$-$Q^5$-$Q^4$-$Q^3$-$Q^2$-$Q^1$-$L^3$-$L^2$-$L^1$.

(II) The fully protected peptides (module A, module B and linker L) were assembled on solid support according to method I as described above.

The peptides were synthesized starting with an appropriately protected Fmoc-amino acid, which was used in the first coupling cycle for grafting the amino acid residue at $X^{12}$ to Sieber amide resin, and using Fmoc-Glu(Allyl)-OH for addition of the amino acid residue at $P^5$. Coupling of the protected peptide fragment (module B and linker L) was performed as indicated in the corresponding section of procedure A above by formation of an amide bond between the γ-carboxyl group of Glu at $P^5$ and the α-amino group of Dab at C. Assembly of the peptides was in the following sequence, showing only residues of module A:

Resin-$X^{12}$-$P^{11}$-$P^{10}$-$P^9$-$P^8$-$P^7$-$P^6$-$P^5$-$P^4$-$P^3$-$P^2$-$P^1$.

Subsequently, cleavage of the peptides from the resin, formation of the disulfide interstrand linkage between $P^2$ and $P^{11}$, and full deprotection were performed as indicated in procedure L above. Finally, the peptides were purified, as described above, and characterized by HPLC-MS. For analytical data, see Ex. 43, 47, 48, 50 and 51 in Table 2.

Example 52 is shown in Table 1.

Procedure F, as described above, was used for the preparation of the peptide, applying an on-resin fragment coupling strategy.

(I) The protected peptide fragment (module B and linker L) was synthesized as described above in the corresponding section in the synthesis of Ex. 1.

Assembly of the peptide fragment was in the following sequence:

Resin-Thr-$Q^6$-$Q^5$-$Q^4$-$Q^3$-$Q^2$-$Q^1$-$L^3$-$L^2$-$L^1$.

(II) The fully protected peptide (module A, module B and linker L) was assembled on solid support according to method G as described above.

The peptide was synthesized starting with the amino acid Fmoc-Ser(tBu)-OH, which was grafted to the resin (Fmoc-Ser(tBu)-2-chlorotrityl resin) and using Fmoc-Glu(Allyl)-OH for addition of the amino acid residue at $P^5$. Coupling of the protected peptide fragment (module B and linker L) was performed as indicated in the corresponding section of procedure A above by formation of an amide bond between the γ-carboxyl group of Glu at $P^5$ and the α-amino group of Dab at $L^1$. Assembly of the peptide was in the following sequence, showing only residues of module A:

Resin-Ser-$P^{11}$-$P^{10}$-$P^9$-$P^8$-$P^7$-$P^6$-$P^5$-$P^4$-$P^3$-$P^2$-$P^1$.

Subsequently, acylation with acetic acid at $P^1$, cleavage of the peptide from the resin, formation of the disulfide interstrand linkage between $P^2$ and $P^{11}$, and full deprotection were performed as indicated in procedure F above. Finally, the peptide was purified, as described above, and characterized by HPLC-MS. For analytical data, see Ex. 52 in Table 2.

Examples 53 and 54 are shown in Table 1.

Procedure E, as described above, was used for the preparation of the peptides, applying an on-resin fragment coupling strategy.

(I) The protected peptide fragment (module B and linker L) was synthesized as described above in the corresponding section in the synthesis of Ex. 1.

Assembly of the peptide fragment was in the following sequence:

Resin-Thr-$Q^6$-$Q^5$-$Q^4$-$Q^3$-$Q^2$-$Q^1$-$L^3$-$L^2$-$L^1$.

(II) The fully protected peptides (module A, module B and linker L) were assembled on solid support according to method F as described above.

The peptides were synthesized starting with the amino acid Fmoc-Ser(tBu)-OH, which was grafted to the resin (Fmoc-Ser(tBu)-2-chlorotrityl resin) and using Fmoc-Glu(Allyl)-OH for addition of the amino acid residue at $P^5$. Coupling of the protected peptide fragment (module B and linker L) was performed as indicated in the corresponding section of procedure A above by formation of an amide bond between the γ-carboxyl group of Glu at $P^5$ and the α-amino group of Dab at $L^1$. Assembly of the peptides was in the following sequence, showing only residues of module A:

Resin-Ser-$P^{11}$-$P^{10}$-$P^9$-$P^8$-$P^7$-$P^6$-$P^5$-$P^4$-$P^3$-$P^2$-$P^1$.

Subsequently, cleavage of the peptides from the resin, formation of the disulfide interstrand linkage between $P^2$ and $P^{11}$, and full deprotection were performed as indicated in procedure E above. Finally, the peptides were purified, as described above, and characterized by HPLC-MS. For analytical data, see Ex. 53 and 54 in Table 2.

Examples 55 and 56 are shown in Table 1.

Procedure G, as described above, was used for the preparation of the peptides, applying an on-resin fragment coupling strategy.

(I) The protected peptide fragment (module B and linker L) was synthesized as described above in the corresponding section in the synthesis of Ex. 1.

Assembly of the peptide fragment was in the following sequence:

Resin-Thr-$Q^6$-$Q^5$-$Q^4$-$Q^3$-$Q^2$-$Q^1$-$L^3$-$L^2$-$L^1$.

(II) The fully protected peptides (module A, module B and linker L) were assembled on solid support according to method F as described above.

The peptides were synthesized starting with the amino acid Fmoc-Ser(tBu)-OH, which was grafted to the resin (Fmoc-Ser(tBu)-2-chlorotrityl resin) and using Fmoc-Glu(Allyl)-OH for addition of the amino acid residue at $P^5$. Coupling of the protected peptide fragment (module B and linker L) was performed as indicated in the corresponding section of procedure A above by formation of an amide bond between the γ-carboxyl group of Glu at $P^5$ and the α-amino group of Dab at $L^1$. Assembly of the peptide was in the following sequence, showing only residues of module A:

Resin-Ser-$P^{11}$-$P^{10}$-$P^9$-$P^8$-$P^7$-$P^6$-$P^5$-$P^4$-$P^3$-$P^2$-$P^1$.

Subsequently, allyl deprotection at $P^2$, ivDde deprotection at $P^{11}$, and formation of the lactam interstrand linkage by an amide bond between the liberated side-chain functional groups of the amino acid residue at $P^2$ and Dab at $P^{11}$, cleavage of the peptides from the resin, and full deprotection were performed as indicated in procedure G above. Finally, the peptides were purified, as described above, and characterized by HPLC-MS. For analytical data, see Ex. 55 and 56 in Table 2.

Examples 58, 60, 61, 74 to 76, 78 to 85, 87 to 91 and 104 to 112 are shown in Table 1. Procedure D, as described above, was used for the preparation of the peptides, applying an on-resin fragment coupling strategy.

(I) The protected peptide fragments (module B and linker L) were synthesized as indicated above in the corresponding section in the synthesis of Ex. 1.

Assembly of the peptide fragment was in the following sequence:

Resin-Thr-$Q^6$-$Q^5$-$Q^4$-$Q^3$-$Q^2$-$Q^1$-$L^3$-$L^2$-$L^1$.

(II) The fully protected peptides (module A, module B and linker L) were assembled on solid support according to method E as described above.

The peptides were synthesized starting with the amino alcohol Fmoc-Throl(tBu), which was grafted to the resin (Fmoc-Throl(tBu)-2-chlorotrityl resin), using Fmoc-Glu(Allyl)-OH for addition of the amino acid residue at $P^5$, and using alpha-hydroxyisovaleric acid (Hiv) for addition of the hydroxy acid residue at $P^1$. Coupling of the protected peptide fragment (module B and linker L) was performed as indicated in the corresponding section of procedure A above by formation of an amide bond between the γ-carboxyl group of Glu at $P^5$ and the α-amino group of Dab at $L^1$. Assembly of the peptides was in the following sequence, showing only residues of module A:

Resin-Throl-$P^{11}$-$P^{10}$-$P^9$-$P^8$-$P^7$-$P^6$-$P^5$-$P^4$-$P^3$-$P^2$-$P^1$.

Subsequently, cleavage of the peptides from the resin, formation of the disulfide interstrand linkage between $P^2$ and $P^{11}$, and full deprotection were performed as indicated in procedure D above. Finally, the peptides were purified, as described above, and characterized by HPLC-MS. For analytical data, see Ex. 58, 60, 61, 74 to 76, 78 to 85, 87 to 91 and 104 to 112 in Table 2.

Examples 59, 72 and 73 are shown in Table 1.

Procedure D, as described above, was used for the preparation of the peptides, applying an on-resin fragment coupling strategy.

(I) The protected peptide fragment (module B and linker L) was synthesized as indicated above in the corresponding section in the synthesis of Ex. 1.

Assembly of the peptide fragment was in the following sequence:

Resin-Thr-$Q^6$-$Q^5$-$Q^4$-$Q^3$-$Q^2$-$Q^1$-$L^3$-$L^2$-$L^1$.

(II) The fully protected peptides (module A, module B and linker L) were assembled on solid support according to method E as described above.

The peptides were synthesized starting with the amino alcohol Fmoc-Glyol, which was grafted to the resin (Fmoc-Glyol-2-chlorotrityl resin), using Fmoc-Glu(Allyl)-OH for addition of the amino acid residue at $P^5$, and using alpha-hydroxyisovaleric acid (Hiv) for addition of the hydroxy acid residue at $P^1$. Coupling of the protected peptide fragment (module B and linker L) was performed as indicated in the corresponding section of procedure A above by formation of an amide bond between the γ-carboxyl group of Glu at $P^5$ and the α-amino group of Dab at $L^1$. Assembly of the peptides was in the following sequence, showing only residues of module A:

Resin-Glyol-$P^{11}$; $P^{10}$; $P^9$; $P^8$; $P^7$; $P^6$; $P^5$; $P^4$; $P^3$; $P^2$-Hiv.

Subsequently, cleavage of the peptides from the resin, formation of the disulfide interstrand linkage between $P^2$ and $P^{11}$, and full deprotection were performed as indicated in procedure D above. Finally, the peptides were purified, as described above, and characterized by HPLC-MS. For analytical data, see Ex. 59, 72 and 73 in Table 2.

Examples 69 and 70 are shown in Table 1.

Procedure D, as described above, was used for the preparation of the peptides, applying an on-resin fragment coupling strategy.

(I) The protected peptide fragment (module B and linker L) was synthesized as indicated above in the corresponding section in the synthesis of Ex. 1.

Assembly of the peptide fragment was in the following sequence:

Resin-Thr-$Q^6$-$Q^5$-$Q^4$-$Q^3$-$Q^2$-$Q^1$-$L^3$-$L^2$-$L^1$.

(II) The fully protected peptides (module A, module B and linker L) were assembled on solid support according to method E as described above.

The peptides were synthesized starting with the amino alcohol Fmoc-Glyol, which was grafted to the resin (Fmoc-Glyol-2-chlorotrityl resin), using Fmoc-Glu(Allyl)-OH for addition of the amino acid residue at $P^5$, and using alpha-hydroxyisovaleric acid (Hiv) for addition of the hydroxy acid residue at $P^1$. Coupling of the protected peptide fragment (module B and linker L) was performed as indicated in the corresponding section of procedure A above by formation of an amide bond between the γ-carboxyl group of Glu at $P^5$ and the α-amino group of Dab at $L^1$. Assembly of the peptide was in the following sequence, showing only residues of module A:

Resin-Glyol-$X^{12}$-$P^{11}$-$P^{10}$-$P^9$-$P^8$-$P^7$-$P^6$-$P^5$-$P^4$-$P^3$-$P^2$-Hiv.

Subsequently, cleavage of the peptides from the resin, formation of the disulfide interstrand linkage between $P^2$ and $P^{11}$, and full deprotection were performed as indicated in procedure D above. Finally, the peptides were purified, as described above, and characterized by HPLC-MS. For analytical data, see Ex. 69 and 70 in Table 2.

Example 71 is shown in Table 1.

Procedure B, as described above, was used for the preparation of the peptide, applying an on-resin fragment coupling strategy.

(I) The protected peptide fragment (module B and linker L) was synthesized as indicated above in the corresponding section in the synthesis of Ex. 1.

Assembly of the peptide fragment was in the following sequence:

Resin-Thr-$Q^6$-$Q^5$-$Q^4$-$Q^3$-$Q^2$-$Q^1$-$L^3$-$L^2$-$L^1$.

(II) The fully protected peptide (module A, module B and linker L) was assembled on solid support according to method C as described above.

The peptide was synthesized starting with the amino alcohol Fmoc-Glyol, which was grafted to the resin (Fmoc-Glyol-2-chlorotrityl resin) and using Fmoc-Glu(Allyl)-OH for addition of the amino acid residue at $P^5$. Coupling of the protected peptide fragment (module B and linker L) was performed as indicated in the corresponding section of procedure A above by formation of an amide bond between the γ-carboxyl group of Glu at $P^5$ and the α-amino group of Dab at C. Assembly of the peptide was in the following sequence, showing only residues of module A:

Resin-Glyol-$X^{12}$-$P^{11}$-$P^{10}$-$P^9$-$P^8$-$P^7$-$P^6$-$P^5$-$P^4$-$P^3$-$P^2$-$P^1$.

Subsequently, acylation with acetic acid at $P^1$, cleavage of the peptide from the resin, formation of the disulfide interstrand linkage between $P^2$ and $P^{11}$, and full deprotection were performed as indicated in procedure B above. Finally, the peptide was purified, as described above, and characterized by HPLC-MS. For analytical data, see Ex. 71 in Table 2.

Example 77 is shown in Table 1.

Procedure A, as described above, was used for the preparation of the peptide, applying an on-resin fragment coupling strategy.

(I) The protected peptide fragment (module B and linker L) was synthesized as indicated above in the corresponding section in the synthesis of Ex. 1.

Assembly of the peptide fragment was in the following sequence:

Resin-Thr-$Q^6$-$Q^5$-$Q^4$-$Q^3$-$Q^2$-$Q^1$-$L^3$-$L^2$-$L^1$.

(II) The fully protected peptide (module A, module B and linker L) was assembled on solid support according to method B as described above.

The peptide was synthesized starting with the amino alcohol Fmoc-Throl(tBu), which was grafted to the resin (Fmoc-Throl(tBu)-2-chlorotrityl resin) and using Fmoc-Glu(Allyl)-OH for addition of the amino acid residue at $P^5$. Coupling of the protected peptide fragment (module B and linker L) was performed as indicated in the corresponding section of procedure A above by formation of an amide bond between the γ-carboxyl group of Glu at $P^5$ and the α-amino group of Dab at $L^1$. Assembly of the peptide was in the following sequence, showing only residues of module A:

Resin-Throl-$P^{11}$-$P^{10}$-$P^9$-$P^8$-$P^7$-$P^6$-$P^5$-$P^4$-$P^3$-$P^2$-$P^1$.

Subsequently, cleavage of the peptide from the resin, formation of the disulfide interstrand linkage between $P^2$ and $P^{11}$, and full deprotection were performed as indicated in procedure A above. Finally, the peptide was purified, as described above, and characterized by HPLC-MS. For analytical data, see Ex. 77 in Table 2.

Examples 86, 123 and 129 are shown in Table 1.

Procedure B, as described above, was used for the preparation of the peptides, applying an on-resin fragment coupling strategy.

(I) The protected peptide fragments (module B and linker L) were synthesized as indicated above in the corresponding section in the synthesis of Ex. 1.

Assembly of the peptide fragments was in the following sequence:

Resin-Thr-$Q^6$-$Q^5$-$Q^4$-$Q^3$-$Q^2$-$Q^1$-$L^3$-$L^2$-$L^1$.

(II) The fully protected peptides (module A, module B and linker L) were assembled on solid support according to method C as described above.

The peptides were synthesized starting with the amino alcohol Fmoc-Throl(tBu), which was grafted to the resin (Fmoc-Throl(tBu)-2-chlorotrityl resin) and using Fmoc-Glu(Allyl)-OH for addition of the amino acid residue at $P^5$. Coupling of the protected peptide fragment (module B and linker L) was performed as indicated in the corresponding section of procedure A above by formation of an amide bond between the γ-carboxyl group of Glu at $P^5$ and the α-amino group of Dab at $L^1$. Assembly of the peptides was in the following sequence, showing only residues of module A:

Resin-Throl-$P^{11}$-$P^{10}$-$P^9$-$P^8$-$P^7$-$P^6$-$P^5$-$P^4$-$P^3$-$P^2$-$P^1$.

Subsequently, acylation with acetic acid at $P^1$, cleavage of the peptides from the resin, formation of the disulfide interstrand linkage between $P^2$ and $P^{11}$, and full deprotection were performed as indicated in procedure B above. Finally, the peptides were purified, as described above, and characterized by HPLC-MS. For analytical data, see Ex. 86, 123 and 129 in Table 2.

Examples 92 and 93 are shown in Table 1.

Procedure D, as described above, was used for the preparation of the peptides, applying an on-resin fragment coupling strategy.

(I) The protected peptide fragment (module B and linker L) was synthesized as indicated above in the corresponding section in the synthesis of Ex. 1.

Assembly of the peptide fragment was in the following sequence:

Resin-Thr-$Q^6$-$Q^5$-$Q^4$-$Q^3$-$Q^2$-$Q^1$-$L^3$-$L^2$-$L^1$.

(II) The fully protected peptides (module A, module B and linker L) were assembled on solid support according to method E as described above.

The peptides were synthesized starting with the amino alcohol Fmoc-Tyrol(tBu), which was grafted to the resin (Fmoc-Tyrol(tBu)-2-chlorotrityl resin), using Fmoc-Glu(Allyl)-OH for addition of the amino acid residue at $P^5$, and using alpha-hydroxyisovaleric acid (Hiv) for addition of the hydroxy acid residue at $P^1$. Coupling of the protected peptide fragment (module B and linker L) was performed as indicated in the corresponding section of procedure A above by formation of an amide bond between the γ-carboxyl group of Glu at $P^5$ and the α-amino group of Dab at $L^1$. Assembly of the peptide was in the following sequence, showing only residues of module A:

Resin-Throl-$P^{11}$-$P^{10}$-$P^9$-$P^8$-$P^7$-$P^6$-$P^5$-$P^4$-$P^3$-$P^2$-$P^1$.

Subsequently, cleavage of the peptides from the resin, formation of the disulfide interstrand linkage between $P^2$ and $P^{11}$, and full deprotection were performed as indicated in procedure D above. Finally, the peptides were purified, as described above, and characterized by HPLC-MS. For analytical data, see Ex. 92 and 93 in Table 2.

Example 94 is shown in Table 1.

Procedure B, as described above, was used for the preparation of the peptide, applying an on-resin fragment coupling strategy.

(I) The protected peptide fragment (module B and linker L) was synthesized as indicated above in the corresponding section in the synthesis of Ex. 1.

Assembly of the peptide fragment was in the following sequence:

Resin-Thr-$Q^6$-$Q^5$-$Q^4$-$Q^3$-$Q^2$-$Q^1$-$L^3$-$L^2$-$L^1$.

(II) The fully protected peptide (module A, module B and linker L) was assembled on solid support according to method C as described above.

The peptide was synthesized starting with the amino alcohol Fmoc-Tyrol(tBu), which was grafted to the resin (Fmoc-Tyrol(tBu)-2-chlorotrityl resin) and using Fmoc-Glu(Allyl)-OH for addition of the amino acid residue at $P^5$. Coupling of the protected peptide fragment (module B and linker L) was performed as indicated in the corresponding section of procedure A above by formation of an amide bond between the γ-carboxyl group of Glu at $P^5$ and the α-amino group of Dab at $L^1$. Assembly of the peptide was in the following sequence, showing only residues of module A:

Resin-Tyrol-$P^{11}$-$P^{10}$-$P^9$-$P^8$-$P^7$-$P^6$-$P^5$-$P^4$-$P^3$-$P^2$-$P^1$.

Subsequently, acylation with acetic acid at $P^1$, cleavage of the peptide from the resin, formation of the disulfide interstrand linkage between $P^2$ and $P^{11}$, and full deprotection were performed as indicated in procedure B above. Finally, the peptide was purified, as described above, and characterized by HPLC-MS. For analytical data, see Ex. 94 in Table 2.

Examples 95, 97 and 101 to 103 are shown in Table 1.

Procedure D, as described above, was used for the preparation of the peptides, applying an on-resin fragment coupling strategy.

(I) The protected peptide fragments (module B and linker L) were synthesized as indicated above in the corresponding section in the synthesis of Ex. 1.

Assembly of the peptide fragments were in the following sequence:

Resin-Thr-$Q^6$-$Q^5$-$Q^4$-$Q^3$-$Q^2$-$Q^1$-$L^3$-$L^2$-$L^1$.

(II) The fully protected peptides (module A, module B and linker L) were assembled on solid support according to method E as described above.

The peptides were synthesized starting with the amino alcohol Fmoc-Serol(tBu), which was grafted to the resin (Fmoc-Serol(tBu)-2-chlorotrityl resin), using Fmoc-Glu(Allyl)-OH for addition of the amino acid residue at $P^5$, and using alpha-hydroxyisovaleric acid (Hiv) for addition of the hydroxy acid residue at $P^1$. Coupling of the protected peptide fragment (module B and linker L) was performed as indicated in the corresponding section of procedure A above by formation of an amide bond between the γ-carboxyl group of Glu at $P^5$ and the α-amino group of Dab at $L^1$. Assembly of the peptides was in the following sequence, showing only residues of module A:

Resin-Serol-$P^{11}$-$P^{10}$-$P^9$-$P^8$-$P^7$-$P^6$-$P^5$-$P^4$-$P^3$-$P^2$-$P^1$.

Subsequently, cleavage of the peptides from the resin, formation of the disulfide interstrand linkage between $P^2$ and $P^{11}$, and full deprotection were performed as indicated in procedure D above. Finally, the peptides were purified, as described above, and characterized by HPLC-MS. For analytical data, see Ex. 95, 97 and 101 to 103 in Table 2.

Examples 96, 98 and 116 are shown in Table 1.

Procedure B, as described above, was used for the preparation of the peptides, applying an on-resin fragment coupling strategy.

(I) The protected peptide fragments (module B and linker L) were synthesized as indicated above in the corresponding section in the synthesis of Ex. 1. Assembly of the peptide fragments was in the following sequence:

Resin-Thr-$Q^6$-$Q^5$-$Q^4$-$Q^3$-$Q^2$-$Q^1$-$L^3$-$L^2$-$L^1$.

(II) The fully protected peptides (module A, module B and linker L) were assembled on solid support according to method C as described above.

The peptides were synthesized starting with the amino alcohol Fmoc-Serol(tBu), which was grafted to the resin (Fmoc-Serol(tBu)-2-chlorotrityl resin) and using Fmoc-Glu(Allyl)-OH for addition of the amino acid residue at $P^5$. Coupling of the protected peptide fragment (module B and linker L) was performed as indicated in the corresponding section of procedure A above by formation of an amide bond between the γ-carboxyl group of Glu at $P^5$ and the α-amino group of Dab at $L^1$. Assembly of the peptides was in the following sequence, showing only residues of module A:

Resin-Serol-$P^{11}$-$P^{10}$-$P^9$-$P^8$-$P^7$-$P^6$-$P^5$-$P^4$-$P^3$-$P^2$-$P^1$.

Subsequently, acylation with acetic acid at $P^1$, cleavage of the peptides from the resin, formation of the disulfide interstrand linkage between $P^2$ and $P^{11}$, and full deprotection were performed as indicated in procedure B above. Finally, the peptides were purified, as described above, and characterized by HPLC-MS. For analytical data, see Ex. 96, 98 and 116 in Table 2.

Example 99, 115, 157, 270, 271, 274, 277, 301, 340, and 344 are shown in Table 1. Procedure O, as described above, was used for the preparation of the peptides, applying an on-resin fragment coupling strategy.

(I) The protected peptide fragment (module B and linker L) was synthesized as indicated above in the corresponding section in the synthesis of Ex. 1.

Assembly of the peptide fragment was in the following sequence:

Resin-Thr-$Q^6$-$Q^5$-$Q^4$-$Q^3$-$Q^2$-$Q^1$-$L^3$-$L^2$-$L^1$.

(II) The fully protected peptides (module A, module B and linker L) were assembled on solid support according to method K as described above.

The peptides were synthesized starting with an appropriately protected Fmoc amino acid which was used in the first coupling cycle for grafting the amino acid residue at $X^{12}$ to Sieber amide resin, using Fmoc-Glu(Allyl)-OH for addition of the amino acid residue at $P^5$, and using alpha-hydroxy-isovaleric acid (Hiv) for addition of the hydroxy acid residue at $P^1$. Coupling of the protected peptide fragment (module B and linker L) was performed as indicated in the corresponding section of procedure A above by formation of an amide bond between the γ-carboxyl group of Glu at $P^5$ and the α-amino group of Dab at $L^1$. Assembly of the peptides was in the following sequence, showing only residues of module A:

Resin-$X^{12}$-$P^{11}$-$P^{10}$-$P^9$-$P^8$-$P^7$-$P^6$-$P^5$-$P^4$-$P^3$-$P^2$-$P^1$.

Subsequently, cleavage of the peptides from the resin, formation of the disulfide interstrand linkage between $P^2$ and $P^{11}$, and full deprotection were performed as indicated in procedure O above. Finally, the peptides were purified, as described above, and characterized by HPLC-MS. For analytical data, see Ex. 99, 115, 157, 270, 271, 274, 277, 301, 340, and 344 in Table 2.

Example 122 is shown in Table 1.

Procedure I, as described above, was used for the preparation of the peptide, applying an on-resin fragment coupling strategy.

(I) The protected peptide fragment (module B and linker L) was synthesized as described above in the corresponding section in the synthesis of Ex. 1.

Assembly of the peptide fragment was in the following sequence:

Resin-Thr-$Q^6$-$Q^5$-$Q^4$-$Q^3$-$Q^2$-$Q^1$-$L^3$-$L^2$-$L^1$.

(II) The fully protected peptide (module A, module B and linker L) was assembled on solid support according to method G as described above.

The peptide was synthesized starting with the amino acid Fmoc-Ser(tBu)-OH, which was grafted to the resin (Fmoc-Ser(tBu)-2-chlorotrityl resin) and using Fmoc-Glu(Allyl)-OH for addition of the amino acid residue at $P^5$. Coupling of the protected peptide fragment (module B and linker L) was performed as indicated in the corresponding section of procedure A above by formation of an amide bond between the γ-carboxyl group of Glu at $P^5$ and the α-amino group of Dab at $L^1$. Assembly of the peptide was in the following sequence, showing only residues of module A:

Resin-Ser-$P^{11}$-$P^{10}$-$P^9$-$P^8$-$P^7$-$P^6$-$P^5$-$P^4$-$P^3$-$P^2$-$P^1$.

Subsequently, cleavage of the peptide from resin and formation of the isopropyl ester of the liberated α-carboxyl group of Ser at $X^{12}$, formation of the disulfide interstrand linkage between $P^2$ and $P^{11}$, and full deprotection were performed as indicated in procedure I above. Finally, the peptide was purified, as described above, and characterized by HPLC-MS. For analytical data, see Ex. 122 in Table 2.

Example 124 is shown in Table 1.

Procedure B, as described above, was used for the preparation of the peptide, applying an on-resin fragment coupling strategy.

(I) The protected peptide fragment (module B and linker L) was synthesized as indicated above in the corresponding section in the synthesis of Ex. 1.

Assembly of the peptide fragment was in the following sequence:

Resin-Thr-$Q^6$-$Q^5$-$Q^4$-$Q^3$-$Q^2$-$Q^1$-$L^3$-$L^2$-$L^1$.

(II) The fully protected peptide (module A, module B and linker L) was assembled on solid support according to method C as described above.

The peptide was synthesized starting with the amino alcohol Fmoc-$^D$Throl(tBu), which was grafted to the resin (Fmoc-$^D$Throl(tBu)-2-chlorotrityl resin) and using Fmoc-Glu(Allyl)-OH for addition of the amino acid residue at $P^5$. Coupling of the protected peptide fragment (module B and linker L) was performed as indicated in the corresponding section of procedure A above by formation of an amide bond between the γ-carboxyl group of Glu at $P^5$ and the α-amino group of Dab at $L^1$. Assembly of the peptide was in the following sequence, showing only residues of module A:

Resin-$^D$Throl-$P^{11}$-$P^{10}$-$P^9$-$P^8$-$P^7$-$P^6$-$P^5$-$P^4$-$P^3$-$P^2$-$P^1$.

Subsequently, acylation with acetic acid at $P^1$, cleavage of the peptide from the resin, formation of the disulfide interstrand linkage between $P^2$ and $P^{11}$, and full deprotection were performed as indicated in procedure B above. Finally, the peptide was purified, as described above, and characterized by HPLC-MS. For analytical data, see Ex. 124 in Table 2.

Examples 125 and 126 are shown in Table 1.

Procedure M1, as described above, was used for the preparation of the peptides, applying an on-resin fragment coupling strategy.

(I) The protected peptide fragment (module B and linker L) was synthesized as described above in the corresponding section in the synthesis of Ex. 1.

Assembly of the peptide fragment was in the following sequence:

Resin-Thr-$Q^6$-$Q^5$-$Q^4$-$Q^3$-$Q^2$-$Q^1$-$L^3$-$L^2$-$L^1$.

(II) The fully protected peptides (module A, module B and linker L) were assembled on solid support according to method J as described above.

The peptides were synthesized starting with an appropriately protected Fmoc-amino acid, which was used in the first coupling cycle for grafting the amino acid residue at $P^{11}$ to Sieber amide resin, and using Fmoc-Glu(Allyl)-OH for addition of the amino acid residue at $P^5$. Coupling of the protected peptide fragment (module B and linker L) was performed as indicated in the corresponding section of procedure A above by formation of an amide bond between the γ-carboxyl group of Glu at $P^5$ and the α-amino group of Dab at $L^1$. Assembly of the peptide was in the following sequence, showing only residues of module A:

Resin-$P^{11}$-$P^{10}$-$P^9$-$P^8$-$P^7$-$P^6$-$P^5$-$P^4$-$P^3$-$P^2$-$P^1$.

Subsequently, acylation with acetic acid at $X^{14}$, cleavage of the peptides from the resin, formation of the disulfide interstrand linkage between $P^2$ and $P^{11}$, and full deprotection were performed as indicated in procedure M1 above. Finally, the peptides were purified, as described above, and characterized by HPLC-MS. For analytical data, see Ex. 125 and 126 in Table 2.

Example 127 is shown in Table 1.

Procedure D, as described above, was used for the preparation of the peptide, applying an on-resin fragment coupling strategy.

(I) The protected peptide fragment (module B and linker L) was synthesized as indicated above in the corresponding section in the synthesis of Ex. 1.

Assembly of the peptide fragment was in the following sequence:

Resin-Thr-$Q^6$-$Q^5$-$Q^4$-$Q^3$-$Q^2$-$Q^1$-$L^1$.

(II) The fully protected peptide (module A, module B and linker L) was assembled on solid support according to method E as described above.

The peptide was synthesized starting with the amino alcohol Fmoc-Throl(tBu), which was grafted to the resin (Fmoc-Throl(tBu)-2-chlorotrityl resin), using Fmoc-Glu (Allyl)-OH for addition of the amino acid residue at $P^5$, and using alpha-hydroxyisovaleric acid (Hiv) for addition of the hydroxy acid residue at $P^1$. Coupling of the protected peptide fragment (module B and linker L) was performed as indicated in the corresponding section of procedure A above by formation of an amide bond between the γ-carboxyl group of Glu at $P^5$ and the α-amino group of Dab at $L^1$. Assembly of the peptide was in the following sequence, showing only residues of module A:

Resin-Throl-$P^{11}$-$P^{10}$-$P^9$-$P^8$-$P^7$-$P^6$-$P^5$-$P^4$-$P^3$-$P^2$-$P^1$.

Subsequently, cleavage of the peptide from the resin, formation of the disulfide interstrand linkage between $P^2$ and $P^{11}$, and full deprotection were performed as indicated in procedure D above. Finally, the peptide was purified, as described above, and characterized by HPLC-MS. For analytical data, see Ex. 127 in Table 2.

Example 145 is shown in Table 1.

Procedure H, as described above, was used for the preparation of the peptide, applying an on-resin fragment coupling strategy.

(I) The protected peptide fragment (module B and linker L) was synthesized as described above in the corresponding section in the synthesis of Ex. 1.

Assembly of the peptide fragment was in the following sequence:

Resin-Thr-$Q^6$-$Q^5$-$Q^4$-$Q^3$-$Q^2$-$Q^1$-$L^3$-$L^2$-$L^1$.

(II) The fully protected peptide (module A, module B and linker L) was assembled on solid support according to method G as described above.

The peptide was synthesized starting with the amino acid Fmoc-Ser(tBu)-OH, which was grafted to the resin (Fmoc-Ser(tBu)-2-chlorotrityl resin) and using Fmoc-Glu(Allyl)-OH for addition of the amino acid residue at $P^5$. Coupling of the protected peptide fragment (module B and linker L) was performed as indicated in the corresponding section of procedure A above by formation of an amide bond between the γ-carboxyl group of Glu at $P^5$ and the α-amino group of Dab at $L^1$. Assembly of the peptide was in the following sequence, showing only residues of module A:

Resin-Ser-$P^{11}$-$P^{10}$-$P^9$-$P^8$-$P^7$-$P^6$-$P^5$-$P^4$-$P^3$-$P^2$-$P^1$.

Subsequently, cleavage of the peptide from resin, formation of the N-methylamide of the liberated α-carboxyl group of Ser at $X^{12}$, formation of the disulfide interstrand linkage between $P^2$ and $P^{11}$, and full deprotection were performed as indicated in procedure H above. Finally, the peptide was purified, as described above, and characterized by HPLC-MS. For analytical data, see Ex. 145 in Table 2.

Examples 146 and 147 are shown in Table 1.

Procedure N1, as described above, was used for the preparation of the peptides, applying an on-resin fragment coupling strategy.

(I) The protected peptide fragment (module B and linker L) was synthesized as described above in the corresponding section in the synthesis of Ex. 1.

Assembly of the peptides fragment was in the following sequence:

Resin-Thr-$Q^6$-$Q^5$-$Q^4$-$Q^3$-$Q^2$-$Q^1$-$L^3$-$L^2$-$L^1$.

(II) The fully protected peptides (module A, module B and linker L) were assembled on solid support according to method J as described above.

The peptides were synthesized starting with an appropriately protected Fmoc-amino acid, which was used in the first coupling cycle for grafting the amino acid residue at $X^{12}$ to Sieber amide resin, using Fmoc-Glu(2-PhiPr)-OH for addition of the amino acid residue at $P^{11}$ and using Fmoc-Glu (Allyl)-OH for addition of the amino acid residue at $P^5$. Coupling of the protected peptide fragment (module B and linker L) was performed as indicated in the corresponding section of procedure A above by formation of an amide bond between the γ-carboxyl group of Glu at $P^5$ and the α-amino group of Dab at C. Assembly of the peptide was in the following sequence, showing only residues of module A:

Resin-$X^{12}$-$P^{11}$-$P^{10}$-$P^9$-$P^8$-$P^7$-$P^6$-$P^5$-$P^4$-$P^3$-$P^2$-$P^1$.

Subsequently, acylation with acetic acid at $P^1$, removal of the alloc protecting group at $P^2$, cleavage of the peptides from resin and removal of the 2-phenyl-isopropyl protecting group at $P^{11}$, formation of the lactam interstrand linkage by an amide bond between the liberated side-chain functional groups of the residues at $P^2$ and at $P^{11}$, and full deprotection were performed as indicated in procedure N1 above. Finally, the peptides were purified, as described above, and characterized by HPLC-MS. For analytical data, see Ex. 146 and 147 in Table 2.

Examples 148, 149, 265, 273, 279, 287, 290, 291, 293, 302, 303, 319 to 327, 341, 346, 348, 349 and 351 are shown in Table 1.

Procedure N1, as described above, was used for the preparation of the peptides, applying an on-resin fragment coupling strategy.

(I) The protected peptide fragments (module B and linker L) were synthesized as described above in the corresponding section in the synthesis of Ex. 1.

Assembly of the peptide fragments was in the following sequence:

Resin-Thr-$Q^6$-$Q^5$-$Q^4$-$Q^3$-$Q^2$-$Q^1$-$L^3$-$L^2$-$L^1$.

(II) The fully protected peptides (module A, module B and linker L) were assembled on solid support according to method J as described above.

The peptides were synthesized starting with an appropriately protected Fmoc-amino acid, which was used in the first coupling cycle for grafting the amino acid residue at $X^{12}$ to Sieber amide resin, using Fmoc-Glu(Allyl)-OH for addition of the amino acid residue at $P^5$ and using Fmoc-Asp(2-PhiPr)-OH for addition of the amino acid residue at $P^{11}$. Coupling of the protected peptide fragment (module B and linker L) was performed as indicated in the corresponding section of procedure A above by formation of an amide bond between the γ-carboxyl group of Glu at $P^5$ and the α-amino group of Dab at C. Assembly of the peptides was in the following sequence, showing only residues of module A:

Resin-$X^{12}$-$P^{11}$-$P^{10}$-$P^9$-$P^8$-$P^7$-$P^6$-$P^5$-$P^4$-$P^3$-$P^2$-$P^1$.

Subsequently, acylation with acetic acid at $P^1$, removal of the alloc protecting group at $P^2$, cleavage of the peptides from the resin and removal of the 2-phenyl-isopropyl protecting group at $P^{11}$, formation of the lactam interstrand linkage by an amide bond between the liberated side-chain functional groups of the residues at $P^2$ and at $P^{11}$, and full deprotection were performed as indicated in procedure N1 above. Finally, the peptides were purified, as described above, and characterized by HPLC-MS. For analytical data, see Ex. 148, 149, 265, 273, 279, 287, 290, 291, 293, 302, 303, 319 to 327, 341, 346, 348, 349 and 351 in Table 2.

Example 160 is shown in Table 1.

Procedure O, as described above, was used for the preparation of the peptide, applying an on-resin fragment coupling strategy.

(I) The protected peptide fragment (module B and linker L) was synthesized as indicated above in the corresponding section in the synthesis of Ex. 1.

Assembly of the peptide fragment was in the following sequence:

Resin-Thr-$Q^6$-$Q^5$-$Q^4$-$Q^3$-$Q^2$-$Q^1$-$L^3$-$L^2$-$L^1$.

(II) The fully protected peptide (module A, module B and linker L) was assembled on solid support according to method K as described above.

The peptide was synthesized starting with an appropriately protected Fmoc amino acid which was used in the first coupling cycle for grafting the amino acid residue at $X^{12}$ to Sieber amide resin, using Fmoc-Glu(Allyl)-OH for addition of the amino acid residue at $P^6$, and using alpha-hydroxyisovaleric acid (Hiv) for addition of the hydroxy acid residue at $P^1$. Coupling of the protected peptide fragment (module B and linker L) was performed as indicated in the corresponding section of procedure A above by formation of an amide bond between the γ-carboxyl group of Glu at $P^6$ and the α-amino group of Dab at $L^1$. Assembly of the peptide was in the following sequence, showing only residues of module A:

Resin-$X^{12}$-$P^{11}$-$P^{10}$-$P^9$-$P^8$-$P^7$-$P^6$-$P^5$-$P^4$-$P^3$-$P^2$-$P^1$.

Subsequently, cleavage of the peptide from the resin, formation of the disulfide interstrand linkage between $P^2$ and $P^{11}$, and full deprotection were performed as indicated in procedure O above. Finally, the peptide was purified, as described above, and characterized by HPLC-MS. For analytical data, see Ex. 160 in Table 2.

Example 161 is shown in Table 1.

Procedure O, as described above, was used for the preparation of the peptide, applying an on-resin fragment coupling strategy.

(I) The protected peptide fragment (module B and linker L) was synthesized as indicated above in the corresponding section in the synthesis of Ex. 1.

Assembly of the peptide fragment was in the following sequence:

Resin-Thr-$Q^6$-$Q^5$-$Q^4$-$Q^3$-$Q^2$-$Q^1$-$L^3$-$L^2$-$L^1$.

(II) The fully protected peptide (module A, module B and linker L) was assembled on solid support according to method K as described above.

The peptide was synthesized starting with an appropriately protected Fmoc amino acid which was used in the first coupling cycle for grafting the amino acid residue at $X^{12}$ to Sieber amide resin, using Fmoc-$^D$Glu(Allyl)-OH for addition of the amino acid residue at $P^6$, and using alpha-hydroxyisovaleric acid (Hiv) for addition of the hydroxy acid residue at $P^1$. Coupling of the protected peptide fragment (module B and linker L) was performed as indicated in the corresponding section of procedure A above by formation of an amide bond between the γ-carboxyl group of $^D$Glu at $P^6$ and the α-amino group of Dab at $L^1$. Assembly of the peptide was in the following sequence, showing only residues of module A:

Resin-$X^{12}$-$P^{11}$-$P^{10}$-$P^9$-$P^8$-$P^7$-$P^6$-$P^5$-$P^4$-$P^3$-$P^2$-$P^1$.

Subsequently, cleavage of the peptide from the resin, formation of the disulfide interstrand linkage between $P^2$ and $P^{11}$, and full deprotection were performed as indicated in procedure O above. Finally, the peptide was purified, as described above, and characterized by HPLC-MS. For analytical data, see Ex. 161 in Table 2.

Example 162 is shown in Table 1.

Procedure D, as described above, was used for the preparation of the peptide, applying an on-resin fragment coupling strategy.

(I) The protected peptide fragment (module B and linker L) was synthesized as indicated above in the corresponding section in the synthesis of Ex. 1.

Assembly of the peptide fragment was in the following sequence:

Resin-Thr-$Q^6$-$Q^5$-$Q^4$-$Q^3$-$Q^2$-$Q^1$-$L^3$-$L^2$-$L^1$.

(II) The fully protected peptide (module A, module B and linker L) was assembled on solid support according to method E as described above.

The peptide was synthesized starting with the amino alcohol Fmoc-Serol(tBu), which was grafted to the resin (Fmoc-Serol(tBu)-2-chlorotrityl resin), using Fmoc-Glu(Allyl)-OH for addition of the amino acid residue at $P^6$, and using alpha-hydroxyisovaleric acid (Hiv) for addition of the hydroxy acid residue at $P^1$. Coupling of the protected peptide fragment (module B and linker L) was performed as indicated in the corresponding section of procedure A above by formation of an amide bond between the γ-carboxyl group of Glu at $P^6$ and the α-amino group of Dab at $L^1$. Assembly of the peptide was in the following sequence, showing only residues of module A:

Resin-Serol-$P^{11}$-$P^{10}$-$P^9$-$P^8$-$P^7$-$P^6$-$P^5$-$P^4$-$P^3$-$P^2$-$P^1$.

Subsequently, cleavage of the peptide from the resin, formation of the disulfide interstrand linkage between $P^2$ and $P^{11}$, and full deprotection were performed as indicated in procedure D above. Finally, the peptide was purified, as described above, and characterized by HPLC-MS. For analytical data, see Ex. 162 in Table 2.

Example 163 is shown in Table 1.

Procedure D, as described above, was used for the preparation of the peptide, applying an on-resin fragment coupling strategy.

(I) The protected peptide fragment (module B and linker L) was synthesized as indicated above in the corresponding section in the synthesis of Ex. 1.

Assembly of the peptide fragment was in the following sequence:

Resin-Thr-$Q^6$-$Q^5$-$Q^4$-$Q^3$-$Q^2$-$Q^1$-$L^3$-$L^2$-$L^1$.

(II) The fully protected peptide (module A, module B and linker L) was assembled on solid support according to method E as described above.

The peptide was synthesized starting with the amino alcohol Fmoc-Serol(tBu), which was grafted to the resin (Fmoc-Serol(tBu)-2-chlorotrityl resin), using Fmoc-$^D$Glu(Allyl)-OH for addition of the amino acid residue at $P^6$, and using alpha-hydroxyisovaleric acid (Hiv) for addition of the hydroxy acid residue at $P^1$. Coupling of the protected peptide fragment (module B and linker L) was performed as indicated in the corresponding section of procedure A above by formation of an amide bond between the γ-carboxyl group of $^D$Glu at $P^6$ and the α-amino group of Dab at $L^1$. Assembly of the peptide was in the following sequence, showing only residues of module A:

Resin-Serol-$P^{11}$-$P^{10}$-$P^9$-$P^8$-$P^7$-$P^6$-$P^5$-$P^4$-$P^3$-$P^2$-$P^1$.

Subsequently, cleavage of the peptide from the resin, formation of the disulfide interstrand linkage between $P^2$ and $P^{11}$, and full deprotection were performed as indicated in procedure D above. Finally, the peptide was purified, as described above, and characterized by HPLC-MS. For analytical data, see Ex. 163 in Table 2.

Example 164 is shown in Table 1.

Procedure O, as described above, was used for the preparation of the peptide, applying an on-resin fragment coupling strategy.

(I) The protected peptide fragment (module B and linker L) was synthesized as indicated above in the corresponding section in the synthesis of Ex. 1.

Assembly of the peptide fragment was in the following sequence:

Resin-Thr-$Q^6$-$Q^5$-$Q^4$-$Q^3$-$Q^2$-$Q^1$-$L^1$.

(II) The fully protected peptide (module A, module B and linker L) was assembled on solid support according to method K as described above.

The peptide was synthesized starting with an appropriately protected Fmoc amino acid which was used in the first coupling cycle for grafting the amino acid residue at $X^{12}$ to Sieber amide resin, using Fmoc-Glu(Allyl)-OH for addition of the amino acid residue at $P^6$, and using alpha-hydroxyisovaleric acid (Hiv) for addition of the hydroxy acid residue at $P^1$. Coupling of the protected peptide fragment (module B and linker L) was performed as indicated in the corresponding section of procedure A above by formation of an amide bond between the γ-carboxyl group of Glu at $P^6$ and the α-amino group of Dab at $L^1$. Assembly of the peptide was in the following sequence, showing only residues of module A:

Resin-$X^{12}$-$P^{11}$-$P^{10}$-$P^9$-$P^8$-$P^7$-$P^6$-$P^5$-$P^4$-$P^3$-$P^2$-$P^1$.

Subsequently, cleavage of the peptide from the resin, formation of the disulfide interstrand linkage between $P^2$ and $P^{11}$, and full deprotection were performed as indicated in procedure O above. Finally, the peptide was purified, as described above, and characterized by HPLC-MS. For analytical data, see Ex. 164 in Table 2.

Example 165 is shown in Table 1.

Procedure O, as described above, was used for the preparation of the peptide, applying an on-resin fragment coupling strategy.

(I) The protected peptide fragment (module B and linker L) was synthesized as indicated above in the corresponding section in the synthesis of Ex. 1.

Assembly of the peptide fragment was in the following sequence:

Resin-Thr-$Q^6$-$Q^5$-$Q^4$-$Q^3$-$Q^2$-$Q^1$-$L^1$.

(II) The fully protected peptide (module A, module B and linker L) was assembled on solid support according to method K as described above.

The peptide was synthesized starting with an appropriately protected Fmoc amino acid which was used in the first coupling cycle for grafting the amino acid residue at $X^{12}$ to Sieber amide resin, using Fmoc-$^D$Glu(Allyl)-OH for addition of the amino acid residue at $P^6$, and using alpha-hydroxyisovaleric acid (Hiv) for addition of the hydroxy acid residue at $P^1$. Coupling of the protected peptide fragment (module B and linker L) was performed as indicated in the corresponding section of procedure A above by formation of an amide bond between the γ-carboxyl group of $^D$Glu at $P^6$ and the α-amino group of Dab at $L^1$. Assembly of the peptide was in the following sequence:

Resin-$X^{12}$-$P^{11}$-$P^{10}$-$P^9$-$P^8$-$P^7$-$P^6$-$P^5$-$P^4$-$P^3$-$P^2$-$P^1$.

Subsequently, cleavage of the peptide from the resin, formation of the disulfide interstrand linkage between $P^2$ and $P^{11}$, and full deprotection were performed as indicated in procedure O above. Finally, the peptide was purified, as described above, and characterized by HPLC-MS. For analytical data, see Ex. 165 in Table 2.

Examples 166, 167 and 168 are shown in Table 1.

Procedure O, as described above, was used for the preparation of the peptides, applying an on-resin fragment coupling strategy.

(I) The protected peptide fragment (module B and linker L) was synthesized as indicated above in the corresponding section in the synthesis of Ex. 1.

Assembly of the peptide fragment was in the following sequence:

Resin-Thr-$Q^6$-$Q^5$-$Q^4$-$Q^3$-$Q^2$-$Q^1$-$L^3$-$L^2$-$L^1$.

(II) The fully protected peptides (module A, module B and linker L) were assembled on solid support according to method K as described above.

The peptides were synthesized starting with an appropriately protected Fmoc amino acid which was used in the first coupling cycle for grafting the amino acid residue at $X^{12}$ to Sieber amide resin, using Fmoc-Glu(Allyl)-OH for addition of the amino acid residue at $P^7$, and using alpha-hydroxyisovaleric acid (Hiv) for addition of the hydroxy acid residue at $P^1$. Coupling of the protected peptide fragment (module B and linker L) was performed as indicated in the corresponding section of procedure A above by formation of an amide bond between the γ-carboxyl group of Glu at $P^7$ and the α-amino group of Dab at $L^1$. Assembly of the peptides was in the following sequence, showing only residues of module A:

Resin-$X^{12}$-$P^{11}$-$P^{10}$-$P^9$-$P^8$-$P^7$-$P^6$-$P^5$-$P^4$-$P^3$-$P^2$-$P^1$.

Subsequently, cleavage of the peptides from the resin, formation of the disulfide interstrand linkage between $P^2$ and $P^{11}$, and full deprotection were performed as indicated in procedure O above. Finally, the peptides were purified, as described above, and characterized by HPLC-MS. For analytical data, see Ex. 166, 167 and 168 in Table 2.

Examples 169, 170 and 171 are shown in Table 1.

Procedure O, as described above, was used for the preparation of the peptides, applying an on-resin fragment coupling strategy.

(I) The protected peptide fragment (module B and linker L) was synthesized as indicated above in the corresponding section in the synthesis of Ex. 1.

Assembly of the peptide fragment was in the following sequence:

Resin-Thr-$Q^6$-$Q^5$-$Q^4$-$Q^3$-$Q^2$-$Q^1$-$L^3$-$L^2$-$L^1$.

(II) The fully protected peptides (module A, module B and linker L) were assembled on solid support according to method K as described above.

The peptides were synthesized starting with an appropriately protected Fmoc amino acid which was used in the first coupling cycle for grafting the amino acid residue at $X^{12}$ to Sieber amide resin, using Fmoc-$^D$Glu(Allyl)-OH for addition of the amino acid residue at $P^7$, and using alpha-hydroxyisovaleric acid (Hiv) for addition of the hydroxy acid residue at $P^1$. Coupling of the protected peptide fragment (module B and linker L) was performed as indicated in the corresponding section of procedure A above by formation of an amide bond between the γ-carboxyl group of $^D$Glu at $P^7$ and the α-amino group of Dab at C. Assembly of the peptides was in the following sequence, showing only residues of module A:

Resin-$X^{12}$-$P^{11}$-$P^{10}$-$P^9$-$P^8$-$P^7$-$P^6$-$P^5$-$P^4$-$P^3$-$P^2$-$P^1$.

Subsequently, cleavage of the peptides from the resin, formation of the disulfide interstrand linkage between $P^2$ and $P^{11}$, and full deprotection were performed as indicated in procedure O above. Finally, the peptides were purified, as described above, and characterized by HPLC-MS. For analytical data, see Ex. 169, 170 and 171 in Table 2.

Examples 172, 173 and 174 are shown in Table 1.

Procedure D, as described above, was used for the preparation of the peptides, applying an on-resin fragment coupling strategy.

(I) The protected peptide fragment (module B and linker L) was synthesized as indicated above in the corresponding section in the synthesis of Ex. 1.

Assembly of the peptide fragment was in the following sequence:

Resin-Thr-$Q^6$-$Q^5$-$Q^4$-$Q^3$-$Q^2$-$Q^1$-$L^3$-$L^2$-$L^1$.

(II) The fully protected peptides (module A, module B and linker L) were assembled on solid support according to method E as described above.

The peptides were synthesized starting with the amino alcohol Fmoc-Serol(tBu), which was grafted to the resin (Fmoc-Serol(tBu)-2-chlorotrityl resin), using Fmoc-Glu(Allyl)-OH for addition of the amino acid residue at $P^7$, and using alpha-hydroxyisovaleric acid (Hiv) for addition of the hydroxy acid residue at $P^1$. Coupling of the protected peptide fragment (module B and linker L) was performed as indicated in the corresponding section of procedure A above by formation of an amide bond between the γ-carboxyl group of Glu at $P^7$ and the α-amino group of Dab at $L^1$. Assembly of the peptides was in the following sequence, showing only residues of module A:

Resin-Serol-$P^{11}$-$P^{10}$-$P^9$-$P^8$-$P^7$-$P^6$-$P^5$-$P^4$-$P^3$-$P^2$-$P^1$.

Subsequently, cleavage of the peptides from the resin, formation of the disulfide interstrand linkage between $P^2$ and $P^{11}$, and full deprotection were performed as indicated in procedure D above. Finally, the peptides were purified, as described above, and characterized by HPLC-MS. For analytical data, see Ex. 172, 173 and 174 in Table 2.

Example 175 is shown in Table 1.

Procedure M1, as described above, was used for the preparation of the peptides, applying an on-resin fragment coupling strategy.

(I) The protected peptide fragments (module B and linker L) were synthesized as described above in the corresponding section in the synthesis of Ex. 1.

Assembly of the peptide fragments was in the following sequence:

Resin-Thr-$Q^6$-$Q^5$-$Q^4$-$Q^3$-$Q^2$-$Q^1$.

(II) The fully protected peptides (module A, module B and linker L) were assembled on solid support according to method J as described above.

The peptides were synthesized starting with an appropriately protected Fmoc-amino acid, which was used in the first coupling cycle for grafting the amino acid residue at $X^{12}$ to Sieber amide resin, and using Fmoc-Glu(Allyl)-OH for addition of the amino acid residue at $P^5$. Coupling of the protected peptide fragment (module B and linker L) was performed as indicated in the corresponding section of procedure A above by formation of an amide bond between the γ-carboxyl group of Glu at $P^5$ and the α-amino group of Dab at $L^1$. Assembly of the peptides was in the following sequence, showing only residues of module A:

Resin-$X^{12}$-$P^{11}$-$P^{10}$-$P^9$-$P^8$-$P^7$-$P^6$-$P^5$-$P^4$-$P^3$-$P^2$-$P^1$.

Subsequently, acylation with acetic acid at $P^1$, cleavage of the peptides from the resin, formation of the disulfide interstrand linkages between $P^2$ and $P^{11}$ and between $P^4$ and $P^9$, and full deprotection were performed as indicated in procedure M1 above. Finally, the peptides were purified, as described above, and characterized by HPLC-MS. For analytical data, see Ex. 175 in Table 2.

Examples 176 and 177 are shown in Table 1.

Procedure L, as described above, was used for the preparation of the peptides, applying an on-resin fragment coupling strategy.

(I) The protected peptide fragment (module B and linker L) was synthesized as described above in the corresponding section in the synthesis of Ex. 1.

Assembly of the peptide fragment was in the following sequence:

Resin-Thr-$Q^6$-$Q^5$-$Q^4$-$Q^3$-$Q^2$-$Q^1$-$L^3$-$L^2$-$L^1$.

(II) The fully protected peptides (module A, module B and linker L) were assembled on solid support according to method I as described above.

The peptide was synthesized starting with an appropriately protected Fmoc-amino acid, which was used in the first coupling cycle for grafting the amino acid residue at $X^{12}$ to Sieber amide resin, and using Fmoc-Glu(Allyl)-OH for addition of the amino acid residue at $P^5$. Coupling of the protected peptide fragment (module B and linker L) was performed as indicated in the corresponding section of procedure A above by formation of an amide bond between the γ-carboxyl group of Glu at $P^5$ and the α-amino group of Dab at $L^1$. Assembly of the peptides was in the following sequence, showing only residues of module A:

Resin-$X^{12}$-$P^{11}$-$P^{10}$-$P^9$-$P^8$-$P^7$-$P^6$-$P^5$-$P^4$-$P^3$-$P^2$-$P^1$.

Subsequently, cleavage of the peptides from the resin, formation of the disulfide interstrand linkages between $P^2$ and $P^{11}$ and between $P^4$ and $P^9$, and full deprotection were performed as indicated in procedure L above. Finally, the peptides were purified, as described above, and characterized by HPLC-MS. For analytical data, see Ex. 176 and 177 in Table 2.

Examples 178, 179, 205 to 208 and 215 are shown in Table 1.

Procedure M1, as described above, was used for the preparation of the peptides, applying an on-resin fragment coupling strategy.

(I) The protected peptide fragments (module B and linker L) were synthesized as described above in the corresponding section in the synthesis of Ex. 1.

Assembly of the peptide fragments was in the following sequence:

Resin-Thr-$Q^6$-$Q^5$-$Q^4$-$Q^3$-$Q^2$-$Q^1$-$L^3$-$L^2$-$L^1$.

(II) The fully protected peptides (module A, module B and linker L) were assembled on solid support according to method J as described above.

The peptides were synthesized starting with an appropriately protected Fmoc-amino acid, which was used in the first coupling cycle for grafting the amino acid residue at $X^{12}$ to Sieber amide resin, and using Fmoc-Glu(Allyl)-OH for addition of the amino acid residue at $P^5$. Coupling of the protected peptide fragment (module B and linker L) was performed as indicated in the corresponding section of procedure A above by formation of an amide bond between the γ-carboxyl group of Glu at $P^5$ and the α-amino group of Dab at C. Assembly of the peptide was in the following sequence, showing only residues of module A:

Resin-$X^{12}$-$P^{11}$-$P^{10}$-$P^9$-$P^8$-$P^7$-$P^6$-$P^5$-$P^4$-$P^3$-$P^2$-$P^1$.

Subsequently, acylation with acetic acid at $P^1$, cleavage of the peptides from the resin, formation of the disulfide interstrand linkage between $P^4$ and $P^9$, and full deprotection were performed as indicated in procedure M1 above. Finally, the peptides were purified, as described above, and characterized by HPLC-MS. For analytical data, see Ex. 178, 179, 205 to 208 and 215 in Table 2.

Examples 219 to 227 and 266 are shown in Table 1.

Procedure M2, as described above, was used for the preparation of the peptides, applying an on-resin fragment coupling strategy.

(I) The protected peptide fragments (module B and linker L) were synthesized as described above in the corresponding section in the synthesis of Ex. 1.

Assembly of the peptide fragments was in the following sequence:

Resin-Thr-$Q^6$-$Q^5$-$Q^4$-$Q^3$-$Q^2$-$Q^1$-$L^3$-$L^2$-$L^1$ (II) The fully protected peptides (module A, module B and linker L) were assembled on solid support according to method J as described above.

The peptides were synthesized starting with an appropriately protected Fmoc-amino acid, which was used in the first coupling cycle for grafting the amino acid residue at $X^{12}$ to Sieber amide resin, and using Fmoc-Glu(Allyl)-OH for addition of the amino acid residue at $P^5$. Coupling of the protected peptide fragment (module B and linker L) was performed as indicated in the corresponding section of procedure A above by formation of an amide bond between the γ-carboxyl group of Glu at $P^5$ and the α-amino group of Dab at C. Assembly of the peptide was in the following sequence, showing only residues of module A:

Resin-$X^{12}$-$P^{11}$-$P^{10}$-$P^9$-$P^8$-$P^7$-$P^6$-$P^5$-$P^4$-$P^3$-$P^2$-$P^1$.

Subsequently, acylation with acetic acid at $P^1$, cleavage of the peptides from the resin, full deprotection and formation of the disulfide interstrand linkage between $P^4$ and $P^9$ were performed as indicated in procedure M2 above. Finally, the peptides were purified, as described above, and characterized by HPLC-MS. For analytical data, see Ex. 219 to 227 and 266 in Table 2.

Examples 180 to 185 are shown in Table 1.

Procedure L, as described above, was used for the preparation of the peptides, applying an on-resin fragment coupling strategy.

(I) The protected peptide fragments (module B and linker L) were synthesized as described above in the corresponding section in the synthesis of Ex. 1.

Assembly of the peptide fragments was in the following sequence:

Resin-Thr-$Q^6$-$Q^5$-$Q^4$-$Q^3$-$Q^2$-$Q^1$-$L^3$-$L^2$-$L^1$.

(II) The fully protected peptides (module A, module B and linker L) were assembled on solid support according to method I as described above.

The peptides were synthesized starting with an appropriately protected Fmoc-amino acid, which was used in the first coupling cycle for grafting the amino acid residue at $X^{12}$ to Sieber amide resin, and using Fmoc-Glu(Allyl)-OH for addition of the amino acid residue at $P^5$. Coupling of the protected peptide fragment (module B and linker L) was performed as indicated in the corresponding section of procedure A above by formation of an amide bond between the γ-carboxyl group of Glu at $P^5$ and the α-amino group of Dab at $L^1$. Assembly of the peptides was in the following sequence, showing only residues of module A:

Resin-$X^{12}$-$P^{11}$-$P^{10}$-$P^9$-$P^8$-$P^7$-$P^6$-$P^5$-$P^4$-$P^3$-$P^2$-$P^1$.

Subsequently, cleavage of the peptides from the resin, formation of the disulfide interstrand linkage between $P^4$ and $P^9$, and full deprotection were performed as indicated in procedure L above. Finally, the peptides were purified, as described above, and characterized by HPLC-MS. For analytical data, see Ex. 180 to 185 in Table 2.

Example 186 is shown in Table 1.

Procedure E, as described above, was used for the preparation of the peptide, applying an on-resin fragment coupling strategy.

(I) The protected peptide fragment (module B and linker L) was synthesized as described above in the corresponding section in the synthesis of Ex. 1.

Assembly of the peptide fragment was in the following sequence:

Resin-Thr-$Q^6$-$Q^5$-$Q^4$-$Q^3$-$Q^2$-$Q^1$.

(II) The fully protected peptide (module A, module B and linker L) was assembled on solid support according to method F as described above.

The peptide was synthesized starting with the amino acid Fmoc-Ser(tBu)-OH, which was grafted to the resin (Fmoc-Ser(tBu)-2-chlorotrityl resin) and using Fmoc-Glu(Allyl)-OH for addition of the amino acid residue at $P^5$. Coupling of the protected peptide fragment (module B and linker L) was performed as indicated in the corresponding section of procedure A above by formation of an amide bond between the γ-carboxyl group of Glu at $P^5$ and the α-amino group of Dab at $L^1$. Assembly of the peptides was in the following sequence, showing only residues of module A:

Resin-Ser-$P^{11}$-$P^{10}$-$P^9$-$P^8$-$P^7$-$P^6$-$P^5$-$P^4$-$P^3$-$P^2$-$P^1$.

Subsequently, cleavage of the peptide from the resin, formation of the disulfide interstrand linkage between $P^4$ and $P^9$, and full deprotection were performed as indicated in procedure E above. Finally, the peptide was purified, as described above, and characterized by HPLC-MS. For analytical data, see Ex. 186 in Table 2.

Example 187 is shown in Table 1.

Procedure N2, as described above, was used for the preparation of the peptide, applying an on-resin fragment coupling strategy.

(I) The protected peptide fragment (module B and linker L) was synthesized as described above in the corresponding section in the synthesis of Ex. 1.

Assembly of the peptide fragment was in the following sequence:

Resin-Thr-$Q^6$-$Q^5$-$Q^4$-$Q^3$-$Q^2$-$Q^1$-$L^3$-$L^2$-$L^1$.

(II) The fully protected peptide (module A, module B and linker L) was assembled on solid support according to method J as described above.

The peptide was synthesized starting with an appropriately protected Fmoc-amino acid, which was used in the first coupling cycle for grafting the amino acid residue at) $X^{12}$ to Sieber amide resin, using Fmoc-Glu(Allyl)-OH for addition of the amino acid residue at $P^5$, and using Fmoc-Asp(2-PhiPr)-OH for addition of the amino acid residue at $P^4$. Coupling of the protected peptide fragment (module B and linker L) was performed as indicated in the corresponding section of procedure A above by formation of an amide bond between the γ-carboxyl group of Glu at $P^5$ and the α-amino group of Dab at $L^1$. Assembly of the peptide was in the following sequence, showing only residues of module A:

Resin-$X^{12}$-$P^{11}$-$P^{10}$-$P^9$-$P^8$-$P^7$-$P^6$-$P^5$-$P^4$-$P^3$-$P^2$-$P^1$.

Subsequently, acylation with acetic acid at $P^1$, ivDde deprotection at $P^9$, cleavage of the peptide from the resin and removal of the 2-phenyl-isopropyl protecting group at $P^4$, formation of a lactam interstrand linkage by an amide bond between the liberated β-carboxyl group of Asp at $P^4$ and the γ-amino group of Dab at $P^9$, and full deprotection were performed as indicated in procedure N2 above. Finally, the peptide was purified, as described above, and characterized by HPLC-MS. For analytical data, see Ex. 187 in Table 2.

Example 188 to 195, 198 to 202 and 204 are shown in Table 1.

Procedure D, as described above, was used for the preparation of the peptides, applying an on-resin fragment coupling strategy.

(I) The protected peptide fragments (module B and linker L) were synthesized as indicated above in the corresponding section in the synthesis of Ex. 1.

Assembly of the peptide fragments was in the following sequence:

Resin-Thr-$Q^6$-$Q^5$-$Q^4$-$Q^3$-$Q^2$-$Q^1$-$L^3$-$L^2$-$L^1$.

(II) The fully protected peptides (module A, module B and linker L) were assembled on solid support according to method E as described above.

The peptides were synthesized starting with the amino alcohol Fmoc-Throl(tBu), which was grafted to the resin (Fmoc-Throl(tBu)-2-chlorotrityl resin), using Fmoc-Glu (Allyl)-OH for addition of the amino acid residue at $P^5$, and using alpha-hydroxyisovaleric acid (Hiv) for addition of the hydroxy acid residue at $P^1$. Coupling of the protected peptide fragment (module B and linker L) was performed as indicated in the corresponding section of procedure A above by formation of an amide bond between the γ-carboxyl group of Glu at $P^5$ and the α-amino group of Dab at $L^1$. Assembly of the peptides was in the following sequence, showing only residues of module A:

Resin-Throl-$P^{11}$-$P^{10}$-$P^9$-$P^8$-$P^7$-$P^6$-$P^5$-$P^4$-$P^3$-$P^2$-$P^1$.

Subsequently, cleavage of the peptides from the resin, formation of the disulfide interstrand linkage between $P^4$ and $P^9$, and full deprotection were performed as indicated in procedure D above. Finally, the peptides were purified, as described above, and characterized by HPLC-MS. For analytical data, see Ex. 188 to 195, 198 to 202 and 204 in Table 2.

Example 196 is shown in Table 1.

Procedure B, as described above, was used for the preparation of the peptide, applying an on-resin fragment coupling strategy.

(I) The protected peptide fragment (module B and linker L) was synthesized as indicated above in the corresponding section in the synthesis of Ex. 1.

Assembly of the peptide fragment was in the following sequence:

Resin-Thr-$Q^6$-$Q^5$-$Q^4$-$Q^3$-$Q^2$-$Q^1$-$L^3$-$L^2$-$L^1$.

(II) The fully protected peptide (module A, module B and linker L) was assembled on solid support according to method C as described above.

The peptide was synthesized starting with the amino alcohol Fmoc-Serol(tBu), which was grafted to the resin (Fmoc-Serol(tBu)-2-chlorotrityl resin) and using Fmoc-Glu (Allyl)-OH for addition of the amino acid residue at $P^5$. Coupling of the protected peptide fragment (module B and linker L) was performed as indicated in the corresponding section of procedure A above by formation of an amide bond between the γ-carboxyl group of Glu at $P^5$ and the α-amino group of Dab at $L^1$. Assembly of the peptide was in the following sequence, showing only residues of module A:

Resin-Serol-$P^{11}$-$P^{10}$-$P^9$-$P^8$-$P^7$-$P^6$-$P^5$-$P^4$-$P^3$-$P^2$-$P^1$.

Subsequently, acylation with acetic acid at $P^1$, cleavage of the peptide from the resin, formation of the disulfide interstrand linkage between $P^4$ and $P^9$, and full deprotection were performed as indicated in procedure B above. Finally, the peptide was purified, as described above, and characterized by HPLC-MS. For analytical data, see Ex. 196 in Table 2.

Example 197 is shown in Table 1.

Procedure D, as described above, was used for the preparation of the peptide, applying an on-resin fragment coupling strategy.

(I) The protected peptide fragment (module B and linker L) were synthesized as indicated above in the corresponding section in the synthesis of Ex. 1.

Assembly of the peptide fragment was in the following sequence:

Resin-Thr-$Q^6$-$Q^5$-$Q^4$-$Q^3$-$Q^2$-$Q^1$-$L^3$-$L^2$-$L^1$.

(II) The fully protected peptide (module A, module B and linker L) was assembled on solid support according to method E as described above.

The peptide was synthesized starting with the amino alcohol Fmoc-Serol(tBu), which was grafted to the resin (Fmoc-Serol(tBu)-2-chlorotrityl resin), using Fmoc-Glu(Allyl)-OH for addition of the amino acid residue at $P^5$, and using alpha-hydroxyisovaleric acid (Hiv) for addition of the hydroxy acid residue at $P^1$. Coupling of the protected peptide fragment (module B and linker L) was performed as indicated in the corresponding section of procedure A above by formation of an amide bond between the γ-carboxyl group of Glu at $P^5$ and the α-amino group of Dab at $L^1$. Assembly of the peptide was in the following sequence, showing only residues of module A:

Resin-Serol-$P^{11}$-$P^{10}$-$P^9$-$P^8$-$P^7$-$P^6$-$P^5$-$P^4$-$P^3$-$P^2$-Hiv.

Subsequently, cleavage of the peptide from the resin, formation of the disulfide interstrand linkage between $P^4$ and $P^9$, and full deprotection were performed as indicated in procedure D above. Finally, the peptide was purified, as described above, and characterized by HPLC-MS. For analytical data, see Ex. 197 in Table 2.

Example 203 is shown in Table 1.

Procedure D, as described above, was used for the preparation of the peptide, applying an on-resin fragment coupling strategy.

(I) The protected peptide fragment (module B and linker L) was synthesized as indicated above in the corresponding section in the synthesis of Ex. 1.

Assembly of the peptide fragment was in the following sequence:

Resin-Thr-$Q^6$-$Q^5$-$Q^4$-$Q^3$-$Q^2$-$Q^1$-$L^3$-$L^2$-$L^1$.

(II) The fully protected peptide (module A, module B and linker L) was assembled on solid support according to method E as described above.

The peptide was synthesized starting with the amino alcohol Fmoc-Throl(tBu), which was grafted to the resin (Fmoc-Throl(tBu)-2-chlorotrityl resin), using Fmoc-Glu (Allyl)-OH for addition of the amino acid residue at $P^7$, and using alpha-hydroxyisovaleric acid (Hiv) for addition of the hydroxy acid residue at $P^1$. Coupling of the protected peptide fragment (module B and linker L) was performed as indicated in the corresponding section of procedure A above by formation of an amide bond between the γ-carboxyl group of Glu at $P^7$ and the α-amino group of Dab at $L^1$. Assembly of the peptide was in the following sequence, showing only residues of module A:

Resin-Throl-$P^{11}$-$P^{10}$-$P^9$-$P^8$-$P^7$-$P^6$-$P^5$-$P^4$-$P^3$-$P^2$-Hiv.

Subsequently, cleavage of the peptide from the resin, formation of the disulfide interstrand linkage between $P^4$ and $P^9$, and full deprotection were performed as indicated in procedure D above. Finally, the peptide was purified, as described above, and characterized by HPLC-MS. For analytical data, see Ex. 203 in Table 2.

Example 209 is shown in Table 1.

Procedure D, as described above, was used for the preparation of the peptide, applying an on-resin fragment coupling strategy.

(I) The protected peptide fragment (module B and linker L) was synthesized as indicated above in the corresponding section in the synthesis of Ex. 1.

Assembly of the peptide fragment was in the following sequence:

Resin-Thr-$Q^6$-$Q^5$-$Q^4$-$Q^3$-$Q^2$-$Q^1$-$L^3$-$L^2$-$L^1$.

(II) The fully protected peptide (module A, module B and linker L) was assembled on solid support according to method E as described above.

The peptide was synthesized starting with the amino alcohol Fmoc-Throl(tBu), which was grafted to the resin (Fmoc-Throl(tBu)-2-chlorotrityl resin), using Fmoc-Glu (Allyl)-OH for addition of the amino acid residue at $P^6$, and using alpha-hydroxyisovaleric acid (Hiv) for addition of the hydroxy acid residue at $P^1$. Coupling of the protected peptide fragment (module B and linker L) was performed as indicated in the corresponding section of procedure A above by formation of an amide bond between the γ-carboxyl group of Glu at $P^6$ and the α-amino group of Dab at $L^1$. Assembly of the peptide was in the following sequence, showing only residues of module A:

Resin-Throl-$P^{11}$-$P^{10}$-$P^9$-$P^8$-$P^7$-$P^6$-$P^5$-$P^4$-$P^3$-$P^2$-$P^1$.

Subsequently, cleavage of the peptide from the resin, formation of the disulfide interstrand linkage between $P^4$ and $P^9$, and full deprotection were performed as indicated in procedure D above. Finally, the peptide was purified, as described above, and characterized by HPLC-MS. For analytical data, see Ex. 209 in Table 2.

Example 210 is shown in Table 1.

Procedure D, as described above, was used for the preparation of the peptide, applying an on-resin fragment coupling strategy.

(I) The protected peptide fragment (module B and linker L) was synthesized as indicated above in the corresponding section in the synthesis of Ex. 1. Assembly of the peptide fragment was in the following sequence:

Resin-Thr-$Q^6$-$Q^5$-$Q^4$-$Q^3$-$Q^2$-$Q^1$-$L^3$-$L^2$-$L^1$.

(II) The fully protected peptide (module A, module B and linker L) was assembled on solid support according to method E as described above.

The peptide was synthesized starting with the amino alcohol Fmoc-Throl(tBu), which was grafted to the resin (Fmoc-Throl(tBu)-2-chlorotrityl resin), using Fmoc-$^D$Glu(Allyl)-OH for addition of the amino acid residue at $P^6$, and using alpha-hydroxyisovaleric acid (Hiv) for addition of the hydroxy acid residue at $P^1$. Coupling of the protected peptide fragment (module B and linker L) was performed as indicated in the corresponding section of procedure A above by formation of an amide bond between the γ-carboxyl group of $^D$Glu at $P^6$ and the α-amino group of Dab at $L^1$. Assembly of the peptide was in the following sequence, showing only residues of module A:

Resin-Throl-$P^{11}$-$P^{10}$-$P^9$-$P^8$-$P^7$-$P^6$-$P^5$-$P^4$-$P^3$-$P^2$-Hiv.

Subsequently, cleavage of the peptide from the resin, formation of the disulfide interstrand linkage between $P^4$ and $P^9$, and full deprotection were performed as indicated in procedure D above. Finally, the peptide was purified, as described above, and characterized by HPLC-MS. For analytical data, see Ex. 210 in Table 2.

Example 211, 212 and 213 are shown in Table 1.

Procedure D, as described above, was used for the preparation of the peptides, applying an on-resin fragment coupling strategy.

(I) The protected peptide fragment (module B and linker L) was synthesized as indicated above in the corresponding section in the synthesis of Ex. 1.

Assembly of the peptide fragment was in the following sequence:

Resin-Thr-$Q^6$-$Q^5$-$Q^4$-$Q^3$-$Q^2$-$Q^1$-$L^3$-$L^2$-$L^1$.

(II) The fully protected peptides (module A, module B and linker L) were assembled on solid support according to method E as described above.

The peptides were synthesized starting with the amino alcohol Fmoc-Throl(tBu), which was grafted to the resin (Fmoc-Throl(tBu)-2-chlorotrityl resin), using Fmoc-Glu(Allyl)-OH for addition of the amino acid residue at $P^7$, and using alpha-hydroxyisovaleric acid (Hiv) for addition of the hydroxy acid residue at $P^1$. Coupling of the protected peptide fragment (module B and linker L) was performed as indicated in the corresponding section of procedure A above by formation of an amide bond between the γ-carboxyl group of Glu at $P^7$ and the α-amino group of Dab at $L^1$. Assembly of the peptide was in the following sequence, showing only residues of module A:

Resin-Throl-$P^{11}$-$P^{10}$-$P^9$-$P^8$-$P^7$-$P^6$-$P^5$-$P^4$-$P^3$-$P^2$-Hiv.

Subsequently, cleavage of the peptides from the resin, formation of the disulfide interstrand linkage between $P^4$ and $P^9$, and full deprotection were performed as indicated in procedure D above. Finally, the peptides were purified, as described above, and characterized by HPLC-MS. For analytical data, see Ex. 211, 212 and 213 in Table 2.

Example 214 is shown in Table 1.

Procedure D, as described above, was used for the preparation of the peptide, applying an on-resin fragment coupling strategy.

(I) The protected peptide fragment (module B and linker L) was synthesized as indicated above in the corresponding section in the synthesis of Ex. 1.

Assembly of the peptide fragment was in the following sequence:

Resin-Thr-$Q^6$-$Q^5$-$Q^4$-$Q^3$-$Q^2$-$Q^1$-$L^3$-$L^2$-$L^1$.

(II) The fully protected peptide (module A, module B and linker L) was assembled on solid support according to method E as described above.

The peptide was synthesized starting with the amino alcohol Fmoc-Throl(tBu), which was grafted to the resin (Fmoc-Throl(tBu)-2-chlorotrityl resin), using Fmoc-$^D$Glu(Allyl)-OH for addition of the amino acid residue at $P^7$, and using alpha-hydroxyisovaleric acid (Hiv) for addition of the hydroxy acid residue at $P^1$. Coupling of the protected peptide fragment (module B and linker L) was performed as indicated in the corresponding section of procedure A above by formation of an amide bond between the γ-carboxyl group of $^D$Glu at $P^7$ and the α-amino group of Dab at $L^1$. Assembly of the peptide was in the following sequence, showing only residues of module A:

Resin-Throl-$P^{11}$-$P^{10}$-$P^9$-$P^8$-$P^7$-$P^6$-$P^5$-$P^4$-$P^3$-$P^2$-Hiv.

Subsequently, cleavage of the peptide from the resin, formation of the disulfide interstrand linkage between $P^4$ and $P^9$, and full deprotection were performed as indicated in procedure D above. Finally, the peptide was purified, as described above, and characterized by HPLC-MS. For analytical data, see Ex. 214 in Table 2.

Example 216 is shown in Table 1.

Procedure D, as described above, was used for the preparation of the peptide, applying an on-resin fragment coupling strategy.

(I) The protected peptide fragment (module B and linker L) was synthesized as indicated above in the corresponding section in the synthesis of Ex. 1.

Assembly of the peptide fragment was in the following sequence:

Resin-Thr-$Q^6$-$Q^5$-$Q^4$-$Q^3$-$Q^2$-$Q^1$-$L^1$.

(II) The fully protected peptide (module A, module B and linker L) was assembled on solid support according to method E as described above.

The peptide was synthesized starting with the amino alcohol Fmoc-Throl(tBu), which was grafted to the resin (Fmoc-Throl(tBu)-2-chlorotrityl resin), using Fmoc-Glu(Allyl)-OH for addition of the amino acid residue at $P^6$, and using alpha-hydroxyisovaleric acid (Hiv) for addition of the hydroxy acid residue at $P^1$. Coupling of the protected peptide fragment (module B and linker L) was performed as indicated in the corresponding section of procedure A above by formation of an amide bond between the γ-carboxyl group of Glu at $P^6$ and the α-amino group of Dab at $L^1$. Assembly of the peptide was in the following sequence, showing only residues of module A:

Resin-Throl-$P^{11}$-$P^{10}$-$P^9$-$P^8$-$P^7$-$P^6$-$P^5$-$P^4$-$P^3$-$P^2$-$P^1$.

Subsequently, cleavage of the peptide from the resin, formation of the disulfide interstrand linkage between $P^4$ and $P^9$, and full deprotection were performed as indicated in procedure D above. Finally, the peptide was purified, as described above, and characterized by HPLC-MS. For analytical data, see Ex. 216 in Table 2.

Example 217 is shown in Table 1.

Procedure D, as described above, was used for the preparation of the peptide, applying an on-resin fragment coupling strategy.

(I) The protected peptide fragment (module B and linker L) was synthesized as indicated above in the corresponding section in the synthesis of Ex. 1.

Assembly of the peptide fragment was in the following sequence:

Resin-Thr-$Q^6$-$Q^5$-$Q^4$-$Q^3$-$Q^2$-$Q^1$-$L^1$.

(II) The fully protected peptide (module A, module B and linker L) was assembled on solid support according to method E as described above.

The peptide was synthesized starting with the amino alcohol Fmoc-Throl(tBu), which was grafted to the resin (Fmoc-Throl(tBu)-2-chlorotrityl resin), using Fmoc-$^D$Glu(Allyl)-OH for addition of the amino acid residue at $P^6$, and using alpha-hydroxyisovaleric acid (Hiv) for addition of the hydroxy acid residue at $P^1$. Coupling of the protected peptide fragment (module B and linker L) was performed as indicated in the corresponding section of procedure A above by formation of an amide bond between the γ-carboxyl group of $^D$Glu at $P^6$ and the α-amino group of Dab at $L^1$. Assembly of the peptide was in the following sequence, showing only residues of module A:

Resin-Throl-$P^{11}$-$P^{10}$-$P^9$-$P^8$-$P^7$-$P^6$-$P^5$-$P^4$-$P^3$-$P^2$-Hiv.

Subsequently, cleavage of the peptide from the resin, formation of the disulfide interstrand linkage between $P^4$ and $P^9$, and full deprotection were performed as indicated in procedure D above. Finally, the peptide was purified, as described above, and characterized by HPLC-MS. For analytical data, see Ex. 217 in Table 2.

Example 218 is shown in Table 1.

Procedure M1, as described above, was used for the preparation of the peptide, applying an on-resin fragment coupling strategy.

(I) The protected peptide fragment (module B and linker L) was synthesized as described above in the corresponding section in the synthesis of Ex. 1.

Assembly of the peptide fragment was in the following sequence:

Resin-Thr-$Q^6$-$Q^5$-$Q^4$-$Q^3$-$Q^2$-$Q^1$-$L^3$-$L^2$-$L^1$.

(II) The fully protected peptide (module A, module B and linker L) was assembled on solid support according to method J as described above.

The peptide was synthesized starting with an appropriately protected Fmoc-amino acid, which was used in the first coupling cycle for grafting the amino acid residue at $P^{11}$ to Sieber amide resin, and using Fmoc-Glu(Allyl)-OH for addition of the amino acid residue at $P^5$. Coupling of the protected peptide fragment (module B and linker L) was performed as indicated in the corresponding section of procedure A above by formation of an amide bond between the γ-carboxyl group of Glu at $P^5$ and the α-amino group of Dab at C. Assembly of the peptide was in the following sequence, showing only residues of module A:

Resin-$P^{11}$-$P^{10}$-$P^9$-$P^8$-$P^7$-$P^6$-$P^5$-$P^4$-$P^3$-$P^2$-$P^1$.

Subsequently, acylation with acetic acid at $X^{14}$, cleavage of the peptide from the resin, formation of the disulfide interstrand linkage between $P^4$ and $P^9$, and full deprotection were performed as indicated in procedure M1 above. Finally, the peptide was purified, as described above, and characterized by HPLC-MS. For analytical data, see Ex. 218 in Table 2.

Example 228 is shown in Table 1.

Procedure M1, as described above, was used for the preparation of the peptide, applying an on-resin fragment coupling strategy.

(I) The protected peptide fragment (module B and linker L) was synthesized as described above in the corresponding section in the synthesis of Ex. 1.

Assembly of the peptide fragment was in the following sequence:

Resin-Thr-$Q^6$-$Q^5$-$Q^4$-$Q^3$-$Q^2$-$Q^1$-$L^3$-$L^2$-$L^1$.

(II) The fully protected peptide (module A, module B and linker L) was assembled on solid support according to method J as described above.

The peptide was synthesized starting with an appropriately protected Fmoc-amino acid, which was used in the first coupling cycle for grafting the amino acid residue at $X^{12}$ to Sieber amide resin, and using Fmoc-Glu(Allyl)-OH for addition of the amino acid residue at $P^5$. Coupling of the protected peptide fragment (module B and linker L) was performed as indicated in the corresponding section of procedure A above by formation of an amide bond between the γ-carboxyl group of Glu at $P^5$ and the α-amino group of Dab at C. Assembly of the peptide was in the following sequence, showing only residues of module A:

Resin-$X^{12}$-$P^{11}$-$P^{10}$-$P^9$-$P^8$-$P^7$-$P^6$-$P^5$-$P^4$-$P^3$-$P^2$-$P^1$.

Subsequently, acylation with acetic acid at $P^1$, cleavage of the peptide from the resin, formation of the disulfide interstrand linkage between $P^1$ and $X^{12}$, and full deprotection were performed as indicated in procedure M1 above. Finally, the peptide was purified, as described above, and characterized by HPLC-MS. For analytical data, see Ex. 228 in Table 2.

Examples 229, and 230 are shown in Table 1.

Procedure Q, as described above, was used for the preparation of the peptides, applying an on-resin fragment coupling strategy.

(I) The protected peptide fragment (module B and linker L) was synthesized as described above in the corresponding section in the synthesis of Ex. 1.

Assembly of the peptide fragment was in the following sequence:

Resin-Thr-$Q^6$-$Q^5$-$Q^4$-$Q^3$-$Q^2$-$Q^1$-$L^3$-$L^2$-$L^1$.

(II) The fully protected peptide (module A, module B and linker L) was assembled on solid support according to method J as described above.

The peptide was synthesized starting with an appropriately protected Fmoc-amino acid, which was used in the first coupling cycle for grafting the amino acid residue at $X^{12}$ to Sieber amide resin, and using Fmoc-Glu(Allyl)-OH for addition of the amino acid residue at $P^5$. Coupling of the protected peptide fragment (module B and linker L) was performed as indicated in the corresponding section of procedure A above by formation of an amide bond between the γ-carboxyl group of Glu at $P^5$ and the α-amino group of Dab at $L^1$. Assembly of the peptides was in the following sequence, showing only residues of module A:

Resin-$X^{12}$-$P^{11}$-$P^{10}$-$P^9$-$P^8$-$P^7$-$P^6$-$P^5$-$P^4$-$P^3$-$P^2$-$P^1$.

Subsequently, acylation with acetic acid at $P^1$, cleavage of the peptides from the resin, and full deprotection were performed as indicated in procedure Q above. Finally, the peptides were purified, as described above, and characterized by HPLC-MS. For analytical data, see Ex. 229, and 230 in Table 2.

Examples 232 and 233 are shown in Table 1.

Procedure A, as described above, was used for the preparation of the peptides, applying an on-resin fragment coupling strategy.

(I) The protected peptide fragment (module B and linker L) was synthesized as indicated above in the corresponding section in the synthesis of Ex. 1.

Assembly of the peptide fragment was in the following sequence:

Resin-Thr-$Q^6$-$Q^5$-$Q^4$-$Q^3$-$Q^2$-$Q^1$.

(II) The fully protected peptides (module A, module B and linker L) were assembled on solid support according to method B as described above.

The peptides were synthesized starting with the amino alcohol Fmoc-Throl(tBu), which was grafted to the resin (Fmoc-Throl(tBu)-2-chlorotrityl resin) and using Fmoc-Glu (Allyl)-OH for addition of the amino acid residue at $P^5$. Coupling of the protected peptide fragment (module B and linker L) was performed as indicated in the corresponding section of procedure A above by formation of an amide bond between the γ-carboxyl group of Glu at $P^5$ and the α-amino group of Dab at $L^1$. Assembly of the peptides was in the following sequence, showing only residues of module A:

Resin-Throl-$P^{11}$-$P^{10}$-$P^9$-$P^8$-$P^7$-$P^6$-$P^5$-$P^4$-$P^3$-$P^2$-$P^1$-$X^{14}$.

Subsequently, cleavage of the peptide from the resin, formation of the disulfide interstrand linkage between $P^2$ and $P^{11}$, and full deprotection were performed as indicated in procedure A above. Finally, the peptides were purified, as described above, and characterized by HPLC-MS. For analytical data, see Ex. 232 and 233 in Table 2.

Examples 234 and 235 are shown in Table 1.

Procedure M1, as described above, was used for the preparation of the peptides, applying an on-resin fragment coupling strategy.

(I) The protected peptide fragment (module B and linker L) was synthesized as described above in the corresponding section in the synthesis of Ex. 1.

Assembly of the peptide fragment was in the following sequence:

Resin-Thr-$Q^6$-$Q^5$-$Q^4$-$Q^3$-$Q^2$-$Q^1$-$L^3$-$L^2$-$L^1$.

(II) The fully protected peptides (module A, module B and linker L) were assembled on solid support according to method J as described above.

The peptides were synthesized starting with an appropriately protected Fmoc-amino acid, which was used in the first coupling cycle for grafting the amino acid residue at $X^{12}$ to Sieber amide resin, and using Fmoc-Glu(Allyl)-OH for addition of the amino acid residue at $P^5$. Coupling of the protected peptide fragment (module B and linker L) was performed as indicated in the corresponding section of procedure A above by formation of an amide bond between the γ-carboxyl group of Glu at $P^5$ and the α-amino group of Dab at $L^1$. Assembly of the peptides was in the following sequence, showing only residues of module A:

Resin-$X^{12}$-$P^{11}$-$P^{10}$-$P^9$-$P^8$-$P^7$-$P^6$-$P^5$-$P^4$-$P^3$-$P^2$-$P^1$-$X^{14}$.

Subsequently, acylation with acetic acid at $X^{14}$, cleavage of the peptides from the resin, formation of the disulfide interstrand linkages between $P^2$ and $P^{11}$ and between $P^4$ and $P^9$, and full deprotection were performed as indicated in procedure M1 above. Finally, the peptides were purified, as described above, and characterized by HPLC-MS. For analytical data, see Ex. 234 and 235 in Table 2.

Example 236 is shown in Table 1.

Procedure D, as described above, was used for the preparation of the peptide, applying an on-resin fragment coupling strategy.

(I) The protected peptide fragment (module B and linker L) was synthesized as indicated above in the corresponding section in the synthesis of Ex. 1.

Assembly of the peptide fragment was in the following sequence:

Resin-Thr-$Q^6$-$Q^5$-$Q^4$-$Q^3$-$Q^2$-$Q^1$-$L^3$-$L^2$-$L^1$.

(II) The fully protected peptide (module A, module B and linker L) was assembled on solid support according to method E as described above.

The peptide was synthesized starting with the amino alcohol Fmoc-Glyol, which was grafted to the resin (Fmoc-Glyol-2-chlorotrityl resin), using Fmoc-Glu(Allyl)-OH for addition of the amino acid residue at $P^5$, and using alpha-hydroxyisovaleric acid (Hiv) for addition of the hydroxy acid residue at $P^1$. Coupling of the protected peptide fragment (module B and linker L) was performed as indicated in the corresponding section of procedure A above by formation of an amide bond between the γ-carboxyl group of Glu at $P^5$ and the α-amino group of Dab at $L^1$. Assembly of the peptide was in the following sequence, showing only residues of module A:

Resin-Glyol-$X^{12}$-$P^{11}$-$P^{10}$-$P^9$-$P^8$-$P^7$-$P^6$-$P^5$-$P^4$-$P^3$-$P^2$-Hiv.

Subsequently, cleavage of the peptide from the resin, formation of the disulfide interstrand linkage between $P^4$ and $P^9$, and full deprotection were performed as indicated in procedure D above. Finally, the peptide was purified, as described above, and characterized by HPLC-MS. For analytical data, see Ex. 236 in Table 2.

Examples 237 to 240 are shown in Table 1.

Procedure M1, as described above, was used for the preparation of the peptide, applying an on-resin fragment coupling strategy.

(I) The protected peptide fragment (module B and linker L) was synthesized as described above in the corresponding section in the synthesis of Ex. 1.

Assembly of the peptide fragment was in the following sequence:

Resin-Thr-$Q^6$-$Q^5$-$Q^4$-$Q^3$-$Q^2$-$Q^1$-$L^3$-$L^2$-$L^1$.

(II) The fully protected peptides (module A, module B and linker L) were assembled on solid support according to method J as described above.

The peptides were synthesized starting with an appropriately protected Fmoc-amino acid, which was used in the first coupling cycle for grafting the amino acid residue at $X^{12}$ to Sieber amide resin, and using Fmoc-Glu(Allyl)-OH for addition of the amino acid residue at $P^5$. Coupling of the protected peptide fragment (module B and linker L) was performed as indicated in the corresponding section of procedure A above by formation of an amide bond between the γ-carboxyl group of Glu at $P^5$ and the α-amino group of Dab at $L^1$. Assembly of the peptides was in the following sequence, showing only residues of module A:

Resin-$X^{12}$-$P^{11}$-$P^{10}$-$P^9$-$P^8$-$P^7$-$P^6$-$P^5$-$P^4$-$P^3$-$P^2$-$P^1$-$X^{14}$.

Subsequently, acylation with acetic acid at $X^{14}$, cleavage of the peptides from the resin, formation of the disulfide interstrand linkage between $P^4$ and $P^9$, and full deprotection were performed as indicated in procedure M1 above. Finally, the peptides were purified, as described above, and characterized by HPLC-MS. For analytical data, see Ex. 237 to 240 in Table 2.

Example 243 is shown in Table 1.

Procedure M1, as described above, was used for the preparation of the peptide, applying an on-resin fragment coupling strategy.

(I) The protected peptide fragment (module B and linker L) was synthesized as described above in the corresponding section in the synthesis of Ex. 1.

Assembly of the peptide fragment was in the following sequence:

Resin-Thr-$Q^6$-$Q^5$-$Q^4$-$Q^3$-$Q^2$-$Q^1$-$L^3$-$L^2$-$L^1$.

(II) The fully protected peptide (module A, module B and linker L) was assembled on solid support according to method J as described above.

The peptide was synthesized starting with an appropriately protected Fmoc-amino acid, which was used in the first coupling cycle for grafting the amino acid residue at $X^{13}$ to Sieber amide resin, and using Fmoc-Glu(Allyl)-OH for addition of the amino acid residue at $P^5$. Coupling of the protected peptide fragment (module B and linker L) was performed as indicated in the corresponding section of procedure A above by formation of an amide bond between the γ-carboxyl group of Glu at $P^5$ and the α-amino group of Dab at $L^1$. Assembly of the peptide was in the following sequence, showing only residues of module A:

Resin-$X^{13}$-$X^{12}$-$P^{11}$-$P^{10}$-$P^9$-$P^8$-$P^7$-$P^6$-$P^5$-$P^4$-$P^3$-$P^2$-$P^1$-$X^{14}$.

Subsequently, acylation with acetic acid at $X^{14}$, cleavage of the peptides from the resin, formation of the disulfide interstrand linkage between $P^2$ and $P^{11}$, and full deprotection were performed as indicated in procedure M1 above. Finally, the peptide was purified, as described above, and characterized by HPLC-MS. For analytical data, see Ex. 243 in Table 2.

Example 241 is shown in Table 1.

Procedure E, as described above, was used for the preparation of the peptide, applying an on-resin fragment coupling strategy.

(I) The protected peptide fragment (module B and linker L) was synthesized as described above in the corresponding section in the synthesis of Ex. 1.

Assembly of the peptide fragment was in the following sequence:

Resin-Thr-$Q^6$-$Q^5$-$Q^4$-$Q^3$-$Q^2$-$Q^1$-$L^3$-$L^2$-$L^1$.

(II) The fully protected peptide (module A, module B and linker L) was assembled on solid support according to method F as described above.

The peptide was synthesized starting with the amino acid Fmoc-$^D$Ala-OH, which was grafted to the resin (Fmoc-$^D$Ala-2-chlorotrityl resin) and using Fmoc-Glu(Allyl)-OH for addition of the amino acid residue at $P^5$. Coupling of the protected peptide fragment (module B and linker L) was performed as indicated in the corresponding section of procedure A above by formation of an amide bond between the γ-carboxyl group of Glu at $P^5$ and the α-amino group of Dab at $L^1$. Assembly of the peptide was in the following sequence, showing only residues of module A:

Resin-$^D$Ala-$X^{12}$-$P^{11}$-$P^{10}$-$P^9$-$P^8$-$P^7$-$P^6$-$P^5$-$P^4$-$P^3$-$P^2$-$P^1$-$X^{14}$.

Subsequently, cleavage of the peptide from the resin, formation of the disulfide interstrand linkage between $P^2$ and $P^{11}$, and full deprotection were performed as indicated in procedure E above. Finally, the peptide was purified, as described above, and characterized by HPLC-MS. For analytical data, see Ex. 241 in Table 2.

Example 242 is shown in Table 1.

Procedure E, as described above, was used for the preparation of the peptide, applying an on-resin fragment coupling strategy.

(I) The protected peptide fragment (module B and linker L) was synthesized as described above in the corresponding section in the synthesis of Ex. 1.

Assembly of the peptide fragment was in the following sequence:

Resin-Thr-$Q^6$-$Q^5$-$Q^4$-$Q^3$-$Q^2$-$Q^1$-$L^3$-$L^2$-$L^1$.

(II) The fully protected peptide (module A, module B and linker L) was assembled on solid support according to method F as described above.

The peptide was synthesized starting with the amino acid Fmoc-$^D$Ser(tBu)-OH, which was grafted to the resin (Fmoc-$^D$Ser(tBu)-2-chlorotrityl resin) and using Fmoc-Glu(Allyl)-OH for addition of the amino acid residue at $P^5$. Coupling of the protected peptide fragment (module B and linker L) was performed as indicated in the corresponding section of procedure A above by formation of an amide bond between the γ-carboxyl group of Glu at $P^5$ and the α-amino group of Dab at $L^1$. Assembly of the peptide was in the following sequence, showing only residues of module A:

Resin-$^D$Ser-$X^{12}$-$P^{11}$-$P^{10}$-$P^9$-$P^8$-$P^7$-$P^6$-$P^5$-$P^4$-$P^3$-$P^2$-$P^1$-$X^{14}$.

Subsequently, cleavage of the peptide from the resin, formation of the disulfide interstrand linkage between $P^2$ and $P^{11}$, and full deprotection were performed as indicated in procedure E above. Finally, the peptide was purified, as described above, and characterized by HPLC-MS. For analytical data, see Ex. 242 in Table 2.

Example 244 is shown in Table 1.

Procedure M1, as described above, was used for the preparation of the peptide, applying an on-resin fragment coupling strategy.

(I) The protected peptide fragment (module B and linker L) was synthesized as described above in the corresponding section in the synthesis of Ex. 1.

Assembly of the peptide fragment was in the following sequence:

Resin-Thr-$Q^6$-$Q^5$-$Q^4$-$Q^3$-$Q^2$-$Q^1$-$L^3$-$L^2$-$L^1$.

(II) The fully protected peptide (module A, module B and linker L) was assembled on solid support according to method J as described above.

The peptide was synthesized starting with an appropriately protected Fmoc-amino acid, which was used in the first coupling cycle for grafting the amino acid residue at $X^{13}$ to Sieber amide resin, and using Fmoc-Glu(Allyl)-OH for addition of the amino acid residue at $P^5$. Coupling of the protected peptide fragment (module B and linker L) was performed as indicated in the corresponding section of procedure A above by formation of an amide bond between the γ-carboxyl group of Glu at $P^5$ and the α-amino group of Dab at $L^1$. Assembly of the peptide was in the following sequence, showing only residues of module A:

Resin-$X^{13}$-$X^{12}$-$P^{11}$-$P^{10}$-$P^9$-$P^8$-$P^7$-$P^6$-$P^5$-$P^4$-$P^3$-$P^2$-$P^1$-$X^{14}$.

Subsequently, acylation with acetic acid at $X^{14}$, cleavage of the peptide from the resin, formation of the disulfide interstrand linkage between $X^{13}$ and $X^{14}$, and full deprotection were performed as indicated in procedure M1 above. Finally, the peptide was purified, as described above, and characterized by HPLC-MS. For analytical data, see Ex. 244 in Table 2.

Examples 245, 250, and 383 are shown in Table 1.

Procedure P, as described above, was used for the preparation of the peptides, applying an on-resin fragment coupling strategy.

(I) The protected peptide fragment (module B and linker L) was synthesized as described above in the corresponding section in the synthesis of Ex. 1.

Assembly of the peptide fragment was in the following sequence:

Resin-Thr-$Q^6$-$Q^5$-$Q^4$-$Q^3$-$Q^2$-$Q^1$-$L^3$-$L^2$-$L^1$.

(II) The fully protected peptides (module A, module B and linker L) were assembled on solid support according to method L as described above.

The peptides were synthesized starting with an appropriately protected Fmoc-amino acid, which was used in the first coupling cycle for grafting the amino acid residue at $X^{13}$ to Sieber amide resin, using Fmoc-Glu(Allyl)-OH for addition of the amino acid residue at $P^5$ and using 3-(tritylthio) propionic acid for addition of the thiol-substituted acyl residue at $X^{14}$. Coupling of the protected peptide fragment (module B and linker L) was performed as indicated in the corresponding section of procedure A above by formation of an amide bond between the γ-carboxyl group of Glu at $P^5$ and the α-amino group of Dab at $L^1$. Assembly of the peptides was in the following sequence, showing only residues of module A:

Resin-$X^{13}$-$X^{12}$-$P^{11}$-$P^{10}$-$P^9$-$P^8$-$P^7$-$P^6$-$P^5$-$P^4$-$P^3$-$P^2$-$P^1$-$X^{14}$.

Subsequently, cleavage of the peptides from the resin, formation of the disulfide interstrand linkage between $X^{13}$ and $X^{14}$, and full deprotection were performed as indicated in procedure P above. Finally, the peptides were purified, as described above, and characterized by HPLC-MS. For analytical data, see Ex. 245, 250, and 383 in Table 2.

Example 246 is shown in Table 1.

Procedure M1, as described above, was used for the preparation of the peptide, applying an on-resin fragment coupling strategy.

(I) The protected peptide fragment (module B and linker L) was synthesized as described above in the corresponding section in the synthesis of Ex. 1.

Assembly of the peptide fragment was in the following sequence:

Resin-Thr-$Q^6$-$Q^5$-$Q^4$-$Q^3$-$Q^2$-$Q^1$-$L^3$-$L^2$-$L^1$.

(II) The fully protected peptide (module A, module B and linker L) was assembled on solid support according to method J as described above.

The peptide was synthesized starting with an appropriately protected Fmoc-amino acid, which was used in the first coupling cycle for grafting the amino acid residue at $X^{13}$ to Sieber amide resin, and using Fmoc-Glu(Allyl)-OH for addition of the amino acid residue at $P^5$. Coupling of the protected peptide fragment (module B and linker L) was performed as indicated in the corresponding section of procedure A above by formation of an amide bond between the γ-carboxyl group of Glu at $P^5$ and the α-amino group of Dab at $L^1$. Assembly of the peptide was in the following sequence, showing only residues of module A:

Resin-$X^{13}$-$X^{12}$-$P^{11}$-$P^{10}$-$P^9$-$P^8$-$P^7$-$P^6$-$P^5$-$P^4$-$P^3$-$P^2$-$P^1$-$X^{14}$.

Subsequently, acylation with acetic acid at $X^{14}$, cleavage of the peptide from the resin, formation of the disulfide interstrand linkage between $P^2$ and $P^9$, and full deprotection were performed as indicated in procedure M1 above. Finally, the peptide was purified, as described above, and characterized by HPLC-MS. For analytical data, see Ex. 246 in Table 2.

Example 247, 248 and 249 are shown in Table 1.

Procedure Q, as described above, was used for the preparation of the peptides, applying an on-resin fragment coupling strategy.

(I) The protected peptide fragment (module B and linker L) was synthesized as described above in the corresponding section in the synthesis of Ex. 1.

Assembly of the peptide fragment was in the following sequence:

Resin-Thr-$Q^6$-$Q^5$-$Q^4$-$Q^3$-$Q^2$-$Q^1$-$L^3$-$L^2$-$L^1$.

(II) The fully protected peptide (module A, module B and linker L) was assembled on solid support according to method J as described above.

The peptide was synthesized starting with an appropriately protected Fmoc-amino acid, which was used in the first coupling cycle for grafting the amino acid residue at $X^{13}$ to Sieber amide resin, and using Fmoc-Glu(Allyl)-OH for addition of the amino acid residue at $P^5$. Coupling of the protected peptide fragment (module B and linker L) was performed as indicated in the corresponding section of procedure A above by formation of an amide bond between the γ-carboxyl group of Glu at $P^5$ and the α-amino group of Dab at $L^1$. Assembly of the peptides was in the following sequence, showing only residues of module A:

Resin-$X^{13}$-$X^{12}$-$P^{11}$-$P^{10}$-$P^9$-$P^8$-$P^7$-$P^6$-$P^5$-$P^4$-$P^3$-$P^2$-$P^1$-$X^{14}$.

Subsequently, acylation with acetic acid at $X^{14}$, cleavage of the peptides from the resin, and full deprotection were performed as indicated in procedure Q above. Finally, the peptides were purified, as described above, and characterized by HPLC-MS. For analytical data, see Ex. 247, 248 and 249 in Table 2.

Examples 367 to 371, 373, 374, 375, 377, 378, and 380 are shown in Table 1. Procedure M2, as described above, was used for the preparation of the peptides, applying an on-resin fragment coupling strategy.

(I) The protected peptide fragments (module B and linker L) were synthesized as described above in the corresponding section in the synthesis of Ex. 1.

Assembly of the peptide fragments was in the following sequence:

Resin-Thr-$Q^6$-$Q^5$-$Q^4$-$Q^3$-$Q^2$-$Q^1$-$L^3$-$L^2$-$L^1$.

(II) The fully protected peptides (module A, module B and linker L) were assembled on solid support according to method J as described above.

The peptides were synthesized starting with an appropriately protected Fmoc-amino acid, which was used in the first coupling cycle for grafting the amino acid residue at $X^{13}$ to Sieber amide resin, and using Fmoc-Glu(Allyl)-OH for addition of the amino acid residue at $P^5$. Coupling of the protected peptide fragment (module B and linker L) was performed as indicated in the corresponding section of procedure A above by formation of an amide bond between the γ-carboxyl group of Glu at $P^5$ and the α-amino group of Dab at $L^1$. Assembly of the peptides was in the following sequence, showing only residues of module A:

Resin-$X^{13}$-$X^{12}$-$P^{11}$-$P^{10}$-$P^9$-$P^8$-$P^7$-$P^6$-$P^5$-$P^4$-$P^3$-$P^2$-$P^1$-$X^{14}$.

Subsequently, acylation with acetic acid at $P^1$, cleavage of the peptides from the resin, full deprotection, and formation of the disulfide interstrand linkage between $P^2$ and $P^{11}$ were performed as indicated in procedure M2 above. Finally, the peptides were purified, as described above, and characterized by HPLC-MS. For analytical data, see Ex. 367 to 371, 373, 374, 375, 377, 378, and 380 in Table 2.

Example 372, 376, 379, 381, and 382 are shown in Table 1.

Procedure O, as described above, was used for the preparation of the peptides, applying an on-resin fragment coupling strategy.

(I) The protected peptide fragments (module B and linker L) were synthesized as indicated above in the corresponding section in the synthesis of Ex. 1.

Assembly of the peptide fragments was in the following sequence:

Resin-Thr-$Q^6$-$Q^5$-$Q^4$-$Q^3$-$Q^2$-$Q^1$-$L^3$-$L^2$-$L^1$.

(II) The fully protected peptides (module A, module B and linker L) were assembled on solid support according to method K as described above.

The peptides were synthesized starting with an appropriately protected Fmoc amino acid which was used in the first coupling cycle for grafting the amino acid residue at $X^{13}$ to Sieber amide resin, using Fmoc-Glu(Allyl)-OH for addition of the amino acid residue at $P^5$, and using alpha-hydroxyisovaleric acid (Hiv) for addition of the hydroxy acid residue at $P^1$. Coupling of the protected peptide fragment (module B and linker L) was performed as indicated in the corresponding section of procedure A above by formation of an amide bond between the γ-carboxyl group of Glu at $P^5$ and the α-amino group of Dab at $L^1$. Assembly of the peptides was in the following sequence, showing only residues of module A:

Resin-$X^{13}$-$X^{12}$-$P^{11}$-$P^{10}$-$P^9$-$P^8$-$P^7$-$P^6$-$P^5$-$P^4$-$P^3$-$P^2$-$P^1$-$X^{14}$.

Subsequently, cleavage of the peptides from the resin, formation of the disulfide interstrand linkage between $P^2$ and $P^{11}$, and full deprotection were performed as indicated in procedure O above. Finally, the peptides were purified, as described above, and characterized by HPLC-MS. For analytical data, see Ex. 372, 376, 379, 381, and 382 in Table 2.

Examples 285, 286, 288 and 292 are shown in Table 1.

Procedure R as described above, was used for the preparation of the peptides, applying an on-resin fragment coupling strategy.

(I) The protected peptide fragments (module B and linker L) were synthesized as described above in the corresponding section in the synthesis of Ex. 1.

Assembly of the peptide fragments was in the following sequence:

Resin-Thr-$Q^6$-$Q^5$-$Q^4$-$Q^3$-$Q^2$-$Q^1$-$L^3$-$L^2$-$L^1$.

(II) The fully protected peptides (module A, module B and linker L) were assembled on solid support according to method J as described above.

The peptides were synthesized starting with the amino acid Fmoc-Ser(tBu)-OH, which was used in the first coupling cycle for grafting the amino acid residue at $X^{12}$ to Sieber amide resin and using Fmoc-Glu(Allyl)-OH for addition of the amino acid residue at $P^5$. Coupling of the protected peptide fragment (module B and linker L) was performed as indicated in the corresponding section of procedure A above by formation of an amide bond between the γ-carboxyl group of Glu at $P^5$ and the α-amino group of Dab at $L^1$.

Assembly of the peptide was in the following sequence, showing only residues of module A:

Resin-Ser-$P^{11}$-$P^{10}$-$P^9$-$P^8$-$P^7$-$P^6$-$P^5$-$P^4$-$P^3$-$P^2$-$P^1$.

Subsequently, acylation with acetic acid at $P^1$, allyl deprotection at $P^2$, ivDde deprotection at $P^{11}$, and formation of the lactam interstrand linkage by an amide bond between the liberated side-chain functional groups of the amino acid residue at $P^2$ and Dab at $P^{11}$, cleavage of the peptides from the resin, and full deprotection were performed as indicated in procedure P above. Finally, the peptides were purified, as described above, and characterized by HPLC-MS. For analytical data, see Ex. 285, 286, 288 and 292 in Table 2.

Examples 304 and 347 are shown in Table 1.

Procedure S, as described above, was used for the preparation of the peptides, applying an on-resin fragment coupling strategy.

(I) The protected peptide fragments (module B and linker L) were synthesized as described above in the corresponding section in the synthesis of Ex. 1.

Assembly of the peptide fragments was in the following sequence:

Resin-Thr-$Q^6$-$Q^5$-$Q^4$-$Q^3$-$Q^2$-$Q^1$-$L^3$-$L^2$-$L^1$.

(II) The fully protected peptides (module A, module B and linker L) were assembled on solid support according to method J as described above.

The peptides were synthesized starting with the amino acid Fmoc-Ser(tBu)-OH, which was used in the first coupling cycle for grafting the amino acid residue at $X^{12}$ to Sieber amide resin, using Fmoc-Glu(Allyl)-OH for addition of the amino acid residue at $P^5$, using Fmoc-Asp(2-PhiPr)-OH for addition of the amino acid residue at $P^{11}$, and using alpha-hydroxyisovaleric acid (Hiv) for addition of the hydroxy acid residue at $P^1$. Coupling of the protected peptide fragment (module B and linker L) was performed as indicated in the corresponding section of procedure A above by formation of an amide bond between the γ-carboxyl group of Glu at $P^5$ and the α-amino group of Dab at $L^1$. Assembly of the peptides was in the following sequence, showing only residues of module A:

Resin-$X^{12}$-$P^{11}$-$P^{10}$-$P^9$-$P^8$-$P^7$-$P^6$-$P^5$-$P^4$-$P^3$-$P^2$-$P^1$.

Subsequently, removal of the alloc protecting group at $P^2$, cleavage of the peptides from the resin and removal of the 2-phenyl-isopropyl protecting group at $P^{11}$, formation of the lactam interstrand linkage by an amide bond between the liberated side-chain functional groups of the residues at $P^2$ and at $P^{11}$, and full deprotection were performed as indicated in procedure Q above. Finally, the peptides were purified, as described above, and characterized by HPLC-MS. For analytical data, see Ex. 304 and 347, in Table 2.

Examples 366 is shown in Table 1.

Procedure M2, as described above, was used for the preparation of the peptide, applying an on-resin fragment coupling strategy.

(I) The protected peptide fragment (module B and linker L) was synthesized as described above in the corresponding section in the synthesis of Ex. 1.

Assembly of the peptide fragment was in the following sequence:

Resin-Thr-$Q^6$-$Q^5$-$Q^4$-$Q^3$-$Q^2$-$Q^1$-$L^3$-$L^2$-$L^1$.

(II) The fully protected peptide (module A, module B and linker L) was assembled on solid support according to method J as described above.

The peptides was synthesized starting with an appropriately protected Fmoc-amino acid, which was used in the first coupling cycle for grafting the amino acid residue at $X^{12}$ to Sieber amide resin, and using Fmoc-$^D$Glu(Allyl)-OH for addition of the amino acid residue at $P^7$. Coupling of the protected peptide fragment (module B and linker L) was performed as indicated in the corresponding section of procedure A above by formation of an amide bond between the γ-carboxyl group of $^D$Glu at $P^7$ and the α-amino group of Dab at $L^1$. Assembly of the peptide was in the following sequence, showing only residues of module A:

Resin-$X^{12}$-$P^{11}$-$P^{10}$-$P^9$-$P^8$-$P^7$-$P^6$-$P^5$-$P^4$-$P^3$-$P^2$-$P^1$.

Subsequently, acylation with acetic acid at $P^1$, cleavage of the peptide from the resin, full deprotection, and formation of the disulfide interstrand linkage between $P^2$ and $P^{11}$ were performed as indicated in procedure M2 above. Finally, the peptide was purified, as described above, and characterized by HPLC-MS. For analytical data, see Ex. 366 in Table 2.

Examples 354 to 365 are shown in Table 1.

Procedure M2, as described above, was used for the preparation of the peptides, applying an on-resin fragment coupling strategy.

(I) The protected peptide fragments (module B and linker L) were synthesized as described above in the corresponding section in the synthesis of Ex. 1.

Assembly of the peptide fragments was in the following sequence:

Resin-Thr-$Q^6$-$Q^5$-$Q^4$-$Q^3$-$Q^2$-$Q^1$-$L^3$-$L^2$-$L^1$.

(II) The fully protected peptides (module A, module B and linker L) were assembled on solid support according to method J as described above.

The peptides were synthesized starting with an appropriately protected Fmoc-amino acid, which was used in the first coupling cycle for grafting the amino acid residue at $X^{12}$ to Sieber amide resin, and using Fmoc-Glu(Allyl)-OH for addition of the amino acid residue at $P^7$. Coupling of the protected peptide fragment (module B and linker L) was performed as indicated in the corresponding section of procedure A above by formation of an amide bond between the γ-carboxyl group of Glu at $P^7$ and the α-amino group of Dab at $L^1$. Assembly of the peptides was in the following sequence, showing only residues of module A:

Resin-$X^{12}$-$P^{11}$-$P^{10}$-$P^9$-$P^8$-$P^7$-$P^6$-$P^5$-$P^4$-$P^3$-$P^2$-$P^1$.

Subsequently, acylation with acetic acid at $P^1$, cleavage of the peptides from the resin, full deprotection, and formation of the disulfide interstrand linkage between $P^2$ and $P^{11}$ were performed as indicated in procedure M2 above. Finally, the peptides were purified, as described above, and characterized by HPLC-MS. For analytical data, see Ex. 354 to 365 in Table 2.

Example 384 is shown in Table 1.

Procedure F, as described above, was used for the preparation of the peptide, applying an on-resin fragment coupling strategy.

(I) The protected peptide fragment (module B and linker L) was synthesized as described above in the corresponding section in the synthesis of Ex. 1.

Assembly of the peptide fragment was in the following sequence:

Resin-Thr-$Q^6$-$Q^5$-$Q^4$-$Q^3$-$Q^2$-$Q^1$-$L^3$-$L^2$-$L^1$.

(II) The fully protected peptide (module A, module B and linker L) was assembled on solid support according to method G as described above.

The peptide was synthesized starting with the amino acid Fmoc-Cys(Trityl)-OH, which was grafted to the resin (Fmoc-Cys(Trityl)-2-chlorotrityl resin) and using Fmoc-Glu(Allyl)-OH for addition of the amino acid residue at $P^5$. Coupling of the protected peptide fragment (module B and linker L) was performed as indicated in the corresponding section of procedure A above by formation of an amide bond between the γ-carboxyl group of Glu at $P^5$ and the α-amino group of Dab at $L^1$. Assembly of the peptide was in the following sequence, showing only residues of module A:

Resin-Cys-$P^{10}$-$P^9$-$P^8$-$P^7$-$P^6$-$P^5$-$P^4$-$P^3$-$P^2$-$P^1$.

Subsequently, acylation with acetic acid at $P^1$, cleavage of the peptide from the resin, formation of the disulfide interstrand linkage between $P^2$ and $P^{11}$, and full deprotection were performed as indicated in procedure F above. Finally, the peptide was purified, as described above, and characterized by HPLC-MS. For analytical data, see 384 in Table 2.

Example 385 is shown in Table 1.

Procedure F, as described above, was used for the preparation of the peptide, applying an on-resin fragment coupling strategy.

(I) The protected peptide fragment (module B and linker L) was synthesized as described above in the corresponding section in the synthesis of Ex. 1.

Assembly of the peptide fragment was in the following sequence:

Resin-Thr-$Q^6$-$Q^5$-$Q^4$-$Q^3$-$Q^2$-$Q^1$-$L^3$-$L^2$-$L^1$.

(II) The fully protected peptide (module A, module B and linker L) was assembled on solid support according to method G as described above.

The peptide was synthesized starting with the amino acid Fmoc-Leu(3R)OtBu-OH, which was grafted to the resin (Fmoc-Leu(3R)OtBu-2-chlorotrityl resin) and using Fmoc-Glu(Allyl)-OH for addition of the amino acid residue at $P^5$. Coupling of the protected peptide fragment (module B and linker L) was performed as indicated in the corresponding section of procedure A above by formation of an amide bond between the γ-carboxyl group of Glu at $P^5$ and the α-amino group of Dab at $L^1$. Assembly of the peptide was in the following sequence, showing only residues of module A:

Resin-Leu(3R)OH—$P^{11}$-$P^{10}$-$P^9$-$P^8$-$P^7$-$P^6$-$P^5$-$P^4$-$P^3$-$P^2$-$P^1$.

Subsequently, acylation with acetic acid at $P^1$, cleavage of the peptide from the resin, formation of the disulfide interstrand linkage between $P^2$ and $P^{11}$, and full deprotection were performed as indicated in procedure F above. Finally, the peptide was purified, as described above, and characterized by HPLC-MS. For analytical data, see 385 in Table 2.

TABLE 1

Examples (Ex.)

In the below-mentioned examples, amino acid residues are connected in either direction from the α carbonyl (C=O) point of attachment to the α nitrogen (N) of the next element, unless otherwise indicated. Other linkages, residues, connection of residues and modifications are as specified.

| Ex. No. | Sequence |
|---|---|
| Ex. 1[a) b) c)] | 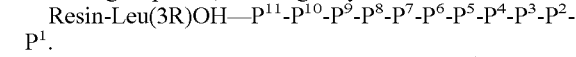 |

TABLE 1-continued
Examples (Ex.)
In the below-mentioned examples, amino acid residues are connected in either direction from the α carbonyl (C=O) point of attachment to the α nitrogen (N) of the next element, unless otherwise indicated. Other linkages, residues, connection of residues and modifications are as specified.
| Ex. No. | Sequence |
|---|---|
| Ex. 2[a) b) c)] | 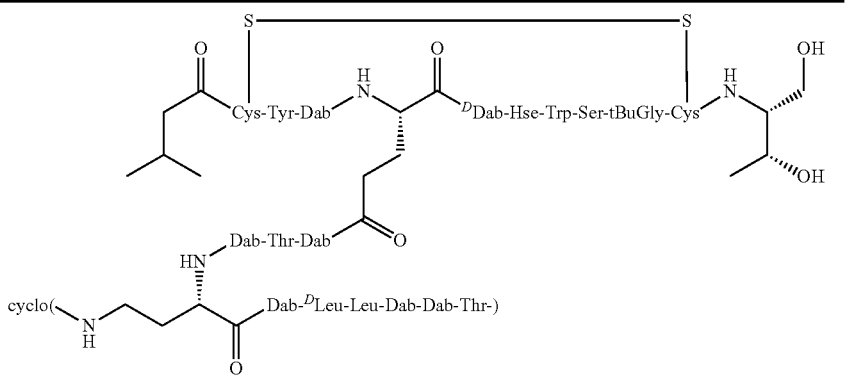 |
| Ex. 3[a) b) c)] | 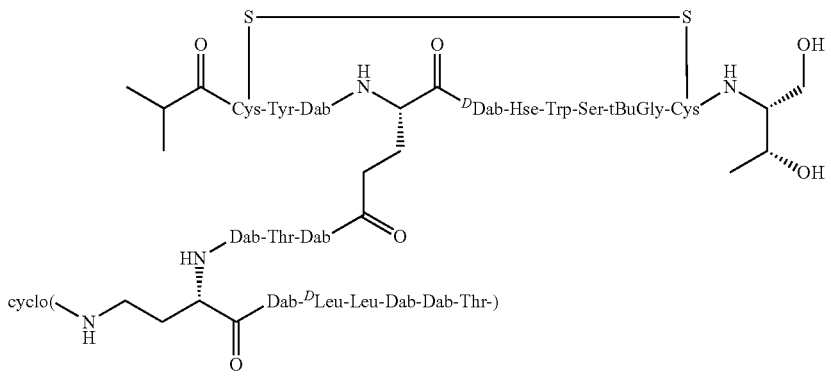 |
| Ex. 4[a) b) c)] | 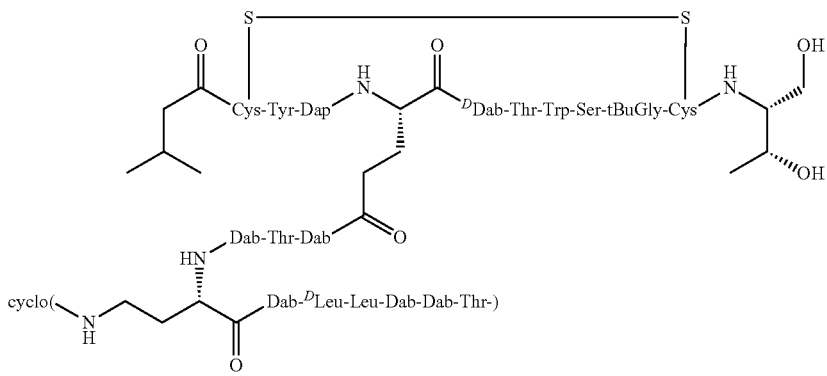 |
| Ex. 5[a) b) c)] | 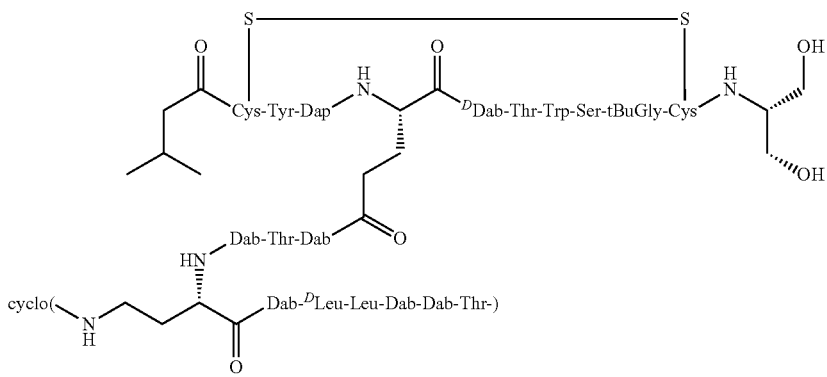 |

TABLE 1-continued
Examples (Ex.)
In the below-mentioned examples, amino acid residues are connected in either
direction from the α carbonyl (C=O) point of attachment to the α nitrogen (N) of the
next element, unless otherwise indicated. Other linkages, residues, connection of
residues and modifications are as specified.
| Ex. No. | Sequence |
|---|---|
Ex. 6[a)]
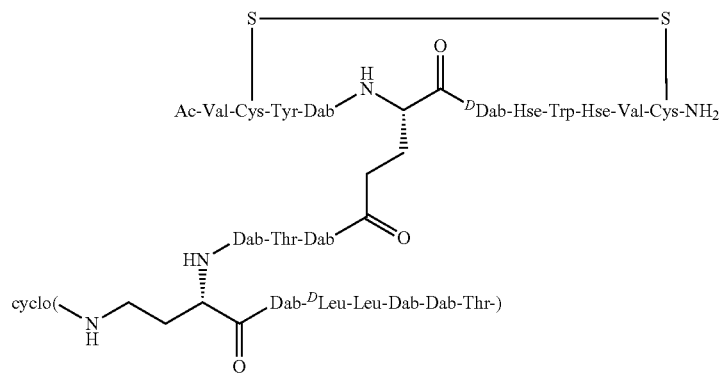
Ex. 7[a) e)]
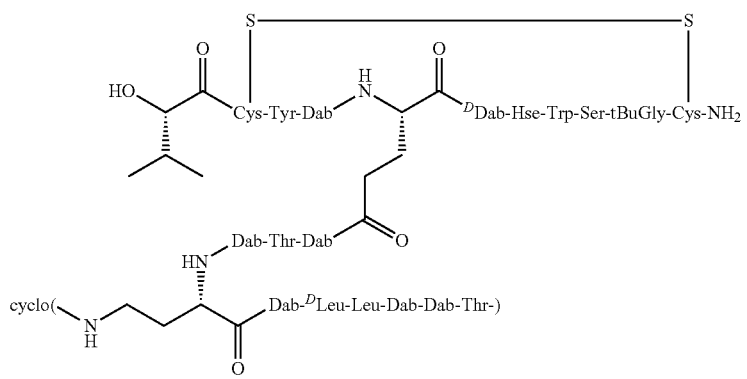
Ex. 8[a)]
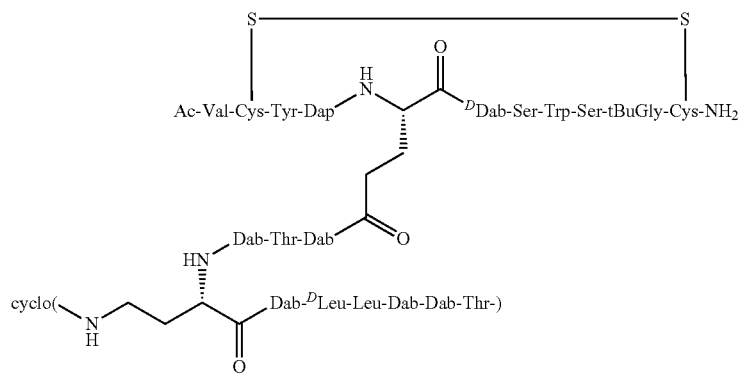

TABLE 1-continued
Examples (Ex.)
In the below-mentioned examples, amino acid residues are connected in either
direction from the α carbonyl (C=O) point of attachment to the α nitrogen (N) of the
next element, unless otherwise indicated. Other linkages, residues, connection of
residues and modifications are as specified.
| Ex. No. | Sequence |
|---|---|
| Ex. 9[a)] | 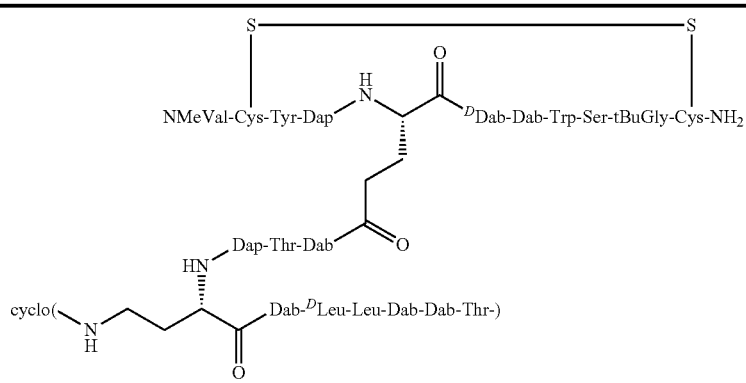 |
| Ex. 10[a)] | 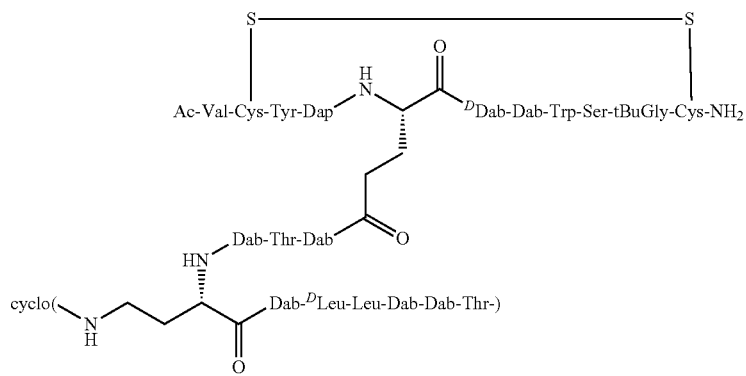 |
| Ex. 11[a)] | 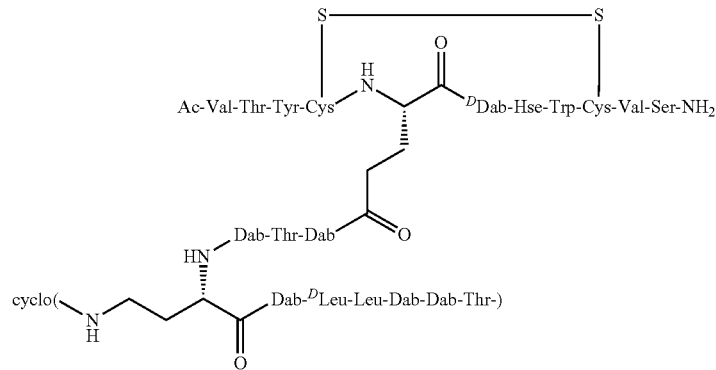 |
| Ex. 12[a)] | 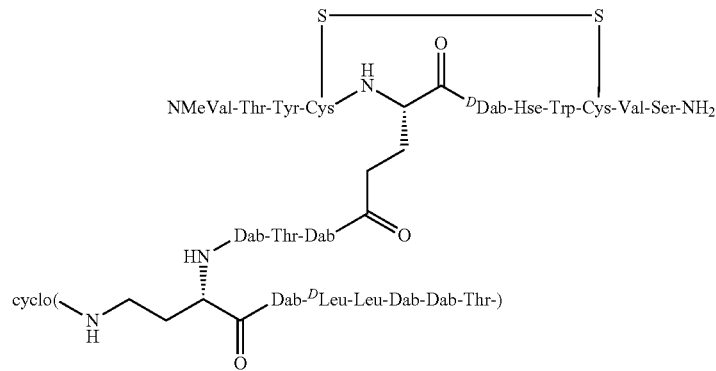 |

TABLE 1-continued
Examples (Ex.)
In the below-mentioned examples, amino acid residues are connected in either direction from the α carbonyl (C=O) point of attachment to the α nitrogen (N) of the next element, unless otherwise indicated. Other linkages, residues, connection of residues and modifications are as specified.
| Ex. No. | Sequence |
| --- | --- |
Ex. 13[a)]
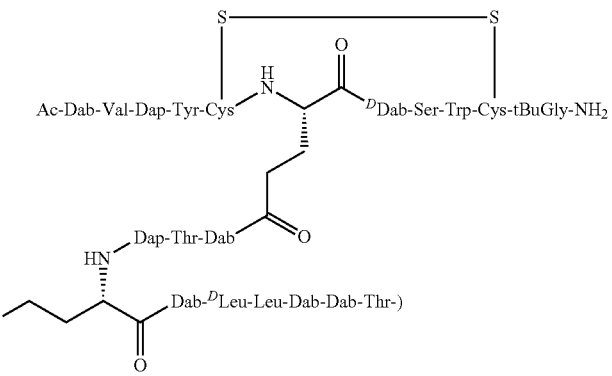
Ex. 14[a)]
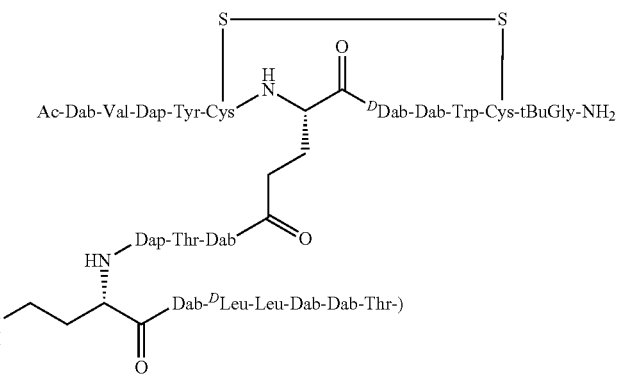
Ex. 15[f)]
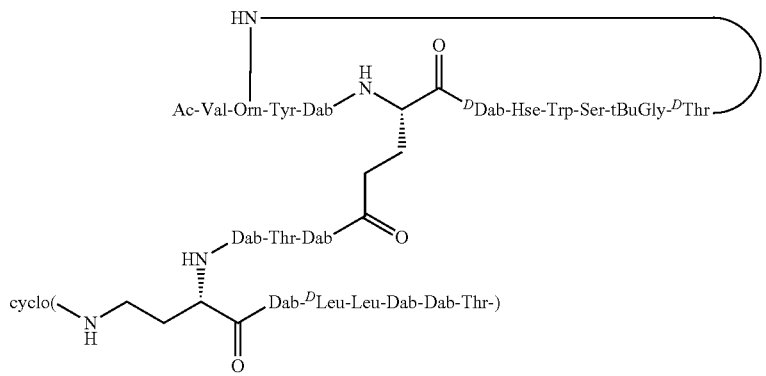

TABLE 1-continued
Examples (Ex.)
In the below-mentioned examples, amino acid residues are connected in either
direction from the α carbonyl (C=O) point of attachment to the α nitrogen (N) of the
next element, unless otherwise indicated. Other linkages, residues, connection of
residues and modifications are as specified.
| Ex. No. | Sequence |
|---|---|
| Ex. 16[f] | 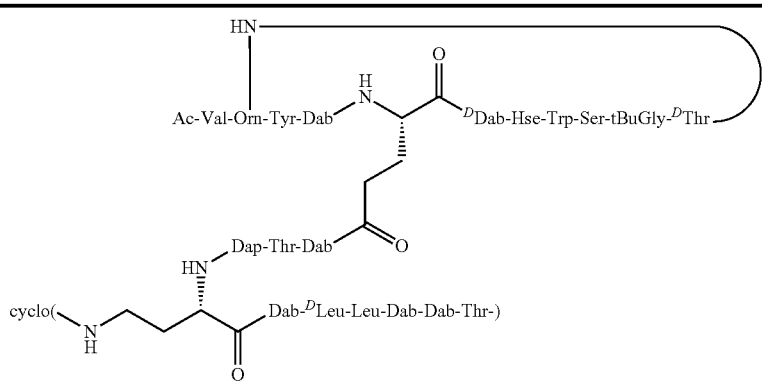 |
| Ex. 17[f] | 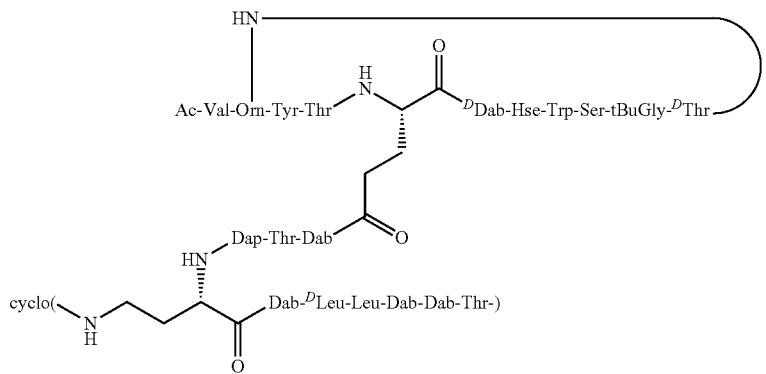 |
| Ex. 18[f] | 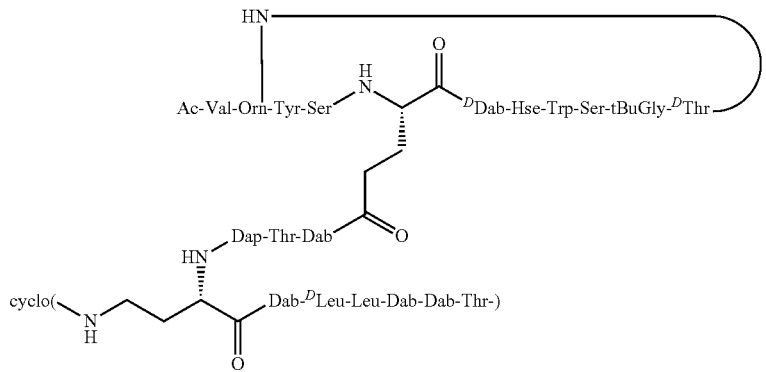 |
| Ex. 19[f] | 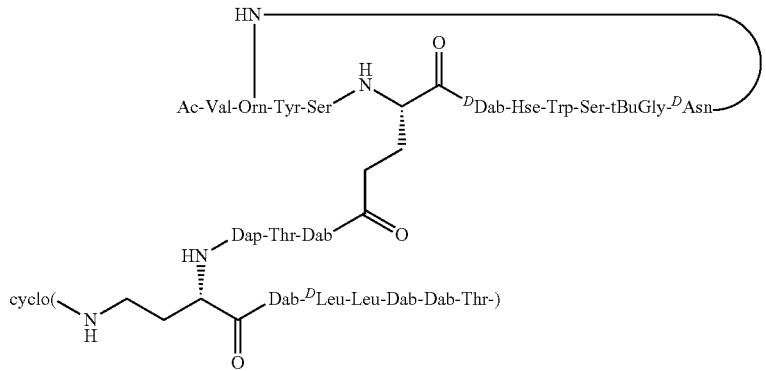 |

TABLE 1-continued
Examples (Ex.)
In the below-mentioned examples, amino acid residues are connected in either direction from the α carbonyl (C=O) point of attachment to the α nitrogen (N) of the next element, unless otherwise indicated. Other linkages, residues, connection of residues and modifications are as specified.
| Ex. No. | Sequence |
| --- | --- |
Ex. 20[f]
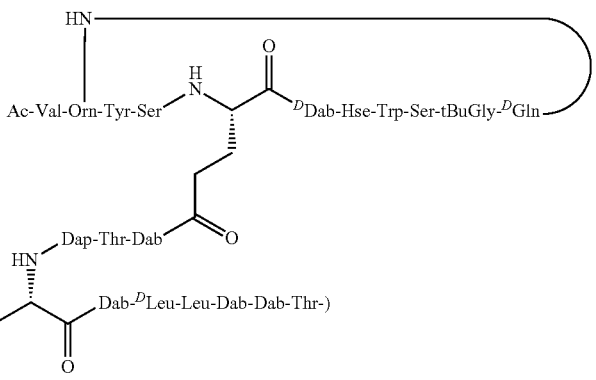
Ex. 21[f]
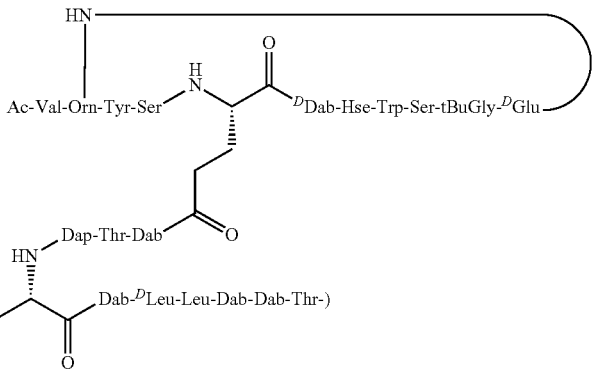
Ex. 22[f]
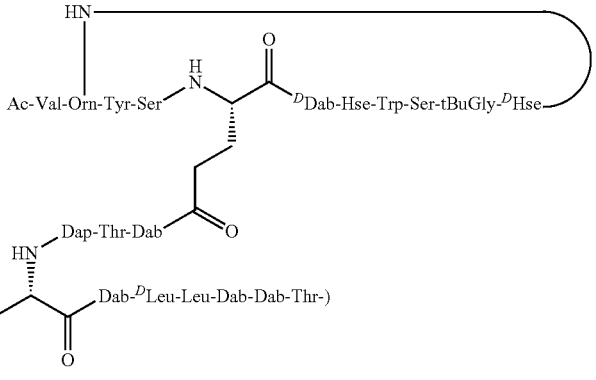

TABLE 1-continued
Examples (Ex.)
In the below-mentioned examples, amino acid residues are connected in either
direction from the α carbonyl (C=O) point of attachment to the α nitrogen (N) of the
next element, unless otherwise indicated. Other linkages, residues, connection of
residues and modifications are as specified.
| Ex. No. | Sequence |
|---|---|
| Ex. 23[f) | 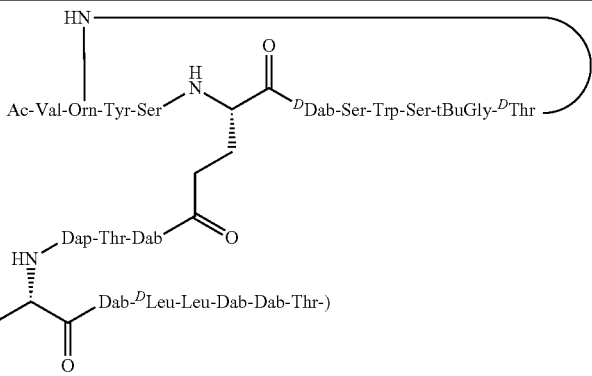 |
| Ex. 24[e) f) | 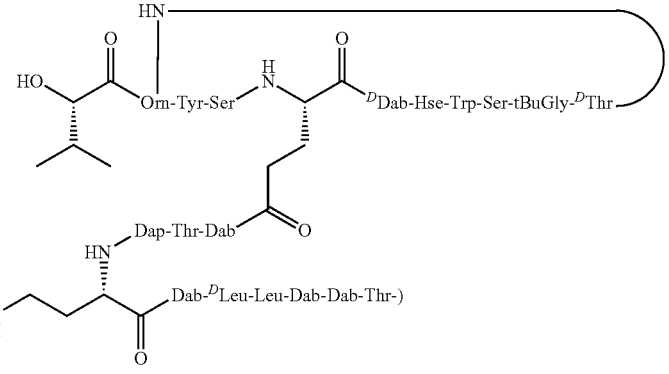 |
| Ex. 25[f) | 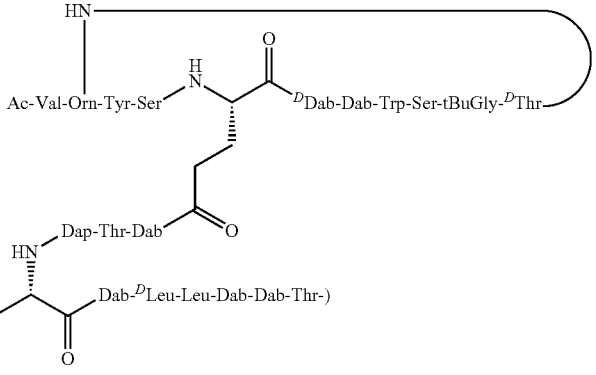 |
| Ex. 26[f) | 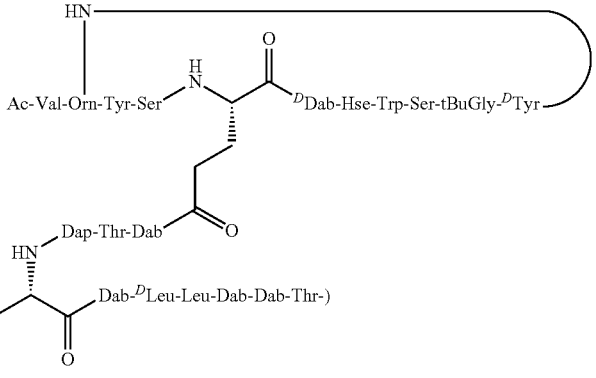 |

TABLE 1-continued
Examples (Ex.)
In the below-mentioned examples, amino acid residues are connected in either direction from the α carbonyl (C=O) point of attachment to the α nitrogen (N) of the next element, unless otherwise indicated. Other linkages, residues, connection of residues and modifications are as specified.
| Ex. No. | Sequence |
| --- | --- |
Ex. 27[f]
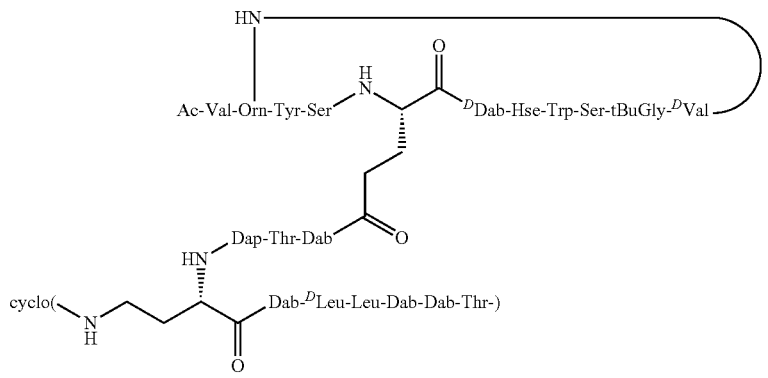
Ex. 28[f]
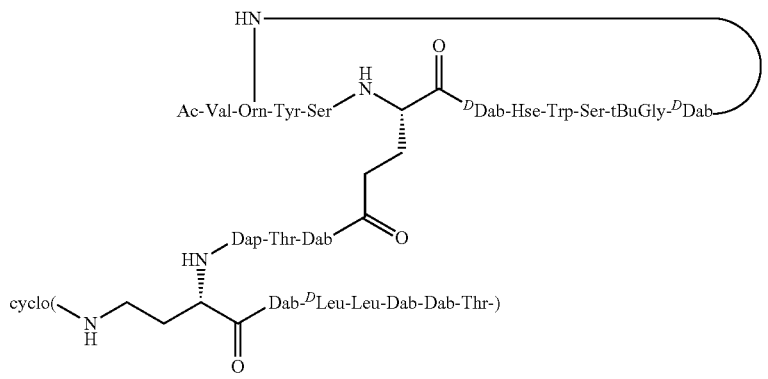
Ex. 29[f]
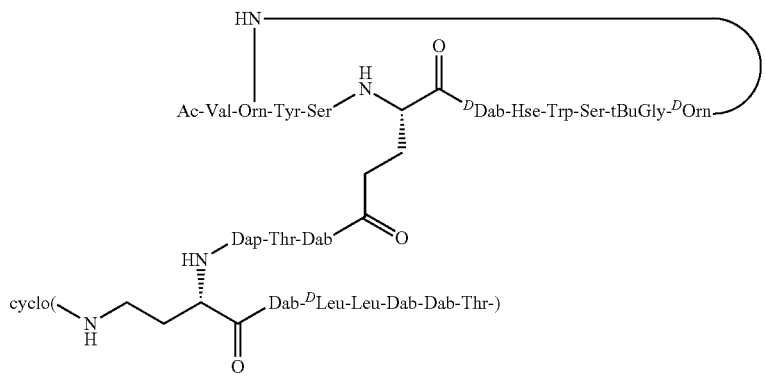

TABLE 1-continued
Examples (Ex.)
In the below-mentioned examples, amino acid residues are connected in either
direction from the α carbonyl (C=O) point of attachment to the α nitrogen (N) of the
next element, unless otherwise indicated. Other linkages, residues, connection of
residues and modifications are as specified.
| Ex. No. | Sequence |
|---|---|
| Ex. 30[f] | 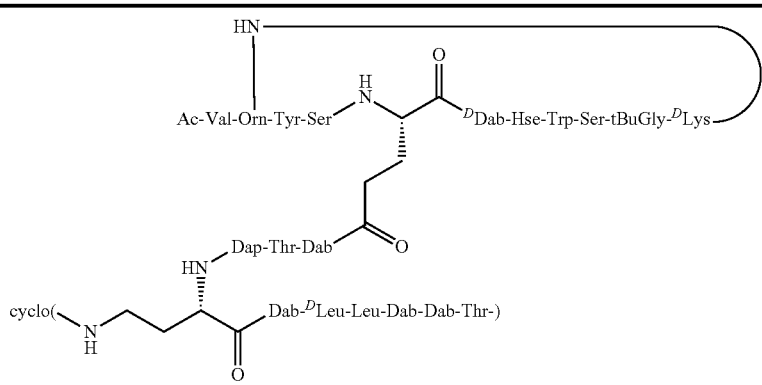 |
| Ex. 31[f] | 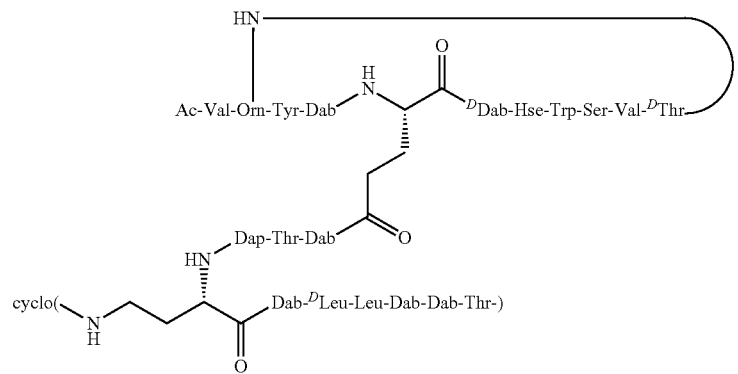 |
| Ex. 32[f] | 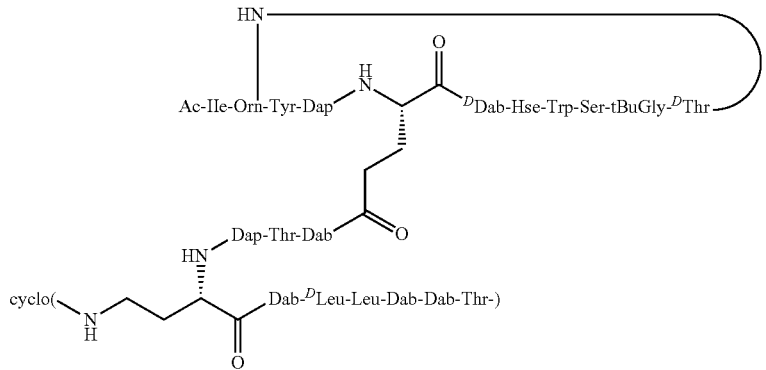 |
| Ex. 33[f] | 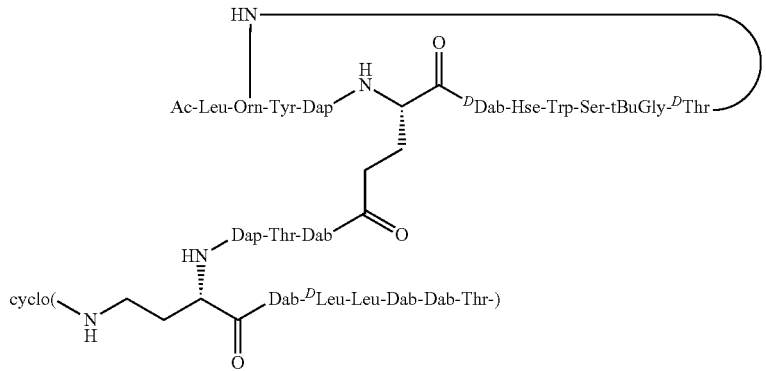 |

TABLE 1-continued
Examples (Ex.)
In the below-mentioned examples, amino acid residues are connected in either
direction from the α carbonyl (C=O) point of attachment to the α nitrogen (N) of the
next element, unless otherwise indicated. Other linkages, residues, connection of
residues and modifications are as specified.
| Ex. No. | Sequence |
|---|---|
Ex. 34[f]
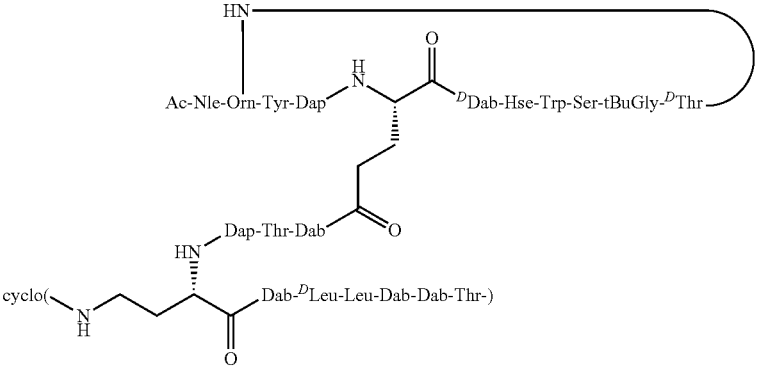
Ex. 35[f]
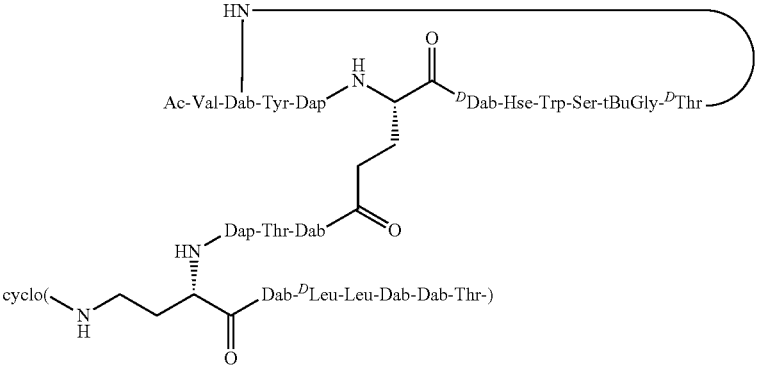
Ex. 36[f]
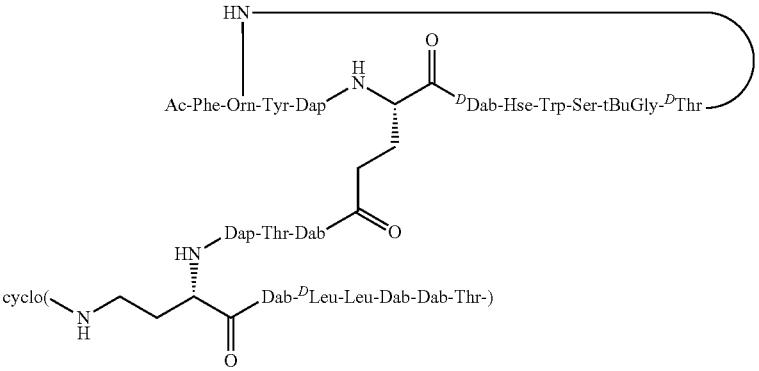

TABLE 1-continued
Examples (Ex.)
In the below-mentioned examples, amino acid residues are connected in either
direction from the α carbonyl (C=O) point of attachment to the α nitrogen (N) of the
next element, unless otherwise indicated. Other linkages, residues, connection of
residues and modifications are as specified.
| Ex. No. | Sequence |
| --- | --- |
| Ex. 37[f] | 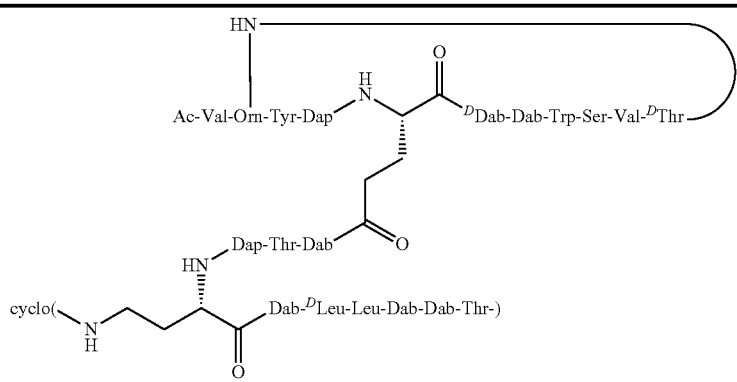 |
| Ex. 38[f] | 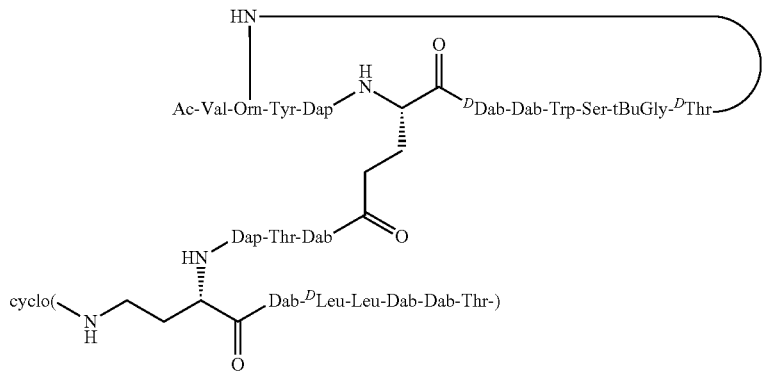 |
| Ex. 39[a] | 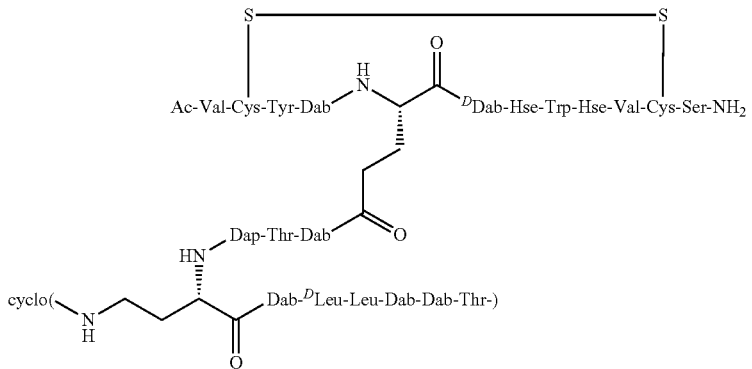 |
| Ex. 40[a] | 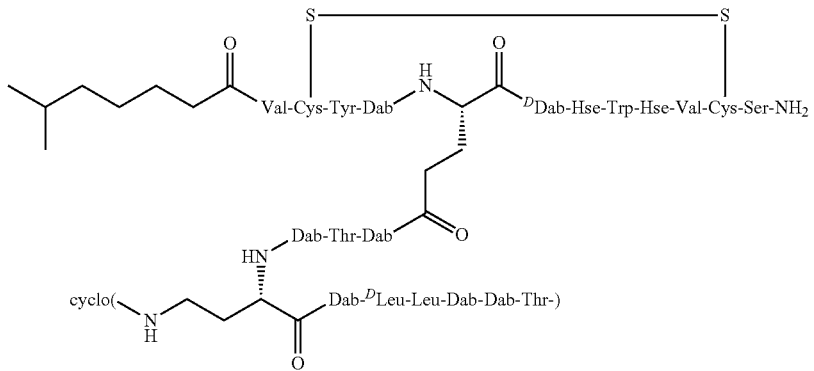 |

TABLE 1-continued
Examples (Ex.)
In the below-mentioned examples, amino acid residues are connected in either direction from the α carbonyl (C=O) point of attachment to the α nitrogen (N) of the next element, unless otherwise indicated. Other linkages, residues, connection of residues and modifications are as specified.
| Ex. No. | Sequence |
| --- | --- |
Ex. 41[a)]
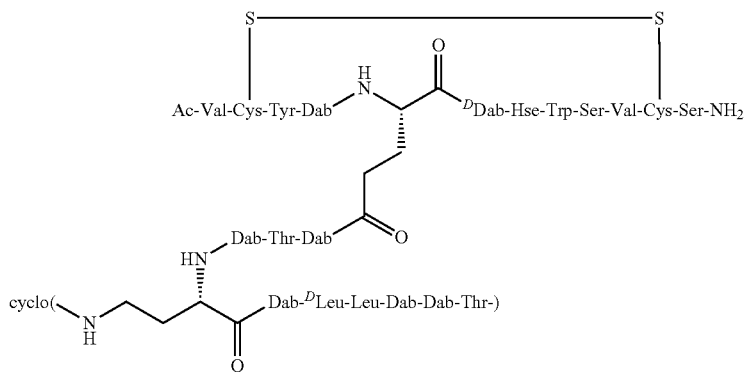
Ex. 42[a)]
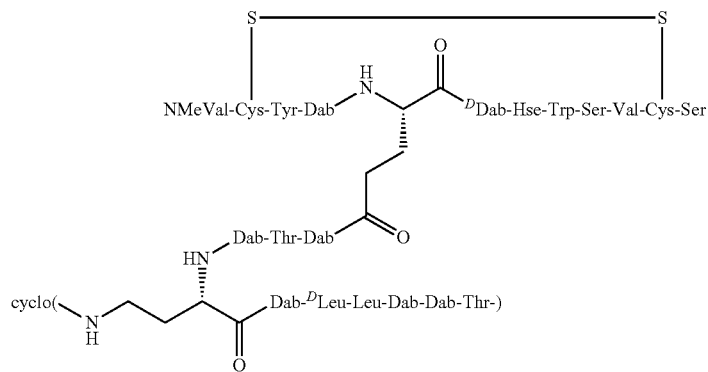
Ex. 43[a)]
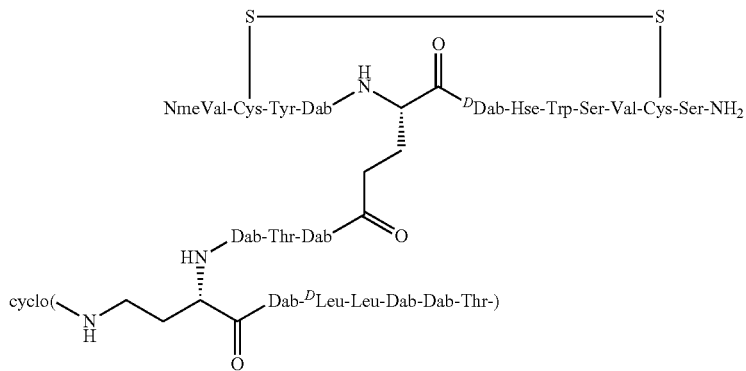

TABLE 1-continued
Examples (Ex.)
In the below-mentioned examples, amino acid residues are connected in either
direction from the α carbonyl (C=O) point of attachment to the α nitrogen (N) of the
next element, unless otherwise indicated. Other linkages, residues, connection of
residues and modifications are as specified.
| Ex. No. | Sequence |
|---|---|
| Ex. 44[a)] | 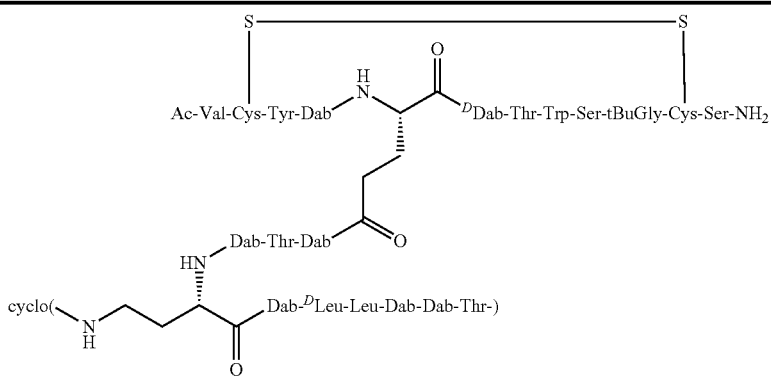 |
| Ex. 45[a)] | 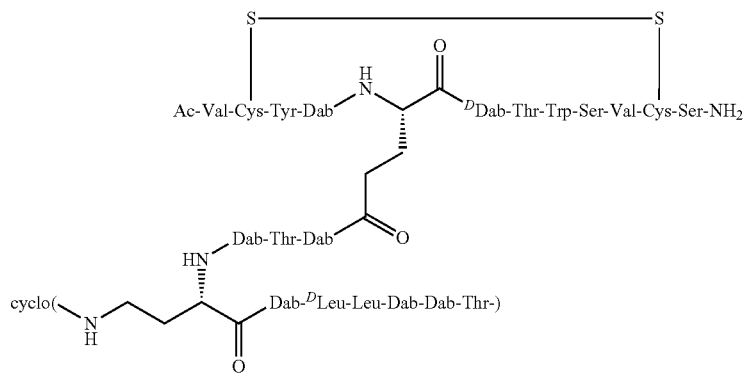 |
| Ex. 46[a)] | 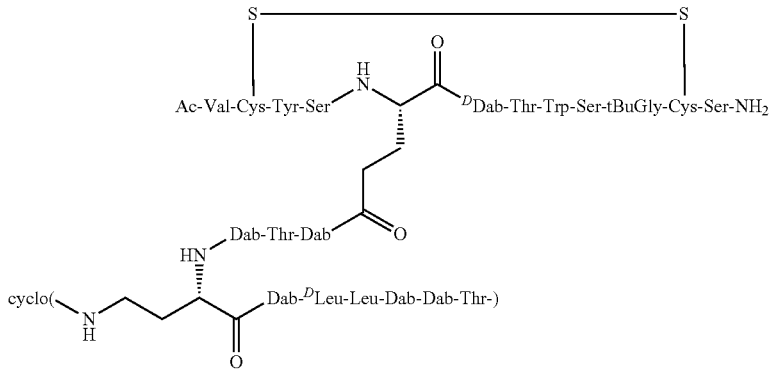 |
| Ex. 47[a)] | 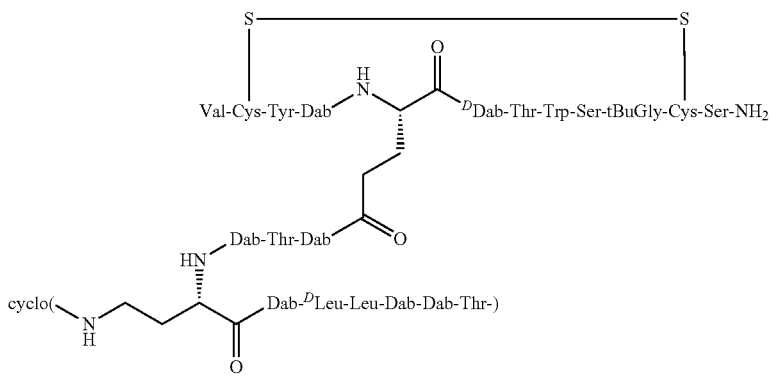 |

TABLE 1-continued
Examples (Ex.)
In the below-mentioned examples, amino acid residues are connected in either direction from the α carbonyl (C=O) point of attachment to the α nitrogen (N) of the next element, unless otherwise indicated. Other linkages, residues, connection of residues and modifications are as specified.
| Ex. No. | Sequence |
|---|---|
| Ex. 48[a)] | 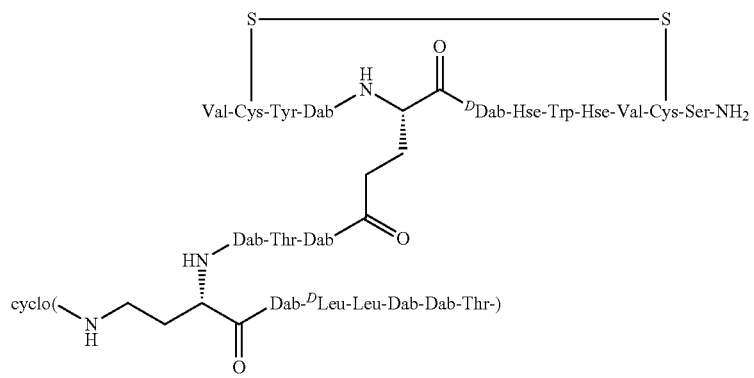 |
| Ex. 49[a)] | 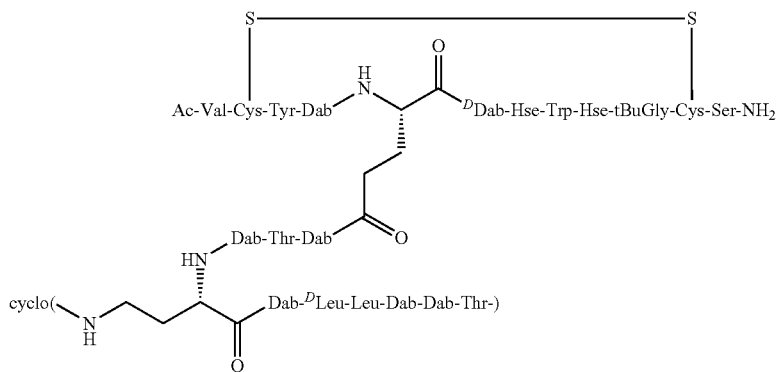 |
| Ex. 50[a)] | 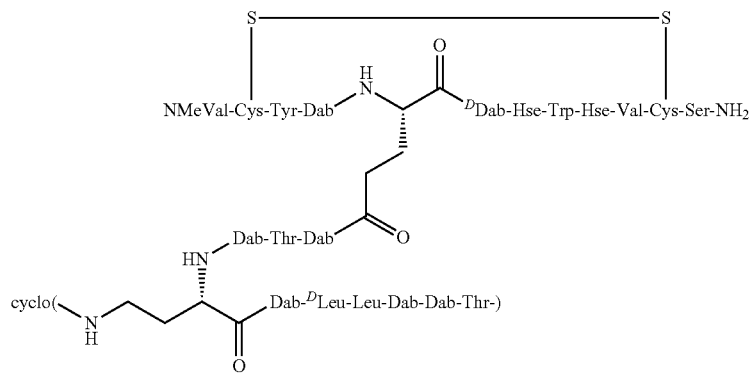 |

TABLE 1-continued
Examples (Ex.)
In the below-mentioned examples, amino acid residues are connected in either
direction from the α carbonyl (C=O) point of attachment to the α nitrogen (N) of the
next element, unless otherwise indicated. Other linkages, residues, connection of
residues and modifications are as specified.
| Ex. No. | Sequence |
|---|---|
| Ex. 51[a)] | 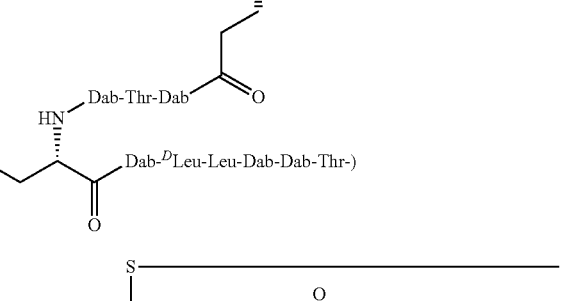 |
| Ex. 52[a)] | 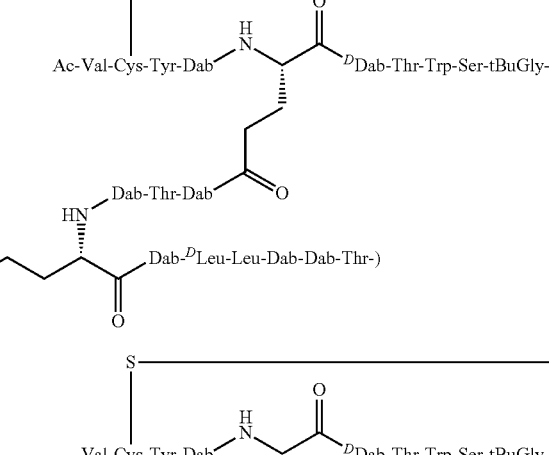 |
| Ex. 53[a)] | 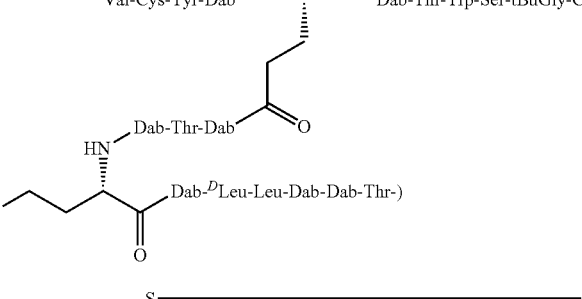 |
| Ex. 54[a)] | 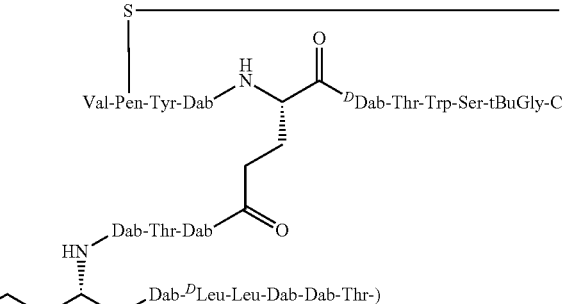 |

TABLE 1-continued
Examples (Ex.)
In the below-mentioned examples, amino acid residues are connected in either direction from the α carbonyl (C=O) point of attachment to the α nitrogen (N) of the next element, unless otherwise indicated. Other linkages, residues, connection of residues and modifications are as specified.
| Ex. No. | Sequence |
| --- | --- |
Ex. 55[g)]
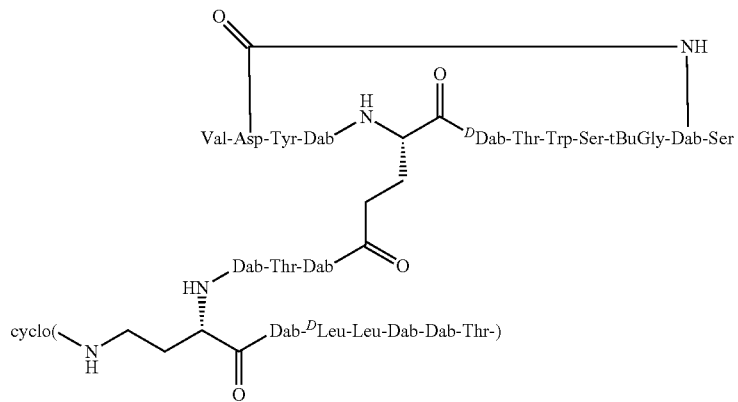
Ex. 56[g)]
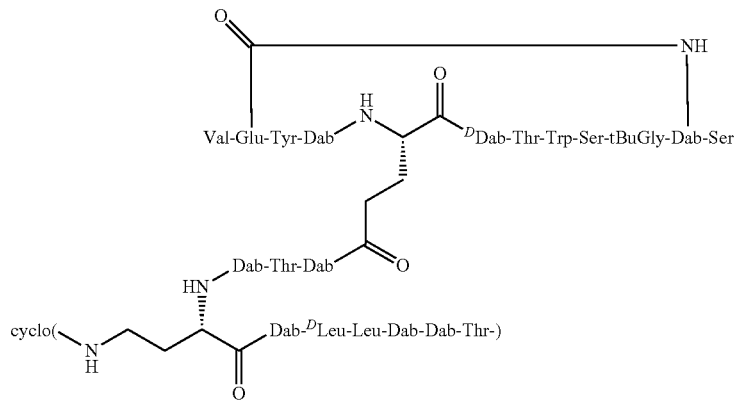
Ex. 57[a)]
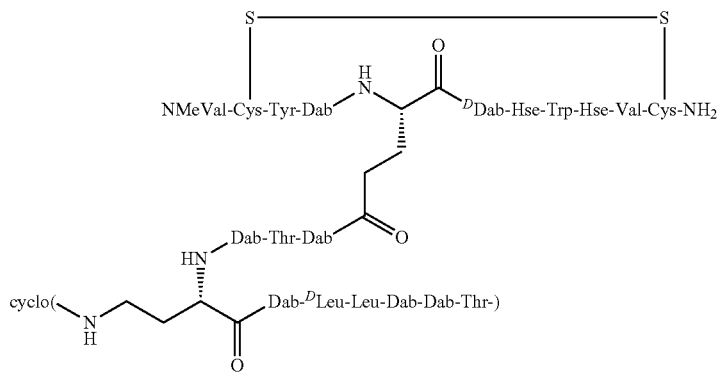

TABLE 1-continued
Examples (Ex.)
In the below-mentioned examples, amino acid residues are connected in either
direction from the α carbonyl (C=O) point of attachment to the α nitrogen (N) of the
next element, unless otherwise indicated. Other linkages, residues, connection of
residues and modifications are as specified.
| Ex. No. | Sequence |
| --- | --- |
| Ex. 58[a) h)] | 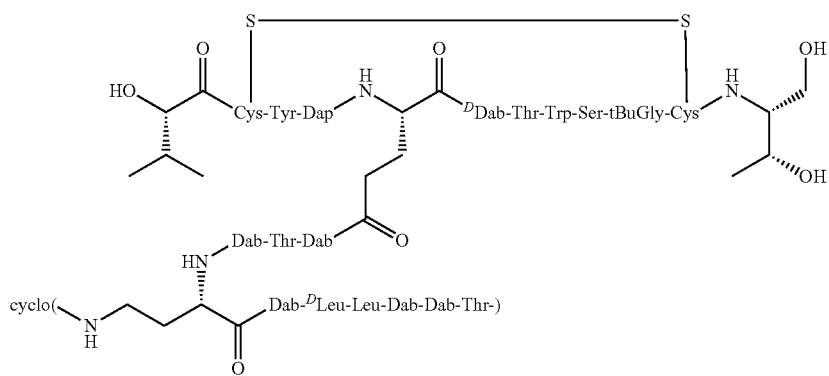 |
| Ex. 59[a) h)] | 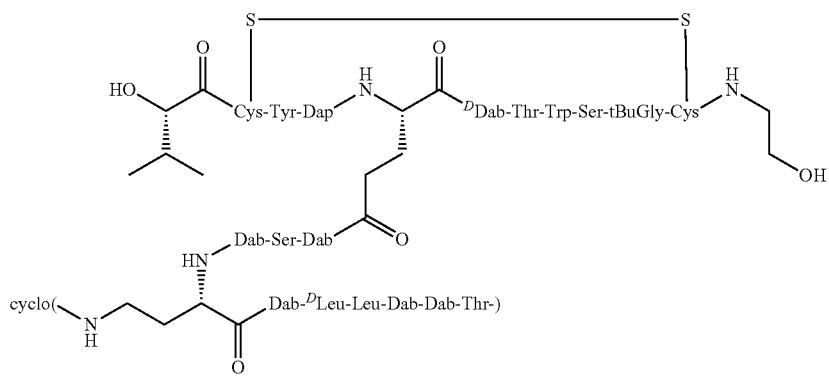 |
| Ex. 60[a) h)] | 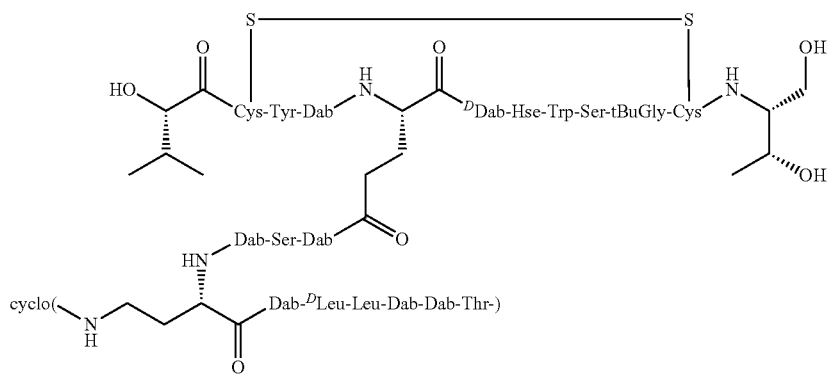 |

TABLE 1-continued
Examples (Ex.)
In the below-mentioned examples, amino acid residues are connected in either
direction from the α carbonyl (C=O) point of attachment to the α nitrogen (N) of the
next element, unless otherwise indicated. Other linkages, residues, connection of
residues and modifications are as specified.
| Ex. No. | Sequence |
|---|---|
| Ex. 61[a) h)] | 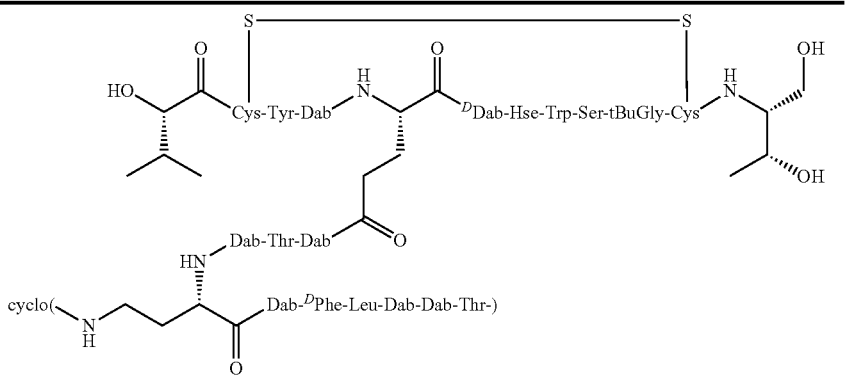 |
| Ex. 62[a)] | 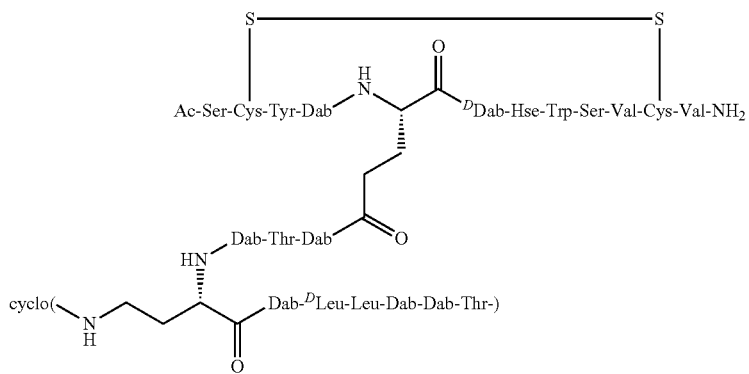 |
| Ex. 63[a)] | 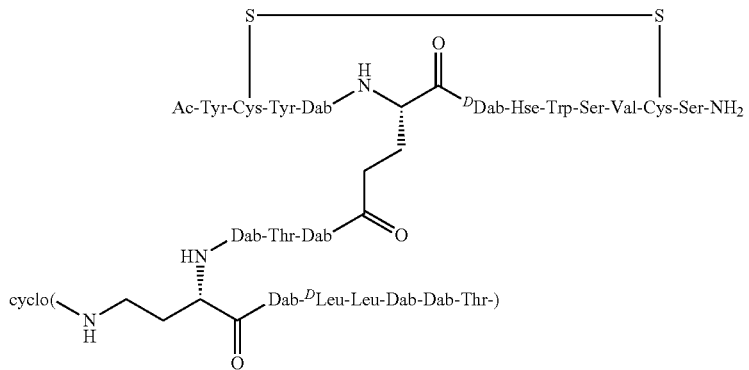 |
| Ex. 64[a)] | 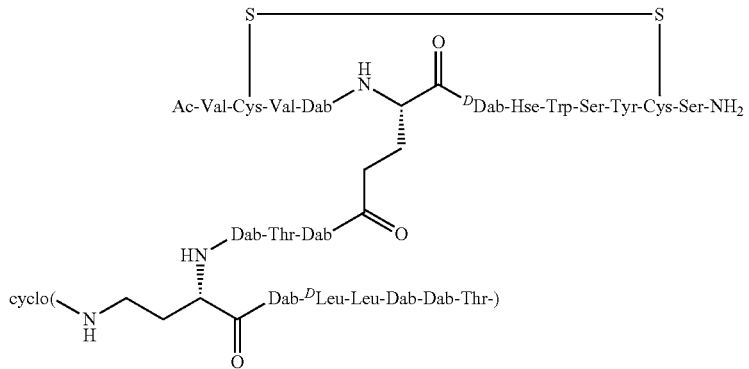 |

TABLE 1-continued
Examples (Ex.)
In the below-mentioned examples, amino acid residues are connected in either
direction from the α carbonyl (C=O) point of attachment to the α nitrogen (N) of the
next element, unless otherwise indicated. Other linkages, residues, connection of
residues and modifications are as specified.
| Ex. No. | Sequence |
| --- | --- |
Ex. 65[a)]
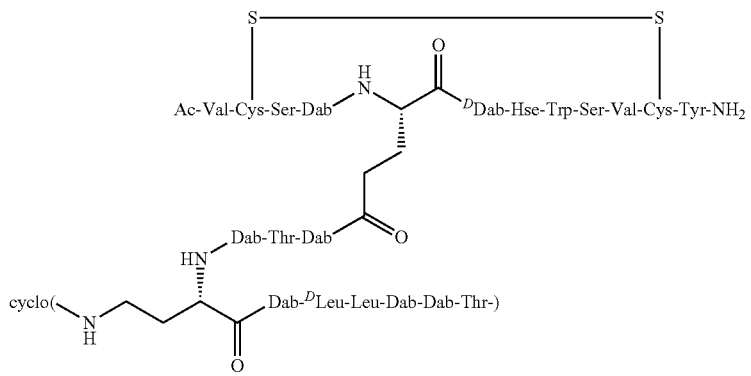
Ex. 66[a)]
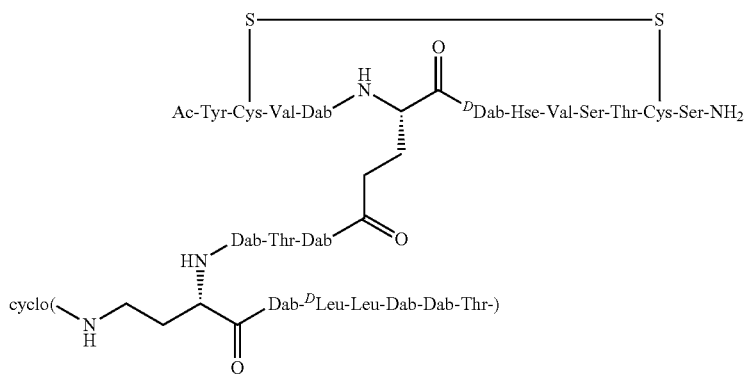
Ex. 67[a)]
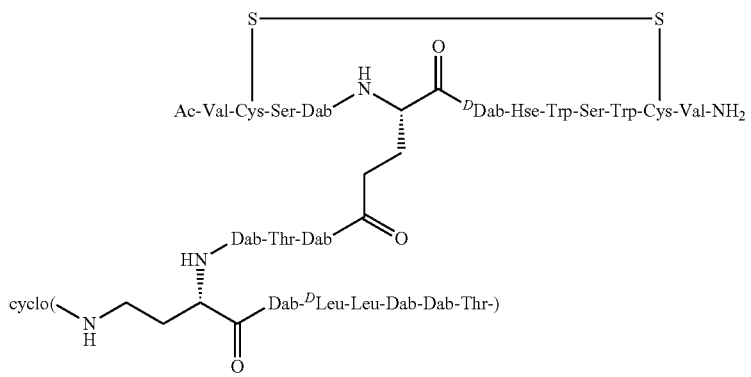

TABLE 1-continued
Examples (Ex.)
In the below-mentioned examples, amino acid residues are connected in either
direction from the α carbonyl (C=O) point of attachment to the α nitrogen (N) of the
next element, unless otherwise indicated. Other linkages, residues, connection of
residues and modifications are as specified.
| Ex. No. | Sequence |
| --- | --- |
Ex. 68[a)]
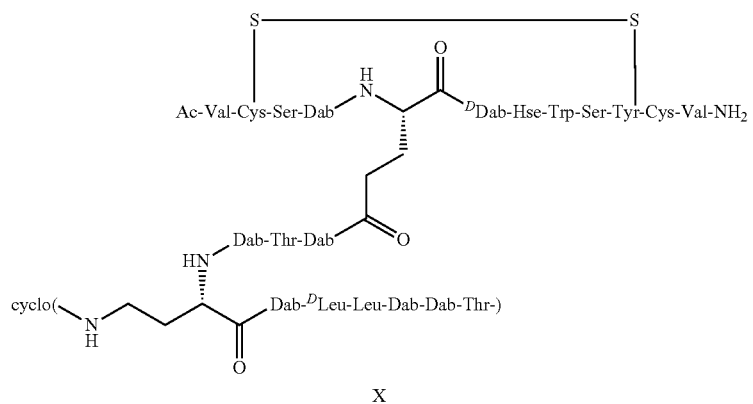
X
Ex. 69[a) h)]
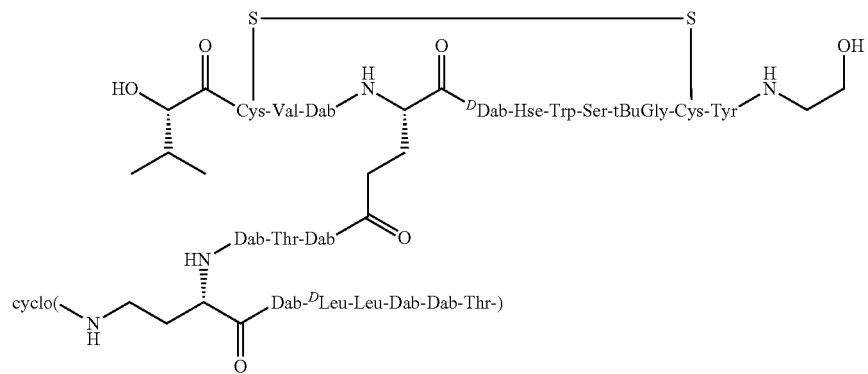
Ex. 70[a) h)]
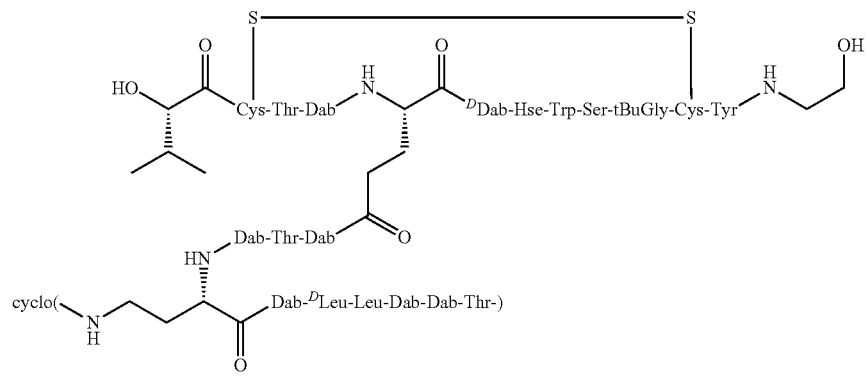

TABLE 1-continued
Examples (Ex.)
In the below-mentioned examples, amino acid residues are connected in either
direction from the α carbonyl (C=O) point of attachment to the α nitrogen (N) of the
next element, unless otherwise indicated. Other linkages, residues, connection of
residues and modifications are as specified.
| Ex. No. | Sequence |
| --- | --- |
Ex. 71[a) b)]
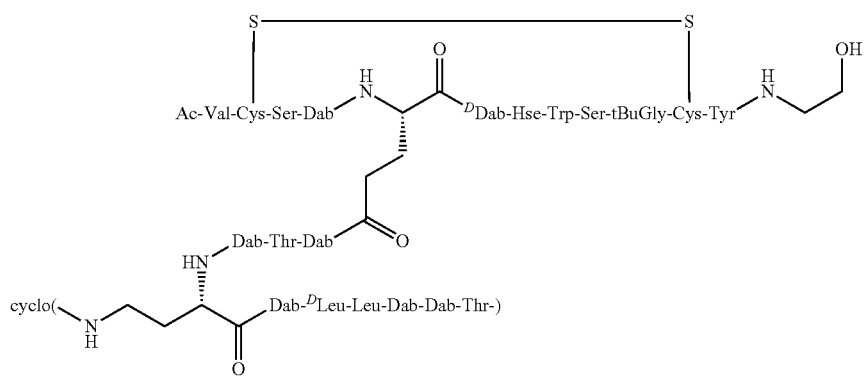
Ex. 72[a) h)]
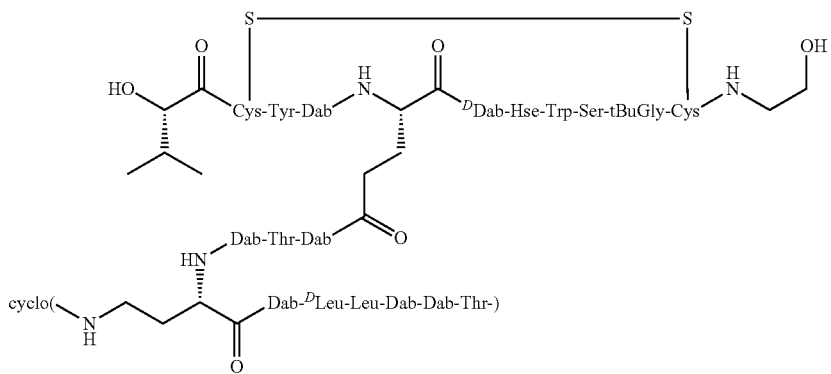
Ex. 73[a) h)]
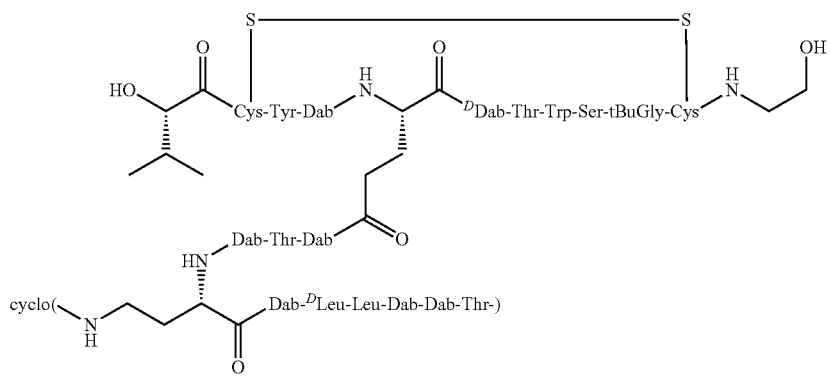

TABLE 1-continued
Examples (Ex.)
In the below-mentioned examples, amino acid residues are connected in either
direction from the α carbonyl (C=O) point of attachment to the α nitrogen (N) of the
next element, unless otherwise indicated. Other linkages, residues, connection of
residues and modifications are as specified.
| Ex. No. | Sequence |
|---|---|
| Ex. 74[a) h)] | 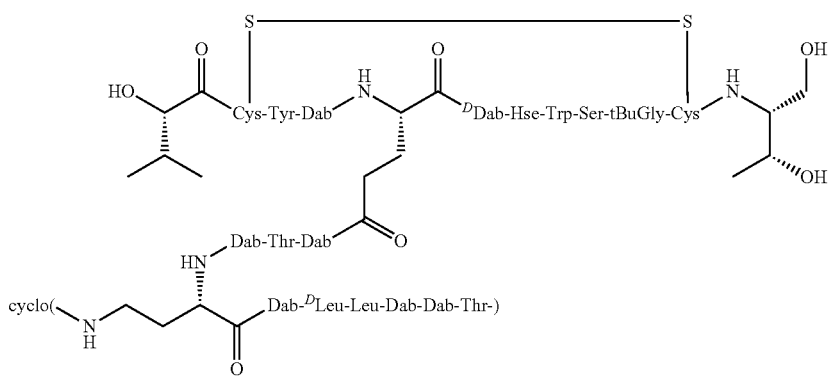 |
| Ex. 75[a) h)] | 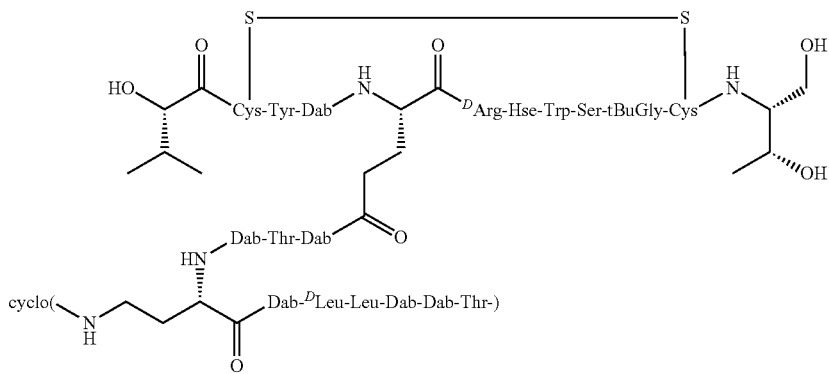 |
| Ex. 76[a) h)] | 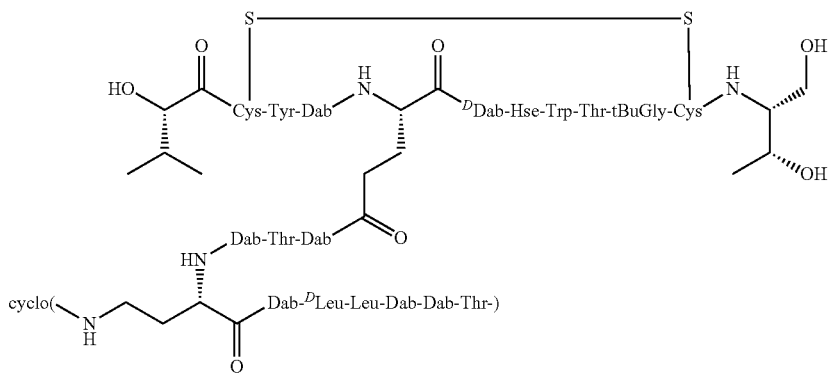 |

TABLE 1-continued
Examples (Ex.)
In the below-mentioned examples, amino acid residues are connected in either
direction from the α carbonyl (C=O) point of attachment to the α nitrogen (N) of the
next element, unless otherwise indicated. Other linkages, residues, connection of
residues and modifications are as specified.
| Ex. No. | Sequence |
|---|---|
| Ex. 77[a) b)] | 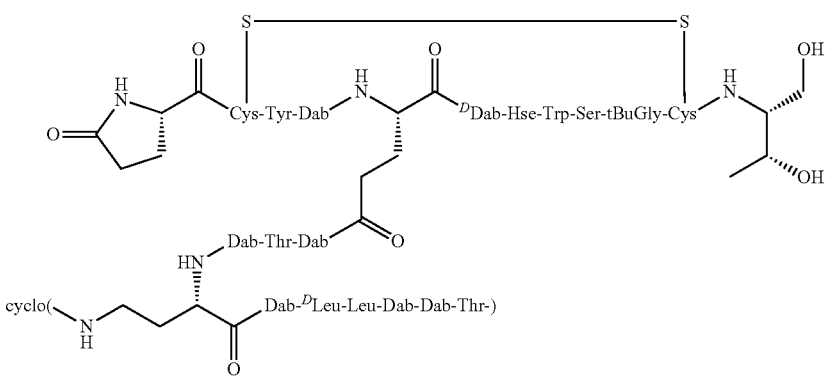 |
| Ex. 78[a) h)] | 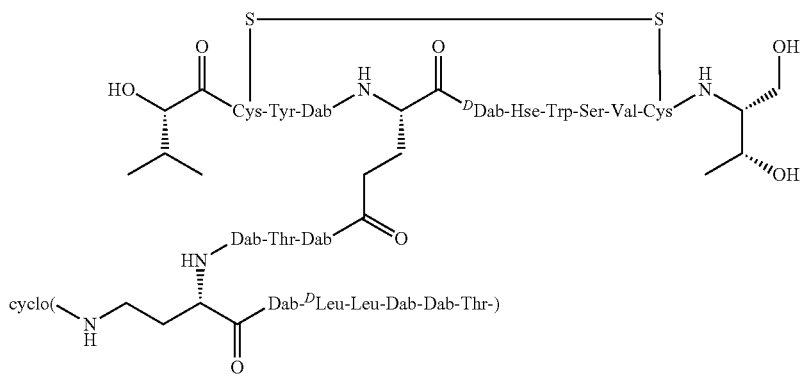 |
| Ex. 79[a) h)] | 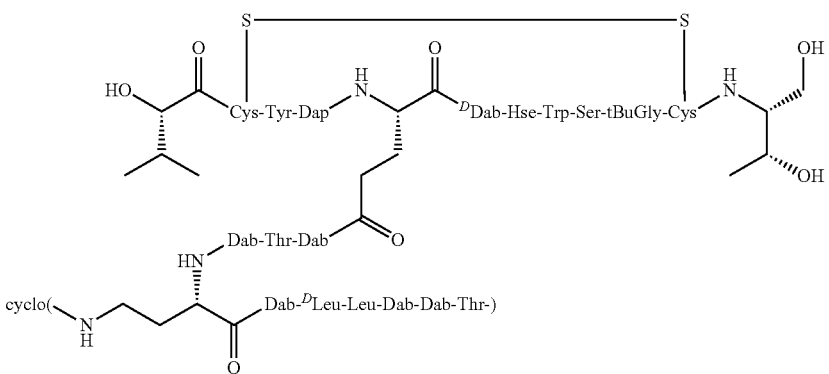 |

TABLE 1-continued
Examples (Ex.)
In the below-mentioned examples, amino acid residues are connected in either
direction from the α carbonyl (C=O) point of attachment to the α nitrogen (N) of the
next element, unless otherwise indicated. Other linkages, residues, connection of
residues and modifications are as specified.
| Ex. No. | Sequence |
| --- | --- |
| Ex. 80[a) h)] | 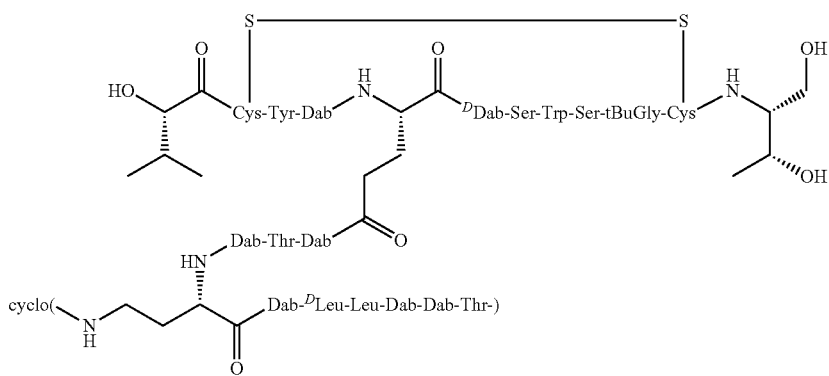 |
| Ex. 81[a) h)] | 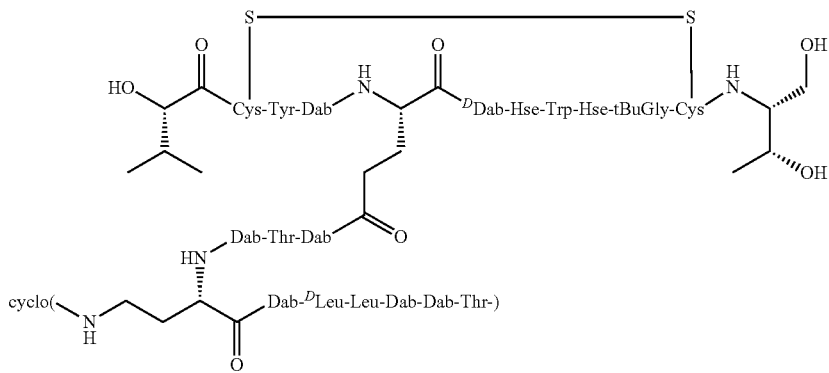 |
| Ex. 82[a) h)] |  |

TABLE 1-continued

Examples (Ex.)
In the below-mentioned examples, amino acid residues are connected in either direction from the α carbonyl (C=O) point of attachment to the α nitrogen (N) of the next element, unless otherwise indicated. Other linkages, residues, connection of residues and modifications are as specified.

| Ex. No. | Sequence |
|---|---|
| Ex. 83[a) h)] | HO-CH(iPr)-C(O)-Cys-Tyr-Dab-NH-CH(-C(O)-DDab-Ser-Trp-Hse-tBuGly-Cys-NH-CH(CH(OH)CH3)-CH2OH; S-S bridge between Cys and Cys; side-chain of central Dab connects via -CH2CH2-NH- to Dab-Thr-Dab-; glutamyl side chain C(O) connects to cyclo(-NH-CH2CH2-CH(NH-)-C(O)-Dab-DLeu-Leu-Dab-Dab-Thr-) |
| Ex. 84[a) h)] | HO-CH(iPr)-C(O)-Pen-Tyr-Dab-NH-CH(-C(O)-DDab-Hse-Trp-Ser-tBuGly-Cys-NH-CH(CH(OH)CH3)-CH2OH; S-S bridge between Pen and Cys; Dab-Thr-Dab- side chain; cyclo(-NH-CH2CH2-CH(NH-)-C(O)-Dab-DLeu-Leu-Dab-Dab-Thr-) |
| Ex. 85[a) h)] | HO-CH(iPr)-C(O)-Cys-Tyr-Dab-NH-CH(-C(O)-DDab-Hse-Trp-Ser-tBuGly-Pen-NH-CH(CH(OH)CH3)-CH2OH; S-S bridge between Cys and Pen; Dab-Thr-Dab- side chain; cyclo(-NH-CH2CH2-CH(NH-)-C(O)-Dab-DLeu-Leu-Dab-Dab-Thr-) |
| Ex. 86[a) b)] | Ac-DVal-Cys-Tyr-Dab-NH-CH(-C(O)-DDab-Hse-Trp-Ser-tBuGly-Cys-NH-CH(CH(OH)CH3)-CH2OH; S-S bridge between Cys and Cys; Dab-Thr-Dab- side chain; cyclo(-NH-CH2CH2-CH(NH-)-C(O)-Dab-DLeu-Leu-Dab-Dab-Thr-) |

TABLE 1-continued

Examples (Ex.)
In the below-mentioned examples, amino acid residues are connected in either direction from the α carbonyl (C=O) point of attachment to the α nitrogen (N) of the next element, unless otherwise indicated. Other linkages, residues, connection of residues and modifications are as specified.

| Ex. No. | Sequence |
| --- | --- |
| Ex. 87[a) h)] | cyclo(HO-Val-Cys-Tyr-Dab-Glu(-Dab-Thr-Dab-)-DDab-Hse-Trp-Gly-tBuGly-Cys-Thr(ol)(OH), Dab(-NH-)-Dab-DLeu-Leu-Dab-Dab-Thr-), disulfide Cys-Cys |
| Ex. 88[a) h)] | cyclo(HO-Val-Cys-Tyr-Ser-Glu(-Dab-Thr-Dab-)-DDab-Hse-Trp-Ser-tBuGly-Cys-Thr(ol)(OH), Dab(-NH-)-Dab-DLeu-Leu-Dab-Dab-Thr-), disulfide Cys-Cys |
| Ex. 89[a) h)] | cyclo(HO-Val-Cys-Val-Dab-Glu(-Dab-Thr-Dab-)-DDab-Hse-Trp-Ser-Tyr-Cys-Thr(ol)(OH), Dab(-NH-)-Dab-DLeu-Leu-Dab-Dab-Thr-), disulfide Cys-Cys |

TABLE 1-continued
Examples (Ex.)
In the below-mentioned examples, amino acid residues are connected in either direction from the α carbonyl (C=O) point of attachment to the α nitrogen (N) of the next element, unless otherwise indicated. Other linkages, residues, connection of residues and modifications are as specified.
| Ex. No. | Sequence |
|---|---|
| Ex. 90[a) h)] | 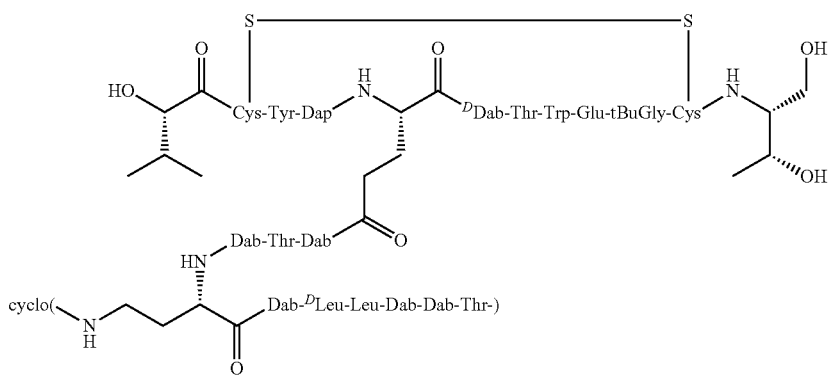 |
| Ex. 91[a) h)] | 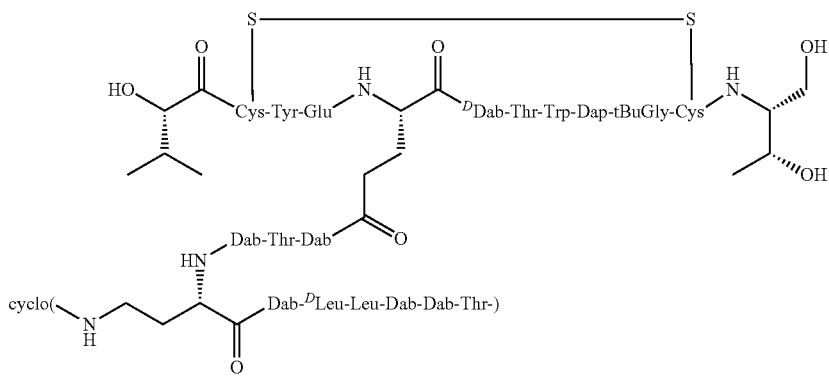 |
| Ex. 92[a) h)] | 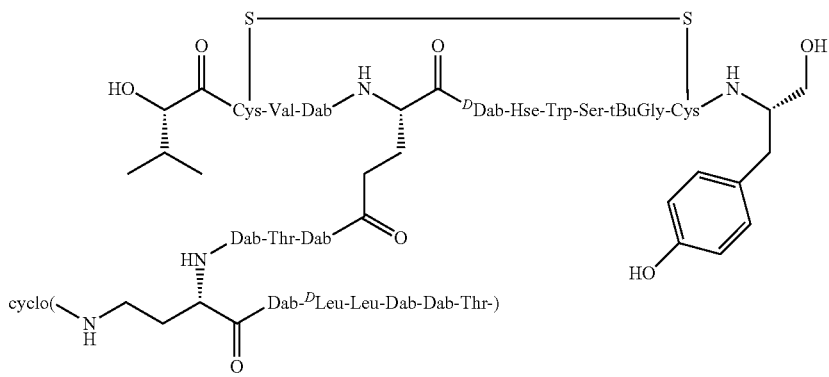 |

TABLE 1-continued
Examples (Ex.)
In the below-mentioned examples, amino acid residues are connected in either
direction from the α carbonyl (C=O) point of attachment to the α nitrogen (N) of the
next element, unless otherwise indicated. Other linkages, residues, connection of
residues and modifications are as specified.
| Ex. No. | Sequence |
|---|---|
| Ex. 93[a) h)] | 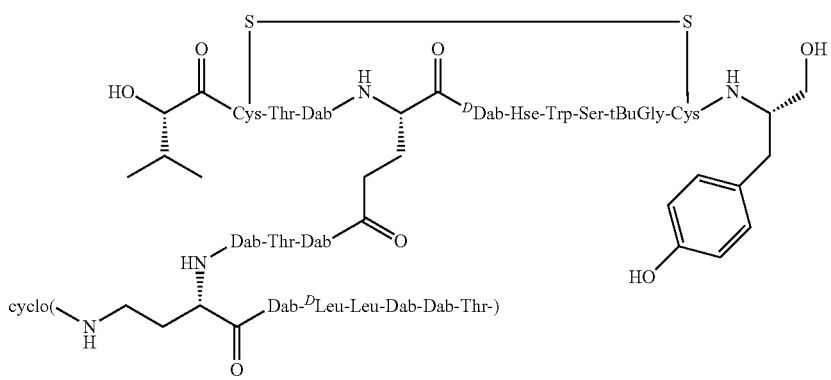 |
| Ex. 94[a) b)] | 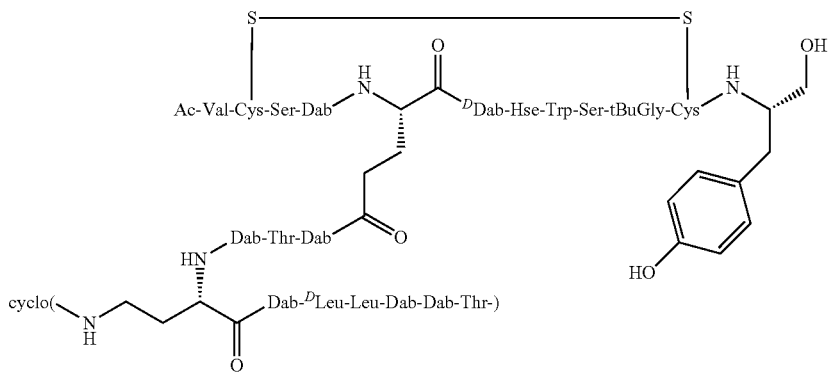 |
| Ex. 95[a) h)] | 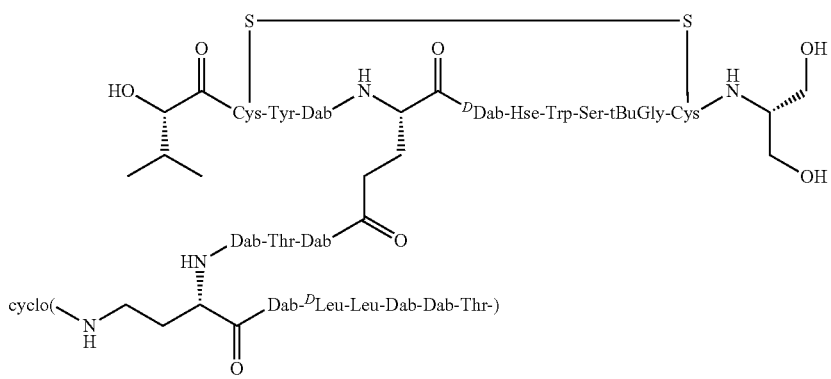 |

TABLE 1-continued

Examples (Ex.)
In the below-mentioned examples, amino acid residues are connected in either direction from the α carbonyl (C=O) point of attachment to the α nitrogen (N) of the next element, unless otherwise indicated. Other linkages, residues, connection of residues and modifications are as specified.

| Ex. No. | Sequence |
|---|---|
| Ex. 96[a) b)] | Ac-Tyr-Cys-Val-Dab-[N(H)]-C(=O)-[D]Dab-Hse-Trp-Ser-tBuGly-Cys-N(H)-CH(CH₂OH)(CH₂OH); S-S bridge between the two Cys; side chain of central residue extends to Dab-Thr-Dab-C(=O)-NH-cyclo(-NH-CH-C(=O)-Dab-[D]Leu-Leu-Dab-Dab-Thr-) |
| Ex. 97[a) h)] | HO-CH(iPr)-C(=O)-S-Cys-Val-Dab-[N(H)]-C(=O)-[D]Dab-Hse-Trp-Ser-Tyr-Cys-N(H)-CH(CH₂OH)(CH₂OH); S-S bridge; side chain extends to Dab-Thr-Dab-C(=O)-NH-cyclo(-NH-CH-C(=O)-Dab-[D]Leu-Leu-Dab-Dab-Thr-) |
| Ex. 98[a) b)] | Ac-Tyr-Cys-Val-Dab-[N(H)]-C(=O)-[D]Dab-Hse-Val-Ser-Trp-Cys-N(H)-CH(CH₂OH)(CH₂OH); S-S bridge; side chain extends to Dab-Thr-Dab-C(=O)-NH-cyclo(-NH-CH-C(=O)-Dab-[D]Leu-Leu-Dab-Dab-Thr-) |
| Ex. 99[a) e)] | HO-CH(iPr)-C(=O)-S-Cys-Tyr-Dap-[N(H)]-C(=O)-[D]Dab-Thr-Trp-Ser-tBuGly-Cys-Thr-NH₂; S-S bridge; side chain extends to Dab-Thr-Dab-C(=O)-NH-cyclo(-NH-CH-C(=O)-Dab-[D]Leu-Leu-Dab-Dab-Thr-) |

TABLE 1-continued
Examples (Ex.)
In the below-mentioned examples, amino acid residues are connected in either
direction from the α carbonyl (C=O) point of attachment to the α nitrogen (N) of the
next element, unless otherwise indicated. Other linkages, residues, connection of
residues and modifications are as specified.
| Ex. No. | Sequence |
|---|---|
| Ex. 100[a)] | 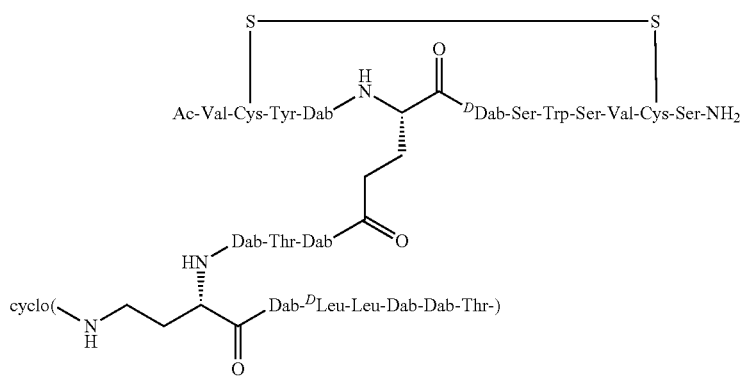 |
| Ex. 101[a) h)] | 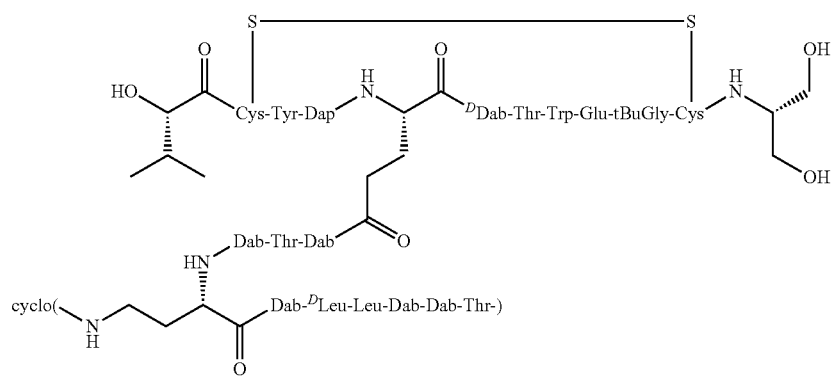 |
| Ex. 102[a) h)] | 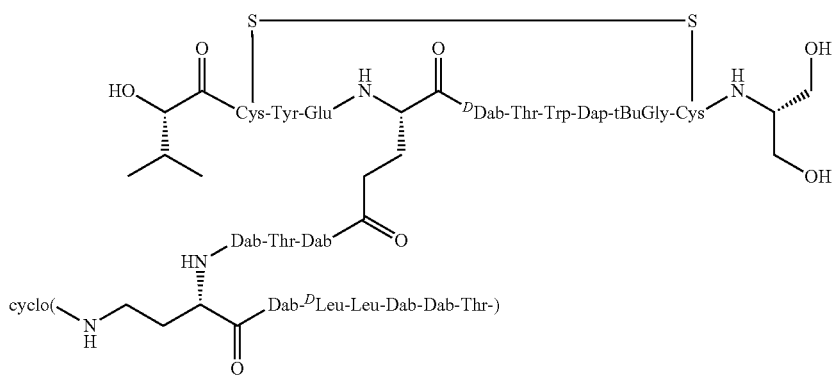 |

TABLE 1-continued
Examples (Ex.)
In the below-mentioned examples, amino acid residues are connected in either
direction from the α carbonyl (C=O) point of attachment to the α nitrogen (N) of the
next element, unless otherwise indicated. Other linkages, residues, connection of
residues and modifications are as specified.
| Ex. No. | Sequence |
|---|---|
| Ex. 103[a) h)] | 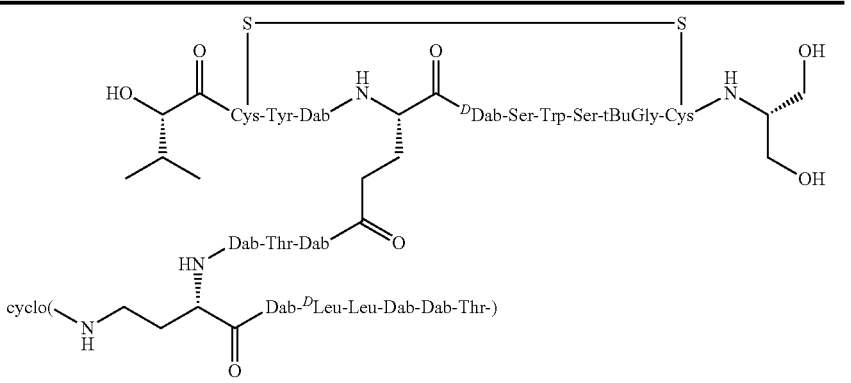 |
| Ex. 104[a) h)] | 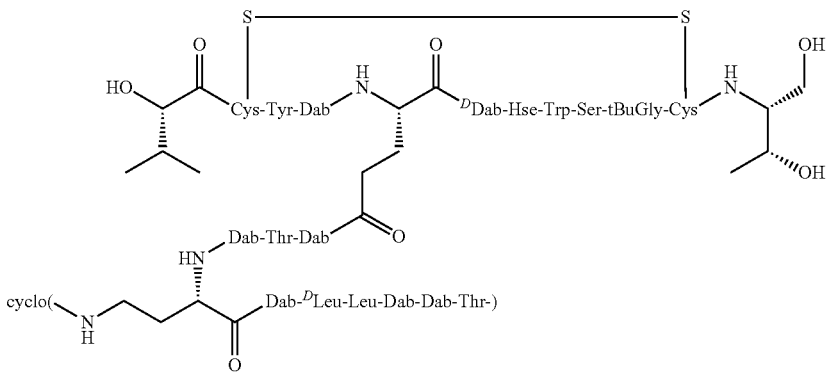 |
| Ex. 105[a) h)] | 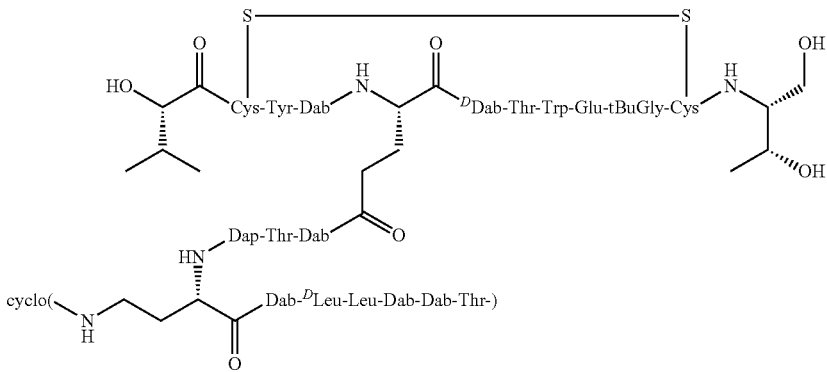 |
| Ex. 106[a) h)] | 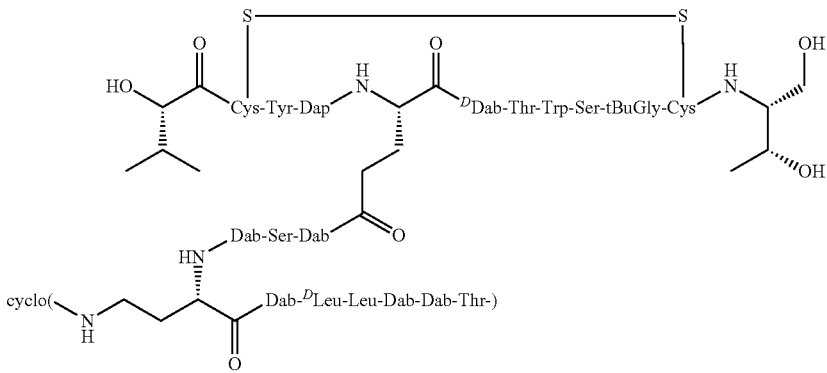 |

TABLE 1-continued

Examples (Ex.)
In the below-mentioned examples, amino acid residues are connected in either
direction from the α carbonyl (C=O) point of attachment to the α nitrogen (N) of the
next element, unless otherwise indicated. Other linkages, residues, connection of
residues and modifications are as specified.

| Ex. No. | Sequence |
| --- | --- |
| Ex. 107[a) h)] | (structure: HO-Val-Cys-Tyr-Dap-N(H)-Glu-DDab-Thr-Trp-Ser-tBuGly-Cys-NH-Thr(OH)-CH2OH, with S-S bridge between the two Cys; side chain of Glu connected via C(=O) to HN-Dab-Thr-Dab-cyclo(-NH-CH2-CH2-CH(—)-C(=O)-Dab-DLeu-Leu-Dab-Dab-Thr-)) |
| Ex. 108[a) h)] | (structure: HO-Val-Cys-Tyr-Ser-N(H)-Glu-DDab-Dab-Trp-Ser-tBuGly-Cys-NH-Thr(OH)-CH2OH, with S-S bridge between the two Cys; side chain of Glu connected via C(=O) to HN-Dab-Thr-Dab-cyclo(-NH-CH2-CH2-CH(—)-C(=O)-Dab-DLeu-Leu-Dab-Dab-Thr-)) |
| Ex. 109[a) h)] | (structure: HO-Val-Cys-Tyr-Dap-N(H)-Glu-DDab-Hse-Trp-Ser-tBuGly-Cys-NH-Thr(OH)-CH2OH, with S-S bridge between the two Cys; side chain of Glu connected via C(=O) to HN-Dab-Thr-Dab-cyclo(-NH-CH2-CH2-CH(—)-C(=O)-Dab-DLeu-Abu-Dab-Dab-Thr-)) |

TABLE 1-continued
Examples (Ex.)
In the below-mentioned examples, amino acid residues are connected in either
direction from the α carbonyl (C=O) point of attachment to the α nitrogen (N) of the
next element, unless otherwise indicated. Other linkages, residues, connection of
residues and modifications are as specified.
| Ex. No. | Sequence |
| --- | --- |
| Ex. 110[a) h)] | 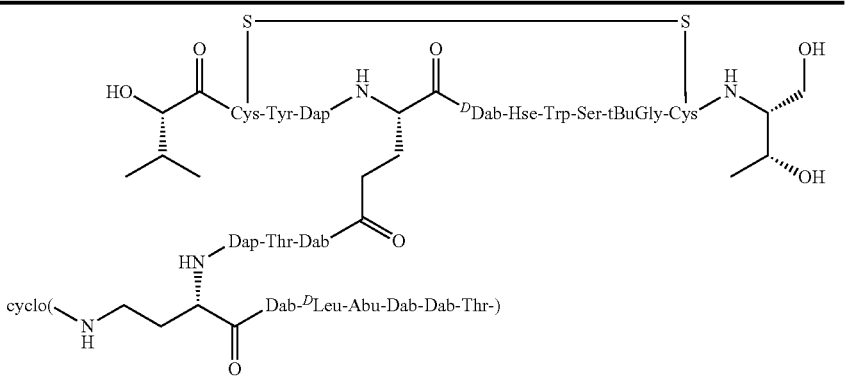 |
| Ex. 111[a) h)] | 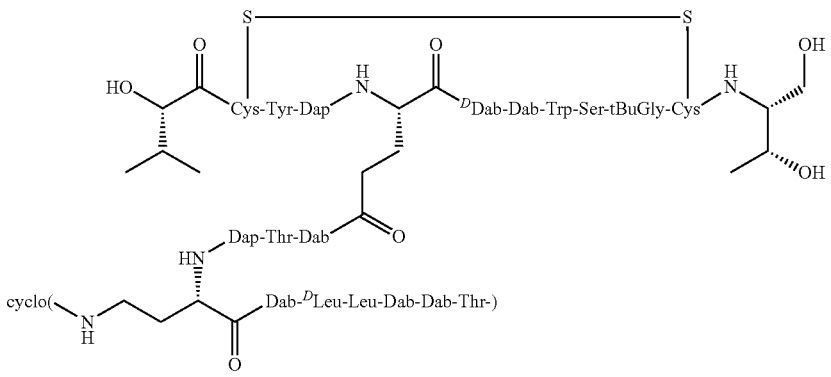 |
| Ex. 112[a) h)] | 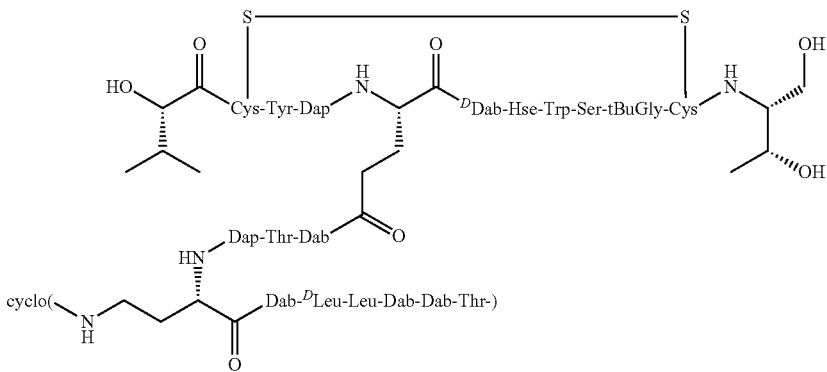 |
| Ex. 113[a)] | 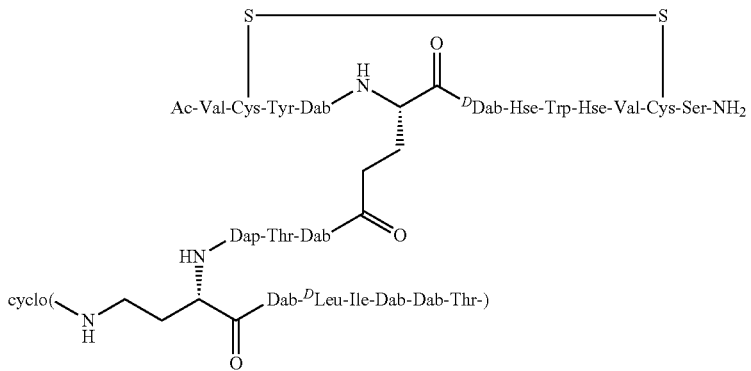 |

TABLE 1-continued
Examples (Ex.)
In the below-mentioned examples, amino acid residues are connected in either
direction from the α carbonyl (C=O) point of attachment to the α nitrogen (N) of the
next element, unless otherwise indicated. Other linkages, residues, connection of
residues and modifications are as specified.
| Ex. No. | Sequence |
|---|---|
Ex. 114[a)]
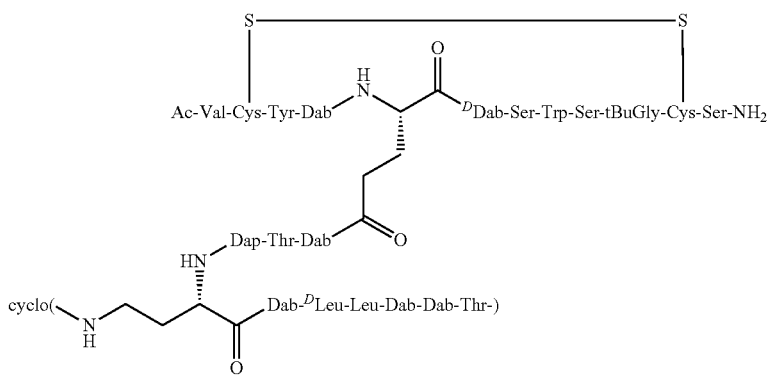
Ex. 115[a) e)]
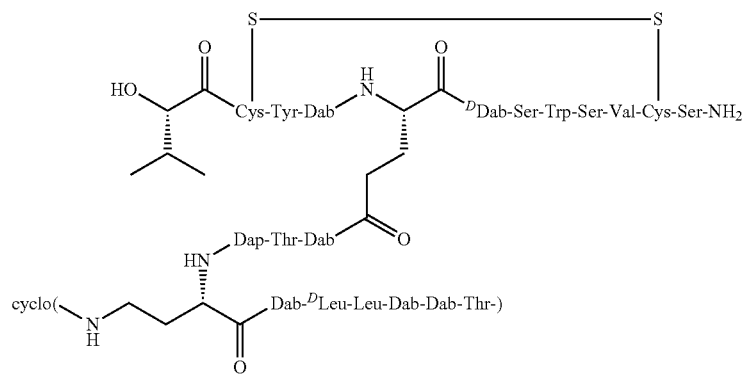
Ex. 116[a) b)]
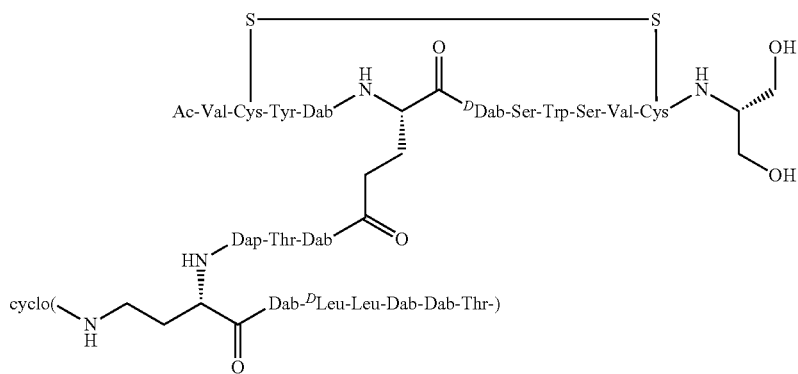

TABLE 1-continued
Examples (Ex.)
In the below-mentioned examples, amino acid residues are connected in either direction from the α carbonyl (C=O) point of attachment to the α nitrogen (N) of the next element, unless otherwise indicated. Other linkages, residues, connection of residues and modifications are as specified.
| Ex. No. | Sequence |
| --- | --- |
| Ex. 117[a)] | 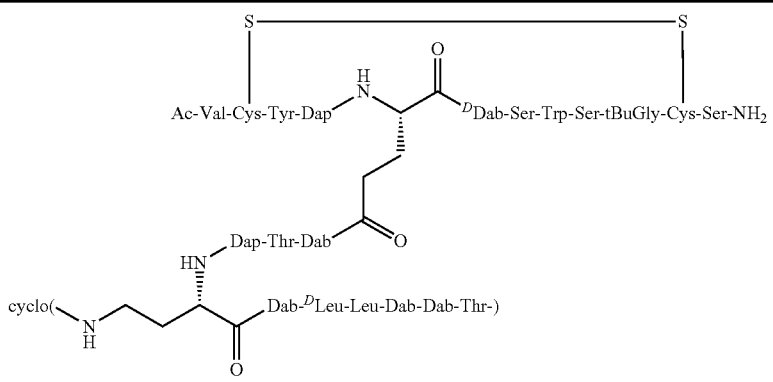 |
| Ex. 119[a)] | 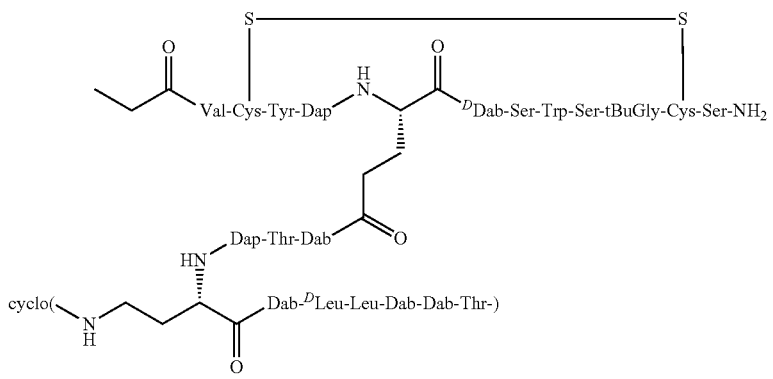 |
| Ex. 120[a)] | 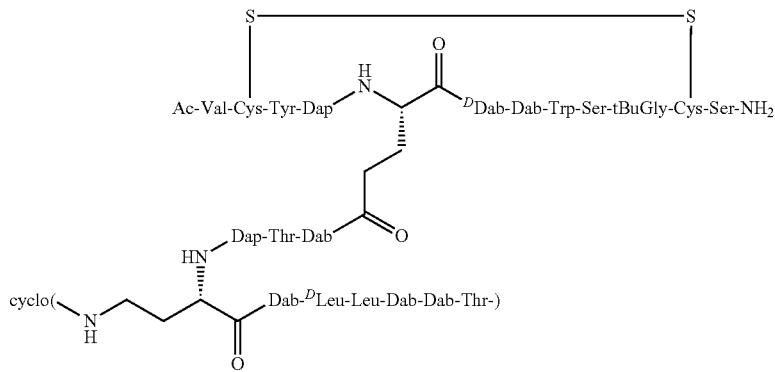 |
| Ex. 121[a)] | 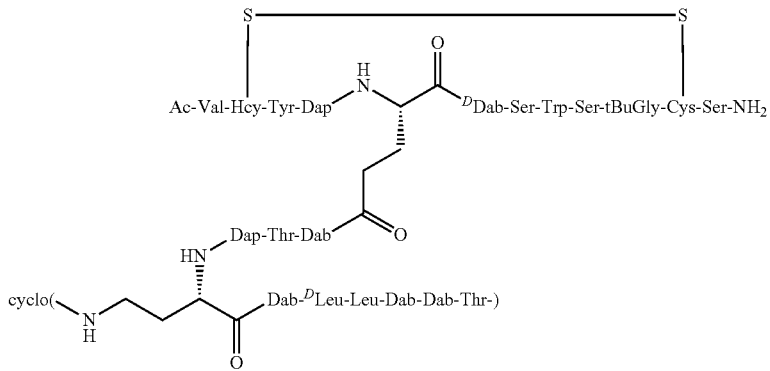 |

TABLE 1-continued
Examples (Ex.)
In the below-mentioned examples, amino acid residues are connected in either
direction from the α carbonyl (C=O) point of attachment to the α nitrogen (N) of the
next element, unless otherwise indicated. Other linkages, residues, connection of
residues and modifications are as specified.
| Ex. No. | Sequence |
|---|---|
| Ex. 122[a)] | 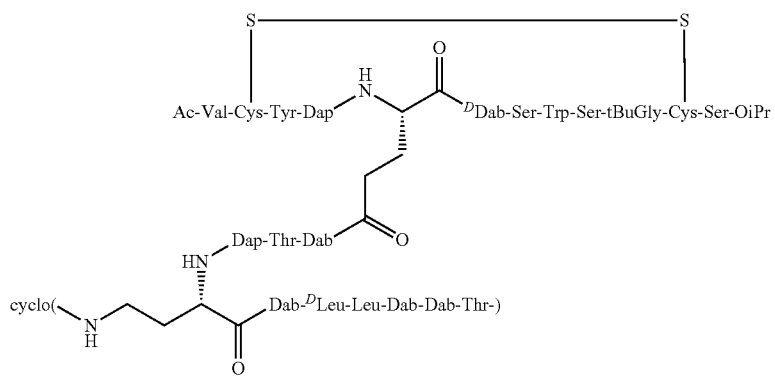 |
| Ex. 123[a) b)] | 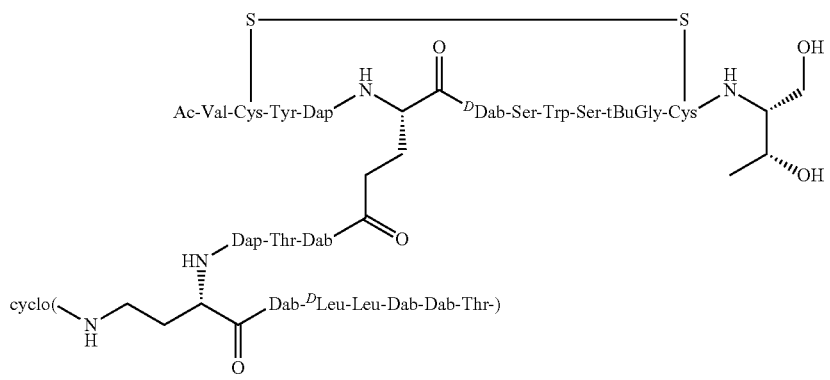 |
| Ex. 124[a) b)] | 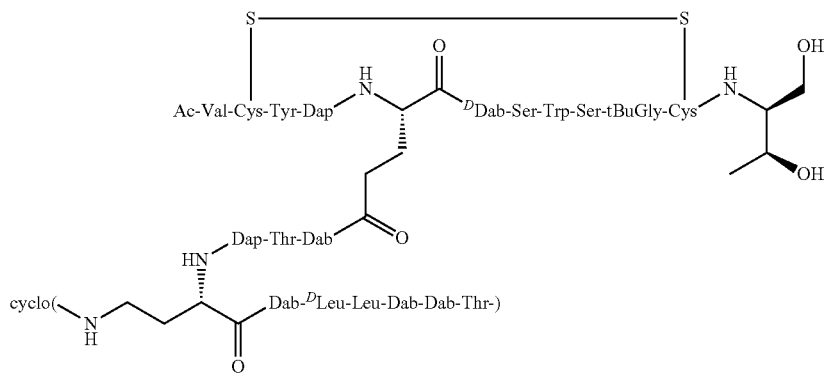 |

TABLE 1-continued
Examples (Ex.)
In the below-mentioned examples, amino acid residues are connected in either direction from the α carbonyl (C═O) point of attachment to the α nitrogen (N) of the next element, unless otherwise indicated. Other linkages, residues, connection of residues and modifications are as specified.
| Ex. No. | Sequence |
|---|---|
| Ex. 125[a)] | 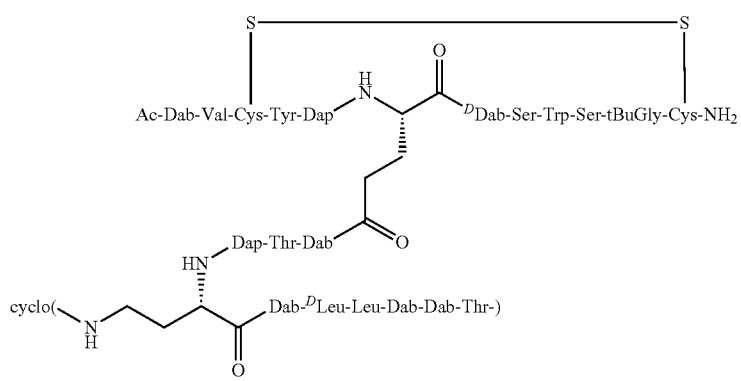 |
| Ex. 126[a)] | 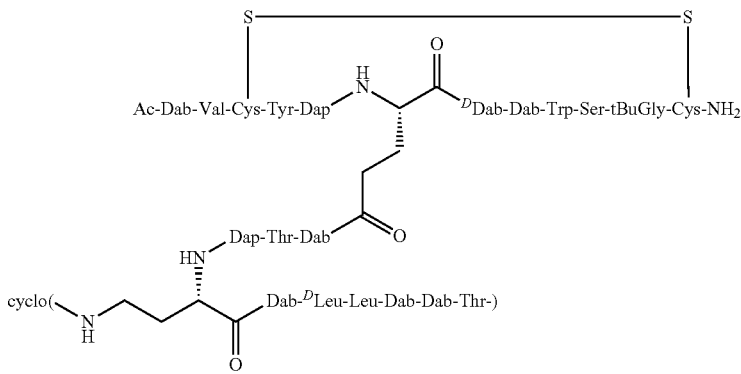 |
| Ex. 127[a) h)] | 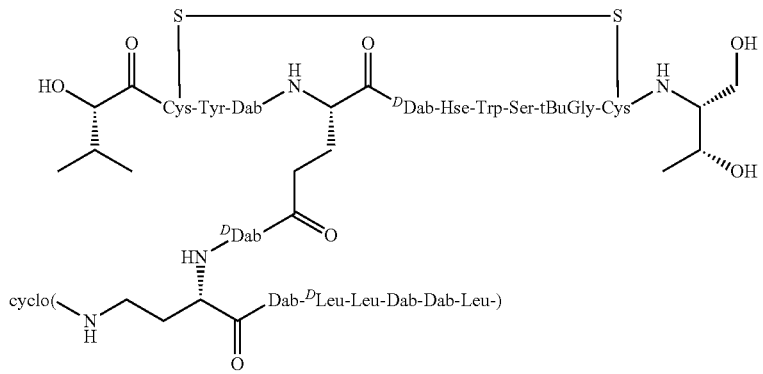 |

TABLE 1-continued
Examples (Ex.)
In the below-mentioned examples, amino acid residues are connected in either
direction from the α carbonyl (C=O) point of attachment to the α nitrogen (N) of the
next element, unless otherwise indicated. Other linkages, residues, connection of
residues and modifications are as specified.
| Ex. No. | Sequence |
|---|---|
| Ex. 128[a)] | 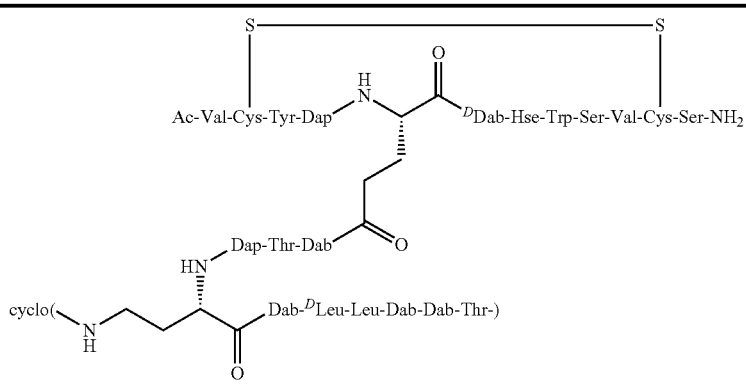 |
| Ex. 129[a) b)] | 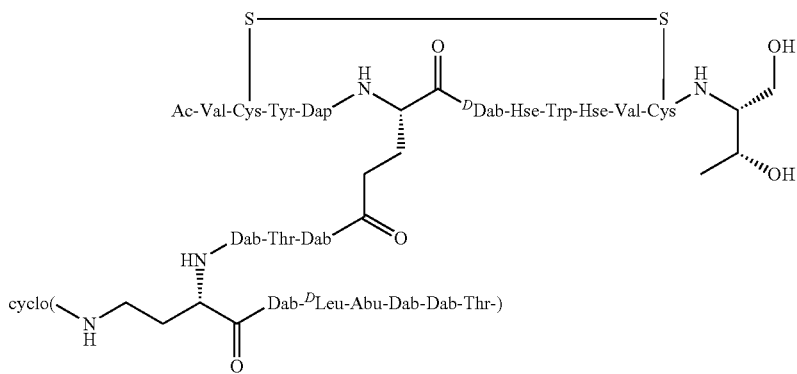 |
| Ex. 130[a)] | 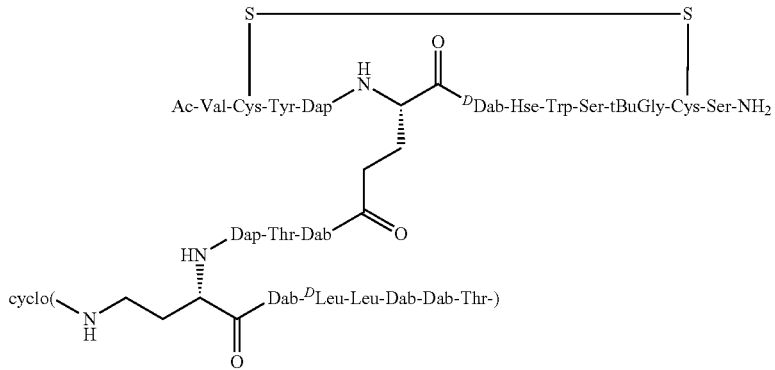 |
| Ex. 131[a)] | 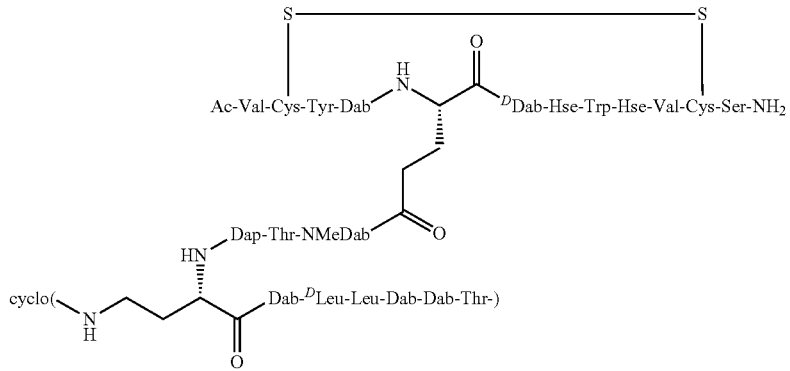 |

TABLE 1-continued
Examples (Ex.)
In the below-mentioned examples, amino acid residues are connected in either direction from the α carbonyl (C=O) point of attachment to the α nitrogen (N) of the next element, unless otherwise indicated. Other linkages, residues, connection of residues and modifications are as specified.
| Ex. No. | Sequence |
| --- | --- |
| Ex. 132[a)] | 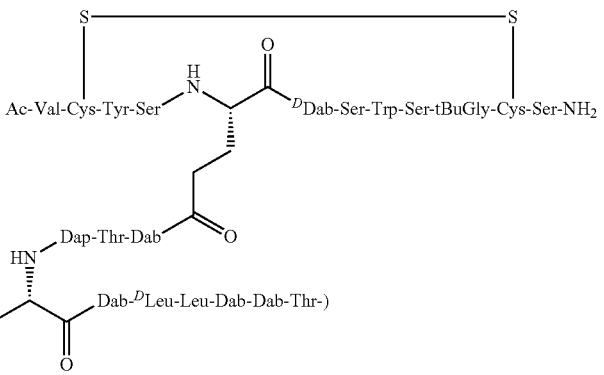 |
| Ex. 133[a)] | 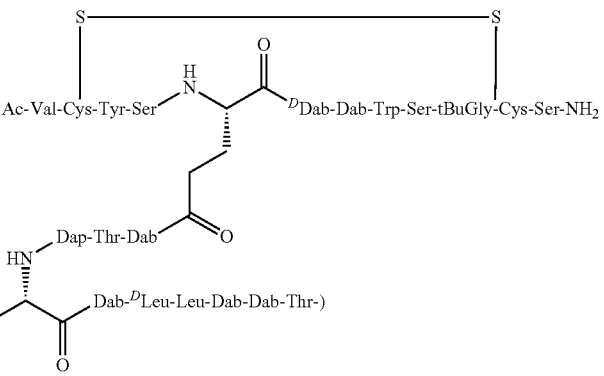 |
| Ex. 134[a)] | 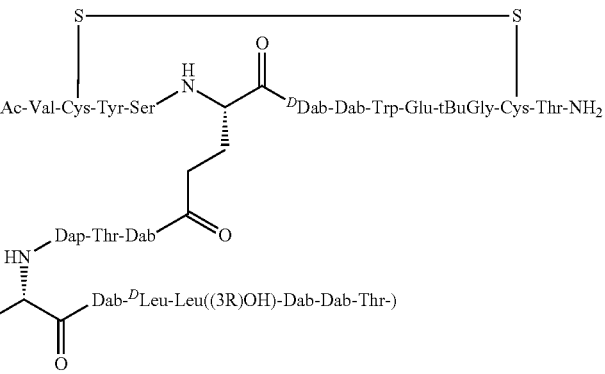 |

TABLE 1-continued
Examples (Ex.)
In the below-mentioned examples, amino acid residues are connected in either
direction from the α carbonyl (C=O) point of attachment to the α nitrogen (N) of the
next element, unless otherwise indicated. Other linkages, residues, connection of
residues and modifications are as specified.
| Ex. No. | Sequence |
|---|---|
| Ex. 135[a)] | 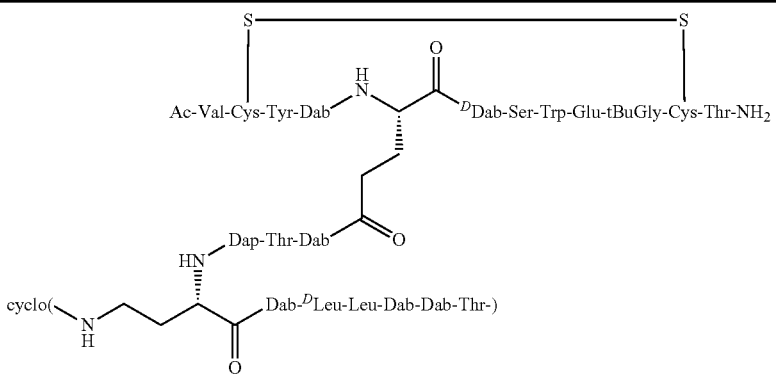 |
| Ex. 136[a)] | 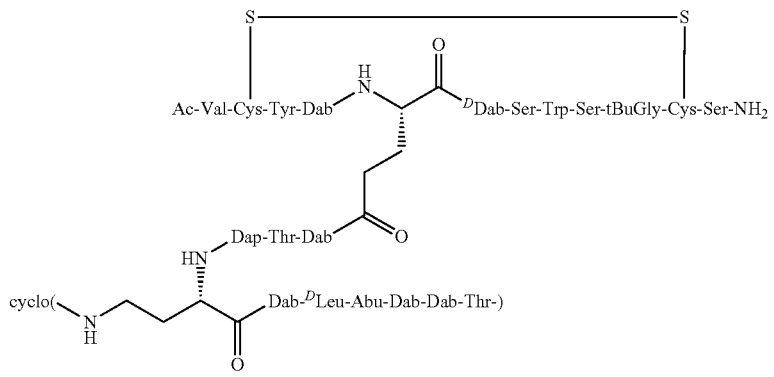 |
| Ex. 137[a)] | 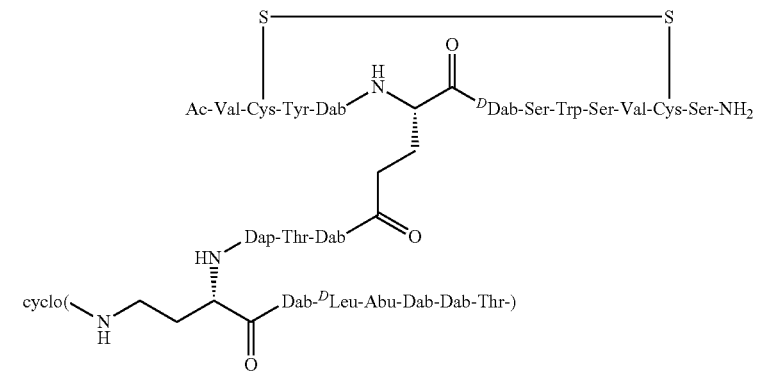 |
| Ex. 138[a)] | 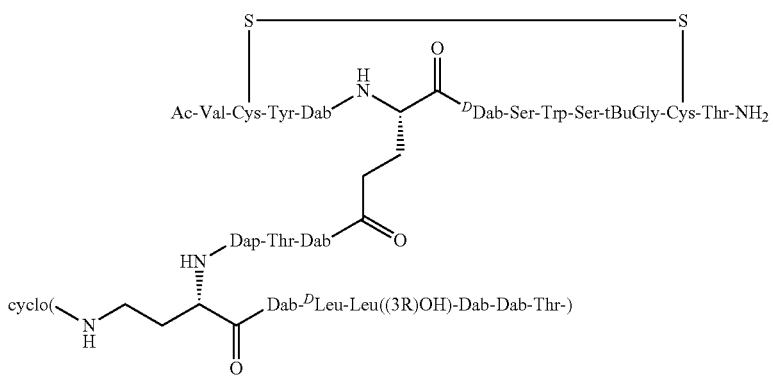 |

TABLE 1-continued

Examples (Ex.)
In the below-mentioned examples, amino acid residues are connected in either
direction from the α carbonyl (C=O) point of attachment to the α nitrogen (N) of the
next element, unless otherwise indicated. Other linkages, residues, connection of
residues and modifications are as specified.

| Ex. No. | Sequence |
|---|---|
| Ex. 139<sup>a)</sup> | 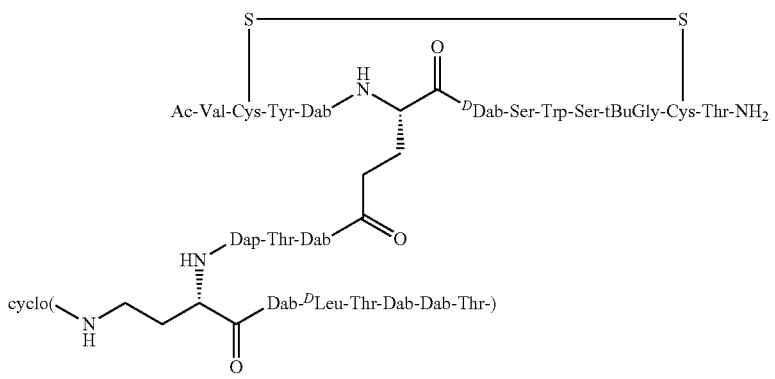 |
| Ex. 140<sup>a)</sup> | 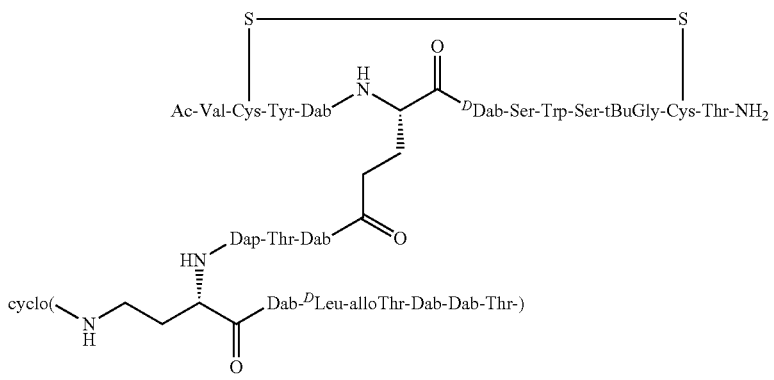 |
| Ex. 141<sup>a)</sup> | 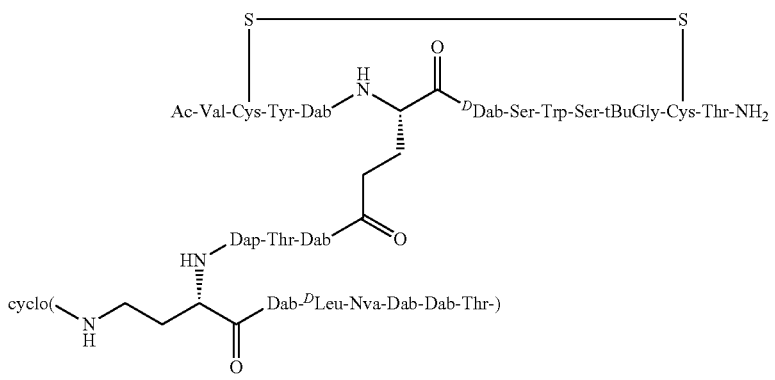 |

TABLE 1-continued
Examples (Ex.)
In the below-mentioned examples, amino acid residues are connected in either direction from the α carbonyl (C=O) point of attachment to the α nitrogen (N) of the next element, unless otherwise indicated. Other linkages, residues, connection of residues and modifications are as specified.
| Ex. No. | Sequence |
| --- | --- |
Ex. 142[a)]
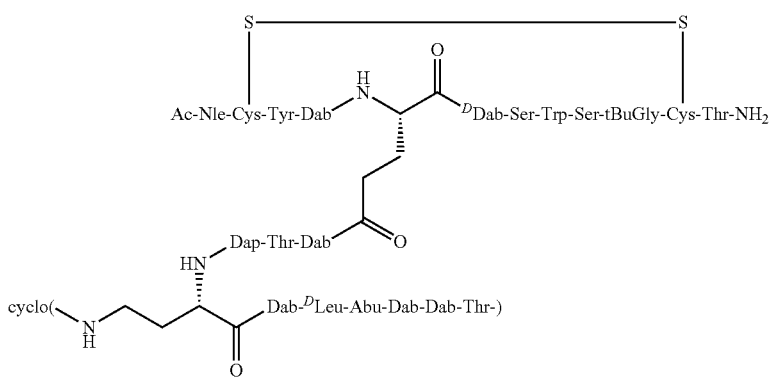
Ex. 143[a)]
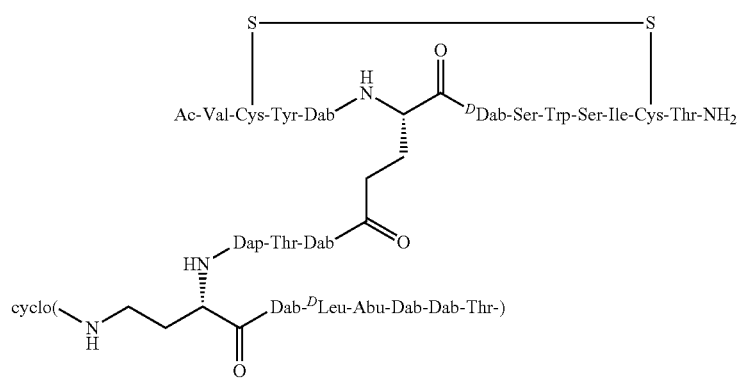
Ex. 144[a)]
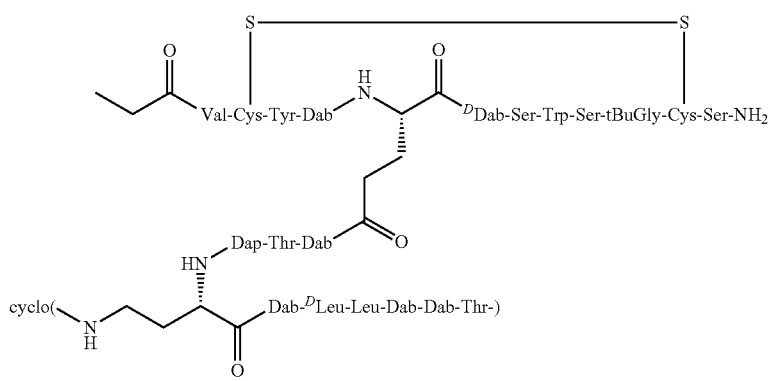

TABLE 1-continued
Examples (Ex.)
In the below-mentioned examples, amino acid residues are connected in either
direction from the α carbonyl (C=O) point of attachment to the α nitrogen (N) of the
next element, unless otherwise indicated. Other linkages, residues, connection of
residues and modifications are as specified.
| Ex. No. | Sequence |
|---|---|
| Ex. 145[a)] | 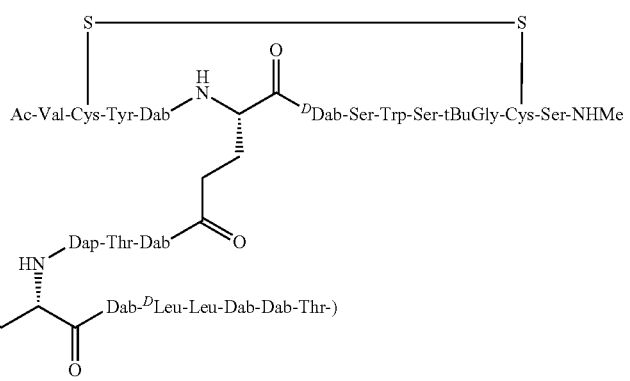 |
| Ex. 146[g)] | 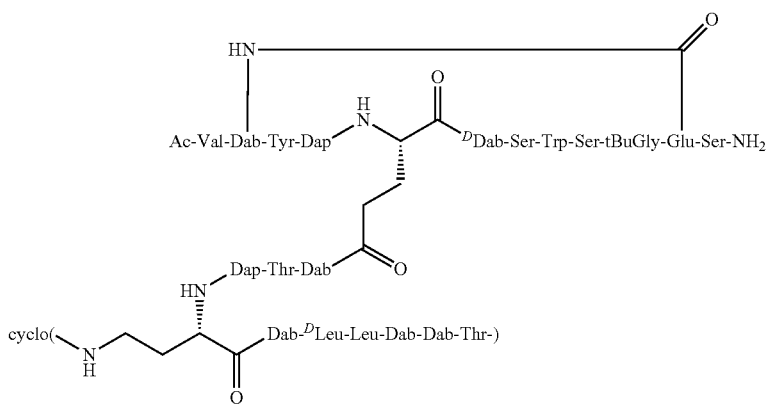 |
| Ex. 147[g)] | 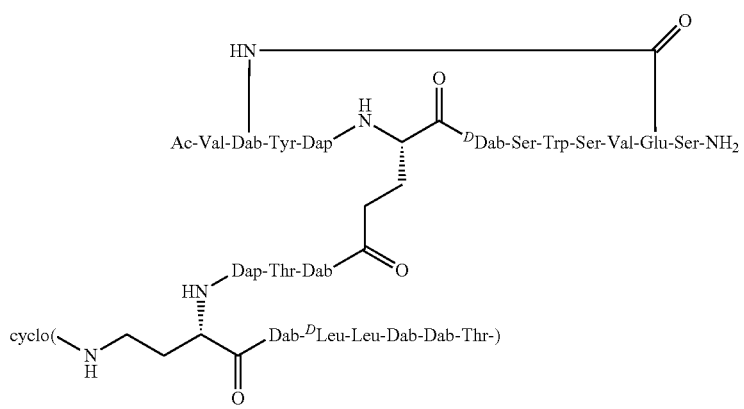 |

TABLE 1-continued
Examples (Ex.)
In the below-mentioned examples, amino acid residues are connected in either direction from the α carbonyl (C=O) point of attachment to the α nitrogen (N) of the next element, unless otherwise indicated. Other linkages, residues, connection of residues and modifications are as specified.
| Ex. No. | Sequence |
|---|---|
| Ex. 148[g)] | 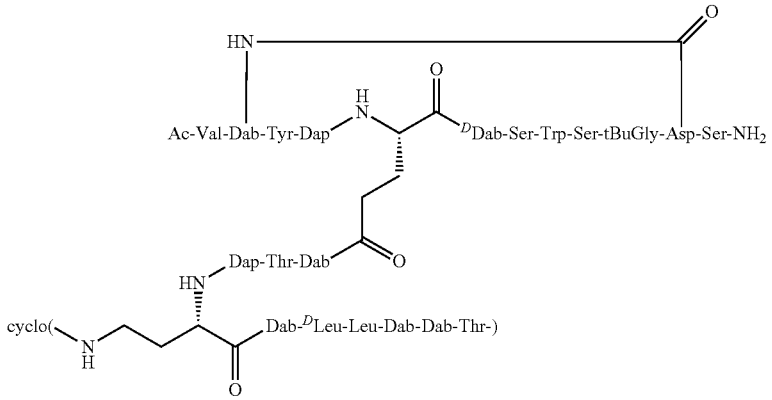 |
| Ex. 149[g)] | 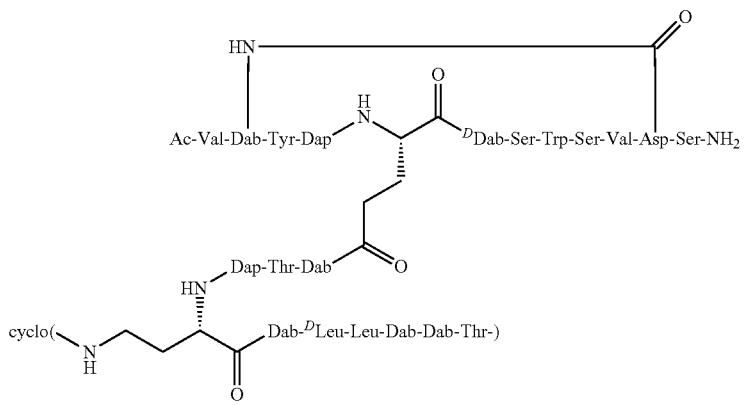 |
| Ex. 150[a)] | 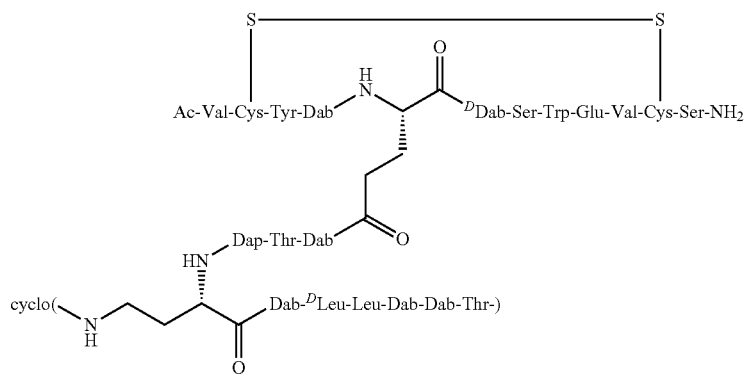 |

TABLE 1-continued
Examples (Ex.)
In the below-mentioned examples, amino acid residues are connected in either
direction from the α carbonyl (C=O) point of attachment to the α nitrogen (N) of the
next element, unless otherwise indicated. Other linkages, residues, connection of
residues and modifications are as specified.
| Ex. No. | Sequence |
|---|---|
| Ex. 151[a)] | 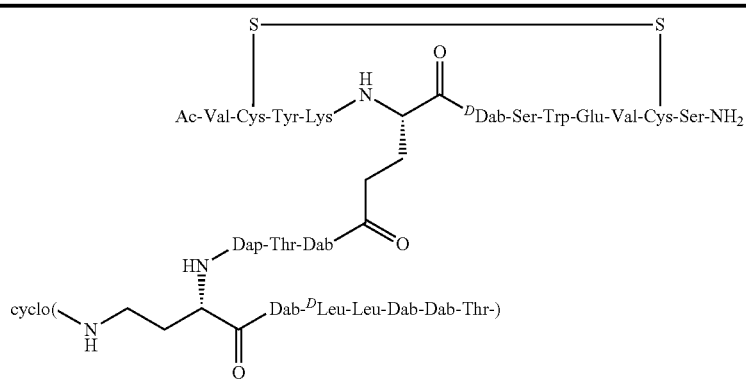 |
| Ex. 152[a)] | 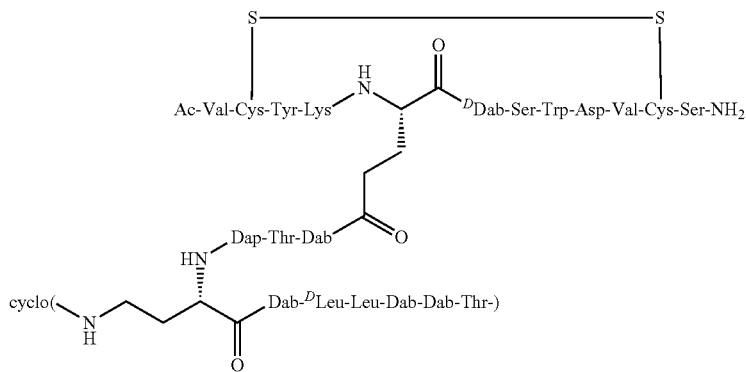 |
| Ex. 153[a)] | 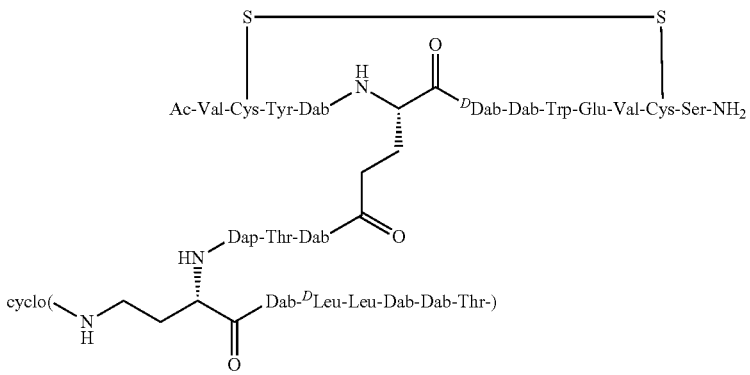 |
| Ex. 154[a)] | 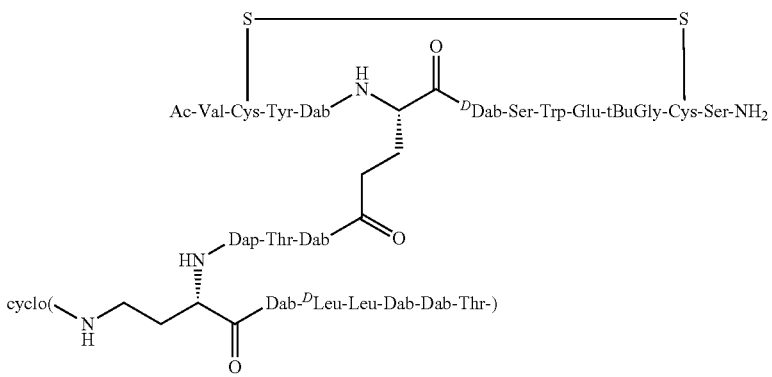 |

TABLE 1-continued
Examples (Ex.)
In the below-mentioned examples, amino acid residues are connected in either direction from the α carbonyl (C=O) point of attachment to the α nitrogen (N) of the next element, unless otherwise indicated. Other linkages, residues, connection of residues and modifications are as specified.
| Ex. No. | Sequence |
| --- | --- |
| Ex. 155[a)] | 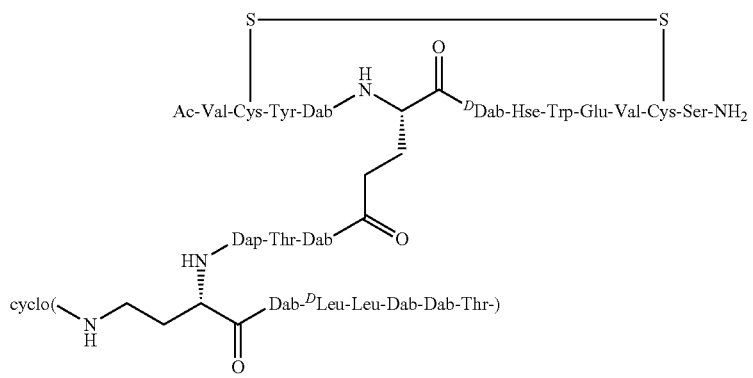 |
| Ex. 156[a)] | 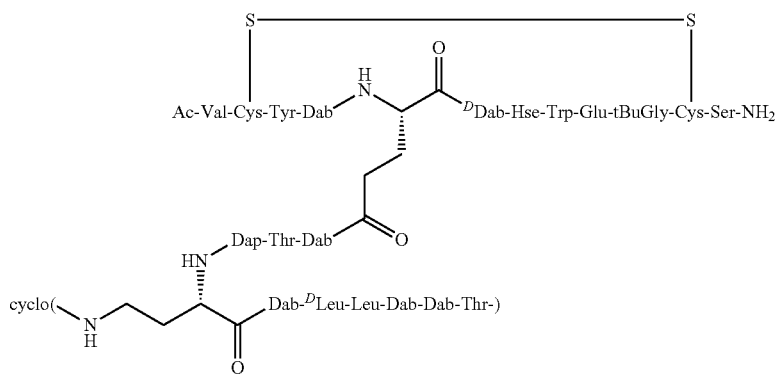 |
| Ex. 157[a) e)] | 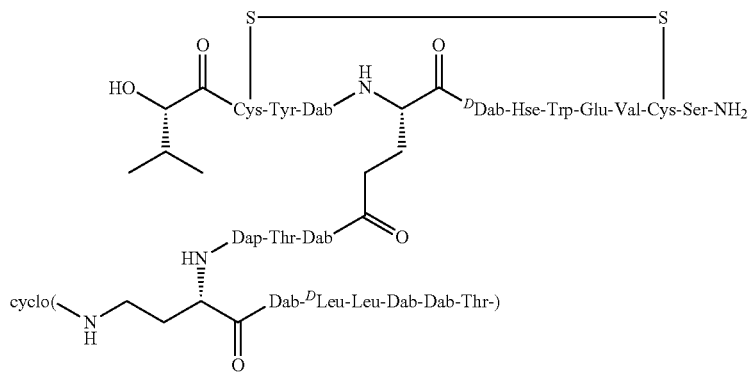 |

TABLE 1-continued
Examples (Ex.)
In the below-mentioned examples, amino acid residues are connected in either direction from the α carbonyl (C=O) point of attachment to the α nitrogen (N) of the next element, unless otherwise indicated. Other linkages, residues, connection of residues and modifications are as specified.
| Ex. No. | Sequence |
|---|---|
| Ex. 158[a)] | 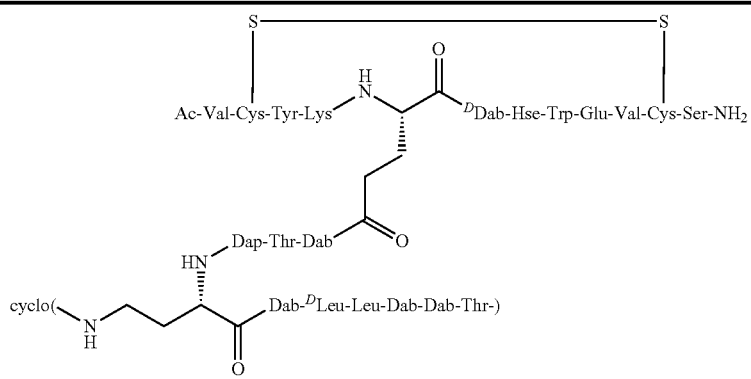 |
| Ex. 159[a)] | 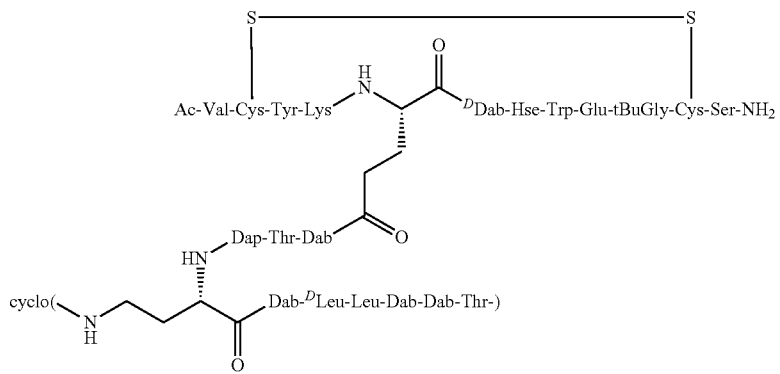 |
| Ex. 160[a) e)] | 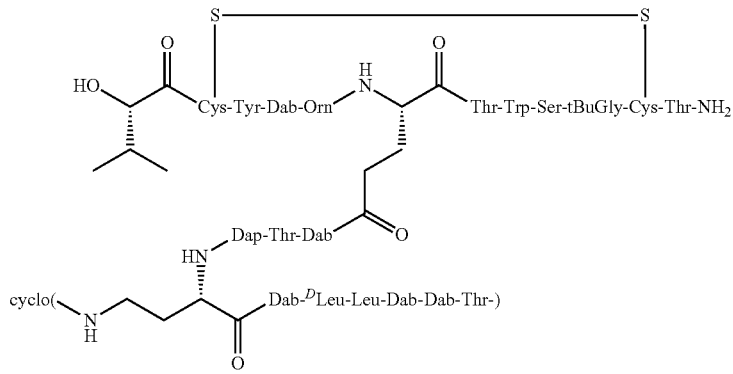 |
| Ex. 161[a) e)] | 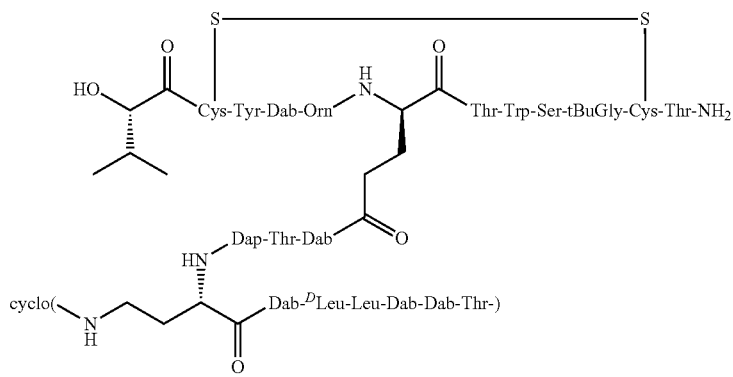 |

TABLE 1-continued
Examples (Ex.)
In the below-mentioned examples, amino acid residues are connected in either direction from the α carbonyl (C=O) point of attachment to the α nitrogen (N) of the next element, unless otherwise indicated. Other linkages, residues, connection of residues and modifications are as specified.
| Ex. No. | Sequence |
|---|---|
| Ex. 162[a) h)] |  |
| Ex. 163[a) h)] | 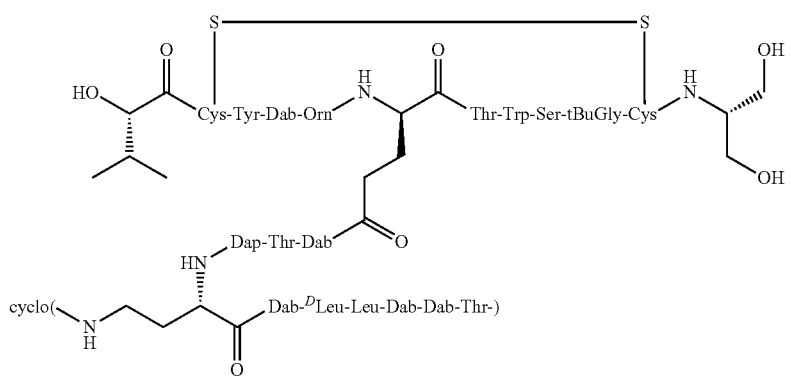 |
| Ex. 164[a) e)] | 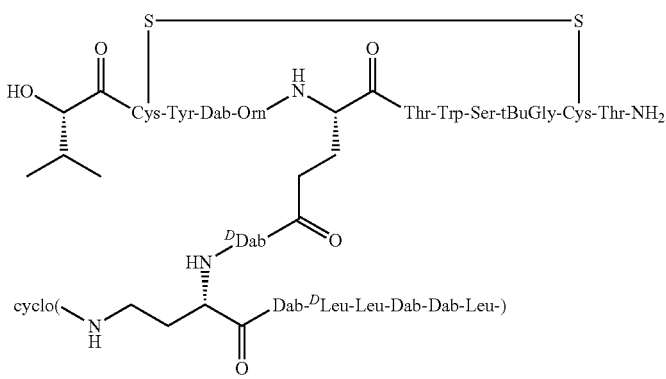 |

TABLE 1-continued
Examples (Ex.)
In the below-mentioned examples, amino acid residues are connected in either
direction from the α carbonyl (C=O) point of attachment to the α nitrogen (N) of the
next element, unless otherwise indicated. Other linkages, residues, connection of
residues and modifications are as specified.
| Ex. No. | Sequence |
|---|---|
| Ex. 165[a) e)] | 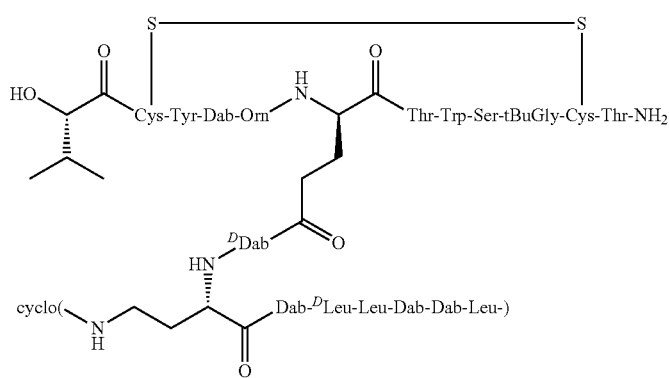 |
| Ex. 166[a) e)] | 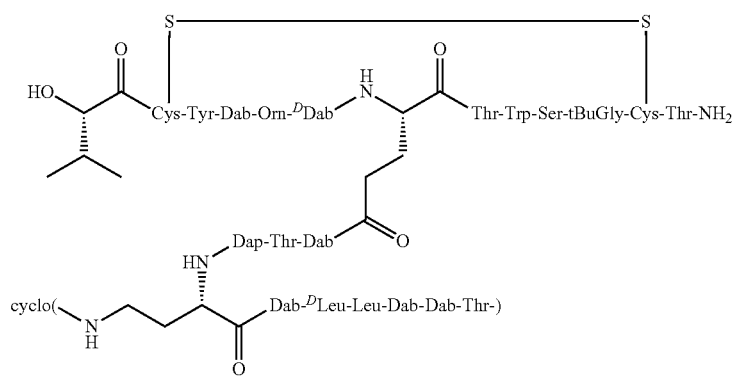 |
| Ex. 167[a) e)] | 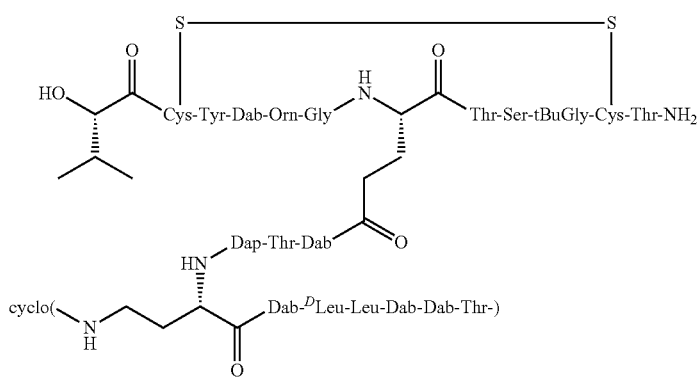 |

TABLE 1-continued
Examples (Ex.)
In the below-mentioned examples, amino acid residues are connected in either direction from the α carbonyl (C=O) point of attachment to the α nitrogen (N) of the next element, unless otherwise indicated. Other linkages, residues, connection of residues and modifications are as specified.
| Ex. No. | Sequence |
|---|---|
| Ex. 168[a) e)] | 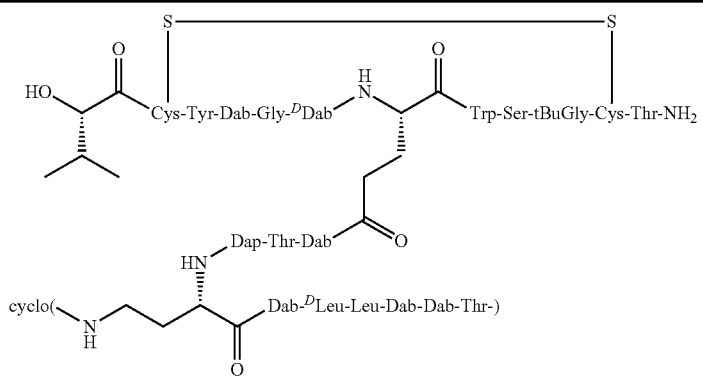 |
| Ex. 169[a) e)] | 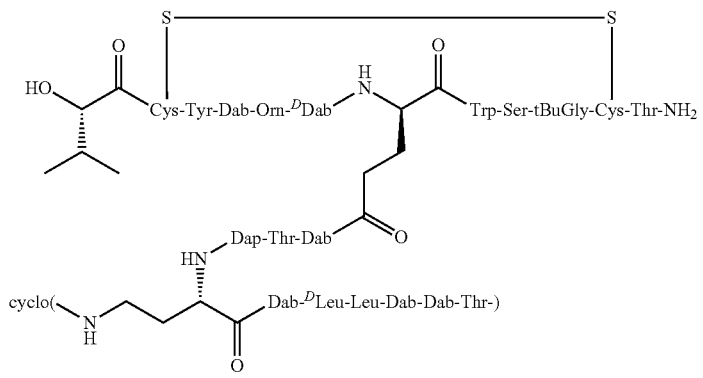 |
| Ex. 170[a) e)] | 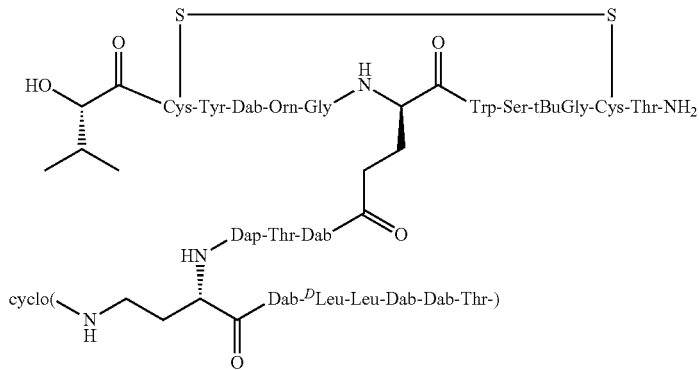 |
| Ex. 171[a) e)] | 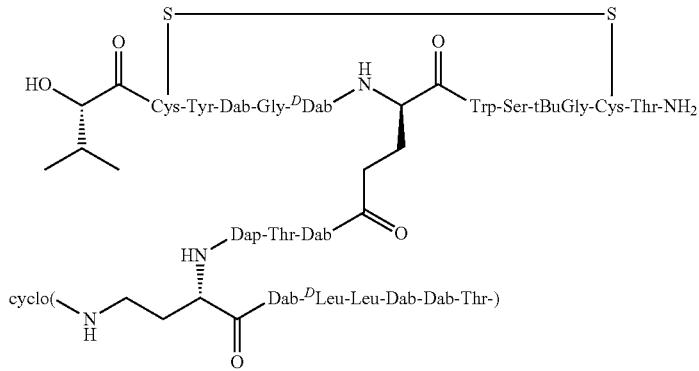 |

TABLE 1-continued
Examples (Ex.)
In the below-mentioned examples, amino acid residues are connected in either
direction from the α carbonyl (C=O) point of attachment to the α nitrogen (N) of the
next element, unless otherwise indicated. Other linkages, residues, connection of
residues and modifications are as specified.
| Ex. No. | Sequence |
|---|---|
| Ex. 172[a) h)] | 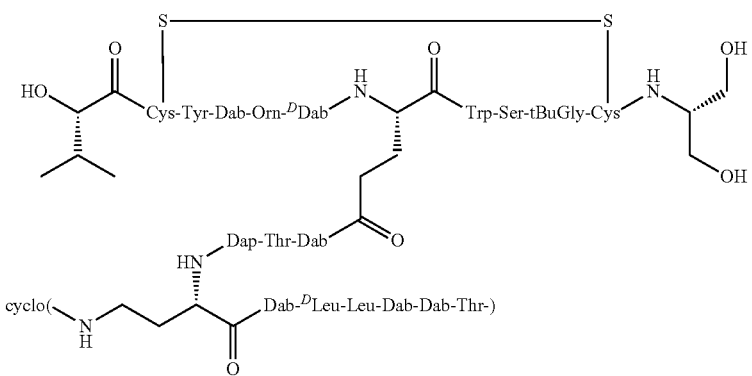 |
| Ex. 173[a) h)] | 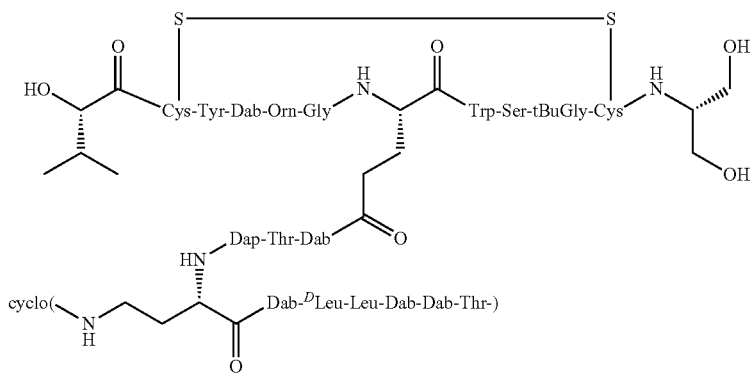 |
| Ex. 174[a) h)] | 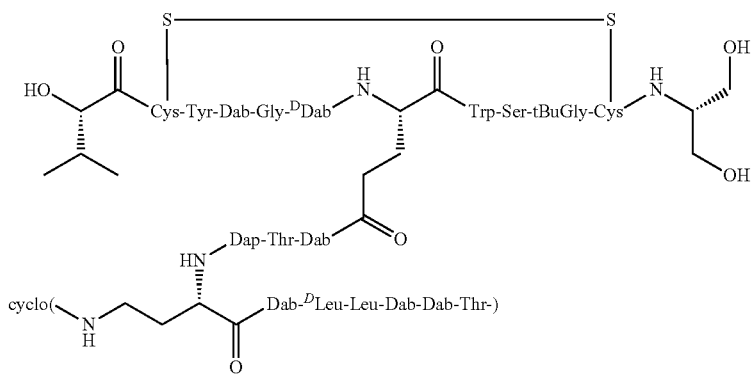 |

TABLE 1-continued
Examples (Ex.)
In the below-mentioned examples, amino acid residues are connected in either direction from the α carbonyl (C=O) point of attachment to the α nitrogen (N) of the next element, unless otherwise indicated. Other linkages, residues, connection of residues and modifications are as specified.
| Ex. No. | Sequence |
|---|---|
| Ex. 175[a)] | 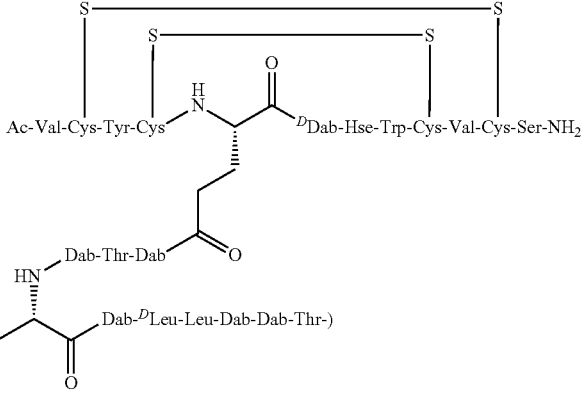 |
| Ex. 176[a)] | 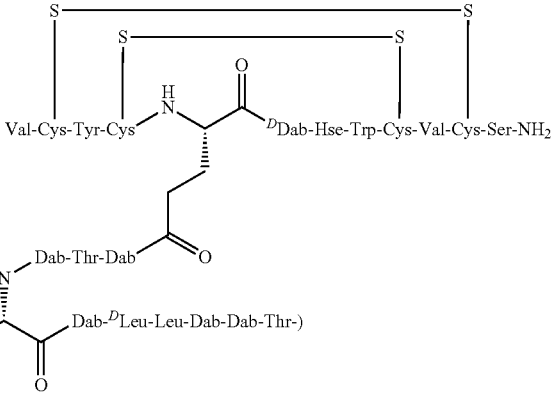 |
| Ex. 177[a)] | 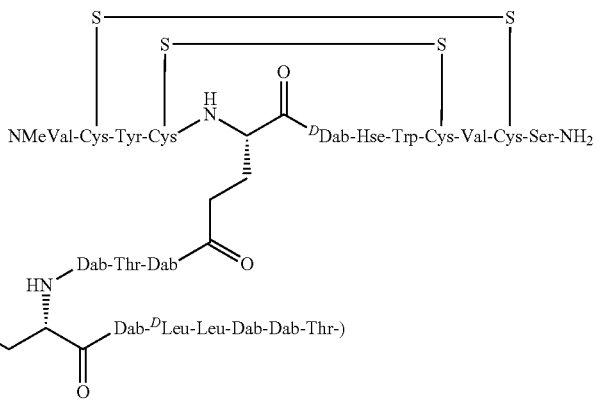 |

TABLE 1-continued
Examples (Ex.)
In the below-mentioned examples, amino acid residues are connected in either
direction from the α carbonyl (C=O) point of attachment to the α nitrogen (N) of the
next element, unless otherwise indicated. Other linkages, residues, connection of
residues and modifications are as specified.
| Ex. No. | Sequence |
|---|---|
| Ex. 178[a)] | 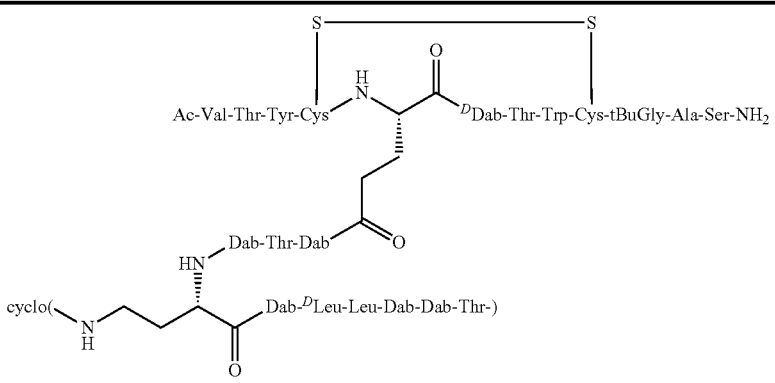 |
| Ex. 179[a)] | 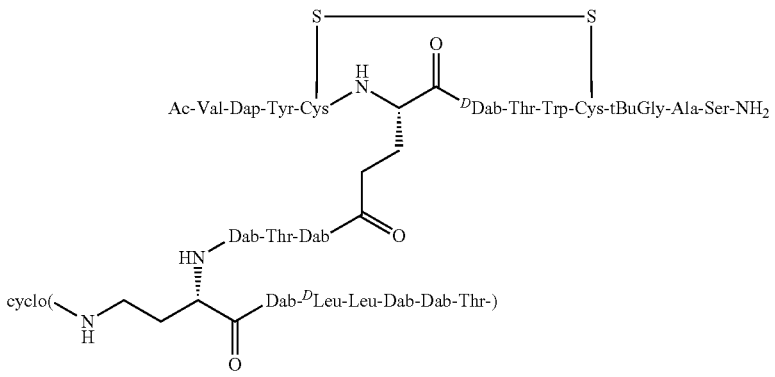 |
| Ex. 180[a)] | 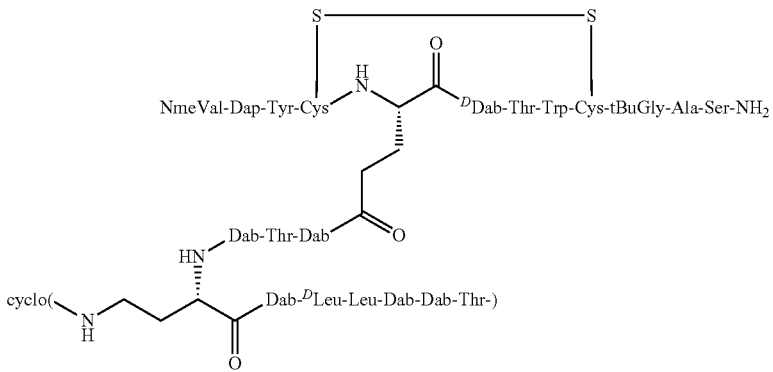 |
| Ex. 181[a)] | 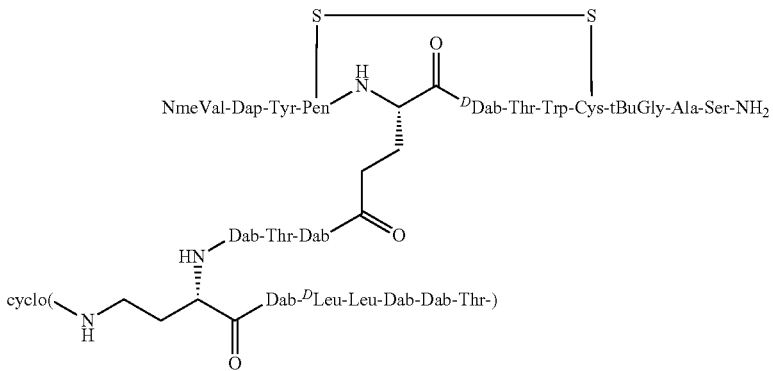 |

TABLE 1-continued
Examples (Ex.)
In the below-mentioned examples, amino acid residues are connected in either
direction from the α carbonyl (C=O) point of attachment to the α nitrogen (N) of the
next element, unless otherwise indicated. Other linkages, residues, connection of
residues and modifications are as specified.
| Ex. No. | Sequence |
| --- | --- |
| Ex. 182[a)] | 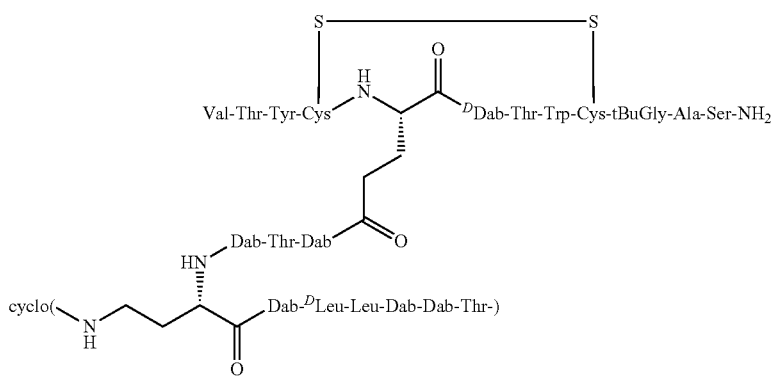 |
| Ex. 183[a)] | 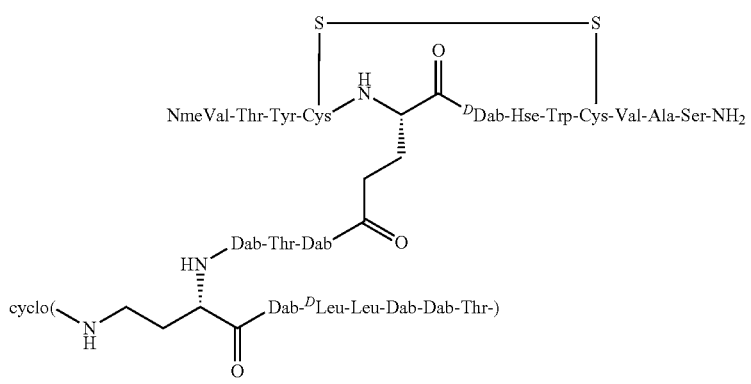 |
| Ex. 184[a)] | 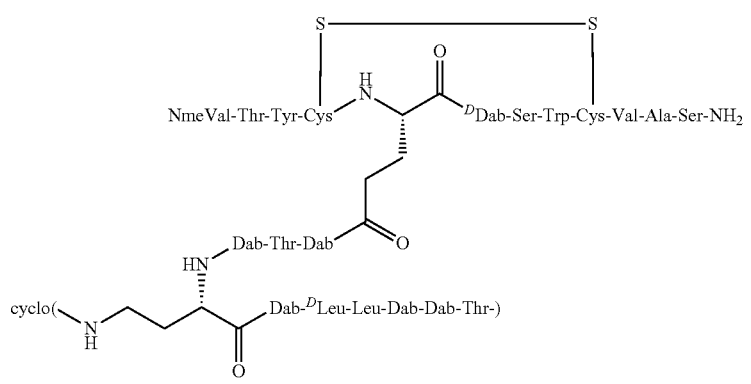 |

TABLE 1-continued

Examples (Ex.)
In the below-mentioned examples, amino acid residues are connected in either
direction from the α carbonyl (C=O) point of attachment to the α nitrogen (N) of the
next element, unless otherwise indicated. Other linkages, residues, connection of
residues and modifications are as specified.

| Ex. No. | Sequence |
|---|---|
| Ex. 185<sup>a)</sup> | 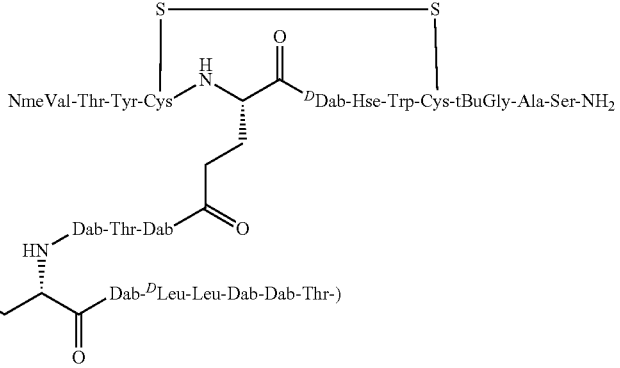 |
| Ex. 186<sup>a)</sup> | 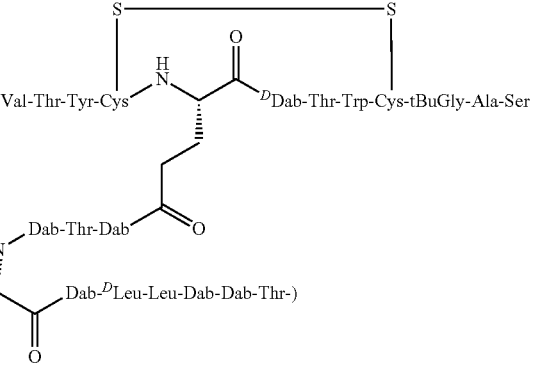 |
| Ex. 187<sup>g)</sup> | 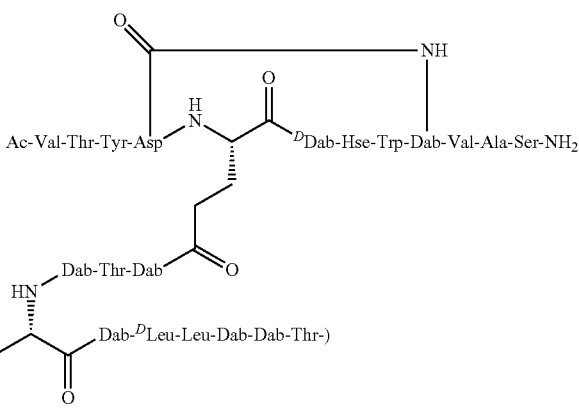 |

| Ex. No. | Sequence |
|---|---|
| Ex. 188[a) h)] | 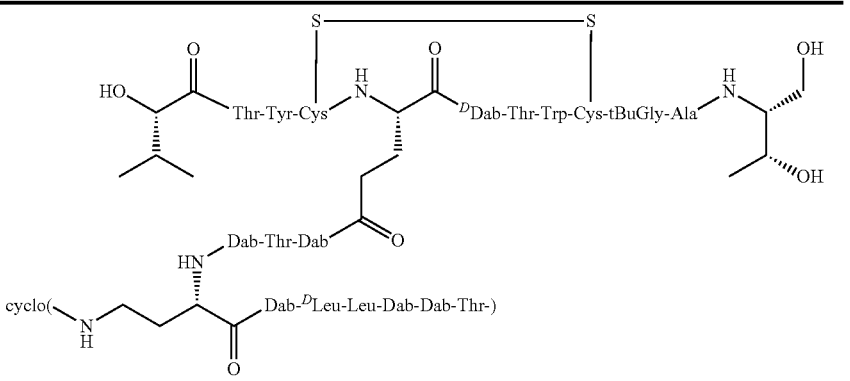 |
| Ex. 189[a) h)] | 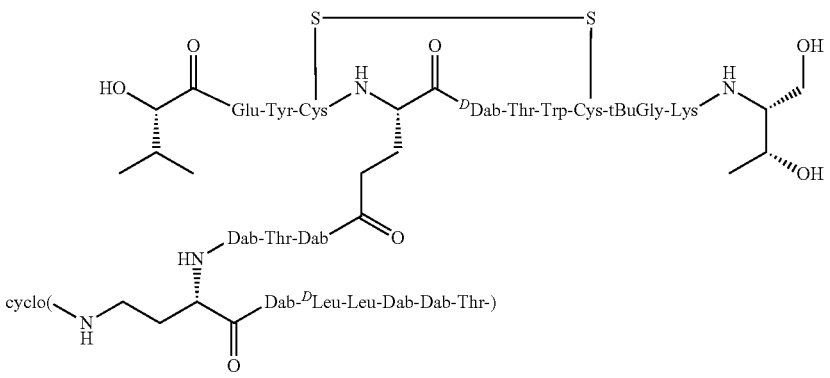 |
| Ex. 190[a) h)] | 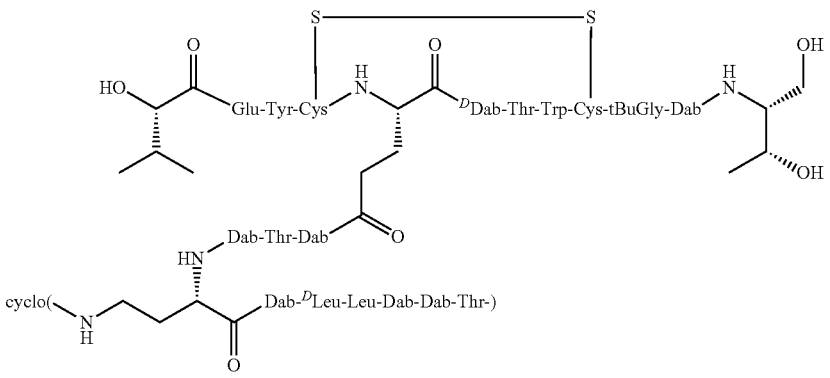 |
| Ex. 191[a) h)] | 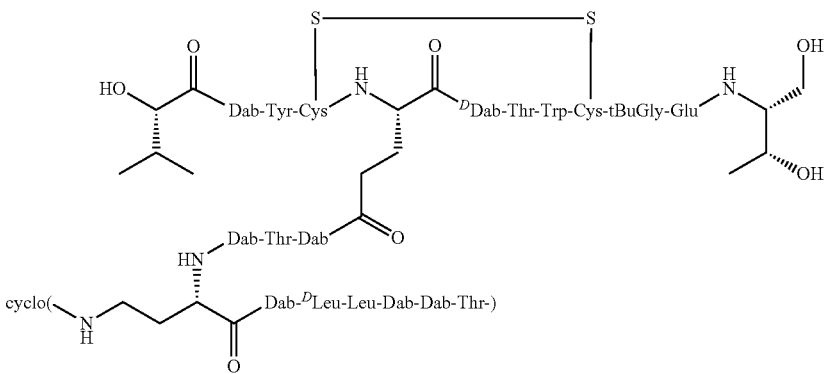 |

TABLE 1-continued

Examples (Ex.)
In the below-mentioned examples, amino acid residues are connected in either
direction from the α carbonyl (C=O) point of attachment to the α nitrogen (N) of the
next element, unless otherwise indicated. Other linkages, residues, connection of
residues and modifications are as specified.

| Ex. No. | Sequence |
|---|---|
| Ex. 192[a) h)] | HO-[Val]-Asp-Tyr-Cys(S-S)-[DGlu]-N-DDab-Thr-Trp-Cys-tBuGly-Lys-[Thr-ol with OH]; side chain: Dab-Thr-Dab-HN-cyclo(-NH-[Dab]-Dab-DLeu-Leu-Dab-Dab-Thr-) |
| Ex. 193[a) h)] | HO-[Val]-Thy-Tyr-Cys(S-S)-[DGlu]-N-DDab-Hse-Trp-Cys-tBuGly-Ala-[Thr-ol with OH]; side chain: Dab-Thr-Dab-HN-cyclo(-NH-[Dab]-Dab-DLeu-Leu-Dab-Dab-Thr-) |
| Ex. 194[a) h)] | HO-[Val]-Thr-Tyr-Pen(S-S)-[DGlu]-N-DDab-Hse-Trp-Cys-tBuGly-Ala-[Thr-ol with OH]; side chain: Dab-Thr-Dab-HN-cyclo(-NH-[Dab]-Dab-DLeu-Leu-Dab-Dab-Thr-) |

TABLE 1-continued
Examples (Ex.)
In the below-mentioned examples, amino acid residues are connected in either
direction from the α carbonyl (C=O) point of attachment to the α nitrogen (N) of the
next element, unless otherwise indicated. Other linkages, residues, connection of
residues and modifications are as specified.
| Ex. No. | Sequence |
|---|---|
| Ex. 195[a) h)] | 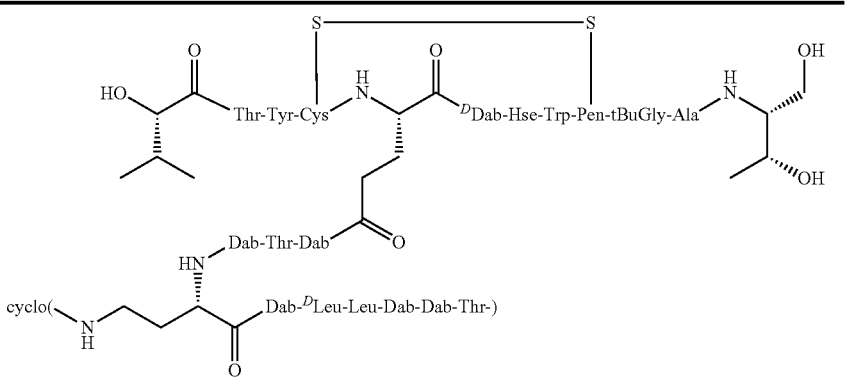 |
| Ex. 196[a) b)] | 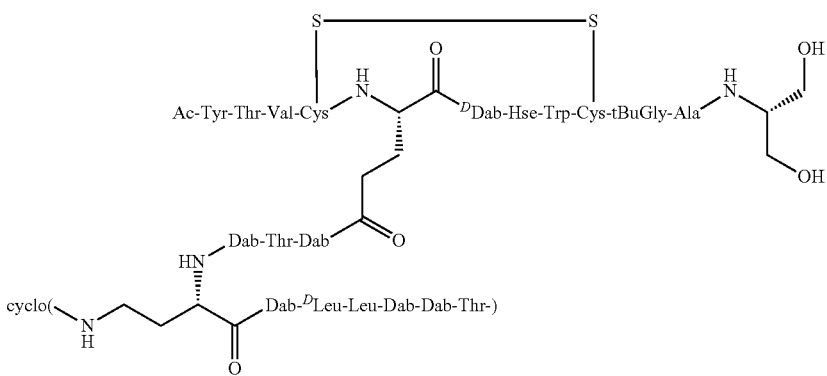 |
| Ex. 197[a) h)] | 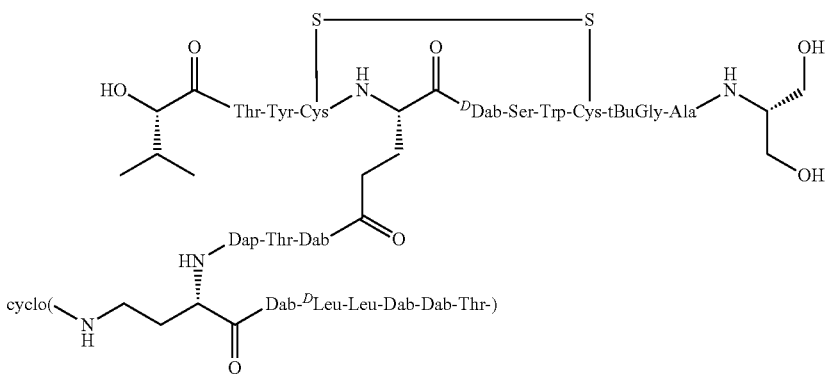 |
| Ex. 198[a) h)] | 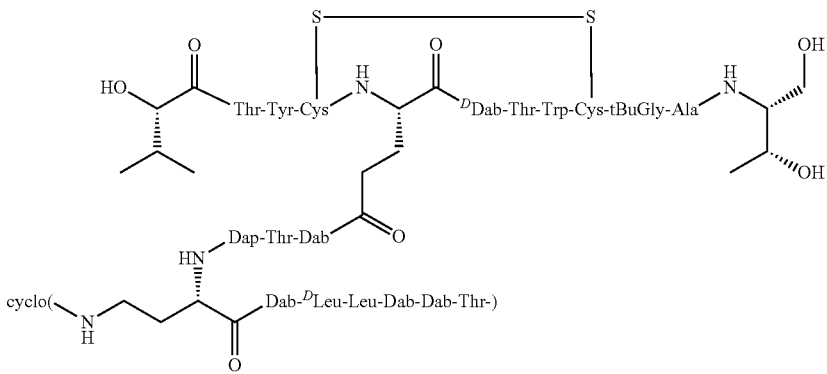 |

TABLE 1-continued

Examples (Ex.)
In the below-mentioned examples, amino acid residues are connected in either direction from the α carbonyl (C=O) point of attachment to the α nitrogen (N) of the next element, unless otherwise indicated. Other linkages, residues, connection of residues and modifications are as specified.

| Ex. No. | Sequence |
| --- | --- |
| Ex. 199[a) h)] | cyclo(-NH-CH(CH(CH3)2)-C(=O)-Thr-Tyr-Cys(S-S)-NH-CH(CH2CH2-C(=O)-Dab-Thr-Dap-NH)-C(=O)-DDab-Thr-Trp-Cys(S-S)-tBuGly-Ala-NH-CH(CH(OH)CH3)-CH2OH ; cyclo(-NH-CH2CH2-CH(NH-)-C(=O)-Dab-DLeu-Leu-Dab-Dab-Thr-) |
| Ex. 200[a) h)] | (same as Ex. 199 but with Dab-Thr-Dab in place of Dap-Thr-Dab in the side chain) |
| Ex. 201[a) h)] | (same as Ex. 199 but with Ala-Tyr-Cys and DDab-Dab-Trp-Cys-tBuGly-Ala) |

TABLE 1-continued
Examples (Ex.)
In the below-mentioned examples, amino acid residues are connected in either
direction from the α carbonyl (C=O) point of attachment to the α nitrogen (N) of the
next element, unless otherwise indicated. Other linkages, residues, connection of
residues and modifications are as specified.
| Ex. No. | Sequence |
|---|---|
| Ex. 202[a) h)] | 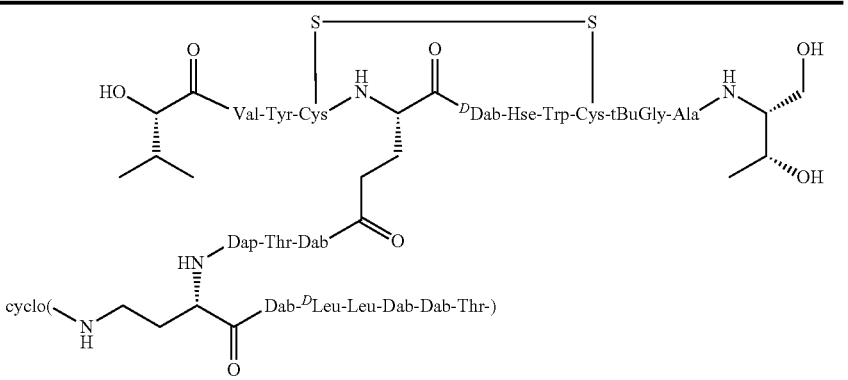 |
| Ex. 203[a) h)] | 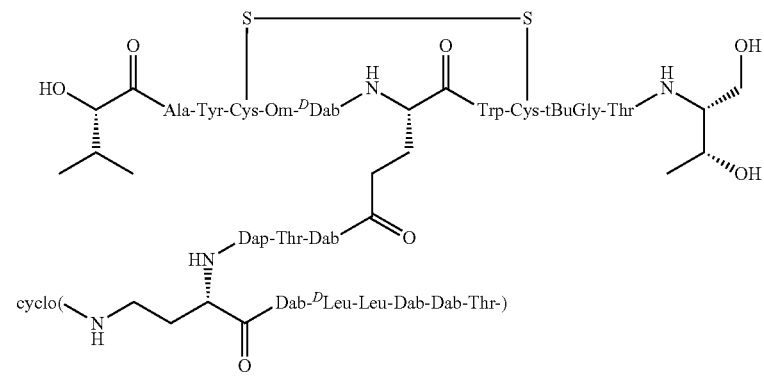 |
| Ex. 204[a) h)] | 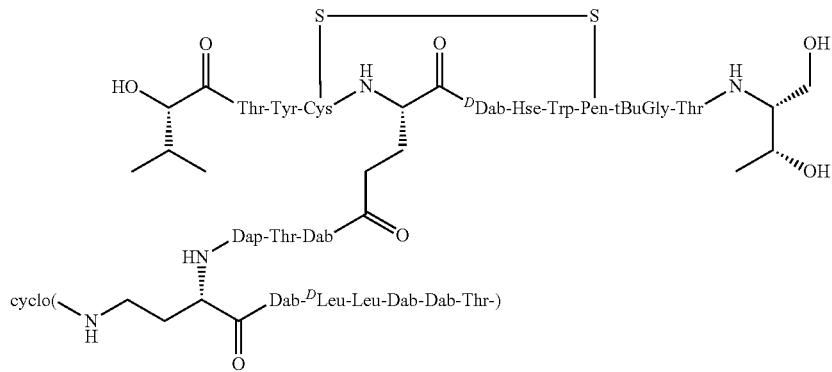 |
| Ex. 205[a)] | 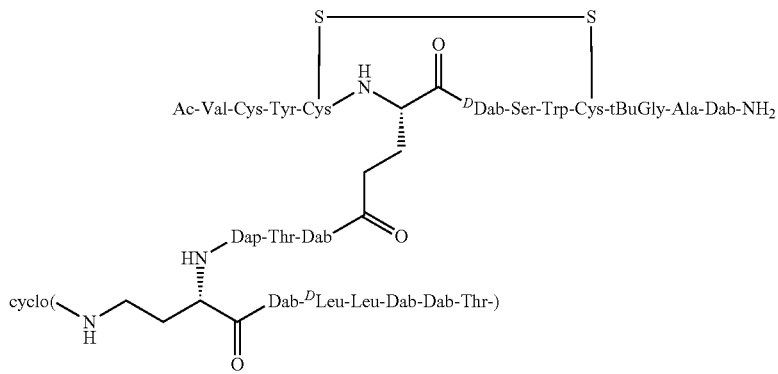 |

TABLE 1-continued
Examples (Ex.)
In the below-mentioned examples, amino acid residues are connected in either
direction from the α carbonyl (C=O) point of attachment to the α nitrogen (N) of the
next element, unless otherwise indicated. Other linkages, residues, connection of
residues and modifications are as specified.
| Ex. No. | Sequence |
| --- | --- |
Ex. 206[a)]
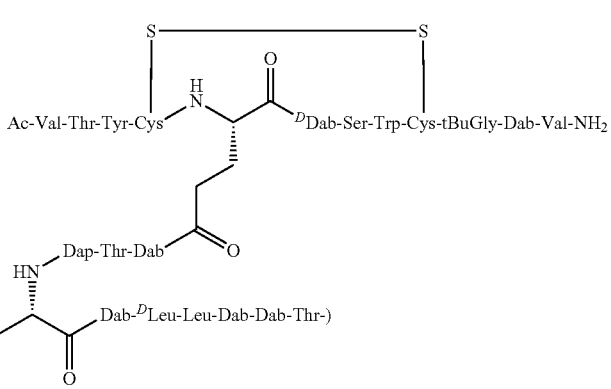
Ex. 207[a)]
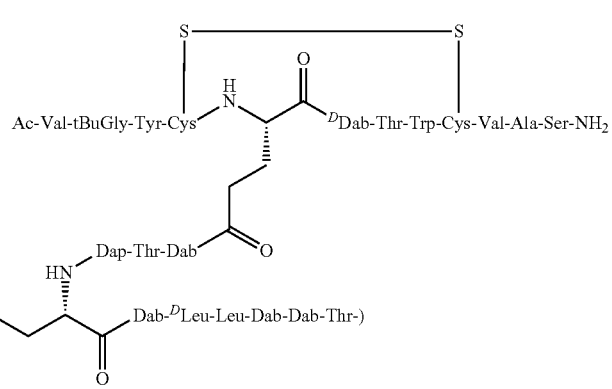
Ex. 208[a)]
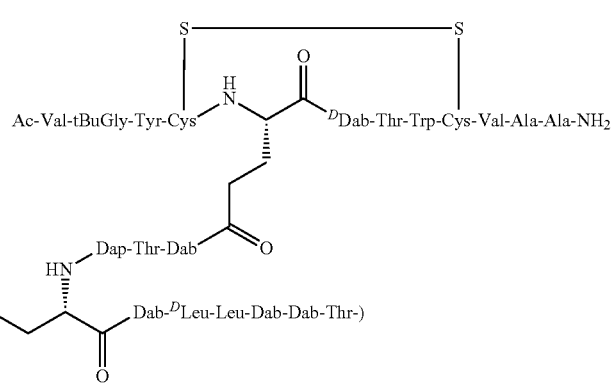

TABLE 1-continued
Examples (Ex.)
In the below-mentioned examples, amino acid residues are connected in either
direction from the α carbonyl (C=O) point of attachment to the α nitrogen (N) of the
next element, unless otherwise indicated. Other linkages, residues, connection of
residues and modifications are as specified.
| Ex. No. | Sequence |
|---|---|
| Ex. 209[a) h)] | 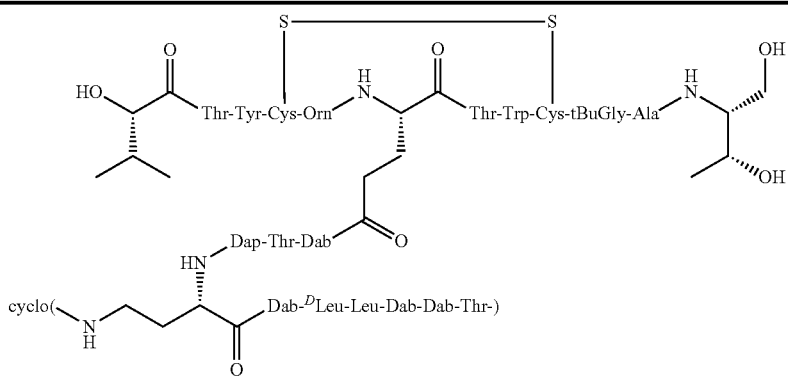 |
| Ex. 210[a) h)] | 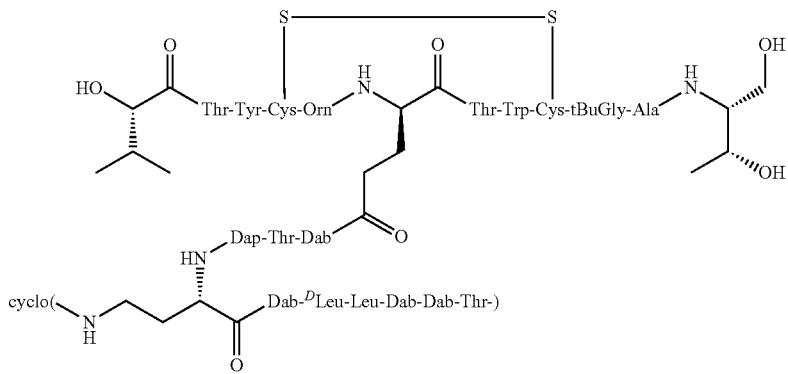 |
| Ex. 211[a) h)] | 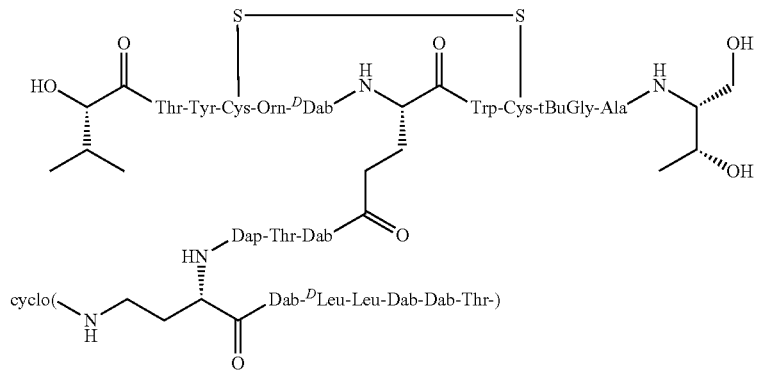 |
| Ex. 212[a) h)] | 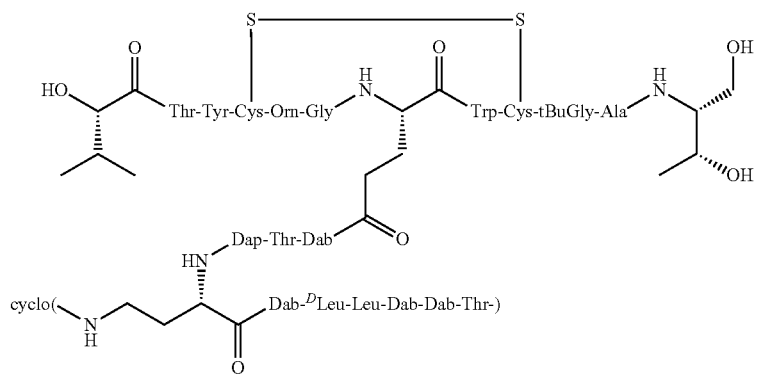 |

TABLE 1-continued
Examples (Ex.)
In the below-mentioned examples, amino acid residues are connected in either
direction from the α carbonyl (C=O) point of attachment to the α nitrogen (N) of the
next element, unless otherwise indicated. Other linkages, residues, connection of
residues and modifications are as specified.
| Ex. No. | Sequence |
| --- | --- |
Ex. 213[a) h)]
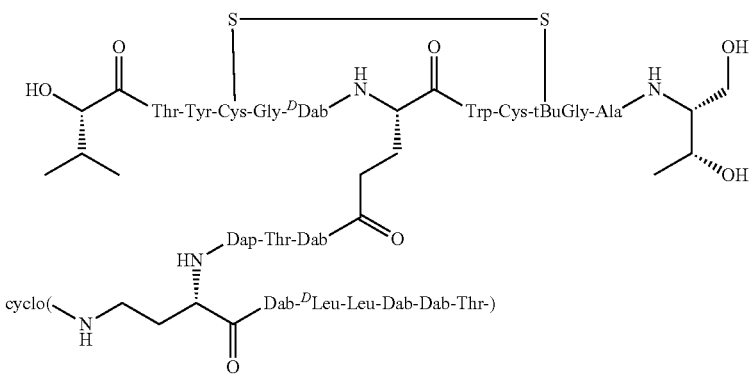
Ex. 214[a) h)]
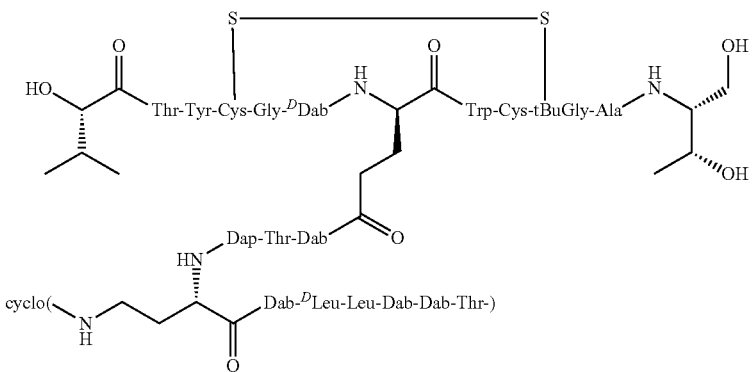
Ex. 215[a)]
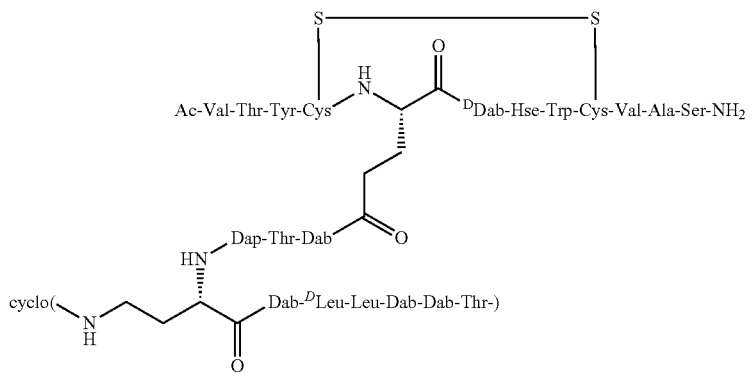

TABLE 1-continued
Examples (Ex.)
In the below-mentioned examples, amino acid residues are connected in either direction from the α carbonyl (C=O) point of attachment to the α nitrogen (N) of the next element, unless otherwise indicated. Other linkages, residues, connection of residues and modifications are as specified.
| Ex. No. | Sequence |
|---|---|
| Ex. 216[a) h)] | 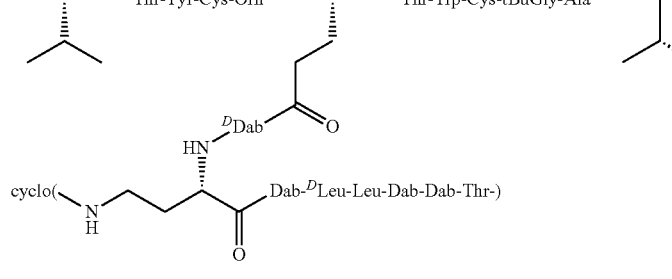 |
| Ex. 217[a) h)] | 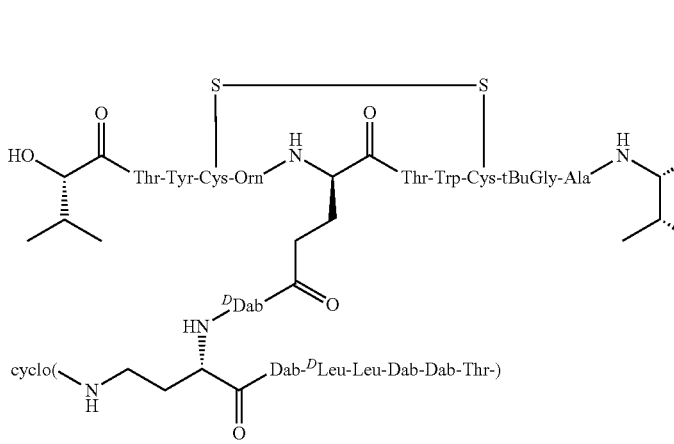 |
| Ex. 218[a)] | 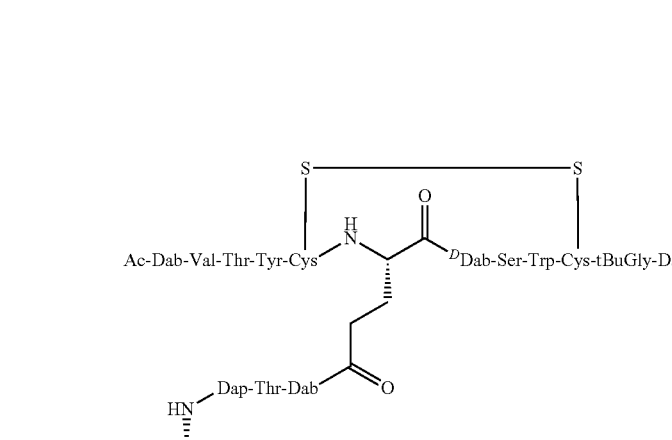 |

TABLE 1-continued
Examples (Ex.)
In the below-mentioned examples, amino acid residues are connected in either
direction from the α carbonyl (C=O) point of attachment to the α nitrogen (N) of the
next element, unless otherwise indicated. Other linkages, residues, connection of
residues and modifications are as specified.
| Ex. No. | Sequence |
| --- | --- |
| Ex. 219[a)] | 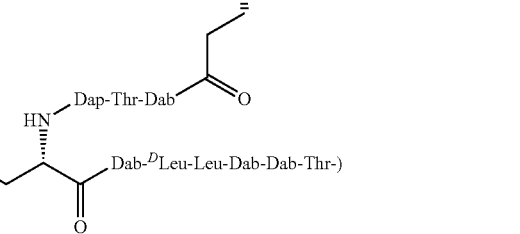 |
| Ex. 220[a)] | 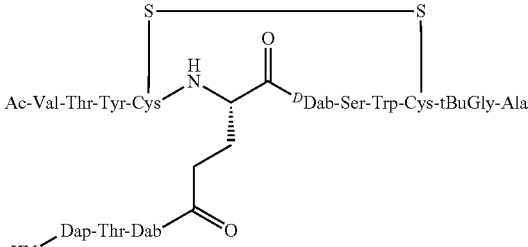 |
| Ex. 221[a)] | 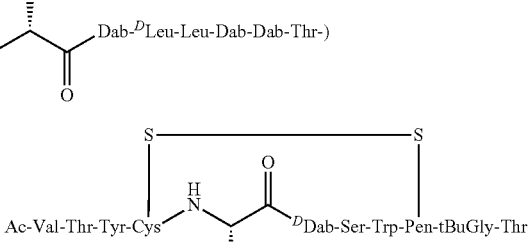 |
| Ex. 222[a)] | 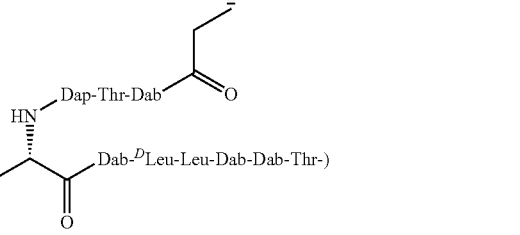 |

TABLE 1-continued
Examples (Ex.)
In the below-mentioned examples, amino acid residues are connected in either
direction from the α carbonyl (C=O) point of attachment to the α nitrogen (N) of the
next element, unless otherwise indicated. Other linkages, residues, connection of
residues and modifications are as specified.
| Ex. No. | Sequence |
| --- | --- |
Ex. 223[a)]
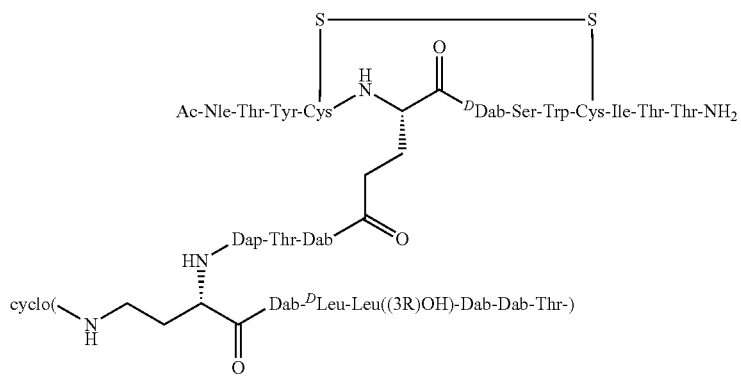
Ex. 224[a)]
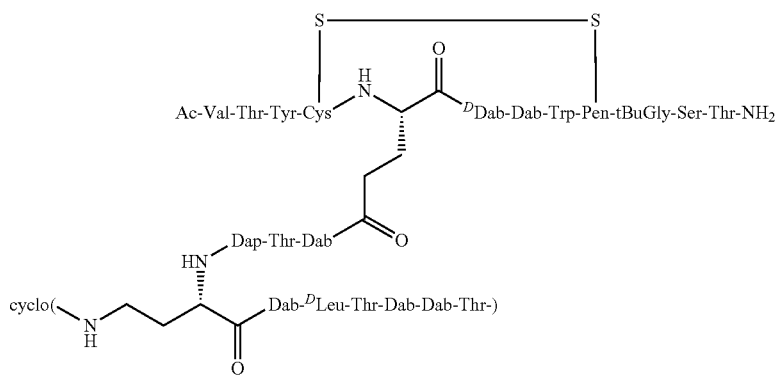
Ex. 225[a)]
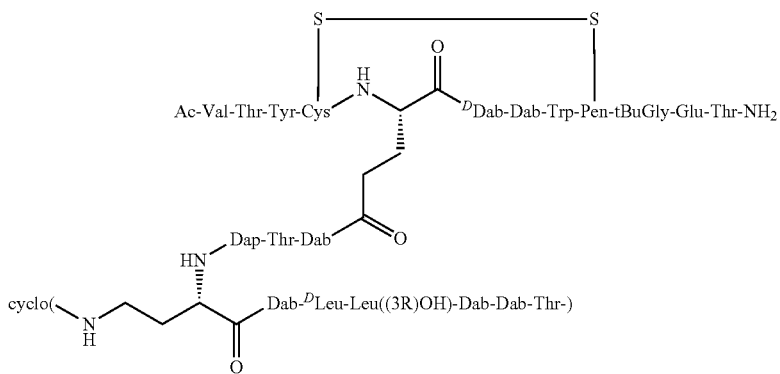

TABLE 1-continued
Examples (Ex.)
In the below-mentioned examples, amino acid residues are connected in either
direction from the α carbonyl (C=O) point of attachment to the α nitrogen (N) of the
next element, unless otherwise indicated. Other linkages, residues, connection of
residues and modifications are as specified.
| Ex. No. | Sequence |
|---|---|
| Ex. 226[a)] | 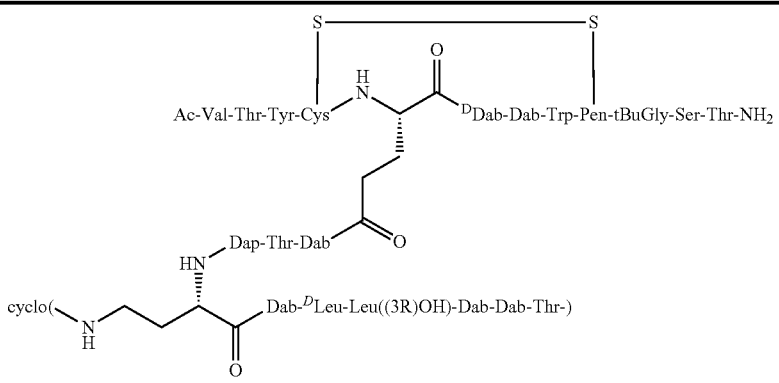 |
| Ex. 227[a)] | 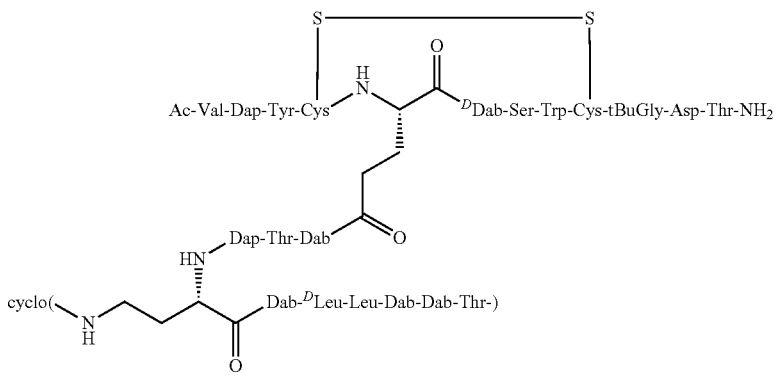 |
| Ex. 228[a)] | 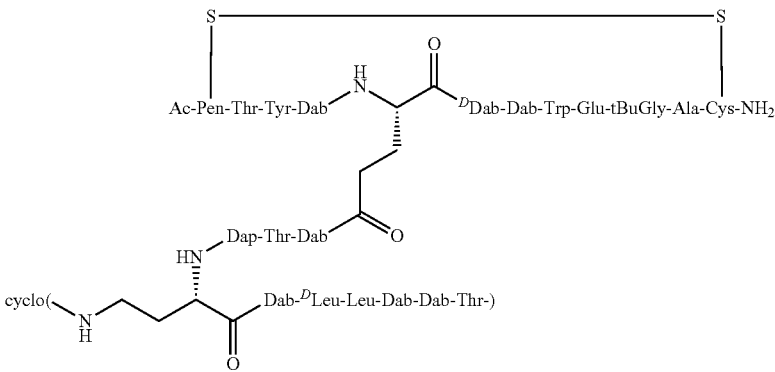 |
| Ex. 229 | 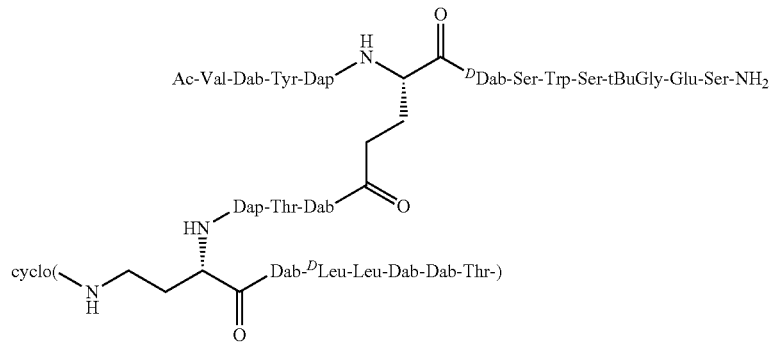 |

TABLE 1-continued
Examples (Ex.)
In the below-mentioned examples, amino acid residues are connected in either
direction from the α carbonyl (C=O) point of attachment to the α nitrogen (N) of the
next element, unless otherwise indicated. Other linkages, residues, connection of
residues and modifications are as specified.
| Ex. No. | Sequence |
| --- | --- |
| Ex. 230 | 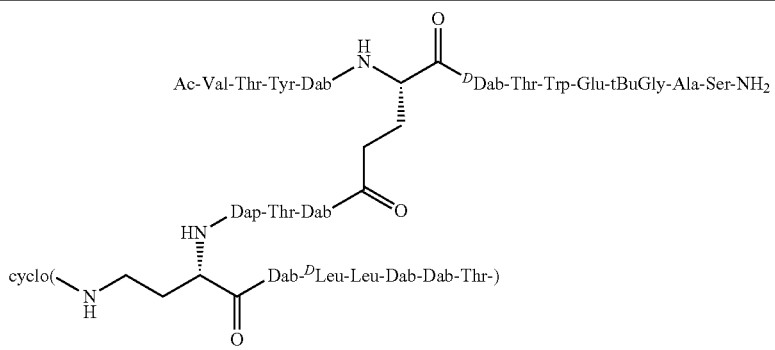 |
| Ex. 232[a) b)] | 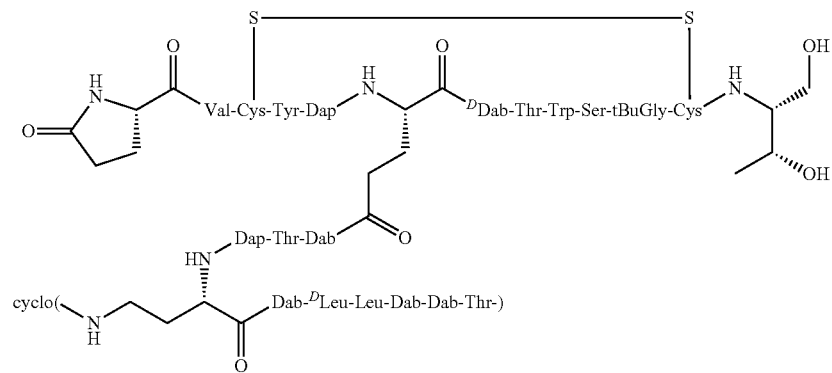 |
| Ex. 233[a) b)] | 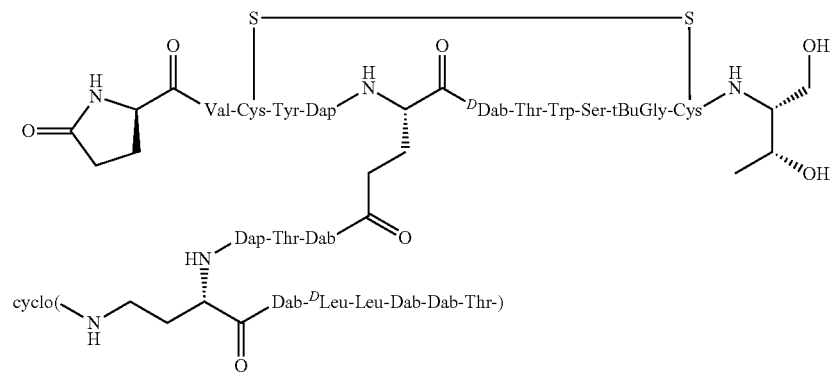 |
| Ex. 234[a)] | 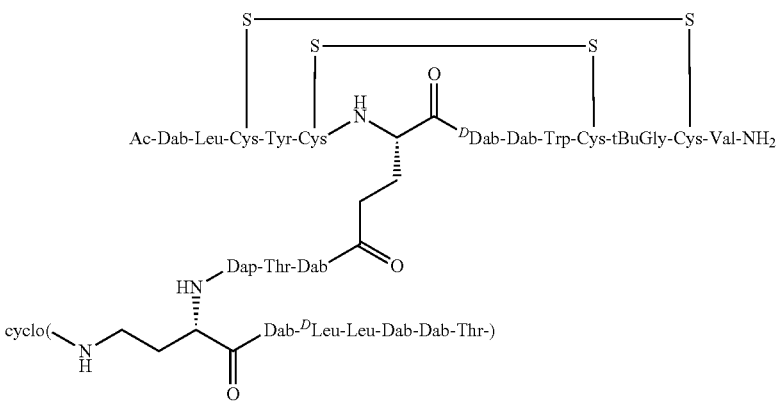 |

TABLE 1-continued
Examples (Ex.)
In the below-mentioned examples, amino acid residues are connected in either
direction from the α carbonyl (C=O) point of attachment to the α nitrogen (N) of the
next element, unless otherwise indicated. Other linkages, residues, connection of
residues and modifications are as specified.
| Ex. No. | Sequence |
| --- | --- |
Ex. 235[a)]
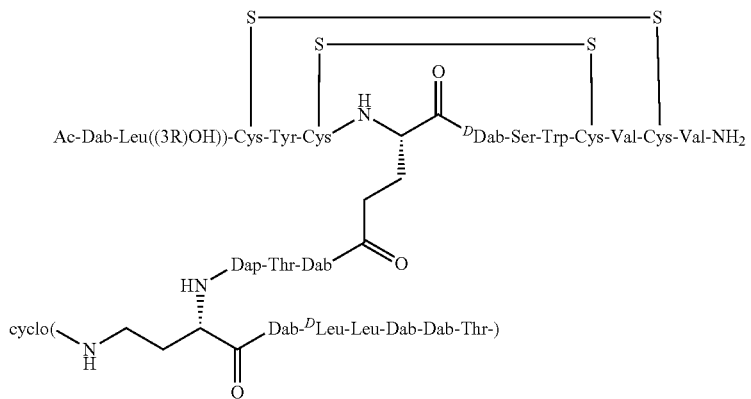
Ex. 236[a) h)]
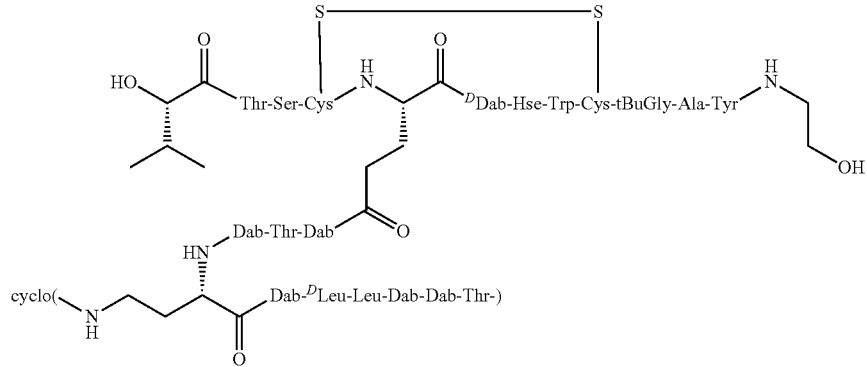
Ex. 237[a)]
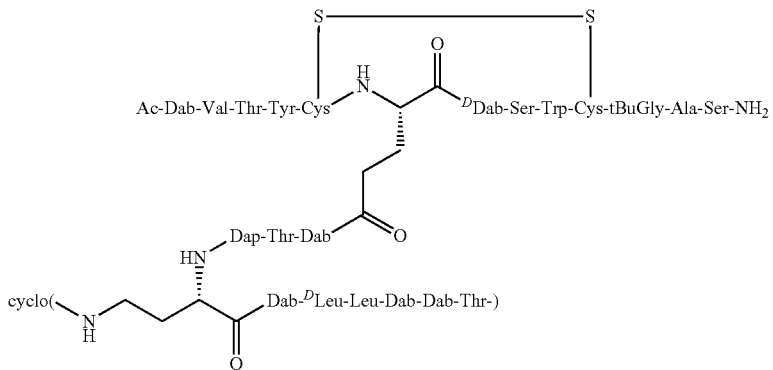

TABLE 1-continued

Examples (Ex.)
In the below-mentioned examples, amino acid residues are connected in either
direction from the α carbonyl (C=O) point of attachment to the α nitrogen (N) of the
next element, unless otherwise indicated. Other linkages, residues, connection of
residues and modifications are as specified.

| Ex. No. | Sequence |
|---|---|
| Ex. 238[a)] | Ac-Dab-Val-Thr-Tyr-Cys(S—S)-NH-CH(C(O)-$^D$Dab-Ser-Trp-Cys-tBuGly-Ala-Val-NH$_2$)-CH$_2$CH$_2$-C(O)-Dap-Thr-Dab-NH-[cyclo(-NH-CH$_2$CH$_2$-CH(NH-)-C(O)-Dab-$^D$Leu-Leu-Dab-Dab-Thr-)] |
| Ex. 239[a)] | Ac-Dab-Leu-Thr-Tyr-Cys(S—S)-NH-CH(C(O)-$^D$Dab-Dab-Trp-Cys-tBuGly-Ala-Val-NH$_2$)-CH$_2$CH$_2$-C(O)-Dap-Thr-Dab-NH-[cyclo(-NH-CH$_2$CH$_2$-CH(NH-)-C(O)-Dab-$^D$Leu-Leu-Dab-Dab-Thr-)] |
| Ex. 240[a)] | Ac-Dab-Leu((3R)OH)-Thr-Tyr-Cys(S—S)-NH-CH(C(O)-$^D$Dab-Dab-Trp-Cys-tBuGly-Ala-Val-NH$_2$)-CH$_2$CH$_2$-C(O)-Dap-Thr-Dab-NH-[cyclo(-NH-CH$_2$CH$_2$-CH(NH-)-C(O)-Dab-$^D$Leu-Leu-Dab-Dab-Thr-)] |
| Ex. 241[a)] | $^D$Ser-Val-Cys-Tyr-Dab(S—S)-NH-CH(C(O)-$^D$Dab-Thr-Trp-Ser-tBuGly-Cys-Ser-$^D$Ala)-CH$_2$CH$_2$-C(O)-Dab-Thr-Dab-NH-[cyclo(-NH-CH$_2$CH$_2$-CH(NH-)-C(O)-Dab-$^D$Leu-Leu-Dab-Dab-Thr-)] |

TABLE 1-continued
Examples (Ex.)
In the below-mentioned examples, amino acid residues are connected in either direction from the α carbonyl (C=O) point of attachment to the α nitrogen (N) of the next element, unless otherwise indicated. Other linkages, residues, connection of residues and modifications are as specified.
| Ex. No. | Sequence |
| --- | --- |
Ex. 242[a)]
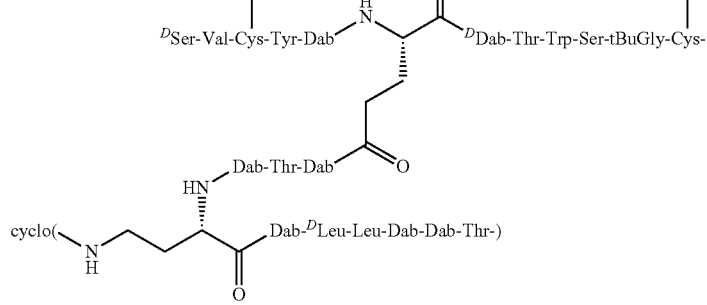
Ex. 243[a)]
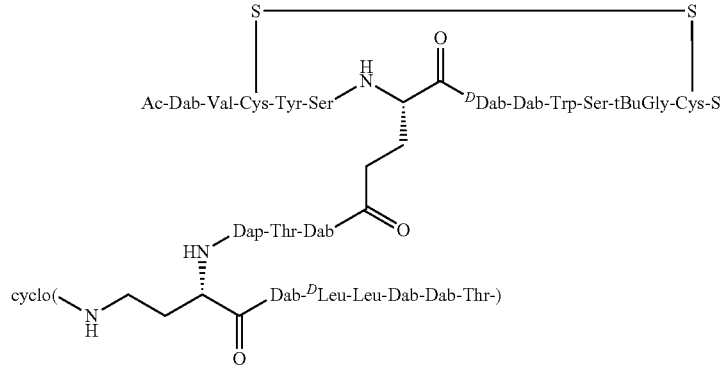
Ex. 244[a)]
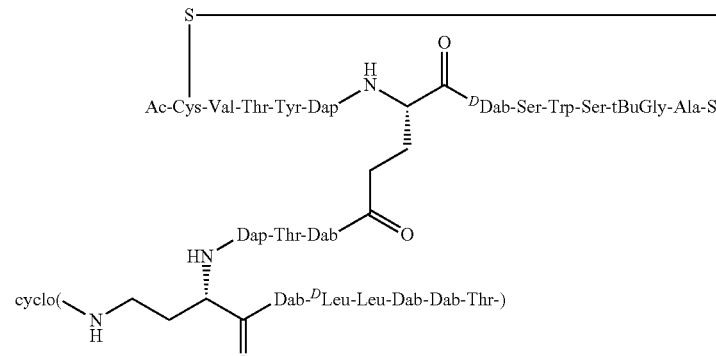

TABLE 1-continued
Examples (Ex.)
In the below-mentioned examples, amino acid residues are connected in either
direction from the α carbonyl (C=O) point of attachment to the α nitrogen (N) of the
next element, unless otherwise indicated. Other linkages, residues, connection of
residues and modifications are as specified.
| Ex. No. | Sequence |
|---|---|
| Ex. 245[a) c) i)] | 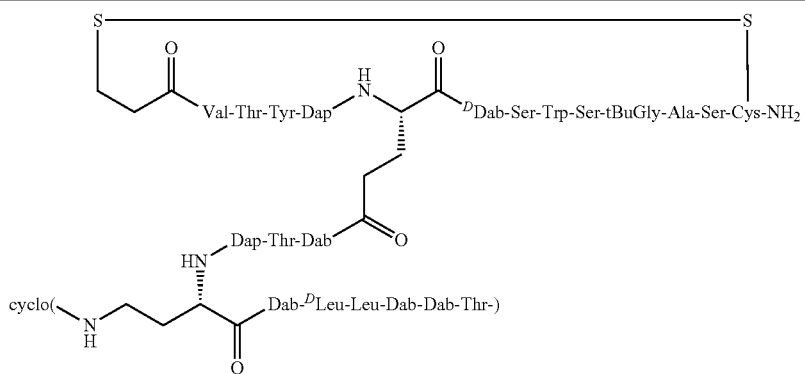 |
| Ex. 246[a)] | 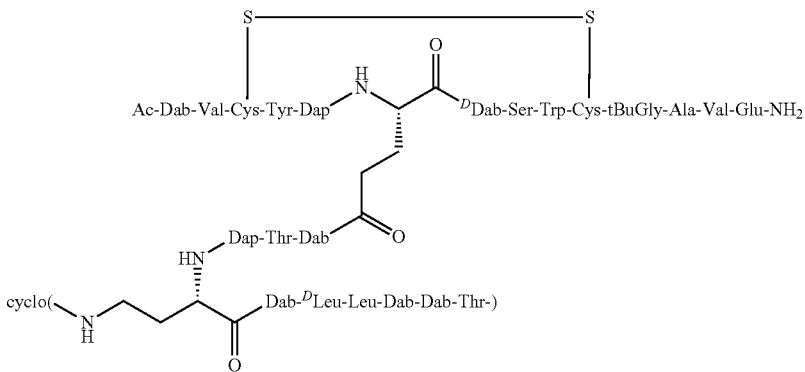 |
| Ex. 247 | 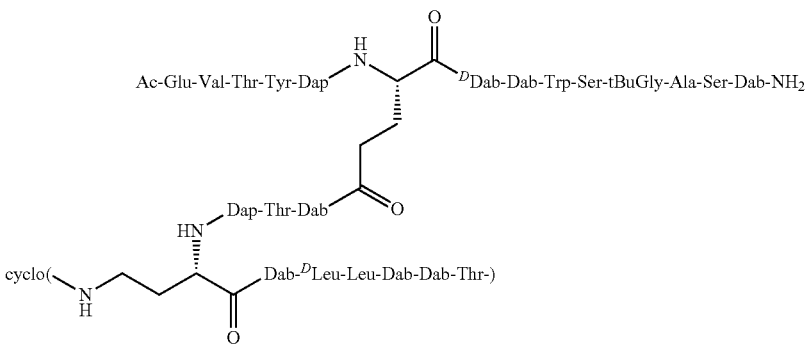 |
| Ex. 248 | 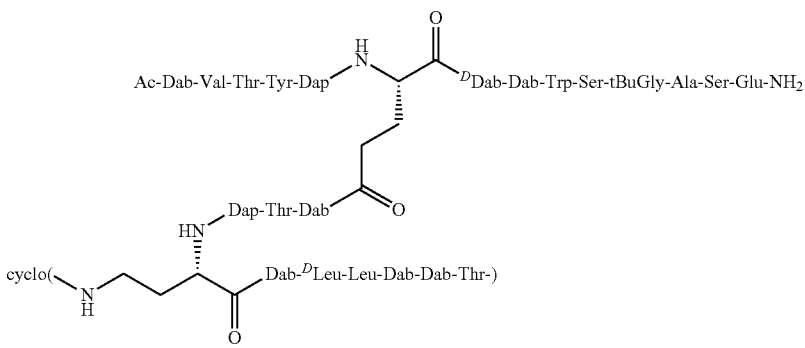 |

TABLE 1-continued
Examples (Ex.)
In the below-mentioned examples, amino acid residues are connected in either
direction from the α carbonyl (C=O) point of attachment to the α nitrogen (N) of the
next element, unless otherwise indicated. Other linkages, residues, connection of
residues and modifications are as specified.
| Ex. No. | Sequence |
|---|---|
| Ex. 249 | 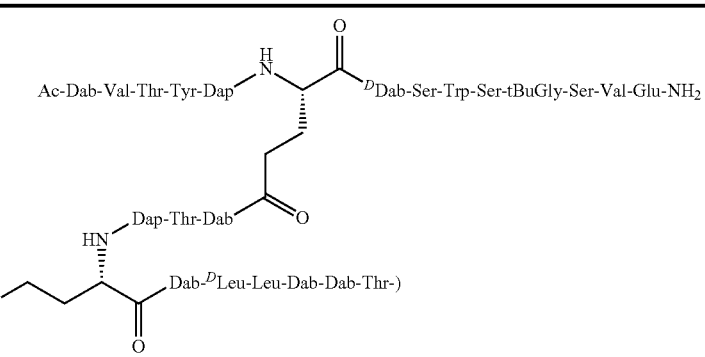 |
| Ex. 250[a) c) i)] | 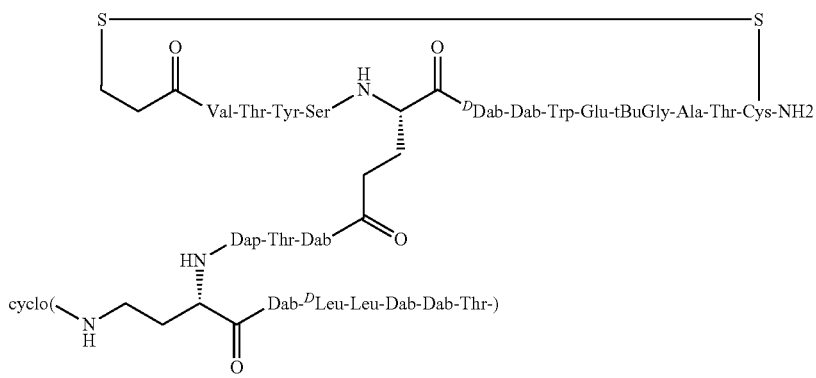 |
| Ex. 251[a)] | 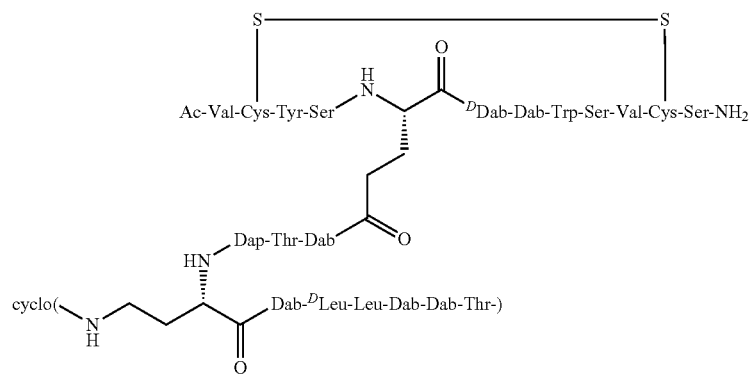 |
| Ex. 252[a)] | 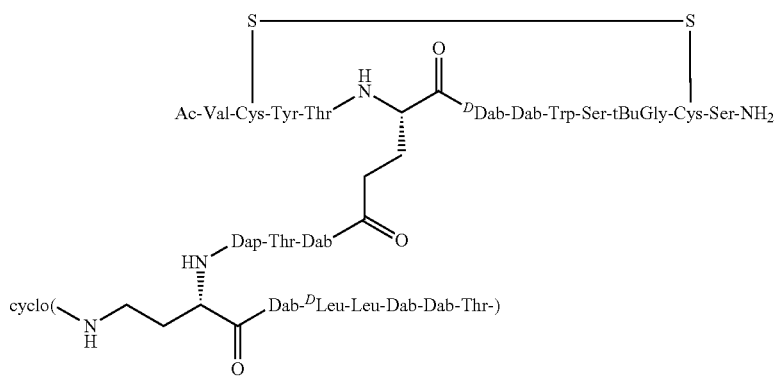 |

TABLE 1-continued
Examples (Ex.)
In the below-mentioned examples, amino acid residues are connected in either direction from the α carbonyl (C=O) point of attachment to the α nitrogen (N) of the next element, unless otherwise indicated. Other linkages, residues, connection of residues and modifications are as specified.
| Ex. No. | Sequence |
|---|---|
| Ex. 253[a)] | 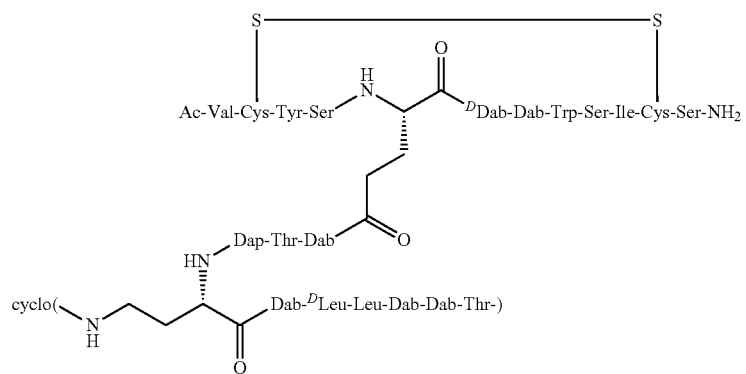 |
| Ex. 254[a)] | 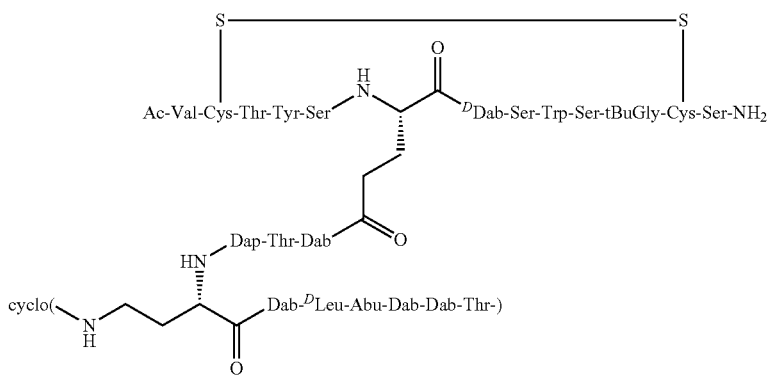 |
| Ex. 255[a)] | 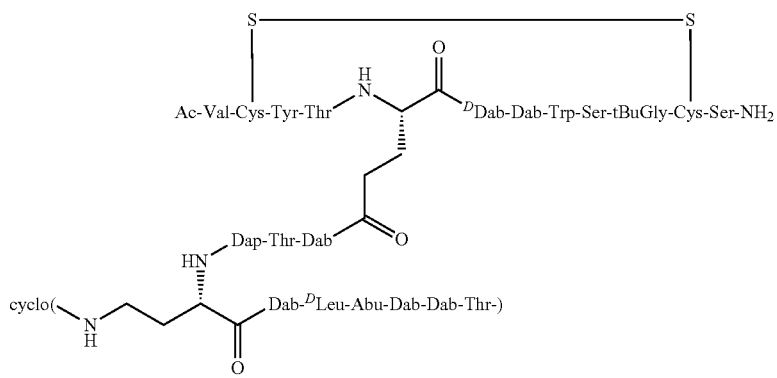 |

TABLE 1-continued
Examples (Ex.)
In the below-mentioned examples, amino acid residues are connected in either
direction from the α carbonyl (C=O) point of attachment to the α nitrogen (N) of the
next element, unless otherwise indicated. Other linkages, residues, connection of
residues and modifications are as specified.
| Ex. No. | Sequence |
|---|---|
| Ex. 256[a)] | 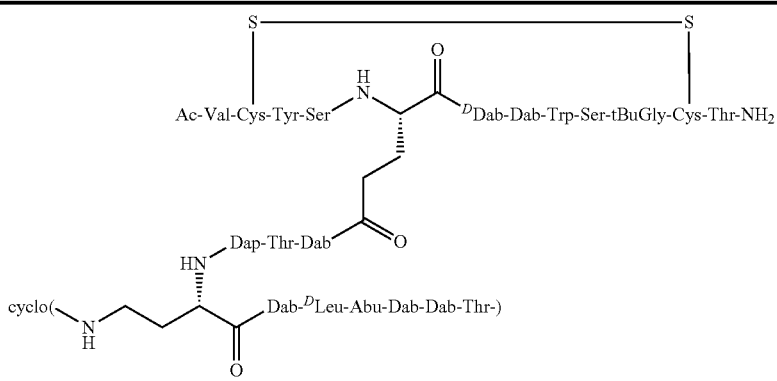 |
| Ex. 257[a)] | 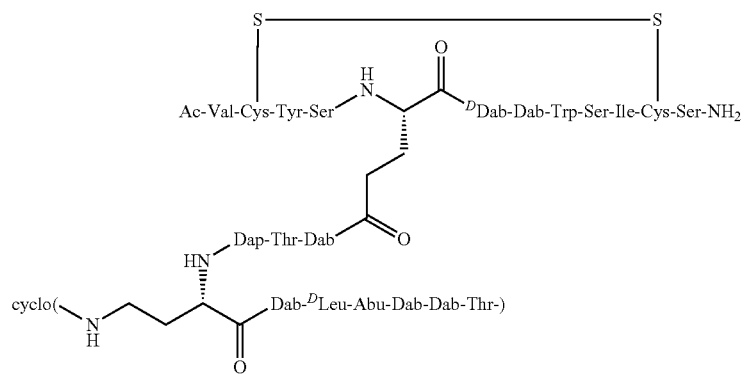 |
| Ex. 258[a)] | 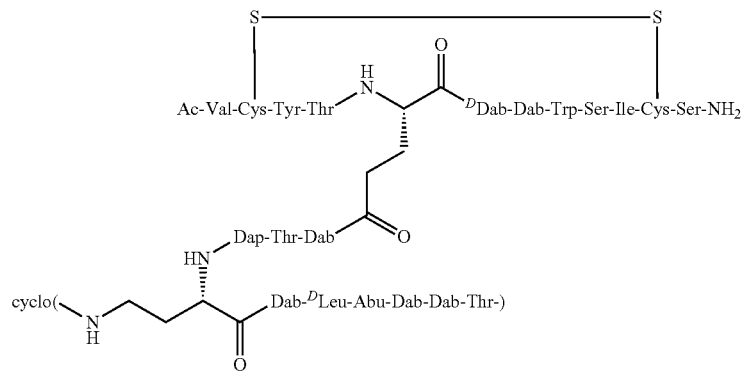 |
| Ex. 259[a)] | 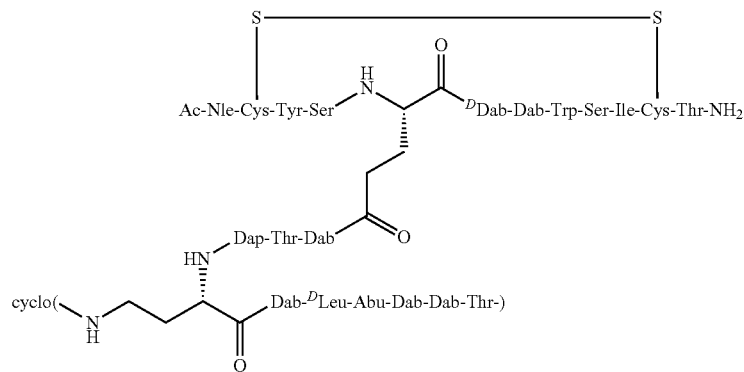 |

TABLE 1-continued
Examples (Ex.)
In the below-mentioned examples, amino acid residues are connected in either
direction from the α carbonyl (C=O) point of attachment to the α nitrogen (N) of the
next element, unless otherwise indicated. Other linkages, residues, connection of
residues and modifications are as specified.
| Ex. No. | Sequence |
|---|---|
| Ex. 260[a)] | 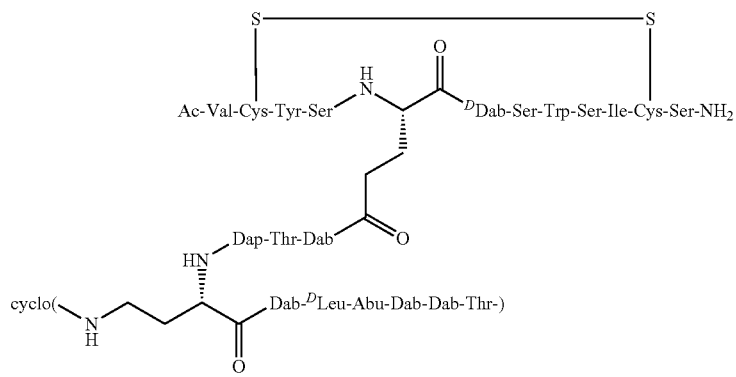 |
| Ex. 261[a)] | 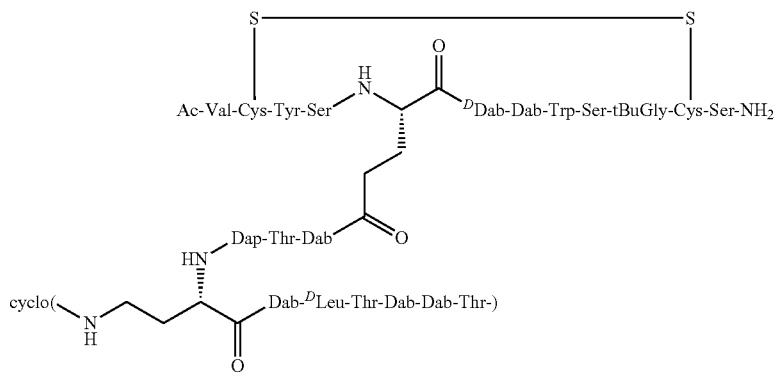 |
| Ex. 262[a)] | 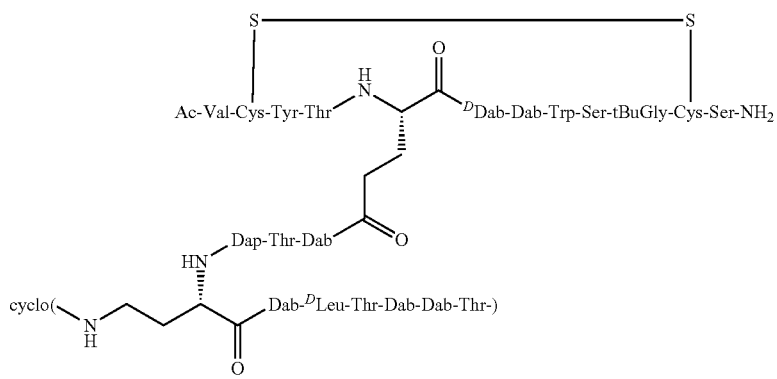 |

TABLE 1-continued
Examples (Ex.)
In the below-mentioned examples, amino acid residues are connected in either direction from the α carbonyl (C=O) point of attachment to the α nitrogen (N) of the next element, unless otherwise indicated. Other linkages, residues, connection of residues and modifications are as specified.
| Ex. No. | Sequence |
|---|---|
| Ex. 263[a)] | 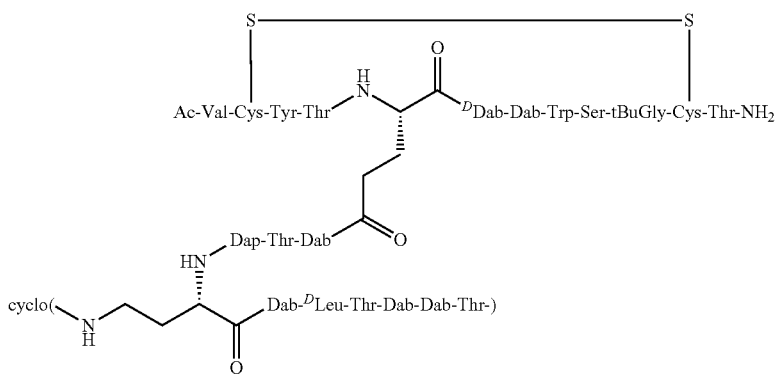 |
| Ex. 264[a)] | 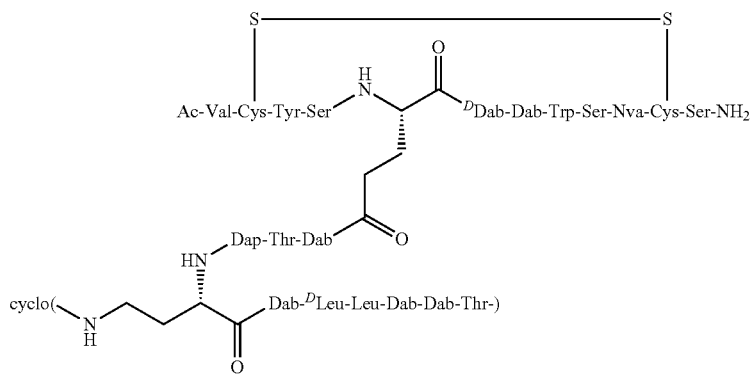 |
| Ex. 265[g)] | 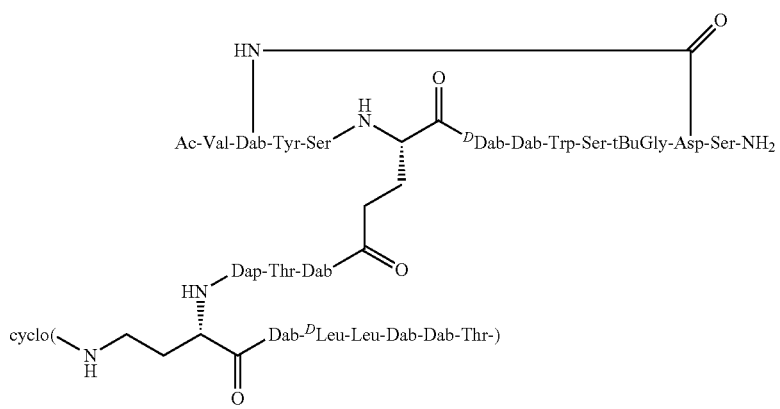 |

TABLE 1-continued
Examples (Ex.)
In the below-mentioned examples, amino acid residues are connected in either
direction from the α carbonyl (C=O) point of attachment to the α nitrogen (N) of the
next element, unless otherwise indicated. Other linkages, residues, connection of
residues and modifications are as specified.
| Ex. No. | Sequence |
|---|---|
| Ex. 266[a)] | 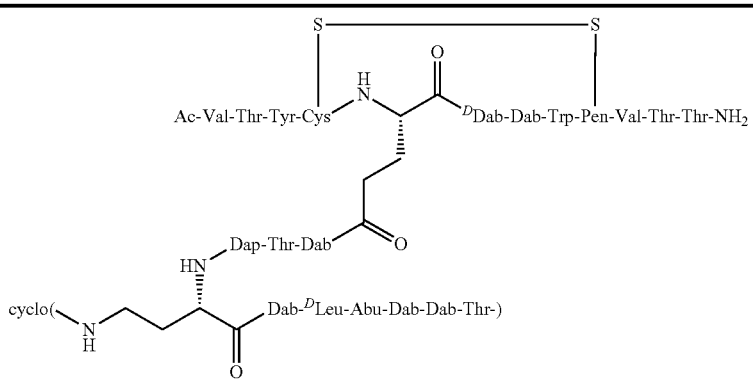 |
| Ex. 267[a)] | 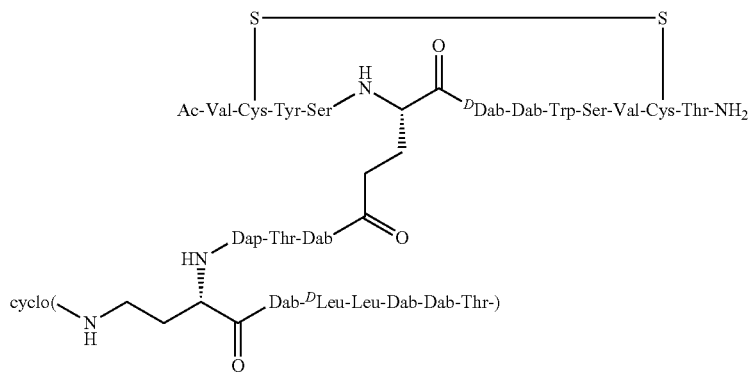 |
| Ex. 268[a)] | 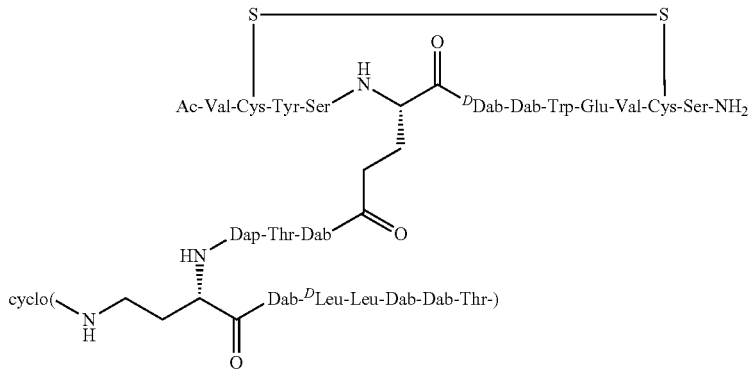 |
| Ex. 269[a)] | 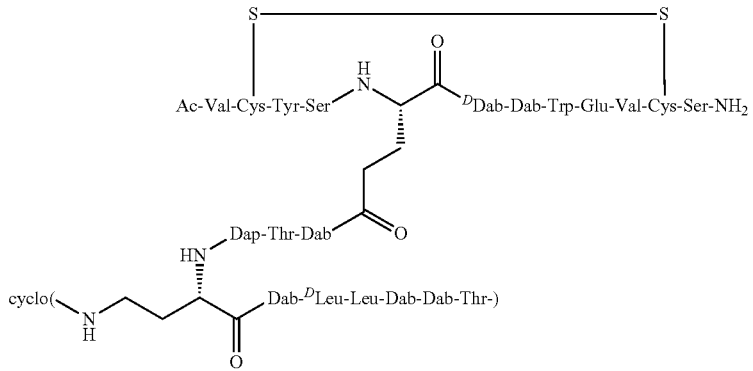 |

TABLE 1-continued
Examples (Ex.)
In the below-mentioned examples, amino acid residues are connected in either
direction from the α carbonyl (C=O) point of attachment to the α nitrogen (N) of the
next element, unless otherwise indicated. Other linkages, residues, connection of
residues and modifications are as specified.
| Ex. No. | Sequence |
| --- | --- |
Ex. 270[a) e)]
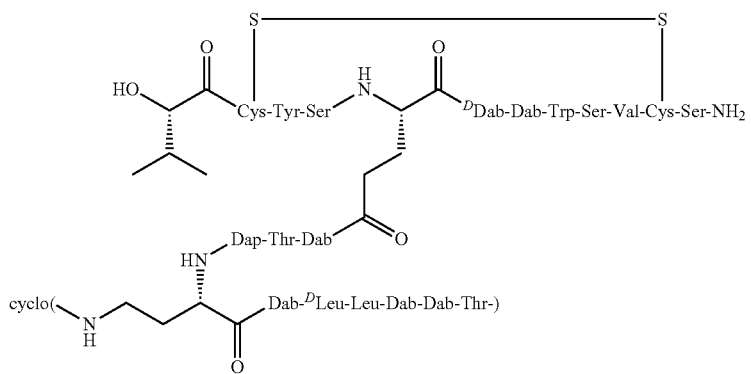
Ex. 271[a) e)]
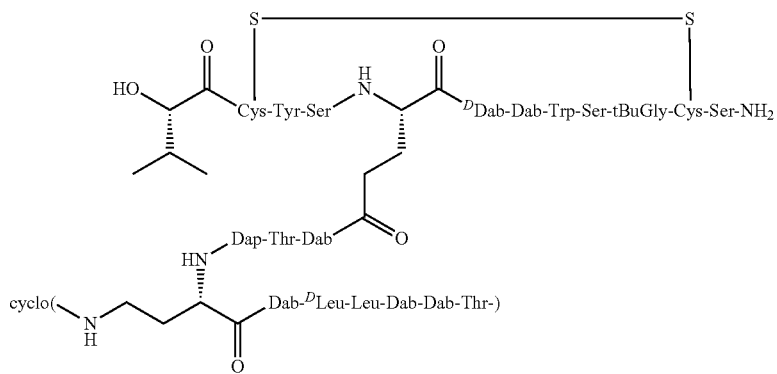
Ex. 272[a)]
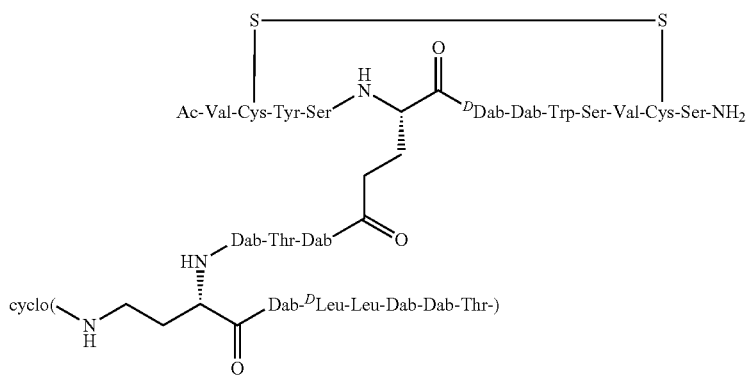

TABLE 1-continued
Examples (Ex.)
In the below-mentioned examples, amino acid residues are connected in either
direction from the α carbonyl (C=O) point of attachment to the α nitrogen (N) of the
next element, unless otherwise indicated. Other linkages, residues, connection of
residues and modifications are as specified.
| Ex. No. | Sequence |
| --- | --- |
Ex. 273[g)]
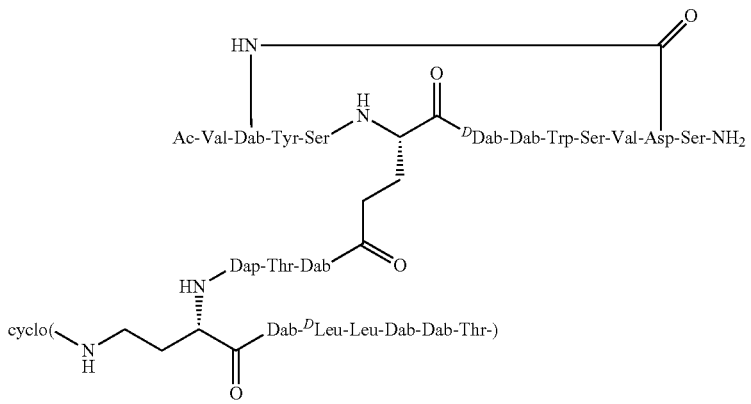
Ex. 274[a) e)]
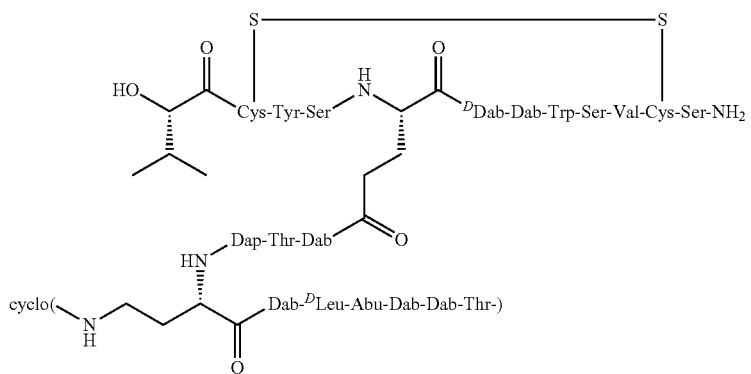
Ex. 275[a)]
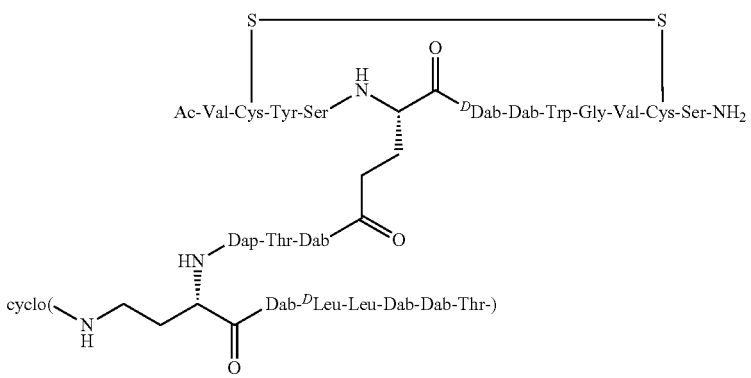

TABLE 1-continued
Examples (Ex.)
In the below-mentioned examples, amino acid residues are connected in either direction from the α carbonyl (C=O) point of attachment to the α nitrogen (N) of the next element, unless otherwise indicated. Other linkages, residues, connection of residues and modifications are as specified.
| Ex. No. | Sequence |
|---|---|
| Ex. 276[a)] | 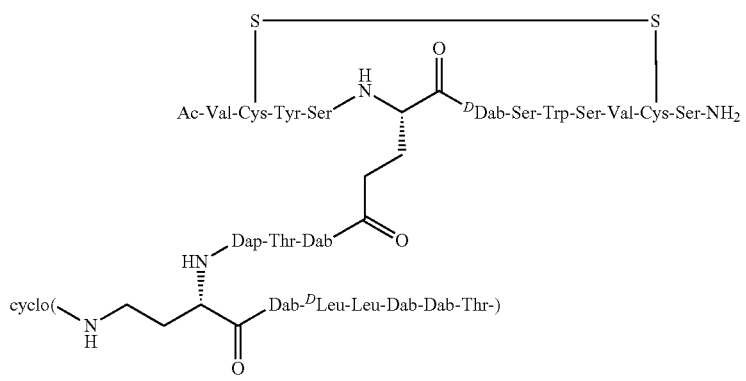 |
| Ex. 277[a) e)] | 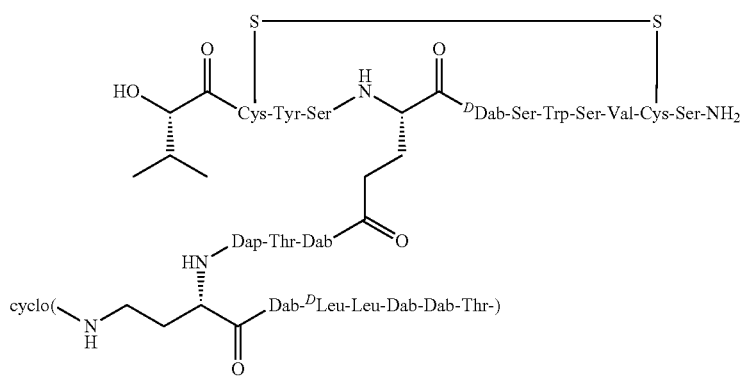 |
| Ex. 278[a)] | 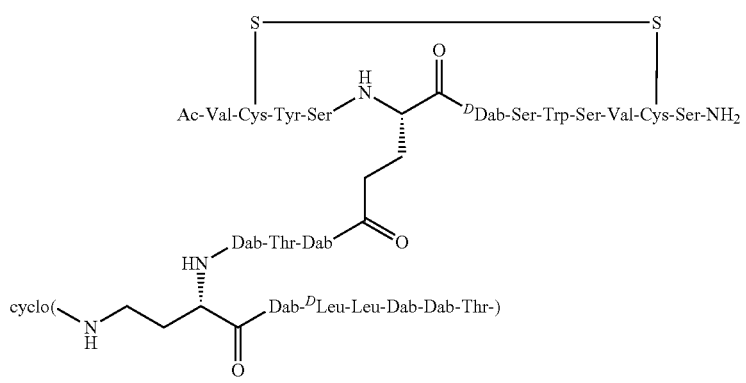 |

TABLE 1-continued
Examples (Ex.)
In the below-mentioned examples, amino acid residues are connected in either
direction from the α carbonyl (C=O) point of attachment to the α nitrogen (N) of the
next element, unless otherwise indicated. Other linkages, residues, connection of
residues and modifications are as specified.
| Ex. No. | Sequence |
| --- | --- |
| Ex. 279[g)] | 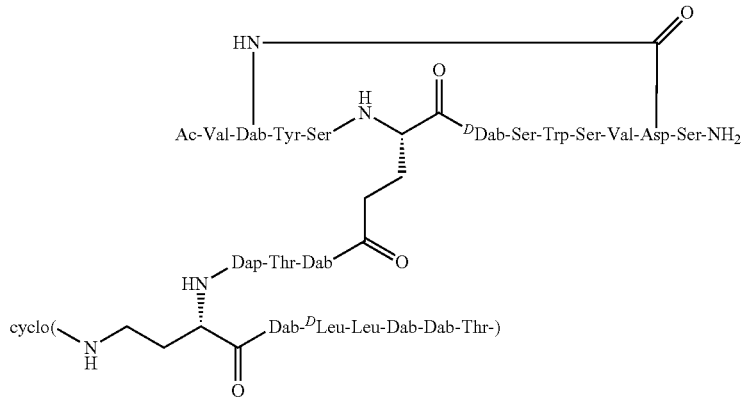 |
| Ex. 280[a)] | 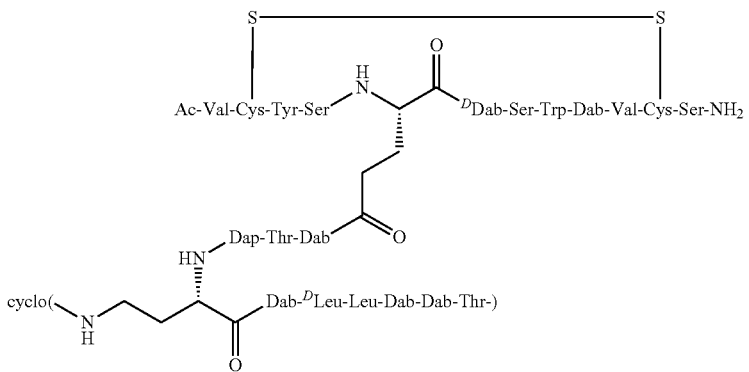 |
| Ex. 281[a)] | 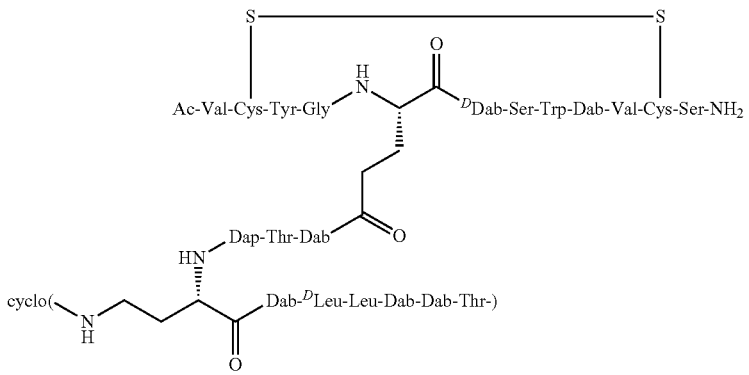 |

TABLE 1-continued
Examples (Ex.)
In the below-mentioned examples, amino acid residues are connected in either
direction from the α carbonyl (C=O) point of attachment to the α nitrogen (N) of the
next element, unless otherwise indicated. Other linkages, residues, connection of
residues and modifications are as specified.
| Ex. No. | Sequence |
|---|---|
| Ex. 282[a)] | 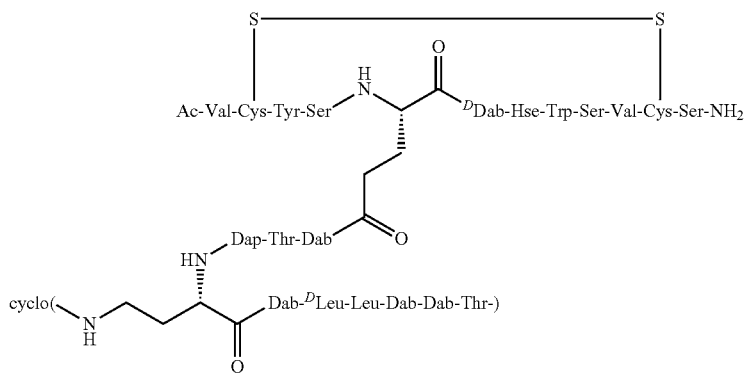 |
| Ex. 283[a)] | 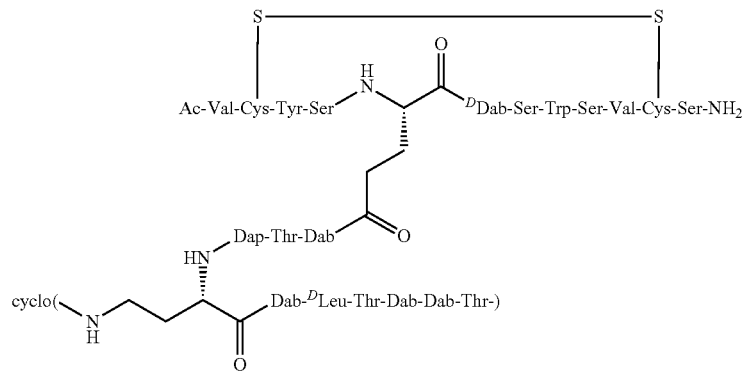 |
| Ex. 284[a)] | 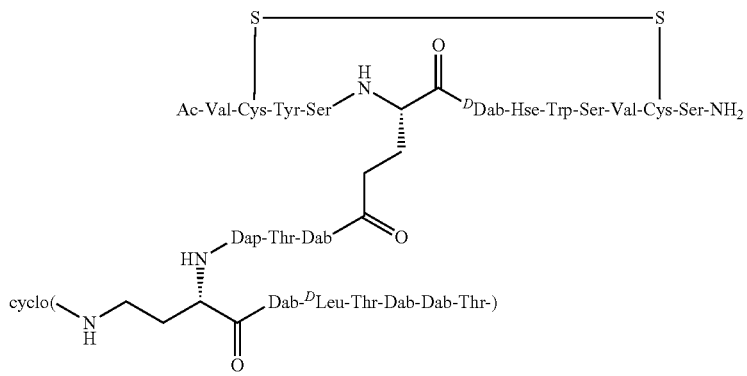 |

TABLE 1-continued
Examples (Ex.)
In the below-mentioned examples, amino acid residues are connected in either direction from the α carbonyl (C=O) point of attachment to the α nitrogen (N) of the next element, unless otherwise indicated. Other linkages, residues, connection of residues and modifications are as specified.
| Ex. No. | Sequence |
| --- | --- |
| Ex. 285[g)] | 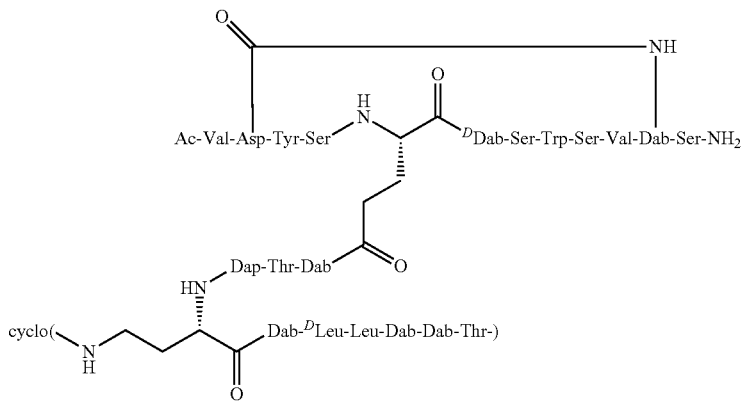 |
| Ex. 286[g)] | 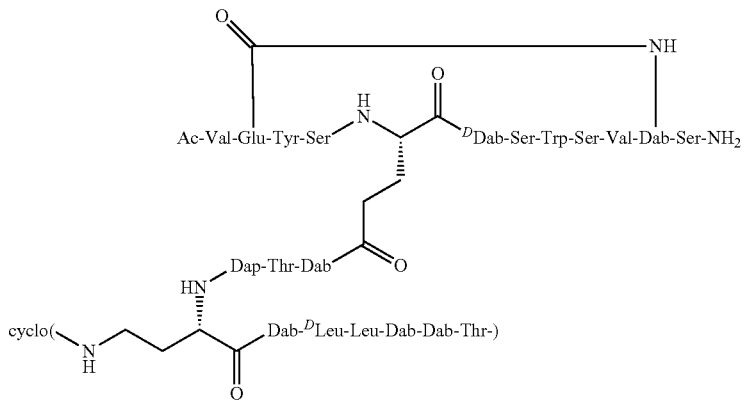 |
| Ex. 287[g)] | 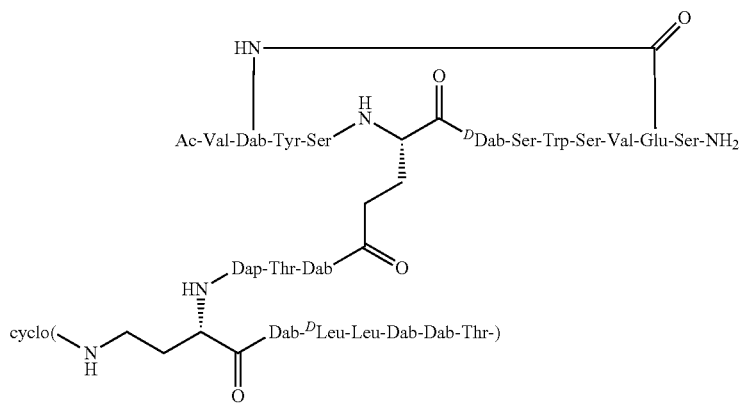 |

TABLE 1-continued

Examples (Ex.)
In the below-mentioned examples, amino acid residues are connected in either direction from the α carbonyl (C=O) point of attachment to the α nitrogen (N) of the next element, unless otherwise indicated. Other linkages, residues, connection of residues and modifications are as specified.

| Ex. No. | Sequence |
| --- | --- |
| Ex. 288[g] | Ac-Val-Asp-Tyr-Ser—[N]—...—[D]Dab-Ser-Trp-Ser-Val-Dab-Ser-NH$_2$, with branch Dab-Thr-Dab and cyclo(-NH-...-Dab-[D]Leu-Leu-Dab-Dab-Thr-) |
| Ex. 289[a] | Ac-Val-Cys-Tyr-Ser—[N]—...—[D]Dab-Gly-Trp-Ser-Val-Cys-Ser-NH$_2$ (S—S bridge), with branch Dap-Thr-Dab and cyclo(-NH-...-Dab-[D]Leu-Leu-Dab-Dab-Thr-) |
| Ex. 290[g] | Ac-Val-Dab-Tyr-Ser—[N]—...—[D]Dab-Gly-Trp-Ser-Val-Asp-Ser-NH$_2$, with branch Dap-Thr-Dab and cyclo(-NH-...-Dab-[D]Leu-Leu-Dab-Dab-Thr-) |

TABLE 1-continued
Examples (Ex.)
In the below-mentioned examples, amino acid residues are connected in either
direction from the α carbonyl (C=O) point of attachment to the α nitrogen (N) of the
next element, unless otherwise indicated. Other linkages, residues, connection of
residues and modifications are as specified.
| Ex. No. | Sequence |
| --- | --- |
| Ex. 291[g)] | 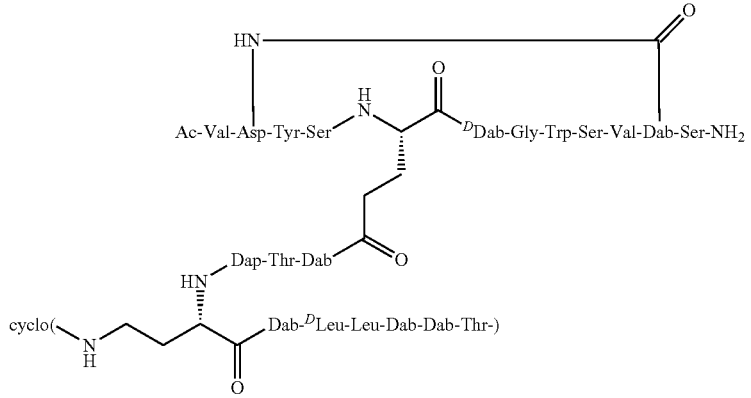 |
| Ex. 292[g)] | 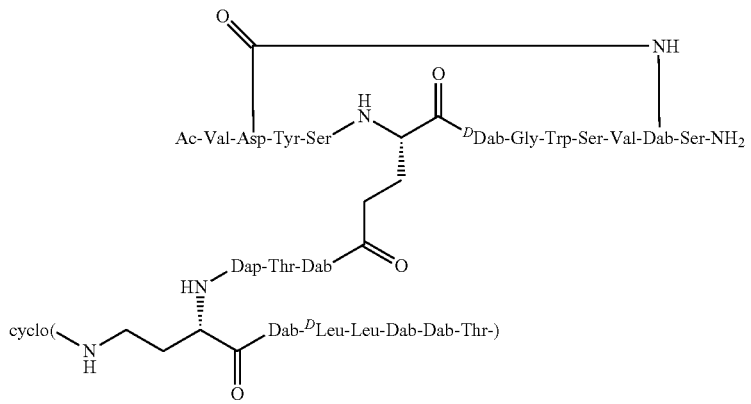 |
| Ex. 293[g)] | 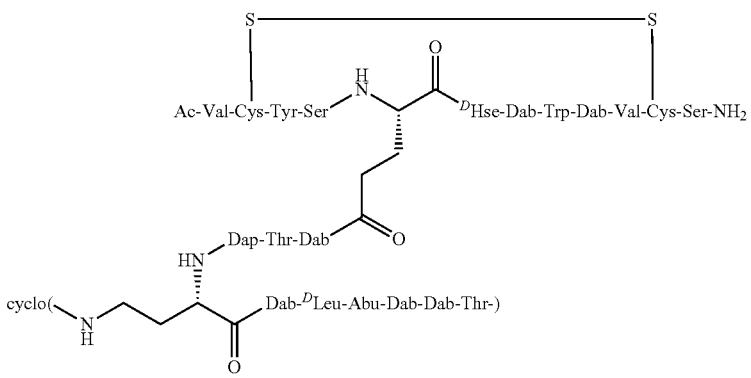 |

TABLE 1-continued
Examples (Ex.)
In the below-mentioned examples, amino acid residues are connected in either
direction from the α carbonyl (C=O) point of attachment to the α nitrogen (N) of the
next element, unless otherwise indicated. Other linkages, residues, connection of
residues and modifications are as specified.
| Ex. No. | Sequence |
|---|---|
| Ex. 294[a)] | 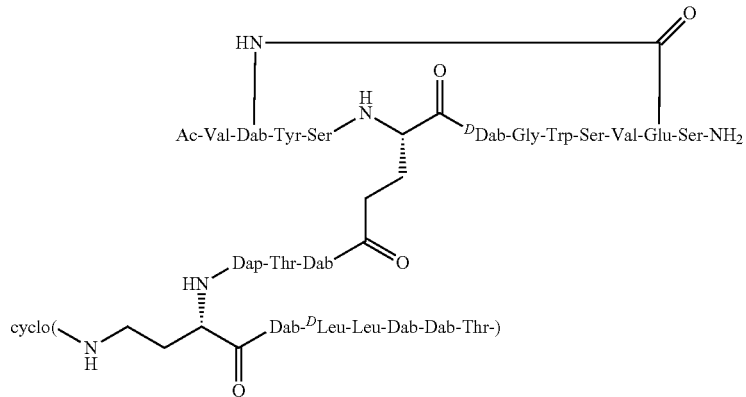 |
| Ex. 295[a)] | 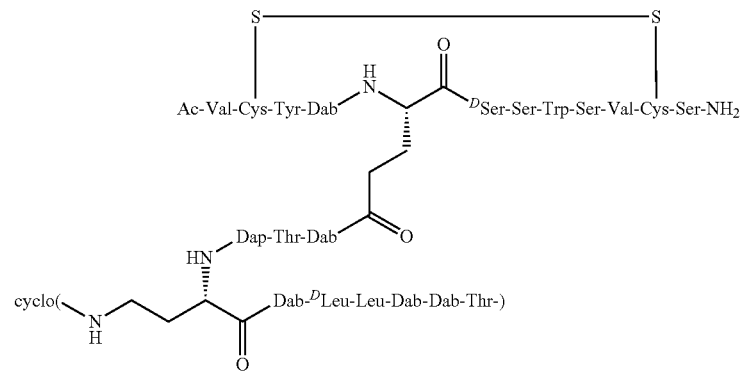 |
| Ex. 296[a)] | 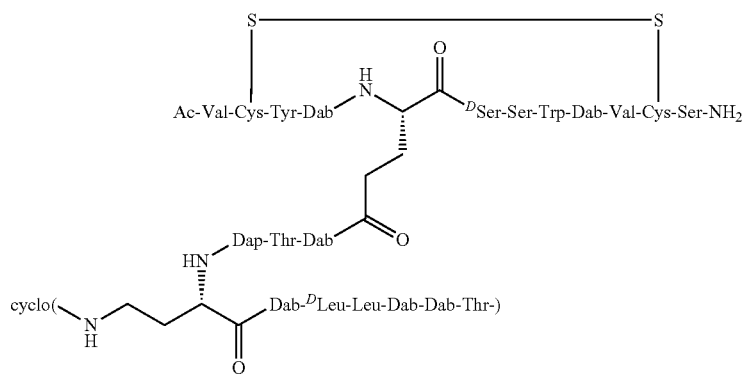 |

TABLE 1-continued
Examples (Ex.)
In the below-mentioned examples, amino acid residues are connected in either
direction from the α carbonyl (C=O) point of attachment to the α nitrogen (N) of the
next element, unless otherwise indicated. Other linkages, residues, connection of
residues and modifications are as specified.
| Ex. No. | Sequence |
|---|---|
| Ex. 297[a)] | 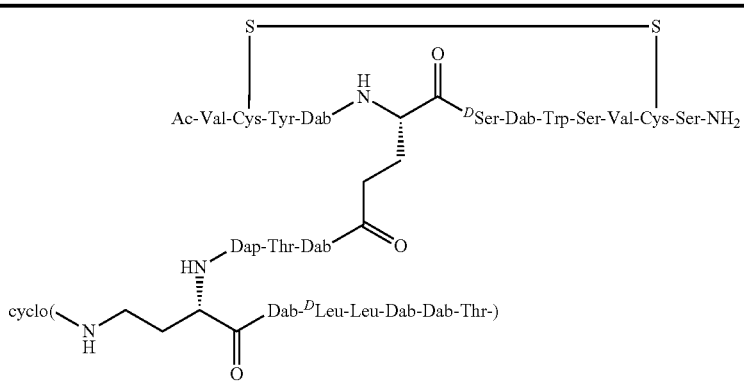 |
| Ex. 298[a)] | 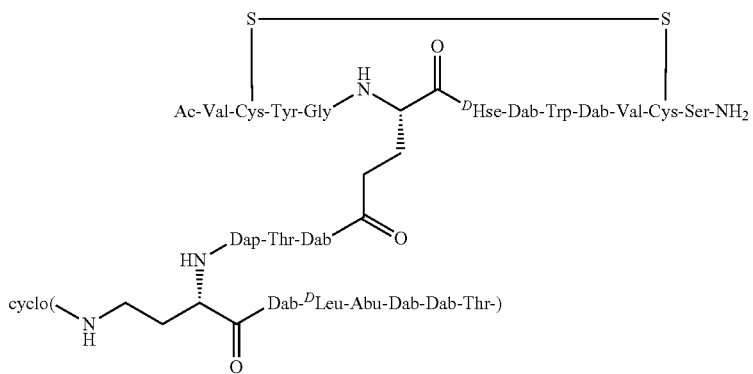 |
| Ex. 299[a)] | 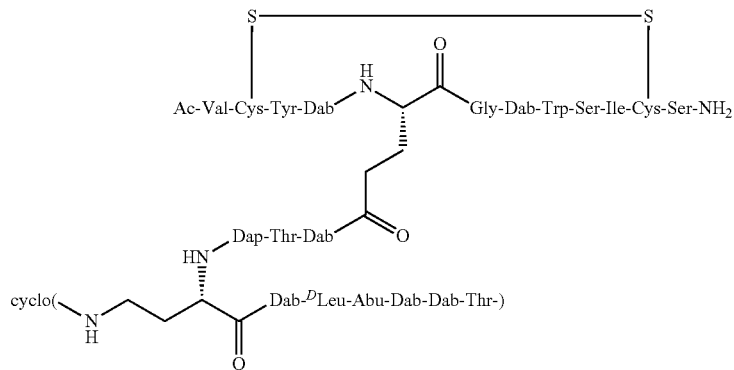 |
| Ex. 300[a)] | 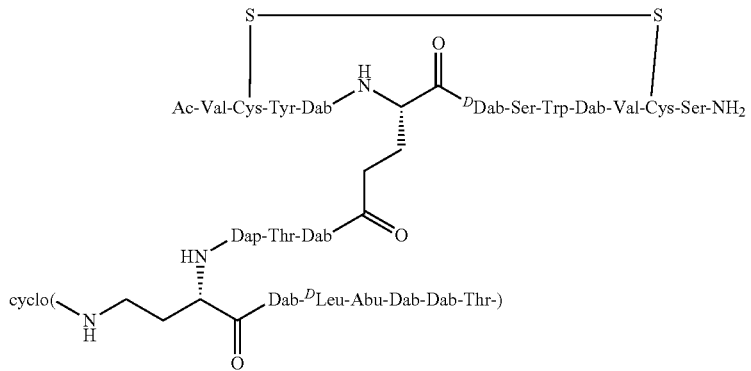 |

TABLE 1-continued
Examples (Ex.)
In the below-mentioned examples, amino acid residues are connected in either
direction from the α carbonyl (C=O) point of attachment to the α nitrogen (N) of the
next element, unless otherwise indicated. Other linkages, residues, connection of
residues and modifications are as specified.
| Ex. No. | Sequence |
| --- | --- |
Ex. 301[a) e)]
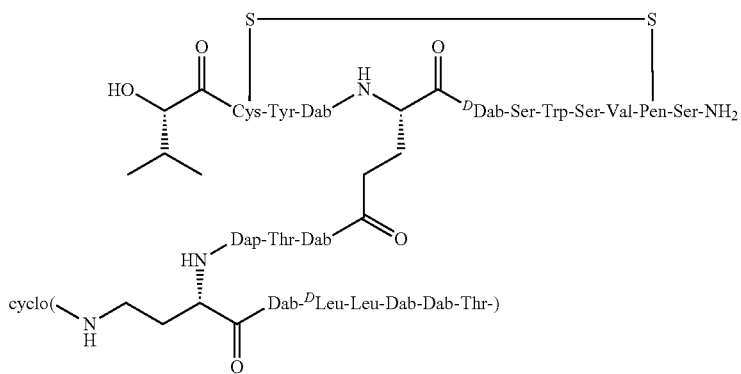
Ex. 302[g)]
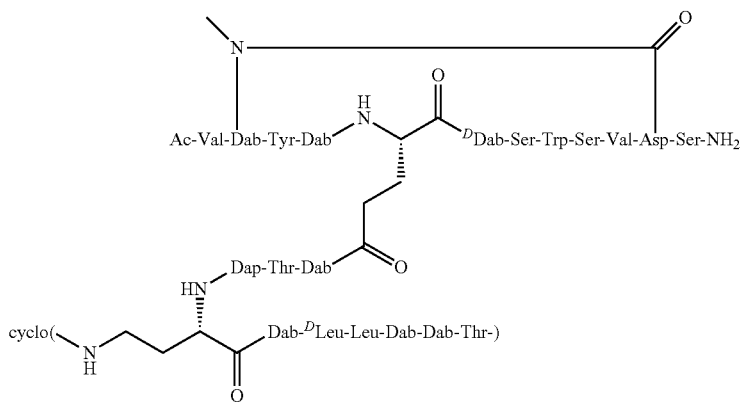
Ex. 303[g)]
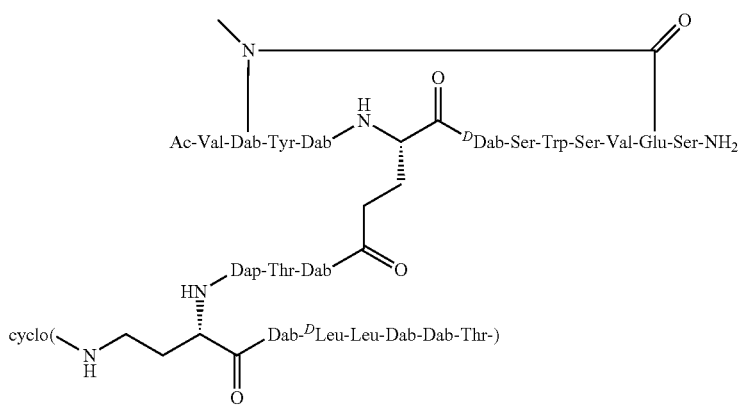

TABLE 1-continued
Examples (Ex.)
In the below-mentioned examples, amino acid residues are connected in either
direction from the α carbonyl (C=O) point of attachment to the α nitrogen (N) of the
next element, unless otherwise indicated. Other linkages, residues, connection of
residues and modifications are as specified.
| Ex. No. | Sequence |
| --- | --- |
Ex. 304[g) e)]
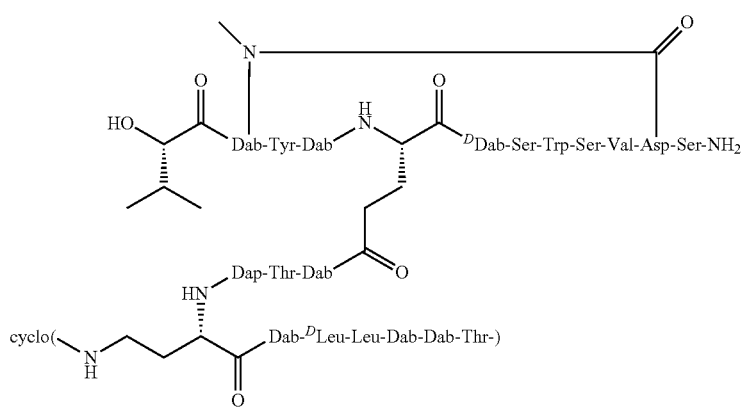
Ex. 305[a)]
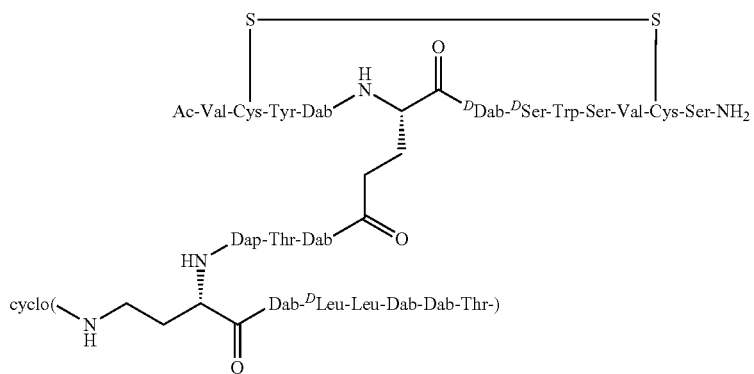
Ex. 306[a)]
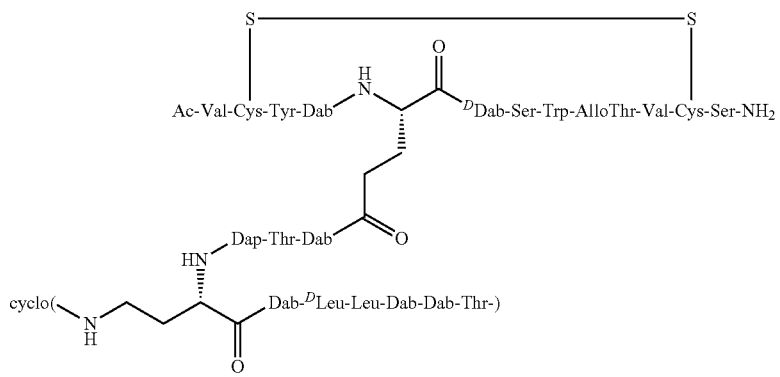

TABLE 1-continued
Examples (Ex.)
In the below-mentioned examples, amino acid residues are connected in either
direction from the α carbonyl (C=O) point of attachment to the α nitrogen (N) of the
next element, unless otherwise indicated. Other linkages, residues, connection of
residues and modifications are as specified.
| Ex. No. | Sequence |
| --- | --- |
| Ex. 307[a)] | 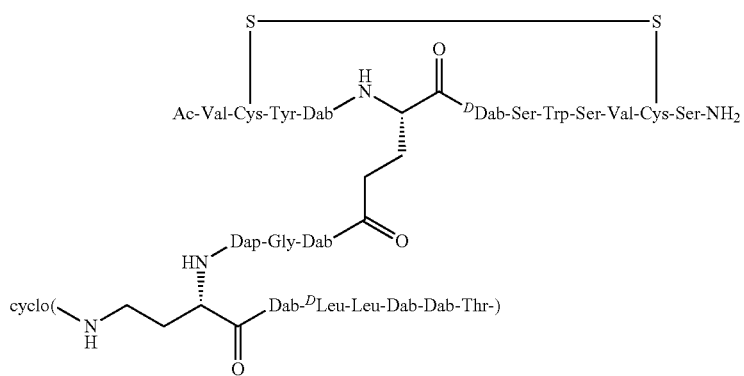 |
| Ex. 308[a)] | 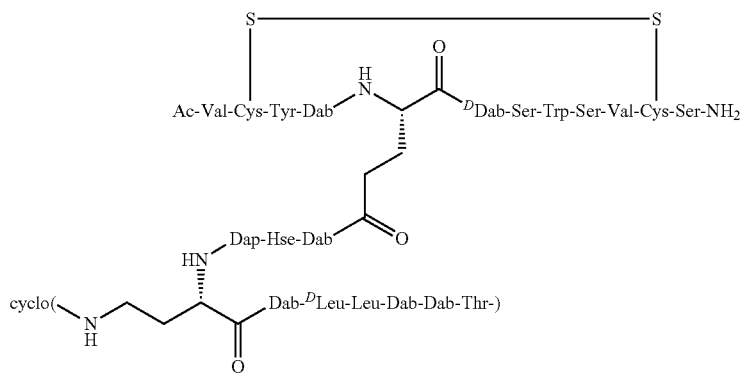 |
| Ex. 309[a)] | 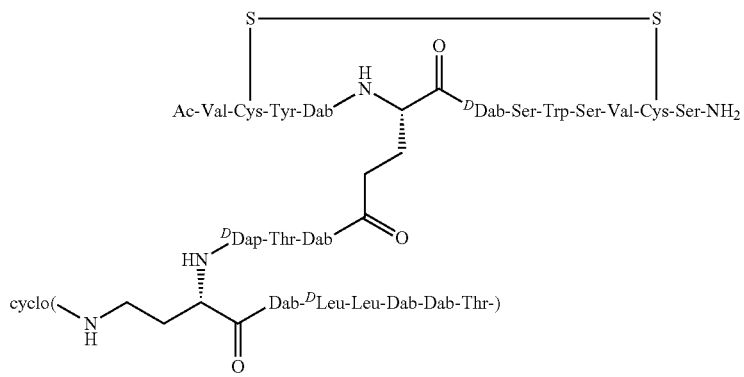 |

TABLE 1-continued
Examples (Ex.)
In the below-mentioned examples, amino acid residues are connected in either
direction from the α carbonyl (C=O) point of attachment to the α nitrogen (N) of the
next element, unless otherwise indicated. Other linkages, residues, connection of
residues and modifications are as specified.
| Ex. No. | Sequence |
| --- | --- |
| Ex. 310[a)] | 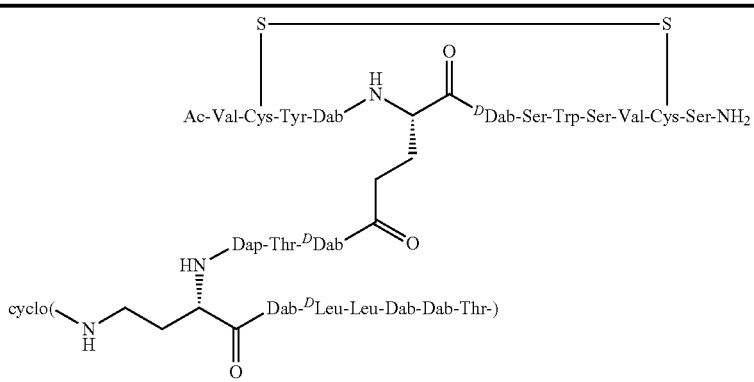 |
| Ex. 311[a)] | 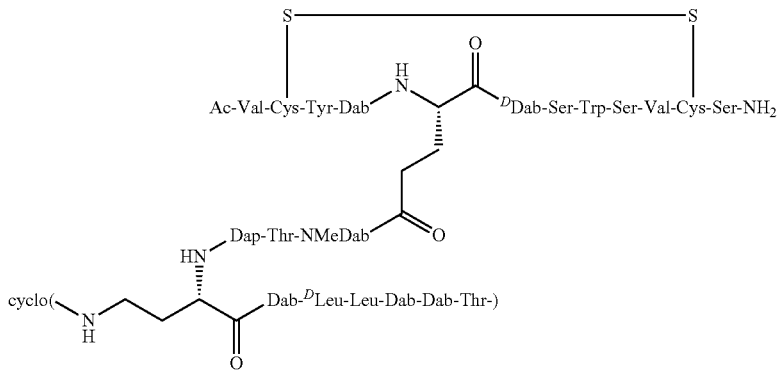 |
| Ex. 312[a)] | 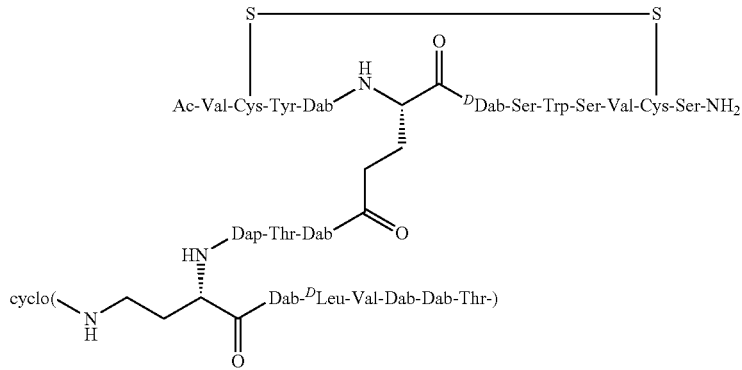 |
| Ex. 313[a)] | 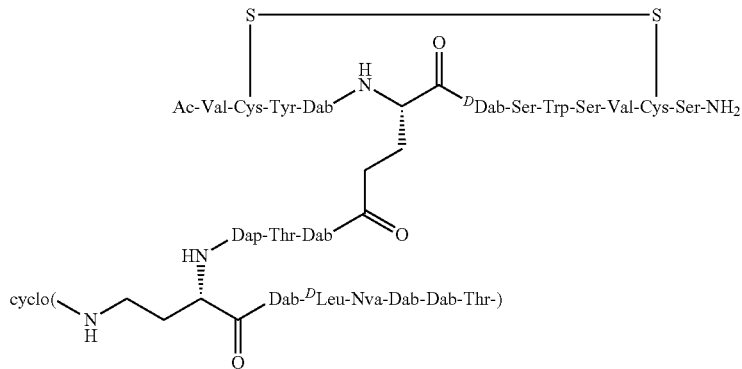 |

TABLE 1-continued
Examples (Ex.)
In the below-mentioned examples, amino acid residues are connected in either direction from the α carbonyl (C=O) point of attachment to the α nitrogen (N) of the next element, unless otherwise indicated. Other linkages, residues, connection of residues and modifications are as specified.
| Ex. No. | Sequence |
|---|---|
| Ex. 314[a)] | 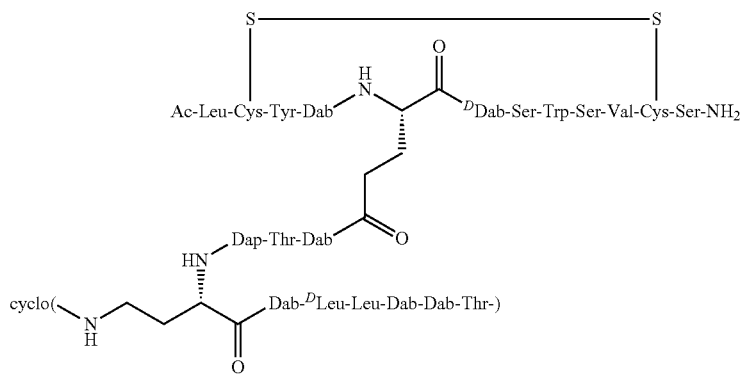 |
| Ex. 315[a)] | 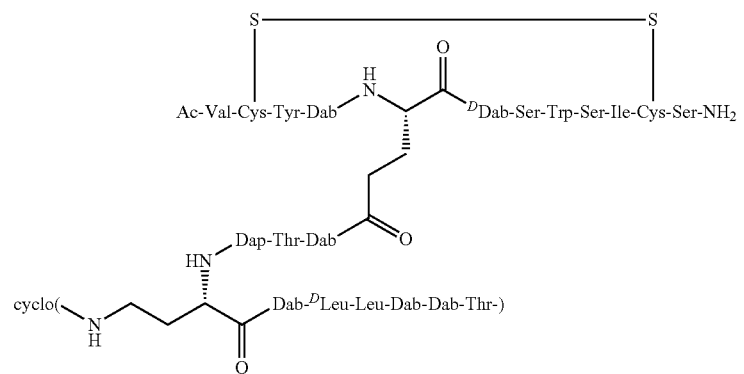 |
| Ex. 316[a)] | 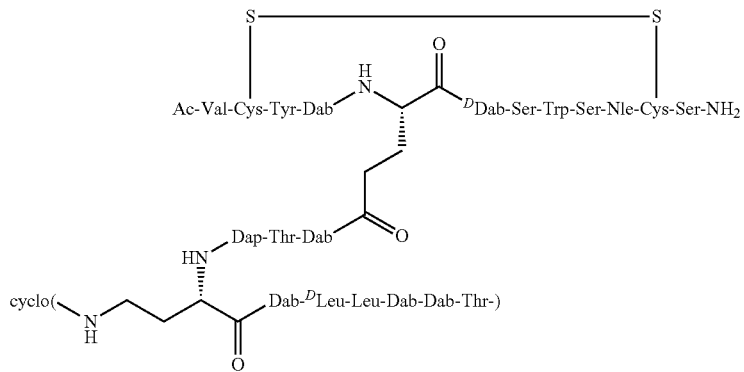 |

TABLE 1-continued
Examples (Ex.)
In the below-mentioned examples, amino acid residues are connected in either
direction from the α carbonyl (C=O) point of attachment to the α nitrogen (N) of the
next element, unless otherwise indicated. Other linkages, residues, connection of
residues and modifications are as specified.
| Ex. No. | Sequence |
|---|---|
| Ex. 317[a)] | 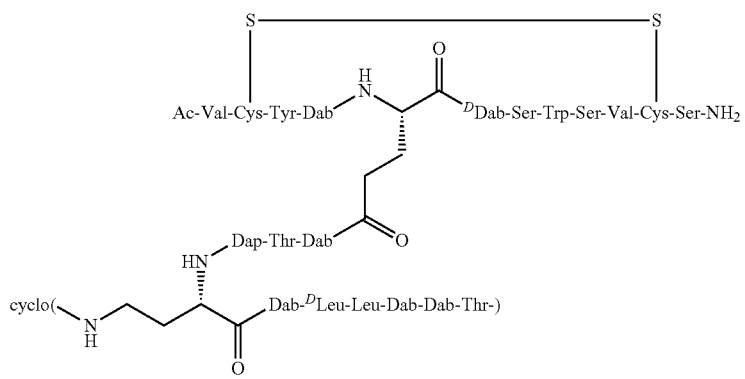 |
| Ex. 318[a)] | 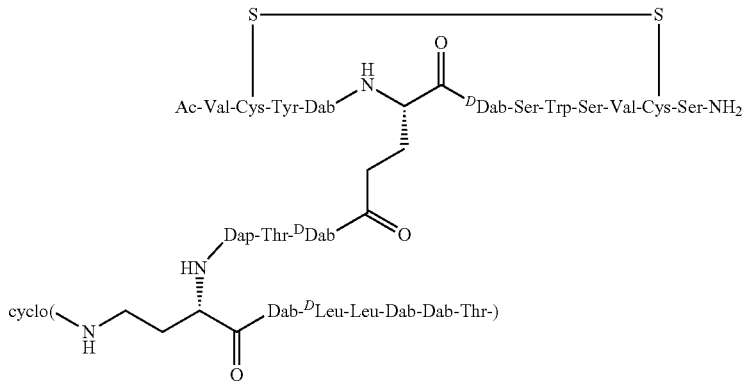 |
| Ex. 319[g)] | 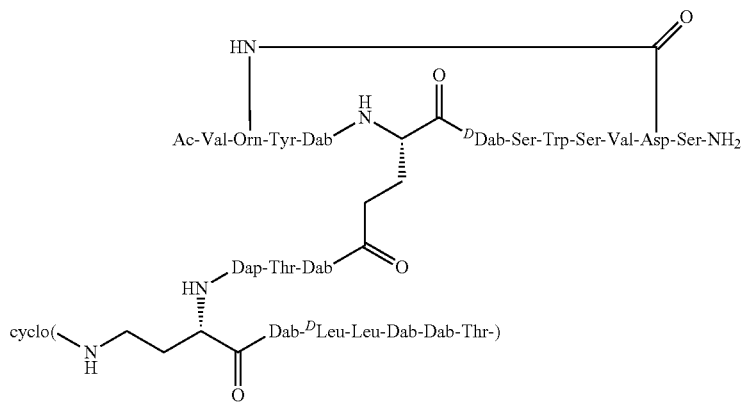 |

TABLE 1-continued
Examples (Ex.)
In the below-mentioned examples, amino acid residues are connected in either direction from the α carbonyl (C=O) point of attachment to the α nitrogen (N) of the next element, unless otherwise indicated. Other linkages, residues, connection of residues and modifications are as specified.
| Ex. No. | Sequence |
| --- | --- |
Ex. 320[g)]
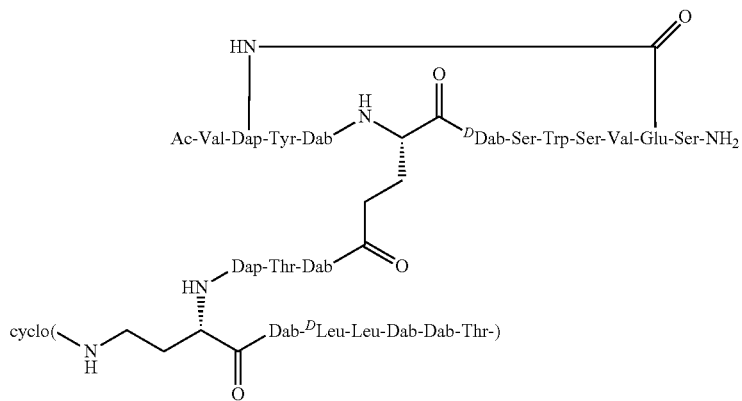
Ex. 321[g)]
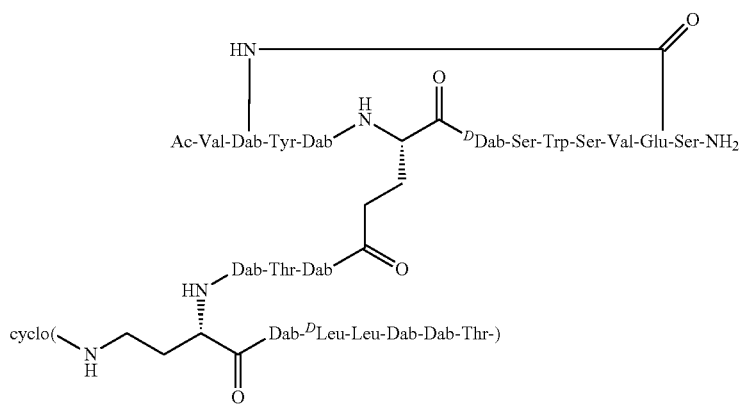
Ex. 322[g)]
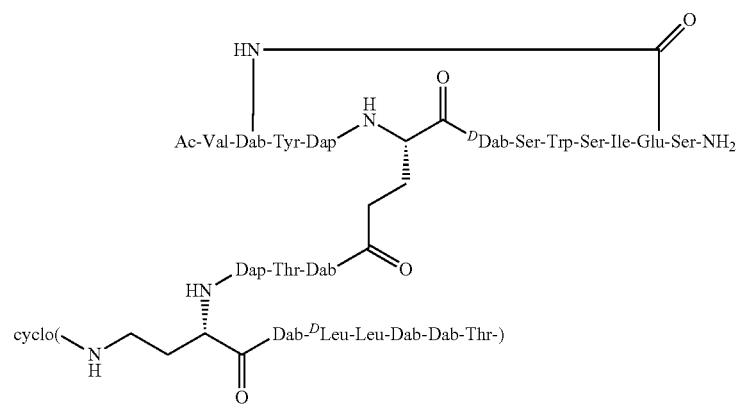

TABLE 1-continued

Examples (Ex.)
In the below-mentioned examples, amino acid residues are connected in either direction from the α carbonyl (C=O) point of attachment to the α nitrogen (N) of the next element, unless otherwise indicated. Other linkages, residues, connection of residues and modifications are as specified.

| Ex. No. | Sequence |
| --- | --- |

Ex. 323[g)]

Ac-Val-Dab-Tyr-Dab-[cyclo(-NH-...-Dab-$^D$Leu-Leu-Dab-Dab-Thr-)-Dap-Thr-Dab-]-$^D$Dab-Ser-Trp-Ser-Ile-Asp-Ser-NH$_2$ Ex. 324[g)]

Ac-Val-Dab-Tyr-Dab-[cyclo(-NH-...-Dab-$^D$Leu-Leu-Dab-Dab-Thr-)-Dap-Thr-Dab-]-$^D$Dab-Ser-Trp-Ser-Ile-Glu-Ser-NH$_2$ Ex. 325[g)]

Ac-Val-Dab-Tyr-Dab-[cyclo(-NH-...-Dab-$^D$Leu-Leu-Dab-Dab-Thr-)-Dap-Thr-Dab-]-$^D$Dab-Ser-Trp-Ser-Nle-Asp-Ser-NH$_2$ TABLE 1-continued
Examples (Ex.)
In the below-mentioned examples, amino acid residues are connected in either direction from the α carbonyl (C=O) point of attachment to the α nitrogen (N) of the next element, unless otherwise indicated. Other linkages, residues, connection of residues and modifications are as specified.
| Ex. No. | Sequence |
| --- | --- |
| Ex. 326[g)] | 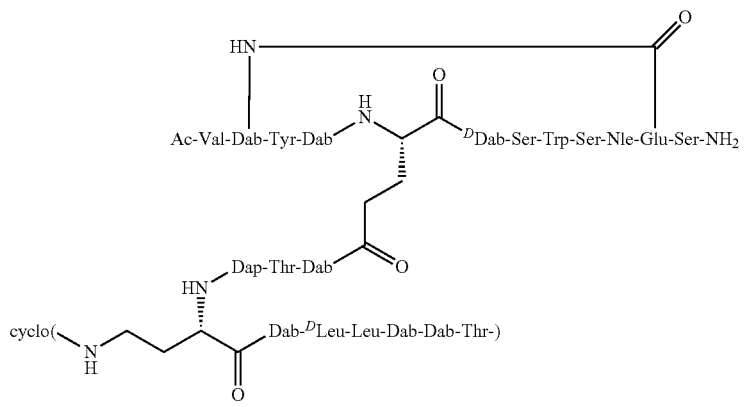 |
| Ex. 327[g)] | 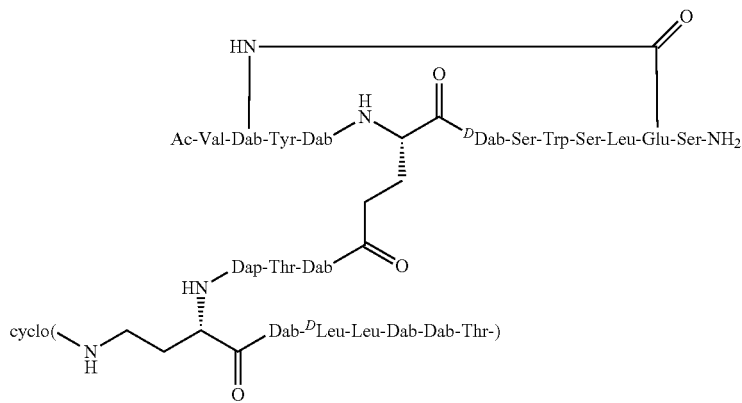 |
| Ex. 328[a)] | 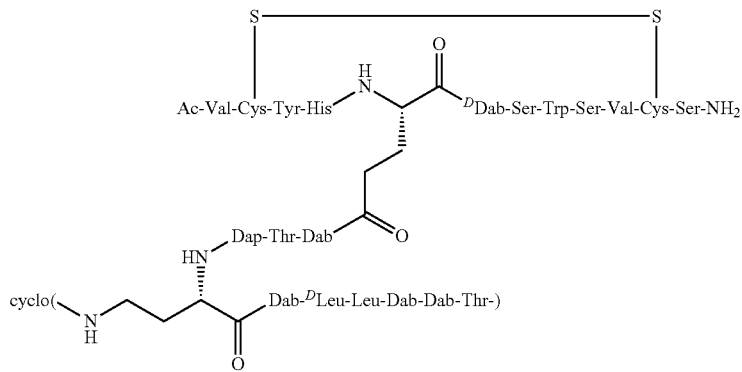 |

TABLE 1-continued
Examples (Ex.)
In the below-mentioned examples, amino acid residues are connected in either
direction from the α carbonyl (C=O) point of attachment to the α nitrogen (N) of the
next element, unless otherwise indicated. Other linkages, residues, connection of
residues and modifications are as specified.
| Ex. No. | Sequence |
| --- | --- |
| Ex. 329[a)] | 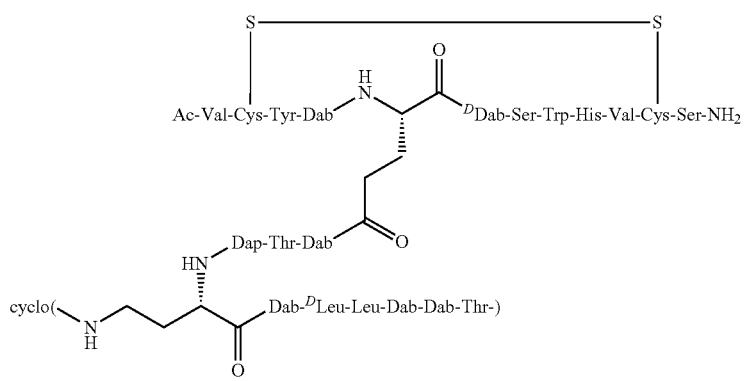 |
| Ex. 330[a)] | 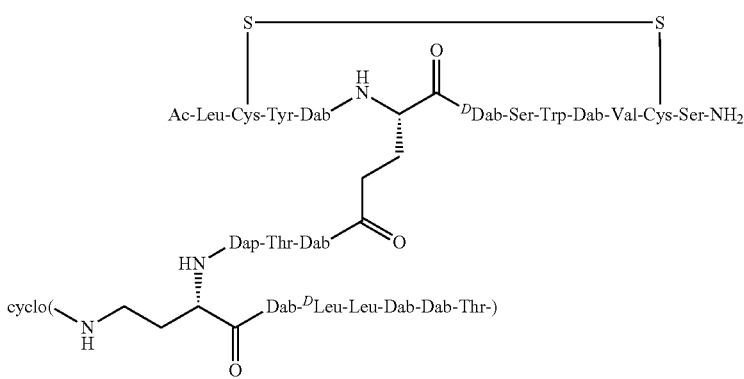 |
| Ex. 331[a)] | 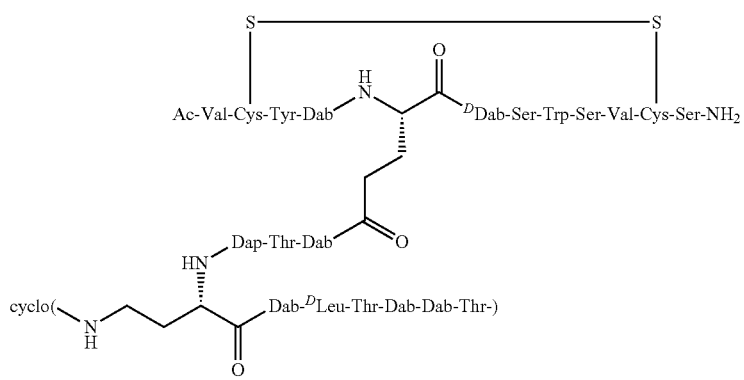 |

TABLE 1-continued
Examples (Ex.)
In the below-mentioned examples, amino acid residues are connected in either
direction from the α carbonyl (C=O) point of attachment to the α nitrogen (N) of the
next element, unless otherwise indicated. Other linkages, residues, connection of
residues and modifications are as specified.
| Ex. No. | Sequence |
| --- | --- |
| Ex. 332[a)] | 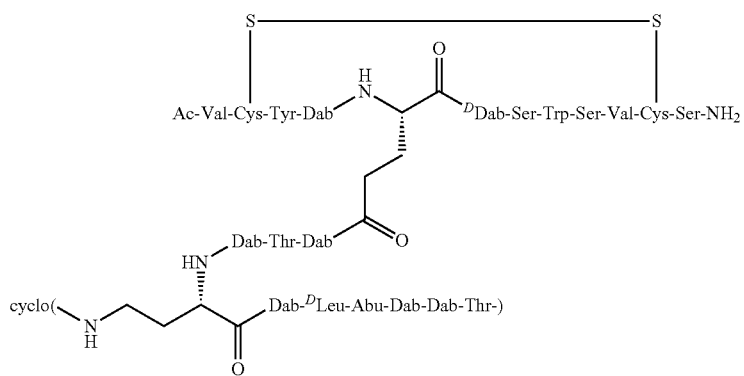 |
| Ex. 333[a)] | 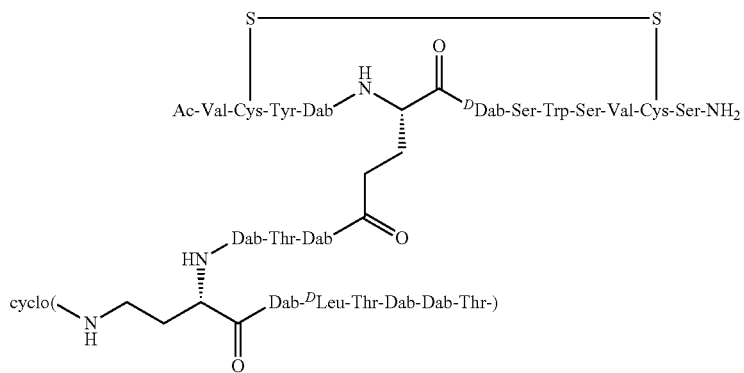 |
| Ex. 334[a)] | 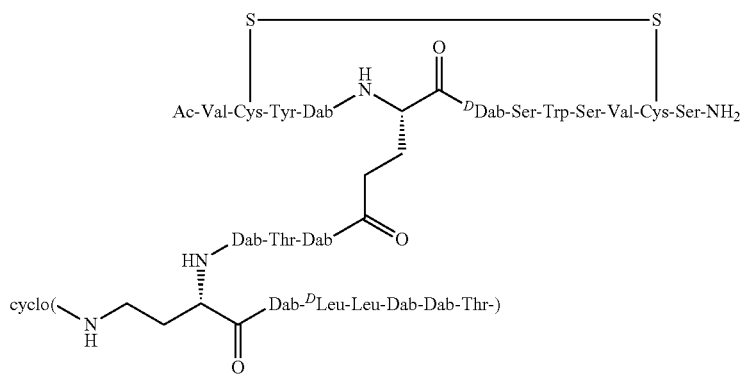 |

TABLE 1-continued
Examples (Ex.)
In the below-mentioned examples, amino acid residues are connected in either direction from the α carbonyl (C=O) point of attachment to the α nitrogen (N) of the next element, unless otherwise indicated. Other linkages, residues, connection of residues and modifications are as specified.
| Ex. No. | Sequence |
|---|---|
| Ex. 335[a)] | 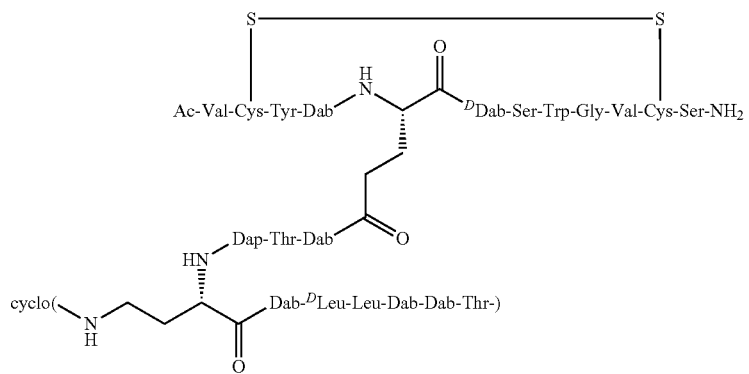 |
| Ex. 336[a)] | 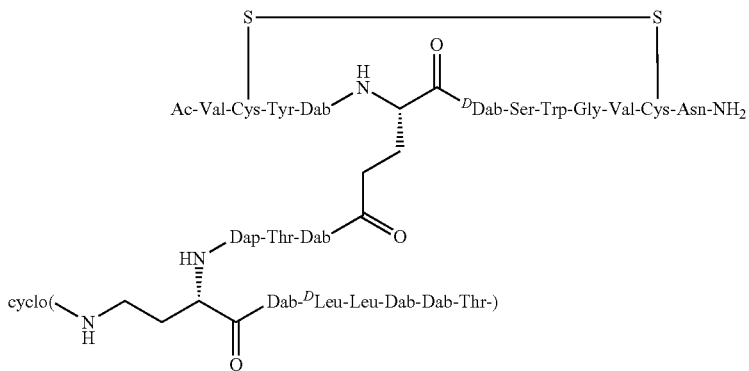 |
| Ex. 337[a)] | 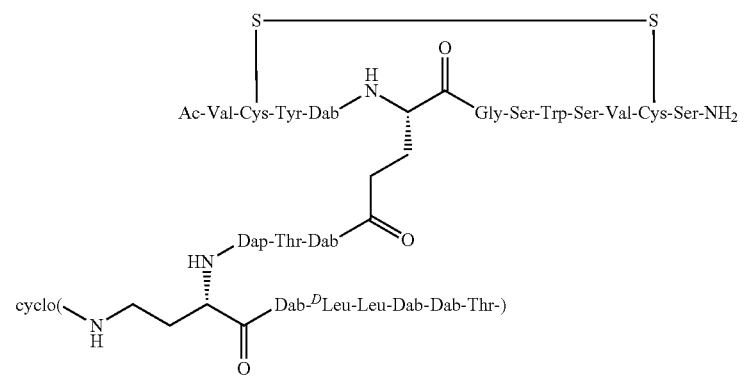 |

TABLE 1-continued
Examples (Ex.)
In the below-mentioned examples, amino acid residues are connected in either direction from the α carbonyl (C═O) point of attachment to the α nitrogen (N) of the next element, unless otherwise indicated. Other linkages, residues, connection of residues and modifications are as specified.
| Ex. No. | Sequence |
|---|---|
| Ex. 338[a)] | 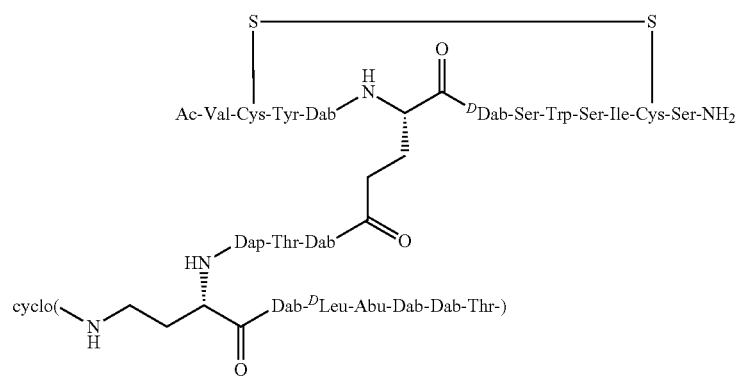 |
| Ex. 339[a)] | 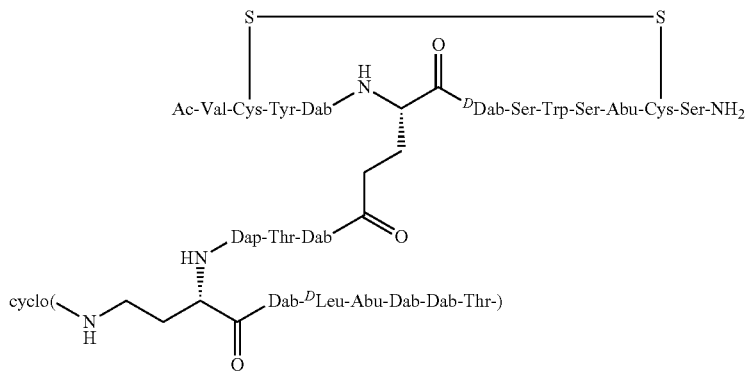 |
| Ex. 340[a) e)] | 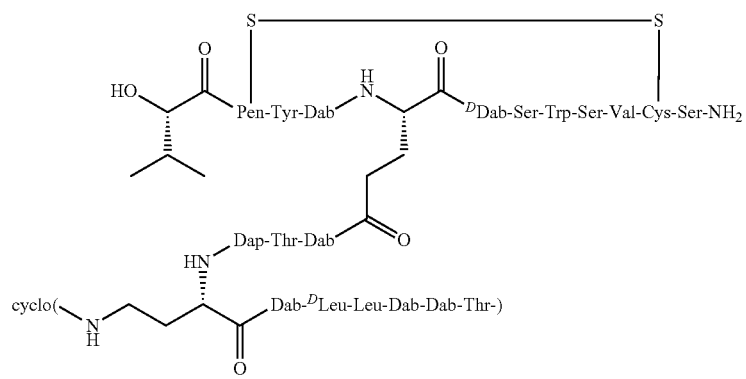 |

TABLE 1-continued
Examples (Ex.)
In the below-mentioned examples, amino acid residues are connected in either
direction from the α carbonyl (C=O) point of attachment to the α nitrogen (N) of the
next element, unless otherwise indicated. Other linkages, residues, connection of
residues and modifications are as specified.
| Ex. No. | Sequence |
|---|---|
| Ex. 341[g)] | 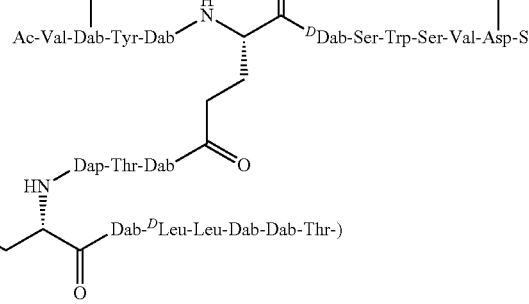 |
| Ex. 342[a)] | 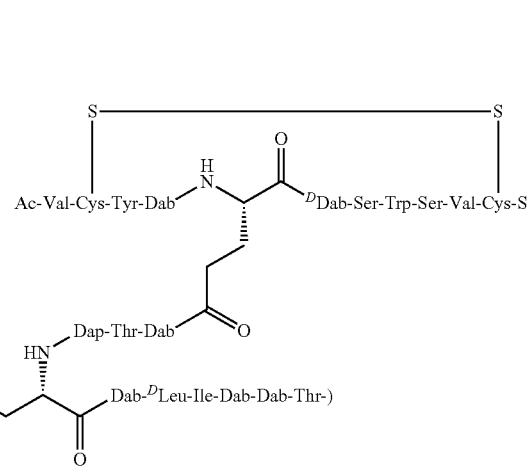 |
| Ex. 343[a)] | 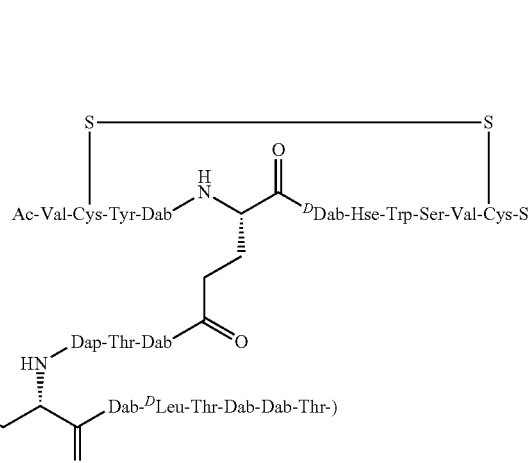 |

TABLE 1-continued
Examples (Ex.)
In the below-mentioned examples, amino acid residues are connected in either
direction from the α carbonyl (C=O) point of attachment to the α nitrogen (N) of the
next element, unless otherwise indicated. Other linkages, residues, connection of
residues and modifications are as specified.
| Ex. No. | Sequence |
|---|---|
| Ex. 344[a) e)] | 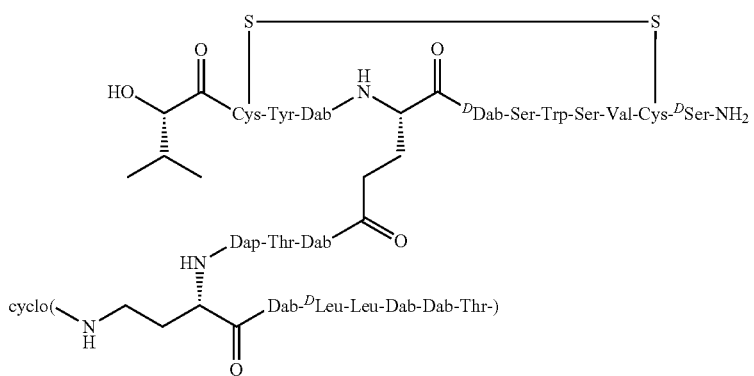 |
| Ex. 345[a)] | 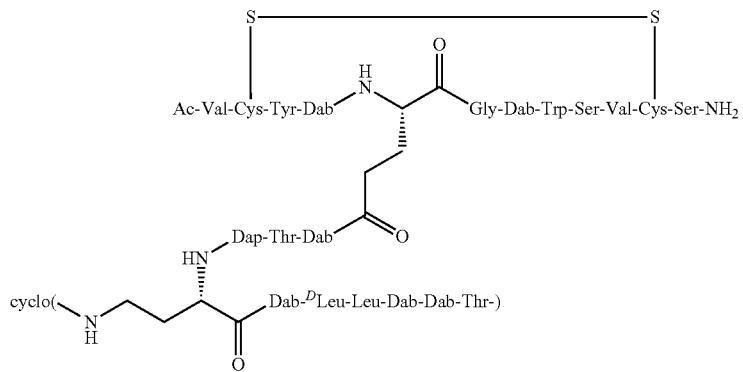 |
| Ex. 346[g)] | 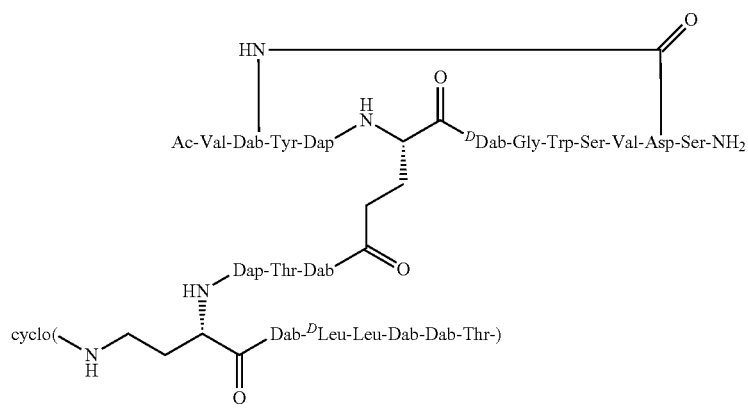 |

TABLE 1-continued
Examples (Ex.)
In the below-mentioned examples, amino acid residues are connected in either
direction from the α carbonyl (C=O) point of attachment to the α nitrogen (N) of the
next element, unless otherwise indicated. Other linkages, residues, connection of
residues and modifications are as specified.
| Ex. No. | Sequence |
|---|---|
| Ex. 347[g) e)] | 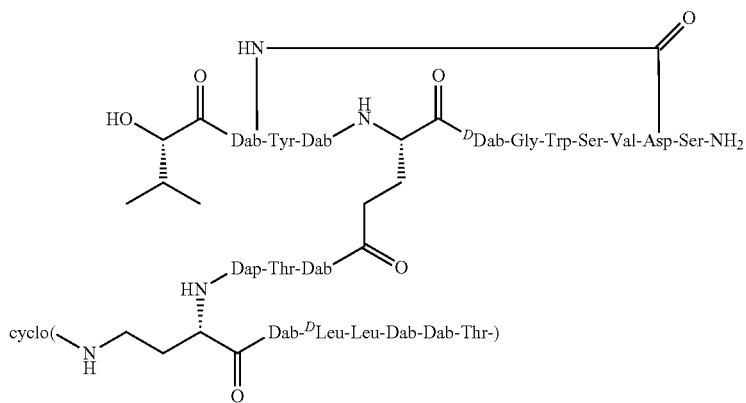 |
| Ex. 348[g)] | 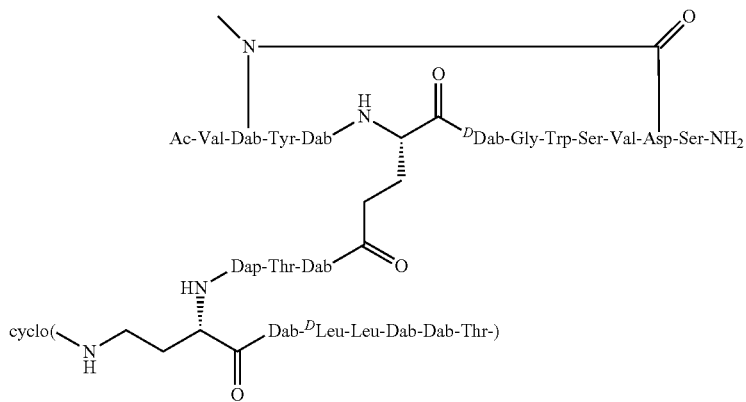 |
| Ex. 349[g)] | 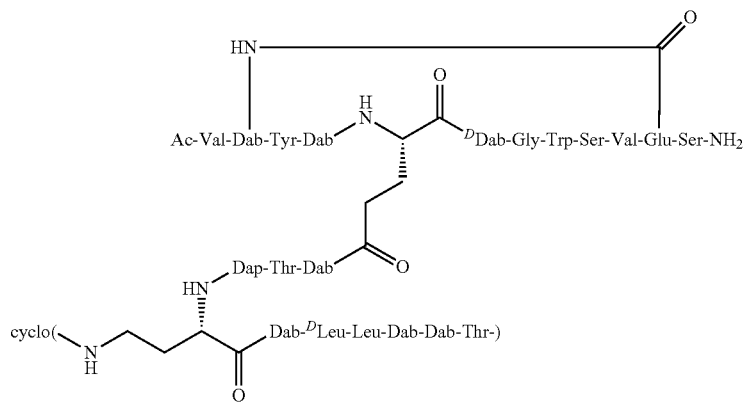 |

TABLE 1-continued
Examples (Ex.)
In the below-mentioned examples, amino acid residues are connected in either direction from the α carbonyl (C=O) point of attachment to the α nitrogen (N) of the next element, unless otherwise indicated. Other linkages, residues, connection of residues and modifications are as specified.
| Ex. No. | Sequence |
| --- | --- |
Ex. 350[a)]
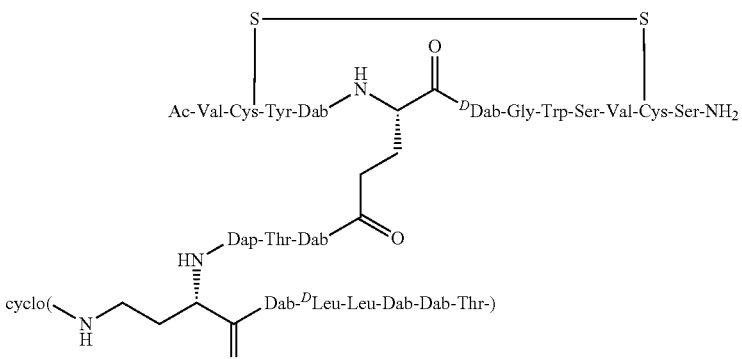
Ex. 351[g)]
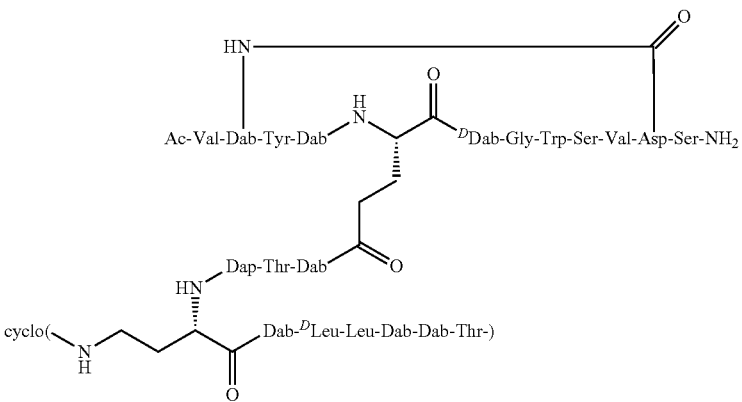
Ex. 352[a)]
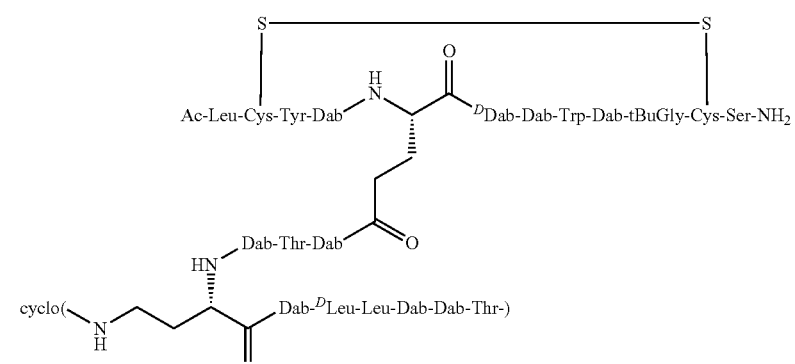

TABLE 1-continued
Examples (Ex.)
In the below-mentioned examples, amino acid residues are connected in either
direction from the α carbonyl (C=O) point of attachment to the α nitrogen (N) of the
next element, unless otherwise indicated. Other linkages, residues, connection of
residues and modifications are as specified.
| Ex. No. | Sequence |
| --- | --- |
| Ex. 353[a)] | 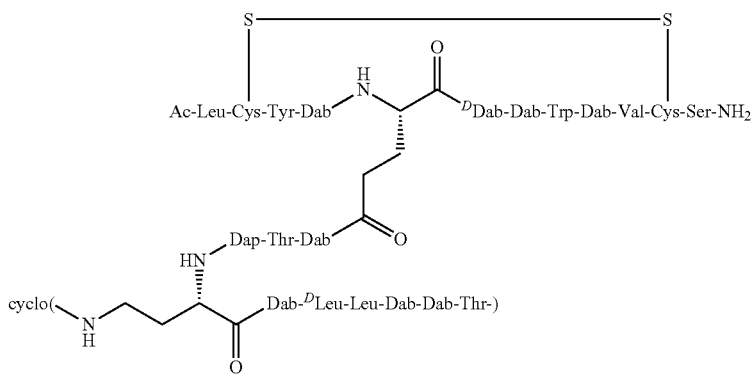 |
| Ex. 354[a)] | 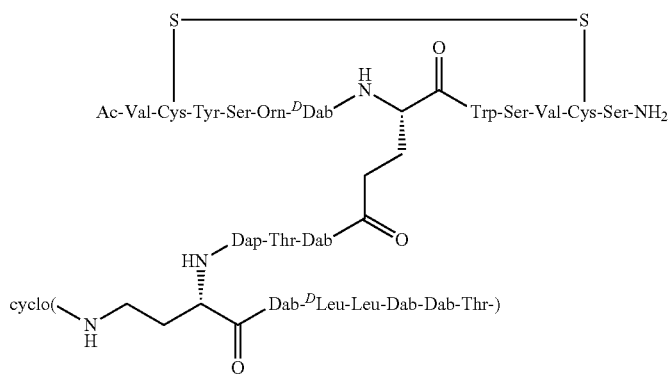 |
| Ex. 355[a)] | 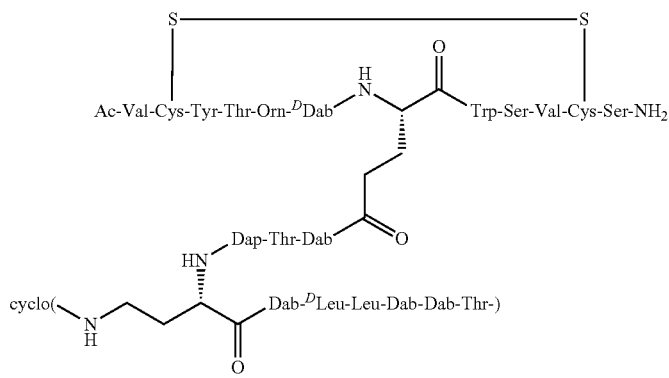 |

TABLE 1-continued
Examples (Ex.)
In the below-mentioned examples, amino acid residues are connected in either
direction from the α carbonyl (C=O) point of attachment to the α nitrogen (N) of the
next element, unless otherwise indicated. Other linkages, residues, connection of
residues and modifications are as specified.
| Ex. No. | Sequence |
|---|---|
| Ex. 356[a)] | 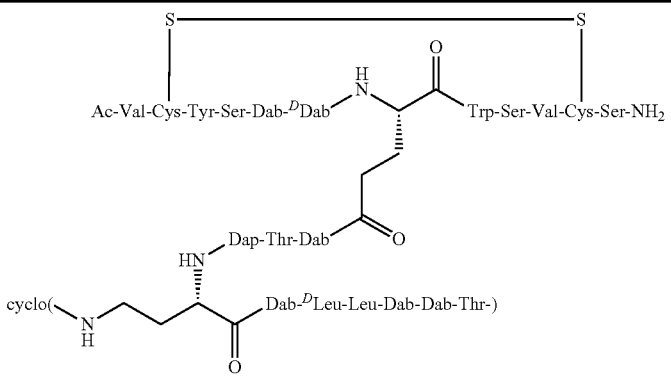 |
| Ex. 357[a)] | 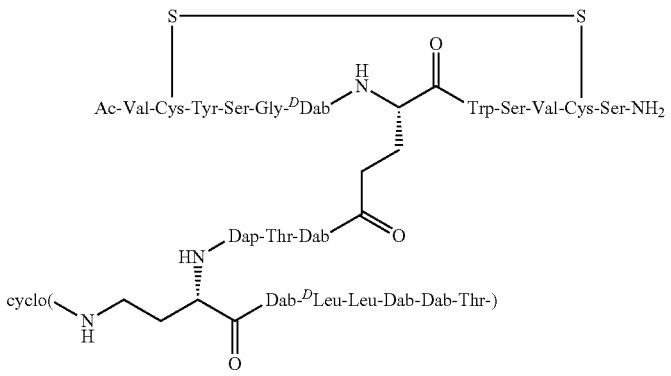 |
| Ex. 358[a)] | 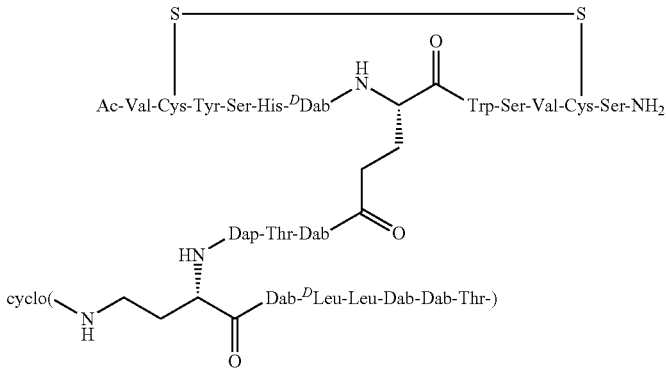 |
| Ex. 359[a)] | 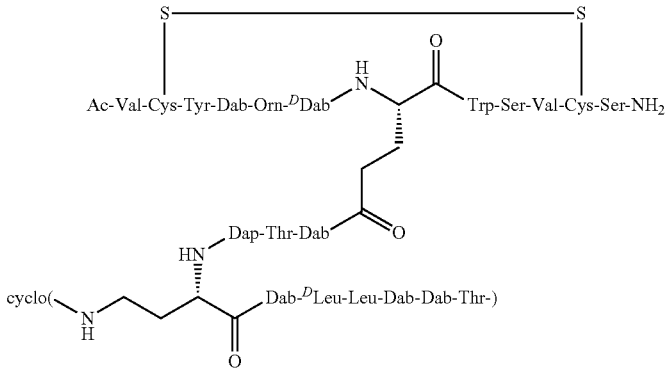 |

TABLE 1-continued
Examples (Ex.)
In the below-mentioned examples, amino acid residues are connected in either
direction from the α carbonyl (C=O) point of attachment to the α nitrogen (N) of the
next element, unless otherwise indicated. Other linkages, residues, connection of
residues and modifications are as specified.
| Ex. No. | Sequence |
| --- | --- |
| Ex. 360[a)] | 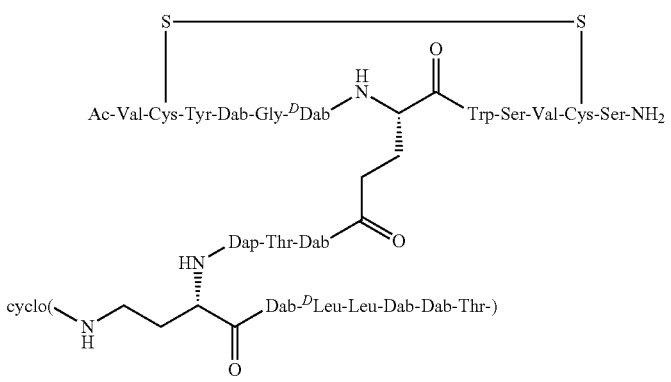 |
| Ex. 361[a)] | 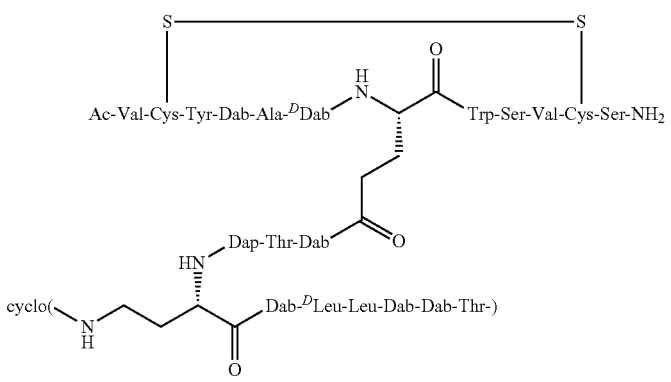 |
| Ex. 362[a)] | 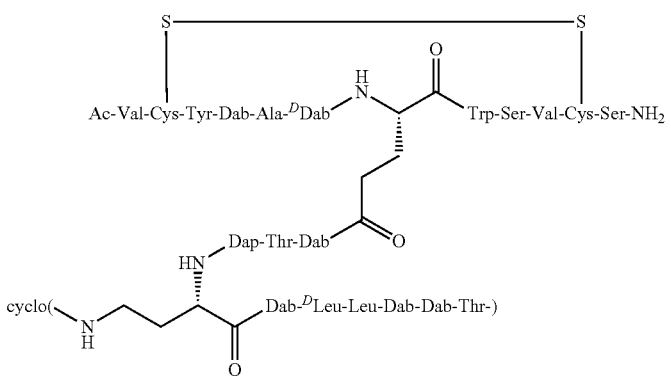 |

TABLE 1-continued
Examples (Ex.)
In the below-mentioned examples, amino acid residues are connected in either
direction from the α carbonyl (C=O) point of attachment to the α nitrogen (N) of the
next element, unless otherwise indicated. Other linkages, residues, connection of
residues and modifications are as specified.
| Ex. No. | Sequence |
|---|---|
| Ex. 363[a)] | 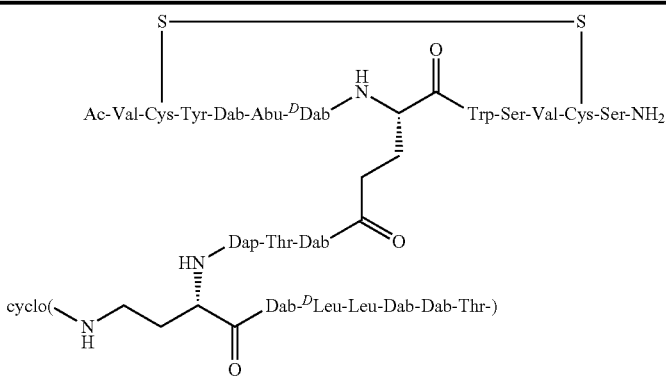 |
| Ex. 364[a)] | 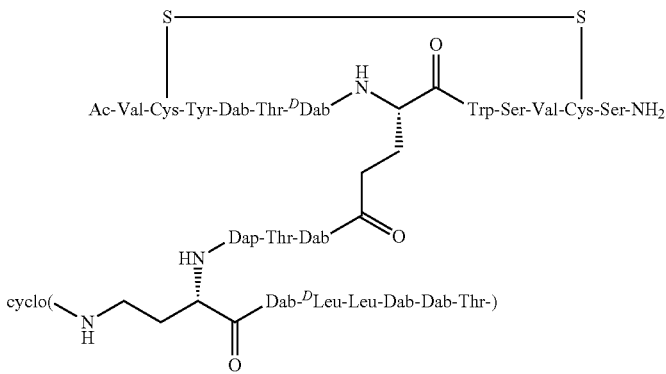 |
| Ex. 365[a)] | 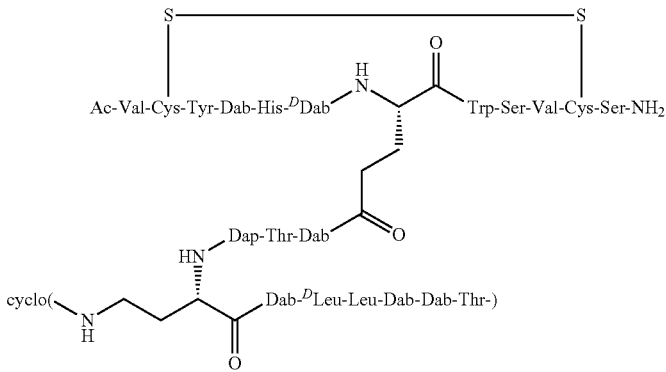 |
| Ex. 366[a)] | 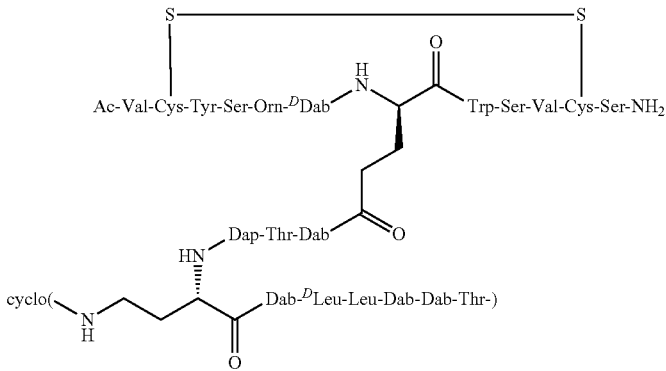 |

TABLE 1-continued
Examples (Ex.)
In the below-mentioned examples, amino acid residues are connected in either
direction from the α carbonyl (C=O) point of attachment to the α nitrogen (N) of the
next element, unless otherwise indicated. Other linkages, residues, connection of
residues and modifications are as specified.
| Ex. No. | Sequence |
|---|---|
| Ex. 367[a)] | 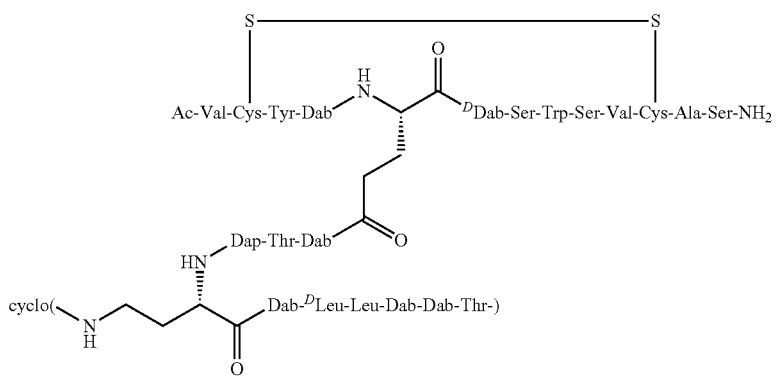 |
| Ex. 368[a)] | 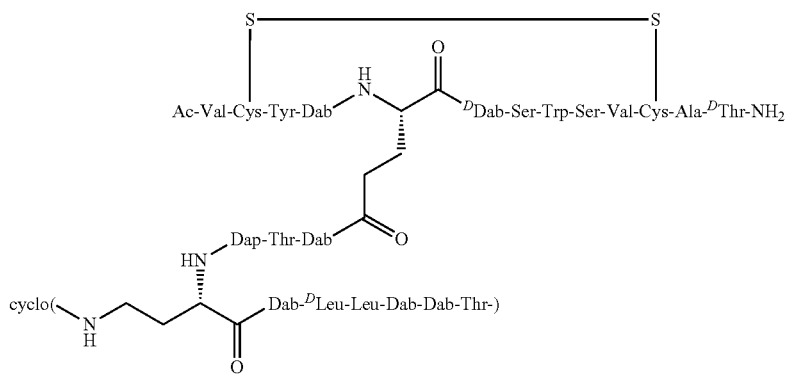 |
| Ex. 369[a)] | 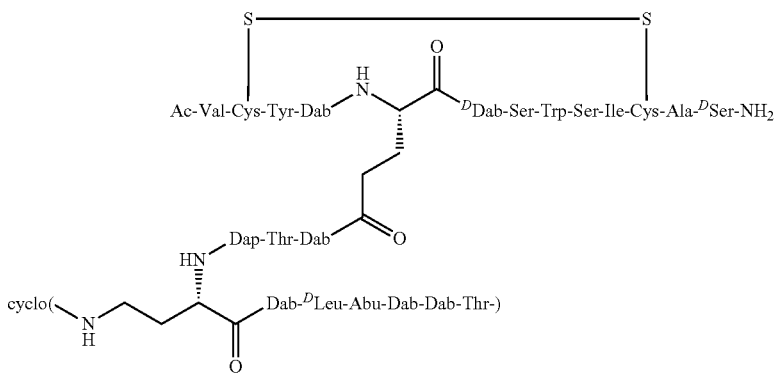 |

TABLE 1-continued
Examples (Ex.)
In the below-mentioned examples, amino acid residues are connected in either
direction from the α carbonyl (C=O) point of attachment to the α nitrogen (N) of the
next element, unless otherwise indicated. Other linkages, residues, connection of
residues and modifications are as specified.
| Ex. No. | Sequence |
| --- | --- |
| Ex. 370[a)] | 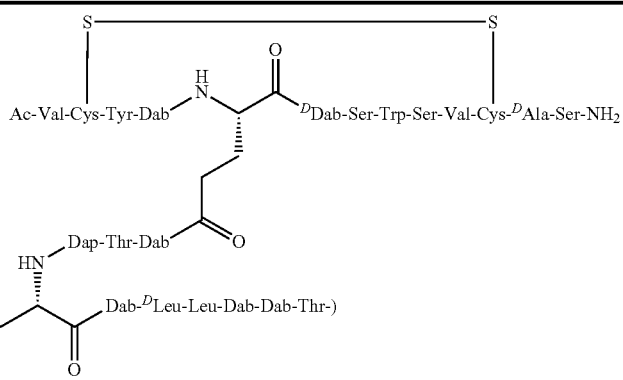 |
| Ex. 371[a)] | 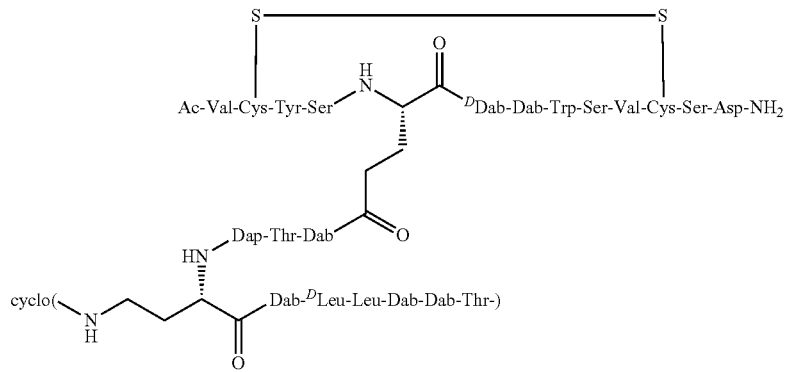 |
| Ex. 372[a) e)] | 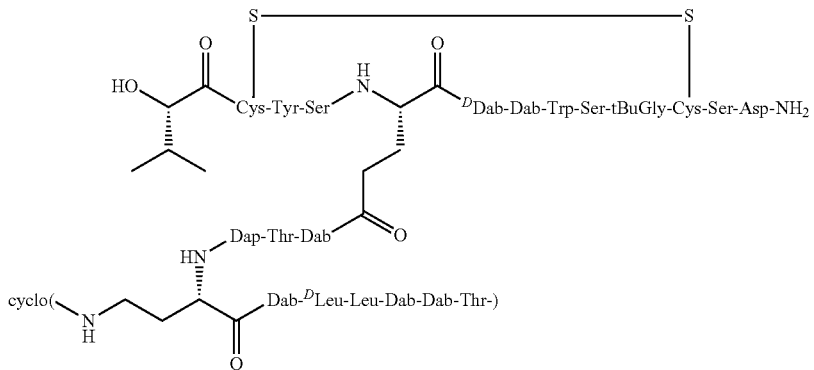 |
| Ex. 373[a)] | 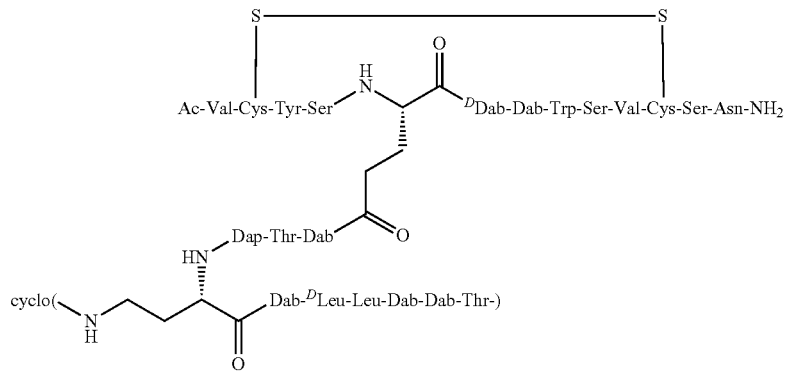 |

TABLE 1-continued

Examples (Ex.)
In the below-mentioned examples, amino acid residues are connected in either
direction from the α carbonyl (C=O) point of attachment to the α nitrogen (N) of the
next element, unless otherwise indicated. Other linkages, residues, connection of
residues and modifications are as specified.

| Ex. No. | Sequence |
|---|---|
| Ex. 374[a)] | Ac-Val-Cys-Tyr-Dab-[NH-CH(-)-C(=O)]-DDab-Ser-Trp-Ser-Val-Cys-Ser-DAsp-NH2, with S–S bridge between the two Cys residues; side chain of central residue extends as -CH2-CH2-C(=O)-Dab-Thr-Dap-NH- linked to cyclo(-NH-CH2-CH2-CH(NH-)-C(=O)-Dab-DLeu-Leu-Dab-Dab-Thr-) |
| Ex. 375[a)] | Ac-Val-Cys-Tyr-Dab-[NH-CH(-)-C(=O)]-DDab-Ser-Trp-Ser-Val-Cys-Ser-DSer-NH2, with S–S bridge between the two Cys residues; side chain of central residue extends as -CH2-CH2-C(=O)-Dab-Thr-Dap-NH- linked to cyclo(-NH-CH2-CH2-CH(NH-)-C(=O)-Dab-DLeu-Leu-Dab-Dab-Thr-) |
| Ex. 376[a) e)] | HO-CH(iPr)-C(=O)-Cys-Tyr-Dab-[NH-CH(-)-C(=O)]-DDab-Gly-Trp-Ser-Ile-Cys-Ser-DSer-NH2, with S–S bridge between the two Cys residues; side chain of central residue extends as -CH2-CH2-C(=O)-Dab-Thr-Dap-NH- linked to cyclo(-NH-CH2-CH2-CH(NH-)-C(=O)-Dab-DLeu-Abu-Dab-Dab-Thr-) |

TABLE 1-continued
Examples (Ex.)
In the below-mentioned examples, amino acid residues are connected in either
direction from the α carbonyl (C=O) point of attachment to the α nitrogen (N) of the
next element, unless otherwise indicated. Other linkages, residues, connection of
residues and modifications are as specified.
| Ex. No. | Sequence |
|---|---|
| Ex. 377[a)] | 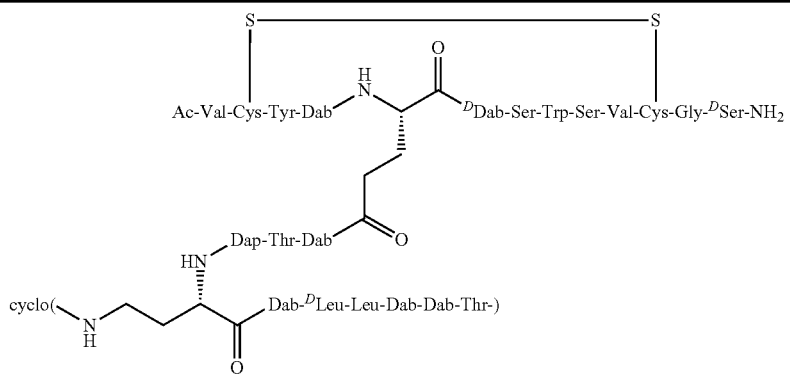 |
| Ex. 378[a)] | 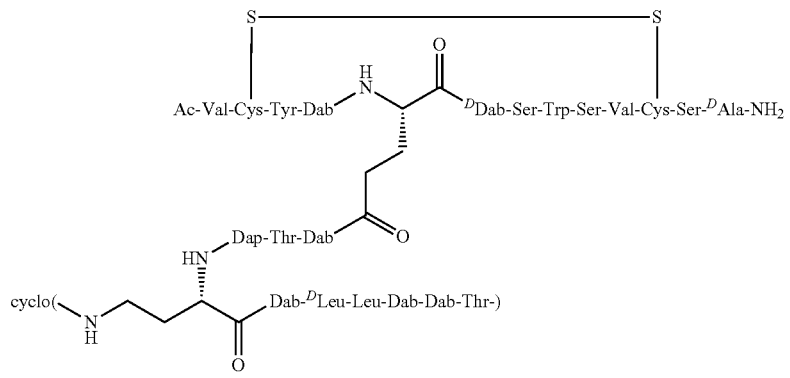 |
| Ex. 379[a) e)] | 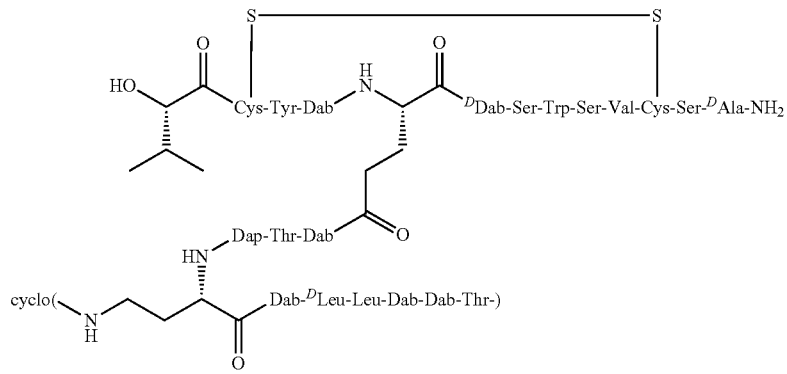 |
| Ex. 380[a)] | 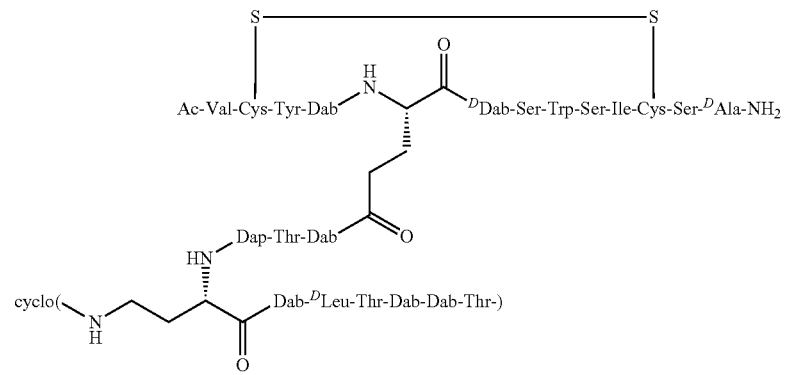 |

TABLE 1-continued
Examples (Ex.)
In the below-mentioned examples, amino acid residues are connected in either
direction from the α carbonyl (C=O) point of attachment to the α nitrogen (N) of the
next element, unless otherwise indicated. Other linkages, residues, connection of
residues and modifications are as specified.
| Ex. No. | Sequence |
| --- | --- |
Ex. 381[a) e)]
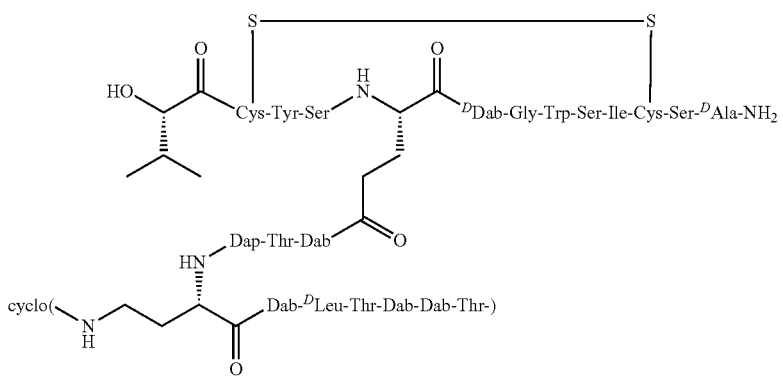
Ex. 382[a) e)]
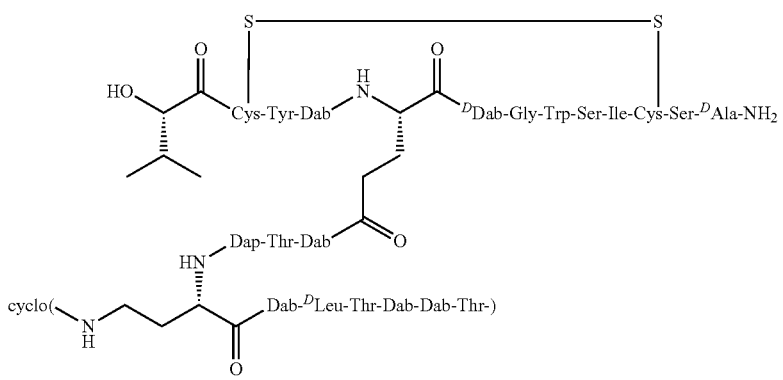
Ex. 383[a)]
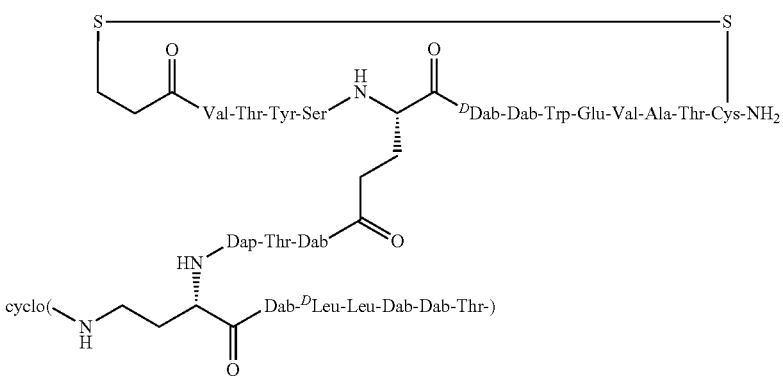

TABLE 1-continued

Examples (Ex.)
In the below-mentioned examples, amino acid residues are connected in either
direction from the α carbonyl (C═O) point of attachment to the α nitrogen (N) of the
next element, unless otherwise indicated. Other linkages, residues, connection of
residues and modifications are as specified.

| Ex. No. | Sequence |
|---|---|
| Ex. 384[a)] | |

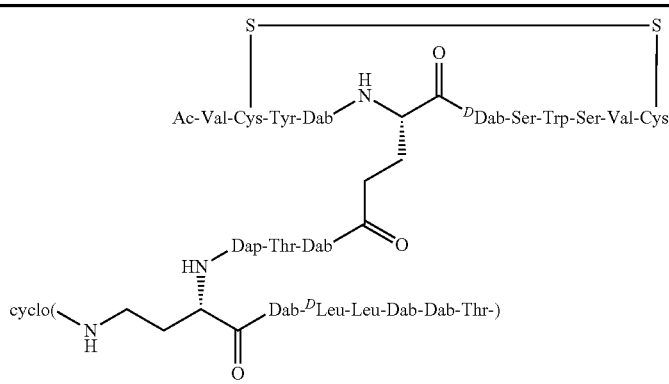

| Ex. 385[a)] | |

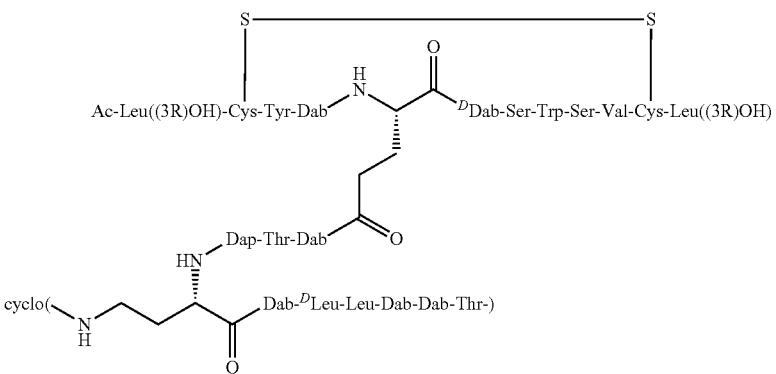

[a)]Disulfide interstrand linkage(s) between indicated amino acid residues in module A, involving disulfide bond(s) between a pair(s) of side-chain thiol groups as specified.
[b)]1,2-amino alcohol residue attached to the C-terinal amino acid residue of module A, involving an amide bond between the α-carboxyl group of the C-terminal amino acid residue and the amino group of the amino alcohol residue.
[c)]Acid residue attached to the N-terminal amino acid residue of a module A, involving an amide bond between the carboxy group of the acid residue and the α-amino group of the N-terminal amino acid residue.
[e)]α-hydroxy acid residue attached to the N-terminal amino acid residue of module A, involving an amide bond between the carboxyl group of the hydroxy acid residue and the α-amino group of the N-terminal amino acid residue.
[f)]Lactam linkage between the two indicated amino acid residues in a module A, involving an amide bond between the side-chain amino group of the residue at $P^2$ and the α-carboxyl group of the residue at $P^{11}$.
[g)]Lactam interstrand linkage between the two indicated amino acid residues in module A, involving an amide bond between a side-chain amino group and a side-chain carboxyl group.
[h)]1,2-amino alcohol residue attached to the C-terminal amino acid residue of module A, involving an amide bond between and the α-carboxyl group of the C-terminal amino acid residue and the amino group of the amino alcohol residue, and α-hydroxy acid residue attached to the N-terminal amino acid residue of module A, involving an amide bond between the carboxyl group of the hydroxy acid residue and the α-amino group of the N-terminal amino acid residue.
[i)]Disulfide interstrand linkage between the indicated amino acid residue and the indicated acid residue in module A, involving a disulfide bond between a pair of side-chain thiol groups as specified.

TABLE 2

| Analytical data Ex. | Meth. [a)] | MS | RT [b)] | Pur. [c)] |
|---|---|---|---|---|
| 1 | A | 776.7 [g)] | 4.11 | 87 |
| 2 | A | 795.8 [g)] | 3.98 | 83 |
| 3 | B | 791.3 [g)] | 3.55 | 80 |
| 4 | B | 791.3 [g)] | 3.69 | 90 |
| 5 | A | 589.9 [h)] | 3.93 | 91 |
| 6 | A | 785.4 [g)] | 3.81 | 92 |
| 7 | A | 771.8 [g)] | 3.96 | 92 |
| 8 | A | 771.4 [g)] | 3.95 | 90 |
| 9 | A | 766.4 [g)] | 3.52 | 88 |
| 10 | A | 775.8 [g)] | 3.89 | 91 |
| 11 | A | 780.9 [g)] | 3.75 | 79 |
| 12 | A | 771.9 [g)] | 3.45 | 92 |
| 13 | A | 775.7 [g)] | 3.69 | 77 |
| 14 | A | 780.0 [g)] | 3.62 | 85 |
| 15 | B | 783.3 [g)] | 3.62 | 94 |
| 16 [d)] | A | 778.8 [g)] | 4.12 | 95 |
| 17 | B | 779.2 [g)] | 3.99 | 74 |
| 18 | A | 774.3 [g)] | 4.37 | 82 |
| 19 | A | 778.5 [g)] | 4.11 | 83 |
| 20 | B | 783.5 [g)] | 3.75 | 76 |
| 21 | A | 783.5 [g)] | 4.29 | 77 |
| 22 | A | 774.3 [g)] | 4.22 | 75 |
| 23 | A | 769.5 [g)] | 4.37 | 71 |
| 24 | B | 760.5 [g)] | 3.80 | 70 |

TABLE 2-continued

| Ex. | Meth.[a] | MS | RT[b] | Pur.[c] |
|---|---|---|---|---|
| 25 | A | 773.9[g] | 4.34 | 84 |
| 26 | A | 795.2[g] | 4.51 | 83 |
| 27 | A | 773.9[g] | 4.85 | 83 |
| 28 | A | 773.9[g] | 3.92 | 77 |
| 29 | B | 778.7[g] | 3.55 | 75 |
| 30 | A | 783.2[g] | 3.96 | 80 |
| 31[d] | E | 774.3[g] | 6.84 | 95 |
| 32 | B | 778.5[g] | 3.90 | 73 |
| 33 | A | 778.8[g] | 4.35 | 81 |
| 34 | A | 778.5[g] | 4.31 | 82 |
| 35 | B | 769.2[g] | 3.82 | 77 |
| 36 | A | 790.2[g] | 4.34 | 80 |
| 37 | A | 768.9[g] | 3.92 | 76 |
| 38 | A | 773.8[g] | 4.09 | 80 |
| 39[d] | A | 814.7[g] | 3.64 | 95 |
| 40 | A | 842.3[g] | 4.76 | 92 |
| 41[d] | B | 809.7[g] | 3.28 | 92 |
| 42[d] | B | 800.7[g] | 3.21 | 95 |
| 43[d] | B | 600.5[h] | 3.03 | 92 |
| 44 | C | 814.4[g] | 2.83 | 93 |
| 45 | C | 809.7[g] | 2.79 | 95 |
| 46 | C | 810.3[g] | 2.94 | 93 |
| 47 | C | 600.7[h] | 2.62 | 95 |
| 48 | C | 600.4[h] | 2.55 | 94 |
| 49 | C | 819.0[g] | 2.78 | 92 |
| 50 | A | 603.9[h] | 3.34 | 90 |
| 51 | C | 607.4[h] | 2.62 | 84 |
| 52 | A | 814.5[g] | 3.86 | 81 |
| 53 | C | 600.9[h] | 2.70 | 92 |
| 54 | C | 607.9[h] | 2.70 | 91 |
| 55 | A | 798.4[g] | 3.54 | 93 |
| 56 | A | 803.0[g] | 3.40 | 83 |
| 57 | A | 776.0[g] | 3.40 | 88 |
| 58[d] | B | 796.5[g] | 3.59 | 95 |
| 59 | A | 777.0[g] | 3.97 | 80 |
| 60 | A | 796.5[g] | 3.88 | 84 |
| 61 | A | 812.4[g] | 3.92 | 81 |
| 62 | A | 809.9[g] | 3.74 | 88 |
| 63 | A | 809.8[g] | 3.57 | 89 |
| 64 | A | 809.8[g] | 3.57 | 84 |
| 65 | A | 607.5[h] | 3.82 | 93 |
| 66 | A | 809.7[g] | 3.53 | 92 |
| 67 | A | 809.7[g] | 3.81 | 89 |
| 68 | A | 809.9[g] | 3.72 | 71 |
| 69 | A | 819.4[g] | 3.90 | 92 |
| 70 | A | 820.0[g] | 3.85 | 85 |
| 71 | A | 829.2[g] | 3.87 | 92 |
| 72 | A | 786.4[g] | 3.93 | 80 |
| 73 | A | 781.9[g] | 3.97 | 78 |
| 74 | A | 801.3[g] | 3.86 | 80 |
| 75 | A | 819.8[g] | 3.85 | 79 |
| 76 | A | 806.0[g] | 3.86 | 90 |
| 77 | A | 804.9[g] | 3.57 | 93 |
| 78 | A | 796.7[g] | 3.79 | 87 |
| 79 | A | 796.5[g] | 3.89 | 86 |
| 80 | A | 796.5[g] | 3.84 | 82 |
| 81 | A | 805.8[g] | 3.84 | 87 |
| 82 | A | 806.0[g] | 3.83 | 84 |
| 83 | A | 801.0[g] | 3.82 | 85 |
| 84 | A | 607.9[h] | 3.98 | 78 |
| 85 | B | 810.4[g] | 3.77 | 78 |
| 86 | A | 815.0[g] | 3.87 | 92 |
| 87 | A | 593.4[h] | 3.98 | 84 |
| 88 | A | 796.7[g] | 3.98 | 87 |
| 89 | A | 796.4[g] | 3.69 | 81 |
| 90 | B | 810.4[g] | 3.59 | 81 |
| 91 | A | 810.4[g] | 3.87 | 87 |
| 92[d] | A | 800.5[g] | 4.05 | 95 |
| 93 | B | 801.3[g] | 3.72 | 82 |
| 94 | A | 810.0[g] | 3.96 | 91 |
| 95 | A | 796.4[g] | 3.78 | 88 |
| 96[d] | A | 810.2[g] | 3.67 | 95 |
| 97 | A | 791.8[g] | 3.62 | 82 |
| 98 | A | 805.4[g] | 3.57 | 88 |
| 99 | A | 796.3[g] | 3.83 | 90 |
| 100 | A | 800.4[g] | 3.68 | 93 |
| 101 | A | 801.0[g] | 3.82 | 73 |
| 102 | A | 801.0[g] | 3.79 | 88 |
| 103 | A | 787.0[g] | 3.77 | 82 |
| 104 | A | 796.4[g] | 3.88 | 84 |
| 105[d] | A | 815.2[g] | 3.85 | 95 |
| 106[d] | B | 791.8[g] | 3.57 | 95 |
| 107[d] | B | 791.8[g] | 3.59 | 95 |
| 108[d] | A | 791.8[g] | 3.90 | 95 |
| 109[d] | A | 782.4[g] | 3.60 | 95 |
| 110[d] | A | 797.2[g] | 3.79 | 95 |
| 111[d] | A | 791.5[g] | 3.82 | 95 |
| 112[d] | A | 791.8[g] | 3.91 | 95 |
| 113[d] | A | 814.4[g] | 3.55 | 95 |
| 114[d] | A | 805.0[g] | 3.76 | 95 |
| 115[d] | A | 786.7[g] | 3.68 | 95 |
| 116[d] | A | 796.0[g] | 3.71 | 95 |
| 117[d] | A | 800.7[g] | 3.78 | 95 |
| 119 | A | 805.0[g] | 3.91 | 87 |
| 120 | A | 804.7[g] | 3.72 | 81 |
| 121 | A | 805.2[g] | 3.97 | 81 |
| 122 | A | 814.7[g] | 4.51 | 78 |
| 123 | A | 800.8[g] | 3.92 | 87 |
| 124 | A | 800.7[g] | 3.91 | 75 |
| 125 | A | 805.2[g] | 3.69 | 82 |
| 126 | A | 809.0[g] | 3.62 | 79 |
| 127 | A | 738.3[g] | 4.25 | 85 |
| 128[d] | A | 805.2[g] | 3.74 | 95 |
| 129[d] | E | 814.9[g] | 6.50 | 95 |
| 130[d] | E | 1193.2[f] | 6.01 | 95 |
| 131[d] | E | 819.3[g] | 6.28 | 95 |
| 132[d] | A | 800.8[g] | 3.90 | 95 |
| 133[d] | A | 805.2[g] | 3.87 | 95 |
| 134[d] | A | 829.8[g] | 3.71 | 95 |
| 135[d] | A | 823.8[g] | 3.72 | 95 |
| 136[d] | A | 795.8[g] | 3.41 | 95 |
| 137[d] | B | 790.8[g] | 3.03 | 95 |
| 138[d] | D | 814.9[g] | 3.55 | 94 |
| 139[d] | A | 805.5[g] | 3.41 | 95 |
| 140[d] | D | 805.5[g] | 3.25 | 95 |
| 141[d] | A | 805.2[g] | 3.68 | 95 |
| 142[d] | A | 805.2[g] | 3.75 | 95 |
| 143[d] | A | 800.3[g] | 3.57 | 94 |
| 144[d] | A | 809.8[g] | 3.89 | 95 |
| 145[d] | A | 809.8[g] | 3.86 | 95 |
| 146 | A | 802.8[g] | 3.70 | 89 |
| 147 | A | 1196.8[f] | 3.56 | 84 |
| 148 | A | 798.2[g] | 3.74 | 88 |
| 149 | A | 793.3[g] | 3.63 | 82 |
| 150[d] | A | 814.4[g] | 3.66 | 95 |
| 151[d] | A | 823.9[g] | 3.64 | 95 |
| 152[d] | A | 819.3[g] | 3.67 | 95 |
| 153[d] | A | 818.8[g] | 3.63 | 95 |
| 154[d] | A | 819.2[g] | 3.72 | 94 |
| 155 | B | 819.2[g] | 3.38 | 80 |
| 156 | A | 823.9[g] | 3.74 | 82 |
| 157 | B | 805.5[g] | 3.40 | 76 |
| 158 | A | 828.5[g] | 3.67 | 89 |
| 159 | A | 833.2[g] | 3.75 | 90 |
| 160 | A | 604.4[h] | 3.98 | 87 |
| 161 | B | 604.3[h] | 3.64 | 90 |
| 162 | A | 597.5[h] | 3.97 | 88 |
| 163 | A | 796.4[g] | 3.88 | 82 |
| 164 | A | 747.3[g] | 4.37 | 88 |
| 165 | A | 746.9[g] | 4.24 | 91 |
| 166 | A | 604.0[h] | 3.79 | 90 |
| 167 | A | 593.3[h] | 3.88 | 91 |
| 168 | A | 589.8[h] | 4.04 | 89 |
| 169 | A | 604.2[h] | 3.86 | 85 |
| 170 | A | 593.2[h] | 3.92 | 87 |
| 171 | A | 786.3[g] | 4.01 | 83 |
| 172 | A | 597.3[h] | 3.76 | 91 |
| 173 | A | 781.8[g] | 3.86 | 82 |
| 174 | A | 776.9[g] | 3.97 | 79 |
| 175 | A | 815.3[g] | 3.82 | 89 |
| 176 | C | 601.3[h] | 2.71 | 84 |
| 177 | C | 604.5[h] | 2.74 | 82 |

TABLE 2-continued

| Ex. | Meth.[a)] | MS | RT[b)] | Pur.[c)] |
|---|---|---|---|---|
| 178 | C | 809.4[g)] | 2.88 | 95 |
| 179 | C | 804.4[g)] | 2.82 | 95 |
| 180 | A | 795.0[g)] | 3.54 | 79 |
| 181 | A | 804.4[g)] | 3.51 | 82 |
| 182 | C | 795.4[g)] | 2.68 | 94 |
| 183 | A | 795.4[g)] | 3.49 | 76 |
| 184 | C | 593.2[h)] | 2.62 | 82 |
| 185 | A | 800.0[g)] | 3.59 | 76 |
| 186 | C | 795.7[g)] | 2.74 | 92 |
| 187 | A | 802.3[g)] | 3.74 | 85 |
| 188[d)] | B | 796.3[g)] | 3.63 | 95 |
| 189 | A | 824.4[g)] | 3.64 | 89 |
| 190 | A | 611.5[h)] | 3.64 | 94 |
| 191[d)] | A | 815.0[g)] | 3.76 | 95 |
| 192 | B | 614.9[h)] | 3.41 | 81 |
| 193 | B | 796.0[g)] | 3.68 | 75 |
| 194 | A | 805.4[g)] | 4.00 | 88 |
| 195 | A | 1208.8[f)] | 4.05 | 84 |
| 196 | A | 805.2[g)] | 3.81 | 82 |
| 197 | B | 782.0[g)] | 3.60 | 78 |
| 198 | A | 791.4[g)] | 3.98 | 90 |
| 199[d)] | B | 791.3[g)] | 3.66 | 95 |
| 200[d)] | B | 791.4[g)] | 3.65 | 95 |
| 201[d)] | A | 781.2[g)] | 3.89 | 95 |
| 202[d)] | B | 790.8[g)] | 3.90 | 95 |
| 203[d)] | A | 795.8[g)] | 3.95 | 95 |
| 204[d)] | A | 811.2[g)] | 3.96 | 94 |
| 205 | A | 799.4[g)] | 3.58 | 82 |
| 206 | A | 813.7[g)] | 4.00 | 80 |
| 207 | A | 804.2[g)] | 4.03 | 81 |
| 208 | A | 808.4[g)] | 4.29 | 91 |
| 209 | A | 796.0[g)] | 4.13 | 74 |
| 210 | A | 796.4[g)] | 4.07 | 80 |
| 211 | B | 597.0[h)] | 3.64 | 76 |
| 212 | A | 781.7[g)] | 4.03 | 82 |
| 213 | B | 582.8[h)] | 3.75 | 74 |
| 214 | A | 582.9[h)] | 4.02 | 71 |
| 215[d)] | A | 804.8[g)] | 3.76 | 95 |
| 216 | A | 737.7[g)] | 4.54 | 83 |
| 217 | A | 737.5[g)] | 4.40 | 83 |
| 218 | A | 610.7[h)] | 3.51 | 74 |
| 219[d)] | E | 800.3[g)] | 6.60 | 95 |
| 220[d)] | E | 1206.7[f)] | 6.75 | 95 |
| 221[d)] | A | 824.2[g)] | 3.91 | 95 |
| 222[d)] | A | 819.4[g)] | 3.76 | 95 |
| 223[d)] | A | 824.8[g)] | 3.95 | 95 |
| 224[d)] | A | 819.8[g)] | 3.49 | 95 |
| 225[d)] | A | 843.0[g)] | 3.64 | 95 |
| 226[d)] | A | 824.8[g)] | 3.78 | 95 |
| 227[d)] | E | 814.5[g)] | 6.52 | 95 |
| 228 | A | 828.2[g)] | 3.97 | 92 |
| 229 | A | 808.8[g)] | 3.57 | 73 |
| 230 | A | 813.0[g)] | 3.73 | 76 |
| 232 | A | 828.4[g)] | 3.82 | 90 |
| 233 | A | 621.5[h)] | 3.87 | 81 |
| 234 | A | 857.1[g)] | 4.31 | 83 |
| 235 | A | 853.7[g)] | 4.09 | 82 |
| 236 | A | 810.4[g)] | 4.05 | 88 |
| 237 | A | 833.4[g)] | 3.62 | 78 |
| 238 | A | 837.4[g)] | 3.94 | 82 |
| 239 | A | 846.4[g)] | 4.01 | 73 |
| 240 | A | 851.8[g)] | 3.84 | 80 |
| 241 | A | 640.4[h)] | 3.59 | 72 |
| 242 | C | 644.3[h)] | 2.65 | 90 |
| 243[d)] | A | 881.6[g)] | 3.62 | 95 |
| 244 | A | 857.8[g)] | 3.91 | 83 |
| 245 | A | 839.0[g)] | 4.04 | 74 |
| 246 | A | 875.4[g)] | 3.78 | 88 |
| 247 | A | 870.6[g)] | 3.45 | 73 |
| 248 | A | 870.6[g)] | 3.46 | 74 |
| 249 | A | 875.4[g)] | 3.81 | 92 |
| 250[d)] | A | 862.2[g)] | 4.16 | 95 |
| 251[d)] | A | 800.2[g)] | 3.78 | 95 |
| 252[d)] | B | 809.8[g)] | 3.60 | 95 |
| 253[d)] | A | 805.0[g)] | 3.93 | 95 |
| 254[d)] | A | 795.5[g)] | 3.58 | 95 |
| 255[d)] | B | 800.2[g)] | 3.36 | 95 |
| 256[d)] | A | 800.4[g)] | 3.65 | 95 |
| 257[d)] | A | 795.7[g)] | 3.66 | 95 |
| 258[d)] | B | 800.2[g)] | 3.42 | 95 |
| 259[d)] | B | 805.0[g)] | 3.64 | 95 |
| 260[d)] | A | 791.4[g)] | 3.66 | 95 |
| 261[d)] | A | 801.0[g)] | 3.48 | 95 |
| 262[d)] | A | 805.4[g)] | 3.49 | 95 |
| 263[d)] | A | 810.4[g)] | 3.58 | 95 |
| 264[e)] | A | 800.2[g)] | 3.82 | 94 |
| 265[e)] | B | 802.8[g)] | 3.49 | 90 |
| 266[e)] | B | 814.5[g)] | 3.17 | 95 |
| 267[e)] | A | 804.9[g)] | 3.84 | 97 |
| 268[e)] | A | 814.3[g)] | 3.75 | 97 |
| 269[e)] | B | 795.5[g)] | 3.44 | 96 |
| 270[e)] | A | 786.4[g)] | 3.72 | 97 |
| 271[e)] | B | 791.3[g)] | 3.48 | 98 |
| 272[e)] | A | 805[g)] | 3.76 | 96 |
| 273[e)] | A | 797.9[g)] | 3.70 | 98 |
| 274[e)] | A | 772.5[g)] | 3.35 | 96 |
| 275[e)] | H | 790.3[g)] | 6.69 | 96 |
| 276[e)] | B | 795.7[g)] | 3.54 | 97 |
| 277[e)] | B | 782.2[g)] | 3.52 | 95 |
| 278[e)] | A | 800.4[g)] | 3.79 | 96 |
| 279[e)] | B | 793.5[g)] | 3.40 | 92 |
| 280[e)] | I | 800.5[g)] | 6.08 | 92 |
| 281[e)] | H | 790.7[g)] | 6.57 | 96 |
| 282[e)] | A | 800.5[g)] | 3.78 | 89 |
| 283[e)] | A | 791.9[g)] | 3.36 | 93 |
| 284[e)] | A | 796.7[g)] | 3.39 | 86 |
| 285[e)] | G | 793.7[g)] | 3.38 | 98 |
| 286[e)] | A | 798.3[g)] | 3.49 | 96 |
| 287[e)] | G | 798.3[g)] | 3.25 | 98 |
| 288[e)] | G | 798.3[g)] | 3.36 | 99 |
| 289[e)] | G | 785.8[g)] | 3.51 | 98 |
| 290[e)] | G | 783.7[g)] | 3.38 | 96 |
| 291[e)] | G | 788.3[g)] | 3.36 | 99 |
| 292[e)] | G | 783.5[g)] | 3.40 | 99 |
| 293[e)] | G | 788.3[g)] | 3.29 | 98 |
| 294[d)] | A | 795.5[g)] | 3.41 | 97 |
| 295[e)] | 1 | 597.2[g)] | 6.08 | 97 |
| 296[e)] | H | 800.5[g)] | 6.29 | 96 |
| 297[e)] | 1 | 800.5[g)] | 5.91 | 97 |
| 298[d)] | A | 785.5[g)] | 3.48 | 98 |
| 299[e)] | H | 785.7[g)] | 6.61 | 96 |
| 300[e)] | A | 795.3[g)] | 3.24 | 96 |
| 301[e)] | G | 796[g)] | 3.40 | 97 |
| 302[e)] | G | 802.9[g)] | 3.24 | 95 |
| 303[e)] | A | 807.5[g)] | 3.66 | 99 |
| 304[e)] | G | 789[g)] | 3.17 | 93 |
| 305[e)] | A | 800.3[g)] | 3.87 | 96 |
| 306[e)] | A | 805.3[g)] | 3.62 | 95 |
| 307[e)] | A | 785.7[g)] | 3.66 | 95 |
| 308[e)] | G | 800.7[g)] | 3.26 | 95 |
| 309[e)] | G | 805.3[g)] | 3.31 | 98 |
| 310[e)] | A | 800.5[g)] | 3.68 | 97 |
| 311[e)] | G | 805[g)] | 3.30 | 95 |
| 312 | G | 795.5[g)] | 3.07 | 90 |
| 313 | G | 795.7[g)] | 3.13 | 90 |
| 314 | A | 804.9[g)] | 3.84 | 98 |
| 315[e)] | A | 805[g)] | 3.76 | 95 |
| 316[d)] | A | 805[g)] | 3.84 | 97 |
| 317[e)] | A | 800.4[g)] | 3.67 | 94 |
| 318[e)] | A | 795.9[g)] | 3.65 | 93 |
| 319[e)] | A | 802.8[g)] | 3.62 | 95 |
| 320[e)] | G | 798.3[g)] | 3.15 | 95 |
| 321[e)] | A | 807.5[g)] | 3.41 | 94 |
| 322[e)] | A | 802.8[g)] | 3.59 | 95 |
| 323[e)] | A | 802.9[g)] | 3.67 | 97 |
| 324[e)] | A | 807.3[g)] | 3.54 | 96 |
| 325[e)] | G | 802.9[g)] | 3.32 | 95 |
| 326[e)] | A | 807.4[g)] | 3.59 | 96 |
| 327[e)] | A | 807.5[g)] | 3.59 | 97 |
| 328[e)] | A | 812.8[g)] | 3.65 | 95 |
| 329[e)] | A | 816.8[g)] | 3.53 | 95 |
| 330 | A | 809.3[g)] | 3.74 | 98 |

TABLE 2-continued

| Ex. | Meth. [a] | MS | RT [b] | Pur. [c] |
|---|---|---|---|---|
| 331 [e] | H | 796.7 [g] | 5.64 | 96 |
| 332 [e] | I | 795.9 [g] | 5.43 | 94 |
| 333 [e] | H | 801.3 [g] | 5.60 | 92 |
| 334 [e] | H | 805.3 [g] | 6.32 | 96 |
| 335 [e] | H | 790.5 [g] | 6.60 | 97 |
| 336 [e] | I | 809.5 [g] | 5.80 | 95 |
| 337 [e] | I | 786.4 [g] | 6.36 | 96 |
| 338 [e] | H | 795.9 [g] | 6.06 | 95 |
| 339 [e] | H | 786.5 [g] | 5.68 | 97 |
| 340 [e] | G | 795.9 [g] | 3.38 | 99 |
| 341 [e] | G | 797.9 [g] | 3.16 | 99 |
| 342 [e] | A | 800.5 [g] | 3.57 | 97 |
| 343 [e] | A | 800.8 [g] | 3.21 | 92 |
| 344 [e] | A | 786.5 [g] | 3.69 | 98 |
| 345 [e] | I | 790.7 [g] | 6.30 | 96 |
| 346 [e] | G | 783.3 [g] | 3.24 | 95 |
| 347 [e] | G | 774.4 [g] | 3.14 | 95 |
| 348 [e] | A | 792.9 [g] | 3.76 | 95 |
| 349 [e] | G | 792.9 [g] | 2.75 | 96 |
| 350 [e] | H | 790.7 [g] | 6.53 | 96 |
| 351 [e] | G | 788 [g] | 3.25 | 97 |
| 352 | A | 823.2 [g] | 3.77 | 97 |
| 353 | A | 813.7 [g] | 3.72 | 96 |
| 354 [e] | G | 804.9 [g] | 3.34 | 98 |
| 355 [e] | G | 809.7 [g] | 3.36 | 96 |
| 356 [e] | A | 800.5 [g] | 3.74 | 96 |
| 357 [e] | G | 785.9 [g] | 3.59 | 97 |
| 358 [e] | G | 812.9 [g] | 3.37 | 96 |
| 359 [e] | I | 809.5 [g] | 5.94 | 97 |
| 360 [e] | G | 790.5 [g] | 3.41 | 97 |
| 361 [e] | A | 794.9 [g] | 3.91 | 96 |
| 362 [e] | G | 804.5 [g] | 3.79 | 96 |
| 363 [e] | A | 799.7 [g] | 4.01 | 96 |
| 364 [e] | G | 805 [g] | 3.42 | 96 |
| 365 [e] | G | 816.9 [g] | 3.30 | 98 |
| 366 [e] | G | 804.9 [g] | 3.30 | 98 |
| 367 [e] | B | 823.9 [g] | 3.39 | 98 |
| 368 [e] | A | 828.8 [g] | 3.79 | 97 |
| 369 [e] | A | 819.3 [g] | 3.58 | 96 |
| 370 [e] | F | 824 [g] | 3.17 | 94 |
| 371 [e] | B | 838.9 [g] | 3.46 | 96 |
| 372 [e] | B | 829.5 [g] | 3.39 | 94 |
| 373 [e] | B | 838.4 [g] | 3.40 | 97 |
| 374 [e] | A | 838.9 [g] | 3.61 | 91 |
| 375 [e] | A | 829.3 [g] | 3.59 | 97 |
| 376 [e] | A | 801.2 [g] | 3.52 | 93 |
| 377 [e] | A | 819.5 [g] | 3.65 | 98 |
| 378 [e] | A | 823.9 [g] | 3.66 | 95 |
| 379 [e] | A | 810.3 [g] | 3.69 | 94 |
| 380 [e] | A | 824.9 [g] | 3.45 | 94 |
| 381 [e] | A | 806.5 [g] | 3.33 | 95 |
| 382 [e] | A | 795.9 [g] | 3.65 | 95 |
| 383 [e] | H | 643.4 [g] | 6.95 | 92 |
| 384 [e] | G | 771.5 [g] | 3.45 | 97 |
| 385 [e] | A | 824.5 [g] | 3.91 | 95 |

[a] Analytical method
[b] Retention time in [min]
[c] Purity in [%]
[d] Acetate salt
[e] Chloride salt
[f] MS: m/z for $[M + 2H]^{2+}$
[g] MS: m/z for $[M + 3H]^{3+}$
[h] MS: m/z for $[M + 4H]^{4+}$ 2. Biological Methods 2.1 Preparation of the Peptides Lyophilized peptides were weighed on a Microbalance (Mettler MT5) and dissolved in sterile water to a final concentration of 1 mg/mL. Stock solutions were kept at +4° C., light protected.

2.2 Antimicrobial Activity of the Peptides

The in vitro antimicrobial activities of the peptides were determined in 96-well plates (Greiner, polystyrene) by the standard CLSI broth microdilution method (Clinical and Laboratory Standards Institute 2014. Performance standards for antimicrobial susceptibility testing, 24th informational supplement. Approved standard CLSI M100-S24; Clinical and Laboratory Standards Institute, Wayne, Pa.). The following microorganisms were used to determine antibiotic activity of the peptides: *Escherichia coli* ATCC 25922, *Klebsiella pneumoniae* SSI #3010[a]), *Acinetobacter baumannii* DSM 30008, *Pseudomonas aeruginosa* ATCC 27853 and the clinical isolates *Escherichia coli* 926415[b]), *Klebsiella pneumoniae* 968733[b]), *Acinetobacter baumannii* 872842[b]), *Enterobacter cloacae* 848840[b]) and *Escherichia coli* MCR-1 Af45[c]). Before preparation of inocula, *Escherichia coli* MCR-1 Af45 was subcultured on Mueller-Hinton II (MH-cation adjusted) agar containing 2 μg/mL colistin.

[a]) Obtained from Statens Serum Institut (SSI), Copenhagen, Denmark
[b]) Obtained from International Health Management Associates, Inc. (IHMA Europe Sàrl), Epalinges, Switzerland
[c]) Obtained from Prof. Patrice Nordmann, University of Fribourg, Fribourg, Switzerland Inocula of the microorganisms were diluted into Mueller-Hinton II (MH-cation adjusted) broth and compared with a 0.5 McFarland standard to give appr. $10^6$ colony forming units (CFU)/mL. Aliquots (90 μL) of inoculum were added to 10 μL of MH-II broth+P-80 (Polysorbate 80, 0.002% final concentration, v/v) containing the peptide in serial two-fold dilutions. Antimicrobial activities of the peptides were expressed as the minimal inhibitory concentration (MIC) in μg/mL at which no visible growth was observed after 18-20 hours of incubation at 35° C.

2.3 Hemolysis

The peptides were tested for their hemolytic activity against human red blood cells (hRBC). Fresh hRBC were washed four times with phosphate buffered saline (PBS) and centrifuged for 10 min at 3000×g. Compounds (200 μg/mL) were incubated with 20% hRBC (v/v) for 1 h at 37° C. and shaking at 300 rpm. A value of 0% and 100% cell lysis, respectively, was determined by incubation of hRBC in the presence of PBS containing 10% water and 2% Triton X-100 in H$_2$O, respectively. The samples were centrifuged, the supernatants were ~7.5-fold diluted in PBS buffer and the optical densities (OD) were measured at 540 nm and blank corrected. The 100% lysis value (OD$_{540}$Triton X-100) gave an OD$_{540}$ of approximately 0.5-1.0.

Percent hemolysis was calculated as follows: (OD$_{540}$peptide/OD$_{540}$Triton X-100)×100%.

2.4 Tolerability in a Mouse Model

The tolerability of the peptides was tested in a mouse model at Pharmacology Discovery Services Taiwan Ltd, Taipei, Taiwan. The peptides were administered subcutaneously (s.c.) at 30 mg/kg or 40 mg/kg, respectively; twice at a 12-hr interval, for assessment of possible adverse effects in the Maximum Tolerated Dose (MTD) assay in male ICR (Institute of Cancer Research) mice. The peptides were dissolved in 0.9% NaCl at the concentrations either of 6 or 8 mg/mL, respectively, based on the free base molecular weight. The pH values of dosing solutions were adjusted to 6.5-7.6 before s.c. administration. A dosing volume at 5 mL/kg and a concentration of 6 or 8 mg/mL, respectively, was applied. The fresh prepared stock solution were stored at 4° C. during the study. Male ICR mice weighing 23±3 g were provided by BioLasco Taiwan (under Charles River Laboratories Licensee). Animals were acclimated for 3 days prior to use and were confirmed to be in good health. The peptides were administered s.c. at 30 mg/kg or 40 mg/kg, respectively, twice at a 12-hr interval, to groups of 3 ICR male mice and observed for the presence of acute toxic symptoms (mortality, convulsions, tremors, muscle relaxation, sedation, etc.) and autonomic effects (diarrhea, salivation, lacrimation, vasodilation, piloerection, etc.) during the first 30 min. The peptides were administered again at a 12-hr (two total doses) interval, following the first dose. The animals were then observed again for the presence of acute toxic symptoms and autonomic effects during the first 30 min. Mortality was observed at 0.5 and 12 hr following the first dose and again at 0.5, 1, 3, 24, 48, and 72 hr after the second dose of test articles.

2.5 Nephrotoxicity in a Mouse Model

The nephrotoxicity of the peptides was tested in a mouse model at Fidelta Ltd, Zagreb, Croatia. Colistin B (polymyxin E2, acetate salt, individually synthesized, 95% purity) was provided by Polyphor Ltd (Allschwil, Switzerland). The purpose of the study was to evaluate the toxic potential of the peptides in male CD1 mice after 1 day of subcutaneous dosing (72 mg/kg/day), divided into 6 administrations (12 mg/kg). Stock solutions of the peptides were prepared in saline (7.2 mg/ml), pH adjusted if required to pH 6.5-7.6 before s.c. administration. The peptides were administered to the animals subcutaneously 6 times a day (every 2 hours). The study involved 7 groups of 5 males in control and dose groups. After 24 h from start of the first dosing the animals were euthanized (isoflurane anesthesia-Abbott, Netherlands and exsanguination). All animals were subjected to gross necropsy as rapidly as possible and their main tissues examined macroscopically. The kidneys were fixed in an appropriate fixative and preserved in 10% buffered formaldehyde for histopathological examination. After dehydration and embedding in paraffin wax, sections of the tissues were cut at 5 micrometer thickness and stained with haematoxylin and eosin.

Semi-quantitative scoring of the kidneys was performed according to the following method:

Lesions were rated as follows: mild acute tubular damage with tubular dilation, prominent nuclei and a few pale tubular casts (Grade 1); severe acute tubular damage with necrosis of tubular epithelial cells and numerous tubular casts (Grade 2); necrosis/infarction of tubules and glomeruli with or without papillary necrosis (Grade 3). The grades were given the following scores: grade 1=1, grade 2=4 and grade 3=10. Moreover, the percentages of kidney slides affected were scored as follows:

<1%=0; 1 to 5%=1; 5 to <10%=2; 10 to <20%=3; 20 to <30%=4; 30 to <40%=5; and >40%=6.

Subsequently, the overall kidney histology score was calculated as the product of percentage score and grade score. These scores were then expressed as a semi-quantitative score (SQS) on a scale of 0 to +5 for renal histological changes. These scores were assigned as follows:

SQS 0=no significant change (overall score, <1)

SQS +1=mild damage (overall score, 1 to <15)

SQS +2=mild to moderate damage (overall score, 15 to <30)

SQS +3=moderate damage (overall score, 30 to <45)

SQS +4=moderate to severe damage (overall score, 45 to <60)

SQS +5=severe damage (overall score, >60)

(Yousef, J., Chen, G., Hill, P., Nation, R., Li, J., *Antimicrobial Agents And Chemotherapy* [P], 2011, Vol 55, issue 9, American Society for Microbiology, USA, pp. 4044-4049).

The results of the experiments described in 2.2-2.5 are indicated in Tables 3, 4, 5, 6 and 7 herein below.

TABLE 3

Minimal inhibitory concentrations (MIC) in Mueller-Hinton II broth and Hemolysis

| Ex. | Escherichia coli ATCC 25922 MIC [µg/mL] | Klebsiella pneumoniae SSI #3010 MIC [µg/mL] | Acinetobacter baumannii DSM 30008 MIC [µg/mL] | Pseudomonas aeruginosa ATCC 27853 MIC [µg/mL] | Hemolysis at 200 µg/mL [%] |
|---|---|---|---|---|---|
| 1 | 0.125 | 0.5 | 0.125 | 0.125 | <1 |
| 2 | 0.125 | 0.5 | 0.125 | 0.25 | <1 |
| 3 | 0.125 | 0.125 | 0.0625 | 0.125 | <1 |
| 4 | 0.125 | 0.125 | 0.0625 | 0.125 | 1 |
| 5 | 0.0625 | 0.125 | 0.0625 | 0.125 | <1 |
| 6 | 0.125 | 0.25 | 0.125 | 0.125 | 2 |
| 7 | 0.125 | 0.125 | 0.0625 | 0.125 | <1 |
| 8 | 0.0625 | 0.125 | 0.125 | 0.125 | <1 |
| 9 | 0.125 | 0.125 | 0.125 | 0.125 | <1 |
| 10 | 0.25 | 0.25 | 0.125 | 0.125 | <1 |
| 11 | 0.125 | 0.125 | 0.125 | 0.25 | 1 |
| 12 | 0.0625 | 0.25 | 0.125 | 0.125 | 2 |
| 13 | 0.125 | 0.125 | 0.125 | 0.125 | <1 |
| 14 | 0.25 | 0.5 | 0.5 | 0.25 | <1 |
| 15 | 0.0625 | 0.125 | 0.125 | 0.25 | <1 |
| 16 | 0.0625 | 0.0625 | 0.0625 | 0.25 | <1 |
| 17 | 0.0625 | 0.125 | 0.0625 | 0.25 | <1 |
| 18 | 0.0625 | 0.125 | 0.0625 | 0.25 | 1 |
| 19 | 0.125 | 0.125 | 0.125 | 0.25 | <1 |
| 20 | 0.125 | 0.125 | 0.125 | 0.25 | <1 |
| 21 | 0.25 | 0.5 | 0.5 | 0.5 | <1 |
| 22 | 0.0625 | 0.125 | 0.0625 | 0.5 | <1 |
| 23 | 0.0625 | 0.125 | 0.0625 | 0.25 | <1 |
| 24 | 0.125 | 0.125 | 0.125 | 0.25 | <1 |
| 25 | 0.0625 | 0.125 | 0.0625 | 0.25 | <1 |
| 26 | 0.0625 | 0.125 | 0.03125 | 0.25 | 1 |
| 27 | 0.0625 | 0.25 | 0.0625 | 0.5 | <1 |
| 28 | 0.125 | 0.125 | 0.125 | 0.25 | <1 |
| 29 | 0.0625 | 0.125 | 0.125 | 0.25 | 1 |
| 30 | 0.0625 | 0.125 | 0.125 | 0.25 | <1 |

TABLE 3-continued

Minimal inhibitory concentrations (MIC) in
Mueller-Hinton II broth and Hemolysis

| Ex. | Escherichia coli ATCC 25922 MIC [µg/mL] | Klebsiella pneumoniae SSI #3010 MIC [µg/mL] | Acinetobacter baumannii DSM 30008 MIC [µg/mL] | Pseudomonas aeruginosa ATCC 27853 MIC [µg/mL] | Hemolysis at 200 µg/mL [%] |
|---|---|---|---|---|---|
| 31 | 0.03125 | 0.0625 | 0.03125 | 0.25 | <1 |
| 32 | 0.0625 | 0.125 | 0.0625 | 0.25 | <1 |
| 33 | 0.0625 | 0.125 | 0.0625 | 0.25 | <1 |
| 34 | 0.0625 | 0.125 | 0.03125 | 0.25 | <1 |
| 35 | 0.125 | 0.25 | 0.125 | 0.25 | <1 |
| 36 | 0.0625 | 0.125 | 0.0625 | 0.25 | <1 |
| 37 | 0.25 | 0.25 | 0.125 | 0.5 | 1 |
| 38 | 0.0625 | 0.125 | 0.125 | 0.25 | n.d. |
| 39 | 0.0625 | 0.0625 | 0.0625 | 0.125 | <1 |
| 40 | 0.125 | 0.5 | 1 | 0.25 | 2 |
| 41 | 0.0625 | 0.125 | 0.0625 | 0.25 | <1 |
| 42 | 0.125 | 0.25 | 0.5 | 0.25 | <1 |
| 43 | 0.25 | 0.25 | 0.5 | 0.5 | <1 |
| 44 | 0.0625 | 0.125 | 0.125 | 0.125 | <1 |
| 45 | 0.0625 | 0.125 | 0.0625 | 0.125 | <1 |
| 46 | 0.0625 | 0.125 | 0.0625 | 0.125 | 2 |
| 47 | 0.0625 | 0.125 | 0.125 | 0.125 | <1 |
| 48 | 0.25 | 0.25 | 0.25 | 0.125 | <1 |
| 49 | 0.125 | 0.125 | 0.0625 | 0.125 | <1 |
| 50 | 0.125 | 0.125 | 0.25 | 0.25 | <1 |
| 51 | 0.25 | 0.125 | 0.5 | 0.125 | <1 |
| 52 | 0.25 | 0.25 | 1 | 0.25 | <1 |
| 53 | 0.125 | 0.125 | 0.25 | 0.125 | <1 |
| 54 | 0.0625 | 0.25 | 0.25 | 0.25 | <1 |
| 55 | 0.25 | 0.5 | 0.5 | 0.25 | 2 |
| 56 | 0.5 | 1 | 1 | 0.5 | <1 |
| 57 | 0.125 | 0.25 | 0.125 | 0.25 | 3 |
| 58 | 0.0625 | 0.125 | 0.0625 | 0.25 | 1 |
| 59 | 0.125 | 0.125 | 0.125 | 0.125 | <1 |
| 60 | 0.0625 | 0.125 | 0.0625 | 0.125 | <1 |
| 61 | 0.125 | 0.0625 | 0.0625 | 0.125 | 3 |
| 62 | 0.125 | 0.0625 | 0.0625 | 0.125 | <1 |
| 63 | 0.125 | 0.125 | 0.125 | 0.125 | <1 |
| 64 | 0.125 | 0.125 | 0.0625 | 0.125 | <1 |
| 65 | 0.125 | 0.25 | 0.125 | 0.125 | <1 |
| 66 | 0.0625 | 0.125 | 0.25 | 0.25 | <1 |
| 67 | 0.125 | 0.5 | 0.25 | 0.25 | <1 |
| 68 | 0.25 | 0.125 | 0.25 | 0.5 | <1 |
| 69 | 0.0625 | 0.0625 | 0.0625 | 0.125 | 2 |
| 70 | 0.125 | 0.125 | 0.0625 | 0.125 | <1 |
| 71 | 0.0625 | 0.125 | 0.0625 | 0.125 | 1 |
| 72 | 0.0625 | 0.125 | 0.0625 | 0.125 | <1 |
| 73 | 0.0625 | 0.125 | 0.0625 | 0.25 | <1 |
| 74 | 0.0625 | 0.0625 | 0.0625 | 0.25 | <1 |
| 75 | 0.0625 | 0.125 | 0.0625 | 0.125 | <1 |
| 76 | 0.0625 | 0.125 | 0.0625 | 0.25 | 1 |
| 77 | 0.125 | 0.125 | 0.125 | 0.125 | <1 |
| 78 | 0.03125 | 0.25 | 0.0625 | 0.125 | <1 |
| 79 | 0.0625 | 0.0625 | 0.03125 | 0.125 | <1 |
| 80 | 0.03125 | 0.125 | 0.125 | 0.125 | <1 |
| 81 | 0.0625 | 0.0625 | 0.125 | 0.125 | <1 |
| 82 | 0.0625 | 0.0625 | 0.125 | 0.25 | <1 |
| 83 | 0.0625 | 0.0625 | 0.0625 | 0.125 | <1 |
| 84 | 0.0625 | 0.125 | 0.125 | 0.25 | <1 |
| 85 | 0.0625 | 0.125 | 0.25 | 0.25 | 1 |
| 86 | 0.125 | 0.125 | 0.0625 | 0.125 | <1 |
| 87 | 0.0625 | 0.125 | 0.0625 | 0.125 | <1 |
| 88 | 0.0625 | 0.125 | 0.03125 | 0.125 | <1 |
| 89 | 0.125 | 0.125 | 0.0625 | 0.25 | <1 |
| 90 | 0.0625 | 0.125 | 0.125 | 0.25 | <1 |
| 91 | 0.0625 | 0.25 | 0.125 | 0.25 | <1 |
| 92 | 0.0625 | 0.0625 | 0.125 | 0.125 | <1 |
| 93 | 0.125 | 0.125 | 0.25 | 0.25 | <1 |
| 94 | 0.0625 | 0.0625 | 0.125 | 0.25 | <1 |
| 95 | 0.03125 | 0.125 | 0.0625 | 0.125 | <1 |
| 96 | 0.0625 | 0.125 | 0.125 | 0.125 | <1 |
| 97 | 0.25 | 0.125 | 0.25 | 0.25 | <1 |
| 98 | 0.125 | 0.25 | 0.25 | 0.25 | <1 |
| 99 | 0.0625 | 0.125 | 0.0625 | 0.125 | 1 |
| 100 | 0.03125 | 0.125 | 0.0625 | 0.125 | <1 |
| 101 | 0.0625 | 0.125 | 0.0625 | 0.125 | <1 |

TABLE 3-continued

Minimal inhibitory concentrations (MIC) in
Mueller-Hinton II broth and Hemolysis

| Ex. | Escherichia coli ATCC 25922 MIC [µg/mL] | Klebsiella pneumoniae SSI #3010 MIC [µg/mL] | Acinetobacter baumannii DSM 30008 MIC [µg/mL] | Pseudomonas aeruginosa ATCC 27853 MIC [µg/mL] | Hemolysis at 200 µg/mL [%] |
|---|---|---|---|---|---|
| 102 | 0.0625 | 0.25 | 0.0625 | 0.25 | <1 |
| 103 | 0.0625 | 0.125 | 0.0625 | 0.125 | 1 |
| 104 | 0.0625 | 0.125 | 0.125 | 0.25 | 1 |
| 105 | 0.0625 | 0.0625 | 0.03125 | 0.125 | <1 |
| 106 | 0.0625 | 0.125 | 0.0625 | 0.125 | <1 |
| 107 | 0.0625 | 0.125 | 0.0625 | 0.125 | <1 |
| 108 | 0.0625 | 0.0625 | 0.03125 | 0.125 | 2 |
| 109 | 0.03125 | 0.0625 | 0.03125 | 0.125 | <1 |
| 110 | 0.0625 | 0.0625 | 0.0625 | 0.125 | 2 |
| 111 | 0.125 | 0.125 | 0.03125 | 0.25 | <1 |
| 112 | 0.0625 | 0.0625 | 0.0625 | 0.125 | <1 |
| 113 | 0.0625 | 0.0625 | 0.125 | 0.125 | <1 |
| 114 | 0.03125 | 0.0625 | 0.0625 | 0.125 | <1 |
| 115 | 0.0625 | 0.0625 | 0.0625 | 0.125 | <1 |
| 116 | 0.03125 | 0.03125 | 0.03125 | 0.125 | <1 |
| 117 | 0.0625 | 0.0625 | 0.015625 | 0.125 | 2 |
| 119 | 0.0625 | 0.0625 | 0.0625 | 0.125 | <1 |
| 120 | 0.125 | 0.0625 | 0.0625 | 0.125 | 1 |
| 121 | 0.0625 | 0.125 | 0.0625 | 0.125 | <1 |
| 122 | 0.25 | 0.5 | 0.25 | 0.5 | 1 |
| 123 | 0.015625 | 0.0625 | 0.015625 | 0.0625 | <1 |
| 124 | 0.0625 | 0.125 | 0.0625 | 0.125 | 2 |
| 125 | 0.0625 | 0.0625 | 0.125 | 0.125 | 2 |
| 126 | 0.125 | 0.125 | 0.125 | 0.25 | <1 |
| 127 | 0.0625 | 0.25 | 0.0625 | 0.5 | 2 |
| 128 | 0.03125 | 0.0625 | 0.03125 | 0.125 | <1 |
| 129 | 0.03125 | 0.0625 | 0.0625 | 0.25 | <1 |
| 130 | 0.03125 | 0.0625 | 0.015625 | 0.125 | 1 |
| 131 | 0.0625 | 0.125 | 0.25 | 0.25 | <1 |
| 132 | 0.03125 | 0.125 | 0.03125 | 0.125 | 2 |
| 133 | 0.03125 | 0.125 | 0.0625 | 0.25 | 2 |
| 134 | 0.03125 | 0.03125 | 0.03125 | 0.125 | 3 |
| 135 | 0.03125 | 0.0625 | 0.03125 | 0.125 | <1 |
| 136 | 0.03125 | 0.0625 | 0.03125 | 0.25 | 3 |
| 137 | 0.03125 | 0.0625 | 0.0625 | 0.125 | 1 |
| 138 | 0.03125 | 0.03125 | 0.03125 | 0.125 | <1 |
| 139 | 0.0625 | 0.0625 | 0.0625 | 0.25 | 2 |
| 140 | 0.125 | 0.125 | 0.125 | 0.25 | <1 |
| 141 | 0.03125 | 0.03125 | 0.03125 | 0.125 | 2 |
| 142 | 0.0625 | 0.03125 | 0.03125 | 0.125 | <1 |
| 143 | 0.03125 | 0.0625 | 0.0625 | 0.125 | 2 |
| 144 | 0.03125 | 0.0625 | 0.0625 | 0.125 | <1 |
| 145 | 0.0625 | 0.125 | 0.0625 | 0.125 | 2 |
| 146 | 0.0625 | 0.0625 | 0.0625 | 0.125 | <1 |
| 147 | 0.0625 | 0.0625 | 0.0625 | 0.125 | <1 |
| 148 | 0.03125 | 0.0625 | 0.03125 | 0.125 | <1 |
| 149 | 0.0625 | 0.125 | 0.0625 | 0.125 | <1 |
| 150 | 0.03125 | 0.125 | 0.0625 | 0.125 | <1 |
| 151 | 0.03125 | 0.0625 | 0.0625 | 0.125 | <1 |
| 152 | 0.125 | 0.25 | 0.125 | 0.25 | <1 |
| 153 | 0.0625 | 0.0625 | 0.03125 | 0.125 | <1 |
| 154 | 0.03125 | 0.0625 | 0.015625 | 0.125 | <1 |
| 155 | 0.0625 | 0.125 | 0.0625 | 0.125 | 1 |
| 156 | 0.03125 | 0.125 | 0.0625 | 0.125 | <1 |
| 157 | 0.0625 | 0.125 | 0.125 | 0.25 | <1 |
| 158 | 0.0625 | 0.125 | 0.0625 | 0.25 | <1 |
| 159 | 0.0625 | 0.125 | 0.0625 | 0.125 | <1 |
| 160 | 0.125 | 0.25 | 0.125 | 0.25 | <1 |
| 161 | 0.125 | 0.125 | 0.125 | 0.25 | 1 |
| 162 | 0.125 | 0.5 | 0.25 | 0.25 | <1 |
| 163 | 0.125 | 0.25 | 0.125 | 0.25 | 1 |
| 164 | 0.5 | 0.5 | 0.5 | 1 | <1 |
| 165 | 0.25 | 0.25 | 1 | 0.5 | <1 |
| 166 | 0.125 | 0.125 | 0.0625 | 0.25 | <1 |
| 167 | 0.0625 | 0.125 | 0.0625 | 0.25 | <1 |
| 168 | 0.0625 | 0.125 | 0.125 | 0.25 | <1 |
| 169 | 0.25 | 0.5 | 0.25 | 0.25 | <1 |
| 170 | 0.125 | 0.5 | 0.25 | 0.5 | <1 |
| 171 | 0.125 | 0.125 | 0.0625 | 0.25 | <1 |
| 172 | 0.125 | 0.125 | 0.125 | 0.25 | <1 |
| 173 | 0.125 | 0.125 | 0.0625 | 0.5 | <1 |

TABLE 3-continued

Minimal inhibitory concentrations (MIC) in Mueller-Hinton II broth and Hemolysis

| Ex. | Escherichia coli ATCC 25922 MIC [µg/mL] | Klebsiella pneumoniae SSI #3010 MIC [µg/mL] | Acinetobacter baumannii DSM 30008 MIC [µg/mL] | Pseudomonas aeruginosa ATCC 27853 MIC [µg/mL] | Hemolysis at 200 µg/mL [%] |
|---|---|---|---|---|---|
| 174 | 0.0625 | 0.0625 | 0.0625 | 0.125 | <1 |
| 175 | 0.0625 | 0.125 | 0.125 | 0.125 | 1 |
| 176 | 0.0625 | 0.125 | 0.125 | 0.125 | <1 |
| 177 | 0.0625 | 0.25 | 0.0625 | 0.125 | <1 |
| 178 | 0.125 | 0.125 | 0.0625 | 0.125 | <1 |
| 179 | 0.125 | 0.25 | 0.0625 | 0.25 | <1 |
| 180 | 0.125 | 0.5 | 0.25 | 0.125 | <1 |
| 181 | 0.25 | 0.5 | 0.25 | 0.5 | <1 |
| 182 | 0.03125 | 0.125 | 0.0625 | 0.125 | <1 |
| 183 | 0.125 | 0.25 | 0.25 | 0.125 | <1 |
| 184 | 0.125 | 0.25 | 0.125 | 0.25 | <1 |
| 185 | 0.125 | 0.125 | 0.125 | 0.125 | <1 |
| 186 | 0.125 | 0.125 | 0.0625 | 0.125 | <1 |
| 187 | 0.125 | 0.25 | 0.5 | 0.5 | <1 |
| 188 | 0.0625 | 0.25 | 0.125 | 0.5 | <1 |
| 189 | 0.125 | 0.125 | 0.125 | 0.25 | <1 |
| 190 | 0.0625 | 0.125 | 0.0625 | 0.25 | <1 |
| 191 | 0.125 | 0.25 | 0.125 | 0.25 | 1 |
| 192 | 0.25 | 0.5 | 0.5 | 0.5 | <1 |
| 193 | 0.125 | 0.25 | 0.0625 | 0.25 | <1 |
| 194 | 0.0625 | 0.0625 | 0.0625 | 0.125 | <1 |
| 195 | 0.0625 | 0.125 | 0.0625 | 0.125 | <1 |
| 196 | 0.25 | 0.25 | 0.125 | 0.25 | <1 |
| 197 | 0.0625 | 0.125 | 0.0625 | 0.125 | <1 |
| 198 | 0.0625 | 0.125 | 0.0625 | 0.25 | <1 |
| 199 | 0.125 | 0.125 | 0.0625 | 0.25 | <1 |
| 200 | 0.125 | 0.5 | 0.25 | 0.25 | <1 |
| 201 | 0.0625 | 0.125 | 0.125 | 0.125 | <1 |
| 202 | 0.125 | 0.125 | 0.125 | 0.125 | <1 |
| 203 | 0.0625 | 0.125 | 0.0625 | 0.25 | <1 |
| 204 | 0.0625 | 0.125 | 0.0625 | 0.125 | 1 |
| 205 | 0.25 | 0.25 | 0.25 | 0.25 | <1 |
| 206 | 0.03125 | 0.0625 | 0.0625 | 0.125 | 1 |
| 207 | 0.125 | 0.125 | 0.0625 | 0.125 | 1 |
| 208 | 0.125 | 0.125 | 0.125 | 0.125 | 2 |
| 209 | 0.125 | 0.25 | 0.25 | 0.5 | <1 |
| 210 | 0.125 | 0.25 | 0.25 | 0.25 | <1 |
| 211 | 0.0625 | 0.0625 | 0.03125 | 0.125 | <1 |
| 212 | 0.0625 | 0.25 | 0.125 | 0.25 | 1 |
| 213 | 0.125 | 0.125 | 0.0625 | 0.25 | <1 |
| 214 | 0.0625 | 0.25 | 0.125 | 0.5 | <1 |
| 215 | 0.125 | 0.25 | 0.125 | 0.25 | 3 |
| 216 | 0.5 | 1 | 1 | 2 | <1 |
| 217 | 0.25 | 0.5 | 2 | 2 | <1 |
| 218 | 0.125 | 0.125 | 0.125 | 0.125 | <1 |
| 219 | 0.03125 | 0.0625 | 0.03125 | 0.125 | <1 |
| 220 | 0.03125 | 0.0625 | 0.03125 | 0.125 | <1 |
| 221 | 0.0625 | 0.125 | 0.0625 | 0.125 | 2 |
| 222 | 0.03125 | 0.0625 | 0.0625 | 0.125 | 1 |
| 223 | 0.03125 | 0.0625 | 0.03125 | 0.125 | <1 |
| 224 | 0.03125 | 0.125 | 0.0625 | 0.125 | 1 |
| 225 | 0.0625 | 0.0625 | 0.125 | 0.125 | <1 |
| 226 | 0.03125 | 0.125 | 0.03125 | 0.125 | 1 |
| 227 | 0.03125 | 0.125 | 0.03125 | 0.125 | <1 |
| 228 | 0.5 | 0.25 | 1 | 0.25 | <1 |
| 229 | 0.125 | 0.125 | 0.5 | 0.5 | 2 |
| 230 | 0.25 | 0.5 | 1 | 1 | <1 |
| 232 | 0.0625 | 0.125 | 0.0625 | 0.125 | <1 |
| 233 | 0.03125 | 0.0625 | 0.0625 | 0.125 | <1 |
| 234 | 0.125 | 0.25 | 0.25 | 0.5 | 9 |
| 235 | 0.0625 | 0.25 | 0.0625 | 0.25 | 4 |
| 236 | 0.25 | 0.25 | 0.25 | 0.25 | <1 |
| 237 | 0.0625 | 0.0625 | 0.03125 | 0.125 | <1 |
| 238 | 0.0625 | 0.125 | 0.03125 | 0.125 | 2 |
| 239 | 0.125 | 0.125 | 0.0625 | 0.25 | 1 |
| 240 | 0.0625 | 0.125 | 0.03125 | 0.25 | 1 |
| 241 | 0.125 | 0.125 | 0.125 | 0.25 | <1 |
| 242 | 0.0625 | 0.125 | 0.125 | 0.125 | <1 |
| 243 | 0.0625 | 0.0625 | 0.0625 | 0.25 | <1 |
| 244 | 0.03125 | 0.0625 | 0.03125 | 0.25 | 1 |
| 245 | 0.0625 | 0.125 | 0.03125 | 0.25 | 1 |

TABLE 3-continued

Minimal inhibitory concentrations (MIC) in
Mueller-Hinton II broth and Hemolysis

| Ex. | Escherichia coli ATCC 25922 MIC [µg/mL] | Klebsiella pneumoniae SSI #3010 MIC [µg/mL] | Acinetobacter baumannii DSM 30008 MIC [µg/mL] | Pseudomonas aeruginosa ATCC 27853 MIC [µg/mL] | Hemolysis at 200 µg/mL [%] |
|---|---|---|---|---|---|
| 246 | 0.25 | 0.25 | 0.5 | 0.25 | <1 |
| 247 | 0.125 | 0.25 | 0.125 | 0.25 | <1 |
| 248 | 0.125 | 0.125 | 0.5 | 0.25 | <1 |
| 249 | 0.03125 | 0.0625 | 0.03125 | 0.125 | 2 |
| 250 | 0.03125 | 0.0625 | 0.03125 | 0.125 | 1 |
| 251 | 0.03125 | 0.03125 | 0.015625 | 0.0625 | 1 |
| 252 | 0.0625 | 0.03125 | 0.0625 | 0.0625 | 2 |
| 253 | 0.03125 | 0.0625 | 0.03125 | 0.0625 | 2 |
| 254 | 0.03125 | 0.03125 | 0.03125 | 0.0625 | 1 |
| 255 | 0.0625 | 0.03125 | 0.03125 | 0.0625 | 1 |
| 256 | 0.03125 | 0.03125 | 0.03125 | 0.0625 | 1 |
| 257 | 0.03125 | 0.03125 | 0.03125 | 0.0625 | 1 |
| 258 | 0.0625 | 0.03125 | 0.03125 | 0.0625 | 2 |
| 259 | 0.015625 | 0.03125 | 0.015625 | 0.0625 | 2 |
| 260 | 0.015625 | 0.0625 | 0.015625 | 0.0625 | <1 |
| 261 | 0.03125 | 0.0625 | 0.03125 | 0.125 | 1 |
| 262 | 0.03125 | 0.03125 | 0.0625 | 0.125 | 1 |
| 263 | 0.03125 | 0.03125 | 0.03125 | 0.125 | 1 |
| 264 | 0.03125 | 0.125 | 0.0625 | 0.25 | <1 |
| 265 | 0.0625 | 0.0625 | 0.0625 | 0.125 | <1 |
| 266 | 0.03125 | 0.0625 | 0.0625 | 0.125 | 1 |
| 267 | 0.03125 | 0.0625 | 0.0625 | 0.0625 | <1 |
| 268 | 0.0625 | 0.0625 | 0.03125 | 0.125 | <1 |
| 269 | 0.015625 | 0.0625 | 0.015625 | 0.0625 | <1 |
| 270 | 0.0625 | 0.0625 | 0.0625 | 0.125 | <1 |
| 271 | 0.03125 | 0.0625 | 0.03125 | 0.0625 | <1 |
| 272 | 0.0625 | 0.0625 | 0.0625 | 0.125 | <1 |
| 273 | 0.0625 | 0.125 | 0.0625 | 0.0625 | <1 |
| 274 | 0.015625 | 0.03125 | 0.03125 | 0.0625 | <1 |
| 275 | 0.0625 | 0.0625 | 0.0625 | 0.125 | <1 |
| 276 | 0.03125 | 0.0625 | 0.03125 | 0.0625 | <1 |
| 277 | 0.0625 | 0.125 | 0.0625 | 0.125 | <1 |
| 278 | 0.03125 | 0.125 | 0.0625 | 0.0625 | 1 |
| 279 | 0.0625 | 0.125 | 0.125 | 0.125 | <1 |
| 280 | 0.03125 | 0.0625 | 0.0625 | 0.125 | <1 |
| 281 | 0.03125 | 0.125 | 0.0625 | 0.125 | <1 |
| 282 | 0.03125 | 0.0625 | 0.015625 | 0.0625 | <1 |
| 283 | 0.0625 | 0.0625 | 0.0625 | 0.125 | <1 |
| 284 | 0.0625 | 0.0625 | 0.0625 | 0.125 | <1 |
| 285 | 0.0625 | 0.0625 | 0.125 | 0.25 | <1 |
| 286 | 0.0625 | 0.0625 | 0.125 | 0.25 | <1 |
| 287 | 0.0625 | 0.0625 | 0.0625 | 0.25 | <1 |
| 288 | 0.0625 | 0.125 | 0.25 | 0.25 | <1 |
| 289 | 0.03125 | 0.0625 | 0.03125 | 0.125 | <1 |
| 290 | 0.0625 | 0.125 | 0.125 | 0.25 | <1 |
| 291 | 0.0625 | 0.125 | 0.25 | 0.25 | <1 |
| 292 | 0.0625 | 0.25 | 0.125 | 0.125 | <1 |
| 293 | 0.0625 | 0.0625 | 0.0625 | 0.25 | <1 |
| 294 | 0.0625 | 0.0625 | 0.0625 | 0.25 | <1 |
| 295 | 0.0625 | 0.0625 | 0.0625 | 0.125 | <1 |
| 296 | 0.125 | 0.0625 | 0.125 | 0.25 | <1 |
| 297 | 0.03125 | 0.0625 | 0.03125 | 0.125 | <1 |
| 298 | 0.03125 | 0.0625 | 0.0625 | 0.25 | <1 |
| 299 | 0.0625 | 0.0625 | 0.0625 | 0.25 | <1 |
| 300 | 0.125 | 0.0625 | 0.125 | 0.125 | <1 |
| 301 | 0.0625 | 0.125 | 0.0625 | 0.125 | 2 |
| 302 | 0.0625 | 0.125 | 0.125 | 0.125 | 3 |
| 303 | 0.0625 | 0.0625 | 0.25 | 0.25 | <1 |
| 304 | 0.125 | 0.0625 | 0.25 | 0.25 | <1 |
| 305 | 0.0625 | 0.0625 | 0.0625 | 0.125 | 3 |
| 306 | 0.03125 | 0.0625 | 0.0625 | 0.0625 | <1 |
| 307 | 0.125 | 0.125 | 0.25 | 0.125 | <1 |
| 308 | 0.0625 | 0.25 | 0.125 | 0.125 | <1 |
| 309 | 0.015625 | 0.0625 | 0.0625 | 0.125 | <1 |
| 310 | 0.03125 | 0.0625 | 0.0625 | 0.125 | <1 |
| 311 | 0.0625 | 0.0625 | 0.0625 | 0.25 | <1 |
| 312 | 0.03125 | 0.0625 | 0.03125 | 0.125 | <1 |
| 313 | 0.015625 | 0.0625 | 0.03125 | 0.125 | <1 |
| 314 | 0.015625 | 0.125 | 0.015625 | 0.25 | 2 |
| 315 | 0.015625 | 0.0625 | 0.015625 | 0.0625 | 2 |
| 316 | 0.015625 | 0.0625 | 0.015625 | 0.0625 | <1 |

TABLE 3-continued

Minimal inhibitory concentrations (MIC) in Mueller-Hinton II broth and Hemolysis

| Ex. | Escherichia coli ATCC 25922 MIC [µg/mL] | Klebsiella pneumoniae SSI #3010 MIC [µg/mL] | Acinetobacter baumannii DSM 30008 MIC [µg/mL] | Pseudomonas aeruginosa ATCC 27853 MIC [µg/mL] | Hemolysis at 200 µg/mL [%] |
|---|---|---|---|---|---|
| 317 | 0.015625 | 0.125 | 0.015625 | 0.125 | <1 |
| 318 | 0.015625 | 0.0625 | 0.03125 | 0.125 | 1 |
| 319 | 0.0625 | 0.25 | 0.125 | 0.125 | <1 |
| 320 | 0.0625 | 0.125 | 0.5 | 0.25 | <1 |
| 321 | 0.0625 | 0.125 | 0.125 | 0.125 | 0 |
| 322 | 0.0625 | 0.125 | 0.0625 | 0.125 | <1 |
| 323 | 0.0625 | 0.125 | 0.0625 | 0.125 | <1 |
| 324 | 0.0625 | 0.0625 | 0.0625 | 0.0625 | <1 |
| 325 | 0.0625 | 0.0625 | 0.0625 | 0.125 | <1 |
| 326 | 0.0625 | 0.0625 | 0.0625 | 0.0625 | <1 |
| 327 | 0.0625 | 0.0625 | 0.0625 | 0.125 | <1 |
| 328 | 0.015625 | 0.125 | 0.015625 | 0.0625 | 1 |
| 329 | 0.0625 | 0.125 | 0.0625 | 0.125 | <1 |
| 330 | 0.0625 | 0.0625 | 0.25 | 0.25 | 1 |
| 331 | 0.0625 | 0.0625 | 0.125 | 0.125 | <1 |
| 332 | 0.03125 | 0.0625 | 0.0625 | 0.25 | 2 |
| 333 | 0.0625 | 0.0625 | 0.125 | 0.25 | 2 |
| 334 | 0.03125 | 0.0625 | 0.03125 | 0.125 | <1 |
| 335 | 0.0625 | 0.0625 | 0.0625 | 0.125 | <1 |
| 336 | 0.0625 | 0.25 | 0.0625 | 0.125 | <1 |
| 337 | 0.0625 | 0.125 | 0.125 | 0.25 | 2 |
| 338 | 0.03125 | 0.03125 | 0.03125 | 0.125 | <1 |
| 339 | 0.0625 | 0.0625 | 0.0625 | 0.125 | <1 |
| 340 | 0.03125 | 0.0625 | 0.0625 | 0.25 | <1 |
| 341 | 0.0625 | 0.0625 | 0.0625 | 0.125 | <1 |
| 342 | 0.0625 | 0.0625 | n.d. | 0.0625 | n.d. |
| 343 | 0.03125 | 0.0625 | 0.0625 | 0.125 | <1 |
| 344 | 0.0625 | 0.0625 | 0.125 | 0.125 | <1 |
| 345 | 0.0625 | 0.0625 | 0.0625 | 0.125 | <1 |
| 346 | 0.0625 | 0.0625 | 0.0625 | 0.125 | <1 |
| 347 | 0.0625 | 0.0625 | 0.125 | 0.125 | <1 |
| 348 | 0.0625 | 0.0625 | 0.125 | 0.125 | <1 |
| 349 | 0.0625 | 0.125 | 0.0625 | 0.125 | <1 |
| 350 | 0.03125 | 0.125 | 0.03125 | 0.125 | <1 |
| 351 | 0.0625 | 0.0625 | 0.0625 | 0.125 | <1 |
| 352 | 0.125 | 0.125 | 1 | 0.25 | <1 |
| 353 | 0.125 | 0.125 | 1 | 0.25 | <1 |
| 354 | 0.0625 | 0.0625 | 0.03125 | 0.125 | 1 |
| 355 | 0.03125 | 0.0625 | 0.03125 | 0.125 | 6 |
| 356 | 0.0625 | 0.0625 | 0.0625 | 0.125 | 2 |
| 357 | 0.0625 | 0.125 | 0.0625 | 0.25 | <1 |
| 358 | 0.03125 | 0.125 | 0.03125 | 0.125 | 1 |
| 359 | 0.0625 | 0.125 | 0.0625 | 0.125 | 1 |
| 360 | 0.0625 | 0.0625 | 0.0625 | 0.125 | 2 |
| 361 | 0.0625 | 0.0625 | 0.0625 | 0.125 | <1 |
| 362 | 0.0625 | 0.0625 | 0.0625 | 0.125 | 2 |
| 363 | 0.0625 | 0.0625 | 0.0625 | 0.125 | 2 |
| 364 | 0.0625 | 0.0625 | 0.0625 | 0.125 | <1 |
| 365 | 0.03125 | 0.0625 | 0.0625 | 0.125 | <1 |
| 366 | 0.125 | 0.25 | 0.25 | 0.25 | 4 |
| 367 | 0.015625 | 0.03125 | 0.007813 | 0.0625 | <1 |
| 368 | 0.015625 | 0.03125 | 0.007813 | 0.0625 | 1 |
| 369 | 0.015625 | 0.03125 | 0.007813 | 0.0625 | <1 |
| 370 | 0.0625 | 0.0625 | 0.0625 | 0.125 | 2 |
| 371 | 0.0625 | 0.0625 | 0.0625 | 0.0625 | 0 |
| 372 | 0.0625 | 0.0625 | 0.03125 | 0.0625 | <1 |
| 373 | 0.0625 | 0.0625 | 0.03125 | 0.0625 | <1 |
| 374 | 0.0625 | 0.0625 | 0.0625 | 0.125 | <1 |
| 375 | 0.03125 | 0.0625 | 0.03125 | 0.125 | <1 |
| 376 | 0.0625 | 0.0625 | 0.0625 | 0.125 | <1 |
| 377 | 0.015625 | 0.03125 | 0.015625 | 0.0625 | <1 |
| 378 | 0.0625 | 0.0625 | 0.03125 | 0.0625 | <1 |
| 379 | 0.03125 | 0.0625 | 0.0625 | 0.125 | <1 |
| 380 | 0.03125 | 0.0625 | 0.0625 | 0.125 | <1 |
| 381 | 0.0625 | 0.0625 | 0.0625 | 0.125 | <1 |
| 382 | 0.0625 | 0.0625 | 0.0625 | 0.125 | <1 |
| 383 | 0.03125 | 0.0625 | 0.0625 | 0.125 | <1 |
| 384 | 0.125 | 0.25 | 1 | 0.5 | <1 |
| 385 | 0.015625 | 0.0625 | 0.03125 | 0.125 | <1 | n.d.: not determined

TABLE 4

Minimal inhibitory concentrations (MIC) of selected clinical isolates of Escherichia coli, Klebsiella pneumonia, Acintobacter baumannii and Enterobacter cloacae in Mueller-Hinton II broth

| Ex. | Escherichia coli 926415 MIC [µg/mL] | Klebsiella pneumoniae 968733 MIC [µg/mL] | Acinetobacter baumannii 872842 MIC [µg/mL] | Enterobacter cloacae 848840 MIC [µg/mL] |
|---|---|---|---|---|
| 1 | 1 | 2 | 1 | 4 |
| 2 | 0.125 | 0.25 | 0.125 | 0.5 |
| 3 | 0.25 | 0.25 | 0.125 | 2 |
| 4 | 0.25 | 0.5 | 0.125 | 0.25 |
| 5 | 0.125 | 0.25 | 0.125 | 0.125 |
| 6 | 0.5 | 0.5 | 4 | 4 |
| 7 | 0.5 | 0.25 | 1 | 2 |
| 8 | 0.5 | 0.25 | 0.0625 | 0.25 |
| 9 | 1 | 0.5 | 0.125 | 0.25 |
| 10 | 8 | 0.5 | 0.125 | 0.25 |
| 11 | 4 | 4 | 8 | 2 |
| 12 | 1 | 4 | 1 | 0.5 |
| 15 | 0.25 | 0.25 | 0.25 | 0.125 |
| 16 | 0.25 | 0.125 | 0.25 | 0.25 |
| 17 | 0.5 | 0.5 | 0.125 | 0.25 |
| 18 | 0.25 | 0.5 | 0.25 | 0.125 |
| 20 | 1 | 2 | 0.5 | 0.25 |
| 21 | 8 | 8 | 2 | 0.5 |
| 22 | 0.5 | 1 | 0.25 | 0.125 |
| 23 | 0.5 | 0.5 | 0.25 | 0.125 |
| 24 | 2 | 0.5 | 1 | 0.25 |
| 25 | 0.25 | 0.25 | 0.25 | 0.125 |
| 26 | 0.125 | 0.25 | 0.125 | 0.25 |
| 27 | 1 | 1 | 0.125 | 0.25 |
| 28 | 8 | 8 | 4 | 0.125 |
| 29 | 4 | 8 | 1 | 0.0625 |
| 31 | 0.5 | 0.125 | 0.125 | 0.125 |
| 32 | 0.0625 | 0.25 | 0.0625 | 0.125 |
| 33 | 0.125 | 0.25 | 0.0625 | 0.125 |
| 34 | 0.0625 | 0.125 | 0.0625 | 0.125 |
| 35 | 1 | 0.25 | 0.25 | 0.25 |
| 36 | 0.125 | 0.25 | 0.0625 | 0.125 |
| 37 | 0.5 | 2 | 1 | 0.25 |
| 38 | 0.5 | 0.25 | 0.25 | 0.5 |
| 39 | 0.25 | 0.5 | 0.25 | 0.5 |
| 40 | 1 | 0.25 | 0.5 | 0.5 |
| 41 | 0.25 | 0.125 | 0.125 | 0.25 |
| 42 | 0.5 | 2 | 1 | 4 |
| 43 | 0.5 | 2 | 0.125 | 2 |
| 44 | 0.125 | 0.25 | 0.125 | 0.125 |
| 45 | 0.5 | 0.5 | 0.25 | 0.25 |
| 46 | 0.125 | 0.5 | 0.125 | 0.125 |
| 47 | 0.25 | 1 | 0.125 | 4 |
| 48 | 1 | 8 | 0.5 | 4 |
| 49 | 0.25 | 0.125 | 0.25 | 0.25 |
| 50 | 0.5 | 4 | 1 | 8 |
| 51 | 0.5 | 1 | 0.25 | 0.5 |
| 52 | 2 | 4 | 2 | 2 |
| 53 | 0.5 | 4 | 0.5 | 8 |
| 54 | 0.5 | 4 | 0.5 | 4 |
| 55 | 1 | 8 | 1 | 8 |
| 57 | 0.5 | 4 | 0.5 | 0.25 |
| 58 | 0.125 | 0.25 | 0.0625 | 0.125 |
| 59 | 0.125 | 0.25 | 0.25 | 1 |
| 60 | 0.125 | 0.125 | 0.125 | 4 |
| 61 | 0.25 | 0.125 | 0.125 | 0.125 |
| 62 | 0.25 | 0.125 | 0.125 | 4 |
| 63 | 0.5 | 0.25 | 0.25 | 4 |
| 64 | 0.5 | 1 | 0.5 | 4 |
| 65 | 0.5 | 0.5 | 0.25 | 4 |
| 66 | 1 | 4 | 0.5 | 0.5 |
| 67 | 2 | 2 | 2 | 2 |
| 68 | 2 | 1 | 8 | n.d. |
| 69 | 0.0625 | 0.125 | 0.0625 | 0.125 |
| 70 | 0.5 | 0.25 | 0.25 | 0.125 |
| 71 | 0.25 | 0.25 | 0.125 | 0.25 |
| 72 | 0.125 | 0.125 | 0.0625 | 0.25 |
| 73 | 0.125 | 0.125 | 0.0625 | 0.125 |
| 74 | 0.25 | 0.0625 | 0.0625 | 0.125 |
| 75 | 0.125 | 0.125 | 0.0625 | 0.125 |
| 76 | 0.125 | 0.125 | 0.25 | 0.125 |
| 77 | 0.25 | 0.25 | 0.25 | 0.25 |
| 78 | 0.125 | 0.0625 | 0.125 | 2 |
| 79 | 0.0625 | 0.0625 | 0.0625 | 0.0625 |
| 80 | 0.0625 | 0.125 | 0.0625 | 0.125 |
| 81 | 0.125 | 0.125 | 0.25 | 0.125 |
| 82 | 0.5 | 0.25 | 0.25 | 0.25 |
| 83 | 0.25 | 0.25 | 0.125 | 0.125 |
| 84 | 0.125 | 0.125 | 0.125 | 0.25 |
| 85 | 0.25 | 0.25 | 0.25 | 0.125 |
| 86 | 0.25 | 0.125 | 0.25 | 1 |
| 87 | 0.0625 | 0.125 | 0.25 | 2 |
| 88 | 0.125 | 0.125 | 0.125 | 0.125 |
| 89 | 0.5 | 1 | 0.5 | 0.5 |
| 90 | 0.5 | 0.25 | 0.125 | 0.25 |
| 91 | 2 | 2 | 0.5 | 1 |
| 92 | 0.0625 | 0.125 | 0.125 | 0.25 |
| 93 | 0.25 | 0.5 | 0.5 | 0.25 |
| 94 | 0.25 | 0.25 | 0.25 | 1 |
| 95 | 0.125 | 0.125 | 0.125 | 4 |
| 96 | 0.5 | 0.125 | 0.5 | 8 |
| 97 | 2 | 8 | 2 | n.d. |
| 98 | 2 | 4 | 2 | 2 |
| 99 | 0.125 | 0.0625 | 0.0625 | 0.125 |
| 100 | 0.25 | 0.0625 | 0.125 | 0.125 |
| 101 | 0.5 | 0.5 | 0.125 | 0.25 |
| 102 | 2 | 4 | 0.5 | 0.5 |
| 103 | 0.125 | 0.25 | 0.0625 | 0.125 |
| 104 | 0.0625 | 0.0625 | 0.0625 | 0.125 |
| 105 | 0.25 | 0.25 | 0.125 | 0.125 |
| 106 | 0.125 | 0.25 | 0.25 | 0.25 |
| 107 | 0.125 | 0.125 | 0.0625 | 0.0625 |
| 108 | 0.125 | 0.125 | 0.0625 | 0.125 |
| 109 | 0.0625 | 0.125 | 0.0625 | 0.125 |
| 110 | 0.125 | 0.125 | 0.0625 | 0.0625 |
| 111 | 0.0625 | 0.125 | 0.0625 | 0.125 |
| 112 | 0.0625 | 0.125 | 0.0625 | 0.125 |
| 113 | 0.25 | 0.5 | 0.25 | 0.125 |
| 114 | 0.0625 | 0.0625 | 0.03125 | 0.0625 |
| 115 | 0.125 | 0.25 | 0.125 | 0.0625 |
| 116 | 0.125 | 0.25 | 0.0625 | 0.03125 |
| 117 | 0.0625 | 0.0625 | 0.015625 | 0.0625 |
| 119 | 0.0625 | 0.125 | 0.03125 | 0.0625 |
| 120 | 0.0625 | 0.125 | 0.0625 | 0.25 |
| 121 | 0.125 | 0.25 | 0.0625 | 0.125 |
| 122 | 4 | 2 | 1 | 2 |
| 123 | 0.03125 | 0.0625 | 0.03125 | 0.0625 |
| 124 | 0.25 | 0.25 | 0.0625 | 0.125 |
| 125 | 0.0625 | 0.125 | 0.125 | 0.125 |
| 126 | 0.125 | 0.25 | 0.25 | 0.5 |
| 127 | 0.125 | 0.5 | 0.0625 | 0.125 |
| 128 | 0.125 | 0.0625 | 0.0625 | 0.0625 |
| 129 | 0.25 | 0.125 | 0.125 | 0.125 |
| 130 | 0.125 | 0.125 | 0.125 | 0.0625 |
| 131 | 0.5 | 1 | 1 | 0.25 |
| 132 | 0.0625 | 0.125 | 0.0625 | 0.125 |
| 133 | 0.0625 | 0.125 | 0.03125 | 0.25 |
| 134 | 0.125 | 0.125 | 0.0625 | 0.125 |
| 135 | 0.0625 | 0.125 | 0.03125 | 0.0625 |
| 136 | 0.0625 | 0.0625 | 0.03125 | 0.0625 |
| 137 | 0.125 | 0.125 | 0.125 | 0.0625 |
| 138 | 0.03125 | 0.0625 | 0.03125 | 0.125 |
| 139 | 0.125 | 0.25 | 0.0625 | 0.125 |
| 140 | 0.25 | 0.5 | 0.5 | 0.25 |
| 141 | 0.03125 | 0.03125 | 0.0625 | 0.0625 |
| 142 | 0.03125 | 0.0625 | 0.03125 | 0.125 |
| 143 | 0.125 | 0.0625 | 0.03125 | 0.0625 |
| 144 | 0.0625 | 0.0625 | 0.0625 | 0.125 |
| 145 | 0.0625 | 0.125 | 0.03125 | 0.125 |
| 146 | 0.25 | 0.25 | 0.125 | 0.25 |

TABLE 4-continued

Minimal inhibitory concentrations (MIC) of selected clinical isolates of *Escherichia coli*, *Klebsiella pneumonia*, *Acintobacter baumannii* and *Enterobacter cloacae* in Mueller-Hinton II broth

| Ex. | *Escherichia coli* 926415 MIC [µg/mL] | *Klebsiella pneumoniae* 968733 MIC [µg/mL] | *Acinetobacter baumannii* 872842 MIC [µg/mL] | *Enterobacter cloacae* 848840 MIC [µg/mL] |
|---|---|---|---|---|
| 147 | 0.25 | 0.5 | 0.25 | 0.125 |
| 148 | 0.125 | 0.25 | 0.0625 | 0.0625 |
| 149 | 0.25 | 0.5 | 0.125 | 0.125 |
| 150 | 0.25 | 0.5 | 0.125 | 0.125 |
| 151 | 0.5 | 1 | 0.25 | 0.125 |
| 152 | 2 | 8 | 1 | 0.5 |
| 153 | 0.125 | 0.25 | 0.0625 | 0.125 |
| 154 | 0.125 | 0.25 | 0.0625 | 0.125 |
| 155 | 0.5 | 0.5 | 0.125 | 0.125 |
| 156 | 0.125 | 0.25 | 0.125 | 0.125 |
| 157 | 1 | 1 | 0.5 | 0.25 |
| 158 | 0.5 | 1 | 0.25 | 0.125 |
| 159 | 0.25 | 0.5 | 0.25 | 0.125 |
| 160 | 0.5 | 0.5 | 0.5 | 2 |
| 161 | 0.5 | 0.25 | 0.25 | 1 |
| 162 | 1 | 8 | 0.5 | n.d. |
| 163 | 0.5 | 0.5 | 0.25 | 4 |
| 164 | 0.25 | 1 | 2 | n.d. |
| 165 | 0.125 | 0.5 | 1 | 4 |
| 166 | 0.25 | 0.125 | 0.25 | 0.25 |
| 167 | 0.25 | 0.25 | 0.125 | 2 |
| 168 | 0.125 | 0.5 | 0.125 | 0.25 |
| 169 | 0.5 | 4 | 1 | n.d. |
| 170 | 0.5 | 2 | 2 | n.d. |
| 171 | 0.125 | 0.5 | 0.0625 | 0.5 |
| 172 | 0.25 | 0.5 | 0.125 | 0.25 |
| 173 | 0.25 | 2 | 0.125 | 4 |
| 174 | 0.125 | 0.25 | 0.125 | 0.25 |
| 175 | 0.25 | 0.5 | 0.0625 | 0.25 |
| 176 | 0.25 | 0.25 | 0.125 | 0.5 |
| 177 | 0.25 | 0.5 | 0.125 | 1 |
| 178 | 0.5 | 2 | 0.25 | 0.25 |
| 179 | 0.5 | 4 | 0.25 | 0.5 |
| 181 | 2 | 8 | 2 | 1 |
| 182 | 0.5 | 1 | 0.125 | 0.125 |
| 184 | 2 | 8 | 1 | 1 |
| 185 | 0.25 | 1 | 0.25 | 0.25 |
| 186 | 1 | 8 | 0.25 | 0.25 |
| 188 | 0.5 | 1 | 0.5 | 0.5 |
| 189 | 1 | 4 | 0.5 | 0.25 |
| 190 | 1 | 4 | 0.5 | 0.5 |
| 191 | 1 | 2 | 0.5 | 0.5 |
| 193 | 0.5 | 0.5 | 0.5 | 0.5 |
| 194 | 0.5 | 0.25 | 0.25 | 0.125 |
| 195 | 0.5 | 0.5 | 0.25 | 0.25 |
| 196 | 2 | 2 | 1 | 1 |
| 197 | 0.5 | 0.5 | 0.25 | 0.25 |
| 198 | 0.25 | 0.5 | 0.125 | 0.25 |
| 199 | 0.5 | 0.5 | 0.25 | 0.25 |
| 200 | 2 | 2 | 1 | 2 |
| 201 | 0.25 | 0.25 | 0.125 | 0.125 |
| 202 | 0.25 | 0.25 | 0.25 | 0.125 |
| 203 | 0.5 | 0.25 | 0.125 | 0.5 |
| 204 | 0.5 | 0.5 | 0.25 | 0.125 |
| 206 | 0.0625 | 0.5 | 0.0625 | 0.125 |
| 207 | 0.5 | 1 | 0.25 | 0.5 |
| 208 | 0.25 | 0.5 | 0.125 | 0.25 |
| 209 | 1 | 4 | 2 | n.d. |
| 210 | 2 | 2 | 0.5 | 2 |
| 211 | 0.25 | 0.25 | 0.0625 | 2 |
| 212 | 1 | 2 | 0.5 | 0.5 |
| 213 | 0.5 | 0.5 | 0.125 | 1 |
| 214 | 0.5 | 0.5 | 0.5 | 8 |
| 215 | 2 | 2 | 0.5 | 0.5 |
| 216 | 1 | 4 | 2 | n.d. |
| 217 | 1 | 2 | 4 | n.d. |
| 219 | 0.25 | 0.5 | 0.125 | 0.125 |
| 220 | 0.125 | 0.125 | 0.0625 | 0.125 |
| 221 | 0.125 | 0.25 | 0.0625 | 0.125 |
| 222 | 0.25 | 0.25 | 0.0625 | 0.125 |
| 223 | 0.125 | 0.25 | 0.03125 | 0.0625 |
| 224 | 0.125 | 0.25 | 0.0625 | 0.125 |
| 225 | 0.25 | 1 | 0.25 | 0.125 |
| 226 | 0.0625 | 0.25 | 0.0625 | 0.0625 |
| 227 | 0.125 | 0.5 | 0.125 | 0.125 |
| 228 | 1 | 1 | 4 | 8 |
| 232 | 0.0625 | 0.125 | 0.0625 | 0.125 |
| 233 | 0.0625 | 0.0625 | 0.0625 | 0.125 |
| 234 | 0.25 | 1 | 0.25 | 0.5 |
| 235 | 0.125 | 0.25 | 0.0625 | 0.25 |
| 236 | 2 | 8 | 2 | 1 |
| 237 | 0.25 | 0.5 | 0.125 | 0.125 |
| 238 | 0.125 | 0.25 | 0.0625 | 0.125 |
| 239 | 0.0625 | 0.25 | 0.125 | 0.25 |
| 240 | 0.0625 | 0.5 | 0.0625 | 0.125 |
| 241 | 1 | 1 | 0.125 | 2 |
| 242 | 0.25 | 1 | 0.125 | 4 |
| 243 | 0.125 | 0.125 | 0.0625 | 0.25 |
| 244 | 0.125 | 0.0625 | 0.0625 | 0.0625 |
| 245 | 0.125 | 0.25 | 0.0625 | 0.125 |
| 246 | 2 | 4 | 4 | 2 |
| 247 | 0.5 | 8 | 0.5 | 0.25 |
| 248 | 0.25 | 4 | 1 | 4 |
| 249 | 0.125 | 0.25 | 0.03125 | 0.125 |
| 250 | 0.0625 | 0.125 | 0.03125 | 0.0625 |
| 251 | 0.125 | 0.0625 | 0.03125 | 0.125 |
| 252 | 0.125 | 0.125 | 0.0625 | 0.125 |
| 253 | 0.0625 | 0.0625 | 0.03125 | 0.125 |
| 254 | 0.125 | 0.125 | 0.03125 | 0.0625 |
| 255 | 0.0625 | 0.25 | 0.125 | 0.0625 |
| 256 | 0.0625 | 0.0625 | 0.03125 | 0.0625 |
| 257 | 0.0625 | 0.125 | 0.03125 | 0.0625 |
| 258 | 0.25 | 0.125 | 0.03125 | 0.0625 |
| 259 | 0.125 | 0.0625 | 0.03125 | 0.0625 |
| 260 | 0.5 | 0.5 | 0.0625 | 0.0625 |
| 261 | 0.125 | 0.25 | 0.0625 | 0.125 |
| 262 | 0.25 | 0.25 | 0.0625 | 0.0625 |
| 263 | 0.125 | 0.25 | 0.0625 | 0.125 |
| 264 | 0.125 | 0.125 | 0.0625 | 0.5 |
| 265 | 0.125 | 0.25 | 0.125 | 0.5 |
| 266 | 0.5 | 1 | 0.5 | 0.25 |
| 267 | 0.0625 | 0.125 | 0.0625 | 0.125 |
| 268 | 0.5 | 0.5 | 0.125 | 0.25 |
| 269 | 0.0625 | 0.0625 | 0.03125 | 0.125 |
| 270 | 0.125 | 0.125 | 0.0625 | 0.25 |
| 271 | 0.0625 | 0.0625 | 0.0625 | 0.25 |
| 272 | 0.125 | 0.125 | 0.0625 | 0.25 |
| 273 | 0.5 | 0.5 | 0.0625 | 0.25 |
| 274 | 0.125 | 0.125 | 0.125 | 0.25 |
| 275 | 0.125 | 0.25 | 0.125 | 1 |
| 276 | 0.25 | 0.25 | 0.0625 | 0.125 |
| 277 | 0.25 | 0.25 | 0.125 | 0.125 |
| 278 | 0.25 | 0.25 | 0.125 | 0.125 |
| 279 | 1 | 2 | 0.5 | 0.25 |
| 280 | 0.25 | 0.5 | 0.125 | 0.0625 |
| 281 | 0.25 | 0.25 | 0.25 | 0.125 |
| 282 | 0.125 | 0.25 | 0.125 | 0.0625 |
| 283 | 0.5 | 2 | 0.5 | 0.125 |
| 284 | 1 | 2 | 0.5 | 0.125 |
| 285 | 2 | 4 | 0.5 | 0.25 |
| 286 | 1 | 2 | 0.5 | 0.25 |
| 287 | 1 | 2 | 0.25 | 0.125 |
| 288 | 4 | 8 | 1 | 1 |
| 289 | 0.25 | 0.25 | 0.0625 | 0.125 |
| 290 | 1 | 4 | 0.25 | 0.25 |
| 291 | 2 | 8 | 1 | 1 |
| 292 | 1 | 4 | 0.5 | 1 |
| 293 | 0.5 | 2 | 0.5 | 0.5 |
| 294 | 0.25 | 1 | 0.5 | 0.125 |
| 295 | 0.5 | 0.5 | 0.125 | 0.25 |

TABLE 4-continued

Minimal inhibitory concentrations (MIC) of selected clinical isolates of Escherichia coli, Klebsiella pneumonia, Acintobacter baumannii and Enterobacter cloacae in Mueller-Hinton II broth

| Ex. | Escherichia coli 926415 MIC [μg/mL] | Klebsiella pneumoniae 968733 MIC [μg/mL] | Acinetobacter baumannii 872842 MIC [μg/mL] | Enterobacter cloacae 848840 MIC [μg/mL] |
|---|---|---|---|---|
| 296 | 0.5 | 4 | 0.25 | 0.5 |
| 297 | 0.125 | 0.125 | 0.0625 | 0.125 |
| 298 | 0.5 | 1 | 0.25 | 0.25 |
| 299 | 0.25 | 0.5 | 0.125 | 0.125 |
| 300 | 0.25 | 2 | 1 | 0.125 |
| 301 | 0.125 | 0.5 | 0.25 | 0.125 |
| 302 | 2 | 2 | 0.5 | 0.5 |
| 303 | 1 | 1 | 0.5 | 1 |
| 304 | 2 | 4 | 1 | 2 |
| 305 | 0.25 | 0.25 | 0.125 | 0.25 |
| 306 | 0.0625 | 0.125 | 0.0625 | 0.0625 |
| 307 | 0.5 | 1 | 0.5 | 4 |
| 308 | 0.5 | 1 | 0.5 | 1 |
| 309 | 0.0625 | 0.125 | 0.03125 | 0.0625 |
| 310 | 0.0625 | 0.0625 | 0.0625 | 0.0625 |
| 311 | 0.25 | 0.125 | 0.125 | 0.125 |
| 312 | 0.25 | 0.125 | 0.0625 | 0.0625 |
| 313 | 0.125 | 0.125 | 0.125 | 0.0625 |
| 314 | 0.0625 | 0.125 | 0.0625 | 0.125 |
| 315 | 0.0625 | 0.0625 | 0.0625 | 0.125 |
| 316 | 0.0625 | 0.0625 | 0.03125 | 0.0625 |
| 317 | 0.0625 | 0.125 | 0.03125 | 0.0625 |
| 318 | 0.125 | 0.125 | 0.0625 | 0.125 |
| 319 | 1 | 4 | 0.5 | 1 |
| 320 | 4 | 8 | 1 | 2 |
| 321 | 0.5 | 1 | 0.25 | 0.25 |
| 322 | 0.125 | 0.25 | 0.0625 | 0.0625 |
| 323 | 0.25 | 0.5 | 0.0625 | 0.125 |
| 324 | 0.125 | 0.5 | 0.125 | 0.125 |
| 325 | 0.125 | 0.5 | 0.125 | 0.0625 |
| 326 | 0.125 | 0.5 | 0.125 | 0.0625 |
| 327 | 0.25 | 0.5 | 0.125 | 0.125 |
| 328 | 0.125 | 0.25 | 0.0625 | 0.0625 |
| 329 | 0.125 | 0.25 | 0.125 | 0.125 |
| 330 | 0.25 | 2 | 1 | 0.125 |
| 331 | 0.5 | 0.5 | 0.25 | 0.25 |
| 332 | 0.25 | 0.5 | 0.25 | 0.125 |
| 333 | 0.5 | 1 | 0.5 | 0.25 |
| 334 | 0.25 | 0.25 | 0.125 | 0.125 |
| 335 | 0.25 | 0.5 | 0.25 | 0.25 |
| 336 | 0.5 | 0.5 | 0.125 | 0.125 |
| 337 | 1 | 2 | 0.25 | 0.25 |
| 338 | 0.0625 | 0.125 | 0.0625 | 0.0625 |
| 339 | 0.5 | 0.5 | 0.125 | 0.125 |
| 340 | 0.125 | 0.25 | 0.0625 | 0.125 |
| 341 | 0.5 | 1 | 0.25 | 2 |
| 342 | 0.125 | 0.25 | 0.0625 | |
| 343 | 0.25 | 0.5 | 0.25 | 0.125 |
| 344 | 0.125 | 0.25 | 0.25 | 1 |
| 345 | 0.125 | 0.25 | 0.125 | 0.125 |
| 346 | 0.25 | 0.5 | 0.125 | 0.125 |
| 347 | 0.25 | 1 | 0.25 | 0.5 |
| 348 | 0.5 | 2 | 0.5 | 0.5 |
| 349 | 0.25 | 0.25 | 0.25 | 0.25 |
| 350 | 0.125 | 0.125 | 0.0625 | 0.125 |
| 351 | 0.5 | 1 | 0.25 | 0.25 |
| 352 | 0.25 | 0.5 | 4 | 8 |
| 353 | 0.25 | 4 | 4 | 8 |
| 354 | 0.5 | 0.25 | 0.0625 | 0.125 |
| 355 | 0.25 | 0.25 | 0.0625 | 0.125 |
| 356 | 0.25 | 0.25 | 0.125 | 0.125 |
| 357 | 0.5 | 0.5 | 0.25 | 0.125 |
| 358 | 0.25 | 0.25 | 0.0625 | 0.125 |
| 359 | 0.25 | 0.5 | 0.125 | 0.125 |
| 360 | 0.25 | 0.5 | 0.125 | 0.125 |
| 361 | 0.125 | 0.125 | 0.0625 | 0.0625 |
| 362 | 0.0625 | 0.125 | 0.0625 | 0.0625 |
| 363 | 0.125 | 0.125 | 0.0625 | 0.0625 |
| 364 | 0.25 | 0.125 | 0.125 | 0.125 |
| 365 | 0.125 | 0.125 | 0.0625 | 0.0625 |
| 366 | 0.5 | 2 | 0.5 | 8 |
| 367 | 0.0625 | 0.0625 | 0.03125 | 0.0625 |
| 368 | 0.015625 | 0.0625 | 0.03125 | 0.03125 |
| 369 | 0.0625 | 0.0625 | 0.03125 | 0.03125 |
| 370 | 0.5 | 1 | 0.5 | 0.125 |
| 371 | 0.25 | 0.5 | 0.0625 | 0.5 |
| 372 | 0.125 | 0.25 | 0.125 | 0.25 |
| 373 | 0.125 | 0.125 | 0.0625 | 0.25 |
| 374 | 0.5 | 1 | 0.25 | 0.25 |
| 375 | 0.125 | 0.125 | 0.0625 | 0.25 |
| 376 | 0.25 | 0.5 | 0.25 | 0.0625 |
| 377 | 0.125 | 0.0625 | 0.0625 | 0.0625 |
| 378 | 0.0625 | 0.125 | 0.0625 | 0.0625 |
| 379 | 0.25 | 0.25 | 0.125 | 1 |
| 380 | 0.125 | 0.5 | 0.25 | 0.125 |
| 381 | 0.5 | 1 | 0.25 | 0.5 |
| 382 | 0.125 | 0.25 | 0.25 | 0.125 |
| 383 | 0.25 | 1 | 0.125 | 0.125 |
| 384 | 4 | >8 | 2 | 2 |
| 385 | 0.0625 | 0.125 | 0.0625 | 0.0625 |
| Colistin[1)3)] | 16 | 16 | 64 | >8 |
| Colistin[2)3)] | 8 | >8 | >8 | >8 |

[1)] measured in absence of P-80
[2)] measured in presence of P-80
[3)] Colistin (Colistin sulfate salt, Cat-Nr. C4461, Lot-Nr. SLBK0713V) obtained from Sigma Aldrich, Buchs; Switzerland

TABLE 5

Minimal inhibitory concentrations (MIC) of Escherichia coli MCR-1 Af45 in Mueller-Hinton II broth

| Ex. | Escherichia coli MCR-1 Af45 MIC [μg/mL] | Ex. | Escherichia coli MCR-1 Af45 MIC [μg/mL] |
|---|---|---|---|
| 3 | 0.125 | 132 | 0.125 |
| 41 | 0.125 | 133 | 0.125 |
| 72 | 0.125 | 134 | 0.25 |
| 73 | 0.125 | 135 | 0.125 |
| 79 | 0.125 | 136 | 0.125 |
| 84 | 0.125 | 137 | 0.25 |
| 88 | 0.25 | 138 | 0.125 |
| 92 | 0.25 | 139 | 0.25 |
| 96 | 0.25 | 140 | 0.25 |
| 99 | 0.0625 | 141 | 0.0625 |
| 100 | 0.125 | 142 | 0.125 |
| 103 | 0.0625 | 143 | 0.5 |
| 104 | 0.125 | 144 | 0.125 |
| 105 | 0.5 | 145 | 0.25 |
| 106 | 0.25 | 147 | 0.5 |
| 107 | 0.125 | 148 | 0.25 |
| 108 | 0.0625 | 150 | 0.25 |
| 109 | 0.125 | 151 | 0.5 |
| 110 | 0.125 | 153 | 0.25 |
| 111 | 0.125 | 154 | 0.125 |
| 112 | 0.125 | 156 | 0.25 |
| 113 | 0.5 | 159 | 0.25 |
| 114 | 0.0625 | 161 | 0.25 |
| 115 | 0.25 | 166 | 0.25 |
| 116 | 0.25 | 168 | 0.25 |
| 117 | 0.125 | 172 | 0.125 |
| 119 | 0.125 | 185 | 0.5 |
| 120 | 0.25 | 193 | 0.5 |
| 126 | 0.5 | 199 | 0.5 |
| 128 | 0.25 | 201 | 0.125 |

TABLE 5-continued

Minimal inhibitory concentrations (MIC) of *Escherichia coli* MCR-1 Af45 in Mueller-Hinton II broth

| Ex. | *Escherichia coli* MCR-1 Af45 MIC [µg/mL] | Ex. | *Escherichia coli* MCR-1 Af45 MIC [µg/mL] |
|---|---|---|---|
| 129 | 0.125 | 202 | 0.25 |
| 203 | 0.25 | 282 | 0.25 |
| 204 | 0.25 | 289 | 0.25 |
| 206 | 0.25 | 297 | 0.125 |
| 219 | 0.25 | 310 | 0.0625 |
| 221 | 0.25 | 334 | 0.125 |
| 222 | 0.5 | 340 | 0.0625 |
| 223 | 0.25 | 341 | 0.5 |
| 224 | 0.5 | 350 | 0.25 |
| 225 | 0.25 | 351 | 0.25 |
| 226 | 0.25 | 359 | 0.125 |
| 232 | 0.0625 | 365 | 0.0625 |
| 233 | 0.125 | 375 | 0.125 |
| 250 | 0.125 | 379 | 0.125 |
| 276 | 0.25 | Colistin [1) 3)] | 4 |
| 281 | 0.125 | Colistin [2) 3)] | 2 |

[1)] measured in absence of P-80

[2)] measured in presence of P-80

[3)] Colistin (Colistin sulfate salt, Cat-Nr. C4461, Lot-Nr. SLBK0713V) obtained from Sigma Aldrich, Buchs; Switzerland

TABLE 6

Tolerability in a mouse model

| Ex. | Mortality and dose | Ex. | Mortality and dose |
|---|---|---|---|
| 39 | 0/3 died at 2 × 30 mg/kg | 284 | 0/3 died at 2 × 40 mg/kg |
| 41 | 0/3 died at 2 × 30 mg/kg | 289 | 0/3 died at 2 × 40 mg/kg |
| 42 | 0/3 died at 2 × 30 mg/kg | 293 | 0/3 died at 2 × 40 mg/kg |
| 43 | 0/3 died at 2 × 30 mg/kg | 294 | 0/3 died at 2 × 40 mg/kg |
| 58 | 0/3 died at 2 × 30 mg/kg | 295 | 0/3 died at 2 × 40 mg/kg |
| 65 | 0/3 died at 2 × 30 mg/kg | 296 | 0/3 died at 2 × 40 mg/kg |
| 92 | 0/3 died at 2 × 30 mg/kg | 297 | 0/3 died at 2 × 40 mg/kg |
| 96 | 0/3 died at 2 × 30 mg/kg | 298 | 0/3 died at 2 × 40 mg/kg |
| 100 | 0/3 died at 2 × 30 mg/kg | 299 | 0/3 died at 2 × 40 mg/kg |
| 114 | 0/3 died at 2 × 30 mg/kg | 300 | 0/3 died at 2 × 40 mg/kg |
| 115 | 0/3 died at 2 × 30 mg/kg | 306 | 0/3 died at 2 × 40 mg/kg |
| 116 | 0/3 died at 2 × 30 mg/kg | 309 | 0/3 died at 2 × 40 mg/kg |
| 137 | 0/3 died at 2 × 30 mg/kg | 310 | 0/3 died at 2 × 40 mg/kg |
| 150 | 0/3 died at 2 × 30 mg/kg | 311 | 0/3 died at 2 × 40 mg/kg |
| 161 | 0/3 died at 2 × 30 mg/kg | 331 | 0/3 died at 2 × 40 mg/kg |
| 188 | 0/3 died at 2 × 30 mg/kg | 332 | 0/3 died at 2 × 40 mg/kg |
| 215 | 0/3 died at 2 × 30 mg/kg | 333 | 0/3 died at 2 × 40 mg/kg |
| 219 | 0/3 died at 2 × 30 mg/kg | 334 | 0/3 died at 2 × 40 mg/kg |
| 257 | 0/3 died at 2 × 30 mg/kg | 335 | 0/3 died at 2 × 40 mg/kg |
| 258 | 0/3 died at 2 × 30 mg/kg | 336 | 0/3 died at 2 × 40 mg/kg |
| 259 | 0/3 died at 2 × 30 mg/kg | 337 | 0/3 died at 2 × 40 mg/kg |
| 260 | 0/3 died at 2 × 30 mg/kg | 338 | 0/3 died at 2 × 40 mg/kg |
| 261 | 0/3 died at 2 × 30 mg/kg | 339 | 0/3 died at 2 × 40 mg/kg |
| 266 | 0/3 died at 2 × 30 mg/kg | 340 | 0/3 died at 2 × 40 mg/kg |
| 270 | 0/3 died at 2 × 40 mg/kg | 341 | 0/3 died at 2 × 40 mg/kg |
| 274 | 0/3 died at 2 × 40 mg/kg | 343 | 0/3 died at 2 × 40 mg/kg |
| 275 | 0/3 died at 2 × 40 mg/kg | 344 | 0/3 died at 2 × 40 mg/kg |
| 276 | 0/3 died at 2 × 40 mg/kg | 345 | 0/3 died at 2 × 40 mg/kg |
| 277 | 0/3 died at 2 × 40 mg/kg | 350 | 0/3 died at 2 × 40 mg/kg |
| 278 | 0/3 died at 2 × 40 mg/kg | 351 | 0/3 died at 2 × 40 mg/kg |
| 279 | 0/3 died at 2 × 40 mg/kg | 358 | 0/3 died at 2 × 40 mg/kg |
| 280 | 0/3 died at 2 × 40 mg/kg | 359 | 0/3 died at 2 × 40 mg/kg |
| 281 | 0/3 died at 2 × 40 mg/kg | 361 | 0/3 died at 2 × 40 mg/kg |
| 282 | 0/3 died at 2 × 40 mg/kg | 362 | 0/3 died at 2 × 40 mg/kg |
| 283 | 0/3 died at 2 × 40 mg/kg | 363 | 0/3 died at 2 × 40 mg/kg |
| 364 | 0/3 died at 2 × 40 mg/kg | | |
| 365 | 0/3 died at 2 × 40 mg/kg | | |
| 370 | 0/3 died at 2 × 40 mg/kg | | |
| 375 | 0/3 died at 2 × 40 mg/kg | | |
| 376 | 0/3 died at 2 × 40 mg/kg | | |
| 379 | 0/3 died at 2 × 40 mg/kg | | |
| 380 | 0/3 died at 2 × 40 mg/kg | | |
| 381 | 0/3 died at 2 × 40 mg/kg | | |
| 382 | 0/3 died at 2 × 40 mg/kg | | |
| 383 | 0/3 died at 2 × 40 mg/kg | | |

TABLE 7

Nephrotoxicity in a mouse model

| Ex. | Max Overall Kidney Histology Score | Semi-Quantitative Score (SQS) |
|---|---|---|
| 39 | 1 | +1 |
| 100 | 2 | +1 |
| 113 | 3 | +1 |
| 114 | 6 | +1 |
| 115 | 4 | +1 |
| 128 | 12 | +1 |
| 132 | 12 | +1 |
| 137 | 1 | +1 |
| 260 | 3 | +1 |
| 276 | 2 | +1 |
| 277 | 2 | +1 |
| 278 | 2 | +1 |
| 279 | 1 | +1 |
| 281 | 2 | +1 |
| 282 | 2 | +1 |
| 289 | 0 | 0 |
| 293 | 1 | +1 |
| 297 | 1 | +1 |
| 306 | 3 | +1 |
| 310 | 2 | +1 |
| 334 | 2 | +1 |
| 340 | 3 | +1 |
| 341 | 2 | +1 |
| 350 | 8 | +1 |
| 351 | 3 | +1 |
| Colistin B | 24 | +2 |

The invention claimed is:

1. A β-hairpin peptidomimetic selected from the group consisting of Ex. 1 to 385, the sequences of which are shown in the following Table below:

| Ex. No. | Sequence |
|---|---|
| Ex. 1 | 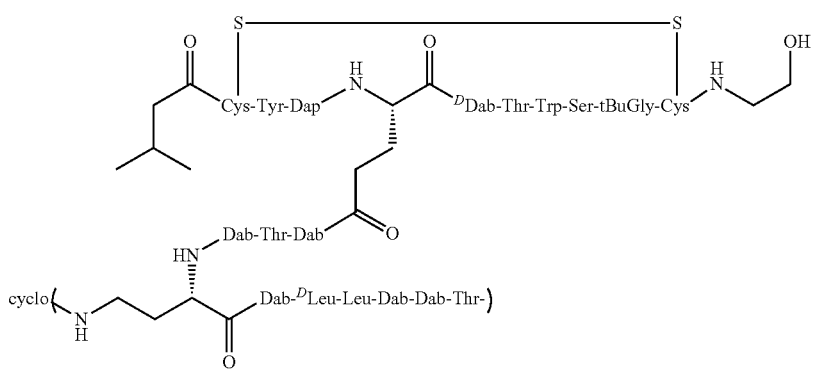 |
| Ex. 2 | 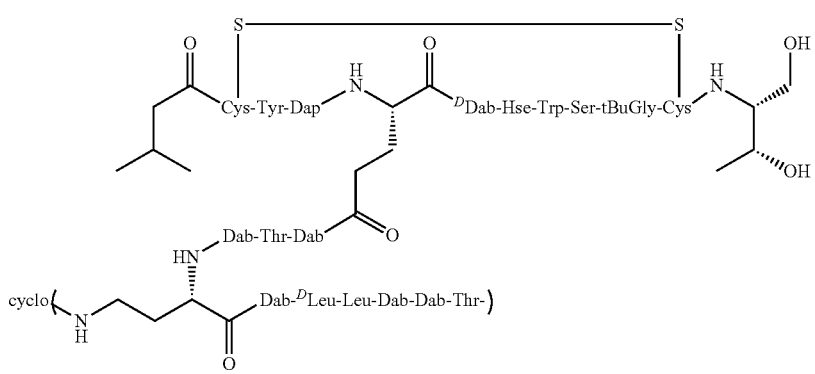 |
| Ex. 3 | 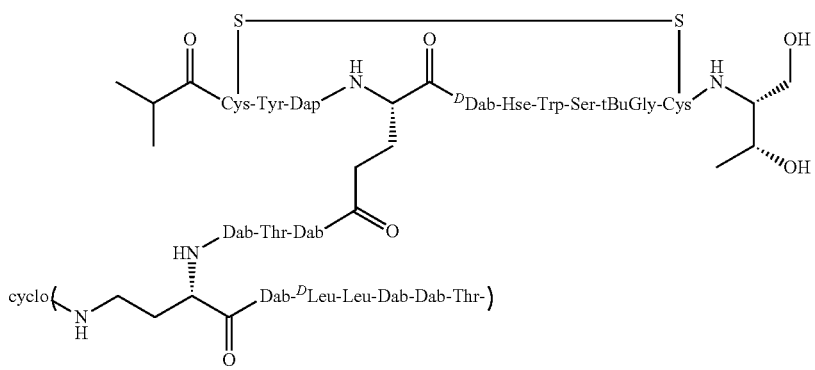 |
| Ex. 4 | 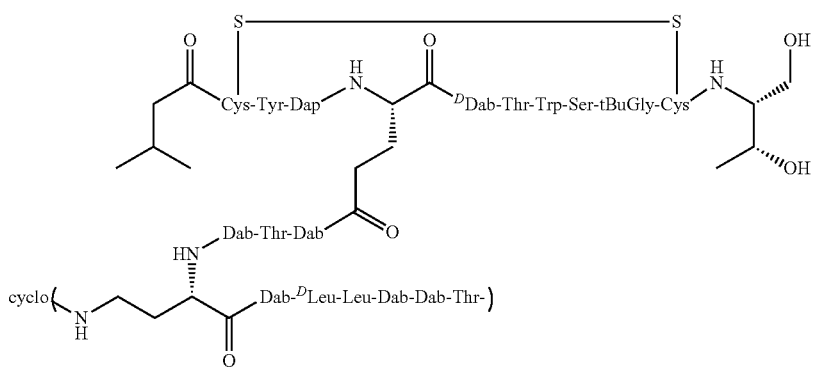 |

| Ex. No. | Sequence |
|---|---|
| Ex. 5 | 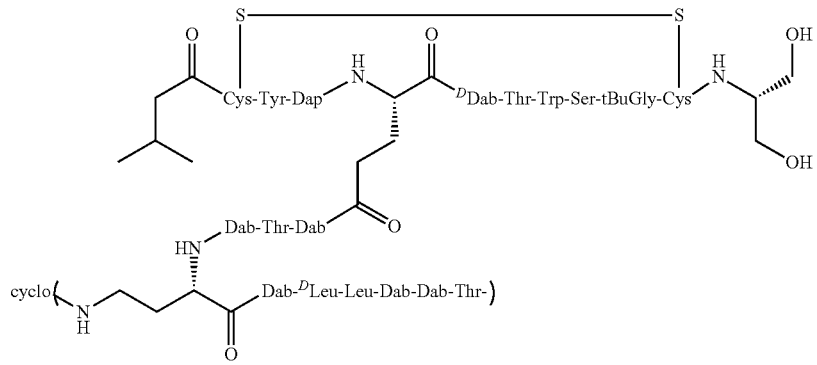 |
| Ex. 6 | 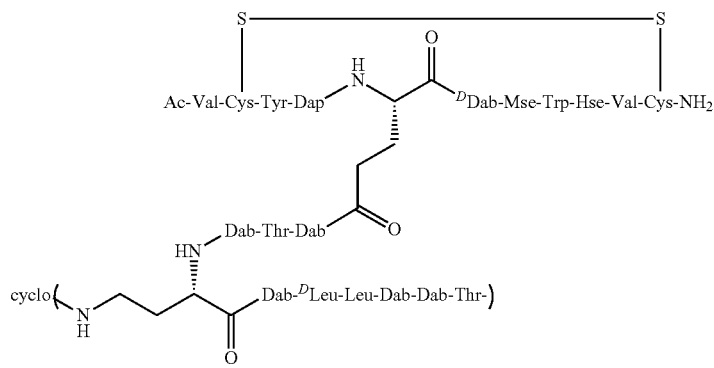 |
| Ex. 7 | 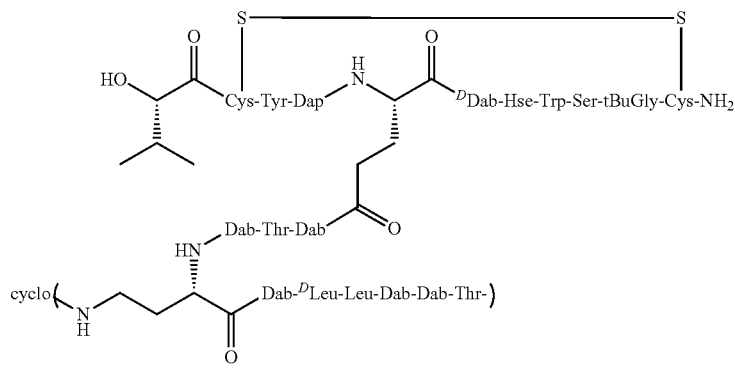 |
| Ex. 8 | 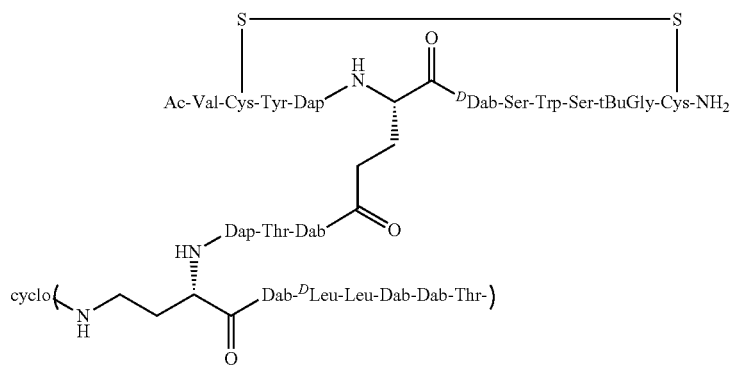 |

-continued
| Ex. No. | Sequence |
|---|---|
| Ex. 9 | 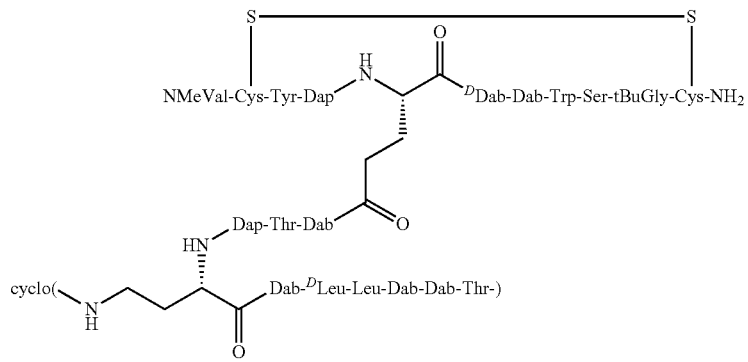 |
| Ex. 10 | 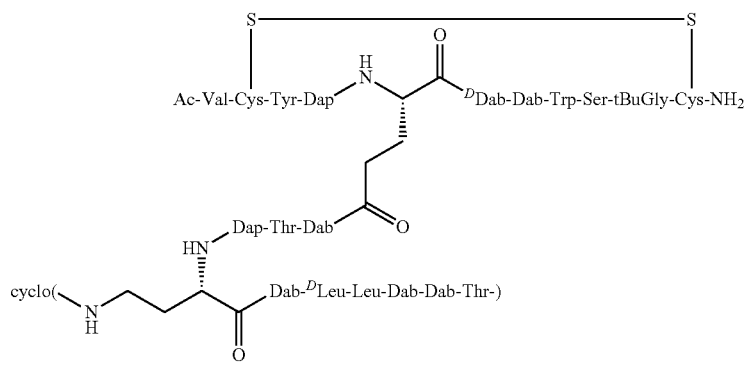 |
| Ex. 11 | 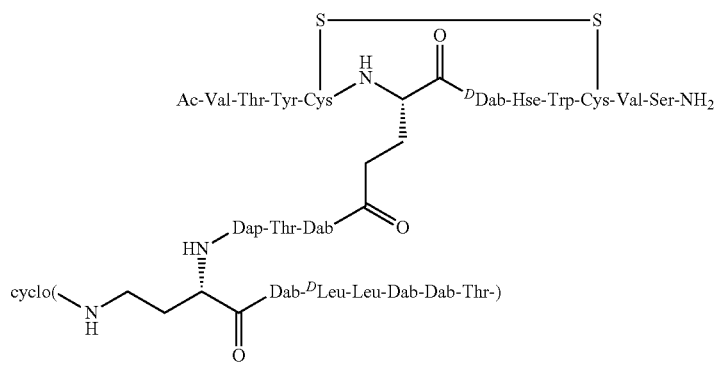 |
| Ex. 12 | 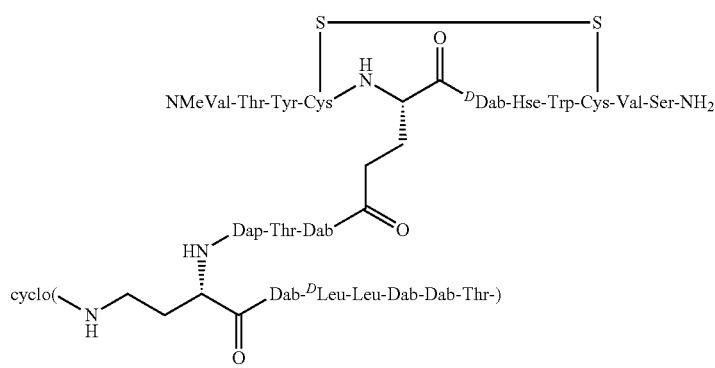 |

| Ex. No. | Sequence |
|---|---|
| Ex. 13 | 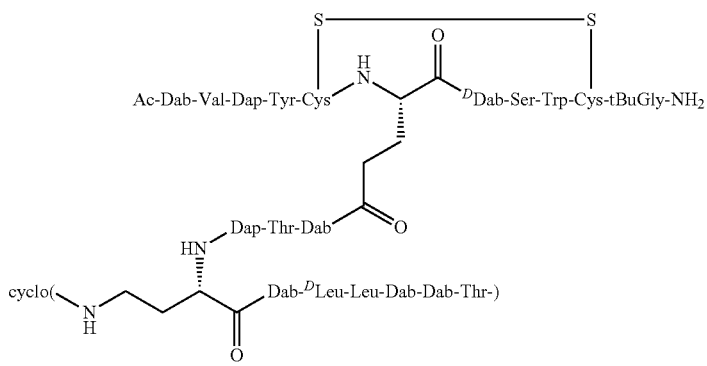 |
| Ex. 14 | 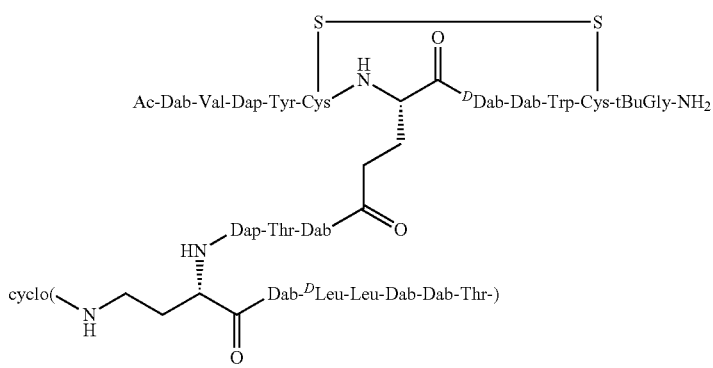 |
| Ex. 15 | 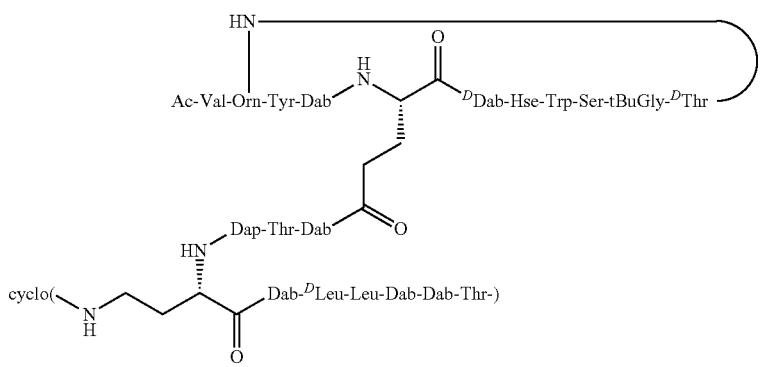 |
| Ex. 16 | 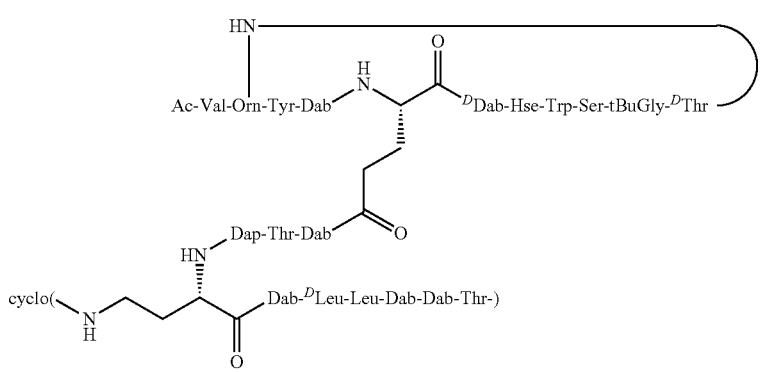 |

| Ex. No. | Sequence |
|---|---|
| Ex. 17 | 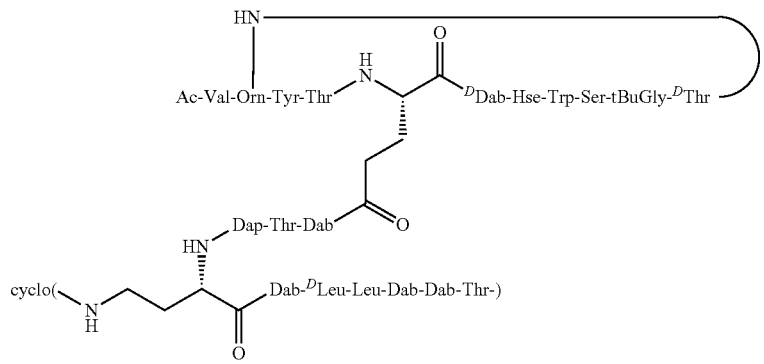 |
| Ex. 18 | 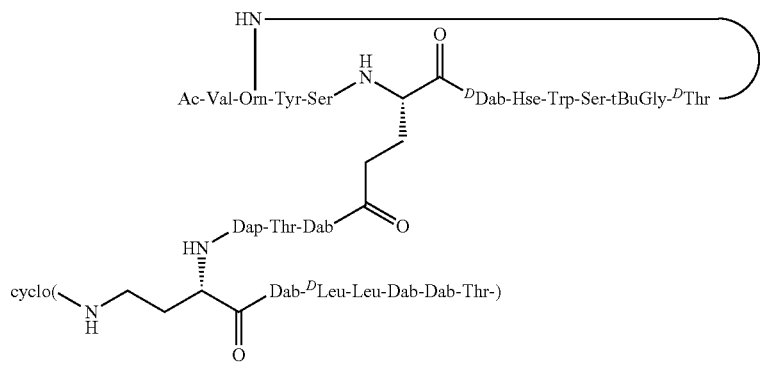 |
| Ex. 19 | 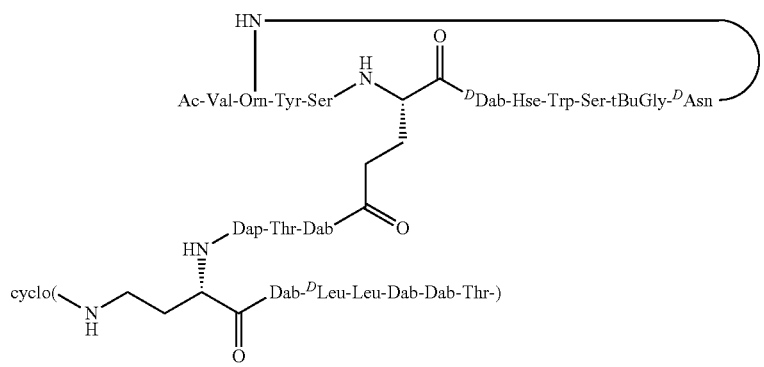 |
| Ex. 20 | 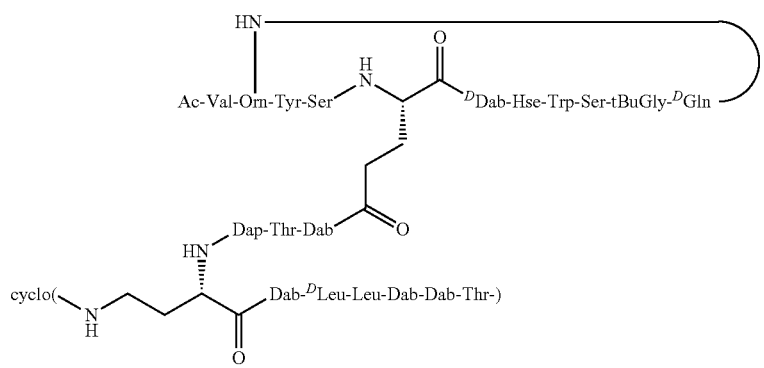 |

| Ex. No. | Sequence |
|---|---|
| Ex. 21 | 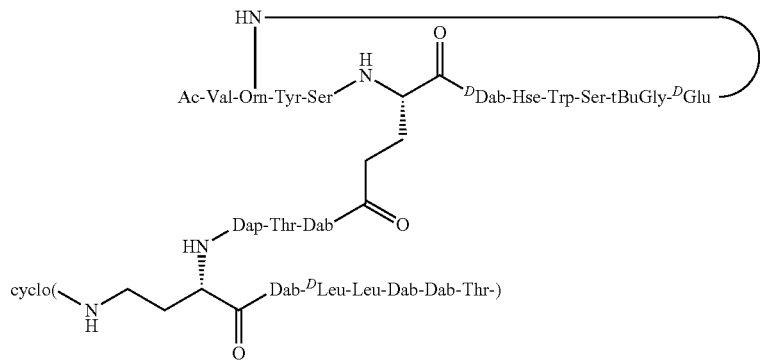 |
| Ex. 22 | 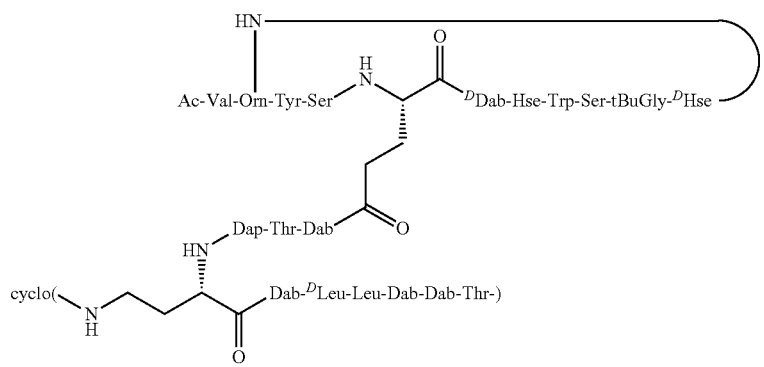 |
| Ex. 23 | 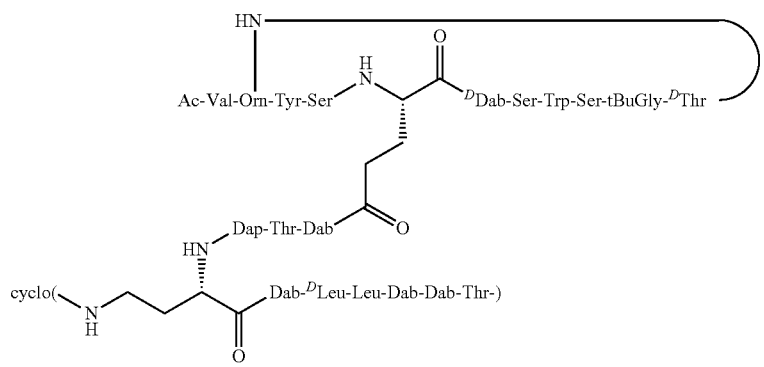 |
| Ex. 24 | 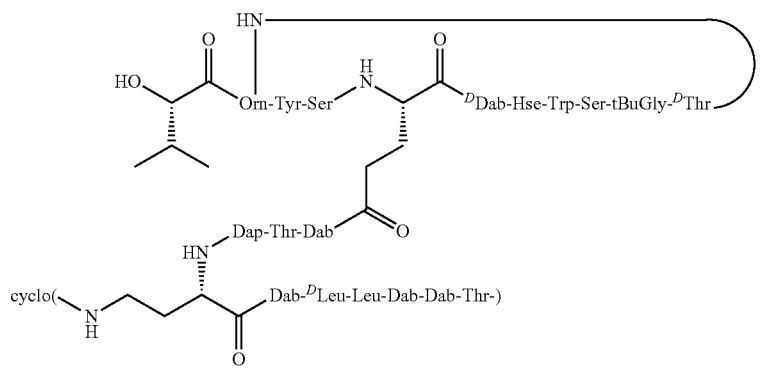 |

| Ex. No. | Sequence |
|---|---|
| Ex. 25 | 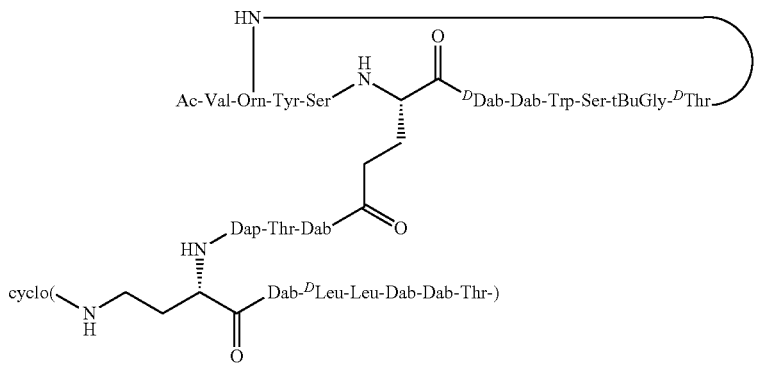 |
| Ex. 26 | 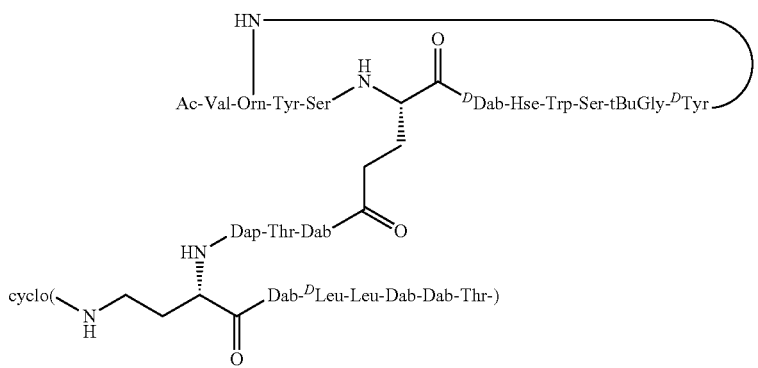 |
| Ex. 27 | 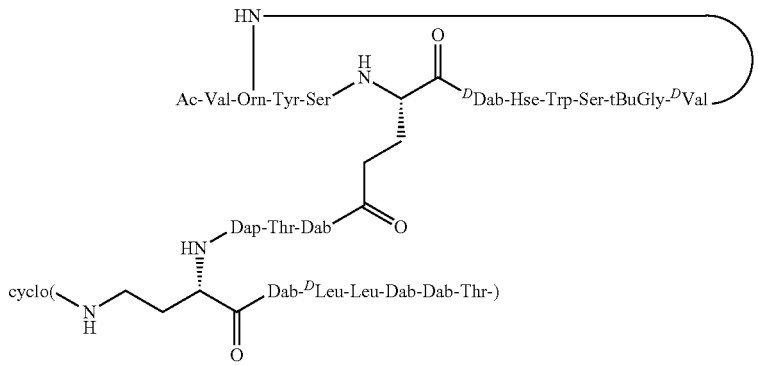 |
| Ex. 28 | 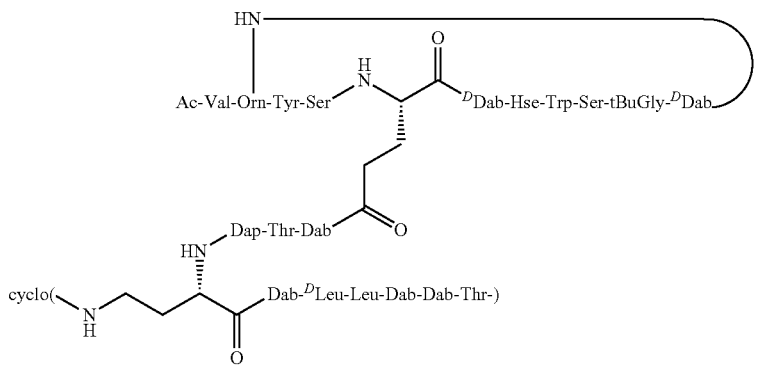 |

| Ex. No. | Sequence |
|---|---|
| Ex. 29 | 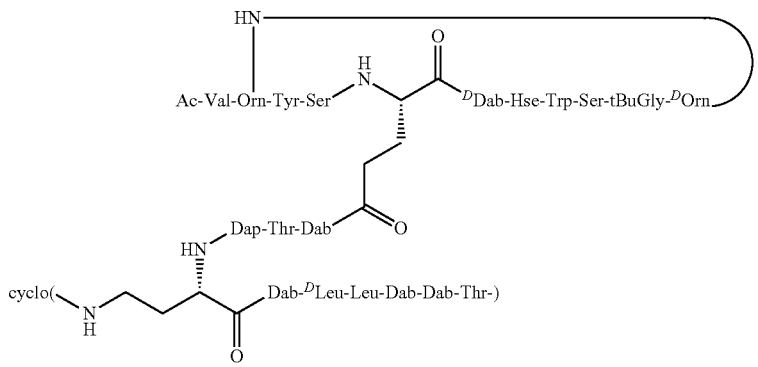 |
| Ex. 30 | 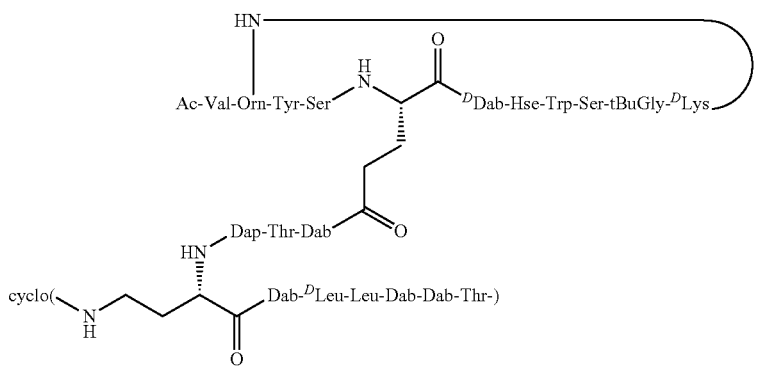 |
| Ex. 31 | 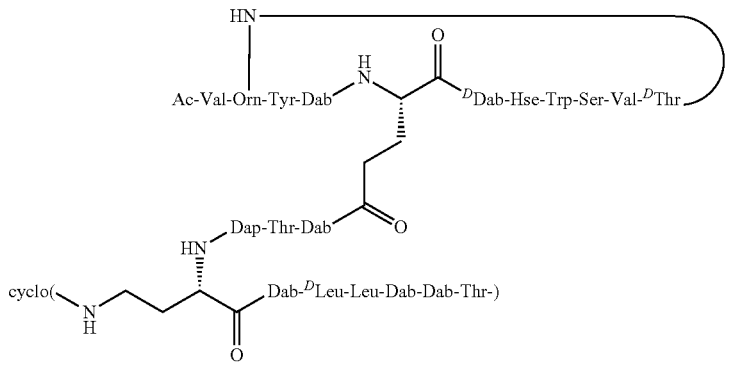 |
| Ex. 32 | 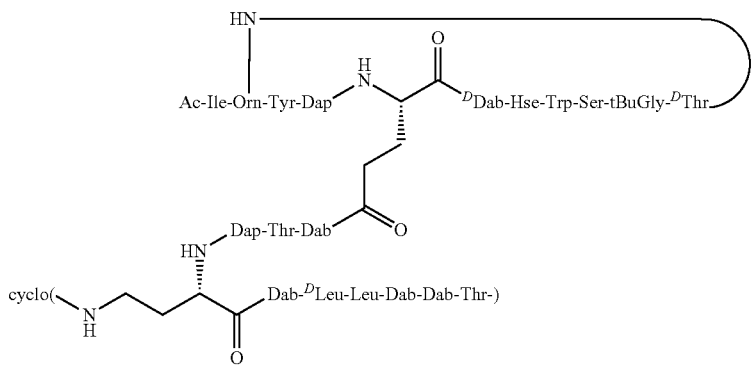 |

| Ex. No. | Sequence |
|---|---|
| Ex. 33 | 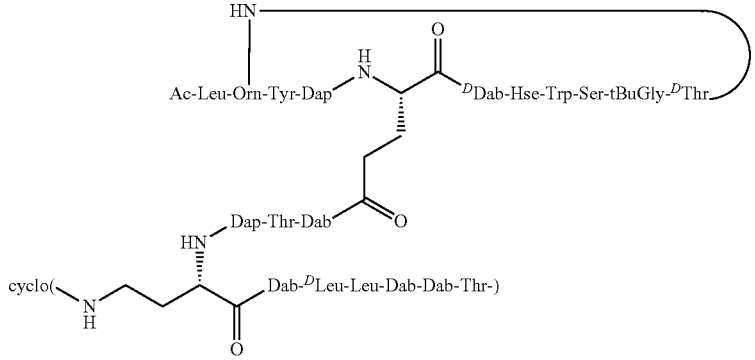 |
| Ex. 34 | 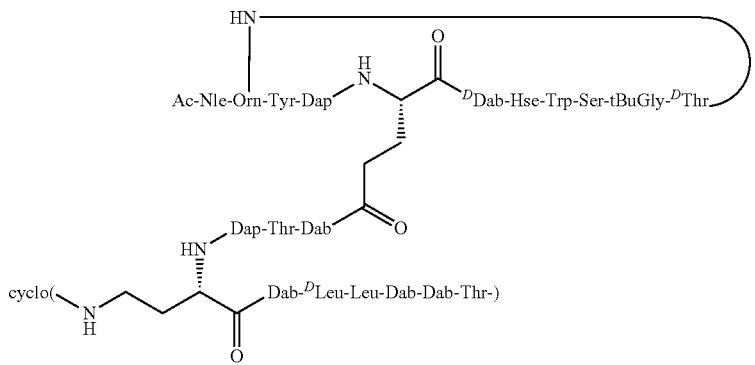 |
| Ex. 35 | 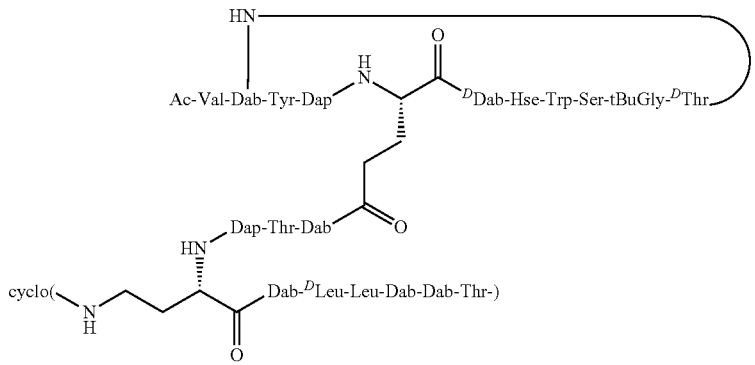 |
| Ex. 36 | 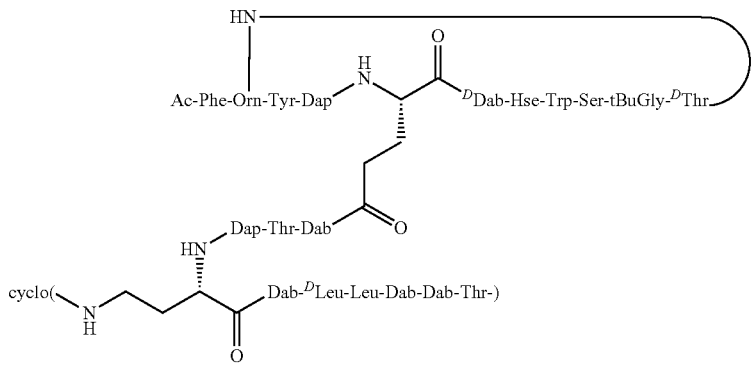 |

| Ex. No. | Sequence |
|---|---|
| Ex. 37 | 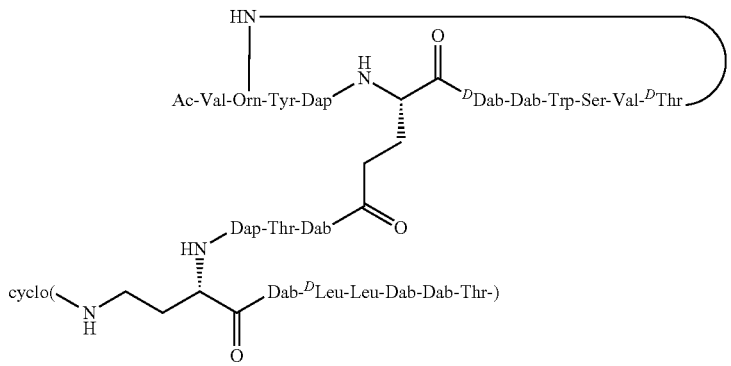 |
| Ex. 38 | 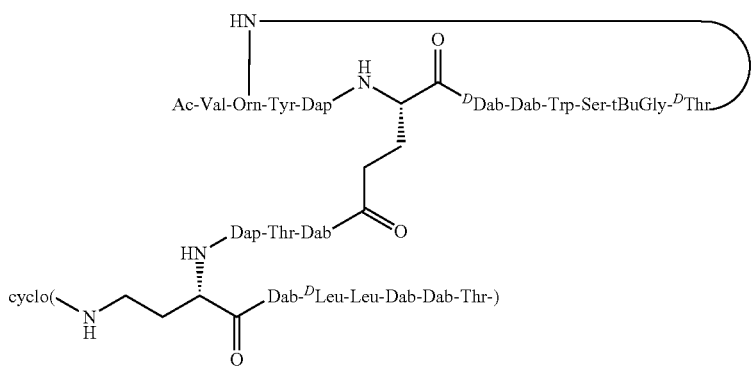 |
| Ex. 39 | 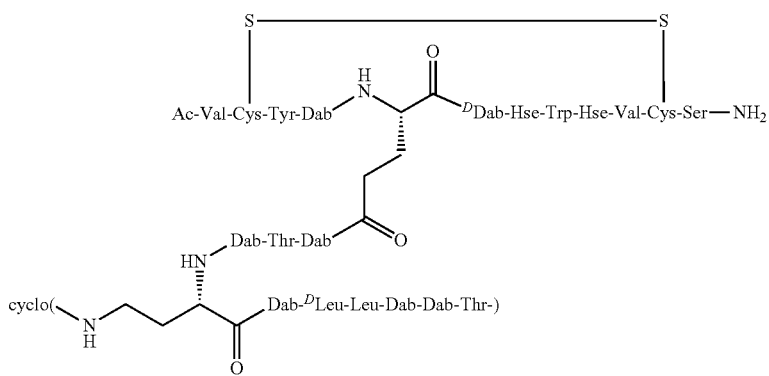 |
| Ex. 40 | 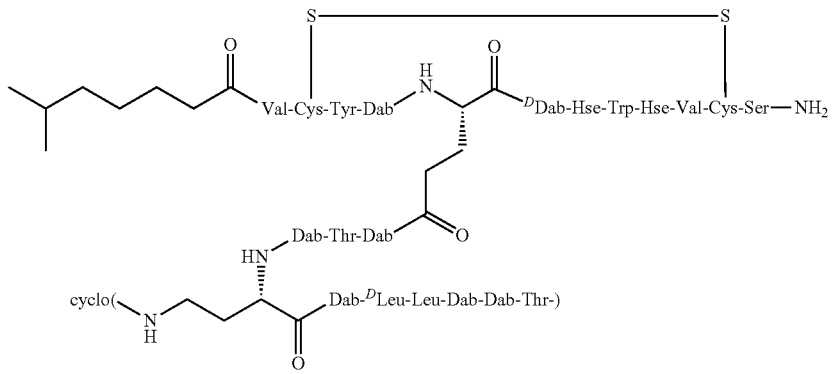 |

| Ex. No. | Sequence |
|---|---|
| Ex. 41 | 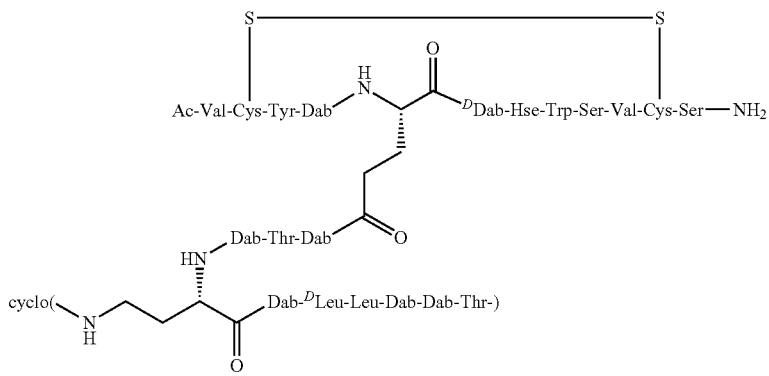 |
| Ex. 42 | 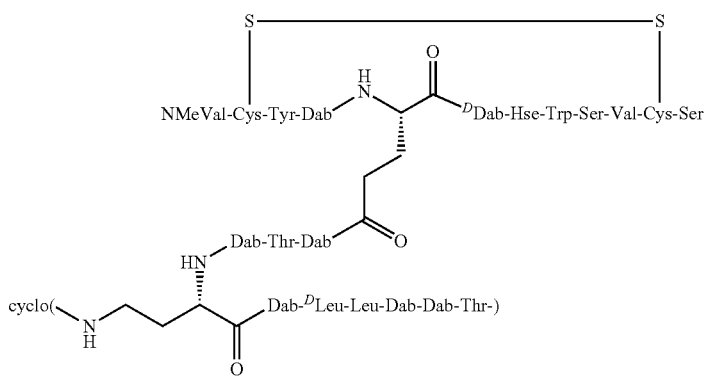 |
| Ex. 43 | 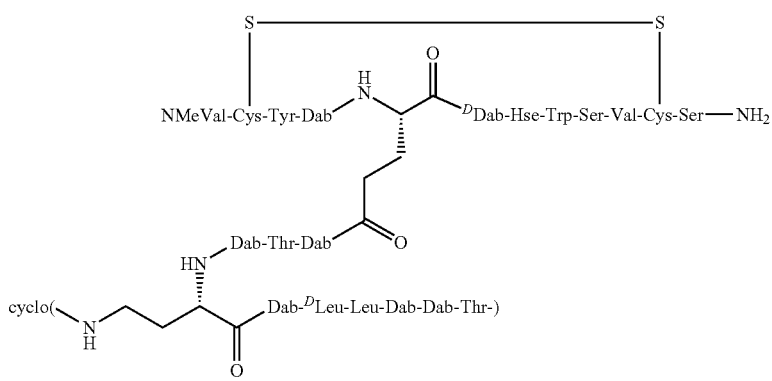 |
| Ex. 44 | 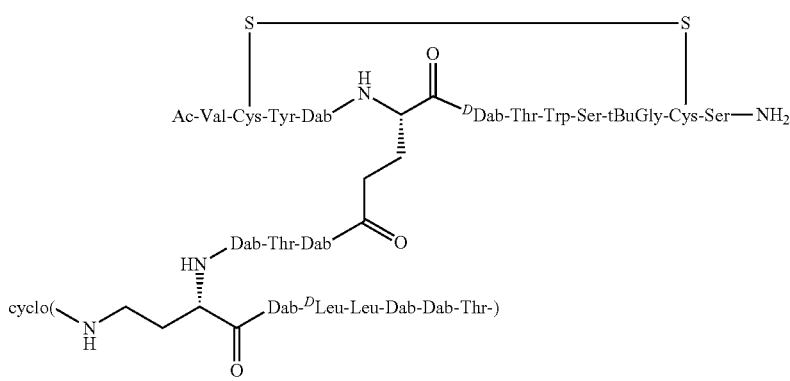 |

| Ex. No. | Sequence |
|---|---|
| Ex. 45 | 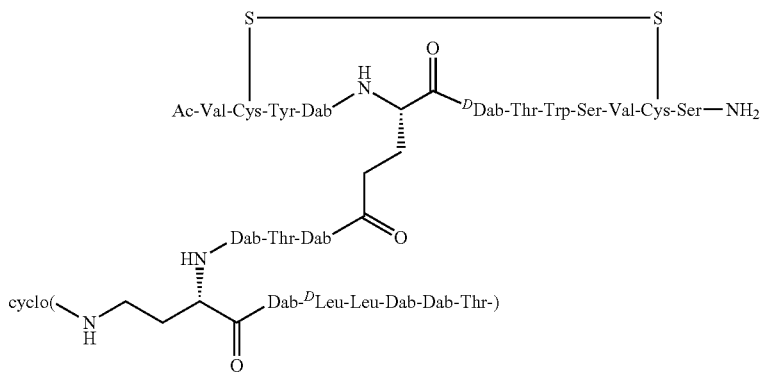 |
| Ex. 46 | 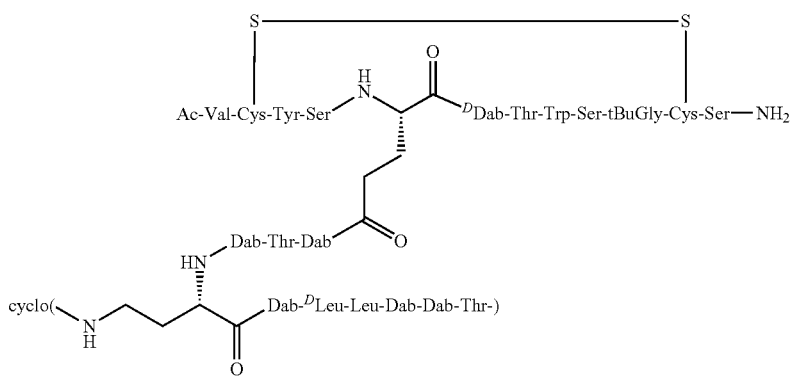 |
| Ex. 47 | 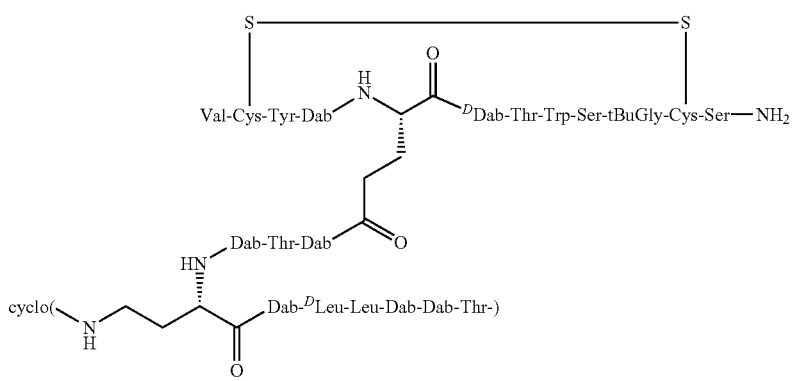 |
| Ex. 48 | 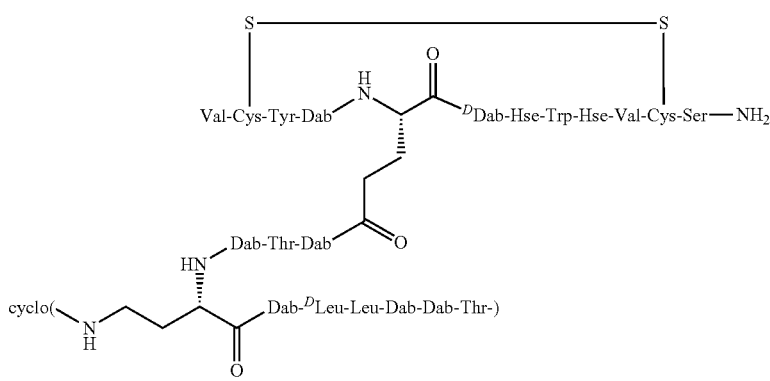 |

| Ex. No. | Sequence |
|---|---|
| Ex. 49 | 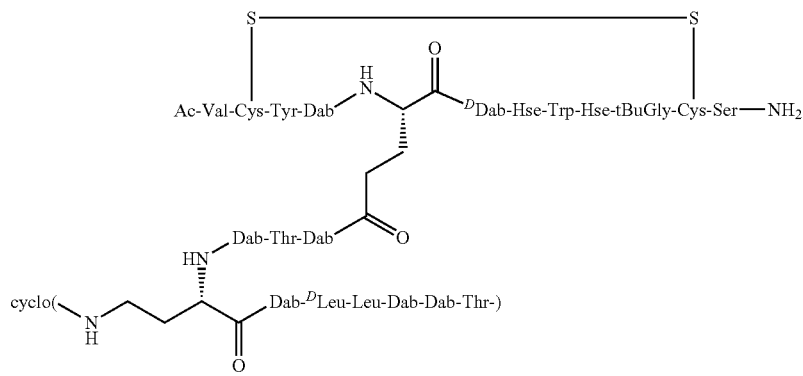 |
| Ex. 50 | 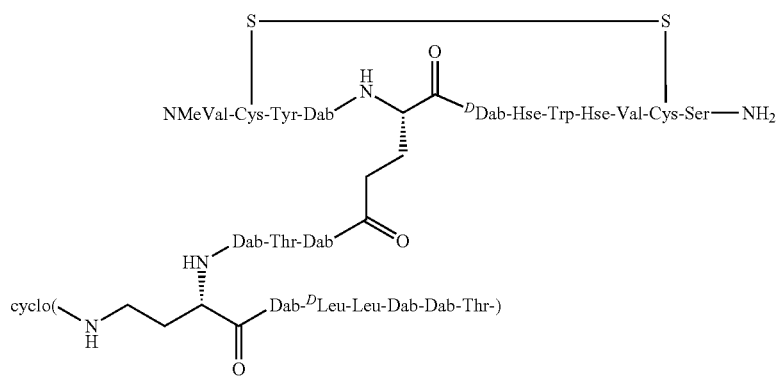 |
| Ex. 51 | 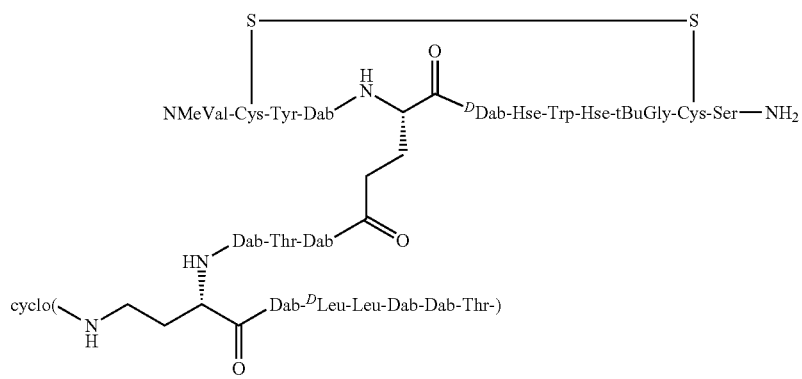 |
| Ex. 52 | 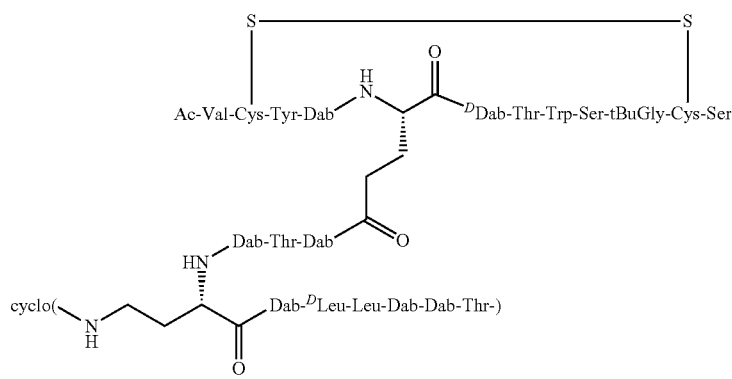 |

| Ex. No. | Sequence |
|---|---|
| Ex. 53 | 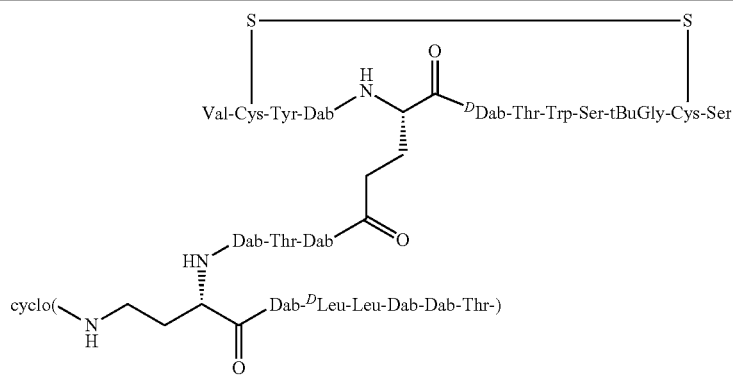 |
| Ex. 54 | 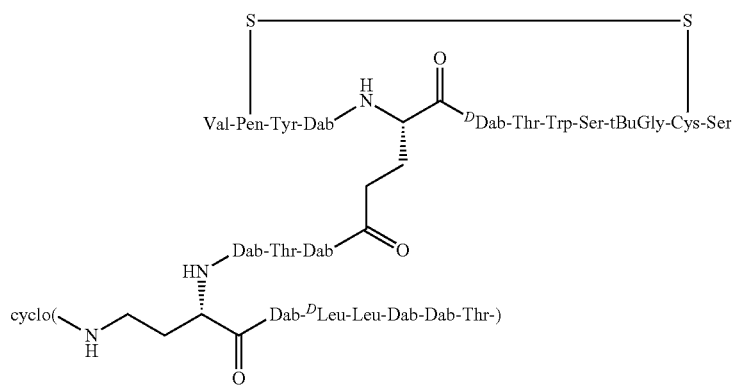 |
| Ex. 55 | 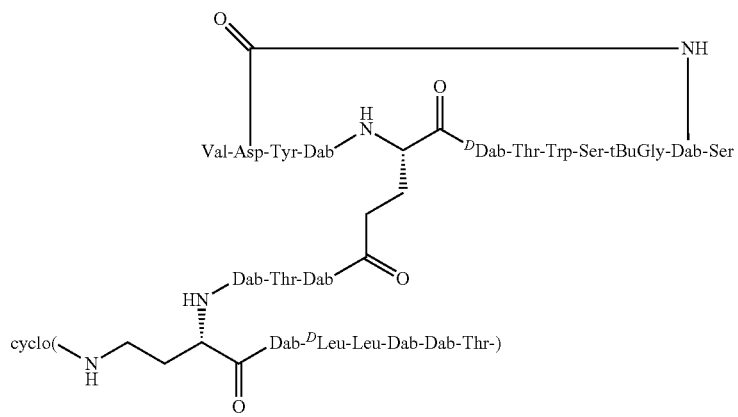 |
| Ex. 56 | 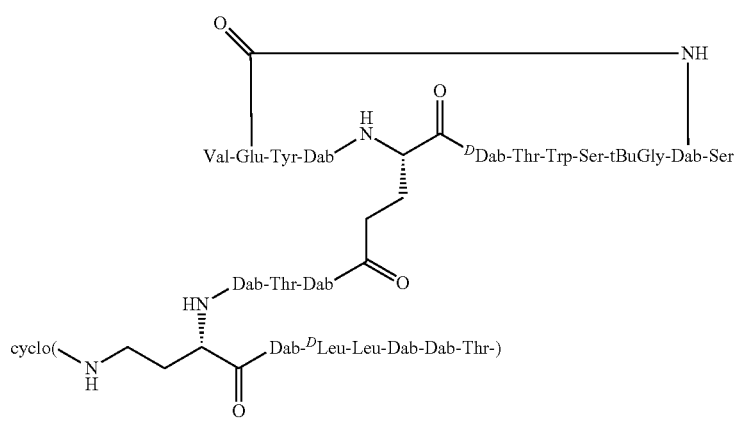 |

| Ex. No. | Sequence |
|---|---|
| Ex. 57 | 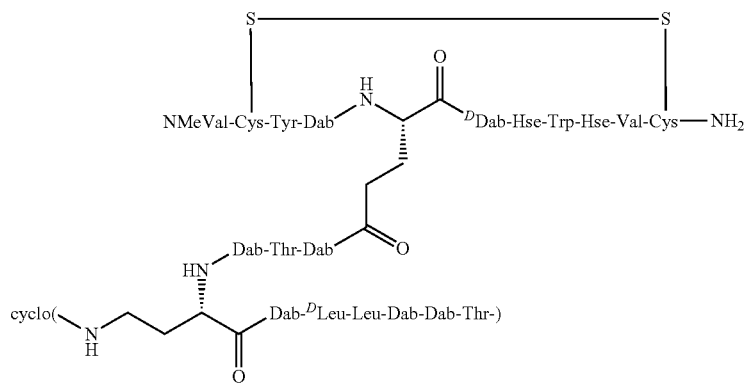 |
| Ex. 58 | 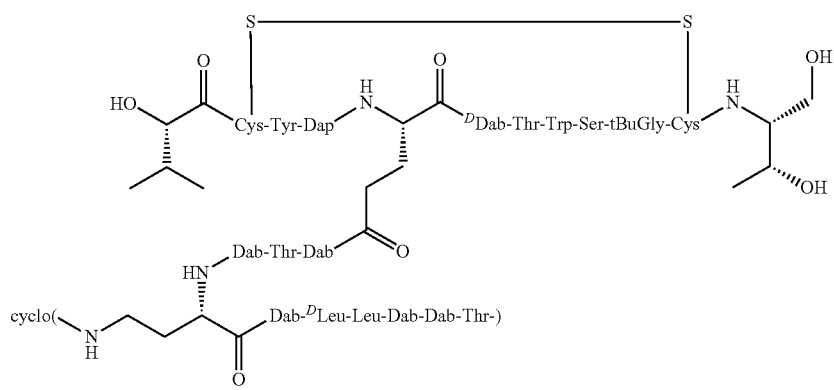 |
| Ex. 59 | 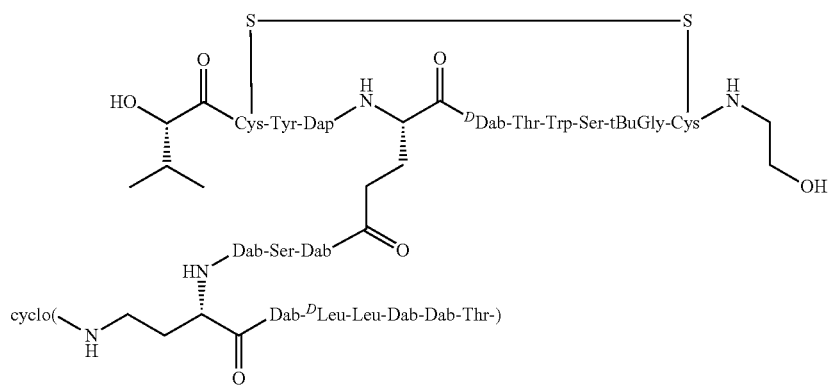 |
| Ex. 60 | 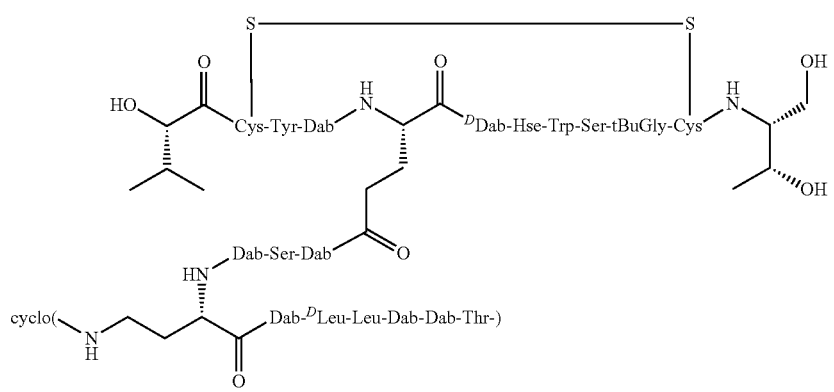 |

| Ex. No. | Sequence |
|---|---|
| Ex. 61 | 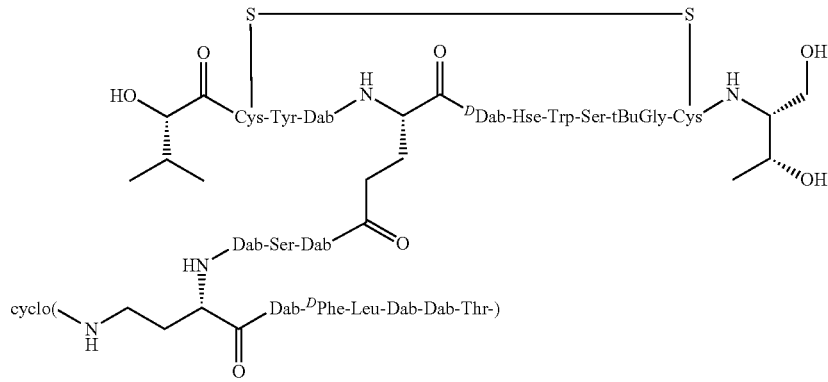 |
| Ex. 62 | 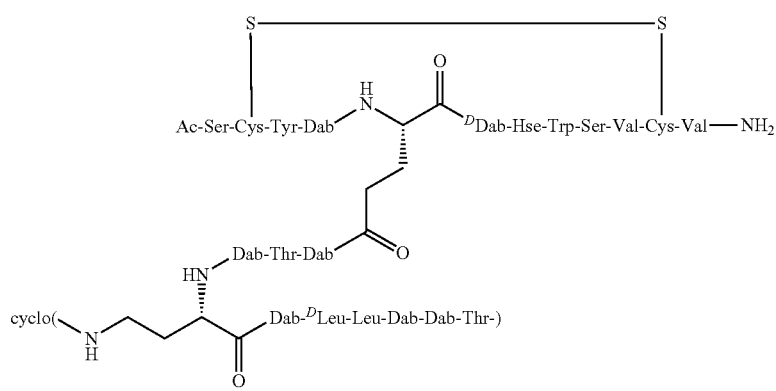 |
| Ex. 63 | 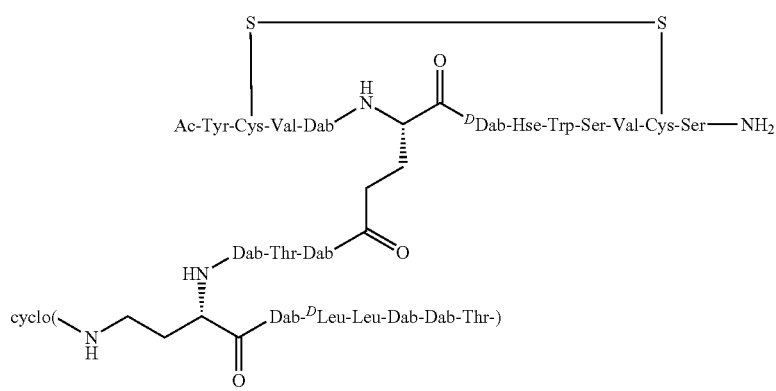 |
| Ex. 64 | 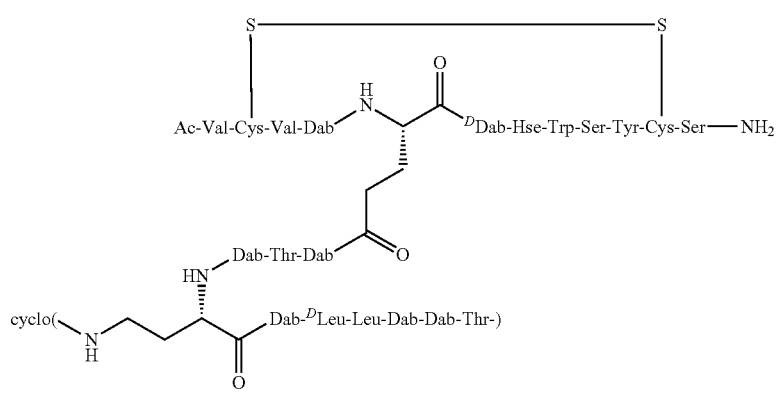 |

| Ex. No. | Sequence |
| --- | --- |
| Ex. 65 | 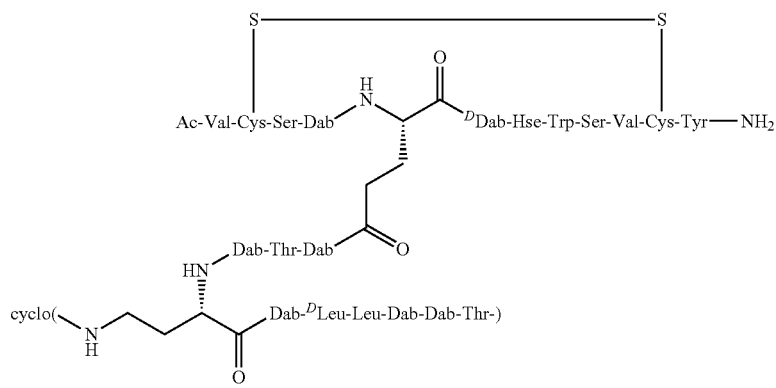 |
| Ex. 66 | 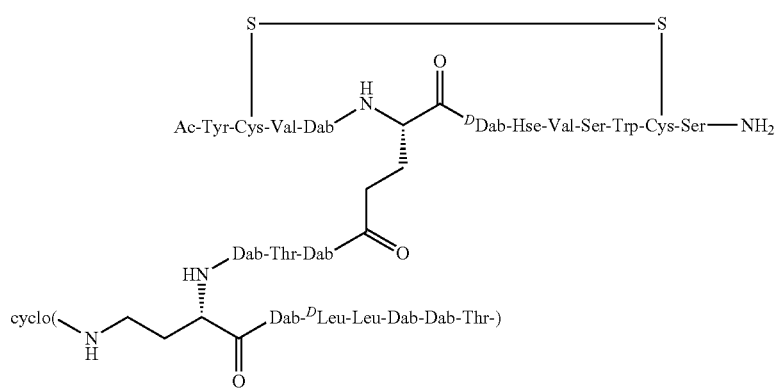 |
| Ex. 67 | 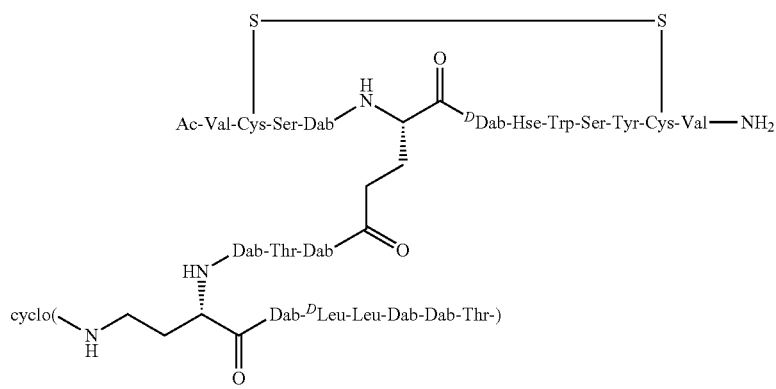 |
| Ex. 68 | 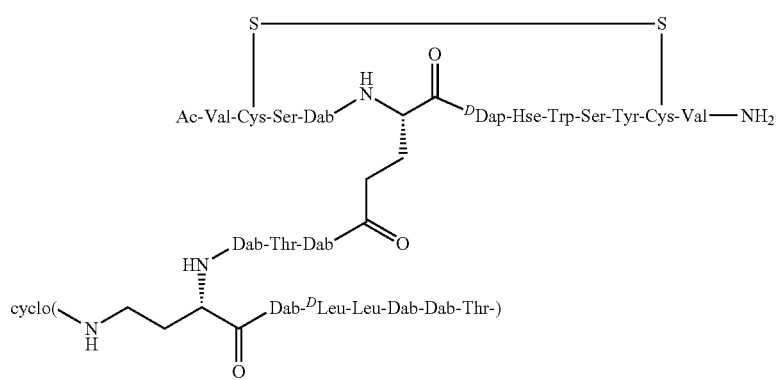 |

| Ex. No. | Sequence |
|---|---|
| Ex. 69 | 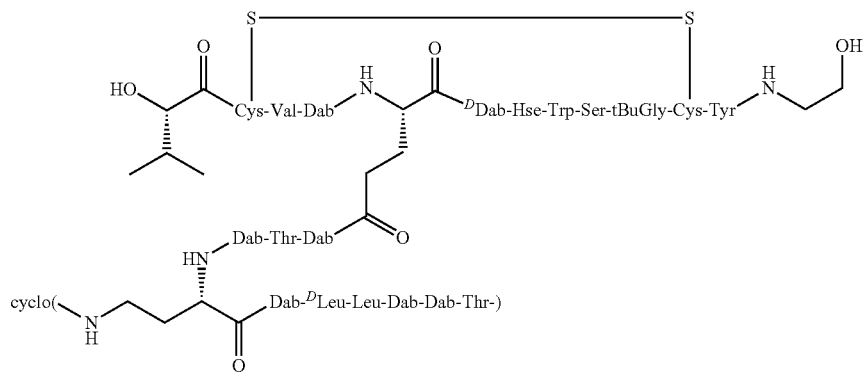 |
| Ex. 70 | 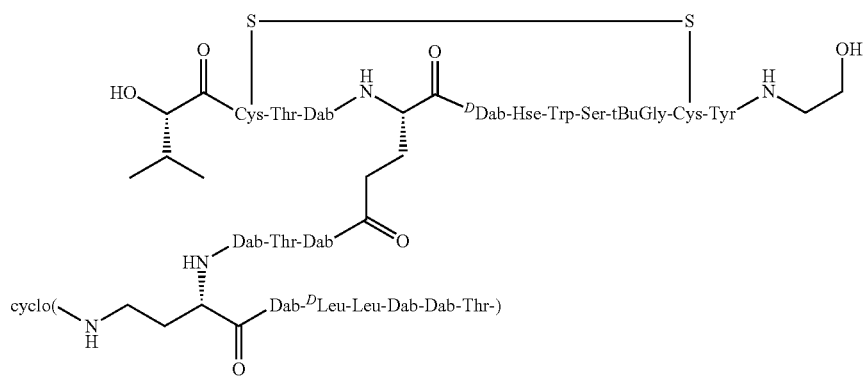 |
| Ex. 71 | 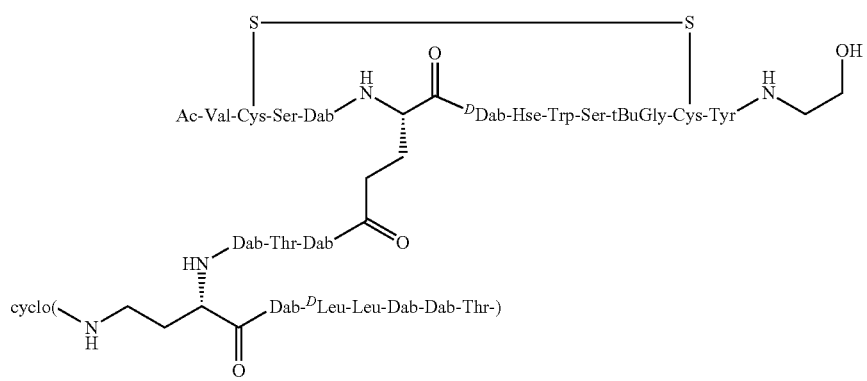 |
| Ex. 72 | 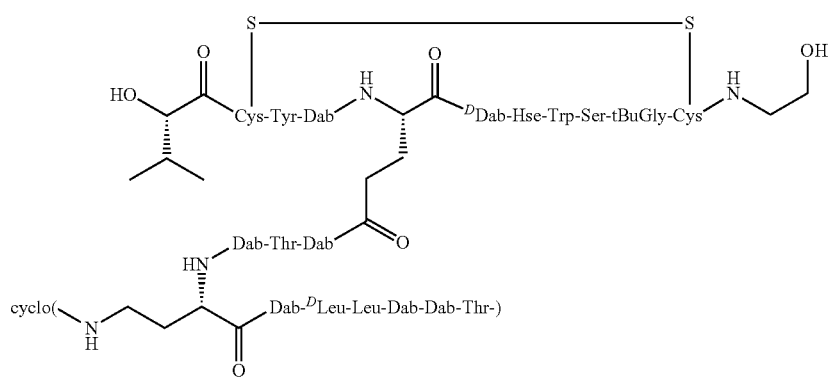 |

| Ex. No. | Sequence |
|---|---|
| Ex. 73 | 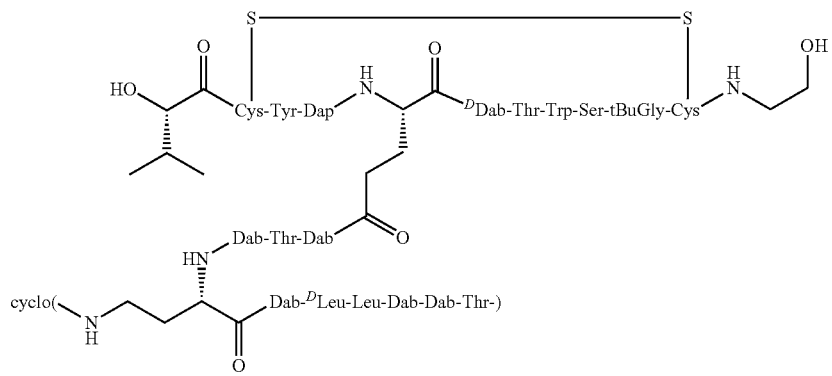 |
| Ex. 74 | 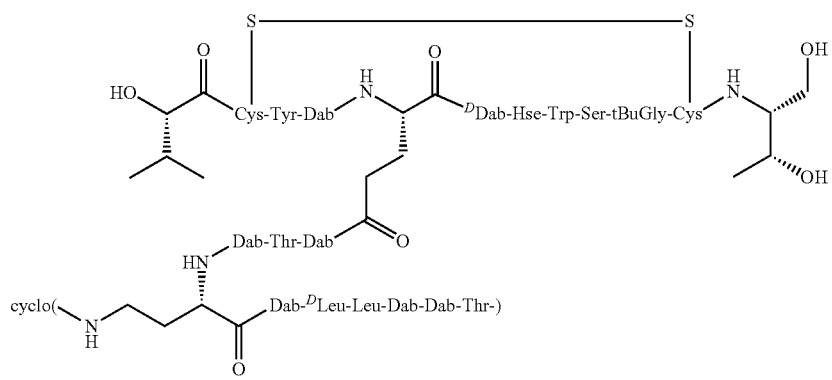 |
| Ex. 75 | 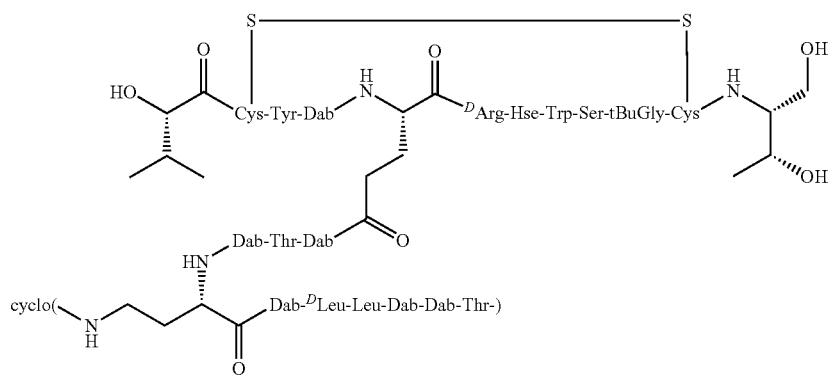 |
| Ex. 76 | 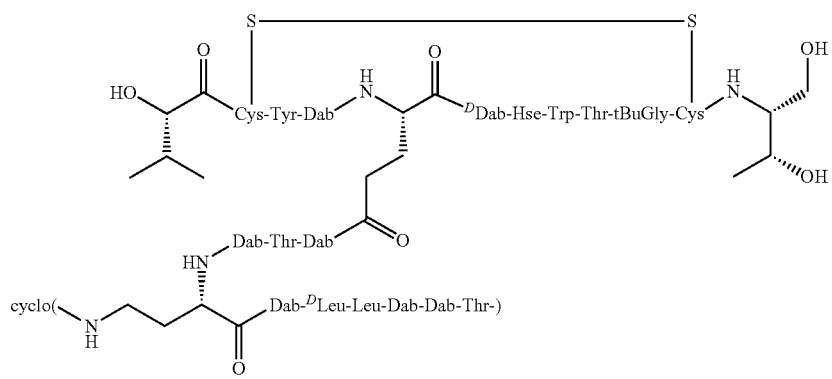 |

| Ex. No. | Sequence |
|---|---|
| Ex. 77 | 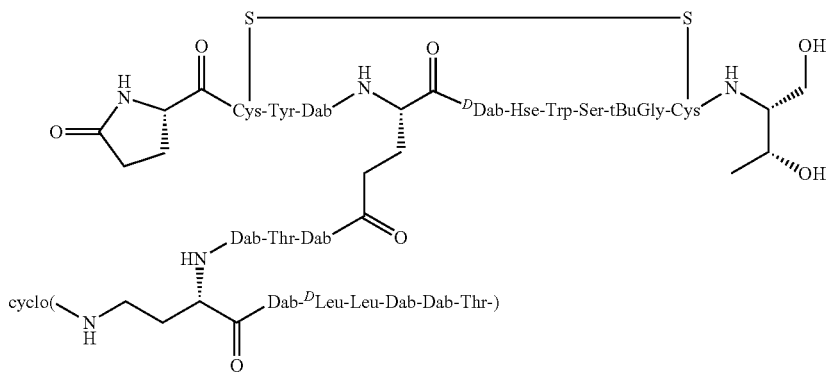 |
| Ex. 78 | 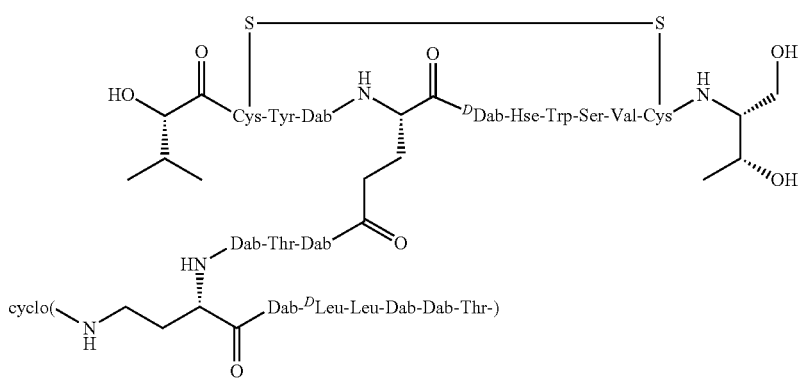 |
| Ex. 79 | 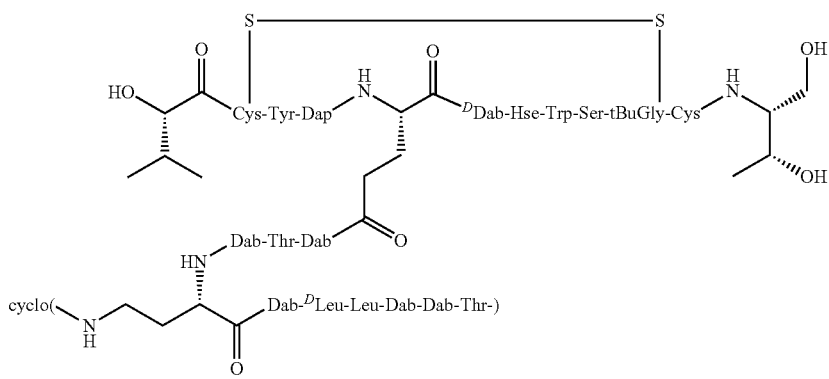 |
| Ex. 80 | 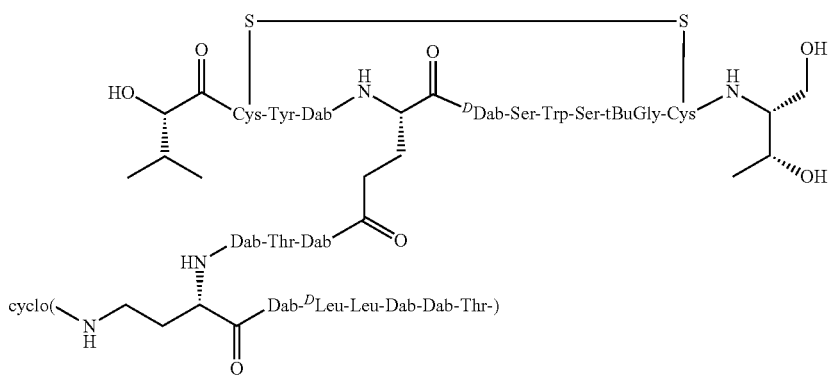 |

| Ex. No. | Sequence |
|---|---|
| Ex. 81 | 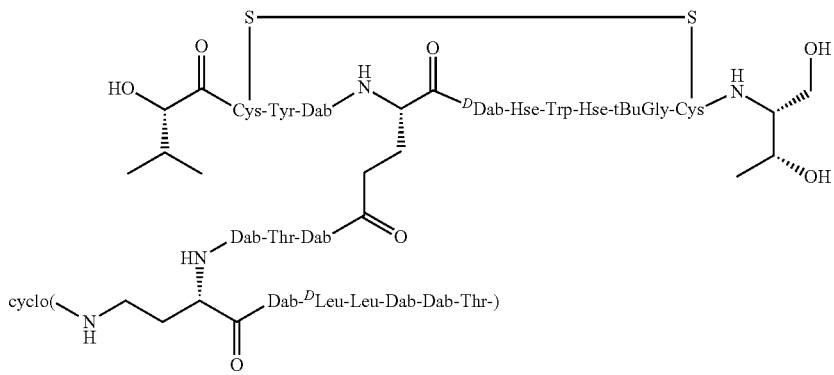 |
| Ex. 82 | 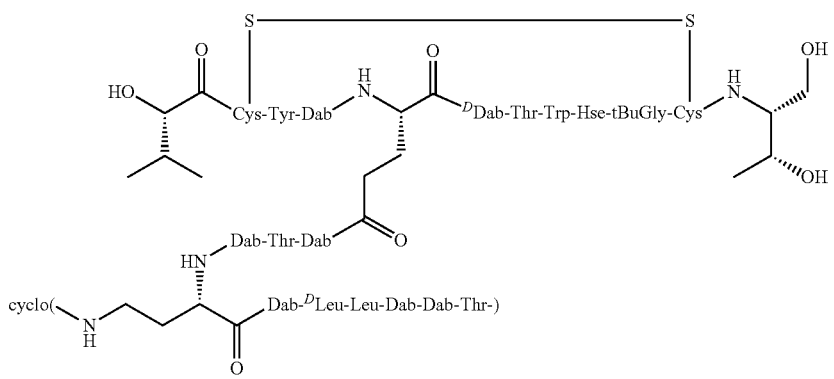 |
| Ex. 83 | 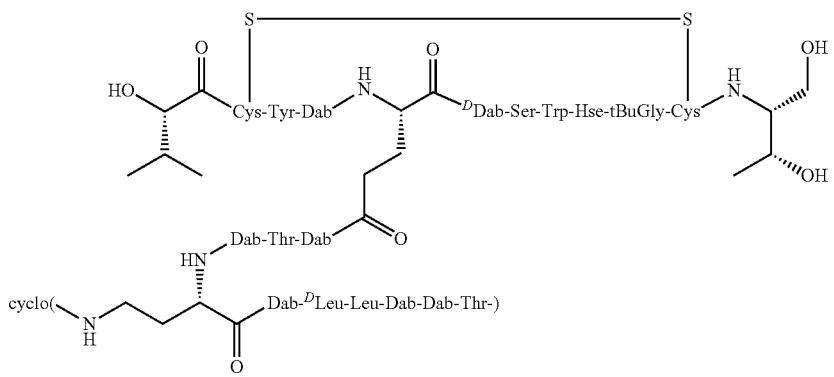 |
| Ex. 84 | 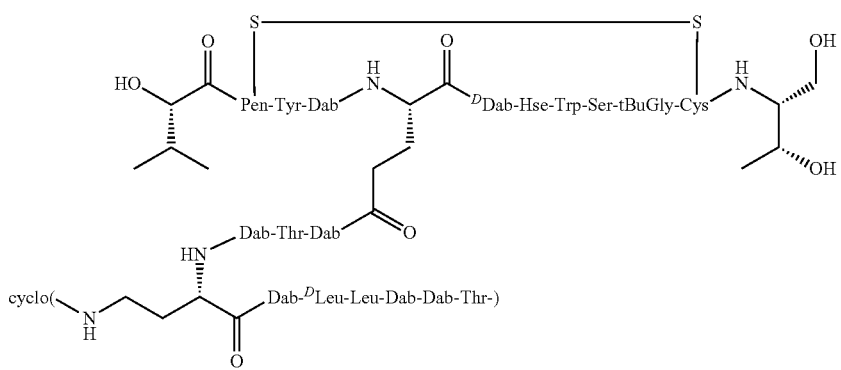 |

| Ex. No. | Sequence |
|---|---|
| Ex. 85 | 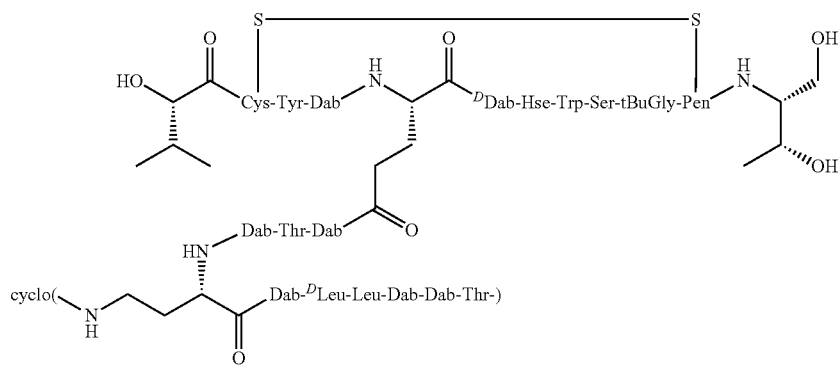 |
| Ex. 86 | 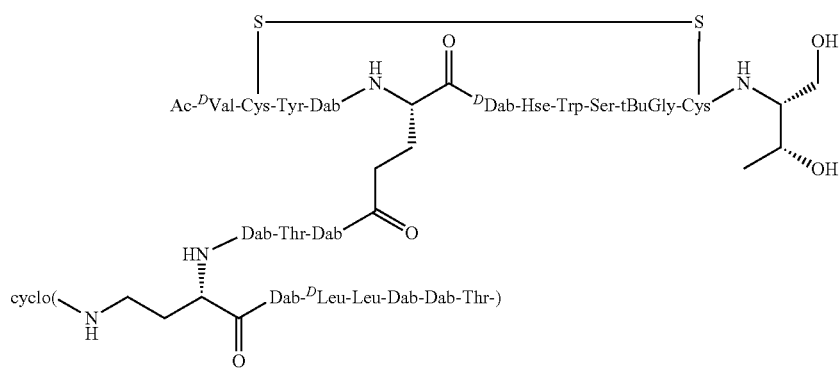 |
| Ex. 87 | 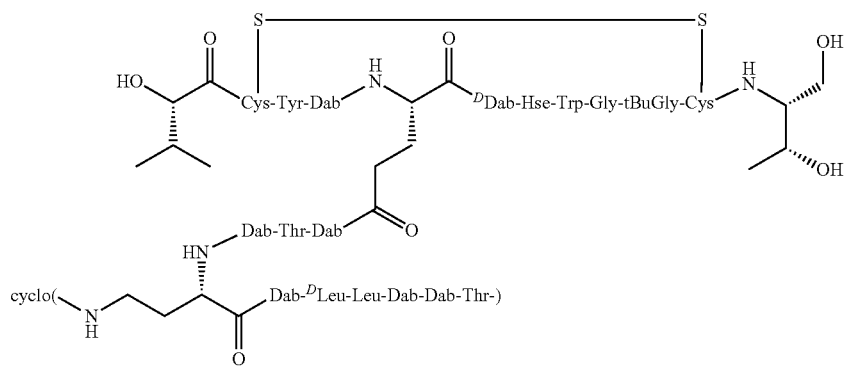 |
| Ex. 88 | 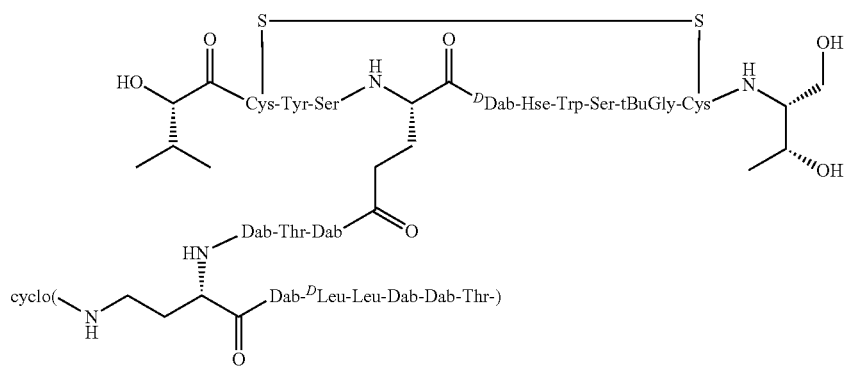 |

| Ex. No. | Sequence |
|---|---|
| Ex. 89 | 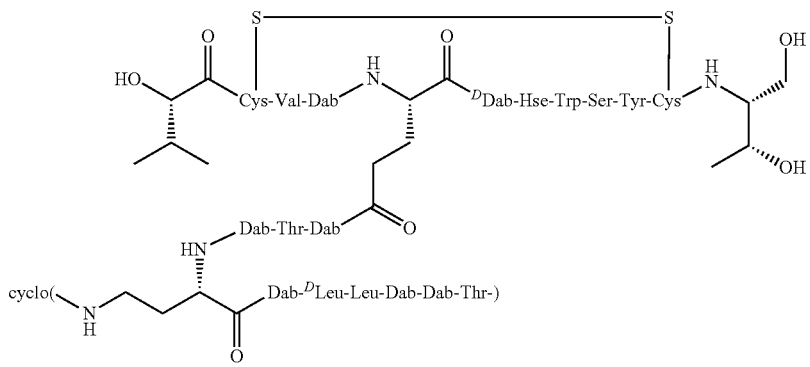 |
| Ex. 90 | 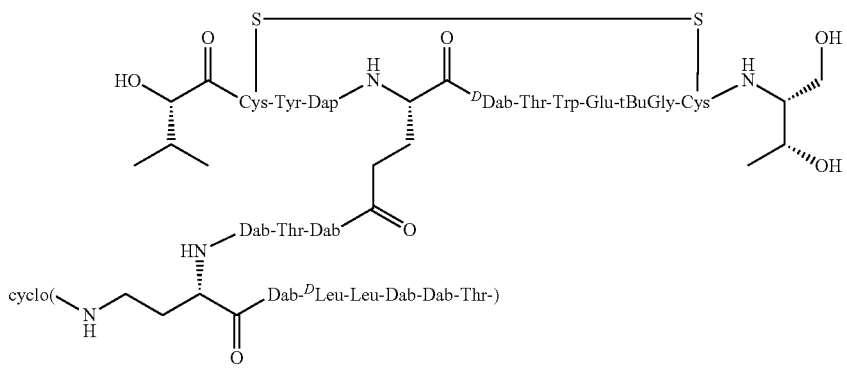 |
| Ex. 91 | 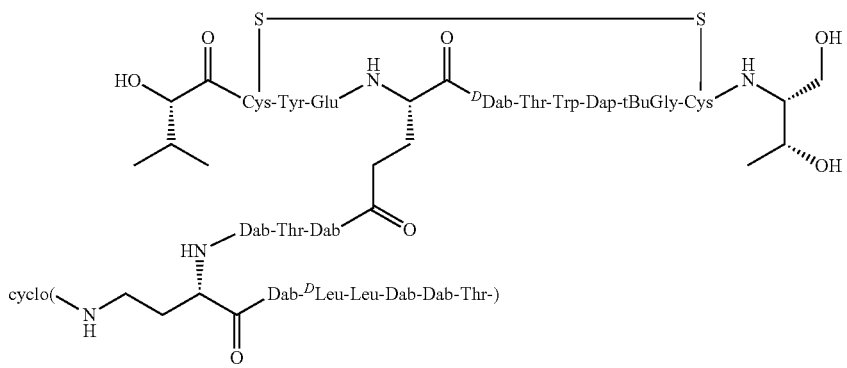 |
| Ex. 92 | 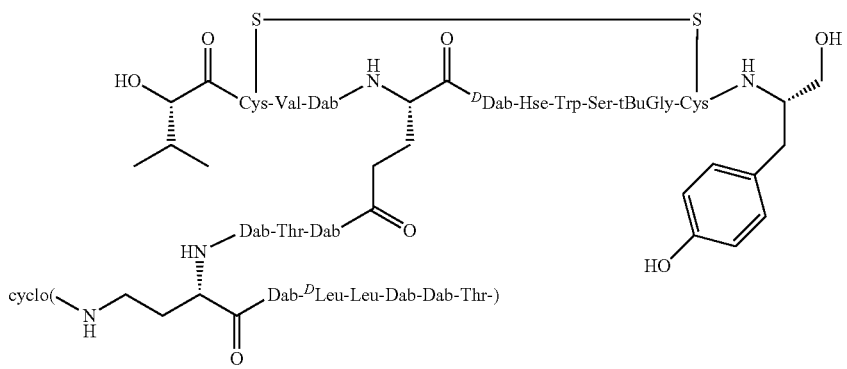 |

| Ex. No. | Sequence |
|---|---|
| Ex. 93 | 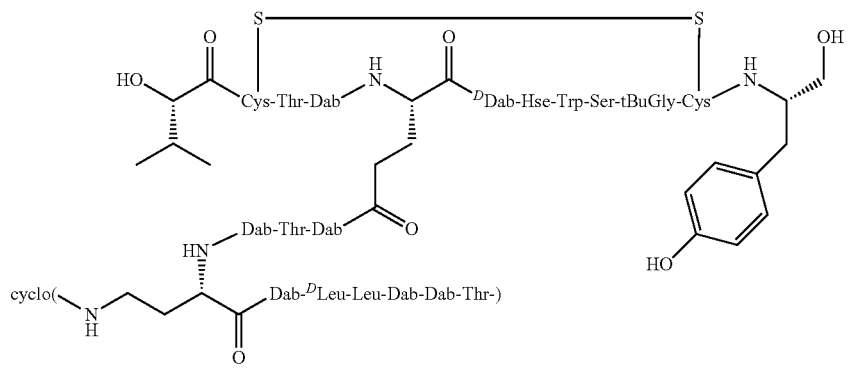 |
| Ex. 94 | 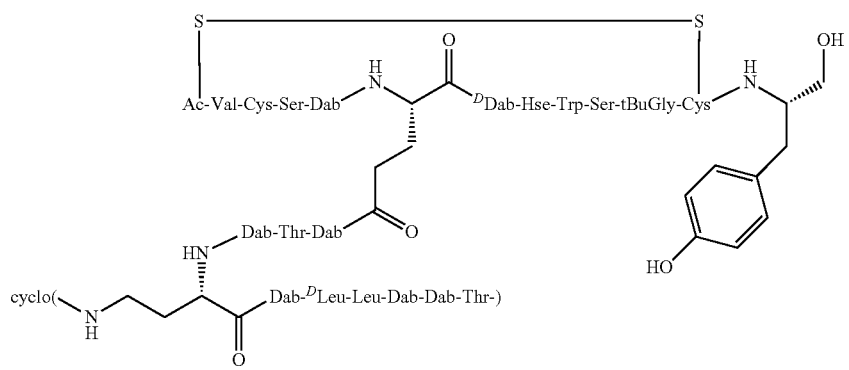 |
| Ex. 95 | 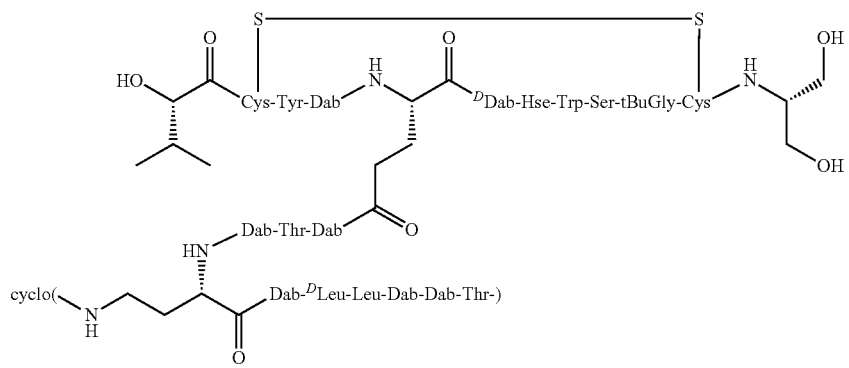 |
| Ex. 96 | 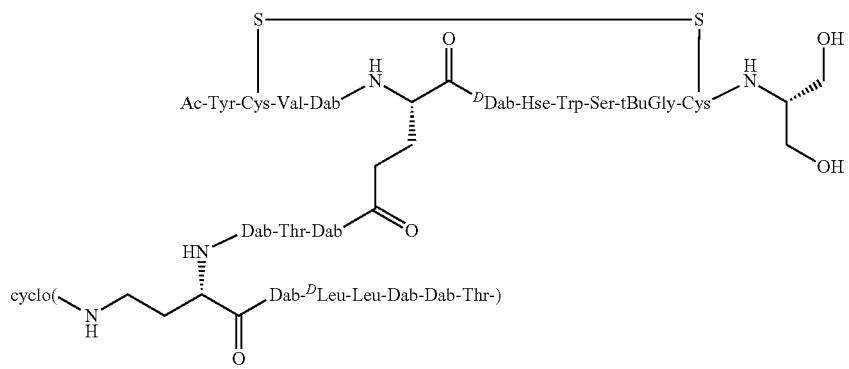 |

| Ex. No. | Sequence |
|---|---|
| Ex. 97 | 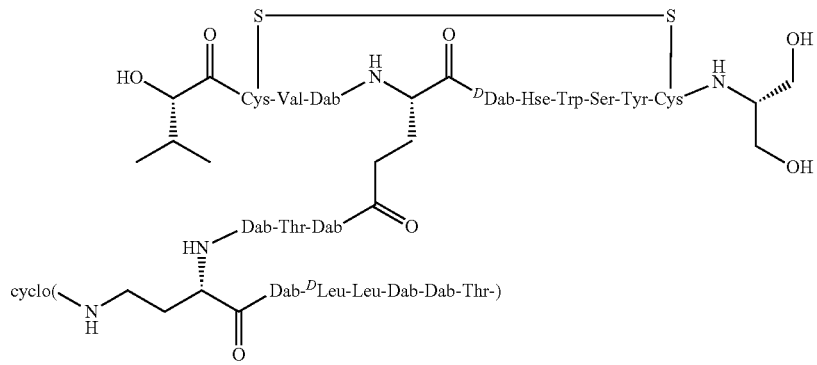 |
| Ex. 98 | 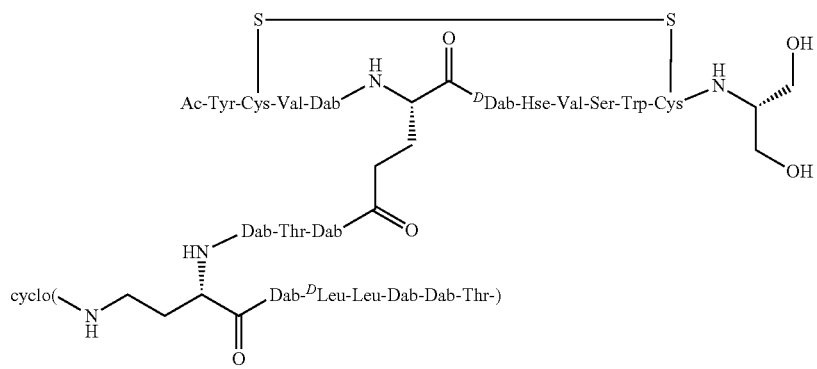 |
| Ex. 99 | 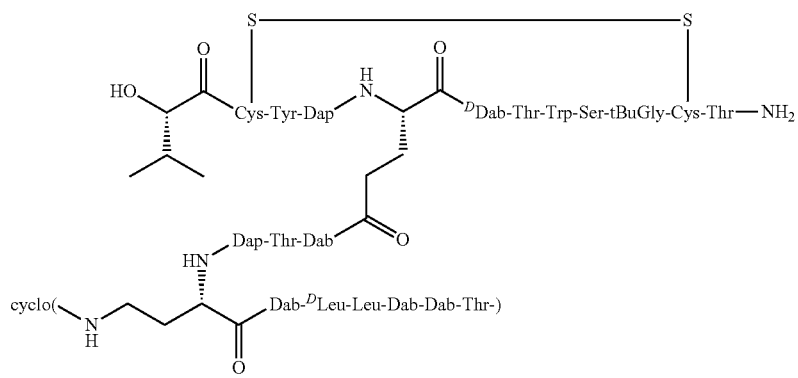 |
| Ex. 100 | 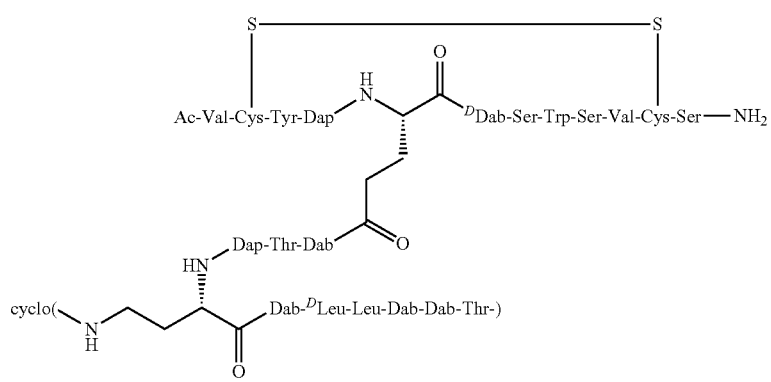 |

| Ex. No. | Sequence |
|---|---|
| Ex. 101 | 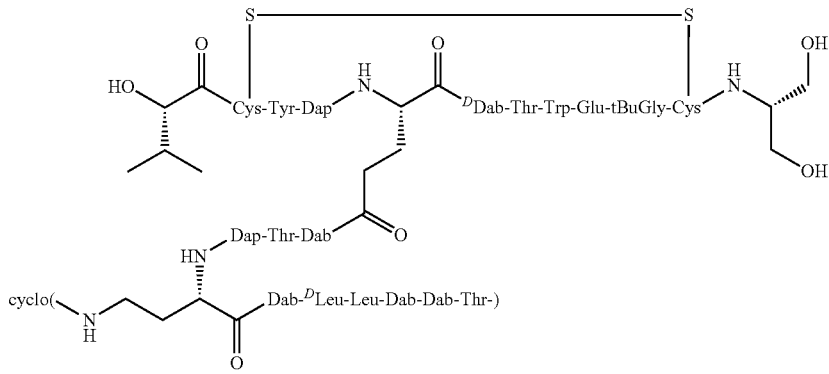 |
| Ex. 102 | 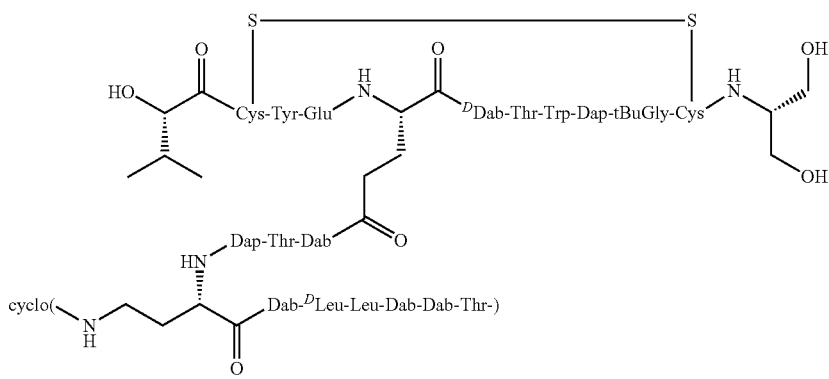 |
| Ex. 103 | 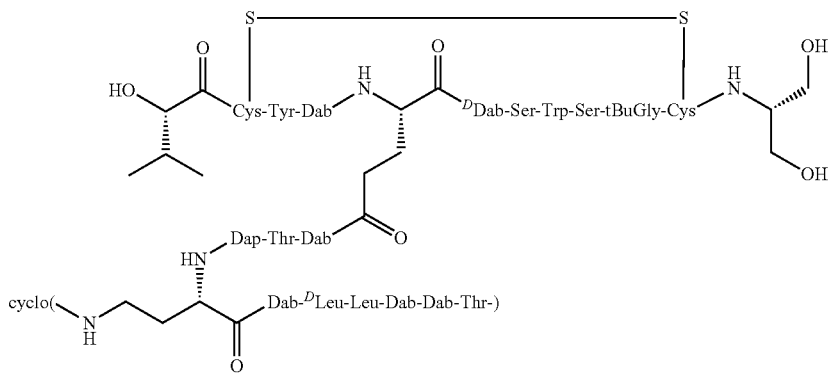 |
| Ex. 104 | 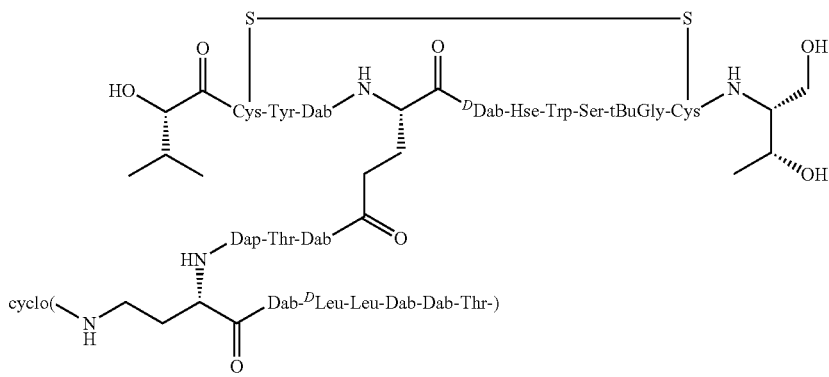 |

-continued
| Ex. No. | Sequence |
|---|---|
| Ex. 105 | 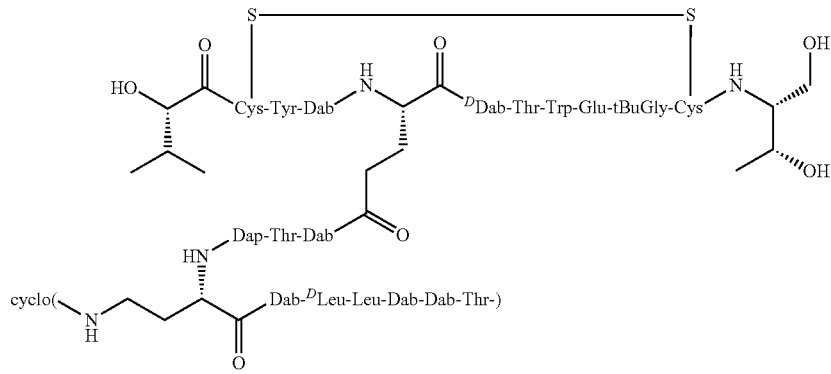 |
| Ex. 106 | 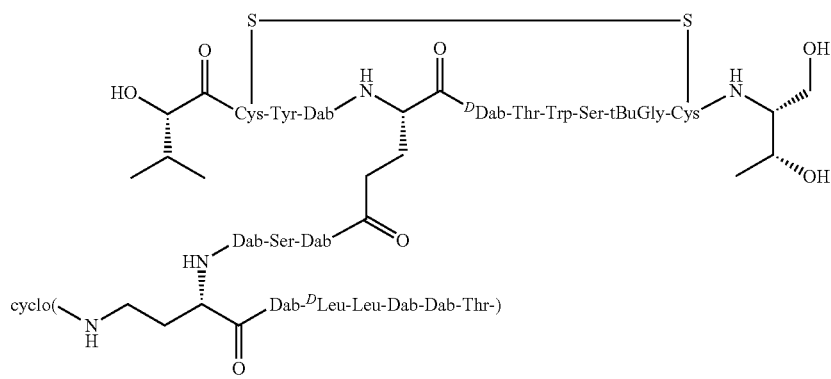 |
| Ex. 107 | 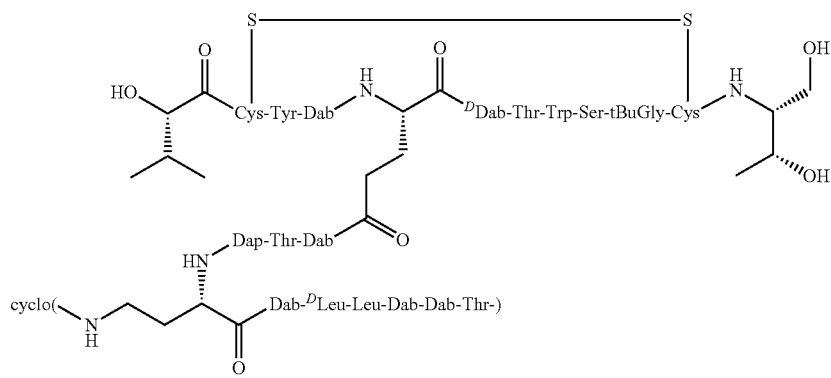 |
| Ex. 108 | 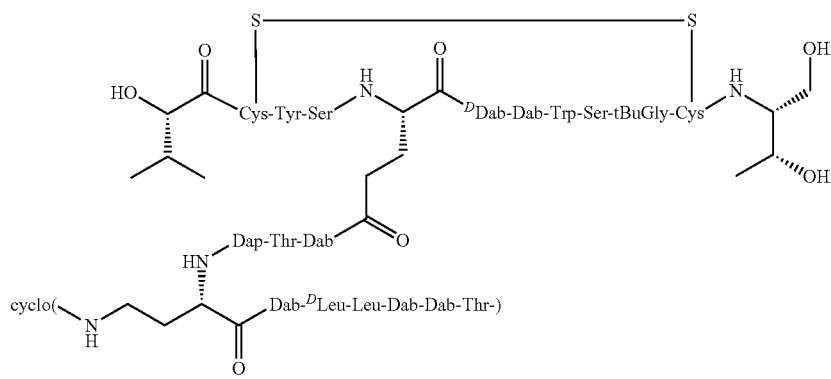 |

| Ex. No. | Sequence |
|---|---|
| Ex. 109 | 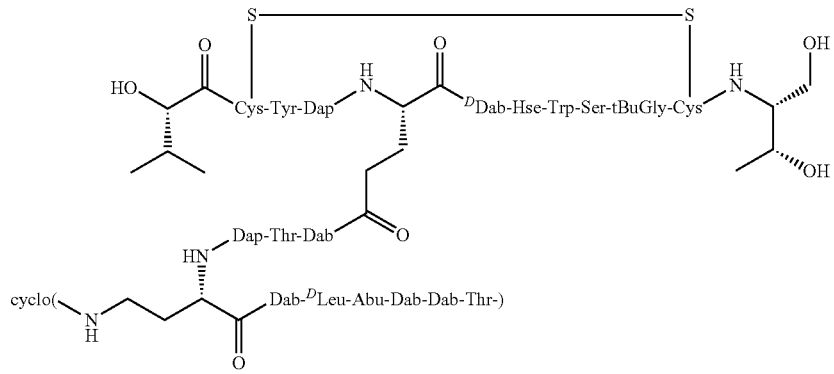 |
| Ex. 110 | 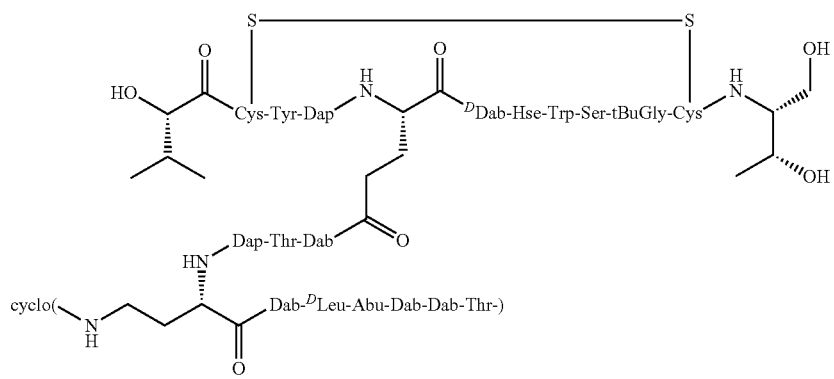 |
| Ex. 111 | 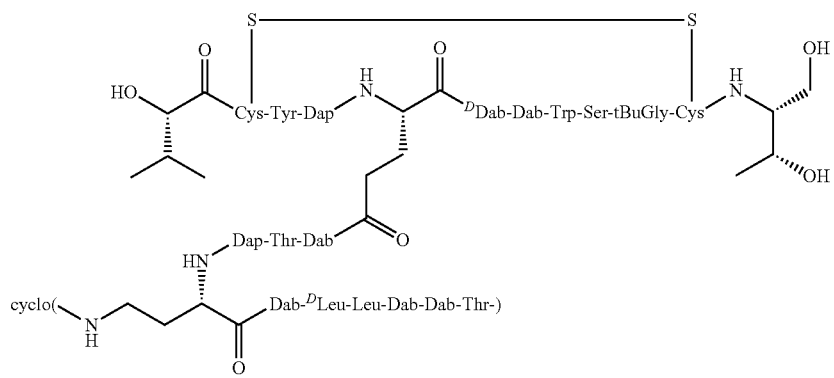 |
| Ex. 112 | 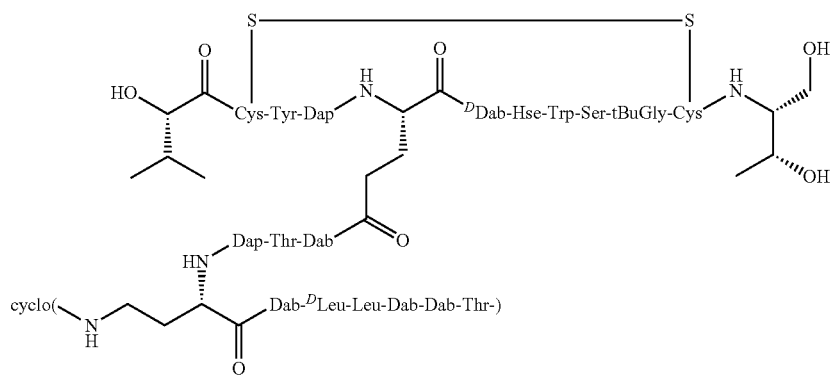 |

| Ex. No. | Sequence |
|---|---|
| Ex. 113 | 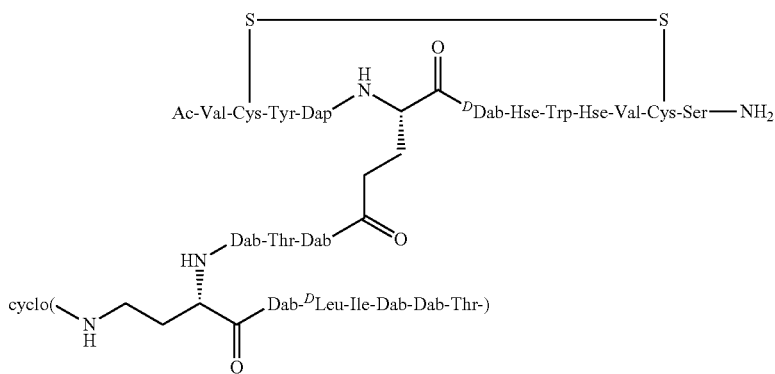 |
| Ex. 114 | 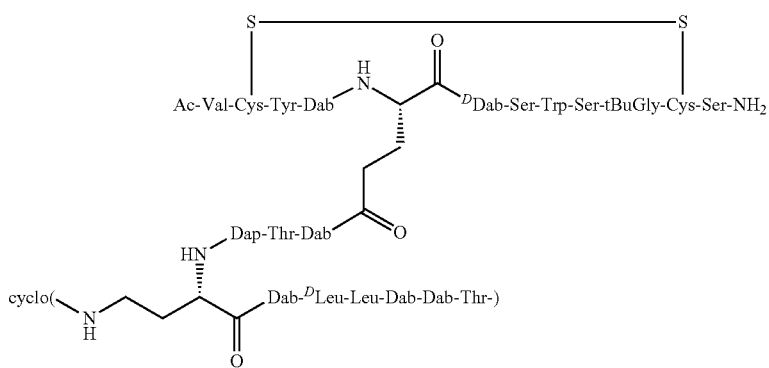 |
| Ex. 115 | 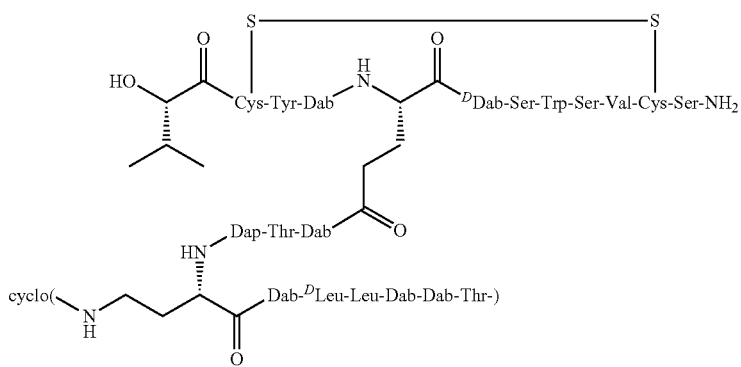 |
| Ex. 116 | 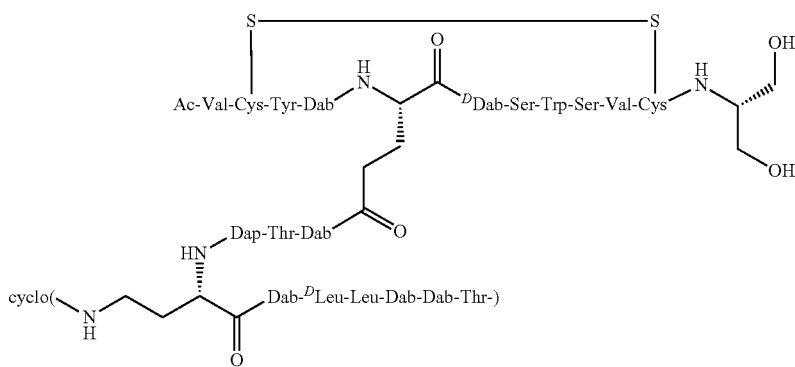 |

| Ex. No. | Sequence |
|---|---|
| Ex. 117 | 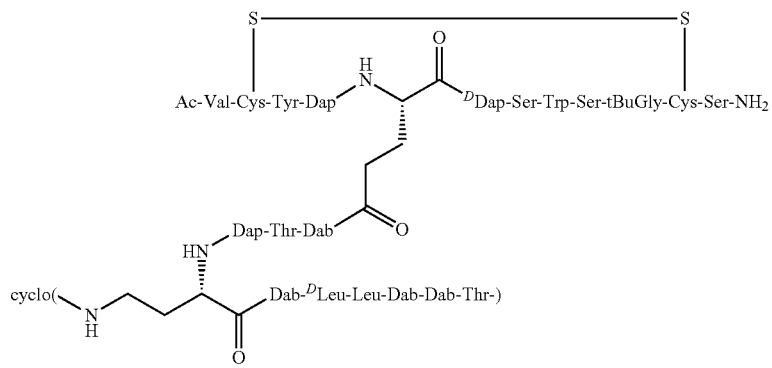 |
| Ex. 119 | 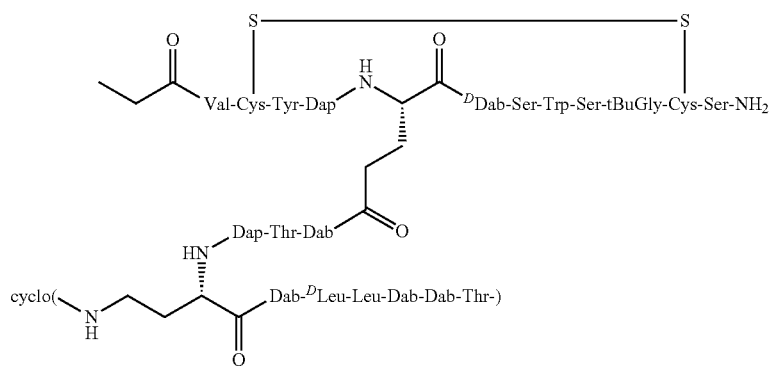 |
| Ex. 120 | 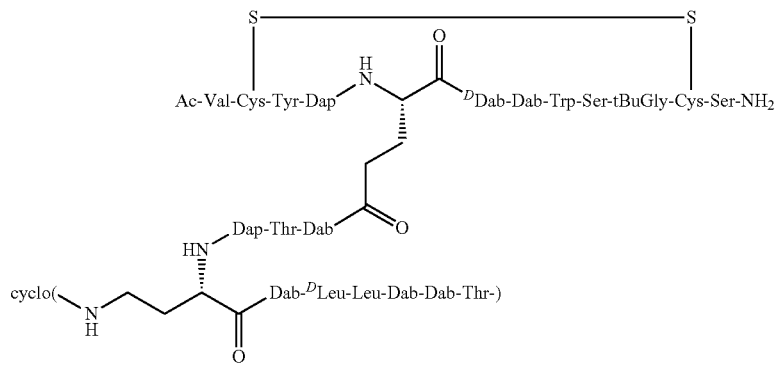 |
| Ex. 121 | 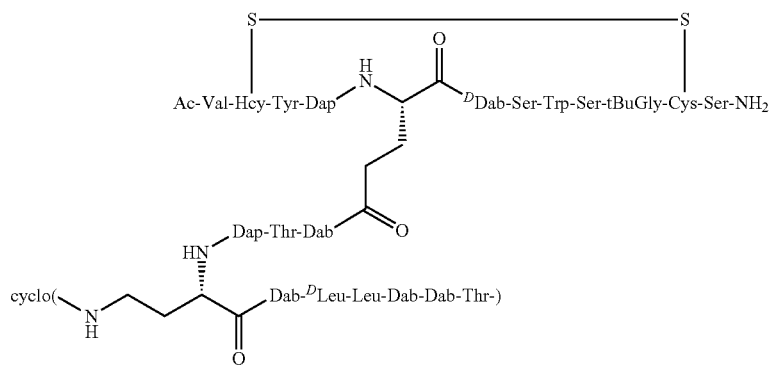 |

| Ex. No. | Sequence |
|---|---|
| Ex. 122 | 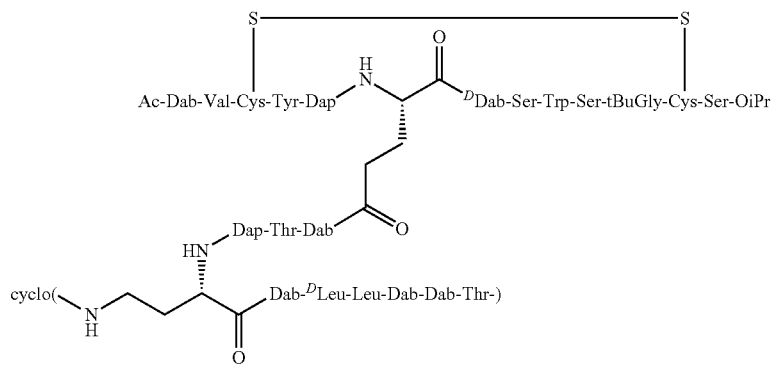 |
| Ex. 123 | 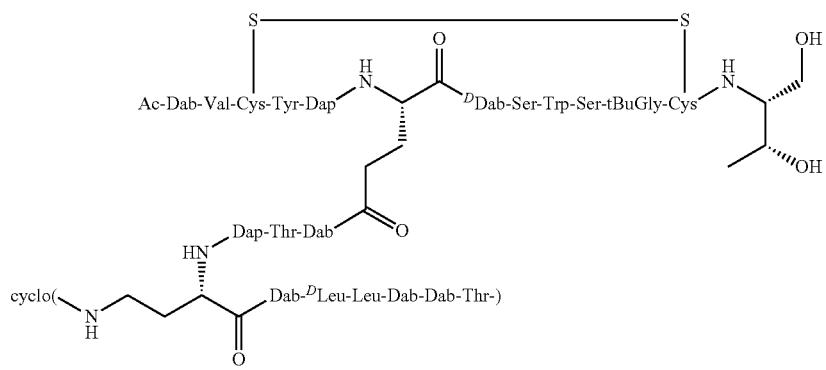 |
| Ex. 124 | 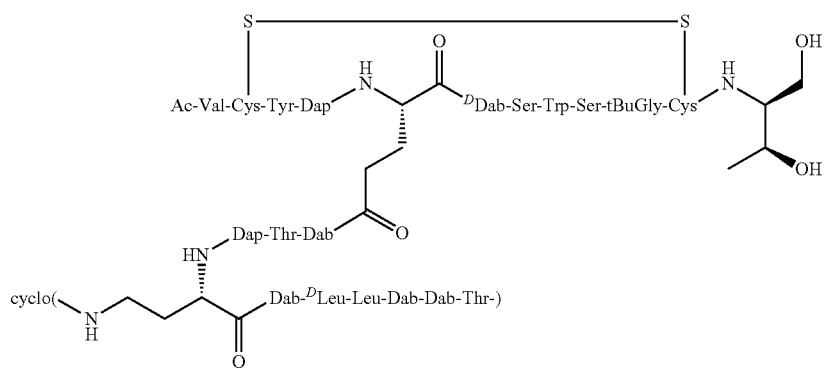 |
| Ex. 125 | 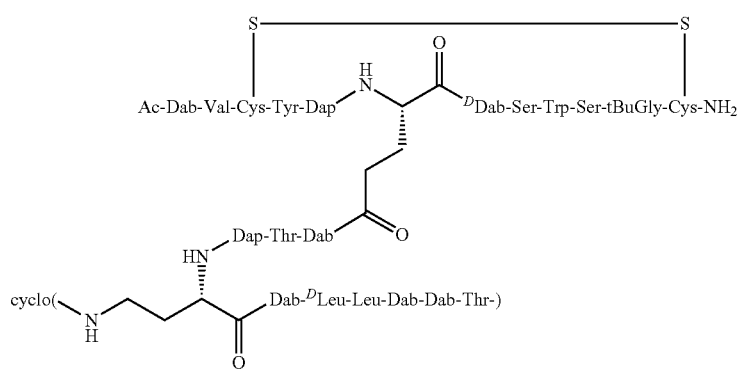 |

| Ex. No. | Sequence |
|---|---|
Ex. 126
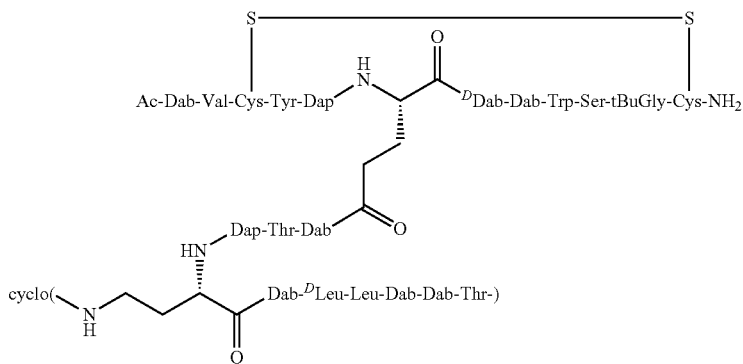
Ex. 127
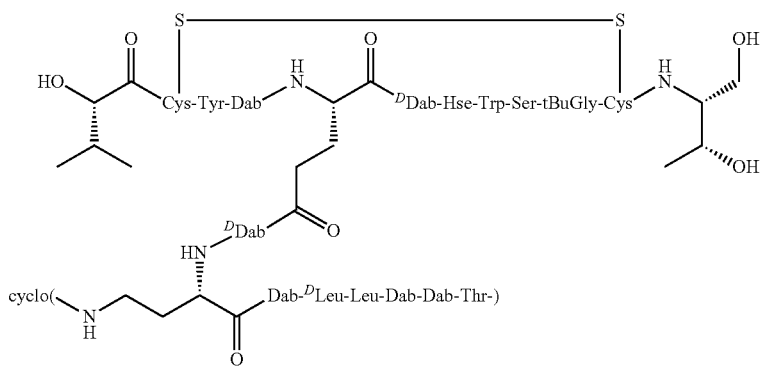
Ex. 128
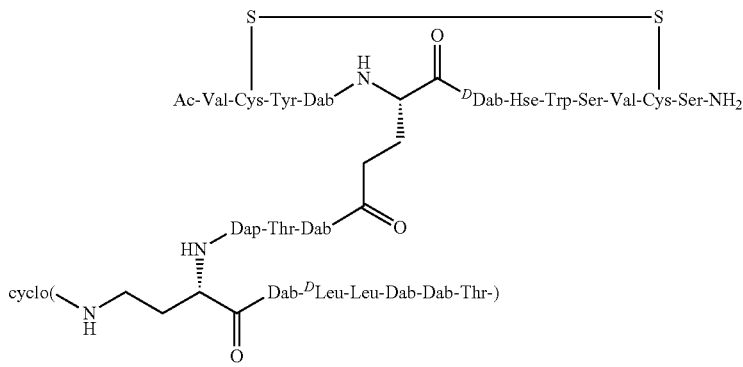
Ex. 129
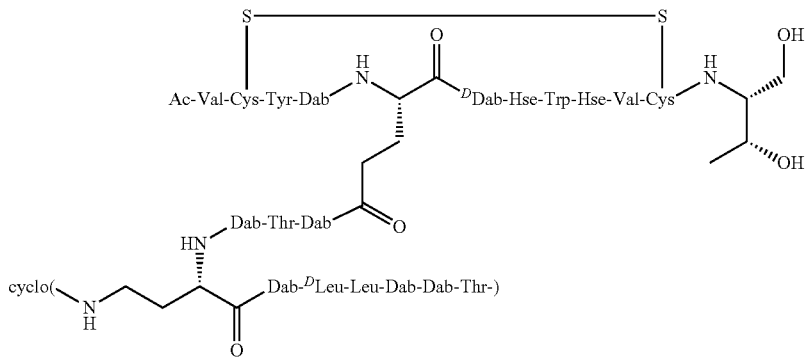

| Ex. No. | Sequence |
|---|---|
| Ex. 130 | 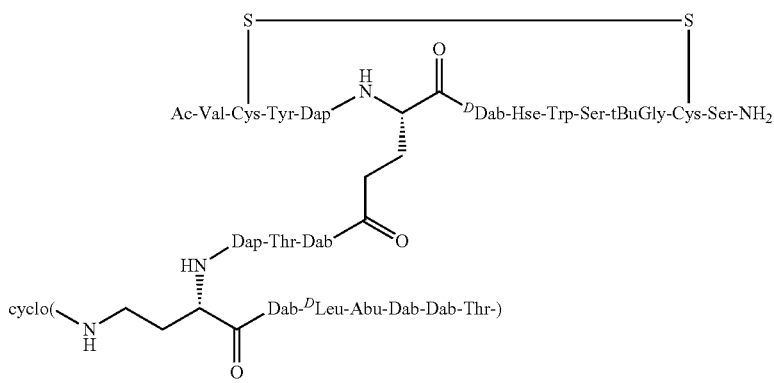 |
| Ex. 131 | 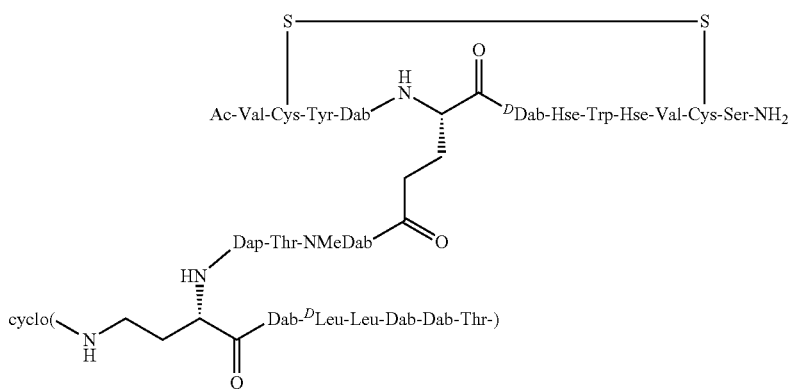 |
| Ex. 132 | 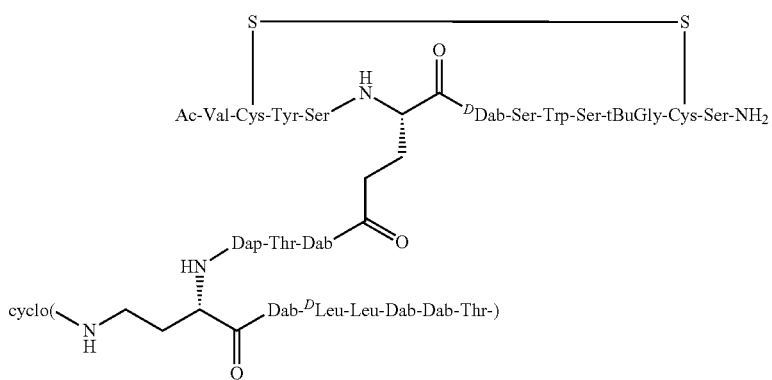 |
| Ex. 133 | 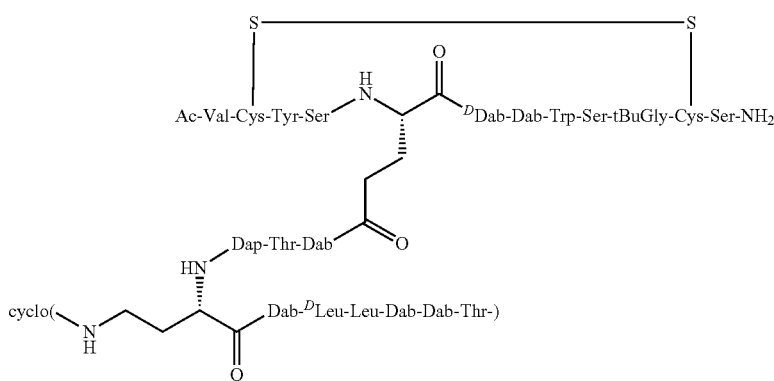 |

| Ex. No. | Sequence |
|---|---|
| Ex. 134 | 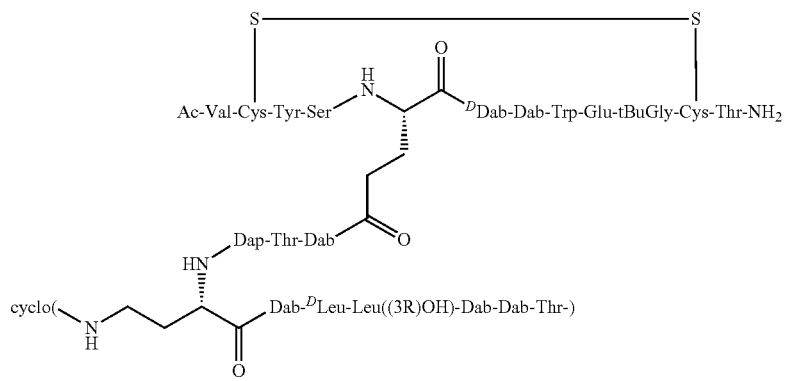 |
| Ex. 135 | 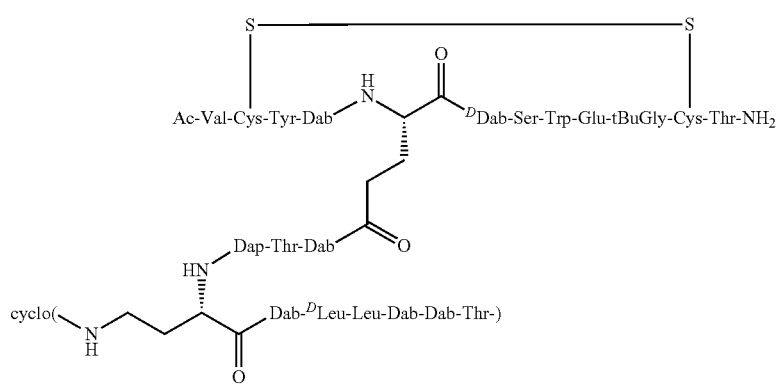 |
| Ex. 136 | 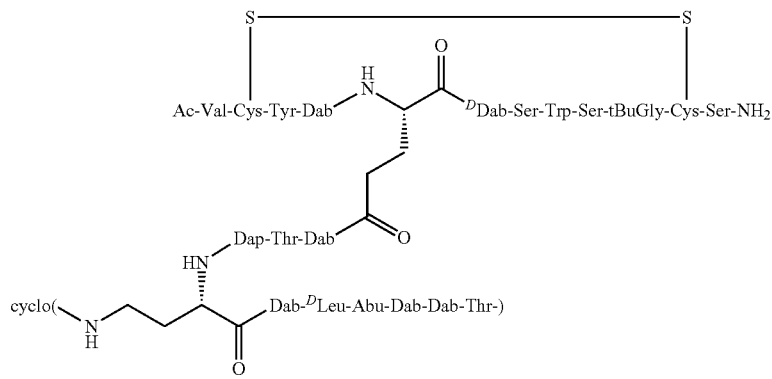 |
| Ex. 137 | 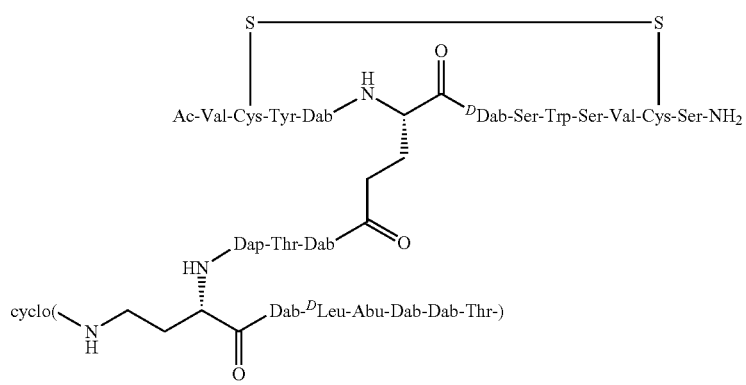 |

| Ex. No. | Sequence |
|---|---|
| Ex. 138 | 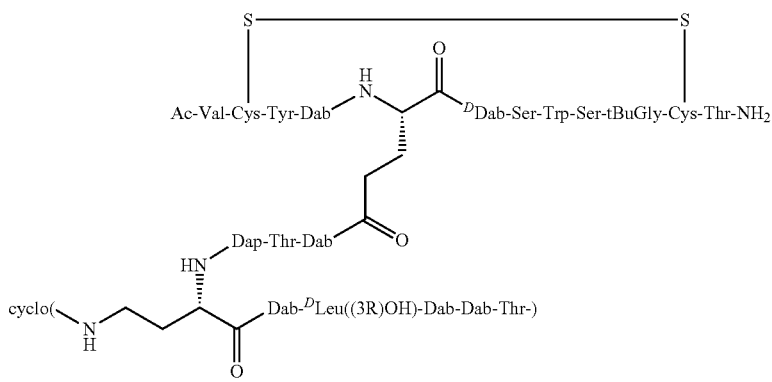 |
| Ex. 139 | 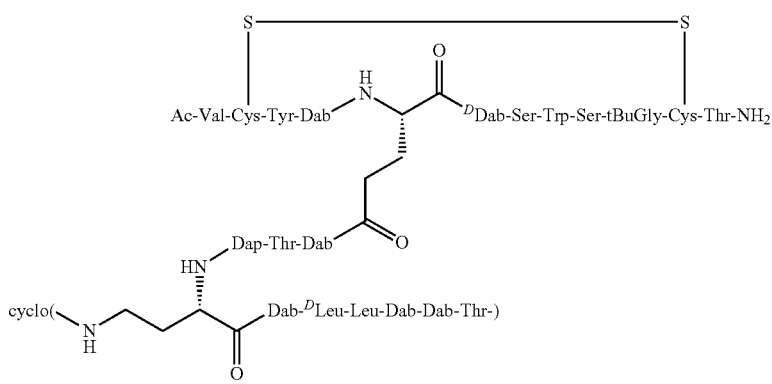 |
| Ex. 140 | 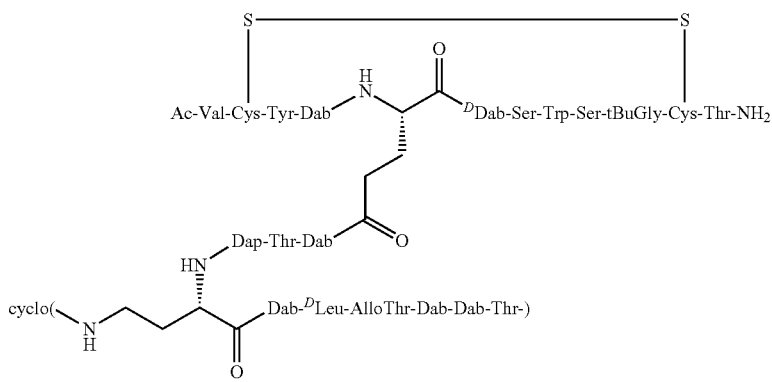 |
| Ex. 141 | 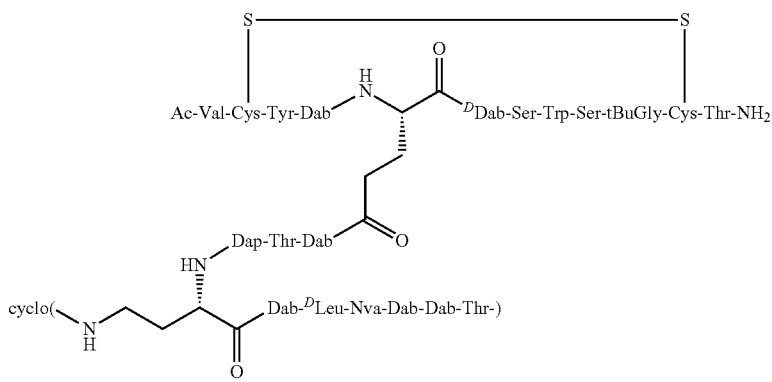 |

| Ex. No. | Sequence |
|---|---|
| Ex. 142 | 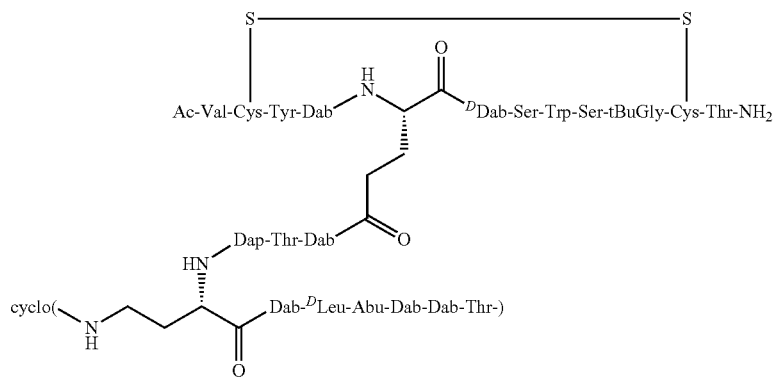 |
| Ex. 143 | 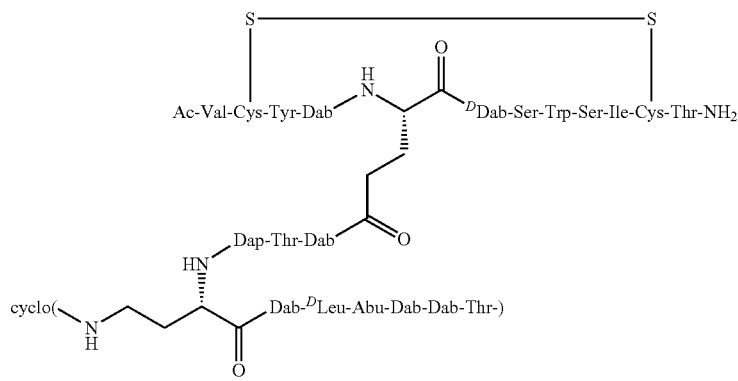 |
| Ex. 144 | 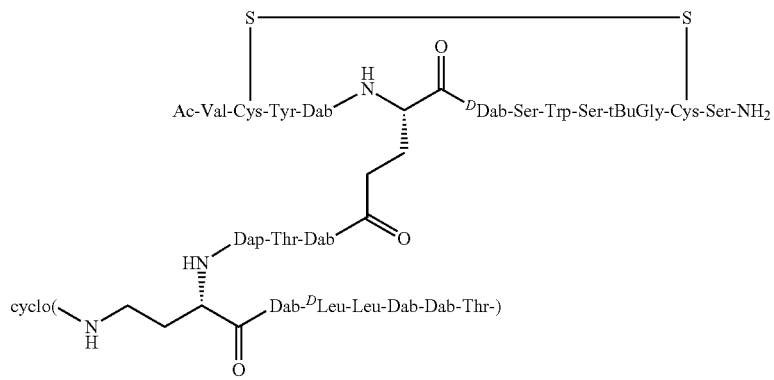 |
| Ex. 145 | 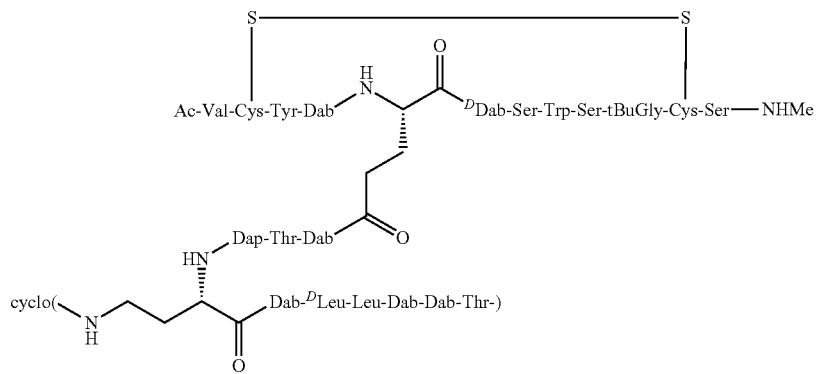 |

-continued
| Ex. No. | Sequence |
|---|---|
| Ex. 146 | 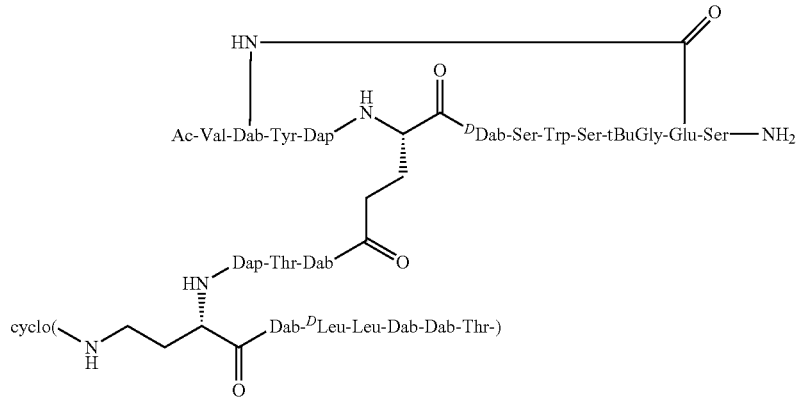 |
| Ex. 147 | 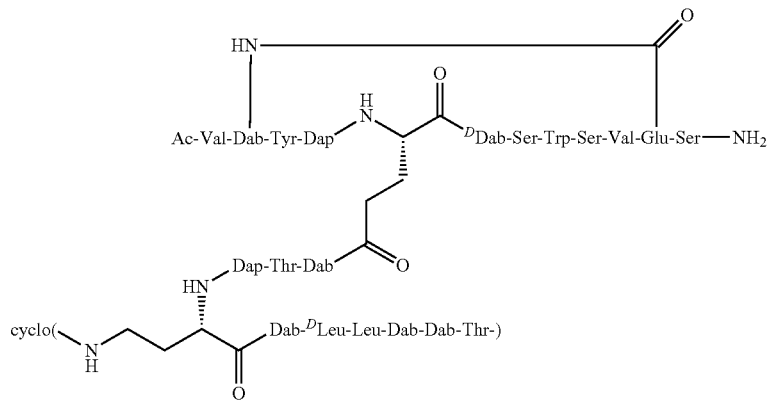 |
| Ex. 148 | 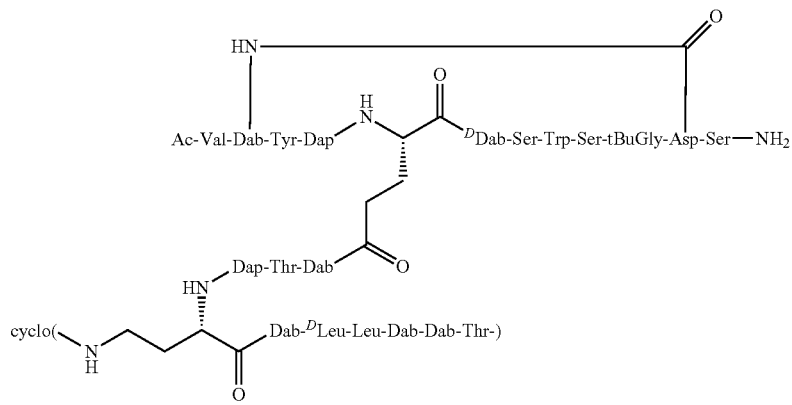 |

| Ex. No. | Sequence |
|---|---|
| Ex. 149 | 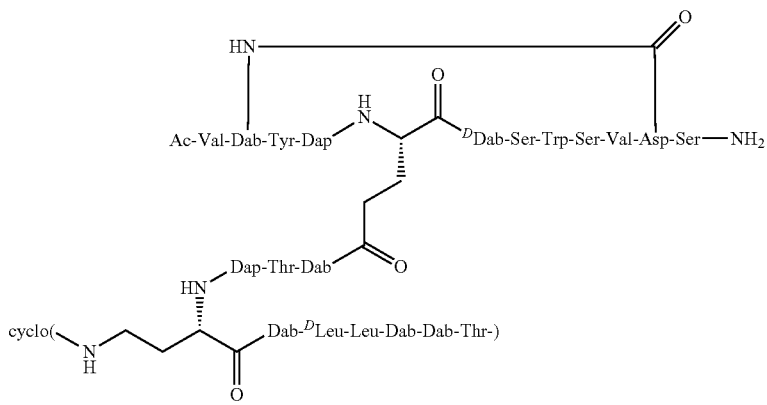 |
| Ex. 150 | 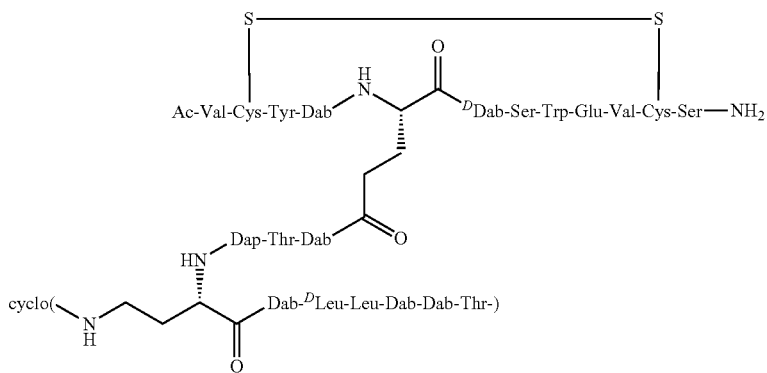 |
| Ex. 151 | 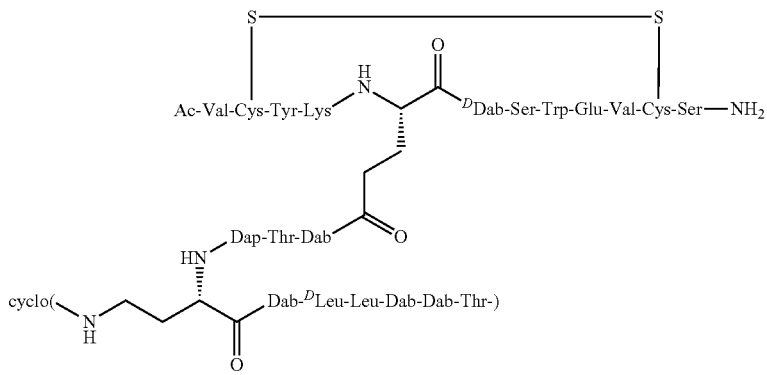 |
| Ex. 152 | 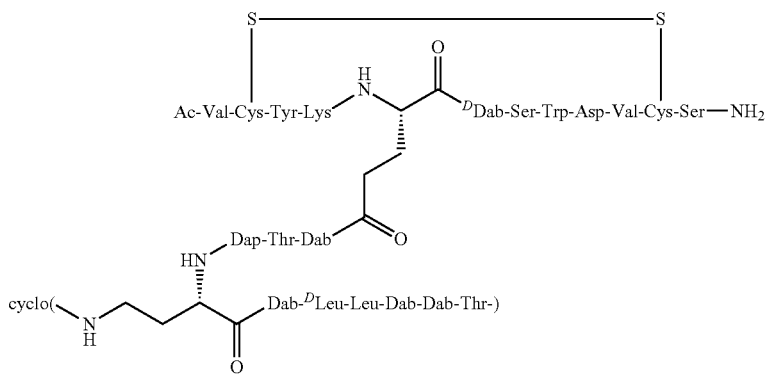 |

| Ex. No. | Sequence |
|---|---|
| Ex. 153 | 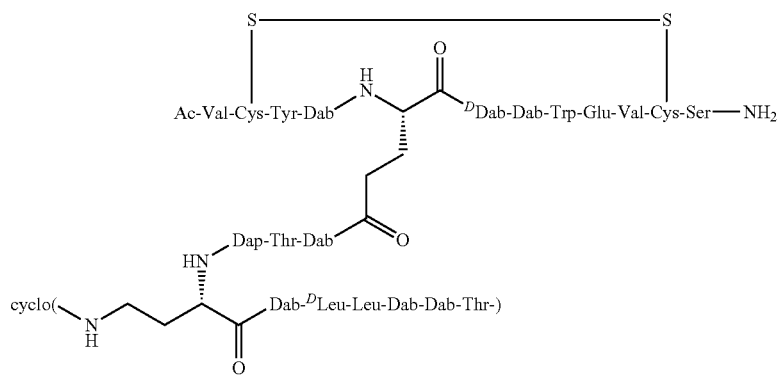 |
| Ex. 154 | 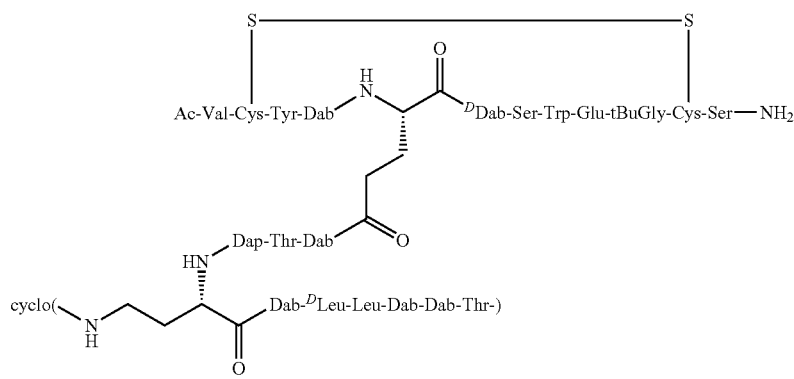 |
| Ex. 155 | 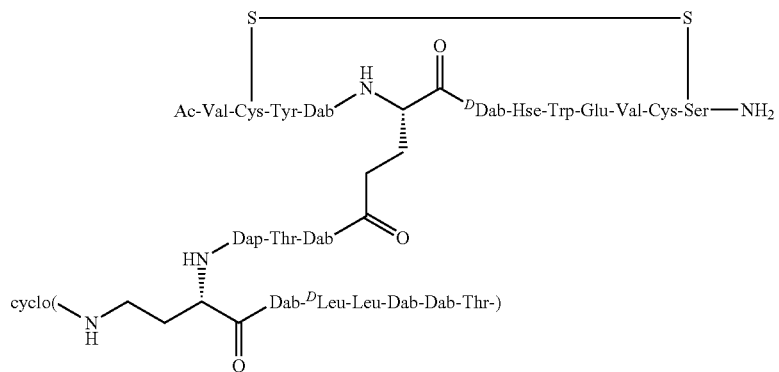 |
| Ex. 156 | 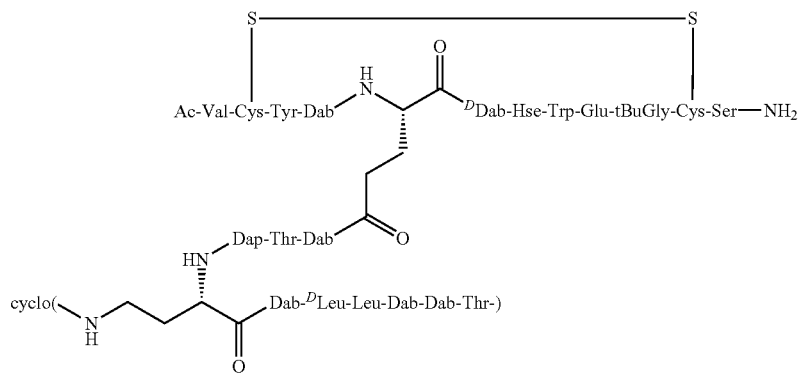 |

| Ex. No. | Sequence |
|---------|----------|
| Ex. 157 | 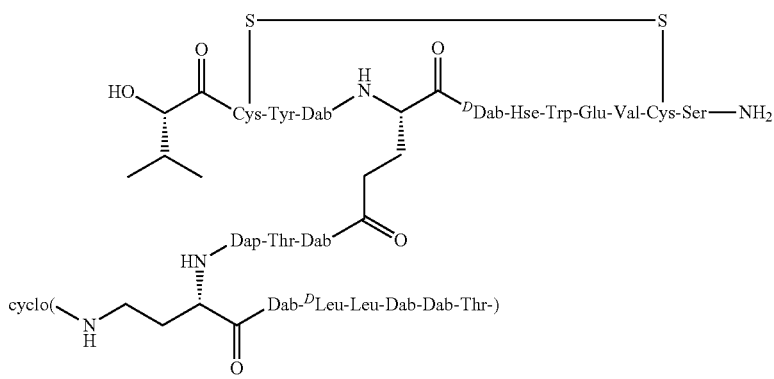 |
| Ex. 158 | 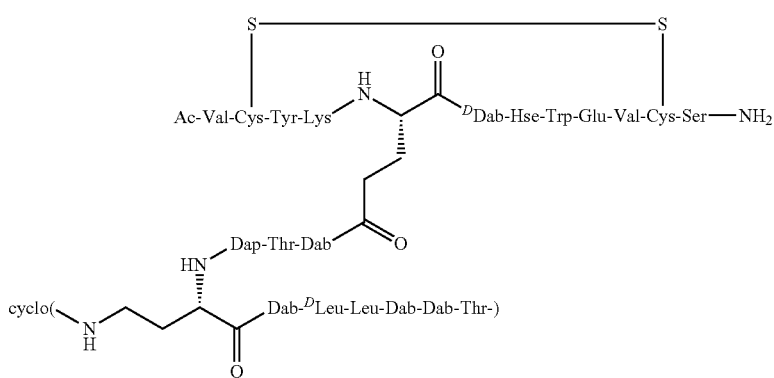 |
| Ex. 159 | 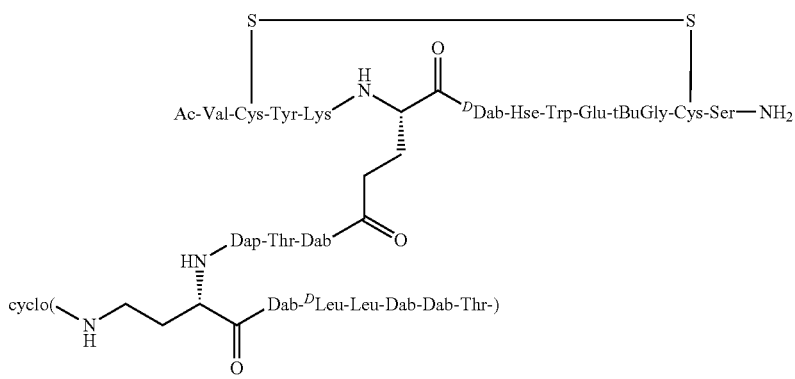 |
| Ex. 160 | 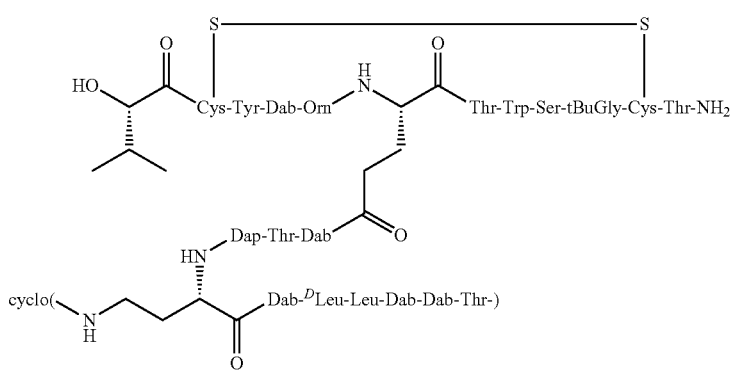 |

| Ex. No. | Sequence |
|---|---|
| Ex. 161 | 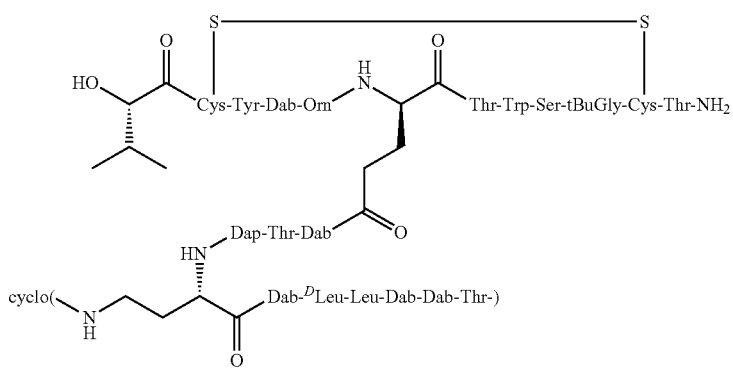 |
| Ex. 162 | 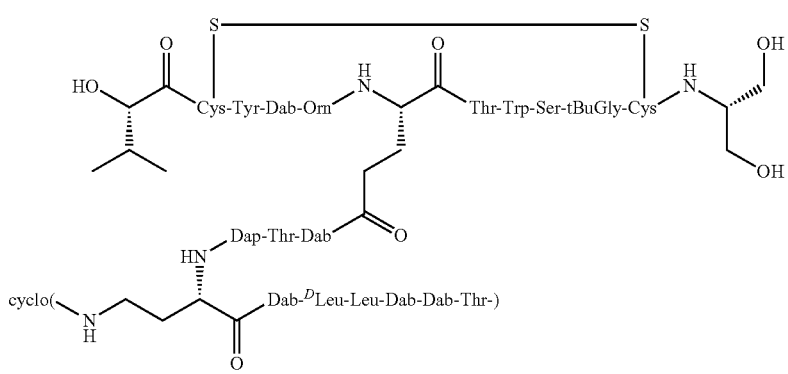 |
| Ex. 163 | 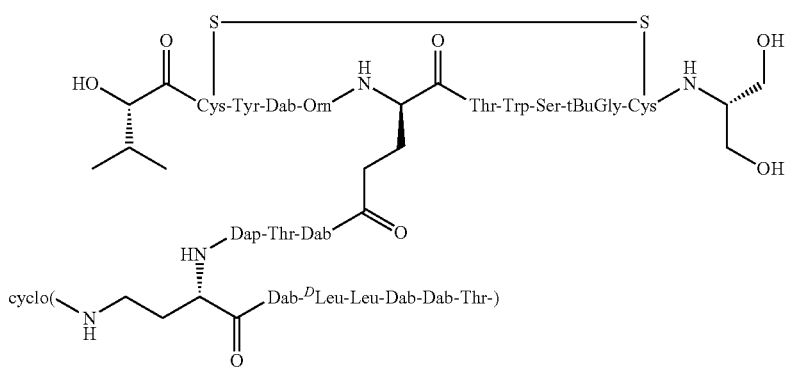 |
| Ex. 164 | 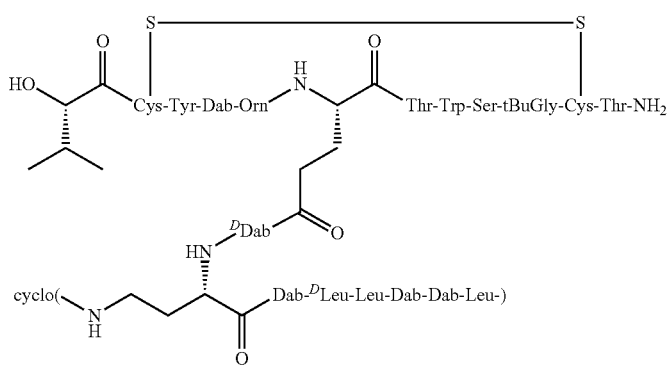 |

| Ex. No. | Sequence |
|---|---|
| Ex. 165 | 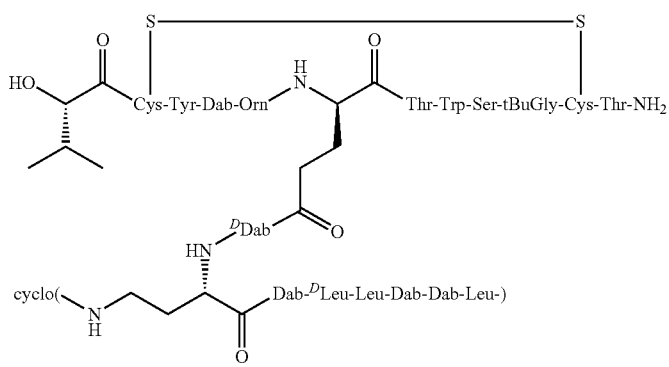 |
| Ex. 166 | 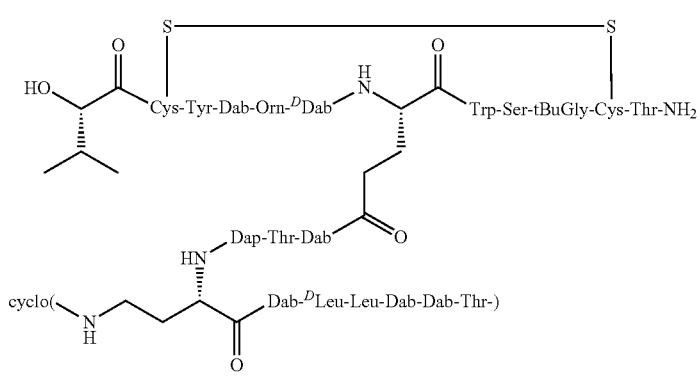 |
| Ex. 167 | 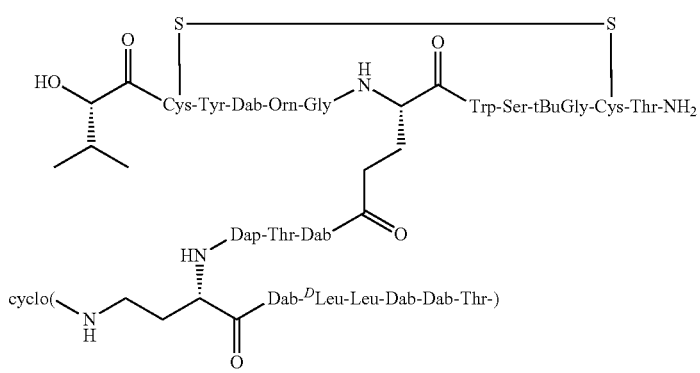 |
| Ex. 168 | 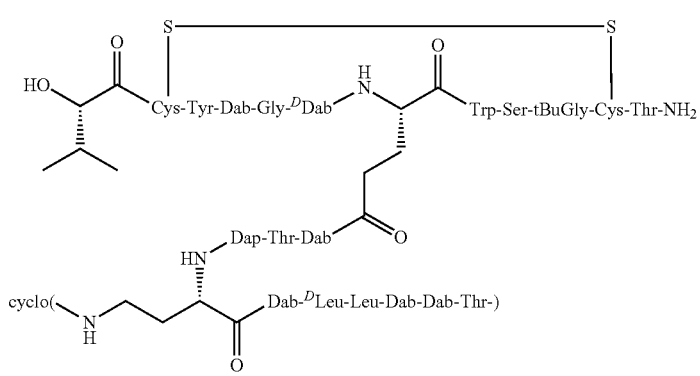 |

| Ex. No. | Sequence |
|---|---|
| Ex. 169 | 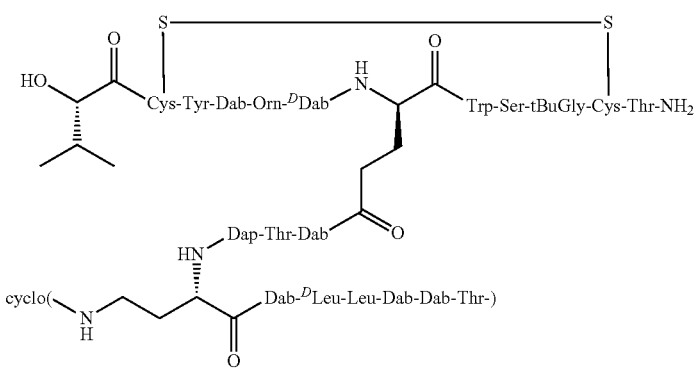 |
| Ex. 170 | 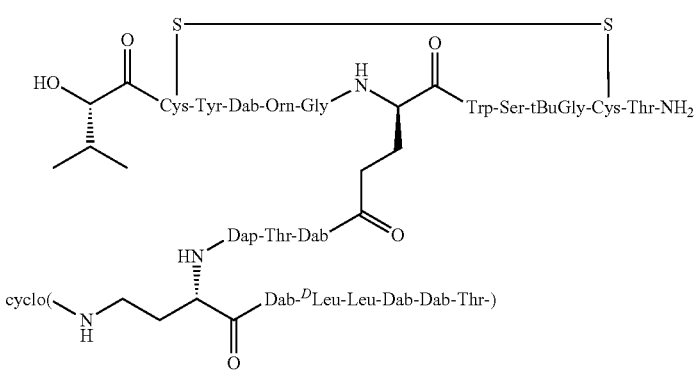 |
| Ex. 171 | 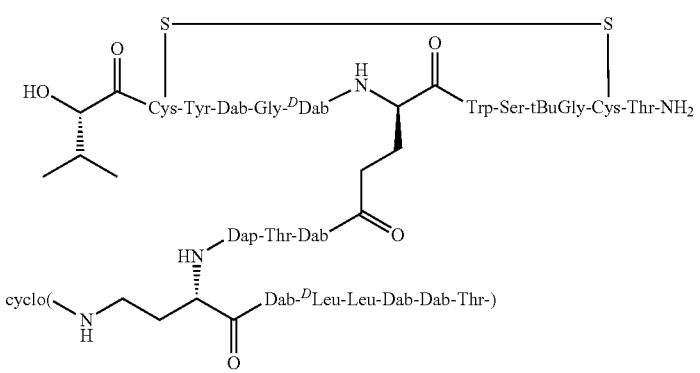 |
| Ex. 172 | 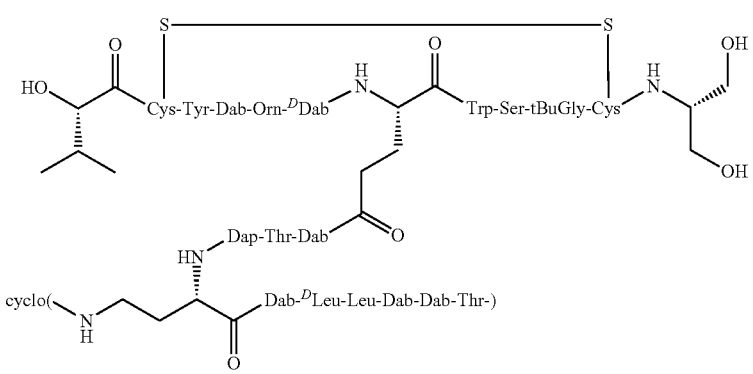 |

| Ex. No. | Sequence |
|---|---|
| Ex. 173 | 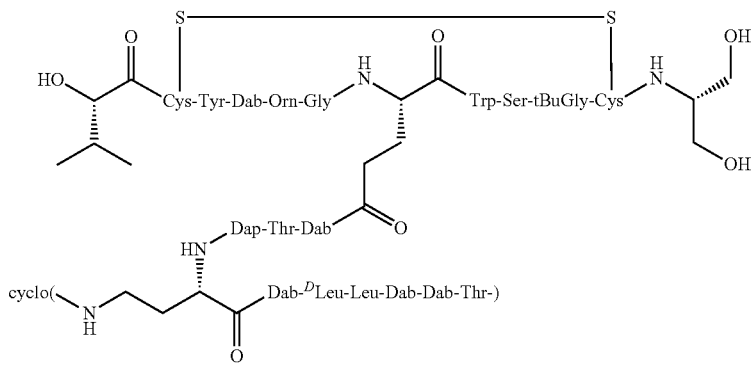 |
| Ex. 174 | 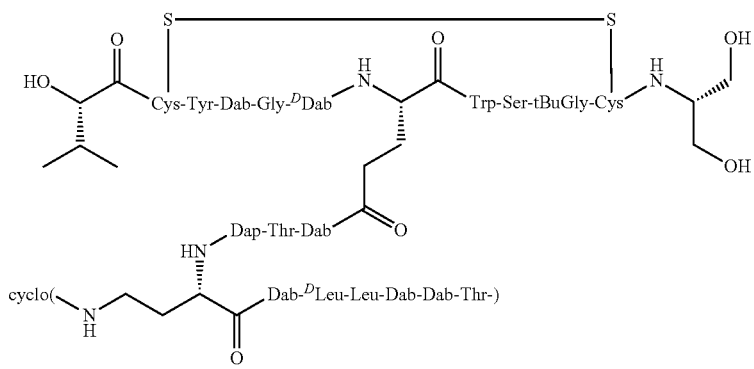 |
| Ex. 175 | 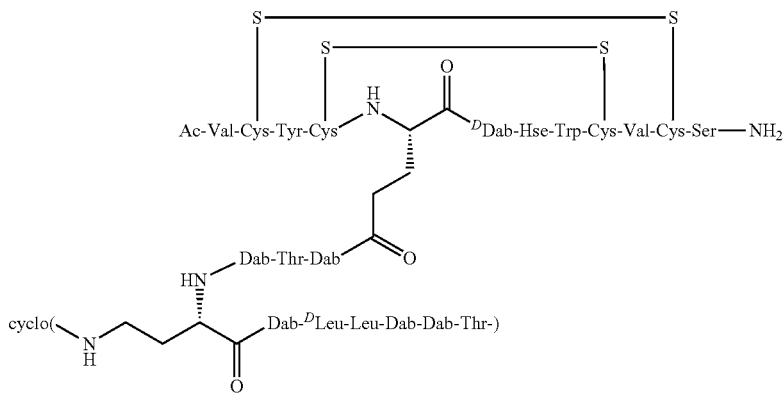 |
| Ex. 176 | 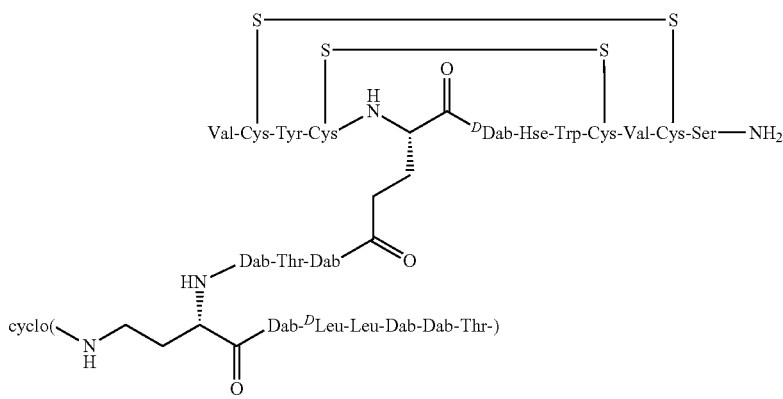 |

| Ex. No. | Sequence |
|---|---|
| Ex. 177 | 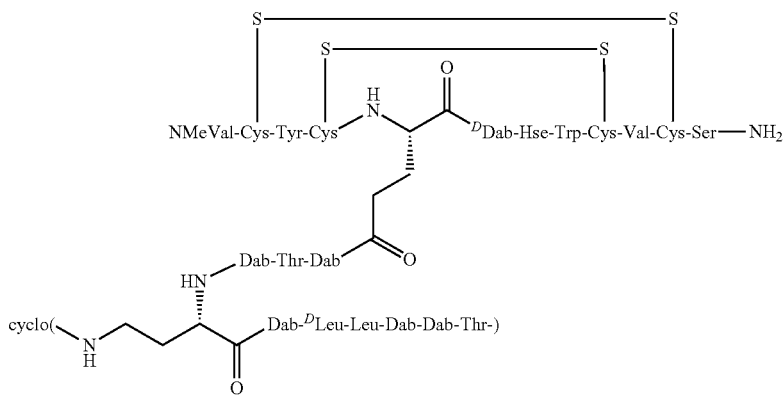 |
| Ex. 178 | 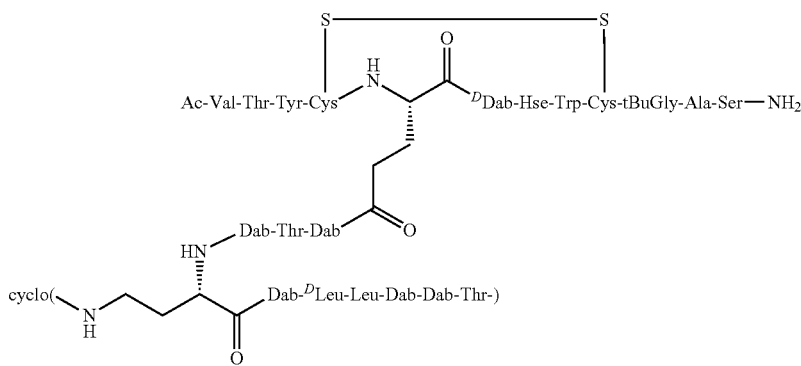 |
| Ex. 179 | 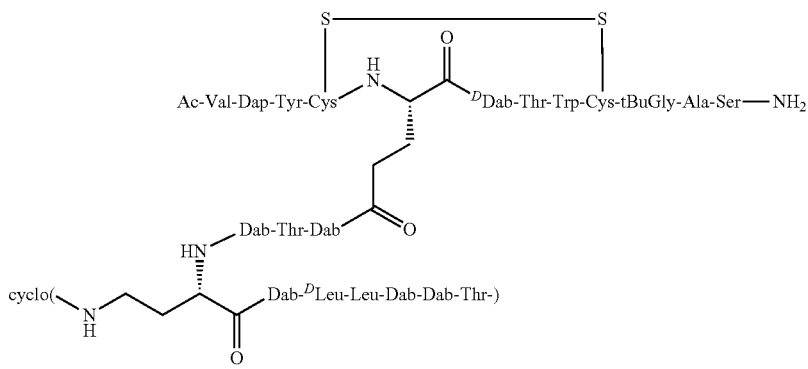 |
| Ex. 180 | 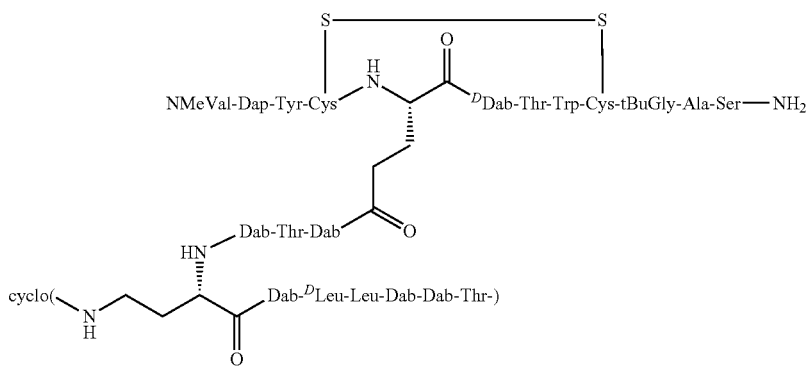 |

-continued
| Ex. No. | Sequence |
|---|---|
| Ex. 181 | 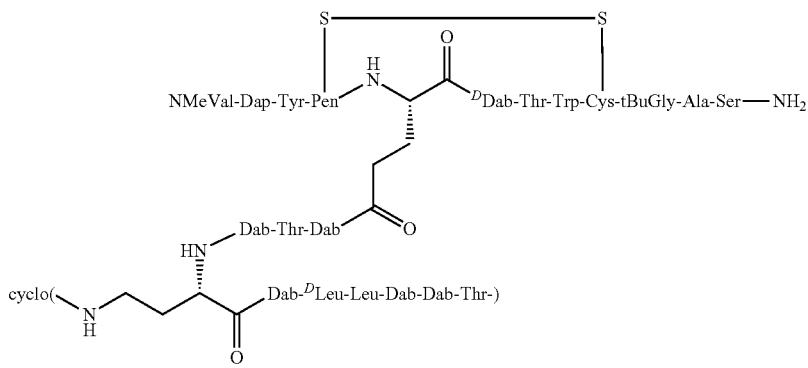 |
| Ex. 182 | 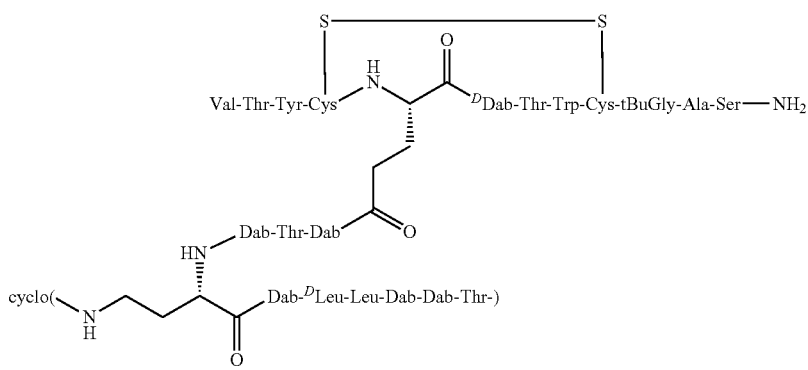 |
| Ex. 183 | 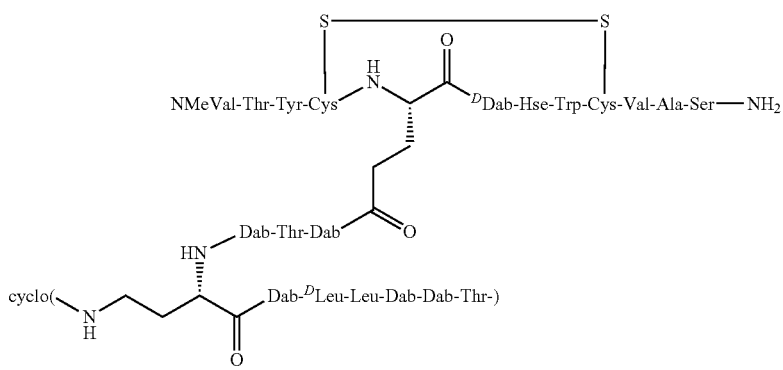 |
| Ex. 184 | 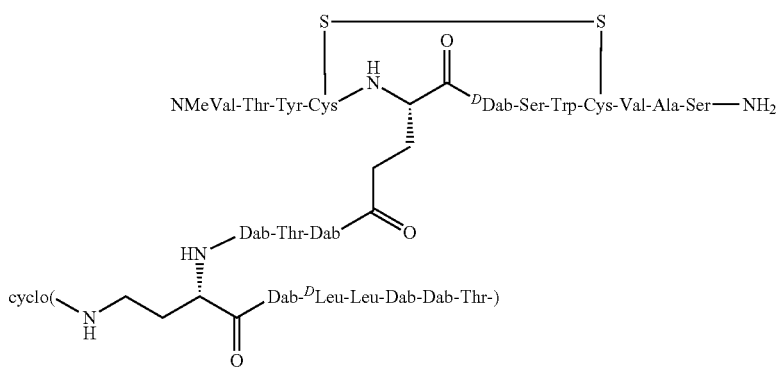 |

| Ex. No. | Sequence |
|---|---|
| Ex. 185 | 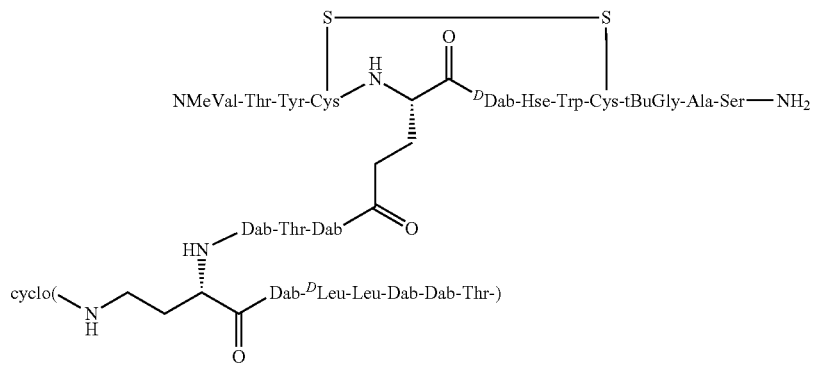 |
| Ex. 186 | 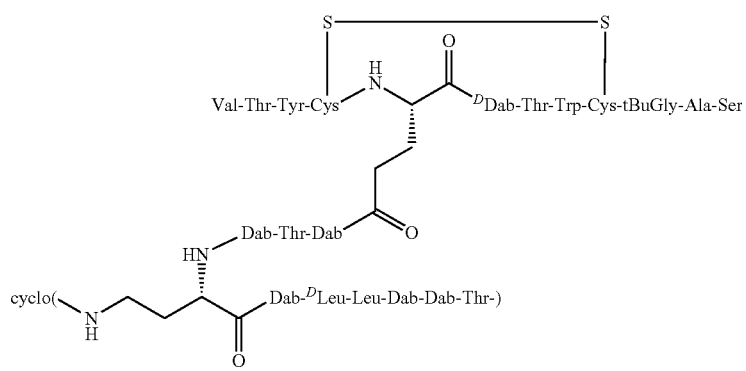 |
| Ex. 187 | 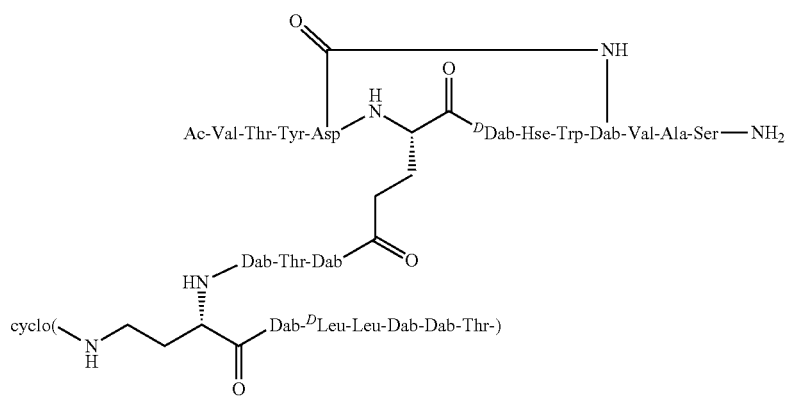 |
| Ex. 188 | 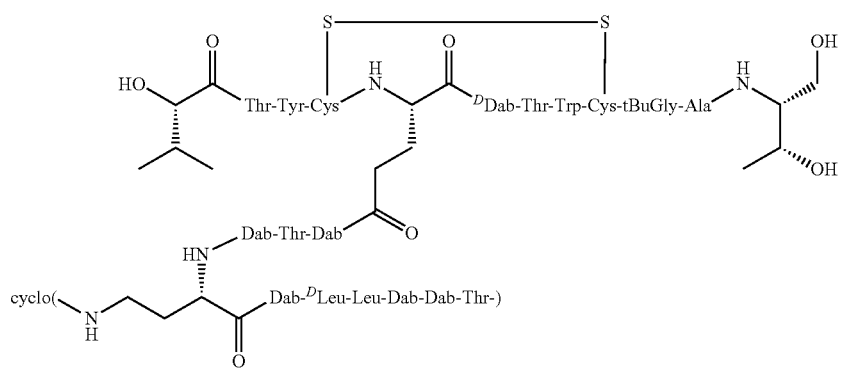 |

| Ex. No. | Sequence |
|---|---|
| Ex. 189 | 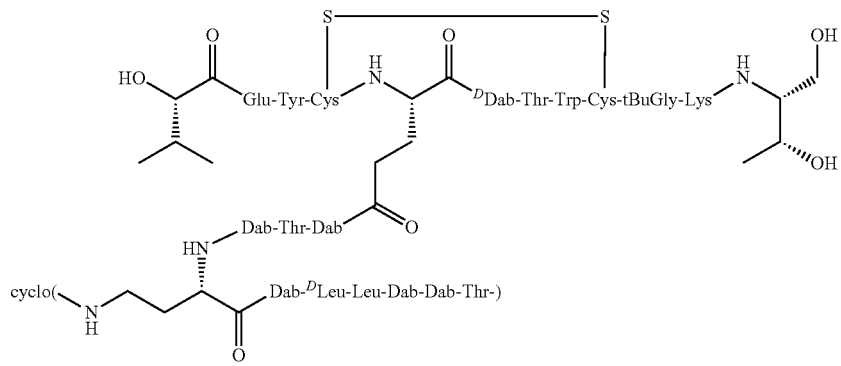 |
| Ex. 190 | 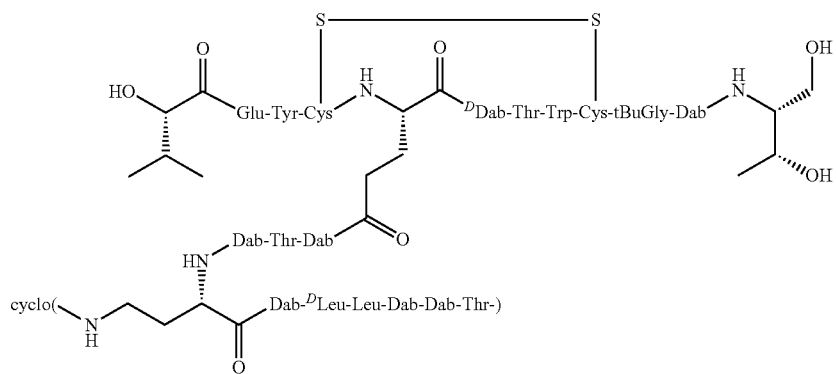 |
| Ex. 191 | 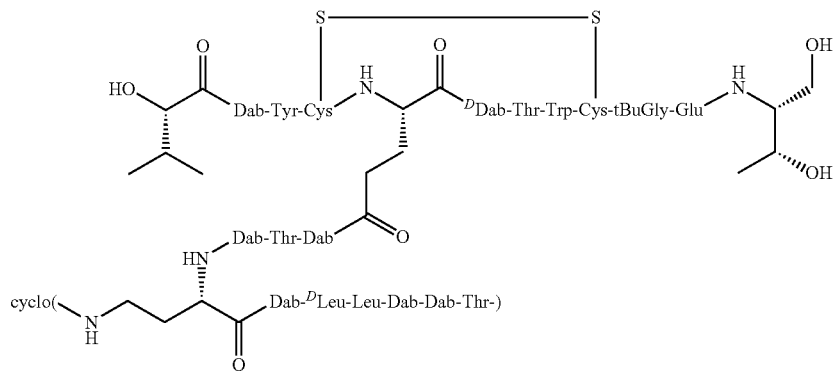 |
| Ex. 192 | 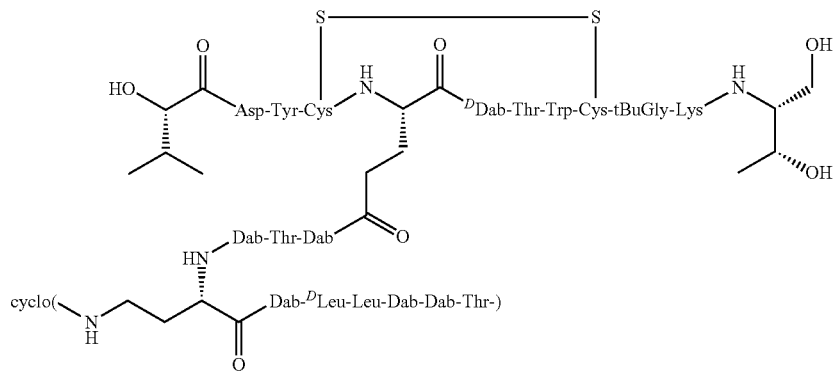 |

| Ex. No. | Sequence |
|---|---|
| Ex. 193 | 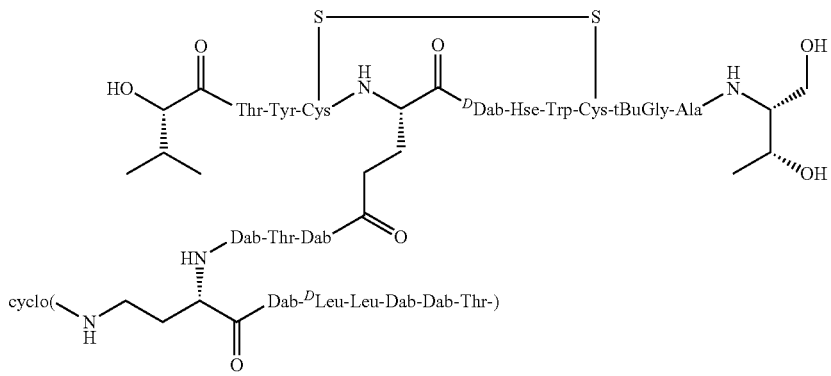 |
| Ex. 194 | 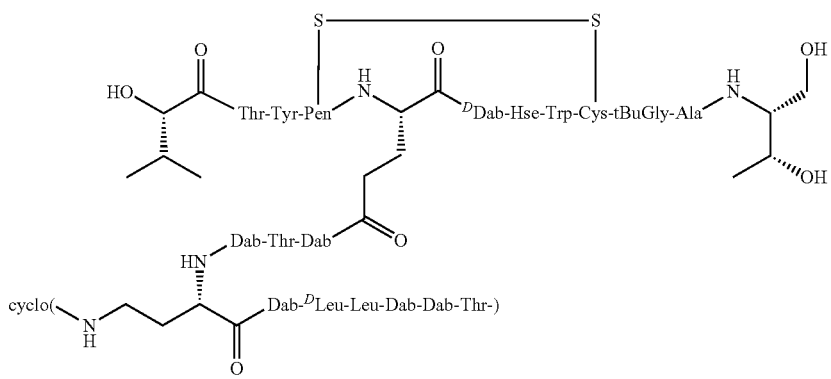 |
| Ex. 195 | 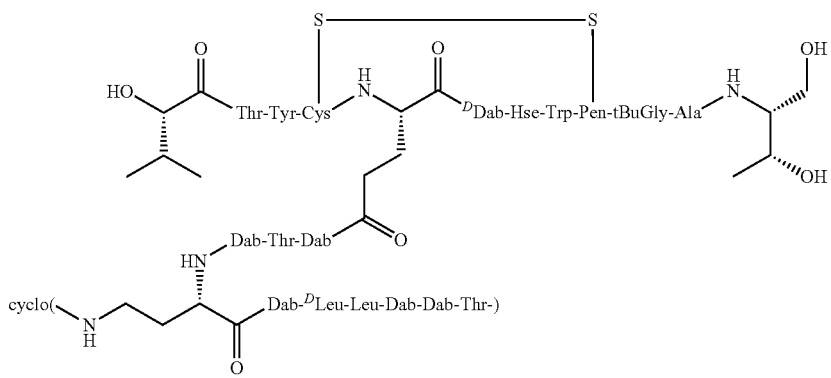 |
| Ex. 196 | 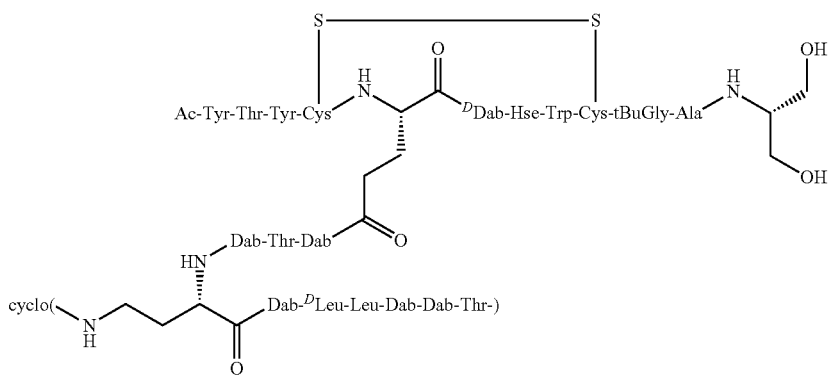 |

| Ex. No. | Sequence |
|---|---|
| Ex. 197 | 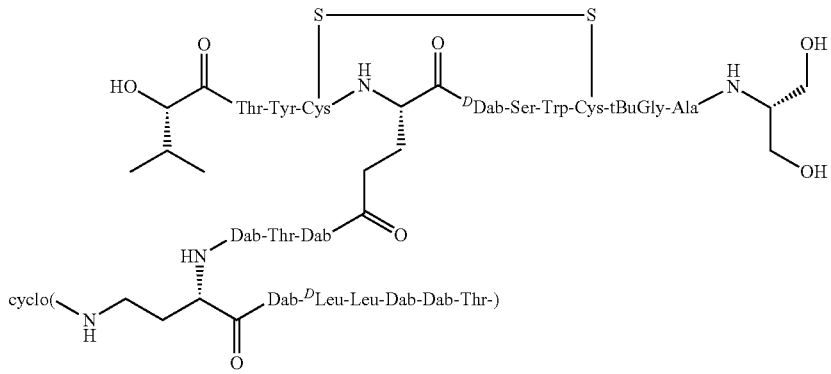 |
| Ex. 198 | 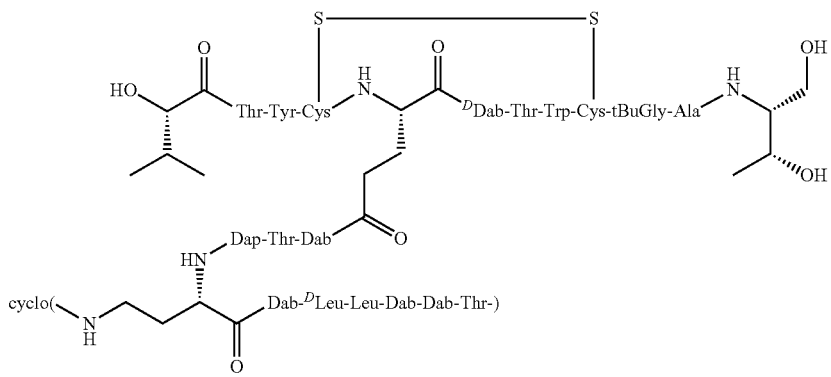 |
| Ex. 199 | 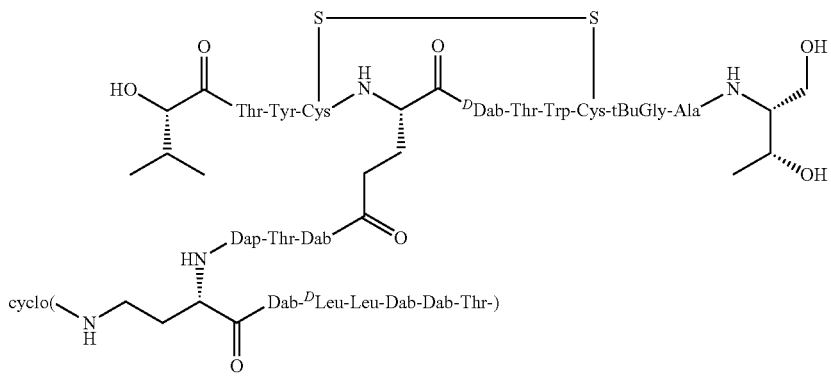 |
| Ex. 200 | 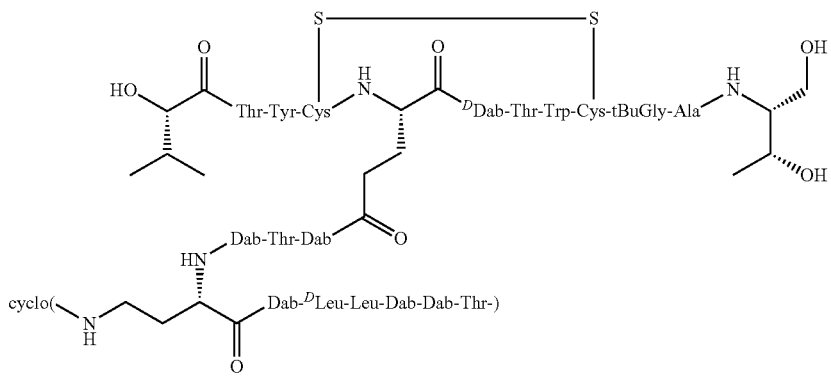 |

| Ex. No. | Sequence |
|---|---|
| Ex. 201 | 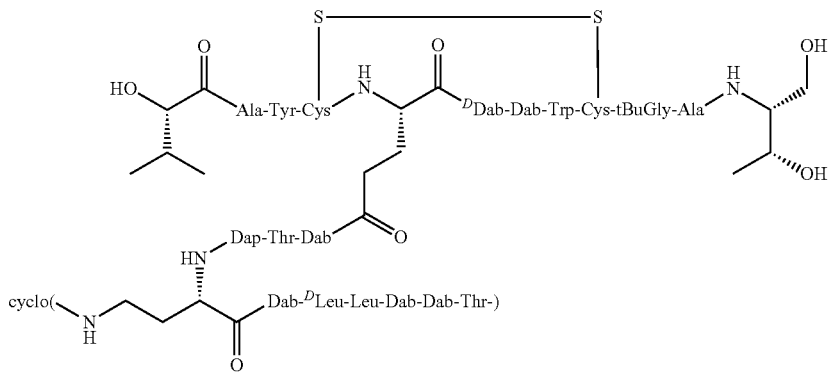 |
| Ex. 202 | 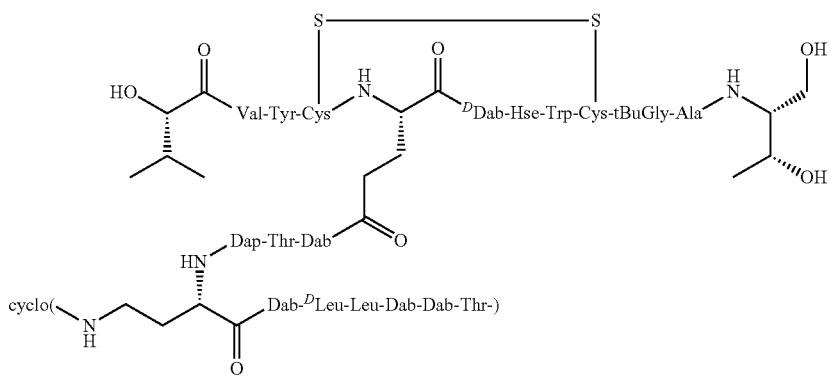 |
| Ex. 203 | 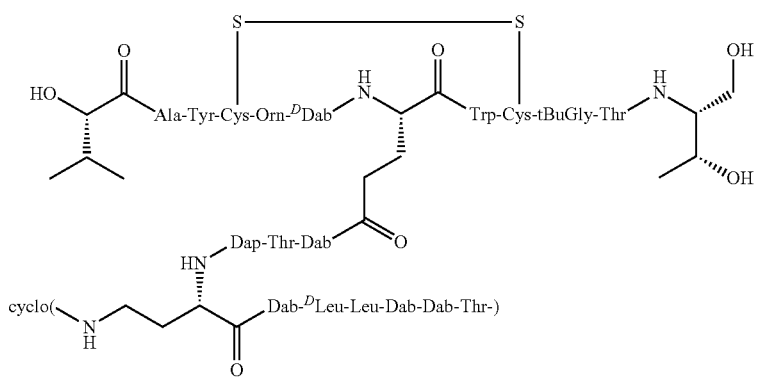 |
| Ex. 204 | 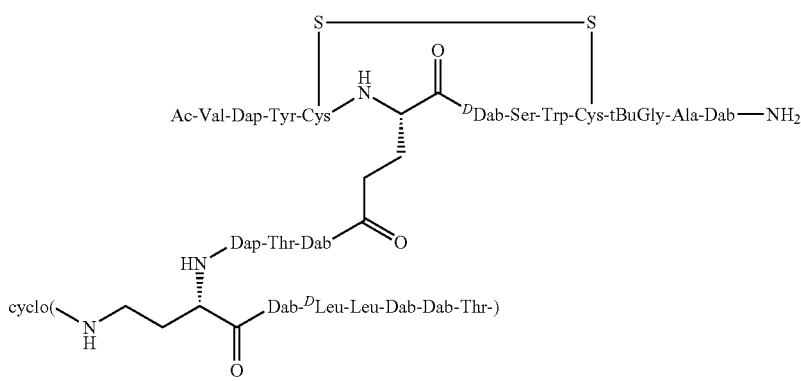 |

-continued
| Ex. No. | Sequence |
|---|---|
| Ex. 205 | 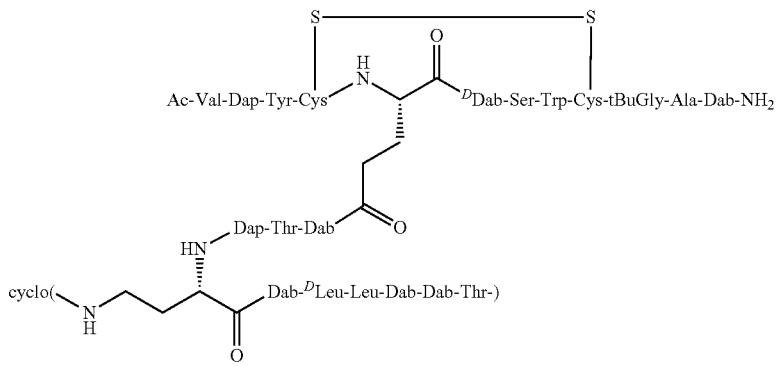 |
| Ex. 206 | 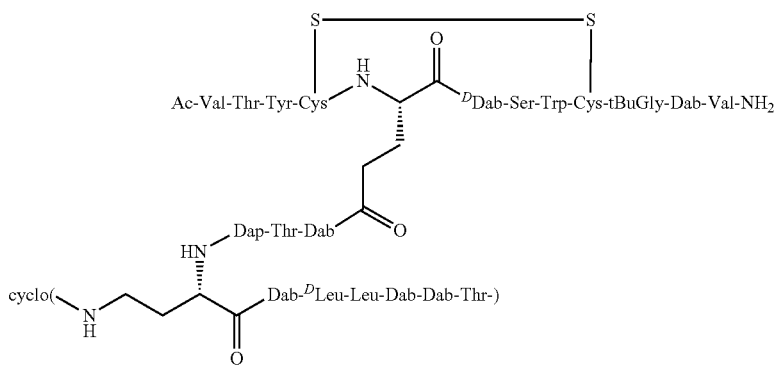 |
| Ex. 207 | 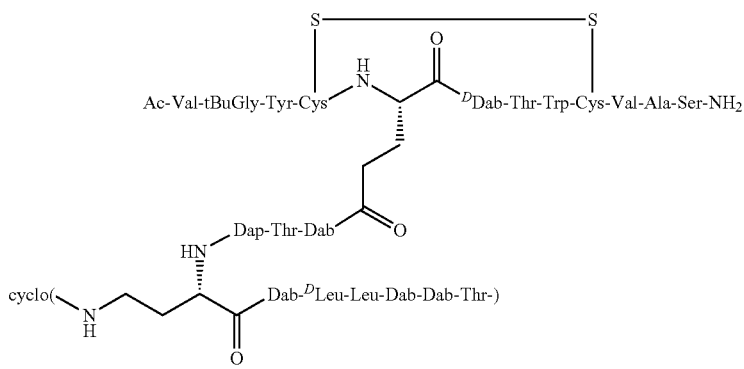 |
| Ex. 208 | 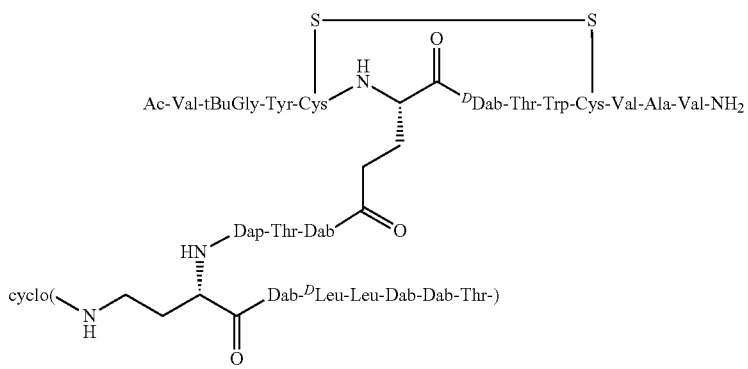 |

| Ex. No. | Sequence |
|---|---|
| Ex. 209 | 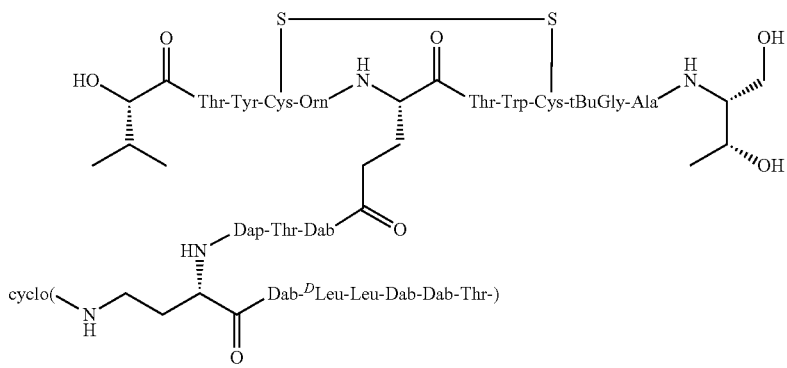 |
| Ex. 210 | 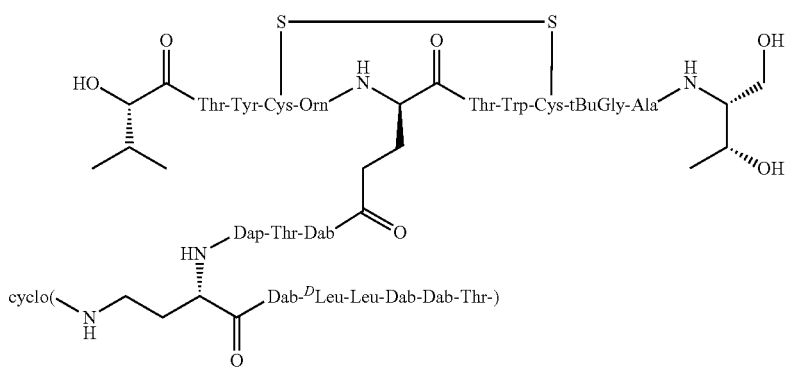 |
| Ex. 211 | 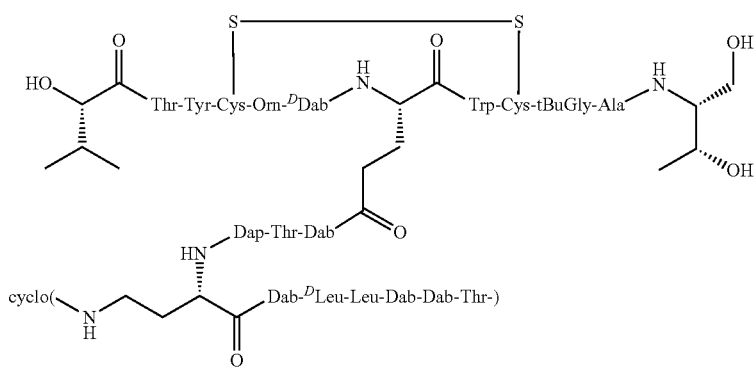 |
| Ex. 212 | 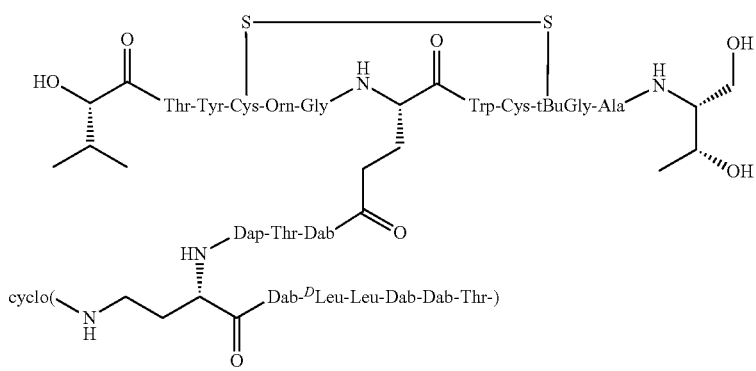 |

| Ex. No. | Sequence |
|---|---|
| Ex. 213 | 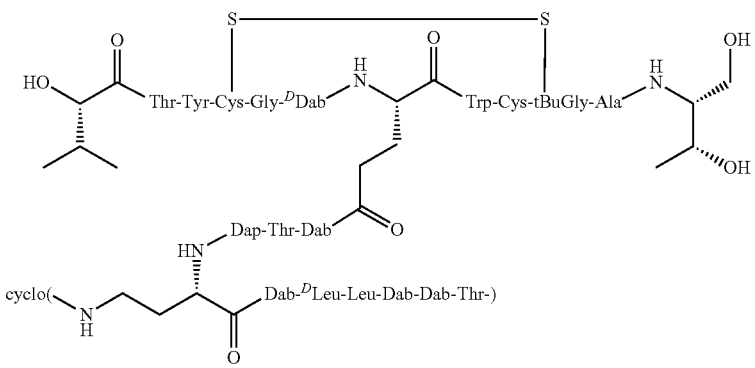 |
| Ex. 214 | 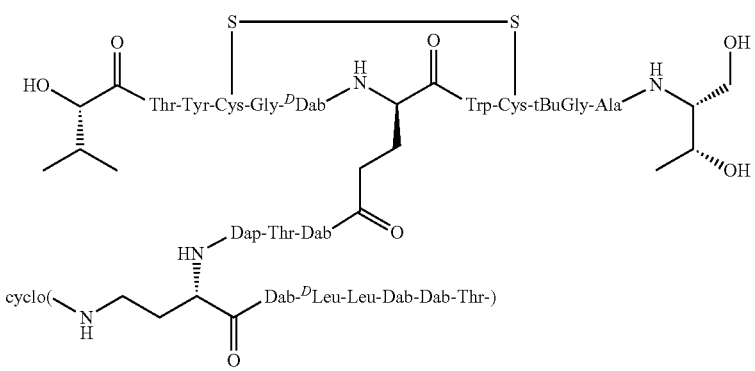 |
| Ex. 215 | 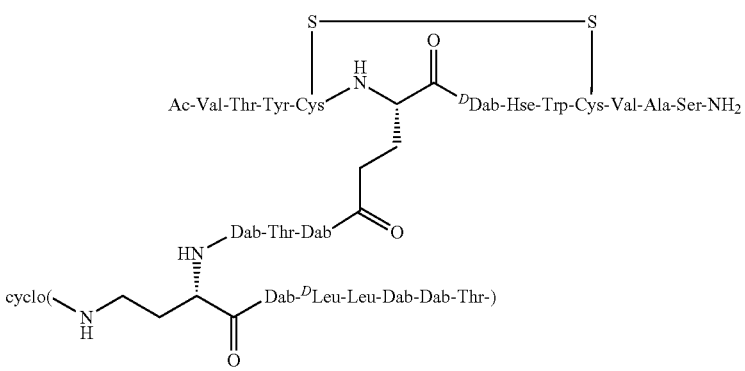 |
| Ex. 216 | 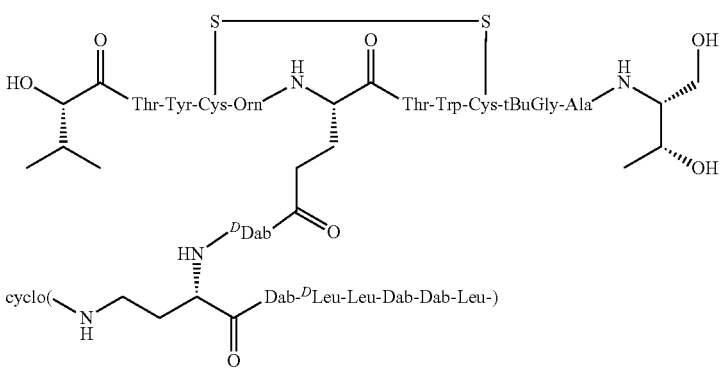 |

| Ex. No. | Sequence |
|---|---|
| Ex. 217 | 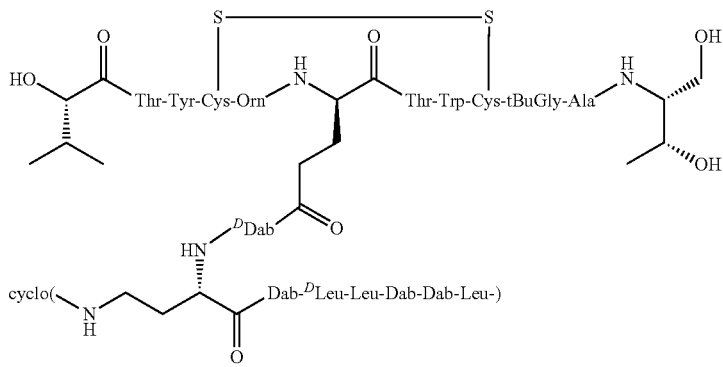 |
| Ex. 218 | 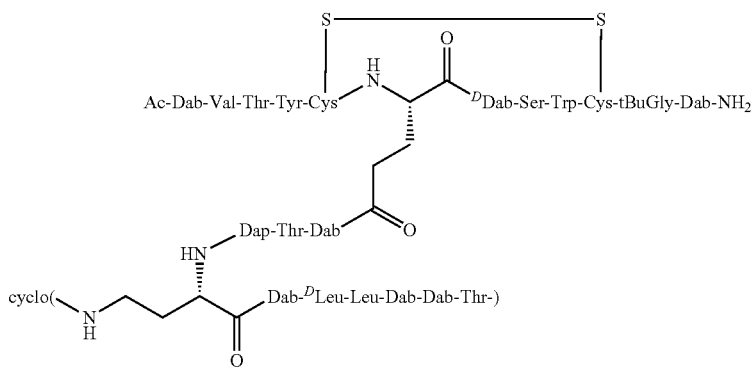 |
| Ex. 219 | 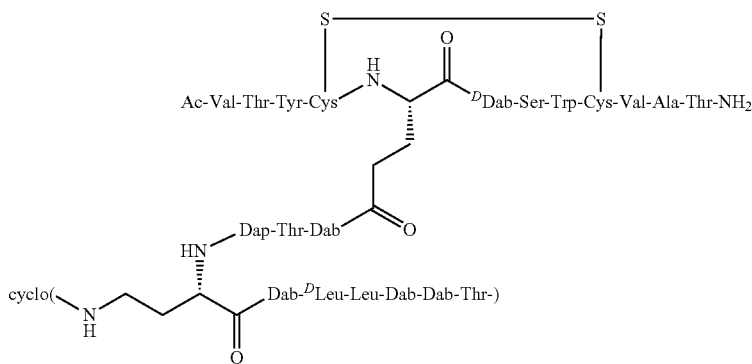 |
| Ex. 220 | 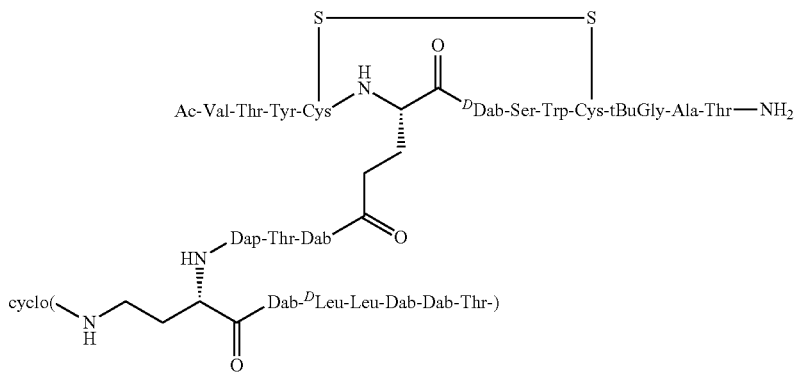 |

| Ex. No. | Sequence |
|---|---|
| Ex. 221 | 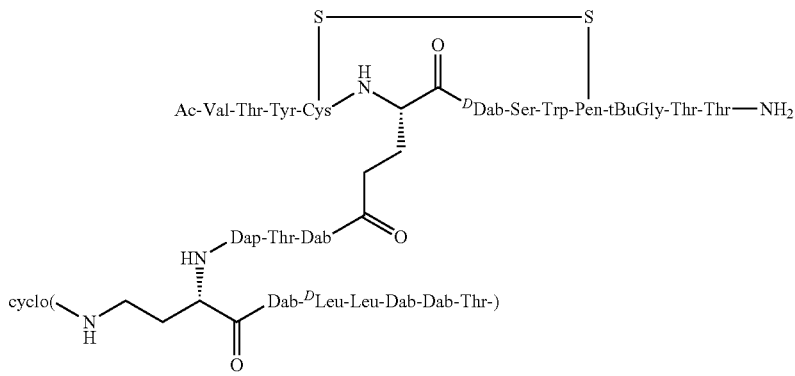 |
| Ex. 222 | 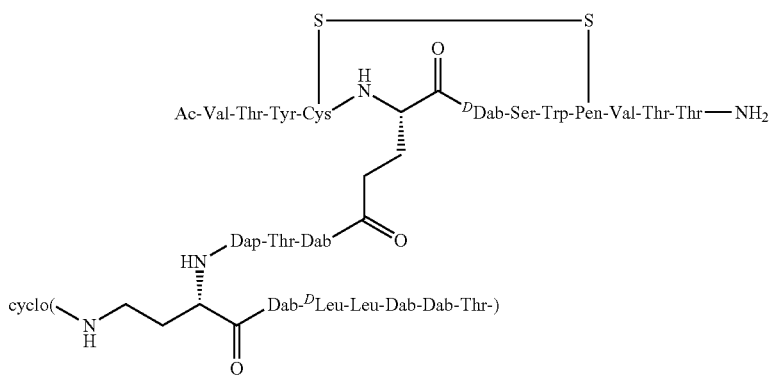 |
| Ex. 223 | 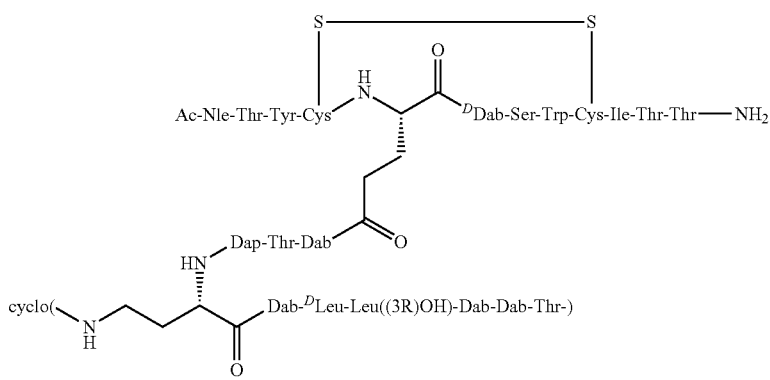 |
| Ex. 224 | 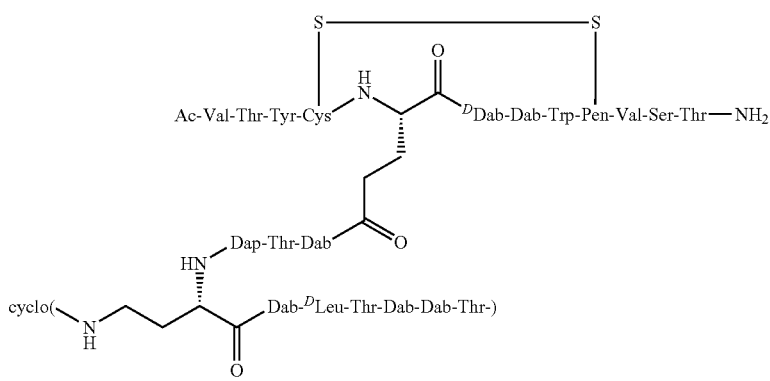 |

-continued
| Ex. No. | Sequence |
|---|---|
| Ex. 225 | 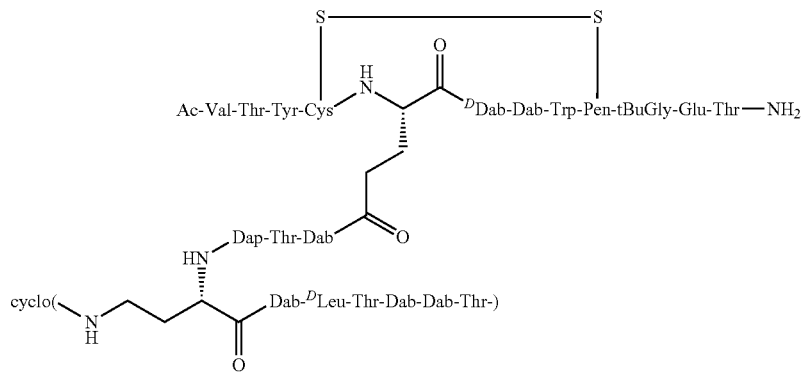 |
| Ex. 226 | 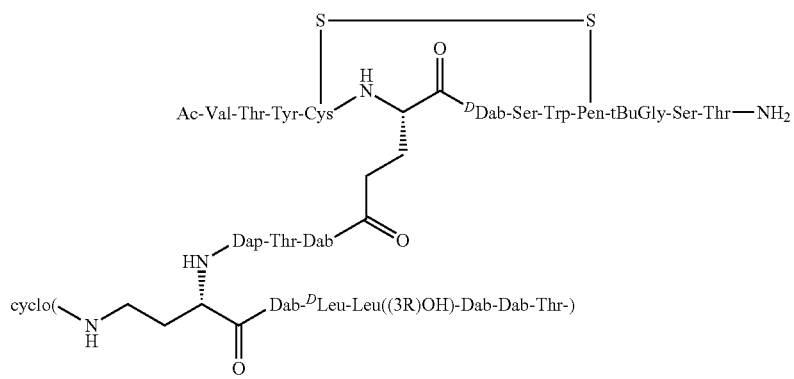 |
| Ex. 227 | 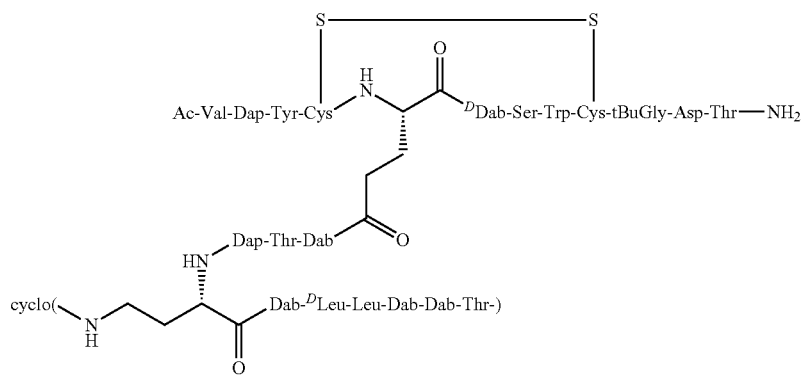 |
| Ex. 228 | 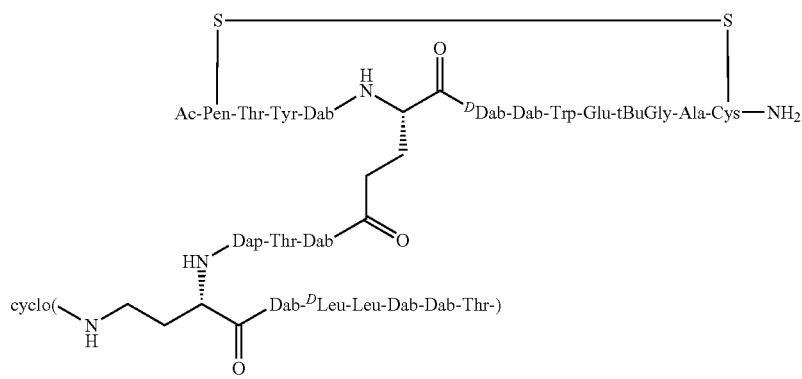 |

| Ex. No. | Sequence |
|---|---|
| Ex. 229 | 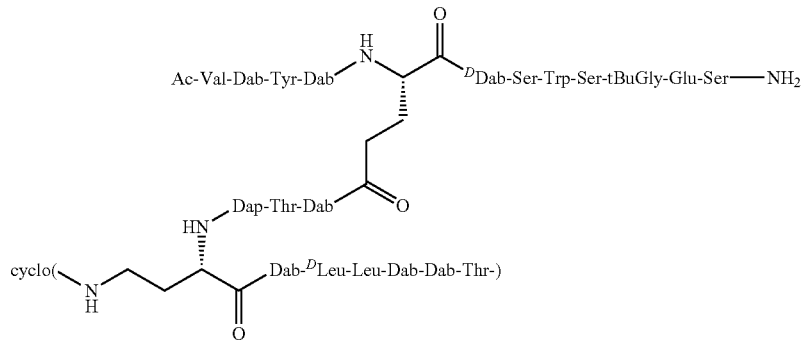 |
| Ex. 230 | 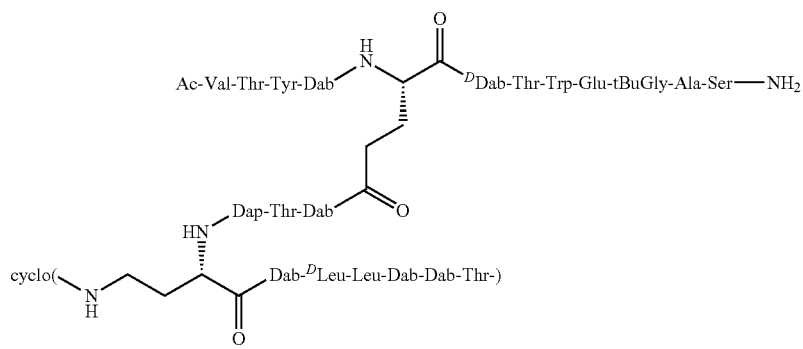 |
| Ex. 232 | 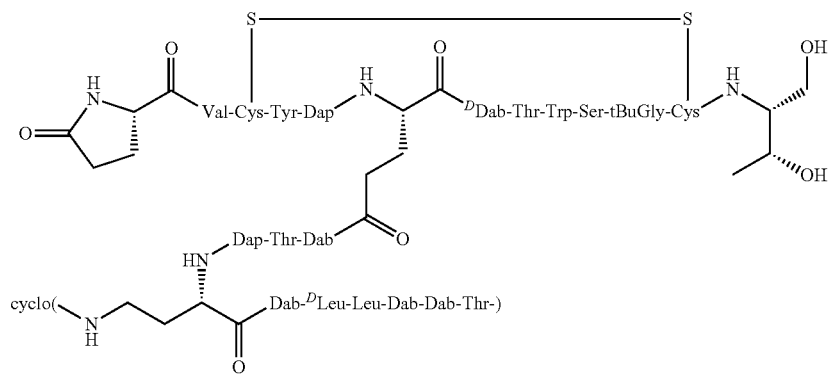 |
| Ex. 233 | 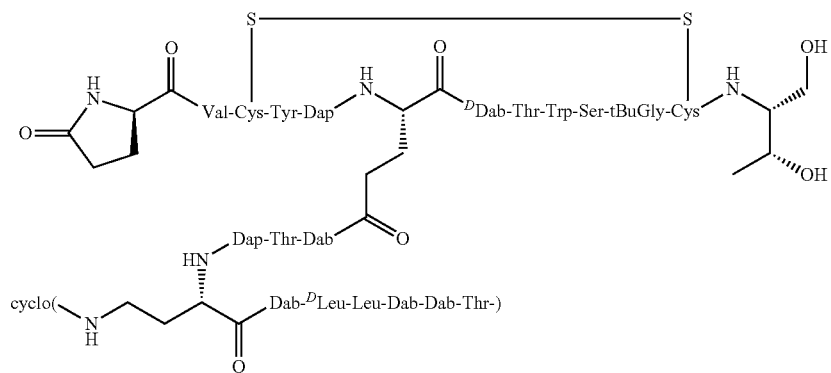 |

| Ex. No. | Sequence |
|---|---|
| Ex. 234 | 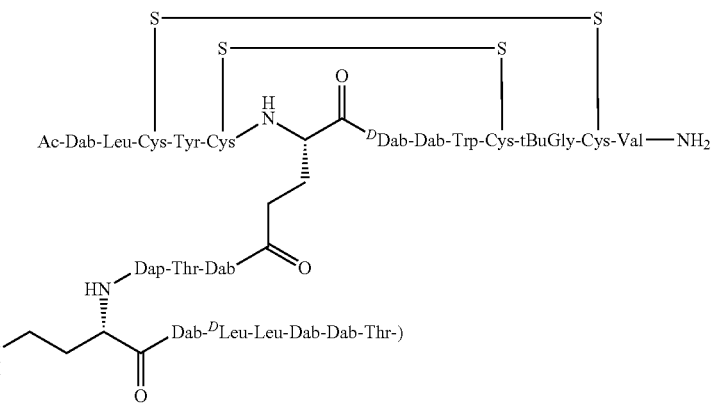 |
| Ex. 235 | 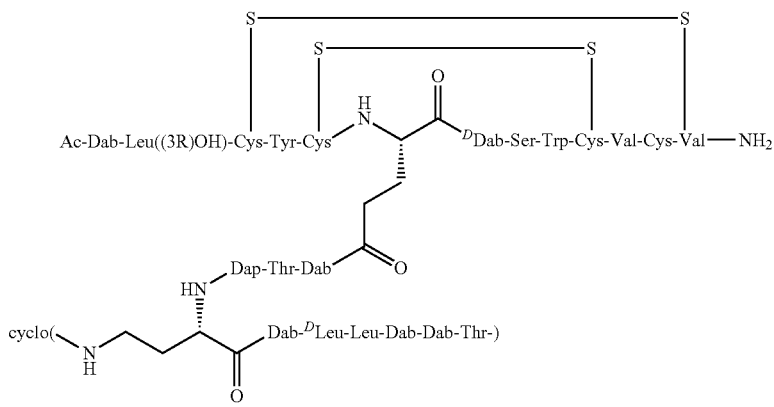 |
| Ex. 236 | 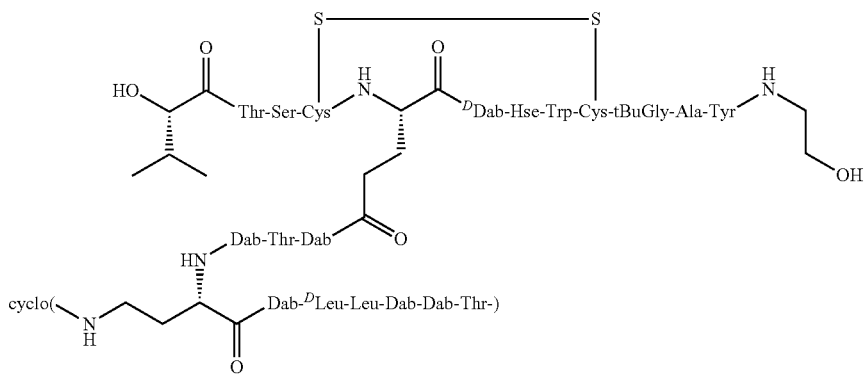 |
| Ex. 237 | 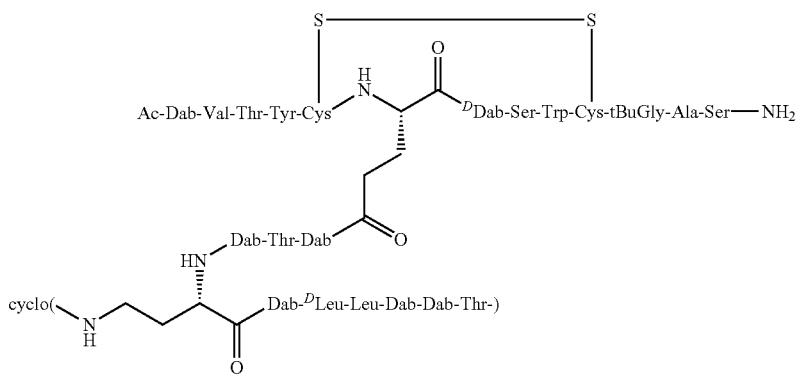 |

| Ex. No. | Sequence |
|---|---|
| Ex. 238 | 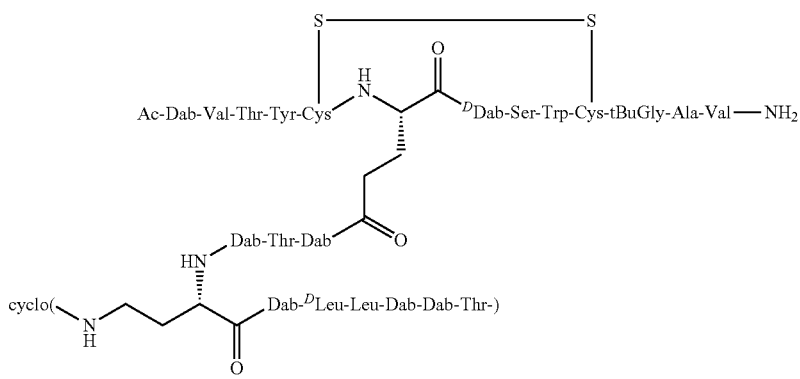 |
| Ex. 239 | 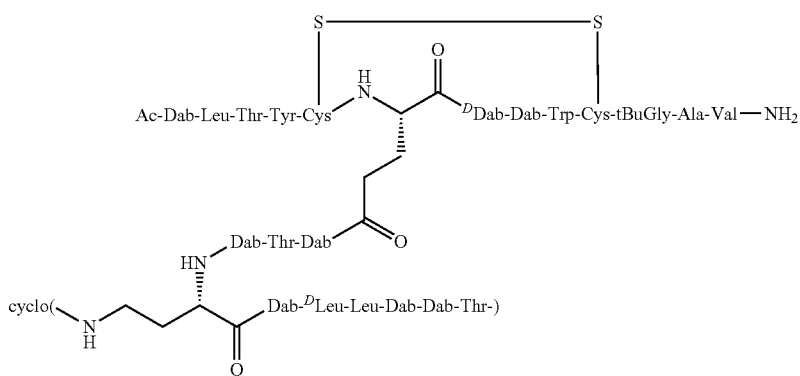 |
| Ex. 240 | 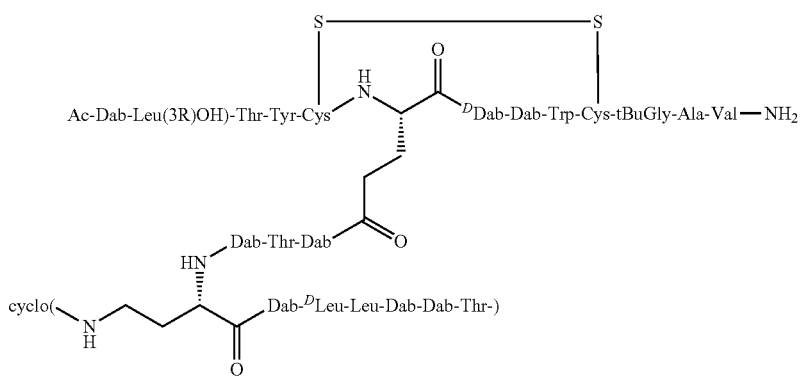 |
| Ex. 241 | 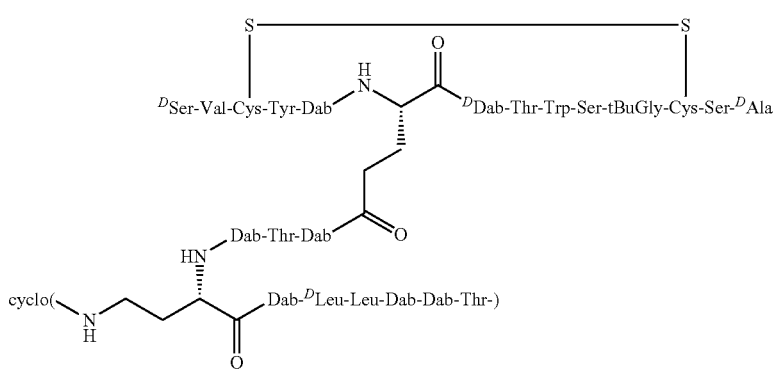 |

| Ex. No. | Sequence |
|---|---|
| Ex. 242 | 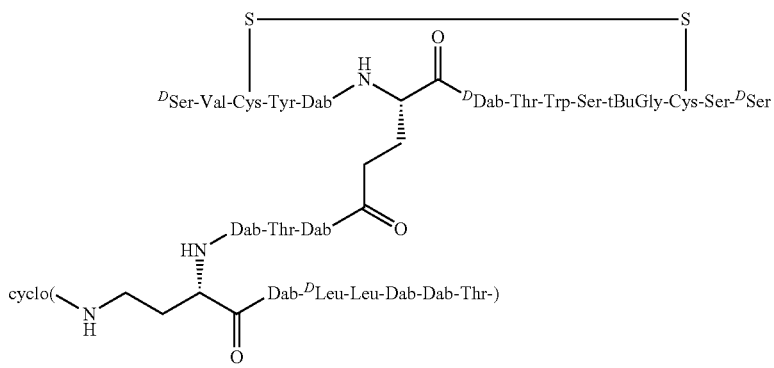 |
| Ex. 243 | 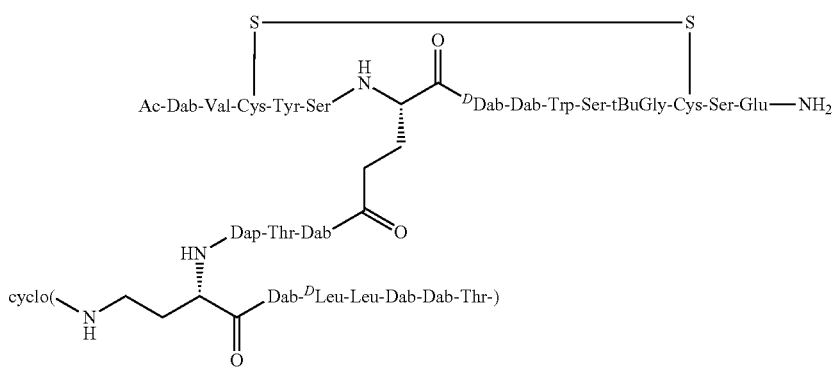 |
| Ex. 244 | 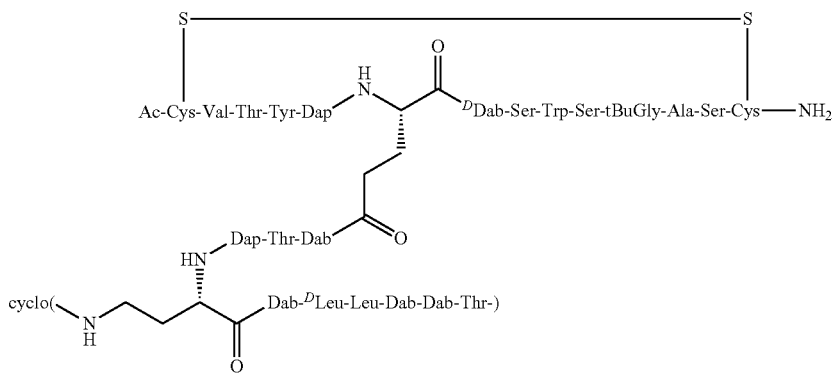 |
| Ex. 245 | 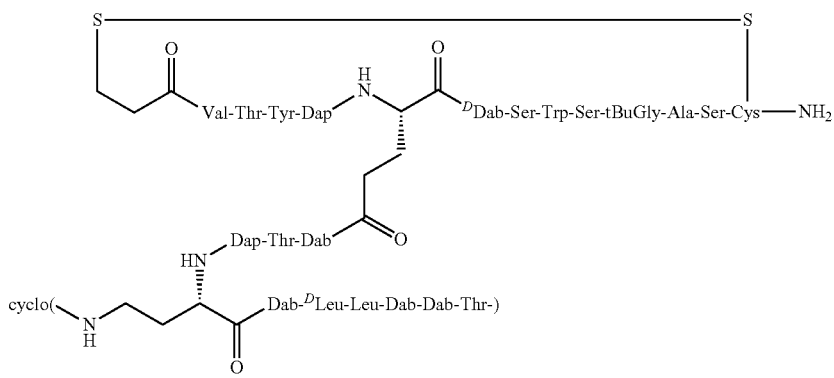 |

| Ex. No. | Sequence |
|---|---|
| Ex. 246 | 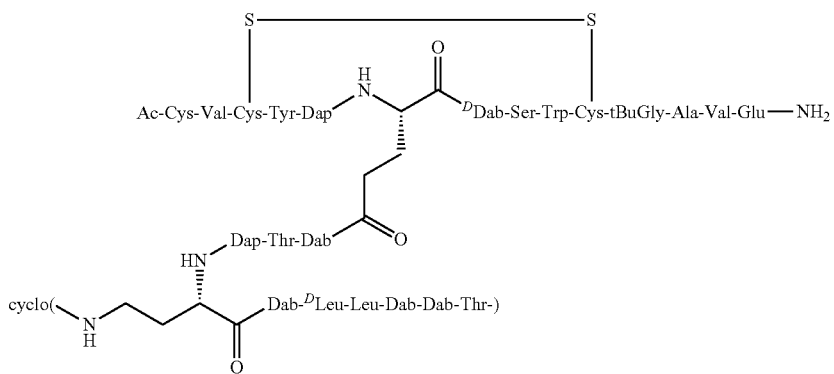 |
| Ex. 247 | 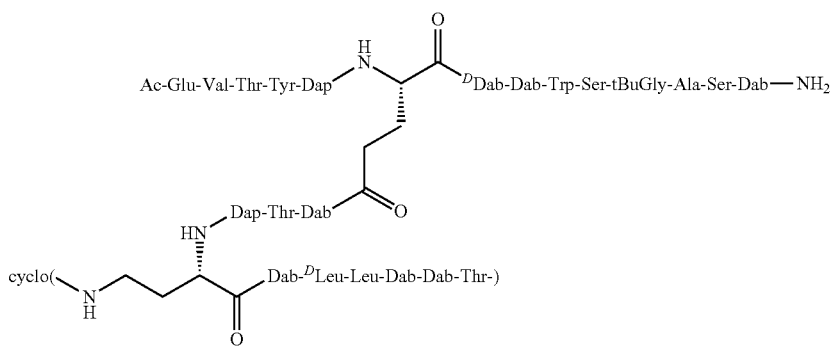 |
| Ex. 248 | 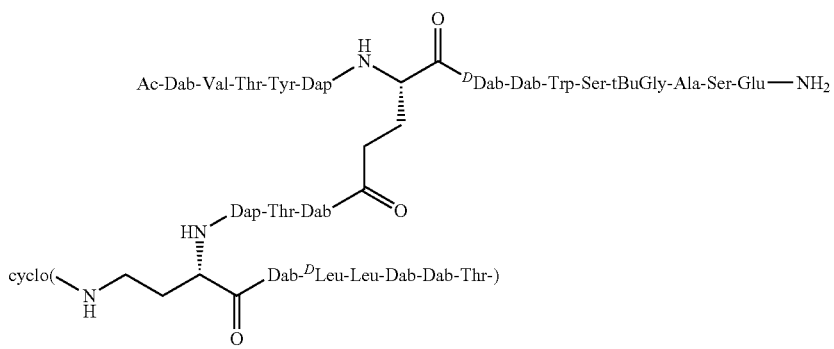 |
| Ex. 249 | 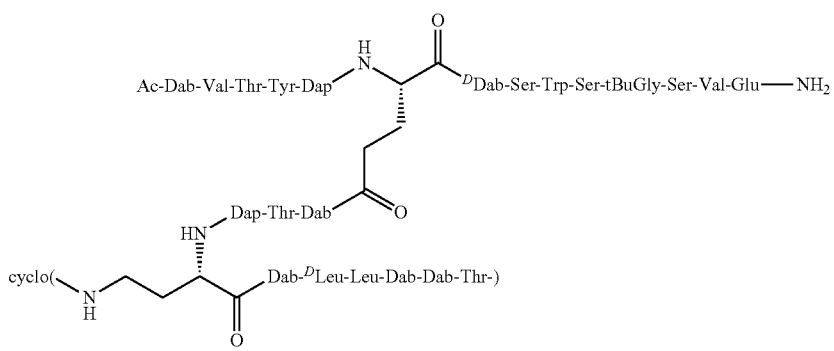 |

| Ex. No. | Sequence |
|---|---|
| Ex. 250 | 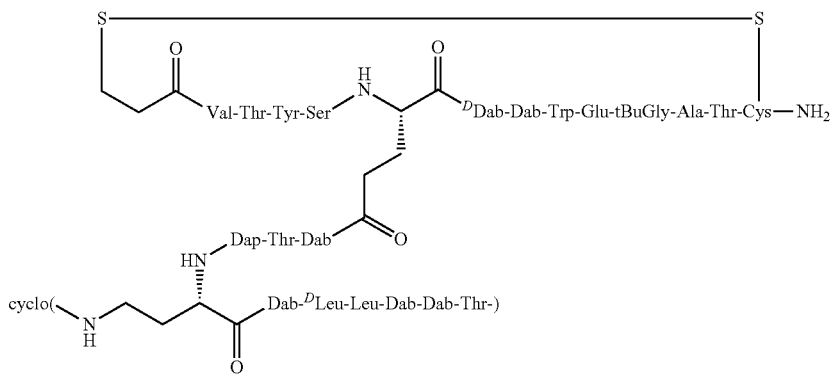 |
| Ex. 251 | 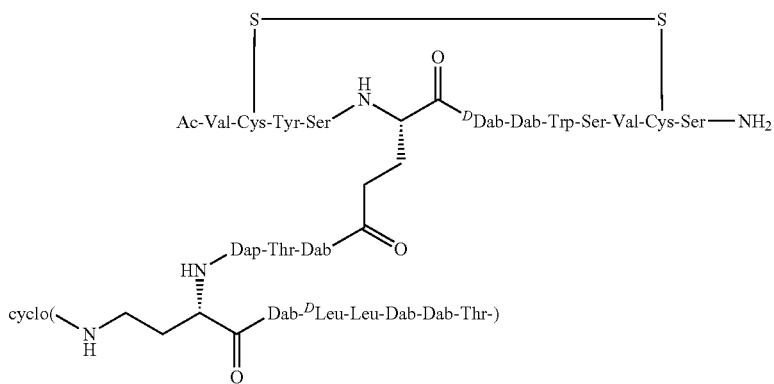 |
| Ex. 252 | 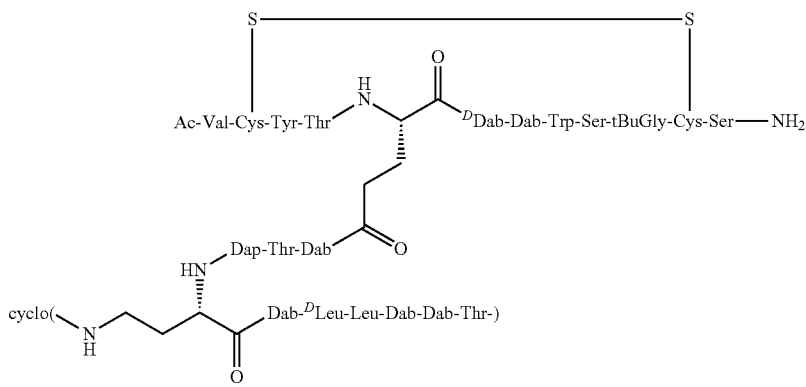 |
| Ex. 253 | 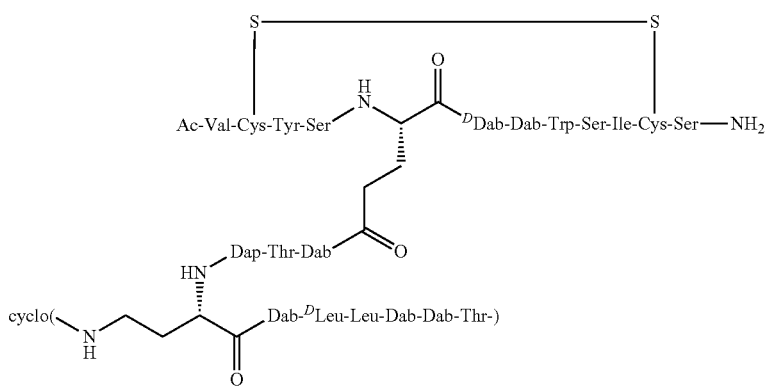 |

| Ex. No. | Sequence |
|---|---|
| Ex. 254 | 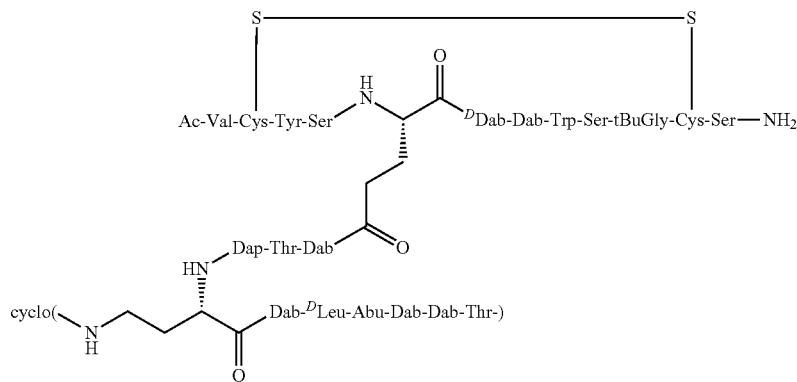 |
| Ex. 255 | 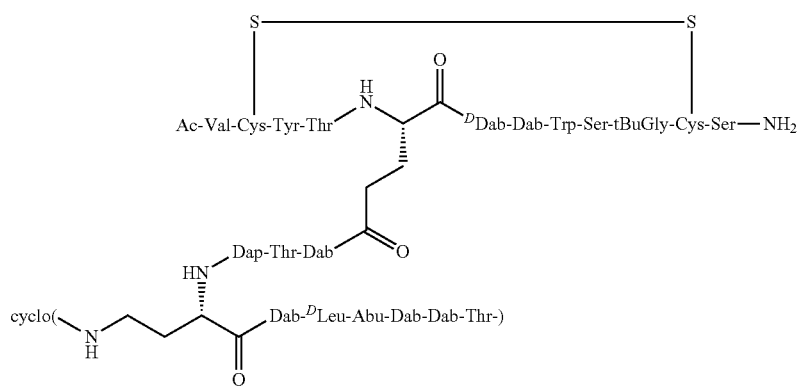 |
| Ex. 256 | 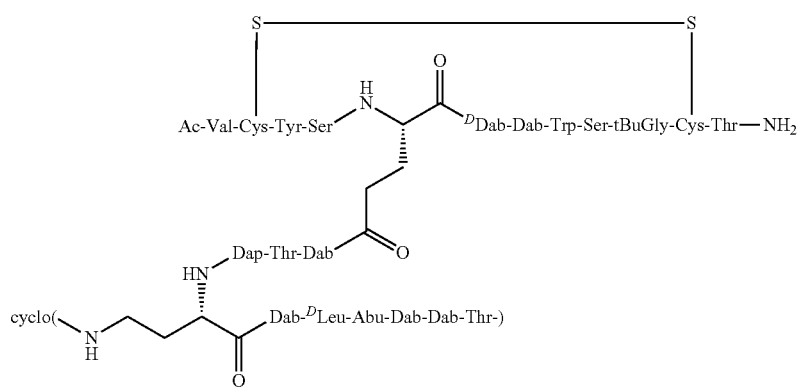 |
| Ex. 257 | 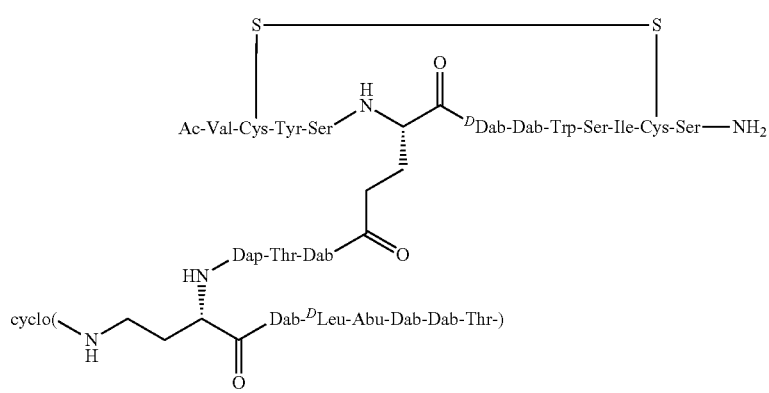 |

| Ex. No. | Sequence |
|---|---|
| Ex. 258 | 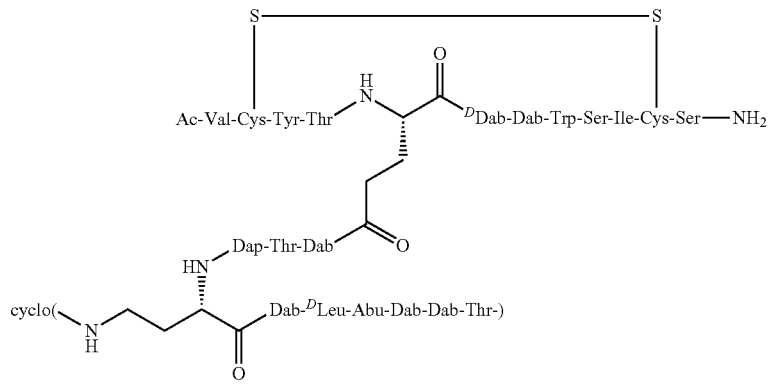 |
| Ex. 259 | 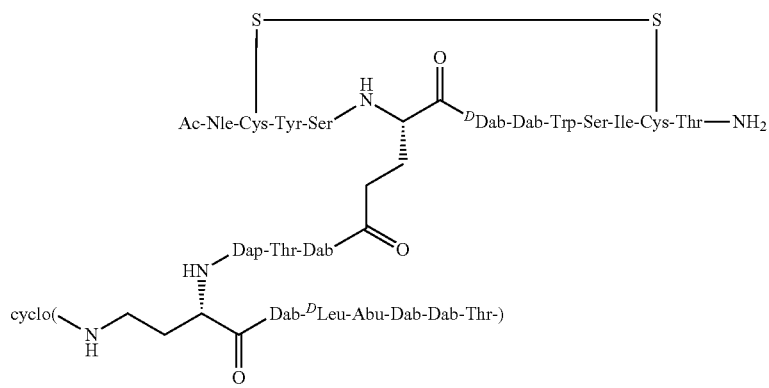 |
| Ex. 260 | 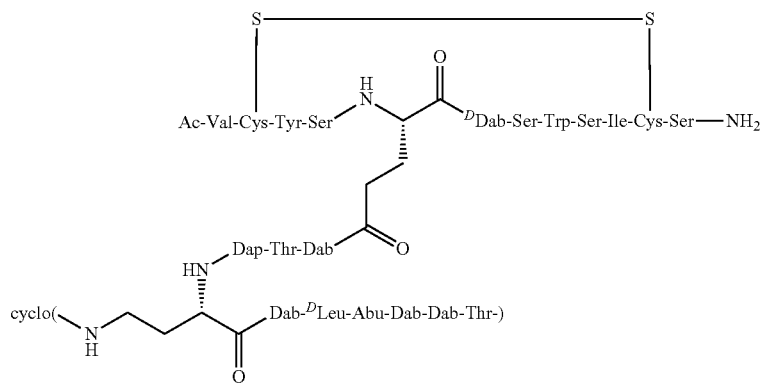 |
| Ex. 261 | 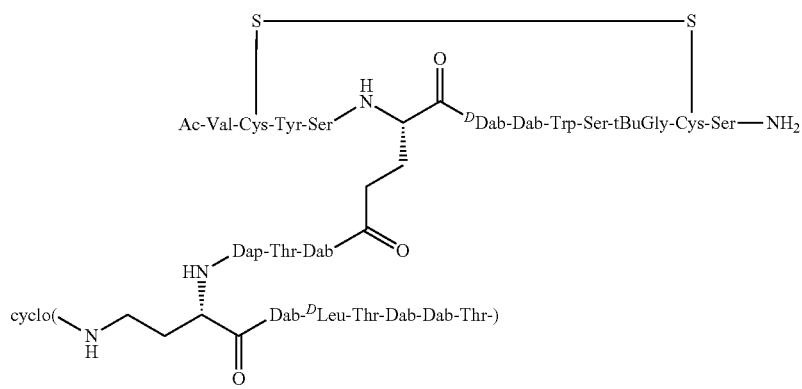 |

| Ex. No. | Sequence |
|---|---|
| Ex. 262 | 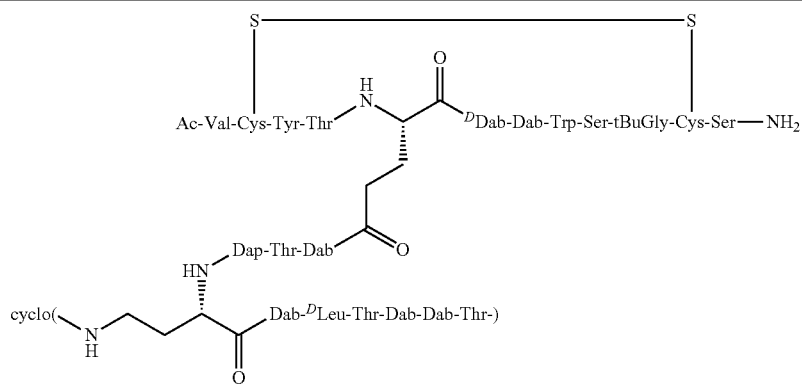 |
| Ex. 263 | 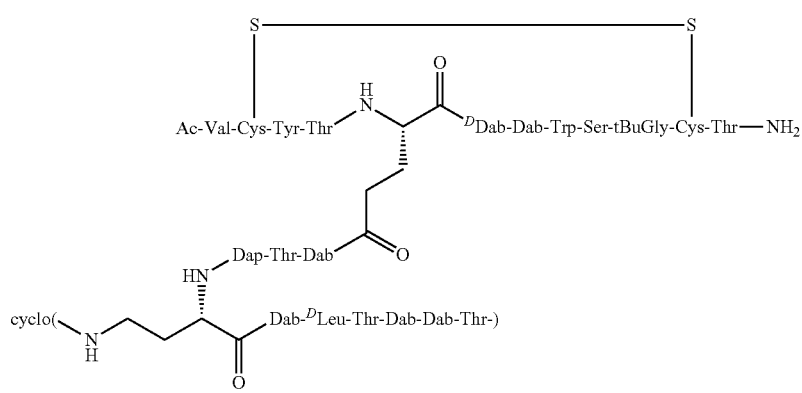 |
| Ex. 264 | 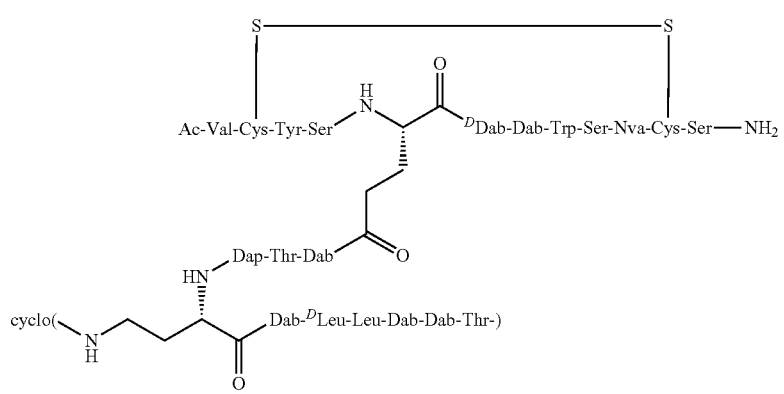 |
| Ex. 265 | 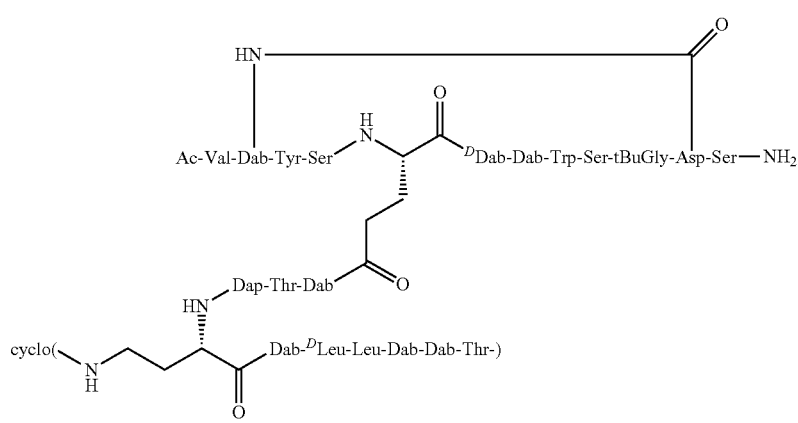 |

| Ex. No. | Sequence |
|---|---|
| Ex. 266 | 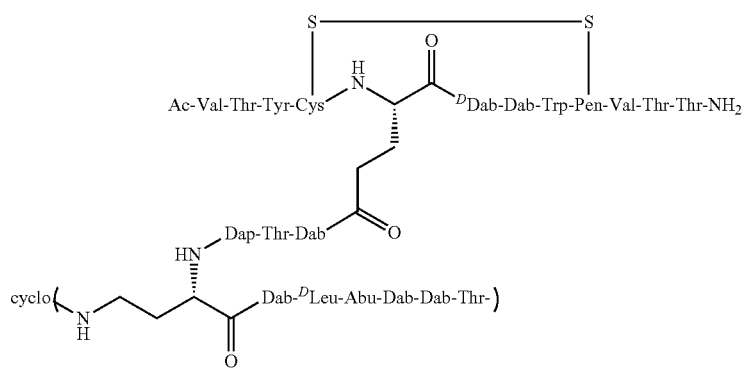 |
| Ex. 267 | 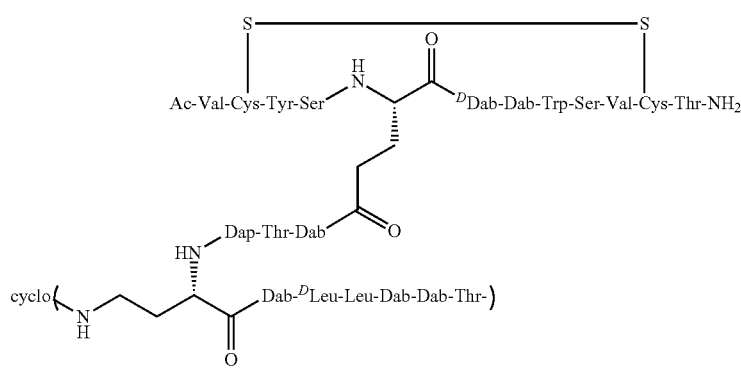 |
| Ex. 268 | 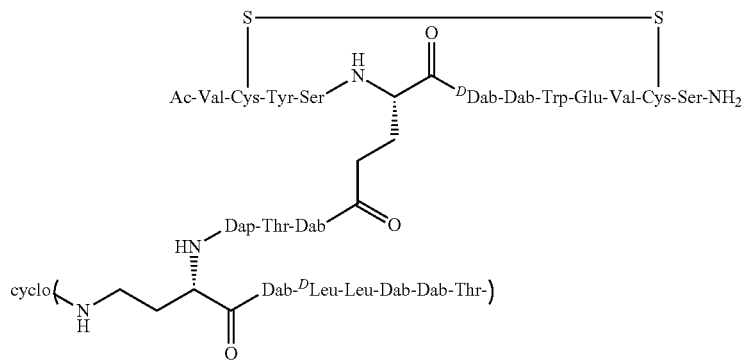 |
| Ex. 269 | 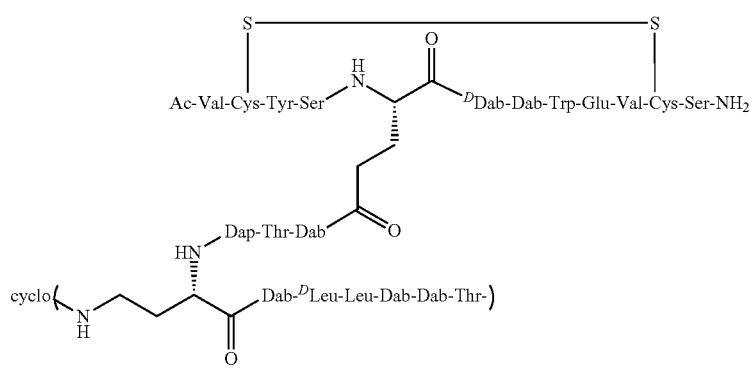 |

| Ex. No. | Sequence |
|---|---|
| Ex. 270 | 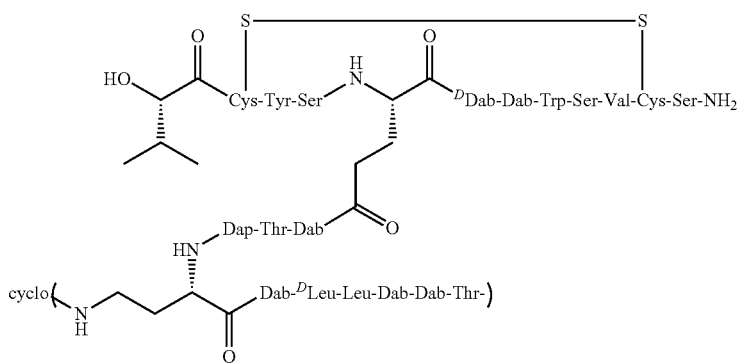 |
| Ex. 271 | 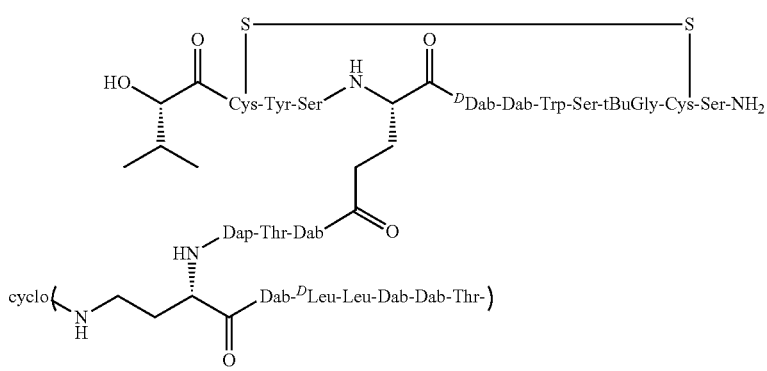 |
| Ex. 272 | 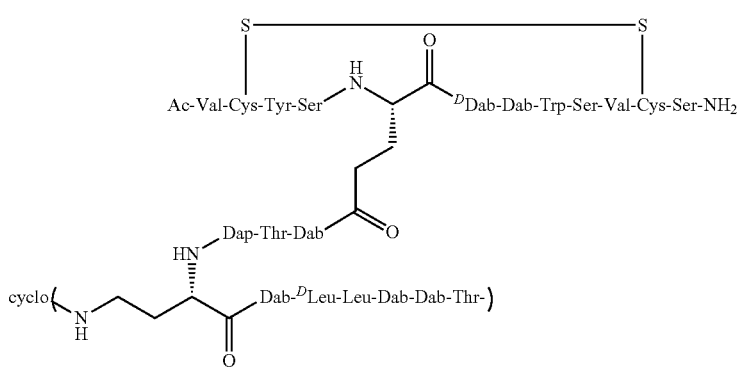 |
| Ex. 273 | 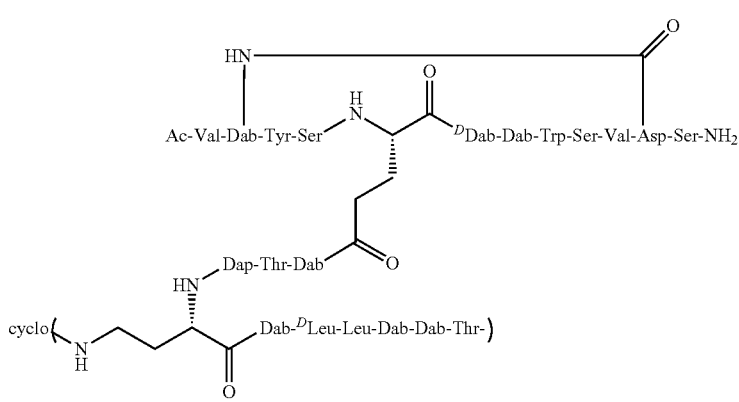 |

| Ex. No. | Sequence |
|---|---|
| Ex. 274 | 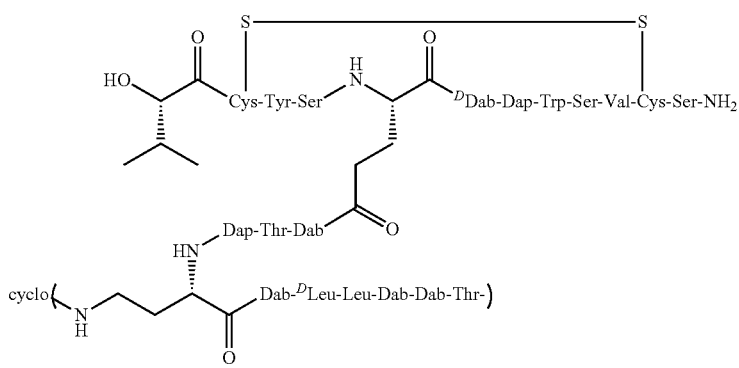 |
| Ex. 275 | 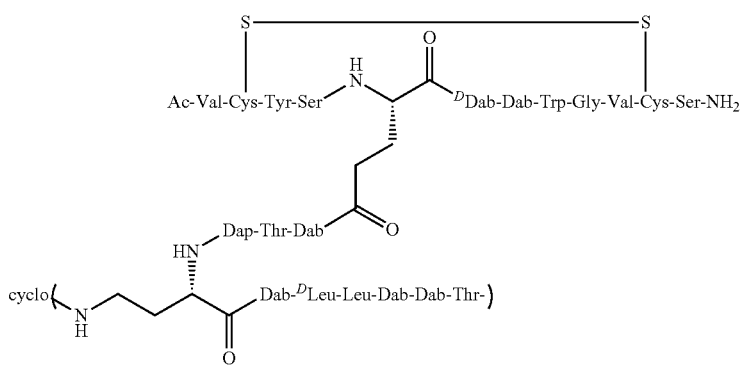 |
| Ex. 276 | 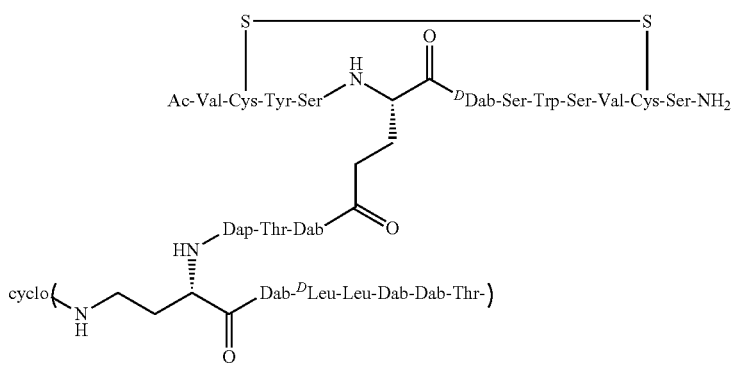 |
| Ex. 277 | 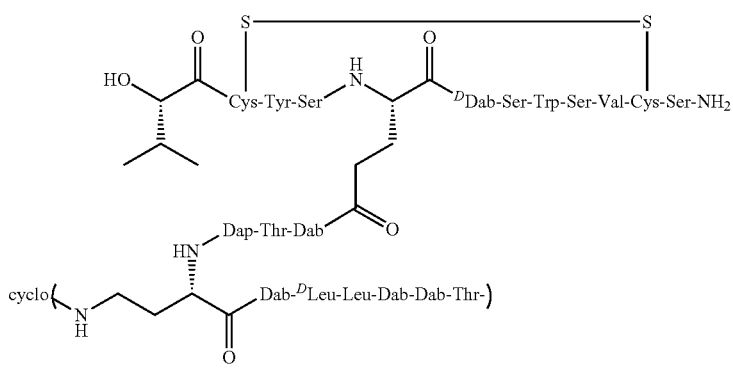 |

| Ex. No. | Sequence |
|---|---|
| Ex. 278 | 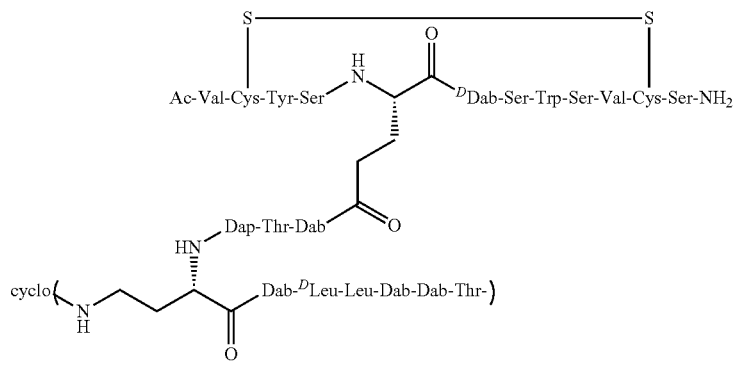 |
| Ex. 279 | 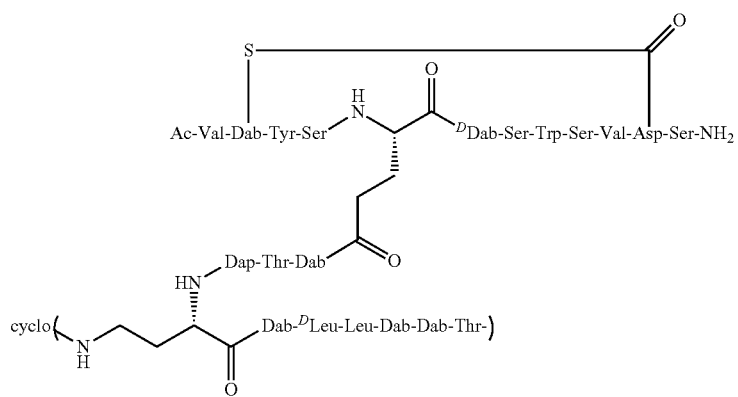 |
| Ex. 280 | 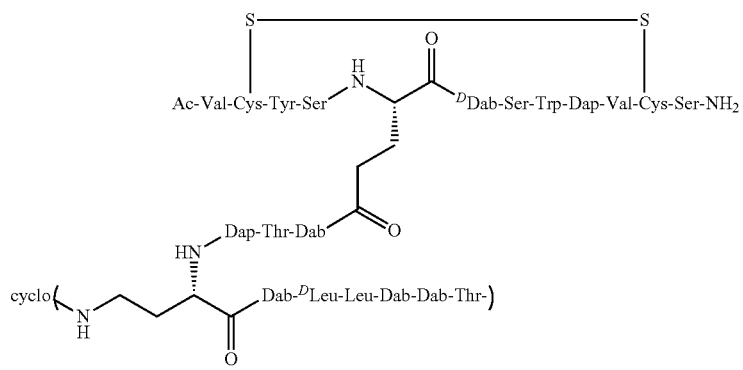 |
| Ex. 281 | 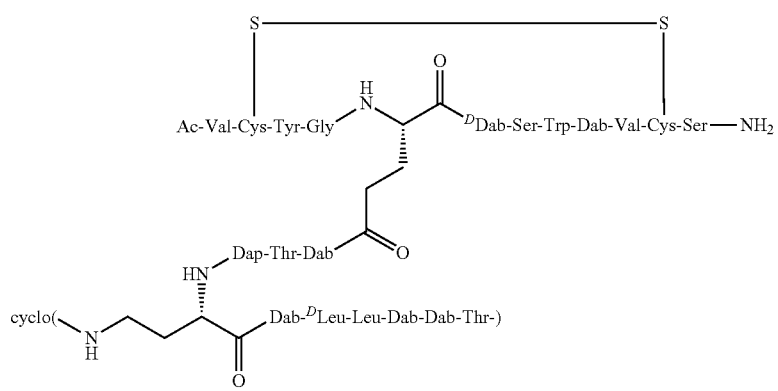 |

| Ex. No. | Sequence |
|---|---|
| Ex. 282 | Ac-Val-Cys-Tyr-Ser-[Glu]-ᴰDab-Hse-Trp-Ser-Val-Cys-Ser—NH₂, with Cys–Cys disulfide; Glu side chain amide to Dap-Thr-Dab-cyclo(NH-...-Dab-ᴰLeu-Leu-Dab-Dab-Thr-) |
| Ex. 283 | Ac-Val-Cys-Tyr-Ser-[Glu]-ᴰDab-Ser-Trp-Ser-Val-Cys-Ser—NH₂, with Cys–Cys disulfide; Glu side chain amide to Dap-Thr-Dab-cyclo(NH-...-Dab-ᴰLeu-Thr-Dab-Dab-Thr-) |
| Ex. 284 | Ac-Val-Cys-Tyr-Ser-[Glu]-ᴰDab-Hse-Trp-Ser-Val-Cys-Ser—NH₂, with Cys–Cys disulfide; Glu side chain amide to Dap-Thr-Dab-cyclo(NH-...-Dab-ᴰLeu-Thr-Dab-Dab-Thr-) |
| Ex. 285 | Ac-Val-Asp-Tyr-Ser-[Glu]-ᴰDab-Ser-Trp-Ser-Val-Dab-Ser—NH₂, with Asp–Dab lactam bridge; Glu side chain amide to Dap-Thr-Dab-cyclo(NH-...-Dab-ᴰLeu-Leu-Dab-Dab-Thr-) |

| Ex. No. | Sequence |
|---|---|
| Ex. 286 | 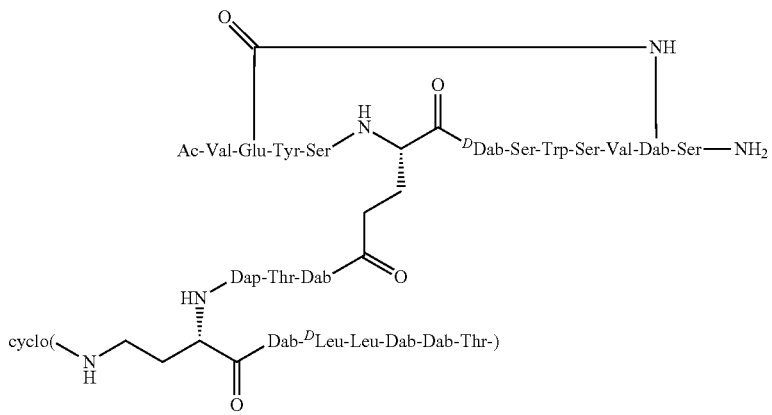 |
| Ex. 287 | 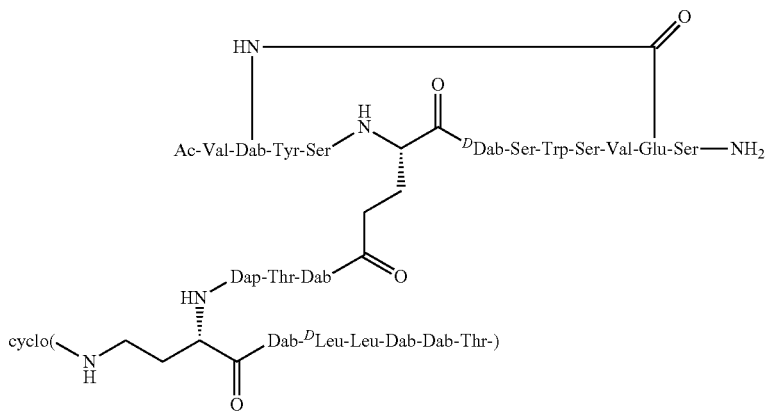 |
| Ex. 288 | 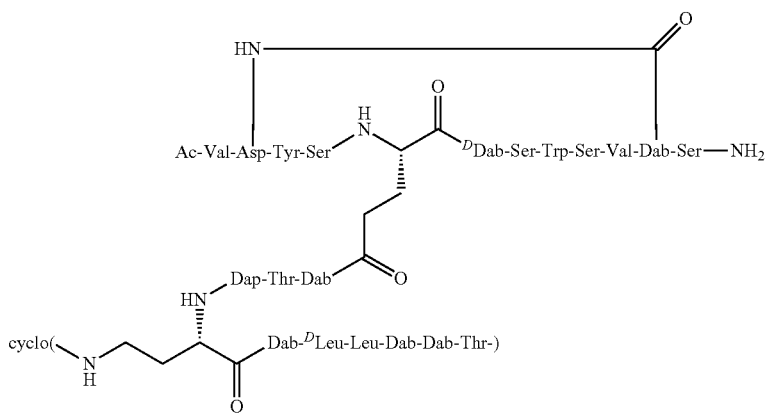 |

| Ex. No. | Sequence |
|---|---|
| Ex. 289 | 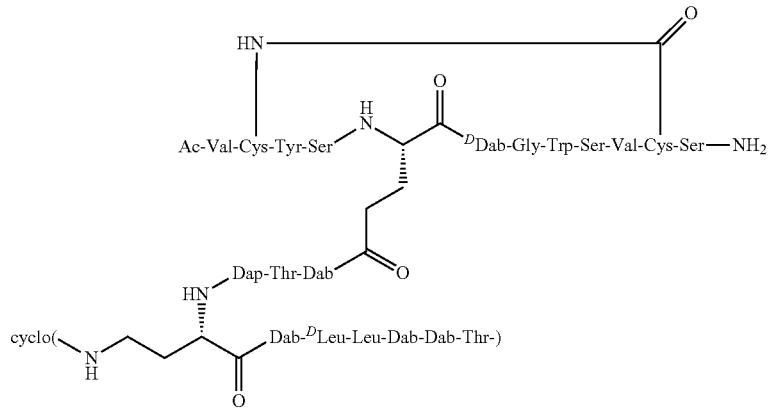 |
| Ex. 290 | 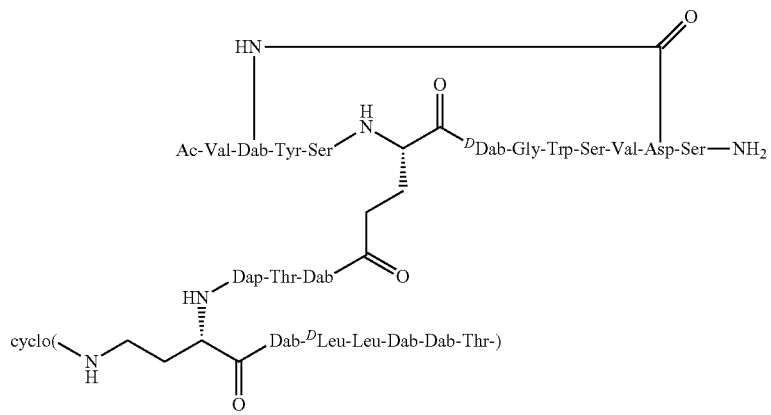 |
| Ex. 291 | 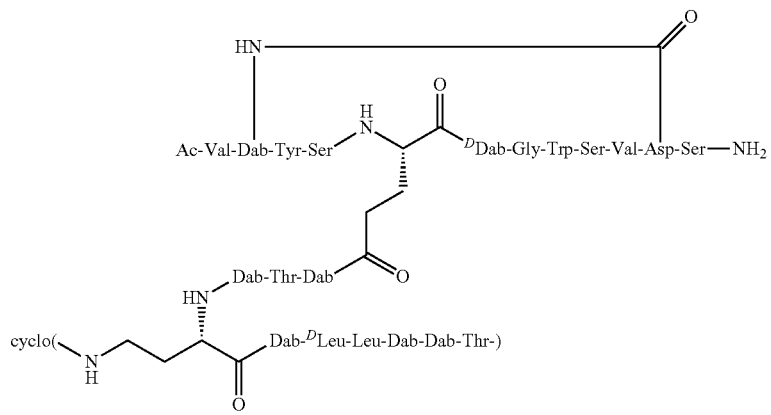 |

| Ex. No. | Sequence |
|---|---|
| Ex. 292 | 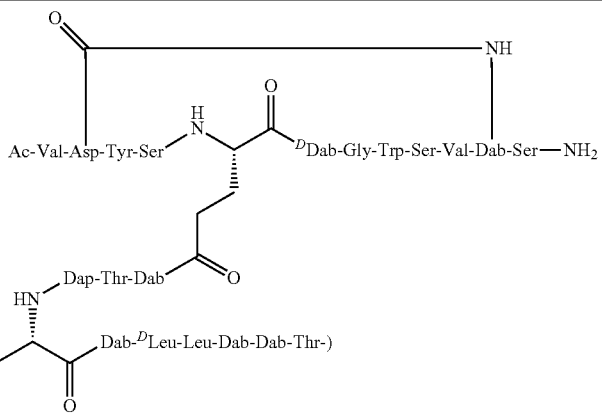 |
| Ex. 293 | 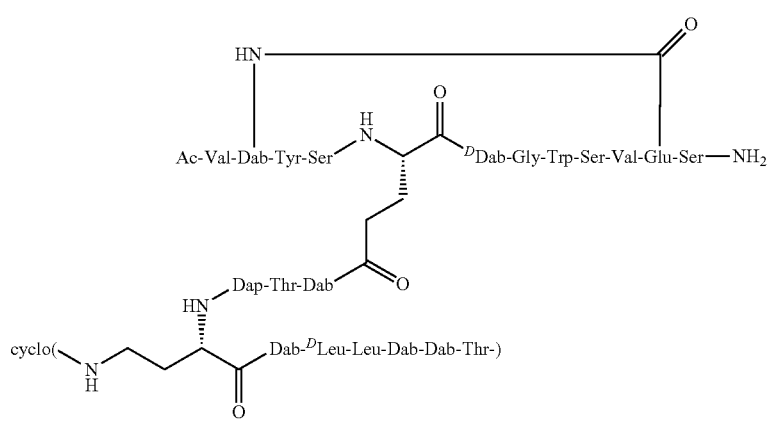 |
| Ex. 294 | 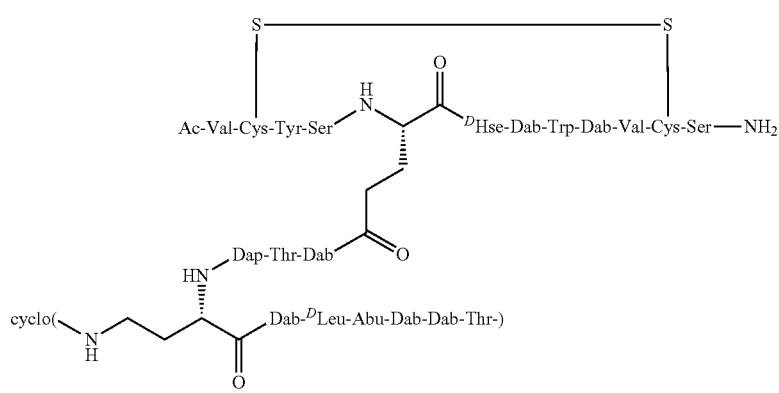 |
| Ex. 295 | 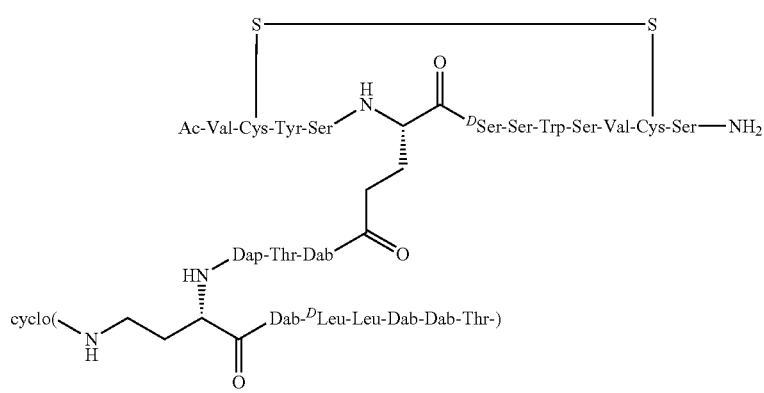 |

| Ex. No. | Sequence |
|---|---|
| Ex. 296 | 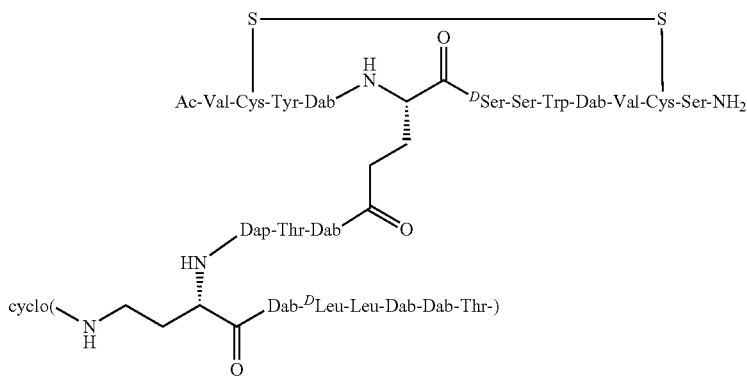 |
| Ex. 297 | 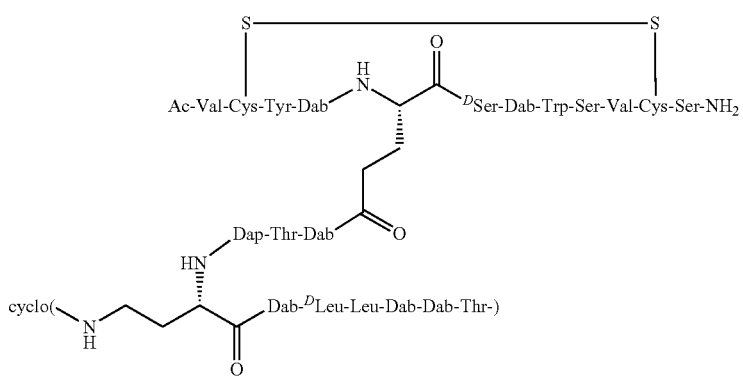 |
| Ex. 298 | 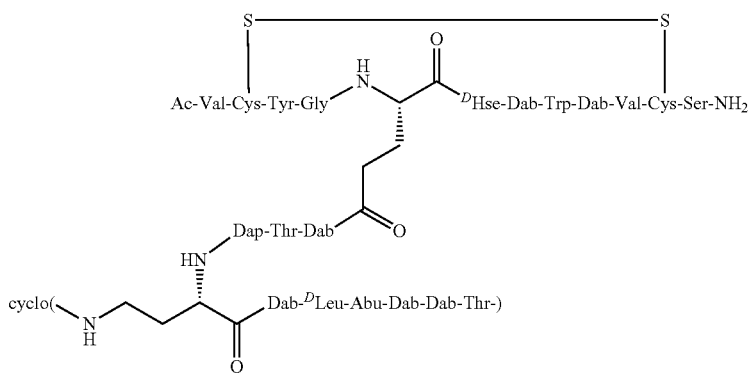 |
| Ex. 299 | 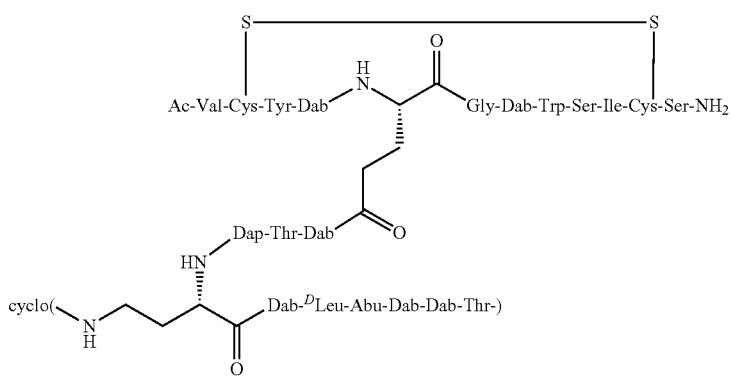 |

| Ex. No. | Sequence |
|---|---|
| Ex. 300 | 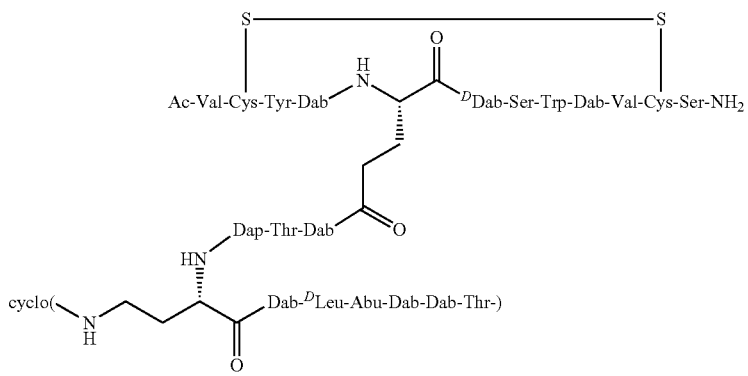 |
| Ex. 301 | 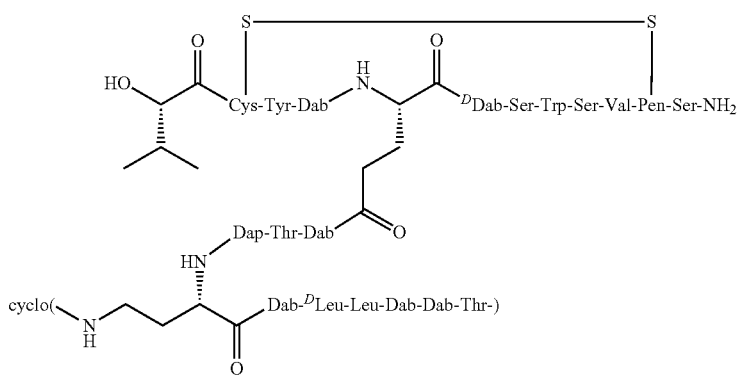 |
| Ex. 302 | 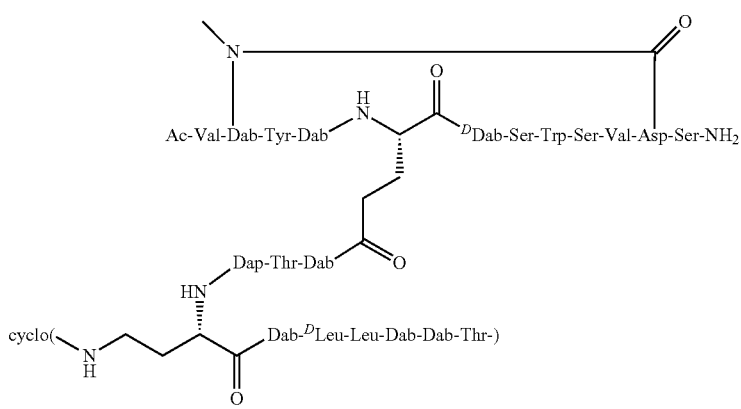 |
| Ex. 303 | 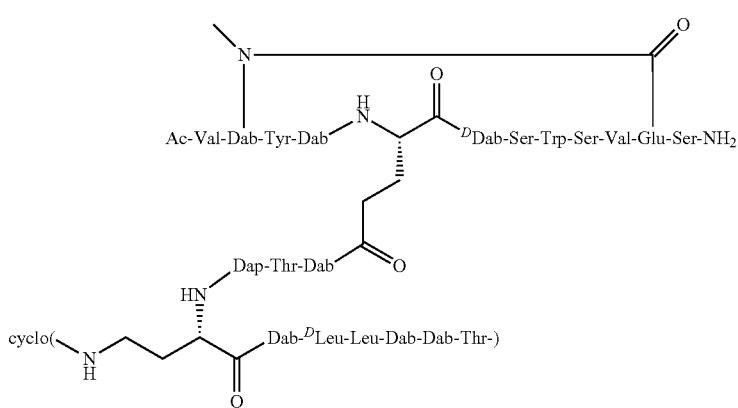 |

| Ex. No. | Sequence |
|---|---|
| Ex. 304 | 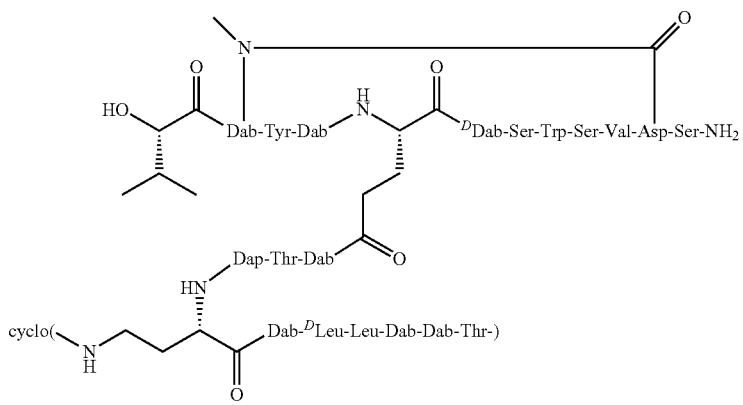 |
| Ex. 305 | 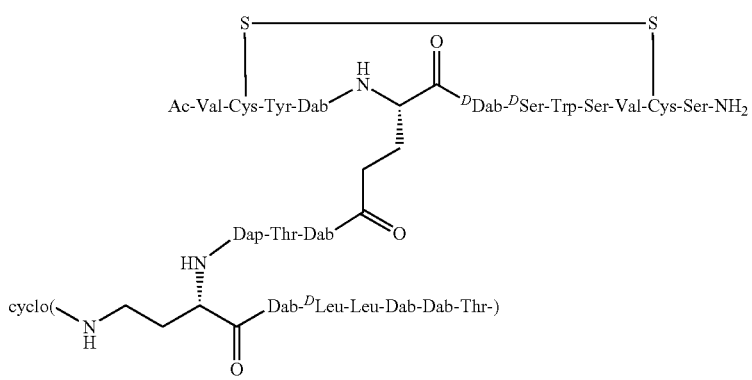 |
| Ex. 306 | 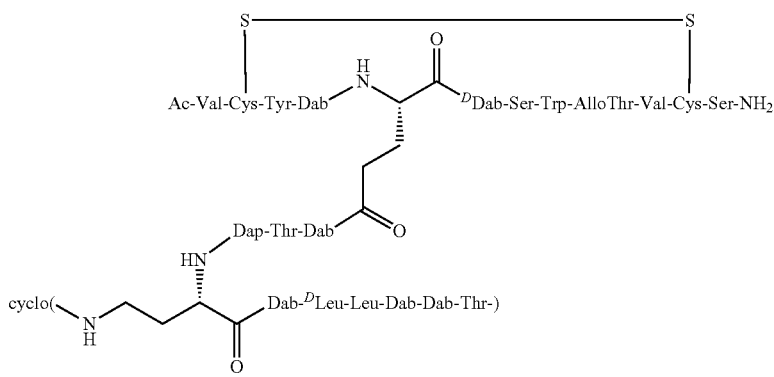 |
| Ex. 307 | 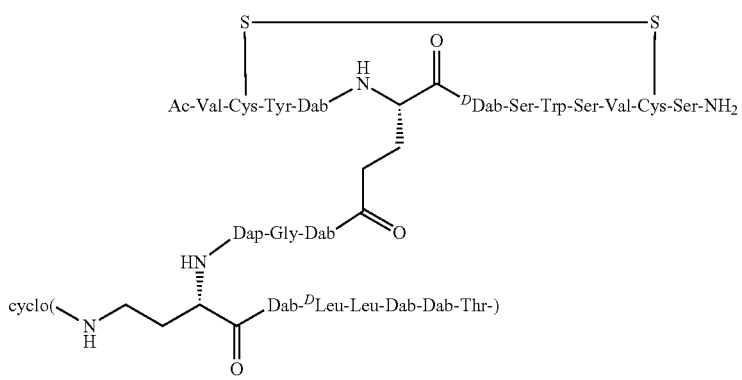 |

| Ex. No. | Sequence |
|---|---|
| Ex. 308 | 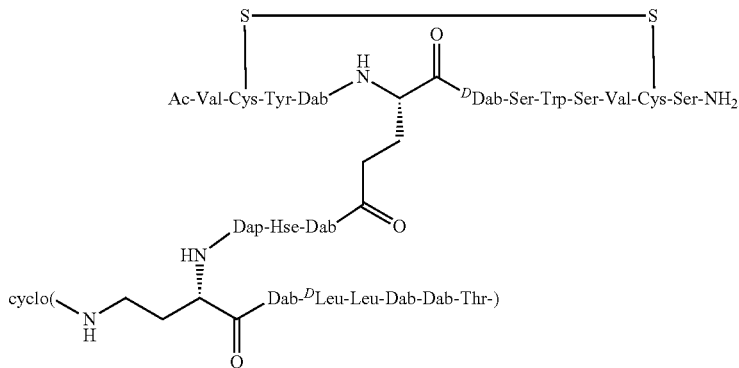 |
| Ex. 309 | 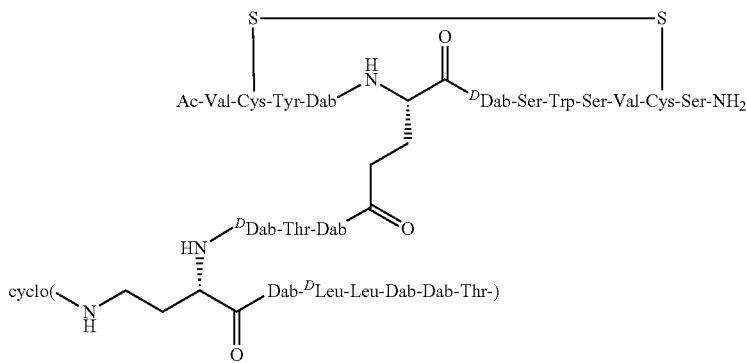 |
| Ex. 310 | 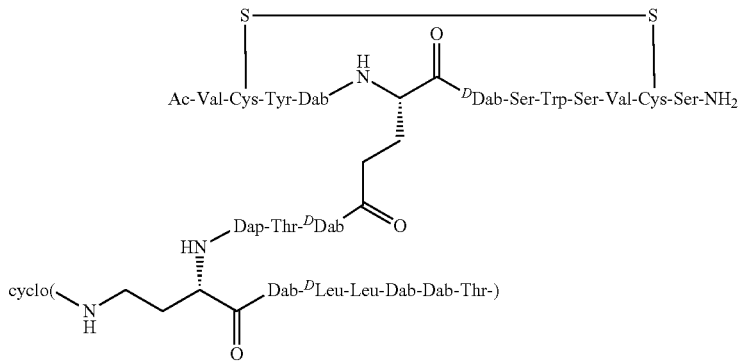 |
| Ex. 311 | 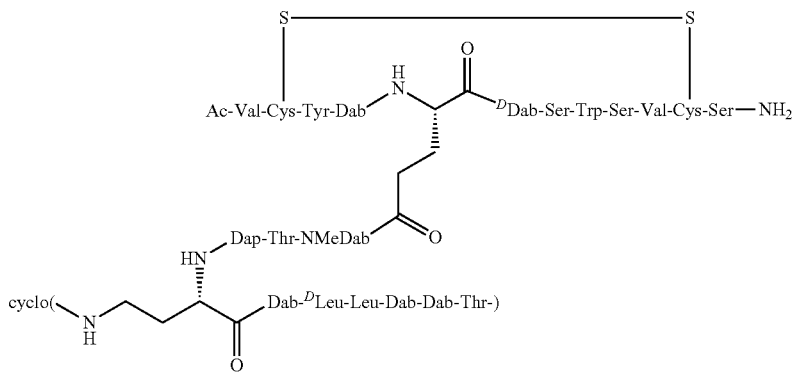 |

| Ex. No. | Sequence |
|---|---|
| Ex. 312 | 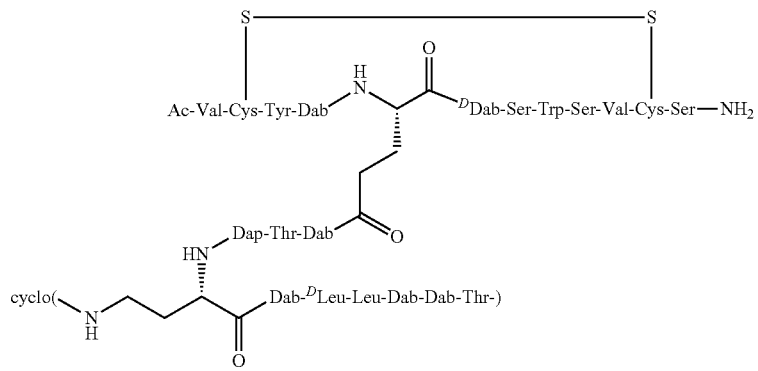 |
| Ex. 313 | 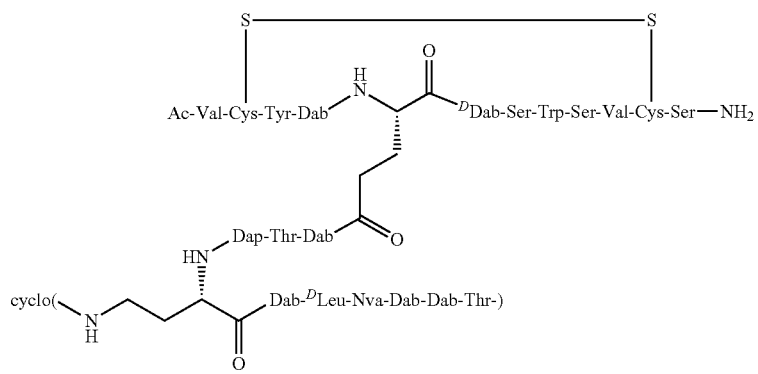 |
| Ex. 314 | 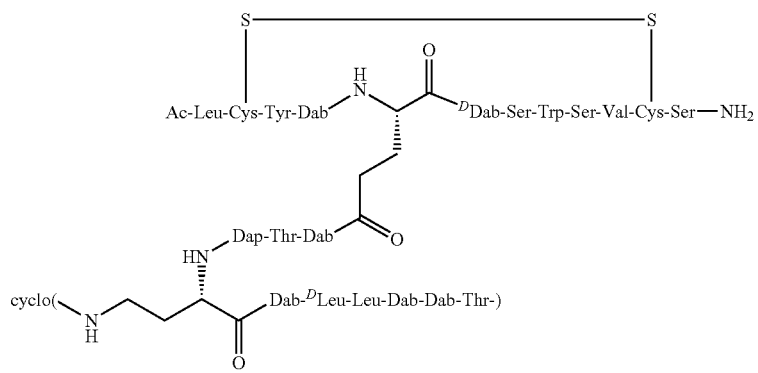 |
| Ex. 315 | 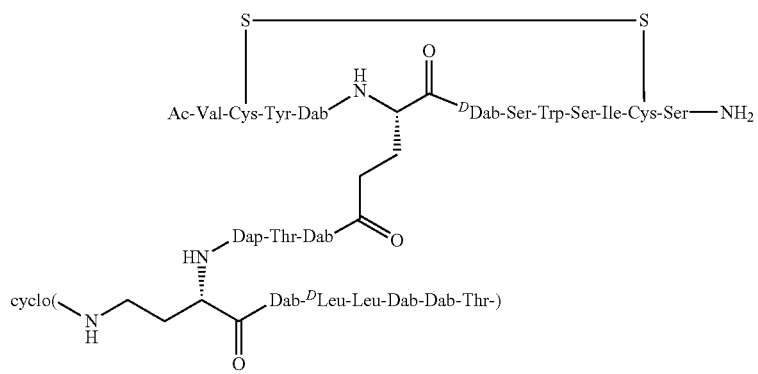 |

| Ex. No. | Sequence |
|---|---|
| Ex. 316 | 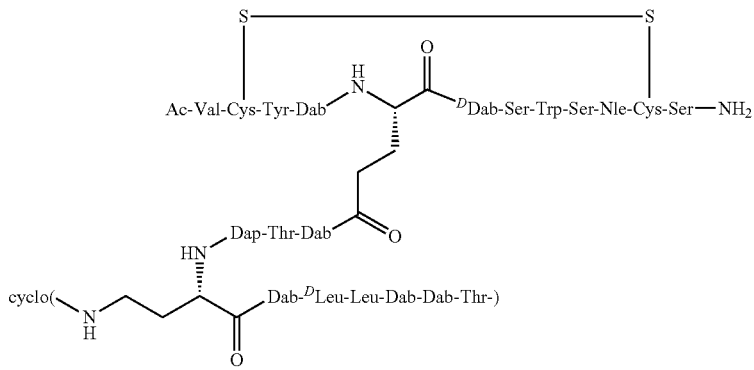 |
| Ex. 317 | 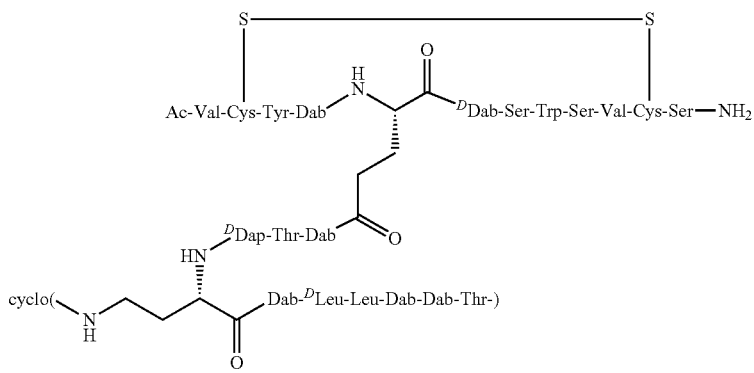 |
| Ex. 318 | 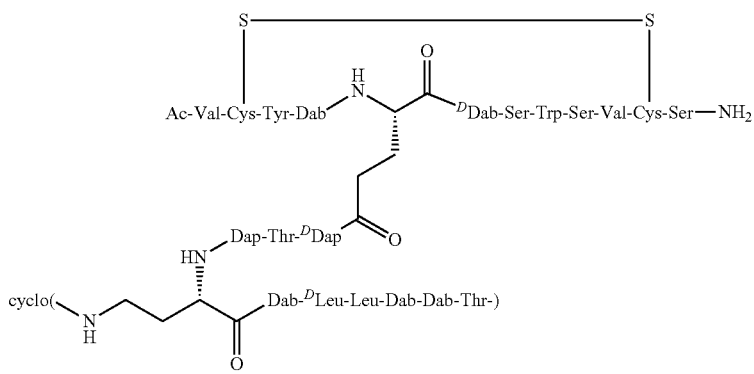 |
| Ex. 319 | 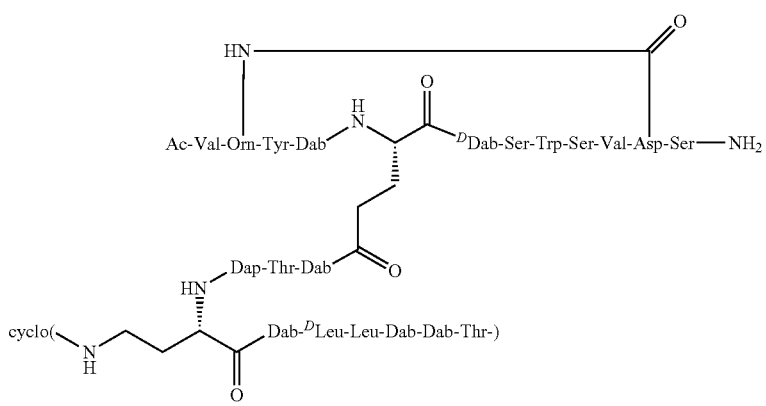 |

| Ex. No. | Sequence |
|---|---|
| Ex. 320 | 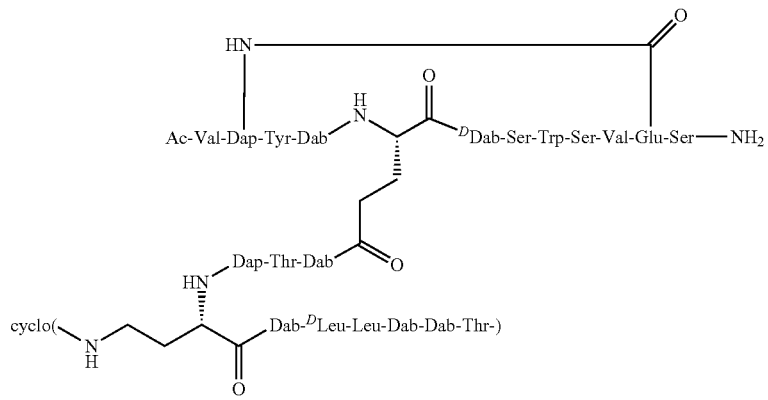 |
| Ex. 321 | 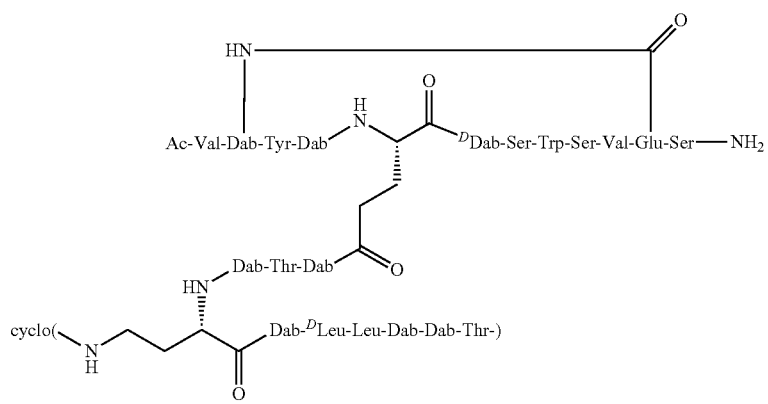 |
| Ex. 322 | 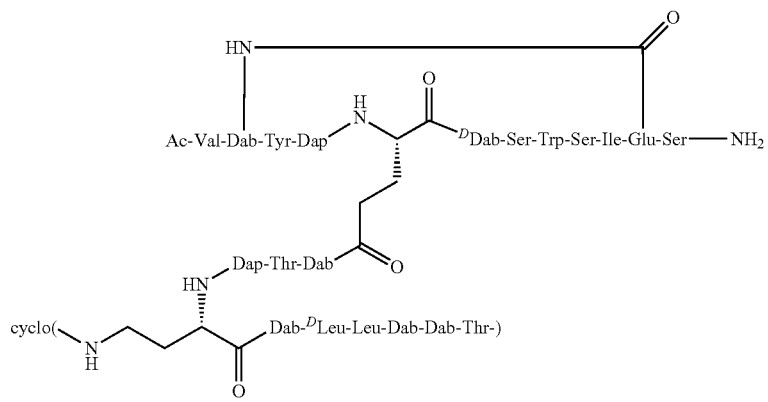 |
| Ex. 323 | 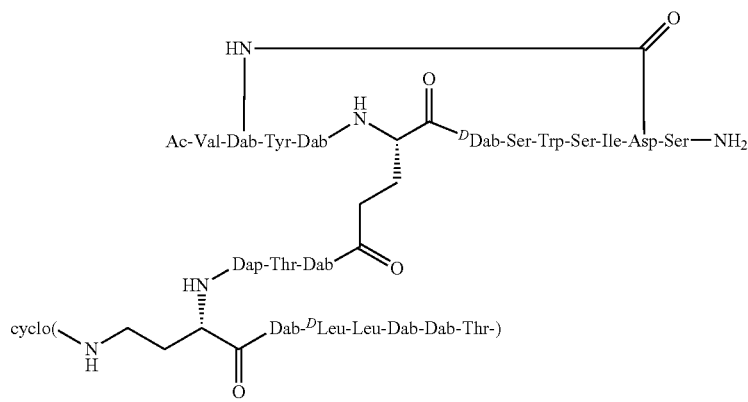 |

| Ex. No. | Sequence |
|---|---|
Ex. 324
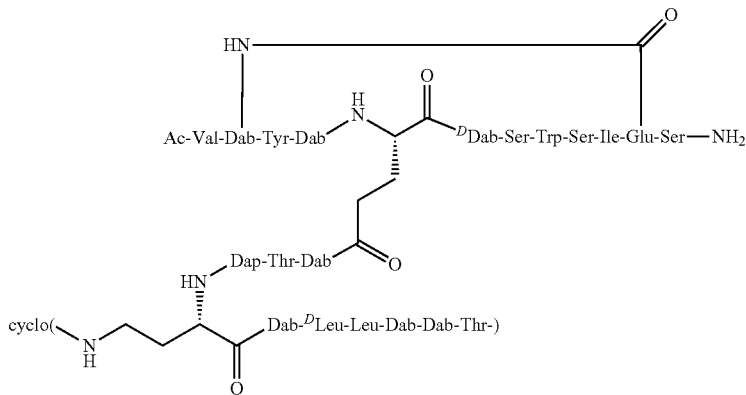
Ex. 325
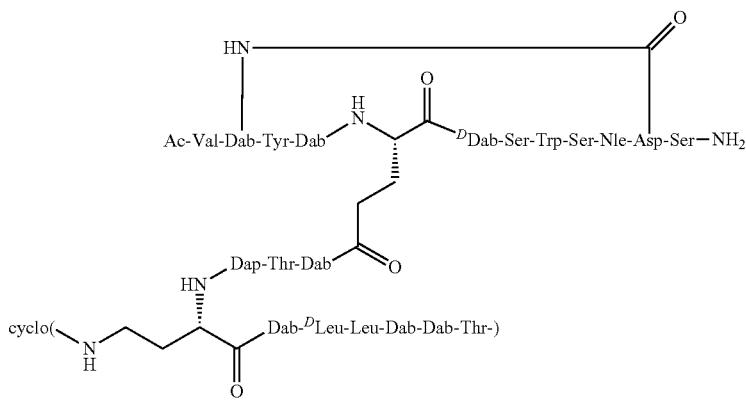
Ex. 326
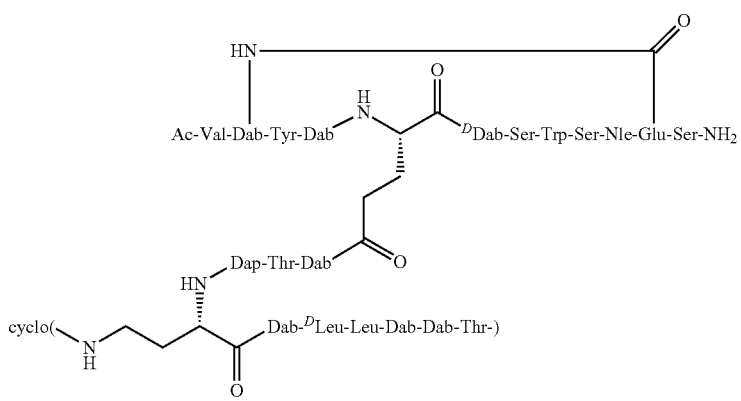

| Ex. No. | Sequence |
|---|---|
| Ex. 327 | 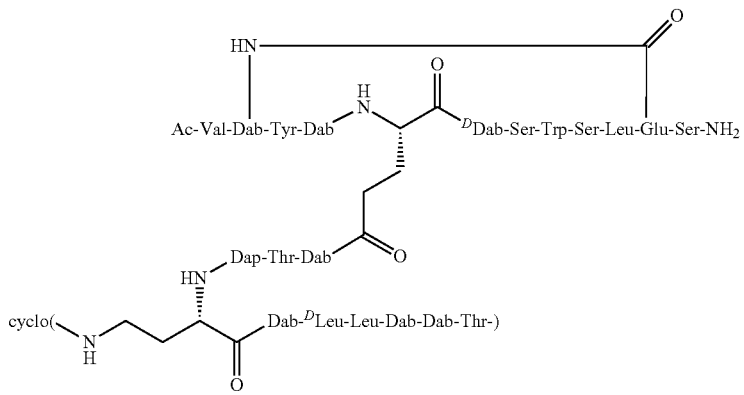 |
| Ex. 328 | 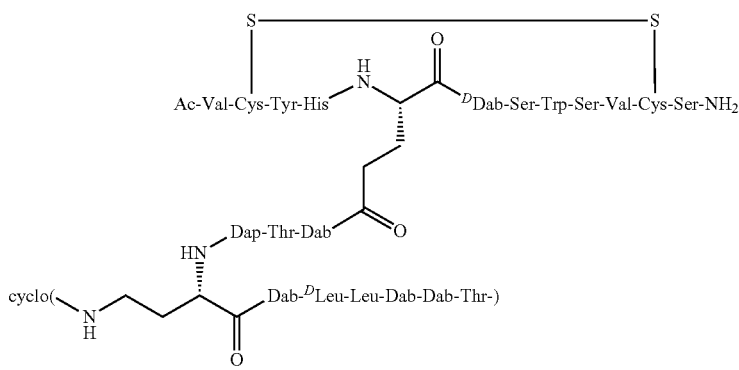 |
| Ex. 329 | 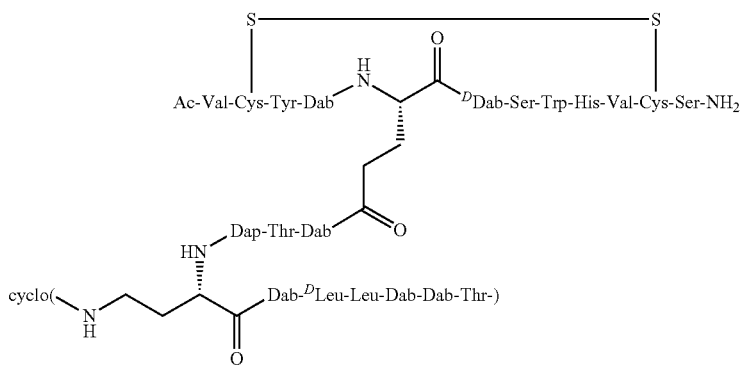 |
| Ex. 330 | 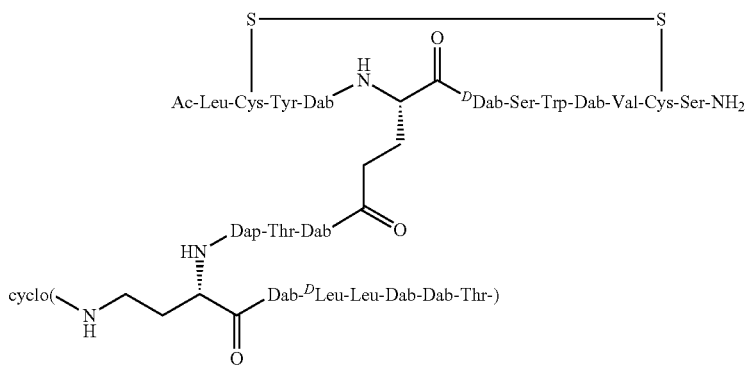 |

| Ex. No. | Sequence |
|---|---|
| Ex. 331 | 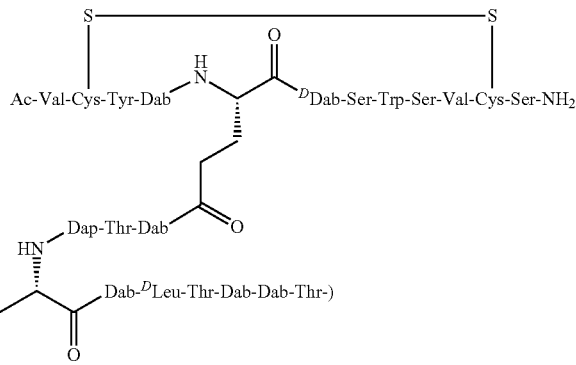 |
| Ex. 332 | 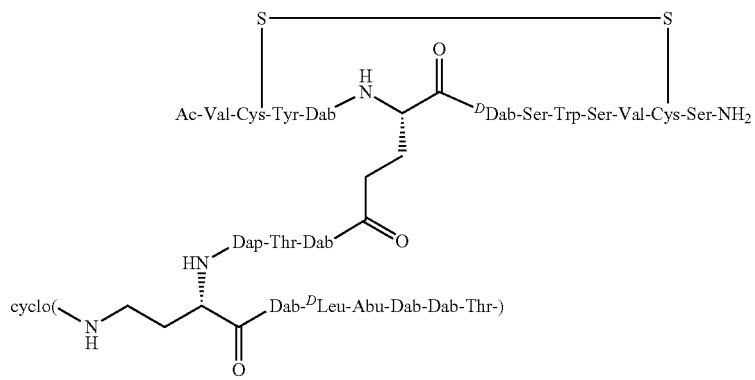 |
| Ex. 333 | 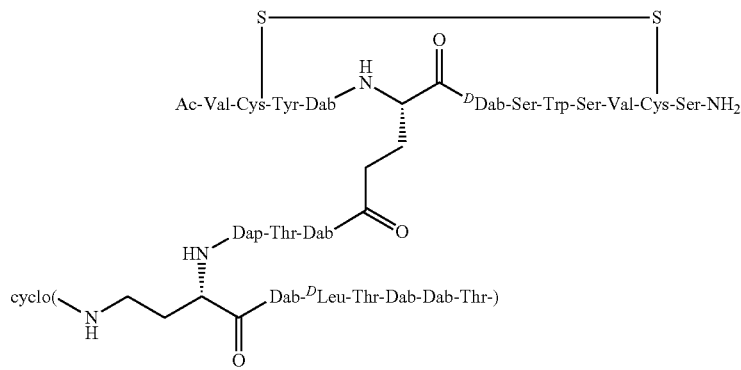 |
| Ex. 334 | 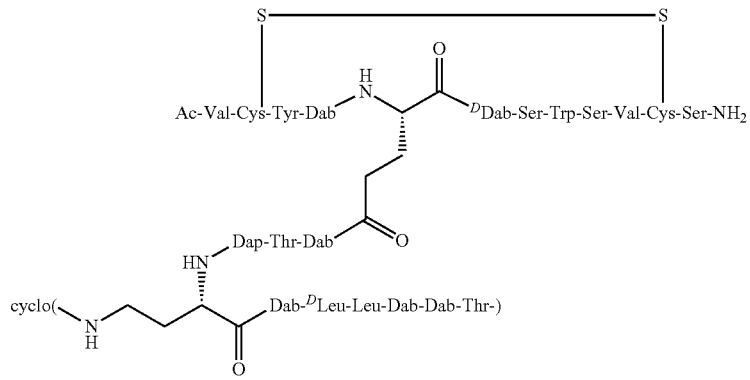 |

| Ex. No. | Sequence |
| --- | --- |
| Ex. 335 | 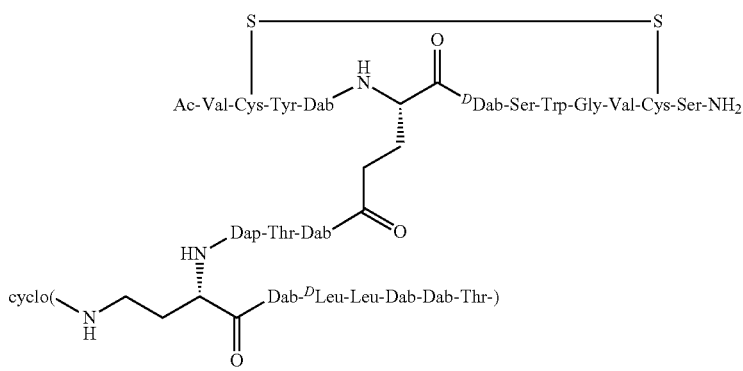 |
| Ex. 336 | 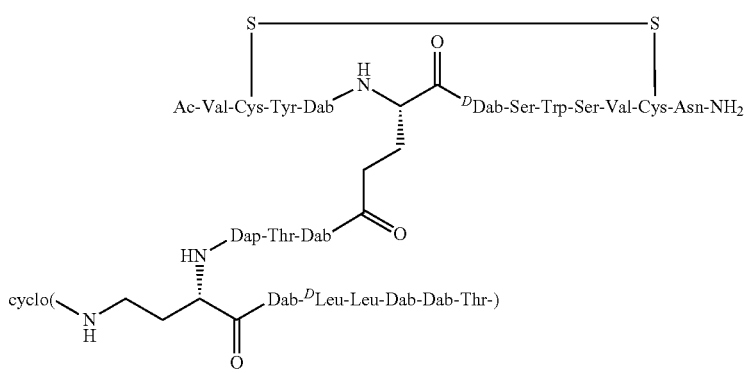 |
| Ex. 337 | 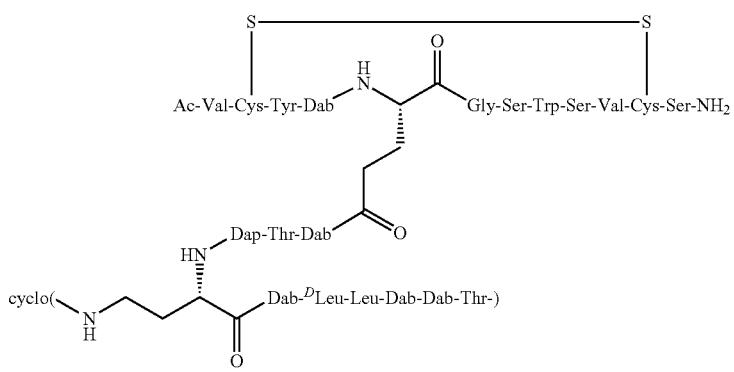 |
| Ex. 338 | 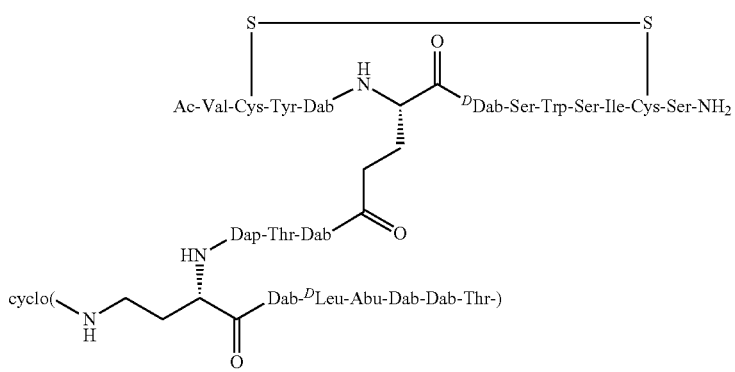 |

| Ex. No. | Sequence |
| --- | --- |
| Ex. 339 | 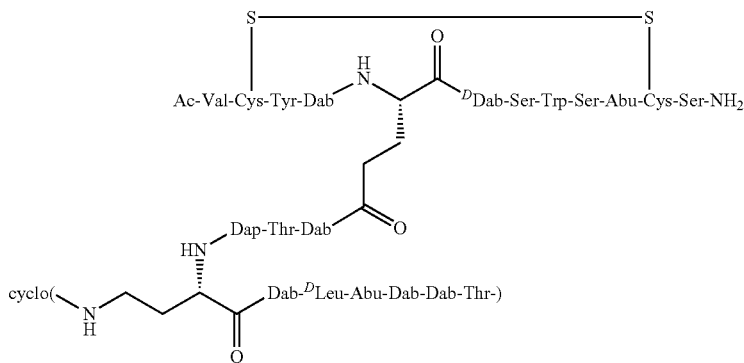 |
| Ex. 340 | 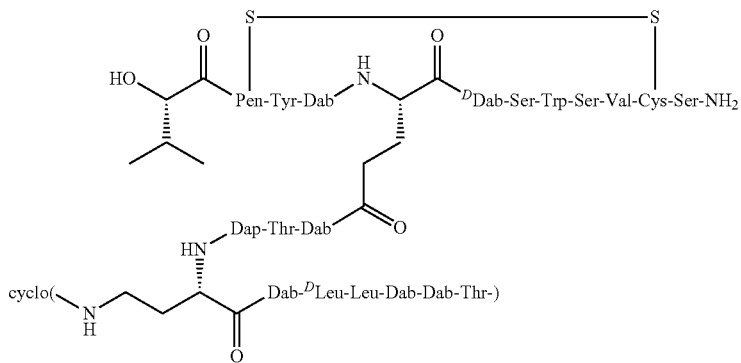 |
| Ex. 341 | 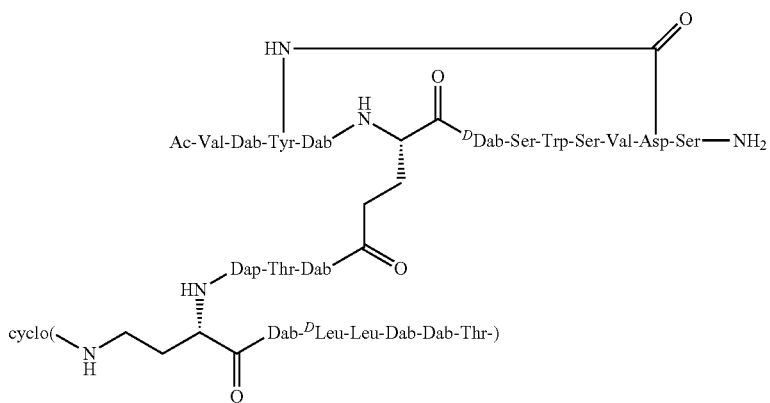 |
| Ex. 342 | 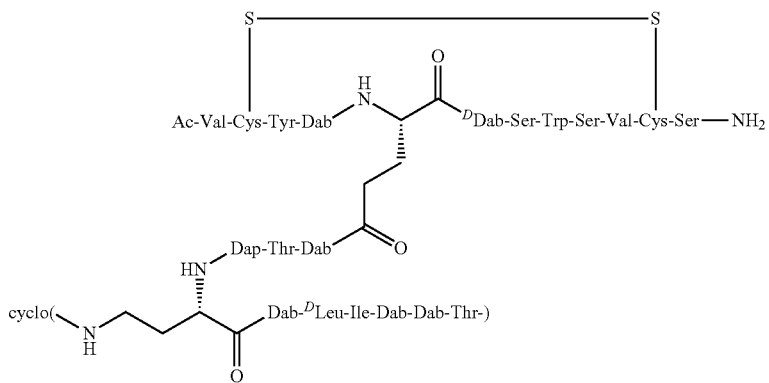 |

| Ex. No. | Sequence |
|---|---|
| Ex. 343 | Ac-Val-Cys-Tyr-Dab-[NH-CH(C=O-DDab-Hse-Trp-Ser-Val-Cys-Ser-NH₂)]-CH₂CH₂-C(=O)-NH-Dap-Thr-Dab-cyclo(-NH-CH(-)-C(=O)-Dab-DLeu-Thr-Dab-Dab-Thr-); Cys-Cys disulfide |
| Ex. 344 | HO-CH(iPr)-C(=O)-Cys-Tyr-Dab-[NH-CH(C=O-DDab-Ser-Trp-Ser-Val-Cys-DSer-NH₂)]-CH₂CH₂-C(=O)-NH-Dap-Thr-Dab-cyclo(-NH-CH(-)-C(=O)-Dab-DLeu-Leu-Dab-Dab-Thr-); Cys-Cys disulfide |
| Ex. 345 | Ac-Val-Cys-Tyr-Dab-[NH-CH(C=O-Gly-Dab-Trp-Ser-Val-Cys-Ser-NH₂)]-CH₂CH₂-C(=O)-NH-Dap-Thr-Dab-cyclo(-NH-CH(-)-C(=O)-Dab-DLeu-Leu-Dab-Dab-Thr-); Cys-Cys disulfide |
| Ex. 346 | Ac-Val-Dab-Tyr-Dab-[NH-CH(C=O-DDab-Gly-Trp-Ser-Val-Asp-Ser-NH₂)]-CH₂CH₂-C(=O)-NH-Dap-Thr-Dab-cyclo(-NH-CH(-)-C(=O)-Dab-DLeu-Leu-Dab-Dab-Thr-); Dab-Asp lactam |

| Ex. No. | Sequence |
|---|---|
| Ex. 347 | 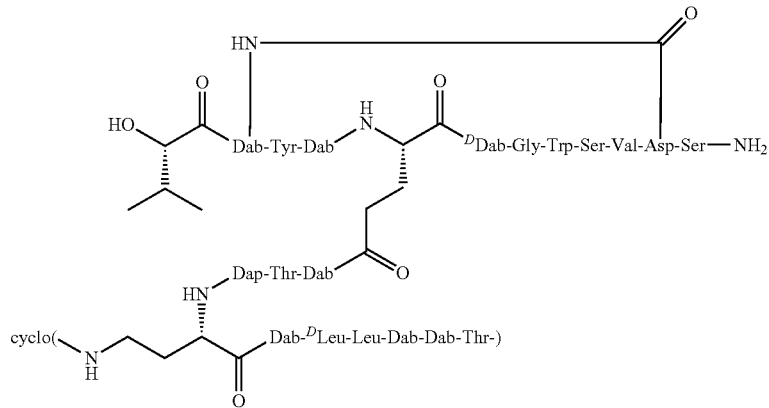 |
| Ex. 348 | 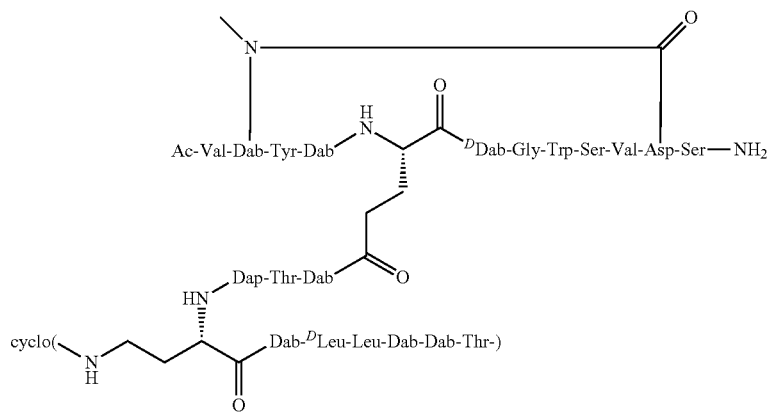 |
| Ex. 349 | 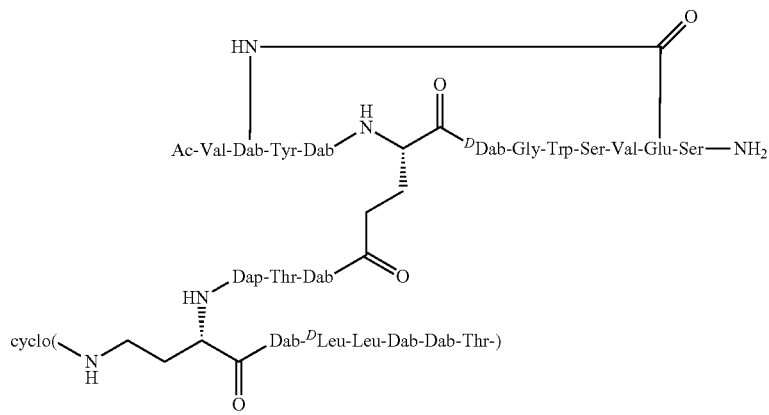 |

| Ex. No. | Sequence |
|---|---|
| Ex. 350 | 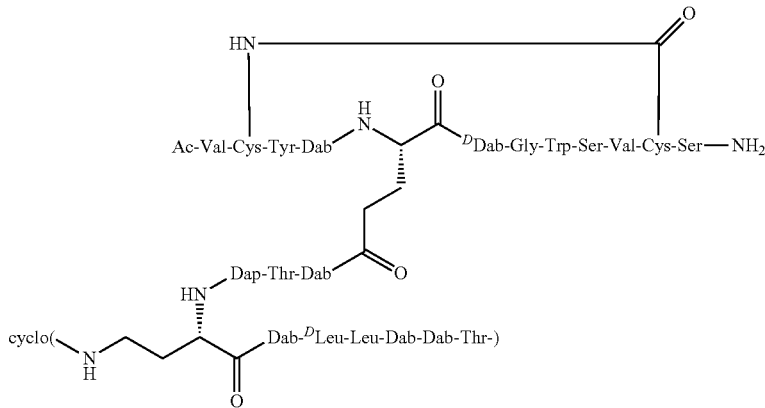 |
| Ex. 351 | 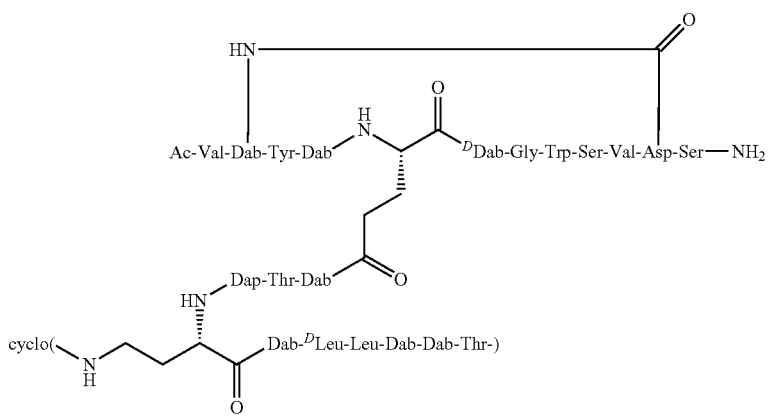 |
| Ex. 352 | 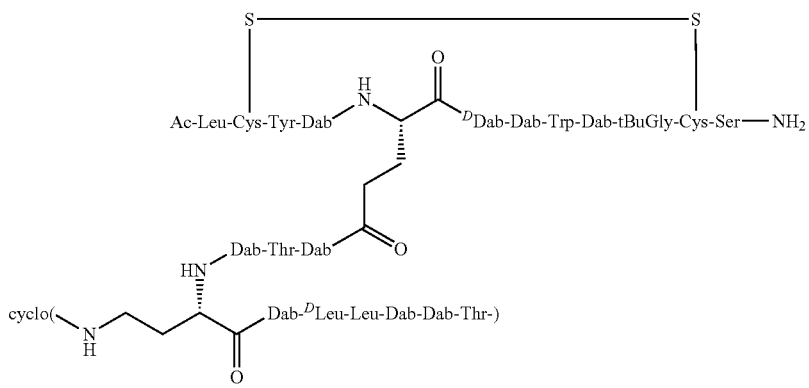 |
| Ex. 353 | 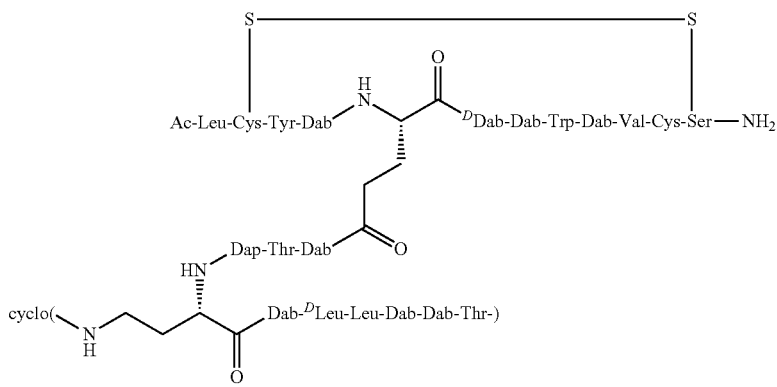 |

| Ex. No. | Sequence |
|---|---|
| Ex. 354 | 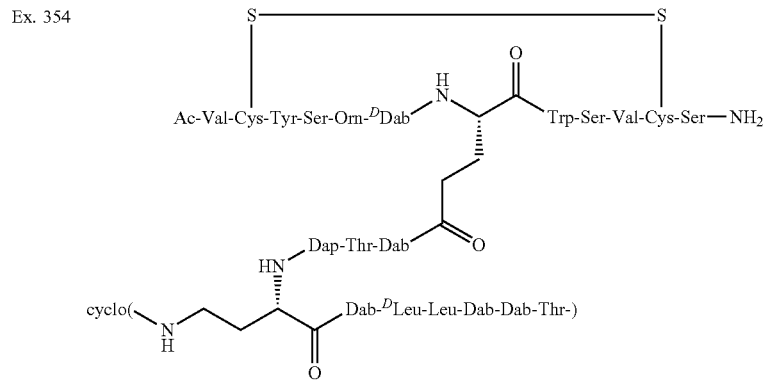 |
| Ex. 355 | 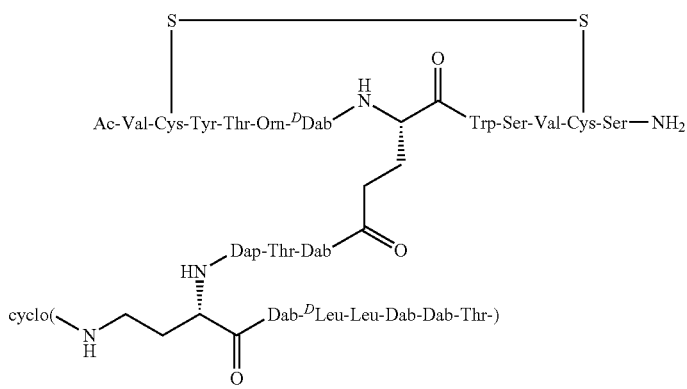 |
| Ex. 356 | 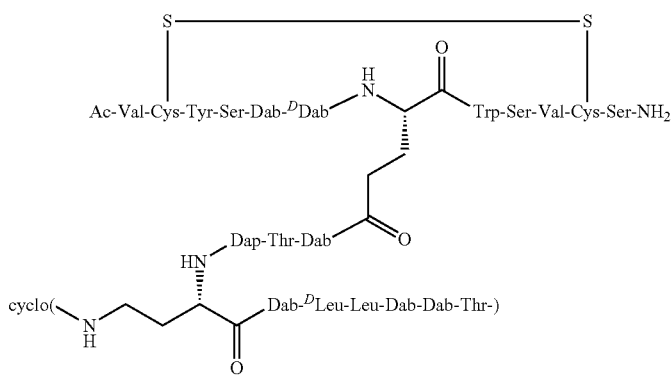 |
| Ex. 357 | 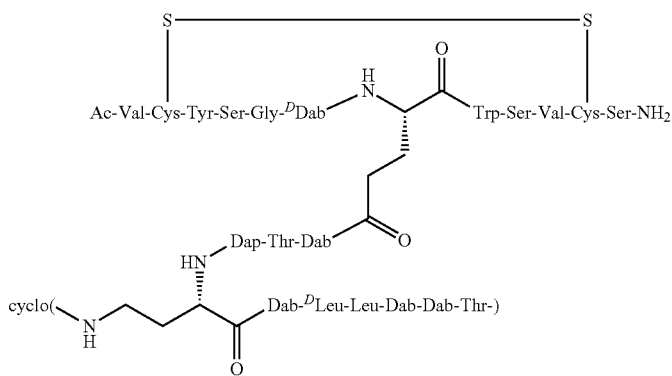 |

-continued
| Ex. No. | Sequence |
|---|---|
| Ex. 358 | 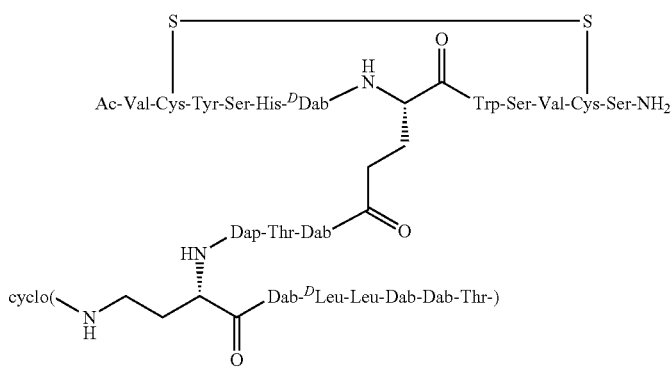 |
| Ex. 359 | 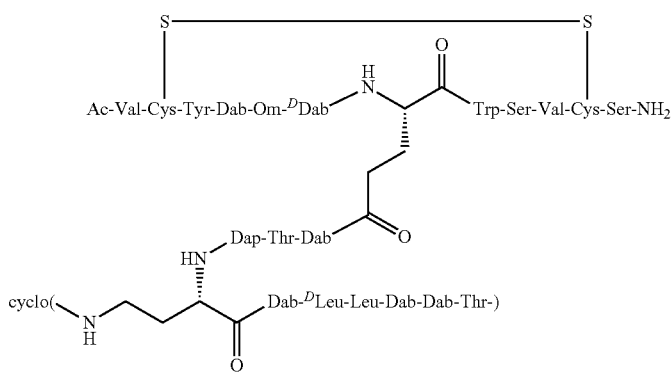 |
| Ex. 360 | 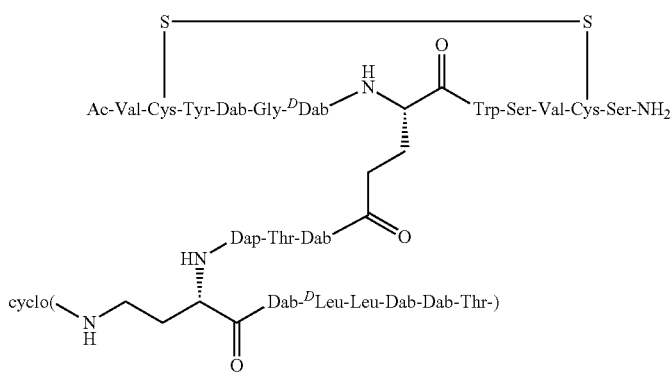 |
| Ex. 361 | 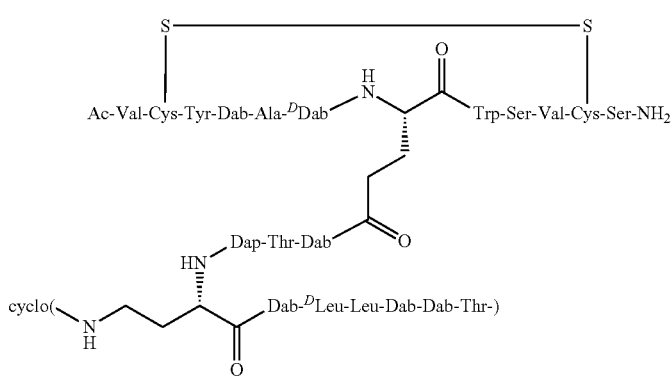 |

| Ex. No. | Sequence |
|---|---|
| Ex. 362 | 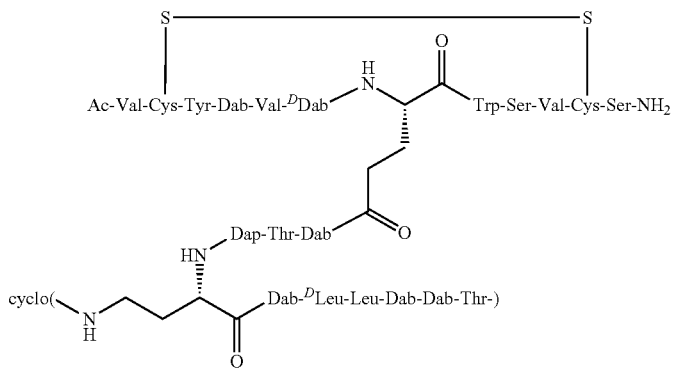 |
| Ex. 363 | 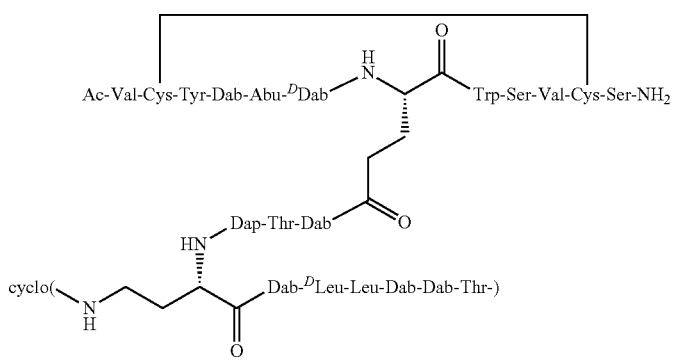 |
| Ex. 364 | 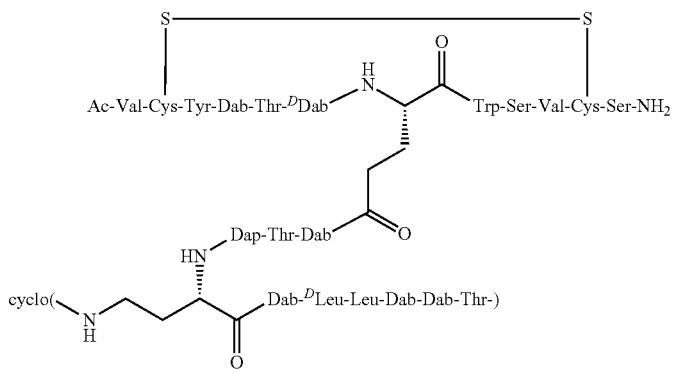 |
| Ex. 365 | 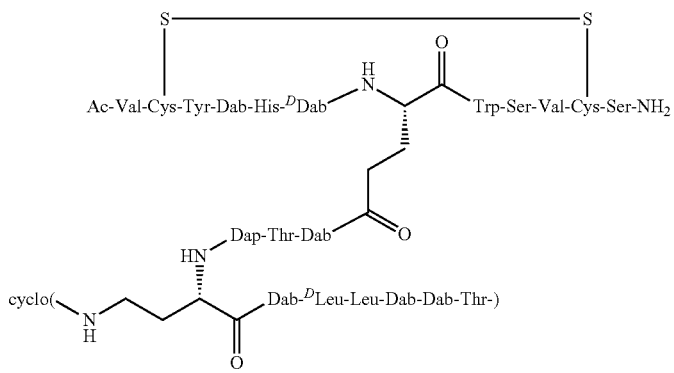 |

| Ex. No. | Sequence |
|---|---|
| Ex. 366 | 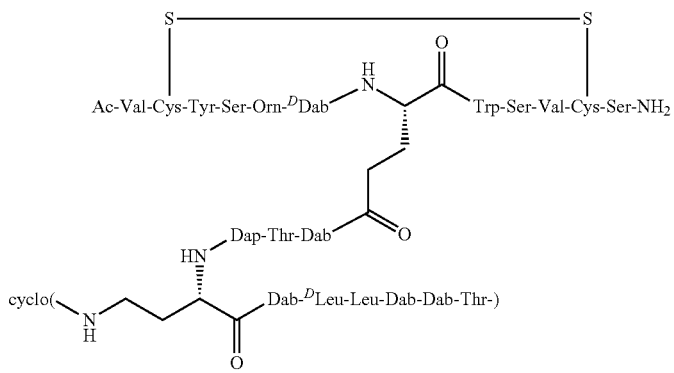 |
| Ex. 367 | 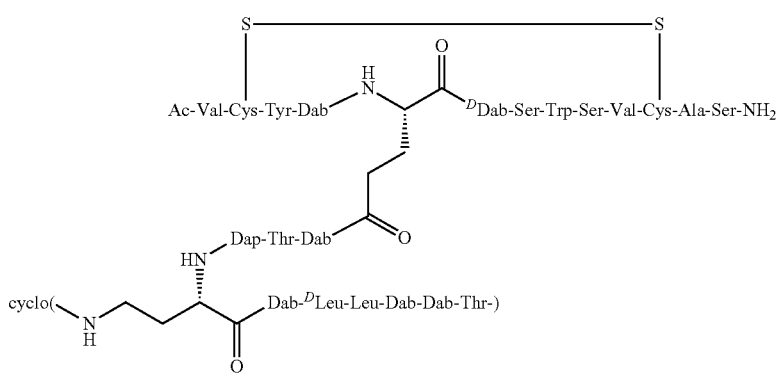 |
| Ex. 368 | 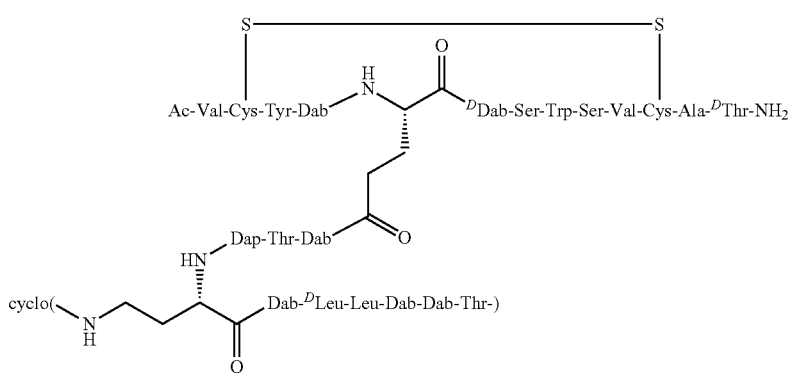 |
| Ex. 369 | 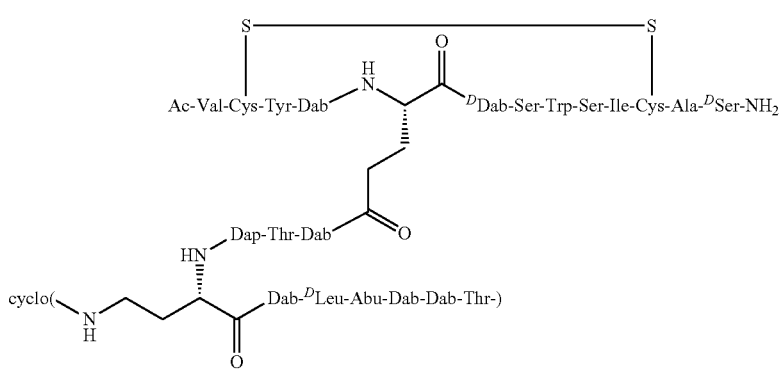 |

-continued
| Ex. No. | Sequence |
|---|---|
| Ex. 370 | 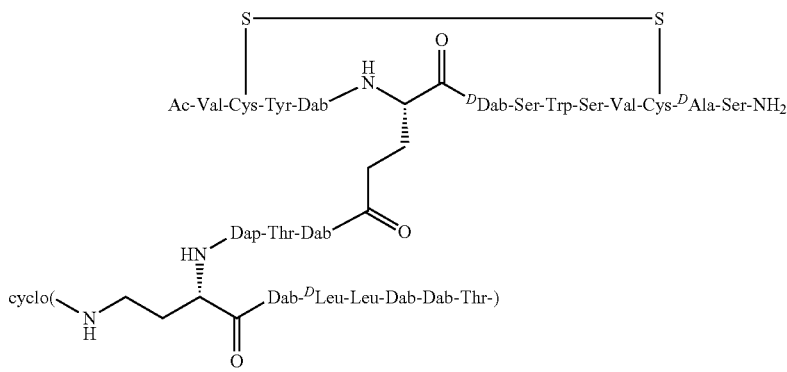 |
| Ex. 371 | 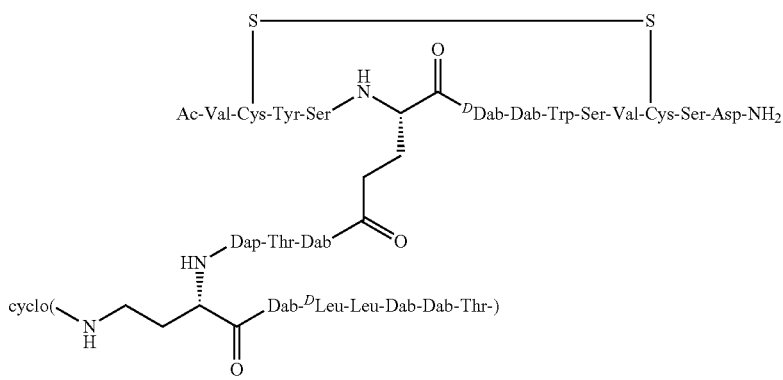 |
| Ex. 372 | 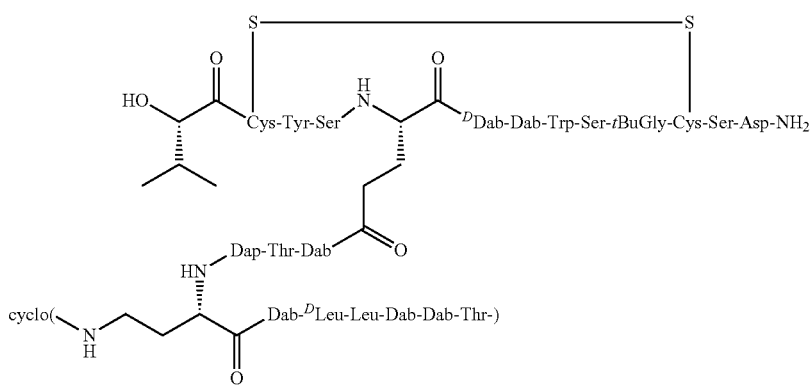 |
| Ex. 373 | 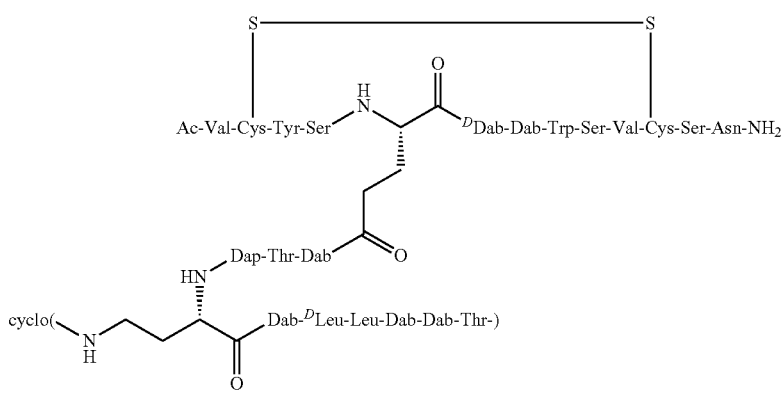 |

| Ex. No. | Sequence |
| --- | --- |
| Ex. 374 | 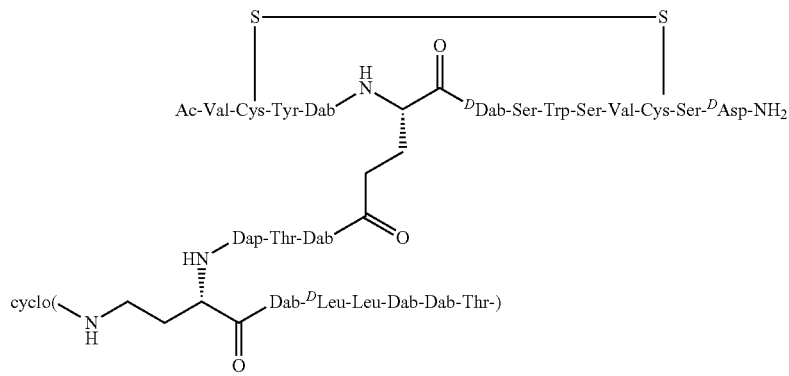 |
| Ex. 375 | 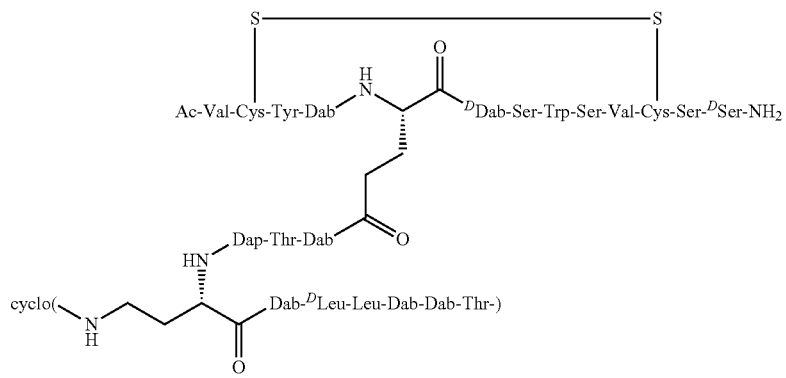 |
| Ex. 376 | 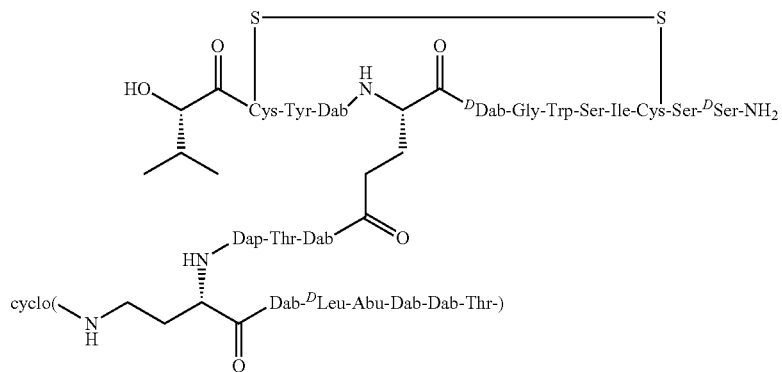 |
| Ex. 377 | 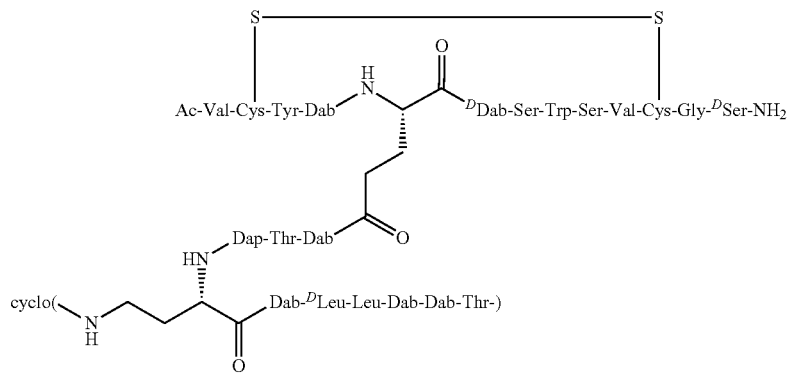 |

-continued
| Ex. No. | Sequence |
|---|---|
| Ex. 378 | 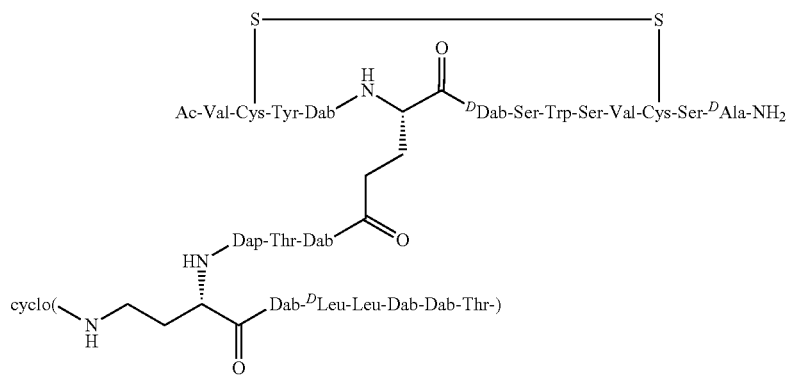 |
| Ex. 379 | 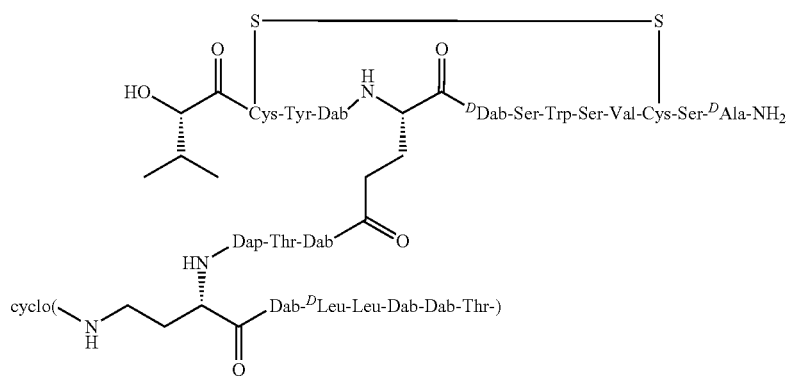 |
| Ex. 380 | 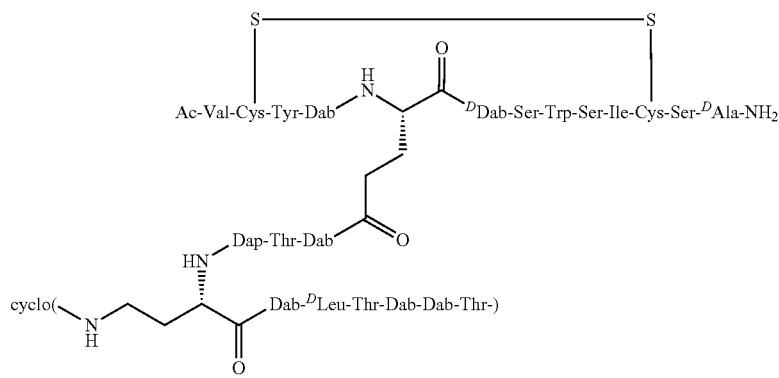 |
| Ex. 381 | 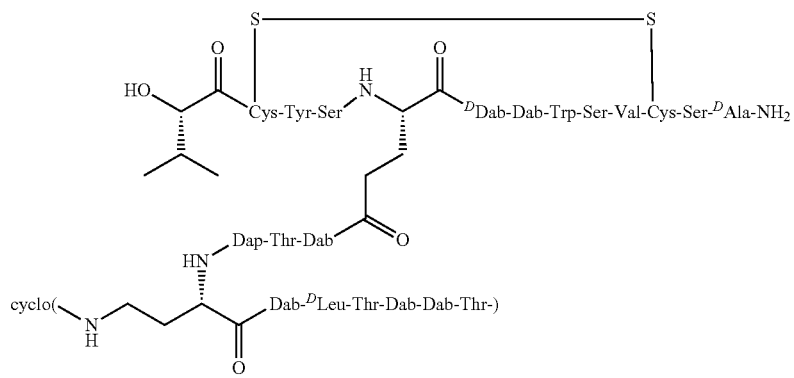 |

| Ex. No. | Sequence |
|---|---|
| Ex. 382 | 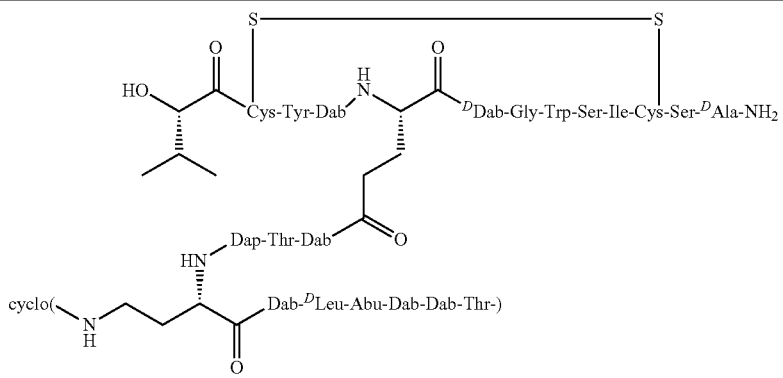 |
| Ex. 383 | 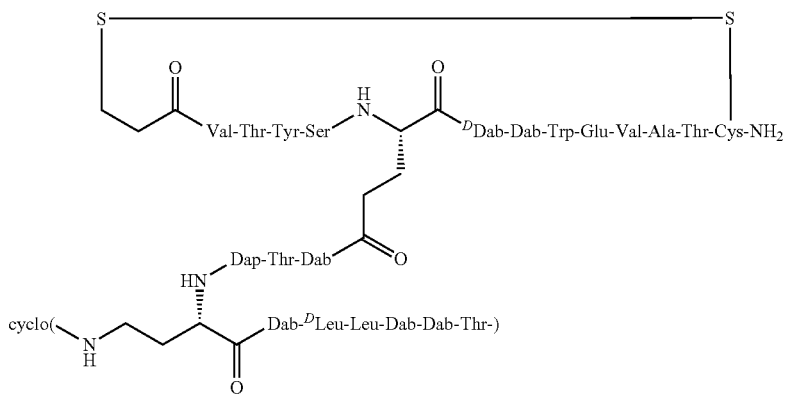 |
| Ex. 384 | 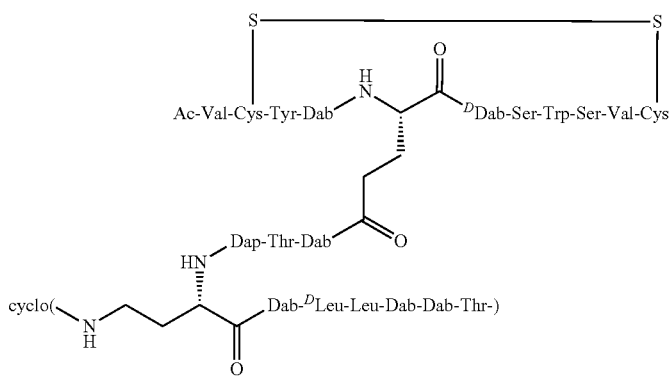 |
| Ex. 385 | 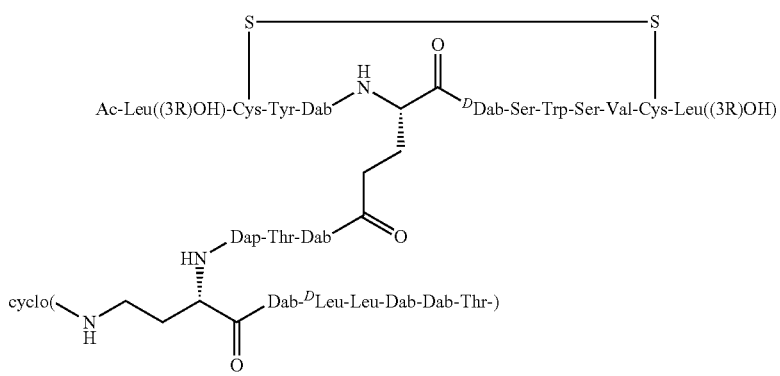 |
or a pharmaceutically acceptable salt thereof.

2. A pharmaceutical composition containing a β-hairpin peptidomimetic or a mixture thereof according to claim 1 and at least one pharmaceutically inert carrier.

3. A pharmaceutical composition according to claim 2 is in a form suitable for oral, topical, injection, pulmonary or inhalation or transdermal administration.

\* \* \* \* \*